US012440706B2

(12) United States Patent
Dragovich et al.

(10) Patent No.: US 12,440,706 B2
(45) Date of Patent: Oct. 14, 2025

(54) CONJUGATED CHEMICAL INDUCERS OF DEGRADATION AND METHODS OF USE

(71) Applicant: Genentech, Inc., South San Francisco, CA (US)

(72) Inventors: Peter Dragovich, South San Francisco, CA (US); Thomas Pillow, South San Francisco, CA (US); Robert Anthony Blake, South San Francisco, CA (US); Ingrid Wertz, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 921 days.

(21) Appl. No.: 17/239,086

(22) Filed: Apr. 23, 2021

(65) Prior Publication Data

US 2023/0067037 A1 Mar. 2, 2023

Related U.S. Application Data

(63) Continuation of application No. PCT/US2019/057878, filed on Oct. 24, 2019.
(Continued)

(51) Int. Cl.

| | |
|---|---|
| ***A61K 47/60*** | (2017.01) |
| ***A61K 31/427*** | (2006.01) |
| ***A61K 31/5517*** | (2006.01) |
| ***A61K 31/661*** | (2006.01) |
| ***A61K 47/68*** | (2017.01) |
| ***A61P 35/00*** | (2006.01) |

(52) U.S. Cl.
CPC ........ *A61K 47/6869* (2017.08); *A61K 31/427* (2013.01); *A61K 31/5517* (2013.01); *A61K 31/661* (2013.01); *A61K 47/6803* (2017.08); *A61P 35/00* (2018.01)

(58) Field of Classification Search
CPC .............. A61K 47/6803; A61K 31/427; A61K 31/5517; A61K 31/661; A61K 47/6869; A61K 47/6855; A61K 47/6867; A61K 47/6849; A61P 35/00
See application file for complete search history.

(56) References Cited

U.S. PATENT DOCUMENTS 11,666,581 B2 * 6/2023 Pillow ..................... A61P 35/00 424/181.1
2016/0015828 A1 1/2016 Torgov et al.
(Continued)

FOREIGN PATENT DOCUMENTS

AU 2004213053 A1 9/2004
CN 106659801 A 5/2017
(Continued)

OTHER PUBLICATIONS

Crew (Crew at al., J. Med. Chem. 2018, 61, 583-598 published online Jul. 10, 2017 (Year: 2017).*
(Continued)

*Primary Examiner* — Clinton A Brooks
*Assistant Examiner* — Izabela Schmidt

(57) ABSTRACT

The subject matter described herein is directed to antibody-CIDE conjugates (Ab-CIDEs), to pharmaceutical compositions containing them, and to their use in treating diseases and conditions where targeted protein degradation is beneficial.

17 Claims, 11 Drawing Sheets

Specification includes a Sequence Listing.

Related U.S. Application Data

(60) Provisional application No. 62/749,812, filed on Oct. 24, 2018.

(56) References Cited

U.S. PATENT DOCUMENTS

| | | | | |
|---|---|---|---|---|
| 2017/0281784 | A1* | 10/2017 | Wang | A61K 38/05 |
| 2018/0125821 | A1 | 5/2018 | Crew et al. | |

FOREIGN PATENT DOCUMENTS

| | | | | |
|---|---|---|---|---|
| CN | 107106700 | A | 8/2017 | |
| JP | 2015-508414 | A | 3/2015 | |
| JP | 2018-509468 | A | 4/2018 | |
| WO | 2004/073656 | A2 | 9/2004 | |
| WO | WO-2013106643 | A2 * | 7/2013 | A61K 31/422 |
| WO | WO-2014139324 | A1 * | 9/2014 | A61P 13/12 |
| WO | 2016/146985 | A1 | 9/2016 | |
| WO | WO-2017201449 | A1 * | 11/2017 | A61K 31/551 |
| WO | 2018/227023 | A1 | 12/2018 | |
| WO | 2019/140003 | A1 | 7/2019 | |

OTHER PUBLICATIONS

Pillow (Pillow et al., Sci., 2017, 8, 366-370 published online Aug. 22, 2016 (Year: 2016).*

Poiani et. al., Bioconjugate Chem. 1994, 5, 621-630 (Year: 1994).*

Blake, R., et al., "GNE-0011, a novel monovalent BRD4 degrader" Abstract (4452 (Mar. 29-Apr. 3, 2019; Cancer Res, vol. 79, 13 Suppl.)) AACR Annual Meeting, Atlanta, GA—US, pp. 1 ( Jul. 1, 2019).

Fidanze, S.D., et al., "Discovery and optimization of novel constrained pyrrolopyridone BET Family inhibitors" Bioorg Med Chem Lett 28(10):1804-1810 (Jun. 1, 2018).

International Preliminary Report on Patentability—PCT/US2019/057878 issued Apr. 27, 2021, pp. 1-11.

International Search Report with Written Opinion—PCT/US2019/057878 mailed Feb. 10, 2020, pp. 1-16.

Zengerle, M., et al., "Selective Small Molecule Induced Degradation of the BET Bromodomain Protein BRD4" ACS Chem Biol 10(8):1770-1777 (Aug. 21, 2015).

* cited by examiner

CONJUGATED CHEMICAL INDUCERS OF DEGRADATION AND METHODS OF USE

CROSS REFERENCE TO RELATED APPLICATIONS

This application is a continuation of International Application No. PCT/US2019/057878 having an International filing date of Oct. 24, 2019, which claims priority to U.S. Patent Application No. 62/749,812 filed on Oct. 24, 2018, the contents of each are incorporated by reference herein in their entirety.

SEQUENCE LISTING

This application contains a Sequence Listing which has been submitted electronically in ASCII format and is hereby incorporated by reference in its entirety. Said ASCII copy, created on Apr. 13, 2021, is named P348.34-US_Sequence_Listing.txt and is 281,410 bytes in size.

FIELD OF THE INVENTION

The subject matter described herein relates generally to degrader conjugates comprising antibody-proteolysis-targeting chimera molecules that are useful for facilitating intracellular degradation of target proteins.

BACKGROUND

Cell maintenance and normal function requires controlled degradation of cellular proteins. For example, degradation of regulatory proteins triggers events in the cell cycle, such as DNA replication, chromosome segregation, etc. Accordingly, such degradation of proteins has implications for the cell's proliferation, differentiation, and death.

While inhibitors of proteins can block or reduce protein activity in a cell, protein degradation in a cell can also reduce activity or remove altogether the target protein. Utilizing a cell's protein degradation pathway can, therefore, provide a means for reducing or removing protein activity. One of the cell's major degradation pathways is known as the ubiquitin-proteasome system. In this system, a protein is marked for degradation by the proteasome by ubiquitinating the protein. The ubiqitinization of the protein is accomplished by an E3 ubiquitin ligase that binds to a protein and adds ubiquitin molecules to the protein. The E3 ubiquitin ligase is part of a pathway that includes E1 and E2 ubiquitin ligases, which make ubiquitin available to the E3 ubiquitin ligase to add to the protein.

To harness this degradation pathway, molecular constructs bring together an E3 ubiquitin ligase with a protein that is to be targeted for degradation and an antibody for targeting. To facilitate a protein for degradation by the proteasome, the molecular construct is comprised of a group that binds to an E3 ubiquitin ligase and a group that binds to the protein target for degradation. These groups are typically connected with a linker. This molecular construct can bring the E3 ubiquitin ligase in proximity with the protein so that it is ubiquitinated and marked for degradation. However, the relatively large size of the molecular construct can be problematic for targeted delivery.

There is an ongoing need in the art for enhanced and targeted delivery of such molecular constructs to cells that contain the protein target. The subject matter described herein addresses this and other shortcomings in the art.

SUMMARY OF THE INVENTION

In one aspect, the subject matter described herein is directed to covalently linked Ab-CIDEs (PACs), wherein the positions of the covalent bonds that connect the components of the Ab-CIDE: Ab, L1 (Linker 1), L2 (Linker 2), protein binding group and the E3 ligase binding group, can be tailored as desired to prepare Ab-CIDEs having desirable properties, such as in vivo pharmacokinetics, stability and solubility.

In one aspect, the subject matter described herein is directed to conjugated Chemical Inducers of Degradation ("CIDE") having the formula:

$$Ab\text{-}(L1\text{-}D)_p,$$

wherein,

D is a CIDE having the structure E3LB-L2-PB;

E3LB is covalently bound to L2, and said E3LB is a group that binds an E3 ligase, wherein said E3 ligase is von Hippel-Lindau (VHL);

L2 is a linker covalently bound to E3LB and PB;

PB is a protein binding group covalently bound to L2, and said PB is a group that binds BRD4 or ERα, including all variants, mutations, splice variants, indels and fusions thereof, Ab is an antibody covalently bound to L1;

L1 is a linker, covalently bound to Ab and D; and p has a value from about 1 to about 8.

Another aspect of the subject matter described herein is a pharmaceutical composition comprising an Ab-CIDE, and one or more pharmaceutically acceptable excipients.

Another aspect of the subject matter described herein is the use of an Ab-CIDE in methods of treating conditions and diseases by administering to a subject a pharmaceutical composition comprising an Ab-CIDE.

Another aspect of the subject matter described herein is a method of making an Ab-CIDE.

Another aspect of the subject matter described herein is an article of manufacture comprising a pharmaceutical composition comprising an Ab-CIDE, a container, and a package insert or label indicating that the pharmaceutical composition can be used to treat a disease or condition.

DETAILED DESCRIPTION

Figure 1:
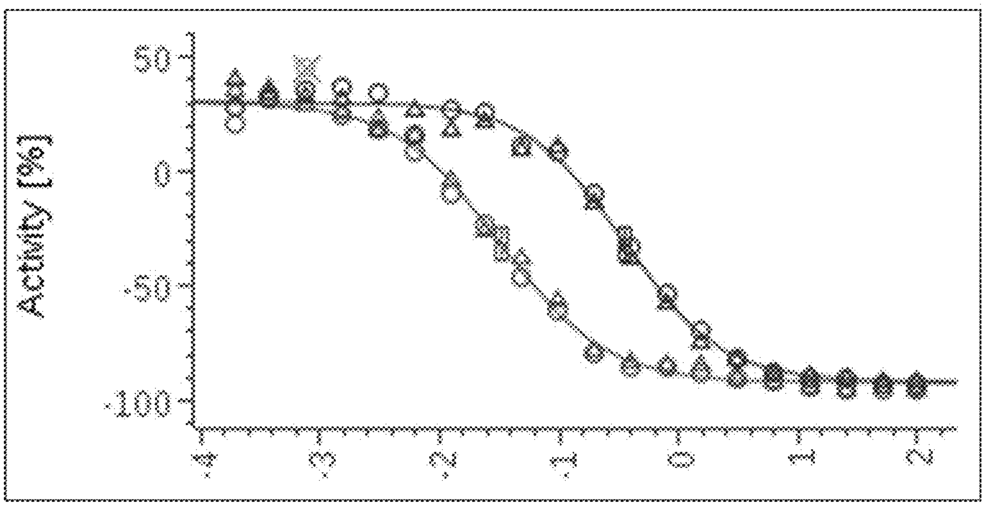
FIG. 1 shows ERα degradation percent activity in MCF7 neo/HER2 cells with ERα targeting Ab-CIDEs. Red curve (bottommost curve)=7C2-HER2-ms-L1EC10, Blue curve (uppermost curve)=CD22-ms-L1EC10.

Disclosed herein, are antibody-Chemical Inducers of Degradation ("CIDE") conjugates, referred to herein as Ab-CIDEs or PACs, that are useful in targeted protein degradation, and the treatment of related diseases and disorders. The subject matter described herein utilizes antibody targeting to direct a CIDE to a target cell or tissue. As described herein, connecting an antibody to a CIDE to form an Ab-CIDE has been shown to deliver the CIDE to a target cell or tissue. As shown herein, e.g. in the Examples, a cell that expresses an antigen can be targeted by an antigen specific Ab-CIDE, whereby the CIDE portion of the Ab-CIDE is delivered intracellularly to the target cell. CIDEs that comprise an antibody directed to an antigen that is not found on the cell do not result in significant intracellular delivery of the CIDE to the cell.

Accordingly, the subject matter described herein is directed to Ab-CIDE compositions that result in the ubiquitination of a target protein and subsequent degradation of the protein. The compositions comprise an antibody covalently linked to a linker (L1), which is covalently linked at any available point of attachment to a CIDE, in which the CIDE comprises an E3 ubiquitin ligase binding (E3LB) moiety, wherein the E3LB moiety recognizes a E3 ubiquitin ligase protein that is VHL or XIAP, and a protein binding moiety (PB) that recognizes a target protein that is Era or BRD4. The subject matter described herein is useful for regulating protein activity, and treating diseases and conditions related to protein activity.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

The term "CIDE" refers to proteolysis-targeting chimera molecules having generally three components, an E3 ubiquitin ligase binding group (E3LB), a linker L2, and a protein binding group (PB).

The terms "residue," "moiety" or "group" refers to a component that is covalently bound or linked to another component. By way of example, a residue of a compound will have an atom or atoms of the compound, such as a hydrogen or hydroxy, replaced with a covalent bond, thereby binding the residue to another component of the CIDE, L1-CIDE or Ab-CIDE. For example a "residue of a CIDE" refers to a CIDE that is covalently linked to one or more groups such as a Linker L2, which itself can be optionally further linked to an antibody.

The term "covalently bound" or "covalently linked" refers to a chemical bond formed by sharing of one or more pairs of electrons.

The term "peptidomimetic" or PM as used herein means a non-peptide chemical moiety. Peptides are short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A peptidomimetic chemical moiety includes non-amino acid chemical moieties. A peptidomimetic chemical moiety may also include one or more amino acid that are separated by one or more non-amino acid chemical units. A peptidomimetic chemical moiety does not contain in any portion of its chemical structure two or more adjacent amino acids that are linked by peptide bonds.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology,* 5th Ed., Garland Publishing, New York). A target antigen generally has numerous binding sites, also called epitopes, recognized by CDRs (complementary determining regions) on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment(s)" as used herein comprises a portion of a full length antibody, generally the antigen binding or variable region thereof. Examples of antibody fragments include Fab, Fab', $F(ab')_2$, and Fv fragments; diabodies; linear antibodies; minibodies (Olafsen et al (2004) *Protein Eng. Design & Sel.* 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the subject matter described herein may be made by the hybridoma method first described by Kohler et al (1975) *Nature,* 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) *Nature,* 352: 624-628; Marks et al (1991) *J. Mol. Biol.,* 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "intact antibody" as used herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used hererin means a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1—H1(L1)—FR2—H2(L2)—FR3—H3(L3)—FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) *J. Immunol.* 161:4083-4090; Lund et al (2000) *Eur. J. Biochem.* 267:7246-7256; US 2005/0048572; US 2004/0229310).

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain that are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. *Cancer Cell* 5:317-328 (2004)).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following. In certain embodiments, an antibody as described herein has dissociation constant (Kd) of ≤1 μM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., $10^{-8}$M or less, e.g. from $10^{-8}$ M to $10^{-13}$ M, e.g., from $10^{-9}$ M to $10^{-13}$ M).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "free cysteine amino acid" as used herein refers to a cysteine amino acid residue which has been engineered into a parent antibody, has a thiol functional group (—SH), and is not paired as an intramolecular or intermolecular disulfide bridge. The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "Linker", "Linker Unit", or "link" as used herein means a chemical moiety comprising a chain of atoms that covalently attaches a CIDE moiety to an antibody, or a component of a CIDE to another component of the CIDE. In various embodiments, a linker is a divalent radical, specified as L1 or L2.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer.

A "patient population" refers to a group of cancer patients. Such populations can be used to demonstrate statistically significant efficacy and/or safety of a drug.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal may be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the subject matter described herein, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g, breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

By "monotherapy" is meant a therapeutic regimen that includes only a single therapeutic agent for the treatment of the cancer or tumor during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "cancer" and "cancerous" refer to or describe the physiological condition in mammals that is typically characterized by unregulated cell growth/proliferation. A "tumor" comprises one or more cancerous cells. Examples of cancer are provided elsewhere herein.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (HIC) score of 2+ or 3+ and/or an in situ hybridization (ISH) amplification ratio$\geq$2.0. The term "HER2-positive cell" refers to a cell that expresses HER2 on its surface.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage IIB, and stage IIIA breast cancers.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor are known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease. A "recurrent" cancer is one which has regrown, either at the initial site or at a distant site, after a response to initial therapy, such as surgery. A "locally recurrent" cancer is cancer that returns after treatment in the same place as a previously treated cancer. An "operable" or "resectable" cancer is cancer which is confined to the primary organ and suitable for surgery (resection). A "non-resectable" or "unresectable" cancer is not able to be removed (resected) by surgery.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin;

ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®, an antisence oligonucleotide); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)—imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor(TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., *Science*, 251: 430-432 (1991); WO 90/11294; Ianeway, *Nature*, 341: 482 (1989); and WO 91/01133); BAFF antagonists such as BAFF antibodies and BR3 antibodies and zTNF4 antagonists (for review, see Mackay and Mackay, *Trends Immunol.*, 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., *Science*, 261: 1328-30 (1993); Mohan et al., *J. Immunol.*, 154: 1470-80 (1995)) and CTLA4-Ig (Finck et al., *Science*, 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the subject matter described herein are used to delay development of a disease or to slow the progression of a disease.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

An "effective amount" of an agent, e.g., a pharmaceutical formulation, refers to an amount effective, at dosages and for periods of time necessary, to achieve the desired therapeutic or prophylactic result. For example, an effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of an Ab-CIDE, as well as salts thereof, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

As used herein, the term "plurality" refers to two or more conjugates. Each conjugate can be the same or different from any other conjugate in the plurality.

A "small molecule" or "small molecular compound" generally refers to an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)$ $(CH_2CH_2CH_3))$, 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene ($—CH_2—$), ethylene ($—CH_2CH_2—$), propylene ($—CH_2CH_2CH_2—$), and the like.

The term "alkenyl" refers to linear or branched-chain monovalent hydrocarbon radical of any length from two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl ($—CH{=}CH_2$), allyl ($—CH_2CH{=}CH_2$), and the like.

The term "alkenylene" refers to linear or branched-chain divalent hydrocarbon radical of any length from two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene ($—CH{=}CH—$), allyl ($—CH_2CH{=}CH—$), and the like.

The term "alkynyl" refers to a linear or branched monovalent hydrocarbon radical of any length from two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl ($—C{\equiv}CH$), propynyl (propargyl, $—CH_2C{\equiv}CH$), and the like.

The term "alkynylene" refers to a linear or branched divalent hydrocarbon radical of any length from two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene ($—C{\equiv}C—$), propynylene (propargylene, $—CH_2C{\equiv}C—$), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_2$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Other terms, definitions and abbreviations herein include: Wild-type ("WT"); Cysteine engineered mutant antibody ("thio"); light chain ("LC"); heavy chain ("HC"); 6-maleimidocaproyl ("MC"); maleimidopropanoyl ("MP"); valine-citrulline ("val-cit" or "vc"), alanine-phenylalanine ("ala-phe"), p-aminobenzyl ("PAB"), and p-aminobenzyloxycarbonyl ("PABC"); A118C (EU numbering)=A121C (Sequential numbering)=A114C (Kabat numbering) of heavy chain K149C (Kabat numbering) of light chain. Still additional definitions and abbreviations are provided elsehwere herein.

II. Chemical Inducers of Degradation

Chemical Inducers of Degradation (CIDE) molecules can be conjugated with an antibody to form an "Ab-CIDE" conjugate. The antibody is conjugated via a linker (L1) to a CIDE ("D"), wherein the CIDE comprises a ubiquitin E3 ligase binding group ("E3LB"), a linker ("L2") and a protein binding group ("PB"). The general formula of an Ab-CIDE molecule is:

$$\text{Ab-(L1-D)}_p,$$

wherein, D is CIDE having the structure E3LB-L2-PB; wherein, E3LB is an E3 ligase binding group covalently bound to L2; L2 is a linker covalently bound to E3LB and PB; PB is a protein binding group covalently bound to L2; Ab is an antibody covalently bound to L1; L1 is a linker, covalently bound to Ab and to D; and p has a value from about 1 to about 50. The variable p reflects that an antibody can be connected to one or more L1-D groups. In one embodiment, p is from about 1 to 8. In another embodiment, p is about 2.

The following sections describe the components that comprise the Ab-CIDE. To obtain a Ab-CIDE having potent efficacy and a desirable therapeutic index, the following components are provided.

1. Antibody (Ab)

As described herein, antibodies, e.g., a monoclonal antibodies (mABs) are used to deliver a CIDE to target cells, e.g., cells that express the specific protein that is targeted by the antibody. The antibody portion of an Ab-CIDE can target a cell that expresses an antigen whereby the antigen specific Ab-CIDE is delivered intracellularly to the target cell, typically through endocytosis. While Ab-CIDEs that comprise an antibody directed to an antigen that is not found on the cell surface may result in less specific intracellular delivery of the CIDE portion into the cell, the Ab-CIDE may still undergo pinocytosis. The Ab-CIDEs and method of their use described herein advantageously utilize antibody recognition of the cellular surface and/or endocytosis of the Ab-CIDE to deliver the CIDE portion inside cells.

a. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

b. Library-Derived Antibodies

Antibodies for use in a Ab-CIDE may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, NJ, 2001) and further described, e.g., in the McCafferty et al., *Nature* 348:552-554; Clackson et al., Nature 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

c. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region.

In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. No. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., Methods 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

d. Multispecific Antibodies

In certain embodiments, an antibody provided herein is a multispecific antibody, e.g. a bispecific antibody. The term "multispecific antibody" as used herein refers to an antibody comprising an antigen-binding domain that has polyepitopic specificity (i.e., is capable of binding to two, or more, different epitopes on one molecule or is capable of binding to epitopes on two, or more, different molecules).

In some embodiments, multispecific antibodies are monoclonal antibodies that have binding specificities for at least two different antigen binding sites (such as a bispecific antibody). In some embodiments, the first antigen-binding domain and the second antigen-binding domain of the multispecific antibody may bind the two epitopes within one and the same molecule (intramolecular binding). For example, the first antigen-binding domain and the second antigen-binding domain of the multispecific antibody may bind to two different epitopes on the same protein molecule. In certain embodiments, the two different epitopes that a multispecific antibody binds are epitopes that are not normally bound at the same time by one monospecific antibody, such as e.g. a conventional antibody or one immunoglobulin single variable domain. In some embodiments, the first antigen-binding domain and the second antigen-binding domain of the multispecific antibody may bind epitopes located within two distinct molecules (intermolecular binding). For example, the first antigen-binding domain of the multispecific antibody may bind to one epitope on one protein molecule, whereas the second antigen-binding domain of the multispecific antibody may bind to another epitope on a different protein molecule, thereby cross-linking the two molecules.

In some embodiments, the antigen-binding domain of a multispecific antibody (such as a bispecific antibody) comprises two VH/VL units, wherein a first VH/VL unit binds to a first epitope and a second VH/VL unit binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, and antibody fragments (such as Fab, Fv, dsFv, scFv, diabodies, bispecific diabodies and triabodies, antibody fragments that have been linked covalently or non-covalently). A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further below.

In certain embodiments, a multispecific antibody provided herein may be a bispecific antibody. The term "bispecific antibody" as used herein refers to a multispecific antibody comprising an antigen-binding domain that is capable of binding to two different epitopes on one molecule or is capable of binding to epitopes on two different molecules. A bispecific antibody may also be referred to herein as having "dual specificity" or as being "dual specific." Exemplary bispecific antibodies may bind both protein and any other antigen. In certain embodiments, one of the binding specificities is for protein and the other is for CD3. See, e.g., U.S. Pat. No. 5,821,337. In certain embodiments, bispecific antibodies may bind to two different epitopes of the same protein molecule. In certain embodiments, bispecific antibodies may bind to two different epitopes on two different protein molecules. Bispecific antibodies may also be used to localize cytotoxic agents to cells which express protein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983), WO 93/08829, and Traunecker et al., *EMBO J.* 10: 3655 (1991)), and "knob-in-hole" engineering (see, e.g., U.S. Pat. No. 5,731,168, WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, *Protein Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J Immunol.* 147: 60 (1991).

Engineered antibodies with three or more functional antigen binding sites, including "Octopus antibodies" or "dual-variable domain immunoglobulins" (DVDs) are also included herein (see, e.g., US 2006/0025576A1, and Wu et al. *Nature Biotechnology* (2007)).). The antibody or fragment herein also includes a "Dual Acting FAb" or "DAF" comprising an antigen binding site that binds to a target protein as well as another, different antigen (see, US 2008/0069820, for example).

e. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. Nat. Med 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med* 9:129-134 (2003); and Hollinger et al., *Proc. Natl. Acad Sci. USA* 90: 6444-6448 (1993). Triabodies and tetrabodies are also described in Hudson et al., *Nat. Med* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

f. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

g. Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including $DHFR^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

Referring now to antibody affinity, in embodiments, the antibody binds to one or more tumor-associated antigens or cell-surface receptors selected from (1)-(53):

(1) BMPR1B (bone morphogenetic protein receptor-type IB, Genbank accession no. NM_001203)

ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358

Figure 4:
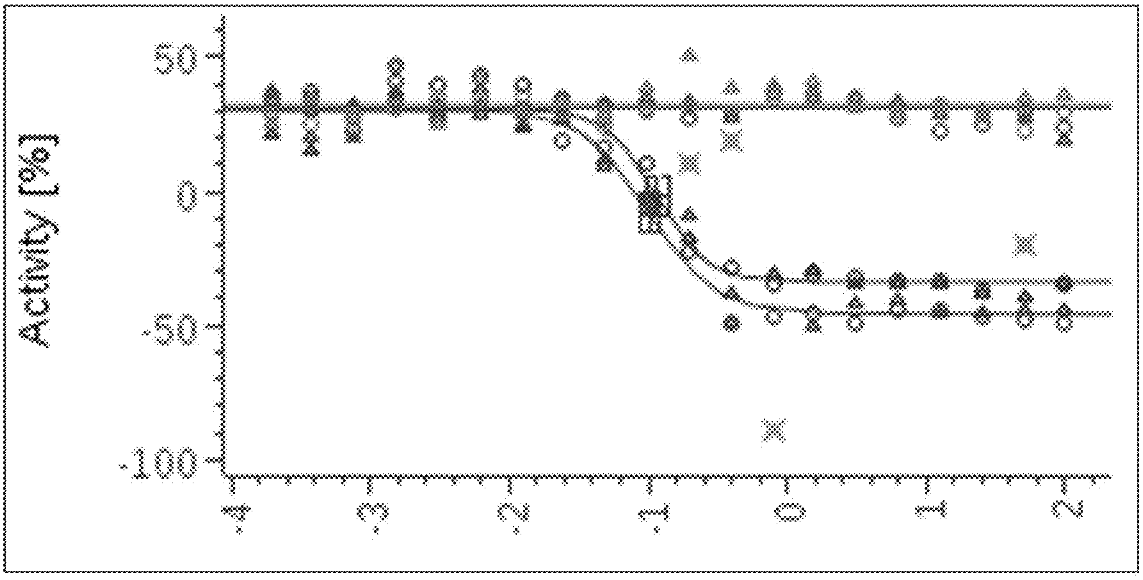
FIG. 4 depicts the degradation assay controls in the degradation assays. Red curve (uppermost curve)=Ab Buffer Only, run #1, Orange curve (uppermost curve, overlapping red curve)=Ab Buffer Only, run #2, Blue curve (middle curve)=7C2-HER2 mAb (high DAR [LC:K149C HC:L174C HC:Y373C]); run #1, Green curve (bottommost curve)=7C2-HER2 mAb (high DAR [LC:K149C HC:L174C HC:Y373C]); run #2.

(Claim 1; Page 183); WO200254940 (Page 100-101); WO200259377(Page 349-350); WO200230268 (Claim 27; Page 376); WO200148204 (Example; FIG. 4)

NP_001194 bone morphogenetic protein receptor, type IB/pid=NP_001194.1-Cross-references: MIM:603248; NP_001194.1; AY065994

(2) E16 (LAT1, SLC7A5, Genbank accession no. NM_003486)

Figure 3:
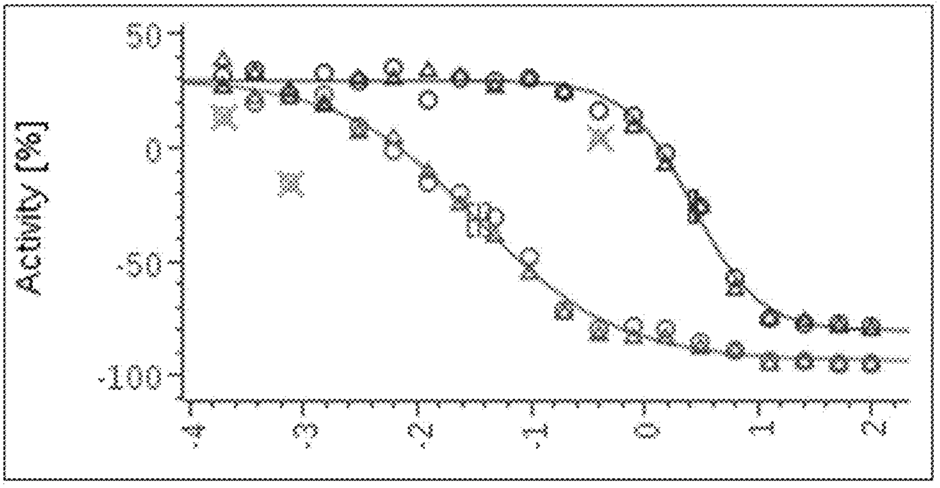
FIG. 3 shows ERα degradation percent activity in MCF7 neo/HER2 cells with ERα targeting Ab-CIDEs. Red curve (bottommost curve)=7C2-HER2-ms-L1EC12, Blue curve (uppermost curve)=CD22-ms-L1EC12.

Biochem. Biophys. Res. Commun. 255 (2), 283-288 (1999), Nature 395 (6699):288-291 (1998), Gaugitsch, H. W., et al (1992) *J. Biol. Chem.* 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);

NP_003477 solute carrier family 7 (cationic amino acid transporter, y+system), member 5/pid=NP_003477.3-*Homo sapiens*

Cross-references: MIM:600182; NP_003477.3; NM_015923; NM_003486_1

(3) STEAP1 (six transmembrane epithelial antigen of prostate, Genbank accession no. NM_012449)

Figure 2:
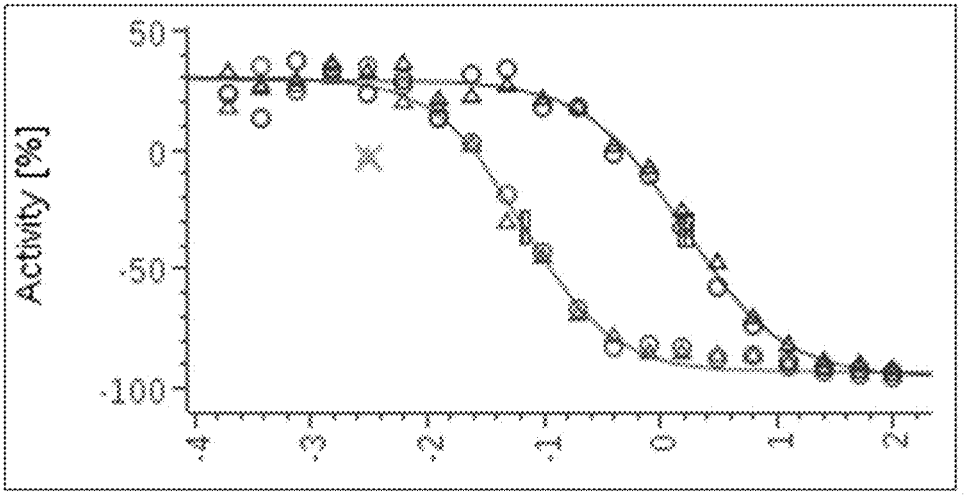
FIG. 2 shows ERα degradation percent activity in MCF7 neo/HER2 cells with ERα targeting Ab-CIDEs. Red curve (bottommost curve)=7C2-HER2-ms-L1EC11, Blue curve (uppermost curve)=CD22-ms-L1EC11.

Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);

NP_036581 six transmembrane epithelial antigen of the prostate

Cross-references: MIM:604415; NP_036581.1; NM_012449_1

(4) 0772P (CA125, MUC16, Genbank accession no. AF361486)

J. Biol. Chem. 276 (29):27371-27375 (2001)); WO2004045553 (Claim 14);

WO200292836 (Claim 6; FIG. 12); WO200283866 (Claim 15; Page 116-121);

US2003124140 (Example 16); US 798959. Cross-references: GI:34501467;

AAK74120.3; AF361486_1

(5) MPF (MPF, MSLN, SMR, megakaryocyte potentiating factor, mesothelin,

Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM: 601051; NP_005814.2; NM_005823_1

(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424)

J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);

Cross-references: MIM:604217; NP 006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11);

Accession: Q9P283; EMBL; AB040878; BAA95969.1. Genew; HGNC:10737;

(8) PSCA hlg (2700050C12Rik, C530008016Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11);

US2003096961 (Claim 11); US2003232056 (Example 5); WO2003105758 (Claim 12);

US2003206918 (Example 5); EP1347046 (Claim 1); WO2003025148 (Claim 20);

Cross-references: GI:37182378; AAQ88991.1; AY358628_1

(9) ETBR (Endothelin type B receptor, Genbank accession no. AY275463);

Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172

(Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

Figure 10:
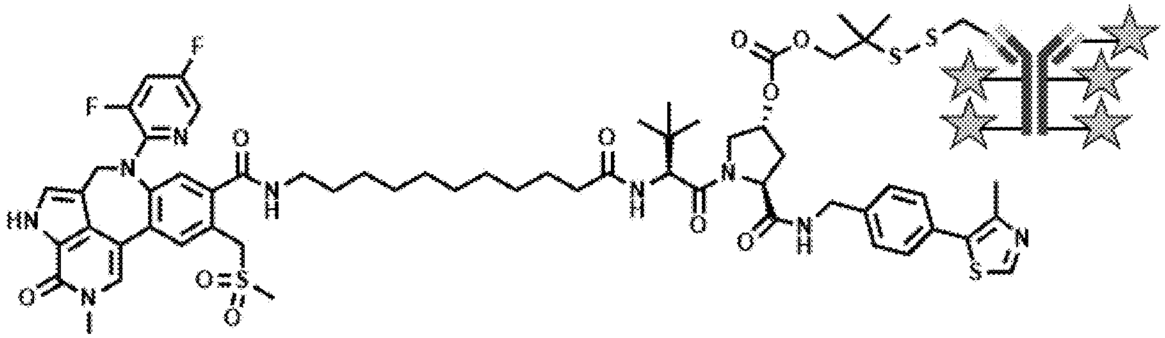
FIG. 10 depicts the structure of a CLL1-targeting Ab-CIDE (PAC), where the stars represent sites of Ab-conjugation (DAR).

Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19): 10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)

Figure 9:
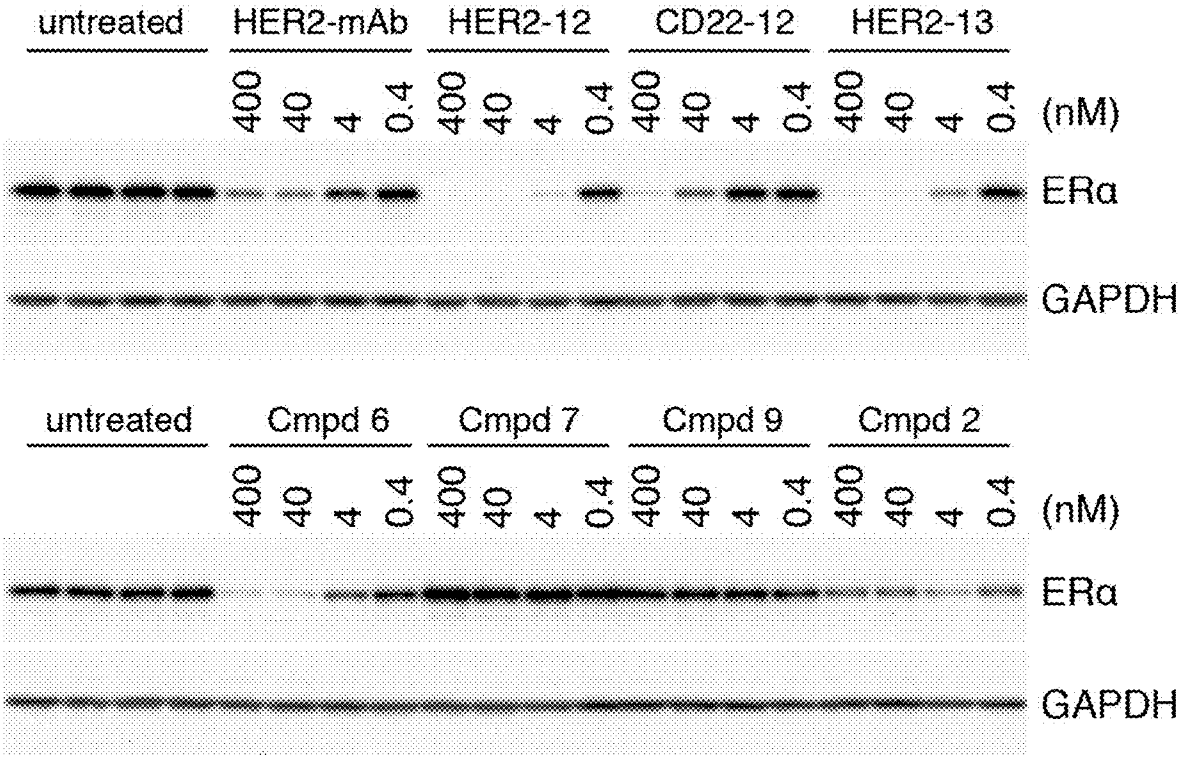
FIG. 9 depicts the in vitro reduction of ERα levels in MCF7-neo/HER2 cells treated with either unconjugated compounds 2, 6, 7, or 9 (lower row, time point=4 h) or conjugates HER2-12, CD22-12, or HER2-13 (upper row, time point=72 h). The activity of the unconjugated HER2-mAb is also depicted (upper row, far left). For the tested conjugates, the depicted concentration refers to the concentration of the corresponding degrader that is present in the experiment (i.e., 400, 40, 4, 0.4 nM degrader concentrations respectively correspond to 10, 1, 0.1 and 0.01 μg/mL concentrations of the DAR6 conjugates).

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9);

WO2004020595 (Claim 1);

Accession: P20023; Q13866; Q14212; EMBL; M26004; AAA35786.1.

(15) CD79b (CD79B, CD790, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP 000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

(17) HER2 (ErbB2, Genbank accession no. M11730)

Figure 5:
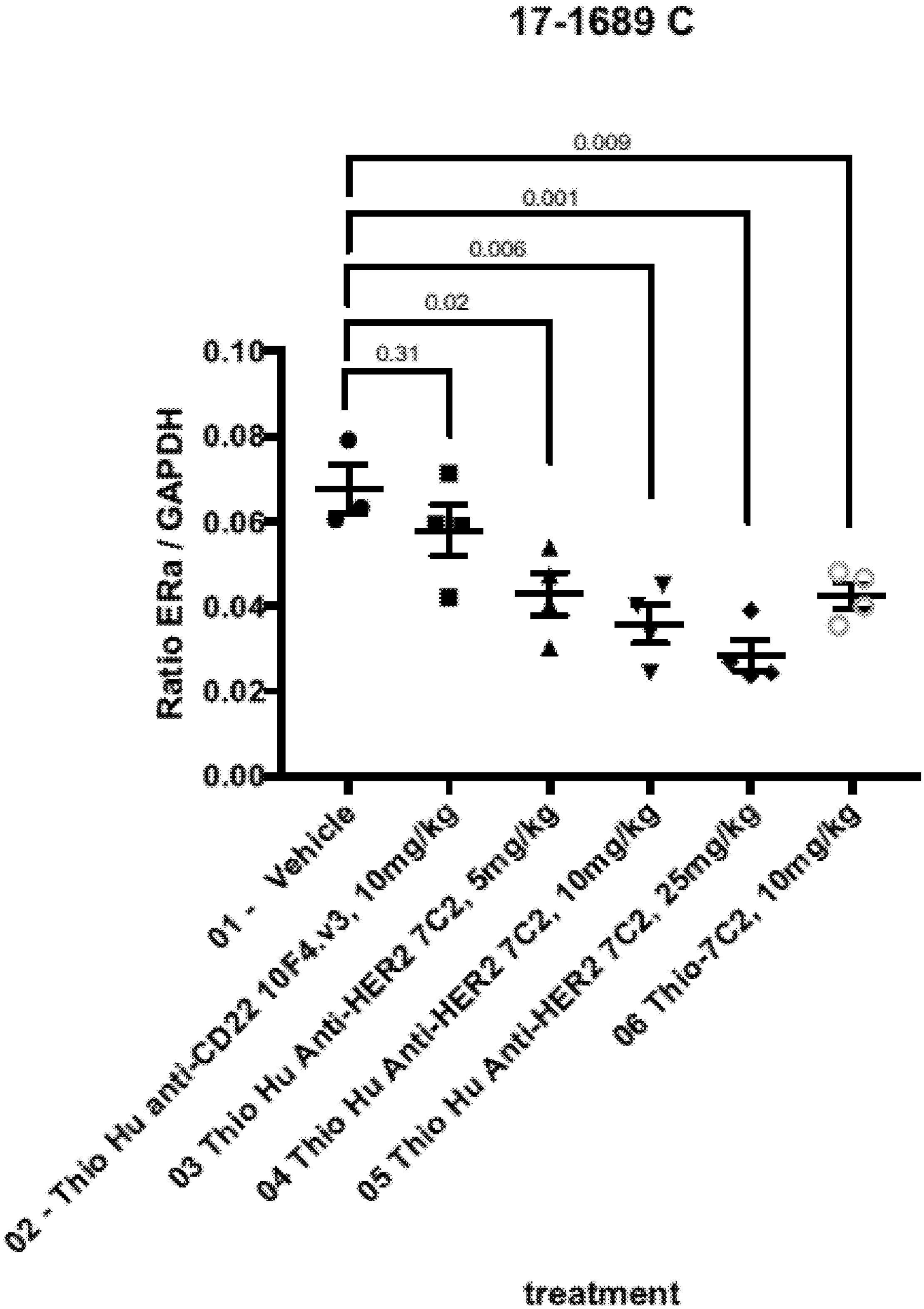
FIG. 5 depicts in vivo reduction of ERα protein levels in MCF7 neo/HER2 xenografts following single IV administration of listed conjugates at the indicated dose. Time point=4 days. Each point represents analysis of an MCF7 neo/HER2 tumor from an individual animal. Group 01=vehicle; Group 02=CD22-ms-L1EC10, 10 mg/kg; Group 03=7C2-HER2-ms-L1EC10, 5 mg/kg; Group 04=7C2-HER2-ms-L1EC10, 10 mg/kg; Group 05=7C2-HER2-ms-L1EC10, 25 mg/kg; Group 06=7C2-HER2-mAb, 10 mg/kg.
Figure 7:
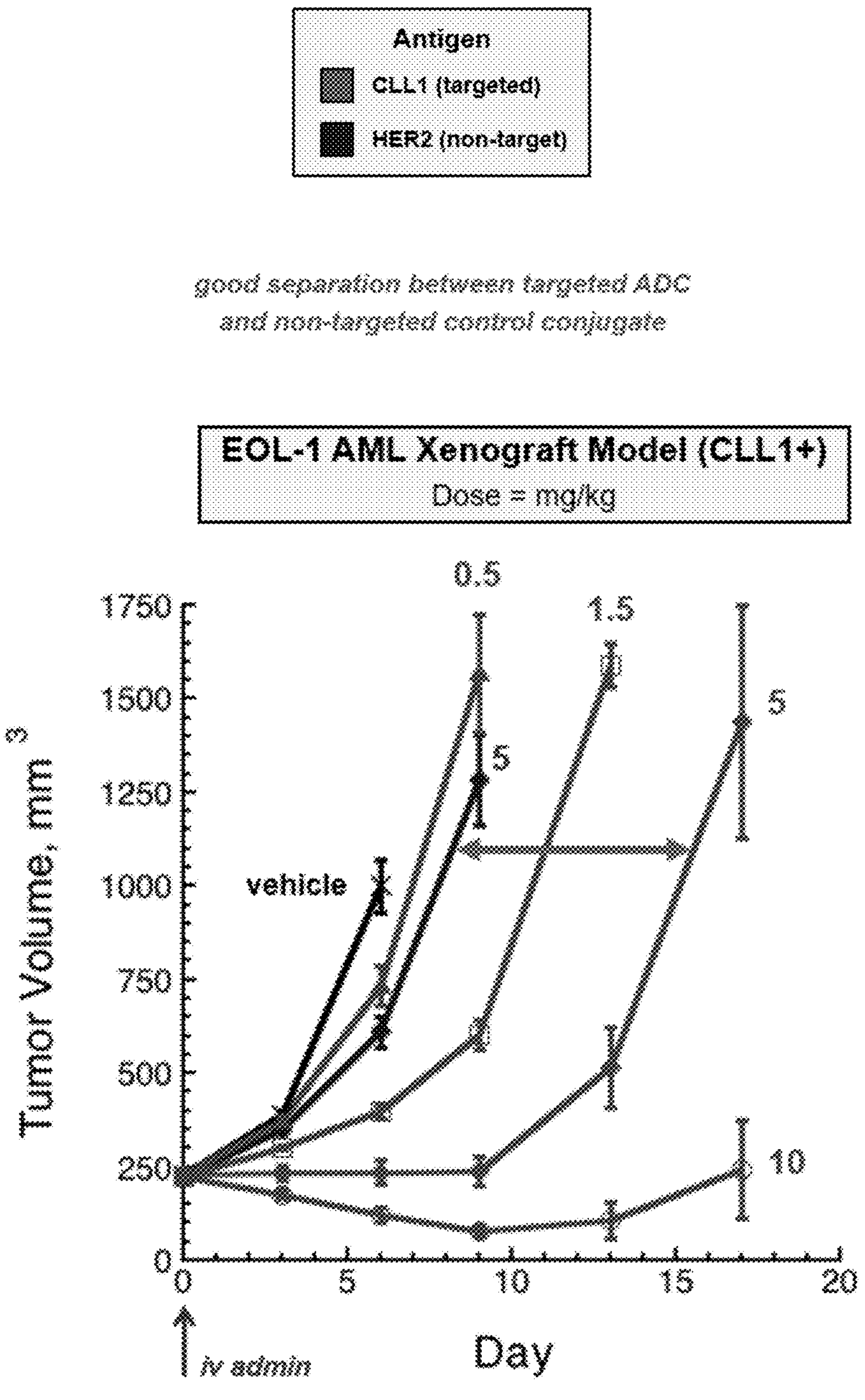
FIG. 7 depicts in vivo dose-dependent efficacy of Anti-CLL1-CIDE conjugate in EOL-1 tumor model.

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2);

WO2004027049 (FIG. 11); WO2004009622; WO2003081210; WO2003089904 (Claim 9); WO2003016475 (Claim 1); US2003118592; WO2003008537 (Claim 1);

WO2003055439 (Claim 29; FIG. 1A-B); WO2003025228 (Claim 37; FIG. 5C);

WO200222636 (Example 13; Page 95-107); WO200212341 (Claim 68; FIG. 7);

WO200213847 (Page 71-74); WO200214503 (Page 114-117); WO200153463 (Claim 2; Page 41-46); WO200141787 (Page 15); WO200044899 (Claim 52; FIG. 7);

WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7);

WO2004022709; WO200100244 (Example 3; FIG. 4);

Accession: P04626; EMBL; M11767; AAA35808.1. EMBL; M11761; AAA35808.1.

(18) NCA (CEACAM6, Genbank accession no. M18728);

Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002;

WO2004063709; EP1439393 (Claim 7); WO2004044178 (Example 4); WO2004031238;

WO2003042661 (Claim 12); WO200278524 (Example 2); WO200286443 (Claim 27; Page 427); WO200260317 (Claim 2);

Accession: P40199; Q14920; EMBL; M29541; AAA59915.1. EMBL; M18728;

(19) MDP (DPEP1, Genbank accession no. BC017023)

Figure 8:
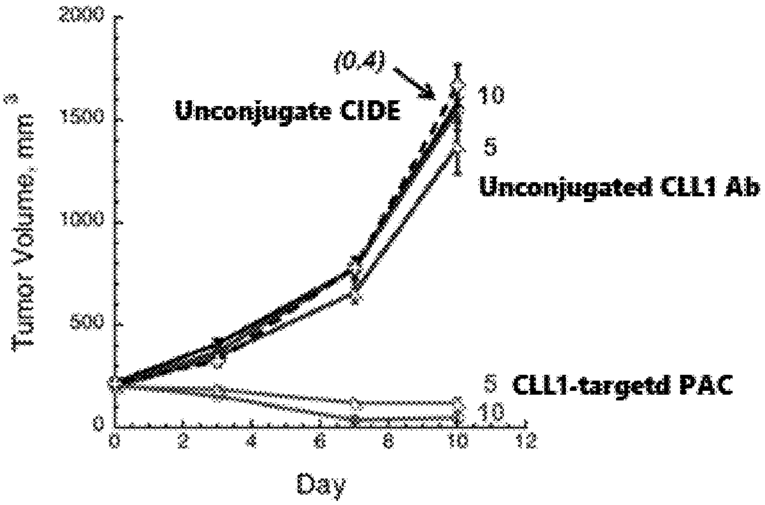
FIG. 8 depicts the in vivo efficacy of an Ab-CIDE (PAC) relative to the unconjugated CIDE.

Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9);

Cross-references: MIM:179780; AAH17023.1; BC017023_1

(20) IL20Rα (IL20Ra, ZCYTOR7, Genbank accession no. AF184971);

Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63);

WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053)

Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1);

US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);

Cross-references: MIM:600997; NP_004433.2; NM_004442_1

(23) ASLG659 (B7 h, Genbank accession no. AX092328)

US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)

Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);

Accession: O43653; EMBL; AF043498; AAC39607.1.

(25) GEDA (Genbank accession No. AY260763);

AAP14954 lipoma HMGIC fusion-partner-like protein/pid=AAP14954.1-*Homo sapiens* Species: *Homo sapiens* (human)

WO2003054152 (Claim 20); WO2003000842 (Claim 1); WO2003023013 (Example 3, Claim 20); US2003194704 (Claim 45);

Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1-*Homo sapiens*

Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);

Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467);

Wilson et al (1991) J. Exp. Med. 173:137-146; WO2003072036 (Claim 1; FIG. 1); Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10)

WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) *Eur. J. Biochem.* 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)

WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2) Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9 p13.3, Genbank accession No. NP_001773.1)

WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)

WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) FCRH5 (IRTA2, Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571.1

WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436

WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1); H7365; C9orf2; C90RF2; U19878; X83961; NM_080655; NM_003692; Harms, P. W. (2003) Genes Dev. 17 (21), 2624-2629; Gery, S. et al (2003) Oncogene 22 (18): 2723-2727;

(39) GDNF-Ral (GDNF family receptor alpha 1; GFRA1; GDNFR; GDNFRA; RETL1; TRNR1; RET1L; GDNFR-alphal; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 cormpiex, locus E; Ly67,RIG-E,SCA-2,TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952; WO 2013/17705;

(41) TMEM46 (shisa homolog 2 (*Xenopus laevis*); SHISA2); NP_001007539.1; NM_001007538.1;

Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;

(47) GPR54 (KISS1 receptor; KISSIR; GPR54; HOT7T175; AXOR12); NP_115940.2; NM_032551.4; Navenot, J. M. et al (2009) Mol. Pharmacol. 75 (6): 1300-1306; Hata, K. et al (2009) Anticancer Res. 29 (2):617-623;

(48) ASPHD1 (aspartate beta-hydroxylase domain containing 1; LOC253982); NP_859069.2; NM_181718.3; Gerhard, D. S. et al (2004) Genome Res. 14 (10B): 2121-2127;

(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;

(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351

(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15): 14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

In an aspect, the antibody of the Ab-CIDE may be an antibody that is directed to a protein that is found on numerous cells or tissue types. Examples of such antibodies include gD and EpCAM. Epithelial cell adhesion molecule (EpCAM) is a transmembrane glycoprotein mediating Ca2+-independent homotypic cell-cell adhesion in epithelia (Litvinov, S. et al. (1994) Journal of Cell Biology 125(2): 437-46). Also known as DIAR5, EGP-2, EGP314, EGP40, ESA, HNPCC8, KS1/4, KSA, M4S1, MIC18, MK-1, TACSTD1, TROP1, EpCAM is also involved in cell signaling, (Maetzel, D. et al. (2009) Nature Cell Biology 11(2):162-71), migration (Osta, W A; et al. (2004) Cancer Res. 64(16):5818-24), proliferation, and differentiation (Litvinov, S. et al. (1996) Am J Pathol. 148(3):865-75). Additionally, EpCAM has oncogenic potential via its capacity to upregulate c-myc, e-fabp, and cyclins A & E (Munz, M. et al. (2004) Oncogene 23(34):5748-58). Since EpCAM is expressed exclusively in epithelia and epithelial-derived neoplasms, EpCAM can be used as a diagnostic marker for various cancers. In other words, a Ab-CIDE can be used to deliver a CIDE to many cells or tissues rather than specific cell types or tissue types as when using a using a targeted antibody.

As described herein, a Ab-CIDE may comprise an antibody, e.g., an antibody selected from:

Anti-Ly6E Antibodies

In certain embodiments, a Ab-CIDE can comprise anti-Ly6E antibodies. Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice (Mao, et al. (1996) *Proc. Natl. Acad. Sci. U.S.A.* 93:5910-5914). In some embodiments, the subject matter described herein provides a Ab-CIDE comprising an anti-Ly6E antibody described in PCT Publication No. WO 2013/177055.

In some embodiments, the subject matter described herein provides a Ab-CIDE comprising an anti-Ly6E antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d)

HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the subject matter described herein provides a Ab-CIDE comprising an antibody that comprises at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the subject matter described herein provides a Ab-CIDE comprising an antibody that comprises at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In one embodiment, the antibody comprises (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, the subject matter described herein provides a Ab-CIDE comprising an antibody that comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In any of the above embodiments, an anti-Ly6E antibody of a Ab-CIDE is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO:8 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs). Optionally, the anti-Ly6E antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-Ly6E antibody of a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity to the amino acid sequence of SEQ ID NO:7 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-Ly6E antibody comprises the VL sequence of SEQ ID NO: 7, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, a Ab-CIDE comprising an anti-Ly6E antibody is provided, wherein the antibody comprises a VH as in any of the embodiments provided above, and a VL as in any of the embodiments provided above.

In one embodiment, a Ab-CIDE is provided, wherein the antibody comprises the VH and VL sequences in SEQ ID NO: 8 and SEQ ID NO: 7, respectively, including post-translational modifications of those sequences.

In a further aspect, provided herein are Ab-CIDEs comprising antibodies that bind to the same epitope as an anti-Ly6E antibody provided herein. For example, in certain embodiments, a Ab-CIDE is provided comprising an antibody that binds to the same epitope as an anti-Ly6E antibody comprising a VH sequence of SEQ ID NO: 8 and a VL sequence of SEQ ID NO: 7, respectively.

In a further aspect, an anti-Ly6E antibody of a Ab-CIDE according to any of the above embodiments is a monoclonal antibody, including a human antibody. In one embodiment, an anti-Ly6E antibody of a Ab-CIDE is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein. In some embodiments, a Ab-CIDE comprises an anti-Ly6E antibody comprising a heavy chain and a light chain comprising the amino acid sequences of SEQ ID NO: 16 and 15, respectively.

Anti-HER2 Antibodies

In certain embodiments, Ab-CIDEs comprise anti-HER2 antibodies. In one embodiment, an anti-HER2 antibody of a Ab-CIDE comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment, an anti-HER2 antibody of a Ab-CIDE comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment, an anti-HER2 antibody of a Ab-CIDE comprises a humanized 7C2 anti-HER2 antibody. A humanized 7C2 antibody is an anti-HER2 antibody.

In some embodiments, described herein are Ab-CIDEs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In some embodiments, described herein are PACs comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, described herein are Ab-CIDEs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In one aspect, described herein are Ab-CIDEs comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24. In a further embodiment, the antibody comprises (a) HVR-H1 comprising the amino acid sequence of SEQ ID NO: 68; (b) HVR-H2 comprising the amino acid sequence of SEQ ID NO: 23, 27, or 28; and (c) HVR-H3 comprising the amino acid sequence of SEQ ID NO: 24 or 29. In a further embodiment, the antibody comprises (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In another aspect, described herein are Ab-CIDEs comprising an antibody that comprises at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, 27, or 28, and (iii) HVR-H3 comprising an amino acid sequence selected from SEQ ID NO: 24 or 29; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21. In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, and (iii) HVR-H3 comprising an amino acid sequence selected from SEQ ID NO: 24; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, described herein are Ab-CIDEs comprising an antibody that comprises (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In another aspect, described herein are Ab-CIDEs comprising an antibody that comprises (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-HER2 antibody of a Ab-CIDE is humanized. In one embodiment, an anti-HER2 antibody of a Ab-CIDE comprises HVRs as in any of the above embodiments, and further comprises a human acceptor framework, e.g. a human immunoglobulin framework or a human consensus framework.

In another aspect, an anti-HER2 antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-HER2 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 22, (b) HVR-H2 comprising the amino acid sequence of SEQ ID NO: 23, and (c) HVR-H3 comprising the amino acid sequence of SEQ ID NO: 24.

In another aspect, an anti-HER2 antibody of a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In certain embodiments, a VL sequence having at least 90%, 91%, 92%, 93%, 94%, 95%, 96%, 97%, 98%, or 99% identity to the amino acid sequence of SEQ ID NO: 17 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 17. In certain embodiments, a total of 1 to 5 amino acids have been substituted, inserted and/or deleted in SEQ ID NO: 17. In certain embodiments, the substitutions, insertions, or deletions occur in regions outside the HVRs (i.e., in the FRs). Optionally, the anti-HER2 antibody comprises the VL sequence of SEQ ID NO: 17, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, a Ab-CIDE comprising an anti-HER2 antibody is provided, wherein the antibody comprises a VH as in any of the embodiments provided above, and a VL as in any of the embodiments provided above.

In one embodiment, a Ab-CIDE comprising an antibody is provided, wherein the antibody comprises the VH and VL sequences in SEQ ID NO: 18 and SEQ ID NO: 17, respectively, including post-translational modifications of those sequences.

In one embodiment, a Ab-CIDE comprising an antibody is provided, wherein the antibody comprises the humanized 7C2.v2.2.LA (hu7C2) K149C kappa light chain sequence of SEQ ID NO: 30

In one embodiment, a Ab-CIDE comprising an antibody is provided, wherein the antibody comprises the Hu7C2 A118C IgG1 heavy chain sequence of SEQ ID NO: 31

In a further aspect, provided herein are PACs comprising antibodies that bind to the same epitope as an anti-HER2 antibody provided herein. For example, in certain embodiments, a Ab-CIDE is provided, comprising an antibody that binds to the same epitope as an anti-HER2 antibody comprising a VH sequence of SEQ ID NO: 18 and a VL sequence of SEQ ID NO: 17, respectively.

In a further aspect, an anti-HER2 antibody of a Ab-CIDE according to any of the above embodiments is a monoclonal antibody, including a human antibody. In one embodiment, an anti-HER2 antibody of a Ab-CIDE is an antibody fragment, e.g., a Fv, Fab, Fab', scFv, diabody, or $F(ab')_2$ fragment. In another embodiment, a Ab-CIDE comprises an antibody that is a substantially full length antibody, e.g., an IgG1 antibody, IgG2a antibody or other antibody class or isotype as defined herein.

Anti-B7-H4 Antibodies

In certain embodiments, an Ab-CIDE can comprise anti-B7-H4 antibodies. B7-H4 is a Type I transmembrane protein and is a member of the B7 superfamily of proteins that provides co-signal in conjunction with a T-cell receptor antigenic signal. B7-H4 is a negative regulator of T-cell function and ligation of T-cells inhibits their growth, cytokine secretion and cytotoxicity. Elimination of B7-H4 in mice does not affect immune cell homeostasis and no signs of autoimmunity. Zhu et al., Blood, 113(8): 1759-1767 (2009); Suh et al., Molecular and Cellular Biology, 26(17): 6403-6411 (2006).The receptor for B7-H4 is unknown and unidentified.

Human B7-H4 is a 282 amino acid protein (including the amino-terminal signal sequence), of which ~227 amino acids are predicted to be in the extracellular space following cleavage of the amino-terminal signal sequence. B7-H4 comprises an Ig-like V-domain, an Ig-like C domain, a transmembrane domain and a short cytoplasmic tail. B7-H4 is a member of the B7-family with the potential of down-regulating the immune system through its co-inhibitory signal in conjunction with antigen-dependent signaling by the T-cell receptor. B7-H4 is nominally expressed in normal human tissues but highly overexpressed in a myriad of human cancers including cancers of the female reproductive system—breast, ovarian, and endometrium. Prevalence of B7-H4 has been reported to be high in invasive ductal and lobular carcinomas comprising both primary (~95%) and metastatic breast cancer (~97%). Although increased B7-H4 staining was associated with negative PR and Her2 status, expression was independent of tumor grade or stage. In addition to the high proportion of B7H4 staining cells in those types of breast cancer, there was also a concomitant decrease in the number of infiltrating lymphocytes. Recently, in a B7-H4 knockout model of pulmonary metastatic breast cancer, the authors reported that B7-H4−/− mice had fewer lung tumor nodules, and showed enhanced survival and memory response to tumor challenge compared to wild type mice. This was attributed to an immunosuppressive effect on CD4 and CD8 cells by tumor associated neutrophils bound to B7-H4-Ig fusion protein. This may also explain why implanted SKOV3 cells over-expressing B7-H4 in SCID mice grew more aggressively than wild-type SKOV3 cells. Furthermore, it was shown that knockdown of B7-H4 mRNA and protein in SKBR3 cells led to increased caspase activity and apoptosis. In some embodiments, the subject matter described herein provides an Ab-CIDE comprising an anti-B7-H4 antibody described in PCT Publication No. WO 2016/040724.

In some embodiments, an anti-B7-H4 antibody of an Ab-CIDE, comprising:

(a) (i) HVR-H3 comprising the amino acid sequence of SEQ ID NO: 128, (ii) HVR-L3 comprising the amino acid sequence of SEQ ID NO: 129, and (iii) HVR-H2 comprising the amino acid sequence of SEQ ID NO: 200; or (b) (i) HVR-H3 comprising the amino acid sequence of SEQ ID NO: 201, (ii) HVR-L3 comprising the amino acid sequence of SEQ ID NO: 129, and (iii) HVR-H2 comprising the amino acid sequence of SEQ ID NO: 200.

In some embodiments, an anti-B7-H4 antibody of an Ab-CIDE comprises:

(a) (i) HVR-H1 comprising the amino acid sequence of SEQ ID NO: 199, (ii) HVR-H2 comprising the amino acid sequence of SEQ ID NO: 200, and (iii) HVR-H3 comprising the amino acid sequence of SEQ ID NO: 128; or (b) (i) HVR-H1 comprising the amino acid sequence of SEQ ID NO: 199, (ii) HVR-H2 comprising the amino acid sequence of SEQ ID NO: 200, and (iii) HVR-H3 comprising the amino acid sequence of SEQ ID NO: 201.

In some embodiments, an anti-B7-H4 antibody of an Ab-CIDE comprises a heavy chain framework FR3 sequence of SEQ ID NO: 213.

In some embodiments, an anti-B7-H4 antibody of an Ab-CIDE comprises: (a) HVR-L1 comprising the amino acid sequence of SEQ ID NO: 202, (b) HVR-L2 comprising the amino acid sequence of SEQ ID NO: 203, and (c) HVR-L3 comprising the amino acid sequence of SEQ ID NO: 129. In some embodiments, an anti-B7-H4 antibody of an Ab-CIDE comprises a light chain framework FR3 sequence of SEQ ID NO: 207.

In some embodiments, an anti-B7-H4 antibody of an Ab-CIDE comprises (a) a VH sequence having at least 95% sequence identity to the amino acid sequence of SEQ ID NO: 198;
(b) a VL sequence having at least 95% sequence identity to the amino acid sequence of SEQ ID NO: 126; or
(c) a VH sequence having at least 95% sequence identity to the amino acid sequence of SEQ ID NO: 127; or
(d) a VH sequence as in (a) and a VL sequence as in (b); or
(e) a VH sequence as in (c) and a VL sequence as in (b).

In some embodiments, an anti-B7-H4 antibody of an Ab-CIDE comprises a VH sequence of SEQ ID NO: 198 or 127. In some embodiments, an anti-B7-H4 antibody of an Ab-CIDE comprises a VL sequence of SEQ ID NO: 126.

In some embodiments, an anti-B7-H4 antibody of an Ab-CIDE, wherein the antibody comprises (a) a VH sequence of SEQ ID NO: 198 and a VL sequence of SEQ ID NO: 126; or (b) a VH sequence of SEQ ID NO: 127 and a VL sequence of SEQ ID NO: 126.

In some embodiments, an anti-B7-H4 antibody of an Ab-CIDE is provided, wherein the antibody comprises:

(a) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 128, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129; or
(b) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 201, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129.

In any of the embodiments described herein, an anti-B7-H4 antibody of an Ab-CIDE may be a monoclonal antibody. In any of the embodiments described herein, an anti-B7-H4 antibody of an Ab-CIDE may be a human, humanized, or chimeric antibody. In any of the embodiments described herein, an anti-B7-H4 antibody of an Ab-CIDE may be an antibody fragment that binds B7-H4. Antibody fragments include, but are not limited to, Fab, Fab', Fab'-SH, $F(ab')_2$, Fv, and scFv fragments, and other fragments described below.

In any of the embodiments described herein, an anti-B7-H4 antibody of an Ab-CIDE may be an IgG1, IgG2a or IgG2b antibody. In any of the embodiments described herein, an anti-B7-H4 antibody of an Ab-CIDE may comprise one or more engineered cysteine amino acids residues. In any of the embodiments described herein, the one or more engineered cysteine amino acids residues may be located in the heavy chain. In any of the embodiments described herein, the one or more engineered cysteine amino acids residues may be located in the light chain. In any of the embodiments described herein, an anti-B7-H4 antibody of an Ab-CIDE may comprise at least one mutation in the heavy chain constant region selected from A118C and S400C. In any of the embodiments described herein, an anti-B7-H4 antibody of an Ab-CIDE may comprise at least one mutation in the light chain constant region selected from K149C and V205C.

In some embodiments, an anti-B7-H4 antibody of an Ab-CIDE is provided, wherein the antibody comprises (a) a heavy chain sequence of SEQ ID NO: 132 and a light chain sequence of SEQ ID NO: 134; or (b) a heavy chain sequence of SEQ ID NO: 133 and a light chain sequence of SEQ ID NO: 134; or (c) a heavy chain sequence of SEQ ID NO: 130 and a light chain sequence of SEQ ID NO: 140; or (d) a heavy chain sequence of SEQ ID NO: 130 and a light chain sequence of SEQ ID NO: 141; or (e) a heavy chain sequence of SEQ ID NO: 131 and a light chain sequence of SEQ ID NO: 140; or (f) a heavy chain sequence of SEQ ID NO: 131 and a light chain sequence of 141; or (g) a heavy chain sequence of SEQ ID NO: 144 and a light chain sequence of SEQ ID NO: 142; or (h) a heavy chain sequence of SEQ ID NO: 144 and a light chain sequence of SEQ ID NO: 143; or (i) a heavy chain sequence of SEQ ID NO: 137 and a light chain sequence of SEQ ID NO: 138; or (j) a heavy chain sequence of SEQ ID NO: 130 and a light chain sequence of SEQ ID NO: 145; or (d) a heavy chain sequence of SEQ ID NO: 130 and a light chain sequence of SEQ ID NO: 146; or (e) a heavy chain sequence of SEQ ID NO: 131 and a light chain sequence of SEQ ID NO: 145; or (f) a heavy chain sequence of SEQ ID NO: 131 and a light chain sequence of 146; or (g) a heavy chain sequence of SEQ ID NO: 144 and a light chain sequence of SEQ ID NO: 147; or (h) a heavy chain sequence of SEQ ID NO: 144 and a light chain sequence of SEQ ID NO: 148.

In some embodiments, an anti-B7-H4 antibody of an Ab-CIDE is a bi-epitopic antibody comprising a first half antibody and a second half antibody is provided, wherein the first half antibody comprises a first VH/VL unit that binds a first epitope of B7-H4, and wherein the second half antibody comprises a second VH/VL unit that binds a second epitope of B7-H4. In some embodiments, the first epitope or the second epitope is an epitope within all or a portion of the B7-H4 Ig-V containing domain. In some embodiments, the first epitope or the second epitope is not within the B7-H4 Ig-V domain or is not entirely within the B7-H4 Ig-V containing domain. In some embodiments, the first epitope is within all or a portion of the B7-H4 Ig-V containing domain and the second epitope is not within the B7-H4 Ig-V domain or is not entirely within the B7-H4 Ig-V containing domain; or wherein the first epitope is not within the B7-H4 Ig-V domain or is not entirely within the B7-H4 Ig-V containing domain, and the second epitope is within all or a portion of the B7-H4 Ig-V containing domain. In some embodiments, the first epitope and the second epitope are each independently selected from:

a) an epitope within all or a portion of the B7-H4 Ig-V containing domain;
b) an epitope within all or a portion of the B7-H4 Ig-C containing domain; and
c) an epitope within all or a portion of the B7-H4 Ig-V and Ig-C containing domains.

In some embodiments, the B7-H4 Ig-V containing domain has the sequence of amino acids 29-157 of SEQ ID NO: 233. In some embodiments, the B7-H4 Ig-C containing domain has the sequence of amino acids 158-250 of SEQ ID NO: 233.

In some embodiments, a) the first half antibody binds an epitope within all or a portion of the B7-H4 Ig-V containing domain and the second half antibody binds an epitope within all or a portion of the B7-H4 Ig-C containing domain; or
b) the first half antibody binds an epitope within all or a portion of the B7-H4 Ig-V containing domain and the second half antibody binds an epitope within all or a portion of the B7-H4 Ig-V and Ig-C containing domains; or
c) the first half antibody binds an epitope within all or a portion of the B7-H4 Ig-C containing domain and the second half antibody binds an epitope within all or a portion of the B7-H4 Ig-V and Ig-C containing domains; or
d) the first half antibody binds an epitope within all or a portion of the B7-H4 Ig-C containing domain and the second half antibody binds an epitope within all or a portion of the B7-H4 Ig-V containing domain; or
e) the first half antibody binds an epitope within all or a portion of the B7-H4 Ig-V and Ig-C containing domains and the second half antibody binds an epitope all or a portion of within the B7-H4 Ig-V containing domain; or
f) the first half antibody binds an epitope within all or a portion of the B7-H4 Ig-V and Ig-C containing domains and the second half antibody binds an epitope within all or a portion of the B7-H4 Ig-C containing domain.

In some embodiments, the first half antibody binds an epitope within all or a portion of the B7-H4 Ig-V containing domain and the second half antibody binds an epitope within all or a portion of the B7-H4 Ig-V and Ig-C containing domains; or wherein the first half antibody binds an epitope within all or a portion of the B7-H4 Ig-V and Ig-C containing domains and the second half antibody binds an epitope within all or a portion of the B7-H4 Ig-V containing domain.

In some embodiments, the first half antibody comprises:

(a) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 128, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129;
(b) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 201, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129;
(c) a VH sequence of SEQ ID NO: 198 and a VL sequence of SEQ ID NO: 126; or
(d) a VH sequence of SEQ ID NO: 127 and a VL sequence of SEQ ID NO: 126.

In some embodiments, the second half antibody comprises:

(a) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 128, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129;
(b) (i) HVR-H1 comprising the amino acid sequence of SEQ ID NO: 199, (ii) HVR-H2 comprising the amino acid sequence of SEQ ID NO: 200, (iii) HVR-H3 comprising the amino acid sequence of SEQ ID NO: 201, (iv) HVR-L1 comprising the amino acid sequence of SEQ ID NO: 202, (v) HVR-L2 comprising the amino acid sequence of SEQ ID NO: 203, and (vi) HVR-L3 comprising the amino acid sequence of SEQ ID NO: 129;
(c) a VH sequence of SEQ ID NO: 198 and a VL sequence of SEQ ID NO: 126; or
(d) a VH sequence of SEQ ID NO: 127 and a VL sequence of SEQ ID NO: 126.

In some embodiments, the first half antibody comprises (a) (i) HVR-H1 comprising the amino acid sequence of SEQ ID NO: 218, (ii) HVR-H2 comprising the amino acid sequence of SEQ ID NO: 219, (iii) HVR-H3 comprising the amino acid sequence of SEQ ID NO: 220, (iv) HVR-L1 comprising the amino acid sequence of SEQ ID NO: 221, (v) HVR-L2 comprising the amino acid sequence of SEQ ID NO: 222, and (vi) HVR-L3 comprising the amino acid sequence of SEQ ID NO: 223; or
(b) a VH sequence of SEQ ID NO: 216 and a VL sequence of SEQ ID NO: 215.

In some embodiments, the second half antibody comprises:

(a) (i) HVR-H1 comprising the amino acid sequence of SEQ ID NO: 218, (ii) HVR-H2 comprising the amino acid sequence of SEQ ID NO: 219, (iii) HVR-H3 comprising the amino acid sequence of SEQ ID NO: 220, (iv) HVR-L1 comprising the amino acid sequence of SEQ ID NO: 221, (v) HVR-L2 comprising the amino acid sequence of SEQ ID NO: 222, and (vi) HVR-L3 comprising the amino acid sequence of SEQ ID NO: 223; or
(b) a VH sequence of SEQ ID NO: 216 and a VL sequence of SEQ ID NO: 215.

In some embodiments, an anti-B7-H4 antibody of an Ab-CIDE is a bi-epitopic antibody which is an IgG1 or IgG4 antibody. In some embodiments, the first half antibody comprises a first heavy chain constant region comprising a knob mutation and the second heavy chain comprises a second heavy chain constant region comprising a hole mutation; or wherein the first half antibody comprises a first heavy chain constant region comprising a hole mutation and the second heavy chain comprises a second heavy chain constant region comprising a knob mutation. In some embodiments, the bi-epitopic antibody is an IgG1 antibody and wherein the knob mutation comprises a T366W mutation. In some embodiments, the bi-epitopic antibody is an IgG1 antibody and wherein the hole mutation comprises at least one, at least two, or three mutations selected from T366S, L368A, and Y407V. In some embodiments, the bi-epitopic antibody is an IgG4 antibody and wherein the knob mutation comprises a T366W mutation. In some embodiments, the bi-epitopic antibody is an IgG4 antibody and wherein the hole mutation comprises at least one, at least two, or three mutations selected from T366S, L368A, and Y407V mutations.

In some embodiments, an anti-B7-H4 antibody of an Ab-CIDE which is a bi-epitopic antibody is provided, wherein:

a) the first half antibody comprises a heavy chain sequence of SEQ ID NO: 159 or 163 and a light chain sequence of SEQ ID NO: 145 or 146;
b) the first half antibody comprises a heavy chain sequence of SEQ ID NO: 160 or 164 and a light chain sequence of SEQ ID NO: 145 or 146;
c) the first half antibody comprises a heavy chain sequence of SEQ ID NO: 161 or 165 and a light chain sequence of SEQ ID NO: 147 or 148;
d) the first half antibody comprises a heavy chain sequence of SEQ ID NO: 162 or 166 and a light chain sequence of SEQ ID NO: 147 or 148;
e) the second half antibody comprises a heavy chain sequence of SEQ ID NO: 159 or 163 and a light chain sequence of SEQ ID NO: 145 or 146;
f) the second half antibody comprises a heavy chain sequence of SEQ ID NO: 160 or 164 and a light chain sequence of SEQ ID NO: 145 or 146;
g) the second half antibody comprises a heavy chain sequence of SEQ ID NO: 161 or 165 and a light chain sequence of SEQ ID NO: 147 or 148; or
h) the second half antibody comprises a heavy chain sequence of SEQ ID NO: 162 or 166 and a light chain sequence of SEQ ID NO: 147 or 148.

In some embodiments, an anti-B7-H4 antibody of an Ab-CIDE which is a bi-epitopic antibody is provided, wherein:

a) the first half antibody comprises a heavy chain sequence of SEQ ID NO: 159 or 163 and a light chain sequence of SEQ ID NO: 145 or 146, and the second half antibody comprises a heavy chain sequence of SEQ ID NO: 162 or 166 and a light chain sequence of SEQ ID NO: 147 or 148; or
b) the first half antibody comprises a heavy chain sequence of SEQ ID NO: 161 or 165 and a light chain sequence of SEQ ID NO: 147 or 148, and the second half antibody comprises a heavy chain sequence of SEQ ID NO: 160 or 164 and a light chain sequence of SEQ ID NO: 145 or 146.

In some embodiments, an anti-B7-H4 antibody of an Ab-CIDE which is a bi-epitopic antibody is provided, comprising a first half antibody and a second half antibody, wherein the first half antibody comprises a first VH/VL unit that binds a first epitope of B7-H4, and wherein the second half antibody comprises a second VH/VL unit that binds a second epitope of B7-H4, wherein the first half antibody comprises a heavy chain sequence of SEQ ID NO: 159 or 163 and a light chain sequence of SEQ ID NO: 145, and the second half antibody comprises a heavy chain sequence of SEQ ID NO: 162 or 166 and a light chain sequence of SEQ ID NO: 147.

In any of the embodiments described herein, B7-H4 may be human B7-H4 of SEQ ID NO: 233.

An exemplary naturally occurring human B7-H4 precursor protein sequence, with signal sequence (amino acids 1-28) is provided in SEQ ID NO: 233, and the corresponding mature B7-H4 protein sequence is shown in SEQ ID NO: 234 (corresponding to amino acids 29-282 of SEQ ID NO: 233).

In certain embodiments, an anti-B7-H4 antibody of an Ab-CIDE has at least one or more of the following characteristics, in any combination:

(a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4), and
(b) binds B7-H4 with an affinity of ≤100 nM, ≤50 nM, ≤10 nM, or ≤9 nM, or ≤8 nM, or ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM.

Nonlimiting exemplary anti-B7-H4 antibody of an Ab-CIDE include hu1D11.v1.9 varC2 and hu1D11.v1.9 varD, described herein. In some embodiments, B7-H4 is human B7-H4. In some embodiments, B7-H4 is selected from human, cynomolgus monkey, mouse, and rat B7-H4.

In some embodiments, an anti-B7-H4 antibody of an Ab-CIDE binds to an epitope within all or a portion of the B7-H4 Ig-V containing domain (amino acids 29-157 of SEQ ID NO: 233). In some embodiments, an anti-B7-H4 antibody of an Ab-CIDE binds to an epitope within all or a portion of the B7-H4 Ig-C containing domain (amino acids 158-250 of SEQ ID NO: 233). In some embodiments, an anti-B7-H4 antibody of an Ab-CIDE binds to an epitope within all or a portion of the B7-H4 Ig-V and Ig-C domains (amino acids 29-250 of SEQ ID NO: 233). In some embodiments, an anti-B7-H4 antibody of an Ab-CIDE binds to an epitope within all or a portion of SEQ ID NO: 234 (mature human B7-H4). In some embodiments, an anti-B7-H4 antibody of an Ab-CIDE binds to an epitope within all or a portion of SEQ ID NO: 233 (precursor human B7-H4). In some such embodiments, an anti-B7-H4 antibody of an Ab-CIDE binds B7-H4 with an affinity of ≤100 nM, ≤50 nM, ≤10 nM, or ≤9 nM, or ≤8 nM, or ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM.

Antibody 1D11v1.9 Variants and Other Embodiments

In some embodiments, an anti-B7-H4 antibody of an Ab-CIDE comprising at least one, two, three, four, five, or six HVRs selected from (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 128; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 129.

In some embodiments, an anti-B7-H4 antibody of an Ab-CIDE comprising at least one, two, three, four, five, or six HVRs selected from (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 201; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 129.

In one aspect, an anti-B7-H4 antibody of an Ab-CIDE comprising at least one, at least two, or all three VH HVR sequences selected from (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 128. In one embodiment, an anti-B7-H4 antibody of an Ab-CIDE comprises HVR-H3 comprising the amino acid sequence of SEQ ID NO: 201. In another embodiment, an anti-B7-H4 antibody of an Ab-CIDE comprises HVR-H3 comprising the amino acid sequence of SEQ ID NO: 128 and HVR-L3 comprising the amino acid sequence of SEQ ID NO: 129. In a further embodiment, an anti-B7-H4 antibody of an Ab-CIDE comprises HVR-H3 comprising the amino acid sequence of SEQ ID NO: 128, HVR-L3 comprising the amino acid sequence of SEQ ID NO: 129, and HVR-H2 comprising the amino acid sequence of SEQ ID NO: 200. In a further embodiment, an anti-B7-H4 antibody of an Ab-CIDE comprises (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 128.

In one aspect, an anti-B7-H4 antibody of an Ab-CIDE comprising at least one, at least two, or all three VH HVR sequences selected from (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 201. In one embodiment, an anti-B7-H4 antibody of an Ab-CIDE comprises HVR-H3 comprising the amino acid sequence of SEQ ID NO: 201. In another embodiment, an anti-B7-H4 antibody of an Ab-CIDE comprises HVR-H3 comprising the amino acid sequence of SEQ ID NO: 201 and HVR-L3 comprising the amino acid sequence of SEQ ID NO: 129. In a further embodiment, an anti-B7-H4 antibody of an Ab-CIDE comprises HVR-H3 comprising the amino acid sequence of SEQ ID NO: 201, HVR-L3 comprising the amino acid sequence of SEQ ID NO: 129, and HVR-H2 comprising the amino acid sequence of SEQ ID NO: 200. In a further embodiment, an anti-B7-H4 antibody of an Ab-CIDE comprises (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 201.

In another aspect, an anti-B7-H4 antibody of an Ab-CIDE comprising at least one, at least two, or all three VL HVR sequences selected from (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 129. In one embodiment, an anti-B7-H4 antibody of an Ab-CIDE comprises (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 129.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 199, (ii) HVR-H2 comprising the amino acid sequence of SEQ ID NO: 200, and (iii) HVR-H3 comprising an amino acid sequence selected from SEQ ID NO: 128; and (b) a VL domain comprising at least one, at least two, or all three VL HVR sequences selected from (i) HVR-L1 comprising the amino acid sequence of SEQ ID NO: 202, (ii) HVR-L2 comprising the amino acid sequence of SEQ ID NO: 203, and (c) HVR-L3 comprising the amino acid sequence of SEQ ID NO: 129.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 199, (ii) HVR-H2 comprising the amino acid sequence of SEQ ID NO: 200, and (iii) HVR-H3 comprising an amino acid sequence selected from SEQ ID NO: 201; and (b) a VL domain comprising at least one, at least two, or all three VL HVR sequences selected from (i) HVR-L1 comprising the amino acid sequence of SEQ ID NO: 202, (ii) HVR-L2 comprising the amino acid sequence of SEQ ID NO: 203, and (c) HVR-L3 comprising the amino acid sequence of SEQ ID NO: 129.

In another aspect, an anti-B7-H4 antibody of an Ab-CIDE comprising (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 128; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 129.

In another aspect, an anti-B7-H4 antibody of an Ab-CIDE comprising (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 201; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 129.

In any of the above embodiments, an anti-B7-H4 antibody of an Ab-CIDE is humanized. In one embodiment, an anti-B7-H4 antibody of an Ab-CIDE comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations: Y49H, V58I, T69R and/or F71Y mutation in the light chain framework region FR3; V67A, I69L, R71A, T73K and/or T75S mutation in the heavy chain framework region FR3.

In some embodiments, an anti-B7-H4 antibody of an Ab-CIDE comprises HVRs as in any of the above embodiments, and further comprises a heavy chain framework FR3 sequence of SEQ ID NO: 213. In some such embodiments, the heavy chain variable domain framework is a modified human $VH_1$ framework having an FR3 sequence of SEQ ID NO: 213.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 198 or 127. In certain embodiments, a VH sequence having at least 90%, 91%, 92%, 93%, 94%, 95%, 96%, 97%, 98%, or 99% identity to the amino acid sequence of SEQ ID NO: 198 or 127 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 198 or 127. In certain embodiments, a total of 1 to 5 amino acids have been substituted, inserted and/or deleted in SEQ ID NO: 198 or 127. In certain embodiments, substitutions, insertions, or deletions occur in regions outside the HVRs (i.e., in the FRs).

Optionally, an anti-B7-H4 antibody of an Ab-CIDE comprises the VH sequence of SEQ ID NO: 198, including post-translational modifications of that sequence. In a particular embodiment, the VH comprises one, two or three HVRs selected from: (a) HVR-H1 comprising the amino acid sequence of SEQ ID NO: 199, (b) HVR-H2 comprising the amino acid sequence of SEQ ID NO: 200, and (c) HVR-H3 comprising the amino acid sequence of SEQ ID NO: 201.

Optionally an anti-B7-H4 antibody of an Ab-CIDE comprises the VH sequence of SEQ ID NO: 127, including post-translational modifications of that sequence. In a particular embodiment, the VH comprises one, two or three HVRs selected from: (a) HVR-H1 comprising the amino acid sequence of SEQ ID NO: 199, (b) HVR-H2 comprising the amino acid sequence of SEQ ID NO: 200, and (c) HVR-H3 comprising the amino acid sequence of SEQ ID NO: 128.

In another aspect, an anti-B7-H4 antibody of an Ab-CIDE, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 126. In certain embodiments, a VL sequence having at least 90%, 91%, 92%, 93%, 94%, 95%, 96%, 97%, 98%, or 99% identity to the amino acid sequence of SEQ ID NO: 126 contains substitutions (e.g., conservative substitutions), insertions, or deletions relative to the reference sequence, but an anti-B7-H4 antibody comprising that sequence retains the ability to bind to B7—H4. In certain embodiments, a total of 1 to 10 amino acids have been substituted, inserted and/or deleted in SEQ ID NO: 126. In certain embodiments, a total of 1 to 5 amino acids have been substituted, inserted and/or deleted in SEQ ID NO: 126. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 126, including post-translational modifications of that sequence. In a particular embodiment, the VL comprises one, two or three HVRs selected from (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 129.

In another aspect, an anti-B7-H4 antibody of an Ab-CIDE is provided, wherein the antibody comprises a VH as in any of the embodiments provided above, and a VL as in any of the embodiments provided above.

In one embodiment, an anti-B7-H4 antibody of an Ab-CIDE comprises the VH and VL sequences in SEQ ID NO: 198 and SEQ ID NO: 126, respectively, including post-translational modifications of those sequences. In one embodiment, an anti-B7-H4 antibody of an Ab-CIDE comprises the VH and VL sequences in SEQ ID NO: 127 and SEQ ID NO: 126, respectively, including post-translational modifications of those sequences.

In certain embodiments, an anti-B7-H4 antibody of an Ab-CIDE according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4). In some embodiments, an anti-B7-H4 antibody of an Ab-CIDE has at least one or more of the following characteristics, in any combination: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4).

In a further aspect, an anti-B7-H4 antibody of an Ab-CIDE according to any of the above embodiments is a monoclonal antibody, including a chimeric, humanized or human antibody. In one embodiment, an anti-B7-H4 antibody of an Ab-CIDE is an antibody fragment, e.g., a Fv, Fab, Fab', scFv, diabody, or $F(ab')_2$ fragment. In another embodiment, an anti-B7-H4 antibody of an Ab-CIDE is a substantially full length antibody, e.g., an IgG1 antibody or other antibody class or isotype as defined herein.

Antibody 1D11 and Other Embodiments

In some embodiments, an anti-B7-H4 antibody of an Ab-CIDE comprising at least one, two, three, four, five, or six HVRs selected from (a) HVR-H1 comprising the amino acid sequence of SEQ ID NO: 5; (b) HVR-H2 comprising the amino acid sequence of SEQ ID NO: 6; (c) HVR-H3 comprising the amino acid sequence of SEQ ID NO: 167; (d) HVR-L1 comprising the amino acid sequence of SEQ ID NO: 168; (e) HVR-L2 comprising the amino acid sequence of SEQ ID NO: 169; and (f) HVR-L3 comprising the amino acid sequence of SEQ ID NO: 10. In another embodiment, the an anti-B7-H4 antibody of an Ab-CIDE comprising at least one, two, three, four, five, or six HVRs selected from (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 201; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 204.

In one aspect, an anti-B7-H4 antibody of an Ab-CIDE comprising at least one, at least two, or all three VH HVR sequences selected from (a) HVR-H1 comprising the amino acid sequence of SEQ ID NO: 5; (b) HVR-H2 comprising the amino acid sequence of SEQ ID NO: 6; and (c) HVR-H3 comprising the amino acid sequence of SEQ ID NO: 167. In one embodiment, an anti-B7-H4 antibody of an Ab-CIDE comprises HVR-H3 comprising the amino acid sequence of SEQ ID NO: 167. In another embodiment, an anti-B7-H4 antibody of an Ab-CIDE comprises HVR-H3 comprising the amino acid sequence of SEQ ID NO: 167 and HVR-L3 comprising the amino acid sequence of SEQ ID NO: 170. In a further embodiment, an anti-B7-H4 antibody of an Ab-CIDE comprises HVR-H3 comprising the amino acid sequence of SEQ ID NO: 167, HVR-L3 comprising the amino acid sequence of SEQ ID NO: 170, and HVR-H2 comprising the amino acid sequence of SEQ ID NO: 6. In a further embodiment, an anti-B7-H4 antibody of an Ab-CIDE comprises (a) HVR-H1 comprising the amino acid sequence of SEQ ID NO: 5; (b) HVR-H2 comprising the amino acid sequence of SEQ ID NO: 6; and (c) HVR-H3 comprising the amino acid sequence of SEQ ID NO: 167.

In one aspect, an anti-B7-H4 antibody of an Ab-CIDE comprising at least one, at least two, or all three VH HVR sequences selected from (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 201. In one embodiment, an anti-B7-H4 antibody of an Ab-CIDE comprises HVR-H3 comprising the amino acid sequence of SEQ ID NO: 201. In another embodiment, an anti-B7-H4 antibody of an Ab-CIDE comprises HVR-H3 comprising the amino acid sequence of SEQ ID NO: 201 and HVR-L3 comprising the amino acid sequence of SEQ ID NO: 204. In a further embodiment, an anti-B7-H4 antibody of an Ab-CIDE comprises HVR-H3 comprising the amino acid sequence of SEQ ID NO: 201, HVR-L3 comprising the amino acid sequence of SEQ ID NO: 204, and HVR-H2 comprising the amino acid sequence of SEQ ID NO: 200. In a further embodiment, an anti-B7-H4 antibody of an Ab-CIDE comprises (a) HVR-H1 comprising the amino acid sequence of SEQ ID NO: 199; (b) HVR-H2 comprising the amino acid sequence of SEQ ID NO: 200; and (c) HVR-H3 comprising the amino acid sequence of SEQ ID NO: 201.

In another aspect, an anti-B7-H4 antibody of an Ab-CIDE comprising at least one, at least two, or all three VL HVR sequences selected from (a) HVR-L1 comprising the amino acid sequence of SEQ ID NO: 168; (b) HVR-L2 comprising the amino acid sequence of SEQ ID NO: 169; and (c) HVR-L3 comprising the amino acid sequence of SEQ ID NO: 170. In one embodiment, an anti-B7-H4 antibody of an Ab-CIDE comprises (a) HVR-L1 comprising the amino acid sequence of SEQ ID NO: 168; (b) HVR-L2 comprising the amino acid sequence of SEQ ID NO: 169; and (c) HVR-L3 comprising the amino acid sequence of SEQ ID NO: 170.

In another aspect, an anti-B7-H4 antibody of an Ab-CIDE comprising at least one, at least two, or all three VL HVR sequences selected from (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 204. In one embodiment, the antibody comprises (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 204.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 5, (ii) HVR-H2 comprising the amino acid sequence of SEQ ID NO: 6, and (iii) HVR-H3 comprising an amino acid sequence selected from SEQ ID NO: 167; and (b) a VL domain comprising at least one, at least two, or all three VL HVR sequences selected from (i) HVR-L1 comprising the amino acid sequence of SEQ ID NO: 168, (ii) HVR-L2 comprising the amino acid sequence of SEQ ID NO: 169, and (c) HVR-L3 comprising the amino acid sequence of SEQ ID NO: 170.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 199, (ii) HVR-H2 comprising the amino acid sequence of SEQ ID NO: 200, and (iii) HVR-H3 comprising an amino acid sequence selected from SEQ ID NO: 201; and (b) a VL domain comprising at least one, at least two, or all three VL HVR sequences selected from (i) HVR-L1 comprising the amino acid sequence of SEQ ID NO: 202, (ii) HVR-L2 comprising the amino acid sequence of SEQ ID NO: 203, and (c) HVR-L3 comprising the amino acid sequence of SEQ ID NO: 204.

In another aspect, an anti-B7-H4 antibody of an Ab-CIDE comprising (a) HVR-H1 comprising the amino acid sequence of SEQ ID NO: 5; (b) HVR-H2 comprising the amino acid sequence of SEQ ID NO: 6; (c) HVR-H3 comprising the amino acid sequence of SEQ ID NO: 167; (d) HVR-L1 comprising the amino acid sequence of SEQ ID NO: 168; (e) HVR-L2 comprising the amino acid sequence of SEQ ID NO: 169; and (f) HVR-L3 comprising the amino acid sequence of SEQ ID NO: 170.

In another aspect, an anti-B7-H4 antibody of an Ab-CIDE comprising (a) HVR-H1 comprising the amino acid sequence of SEQ ID NO: 199; (b) HVR-H2 comprising the amino acid sequence of SEQ ID NO: 200; (c) HVR-H3 comprising the amino acid sequence of SEQ ID NO: 201; (d) HVR-L1 comprising the amino acid sequence of SEQ ID NO: 202; (e) HVR-L2 comprising the amino acid sequence of SEQ ID NO: 203; and (f) HVR-L3 comprising the amino acid sequence of SEQ ID NO: 204.

In any of the above embodiments, an anti-B7-H4 antibody of an Ab-CIDE is humanized. In one embodiment, an anti-B7-H4 antibody of an Ab-CIDE comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations: Y49H, V58I, T69R and/or F71Y mutation in the light chain framework region FR3; V67A, I69L, R71A, T73K and/or T75S mutation in the heavy chain framework region FR3.

In some embodiments, an anti-B7-H4 antibody of an Ab-CIDE comprises HVRs as in any of the above embodiments, and further comprises a heavy chain framework FR3 sequence of SEQ ID NO: 211, 212 or 213. In some such embodiments, the heavy chain variable domain framework is a modified human $VH_1$ framework having an FR3 sequence of SEQ ID NO: 211, 212 or 213.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4. In certain embodiments, a VH sequence having at least 90%, 91%, 92%, 93%, 94%, 95%, 96%, 97%, 98%, or 99% identity to the amino acid sequence of SEQ ID NO: 4 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 4. In certain embodiments, a total of 1 to 5 amino acids have been substituted, inserted and/or deleted in SEQ ID NO: 4. In certain embodiments, substitutions, insertions, or deletions occur in regions outside the HVRs (i.e., in the FRs). Optionally, an anti-B7-H4 antibody of an Ab-CIDE comprises the VH sequence of SEQ ID NO: 4, including post-translational modifications of that sequence. In a particular embodiment, the VH comprises one, two or three HVRs selected from: (a) HVR-H1 comprising the amino acid sequence of SEQ ID NO: 5, (b) HVR-H2 comprising the amino acid sequence of SEQ ID NO: 6, and (c) HVR-H3 comprising the amino acid sequence of SEQ ID NO: 167.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 196, 197, 198, 99, 100, 101, 102 or 103. In certain embodiments, a VH sequence having at least 90%, 91%, 92%, 93%, 94%, 95%, 96%, 97%, 98%, or 99% identity to the amino acid sequence of SEQ ID NO: 196, 197, 198, 99, 100, 101, 102 or 103 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 196, 197, 198, 99, 100, 101, 102 or 103. In certain embodiments, a total of 1 to 5 amino acids have been substituted, inserted and/or deleted in SEQ ID NO: 196, 197, 198, 99, 100, 101, 102 or 103.

In certain embodiments, substitutions, insertions, or deletions occur in regions outside the HVRs (i.e., in the FRs). Optionally, an anti-B7-H4 antibody of an Ab-CIDE comprises the VH sequence of SEQ ID NO: 196, 197, 198, 99, 100, 101, 102 or 103, including post-translational modifications of that sequence. In a particular embodiment, the VH comprises one, two or three HVRs selected from: (a) HVR-H1 comprising the amino acid sequence of SEQ ID NO: 199, (b) HVR-H2 comprising the amino acid sequence of SEQ ID NO: 200, and (c) HVR-H3 comprising the amino acid sequence of SEQ ID NO: 201.

In another aspect, an anti-B7-H4 antibody of an Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 3. In certain embodiments, a VL sequence having at least 90%, 91%, 92%, 93%, 94%, 95%, 96%, 97%, 98%, or 99% identity to the amino acid sequence of SEQ ID NO: 3 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 3. In certain embodiments, a total of 1 to 5 amino acids have been substituted, inserted and/or deleted in SEQ ID NO: 3. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 3, including post-translational modifications of that sequence. In a particular embodiment, the VL comprises one, two or three HVRs selected from (a) HVR-L1 comprising the amino acid sequence of SEQ ID NO: 168; (b) HVR-L2 comprising the amino acid sequence of SEQ ID NO:169; and (c) HVR-L3 comprising the amino acid sequence of SEQ ID NO: 170.

In another aspect, an anti-B7-H4 antibody of an Ab-CIDE, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 195, 253, 254, 255, 256, 257 or 258. In certain embodiments, a VL sequence having at least 90%, 91%, 92%, 93%, 94%, 95%, 96%, 97%, 98%, or 99% identity to the amino acid sequence of SEQ ID NO: 195, 253, 254, 255, 256, 257 or 258 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 195, 253, 254, 255, 256, 257 or 258. In certain embodiments, a total of 1 to 5 amino acids have been substituted, inserted and/or deleted in SEQ ID NO: 195, 253, 254, 255, 256, 257 or 258. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 195, 253, 254, 255, 256, 257 or 258, including post-translational modifications of that sequence. In a particular embodiment, the VL comprises one, two or three HVRs selected from (a) HVR-L1 comprising the amino acid sequence of SEQ ID NO: 202; (b) HVR-L2 comprising the amino acid sequence of SEQ ID NO: 203; and (c) HVR-L3 comprising the amino acid sequence of SEQ ID NO: 204.

In another aspect, an anti-B7-H4 antibody of an Ab-CIDE is provided, wherein the antibody comprises a VH as in any of the embodiments provided above, and a VL as in any of the embodiments provided above.

In one embodiment, an anti-B7-H4 antibody of an Ab-CIDE comprises the VH and VL sequences in SEQ ID NO: 4 and SEQ ID NO: 3, respectively, including post-translational modifications of those sequences. In one embodiment, an anti-B7-H4 antibody of an Ab-CIDE comprises the VH and VL sequences in SEQ ID NO: 101 and SEQ ID NO: 253, respectively, including post-translational modifications of those sequences. In one embodiment, an anti-B7-H4 antibody of an Ab-CIDE comprises the VH and VL sequences in SEQ ID NO: 101 and SEQ ID NO: 257, respectively, including post-translational modifications of those sequences. In one embodiment, an anti-B7-H4 antibody of an Ab-CIDE comprises the VH and VL sequences in SEQ ID NO: 102 and SEQ ID NO: 258, respectively, including post-translational modifications of those sequences. In one embodiment, an anti-B7-H4 antibody of an Ab-CIDE comprises the VH and VL sequences in SEQ ID NO: 103 and SEQ ID NO: 258, respectively, including post-translational modifications of those sequences. In one embodiment, an anti-B7-H4 antibody of an Ab-CIDE comprises the VH and VL sequences in SEQ ID NO: 101 and SEQ ID NO: 256, respectively, including post-translational modifications of those sequences. In one embodiment, an anti-B7-H4 antibody of an Ab-CIDE comprises the VH and VL sequences in SEQ ID NO: 101 and SEQ ID NO: 255, respectively, including post-translational modifications of those sequences. In one embodiment, an anti-B7-H4 antibody of an Ab-CIDE comprises the VH and VL sequences in SEQ ID NO: 101 and SEQ ID NO: 254, respectively, including post-translational modifications of those sequences. In one embodiment, an anti-B7-H4 antibody of an Ab-CIDE comprises the VH and VL sequences in SEQ ID NO: 100 and SEQ ID NO: 253, respectively, including post-translational modifications of those sequences. In one embodiment, an anti-B7-H4 antibody of an Ab-CIDE comprises the VH and VL sequences in SEQ ID NO: 99 and SEQ ID NO: 253, respectively, including post-translational modifications of those sequences. In one embodiment, an anti-B7-H4 antibody of an Ab-CIDE comprises the VH and VL sequences in SEQ ID NO: 196 and SEQ ID NO: 253, respectively, including post-translational modifications of those sequences. In one embodiment, an anti-B7-H4 antibody of an Ab-CIDE comprises the VH and VL sequences in SEQ ID NO: 196 and SEQ ID NO: 195, respectively, including post-translational modifications of those sequences. In one embodiment, an anti-B7-H4 antibody of an Ab-CIDE comprises the VH and VL sequences in SEQ ID NO: 197 and SEQ ID NO: 195, respectively, including post-translational modifications of those sequences. In one embodiment, an anti-B7-H4 antibody of an Ab-CIDE comprises the VH and VL sequences in SEQ ID NO: 198 and SEQ ID NO: 195, respectively, including post-translational modifications of those sequences.

In a further aspect, an anti-B7-H4 antibody of an Ab-CIDE that binds to the same epitope as an anti-B7-H4 antibody provided herein. For example, in certain embodiments, an anti-B7-H4 antibody of an Ab-CIDE that binds to the same epitope as an anti-B7-H4 antibody comprising a VH sequence of SEQ ID NO: 4 and a VL sequence of SEQ ID NO: 3. In certain embodiments, an anti-B7-H4 antibody of an Ab-CIDE that binds to the same epitope as an anti-B7-H4 antibody comprising a VH sequence of SEQ ID NO: 101 and a VL sequence of SEQ ID NO: 253. In certain embodiments, an anti-B7-H4 antibody of an Ab-CIDE that binds to the same epitope as an anti-B7-H4 antibody comprising a VH sequence of SEQ ID NO: 101 and a VL sequence of SEQ ID NO: 257. In certain embodiments, an anti-B7-H4 antibody of an Ab-CIDE that binds to the same epitope as an anti-B7-H4 antibody comprising a VH sequence of SEQ ID NO: 102 and a VL sequence of SEQ ID NO: 258. In certain embodiments, an anti-B7-H4 antibody of an Ab-CIDE that binds to the same epitope as an anti-B7-H4 antibody comprising a VH sequence of SEQ ID NO: 103 and a VL sequence of SEQ ID NO: 258. In certain embodiments, an anti-B7-H4 antibody of an Ab-CIDE that binds to the same epitope as an anti-B7-H4 antibody comprising a VH sequence of SEQ ID NO: 101 and a VL sequence of SEQ ID NO: 256. In certain embodiments, an anti-B7-H4 antibody of an Ab-CIDE that binds to the same epitope as an anti-B7-H4 antibody comprising a VH sequence of SEQ ID NO: 101 and a VL sequence of SEQ ID NO: 255. In certain embodiments, an anti-B7-H4 antibody of an Ab-CIDE that binds to the same epitope as an anti-B7-H4 antibody comprising a VH sequence of SEQ ID NO: 101 and a VL sequence of SEQ ID NO: 254. In certain embodiments, an anti-B7-H4 antibody of an Ab-CIDE that binds to the same epitope as an anti-B7-H4 antibody comprising a VH sequence of SEQ ID NO: 100 and a VL sequence of SEQ ID NO: 253. In certain embodiments, an anti-B7-H4 antibody of an Ab-CIDE that binds to the same epitope as an anti-B7-H4 antibody comprising a VH sequence of SEQ ID NO: 99 and a VL sequence of SEQ ID NO: 253. In certain embodiments, an anti-B7-H4 antibody of an Ab-CIDE that binds to the same epitope as an anti-B7-H4 antibody comprising a VH sequence of SEQ ID NO: 256 and a VL sequence of SEQ ID NO: 253. In certain embodiments, an anti-B7-H4 antibody of an Ab-CIDE that binds to the same epitope as an anti-B7-H4 antibody comprising a VH sequence of SEQ ID NO: 256 and a VL sequence of SEQ ID NO: 255. In certain embodiments, an anti-B7-H4 antibody of an Ab-CIDE that binds to the same epitope as an anti-B7-H4 antibody comprising a VH sequence of SEQ ID NO: 257 and a VL sequence of SEQ ID NO: 195. In certain embodiments, an anti-B7-H4 antibody of an Ab-CIDE that binds to the same epitope as an anti-B7-H4 antibody comprising a VH sequence of SEQ ID NO: 198 and a VL sequence of SEQ ID NO: 195.

In certain embodiments, an anti-B7-H4 antibody of an Ab-CIDE according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO: 233); or binds to an epitope within all or a portion of SEQ ID NO: 234 (mature human B7-H4); or binds to an epitope within all or a portion of SEQ ID NO: 233 (precursor human B7-114). In some embodiments, an anti-B7-H4 antibody of an Ab-CIDE has at least one or more of the following characteristics, in any combination: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4).

In a further aspect, an anti-B7-H4 antibody of an Ab-CIDE according to any of the above embodiments is a monoclonal antibody, including a chimeric, humanized or human antibody. In one embodiment, an anti-B7-H4 antibody of an Ab-CIDE is an antibody fragment, e.g., a Fv, Fab, Fab', scFv, diabody, or $F(ab')_2$ fragment. In another embodiment, an anti-B7-H4 antibody of an Ab-CIDE is a substantially full length antibody, e.g., an IgG1 antibody or other antibody class or isotype as defined herein.

Antibody 22C10 and Other Embodiments

In one aspect, an anti-B7-H4 antibody of an Ab-CIDE comprising at least one, two, three, four, five, or six HVRs selected from (a) HVR-H1 comprising the amino acid sequence of SEQ ID NO: 189; (b) HVR-H2 comprising the amino acid sequence of SEQ ID NO: 190; (c) HVR-H3 comprising the amino acid sequence of SEQ ID NO: 191; (d) HVR-L1 comprising the amino acid sequence of SEQ ID NO: 192; (e) HVR-L2 comprising the amino acid sequence of SEQ ID NO: 193; and (f) HVR-L3 comprising the amino acid sequence of SEQ ID NO: 194.

In another aspect, an anti-B7-H4 antibody of an Ab-CIDE comprising at least one, two, three, four, five, or six HVRs selected from (a) HVR-H1 comprising the amino acid sequence of SEQ ID NO: 218; (b) HVR-H2 comprising the amino acid sequence of SEQ ID NO: 219; (c) HVR-H3 comprising the amino acid sequence of SEQ ID NO: 220; (d) HVR-L1 comprising the amino acid sequence of SEQ ID NO: 221; (e) HVR-L2 comprising the amino acid sequence of SEQ ID NO: 222; and (f) HVR-L3 comprising the amino acid sequence of SEQ ID NO: 223.

In one aspect, an anti-B7-H4 antibody of an Ab-CIDE comprising at least one, at least two, or all three VH HVR sequences selected from (a) HVR-H1 comprising the amino acid sequence of SEQ ID NO: 189; (b) HVR-H2 comprising the amino acid sequence of SEQ ID NO: 190; and (c) HVR-H3 comprising the amino acid sequence of SEQ ID NO: 191. In one embodiment, an anti-B7-H4 antibody of an Ab-CIDE comprises HVR-H3 comprising the amino acid sequence of SEQ ID NO: 191. In another embodiment, an anti-B7-H4 antibody of an Ab-CIDE comprises HVR-H3 comprising the amino acid sequence of SEQ ID NO: 191, and HVR-L3 comprising the amino acid sequence of SEQ ID NO: 194. In a further embodiment, an anti-B7-H4 antibody of an Ab-CIDE comprises HVR-H3 comprising the amino acid sequence of SEQ ID NO: 191, HVR-L3 comprising the amino acid sequence of SEQ ID NO: 194, and HVR-H2 comprising the amino acid sequence of SEQ ID NO: 190. In a further embodiment, an anti-B7-H4 antibody of an Ab-CIDE comprises (a) HVR-H1 comprising the amino acid sequence of SEQ ID NO: 189; (b) HVR-H2 comprising the amino acid sequence of SEQ ID NO: 190; and (c) HVR-H3 comprising the amino acid sequence of SEQ ID NO:191.

In another aspect, an anti-B7-H4 antibody of an Ab-CIDE comprising at least one, at least two, or all three VH HVR sequences selected from (a) HVR-H1 comprising the amino acid sequence of SEQ ID NO: 218; (b) HVR-H2 comprising the amino acid sequence of SEQ ID NO: 219; and (c) HVR-H3 comprising the amino acid sequence of SEQ ID NO: 220. In one embodiment, an anti-B7-H4 antibody of an Ab-CIDE comprises HVR-H3 comprising the amino acid sequence of SEQ ID NO: 220. In another embodiment, an anti-B7-H4 antibody of an Ab-CIDE comprises HVR-H3 comprising the amino acid sequence of SEQ ID NO: 220, and HVR-L3 comprising the amino acid sequence of SEQ ID NO: 223. In a further embodiment, an anti-B7-H4 antibody of an Ab-CIDE comprises HVR-H3 comprising the amino acid sequence of SEQ ID NO: 220, HVR-L3 comprising the amino acid sequence of SEQ ID NO: 223, and HVR-H2 comprising the amino acid sequence of SEQ ID NO: 219. In a further embodiment, an anti-B7-H4 antibody of an Ab-CIDE comprises (a) HVR-H1 comprising the amino acid sequence of SEQ ID NO: 218; (b) HVR-H2 comprising the amino acid sequence of SEQ ID NO: 219; and (c) HVR-H3 comprising the amino acid sequence of SEQ ID NO: 220.

In another aspect, an anti-B7-H4 antibody of an Ab-CIDE comprising at least one, at least two, or all three VL HVR sequences selected from (a) HVR-L1 comprising the amino acid sequence of SEQ ID NO: 192; (b) HVR-L2 comprising the amino acid sequence of SEQ ID NO: 193; and (c) HVR-L3 comprising the amino acid sequence of SEQ ID NO: 194. In one embodiment, an anti-B7-H4 antibody of an Ab-CIDE comprises (a) HVR-L1 comprising the amino acid sequence of SEQ ID NO: 192; (b) HVR-L2 comprising the amino acid sequence of SEQ ID NO: 193; and (c) HVR-L3 comprising the amino acid sequence of SEQ ID NO: 194.

In another aspect, an anti-B7-H4 antibody of an Ab-CIDE comprising at least one, at least two, or all three VL HVR sequences selected from (a) HVR-L1 comprising the amino acid sequence of SEQ ID NO: 221; (b) HVR-L2 comprising the amino acid sequence of SEQ ID NO: 222; and (c) HVR-L3 comprising the amino acid sequence of SEQ ID NO: 223. In one embodiment, an anti-B7-H4 antibody of an Ab-CIDE comprises (a) HVR-L1 comprising the amino acid sequence of SEQ ID NO: 221; (b) HVR-L2 comprising the amino acid sequence of SEQ ID NO: 222; and (c) HVR-L3 comprising the amino acid sequence of SEQ ID NO: 223.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 189, (ii) HVR-H2 comprising the amino acid sequence of SEQ ID NO: 190, and (iii) HVR-H3 comprising the amino acid sequence of SEQ ID NO: 191; and (b) a VL domain comprising at least one, at least two, or all three VL HVR sequences selected from (i) HVR-L1 comprising the amino acid sequence of SEQ ID NO: 192, (ii) HVR-L2 comprising the amino acid sequence of SEQ ID NO: 193, and (c) HVR-L3 comprising the amino acid sequence of SEQ ID NO: 194.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 218, (ii) HVR-H2 comprising the amino acid sequence of SEQ ID NO: 219, and (iii) HVR-H3 comprising the amino acid sequence of SEQ ID NO: 220; and (b) a VL domain comprising at least one, at least two, or all three VL HVR sequences selected from (i) HVR-L1 comprising the amino acid sequence of SEQ ID NO: 221, (ii) HVR-L2 comprising the amino acid sequence of SEQ ID NO: 222, and (c) HVR-L3 comprising the amino acid sequence of SEQ ID NO: 223.

In another aspect, an anti-B7-H4 antibody of an Ab-CIDE comprising (a) HVR-H1 comprising the amino acid sequence of SEQ ID NO: 189; (b) HVR-H2 comprising the amino acid sequence of SEQ ID NO: 190; (c) HVR-H3 comprising the amino acid sequence of SEQ ID NO: 191; (d) HVR-L1 comprising the amino acid sequence of SEQ ID NO: 192; (e) HVR-L2 comprising the amino acid sequence of SEQ ID NO: 193; and (f) HVR-L3 comprising an amino acid sequence selected from SEQ ID NO: 194.

In another aspect, an anti-B7-H4 antibody of an Ab-CIDE comprising (a) HVR-H1 comprising the amino acid sequence of SEQ ID NO: 218; (b) HVR-H2 comprising the amino acid sequence of SEQ ID NO: 219; (c) HVR-H3 comprising the amino acid sequence of SEQ ID NO: 220; (d) HVR-L1 comprising the amino acid sequence of SEQ ID NO: 221; (e) HVR-L2 comprising the amino acid sequence of SEQ ID NO: 222; and (f) HVR-L3 comprising an amino acid sequence selected from SEQ ID NO: 223.

In any of the above embodiments, an anti-B7-H4 antibody of an Ab-CIDE is a human antibody.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 188. In certain embodiments, a VH sequence having at least 90%, 91%, 92%, 93%, 94%, 95%, 96%, 97%, 98%, or 99% identity to the amino acid sequence of SEQ ID NO: 188 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 188. In certain embodiments, a total of 1 to 5 amino acids have been substituted, inserted and/or deleted in SEQ ID NO: 188. In certain embodiments, substitutions, insertions, or deletions occur in regions outside the HVRs (i.e., in the FRs). Optionally, an anti-B7-H4 antibody of an Ab-CIDE comprises the VH sequence of SEQ ID NO: 188, including post-translational modifications of that sequence. In a particular embodiment, the VH comprises one, two or three HVRs selected from: (a) HVR-H1 comprising the amino acid sequence of SEQ ID NO: 189, (b) HVR-H2 comprising the amino acid sequence of SEQ ID NO: 190, and (c) HVR-H3 comprising the amino acid sequence of SEQ ID NO: 191.

In another aspect, an anti-B7-H4 antibody of an Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 187. In certain embodiments, a VL sequence having at least 90%, 91%, 92%, 93%, 94%, 95%, 96%, 97%, 98%, or 99% identity to the amino acid sequence of SEQ ID NO: 187 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 187. In certain embodiments, a total of 1 to 10 amino acids have been substituted, inserted and/or deleted in SEQ ID NO: 187. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 187, including post-translational modifications of that sequence. In a particular embodiment, the VL comprises one, two or three HVRs selected from (a) HVR-L1 comprising the amino acid sequence of SEQ ID NO: 192; (b) HVR-L2 comprising the amino acid sequence of SEQ ID NO: 193; and (c) HVR-L3 comprising the amino acid sequence of SEQ ID NO: 194.

In another aspect, an anti-B7-H4 antibody of an Ab-CIDE, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 215, 217, 104, 105 or 106. In certain embodiments, a VL sequence having at least 90%, 91%, 92%, 93%, 94%, 95%, 96%, 97%, 98%, or 99% identity to the amino acid sequence of SEQ ID NO: 215, 217, 104, 105 or 106 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 215, 217, 104, 105 or 106. In certain embodiments, a total of 1 to 10 amino acids have been substituted, inserted and/or deleted in SEQ ID NO: 215, 217, 104, 105 or 106. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 215, 217, 104, 105 or 106, including post-translational modifications of that sequence. In a particular embodiment, the VL comprises one, two or three HVRs selected from (a) HVR-L1 comprising the amino acid sequence of SEQ ID NO: 221; (b) HVR-L2 comprising the amino acid sequence of SEQ ID NO: 222; and (c) HVR-L3 comprising the amino acid sequence of SEQ ID NO: 223.

In another aspect, an anti-B7-H4 antibody of an Ab-CIDE, wherein the antibody comprises a VH as in any of the embodiments provided above, and a VL as in any of the embodiments provided above. In one embodiment, an anti-B7-H4 antibody of an Ab-CIDE comprises the VH and VL sequences in SEQ ID NO: 111 and SEQ ID NO: 104, respectively, including post-translational modifications of those sequences. In one embodiment, an anti-B7-H4 antibody of an Ab-CIDE comprises the VH and VL sequences in SEQ ID NO: 111 and SEQ ID NO: 215, respectively, including post-translational modifications of those sequences. In one embodiment, an anti-B7-H4 antibody of an Ab-CIDE comprises the VH and VL sequences in SEQ ID NO: 112 and SEQ ID NO: 215, respectively, including post-translational modifications of those sequences. In one embodiment, an anti-B7-H4 antibody of an Ab-CIDE comprises the VH and VL sequences in SEQ ID NO: 113 and SEQ ID NO: 215, respectively, including post-translational modifications of those sequences. In one embodiment, an anti-B7-H4 antibody of an Ab-CIDE comprises the VH and VL sequences in SEQ ID NO: 114 and SEQ ID NO: 215, respectively, including post-translational modifications of those sequences. In one embodiment, an anti-B7-H4 antibody of an Ab-CIDE comprises the VH and VL sequences in SEQ ID NO: 111 and SEQ ID NO: 105, respectively, including post-translational modifications of those sequences. In one embodiment, an anti-B7-H4 antibody of an Ab-CIDE comprises the VH and VL sequences in SEQ ID NO: 111 and SEQ ID NO: 106, respectively, including post-translational modifications of those sequences. In one embodiment, an anti-B7-H4 antibody of an Ab-CIDE comprises the VH and VL sequences in SEQ ID NO: 110 and SEQ ID NO: 215, respectively, including post-translational modifications of those sequences. In one embodiment, an anti-B7-H4 antibody of an Ab-CIDE comprises the VH and VL sequences in SEQ ID NO: 109 and SEQ ID NO: 215, respectively, including post-translational modifications of those sequences. In one embodiment, an anti-B7-H4 antibody of an Ab-CIDE comprises the VH and VL sequences in SEQ ID NO: 108 and SEQ ID NO: 215, respectively, including post-translational modifications of those sequences. In one embodiment, an anti-B7-H4 antibody of an Ab-CIDE comprises the VH and VL sequences in SEQ ID NO: 107 and SEQ ID NO: 215, respectively, including post-translational modifications of those sequences. In one embodiment, an anti-B7-H4 antibody of an Ab-CIDE comprises the VH and VL sequences in SEQ ID NO: 216 and SEQ ID NO: 215, respectively, including post-translational modifications of those sequences. In another embodiment, an anti-B7-H4 antibody of an Ab-CIDE comprises the VH and VL sequences in SEQ ID NO: 216 and SEQ ID NO: 217, respectively, including post-translational modifications of those sequences.

In a further aspect, an anti-B7-H4 antibody of an Ab-CIDE that binds to the same epitope as an anti-B7-H4 antibody provided herein. For example, in certain embodiments, an anti-B7-H4 antibody of an Ab-CIDE is provided that binds to the same epitope as an anti-B7-H4 antibody comprising a VH sequence of SEQ ID NO: 188 and a VL sequence of SEQ ID NO: 187. In certain embodiments, an anti-B7-H4 antibody of an Ab-CIDE is provided that binds to the same epitope as an anti-B7-H4 antibody comprising a VH sequence of SEQ ID NO: 111 and a VL sequence of SEQ ID NO: 104. In certain embodiments, an anti-B7-H4 antibody of an Ab-CIDE is provided that binds to the same epitope as an anti-B7-H4 antibody comprising a VH sequence of SEQ ID NO: 111 and a VL sequence of SEQ ID NO: 215. In certain embodiments, an anti-B7-H4 antibody of an Ab-CIDE is provided that binds to the same epitope as an anti-B7-H4 antibody comprising a VH sequence of SEQ ID NO: 112 and a VL sequence of SEQ ID NO: 215. In certain embodiments, an anti-B7-H4 antibody of an Ab-CIDE is provided that binds to the same epitope as an anti-B7-H4 antibody comprising a VH sequence of SEQ ID NO: 113 and a VL sequence of SEQ ID NO: 215. In certain embodiments, an anti-B7-H4 antibody of an Ab-CIDE is provided that binds to the same epitope as an anti-B7-H4 antibody comprising a VH sequence of SEQ ID NO: 114 and a VL sequence of SEQ ID NO: 215. In certain embodiments, an anti-B7-H4 antibody of an Ab-CIDE is provided that binds to the same epitope as an anti-B7-H4 antibody comprising a VH sequence of SEQ ID NO: 111 and a VL sequence of SEQ ID NO: 105. In certain embodiments, an anti-B7-H4 antibody of an Ab-CIDE is provided that binds to the same epitope as an anti-B7-H4 antibody comprising a VH sequence of SEQ ID NO: 111 and a VL sequence of SEQ ID NO: 106. In certain embodiments, an anti-B7-H4 antibody of an Ab-CIDE is provided that binds to the same epitope as an anti-B7-H4 antibody comprising a VH sequence of SEQ ID NO: 110 and a VL sequence of SEQ ID NO: 215. In certain embodiments, an anti-B7-H4 antibody of an Ab-CIDE is provided that binds to the same epitope as an anti-B7-H4 antibody comprising a VH sequence of SEQ ID NO: 109 and a VL sequence of SEQ ID NO: 215. In certain embodiments, an anti-B7-H4 antibody of an Ab-CIDE that binds to the same epitope as an anti-B7-H4 antibody comprising a VH sequence of SEQ ID NO: 108 and a VL sequence of SEQ ID NO: 215. In certain embodiments, an anti-B7-H4 antibody of an Ab-CIDE that binds to the same epitope as an anti-B7-H4 antibody comprising a VH sequence of SEQ ID NO: 107 and a VL sequence of SEQ ID NO: 215. In certain embodiments, an anti-B7-H4 antibody of an Ab-CIDE that binds to the same epitope as an anti-B7-H4 antibody comprising a VH sequence of SEQ ID NO: 216 and a VL sequence of SEQ ID NO: 215. In certain embodiments, an anti-B7-H4 antibody of an Ab-CIDE that binds to the same epitope as an anti-B7-H4 antibody comprising a VH sequence of SEQ ID NO: 216 and a VL sequence of SEQ ID NO: 217.

In certain embodiments, an anti-B7-H4 antibody of an Ab-CIDE according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7—H4). In some embodiments, an anti-B7-H4 antibody of an Ab-CIDE has at least one or more of the following characteristics, in any combination: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4).

In a further aspect, an anti-B7-H4 antibody of an Ab-CIDE according to any of the above embodiments is a monoclonal antibody, including a human antibody. In one embodiment, an anti-B7-H4 antibody of an Ab-CIDE is an antibody fragment, e.g., a Fv, Fab, Fab', scFv, diabody, or $F(ab')_2$ fragment. In another embodiment, an anti-B7-H4 antibody of an Ab-CIDE is a substantially full length antibody, e.g., an IgG2a antibody or other antibody class or isotype as defined herein.

Antibody 32D6 and Other Embodiments

In one aspect, an anti-B7-H4 antibody of an Ab-CIDE comprising at least one, two, three, four, five, or six HVRs selected from (a) HVR-H1 comprising the amino acid sequence of SEQ ID NO: 173; (b) HVR-H2 comprising the amino acid sequence of SEQ ID NO: 174; (c) HVR-H3 comprising the amino acid sequence of SEQ ID NO: 175; (d) HVR-L1 comprising the amino acid sequence of SEQ ID NO: 176; (e) HVR-L2 comprising the amino acid sequence of SEQ ID NO: 177; and (f) HVR-L3 comprising the amino acid sequence of SEQ ID NO: 178.

In one aspect, an anti-B7-H4 antibody of an Ab-CIDE comprising at least one, at least two, or all three VH HVR sequences selected from (a) HVR-H1 comprising the amino acid sequence of SEQ ID NO: 173; (b) HVR-H2 comprising the amino acid sequence of SEQ ID NO: 174; and (c) HVR-H3 comprising the amino acid sequence of SEQ ID NO: 175. In one embodiment, an anti-B7-H4 antibody of an Ab-CIDE comprises HVR-H3 comprising the amino acid sequence of SEQ ID NO: 175. In another embodiment, an anti-B7-H4 antibody of an Ab-CIDE comprises HVR-H3 comprising the amino acid sequence of SEQ ID NO: 175, and HVR-L3 comprising the amino acid sequence of SEQ ID NO: 178. In a further embodiment, an anti-B7—H4 antibody of an Ab-CIDE comprises HVR-H3 comprising the amino acid sequence of SEQ ID NO: 175, HVR-L3 comprising the amino acid sequence of SEQ ID NO: 178, and HVR-H2 comprising the amino acid sequence of SEQ ID NO: 174. In a further embodiment, an anti-B7-H4 antibody of an Ab-CIDE comprises (a) HVR-H1 comprising the amino acid sequence of SEQ ID NO: 173; (b) HVR-H2 comprising the amino acid sequence of SEQ ID NO: 174; and (c) HVR-H3 comprising the amino acid sequence of SEQ ID NO:175.

In another aspect, an anti-B7-H4 antibody of an Ab-CIDE comprising at least one, at least two, or all three VL HVR sequences selected from (a) HVR-L1 comprising the amino acid sequence of SEQ ID NO: 176; (b) HVR-L2 comprising the amino acid sequence of SEQ ID NO: 177; and (c) HVR-L3 comprising the amino acid sequence of SEQ ID NO: 178. In one embodiment, an anti-B7-H4 antibody of an Ab-CIDE comprises (a) HVR-L1 comprising the amino acid sequence of SEQ ID NO: 176; (b) HVR-L2 comprising the amino acid sequence of SEQ ID NO: 177; and (c) HVR-L3 comprising the amino acid sequence of SEQ ID NO: 178.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 173, (ii) HVR-H2 comprising the amino acid sequence of SEQ ID NO: 174, and (iii) HVR-H3 comprising the amino acid sequence of SEQ ID NO: 175; and (b) a VL domain comprising at least one, at least two, or all three VL HVR sequences selected from (i) HVR-L1 comprising the amino acid sequence of SEQ ID NO: 176, (ii) HVR-L2 comprising the amino acid sequence of SEQ ID NO: 177, and (c) HVR-L3 comprising the amino acid sequence of SEQ ID NO: 178.

In another aspect, an anti-B7-H4 antibody of an Ab-CIDE comprising (a) HVR-H1 comprising the amino acid sequence of SEQ ID NO: 173; (b) HVR-H2 comprising the amino acid sequence of SEQ ID NO: 174; (c) HVR-H3 comprising the amino acid sequence of SEQ ID NO: 175; (d) HVR-L1 comprising the amino acid sequence of SEQ ID NO: 176; (e) HVR-L2 comprising the amino acid sequence of SEQ ID NO: 177; and (f) HVR-L3 comprising an amino acid sequence selected from SEQ ID NO: 178.

In any of the above embodiments, an anti-B7-H4 antibody of an Ab-CIDE is a human antibody.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 172. In certain embodiments, a VH sequence having at least 90%, 91%, 92%, 93%, 94%, 95%, 96%, 97%, 98%, or 99% identity to the amino acid sequence of SEQ ID NO: 172 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 172. In certain embodiments, a total of 1 to 5 amino acids have been substituted, inserted and/or deleted in SEQ ID NO: 172. In certain embodiments, substitutions, insertions, or deletions occur in regions outside the HVRs (i.e., in the FRs). Optionally, an anti-B7-H4 antibody of an Ab-CIDE comprises the VH sequence of SEQ ID NO: 172, including post-translational modifications of that sequence. In a particular embodiment, the VH comprises one, two or three HVRs selected from: (a) HVR-H1 comprising the amino acid sequence of SEQ ID NO: 173, (b) HVR-H2 comprising the amino acid sequence of SEQ ID NO: 174, and (c) HVR-H3 comprising the amino acid sequence of SEQ ID NO: 175.

In another aspect, an anti-B7-H4 antibody of an Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 171. In certain embodiments, a VL sequence having at least 90%, 91%, 92%, 93%, 94%, 95%, 96%, 97%, 98%, or 99% identity to the amino acid sequence of SEQ ID NO: 171 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 171. In certain embodiments, a total of 1 to 10 amino acids have been substituted, inserted and/or deleted in SEQ ID NO: 171. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 171, including post-translational modifications of that sequence. In a particular embodiment, the VL comprises one, two or three HVRs selected from (a) HVR-L1 comprising the amino acid sequence of SEQ ID NO: 176; (b) HVR-L2 comprising the amino acid sequence of SEQ ID NO: 177; and (c) HVR-L3 comprising the amino acid sequence of SEQ ID NO: 178.

In another aspect, an anti-B7-H4 antibody of an Ab-CIDE, wherein the antibody comprises a VH as in any of the embodiments provided above, and a VL as in any of the embodiments provided above. In one embodiment, an anti-B7-H4 antibody of an Ab-CIDE comprises the VH and VL sequences in SEQ ID NO: 172 and SEQ ID NO: 171, respectively, including post-translational modifications of those sequences. In another embodiment, an anti-B7-H4 antibody of an Ab-CIDE comprises the VH and VL sequences in SEQ ID NO: 172 and SEQ ID NO: 171, respectively, including post-translational modifications of those sequences.

In a further aspect, an anti-B7-H4 antibody of an Ab-CIDE that binds to the same epitope as an anti-B7-H4 antibody provided herein. For example, in certain embodiments, an anti-B7-H4 antibody of an Ab-CIDE that binds to the same epitope as an anti-B7-H4 antibody comprising a VH sequence of SEQ ID NO: 172 and a VL sequence of SEQ ID NO: 171.

In certain embodiments, an anti-B7-H4 antibody of an Ab-CIDE according to any of the above embodiments is provided that binds to B7-H4 and has at least one of the following characteristics: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4). In some embodiments, an anti-B7-H4 antibody of an Ab-CIDE has at least one or more of the following characteristics, in any combination: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); binds to an epitope within all or a portion of SEQ ID NO: 233 (precursor human B7-H4).

In a further aspect, an anti-B7-H4 antibody of an Ab-CIDE according to any of the above embodiments is a monoclonal antibody, including a human antibody. In one embodiment, an anti-B7-H4 antibody of an Ab-CIDE is an antibody fragment, e.g., a Fv, Fab, Fab', scFv, diabody, or $F(ab')_2$ fragment. In another embodiment, an anti-B7-H4 antibody of an Ab-CIDE is a substantially full length antibody, e.g., an IgG2a antibody or other antibody class or isotype as defined herein.

Antibody 9B9 and Other Embodiments

In one aspect, an anti-B7-H4 antibody of an Ab-CIDE comprising at least one, two, three, four, five, or six HVRs selected from (a) HVR-H1 comprising the amino acid sequence of SEQ ID NO: 181; (b) HVR-H2 comprising the amino acid sequence of SEQ ID NO: 182; (c) HVR-H3 comprising the amino acid sequence of SEQ ID NO: 183; (d) HVR-L1 comprising the amino acid sequence of SEQ ID NO: 184; (e) HVR-L2 comprising the amino acid sequence of SEQ ID NO: 185; and (f) HVR-L3 comprising the amino acid sequence of SEQ ID NO: 186.

In one aspect, an anti-B7-H4 antibody of an Ab-CIDE comprising at least one, at least two, or all three VH HVR sequences selected from (a) HVR-H1 comprising the amino acid sequence of SEQ ID NO: 181; (b) HVR-H2 comprising the amino acid sequence of SEQ ID NO: 182; and (c) HVR-H3 comprising the amino acid sequence of SEQ ID NO: 183. In one embodiment, an anti-B7-H4 antibody of an Ab-CIDE comprises HVR-H3 comprising the amino acid sequence of SEQ ID NO: 183. In another embodiment, an anti-B7-H4 antibody of an Ab-CIDE comprises HVR-H3 comprising the amino acid sequence of SEQ ID NO: 183, and HVR-L3 comprising the amino acid sequence of SEQ ID NO: 186. In a further embodiment, an anti-B7-H4 antibody of an Ab-CIDE comprises HVR-H3 comprising the amino acid sequence of SEQ ID NO: 183, HVR-L3 comprising the amino acid sequence of SEQ ID NO: 186, and HVR-H2 comprising the amino acid sequence of SEQ ID NO: 182. In a further embodiment, an anti-B7-H4 antibody of an Ab-CIDE comprises (a) HVR-H1 comprising the amino acid sequence of SEQ ID NO: 181; (b) HVR-H2 comprising the amino acid sequence of SEQ ID NO: 182; and (c) HVR-H3 comprising the amino acid sequence of SEQ ID NO:183.

In another aspect, an anti-B7-H4 antibody of an Ab-CIDE comprising at least one, at least two, or all three VL HVR sequences selected from (a) HVR-L1 comprising the amino acid sequence of SEQ ID NO: 184; (b) HVR-L2 comprising the amino acid sequence of SEQ ID NO: 185; and (c) HVR-L3 comprising the amino acid sequence of SEQ ID NO: 186. In one embodiment, an anti-B7-H4 antibody of an Ab-CIDE comprises (a) HVR-L1 comprising the amino acid sequence of SEQ ID NO: 184; (b) HVR-L2 comprising the amino acid sequence of SEQ ID NO: 185; and (c) HVR-L3 comprising the amino acid sequence of SEQ ID NO: 186.

In another aspect, an anti-B7-H4 antibody of an Ab-CIDE comprises (a) a VH domain comprising at least one, at least two, or all three VH HVR sequences selected from (i) HVR-H1 comprising the amino acid sequence of SEQ ID NO: 181, (ii) HVR-H2 comprising the amino acid sequence of SEQ ID NO: 182, and (iii) HVR-H3 comprising the amino acid sequence of SEQ ID NO: 183; and (b) a VL domain comprising at least one, at least two, or all three VL HVR sequences selected from (i) HVR-L1 comprising the amino acid sequence of SEQ ID NO: 184, (ii) HVR-L2 comprising the amino acid sequence of SEQ ID NO: 185, and (c) HVR-L3 comprising the amino acid sequence of SEQ ID NO: 186.

In another aspect, an anti-B7-H4 antibody of an Ab-CIDE comprising (a) HVR-H1 comprising the amino acid sequence of SEQ ID NO: 181; (b) HVR-H2 comprising the amino acid sequence of SEQ ID NO: 182; (c) HVR-H3 comprising the amino acid sequence of SEQ ID NO: 183; (d) HVR-L1 comprising the amino acid sequence of SEQ ID NO: 184; (e) HVR-L2 comprising the amino acid sequence of SEQ ID NO: 185; and (f) HVR-L3 comprising an amino acid sequence selected from SEQ ID NO: 186.

In any of the above embodiments, an anti-B7-H4 antibody of an Ab-CIDE is a human antibody.

In another aspect, an anti-B7-H4 antibody of an Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 180. In certain embodiments, a VH sequence having at least 90%, 91%, 92%, 93%, 94%, 95%, 96%, 97%, 98%, or 99% identity to the amino acid sequence of SEQ ID NO: 180 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 10 amino acids have been substituted, inserted and/or deleted in SEQ ID NO: 180. In certain embodiments, a total of 1 to 5 amino acids have been substituted, inserted and/or deleted in SEQ ID NO: 180. In certain embodiments, substitutions, insertions, or deletions occur in regions outside the HVRs (i.e., in the FRs). Optionally, an anti-B7-H4 antibody of an Ab-CIDE comprises the VH sequence of SEQ ID NO: 180, including post-translational modifications of that sequence. In a particular embodiment, the VH comprises one, two or three HVRs selected from: (a) HVR-H1 comprising the amino acid sequence of SEQ ID NO: 181, (b) HVR-H2 comprising the amino acid sequence of SEQ ID NO: 182, and (c) HVR-H3 comprising the amino acid sequence of SEQ ID NO: 183.

In another aspect, an anti-B7-H4 antibody of an Ab-CIDE, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 179. In certain embodiments, a VL sequence having at least 90%, 91%, 92%, 93%, 94%, 95%, 96%, 97%, 98%, or 99% identity to the amino acid sequence of SEQ ID NO: 179 contains substitutions (e.g., conservative substitutions), insertions, or deletions relative to the reference sequence, but an anti-B7-H4 antibody comprising that sequence retains the ability to bind to B7-H4. In certain embodiments, a total of 1 to 5 amino acids have been substituted, inserted and/or deleted in SEQ ID NO: 179. In certain embodiments, a total of 1 to 10 amino acids have been substituted, inserted and/or deleted in SEQ ID NO: 179. In certain embodiments, the substitutions, insertions, or deletions occur in regions outside the HVRs (i.e., in the FRs). Optionally, an anti-B7-H4 antibody of an Ab-CIDE comprises the VL sequence of SEQ ID NO: 171, including post-translational modifications of that sequence. In a particular embodiment, the VL comprises one, two or three HVRs selected from (a) HVR-L1 comprising the amino acid sequence of SEQ ID NO: 184; (b) HVR-L2 comprising the amino acid sequence of SEQ ID NO: 185; and (c) HVR-L3 comprising the amino acid sequence of SEQ ID NO: 186.

In another aspect, an anti-B7-H4 antibody of an Ab-CIDE, wherein the antibody comprises a VH as in any of the embodiments provided above, and a VL as in any of the embodiments provided above. In one embodiment, an anti-B7-H4 antibody of an Ab-CIDE comprises the VH and VL sequences in SEQ ID NO: 180 and SEQ ID NO: 179, respectively, including post-translational modifications of those sequences.

In a further aspect, an anti-B7-H4 antibody of an Ab-CIDE that binds to the same epitope as an anti-B7-H4 antibody provided herein. For example, in certain embodiments, an anti-B7—H4 antibody of an Ab-CIDE is provided that binds to the same epitope as an anti-B7-H4 antibody comprising a VH sequence of SEQ ID NO: 180 and a VL sequence of SEQ ID NO: 179.

In certain embodiments, an anti-B7-H4 antibody of an Ab-CIDE according to any of the above embodiments is provided that to B7-H4 and has at least one of the following characteristics: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4). In some embodiments, an anti-B7-H4 antibody of an Ab-CIDE has at least one or more of the following characteristics, in any combination: (a) binds to an epitope within all or a portion of the B7-H4 Ig-V containing domain (amino acids 29-157 of SEQ ID NO: 233); or binds to an epitope within all or a portion of the B7-H4 Ig-C containing domain (amino acids 158-250 of SEQ ID NO: 233); or binds to an epitope within all or a portion of the B7-H4 Ig-V and Ig-C domains (amino acids 29-250 of SEQ ID NO:233); or binds to an epitope within all or a portion of SEQ ID NO: 234 (mature human B7-H4); or binds to an epitope within all or a portion of SEQ ID NO: 233 (precursor human B7-H4).

In a further aspect, an anti-B7-H4 antibody of an Ab-CIDE according to any of the above embodiments is a monoclonal antibody, including a human antibody. In one embodiment, an anti-B7-H4 antibody of an Ab-CIDE is an antibody fragment, e.g., a Fv, Fab, Fab', scFv, diabody, or $F(ab')_2$ fragment. In another embodiment, an anti-B7-H4 antibody of an Ab-CIDE is a substantially full length antibody, e.g., an IgG2a antibody or other antibody class or isotype as defined herein.

Anti-MUC16 Antibodies

In certain embodiments, Ab-CIDEs comprise anti-MUC16 antibodies.

In some embodiments, described herein are PACs comprising an anti-MUC16 antibody comprising at least one, two, three, four, five, or six HVRs selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33 and (f) HVR-L3 comprising the amino acid sequence of SEQ ID NO: 34.

In one aspect, described herein are Ab-CIDEs comprising an antibody that comprises at least one, at least two, or all three VH HVR sequences selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37. In a further embodiment, the antibody comprises (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37.

In another aspect, described herein are Ab-CIDEs comprising an antibody that comprises at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 35, (ii) HVR-H2 comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, described herein are Ab-CIDEs comprising an antibody that comprises (a) HVR-H1 comprising the amino acid sequence of SEQ ID NO: 35 (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In any of the above embodiments, an anti-MUC16 antibody of a Ab-CIDE is humanized. In one embodiment, an anti-MUC16 antibody comprises HVRs as in any of the above embodiments, and further comprises a human acceptor framework, e.g. a human immunoglobulin framework or a human consensus framework.

In another aspect, an anti-MUC16 antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In certain embodiments, a VH sequence having at least 90%, 91%, 92%, 93%, 94%, 95%, 96%, 97%, 98%, or 99% identity to the amino acid sequence of SEQ ID NO: 39 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 39. In certain embodiments, a total of 1 to 5 amino acids have been substituted, inserted and/or deleted in SEQ ID NO: 39. In certain embodiments, substitutions, insertions, or deletions occur in regions outside the HVRs (i.e., in the FRs). Optionally, the anti-MUC16 antibody comprises the VH sequence of SEQ ID NO: 39, including post-translational modifications of that sequence. In a particular embodiment, the VH comprises one, two or three HVRs selected from: (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 37.

In another aspect, an anti-MUC16 antibody of a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 38. In certain embodiments, a VL sequence having at least 90%, 91%, 92%, 93%, 94%, 95%, 96%, 97%, 98%, or 99% identity to the amino acid sequence of SEQ ID NO:38 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 38. In certain embodiments, a total of 1 to 5 amino acids have been substituted, inserted and/or deleted in SEQ ID NO: 38. In certain embodiments, the substitutions, insertions, or deletions occur in regions outside the HVRs (i.e., in the FRs). Optionally, the anti-MUC16 antibody comprises the VL sequence of SEQ ID NO: 38, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, a Ab-CIDE comprising an anti-MUC16 antibody is provided, wherein the antibody comprises a VH as in any of the embodiments provided above, and a VL as in any of the embodiments provided above.

In one embodiment, a Ab-CIDE is provided, wherein the antibody comprises the VH and VL sequences in SEQ ID NO: 39 and SEQ ID NO: 38, respectively, including post-translational modifications of those sequences.

In a further aspect, provided herein are Ab-CIDEs comprising antibodies that bind to the same epitope as an anti-MUC16 antibody provided herein. For example, in certain embodiments, a PAC is provided comprising an antibody that binds to the same epitope as an anti-MUC16 antibody comprising a VH sequence of SEQ ID NO: 39 and a VL sequence of SEQ ID NO: 38, respectively.

In a further aspect, an anti-MUC16 antibody of a Ab-CIDE according to any of the above embodiments is a monoclonal antibody, including a human antibody. In one embodiment, an anti-MUC16 antibody of a Ab-CIDE is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

Anti-STEAP-1 Antibodies

In certain embodiments, Ab-CIDEs comprise anti-STEAP-1 antibodies.

In some embodiments, described herein are PACs comprising an anti-STEAP-1 antibody comprising at least one, two, three, four, five, or six HVRs selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44 and (f) HVR-L3 comprising the amino acid sequence of SEQ ID NO: 45.

In one aspect, described herein are Ab-CIDEs comprising an antibody that comprises at least one, at least two, or all three VH HVR sequences selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42. In a further embodiment, the antibody comprises (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42.

In another aspect, described herein are Ab-CIDEs comprising an antibody that comprises at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 40, (ii) HVR-H2 comprising the amino acid sequence of SEQ ID NO: 41, and (iii) HVR-H3 comprising an amino acid sequence selected from SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (c) HVR-L3 comprising the amino acid sequence of SEQ ID NO: 45.

In another aspect, described herein are Ab-CIDEs comprising an antibody that comprises (a) HVR-H1 comprising the amino acid sequence of SEQ ID NO: 40 (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In any of the above embodiments, an anti-STEAP-1 antibody of a Ab-CIDE is humanized. In one embodiment, an anti-STEAP-1 antibody comprises HVRs as in any of the above embodiments, and further comprises a human acceptor framework, e.g. a human immunoglobulin framework or a human consensus framework.

In another aspect, an anti-STEAP-1 antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 46. In certain embodiments, a VH sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 46. In certain embodiments, a total of 1 to 5 amino acids have been substituted, inserted and/or deleted in SEQ ID NO: 46. In certain embodiments, substitutions, insertions, or deletions occur in regions outside the HVRs (i.e., in the FRs). Optionally, the anti-STEAP-1 antibody comprises the VH sequence of SEQ ID NO: 46, including post-translational modifications of that sequence. In a particular embodiment, the VH comprises one, two or three HVRs selected from: (a) HVR-H1 comprising the amino acid sequence of SEQ ID NO: 40, (b) HVR-H2 comprising the amino acid sequence of SEQ ID NO: 41, and (c) HVR-H3 comprising the amino acid sequence of SEQ ID NO: 42.

In another aspect, an anti-STEAP-1 antibody of an a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 47. In certain embodiments, a VL sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 47 In certain embodiments, a total of 1 to 5 amino acids have been substituted, inserted and/or deleted in SEQ ID NO: 47. In certain embodiments, the substitutions, insertions, or deletions occur in regions outside the HVRs (i.e., in the FRs). Optionally, the anti-STEAP-1 antibody comprises the VL sequence of SEQ ID NO: 47, including post-translational modifications of that sequence. In a particular embodiment, the VL comprises one, two or three HVRs selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, a Ab-CIDE comprising an anti-STEAP-1 antibody is provided, wherein the antibody comprises a VH as in any of the embodiments provided above, and a VL as in any of the embodiments provided above.

In one embodiment, a Ab-CIDE is provided, wherein the antibody comprises the VH and VL sequences in SEQ ID NO: 46 and SEQ ID NO: 47, respectively, including post-translational modifications of those sequences.

In a further aspect, provided herein are Ab-CIDEs comprising antibodies that bind to the same epitope as an anti-STEAP-1 antibody provided herein. For example, in certain embodiments, a Ab-CIDE is provided comprising an antibody that binds to the same epitope as an anti-STEAP-1 antibody comprising a VH sequence of SEQ ID NO: 46 and a VL sequence of SEQ ID NO: 47, respectively.

In a further aspect, an anti-STEAP-1 antibody of a Ab-CIDE according to any of the above embodiments is a monoclonal antibody, including a human antibody. In one embodiment, an anti-STEAP-1 antibody of a Ab-CIDE is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

Anti-NaPi2b Antibodies

In certain embodiments, a Ab-CIDE comprises anti-NaPi2b antibodies.

In some embodiments, described herein are Ab-CIDEs comprising an anti-NaPi2b antibody comprising at least one, two, three, four, five, or six HVRs selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52 and (f) HVR-L3 comprising the amino acid sequence of SEQ ID NO: 53.

In one aspect, described herein are Ab-CIDEs comprising an antibody that comprises at least one, at least two, or all three VH HVR sequences selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50. In a further embodiment, the antibody comprises (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50.

In another aspect, described herein are Ab-CIDEs comprising an antibody that comprises at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 48, (ii) HVR-H2 comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, described herein are Ab-CIDEs comprising an antibody that comprises (a) HVR-H1 comprising the amino acid sequence of SEQ ID NO: 48 (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In any of the above embodiments, an anti-NaPi2b antibody of a Ab-CIDE is humanized. In one embodiment, an anti-NaPi2b antibody comprises HVRs as in any of the above embodiments, and further comprises a human acceptor framework, e.g. a human immunoglobulin framework or a human consensus framework.

In another aspect, an anti-NaPi2b antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 54. In certain embodiments, a VH sequence having at least 90%, 91%, 92%, 93%, 94%, 95%, 96%, 97%, 98%, or 99% identity to the amino acid sequence of SEQ ID NO: 54 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO: 54. In certain embodiments, a total of 1 to 5 amino acids have been substituted, inserted and/or deleted in SEQ ID NO: 54. In certain embodiments, substitutions, insertions, or deletions occur in regions outside the HVRs (i.e., in the FRs). Optionally, the anti-NaPi2b antibody comprises the VH sequence of SEQ ID NO: 54, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-NaPi2b antibody of a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, or 99% identity to the amino acid sequence of SEQ ID NO: 55 contains substitutions (e.g., conservative substitutions), insertions, or deletions relative to the reference sequence, but an anti-NaPi2b antibody comprising that sequence retains the ability to bind to anti-NaPi2b. In certain embodiments, a total of 1 to 10 amino acids have been substituted, inserted and/or deleted in SEQ ID NO: 55. In certain embodiments, a total of 1 to 5 amino acids have been substituted, inserted and/or deleted in SEQ ID NO: 55. In certain embodiments, the substitutions, insertions, or deletions occur in regions outside the HVRs (i.e., in the FRs). Optionally, the anti-NaPi2b antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, a Ab-CIDE comprising an anti-NaPi2b antibody is provided, wherein the antibody comprises a VH as in any of the embodiments provided above, and a VL as in any of the embodiments provided above.

In one embodiment, a Ab-CIDE is provided, wherein the antibody comprises the VH and VL sequences in SEQ ID NO: 54 and SEQ ID NO: 55, respectively, including post-translational modifications of those sequences.

In a further aspect, provided herein are Ab-CIDEs comprising antibodies that bind to the same epitope as an anti-NaPi2b antibody provided herein. For example, in certain embodiments, a Ab-CIDE is provided comprising an antibody that binds to the same epitope as an anti-NaPi2b antibody comprising a VH sequence of SEQ ID NO: 54 and a VL sequence of SEQ ID NO: 55, respectively.

In a further aspect, an anti-NaPi2b antibody of a Ab-CIDE according to any of the above embodiments is a monoclonal antibody, including a human antibody. In one embodiment, an anti-NaPi2b antibody of a Ab-CIDE is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

Anti-CD79b Antibodies

In certain embodiments, Ab-CIDEs comprise anti-CD79b antibodies.

In some embodiments, described herein are Ab-CIDEs comprising an anti-CD79b antibody comprising at least one, two, three, four, five, or six HVRs selected from (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, described herein are Ab-CIDEs comprising an antibody that comprises at least one, at least two, or all three VH HVR sequences selected from (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60. In a further embodiment, the antibody comprises (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60.

In another aspect, described herein are Ab-CIDEs comprising an antibody that comprises at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, a Ab-CIDE comprises an antibody comprising (a) a VH domain comprising at least one, at least two, or all three VH HVR sequences selected from (i) HVR-H1 comprising the amino acid sequence of SEQ ID NO: 58, (ii) HVR-H2 comprising the amino acid sequence of SEQ ID NO: 59, and (iii) HVR-H3 comprising an amino acid sequence selected from SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (c) HVR-L3 comprising the amino acid sequence of SEQ ID NO: 63.

In another aspect, described herein are Ab-CIDEs comprising an antibody that comprises (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In any of the above embodiments, an anti-CD79b antibody of a Ab-CIDE is humanized. In one embodiment, an anti-CD79b antibody comprises HVRs as in any of the above embodiments, and further comprises a human acceptor framework, e.g. a human immunoglobulin framework or a human consensus framework.

In another aspect, an anti-CD79b antibody of a Ab-CIDE comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 56. In certain embodiments, a VH sequence having at least 90%, 91%, 92%, 93%, 94%, 95%, 96%, 97%, 98%, or 99% identity to the amino acid sequence of SEQ ID NO: 56 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 56. In certain embodiments, a total of 1 to 5 amino acids have been substituted, inserted and/or deleted in SEQ ID NO: 56. In certain embodiments, substitutions, insertions, or deletions occur in regions outside the HVRs (i.e., in the FRs). Optionally, the anti-CD79b antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 58, (b) HVR-H2 comprising the amino acid sequence of SEQ ID NO: 59, and (c) HVR-H3 comprising the amino acid sequence of SEQ ID NO: 60.

In another aspect, an anti-CD79b antibody of a Ab-CIDE is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, or 99% identity to the amino acid sequence of SEQ ID NO: 57 contains substitutions (e.g., conservative substitutions), insertions, or deletions relative to the reference sequence, but an anti-Ly6E antibody comprising that sequence retains the ability to bind to CD79b. In certain embodiments, a total of 1 to 10 amino acids have been substituted, inserted and/or deleted in SEQ ID NO: 57. In certain embodiments, a total of 1 to 5 amino acids have been substituted, inserted and/or deleted in SEQ ID NO: 57. In certain embodiments, the substitutions, insertions, or deletions occur in regions outside the HVRs (i.e., in the FRs). Optionally, the anti-CD79b antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, described herein are Ab-CIDEs comprising an anti-CD79b antibody is provided, wherein the antibody comprises a VH as in any of the embodiments provided above, and a VL as in any of the embodiments provided above.

In one embodiment, a Ab-CIDE is provided, wherein the antibody comprises the VH and VL sequences in SEQ ID NO: 56 and SEQ ID NO: 57, respectively, including post-translational modifications of those sequences.

In a further aspect, provided herein are Ab-CIDEs comprising antibodies that bind to the same epitope as an anti-CD79b antibody provided herein. For example, in certain embodiments, a Ab-CIDE is provided comprising an antibody that binds to the same epitope as an anti-CD79b antibody comprising a VH sequence of SEQ ID NO: 56 and a VL sequence of SEQ ID NO: 57, respectively.

In a further aspect, an anti-CD79b antibody of a Ab-CIDE according to any of the above embodiments is a monoclonal antibody, including a human antibody. In one embodiment, an anti-CD79b antibody of a Ab-CIDE is an antibody fragment, e.g., a Fv, Fab, Fab', scFv, diabody, or $F(ab')_2$ fragment. In another embodiment, the antibody is a substantially full length antibody, e.g., an IgG1 antibody, IgG2a antibody or other antibody class or isotype as defined herein.

Anti-CD22 Antibodies

In certain embodiments, a Ab-CIDE can comprise anti-CD22 antibodies, which comprise three light chain hypervariable regions (HVR-L1, HVR-L2 and HVR-L3) and three heavy chain hypervariable regions (HVR-H1, HVR-H2 and HVR-H3). In one embodiment, the anti-CD22 antibody of a Ab-CIDE comprises three light chain hypervariable regions and three heavy chain hypervariable regions (SEQ ID NO: 66-71), the sequences of which are shown below. In one embodiment, the anti-CD22 antibody of a Ab-CIDE comprises the variable light chain sequence of SEQ ID NO: 72 and the variable heavy chain sequence of SEQ ID NO: 73. In one embodiment, the anti-CD22 antibody of Ab-CIDEs of the present invention comprises the light chain sequence of SEQ ID NO: 74 and the heavy chain sequence of SEQ ID NO: 75:

Anti-CD33 Antibodies

In certain embodiments, a Ab-CIDE can comprise anti-CD33 antibodies, which comprise three light chain hypervariable regions and three heavy chain hypervariable regions, the sequences (SEQ ID NO:76-81) of which are shown below. In one embodiment, the anti-CD33 antibody of a Ab-CIDE comprises the variable light chain sequence of SEQ ID NO: 82 and the variable heavy chain sequence of SEQ ID NO: 83.

In one embodiment, the anti-CD33 antibody of a Ab-CIDE comprises the light chain sequence of SEQ ID NO: 84 and the heavy chain sequence of SEQ ID NO: 85. In one embodiment, the anti-CD33 antibody of a Ab-CIDE comprises three light chain hypervariable regions and three heavy chain hypervariable regions, the sequences (Seq ID NO: 84-89) of which are shown below. In one embodiment, the anti-CD33 antibody of a Ab-CIDE comprises the variable light chain sequence of SEQ ID NO: 90 and the variable heavy chain sequence of SEQ ID NO: 91. In one embodiment, the anti-CD33 antibody of Ab-CIDE comprises the variable light chain sequence of SEQ ID NO: 92 and the variable heavy chain sequence of SEQ ID NO: 93. In one embodiment, the anti-CD33 antibody of the present invention comprises the variable light chain sequence of SEQ ID NO: 94 and the variable heavy chain sequence of SEQ ID NO: 95. In one embodiment, the anti-CD33 antibody of the present invention comprises the variable light chain sequence of SEQ ID NO: 96 and the variable heavy chain sequence of SEQ ID NO: 97.

1. Antibody Affinity

In certain embodiments, an antibody provided herein has a dissociation constant (Kd) of ≤1 μM, ≤100 nM, ≤50 nM, ≤10 nM, ≤5 nM, ≤1 nM, ≤0.1 nM, ≤0.1 nM, or ≤0.001 nM, and optionally is $\geq 10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 l/well of scintillant (MICROSCINT-20 m; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 l/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Linkers (L1)

As described herein, a "linker" (L1, Linker-1) is a bifunctional or multifunctional moiety that can be used to link one or more CIDE moieties (D) to an antibody (Ab) to form a Ab-CIDE. In some embodiments, Ab-CIDEs can be prepared using a L1 having reactive functionalities for covalently attaching to the CIDE and to the antibody. For example, in some embodiments, a cysteine thiol of an antibody (Ab) can form a bond with a reactive functional group of a linker or a linker L1-CIDE group to make a Ab-CIDE. Particularly, the chemical structure of the linker can have significant impact on both the efficacy and the safety of a Ab-CIDE (Ducry & Stump, *Bioconjugate Chem,* 2010, 21, 5-13). Choosing the right linker influences proper drug delivery to the intended cellular compartment of target cells.

Linkers can be generally divided into two categories: cleavable (such as peptide, hydrzone, or disulfide) or non-cleavable (such as thioether). If a linker is a non-cleavable linker, then its position on the E3LB portion is such that it does not interfere with VHL binding. Specifically, the non-cleavable linker is not to be covalently linked at the hydroxyl position on the proline of the VHL-binding domain. Peptide linkers, such as Valine-Citrulline (Val-Cit), that can be hydrolyzed by lysosomal enzymes (such as Cathepsin B) have been used to connect the drug with the antibody (U.S. Pat. No. 6,214,345). They have been particularly useful, due in part to their relative stability in systemic circulation and the ability to efficiently release the drug in tumor. However, the chemical space represented by natural peptides is limited; therefore, it is desirable to have a variety of non-peptide linkers which act like peptides and can be effectively cleaved by lysosomal proteases. The greater diversity of non-peptide structures may yield novel, beneficial properties that are not afforded by the peptide linkers. Provided herein are different types of non-peptide linkers for linker L1 that can be cleaved by lysosomal enzymes.

a. Peptidomimetic Linkers

Provided herein are different types of non-peptide, peptidomimetic linkers for Ab-CIDE that are cleavable by lysosomal enzymes. For example, the amide bond in the middle of a dipeptide (e.g. Val-Cit) was replaced with an amide mimic; and/or entire amino acid (e.g., valine amino acid in Val-Cit dipeptide) was replaced with a non-amino acid moiety (e.g., cycloalkyl dicarbonyl structures (for example, ring size=4 or 5)).

When L1 is a peptidomimetic linker, it is represented by the following formula

-Str-(PM)-Sp, wherein:

Str is a stretcher unit covalently attached to Ab;

Sp is a bond or spacer unit covalently attached to a CIDE moiety; and

PM is a non-peptide chemical moiety selected from the group consisting of:

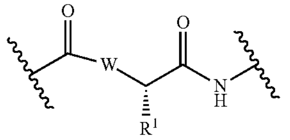

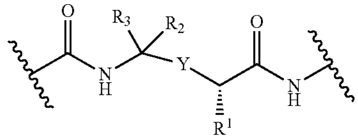

and

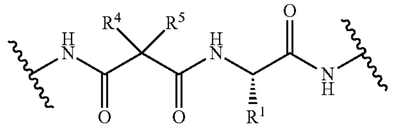

W is —NH-heterocycloalkyl- or heterocycloalkyl;

Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;

each $R^1$ is independently $C_1$-$C_{10}$alkyl, $C_1$-$C_{10}$alkenyl, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and $R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ may form a $C_3$-$C_7$cycloalkyl ring.

It is noted that L1 may be connected to the CIDE through any of the E3LB, L2, or PB groups.

In embodiments, Y is heteroaryl; $R^4$ and $R^5$ together form a cyclobutyl ring.

In embodiments, Y is a moiety selected from the group consisting of:

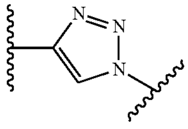

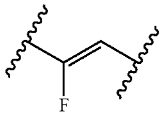

AND

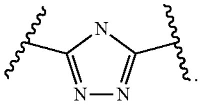

.

In embodiments, Str is a chemical moiety represented by the following formula:

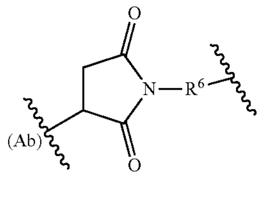

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl; Sp is —Ar—$R^b$—, wherein Ar is aryl or heteroaryl, $R^b$ is ($C_1$-$C_{10}$alkylene) O—.

In embodiments, Str has the formula:

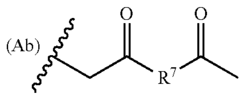

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) and N($R^c$)—($C_2$-$C_6$alkylene); where each $R^c$ is independently H or $C_1$-$C_6$ alkyl; Sp is —Ar—$R^b$—, wherein Ar is aryl or heteroaryl, $R^b$ is ($C_1$-$C_{10}$alkylene)O— or Sp-$C_1$-$C_6$alkylene-C(O) NH—.

In embodiments, L1 is a non-peptide chemical moiety represented by the following formula

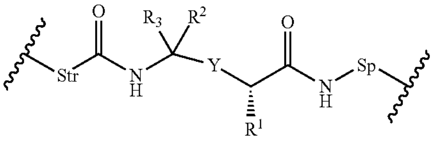

$R^1$ is $C_1$-$C_6$alkyl, $C_1$-$C_6$alkenyl, ($C_1$-$C_6$alkyl)NHC(NH) $NH_2$ or ($C_1$-$C_6$alkyl)NHC(O)$NH_2$;

$R^3$ and $R^2$ are each independently H or $C_1$-$C_{10}$alkyl.

In embodiments, L1 is a non-peptide chemical moiety represented by the following formula

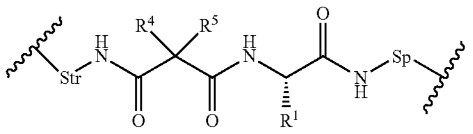

$R^1$ is $C_1$-$C_6$ alkyl, ($C_1$-$C_6$alkyl)NHC(NH)$NH_2$ or ($C_1$-$C_6$alkyl)NHC(O)$NH_2$;

$R^4$ and $R^5$ together form a $C_3$-$C_7$cycloalkyl ring.

In embodiments, L1 is a non-peptide chemical moiety represented by the following formula

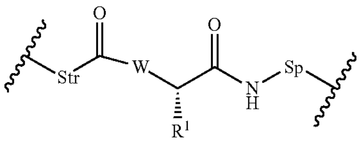

$R^1$ is $C_1$-$C_6$alkyl, ($C_1$-$C_6$alkyl)NHC(NH)$NH_2$ or ($C_1$-$C_6$alkyl)NHC(O)$NH_2$ and W is as defined above.

In some embodiments, the linker may be a peptidomimetic linker such as those described in WO2015/095227, WO2015/095124 or WO2015/095223.

In certain embodiments, the linker is selected from the group consisting of:

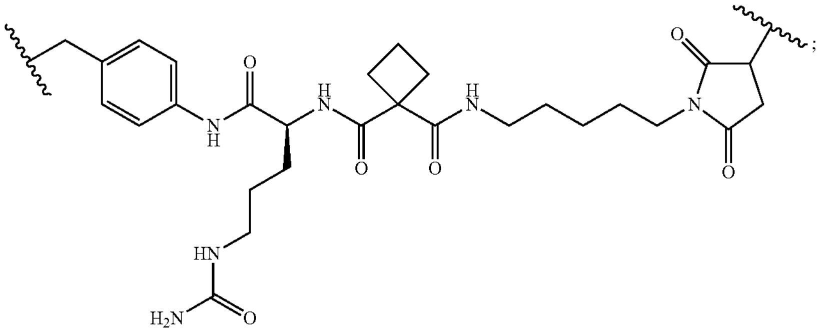

; and

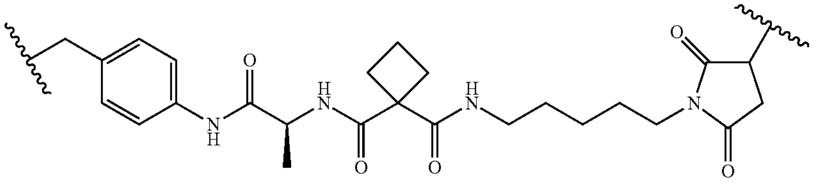

.

b. Non-Peptidomimetic Linkers

In an aspect, a Linker L1 forms a disulfide bond with the antibody. In an aspect, the linker has the structure:

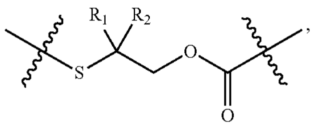

, or

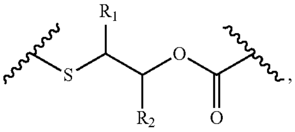

, wherein, $R^1$ and $R^2$ are independently selected from H and $C_1$-$C_6$ alkyl, or $R^1$ and $R^2$ form a 3, 4, 5, or 6-membered cycloalkyl or heterocyclyl group. The linker may be covalently bound to an antibody and a CIDE as follows:

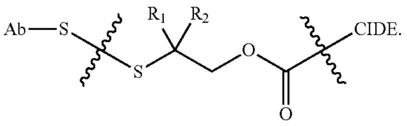

In an aspect, a Linker L1 forms a disulfide bond with the antibody, and the linker has the structure:

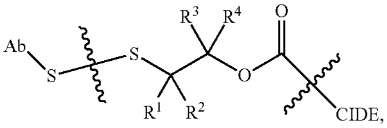

wherein $R^1$, $R^2$, $R^3$, and $R^4$ are independently selected from the group consisting of H, optionally substituted branched or linear $C_1$-$C_5$ alkyl, and optionally substituted $C_3$-$C_6$ cycloalkyl, or $R^1$ and $R^2$ taken together or $R^3$ and $R^4$ taken together with the carbon atom to which they are bound form a $C_3$-$C_6$ cycloalkyl ring.

In one aspect the carbonyl group of the linker is connected to an amine group in the CIDE. It is also noted that the sulfur atom connected to Ab is a sulfur group from a cysteine in the antibody. In another aspect, a linker L1 has a functionality that is capable of reacting with a free cysteine present on an antibody to form a covalent bond. Nonlimiting examples of such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Examples of such electrophilic groups include, but are not limited to, aldehyde and ketone carbonyl groups. In some embodiments, a heteroatom of the reactive functionality of the linker can react with an electrophilic group on an antibody and form a covalent bond to an antibody unit.

Nonlimiting examples of such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a CIDE. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., *Cancer Research* 52:127-131 (1992); U.S. Pat. No. 5,208,020).

In certain embodiments, a linker has the following Formula:

$$-A_a-W_w—Y_y—$$

wherein A is a "stretcher unit", and a is an integer from 0 to 1; W is an "amino acid unit", and w is an integer from 0 to 12; Y is a "spacer unit", and y is 0, 1, or 2. Exemplary embodiments of such linkers are described in U.S. Pat. No. 7,498,298.

In some embodiments, a linker component comprises a "stretcher unit" that links an antibody to another linker component or to a CIDE moiety. Nonlimiting exemplary stretcher units are shown below (wherein the wavy line indicates sites of covalent attachment to an antibody, CIDE, or additional linker components):

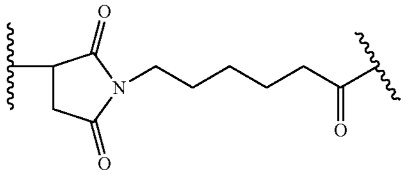

MC

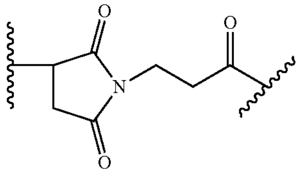

MP

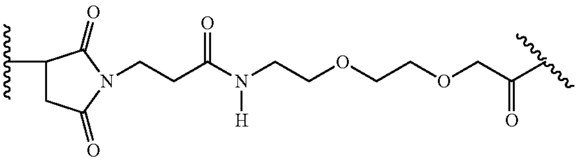

mPEG

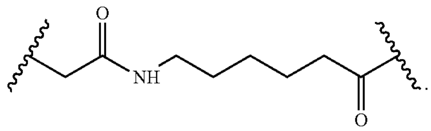

.

In certain embodiments, the linker is:

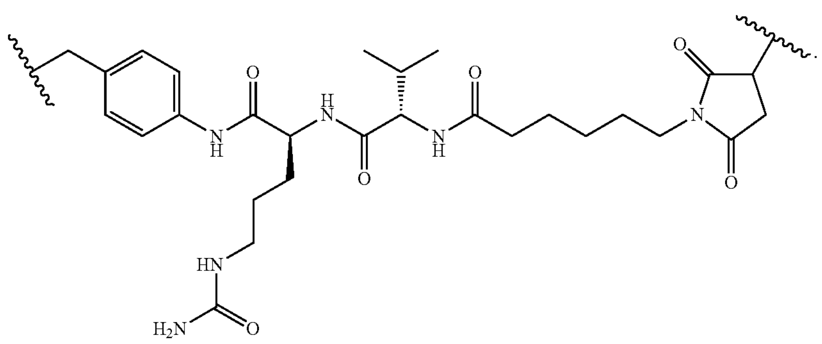 [SMILES: *Cc1ccc(NC(=O)[C@H](CCCNC(N)=O)NC(=O)[C@@H](NC(=O)CCCCCN2C(=O)CC(*)C2=O)C(C)C)cc1]

In certain embodiments, a linker has the following Formula:

$-A_a-Y_y-$ wherein A and Y are defined as above. In certain embodiments, the spacer unit Y may be a phosphate, such as a monophosphate or a bisphosphate. In certain embodiments, the stretcher component A comprises:

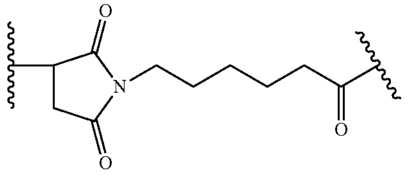

MC

In certain embodiments, the linker is:

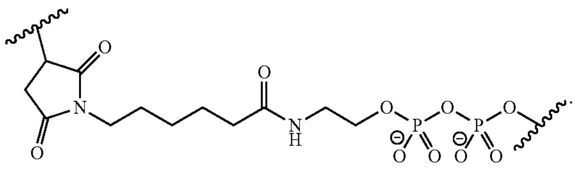 [SMILES: *OP(=O)([O-])OP(=O)([O-])OCCNC(=O)CCCCCN1C(=O)CC(*)C1=O]

3. CIDE ("D")

Useful CIDEs have the general formula described above. CIDEs include those having the Following Components.

a. E3 Ubiquitin Ligases Binding Groups (E3LB)

E3 ubiquitin ligases (of which over 600 are known in humans) confer substrate specificity for ubiquitination. There are known ligands which bind to these ligases. As described herein, an E3 ubiquitin ligase binding group is a peptide or small molecule that can bind an E3 ubiquitin ligase that is selected from the group consisting of von Hippel-Lindau (VHL) and XIAP.

A particular E3 ubiquitin ligase is von Hippel-Lindau (VHL) tumor suppressor, the substrate recognition subunit of the E3 ligase complex VCB, which also consists of elongins B and C, Cul2 and Rbxl. The primary substrate of VHL is Hypoxia Inducible Factor1α (HIF-lα), a transcription factor that upregulates genes such as the pro-angiogenic growth factor VEGF and the red blood cell inducing cytokine erythropoietin in response to low oxygen levels. Compounds that bind VHL may be hydroxyproline compounds such as those disclosed in WO2013/106643, WO2013/106646, and other compounds described in US2016/0045607, WO2014187777, US20140356322, and U.S. Pat. No. 9,249,153.

In one aspect, the subject matter herein is directed to compounds according to the chemical structure:

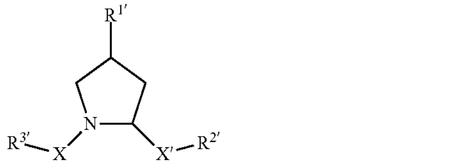

Where $R^{1'}$ is an optionally substituted $C_1$-$C_6$ alkyl group, an optionally substituted $-(CH_2)_nOH$, an optionally substituted $-(CH_2)_nSH$, an optionally substituted $(OH_2)_n-O-(C_1$-$C_6)$alkyl group, an optionally substituted $(CH_2)_n-WCOCW-(C_0$-$C_6)$alkyl group containing an epoxide moiety WCOCW where each W is independently H or a $C_1$-$C_3$ alkyl group, an optionally substituted $-(CH_2)_nCOOH$, an optionally substituted $-(CH_2)_nC(O)-(C_1$-$C_6$ alkyl), an optionally substituted $-(CH_2)_nNHC(O)-R_1$, an optionally substituted $-(CH_2)_nC(O)-NR_1R_2$, an optionally substituted $-(CH_2)_nOC(O)-NR_1R_2$, $-(CH_2O)_nH$, an optionally substituted $-(CH_2)_nOC(O)-(C_1$-$C_6$ alkyl), an optionally substituted $-(CH_2)_nC(O)-O-(C_1$-$C_6$ alkyl), an optionally substituted $-(CH_2O)_nCOOH$, an optionally substituted $-(OCH_2)_nO-(C_1$-$C_6$ alkyl), an optionally substituted $-(CH_2)_nC(O)-O-(C_1$-$C_6$ alkyl), an optionally substituted $-(OCH_2)_nNHC(O)-R_1$, an optionally substituted $-(CH_2O)_nC(O)-NR_1R_2$, $-(CH_2CH_2O)_nH$, an optionally substituted $-(CH_2CH_2O)_nCOOH$, an optionally substituted $-(OCH_2CH_2)_n(O-(C_1$-$C_6$ alkyl), an optionally substituted $-(CH_2CH_2O)$ $C(O)-(C_1$-$C_6$ alkyl), an optionally substituted $-(OCH_2CH_2)_nNHC(O)-R_1$, an optionally substituted $-(CH_2CH_2O)_nC(O)-NRiR_2$, an optionally substituted $-SO_2R_s$, an optionally substituted $S(O)R_s$, $NO_2$, CN or halogen (F, Cl, Br, I, preferably F or Cl);

$R^1$ and $R_2$ are each independently H or a $C_1$-$C_6$ alkyl group which may be optionally substituted with one or two hydroxyl groups or up to three halogen groups (preferably fluorine);

$R_s$ is a $C_1$-$C_6$ alkyl group, an optionally substituted aryl, heteroaryl or heterocycle group or a $-(CH_2)$ $NR_1R_2$ group;

X and X' are each independently C═O, O═S, —S(O), $S(O)_2$, (preferably X and X' are both C═O);

$R^{2'}$ is an optionally substituted $-(CH_2)_n-(C{=}O)_u(NR_1)_v(SO_2)_w$alkyl group, an optionally substituted $-(CH_2)_n-(C{=}O)_u(NR_1)_v(SO_2)_wNR_1NR_2N$ group, an optionally substituted $-(CH_2)_n-(C{=}O)_u(NR_1)_v(SO_2)_w$-Aryl, an optionally substituted $-(CH_2)_n-(C{=}O)_u(NR_1)_v(SO_2)_w$-Heteroaryl, an optionally substituted $-(CH_2)_n-(C{=}O)_vNR_1(SO_2)_w$-Heterocycle, an optionally substituted $-NR^Z-(CH_2)_n-C(O)_u(NR_1)_v(SO_2)_w$-alkyl, an optionally substituted $-NR^Z-(CH_2)_n-C(O)_u(NR_1)_v(SO_2)_w-NR_{1N}NR_{2N}$, an optionally substituted $-NR^Z-(CH_2)_n-C(O)_u(NR_1)_v(SO_2)_w-NR_1C(O)R_{1N}$, an optionally substituted $-NR^Z-(CH_2)_n-(C{=}O)_u(NR_1)_v(SO_2)_w$-Aryl, an optionally substituted $-NR^Z-(CH_2)_n-(C{=}O)_u(NR_1)_v(SO_2)_w$-Heteroaryl, an optionally substituted $-NR^Z-(CH_2)_n-(C{=}O)_vNR_1(SO_2)_w$-Heterocycle, an optionally substituted $-X^{R2'}$-alkyl group, an optionally substituted $-X^{R2'}$-Aryl group, an optionally substituted $-X^{R2'}$-Heteroaryl group, an optionally substituted $-X^{R2'}$-Heterocycle group, $R^{3'}$ is an optionally substituted alkyl, an optionally substituted $-(CH_2)_n-C(O)_u(NR_1)_v(SO_2)_w$-alkyl, an optionally substituted $-(CH_2)_n-C(O)_u(NR_1)_v(SO_2)_w-NR_{1N}R_{2N}$, an optionally substituted $-(CH_2)_n-C(O)_u(NR_1)_v(SO_2)_w-NR_1C(O)R_{1N}$, an optionally substituted $-(CH_2)_n-C(O)_u(NR_1)_v(SO_2)_w-C(O)NR_1R_2$, an optionally substituted $-(CH_2)_n-C(O)_u(NR_1)_v(SO_2)_w$-Aryl, an optionally substituted $-(CH_2)_n-C(O)_u(NR_1)_v(SO_2)_w$-Heteroaryl, an optionally substituted $-(CH_2)_n-C(O)_u(NR_1)_v(SO_2)_w$-Heterocycle, an optionally substituted $-NR^Z-(CH_2)_n-C(O)_u(NR_1)_v(SO_2)_w$-alkyl, an optionally substituted $-NR^Z-(CH_2)_n-C(O)_u(NR_1)_v(SO_2)_w-NR_{1N}R_{2N}$, an optionally substituted $-NR^Z-(CH_2)_n-C(O)_u(NR_1)_v(SO_2)_w-NR_1C(O)R_{1N}$, an optionally substituted $-NR^Z-(CH_2)_n-C(O)_u(NR_1)_v(SO_2)_w$-Aryl, an optionally substituted $-NR^Z-(CH_2)_n-C(O)_u(NR_1)_v(SO_2)_w$-Heteroaryl, an optionally substituted $-NR^Z-(CH_2)_n-C(O)_u(NR_1)_v(SO_2)_w$-Heterocycle, an optionally substituted $-O-(CH_2)_n-(C{=}O)_u(NR_1)_v(SO_2)_w$-alkyl, an optionally substituted $-O-(CH_2)_n-(C{=}O)_u(NR_1)_v(SO_2)_w-NR_{1N}R_{2N}$, an optionally substituted $-O-(CH_2)_n-(C{=}O)_u(NR_1)_v(SO_2)_w-NR_1C(O)R_{1N}$, an optionally substituted $-O-(CH_2)_n-(C{=}O)_u(NR_1)_v(SO_2)_w$-Aryl, an optionally substituted $-O-(CH_2)_n-(C{=}O)_u(NR_1)(SO_2)_w$-Heteroaryl, an optionally substituted $-O-(CH_2)_n-(C{=}O)_u(NR_1)(SO_2)_w$-Heterocycle, an optionally substituted $-(CH_2)_n-(V)_{n'}-(CH_2)_n-(V)_{n'}$-alkyl group, an optionally substituted $-(CH_2)_n-(V)_{n'}-(CH_2)_n-(V)_{n'}$-Aryl group, an optionally substituted $-(CH_2)_n-(V)_{n'}-(CH_2)_n-(V)_{n'}$-Heteroaryl group, an optionally substituted $-(CH_2)_n-(V)_{n'}-(CH_2)_n-(V)_{n'}$-Heterocycle group, an optionally substituted $-(CH_2)_n-N(R_{1'})(C{=}O)_{m'}-(V)_{n'}$-alkyl group, an optionally substituted $-(CH_2)_n-N(R_{1'})(C{=}O)_{m'}-(V)_{n'}$-Aryl group, an optionally substituted $-(CH_2)_n-N(R_{1'})(C{=}O)_{m'}-(V)_{n'}$-Heteroaryl group, an optionally substituted $-(CH_2)_n-N(R_{1'})(C{=}O)_{m'}-(V)_{n'}$-Heterocycle group, an optionally substituted $-X^{R3'}$-alkyl group, an optionally substituted $-X^{R3'}$-Aryl group, an optionally substituted $-X^{R3'}$-Heteroaryl group, an optionally substituted $-X^{R3'}$-Heterocycle group, an optionally substituted Where $R_{1N}$ and $R_{2N}$ are each independently H, $C_1$-$C_6$ alkyl which is optionally substituted with one or two hydroxyl groups and up to three halogen groups or an optionally substituted $-(CH_2)_n$-Aryl, $-(CH_2)_n$-Heteroaryl or $-(CH_2)_n$-Heterocycle group;

$R^Z$ and $R_1$ are each independently H or a $C_1$-$C_3$ alkyl group;

V is O, S or $NR_1$;

$R_1$ is the same as above;

$X^{R2'}$ and $X^{R3'}$ are each independently an optionally substituted $-CH_2)_n-$, $-CH_2)_n-CH(X_V){=}CH(X_V)-$ (cis or trans), $-CH_2)_n-CH{\equiv}CH-$, $-(CH_2CH_2O)_n-$ or a $C_3$-$C_6$ cycloalkyl group, where $X_v$ is H, a halo or a $C_1$-$C_3$ alkyl group which is optionally substituted;

Each m is independently 0, 1, 2, 3, 4, 5, 6;

Each m' is independently 0 or 1;

Each n is independently 0, 1, 2, 3, 4, 5, 6;

Each n' is independently 0 or 1;

Each u is independently 0 or 1;

Each v is independently 0 or 1;

Each w is independently 0 or 1, or

A pharmaceutically acceptable salt, enantiomer, diastereomer, solvate or polymorph thereof.

In alternative aspects, the present invention relates to compounds according to the chemical structure:

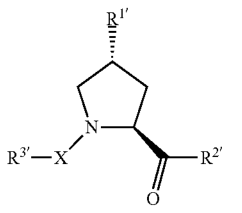

wherein each of $R^{1'}$, $R^{2'}$ and $R^{3'}$ are the same as above and X is C═O, C═S, —S(O) group or a $S(O)_2$ group, more preferably a C═O group, or a pharmaceutically acceptable salt, enantiomer, diastereomer, solvate or polymorph thereof.

In still further preferred aspects of the invention, compounds according to the present invention

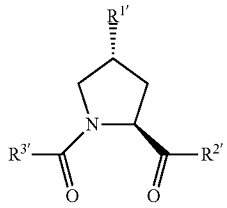

where $R^{1'}$, $R^{2'}$ and $R^{3'}$ are the same as presented above, or a pharmaceutically acceptable enantiomer, diastereomer, solvate or polymorph thereof.

In further preferred aspects of the invention, $R^{1'}$ is preferably a hydroxyl group or a group which may be metabolized to a hydroxyl or carboxylic group, preferably a hydroxyl group, such that the compound represents a prodrug form of an active compound. Exemplary preferred $R^{1'}$ groups include, for example, $-(CH_2)_nOH$, $(CH_2)_n-O-(C_1-C_6)$alkyl group, $-(CH_2)_nCOOH$, $-(CH_2O)_nH$, an optionally substituted $-(CH_2)_nC(O)(C_0-C_6)$alkyl, an optionally substituted $-(CH_2)_nOC(O)-(C_1C_6)$alkyl, or an optionally substituted $-(CH_2)_nC(O)-O-(C_1-C_6)$alkyl, wherein n is 0 or 1. Most often, $R^1$ is hydroxyl.

X and X', where present, are preferably a C═O, C═S, —S(O) group or a $S(O)_2$ group, more preferably a C═O group.

R 2' is preferably an optionally substituted $-NR_1$-T-Aryl, an optionally substituted $-NR_1$-T-Heteroaryl group or an optionally substituted $-NR_1$-T-Heterocycle, where $R^1$ is a $C_1-C_3$ alkyl group, preferably H or $CH_3$, more preferably H and T is an optionally substituted $-(CH_2)_n-$ group, wherein each one of the methylene groups within the alkylene chain may be optionally substituted with one or two substituents, preferably selected from halogen, a $C_1-C_3$ alkyl group or a side chain of an amino acid as otherwise described herein, preferably one or two methyl groups, which may be optionally substituted; and n is 0 to 6, often 0, 1, 2 or 3, preferably 0 or 1. Alternatively, T may also be a $-(CH_2O)_n-$ group, a $-(OCH_2)_n-$ group, a $-(CH_2CH_2O)_n-$ group, a $-(OCH_2CH_2)_n-$ group, all of which groups are optionally substituted.

Preferred Aryl groups for $R^{2'}$ include optionally substituted phenyl or naphthyl groups, preferably phenyl groups, wherein the phenyl group is optionally substituted with a halogen (preferably F or Cl), an amine, monoalkyl- or dialkyl amine (preferably, dimethylamine), F, Cl, OH, SH, COOH, $C_1-C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with at least one of F, Cl, OH, SH, COOH, $CH_3$, $CF_3$, OMe, $OCF_3$, $NO_2$, or CN group, which may be substituted in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

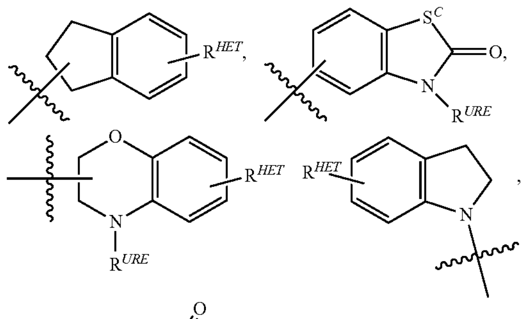

,

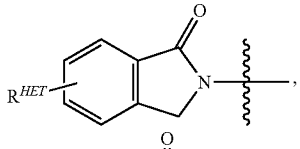

,

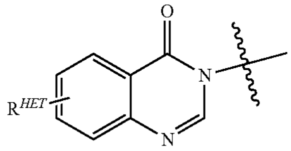

or

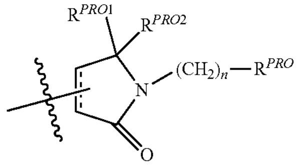

Where $S^c$ is $CHR^{SS}$, $NR^{URE}$, or O;

$R^{HET}$ is H, CN, $NO_2$, halo (preferably Cl or F), optionally substituted $C_1-C_6$ alkyl (preferably substituted with one or two hydroxyl groups or up to three halo groups (e.g. $CF_3$), optionally substituted $O(C_1-C_6alkyl)$ (preferably substituted with one or two hydroxyl groups or up to three halo groups) or an optionally substituted acetylenic group —C≡C—$R_a$ where $R_a$ is H or a $C_1-C_6$ alkyl group (preferably C1-C3 alkyl);

$R^{SS}$ is H, CN, $NO_2$, halo (preferably F or Cl), optionally substituted $C_1-C_6$ alkyl (preferably substituted with one or two hydroxyl groups or up to three halo groups), optionally substituted O—($C_1-C_6$ alkyl) (preferably substituted with one or two hydroxyl groups or up to three halo groups) or an optionally substituted —C(O)($C_1-C_6$ alkyl) (preferably substituted with one or two hydroxyl groups or up to three halo groups);

$R^{URE}$ is H, a $C_1-C_6$ alkyl (preferably H or $C_1-C_3$ alkyl) or a $-C(O)(C_1C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran, among others);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl).

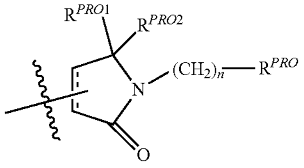

In certain preferred aspects, is a

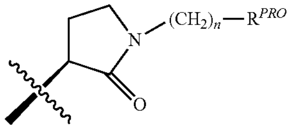

or

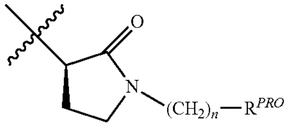

group, where $R^{PRO}$ and n are the same as above.

Preferred heteroaryl groups for $R^{2'}$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

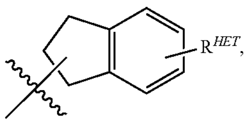

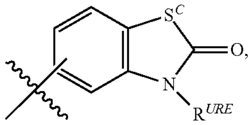

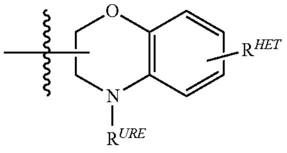

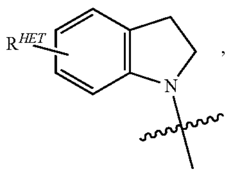

,

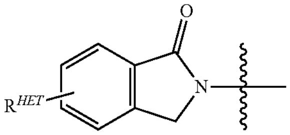

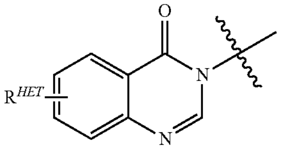

or

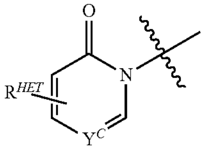

Where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^c$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

Preferred heterocycle groups for $R^{2'}$ include tetrahydroquinoline, piperidine, piperazine, pyrrollidine, morpholine, tetrahydrofuran, tetrahydrothiophene, oxane, thiane, each of which groups may be optionally substituted, or a group according to the chemical structure:

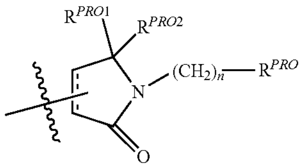

or

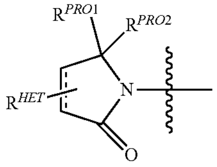

Preferably, a

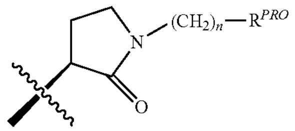

or

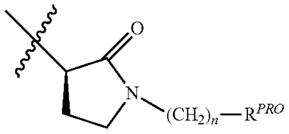

group,

Where $R^{PRO}$ is H, optionally substituted $C_1$-$C_6$ alkyl or an optionally substituted aryl, heteroaryl or heterocyclic group; $R^{PRO1}$ and $R^{PRO2}$ are each independently H, an optionally substituted $C_1$-$C_3$ alkyl group or together form a keto group and Each n is independently 0, 1, 2, 3, 4, 5, or 6 (preferably 0 or 1).

Preferred $R^{2'}$ substituents for use in the present invention also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^3$ is preferably an optionally substituted-T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle, where $R^1$ is a $C_1$-$C_3$ alkyl group, preferably H or $CH_3$, more preferably H, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3, preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ include optionally substituted phenyl or naphthyl groups (including tetrahydronaphthyl), preferably phenyl groups, wherein the phenyl or naphthyl group is optionally substituted with a halogen (preferably F or Cl), an amine, monoalkyl- or dialkyl amine (preferably, dimethylamine), an amido group (preferably a —$(CH_2)_m$—$NR_1C(O)R_2$ group, where m, $R_1$ and $R_2$ are the same as above), a halo (often F, Cl), OH, SH, $CH_3$, $CF_3$, OMe, $OCF_3$, $NO_2$, CN or a $S(O)_2R_s$ group ($R_s$ is a $C_1$-$C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, or CN group, which may be substituted in ortho-, meta- and/or para-positions of the phenyl ring, preferably para-), a naphthyl group, which may be optionally substituted, an optionally substituted heteroaryl, including an optionally substituted isoxazole including a methylsubstituted isoxazole, an optionally substituted oxazole including a methylsubstituted oxazole, an optionally substituted thiazole including a methyl substituted thiazole, an optionally substituted pyrrole, including a methylsubstituted pyrrole, an optionally substituted imidazole including a methylimidazole, an optionally substituted benzylimidazole or methoxybenzylimidazole, an optionally substituted oximidazole or methyloximidazole, an optionally substituted diazole group, including a methyldiazole group, an optionally substituted triazole group, including a methylsubstituted triazole group, a tetrazole group, an optionally substituted pyridine group, including a halo-(preferably, F) or methylsubstitutedpyridine group or an optionally substituted oxapyridine group (where the pyridine group is linked to the phenyl group by an oxygen) or an optionally substituted heterocycle (tetrahydrofuran, terahydrothiophene, pyrrolidine, piperidine, morpholine, piperazine, oxane, thiane or tetrahydroquinoline).

Preferred Heteroaryl groups for $R^{3'}$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

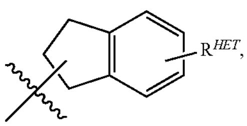

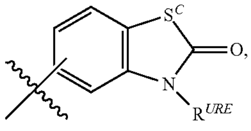

-continued

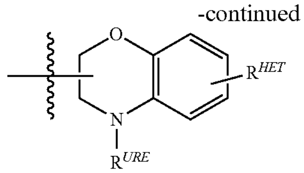

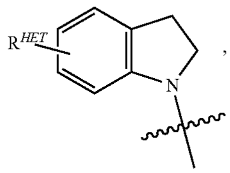

,

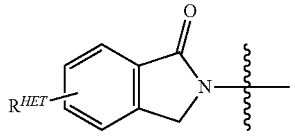

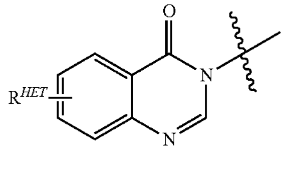

or

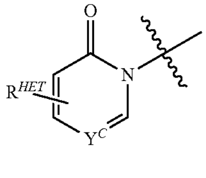

Where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)(C $C_1$-$C_6$ alkyl) (preferably substituted with one or two hydroxyl groups or up to three halo groups);

$R^{URE}$ is H, a C $C_1$-$C_6$ alkyl (preferably H or $C_1$-$C_3$ alkyl) or a —C(O)($C_1$.$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofurari, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

Preferred heterocycle groups for $R^{3'}$ include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

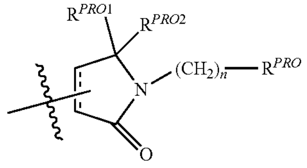

or

-continued

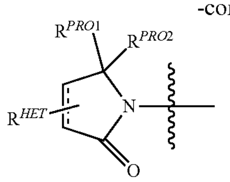

Preferably, a

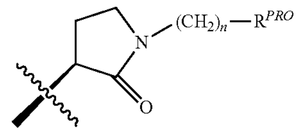

or

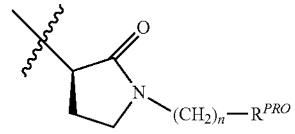

group, where $R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and Each n is 0, 1, 2, 3, 4, 5, or 6 (preferably 0 or 1).

Preferred $R^{3'}$ substituents for use in the present invention also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents which are also disclosed in the present specification, especially including the $R^{2'}$ groups which are presented in the attached figures hereof.

In certain alternative preferred embodiments, $R^{2'}$ is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, Where $R_1$ is H or a $C_1$-$C_3$ alkyl group (preferably H);

$X^{2'}$ is an optionally substituted —$CH_2)_n$—, —$CH_2)_n$—$CH(X_v)$=$CH(X_v)$— (cis or trans), —$CH_2)_n$—CH≡CH—, —$(CH_2CH_2O)_n$— or a $C_3$-$C_6$ cycloalkyl group;

where $X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br); Aryl is an optionally substituted phenyl or naphthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

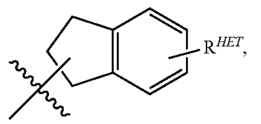
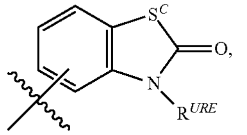
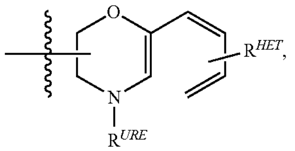
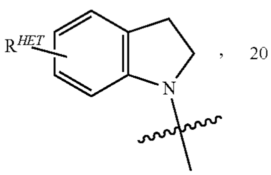
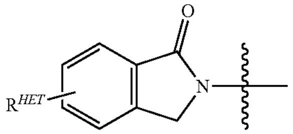
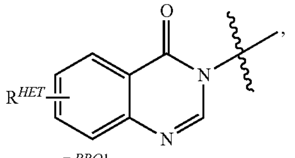
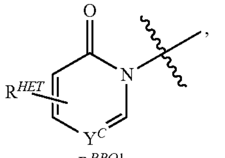
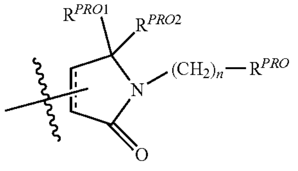
or
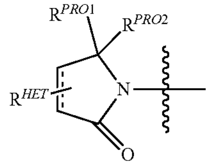

Where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and Each n is independently 0, 1, 2, 3, 4, 5, or 6 (preferably 0 or 1).

In certain alternative preferred embodiments of the present invention, $R^{3'}$ is an optionally substituted —$(CH_2)_n$—(V)n'—$(CH_2)$n—$(V)_{n'}$—$R^{S3}$ group, an optionally substituted —$(CH_2)_n$—$N(R_{1'})(C{=}O)_{m'}$—$(V)_{n'}$—$R^{S3'}$ group, an optionally substituted —$X^{R3'}$-alkyl group, an optionally substituted —$X^{R3'}$-Aryl group; an optionally substituted —$X^{R3}$-HET group, an optionally substituted —$X^{R3}$-Aryl-HET group or an optionally substituted —$X^{R3'}$-HET-Aryl group, Where $R^{S3'}$ is an optionally substituted alkyl group ($C_1$-$Q_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is —$(CH_2)_n$—, —$(CH_2CH_2O)_n$—, —$CH_2)_n$—CH$(X_v)$=CH$(X_v)$— (cis or trans), —$CH_2)_n$—CH≡CH—, or a $C_3$-$C_6$ cycloalkyl group, all optionally substituted;

where $X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br); Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydroiuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

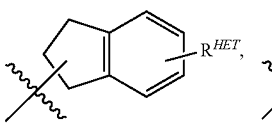
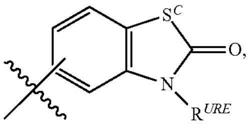

-continued

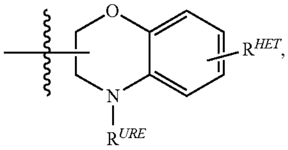
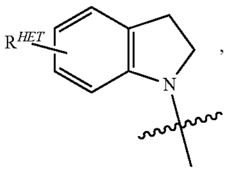
,

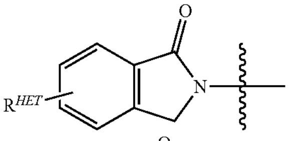

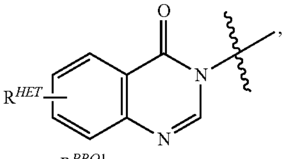
,
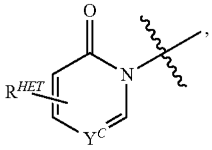
,

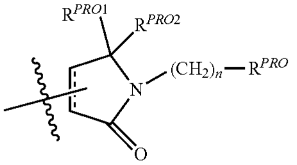
or
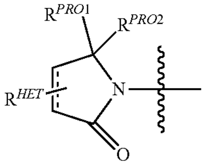

Where $S^c$ is $CHR^{SS}$, $NR^{URE}$, or O;

$R^{HET}$ is H, CN, $NO_2$, halo (preferably Cl or F), optionally substituted Q-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydirofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and Each n is independently 0, 1, 2, 3, 4, 5, or 6 (preferably 0 or 1);

Each m' is 0 or 1; and

Each n' is 0 or 1.

In alternative embodiments, $R^{3'}$ is —$(CH_2)_n$-Aryl, —$(CH_2CH_2O)_n$-Aryl, —$(CH_2)_n$-HET or —$(CH_2CH_2O)_n$-HET;

Where Aryl is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_n$O($C_1$-$C_6$) alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_m$—($C_1$-$C_6$)alkyl group, a —$(V)_m$—$(CH_2CH_2O)_n$—$R^{PEG}$ group where V is O, S or $NR_1$, $R_1$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

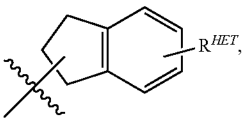
,
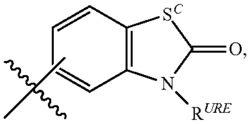
,
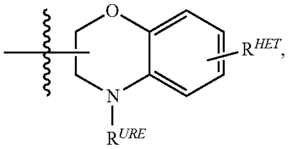
,
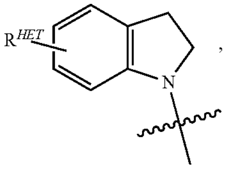
,
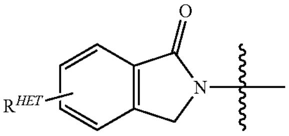

-continued

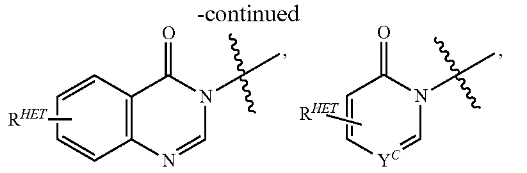

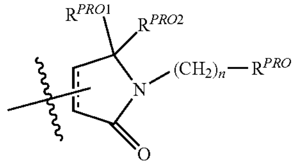

or

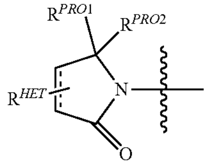

Where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a Ci-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group;

HET is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

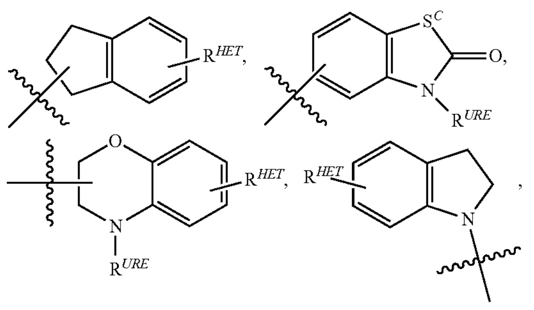

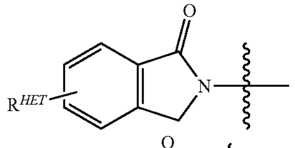

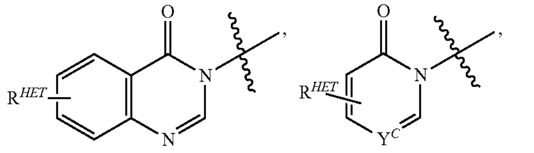

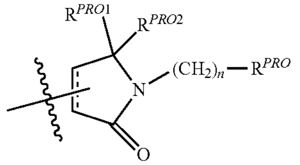

or

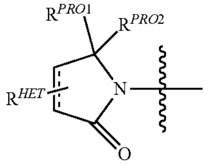

Where $S^c$ is $CHR^{SS}$, NR, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydroftiran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ is H, optionally substituted $C_1$-$C_6$ alkyl or an optionally substituted aryl, heteroaryl or heterocyclic group;

$R^{PRO1}$ and $R^{PRO2}$ are each independently H, an optionally substituted $C_1$-$C_3$ alkyl group or together form a keto group, Each m' is independently 0 or 1, and Each n is independently 0, 1, 2, 3, 4, 5, or 6 (preferably 0 or 1).

In still additional embodiments, preferred compounds include those according to the chemical structure:

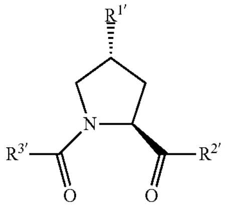

Where $R^{1'}$ is OH or a group which is metabolized in a patient or subject to OH;

$R^{2'}$ is a —NH—$CH_2$-Aryl-HET (preferably, a phenyl linked directly to a methyl substituted thiazole);

$R^{3'}$ is a —$CHR^{CR3'}$—NH—C(O)—$R^{3P1}$ group or a —$CHR^{CR3'}$—$R^{3P2}$ group;

Where $R^{CR3'}$ is a $C_1$-$C_4$ alkyl group, preferably methyl, isopropyl or tert-butyl;

$R^{3P1}$ is $C_1$-$C_3$ alkyl (preferably methyl), an optionally substituted oxetane group (preferably methyl substituted, a —$(CH_2)_nOCH_3$ group where n is 1 or 2 (preferably 2), or a

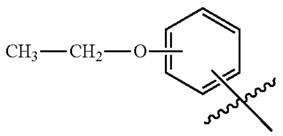

group (the etyl ether group is preferably meta-substituted on the phenyl moiety), a morpholino group (linked to the carbonyl at the 2- or 3-position);

$R^{3P2}$ is a 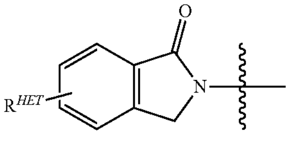

Where Aryl is phenyl;

HET is an optionally substituted thiazole or isothiazole; and $R^{HET}$ is H or a halo group (preferably H), Or a pharmaceutically acceptable salt, stereoisomer, solvate or polymorph thereof. Preferred compositions which pertain to this embodiment of the present application are presented in FIG. 17 hereof.

In another aspect, the compound according to the present invention is based upon an amino acid such as phenylanine as a portion (right hand) of the molecule according to the formula:

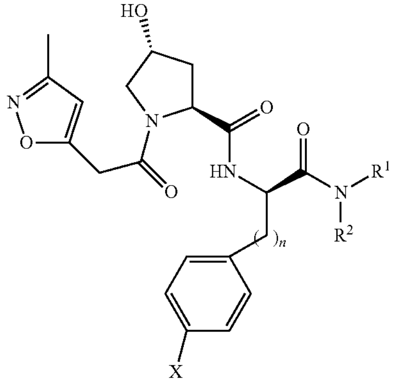

or

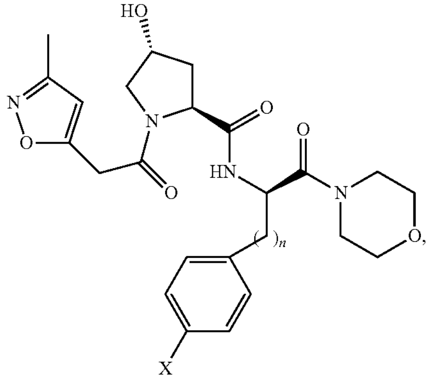

Where X is halogen, $C_1$-$C_3$ alkyl or an optionally substituted heterocycle; and $R^1$ and $R^2$ are each independently H, $C_1$-$C_3$ alkyl optionally substituted with one or two hydroxyl groups, or an optionally substituted phenyl group; and n is 0, 1, 2, or 3, preferably 0 or 1, or a pharmaceutically acceptable salt, enantiomer, diastereomer, solvate or polymorph thereof.

Preferably, the E3LB portion terminates in a —NHCOOH moeity that can be covalently linked to the L2 portion through an amide bond.

In certain embodiments, the E3LB residue is as disclosed in U.S. Patent Application Pub. No. 2019/0300521, which is hereby incorporated by reference in its entirety. The E3LB residue includes those having a structure of:

I-A

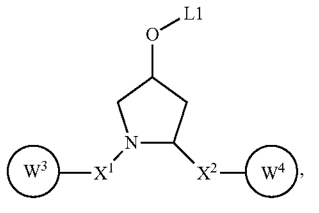

wherein,

L1 is selected from the group consisting of:

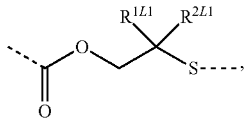

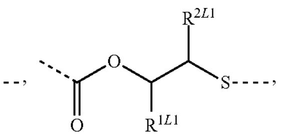

wherein, $R^{1L1}$ and $R^{2L1}$ are independently selected from H and $C_1$-$C_6$ alkyl, or $R^{1L1}$ and $R^{2L1}$ form a 3, 4, 5, or 6-membered cycloalkyl or heterocyclyl group; or is a peptidomimetic linker represented by the following formula:

Str-(PM)-Sp, wherein:

Str is a stretcher unit covalently attached to Ab;

Sp is a bond or spacer unit covalently attached to a CIDE moiety; and

PM is a non-peptide chemical moiety selected from the group consisting of:

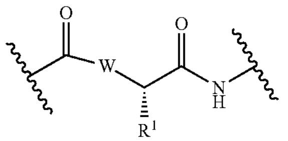

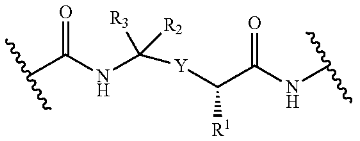

and

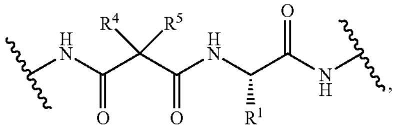

wherein

W is —NH-heterocycloalkyl- or heterocycloalkyl;

Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;

each $R^1$ is independently $C_1$-$C_{10}$alkyl, $C_1$-$C_{10}$alkenyl, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and $R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ may form a $C_3$-$C_7$cycloalkyl ring;

or a linker having the formula:

$-A_a-W_w—Y_y—$ wherein A is a stretcher unit, and a is an integer from 0 to 1; W is an amino acid unit, and w is an integer from 0 to 12; Y is a spacer unit, and y is 0, 1, or 2; or a linker having the formula:

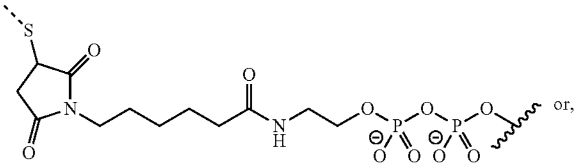

or,

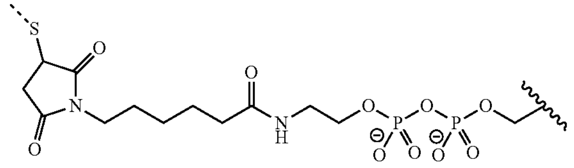

a dashed line indicates the attachment of at least one PB, another E3LB, or a chemical linker moiety coupling at least one PB, antibody, or another E3LB to the other end of the linker;

L1 is a linker as described elsewhere herein; or, in certain embodiments, L1 can be a linker as described elsewhere herein or a hydrogen, when a L1 group is covalently attached to the compound of Formulae I-A, I-B, I-C, I-D, I-E, I-F, I-G, I-H, I-I, I-J, I-K, I-L, I-M-, I-N, I-O, I-P, I-Q, I-R, and L-I, each of which is an E3LB residue, at another position, such as a phenyl ring as depicted in Table 1-L1.

$X^1$, $X^2$ of Formula I-A are each independently selected from the group of a bond, O, $NR^{Y3}$, $CR^{Y3}R^{Y4}$, C═O, C═S, SO, and $SO_2$;

$R^{Y3}$, $R^{Y4}$ of Formula I-A are each independently selected from the group of H, linear or branched $C_{1-6}$ alkyl, optionally substituted by 1 or more halo, optionally substituted $C_{1-6}$ alkoxyl;

$W^3$ of Formula I-A is selected from the group of an optionally substituted T, an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocyclyl, an optionally substituted -T-biheterocyclyl, an optionally substituted $NR^1$-T-Aryl, an optionally substituted $NR^1$-T-Heteroaryl or an optionally substituted $NR^1$-T-Heterocyclyl;

$X^3$ of Formula I-A is C═O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or OH groups, $R^{Y3}$C═O, $R^{Y3}$C═S, $R^{Y3}$SO, $R^{Y3}SO_2$, N($R^{Y3}R^{Y4}$)C═O, N($R^{Y3}R^{Y4}$)C═S, N($R^{Y3}R^{Y4}$)SO, and N($R^{Y3}R^{Y4}$)$SO_2$;

T of Formula I-A is selected from the group of an optionally substituted alkyl, $(CH_2)_n$— group, —$(CH_2)_n$—O—$C_1$-$C_6$ alkyl which is optionally substituted, linear, branched, or —$(CH_2)_n$—O-heterocyclyl which is optionally substituted, wherein each one of the methylene groups is optionally substituted with one or two substituents selected from the group of halogen, methyl, a linear or branched $C_1$-$C_6$ alkyl group optionally substituted by 1 or more halogen or OH groups, an amino acid side chain optionally substituted or an optionally substituted heterocyclyl; $W^4$ of Formula I-A is an optionally substituted —$NR_1$-T-Aryl wherein the aryl group may be optionally substituted with an optionally substituted 5-6 membered heteroaryl or an optionally substituted aryl, an optionally substituted —$NR_1$-T-Heteroaryl group, wherein the heteroaryl is optionally substituted with an optionally substituted aryl or an optionally substituted heteroaryl, or an optionally substituted —$NR_1$-T-Heterocyclyl, where —$NR_1$ is covalently bonded to $X^2$ and $R^1$ is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, optionally substituted alkoxy, a linear or branched $C_1$-$C_6$ alkyl group optionally substituted by 1 or more halogen, C(O) $NR^1R^{1a}$, or $NR^1R^{1a}$ or $R^1$ and $R^{1a}$ are joined to form an optionally substituted heterocyclyl, or —OH groups or an amino acid side chain optionally substituted; and n is 0 to 6, often 0, 1, 2, or 3, preferably 0 or 1.

In certain embodiments, $W^4$ of Formula I-A is

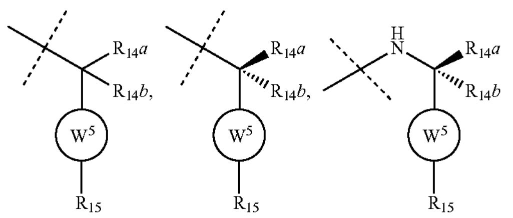

or

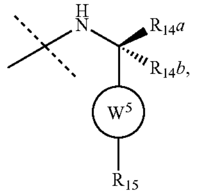

wherein $R_{14a}$, $R_{14b}$, are each independently selected from the group of H, haloalkyl (e.g., fluoroalkyl), optionally substituted alkyl, optionally substituted alkoxy, optionally substituted hydroxyl alkyl, optionally substituted alkylamine, optionally substituted heteroalkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine.

In any of the embodiments, $W^5$ of Formula I-A is selected from the group of an optionally substituted phenyl, an optionally substituted napthyl or an optionally substituted 5-10 membered heteroaryl, $R_{15}$ of Formula I-A is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}$ $SO_2R_{14b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, I-A, is optionally substituted by 0-$3R^P$ groups in the pyrrolidine moiety. Each $R^P$ is independently H, halo, —OH, $C_{1-3}$alkyl, C═O.

In any of the embodiments described herein, the $W^3$, $W^4$ of Formula I-A can independently be covalently coupled to a linker which is attached one or more PB groups.

and wherein the dashed line indicates the site of attachment of at least one PB, another E3LB or a chemical linker moiety coupling at least one PB to E3LB.

In certain embodiments, E3LB is represented by the structure:

I-B

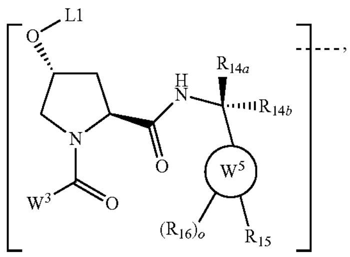

wherein:

$W^3$ of Formula I-B is selected from the group of an optionally substituted aryl, optionally substituted heteroaryl, or

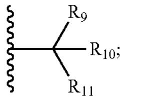

$R_9$ and $R_{10}$ of Formula I-B are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula I-B is selected from the group of an optionally substituted heterocyclyl, optionally substituted alkoxy, optionally substituted heteroaryl, optionally substituted aryl,

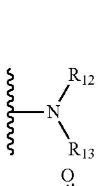

,

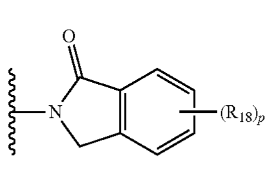

or

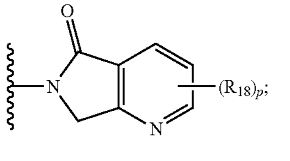

$R_{12}$ of Formula I-B is selected from the group of H or optionally substituted alkyl;

$R_{13}$ of Formula I-B is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula I-B, are each independently selected from the group of H, haloalkyl (e.g. fluoroalkyl), optionally substituted alkyl, optionally substitute alkoxy, aminomethyl, alkylaminomethyl, alkoxymethyl, optionally substituted hydroxyl alkyl, optionally substituted alkylamine, optionally substituted heteroalkyl, optionally substituted alkyl-heterocycloalkyl, optionally substituted alkoxy-heterocycloalkyl, $CONR_{27a}R_{27b}$, $CH_2NHCOR_{26}$, or $(CH_2)N(CH_3)COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$W^5$ of Formula I-B is selected from the group of a phenyl, napthyl, or a 5-10 membered heteroaryl, $R_{15}$ of Formula I-B is selected from the group of H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl;

each $R_{16}$ of Formula I-B is independently selected from the group of halo, CN, optionally substituted alkyl, optionally substituted haloalkyl, hydroxy, or optionally substituted haloalkoxy;

of Formula I-B is 0, 1, 2, 3, or 4;

$R_{18}$ of Formula I-B is independently selected from the group of H, halo, optionally substituted alkoxy, cyano, optionally substituted alkyl, haloalkyl, haloalkoxy or a linker;

each $R_{26}$ is independently selected from H, optionally substituted alkyl or $NR_{27a}R_{27b}$;

each $R_{27a}$ and $R_{27b}$ is independently H, optionally substituted alkyl, or $R_{27a}$ and $R_{27b}$ together with the nitrogen atom to which they are attached form a 4-6 membered heterocyclyl; and p of Formula I-B is 0, 1, 2, 3, or 4, and wherein the dashed line indicates the site of attachment of at least one PB, another E3LB, or a chemical linker moiety coupling at least one PB to E3LB.

In certain embodiments, $R_{15}$ of Formula I-B is

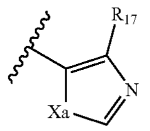

wherein $R_{17}$ is H, halo, optionally substituted $C_{3-6}$ cycloalkyl, optionally substituted $C_{1-6}$ alkyl, optionally substituted $C_{1-6}$ alkenyl, and $C_{1-6}$ haloalkyl; and Xa is S or O.

In certain embodiments, $R_{17}$ of Formula I-B is selected from the group methyl, ethyl, isopropyl, and cyclopropyl.

In certain additional embodiments, $R_{15}$ of Formula I-B is selected from the group consisting of:

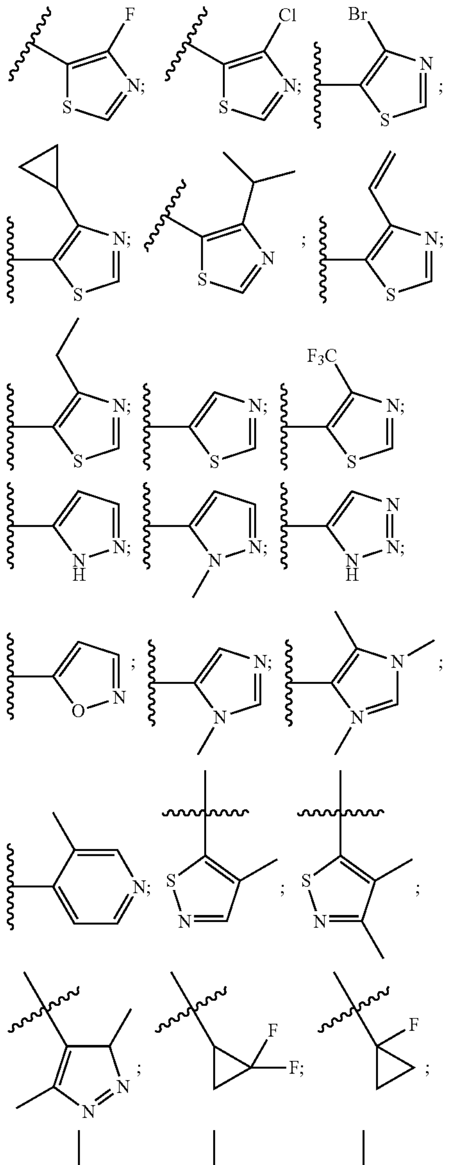

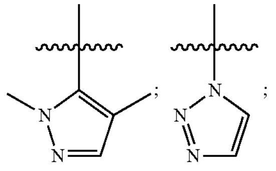

and

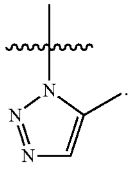

In certain embodiments, $R_{11}$ of Formula I-B is selected from the group consisting of:

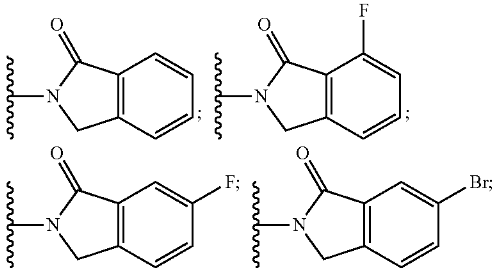

-continued

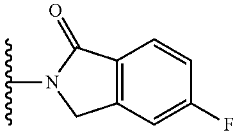 ; 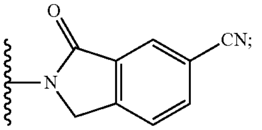

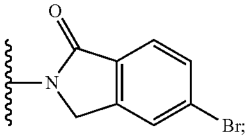 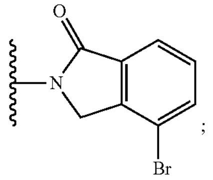

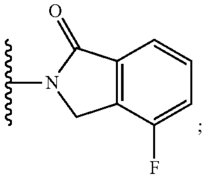 ; 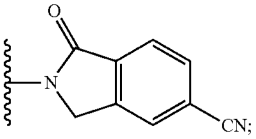

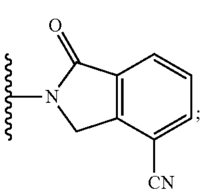 ; 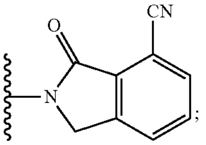

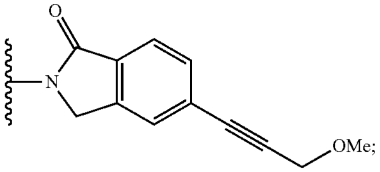

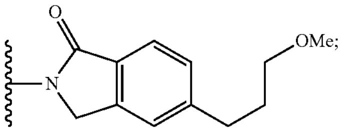

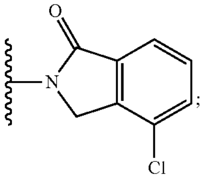 ; 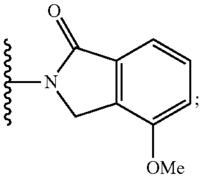

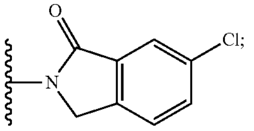 and 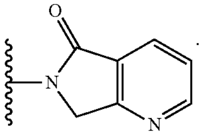

In certain embodiments, $R_{14a}$, $R_{14b}$ of Formula I-B, are each independently selected from the group of H, optionally substituted haloalkyl, optionally substituted alkyl, optionally substituted alkoxy, optionally substituted hydroxyl alkyl, optionally substituted alkylamine, optionally substituted heteroalkyl, optionally substituted alkyl-heterocycloalkyl, optionally substituted alkoxy-heterocycloalkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered cycloalkyl, heterocycloalkyl, spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted; $R_{26}$ and $R_{27}$ are as described above.

In certain embodiments, $R_{15}$ of Formula I-B is selected from H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}SO_2R_{27b}$, optionally substituted alkyl, optionally substituted haloalkyl (e.g. optionally substituted fluoroalkyl), optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

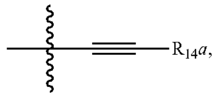

wherein $R_{26}$, $R_{27}$, $R_{30}$ and $R_{14a}$ are as described above.

In certain embodiments, $R_{14a}$, $R_{14b}$ of Formula I-B, are each independently selected from the group of H, optionally substituted haloalkyl, optionally substituted alkyl, $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, or $CH_2NCH_3COR_{26}$; and the other of $R_{14a}$ and $R_{14b}$ is H; or $R_{14a}$, $R_{14b}$, together with the carbon atom to which they are attached, form an optionally substituted 3- to 6-membered spirocycloalkyl or spiroheterocyclyl, wherein the spiroheterocyclyl is not epoxide or aziridine, the said spirocycloalkyl or spiroheterocycloalkyl itself being optionally substituted with an alkyl, a haloalkyl, or —$COR_{33}$ where $R_{33}$ is an alkyl or a haloalkyl, wherein $R_{30}$ is selected from H, alkyl, alkynylalkyl, cycloalkyl, heterocycloalkyl, cycloalkylalkyl, heterocycloalkylalkyl, arylalkyl or heteroarylalkyl further optionally substituted;

$R_{15}$ of Formula I-B is selected from H, halogen, CN, OH, $NO_2$, $NR_{27a}R_{27b}$, $OR_{27a}$, $CONR_{27a}R_{27b}$, $NR_{27a}COR_{27b}$, $SO_2NR_{27a}R_{27b}$, $NR_{27a}$ $SO_2R_{27b}$, optionally substituted alkyl, optionally substituted haloalkyl, optionally substituted haloalkoxy, optionally substituted aryl, optionally substituted heteroaryl, optionally substituted cycloalkyl, or optionally substituted heterocyclyl wherein optional substitution of the said aryl, heteroaryl, cycloalkyl and heterocycloalkyl includes $CH_2OR_{30}$, $CH_2NHR_{30}$, $CH_2NCH_3R_{30}$, $CONR_{27a}R_{27b}$, $CH_2CONR_{27a}R_{27b}$, $CH_2NHCOR_{26}$, $CH_2NCH_3COR_{26}$ or

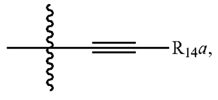

wherein $R_{26}$, $R_{27}$, $R_{30}$ and $R_{14a}$ are as described above.

In certain embodiments, E3LB has a chemical structure selected from the group of:

I-C

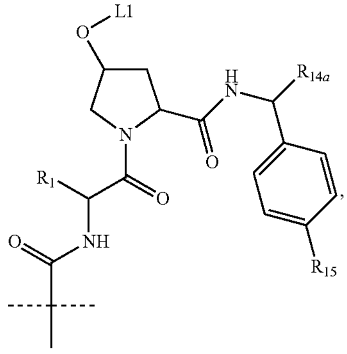

I-D

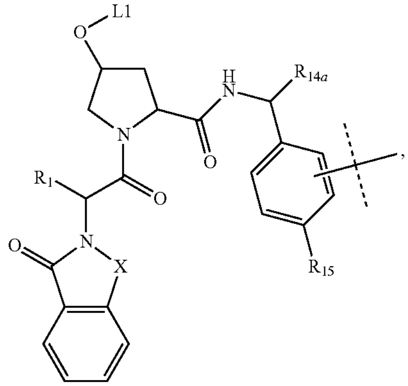

I-E

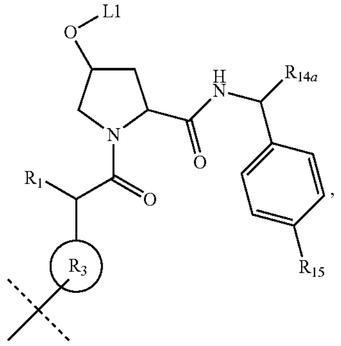

wherein:

$R_1$ of Formulas I-C, I-D, and I-E is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl;

$R_{14a}$ of Formulas I-C, I-D, and I-E is H, haloalkyl, optionally substituted alkyl, methyl, fluoromethyl, hydroxymethyl, ethyl, isopropyl, or cyclopropyl;

$R_{15}$ of Formulas I-C, I-D, and I-E is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, optionally substituted cycloalkyl, or optionally substituted heterocyclyl;

X of Formulas I-C, I-D, and I-E is C, $CH_2$, or C=O $R_3$ of Formulas I-C, I-D, and I-E is absent or an optionally substituted 5 or 6 membered heteroaryl; and the dashed line indicates the site of attachment of at least one PB, another E3LB or a chemical linker moiety coupling at least one PB or another E3LB or both to E3LB.

In certain embodiments, E3LB comprises a group according to the chemical structure:

I-F

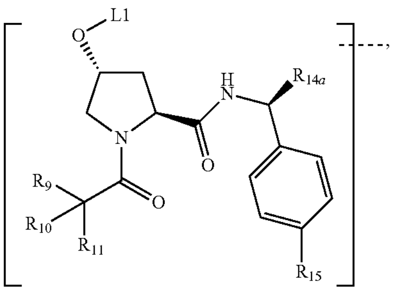

wherein:

$R_{14a}$ of Formula I-F is H, haloalkyl, optionally substituted alkyl, methyl, fluoromethyl, hydroxymethyl, ethyl, isopropyl, or cyclopropyl;

$R_9$ of Formula I-F is H;

$R_{10}$ of Formula I-F is H, ethyl, isopropyl, tert-butyl, sec-butyl, cyclopropyl, cyclobutyl, cyclopentyl, or cyclohexyl;

$R_{11}$ of Formula I-F is

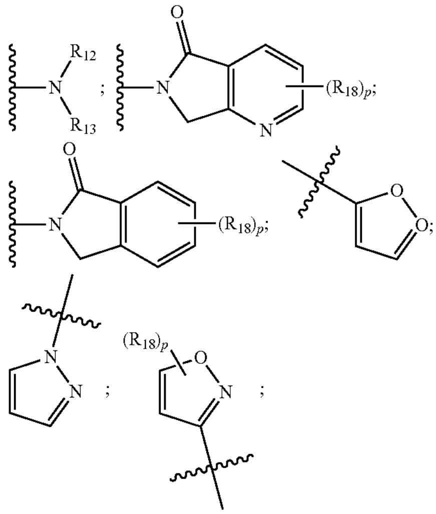

or optionally substituted heteroaryl;

p of Formula I-F is 0, 1, 2, 3, or 4;

each $R_{18}$ of Formula I-F is independently halo, optionally substituted alkoxy, cyano, optionally substituted alkyl, haloalkyl, haloalkoxy or a linker;

$R_{12}$ of Formula I-F is H, C=O;

$R_{13}$ of Formula I-F is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ of Formula I-F is selected from the group consisting of H, halogen, Cl, CN, OH, $NO_2$, optionally substituted haloalkyl, optionally substituted heteroaryl, optionally substituted aryl;

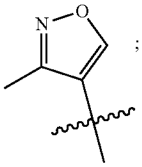 ; 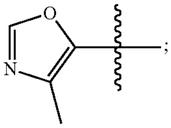 ; 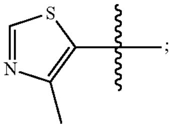 ;

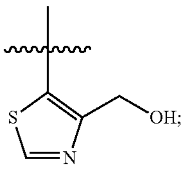 ; 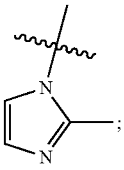 ; 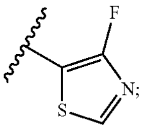 ;

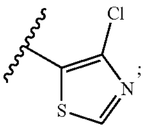 ; 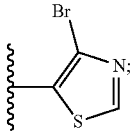 ; 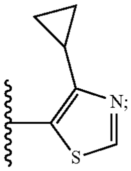 ;

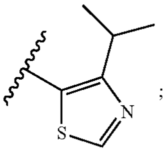 ; 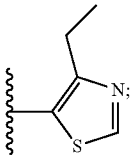 ; 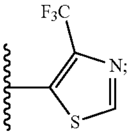 ;

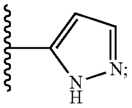 ; 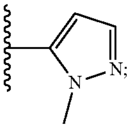 ; 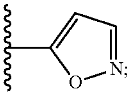 ;

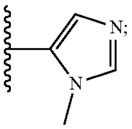 ; 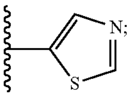 ; 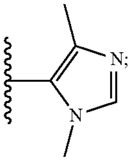 ;

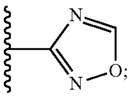 ; 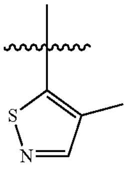 ; 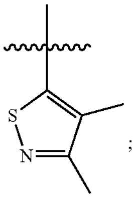 ;

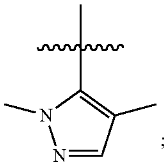 ; 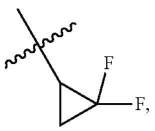 , 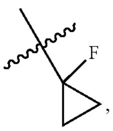 ,

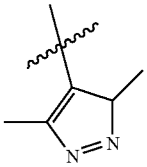 ; 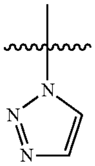 ; 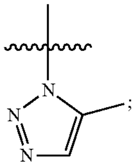 ;

and, wherein the dashed line of Formula I-F indicates the site of attachment of at least one PB, another E3LB or a chemical linker moiety coupling at least one PB or another E3LB or both to E3LB.

In certain embodiments, the E3LB is selected from the following structures:

I-A2

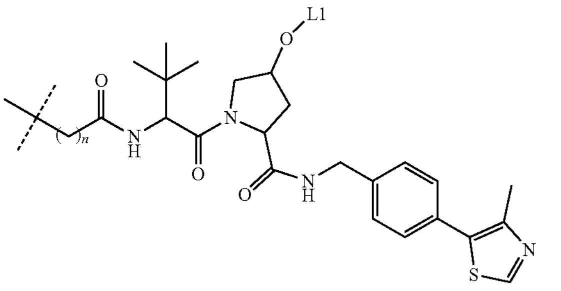

I-A3

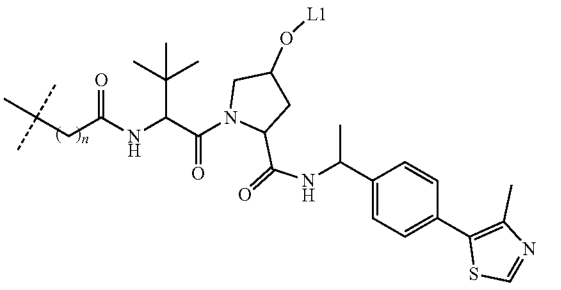

I-A4

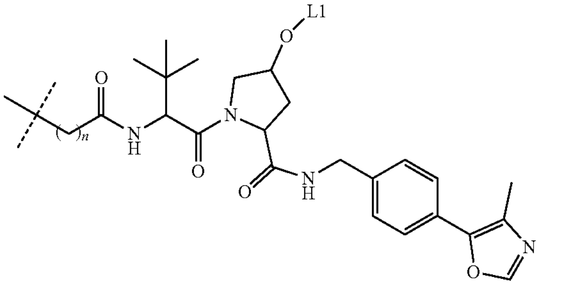

I-A5

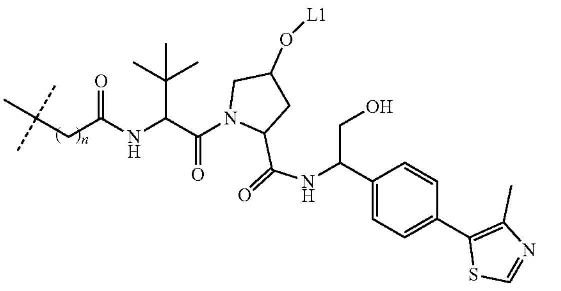

-continued
I-A6
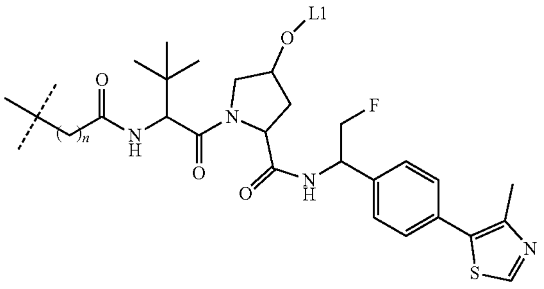
I-A7
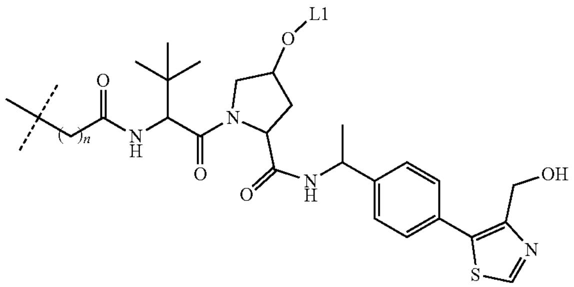
I-A8
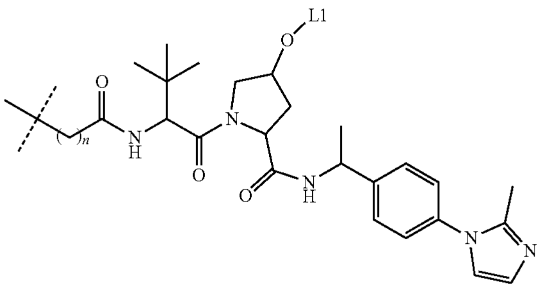
I-A9
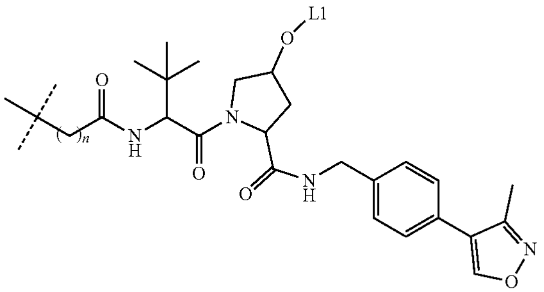
I-A10
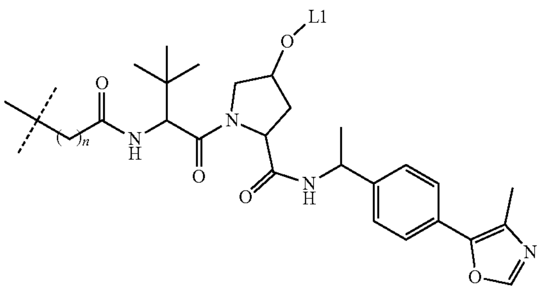
-continued
I-A11
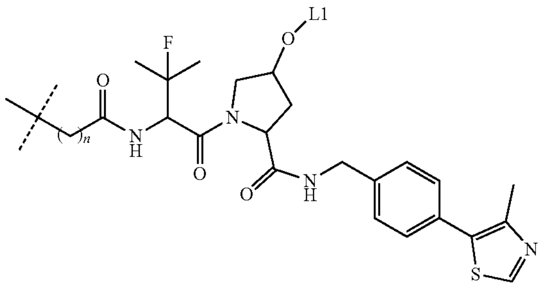
I-A12
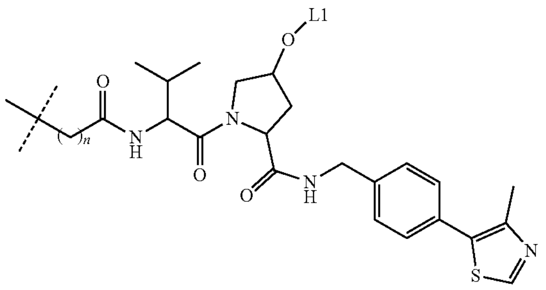
I-A13
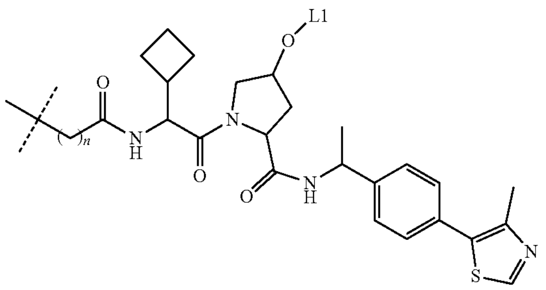
I-A14
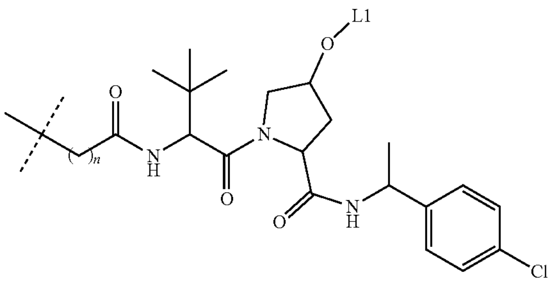
wherein n is 0 or 1.
In certain embodiments, the E3LB is selected from the following structures:

I-A2
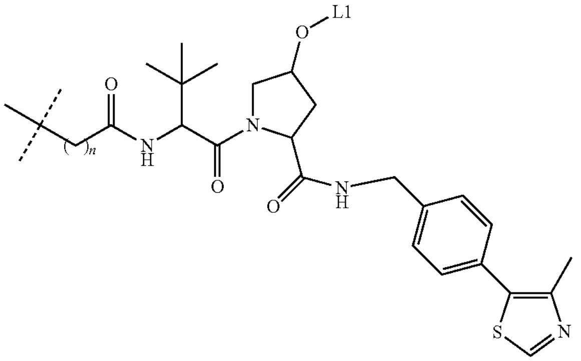
I-A3
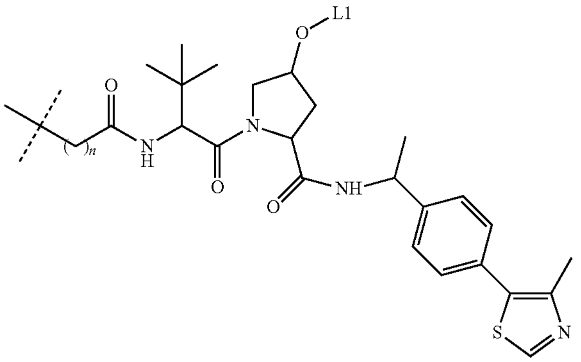
I-A4
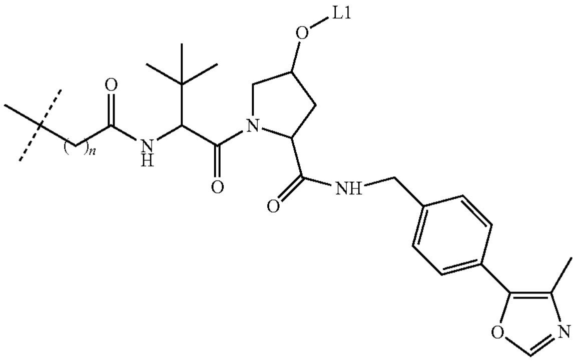
I-A5
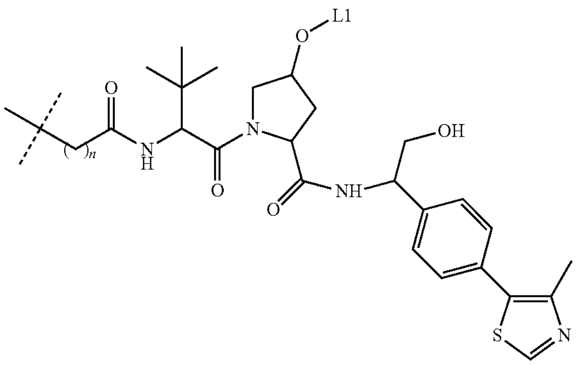
-continued
I-A6
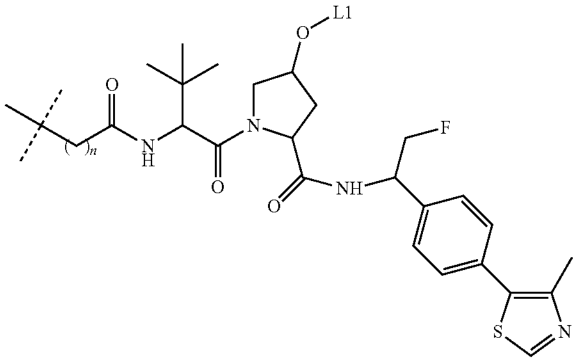
I-A7
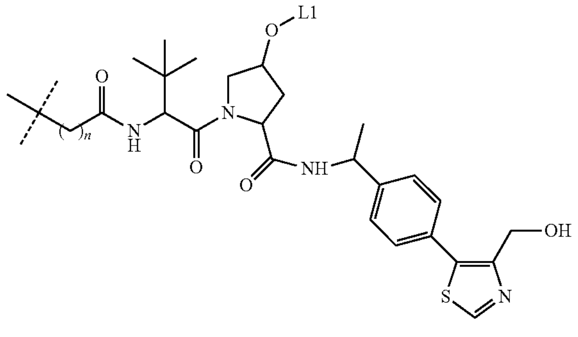
I-A8
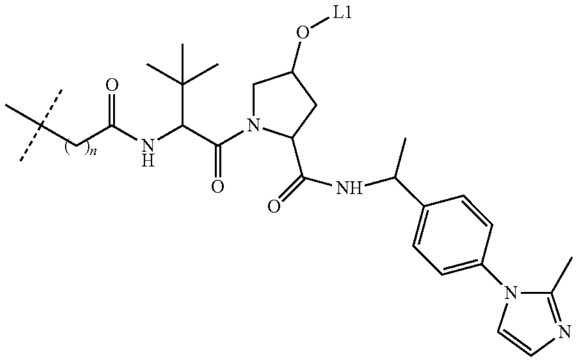
I-A9
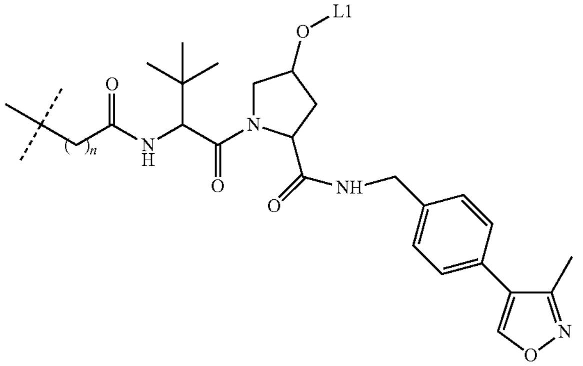

-continued
I-A10
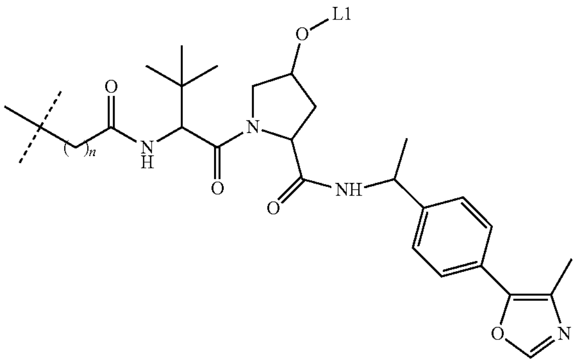
I-A11
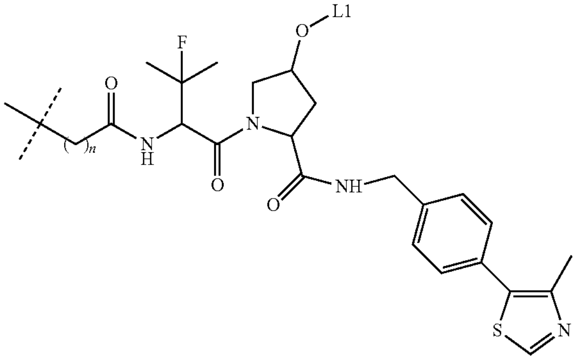
I-A12
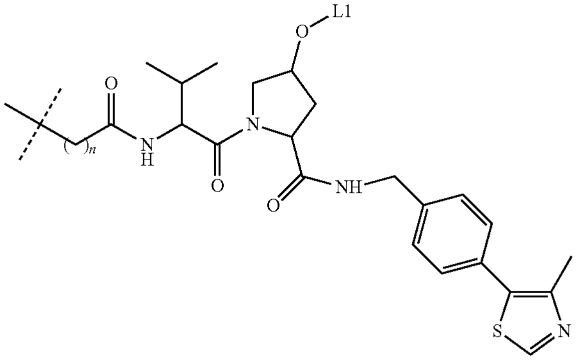
I-A13
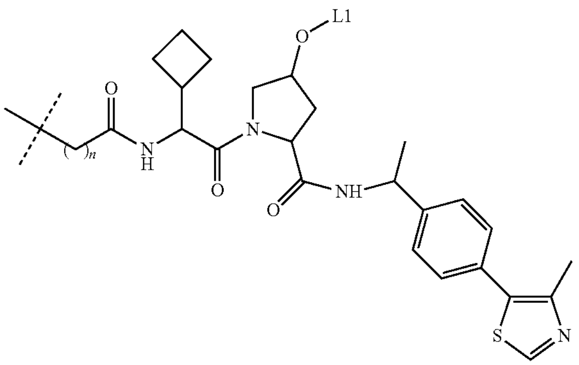
-continued
I-A14
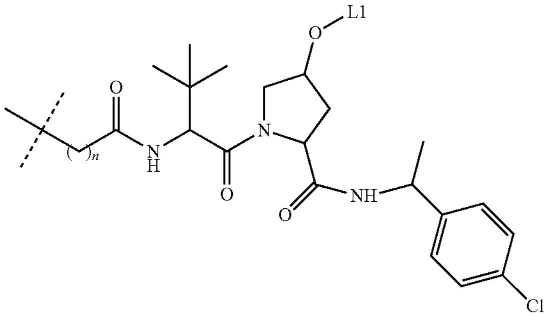
wherein n is 0 or 1.
In certain embodiments, the E3LB is selected from the following structures:
I-B1
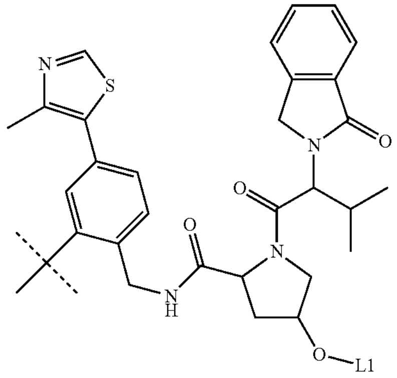
I-B2
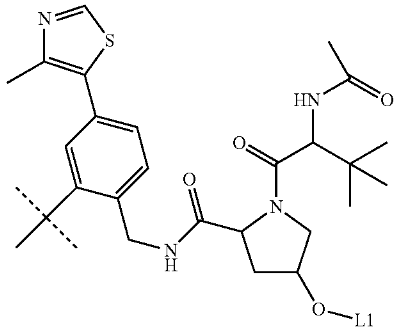
I-B3
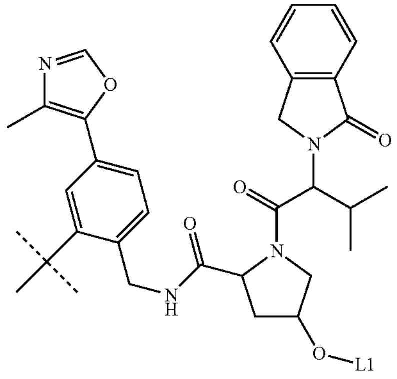

-continued
I-B4
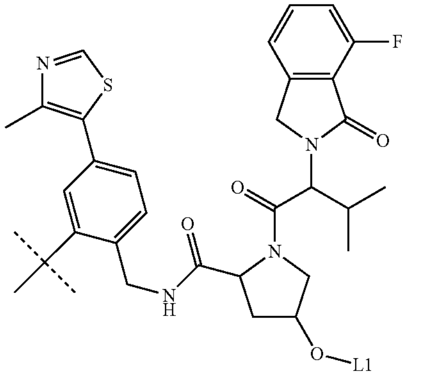
I-B5
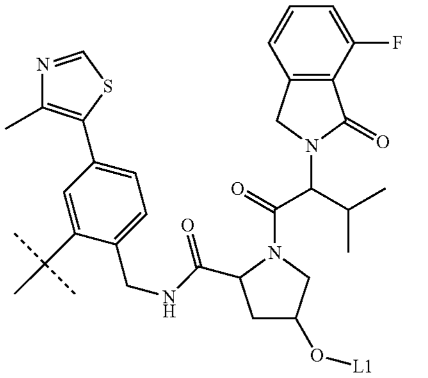
I-B6
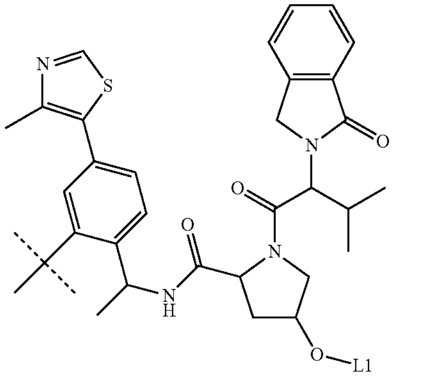
I-B7
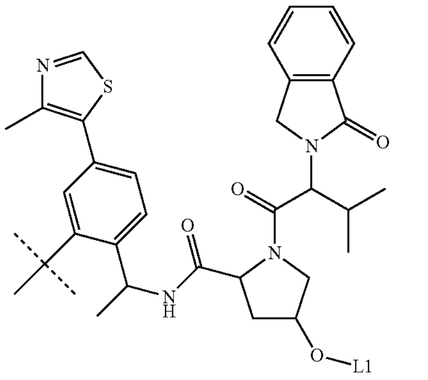
-continued
I-B8
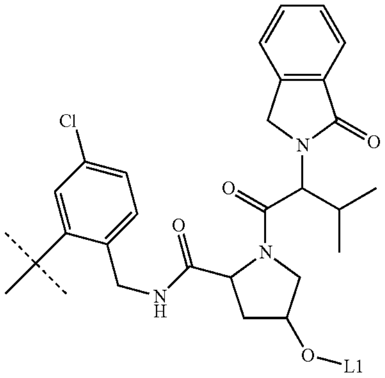
I-B9
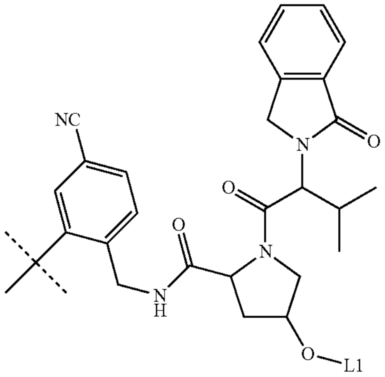
I-B10
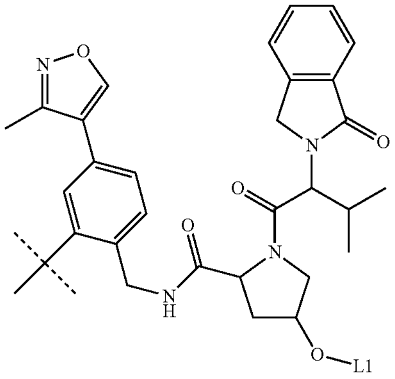
I-B11
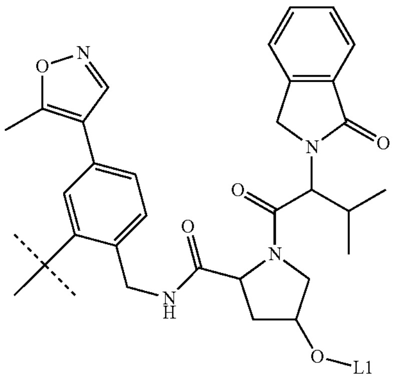

-continued
I-B12
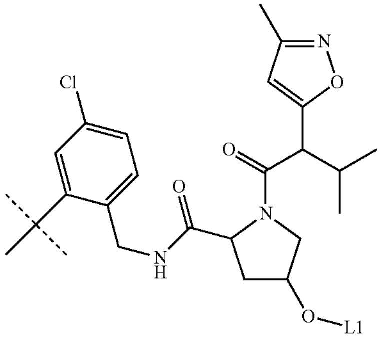
I-C1
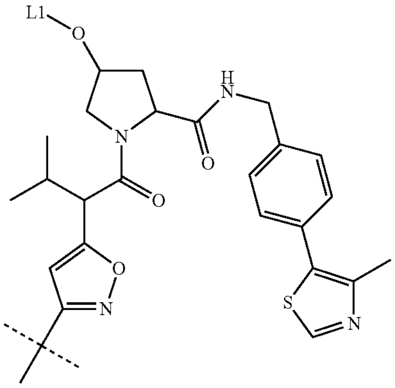
I-C2
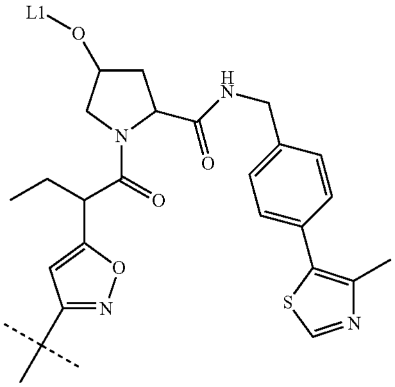
I-C3
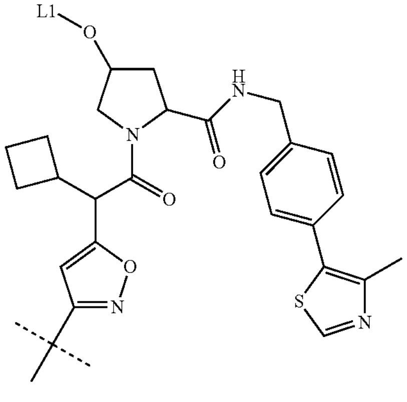
-continued
I-C4
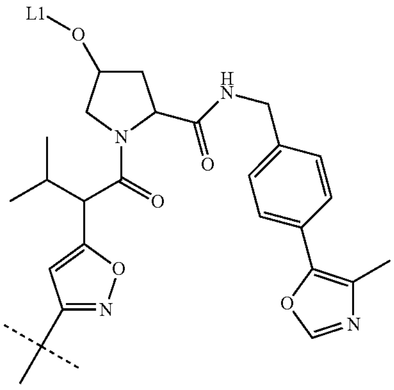
I-C5
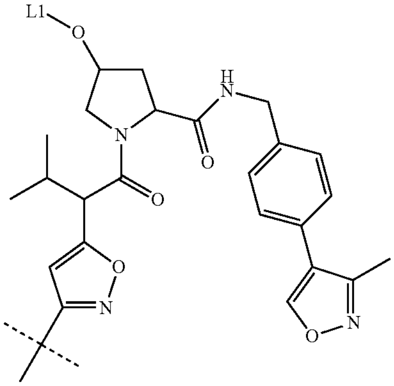
I-C6
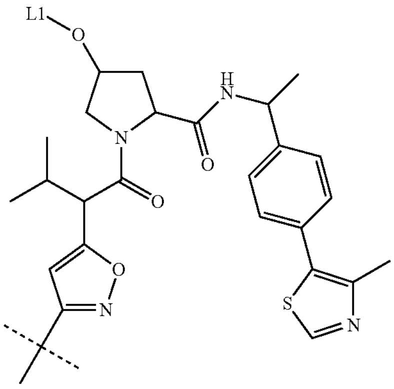
I-C7
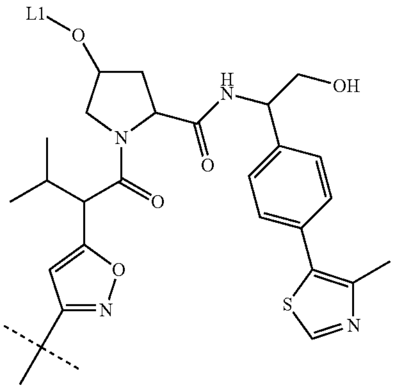

-continued
I-C8
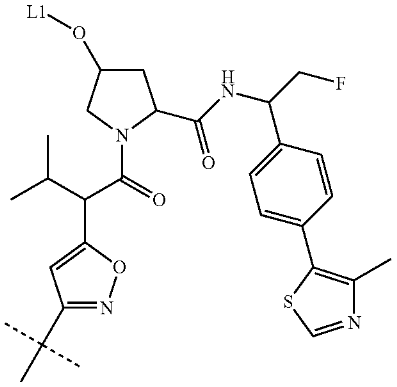
I-C9
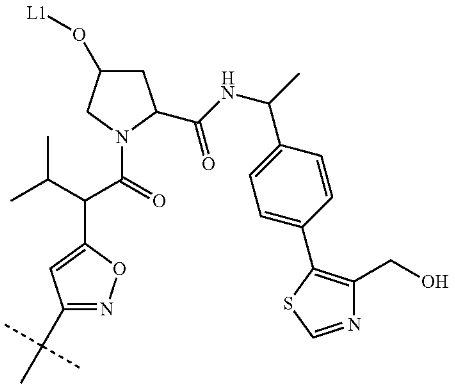
I-C10
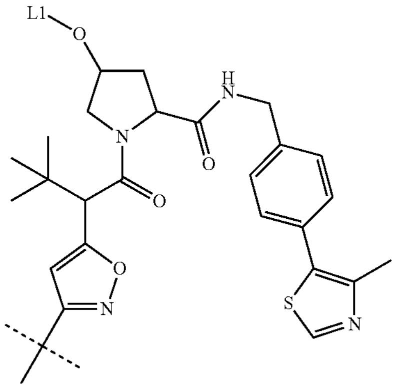
I-C12
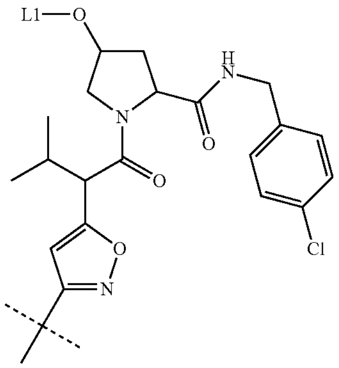
-continued
I-C13
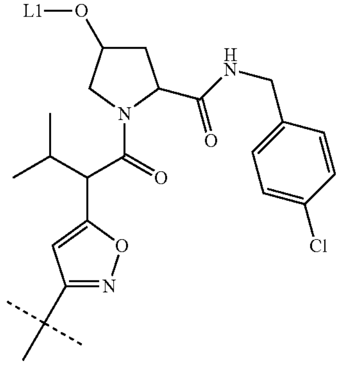
I-C14
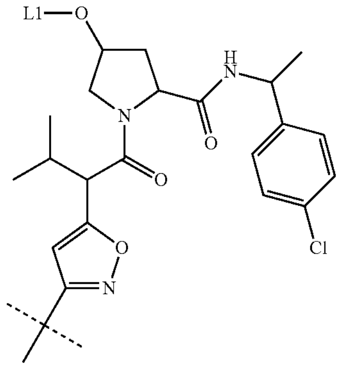
I-C15
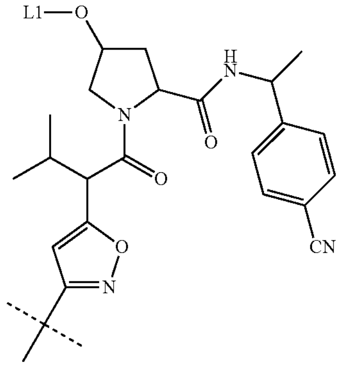
I-D1
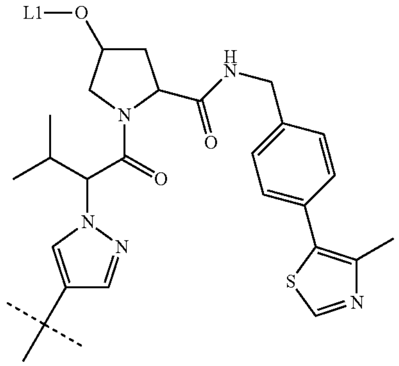

-continued
I-D2
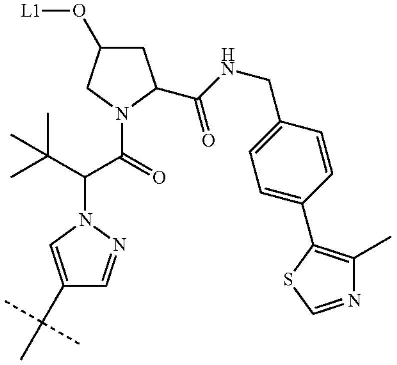
I-D3
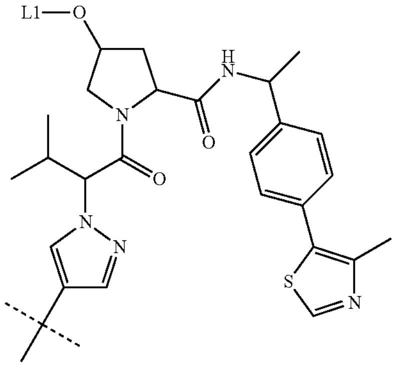
I-D4
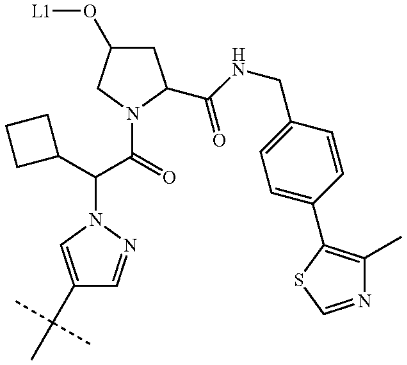
I-D5
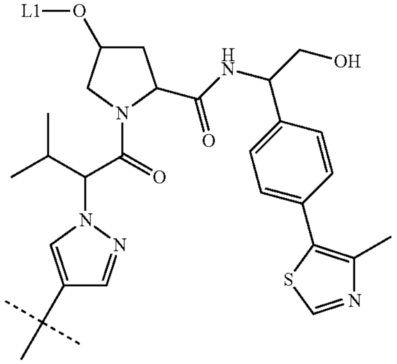
-continued
I-D6
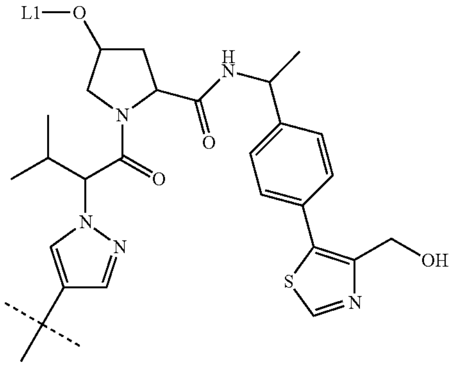
I-D7
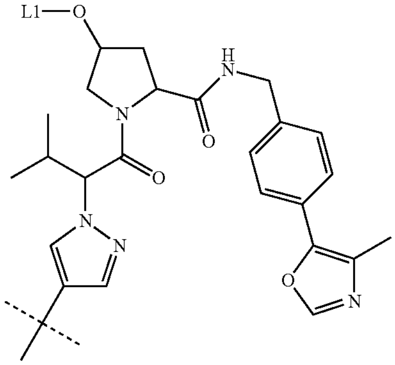
I-D8
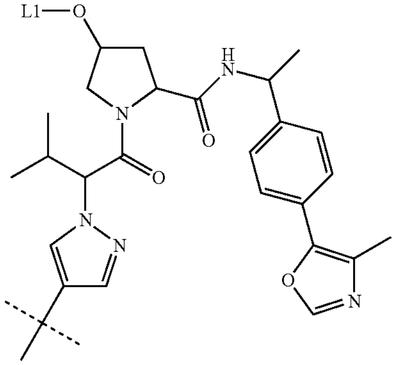
I-D9
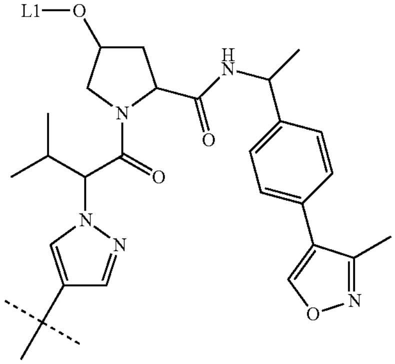
wherein, the phenyl ring in I-A1 through I-A15, I-B1 through I-B12, I-C1 through I-C15 and I-D1 through I-D9 is optionally substituted with fluorine, lower alkyl and alkoxy groups, and wherein the dashed line indicates the site of attachment of at least one PB, another E3LB or a chemical linker moiety coupling at least one PB or another E3LB or both to I-A.

In one embodiment, the phenyl ring in I-A1 through I-A15, I-B1 through I-B12, I-C1 through I-C15 and I-D1 through I-D9 can be functionalized as the ester to make it a part of the prodrug.

In certain embodiments, the hydroxyl group on the pyrrolidine ring of I-A1 through I-A15, I-B1 through I-B12, I-C1 through I-C15 and I-D1 through I-D9, respectively, comprises an ester-linked prodrug moiety.

In any of the aspects or embodiments described herein, the E3LB is a group according to the chemical structure:

I-G

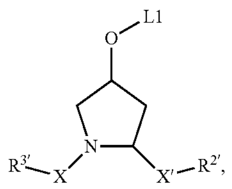

or a pharmaceutically acceptable salt thereof, wherein.

X and X' of I-G are each independently C═O, C═S, —S(O), $S(O)_2$, (preferably X and X' are both C═O);

$R^{2'}$ of I-G is an optionally substituted $—(CH_2)_n—(C═O)_u(NR')_v(SO_2)_w$alkyl group, an optionally substituted $—(CH_2)_n—(C═O)_u(NR'')_v(SO_2)_wNR_{1N}R_{2N}$ group, an optionally substituted $—(CH_2)_n—(C═O)_u(NR')_v(SO_2)_w$-Aryl, an optionally substituted $—(CH_2)_n—(C═O)_u(NR'')_v(SO_2)_w$-Heteroaryl, an optionally substituted $—(CH_2)_n—(C═O)_vNR''(SO_2)_w$-Heterocyclyl, an optionally substituted $—NR''—(CH_2)_n—C(O)_u(NR'')_v(SO_2)_w$-alkyl, an optionally substituted $—NR''—(CH_2)_n—C(O)_u(NR'')_v(SO_2)_w—NR_{1N}R_{2N}$, an optionally substituted $—NR''—(CH_2)_n—C(O)_u(NR'')_v(SO_2)_w—NR''C(O)R_{1N}$, an optionally substituted $—NR''—(CH_2)_n—(C═O)_u(NR')_v(SO_2)_w$-Aryl, an optionally substituted $—NR''—(CH_2)_n—(C═O)_u(NR')_v(SO_2)_w$-Heteroaryl or an optionally substituted $—NR''—(CH_2)_n—(C═O)_vNR''$ $(SO_2)_w$-Heterocyclyl, an optionally substituted $—X^{R2'}$-alkyl group; an optionally substituted $—X^{R2'}$-Aryl group; an optionally substituted $—X^{R2'}$-Heteroaryl group; an optionally substituted $—X^{R2'}$ Heterocyclyl group;

$R^{3'}$ of I-G is an optionally substituted alkyl, an optionally substituted $—(CH_2)_n—(O)_u(NR'')_v(SO_2)_w$-alkyl, an optionally substituted $—(CH_2)_n—C(O)_u(NR'')_v(SO_2)_w—NR_{1N}R_{2N}$, an optionally substituted $—(CH_2)_n—C(O)_u(NR'')_v(SO_2)_w—NR''C(O)R_{1N}$, an optionally substituted $—(CH_2)_n—C(O)_u(NR'')_v(SO_2)_w—C(O)(R'')_2$, an optionally substituted $—(CH_2)_n—C(O)_u(NR'')_v(SO_2)_w$-Aryl, an optionally substituted $—(CH_2)_n—C(O)_u(NR'')_v(SO_2)_w$-Heteroaryl, an optionally substituted $—(CH_2)_n—C(O)—(NR'')_v(SO_2)_w$-Heterocyclyl, an optionally substituted $—NR''—(CH_2)_n—C(O)_u(NR'')_v(SO_2)_w$-alkyl, an optionally substituted $—NR''—(CH_2)_n—C(O)_u(NR'')_v(SO_2)_w—NR_{1N}R_{2N}$, an optionally substituted $—NR''(CH_2)_n—C(O)_u(NR'')_v(SO_2)_w—NR''C(O)R_{1N}$, an optionally substituted $—NR''—(CH_2)_n—C(O)_u(NR'')_v(SO_2)_w$-Aryl, an optionally substituted $—NR''—(CH_2)_n—C(O)_u(NR'')_v(SO_2)_w$-Heteroaryl, an optionally substituted $—NR^1—(CH_2)_n—C(O)_u(NR'')_v(SO_2)_w$-Heterocyclyl, an optionally substituted $—O—(CH_2)n—(C═O)_u(NR'')_v(SO_2)_w$-alkyl, an optionally substituted $—O—(CH_2)n—(C═O)_u(NR'')_v(SO_2)_w—NR_{1N}R_{2N}$, an optionally substituted $—O—(CH_2)n—(C═O)_u(NR'')_v(SO_2)_w—NR''C(O)R_{1N}$, an optionally substituted $—O—(CH_2)n—(C═O)_u(NR'')_v(SO_2)_w$-Aryl, an optionally substituted $—O—(CH_2)_n—(C═O)_u(NR'')_v(SO_2)_w$-Heteroaryl or an optionally substituted $—O—(CH_2)_n—(C═O)_u(NR'')_v(SO_2)_w$-Heterocyclyl; $—(CH_2)_n—(V)_{n'}—(CH_2)_n—(V)_{n'}$-alkyl group, an optionally substituted $—(CH_2)_n—(V)_{n'}—(CH_2)_n—(V)_{n'}$-Aryl group, an optionally substituted $—(CH_2)_n—(V)_{n'}—(CH_2)_n—(V)_{n'}$-Heteroaryl group, an optionally substituted $—(CH_2)_n—(V)_{n'}—(CH_2)_n—(V)_{n'}$-Heterocyclyl' group, an optionally substituted $—(CH_2)_n—N(R_{1'})(C═O)_{m'}—(V)_{n'}$-alkyl group, an optionally substituted $—(CH_2)_n—N(R_{1'})(C═O)_{m'}—(V)_{n'}$-Aryl group, an optionally substituted $—(CH_2)_n—N(R_{1'})(C═O)_{m'}—(V)_{n'}$-Heteroaryl group, an optionally substituted $—(CH_2)_n—N(R_{1'})(C═O)_{m'}—(V)_{n'}$-Heterocyclyl group, an optionally substituted $—X^{R3'}$-alkyl group; an optionally substituted $—X^{R3'}$-Aryl group; an optionally substituted $—X^{R3'}$-Heteroaryl group; an optionally substituted $—X^{R3'}—$ Heterocyclyl group;

$R_{1N}$ and $R_{2N}$ of I-G are each independently H, $C_1$-$C_6$ alkyl which is optionally substituted with one or two hydroxyl groups and up to three halogen groups or an optionally substituted $(CH_2)_n$-Aryl, $—(CH_2)_n$-Heteroaryl or $—(CH_2)_n$-Heterocyclyl group;

V of I-G is O, S or $NR_1$;

each $R_{1'}$ of I-G is independently H or a $C_1$-$C_3$ alkyl group;

$X^{R2'}$ and $X^{R3'}$ of I-G are each independently an optionally substituted $—CH_2)_n—$, $CH_2)_n—CH(X_v)═CH(X_v)—$ (cis or trans), $—CH_2)_n—CH≡CH—$, $—(CH_2CH_2O)_n—$ or a $C_3$-$C_6$ cycloalkyl group, where $X_v$ is H, a halo or a $C_1$-$C_3$ alkyl group which is optionally substituted;

each R'' of I-G is independently H or a $C_1$-$C_6$ alkyl group which may be optionally substituted with one or two hydroxyl groups or up to three halogen groups (preferably fluorine);

$R_S$ of I-G is a $C_1$-$C_6$ alkyl group, an optionally substituted aryl, heteroaryl or heterocyclyl group or a $—(CH_2)_mN(R'')_2$ group;

each m of I-G is independently 0, 1, 2, 3, 4, 5, 6;

each m' of I-G is independently 0 or 1;

each n of I-G is independently 0, 1, 2, 3, 4, 5, 6;

each n' of I-G is independently 0 or 1;

each u of I-G is independently 0 or 1;

each v of I-G is independently 0 or 1;

each w of I-G is independently 0 or 1; and any one or more of $R^{2'}$, $R^{3'}$, X and X' of I-G is optionally modified to be covalently bonded to the PB group through a linker group when PB is not E3LB, or when PB is E3LB, any one or more of $R^{2'}$, $R^{3'}$, X and X' of each of E3LB is optionally modified to be covalently bonded to each other directly or through a linker group, or a pharmaceutically acceptable salt, stereoisomer, solvate or polymorph thereof.

In any of the aspects or embodiments described herein, the E3LB is:

I-H

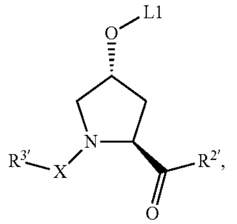

wherein:

each of $R^{2'}$ and $R^{3'}$ of I-H are the same as above and X is C═O, C═S, —S(O) group or a $S(O)_2$ group, more preferably a C═O group, and any one or more of $R^{2'}$ and $R^{3'}$ of I-H are optionally modified to bind a linker group to which is further covalently bonded to the PB group when PB is not E3LB, or when PB is E3LB, any one or more of $R^{2'}$, $R^{3'}$ of each of E3LB are optionally modified to be covalently bonded to each other directly or through a linker group, or a pharmaceutically acceptable salt, enantiomer, diastereomer, solvate or polymorph thereof.

In any of the aspects or embodiments described herein, the E3LB is according to the chemical structure:

I-I

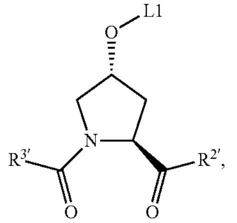

wherein:

any one or more of $R^{2'}$ and $R^{3'}$ of I-I are optionally modified to bind a linker group to which is further covalently bonded to the PB group when PB is not E3LB or when PB is E3LB, any one or more of $R^{2'}$, $R^{3'}$ of each of E3LB is optionally modified to be covalently bonded to each other directly or through a linker group, or a pharmaceutically acceptable salt, enantiomer, diastereomer, solvate or polymorph thereof.

X and X', where present, of I-G and I-H are preferably a C═O, C═S, —S(O) group or a $S(O)_2$ group, more preferably a C═O group;

$R^{2'}$ of I-G through I-I is preferably an optionally substituted —NH-T-Aryl, an optionally substituted —N($CH_3$)-T-Aryl, an optionally substituted —NH-T-Heteroaryl group, an optionally substituted —N($CH_3$)-T-Heteroaryl, an optionally substituted —NH-T-Heterocyclyl, or an optionally substituted —N($CH_3$)-T-Heterocyclyl preferably H and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_3$ alkyl group, preferably one or two methyl groups, which may be optionally substituted; and n is 0 to 6, often 0, 1, 2 or 3, preferably 0 or 1.

Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

Preferred Aryl groups for $R^{2'}$ of I-G through I-I include optionally substituted phenyl or naphthyl groups, preferably phenyl groups, wherein the phenyl or naphthyl group is connected to a PB (including a E3LB group) with a linker group and/or optionally substituted with a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is optionally connected to a PB group, including a E3LB, with a linker group), and/or optionally substituted with at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

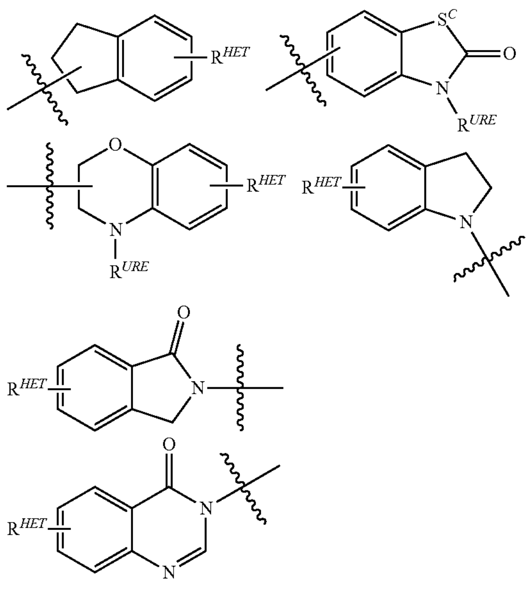

-continued

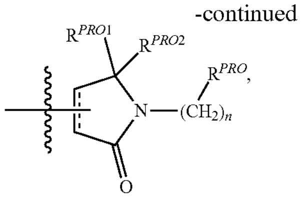

wherein:

$S^c$ of I-G through I-I is $CHR^{SS}$, $NR^{URE}$ or O;

$R^{HET}$ of I-G through I-I is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R^a$ where $R^a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocyclyl, preferably for example piperidine, morpholine, pyrrolidine, tetrahydrofuran);

$R^{PRO}$ of I-G through I-I is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of I-G through I-I are each independently H, an optionally substituted $C_1$-$C_3$ alkyl group or together form a keto group; and each n of I-G through I-I is independently 0, 1, 2, 3, 4, 5, or 6 (preferably 0 or 1), or an optionally substituted heterocyclyl, preferably tetrahydrofuran, tetrahydrothiene, piperidine, piperazine or morpholine (each of which groups when substituted, are preferably substituted with a methyl or halo (F, Br, Cl), each of which groups may be optionally attached to a PB group (including a E3LB group) via a linker group.

In certain preferred aspects,

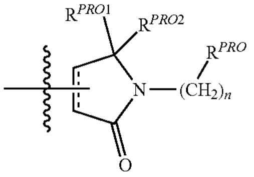

of I-G through I-I is a

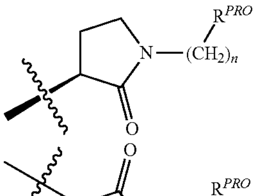

or

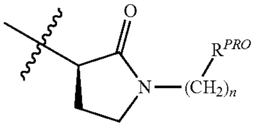

group, where $R^{PRO}$ and n of I-G through I-I are the same as above.

Preferred heteroaryl groups for $R^{2'}$ of I-G through I-I include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

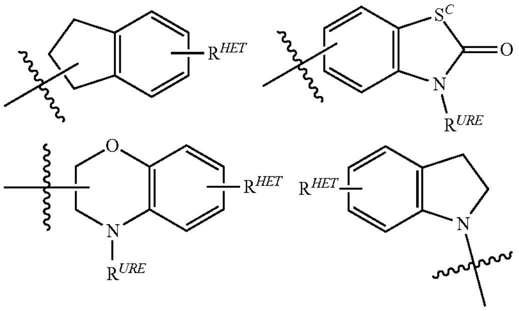

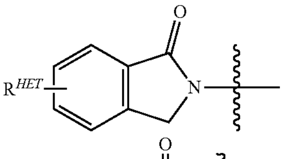

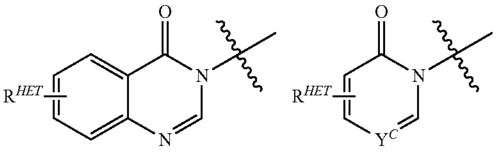

wherein:

$S^c$ of I-G through I-I is $CHR^{SS}$, $NR^{URE}$ or O;

$R^{HET}$ of I-G through I-I is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$, where $R_a$ of I-G through I-I is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted, and $Y^C$ of I-G through I-I is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PB group (including a E3LB group) via a linker group.

Preferred heterocyclylheterocyclyl groups for $R^{2'}$ of I-G through I-I include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

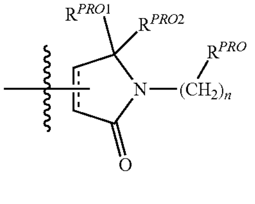

or

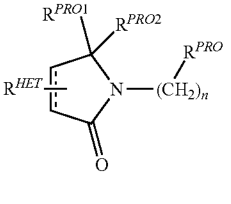

preferably,

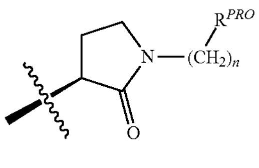

or

-continued

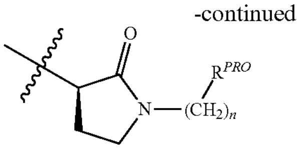

a group, wherein:

$R^{PRO}$ of I-G through I-I is H, optionally substituted $C_1$-$C_6$ alkyl or an optionally substituted aryl, heteroaryl or heterocyclyl group;

$R^{PRO1}$ and $R^{PRO2}$ of I-G through I-I are each independently H, an optionally substituted $C_1$-$C_3$ alkyl group or together form a keto group and each n of I-G through I-I is independently 0, 1, 2, 3, 4, 5, or 6 (often 0 or 1), each of which groups may be optionally connected to a PB group (including a E3LB group) via a linker group.

Preferred $R^{2'}$ substituents of I-G through I-I also include specifically (and without limitation to the specific compound disclosed) the $R^{2'}$ substituents which are found in the identified compounds disclosed herein. Each of these $R^{2'}$ substituents may be used in conjunction with any number of $R^{3'}$ substituents which are also disclosed herein.

$R^{3'}$ of I-G through I-I is preferably an optionally substituted —NH-T-Aryl, an optionally substituted —N($C_1$-$C_3$ alkyl)-T-Aryl, an optionally substituted —NH-T-Heteroaryl group, an optionally substituted —N($C_1$-$C_3$ alkyl)-T-Heteroaryl, an optionally substituted —NH-T-Heterocyclyl, or an optionally substituted —N($C_1$-$C_3$ alkyl)-T-Heterocyclyl, wherein T is an optionally substituted $-(CH_2)_n-$ group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a $-(CH_2O)_n-$ group, a $-(OCH_2)_n-$ group, a $-(CH_2CH_2O)_n-$ group, a $-(OCH_2CH_2)_n-$ group, each of which groups is optionally substituted.

Preferred aryl groups for $R^{3'}$ of I-G through I-I include optionally substituted phenyl or naphthyl groups, preferably phenyl groups, wherein the phenyl or naphthyl group is optionally connected to a PB group (including a E3LB group) via a linker group and/or optionally substituted with a halogen (preferably F or Cl), an amine, monoalkyl- or dialkyl amine (preferably, dimethylamine), an amido group (preferably a $-(CH_2)_m-NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocyclyl group or a $-(CH_2)_m(R'')_2$ group), each of which may be substituted in ortho-, meta- and/or para-positions of the phenyl ring, preferably para-), or an Aryl (preferably phenyl), Heteroaryl or Heterocyclyl. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PB group (including a E3LB group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocyclyl (tetrahydrofuran, tetrahydrothiophene, pyrrolidine, piperidine, morpholine, piperazine, tetrahydroquinoline, oxane or thiane. Each of the aryl, heteroaryl or heterocyclyl groups may be optionally connected to a PB group (including a E3LB group) via a linker group.

Preferred Heteroaryl groups for $R^{3'}$ of I-G through I-I include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted $-(CH_2)_m-O-C_1-C_6$ alkyl group or an optionally substituted $-(CH_2)_m-C(O)-O-C_1-C_6$ alkyl group), an optionally substituted pyridine (2-, 3, or 4-pyridine) or a group according to the chemical structure:

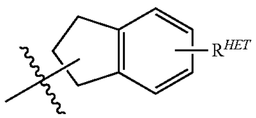

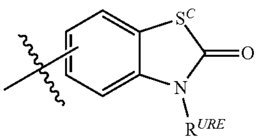

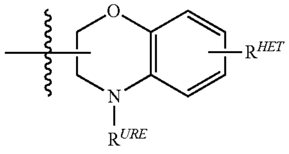

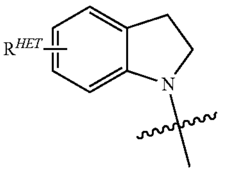

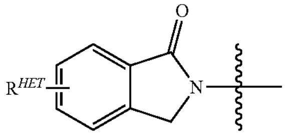

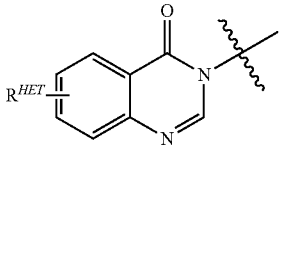

or

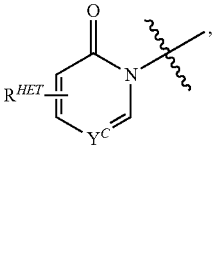

, wherein:

$S^c$ of I-G through I-I is $CHR^{SS}$, $NR^{URE}$ or O;

$R^{HET}$ of I-G through I-I is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a $-C(O)(C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted, and $Y^C$ of I-G through I-I is N or $C-R^{YC}$, where $R^Yc$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl). Each of said heteroaryl groups may be optionally connected to a PB group (including a E3LB group) via a linker group.

Preferred heterocyclyl groups for $R^{3'}$ of I-G through I-I include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

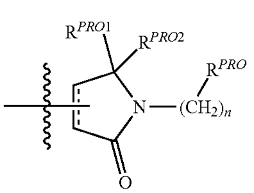

or

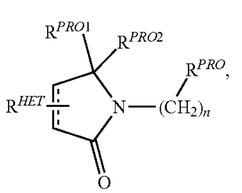

, preferably, a

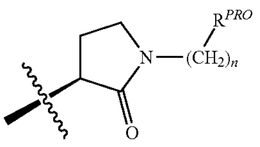

or

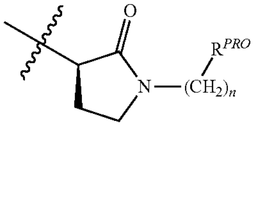

group, wherein:

$R^{PRO}$ of I-G through I-I is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of I-G through I-I are each independently H, an optionally substituted $C_1$-$C_3$ alkyl group or together form a keto group, and each n of I-G through I-I is 0, 1, 2, 3, 4, 5, or 6 (preferably 0 or 1), wherein each of said heterocyclyl groups may be optionally connected to a PB group (including a E3LB group) via a linker group.

In certain alternative preferred embodiments, $R^{2'}$ of I-G through I-I is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:

$R_1$ of I-G through I-I is H or a $C_1$-$C_3$ alkyl group (preferably H);

$X^{R2'}$ of I-G through I-I is an optionally substituted —$CH_2)_n$—, —$CH_2)_n$—$CH(X_v)$=$CH(X_v)$— (cis or trans), —$(CH_2)_n$—CH=CH—, —$(CH_2CH_2O)_n$— or a $C_3$-$C_6$ cycloalkyl group; and $X_v$ of I-G through I-I is H, a halo or a $C_1$-$C_3$ alkyl group which is optionally substituted with one or two hydroxyl groups or up to three halogen groups;

Alkyl of I-G through I-I is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl of I-G through I-I is an optionally substituted phenyl or naphthyl group (preferably, a phenyl group); and HET of I-G through I-I is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

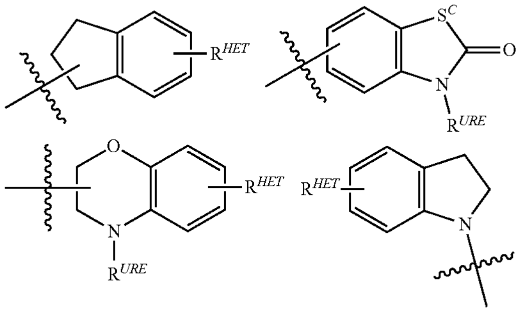

-continued

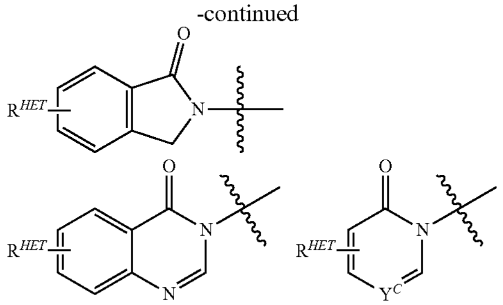

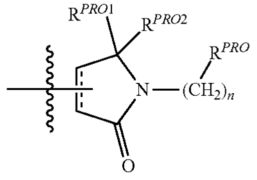

or

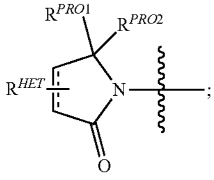

;

$S^c$ of I-G through I-I is $CHR^{SS}$, $NR^{URE}$ or O;

$R^{HET}$ of I-G through I-I is H, CN, $NO_2$, halo(preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of I-G through I-I is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of I-G through I-I is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of I-G through I-I are each independently H, an optionally substituted $C_1$-$C_3$ alkyl group or together form a keto group, and each n of I-G through I-I is independently 0, 1, 2, 3, 4, 5, or 6 (preferably 0 or 1).

Each of said groups may be optionally connected to a PB group (including a E3LB group) via a linker group.

In certain alternative preferred embodiments of the present disclosure, $R^{3'}$ of I-G through I-I is an optionally substituted $-(CH_2)_n-(V)_{n'}-(CH_2)_n-(V)_{n'}-R^{S3'}$ group, an optionally substituted-$(CH_2)_n-N(R_{1'})(C{=}O)_{m'}-(V)_{n'}-R^{S3'}$ group, an optionally substituted $-X^{R3'}$-alkyl group, an optionally substituted $-X^{R3'}$-Aryl group; an optionally substituted $-X^{R3'}$-HET group, an optionally substituted $-X^{R3'}$-Aryl-HET group or an optionally substituted $-X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_{1'}$ is H or a $C_1$-$C_3$ alkyl group (preferably H);

V is O, S or $NR_{1'}$;

$X^{R3'}$ is $-(CH_2)_n-$, $-(CH_2CH_2O)_n-$, $-CH_2)_n-CH(X_v){=}CH(X_v)-$ (cis or trans), $-CH_2)_n-CH{=}CH-$, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$ alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

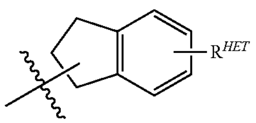

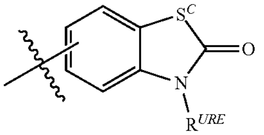

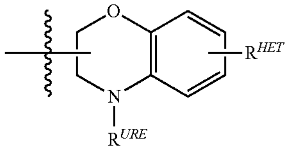

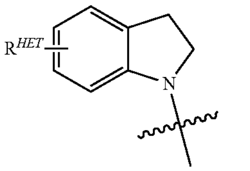

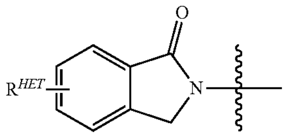

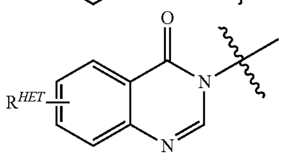

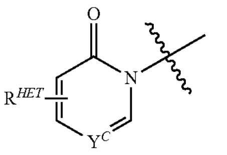

-continued

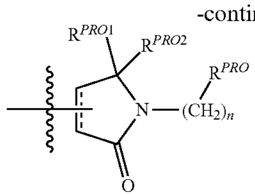

or

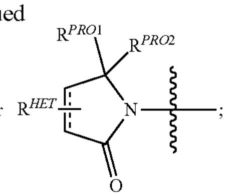

;

$S^c$ of I-G through I-I is $CHR^{SS}$, $NR^{URE}$, or O;

$R^{HET}$ of I-G through I-I is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a $-C(O)(C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of I-G through I-I is N or $C-R^{YC}$, where $R^{Y}c$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C{\equiv}C-R_a$ where $R_a$ is H or a $C_1$-$C_6$ alkyl group (preferably $C_1$-$C_3$ alkyl);

$R^{PRO}$ of I-G through I-I is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of I-G through I-I are each independently H, an optionally substituted $C_1$-$C_3$ alkyl group or together form a keto group;

each n of I-G through I-I is independently 0, 1, 2, 3, 4, 5, or 6 (preferably 0 or 1);

each m' of I-G through I-I is 0 or 1; and each n' of I-G through I-I is 0 or 1;

wherein each of said compounds, preferably on the alkyl, Aryl or Het groups, is optionally connected to a PB group (including a E3LB group) via a linker.

In alternative embodiments, $R^{3'}$ of I-G through I-I is $-(CH_2)_n$-Aryl, $-(CH_2CH_2O)_n$-Aryl, $-(CH_2)_n$-HET or $-(CH_2CH_2O)_n$—HET, wherein:

said Aryl of I-G through I-I is phenyl which is optionally substituted with one or two substitutents, wherein said substituent(s) is preferably selected from $-(CH_2)_nOH$, $C_1$-$C_6$ alkyl which itself is further optionally substituted with CN, halo (up to three halo groups), OH, $-(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, or said Aryl group of I-G through I-I is substituted with $-(CH_2)_nOH$, $-(CH_2)_n-O-(C_1$-$C_6)$alkyl, $-(CH_2)_n-O-(CH_2)_n-(C_1$-$C_6)$alkyl, $-(CH_2)_n-C(O)(C_0$-$C_6)$ alkyl, $-(CH_2)_n-C(O)O(C_0$-$C_6)$alkyl, $-(CH_2)_n-OC(O)(C_0$-$C_6)$alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted $-(CH_2)_n-(V)_{m'}-CH_2)_n-(V)_{m'}-(C_1$-$C_6)$alkyl group, a $-(V)_{m'}-(CH_2CH_2O)_n-R^{PEG}$ group where V is O, S or $NR_{1'}$, $R_{1'}$, is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of I-G through I-I is optionally substituted with a heterocyclyl, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

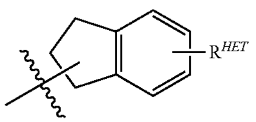
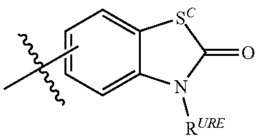
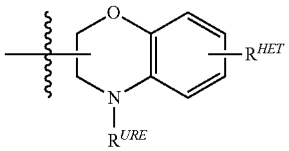
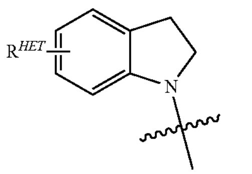
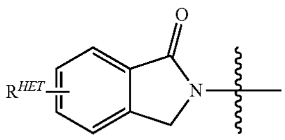
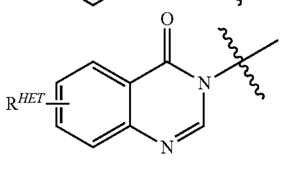
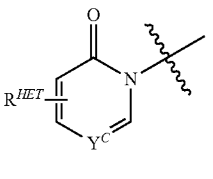

-continued

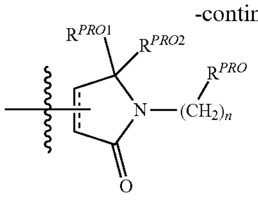
or
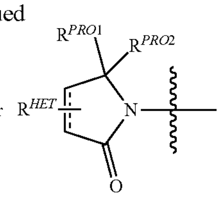

$S^c$ of I-G through I-I is $CHR^{SS}$, $NR^{URE}$ or O;

$R^{HET}$ of I-G through I-I its H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted $O-(C_1$-$C_6$ alkyl) (preferably substituted with one or two hydroxyl groups or up to three halo groups) or an optionally substituted $-C(O)(C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a $-C(O)(C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of I-G through I-I is N or $C-R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group $-C\equiv C-R_a$ where $R_a$ is H or a $C_1$-$C_6$ alkyl group (preferably $C_1$-$C_3$ alkyl);

$R^{PRO}$ of I-G through I-I is H, optionally substituted $C_1$-$C_6$ alkyl or an optionally substituted aryl (phenyl or napthyl), heteroaryl or heterocyclyl group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of I-G through I-I are each independently H, an optionally substituted $C_1$-$C_3$ alkyl group or together form a keto group;

HET of I-G through I-I is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

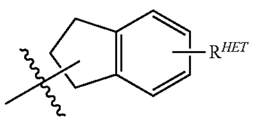
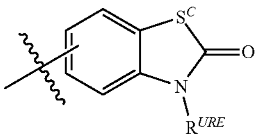
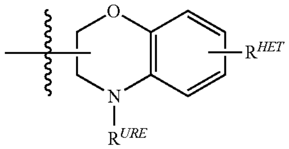
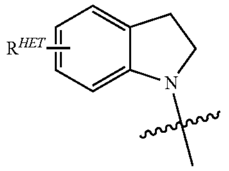
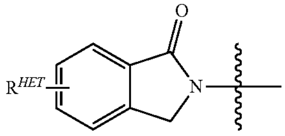
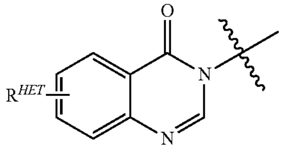
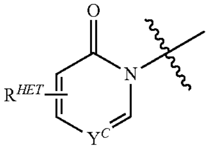
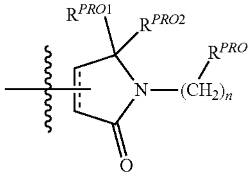
or
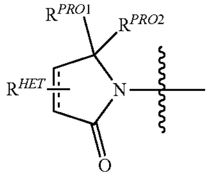

$S^c$ of I-G through I-I is $CHR^{SS}$, $NR^{URE}$ or O;

$R^{HET}$ of I-G through I-I is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$, where $R_a$ is H or a $C_1$-$C_6$ alkyl group (preferably $C_1$-$C_3$ alkyl);

$R^{SS}$ of I-G through I-I is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of I-G through I-I is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocyclyl, for example piperidine, morpholine, pyrrolidine, tetrahydrofuran, tetrahydrothiophene, piperidine, piperazine, each of which is optionally substituted;

$Y^C$ of I-G through I-I is N or C—$R^{YC}$, where $R^Y$c is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of I-G through I-I is H, optionally substituted $C_1$-$C_6$ alkyl or an optionally substituted aryl, heteroaryl or heterocyclyl group;

$R^{PRO1}$ and $R^{PRO2}$ of I-G through I-I are each independently H, an optionally substituted $C_1$-$C_3$ alkyl group or together form a keto group;

each m' of I-G through I-I is independently 0 or 1; and each n of I-G through I-I is independently 0, 1, 2, 3, 4, 5, or 6 (preferably 0 or 1), wherein each of said compounds, preferably on said Aryl or HET groups, is optionally connected to a PB group (including a E3LB group) via a linker group.

In still additional embodiments, preferred compounds include those according to the chemical structure:

L-i

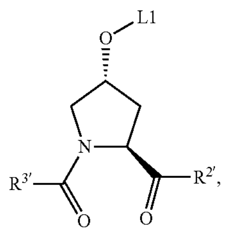

wherein:

$R^{2'}$ of I-I is a —NH—$CH_2$-Aryl-HET (preferably, a phenyl linked directly to a methyl substituted thiazole);

$R^{3'}$ of I-I is a —$CHR^{CR3'}$—NH—C(O)—$R^{3P1}$ group or a —$CHR^{CR3'}$—$R^{3P2}$ group;

$R^{CR3'}$ of I-I is a $C_1$-$C_4$ alkyl group, preferably methyl, isopropyl or tert-butyl;

$R^{3P1}$ of I-I is $C_1$-$C_3$ alkyl (preferably methyl), an optionally substituted oxetane group (preferably methyl substituted, a —$(CH_2)_nOCH_3$ group where n is 1 or 2 (preferably 2), or a

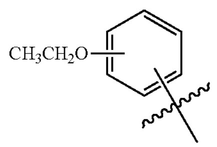

group (the ethyl ether group is preferably meta-substituted on the phenyl moiety), a morpholino group (linked to the carbonyl at the 2- or 3-position;

$R^{3P2}$ of I-I is a

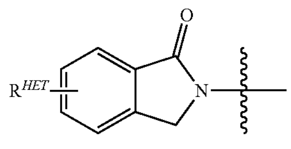

group;

Aryl of I-I is phenyl;

HET of I-I is an optionally substituted thiazole or isothiazole; and $R^{HET}$ of I-I is H or a halo group (preferably H);

or a pharmaceutically acceptable salt, stereoisomer, solvate or polymorph thereof, wherein each of said compounds is optionally connected to a PB group (including a E3LB group) via a linker group.

In certain aspects, bifunctional compounds comprising a ubiquitin E3 ligase binding moiety (E3LB), wherein E3LB is a group according to the chemical structure:

I-J

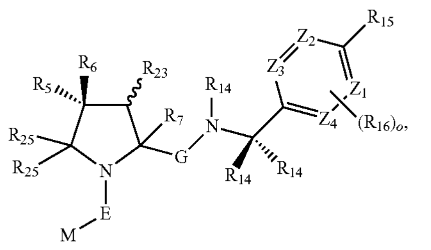

wherein:

each $R_5$ and $R_6$ of I-J is independently OH, SH, or optionally substituted alkyl or $R_5$, $R_6$, and the carbon atom to which they are attached form a carbonyl;

$R_7$ of I-J is H or optionally substituted alkyl;

E of I-J is a bond, C═O, or C═S;

G of I-J is a bond, optionally substituted alkyl, —COOH or C═J;

J of I-J is O or N—$R_8$;

$R_8$ of I-J is H, CN, optionally substituted alkyl or optionally substituted alkoxy;

M of I-J is optionally substituted aryl, optionally substituted heteroaryl, optionally substituted heterocyclyl or

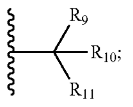

each $R_9$ and $R_{10}$ of I-J is independently H; optionally substituted alkyl, optionally substituted cycloalkyl, optionally substituted hydroxyalkyl, optionally substituted thioalkyl, a disulphide linked I-J, optionally substituted heteroaryl, or haloalkyl; or $R_9$, $R_{10}$, and the carbon atom to which they are attached form an optionally substituted cycloalkyl;

$R_{11}$ of I-J is optionally substituted heterocyclyl, optionally substituted alkoxy, optionally substituted heteroaryl, optionally substituted aryl, or

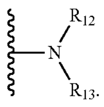

$R_{12}$ of I-J is H or optionally substituted alkyl;

$R_{13}$ of I-J is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each $R_{14}$ of I-J is independently H, haloalkyl, optionally substituted cycloalkyl, optionally substituted alkyl, an azetidine, optionally substituted alkoxy, or optionally substituted heterocyclyl;

$R_{15}$ of I-J is H, CN, optionally substituted heteroaryl, haloalkyl, optionally substituted aryl, optionally substituted alkoxy, or optionally substituted heterocyclyl;

each $R_{16}$ of I-J is independently halo, optionally substituted alkyl, optionally substituted haloalkyl, optionally substituted CN, or optionally substituted haloalkoxy;

each $R_{25}$ of I-J is independently H or optionally substituted alkyl; or both $R_{25}$ groups can be taken together to form an oxo or optionally substituted cycloalkyl group;

$R_{23}$ of I-J is H or OH;

wherein one of $R_{23}$, $R_5$, or $R_6$ is O-L1.

$Z_1$, $Z_2$, $Z_3$, and $Z_4$ of I-J are independently C or N; and of I-J is 0, 1, 2, 3, or 4, or a pharmaceutically acceptable salt, stereoisomer, solvate or polymorph thereof.

In certain embodiments, wherein G of I-J is C=J, J is O, $R_7$ is H, each $R_{14}$ is H, and o is 0.

In certain embodiments, wherein G of I-J is C=J, J is O, $R_7$ is H, each $R_{14}$ is H, $R_{15}$ is optionally substituted heteroaryl, and o is 0. In other instances, E is C═O and M is

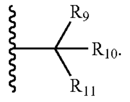

In certain embodiments, wherein E of I-J is C═O, $R_{11}$ is optionally substituted heterocyclyl or

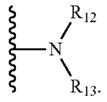

and M is

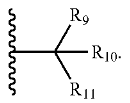

In certain embodiments, wherein E of I-J is C═O, M is

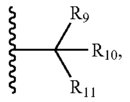

and $R_{11}$ is

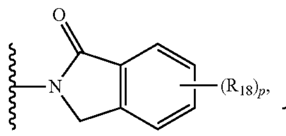 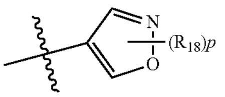 or

-continued

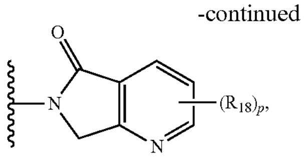

each $R_{18}$ is independently H, halo, optionally substituted alkoxy, cyano, optionally substituted alkyl, haloalkyl, or haloalkoxy; and p is 0, 1, 2, 3, or 4.

In certain embodiments, each $R_{14}$ is independently substituted with at least one of H, hydroxyl, halo, amine, amide, alkoxy, alkyl, haloalkyl, or heterocyclic.

In certain embodiments, $R_{15}$ of I-J is a group according to

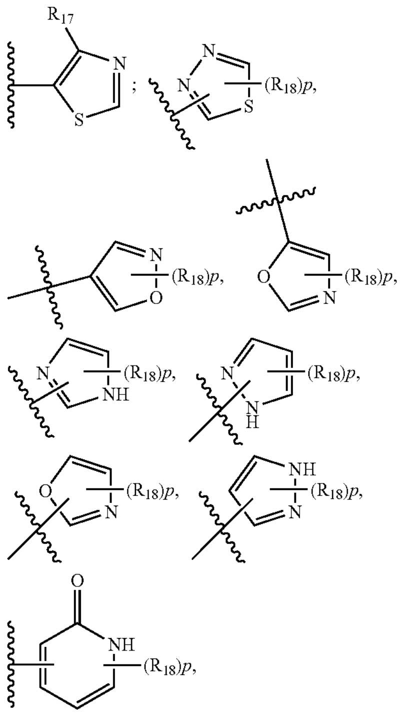

CN, or a haloalkyl, and each $R_{18}$ is independently H, halo, optionally substituted alkoxy, cyano, aminoalkyl, amidoalkyl, optionally substituted alkyl, haloalkyl, or haloalkoxy; and p is 0, 1, 2, 3, or 4.

In certain embodiments, E3LB is a chemical structure:

I-K

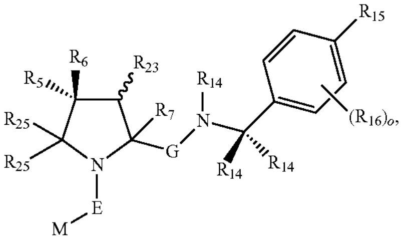

wherein:

G of I-K is C=J, J is O;

$R_7$ of I-K is H;

each $R_{14}$ of I-K is independently H, an amide, an alkyl, e.g., methyl, optionally substituted with one or more $C_1$-$C_6$ alkyl groups or C(O)NR'R";

R' and R" are each independently H, optionally substituted alkyl, or cycloalkyl;

of I-K is 0;

$R_{15}$ of I-K is defined as above for I-J;

$R_{16}$ of I-K is defined is as above for I-J; and $R_{17}$ of I-K is H, halo, optionally substituted cycloalkyl, optionally substituted alkyl, optionally substituted alkenyl, and haloalkyl.

In other instances, $R_{17}$ of I-K is alkyl (e.g., methyl) or cycloalkyl (e.g., cyclopropyl).

In other embodiments, E3LB is according to the chemical structure:

I-K

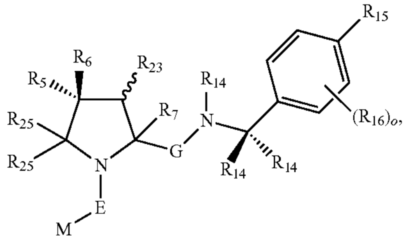

wherein:

G of I-K is C=J, J is O;

$R_7$ of I-K is H;

each R1 of I-K is H;

of I-K is 0; and $R_{15}$ of I-K is selected from the group consisting of optionally substituted:

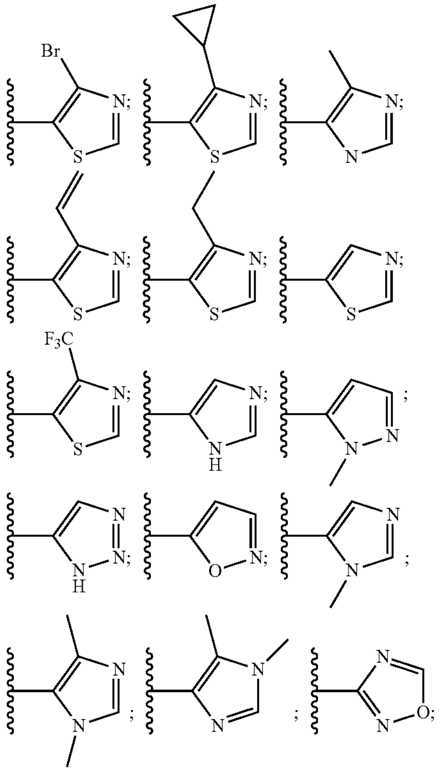

-continued
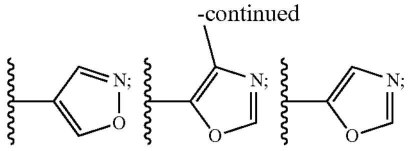
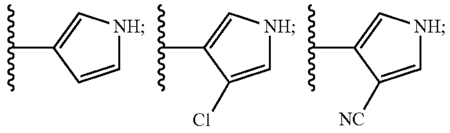
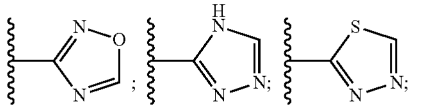
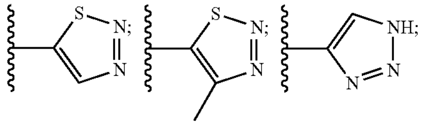
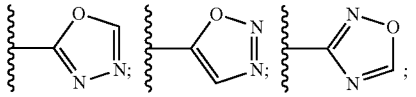
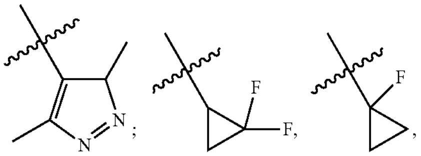
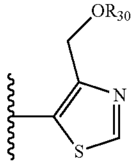
and
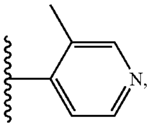
wherein $R_{30}$ of I-K is H or an optionally substituted alkyl.
In other embodiments, E3LB is a group according to the chemical structure:
I-K
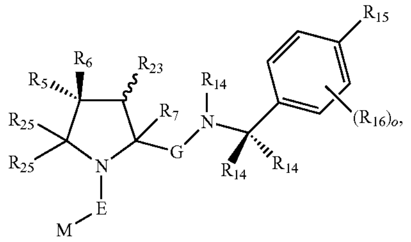
wherein:
E of I-K is C═O;
M of I-K is
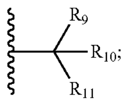
and
$R_{11}$ of I-K is selected from the group consisting of optionally substituted:
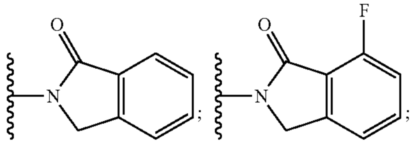
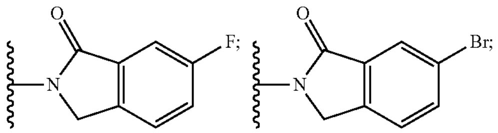
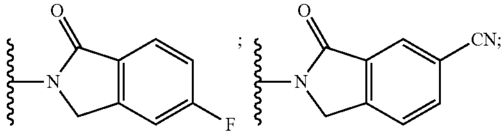
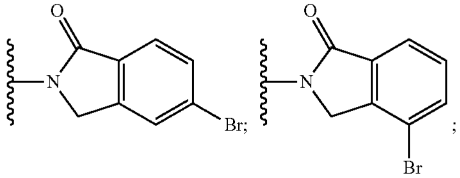
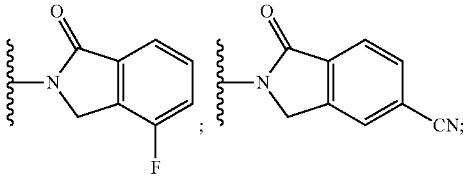
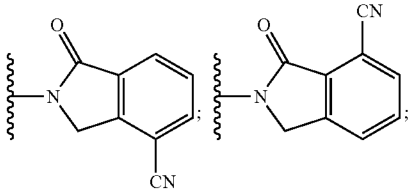
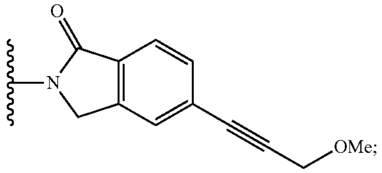
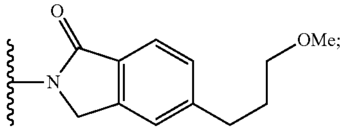
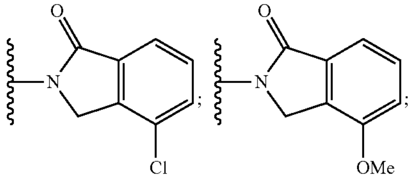
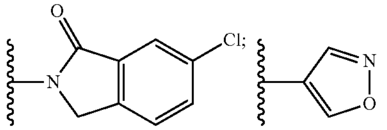
and
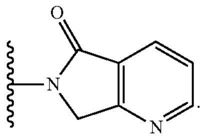 [SMILES: *N1Cc2ncccc2C1=O]

In still other embodiments, a compound of the chemical structure,

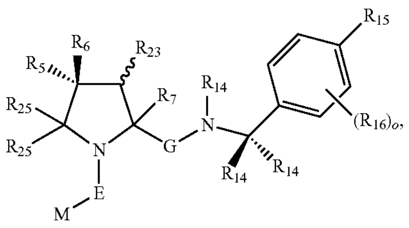

wherein:

E of I-K is C═O;

$R_{11}$ of I-K is

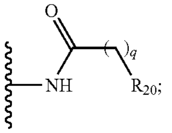

and

M of I-K is

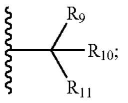

q of I-K is 1 or 2;

$R_{20}$ of I-K is H, optionally substituted alkyl, optionally substituted cycloalkyl, optionally substituted aryl, or

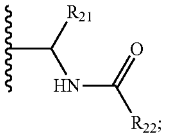

$R_{21}$ of I-K is H or optionally substituted alkyl; and $R_{22}$ of I-K is H, optionally substituted alkyl, optionally substituted alkoxy, or haloalkyl.

In any embodiment described herein, $R_{11}$ of I-J or I-K is selected from the group consisting of.

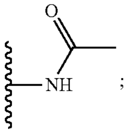 ; 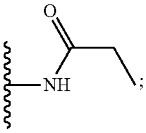 ; 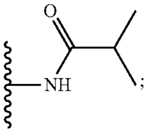 ;

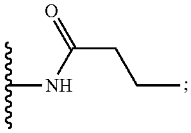 ; 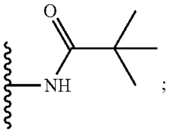 ;

-continued

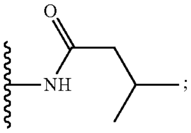 ; 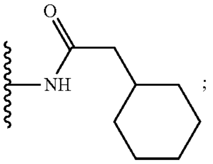 ;

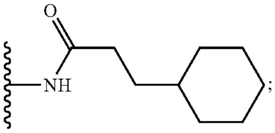 ; 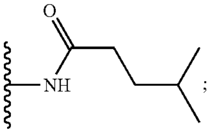 ;

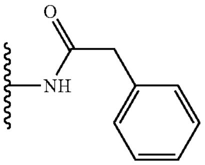 ; 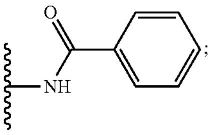 ;

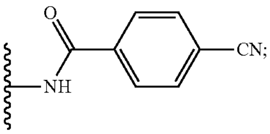 ; 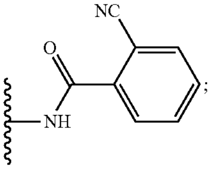 ;

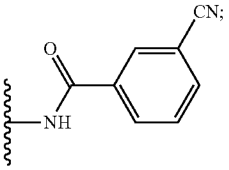

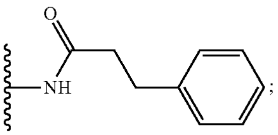 ;

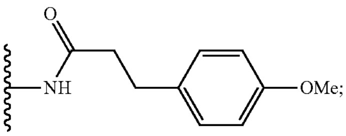

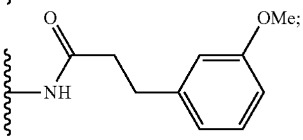

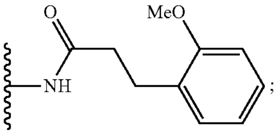 ;

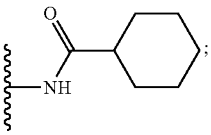 ; 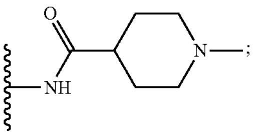 ;

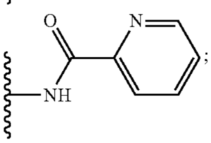 ; 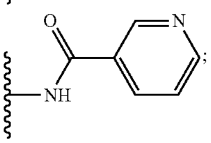 ;

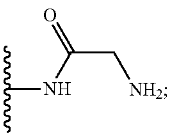 ; 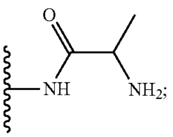 ; 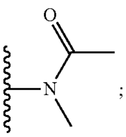 ;

-continued
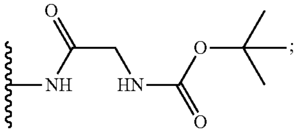
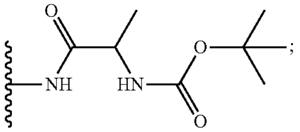
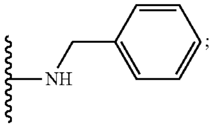
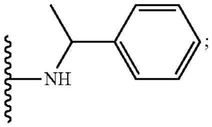
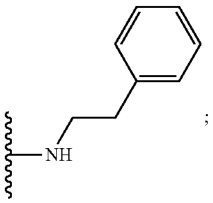
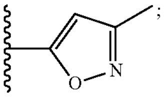
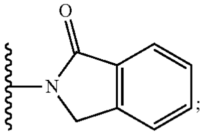
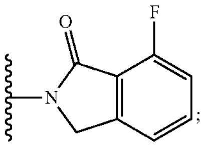
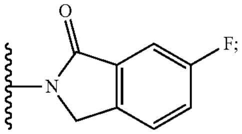
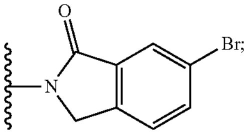
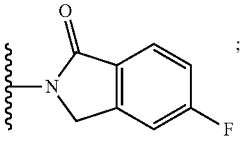
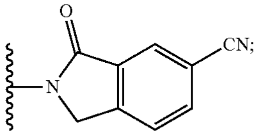
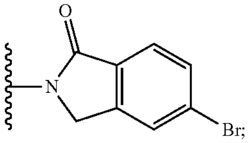
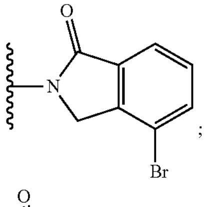
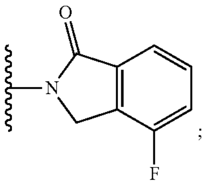
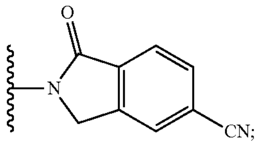
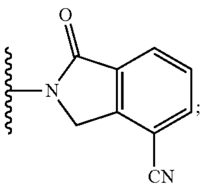
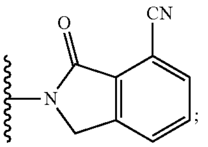
-continued
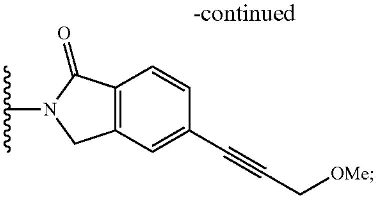
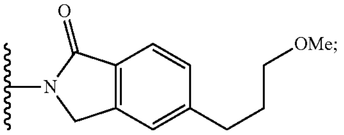
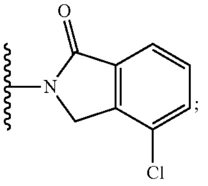
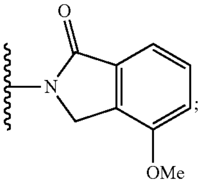
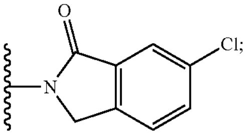
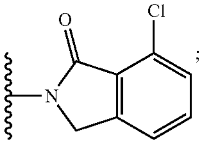
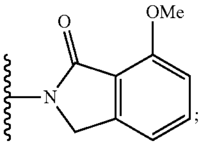
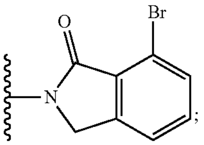
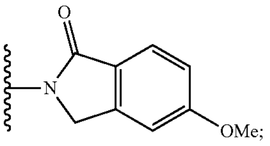
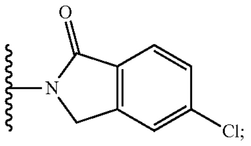
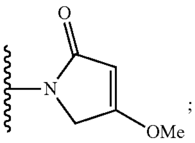
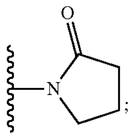
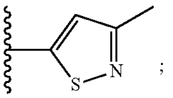
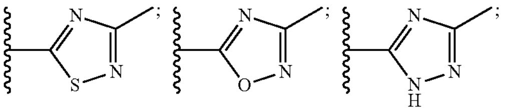
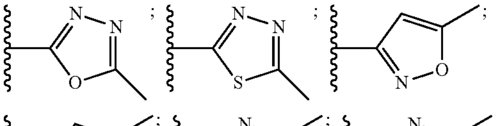
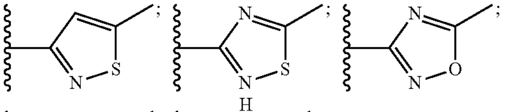
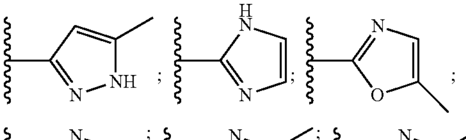
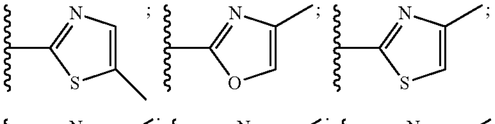
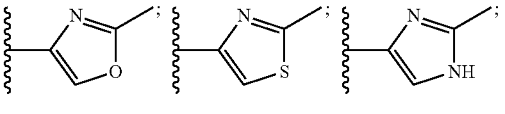

-continued
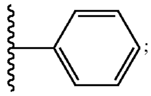 ; 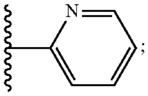 ; 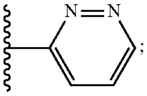 ;
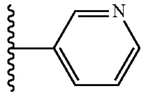 ; 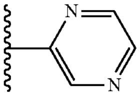 ; 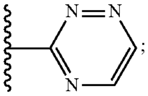 ; and
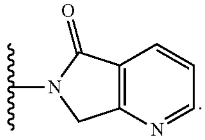 .
In certain embodiments, $R_{11}$ of I-J or I-K is selected from the group consisting of:
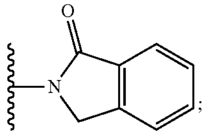 ; 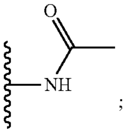 ;
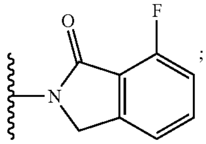 ; 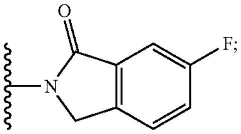
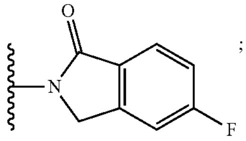 ; 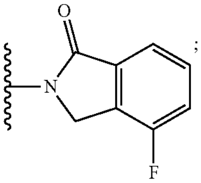 ;
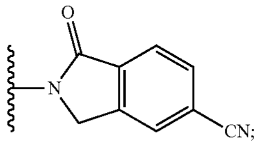 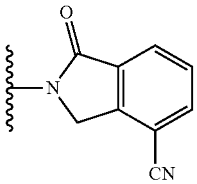 ;
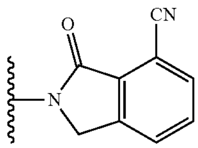 ; 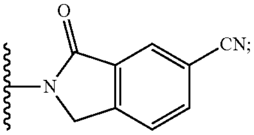
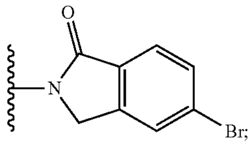 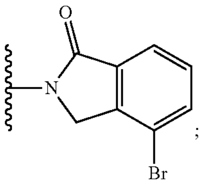 ;
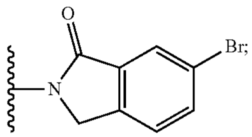 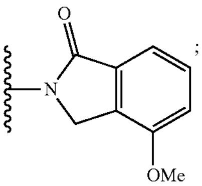 ;
-continued
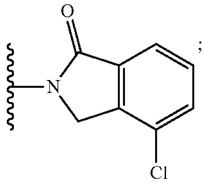 ; 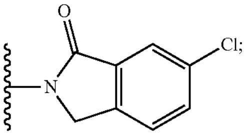
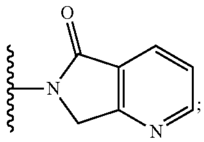 ;
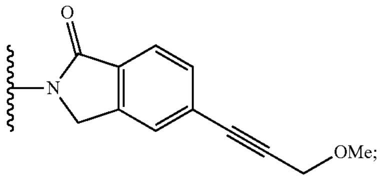
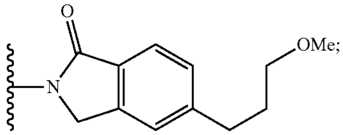
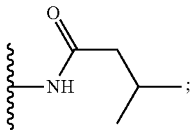 ; 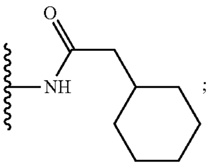 ;
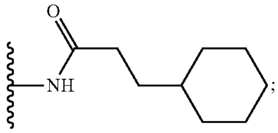 ; 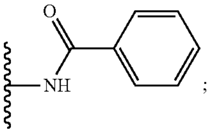 ;
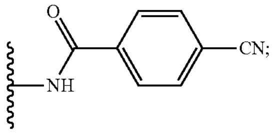
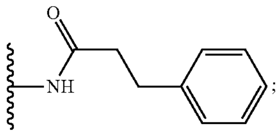 ;
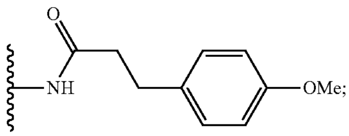
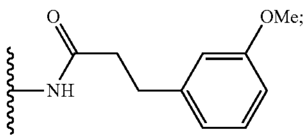
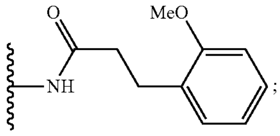 ; 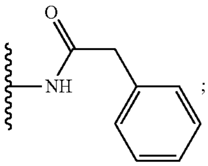 ;

-continued

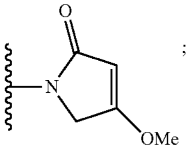
;
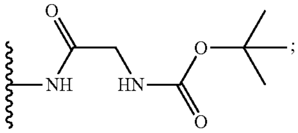
;
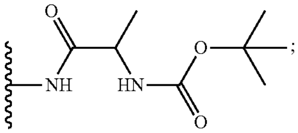
;
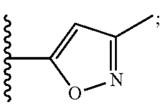
;
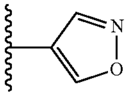
;
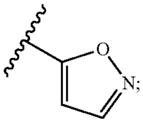
;
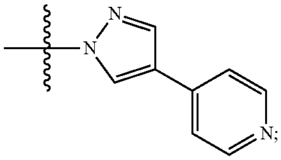
;
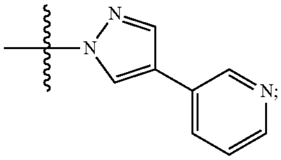
;
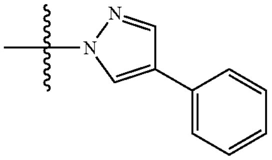
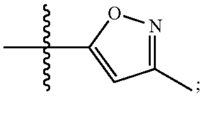
;
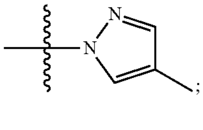
;
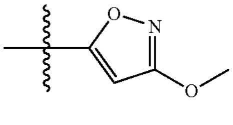
;
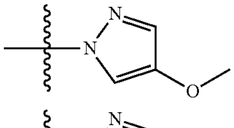
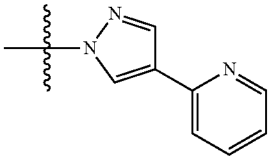
and -continued

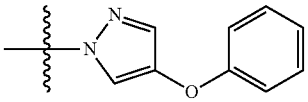

In certain embodiments, E3LB is a group according to the chemical structure:

I-L

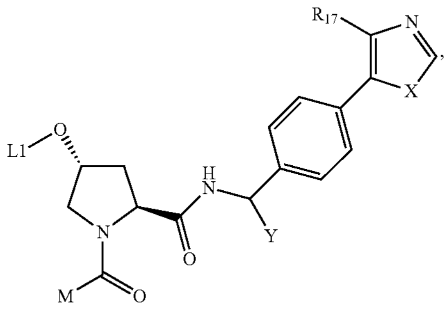
, wherein:

X of I-L is O or S;

Y of I-L is H, methyl or ethyl;

$R_{17}$ of I-L is H, methyl, ethyl, hydoxymethyl or cyclopropyl;

M of I-L is optionally substituted aryl, optionally substituted heteroaryl, or

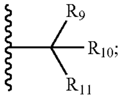
;

$R_9$ of I-L is H;

$R_{10}$ of I-L is H, optionally substituted alkyl, optionally substituted haloalkyl, optionally substituted heteroaryl, optionally substituted aryl, optionally substituted hydroxyalkyl, optionally substituted thioalkyl or cycloalkyl;

$R_{11}$ of I-L is optionally substituted heteroaromatic, optionally substituted heterocyclyl, optionally substituted aryl or

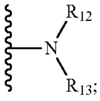
;

$R_{12}$ of I-L is H or optionally substituted alkyl; and $R_{13}$ of I-L is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate.

In some embodiments, E3LB is a group according to the chemical structure:

I-M

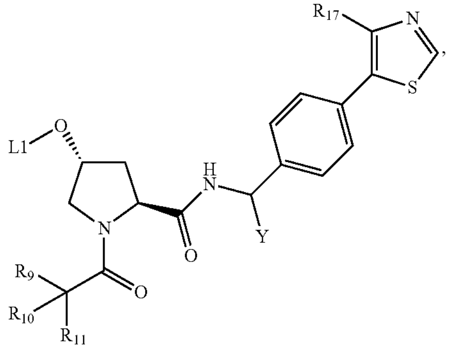

wherein:

Y of I-M is H, methyol or ethyl $R_9$ of I-M is H;

$R_{10}$ is isopropyl, tert-butyl, sec-butyl, cyclopentyl, or cyclohexyl;

$R_{11}$ of I-M is optionally substituted amide, optionally substituted isoindolinone, optionally substituted isooxazole, optionally substituted heterocyclyls.

In other preferred embodiments of the disclosure, E3LB is a group according to the chemical structure:

I-N

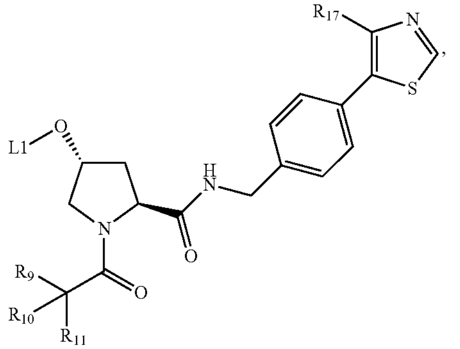

wherein:

$R_{17}$ of I-N is methyl, ethyl, or cyclopropyl; and $R_9$, $R_{10}$, and $R_{11}$ of I-N are as defined above. In other instances, $R_9$ is H; and $R_{10}$ of I-N is H, alkyl, or cycloalkyl (preferably, isopropyl, tert-butyl, sec-butyl, cyclopentyl, or cyclohexyl).

In other preferred embodiments of the disclosure, E3LB is a group according to the chemical structure:

I-O

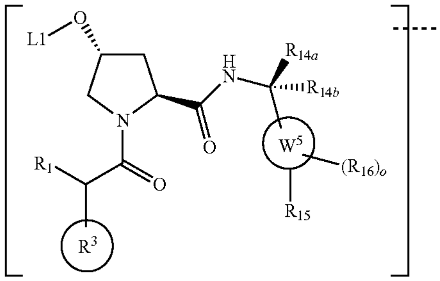

or

-continued

I-P

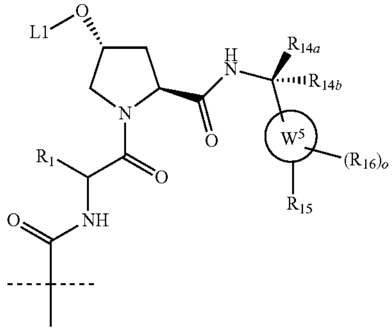

or a pharmaceutically acceptable salt thereof, wherein.

$R^1$ is H, optionally substituted alkyl or optionally substituted cycloalkyl;

$R_3$ is an optionally substituted 5-6 membered heteroaryl;

$W^5$ is optionally substituted phenyl, optionally substituted napthyl or optionally substituted pyridinyl;

one of $R_{14a}$ and $R_{14b}$ is H, optionally substituted alkyl, optionally substituted haloalkyl (e.g., fluoroalkyl), optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR_{26}$, $CONR_{27a}R_{27b}$, $NHCOR_{26}$, or $NHCH_3COR_{26}$; and the other of $R_{14a}$ and $R_{14b}$ is H; or $R_{14a}$, $R_{14b}$, together with the carbon atom to which they are attached, form an optionally substituted 3 to 6 membered cycloalkyl, heterocycloalkyl, spirocycloalkyl or spiroheterocyclyl, wherein the spiroheterocyclyl is not epoxide or aziridine;

$R_{15}$ is CN, optionally substituted fluoroalkyl,

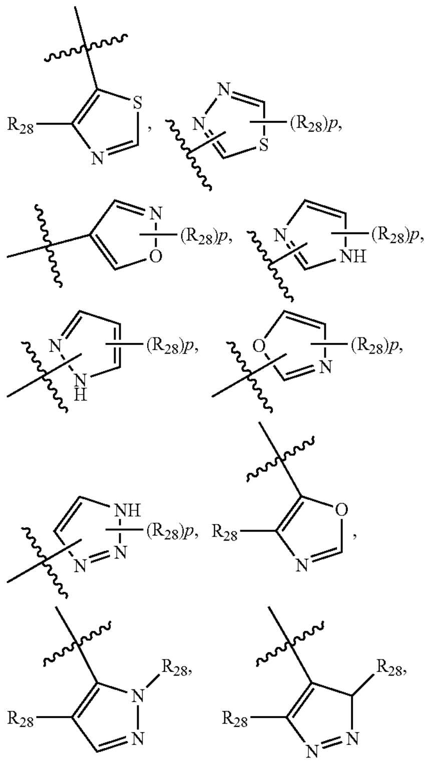

-continued

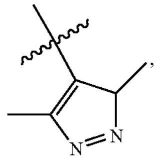
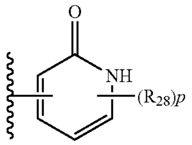

optionally substituted

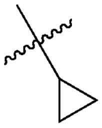
(e.g.,
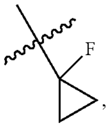
,
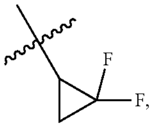

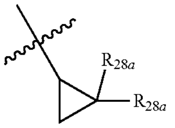
or
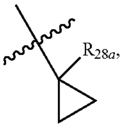

wherein $R_{28a}$ is halo, optionally substituted alkyl or fluoroalkyl, or

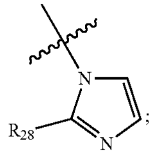
;

each $R_{16}$ is independently selected from halo, CN, optionally substituted alkyl, optionally substituted haloalkyl, hydroxy, or haloalkoxy;

each $R_{26}$ is independently H, optionally substituted alkyl or $NR_{27a}R_{27b}$;

each $R_{27a}$ and $R_{27b}$ is independently H, optionally substituted alkyl, optionally substituted cycloalkyl, or $R_{27a}$ and $R_{27b}$ together with the nitrogen atom to which they are attached form a 4-6 membered heterocyclyl;

each $R_{28}$ is independently H, halogen, CN, optionally substituted aminoalkyl, optionally substituted amidoalkyl, optionally substituted haloalkyl, optionally substituted alkyl, optionally substituted alkoxy, optionally substituted heteroalkyl, optionally substituted alkylamine, optionally substituted hydroxyalkyl, amine, optionally substituted alkynyl, or optionally substituted cycloalkyl;

is 0, 1 or 2; and p is 0, 1, 2, 3, or 4.

In any of the aspects or embodiments described herein, the E3LB is of the formula:

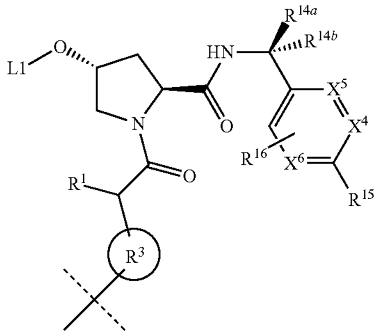
or

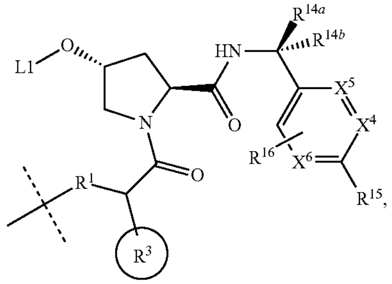

wherein:

each of $X^4$, $X^5$, and $X^6$ is selected from CH and N, wherein no more than 2 are N;

$R^1$ is $C_{1-6}$ alkyl;

$R^3$ is the same as defined for I-O and IP one of $R^{14a}$ and $R^{14b}$ is H, optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H; or $R^{14a}$ and $R^{14b}$, together with the carbon atom to which they are attached, form an optionally substituted 3 to 5 membered cycloalkyl, heterocycloalkyl, spirocycloalkyl or spiroheterocyclyl, wherein the spiroheterocyclyl is not epoxide or aziridine;

each $R_{27a}$ and $R_{27b}$ is independently H $C_{1-6}$ alkyl or cyclolkyl;

q is 1, 2, 3 or 4;

$R^{15}$ is optionally substituted

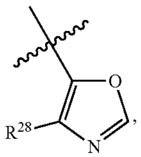
,
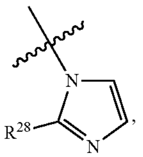
,
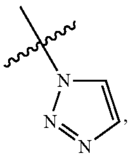
,
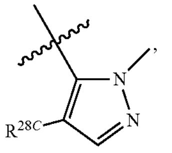

or CN;

$R_{28}$ is H, methyl, $CH_2N(Me)_2$, $CH_2OH$, $CH_2O(C_{1-4}$ alkyl), $CH_2NHC(O)C_{1-4}$ alkyl, $NH_2$,

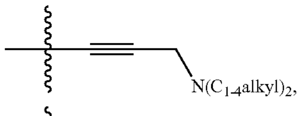

or

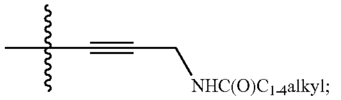

In any aspect or embodiment described herein, $R^{14a}$ and $R^{14b}$ are selected from: H, $C_{1-4}$ alkyl, $C_{1-4}$ cycloalkyl, $C_{1-4}$ haloalkyl, $C_{1-4}$ hydroxyalkyl, $C_{1-4}$ alkyloxyalkyl, $C_{1-4}$ alkyl-$NR_{27a}R_{27b}$ and $CONR_{27a}R_{27b}$.

In any aspect or embodiment described herein, at least one of $R^{14a}$ and $R^{14b}$ is H (e.g., both $R^{14a}$ and $R^{14b}$ are H).

In any aspect or embodiment described herein, at least one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$. Alternatively, in any aspect or embodiment described herein, one of $R^{14a}$ and $R^{14b}$ is optionally substituted alkyl, optionally substituted haloalkyl, optionally substituted alkoxy, optionally substituted hydroxyl alkyl, optionally substituted alkylamine, optionally substituted heterolkyl, optionally substituted alkyl-heterocycloalkyl, optionally substituted alkoxy-heterocycloalkyl, $COR^{26}$, $CONR^{27a}R^{27b}$, $NHCOR^{26}$, or $NHCH_3COR^{26}$; and the other of $R^{14a}$ and $R^{14b}$ is H.

In any aspect or embodiment described herein, $R^{14a}$ and $R^{14b}$ together with the carbon atom to which they are attached form

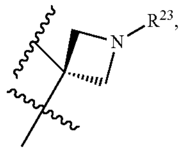

wherein $R^{23}$ is selected from H, $C_{1-4}$ alkyl, $—C(O)C_{1-4}$ alkyl.

In other preferred embodiments of the disclosure, E3LB is a group according to the chemical structure:

I-Q

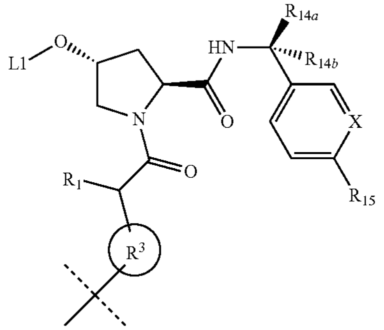

or

-continued

I-R

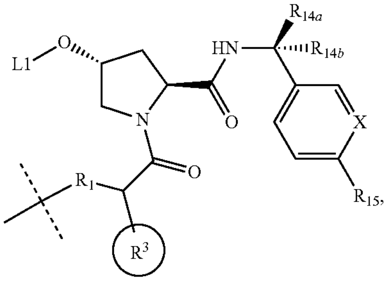

or a pharmaceutically acceptable salt thereof, wherein.

X is CH or N; and $R_1$, $R_3$, $R_{14a}$, $R_{14b}$, and $R_{15}$ of I-Q and I-R are the same as defined for I-O and I-P.

In any of the aspects or embodiments described herein, the E3LB as described herein may be a pharmaceutically acceptable salt, enantiomer, diastereomer, solvate or polymorph thereof. In addition, in any of the aspects or embodiments described herein, the E3LB as described herein may be coupled to a PB directly via a bond or by a chemical linker.

b. BRD4 or ERα Protein Binding Group (PB)

The PB component is a group which binds to a target protein intended to be degraded. PB groups include, for example, any moiety which binds to a protein specifically (binds to a target protein). Accordingly, the PB component of a CIDE is any peptide or small molecule that bind protein targets selected from the group consisting of ERα and BRD4, including all variants, mutations, splice variants, indels and fusions of these target proteins listed. The PB are selected from small molecule target protein binding moieties. Such small molecule target protein binding moieties also include pharmaceutically acceptable salts, enantiomers, solvates and polymorphs of these compositions, as well as other small molecules that may target a protein of interest.

i. BRD4

1. Tetracyclics

In embodiments, the CIDE contains a residue of a tetracyclic bromodomain inhibitor such as the inhibitors described in US2016/0039821. The inhibitor has the following general formula:

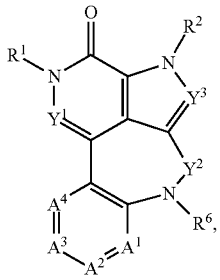

In certain embodiments of formula (I), $Y^1$ is N or CH.

In certain embodiments, $Y^1$ is N.

In certain embodiments, $Y^1$ is CH.

In certain embodiments of formula (I), $R^1$ is $CD_3$, $C_1$-$C_3$ alkyl, or $C_1$-$C_3$ haloalkyl.

In certain embodiments, $R^1$ is $C_1$-$C_3$ alkyl. In some such embodiments, $R^1$ is methyl.

In certain embodiments of formula (I), $R^2$ is H or $C_1$-$C_3$ alkyl.

In certain embodiments, $R^2$ is H or methyl.

In certain embodiments, $R^2$ is H.

In certain embodiments, $R^2$ is $C_1$-$C_3$ alkyl. In some such embodiments, $R^2$ is methyl.

In certain embodiments of formula (I), $Y^3$ is N or $CR^3$.

In certain embodiments, $Y^3$ is N.

In certain embodiments, $Y^3$ is $CR^3$.

In certain embodiments of formula (I), $R^3$ is H, —CN, $C_1$-$C_6$ alkyl, $C_2$-$C_6$ alkenyl, $C_2$-$C_6$ alkynyl, halogen, $C_1$-$C_6$ haloalkyl, —(O)$R^{3a}$, —C(O)O$R^{3a}$, —C(O)N$R^{3b}R^{3c}$, —S(O)$R^{3d}$, —S(O)$_2R^{3a}$, —S(O)$_2$N$R^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{3a}$, —C(O)O$R^{3a}$, —C(O)N$R^{3b}R^{3c}$, —C(O)N($R^{3b}$)N$R^{3b}R^{3c}$, —S(O)$R^{3d}$, —S(O)$_2R^{3a}$, —S(O)$_2$N$R^{3b}R^{3c}$, —O$R^{3a}$, —OC(IO)$R^{3d}$, —N$R^{3b}R^{3c}$, N($R^{3b}$)C(O)$R^{3d}$, N($R^{3a}$)SO$_3R^{3d}$, N($R^{3b}$)C(O)O$R^{3d}$, N($R^{3b}$)C(O)N$R^{3b}R^{3c}$, N($R^{3b}$)SO$_2$N$R^{3b}R^{3c}$, and N($R^{3b}$)C(N$R^{3b}R^{3c}$)N$R^{3b}R^{3c}$.

In certain embodiments, $R^3$ is H, —CN, —C(O)$R^{3c}$, —C(O)O$R^{3a}$, —C(O)N$R^{3b}R^{3c}$, or $C_1$-$C_6$ alkyl, wherein the $C_1$-$C_6$ alkyl is optionally substituted with a substituent selected from the group consisting of $G^1$, —N$R^{3b}R^{3c}$, N($R^{3b}$)C(O)$R^{3d}$, N($R^{3b}$)SO$_2R^{3d}$, N($R^{3b}$)C(O)O$R^{3d}$, N($R^{3b}$)C(O)N$R^{3b}R^{3c}$, and N($R^{3b}$)SO$_2$N$R^{3b}R^{3c}$. In some such embodiments, the $G^1$ group is optionally substituted heterocycle. In some such embodiments, the $C_1$-$C_6$ alkyl is substituted with a $G^1$ group, wherein the $G^1$ group is piperidinyl, piperazinyl, or morpholinyl, each of which is optionally substituted with 1 or 2 $C_1$-$C_6$ alkyl. In some such embodiments, the $C_1$-$C_6$ alkyl is substituted with a $G^1$ group, wherein the $G^1$ group is piperazinyl or morpholinyl, each of which is optionally substituted with 1 or 2 $C_1$-$C_6$ alkyl.

In certain embodiments, $R^3$ is H, —C(O)N$R^{3b}R^{3c}$, —CN, or $C_1$-$C_6$ alkyl which is substituted with a $G^1$ group. In some such embodiments, the $C_1$-$C_6$ alkyl is substituted with a $G^1$ group, wherein the $G^1$ group is an optionally substituted $C_4$-$C_6$ heterocycle. In some such embodiments, the $C_1$-$C_6$ alkyl is substituted with a $G^1$ group, wherein the $G^1$ group is piperidinyl, piperazinyl, or morpholinyl, each of which is optionally substituted with 1 or 2 $C_1$-$C_6$ alkyl.

In certain embodiments, $R^3$ is H, —C(O)$R^{3a}$, or —C(O)N$R^{3b}R^{3c}$. In some such embodiments, $R^{3a}$ is $G^1$. In some such embodiments, $R^{3a}$ is $G^1$ wherein $G^1$ is optionally substituted heterocycle. In some such embodiments, $R^{3b}$ is $G^1$ wherein $G^1$ is piperidinyl, piperazinyl, or morpholinyl, each of which is optionally substituted with 1 or 2 $C_1$-$C_6$ alkyl. In some such embodiments, $R^{3a}$ is $G^1$ wherein $G^1$ is piperazinyl, optionally substituted with 1 or 2 $C_1$-$C_6$ alkyl.

In certain embodiments, $R^3$ is H or —C(O)N$R^{3b}R^{3c}$. In some such embodiments, $R^{3b}$ and $R^{3c}$ are each independently H or $C_1$-$C_6$ alkyl.

In certain embodiments, $R^3$ is H.

In certain embodiments, $R^3$ is —C(O)N$R^{3b}R^{3c}$. In some such embodiments, $R^{3b}$ and $R^{3c}$ are each independently H or $C_1$-$C_3$ alkyl.

In certain embodiments, $R^3$ is $G^1$. In some such embodiments, $G^1$ is optionally substituted monocyclic heteroaryl. In some such embodiments, $G^1$ is optionally substituted pyrazolyl. In some such embodiments, $G^1$ is pyrazolyl substituted with 1 or 2 $C_1$-$C_6$ alkyl.

In certain embodiments of formula (I), $Y^2$ is C(O), S(O)$_2$, or $CR^4R^5$.

In certain embodiments, $Y^2$ is C(O).

In certain embodiments, $Y^2$ is S(O)$_2$.

In certain embodiments, $Y^2$ is $CR^4R^5$.

In certain embodiments of formula (I), $R^4$ is H, deuterium, $C_1$-$C_6$ alkyl, halogen, or $C_1$-$C_6$ haloalkyl.

In certain embodiments, $R^4$ is H or deuterium.

In certain embodiments, $R^4$ is H.

In certain embodiments of formula (I), $R^5$ is H, deuterium, $C_1$-$C_6$ alkyl, $C_2$-$C_6$ alkenyl, $C_2$-$C_6$ alkynyl, halogen, $C_1$-$C_6$ haloalkyl, —C(O)$R^{5a}$, —C(O)O$R^{5a}$, —C(O)N$R^{5b}R^{5c}$, —S(O)$R^{5d}$, —S(O)$_2R^{5a}$, —S(O)$_2$N$R^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —CN, —C(O)$R^{5a}$, —C(O)O$R^{5a}$, —C(O)N$R^{5b}R^{5c}$, —C(O)N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, N($R^{5b}$)SO$_2$N$R^{5b}R^{5c}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, N($R^{5b}$)SO$_2$N$R^{5b}R^{5c}$, and N($R^{5b}$)C(N$R^{5b}R^{5c}$)═N$R^{5b}R^{5c}$.

In certain embodiments, $R^5$ is H, deuterium, $C_1$-$C_6$ alkyl, $C_2$-$C_6$ alkenyl, $C_2$-$C_6$ alkynyl, $C_1$-$C_6$ haloalkyl, —C(O)$R^{5a}$, —C(O)O$R^{5a}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{5a}$, —C(O)O$R^{5a}$, —C(O)N$R^{5b}R^{5c}$, —C(O)N($R^{5b}$)N$R^{3b}R^{4c}$, —O$R^{5a}$, —OC(O)$R^{5d}$, —N$R^{5b}R^{5c}$, N($R^{5b}$)C(O)$R^{5d}$, N($R^{5b}$)SO$_2R^{5d}$, N($R^{5b}$)C(O)O$R^{5d}$, N($R^{5b}$)C(O)N$R^{5b}R^{5c}$, and N($R^{5b}$)SO$_2$N$R^{5b}R^{5c}$.

In certain embodiments, $R^5$ is $C_2$-$C_6$ alkenyl optionally substituted with a $G^1$ group, or $R^5$ is H, deuterium, $C_1$-$C_6$ alkyl, —C(O)$R^{5a}$, —C(O)O$R^{5a}$, —C(O)O$R^{5a}$, or $G^1$; wherein the $C_1$-$C_6$ alkyl is unsubstituted or substituted with a substituent selected from the group consisting of $G^1$, —C(O)$R^{5c}$, —C(O)O$R^{5a}$, —C(O)N$R^{5b}R^{5c}$, —C(O)N($R^{5b}$)N$R^{5b}R^{5c}$, —O$R^{5a}$, —OC(O)$R^{5d}$, —N$R^{5b}R^{5c}$, and N($R^{5b}$)C(N$R^{5b}R^{5c}$)═N$R^{5b}R^{5c}$.

In certain embodiments, $R^5$ is H, deuterium, or $C_1$-$C_6$ alkyl optionally substituted with a substituents selected from the group consisting of —C(O)O$R^{5a}$ or O$R^{5a}$. In some such embodiments, $R^{5a}$ is $C_1$-$C_6$ alkyl.

In certain embodiments, $R^5$ is H.

In certain embodiments of formula (I), $R^6$ is H, $C_1$-$C_6$ alkyl, $C_2$-$C_6$ alkenyl, $C_2$-$C_6$ alkynyl, halogen, $C_1$-$C_6$ haloalkyl, —C(O)$R^{6a}$, —C(O)O$R^{6a}$, —C(O)N$R^{6b}R^{6c}$, —S(O)$_2R^{6c}$, —S(O)$_2$N$R^{6b}R^{6c}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, —CN, —C(O)$R^{6a}$, —C(O)O$R^{6a}$, —C(O)N$R^{6b}R^{6c}$, —C(O)N($R^{6b}$)N$R^{6b}R^{6c}$, —S(O)$R^{6d}$, —S(O)$_2R^{6a}$, —S(O)$_2$N$R^{6b}R^{6c}$, —O$R^{6a}$, —OC(O)$R^{6d}$, —N$R^{6b}R^{6c}$, —N($R^{6b}$)C(O)$R^{6d}$, N($R^{6b}$)SO$_2R^{6d}$, —N($R^{6b}$)C(O)O$R^{6d}$, N($R^{6b}$)C(O)N$R^{6b}R^{6c}$, N($R^{6b}$)SO$_2$N$R^{6b}R^{6c}$, and N($R^{6b}$)C(N$R^{6b}R^{6c}$)═N$R^{6b}R^{6c}$.

In certain embodiments, $R^6$ is H, $C_1$-$C_6$ alkyl, $C_2$-$C_6$ alkenyl, —C(O)$R^{6c}$, —C(O)O$R^6$, —C(O)N$R^{6b}R^{6c}$, —S(O)$_3R^{6a}$, or $G^2$; wherein the $C_1$-$C_6$ alkyl and the $C_2$-$C_6$ alkenyl are each independently unsubstituted or substituted with 1 or 2 substituents independently selected from the group consisting of $G^2$, —CN, —C(O)O$R^{6a}$, —N$R^{6b}R^{6c}$, N($R^{6b}$)C(O)$R^{6d}$, N($R^{6b}$)SO$_2R^{6d}$, N($R^{6b}$)C(O)O$R^{6d}$, N($R^{6c}$)C(O)N$R^{6b}R^{6c}$, and N($R^{6c}$)SO$_2$N$R^{6b}R^{6c}$.

In certain embodiments, $R^6$ is H, $C_1$-$C_6$ alkyl, —C(O)$R^{6a}$, —C(O)O$R^{6a}$, —C(O)N$R^{6b}R^{6c}$, —S(O)$_2R^{6a}$, or $G^2$, wherein the $C_1$-$C_6$ alkyl is unsubstituted or substituted with a substituent selected from the group consisting of $G^2$ and —C(O)O$R^{6a}$ In certain embodiments, $R^6$ is —C(O)$R^{6a}$, —C(O)O$R^{6a}$, —C(O)N$R^{6b}R^{6c}$, $G^2$, or $C_1$-$C_6$ alkyl which is unsubstituted or substituted with a $G^2$ group. In certain embodiments, $R^{6a}$ is $G^2$ or unsubstituted $C_1$-$C_6$ alkyl.

In certain embodiments, $R^6$ is —C(O)O$R^{6c}$. In some embodiments, $R^{6a}$ is $C_1$-$C_6$ alkyl.

In certain embodiments, $R^6$ is $G^2$ or $C_1$-$C_6$ alkyl which is unsubstituted or substituted with a $G^2$ group. In some such embodiments, $R^6$ is optionally substituted aryl, optionally substituted heteroaryl, optionally substituted heterocycle, or optionally substituted cycloalkyl; or $R^6$ is $C_1$-$C_6$ alkyl which is unsubstituted or substituted with a substituent selected from the group consisting of heteroaryl, cycloalkyl, and heterocycle, each of which is optionally substituted. In some such embodiments, $R^6$ is optionally substituted aryl, optionally substituted heteroaryl, or optionally substituted cycloalkyl; or $R^6$ is $C_1$-$C_6$ alkyl which is unsubstituted or substituted with a substituent selected from the group consisting of cycloalkyl and heterocycle, each of which is optionally substituted. In some such embodiments, $R^6$ is phenyl, pyridinyl, pyrimidinyl, pyrazinyl, pyridazinyl, indazolyl, cyclohexyl, tetrahydrofuranyl, tetrahydropyranyl, pyrrolidinyl, piperidinyl, or azepanyl, each of which is optionally substituted, or $R^6$ is $C_1$-$C_6$ alkyl which is unsubstituted or substituted with a $G^1$ group wherein the $G^1$ group is cyclopropyl, cyclohexyl, pyrnolidinyl, piperidinyl, morpholinyl, tetrahydrofuranyl, tetrahydropyranyl, 1,3 dioxolyl, or pyrazolyl, each of which is optionally substituted. In some such embodiments, $R^6$ is optionally substituted phenyl, optionally substituted pyridinyl, or optionally substituted cyclohexyl; or $R^6$ is $C_1$-$C_6$ alkyl which is unsubstituted or substituted with a substituent selected from the group consisting of cyclopropyl and tetrahydrofuranyl, each of which is optionally substituted. In some such embodiments, said optional substituents are independently selected from the group consisting of halogen, —O($C_1$-$C_3$ alkyl), —O($C_1$-$C_3$ haloalkyl), —N(H)C(O)O($C_1$-$C_6$ alkyl), $C_1$-$C_3$ alkyl, and $C_1$-$C_3$ haloalkyl. In some such embodiments, said optional substituents are halogen. In some such embodiments, said halogen if F or Cl.

In certain embodiments of formula (I), $A^1$ is C($R^7$) or N; $A^2$ is C($R^8$) or N; $A^3$ is C($R^9$) or N; and $A^4$ is C($R^{10}$) or N; wherein zero, one, or two or $A^1$, $A^2$, $A^3$, and $A^4$ are N.

In certain embodiments, $A^1$ is C($R^7$), $A^2$ is C($R^8$), $A^2$ is C($R^9$), and $A^4$ is C($R^{10}$).

In certain embodiments, one of $A^1$, $A^2$, $A^3$, and $A^4$ is N. In some such embodiments, $A^1$ is N; $A^2$ is C($R^8$); $A^3$ is C($R^9$); and $A^4$ is C($R^{10}$).

In certain embodiments, two of $A^1$, $A^2$, $A^3$, and $A^4$ are N. In some such embodiments, $A^1$ is N; $A^2$ is C($R^8$); $A^3$ is N; and $A^4$ is C($R^{10}$).

In certain embodiments, $A^1$ is C($R^7$), $A^2$ is C($R^8$), $A^3$ is C($R^9$), and $A^4$ is C($R^{10}$); or $A^1$ is N; $A^2$ is C($R^8$); $A^3$ is C($R^9$); and $A^4$ is C($R^{10}$); or Ai is N; $A^2$ is C($R^8$); $A^3$ is N; and A is C($R^{10}$);

In certain embodiments of formula (I), $R^7$, $R^8$, and $R^9$, are each independently H, $C_1$-$C_6$ alkyl, $C_2$-$C_6$ alkenyl, $C_2$-$C_6$ alkynyl halogen, $C_1$-$C_6$ haloalkyl, —CN, $NO_2$, —O$R^{Y1}$, —OC(O)$R^{Y2}$, —OC(O)N$R^{Y3}R^{Y4}$, —S$R^{Y1}$, —S(O)$_2R^{Y1}$, —S(O)$_2$N$R^{Y3}R^{Y4}$, —C(O)$R^{Y1}$, —C(O)O$R^{Y1}$, —C(O)N$R^{Y3}R^{Y4}$, —N$R^{Y3}R^{Y4}$, —N($R^{Y3}$)C(O)$R^{Y2}$, —N($R^{Y3}$)S(O)$_2R^{Y2}$, —N($R^{Y3}$)C(O)O($R^{Y2}$), —N($R^{Y3}$)C(O)N$R^{Y3}R^{Y4}$, —N($R^{Y3}$)S(O)$_2$N$R^{Y3}R^{Y4}$, $G^3$, —($C_1$-$C_6$ alkylenyl)-CN, —($C_1$-$C_6$ alkylenyl)-O$R^{Y1}$, —($C_1$-$C_6$ alkylenyl)-OC(O)$R^{Y2}$, —($C_1$-$C_6$ alkylenyl)-OC(O)N$R^{Y3}R^{Y4}$, —($C_1$-$C_6$ alkylenyl)-S(O)$_2R^{Y1}$, —($C_1$-$C_6$ alkylenyl)-S(O)$_2$N$R^{Y3}R^{Y4}$, —($C_1$-$C_6$ alkylenyl)-C(O)$R^{Y1}$, —($C_1$-$C_6$ alkylenyl)-C(O)O$R^{Y1}$, —($C_1$-$C_6$ alkylenyl)-C(O)N$R^{Y3}R^{Y4}$, —($C_1$-$C_6$ alkylenyl)-N$R^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)N$R^{Y3}R^{Y4}$, —($C_1$-$C_6$ alkylenyl)-N($R^{Y3}$)S(O)$_2$N$R^{Y3}R^{Y4}$, —($C_1$-$C_6$ alkylenyl)-CN, or ($C_1$-$C_6$ alkylenyl)-$G^3$.

In certain embodiments, $R^7$ is H, halogen, —CN, $C_1$-$C_3$ alkyl, or optionally substituted cyclopropyl.

In certain embodiments, $R^7$ is H, halogen, $C_1$-$C_3$ alkyl, or optionally substituted cyclopropyl. In some such embodiments, the cyclopropyl is optionally substituted with 1, 2, 3, 4, or 5 $R^{4g}$ groups, wherein $R^{4g}$ is $C_1$-$C_2$ alkyl, halogen, or $C_1$-$C_2$ haloalkyl.

In certain embodiments, $R^7$ is H or halogen. In some such embodiments, the halogen is F or Cl. In some such embodiments, the halogen is F.

In certain embodiments, $R^8$ is H, $C_1$-$C_6$ alkyl, halogen, $C_1$-$C_6$ haloalkyl, —CN, optionally substituted heterocycle, —C(O)N$R^{Y3}R^{Y4}$, —($C_1$-$C_6$ alkylenyl)-N$R^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)N$R^{Y3}R^{Y4}$, —($C_1$-$C_6$ alkylenyl)-N($R^{Y3}$)S(O)$_2$N$R^{Y3}R^{Y4}$, or —($C_1$-$C_6$ alkylenyl)-$G^3$ wherein $G^3$ is optionally substituted heterocycle.

In certain embodiments, $R^8$ is H.

In certain embodiments, $R^9$ is H, $C_1$-$C_6$ alkyl, halogen, $C_1$-$C_6$ haloalkyl, —CN, —S(O)$_2R^{Y1}$, —S(O)$_2$N$R^{Y3}$, $R^{Y4}$, —C(O)N$R^{Y3}R^{Y4}$, —N$R^{Y3}R^{Y4}$, —N($R^{Y3}$)C(O)$R^{Y2}$, —N($R^{Y3}$)S(O)$_2R^{Y2}$, —N($R^{Y3}$)C(O)O($R^{Y2}$), —N($R^{Y3}$)C(O)N$R^{Y3}R^{Y4}$, —N($R^{Y3}$)S(O)$_2$N$R^{Y3}R^{Y4}$, —($C_1$-$C_6$ alkylenyl)-CN, —(—($C_1$-$C_6$ alkylenyl)-S(O)$_2R^{Y1}$, —($C_1$-$C_6$ alkylenyl)-S(O)$_2$N$R^{Y3}R^{Y4}$, —($C_1$-$C_6$ alkylenyl)-C(O)N$R^{Y3}R^{Y4}$, —($C_1$-$C_6$ alkylenyl)-N$R^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)N$R^{Y3}R^{Y4}$, or —($C_1$-$C_6$ alkylenyl)-N($R^{Y3}$)S(O)$_2$N$R^{Y3}R^{Y4}$.

In certain embodiments, $R^9$ is H, $C_1$-$C_6$ alkyl, halogen, —S(O)$_2R^{Y1}$, —S(O)$_2$N$R^{Y3}R^{Y4}$, —N$R^{Y3}R^{Y4}$, —N($R^{Y3}$)S(O)$_2R^{Y2}$, —($C_1$-$C_6$ alkylenyl)-CN, or —($C_1$-$C_6$ alkylenyl)-S(O)$_2R^{Y1}$.

In certain embodiments, $R^9$ is H, $C_1$-$C_6$ alkyl, halogen, —S(O)$_2R^{Y1}$, —S(O)$_2$N$R^{Y3}R^{Y4}$, —N$R^{Y3}R^{Y4}$, —N($R^{Y3}$)S(O)$_2R^{Y2}$, or —($C_1$-$C_6$ alkylenyl)-S(O)$_2R^{Y1}$. In some embodiments, $R^{Y1}$, $R^{Y3}$, and $R^{Y4}$, at each occurrence, are each independently H or $C_1$-$C_6$ alkyl, and $R^{Y2}$ is $C_1$-$C_6$ alkyl. In some embodiments, $R^{Y1}$ and $R^{Y2}$ are $C_1$-$C_3$ alkyl, and $R^{Y3}$ and $R^{Y4}$ are hydrogen.

In certain embodiments, $R^9$ is halogen, —N$R^{Y3}R^{Y4}$, —N($R^{Y3}$)C(O)$R^{Y2}$, —N($R^{Y3}$)S(O)$_2R^{Y2}$, or —($C_1$-$C_6$ alkylenyl)-S(O)$_2R^{Y1}$.

In certain embodiments, $R^9$ is halogen, —NR($R^{Y3}$)S(O)$_2R^{Y2}$, or —($C_1$-$C_6$ alkylenyl)-S(O)$_2R^{Y1}$. In some such embodiments, $R^{Y1}$ and $R^{Y2}$ are $C_1$-$C_6$ alkyl, and $R^{Y2}$ is H. In some such embodiments, the halogen is F. In some such embodiments, $R^{Y1}$ and $R^{Y2}$ are each independently methyl or ethyl, and $R^{Y3}$ is H.

In certain embodiments, $R^9$ is —($CH_2$)—S(O)$_2R^{Y1}$. In some embodiments, $R^{Y1}$ is $C_1$-$C_6$ alkyl. In some such embodiments, $R^{Y1}$ is methyl.

In certain embodiments of formula (I), $R^{10}$ is H, $C_1$-$C_3$ alkyl halogen, $C_1$-$C_3$ haloalkyl, or —CN.

In certain embodiments, $R^{10}$ is H, $C_1$-$C_2$ alkyl, or halogen.

In certain embodiments, $R^{10}$ is H.

Various embodiments of substituents $R^1$, $R^2$, $R^4$, $Y^1$, $Y^2$, $Y^3$, $A^1$, $A^2$, $A^3$, and $A^4$ have been discussed above. These substituents embodiments can be combined to form various embodiments of compounds of formula (I). All embodiments of compounds of formula (I), formed by combining the substituent embodiments discussed above are within the scope of the subject matter, and some illustrative embodiments of the compounds of formula (I) are provided below.

In certain embodiments, $Y^1$ is CH; $Y^2$ is $CR^3$; and $Y^2$ is $CR^4R^5$.

In certain embodiments, $Y^1$ is CH; $Y^3$ is $CR^3$; $Y^2$ is $CR^4R^5$; and $R^3$ is H, —CN, —C(O)$R^{3a}$, —C(O)O$R^{3a}$, —C(O)N$R^{3b}R^{3c}$, or $C_1$-$C_6$ alkyl, wherein the $C_1$-$C_6$ alkyl is optionally substituted with a substituent selected from the group consisting of $G^1$, —N$R^{3b}R^{3c}$, N($R^{3b}$)C(O)$R^{3d}$, N($R^{3b}$)$SO_2R^{3d}$, N($R^{3b}$)C(O)O$R^{3d}$, N($R^{3b}$)C(O)N$R^{3b}R^{3c}$, and N($R^{3b}$)$SO_2$N$R^{3b}R^{3c}$.

In some further embodiments, $A^1$ is C($R^y$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $Y^1$ is CH; $Y^3$ is $CR^3$; $Y^2$ is $CR^4R^5$; $R^4$ is H or deuterium; and $R^5$ is H, deuterium, $C_1$-$C_6$ alkyl, $C_2$-$C_6$ alkenyl, $C_2$-$C_6$ alkynyl, $C_1$-$C_6$ haloalkyl, —C(O)$R^{5a}$, —C(O)O$R^{5a}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, —C(O)$R^{5a}$, —C(O)O$R^{5a}$, —C(O)N$R^{5b}R^{5a}$, —C(O)N($R^{4b}$)N$R^{5b}R^{5c}$, —O$R^{5a}$, —OC(O)$R^{5d}$, —N$R^{5b}R^{5c}$, N($R^{5b}$)C(O)$R^{5d}$, N($R^{5b}$)$SO_2R^{5d}$, N($R^{5b}$)C(O)O$R^{5d}$, N($R^{5b}$)C(O)N$R^{5b}R^{5c}$, and N($R^{5b}$)$SO_2$N$R^{5b}R^{5c}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$, and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $Y^1$ is CH; $Y^3$ is $CR^3$; $Y^2$ is $CR^4R^5$; and $R^6$ is H, $C_1$-$C_6$ alkyl, $C_2$-$C_6$ alkenyl, —C(O)$R^{6a}$, —C(O)O$R^{6a}$, —C(O)N$R^{6b}R^{6c}$, —S(O)$_2R^{6a}$, or $G^2$; wherein the $C_1$-$C_6$ alkyl and the $C_2$-$C_6$ alkenyl are each independently unsubstituted or substituted with 1 or 2 substituents independently selected from the group consisting of $G^2$, —CN, —C(O)O$R^{6a}$, —N$R^{6b}R^{6c}$, N($R^{6b}$)C(O)$R^{6d}$, N($R^{6b}$)$SO_2R^{6d}$, N($R^{6b}$)C(O)O$R^{6d}$, N($R^{6b}$)C(O)N$R^{6b}R^{6c}$, and N($R^{6b}$)$SO_2$N$R^{6b}R^{6c}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^2$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $Y^1$ is CH; $Y^3$ is $CR^3$; $Y^2$ is $CR^4R^5$; and $R^9$ is H, $C_1$-$C_6$ alkyl, halogen, $C_1$-$C_6$ ahaloalkyl, —CN, —S(O)$_2R^{Y1}$, —S(O)$_2$N$R^{Y3}R^{Y4}$, —C(O)N$R^{Y3}R^{Y4}$, —N$R^{Y3}R^{Y4}$, —N($R^{Y3}$)C(O)$R^{Y2}$, —N($R^{=3}$)S(O)$_2R^{Y2}$, —N($R^{Y3}$)C(O)O($R^{Y2}$), —N($R^{Y3}$)CX(O)N$R^{Y3}R^{65\ 4}$, N($R^{Y3}$)S(O)$_2$N$R^{Y3}R^{65\ 4}$, —($C_1$-$C_6$ alkylenyl)-S(O)$_2R^{Y1}$, —($C_1$-$C_6$ alkylenyl)-S(O)$_2$N$R^{Y3}R^{Y4}$, —($C_1$-$C_6$ alkylenyl)-C(O)N$R^{Y3}R^{Y4}$, —($C_1$-$C_6$ alkylenyl)-N$R^{Y3}R^{Y4}$, —($C_1$-$C_6$ alkylenyl) N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)N$R^{Y3}R^{Y4}$, or —($C_1$-$C_6$ alkylenyl)-N($R^{Y3}$)S(O)$_2$N$R^{Y3}R^{Y4}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $Y^1$ is CH; $Y^3$ is $CR^3$; $Y^2$ is $CR^4R^5$; and $A^1$ is C($R^7$), $A^2$ is C($R^8$), $A^3$ is C($R^9$), and $A^4$ is C($R^{10}$); or Ai is N, $A^2$ is C($R^8$), $A^3$ is C($R^9$), and $A^4$ is C($R^{10}$); or Ai is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $R^1$ is $C_1$-$C_3$ alkyl; $R^2$ is H; $Y^1$ is CH; $Y^3$ is $CR^3$; and $Y^2$ is $CR^4R^5$.

In some further embodiments, $R^1$ is methyl.

In certain embodiments, $R^1$ is $C_1$-$C_3$ alkyl; $R^2$ is H; $Y^1$ is CH; $Y^3$ is $CR^3$; $Y^2$ is $CR^4R^5$; $R^4$ is H or deuterium; and $R^5$ is $C_2$-$C_6$ alkenyl optionally substituted with a $G^1$ group, or $R^5$ is H, deuterium, $C_1$-$C_6$ alkyl, —C(O)$R^{5a}$, —C(O)O$R^{5a}$, or $G^1$; wherein the $C_1$-$C_6$ alkyl is unsubstituted or substituted with substituent selected from the group consisting of $G^1$, —C(O)$R^{5a}$, —C(O)O$R^{5a}$, —C(O)N$R^{5b}R^{5c}$, —C(O)N($R^{5b}$)N$R^{5b}R^{5c}$, —O$R^{5a}$, —OC(O)$R^{5d}$, —$N^{5b}R^{5c}$, and N($R^{5b}$)C(N$R^{5b}R^{5c}$)═N$R^{5b}R^{5c}$.

In some further embodiments, $R^1$ is methyl.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or Ai is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $R^1$ is $C_1$-$C_3$ alkyl; $R^2$ is H; $Y^1$ is CH; $Y^3$ is $CR^3$; $Y^2$ is $CR^4R^5$; and $R^3$ is H, —C(O)$R^{3a}$, or —C(O)N$R^{3b}R^{3c}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, A1 is N, A2 is C(R8), A3 is C(R9), and A4 is C(R10).

In some further embodiments, $A^1$ is N, $A^2$ is C($R^8$), $A^3$ is N, and $A^4$ is C($R^{10}$).

In some further embodiments, $R^1$ is methyl.

In some further embodiments, $R^1$ is methyl, and $R^{3a}$ is $G^1$.

In yet some further embodiments, $R^1$ is methyl, $R^{3a}$ is $G^1$ wherein $G^1$ is optionally substituted heterocycle.

In certain embodiments, $R^1$ is $C_1$-$C_3$ alkyl; $R^2$ is H; $Y^1$ is CH; $Y^3$ is $CR^3$; $Y^2$ is $CR^4R^5$; and $R^6$ is H, $C_1$-$C_6$ alkyl, —C(O)$R^{6a}$, —C(O)$NR^{6b}R^{6c}$, —S(O)$_2R^{6a}$, or $G^2$; wherein the $C_1$-$C_6$ alkyl is unsubstituted or substituted with a substituent selected from the group consisting of $G^2$ and —C(O)O$R^{6a}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $R^1$ is methyl.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In certain embodiments, $R^1$ is $C_1$-$C_2$ alkyl; $R^2$ is H; $Y^1$ is CH: $Y^3$ is $CR^3$; $Y^3$ is $CR^4R^5$; and $R^9$ is H, $C_1$-$C_6$ alkyl, halogen, —S(O)$_2R^{Y1}$, —S(O)$_2NR^{Y3}R^{Y4}$, —N($R^{Y3}$)S(O)$_2R^{Y2}$, or —($C_1$-$C_6$ alkylenyl)-S(O)$_2R^{Y1}$.

In some further embodiments, $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In some further embodiments, $R^1$ is methyl.

In certain embodiments, $R^1$ is $C_1$-$C_3$ alkyl; $R^2$ is H; $Y^1$ is CH; $Y^3$ is $CR^3$; $Y^2$ is $CR^4R^5$; and $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$).

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In yet some further embodiments, $R^1$ is methyl.

In certain embodiments, $R^1$ is methyl; $R^2$ is H; $Y^1$ is CH; $Y^3$ is $CR^3$; $Y^2$ is $CR^4R^5$; $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$; $R^4$ is H or deuterium; $R^7$ is H, halogen, $C_1$-$C_3$ alkyl, or optionally substituted cyclopropyl; $R^8$ is H, $C_1$-$C_6$ alkyl, halogen, $C_1$-$C_6$ haloalkyl, —CN, optionally substituted heterocycle, —C(O)$NR^{Y3}R^{65\ 4}$, —($C_1$-$C_6$ alkylenyl)-$NR^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_{11}$-$C_6$ alkylenyl)-N($R^{Y3}$)C(O)$NR^{Y3}R^{Y4}$, —($C_1$-$C_6$ alkylenyl)-N($R^{Y3}$)S(O)$_2NR^{Y3}R^{Y4}$, or —($C_1$-$C_6$ alkylenyl)-$G^3$ wherein $G^3$ is optionally substituted heterocycle; and $R^{10}$ is H, $C_1$-$C_3$ alkyl, or halogen.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In one embodiment, the invention is directed to compounds of formula (I), wherein $R^1$ is methyl; $R^2$ is H; $Y^1$ is CH; $Y^3$ is $CR^3$; $Y^2$ is $CR^4R^5$; $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^3$ is N, and $A^4$ is C($R^{10}$); $R^4$ is H or deuterium; $R^7$ is H, halogen, $C_1$-$C_3$ alkyl, or optionally substituted cyclopropyl; $R^8$ is H, $C_1$-$C_6$ alkyl, halogen, $C_1$-$C_6$ haloalkyl, —CN, optionally substituted heterocycle, —C(O)$NR^{Y3}R^{Y4}$, —($C_1$-$C_6$ alkylenyl)-$NR^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)$NR^{Y3}R^{Y4}$, —($C_1$-$C_6$ alkylenyl)-N($R^{Y3}$)S(O)$_2NR^{Y3}R^{Y4}$, or —($C_1$-$C_6$ alkylenyl)-$G^3$ wherein $G^3$ is optionally substituted heterocycle; $R^{10}$ is H, $C_1$-$C_3$ alkyl, or halogen; and $R^3$ is H or —C(O)$NR^{3b}R^{3c}$.

In some further embodiments, $R^{3b}$ and $R^{3c}$ are each independently H or $C_1$-$C_6$ alkyl.

In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In one embodiment, the invention is directed to compounds of formula (I), wherein $R^1$ is methyl; $R^2$ is H; $Y^1$ is CH; $Y^3$ is $CR^3$; $Y^2$ is $CR^4R^5$; $A^1$ is C($R^7$), $A^2$ is C($R^8$), $A^3$ is C($R^9$), and $A^4$ is C($R^{10}$); or $A^1$ is N, $A^2$ is C($R^8$), $A^3$ is C($R^9$), and $A^4$ is C($R^{10}$); or $A^1$ is N, $A^2$ is C($R^8$), $A^2$ is N, and $A^4$ is C($R^{10}$); $R^4$ is H or deuterium; $R^7$ is H, halogen, $C_1$-$C_3$ alkyl, or optionally substituted cyclopropyl; $R^8$ is H, $C_1$-$C_6$ alkyl, halogen, $C_1$-$C_6$ haloalkyl, —CN, optionally substituted heterocycle, —C(O)$NR^{Y7}R^{Y4}$, —($C_1$-$C_6$ alkylenyl)-$NR^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)*N($R^{Y3}$)C(O)O($R^{Y2}$), —($C_1$-$C_6$ alkylenyl)-N($R^{Y3}$)C(O)$NR^{Y3}R^{Y4}$, —($C_1$-$C_6$ alkylenyl)-N($R^{Y3}$)S(O)$_2NR^{Y3}R^{Y4}$, or —($C_1$-$C_6$ alkylenyl)-$G^3$ wherein $G^3$ is optionally substituted heterocycle; $R^{10}$ is H, $C_1$-$C_3$ alkyl, or halogen; and $R^5$ is H, deuterium, or $C_1$-$C_6$ alkyl optionally substituted with a substituent selected from the group consisting of —C(O)O$R^{5a}$ and O$R^{5a}$ In some further embodiments, $A^1$ is C($R^7$), $A^2$ is C($R^8$), $A^3$ is C($R^9$), and $A^4$ is C($R^{10}$).

In some further embodiments, $A^1$ is N, $A^2$ is C($R^8$), $A^3$ is C($R^9$), and $A^4$ is C($R^{10}$).

In some further embodiments, $A^1$ is N, $A^2$ is C($R^8$), $A^3$ is N, and $A^4$ is C($R^{10}$).

In yet some embodiments, $R^{5a}$ is $C_1$-$C_6$ alkyl.

In one embodiment, the invention is directed to compounds of formula (I), wherein $R^1$ is methyl; $R^2$ is H; $Y^1$ is CH; $Y^3$ is $CR^3$; $Y^2$ is $CR^4R^5$; $A^1$ is C($R^7$), $A^2$ is C($R^8$), $A^3$ is C($R^9$), and $A^4$ is C($R^{10}$; or $A^1$ is N, $A^2$ is C($R^8$), $A^3$ is N, and $A^4$ is C($R^{10}$); $A^1$ is N, $A^2$ is C($R^8$), $A^3$ is N, and $A^4$ is C($R^{10}$); $R^4$ is H or deuterium; $R^7$ is H, halogen, $C_1$-$C_3$ alkyl, or optionally substituted cyclopropyl; $R^8$ is H, $C_1$-$C_6$ alkyl, halogen, $C_1$-$C_6$ haloalkyl, —CN, optionally substituted heterocycle, —C(O)$NR^{Y3}R^{Y4}$, —($C_1$-$C_6$ alkylenyl)-$NR^{Y3}R^{Y4}$, —($C_1$-$C_6$ alkylenyl)-N($R^{Y3}$)C(O)$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)$NR^{Y3}R^{Y4}$, —($C_1$-$C_6$ alkylenyl)-N($R^{Y3}$)S(O)$_2NR^{Y3}R^{Y4}$, or —($C_1$-$C_6$ alkylenyl)-$G^3$ wherein $G^3$ is optionally substituted heterocycle; $R^{10}$ is H, $C_1$-$C_3$ alkyl, or halogen; and $R^6$ is —C(O)$R^{6a}$, —C(O)O$R^{6a}$, —C(O)$NR^{6b}R^{6c}$, $G^2$, or $C_1$-$C_6$ alkyl which is unsubstituted or substituted with a $G^2$ group.

In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $A^1$ is N, $A^2$ is $C(R^8)$, $A^3$ is N, and $A^4$ is $C(R^{10})$.

In one embodiment, the invention is directed to compounds of formula (I), wherein $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H, halogen, $C_1$-$C_3$ alkyl, or optionally substituted cyclopropyl; $R^8$ is H, $C_1$-$C_6$ alkyl, halogen, $C_1$-$C_6$ haloalkyl, —CN, optionally substituted heterocycle, —$C(O)NR^{Y3}R^{Y4}$, —($C_1$-$C_6$ alkylenyl)-$NR^{Y3}R^{Y4}$, —($C_1$-$C_6$ alkylenyl)-$N(R^{Y3})C(O)R^{Y2}$, —($C_1$-$C_6$ alkylenyl)-$N(R^{Y3})S(O)_2R^{Y2}$, —($C_1$-$C_6$ alkylenyl)-$N(R^{Y3})C(O)O(R^{Y2})$, —($C_1$-$C_6$ alkylenyl)-$N(R^{Y3})C(O)NR^{Y3}R^{Y4}$, —($C_1$-$C_6$ alkylenyl)-$N(R^{Y3})S(O)_2NR^{Y3}R^{Y4}$, or —($C_1$-$C_6$ alkylenyl)-$G^3$ wherein $G^3$ is optionally substituted heterocycle; $R^{10}$ is H, $C_1$-$C_3$ alkyl, or halogen; and $R^9$ is halogen, —$NR^{Y3}R^{Y4}$, —$N(R^{Y3})C(O)R^{Y2}$, —$N(R^{Y3})S(O)_2R^{Y2}$, or —($C_1$-$C_6$ alkylenyl)-$S(O)_2R^{Y1}$.

In some further embodiments, $A^1$ is $C(R^7)$, $A^2$ is $C(R^8)$, $A^3$ is $C(R^9)$, and $A^4$ is $C(R^{10})$;

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; and $R^{10}$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; and $R^4$ is H or deuterium; $R^7$ is H or halogen; $R^8$ is H; $R^{10}$ is H; and $R^9$ is halogen, —$N(R^{Y3})S(O)_2R^{Y2}$, or —($C_1$-$C_6$ alkylenyl)-$S(O)_2R^{Y\ 1}$.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{Y1}$ and $R^{Y2}$ are $C_1$-$C_6$ alkyl, and $R^{Y3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; $R^{10}$ is H; $R^9$ is halogen, —$N(R^{Y3})S(O)_2R^{Y2}$, or —($C_1$-$C_6$ alkylenyl)-$S(O)_2R^{Y1}$; and $R^6$ is —$C(O)R^{6a}$, —$C(O)OR^{6a}$, —$C(O)NR^{6b}R^{6c}$, $G^2$, or $C_1$-$C_6$ alkyl which is unsubstituted or substituted with a $G^2$ group.

In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{Y1}$ and $R^{Y2}$ are $C_1$-$C_6$ alkyl, and $R^{Y3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; $R^{10}$ is H; $R^9$ is halogen, —$N(R^{Y3})S(O)_2R^{Y2}$, or —($C_1$-$C_6$ alkylenyl)-$S(O)_2R^{Y1}$; $R^6$ is —$C(O)R^{6a}$, —$C(O)OR^{6a}$, —$C(O)NR^{6b}R^{6c}$, $G^2$, or $C_1$-$C_6$ alkyl which is unsubstituted or substituted with a $G^2$ group; and $R^5$ is H, deuterium, or $C_1$-$C_6$ alkyl optionally substituted with substituent selected from the group consisting of —$C(O)OR^{5a}$ or $OR^{5a}$ In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{Y1}$ and $R^{Y2}$ are $C_1$-$C_6$ alkyl, and $R^{Y3}$ is H.

In certain embodiments, $R^1$ is methyl; $R^2$ is H; $Y^1$ is CH; $Y^3$ is $CR^4R^5$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; $R^{10}$ is H; $R^9$ is halogen, —$N(R^{Y3})S(O)_2R^{65\ 2}$, or —($C_1$-$C_6$ alkylenyl)-$S(O)_2R^{Y1}$;

$R^6$ is —$C(O)R^{6a}$, —$C(O)OR^{6a}$, —$C(O)NR^{6b}R^{6c}$, $G^2$, or $C_1$-$C_6$ alkyl which is unsubstituted or substituted with a $G^2$ group; $R^5$ is H, deuterium, or $C_1$-$C_6$ alkyl optionally substituted with a substituent selected from the group consisting of $C(O)OR^{5a}$ and $OR^{5a}$; and $R^3$ is H or $C(O)NR^{3b}R^{3c}$.

In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^5$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; $R^{10}$ is H; $R^9$ is halogen, —$N(R^{Y3})S(O)_2R^{Y2}$, or —($C_1$-$C_6$ alkylenyl)-$S(O)_2R^{Y1}$; $R^6$ is —$C(O)R^{6a}$, —$C(O)OR^{6a}$, —$C(O)NR^{6b}R^{6c}$, $G^2$, or $C_1$-$C_6$ alkyl which is unsubstituted or substituted with a $G^2$ group; $R^5$ is H, deuterium, or $C_1$-$C_6$ alkyl optionally substituted with a substituent selected from the group consisting of $C(O)OR^{5a}$, and $OR^{5a}$; $R^3$ is H or $C(O)NR^{3b}R^{3c}$; $R^{3b}$ and $R^{3c}$ are each independently H or $C_1$-$C_6$ alkyl; $R^{5a}$ is $C_1$-$C_6$ alkyl; $R^{Y1}$ and $R^{Y2}$ are $C_1$-$C_6$ alkyl; and $R^{Y3}$ is H.

In some further embodiments, $R^{6a}$ is $G^2$ or unsubstituted $C_1$-$C_6$ alkyl.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^4$ is H or deuterium; $R^7$ is H or halogen; $R^8$ is H; $R^{10}$ is H; $R^9$ is halogen, —$N(R^{Y3})S(O)_2R^{Y2}$, or —($C_1$-$C_6$ alkylenyl)-$S(O)_2R^{Y1}$; $R^6$ is $G^2$ or $C_1$-$C_6$ alkyl which is unsubstituted or substituted with a $G^2$ group; $R^5$ is H, deuterium, or $C_1$-$C_6$ alkyl optionally substituted with a substituents selected from the group consisting of —$C(O)OR^{5a}$ and $OR^{5a}$; $R^3$ is H or —$C(O)NR^{3b}R^{3c}$; $R^{3b}$ and $R^{3c}$ are each independently H or $C_1$-$C_6$ alkyl; $R^{5a}$ is $C_1$-$C_6$ alkyl; $R^{Y1}$ and $R^{Y2}$ are $C_1$-$C_6$ alkyl; and $R^{Y3}$ is H.

In some further embodiments, $R^6$ is optionally substituted aryl, optionally substituted heteroaryl, or optionally substituted cycloalkyl; or $R^6$ is $C_1$-$C_6$ alkyl which is unsubstituted or substituted with a substituent selected from the group consisting of cycloalkyl and heterocycle, each of which is optionally substituted.

In some further embodiments, $R^6$ is optionally substituted phenyl, optionally substituted cyclohexyl, optionally substituted pyridinyl, or $C_1$-$C_6$ alkyl which is unsubstituted or substituted with a $G^2$ group wherein $G^2$ is cyclopropyl or tetrahydrofuranyl, each of which is optionally substituted.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is H, —$C(O)NR^{3b}R^{3c}$, —CN, or $C_1$-$C_6$ alkyl which is substituted with a $G^1$ group; wherein $G^1$ is an optionally substituted $C_4$-$C_6$ heterocycle; $R^4$ is H or deuterium; $R^7$ is H, halogen, —CN, $C_1$-$C_3$ alkyl, or optionally substituted cyclopropyl; $R^8$ is H; $R^9$ is halogen, —$N(R^{Y3})S(O)_2R^{Y2}$, or —($C_1$-$C_6$ alkylenyl)-$S(O)_2R^{Y1}$; and $R^{10}$ is H.

In some further embodiments, $A^1$ is $C(R^7)$, $A^2$ is $C(R^3)$, $A^3$ is $C(^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{3b}$ is H or $C_1$-$C_6$ alkyl; and $R^{3c}$ is H, $C_1$-$C_6$ alkyl, $C_1$-$C_6$ haloalkyl, $G^1$, or —($C_1$-$C_6$ alkylenyl)-$G^1$.

In some embodiments, $R^{3b}$ and $R^{3c}$ are each independently H or $C_1$-$C_6$ alkyl.

In some further embodiments, $R^{Y1}$ and $R^{Y2}$ are $C_1$-$C_6$ alkyl; and $R^{Y3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is H, —$C(O)NR^{3b}R^{3c}$, —CN, or $C_1$-$C_6$ alkyl which is substituted with a $G^1$ group; wherein $G^1$ is an optionally substituted $C_4$-$C_6$ heterocycle; $R^4$ is H or deuterium; $R^7$ is H, halogen, —CN, $C_1$-$C_3$ alkyl, or optionally substituted cyclopropyl; $R^8$ is H; $R^9$ is halogen, —$N(R^{Y3})S(O)_2R^{Y2}$, or —($C_1$-$C_6$ alkylenyl)-$S(O)_2R^{Y1}$; $R^{10}$ is H; and $R^8$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{3b}$ and $R^{3c}$ are each independently H or $C_1$-$C_6$ alkyl.

In some further embodiments, $R^{Y1}$ and $R^{Y2}$ are $C_1$-$C_6$ alkyl; and $R^{Y3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is H, —$C(O)NR^{3b}R^{3c}$, —CN, or $C_1$-$C_6$ alkyl which is substituted with a $G^1$ group; wherein $G^1$ is an optionally substituted $C_4$-$C_6$ heterocycle; $R^4$ is H or deuterium; $R^7$ is H, halogen, —CN, $C_1$-$C_3$ alkyl, or optionally substituted cyclopropyl; $R^8H$; $R^9$ is halogen, —$N(R^{Y3})S(O)_2R^{Y2}$, or —($C_1$-$C_6$ alkylenyl)-$S(O)_2R^{Y1}$; $R^{10}$ is H; $R^5$ is H; and $R^6$ is phenylk, pyridinyl, or cyclohexly; each of which is optionally substituted; or $R^6$ is —$C(O)O(C_1$-$C_6$ alkyl); or $R^6$ is $CH_2$-(optionally substituted tetrahydropyranyl).

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{3b}$ and $R^{3c}$ are each independently H or $C_1$-$C_6$ alkyl.

In some further embodiments, $R^{Y1}$ and $R^{Y2}$ are $C_1$-$C_6$ alkyl; and $R^{Y3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is $G^1$; $R^4$ is H or deuterium; $R^7$ is H, halogen, —CN, $C_1$-$C_3$ alkyl, or optionally substituted cyclopropyl; $R^8$ is H; $R^9$ is —$S(O)_2R^{Y1}$, —$N(R^{Y3})S(O)_2R^{Y2}$, or —($C_1$-$C_6$ alkylenyl)-$S(O)_2R^{Y1}$; and $R^{10}$ is H.

In some further embodiments, $A^1$ is $C(R^7)$, $A^2$ is $C(R^8)$, $A^3$ is $C(R^9)$, and $A^4$ is $C(R^{10})$ In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{Y1}$ and $R^{Y2}$ are $C_1$-$C_6$ alkyl; and $R^{Y3}$ is H.

In certain embodiments, $R^1$ is methyl; $R^2$ is H; $Y^1$ is CH; $Y^2$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is $G^1$; wherein $G^1$ is optionally substituted heteroaryl; $R^4$ is H or deuterium; $R^7$ is H, halogen, —CN, $C_1$-$C_3$ alkyl, or optionally substituted cyclopropyl; $R^8$ is H; $R^9$ is —$S(O)_2R^{Y1}$, —$N(R^{Y3})S(O)_2R^{Y2}$, or —($C_1$-$C_6$ alkylenyl)-$S(O)_2R^{Y1}$; $R^{10}$ is H; and $R^5$ is H.

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{\gamma1}$ and $R^{\gamma2}$ are $C_1$-$C_6$ alkyl; and $R^{\gamma3}$ is H.

In certain embodiments, $R^1$ is methyl; $R^2$ is H; $Y^1$ is CH; $Y^3$ is $CR^3$; $Y^2$ is $CR^4R^5$; $A^1$ is $C(R^7)$, $A^2$ is $C(R^8)$, $A^3$ is $C(R^9)$, and $A^4$ is $C(R^{10})$; or $A^1$ is N, $A^2$ is $C(R^8)$, $A^3$ is $C(R^9)$, and $A^4$ is $C(R^{10})$; or $A^1$ is N, $A^2$ is $C(R^8)$, $A^3$ is N, and $A^4$ is $C(R^{10})$; $R^3$ is $G^1$; wherein $G^1$ is optionally substituted pyrazolyl; $R^4$ is H or deuterium; $R^7$ is H, halogen, —CN, $C_1$-$C_3$ alkyl, or optionally substituted cyclopropyl; $R^8$ is H; $R^9$ is $—S(O)_2R^{\gamma1}$; $R^{10}$ is H; $R^5$ is H; and $R^6$ is phenyl, pyridinyl, or cyclohexyl; each of which is optionally substituted; or $R^6$ is $—C(O)O(C_1$-$C_6$ alkyl); or $R^6$ is $—CH_2$-(optionally substituted tetrahydropyranyl).

In some further embodiments, $A^1$ is $C(R^7)$, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is $C(R^9)$, and $A^4$ is $C(R^{10})$.

In some further embodiments, $A^1$ is N, $A^2$ is $C(R^8)$, $A^3$ is N, and $A^4$ is $C(R^{10})$.

In some further embodiments, $R^{\gamma1}$ is $C_1$-$C_6$ alkyl.

In certain embodiments, $Y^1$ is N or CH; $R^1$ is $CD_3$, $C_1$-$C_3$ alkyl, or $C_1$-$C_3$ haloalkyl; $R^2$ is H or $C_1$-$C_3$ alkyl; $Y^3$ is N or $CR^3$; $R^3$ is H, $C_1$-$C_6$ alkyl, $C_2$-$C_6$ alkenyl, $C_2$-$C_6$ alkynyl, halogen, $C_1$-$C_6$ haloalkyl, $—C(O)R^{3a}$, $—C(O)OR^{3a}$, $—C(O)NR^{3b}R^{3c}$, $—S(O)R^{3d}$, $—S(O)_2R^{3a}$, $—S(O)_2NR^{3b}R^{3c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, $—C(O)R^{3a}$, $—C(O)OR^{3a}$, $—C(O)NR^{3b}R^{3c}$, $—C(O)N(R^{3b})NR^{3b}R^{3c}$, $—S(O)R^{3d}$, $—S(O)_2R^{3a}$, $—S(O)_2NR^{3b}R^{3c}$, $—OR^{3a}$, $—OC(O)R^{3d}$, $—NR^{3b}R^{3c}$, $N(R^{3b})C(O)R^{3d}$, $N(R^{3b})SO_2R^{3d}$, $N(R^{3b})$, $—N(R^{3b})C(O)OR^{3d}$, $N(R^{3b})C(O)NR^{3b}R^{3c}$, $N(R^{3b})SO_2NR^{3b}R^{3c}$, and $N(R^{3b})C(NR^{3b}R^{3c})═NR^{3b}R^{3c}$; $Y^2$ is $C(O)_2S(O)_2$, or $CR^4R^5$; $R^4$ is H, deuterium, $C_1$-$C_6$ alkyl, halogen, or $C_1$-$C_6$ haloalkyl; $R^5$ is H, deuterium, $C_1$-$C_6$ alkyl, $C_2$-$C_6$ alkenyl, $C_2$-$C_6$ alkynyl, halogen, $C_1$-$C_6$ haloalkyl, $—C(O)R^{5a}$, $—C(O)OR^{5a}$, $—C(O)NR^{5b}R^{5c}$, $—S(O)R^{5d}$, $—S(O)_2R^{5a}$, $—S(O)_2NR^{5b}R^{5c}$, or $G^1$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^1$, $—C(O)R^{5a}$, $—C(O)OR^{5a}$, $—C(O)NR^{5b}R^{5c}$, $—C(O)N(R^{5b}R^{5c}$, $—S(O)R^{5d}$, $—S(O)_2R^{5a}$, $—S(O)_2NR^{5b}R^{5c}$, $—OR^{5a}$, $—OC(O)R^{5d}$, $—NR^{5b}R^{5c}$, $N(R^{5b})C(O)R^{5d}$, $N(R^{5b})SO_2R^{5d}$, $N(R^{5b})C(O)OR^{5d}$, $N(R^{5b})C(O)NR^{5b}R^{5c}$, $N(R^{5b})SO_2NR^{5b}R^{5c}$, and $N(R^{5b})C(NR^{5b}R^{5c})═NR^{5b}R^{5c}$; $R^{3a}$, $R^{3b}$, $R^{3c}$, $R^{5a}$, $R^{5b}$, and $R^{5c}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^1$, or $—(C_1$-$C_6$ alkylenyl)-$G^1$; $R^{3d}$ and $R^{5d}$, are each occurrence, are each independently $C_1$-$C_6$ alkyl, $C_2$-$C_6$ alkenyl, $C_2$-$C_6$ alkynyl, $C_1$-$C_6$ haloalkyl, $G^1$, or $—(C_1$-$C_6$ alkylenyl)-$G^1$; $G^1$, at each occurrence, is independently aryl, heteroaryl, heterocycle, cycloalkyl, or cycloalkenyl; and each $G^1$ is optionally substituted with 1, 2, 3, 4, or 5 $R^1$ groups; $R^6$ is H, $C_1$-$C_6$ alkyl, $C_2$-$C_6$ alkenyl, $C_2$-$C_6$ alkynyl, halogen, $C_1$-$C_6$ haloalkyl, $—C(O)R^{6a}$, $—C(O)OR^{6a}$, $—C(O)NR^{6b}R^{6c}$, $—S(O)_2R^{6a}$, $—S(O)_2NR^{6b}R^{6c}$, or $G^2$; wherein the $C_1$-$C_6$ alkyl, $C_2$-$C_6$ alkenyl, and $C_2$-$C_6$ alkynyl are each independently unsubstituted or substituted with 1 or 2 substituents independently selected from the group consisting of $G^2$, $—C(O)R^{6a}$, $—C(O)OR^{6a}$, $—C(O)NR^{6b}R^{6c}$, $—C(O)N(R^{6b})NR^{6b}R^{6c}$, $—S(O)R^{6d}$, $—S(O)_2R^{6a}$, $—S(O)_2NR^{6b}R^{6c}$, $—OR^{6a}$, $—OC(O)R^{6d}$, $—NR^{6b}R^{6c}$, $N(R^{6b})C(O)R^{6d}$, $N(R^{6b})SO_2R^{6d}$, $N(R^{6b})C(O)OR^{6d}$, $N(R^{6b})C(O)NR^{6b}R^{6c}$, $N(R^{6b})SO_2NR^{6b}R^{6c}$, and $N(R^{6b})C(NR^{6b}R^{6c})═NR^{6b}R^{6c}$; $R^{6a}$, $R^{6b}$, and $R^{6c}$, at each occurrence, are each independently H, alkyl, $C_2$-$C_6$ alkenyl, $C_2$-$C_6$ alkynyl, haloalkyl, $G^2$, $—(C_2$-$C_6$ alkylenyl)-$G^2$, $—(C_1$-$C_6$ alkylenyl)-$OR^a$, $—(C_1$-$C_6$ alkylenyl)-$S(O)_2R^a$, $—(C_1$-$C_6$ alkylenyl)-$S(O)_2NR^cR^d$, $—(C_1$-$C_6$ alkylenyl)-$C(O)R^a$, $—(C_1$-$C_6$ alkylenyl)-$C(O)OR^a$, $—(C_1$-$C_6$ alkylenyl)-$C(O)NR^cR^d$, $—(C_1$-$C_6$ alkylenyl)-$NR^cR^d$, $—(C_1$-$C_6$ alkylenyl)-$N(R^c)C(O)O(R^b)$, $—(C_1$-$C_6$ alkylenyl)-$N(R^c)S(O)_2R^b$, $—(C_1$-$C_6$ alkylenyl)-$N(R^c)C(O)O(R^b)$, $—(C_1$-$C_6$ alkylenyl)-$N(R^c)C(O)NR^cR^d$, or $—(C_1$-$C_6$ alkylenyl)-$N(R^c)S(O)_2NR^cR^d$; $R^{6d}$, at each occurrence, is independently alkyl, $C_2$-$C_6$ alkenyl, $C_2$-$C_6$ alkynyl, haloalkyl, $G^2$, $—(C_1$-$C_6$ alkylenyl)-$G^2$, $—(C_1$-$C_6$ alkylenyl)-$OR^a$, $—(C_1$-$C_6$ alkylenyl)-$S(O)_2R^a$, $—(C_1$-$C_6$ alkylenyl)-$S(O)_2NR^cR^d$, $—(C_1$-$C_6$ alkylenyl)-$C(O)R^a$, $—(C_1$-$C_6$ alkylenyl)-$C(O)OR^a$, $—(C_1$-$C_6$ alkylenyl)-$C(O)NR^cR^d$, $—(C_1$-$C_6$ alkylenyl)-$NR^cR^d$, $—(C_1$-$C_6$ alkylenyl)-$N(R^c)C(O)R^b$, $—(C_1$-$C_6$ alkylenyl)-$N(R^c)S(O)_2R^b$, $—(C_1$-$C_6$ alkylenyl) $N(R^c)C(O)O(R^b)$, $—(C_1$-$C_6$ alkylenyl)-$N(R^c)C(O)NR^cR^d$, or $—(C_1$-$C_6$ alkylenyl)-$N(R^c)S(O)_2NR^cR^d$; $G^2$, at each occurrence, is independently aryl, heteroaryl, heterocycle, cycloalkyl, or cycloalkenyl; and each $G^2$ is optionally substituted with 1, 2, 3, 4, or 5 $R^{2g}$ groups; $A^1$ is $C(R^7)$ or N; $A^2$ is $C(R^8)$ or N; $A^3$ is $C(R^9)$ or N; and $A^4$ is $C(R^{10})$ or N; wherein zero, one, or two of $A^1$, $A^2$, $A^3$, and $A^4$ are N; $R^7$, $R^8$, and $R^9$, are each independently H, $C_1$-$C_6$ alkyl, $C_2$-$C_6$ alkenyl, $C_2$-$C_6$ alkynyl, halogen, $C_1$-$C_6$ haloalkyl, —CN, $NO_2$, $—OR^{\gamma1}$, $—OC(O)R^{\gamma2}$, $—OC(O)NR^{\gamma3}R^{\gamma4}$, $—SR^{\gamma1}$, $—S(O)_2R^{\gamma1}$, $—S(O)_2NR^{\gamma3}R^{\gamma4}$, $—C(O)R^{\gamma1}$, $—C(O)OR^{\gamma1}$, $—C(O)NR^{\gamma3}R^{\gamma4}$, $—NR^{\gamma3}R^{\gamma4}$, $—N(R^{\gamma3})C(O)R^{\gamma2}$, $—N(R^{\gamma3})S(O)_2R^{\gamma2}$, $—N(R^{\gamma3})C(O)O(R^{\gamma1})$, $—N(R^{\gamma3})C(O)NR^{\gamma3}R^{\gamma4}$, $—N(R^{\gamma3})S(O)_2NR^{\gamma3}R^{\gamma4}$, $G^3$, $—(C_1$-$C_6$ alkylenyl)-CN, $—(C_1$-$C_6$ alkylenyl)-$OR^{\gamma1}$, $—(C_1$-$C_6$ alkylenyl)-$OC(O)R^{\gamma2}$, $—(C_1$-$C_6$ alkylenyl)-$OC(O)NR^{\gamma3}R^{\gamma4}$, $—(C_1$-$C_6$ alkylenyl)-$S(O)_2R^{\gamma1}$, $—(C_1$-$C_6$ alkylenyl)-$S(O)_2NR^{\gamma3}R^{\gamma4}$, $—(C_1$-$C_6$ alkylenyl)-$C(O)R^{\gamma1}$, $—(C_1$-$C_6$ alkylenyl)-$C(O)OR^{\gamma1}$, $—(C_1$-$C_6$ alkylenyl)-$C(O)NR^{\gamma3}R^{\gamma4}$, $—(C_1$-$C_6$ alkylenyl)-$NR^{\gamma3}R^{\gamma4}$, $—(C_1$-$C_6$ alkylenyl)-$N(R^{\gamma3})C(O)R^{\gamma2}$, $—(C_1$-$C_6$ alkylenyl)-$N(R^{\gamma3})S(O)_2R^{\gamma2}$, $—(C_1$-$C_6$ alkylenyl)-$N(R^{\gamma3})C(O)O(R^{\gamma2})$, $—(C_1$-$C_6$ alkylenyl)-$N(R^{\gamma3})C(O)NR^{\gamma3}R^{\gamma4}$, $—(C_1$-$C_6$ alkylenyl)-$N(R^{\gamma3})S(O)_2NR^{\gamma3}R^{\gamma4}$, $—(C_1$-$C_6$ alkylenyl)-CN, or $—(C_1$-$C_6$ alkylenyl)-$G^3$; $R^{\gamma1}$, $R^{\gamma3}$, and $R^{\gamma4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, $—(C_1$-$C_6$ alkylenyl)-$G^3$, $—(C_1$-$C_6$ alkylenyl)-$OR^a$, $—(C_1$-$C_6$ alkylenyl) $S(O)_2R^a$, $—(C_1$-$C_6$ alkylenyl)-$S(O)_2NR^cR^d$, $—(C_1$-$C_6$ alkylenyl)-$C(O)R^a$, $—(C_1$-$C_6$ alkylenyl)-$C(O)OR^a$, $(C_1$-$C_6$ alkylenyl)-$C(O)NR^cR^d$, $—(C_1$-$C_6$ alkylenyl)-$NR^cR^d$, $(C_1$-$C_6$ alkylenyl)-$N(R^c)C(O)R^b$, $—(C_1$-$C_6$ alkylenyl)-$N(R^c)S(O)_2R^b$, $—(C_1$-$C_6$ alkylenyl)-$N(R^c)C(O)O(R^b)$, $—(C_1$-$C_6$ alkylenyl)-$N(R^c)C(O)NR^cR^d$, or $—(C_1$-$C_6$ alkylenyl)-$N(R^c)S(O)_2NR^cR^d$, $R^{\gamma2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, $—(C_1$-$C_6$ alkylenyl)-$G^3$, $—(C_1$-$C_6$ alkylenyl)-$OR^a$, $—(C_1$-$C_6$ alkylenyl)-$S(O)_2R^a$, $—(C_1$-$C_6$ alkylenyl)-$S(O)_2NR^cR^d$, $—(C_1$-$C_6$ alkylenyl)-$C(O)R^a$, $—(C_1$-$C_6$ alkylenyl)-$C(O)OR^a$, $—(C_1$-$C_6$ alkylenyl)-$C(O)NR^cR^d$, $—(C_1$-$C_6$ alkylenyl)-$NR^cR^d$, $—(C_1$-$C_6$ alkylenyl)-$N(R^c)C(O)R^b$, $—(C_1$-$C_6$ alkylenyl)-$N(R^c)S(O)_2R^b$, $—(C_1$-$C_6$ alkylenyl)-$N(R^c)C(O)O(R^b)$, $—(C_1$-$C_6$ alkylenyl)-$N(R^c)C(O)NR^cR^d$, or $—(C_1$-$C_6$ alkylenyl)-$N(R^c)S(O)_2NR^cR^d$; $G^3$, at each occurrence, is independently aryl, heteroaryl, cycloalkyl, cycloalkenyl, or heterocycle; and each $G^3$ group is optionally substituted with 1, 2, 3, 4, or 5 $R^{6g}$ groups; $R^{10}$ is H, $C_1$-$C_3$ alkyl, halogen, $C_1$-$C_3$ haloalkyl, or CN; $R^{1g}$, $R^{2g}$, and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^{3a}$, $—OR^a$, $—OC(O)R^b$, $—OC(O)NR^cR^d$, $—SR^a$, $—S(O)_2R^a$, $—S(O)_2NR^cR^d$, $—C(O)R^a$, —C(O)OR$^a$, —C(O)NR$^c$R$^d$, —NR$^c$R$^d$, —(R$^c$C(O)R$^b$, —N(R$^c$)S(O)$_2$R$^b$, —N(R$^c$)C(O)O(R$^b$), —N(R$^c$)C(O)NR$^c$R$^d$, —N(R$^c$)S(O)$_2$NR$^c$R$^d$, (C$_1$-C$_6$ alkylenyl)-CN, —(C$_1$-C$_6$ alkylenyl)-G$^{2a}$, —(C$_1$-C$_6$ alkylenyl)-OR$^a$, —(C$_1$-C$_6$ alkylenyl)-OC(O)R$^b$, —(C$_1$-C$_6$ alkylenyl)-OC(O)NR$^c$R$^d$, —(C$_1$-C$_6$ alkylenyl)-S(O)$_2$R$^a$, —(C$_1$—C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^c$)C(O)R$^b$, —(C$_1$-C$_6$ alkylenyl)-N(R$^c$)S(O)$_2$R$^b$, —(C$_1$-C$_6$ alkylenyl)-N(R$^c$C(O)O(R$^b$), —(C$_1$-C$_6$ alkylenyl)-N(R$^c$)C(O)NR$^c$R$^d$, —(C$_1$-C$_6$ alkylenyl)-N(R$^c$)S(O)$_2$NR$^c$R$^d$, or —(C$_1$-C$_6$ alkylenyl)-CN; R$^a$, R$^c$, R$^d$, and R$^c$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^{2a}$, or —(C$_1$-C$_6$ alkylenyl)-G$^{2a}$; R$^b$, at each occurrence, is independently C$_1$-C$_6$ alkyl, C$_2$-C$_6$ alkenyl, C$_2$-C$_6$ alkynyl, C$_1$-C$_6$ haloalkyl, G$^{3a}$, or (C$_1$-C$_6$ alkylenyl)-G$^{2a}$; G$^{2a}$, at each occurrence, are each independently aryl, heteroaryl, heterocycle, cycloalkyl, or cycloalkenyl; and each G$^{2a}$ group is optionally substituted with 1, 2, 3, 4, or 5 R$^{3g}$ groups; R$^{3g}$, at each occurrence, is independently oxo, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{x1}$, —OC(O)R$^{x2}$, —OC(O)NR$^{x1}$R$^{x1}$, —SR$^{x1}$, —S(O)$_2$R$^{x1}$, —S(O)$_2$NR$^{x3}$R$^{x4}$, —C(O)R$^{x1}$, —C(O)OR$^{x1}$, —C(O)NR$^{x3}$R$^{x4}$, —NR$^{x3}$R$^{x4}$, —N(R$^{x3}$)C(O)R$^{x2}$, N(R$^{x1}$)S(O)$_2$R$^{x2}$, N(R$^{x1}$)C(O)O(R$^{x2}$), N(R$^{x1}$)C(O)NR$^{x3}$R$^{x4}$, —N(R$^{x3}$)S(O)$_2$NR$^{x3}$R$^{x4}$, —(C$_1$-C$_6$ alkylenyl)-OR$^{x1}$, —(C$_1$-C$_6$ alkylenyl)-OC(O)R$^{x2}$, —(C$_1$-C$_6$ alkylenyl)-OC(O)NR$^{x3}$R$^{x4}$, —(C$_1$-C$_6$ alkylenyl)-S(O)$_2$R$^{x1}$, —(C$_1$-C$_6$ alkylenyl)-S(O)$_2$NR$^{x3}$R$^{x4}$, —(C$_1$-C$_6$ alkylenyl)-C(O)R$^{x1}$, —(C$_1$-C$_4$ alkylenyl)-C(O)OR$^{x1}$, —(C$_1$-C$_6$ alkylenyl)-C(O)NR$^{x3}$R$^{x4}$, —(C$_1$-C$_6$ alkylenyl)-NR$^{x3}$R$^{x4}$, —(C$_1$-C$_6$ alkylenyl)-N(R$^{x3}$)C(O)R$^{x2}$, —(C$_1$-C$_6$ alkylenyl)-N(R$^{x3}$)S(O)$_2$R$^{x2}$, —(C$_1$-C$_6$ alkylenyl)-N(R$^{x3}$)C(O)O(R$^{x2}$), —(C$_1$-C$_6$ alkylenyl)-N(R$^{x3}$)C(O)NR$^{x3}$R$^{x4}$, —(C$_1$-C$_6$ alkylenyl)-N(R$^{x3}$)S(O)$_2$NR$^{x3}$R$^{x4}$, or —(C$_1$-C$_6$ alkylenyl)-CN; R$^{x1}$, R$^{x3}$, and R$^{x4}$, at each occurrence, are each independently H, C$_1$-C$_6$ alkyl, C$_2$-C$_6$ alkenyl, C$_2$-C$_6$ alkynyl, or C$_1$-C$_6$ haloalkyl; and R$^{x2}$, at each occurrence, is independently C$_1$-C$_6$ alkyl, C$_2$-C$_6$ alkenyl, C$_2$-C$_6$ alkynyl, or C$_1$-C$_6$ haloalkyl.

In certain embodiments, Y$^1$ is N or CH; R$^1$ is CD$_3$, C$_1$-C$_3$ alkyl, or C$_1$-C$_3$ haloalkyl; R$^2$ is H or C$_1$-C$_3$ alkyl; Y$^3$ is N or CR$^3$; R$^3$ is H, C$_1$-C$_6$ alkyl, C$_2$-C$_6$ alkenyl, C$_2$-C$_6$ alkynyl, halogen, C$_1$-C$_6$ haloalkyl, —CN, —C(O)R$^{3a}$, —C(O)OR$^{3a}$, —C(O)NR$^{3b}$R$^{3c}$, —S(O)R$^{3d}$, —SO)$_2$R$^{3a}$, —S(O)$_2$NR$^{3b}$R$^{3c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —CN, —C(O)R$^{3a}$, —C(O)OR$^{3a}$, —C(O)NR$^{3b}$R$^{3c}$, —C(O)N(R$^{3b}$)NR$^{3b}$R$^{3c}$, —S(O)R$^{3d}$, —S(O)$_2$R$^{3a}$, —S(O)$_2$NR$^{3b}$R$^{3c}$, —OR$^{3a}$, —OC(O)R$^{3d}$, —NR$^{3b}$R$^{3c}$, —N(R$^{3b}$)C(O)R$^{3d}$, N(R$^{3b}$)SO$_2$R$^{3d}$, N(R$^{3b}$)C(O)OR$^{3d}$, N(R$^{3b}$)C(O)NR$^{3b}$R$^{3c}$, N(R$^{3b}$)SO$_2$NR$^{3b}$R$^{3c}$, and N(R$^{3b}$)C(NR$^{3b}$R$^{3c}$)'NR$^{3b}$R$^{3c}$; Y$^2$ is C(O), S(O)$_2$, or CR$^4$R$^5$; R$^4$ is H, deuterium, C$_1$-C$_6$ alkyl, halogen, or C$_1$-C$_6$ haloalkyl; R$^5$ is H, deuterium, C$_1$-C$_6$ alkyl, C$_2$-C$_6$ alkenyl, C$_2$-C$_6$ alkynyl, halogen, C$_1$-C$_6$ haloalkyl, —C(O)R$^{5a}$, —C(O)OR$^{5a}$, —C(O)NR$^{5b}$R$^{5c}$, —S(O)R$^{5d}$, —S(O)$_2$R$^{5a}$, —S(O)$_2$NR$^{5b}$R$^{5c}$, or G$^1$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^1$, —C(O)R$^{5a}$, —C(O)OR$^{5a}$, —C(O)NR$^{5b}$R$^{5c}$, —C(O)N(R$^{5b}$)NR$^{5b}$R$^{5c}$, —S(O)R$^{5d}$, —S(O)$_2$R$^{5a}$, —S(O)$_2$NR$^{5b}$R$^{5c}$, —OR$^{5a}$, —OC(O)R$^{5d}$, —NR$^{5b}$R$^{5c}$, —N(R$^{5b}$)C(O)R$^{5d}$, —N(R$^{5b}$)SO$_2$R$^{5d}$, N(R$^{5b}$)C(O)OR$^{5d}$, N(R$^{5b}$)C(O)NR$^{5b}$R$^{5c}$, N(R$^{5b}$)SO$_2$NR$^{5b}$R$^{5c}$, and N(R$^{5b}$)C(NR$^{5b}$R$^{5c}$)═NR$^{5b}$R$^{5c}$; R$^{3a}$, R$^{3b}$, R$^{3c}$, R$^{5a}$, and R$^{5b}$, at each occurrence, are each independently H, C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$; R$^{5c}$ at each occurrence, is independently H, C$_1$-C$_6$ alkyl, C$_2$-C$_6$ alkenyl, C$_2$-C$_6$ alkynyl, C$_1$-C$_6$ haloalkyl, G$^1$, —(C$_1$-C$_6$ alkylenyl)-G$^1$, —(C$_1$-C$_6$ alkylenyl)-CN, —(C$_1$-C$_6$ alkylenyl)-OR$^a$, or —(C$_1$-C$_6$ alkylenyl)-C(O)OR$^a$; R$^{3d}$, at each occurrence is independently C$_1$-C$_6$ alkyl, C$_2$-C$_6$ alkenyl, C$_2$-C$_6$ alkynyl, C$_1$-C$_6$ haloalkyl, G$^1$, or —(C$_1$-C$_6$ alkylenyl)-G$^1$; R$^{5d}$, at each occurrence, is independently C$_1$-C$_6$ alkyl, C$_2$-C$_6$ alkenyl, C$_2$-C$_6$ alkynyl, C$_1$-C$_6$ haloalkyl, G$^1$, —(C$_1$-C$_6$ alkylenyl)-G$^1$, —(C$_1$-C$_6$ alkylenyl)-NR$^c$R$^d$, or —(C$_1$-C$_6$ alkylenyl)-N(R$^c$)C(O)O(R$^b$); G$^1$, at each occurrence, is independently aryl, heteroaryl, heterocycle, cycloalkyl, or cycloalkenyl; and each G$^1$ is optionally substituted with 1, 2, 3, 4, or 5 R$^{1g}$ groups;

R$^6$ is H, C$_1$-C$_6$ alkyl, C$_2$-C$_6$ alkenyl, C$_2$-C$_6$ alkynyl, halogen, C$_1$-C$_6$ haloalkyl, —C(O)R$^{6a}$, —C(O)OR$^{6a}$, —C(O)NR$^{6b}$R$^{6c}$, —S(O)$_2$R$^{6a}$, —S(O)$_2$NR$^{6b}$R$^{6c}$, or G$^2$; wherein the C$_1$-C$_6$ alkyl, C$_2$-C$_6$ alkenyl, and C$_2$-C$_6$ alkynyl are each independently unsubstituted or substituted with 1 or 2 substituents independently selected from the group consisting of G$^2$, —C(O)R$^{6a}$, —C(O)OR$^{6a}$, —C(O)NR$^{6b}$R$^{6c}$, —C(O)N(R$^{6b}$)NR$^{6b}$R$^{6c}$, —S(O)R$^{6d}$, —S(O)$_2$R$^{6a}$, —S(O)$_2$NR$^{6b}$R$^{6c}$, —OR$^{6a}$, —OC(O)R$^{6d}$, —NR$^{6b}$R$^{6c}$, N(R$^{6b}$)C(O)R$^{6d}$, N(R$^{6a}$)SO$_2$R$^{6d}$, N(R$^{6b}$)C(O)OR$^{6d}$, N(R$^{6b}$)C(O)NR$^{6b}$R$^{6c}$, N(R$^{6b}$)SO$_2$NR$^{6b}$R$^{6c}$, and N(R$^{6b}$)C(NR$^{6b}$R$^{6c}$)═NR$^{6b}$R$^{6c}$; R$^{6a}$, R$^{6b}$, and R$^{6c}$, at each occurrence, are each independently H, alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^c$)C(O)R$^b$, (C$_1$-C$_6$ alkylenyl)-N(R$^c$S(O)$_2$R$^b$, —(C$_1$-C$_6$ alkylenyl)-N(R$^c$)C(O)O(R$^b$), —(C$_1$-C$_6$ alkylenyl)-N(R$^c$)C(O)NR$^c$R$^d$, or —(C$_1$-C$_6$ alkylenyl)-N(R$^c$)S(O)$_2$NR$^c$R$^d$; R$^{6d}$, at each occurrence, is independently alkyl, C$_2$-C$_6$ alkenyl, C$_2$-C$_6$ alkynyl, haloalkyl, G$^2$, —(C$_1$-C$_6$ alkylenyl)-G$^2$, —(C$_1$-C$_6$ alkylenyl)-OR$^a$, —(C$_1$-C$_6$ alkylenyl)-S(O)$_2$R$^a$, —(C$_1$-C$_6$ alkylenyl)-S(O)$_2$NR$^c$R$^d$, —(C$_1$-C$_6$ alkylenyl)-C(O)R$^a$, —(C$_1$-C$_6$ alkylenyl)-C(O)OR$^a$, —(C$_1$-C$_6$ alkylenyl)-C(O)NR$^c$R$^d$, —(C$_1$-C$_6$ alkylenyl)-NR$^c$R$^d$, —(C$_1$-C$_6$ alkylenyl)-N(R$^a$)C(O)R$^b$, —(C$_1$-C$_6$ alkylenyl)-N(R$^a$)S(O)$_2$R$^b$, —(C$_1$-C$_6$ alkylenyl)-N(R$^a$)C(O)O(R$^b$), —(C$_1$-C$_6$ alkylenyl)-N(R$^a$)C(O)NR$^c$R$^d$, or —(C$_1$-C$_6$ alkylenyl)-N(R$^c$)S(O)$_2$NR$^c$R$^d$; G$^2$, at each occurrence, is independently aryl, heteroaryl, heterocycle, cycloalkyl, or cycloalkenyl; and each G$^2$ is optionally substituted with 1, 2, 3, 4, or 5 R$^{2g}$ groups; A$^1$ is C(R$^7$) or N; A$^2$ is C(R$^8$) or N; A$^3$ is C(R$^9$) or N; and A$^4$ is C(R$^{10}$) or N; wherein zero, one, or two of Ai, A$^2$, A$^3$, and A$^4$ are N; R$^7$, R$^8$, and R$^9$, are each independently H, C$_1$-C$_6$ alkyl, C$_2$-C$_6$ alkenyl, C$_2$-C$_6$ alkynyl, halogen, C$_1$-C$_6$ haloalkyl, —CN, NO$_2$, —OR$^{Y1}$, —OC(O)R$^{Y2}$, —OC(O)NR$^{Y3}$R$^{Y4}$, —SR$^{Y1}$, —S(O)$_2$R$^{Y1}$, —S(O)$_2$NR$^{Y3}$R$^{Y4}$, —C(O)R$^{Y1}$, —C(O)OR$^{Y1}$, —C(O)NR$^{Y3}$R$^{Y4}$, —NR$^Y$R$^{Y4}$, —N(R$^{Y3}$)C(O)R$^{Y2}$, —N(R$^{Y3}$)S(O)$_2$R$^{Y2}$, —N(R$^{Y3}$)C(O)O(R$^{Y2}$), —N(R$^{Y3}$)C(O)NR$^{Y3}$R$^{Y4}$, —N(R$^{Y3}$)S(O)$_2$NR$^{Y3}$R$^{Y4}$, G$^3$, —(C$_1$-C$_6$ alkylenyl)-CN, —(C$_1$-C$_6$ alkylenyl)-OR$^{Y1}$, —(C$_1$-C$_6$ alkylenyl)-OC(O)R$^{Y2}$, —(C$_1$-C$_6$ alkylenyl)-OC(O)NR$^{Y3}$R$^{Y4}$, —(C$_1$-C$_6$ alkylenyl)-S(O)$_2$R$^{Y1}$, —(C$_1$-C$_6$ alkylenyl)-S(O)$_2$NR$^{Y3}$R$^{Y4}$, —(C$_1$-C$_6$ alkylenyl)-C(O)R$^{Y1}$, —(C$_1$-C$_6$ alkylenyl)-C(O)OR$^{Y1}$, (C$_1$-C$_6$ alkylenyl)-C(O)NR$^{Y3}$R$^{Y4}$, —(C$_1$-C$_6$ alkylenyl)-NR$^{Y3}$R$^{Y4}$, —(C$_1$-C$_6$ alkylenyl)-N(R$^{Y3}$)C(O)

$R^{Y2}$, —($C_1$-$C_6$ alkylenyl)-N($R^{Y3}$)S(O)$_2R^{Y2}$, —($C_1$-$C_6$ alkylenyl)-N($R^{Y3}$)C(O)O($R^{Y2}$), —($C_1$-$C_6$ alkylenyl)-N($R^{Y3}$)C(O)NR$^{Y3}$R$^{Y4}$, —($C_1$-$C_6$ alkylenyl)-N($R^{Y3}$)S(O)$_2$ NR$^{Y3}$R$^{Y4}$, —($C_1$-$C_6$ alkylenyl)-cn, OR—($C_1$-$C_6$ alkylenyl)-$G^3$;

$R^{Y1}$, $R^{Y3}$, and $R^{Y4}$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-OR$^a$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl-C(O) R$^a$, —($C_1$-$C_6$ alkylenyl)-C(O)OR$^a$, —($C_1$-$C_6$ alkylenyl)-C(O)NR$^c$R$^d$, —($C_1$-$C_6$ alkylenyl)-NR$^c$R$^d$, —($C_1$-$C_6$ alkylenyl)-N(R$^c$)C(O)(R$^b$), —($C_1$-$C_6$ alkylenyl)-N (R$^c$)S(O)$_2$R$^b$, —($C_1$-$C_6$ alkylenyl)-N(R$^c$)C(O)O(R$^b$), —($C_1$-$C_6$ alkylenyl)-N(R$^c$)C(O)NR$^c$R$^d$, or —($C_1$-$C_6$ alkylenyl)-N(R$^c$)S(O)$_2$NR$^c$R$^d$; $R^{Y2}$, at each occurrence, is independently $C_1$-$C_6$ alkyl, $C_2$-$C_6$ alkenyl, $C_2$-$C_6$ alkynyl, $C_1$-$C_6$ haloalkyl, $G^3$, —($C_1$-$C_6$ alkylenyl)-$G^3$, —($C_1$-$C_6$ alkylenyl)-OR$^a$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl)-C(O)R$^a$, —($C_1$—$C_6$ alkylenyl)-C(O)OR$^a$, —($C_1$-$C_6$ alkylenyl)-C(O)NR$^c$R$^d$, —($C_1$-$C_6$ alkylenyl)-NR$^c$R$^d$, —($C_1$-$C_6$ alkylenyl)-N(R$^a$)C(O)R$^b$, —($C_1$-$C_6$ alkylenyl)-N(R$^a$)S(O)$_2$R$^b$, —($C_1$-$C_6$ alkylenyl)-N(R$^c$) C(O)O(R$^b$), —($C_1$-$C_6$ alkylenyl)-N(R$^c$)S(O)$_2$R$^b$, —($C_1$-$C_6$ alkylenyl)-N(R$^c$)S(O)$_2$NR$^c$R$^d$; $G^3$, at each occurrence, is independently aryl, heteroaryl, cycloalkyl, cycloalkenyl, or heterocycle; and each $G^3$ group is optionally substituted with 1, 2, 3, 4, or 5 $R^{4g}$ groups; $R^{10}$ is H, $C_1$-$C_3$ alkyl, halogen, $C_1$-$C_3$ haloalkyl, or —CN; $R^{1g}$, $R^{2g}$, and $R^{4g}$, at each occurrence, is independently selected from the group consisting of oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, $G^{2a}$, —OR$^a$, —OC(O) R$^b$, —OC(O)NR$^c$R$^d$, —SR$^a$, —S(O)$_2$R$^a$, —S(O)$_2$ NR$^c$R$^d$, —C(O)R$^a$, —C(O)OR$^a$, —C(O)NR$^c$R$^d$, —NR$^c$R$^d$, —N(R$^a$)C(O)R$^b$, —N(R$^a$)S(O)$_2$R$^b$, —N(R$^a$) C(O)O(R$^b$), —N(R$^c$)C(O)NR$^c$R$^d$, —N(R$^c$)S(O)$_2$ NR$^c$R$^d$, —($C_1$-$C_6$ alkylenyl)-CN, —($C_1$-$C_6$ alkylenyl)-$G^{2a}$, —($C_1$-$C_6$ alkylenyl)-OR$^a$, —($C_1$-$C_6$ alkylenyl)-OC(O)R$^b$, —($C_1$-$C_6$ alkylenyl)-OC(O)NR$^c$R$^d$, —($C_1$-$C_6$ alkylenyl)-S(O)$_2$R$^a$, —($C_1$-$C_6$ alkylenyl)-S(O)$_2$NR$^c$R$^d$, —($C_1$-$C_6$ alkylenyl)-C(O)R$^a$, —($C_1$-$C_6$ alkylenyl)-C(O)OR$^a$, —($C_1$-$C_6$ alkylenyl)-C(O) NR$^c$R$^d$, —($C_1$-$C_6$ alkylenyl)-NR$^c$R$^d$, —($C_1$-$C_6$ alkylenyl)-N(R$^a$)C(O)R$^b$, —($C_1$-$C_6$ alkylenyl)-N(R$^c$) S(O)$_2$R$^b$, —($C_1$-$C_6$ alkylenyl)-N(R$^c$)C(O)O(R$^b$), —($C_1$-$C_6$ alkylenyl)-N(R$^c$)C(O)NR$^c$R$^d$, —($C_1$-$C_6$ alkylenyl)-N(R$^c$)S(O)$_2$NR$^c$R$^d$, or —($C_1$-$C_6$ alkylenyl)-CN; R$^a$, R$^c$, R$^d$, and R$^e$, at each occurrence, are each independently H, $C_1$-$C_6$ alkyl, $C_2$-$C_6$ alkenyl, $C_2$-$C_6$ alkynyl, $C_1$-$C_6$ haloalkyl, $G^{2a}$, or —($C_1$-$C_6$ alkylenyl)-$G^{2a}$; R$^b$, at each occurrence, is independently $C_1$-$C_6$ alkyl, $C_2$-$C_6$ alkenyl, $C_2$-$C_6$ alkynyl, $C_1$-$C_6$ haloalkyl, $G^{2a}$, or —($C_1$-$C_6$ alkylenyl)-$G^{2a}$; $G^{2a}$, at each occurrence, are each independently aryl, heteroaryl, heterocycle, cycloalkyl, or cycloalkenyl; and each $G^{2a}$ group is optionally substituted with 1, 2, 3, 4, or 5 $R^{3g}$ groups; $R^{3g}$, at each occurrence, is independently oxo, $C_1$-$C_6$ alkyl, $C_2$-$C_6$ alkenyl, $C_2$-$C_6$ alkynyl, halogen, $C_1$-$C_6$ haloalkyl, —CN, $NO_2$, —OR$^{x1}$, —OC(O)R$^{x2}$, —OC (O)NR$^{x3}$R$^{x4}$, —SR$^{x1}$, —S(O)$_2$R$^{x1}$, —S(O)$_2$NR$^{x3}$R$^{x4}$, —C(O)R$^{x1}$, —C(O)OR$^{x1}$, —C(O)NR$^{x3}$R$^{x4}$, —NR$^{x3}$R$^{x4}$, —N(R$^{x3}$)C(O)R$^{x2}$, —N(R$^{x3}$)S(O)$_2$R$^{x2}$, —N(R$^{x3}$)C(O)O(R$^{x2}$), —N(R$^{x3}$)C(O)NR$^{x3}$R$^{x4}$, —N(R$^{x3}$)S(O)$_2$NR$^{x3}$R$^{x4}$, —($C_1$-$C_6$ alkylenyl)-OR$^{x1}$, —($C_1$-$C_6$ alkylenyl)-OC(O)R$^{x2}$, —($C_1$-$C_6$ alkylenyl)-OC(O)NR$^{x3}$R$^{x4}$, —($C_1$-$C_6$ alkylenyl)-S(O)$_2$R$^{x1}$, —($C_1$-$C_6$ alkylenyl)-S(O)$_2$NR$^{x3}$R$^{x4}$, —($C_1$-$C_6$ alkylenyl)-C (O)R$^{x1}$, —($C_1$-$C_6$ alkylenyl)-C(O)OR$^{x1}$, —($C_1$-$C_6$ alkylenyl)-C(O)NR$^{x3}$R$^{x4}$, —($C_1$-$C_6$ alkylenyl)-NR$^{x3}$R$^{x4}$, —($C_1$-$C_6$ alkylenyl)-n(r$^{x3}$)C(O)R$^{x2}$, —($C_1$-$C_6$ alkylenyl)-N(R$^{x3}$)S(O)$_2$R$^{x2}$, —($C_1$-$C_6$ alkylenyl)-N (R$^{x3}$)C(O)O(R$^{x2}$), —($C_1$-$C_6$ alkylenyl)-N(R$^{x3}$)C(O) NR$^3$R$^{x4}$, —($C_1$-$C_6$ alkylenyl)-N(R$^{x3}$)S(O)$_2$NR$^{x3}$R$^{x4}$, or —($C_1$-$C_6$ alkylenyl)-CN; R$^{x1}$, R$^{x3}$, and R$^{x4}$, at each occurrence, are each independently H, $C_1$-$C_6$ alkyl, $C_2$-$C_6$ alkenyl, $C_2$-$C_6$ alkynyl, or $C_1$-$C_6$ haloalkyl; and R$^{x2}$, at each occurrence, is independently $C_1$-$C_6$ alkyl, $C_2$-$C_6$ alkenyl, $C_2$-$C_6$ alkynyl, or $C_1$-$C_6$ haloalkyl.

In certain embodiments, the BRD4 inhibitor has the structure:

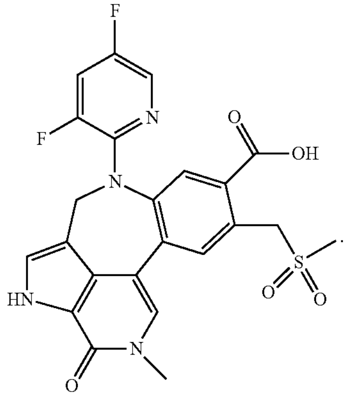 [SMILES: Cn1cc2c3c(c[nH]c3c1=O)CN(c1ncc(F)cc1F)c1cc(C(=O)O)c(CS(C)(=O)=O)cc1-2]

In embodiments, the BRD4 binding fragment is covalently linked to L2 via an amide bond. In embodiments, the BRD4 binding fragment is covalently linked to L2 via an amide bond formed from an amine group in L2 and the —COOH in the structure above. Thus, in certain embodiments, for linking the BRD4 binding fragment to L2, $A^2$ is C($R^8$), where $R^8$ is —C(O)OR$^{Y1}$, where $R^{Y1}$ is a hydrogen.

In embodiments, for linking the BRD4 binding fragment to L2, $A^2$ is C($R^8$), where $R^8$ is —C(O)NR$^{Y3}$R$^{Y4}$, where $R^{Y3}$ and $R^{Y4}$ are each independently selected from the group consisting of hydrogen and $C_1$-$C_6$ alkyl, in the following structure:

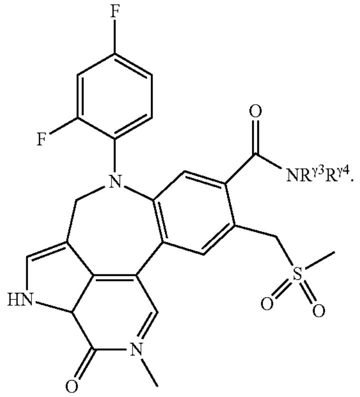

2. JQ1 Inhibitors

In embodiments, the CIDE contains a residue of a JQ1 bromodomain inhibitor, such as the inhibitors described in U.S. Pat. No. 8,981,083, herein incorporated by reference in its entirety. The inhibitor has the following general formula, I:

(I)

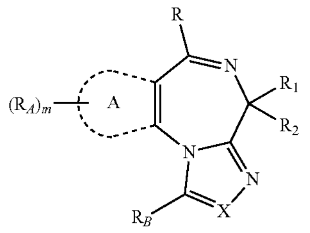

wherein

X is N or $CR_5$;

$R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or COO $R_3$, each of which is optionally substituted;

ring A is aryl or heteroaryl;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

R is alkyl, cycloalkyl, heterocycloalkyl, aryl, or heteroaryl; each of which is optionally substituted;

$R_1$ is $(CH_2)_n$-L, in which n is 0-3 and L is H, —COO—$R_3$, —CO—$R_3$, —CO—$N(R_3R_4)$, —$S(O)_2$—$R_3$, —$S(O)_2$—$N(R_3R_4)$, $N(R_3R_4)$, $N(R_4)C(O)R_3$, optionally substituted aryl, or optionally substituted heteroaryl;

$R_2$ is H, D (deuterium), halogen, or optionally substituted alkyl;

each $R_3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, $N{=}CR_4R_6$;

each $R_4$ is independently H, alkyl, alkyl, cycloalkyl, heterocycloalkyl, aryl, or heteroaryl, each of which is optionally substituted; or $R_3$ and $R_4$ are taken together with the nitrogen atom to which they are attached to form a 4-10-membered ring;

$R_6$ is alkyl, alkenyl, cycloalkyl, cycloalkenyl, heterocycloalkyl, aryl, or heteroaryl, each of which is optionally substituted; or $R_4$ and $R_6$ are taken together with the carbon atom to which they are attached to form a 4-10-membered ring;

m is 0, 1, 2, or 3;

provided that (a) if ring A is thienyl, X is N, R is phenyl or substituted phenyl, $R_2$ is H, $R_B$ is methyl, and $R_1$ is —$(CH_2)_n$-L, in which n is 1 and L is —CO—$N(R_3R_4)$, then $R_3$ and $R_4$ are not taken together with the nitrogen atom to which they are attached to form a morpholino ring;

(b) if ring A is thienyl, X is N, R is substituted phenyl, $R_2$ is H, $R_B$ is methyl, and $R_1$ is —$(CH_2)_n$-L, in which n is 1 and L is —CO—$N(R_3R_4)$, and one of $R_3$ and $R_4$ is H, then the other of $R_3$ and $R_4$ is not methyl, hydroxyethyl, alkoxy, phenyl, substituted phenyl, pyridyl or substituted pyridyl; and (c) if ring A is thienyl, X is N, R is substituted phenyl, $R_2$ is H, $R_B$ is methyl, and $R_1$ is —$(CH_2)_n$-L, in which n is 1 and L is —COO—$R_3$, then $R_3$ is not methyl or ethyl;

or a salt, solvate or hydrate thereof.

In certain embodiments, R is aryl or heteroaryl, each of which is optionally substituted.

In certain embodiments, L is H, —COO—$R_3$, —CO—$N(R_3R_4)$, —$S(O)_2$—$R_3$, —$S(O)_2$—$N(R_3R_4)$, $N(R_3R_4)$, $N(R_4)C(O)R_3$ or optionally substituted aryl. In certain embodiments, each $R_3$ is independently selected from the group consisting of: H, $C_1$-$C_5$ alkyl, which is optionally substituted, containing 0, 1, 2, or 3 heteroatoms selected from O, S, or N; or $NH_2$, $N{=}CR_4R_6$.

In certain embodiments, $R_2$ is H, D, halogen or methyl.

In certain embodiments, $R_B$ is alkyl, hydroxyalkyl, haloalkyl, or alkoxy; each of which is optionally substituted.

In certain embodiments, $R_B$ is methyl, ethyl, hydroxy methyl, methoxymethyl, trifluoromethyl, COOH, COOMe, COOEt, or $COOCH_2OC(O)CH_3$.

In certain embodiments, ring A is a 5 or 6-membered aryl or heteroaryl. In certain embodiments, ring A is thiofuranyl, phenyl, naphthyl, biphenyl, tetrahydronaphthyl, indanyl, pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, or 5,6,7,8-tetrahydroisoquinolinyl.

In certain embodiments, ring A is phenyl or thienyl.

In certain embodiments, m is 1 or 2, and at least one occurrence of $R_A$ is methyl.

In certain embodiments, each $R_A$ is independently H, an optionally substituted alkyl, or any two $R_A$ together with the atoms to which each is attached, can form an aryl.

In some further embodiments, the JQ1 inhibitor is a compound of Formula II:

(II)

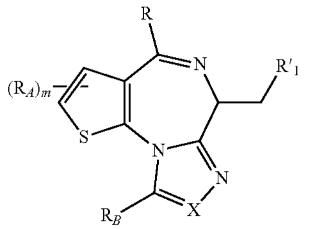

wherein

X is N or $CR^5$;

$R_5$ is H, alkyl, cycloalkyl, heterocycloalkyl, aryl, or heteroaryl, each of which is optionally substituted;

$R_B$ is H, alkyl, hydroxylalkyl, aminoalkyl, alkoxyalkyl, haloalkyl, hydroxy, alkoxy, or —COO—$R_3$, each of which is optionally substituted;

each $R_A$ is independently alkyl, cycloalkyl, heterocycloalkyl, aryl, or heteroaryl, each of which is optionally substituted; or any two $R_A$ together with the atoms to which each is attached, can form a fused aryl or heteroaryl group;

R is alkyl, cycloalkyl, heterocycloalkyl, aryl, or heteroaryl, each of which is optionally substituted;

R'$_1$ is H, —COO—R$_3$, —CO—R$_3$, optionally substituted aryl, or optionally substituted heteroaryl;

each R$_3$ is independently selected from the group consisting of:

(i) H, aryl, substituted aryl, heteroaryl, substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl; —$C_3$-$C_{12}$ cycloalkenyl, or substituted —$C_3$-$C_{12}$ cycloalkenyl; each of which may be optionally substituted;

m is 0, 1, 2, or 3;

provided that if R'$_1$ is —COO—R$_3$, X is N, R is substituted phenyl, and R$_B$ is methyl, then R$_3$ is not methyl or ethyl; or a salt, solvate or hydrate thereof.

In certain embodiments, R is aryl or heteroaryl, each of which is optionally substituted. In certain embodiments, R is phenyl or pyridyl, each of which is optionally substituted. In certain embodiments, R is p-Cl-phenyl, o-Cl-phenyl, m-Cl-phenyl, p-F-phenyl, o-F-phenyl, m-F-phenyl or pyridinyl.

In certain embodiments, R'$_1$ is —COO—R$_3$, optionally substituted aryl, or optionally substituted heteroaryl; and R$_3$ is —$C_1$-$C_5$ alkyl, which contains 0, 1, 2, or 3 heteroatoms selected from O, S, or N, and which may be optionally substituted. In certain embodiments, R'$_1$ is —COO—R$_3$, and R$_3$ is methyl, ethyl, propyl, i-propyl, butyl, sec-butyl, or t-butyl; or R'$_1$ is H or optionally substituted phenyl.

In certain embodiments, R$_B$ is methyl, ethyl, hydroxy methyl, methoxymethyl, trifluoromethyl, COOH, COOMe, COOEt, $COOCH_2OC(O)CH_3$.

In certain embodiments, R$_B$ is methyl, ethyl, hydroxy methyl, methoxymethyl, trifluoromethyl, COOH, COOMe, COOEt, or $COOCH_2OC(O)CH_3$.

In certain embodiments, each R$_A$ is independently an optionally substituted alkyl, or any two R$_A$ together with the atoms to which each is attached, can form a fused aryl.

In certain embodiments, each R$_A$ is methyl.

In further embodiments, the JQ1 inhibitor is a compound of formula IV:

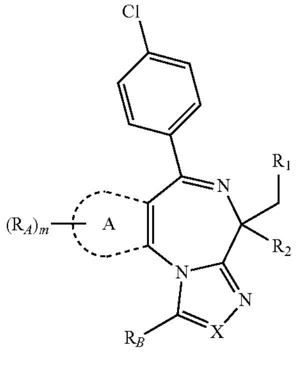

(IV)

wherein

X is N or CR$_5$;

R$_5$ is H, alkyl, cycloalkyl, heterocycloalkyl, aryl, or heteroaryl, each of which is optionally substituted;

R$_B$ is H, alkyl, hydroxylalkyl, aminoalkyl, alkoxyalkyl, haloalkyl, hydroxy, alkoxy, or COO R$_3$, each of which is optionally substituted;

ring A is aryl or heteroaryl;

each R$_A$ is independently alkyl, cycloalkyl, heterocycloalkyl, aryl, or heteroaryl, each of which is optionally substituted; or any two R$_A$ together with the atoms to which each is attached, can form a fused aryl or heteroaryl group;

R$_1$ is —$(CH_2)_n$-L, in which n is 0-3 and L is H, —COO—R$_3$, —CO—R$_3$, —CO—N(R$_3$R$_4$), —$S(O)_2$—R$_3$, —$S(O)_2$—N(R$_3$R$_4$), N(R$_3$R$_4$), N(R$_4$)C(O)R$_3$, optionally substituted aryl, or optionally substituted heteroaryl;

R$_2$ is H, D, halogen, or optionally substituted alkyl;

each R$_3$ is independently selected from the group consisting of:

(i) H, aryl, substituted aryl, heteroaryl, or substituted heteroaryl;

(ii) heterocycloalkyl or substituted heterocycloalkyl;

(iii) —$C_1$-$C_8$ alkyl, —$C_2$-$C_8$ alkenyl or —$C_2$-$C_8$ alkynyl, each containing 0, 1, 2, or 3 heteroatoms selected from O, S, or N; —$C_3$-$C_{12}$ cycloalkyl, substituted —$C_3$-$C_{12}$ cycloalkyl, —$C_3$-$C_{12}$ cycloalkenyl, or substituted —$C_3$-$C_{12}$ cycloalkenyl, each of which may be optionally substituted; and (iv) $NH_2$, N═CR$_4$R$_6$;

each R$_4$ is independently H, alkyl, alkyl, cycloalkyl, heterocycloalkyl, aryl, or heteroaryl, each of which is optionally substituted;

or R$_3$ and R$_4$ are taken together with the nitrogen atom to which they are attached to form a 4-10-membered ring;

R$_6$ is alkyl, alkenyl, cycloalkyl, cycloalkenyl, heterocycloalkyl, aryl, or heteroaryl, each of which is optionally substituted; or R$_4$ and R$_6$ are taken together with the carbon atom to which they are attached to form a 4-10-membered ring;

m is 0, 1, 2, or 3;

provided that (a) if ring A is thienyl, X is N, R$_2$ is H, R$_B$ is methyl, and R$_1$ is —$(CH_2)_n$-L, in which n is 0 and L is —CO—N(R$_3$R$_4$), then R$_3$ and R$_4$ are not taken together with the nitrogen atom to which they are attached to form a morpholino ring;

(b) if ring A is thienyl, X is N, R$_2$ is H, R$_B$ is methyl, and R$_1$ is —$(CH_2)_n$-L, in which n is 0 and L is —CO—N(R$_3$R$_4$), and one of R$_3$ and R$_4$ is H, then the other of R$_3$ and R$_4$ is not methyl, hydroxyethyl, alkoxy, phenyl, substituted phenyl, pyridyl or substituted pyridyl; and (c) if ring A is thienyl, X is N, R$_2$ is H, R$_B$ is methyl, and R$_1$ is $(CH_2)_n$-L, in which n is 0 and L is —COO—R$_3$, then R$_3$ is not methyl or ethyl; or a salt, solvate or hydrate thereof.

In certain embodiments, the JQ1 inhibitor is a compound as described above, wherein R'$_1$ is —COO—R$_3$, wherein R$_3$ is H. In certain embodiments, the JQ1 inhibitor has the structure:

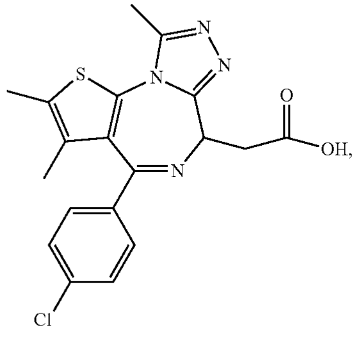

or

-continued

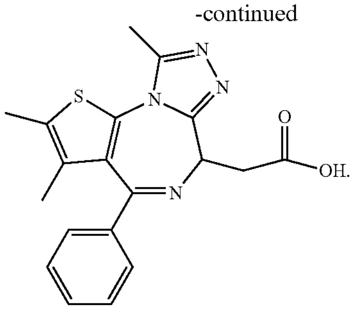

In certain embodiments, the JQ1 binding fragment is covalently linked to L2 via an amide bond formed from an amine group in L2 and the —COOH in the structures above.

When L1 is covalently bound to the JQ1 binding fragment, points of attachment include those shown in the structure below as *, with a particular embodiment shown as

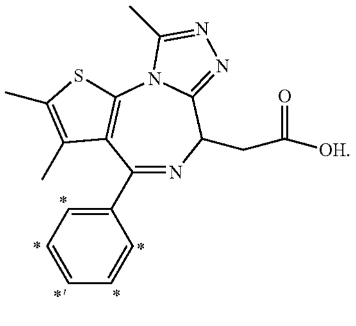 [SMILES: Cc1sc2c(c1C)C(c1ccccc1)=NC(CC(=O)O)c1nnc(C)n1-2]

ii. ERα

In embodiments, the CIDE portion contains a residue of an anti-estrogen compound, for example, a residue of tamoxifen metabolites, 4-hydroxytamoxifen (mixture of E and Z isomers or isolated E or Z isomers) and endoxifen (mixture of E and Z isomers or isolated E or Z isomers), such as a compound having the following formula:

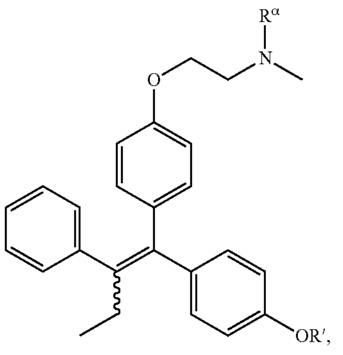

wherein, $R^{a}$ is hydrogen or methyl, and R' is hydrogen, $C_1$-$C_6$ alkyl, benzyl, phenyl, or —($PO_3H_2$).

In embodiments, the CIDE portion contains a residue of endoxifen (mixture of E and Z isomers or isolated E or Z isomers):

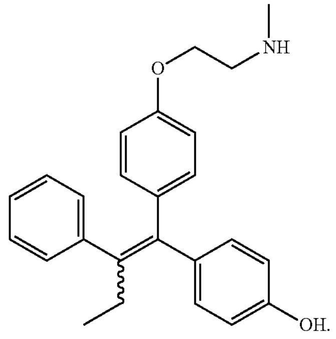 [SMILES: CCC(=C(c1ccc(O)cc1)c1ccc(OCCNC)cc1)c1ccccc1]

c. Linker L2

The E3LB and PB groups of CIDEs as described herein can be connected with linker (L2, Linker L2, Linker-2). In certain embodiments, the Linker L2 is covalently bound to the E3LB portion through an amide bond, formed from a —NH, —$NH_2$, —$NHR^{\alpha}$, —NHCOOH or other moeity on the E3LB portion capable of forming an amide bond with a Linker L2.

In certain embodiments, the linker group L2 is a group comprising one or more covalently connected structural units of A (e.g., -$A_1$ . . . $A_q$-), wherein $A_1$ is a group coupled to at least one of a E3LB, a PB, or a combination thereof. In certain embodiments, $A_1$ links a E3LB, a PB, or a combination thereof directly to another E3LB, PB, or combination thereof. In other embodiments, $A_1$ links a EL3B, a PB, or a combination thereof indirectly to another E3LB, PB, or combination thereof through $A_q$.

In certain embodiments, $A_1$ to $A_q$ are, each independently, a bond, $CR^{La}R^{Lb}$ O, S, SO, $SO_2$, $NR^{Lc}$, $SO_2NR^{Lc}$, $SONR^{Lc}$, $CONR^{Lc}$, $NR^{Lc}CONR^{Ld}$, $NR^{Lc}SO_2NR^{Ld}$, CO, $CR^{La}$=$CR^{Lb}$, C≡C, $SiR^{La}R^{Lb}$, $P(O)R^{La}$, $P(O)OR^{La}$, $NR^{Lc}C$(=NCN)$NR^{Ld}$ $NR^{Lc}C$(=NCN), $NR^{Lc}C$(=$CNO_2$)$NR^{Ld}$, $C_{3-11}$cycloalkyl optionally substituted with 0-6 $R^{La}$ and/or $R^{Lb}$ groups, $C_{3-11}$heterocyclyl optionally substituted with 0-6 $R^{La}$ and/or $R^{Lb}$ groups, aryl optionally substituted with 0-6 $R^{La}$ and/or $R^{Lb}$ groups, heteroaryl optionally substituted with 0-6 $R^{La}$ and/or $R^{Lb}$ groups, where $R^{La}$ or $R^{Lb}$, each independently, can be linked to other A groups to form cycloalkyl and/or heterocyclyl moeity which can be further substituted with 0-4 $R^{Le}$ groups; wherein $R^{La}$, $R^{Lb}$, $R^{Lc}$, $R^{Ld}$ and $R^{Le}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C$(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, SFs, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q is an integer greater than or equal to 0. In certain embodiments, q is an integer greater than or equal to 1.

In certain embodiments, e.g., where q is greater than 2, $A_q$ is a group which is connected to an E3LB moiety, and $A_1$ and $A_q$ are connected via structural units of A (number of such structural units of A: q-2).

In certain embodiments, e.g., where q is 2, $A_q$ is a group which is connected to $A_1$ and to an E3LB moiety.

In certain embodiments, e.g., where q is 1, the structure of the linker group L2 is $-A_1-$, and $A_1$ is a group which is connected to an E3LB moiety and a PB moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker (L2) is selected from the group consisting of:

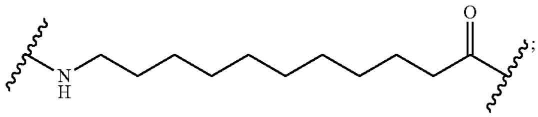
;
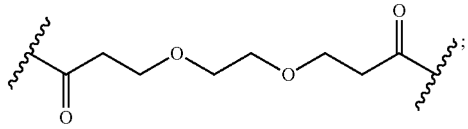
;
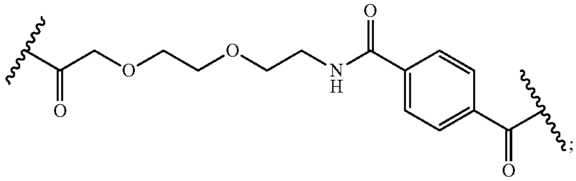
;
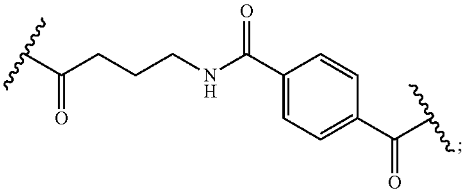
;
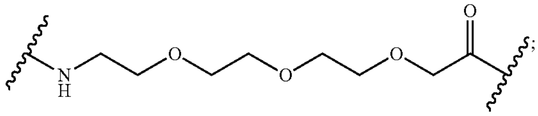
;
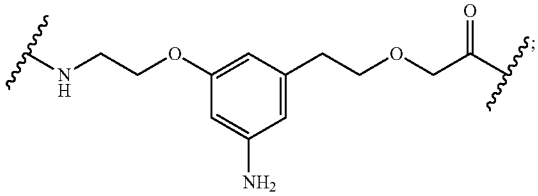
;
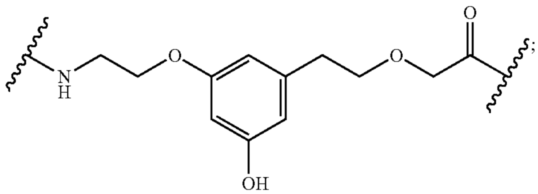
;
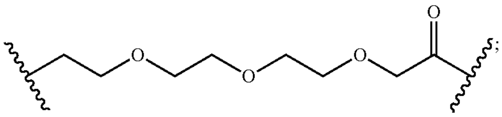
;
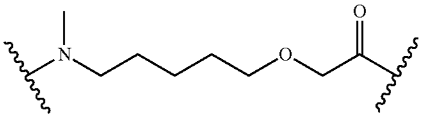
;

-continued

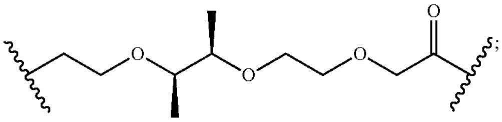
;
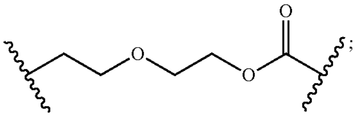
;
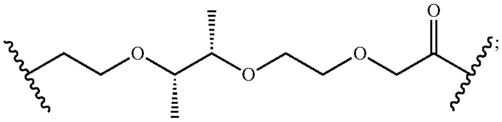
;
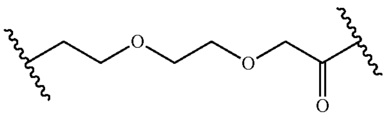
;
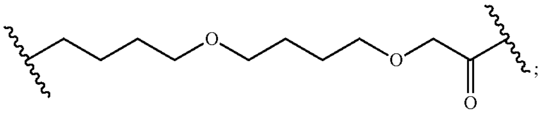
;
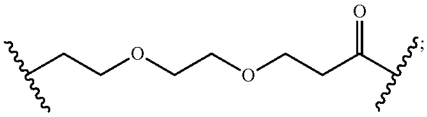
;
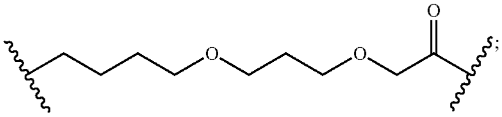
;
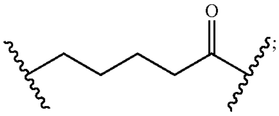
;
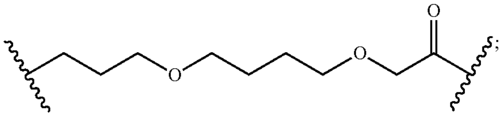
;
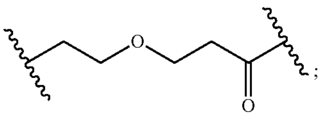
;
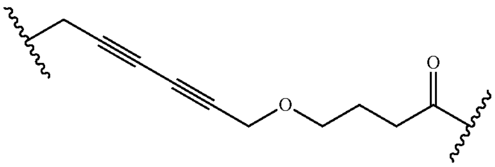
;
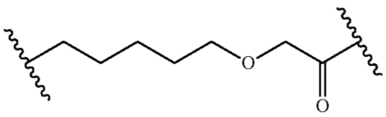
;
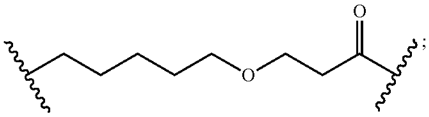
;

-continued

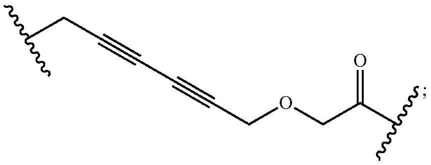

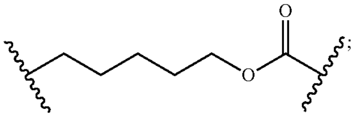

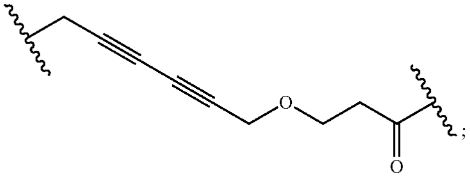

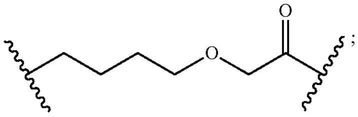

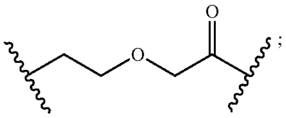

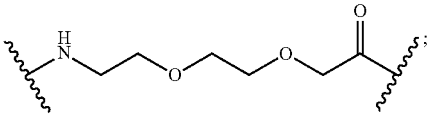

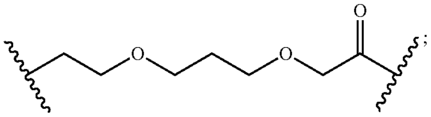

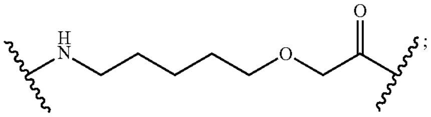

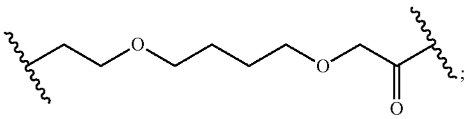

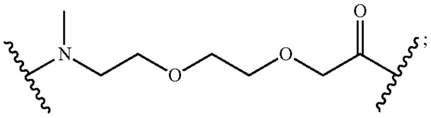

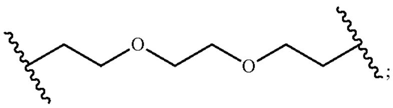

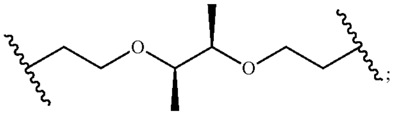

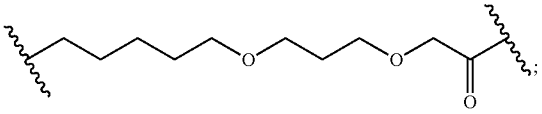

-continued

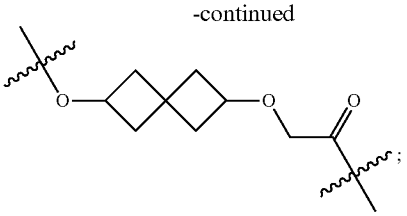

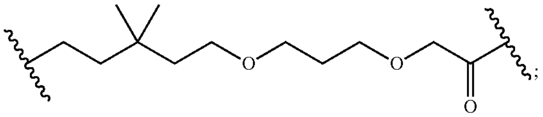

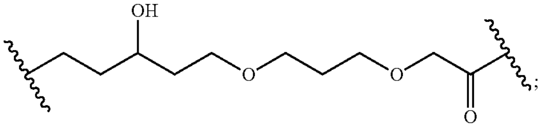

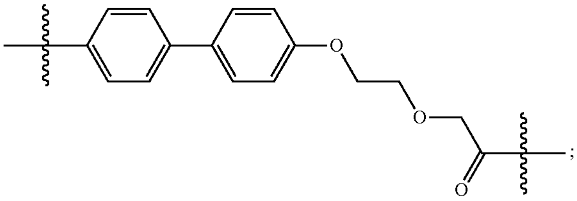

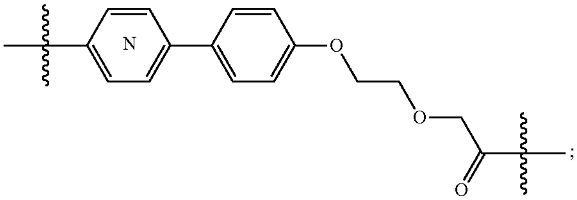

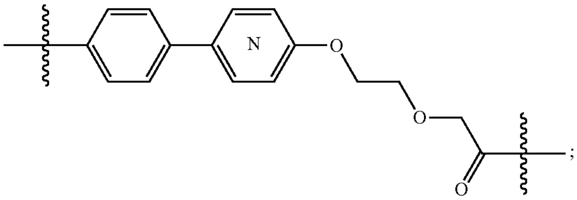

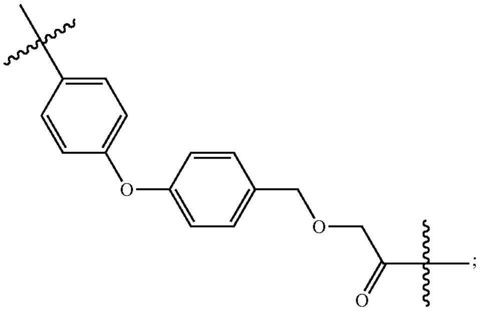

and

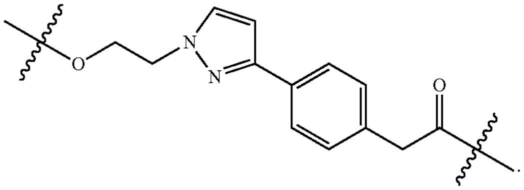 [SMILES: *OCCn1ccc(-c2ccc(CC(*)=O)cc2)n1]

In additional embodiments, the linker group is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

Although the E3LB group and PB group may be covalently linked to the linker group through any group which is appropriate and stable to the chemistry of the linker. The linker is independently covalently bonded to the E3LB group and the PB group preferably through an amide, ester, thioester, keto group, carbamate (urethane), carbon or ether, each of which groups may be inserted anywhere on the E3LB group and PB group to provide maximum binding of the E3LB group on the ubiquitin ligase and the PB group on the target protein to be degraded. In certain aspects where the PB group is an E3LB group, the target protein for degradation may be the ubiquitin ligase itself. In certain aspects, the linker may be linked to an optionally substituted alkyl, alkylene, alkene or alkyne group, an aryl group or a heterocyclic group on the E3LB and/or PB groups. It is noted that an E3LB group or a PB group may need to be derivatized to make a chemical functional group that is reactive with a chemical functional group on the linker. Alternatively, the linker may need to be derivatized to include a chemical functional group that can react with a functional group found on E3LB and/or PB.

L2 can also be represented by the formula:

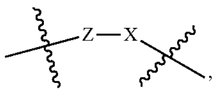

Where Z is a group which links E3LB to X; and X is a group linking Z to group PB.

In embodiments, Z is absent (a bond), —$(CH_2)$i-O, —$(CH_2)$i-S, —$(CH_2)$i-N—R, a $(CH_2)_i$—$X_1Y_1$ group wherein $X_1Y_1$ forms an amide group, or a urethane group, ester or thioester group, or a

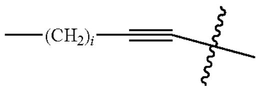

or

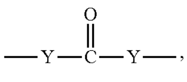

where, each R is H, or a $C_1$-$C_3$ alkyl, an alkanol group or a heterocycle (including a water soluble heterocycle, preferably, a morpholino, piperidine or piperazine group to promote water solubility of the linker group); each Y is independently a bond, O, S or N—R; and each i is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

In embodiments, X is a

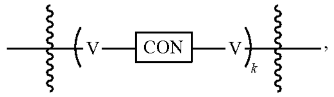

where each V is independently a bond (absent),

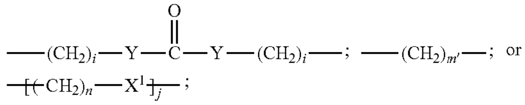

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

k is 1 to 100, 1 to 75, 1 to 60, 1 to 55, 1 to 50, 1 to 45, 1 to 40, 2 to 35, 3 to 30, 1 to 5, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 5, 1 to 10, 1 to 8, 1 to 6, 1, 2, 3, 4 or 5;

$X^1$ is O, S or N—R, preferably 0;

Y is the same as above;

and CON is a connector group (which may be a bond) which connects Z to X, when present in the linker group.

In embodiments, CON is a bond (absent), a heterocycle including a water soluble heterocycle such as a piperazinyl or other group or a group,

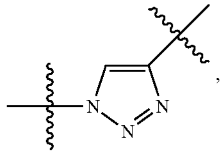,
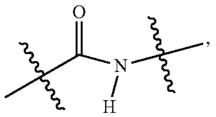,
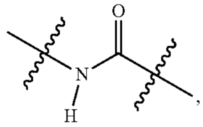,
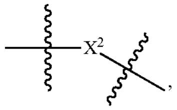,
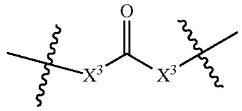
or
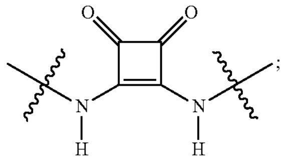;

where $X^2$ is O, S, $NR^4$, S(O), $S(O)_2$, —$S(O)_2O$, —OS$(O)_2$, or $OS(O)_2O$;

$X^3$ is O, S, $CHR^4$, $NR^4$; and

R is H or a $C_1$-$C_3$ alkyl group optionally substituted with one or two hydroxyl groups, or a pharmaceutically acceptable salt, enantiomer or stereoisomer thereof.

In alternative preferred aspects, the linker group is a (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units.

In embodiments, CON is

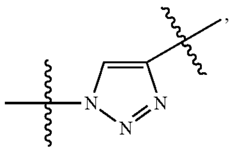 [SMILES: *c1cn(*)nn1]

or an amide group.

Although the E3LB group and PB group may be covalently linked to the linker group through any group which is appropriate and stable to the chemistry of the linker, in preferred aspects, the linker is independently covalently bonded to the E3LB group and the PB group through an amide, ester, thioester, keto group, carbamate (urethane) or ether, each of which groups may be inserted anywhere on the E3LB group and PB group to allow binding of the E3LB group to the ubiquitin ligase and the PB group to the target protein to be degraded. In other words, as shown herein, the linker can be designed and connected to E3LB and PB to minimize, eliminate, or neutralize any impact its presence might have on the binding of E3LB and PB to their respective binding partners. In certain aspects, the targeted protein for degradation may be an ubiquitin ligase.

Additional linkers L2 are disclosed in US Application Publication Nos. 2016/0058872; 2016/0045607; 2014/0356322; and 2015/0291562, and WO2014/063061.

Referring now to a Ab-CIDE, a Ab-CIDE can comprise a single antibody where the single antibody can have more than one CIDE, each CIDE covalently linked to the antibody through a linker L1. The "CIDE loading" is the average number of CIDE moieties per antibody. CIDE loading may range from 1 to 8 CIDE (D) per antibody (Ab). That is, in the Ab-CIDE formula, Ab-(L1-D)p, p has a value from about 1 to about 50, from about 1 to about 8, from about 1 to about 5, from about 1 to about 4, or from about 1 to about 3. Each CIDE covalently linked to the antibody through linker L1 can be the same or different CIDE and can have a linker of the same type or different type as any other L1 covalently linked to the antibody. In one embodiment, Ab is a cysteine engineered antibody and p is about 2.

The average number of CIDEs per antibody in preparations of Ab-CIDEs from conjugation reactions may be characterized by conventional means such as mass spectrometry, ELISA assay, electrophoresis, and HPLC. The quantitative distribution of Ab-CIDEs in terms of p may also be determined. By ELISA, the averaged value of p in a particular preparation of Ab-CIDE may be determined (Hamblett et al (2004) Clin. Cancer Res. 10:7063-7070; Sanderson et al (2005) Clin. Cancer Res. 11:843-852). However, the distribution of the value of p is not discernible by the antibody-antigen binding and detection limitation of ELISA. Also, ELISA assay for detection of Ab-CIDEs does not determine where the CIDE moieties are attached to the antibody, such as the heavy chain or light chain fragments, or the particular amino acid residues. In some instances, separation, purification, and characterization of homogeneous Ab-CIDEs where p is a certain value from Ab-CIDEs with other CIDE loadings may be achieved by means such as reverse phase HPLC or electrophoresis.

For some Ab-CIDEs, p may be limited by the number of attachment sites on the antibody. For example, an antibody may have only one or several cysteine thiol groups, or may have only one or several sufficiently reactive thiol groups through which a linker may be attached. Another reactive site on an Ab to connect L1-Ds are the amine functional group of lysine residues. Values of p include values from about 1 to about 50, from about 1 to about 8, from about 1 to about 5, from about 1 about 4, from about 1 to about 3, and where p is equal to 2. In some embodiments, the subject matter described herein is directed to any the Ab-CIDEs, wherein p is about 1, 2, 3, 4, 5, 6, 7, or 8.

Generally, fewer than the theoretical maximum of CIDE moieties is conjugated to an antibody during a conjugation reaction. An antibody may contain, for example, many lysine residues that do not react with the linker L1-CIDE group (L1-D) or linker reagent. Only the most reactive lysine groups may react with an amine-reactive linker reagent. Also, only the most reactive cysteine thiol groups may react with a thiol-reactive linker reagent or linker L1-CIDE group. Generally, antibodies do not contain many, if any, free and reactive cysteine thiol groups which may be linked to a CIDE moiety. Most cysteine thiol residues in the antibodies of the compounds exist as disulfide bridges and must be reduced with a reducing agent such as dithiothreitol (DTT) or TCEP, under partial or total reducing conditions. However, the CIDE loading (CIDE/antibody ratio, "CAR") of a CAR may be controlled in several different manners, including: (i) limiting the molar excess of linker L1-CIDE group or linker reagent relative to antibody, (ii) limiting the conjugation reaction time or temperature, and (iii) partial or limiting reductive conditions for cysteine thiol modification.

III. L1-CIDE Compounds

The CIDEs described herein can be covalently linked to a linker L1 to prepare L1-CIDE groups. These compounds have the following general formula:

(L1-D), wherein, D is a CIDE having the structure E3-LB-L2-PB; wherein, E3LB is an E3 ligase binding group covalently bound to L2; L2 is a linker covalently bound to E3LB and PB; PB is a protein binding group covalently bound to L2; and L1 is a linker, covalently bound to D. Useful groups for each of these components is as described above.

In particular embodiments, L1 is as described elsewhere herein, including a peptidomimetic linker. In these embodiments, the L1-CIDE has the following formula:

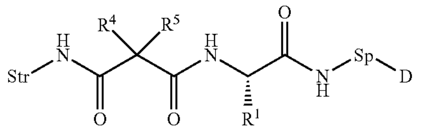

wherein

Str is a stretcher unit;

Sp is a bond or a spacer unit covalently attached to D, i.e., a CIDE moiety;

$R^1$ is $C_1$-$C_{10}$alkyl, ($C_1$-$C_{10}$alkyl)$NHC(NH)NH_2$ or ($C_1$-$C_{10}$alkyl)$NHC(O)NH_2$;

$R^4$ and $R^5$ are each independently $C_1$-$C_{10}$alkyl, arylalkyl, heteroarylalkyl, ($C_1$-$C_{10}$alkyl)$OCH_2$—, or $R^4$ and $R^5$ may form a $C_3$-$C_7$cycloalkyl ring;

D is a CIDE moiety.

An L1-CIDE compound can be represented by the following formula:

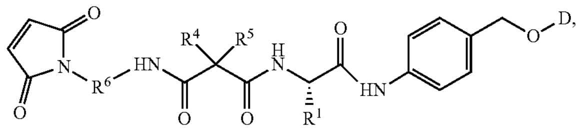

wherein $R_6$ is $C_1$-$C_{10}$alkylene; $R^4$ and $R^5$ together form a $C_3$-$C_7$cycloalkyl ring, and D is a CIDE moeity.

An L1-CIDE compound can be represented by the following formula:

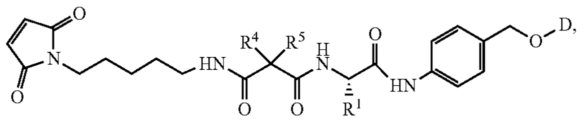

wherein $R^1$, $R^4$ and $R^5$ are as described elsewhere herein, and D is a CIDE moiety.

An L1-CIDE compound can be represented by the following formula:

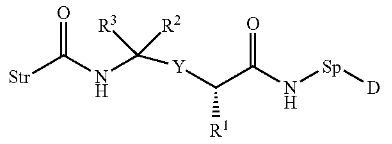

wherein

Str is a stretcher unit;

Sp is an optional spacer unit covalently attached to D, i.e., a CIDE moiety;

Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;

$R^1$ is $C_1$-$C_{10}$alkyl, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, arylalkyl or heteroarylalkyl, or $R^3$ and $R^2$ together may form a $C_3$-$C_7$cycloalkyl; and D is a CIDE moiety.

An L1-CIDE compound can be represented by the following formula:

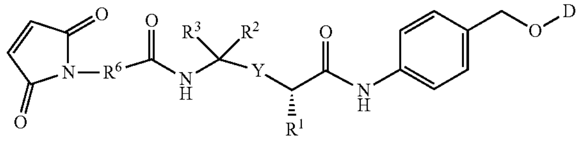

wherein, $R^6$ is $C_1$-$C_{10}$alkylene, and $R^1$, $R^2$ and $R^3$ are as described elsewhere herein, and D is a CIDE moiety An L1-CIDE compound can be represented by the following formula:

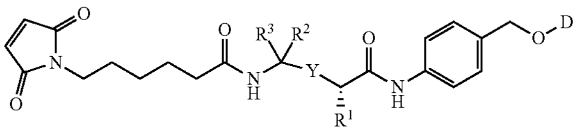

wherein $R^1$, $R^2$ and $R^3$ are as described elsewhere herein, and D is a CIDE moiety.

In any of the above L1-CIDE compounds, Str can have the following formula:

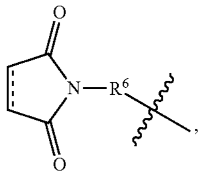

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl aryl, arylalkyl, heteroarylalkyl and heteroaryl; each $R^a$ is independently H or $C_1$-$C_6$alkyl; Sp is —Ar—$R^b$—, wherein Ar is aryl or heteroaryl, $R^b$ is ($C_1$-$C_{10}$alkylene)O—.

In certain L1-CIDE compounds, $R^6$ is $C_1$-$C_{10}$alkylene, Sp is —Ar—$R^b$—, wherein Ar is aryl $R^b$ is ($C_1$-$C_6$alkylene) O—; or $R_6$ is —$(CH_2)$q is 1-10;

In any of the above L1-CIDE compounds, Str can have the following formula:

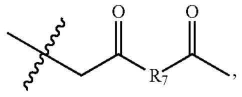

wherein, ⌇ indicates a moiety capable of conjugating to an antibody, $R^7$ is selected from $C_1$-$C_{10}$alkylene, $C_1$-$C_{10}$alkylene-O, N($R^c$)—($C_2$-$C_6$ alkylene)-N($R^c$) and N($R^c$)—($C_2$-$C_6$alkylene); where each $R^c$ is independently H or $C_1$-$C_6$ alkyl;

Sp is —Ar—$R^b$—, wherein Ar is aryl or heteroaryl, $R^b$ is ($C_1$-$C_{10}$ alkylene)O—; or wherein $R^6$ is $C_1$-$C_{10}$ alkylene, Sp is —Ar—$R^b$—, wherein Ar is aryl $R^b$ is ($C_1$-$C_6$ alkylene) O—.

An L1-CIDE can have the following formulae, wherein in each instance, D is a CIDE moiety:

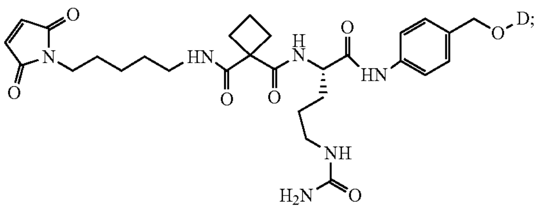

; and

-continued

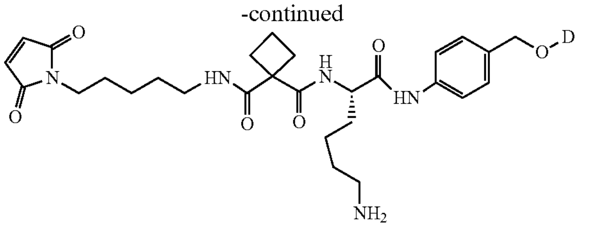

Referring now to the PB group of the CIDE, in particular embodiments, PB is as described elsewhere herein and is selected from the group consisting of Estrogen Receptor alpha (ERα) and BRD4. Referring now to the E3LB group of the CIDE, E3LB is as described elsewhere herein and is selected from the group consisting of VHL and XIAP. Ab-CIDEs can include any combination of PB, E3LB, Ab, L1 and L2, provided that when EL3B is a ligase binding group that binds XIAP, then PB is other than a group that targets ERα.

In view of the subject matter disclosed herein, those of skill in the art would understand that the L1 and L2 points of attachment can vary. Further, portions of the linkers, such as -Str-(PM)-Sp- can be interchanged. Additionally, portions of linkers L1 can be interchanged. Non-limiting examples of L1 linker attachments to the CIDE, to the antibody and to other linkers that can be interchanged include, but are not limited to, those depicted in Table 1-L1.

TABLE 1-L1

| CIDE Portion to which L1 Attached | CIDE Attachment Portion of L1 | Linker Portion of L1 | Antibody Attachment Portion of L1 |
|---|---|---|---|
| E3LB Residue 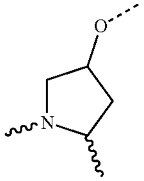 | NA | 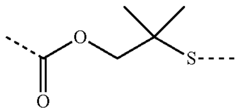 | NA |
| E3LB Residue 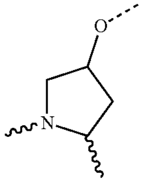 | NA | 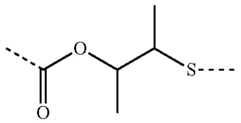 | NA |
| E3LB Residue 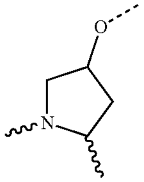 | NA | 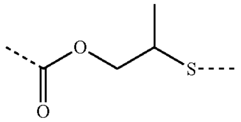 | NA |
| E3LB Residue 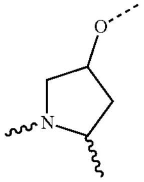 | 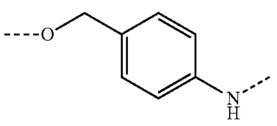 | 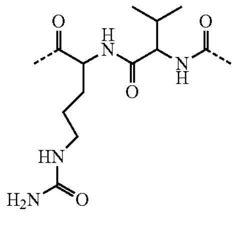 | 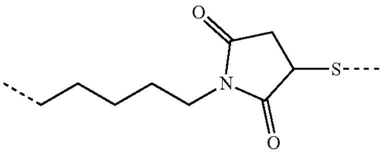 |
| E3LB Residue 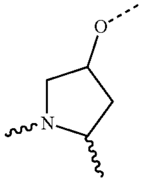 | 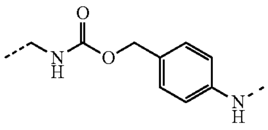 | 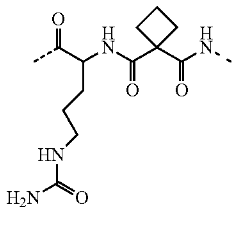 | 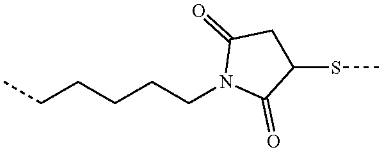 |

TABLE 1-L1-continued
| CIDE Portion to which L1 Attached | CIDE Attachment Portion of L1 | Linker Portion of L1 | Antibody Attachment Portion of L1 |
|---|---|---|---|
| E3LB Residue 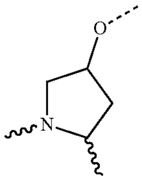 | 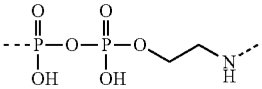 | 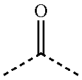 | 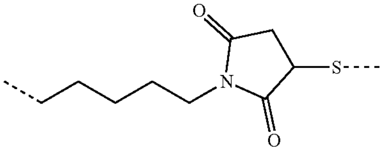 |
| E3LB Residue 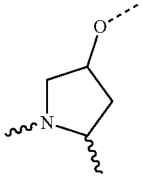 | 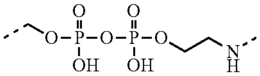 | 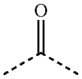 | 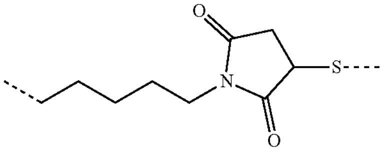 |
| E3LB Residue 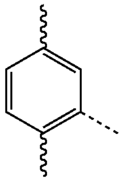 | 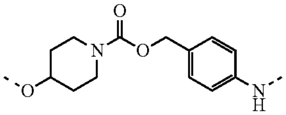 | 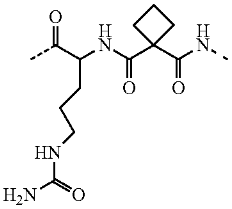 | 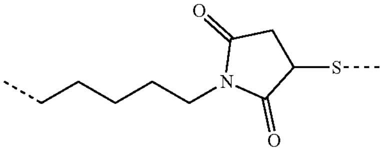 |
| E3LB Residue 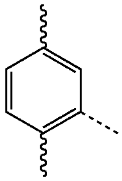 | 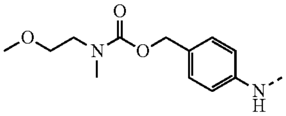 | 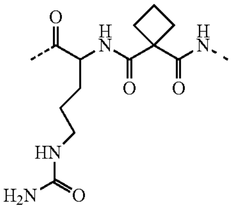 | 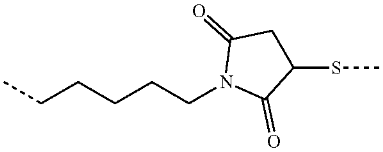 |
| E3LB Residue 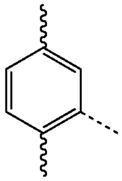 | 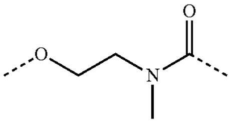 | NA | 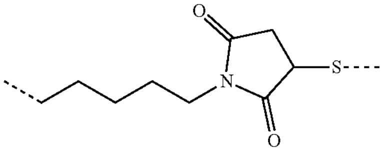 |
| E3LB Residue 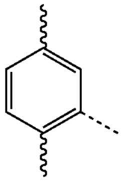 | 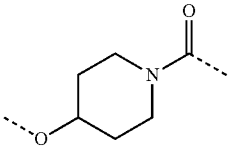 | NA | 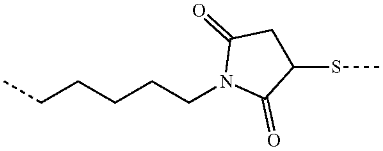 |
| E3LB Residue 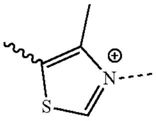 | 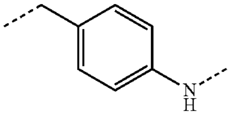 | 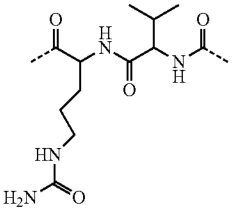 | 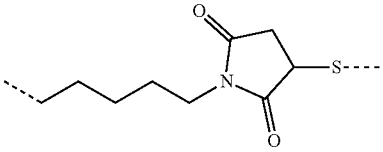 |

TABLE 1-L1-continued
| CIDE Portion to which L1 Attached | CIDE Attachment Portion of L1 | Linker Portion of L1 | Antibody Attachment Portion of L1 |
|---|---|---|---|
| Linker L2 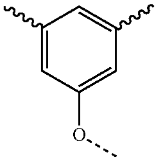 | 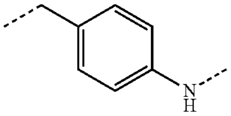 | 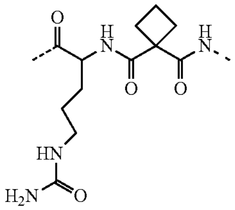 | 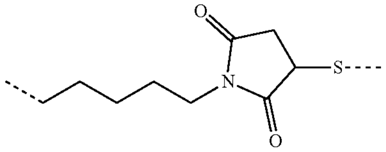 |
| Linker L2 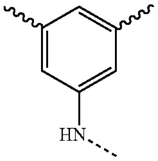 | 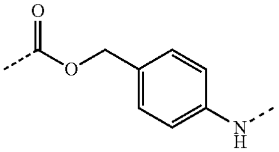 | 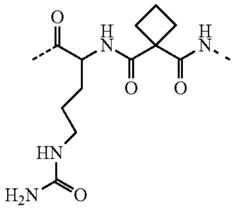 | 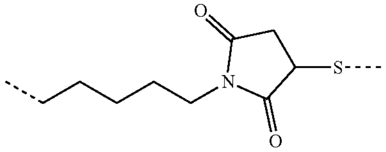 |
| Linker L2 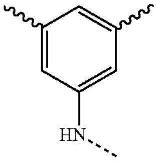 | 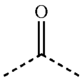 | NA | 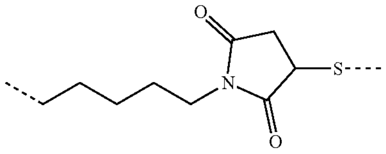 |
| Linker L2 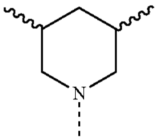 | 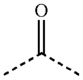 | NA | 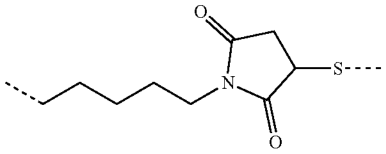 |
| Linker L2 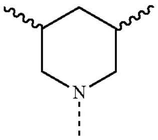 | 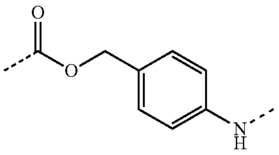 | 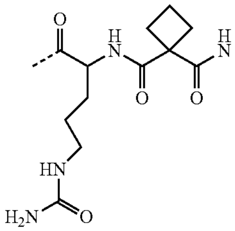 | 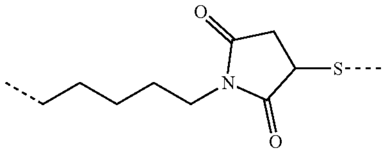 |
| Protein Binding group, PB 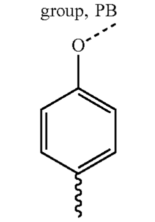 | 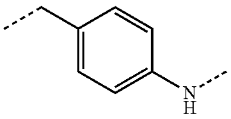 | 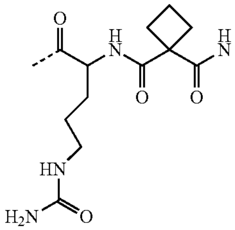 | 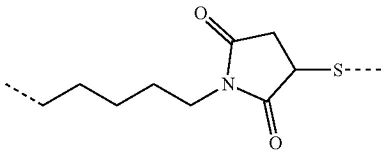 |
| Protein Binding group, PB 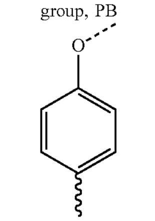 | 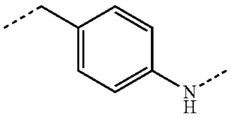 | 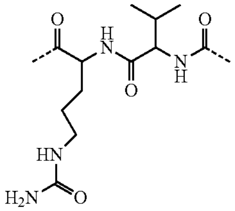 | 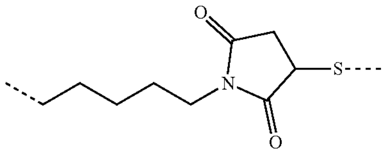 |

TABLE 1-L1-continued

| CIDE Portion to which L1 Attached | CIDE Attachment Portion of L1 | Linker Portion of L1 | Antibody Attachment Portion of L1 |
|---|---|---|---|
| Protein Binding group, PB 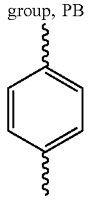 | 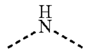 | 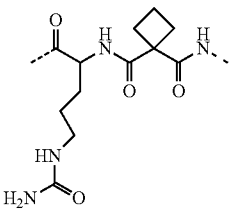 | 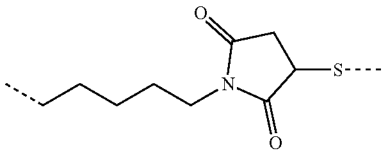 |
| Protein Binding group, PB 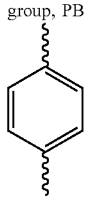 | 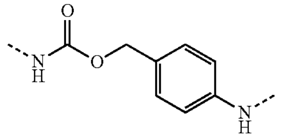 | 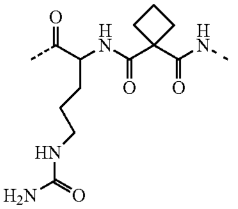 | 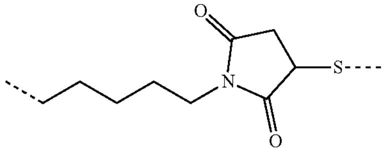 |
| Protein Binding group, PB 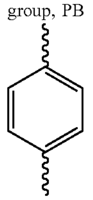 | 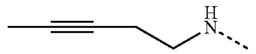 | 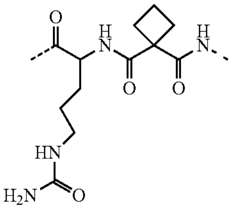 | 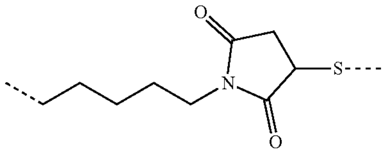 |
| Protein Binding group, PB 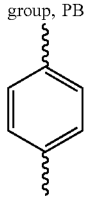 | 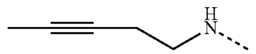 | 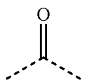 | 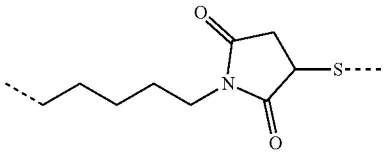 |

In certain embodiments, the linker L1 can be covalently linked to the E3LB residue in different positions, T, U and V:

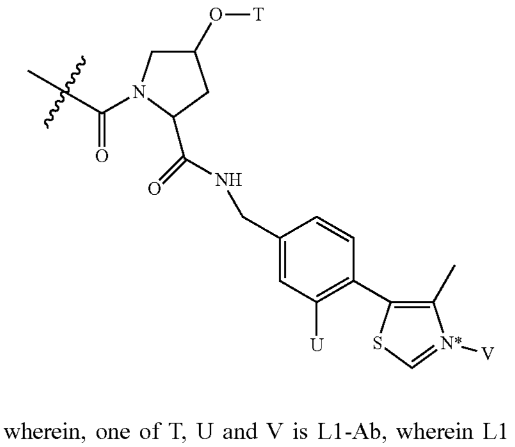

wherein, one of T, U and V is L1-Ab, wherein L1 is a Linker-1; provided that if T is L1, U is hydrogen, and V and * are absent; or if U is L1, T is hydrogen, and V and * are absent; or if V is L1, * is ⊕, and each of T and U is hydrogen; L1 is as described herein.

The Linker-L2 can be attached to any position of an antibody so long as the covalent bond between Linker L2 and the antibody is a disulphide bond. As disclosed herein, L2 can be covalently linked to the PB residue, the E3LB residue and/or Linker-L1. Non-limiting examples include: L1 covalently linked to the PB residue, as in conjugate L1BQ3; L1 covalently linked to a hydroxyl (T position) of E3LB, as in conjugate L1BQ2; L1 covalently linked to a phenyl (U position) of E3LB, as in conjugate L1BQ7; L1 covalently linked to a thiazole N (V position) of E3LB, as in conjugate L1BC1; and L1 covalently linked to the Linker L2 as in L1BQ1.

In embodiments, an antibody, Ab, is conjugated to one to eight Chemical Inducers of Degradation (CIDEs), D, each via a linker, L1.

Ab-(L1-D)p, wherein p is 1 to 8

D comprises an E3 ligase binding (E3LB) ligand linked to a target protein binding (PB) ligand via a linker, L2 as follows:

E3LB-L2-PB

In embodiments, L1 forms a disulfide bond with the sulfur of an engineered Cys residue of the antibody to link the CIDE to the Ab.

In embodiments, the antibody is linked via L1 to the E3LB ligand of the CIDE.

In embodiments, L1 is linked to an E3LB ligand residue of the E3LB ligand of the CIDE.

In embodiments, the E3LB ligand residue comprises

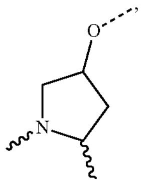

wherein L1 is linked to the residue at 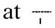.

In embodiments, L1 is linked to the E3LB ligand residue via a linker selected from the group consisting of

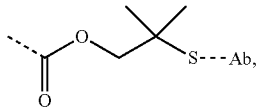

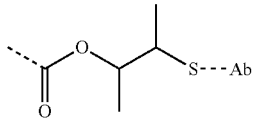 and

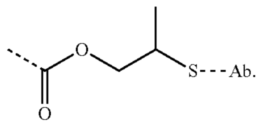

In embodiments, L1 is linked to the E3LB ligand residue via a linker selected from the group consisting of

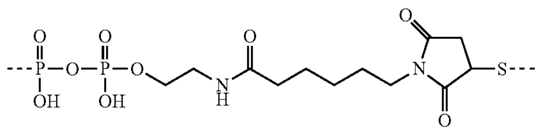 and

-continued

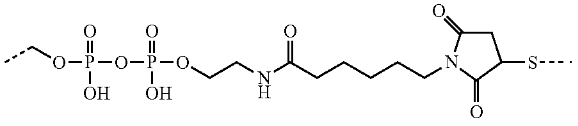

In embodiments, L1 comprises a stretcher unit (Str) linked to a peptidomimetic linker (PM) which is linked to a spacer unit (Sp) as follows:

Str-PM-Sp.

In embodiments, Str is linked to a sulfur of the engineered Cys residue of the antibody and Sp is linked to the E3LB ligand of the CIDE as follows:

Ab-Str-PM-Sp-E3LB-L2-PB.

In embodiments, where the Sp is linked to the E3LB ligand of the CIDE, the Sp is linked to an E3LB ligand residue. In embodiments, the E3LB ligand residue comprises

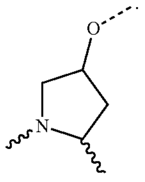

In embodiments, Str is

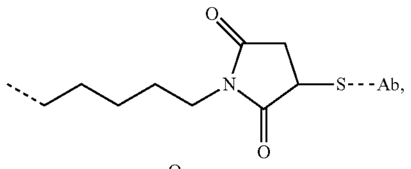 or

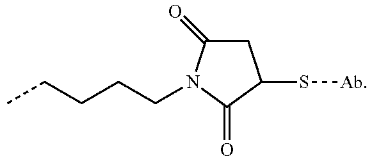

In embodiments, Str-PM-Sp of L1 is selected from the group consisting of

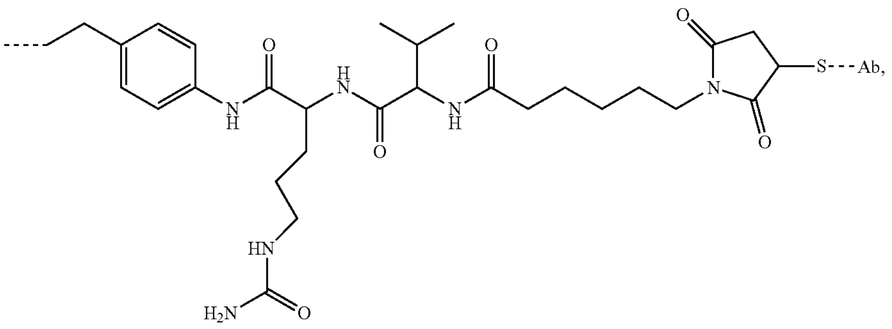

-continued
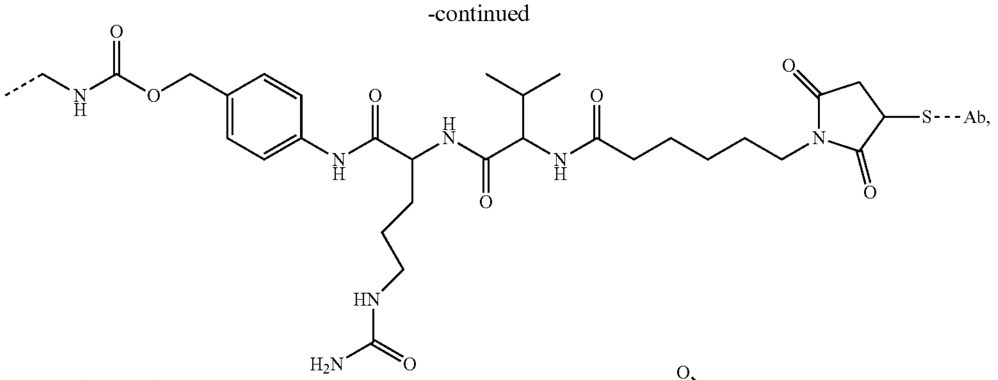
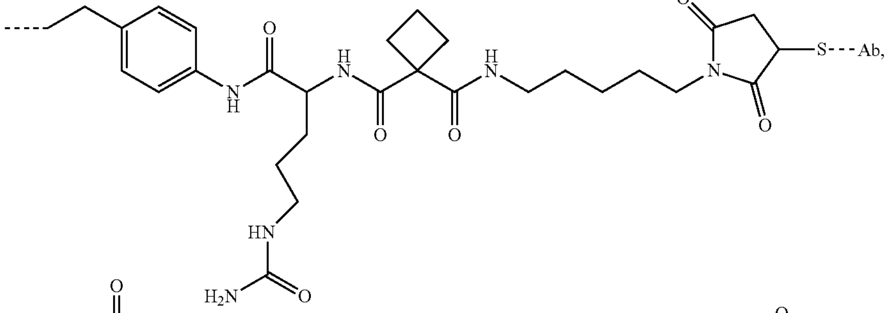
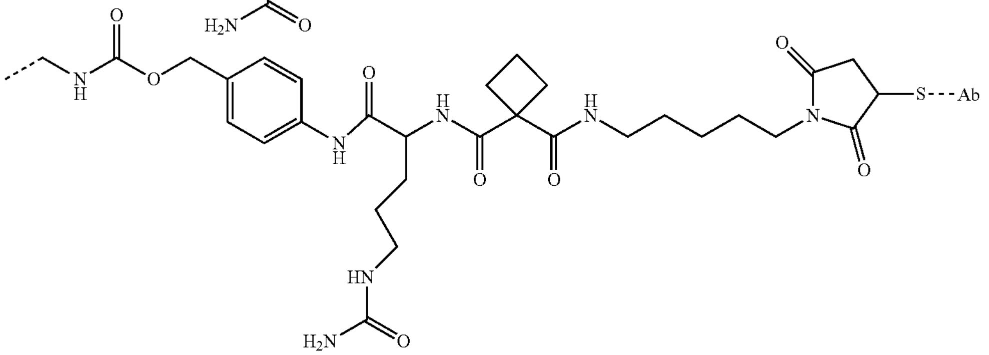
In embodiments, the E3LB ligand residue comprises
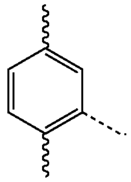
In embodiments, L1 is linked to E3LB ligand residue via a linker selected from the group consisting of
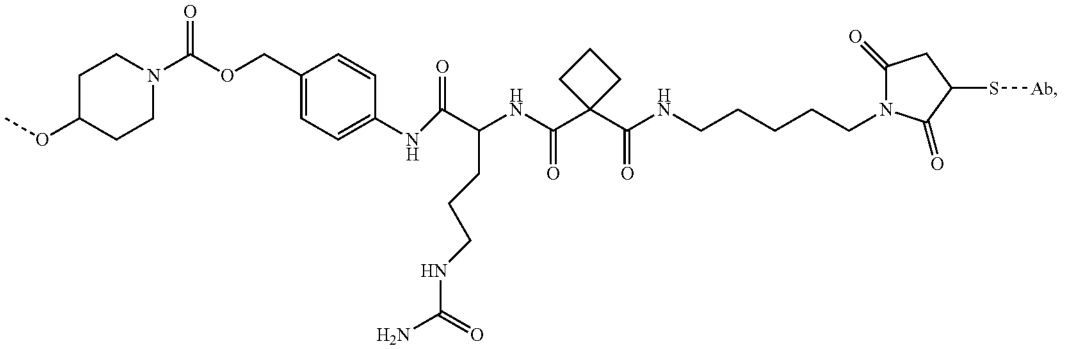

-continued
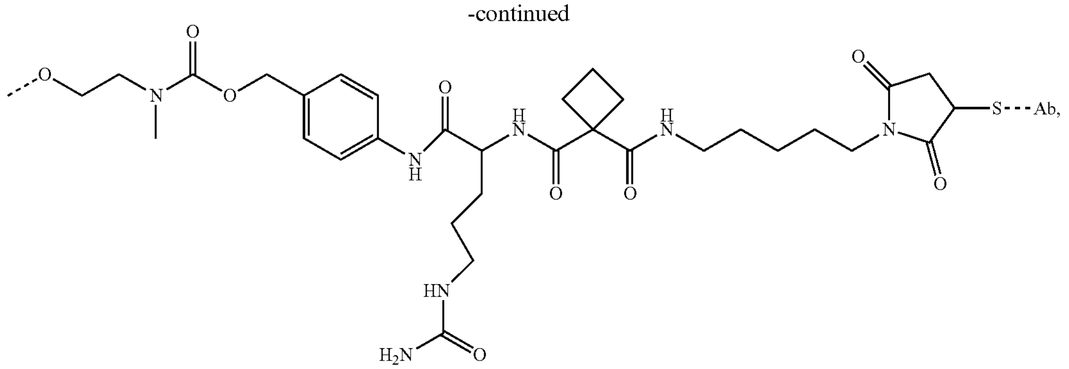
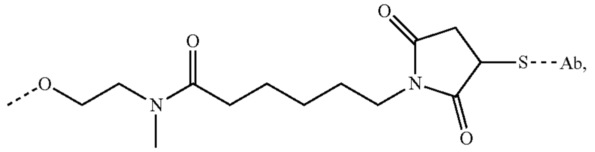
, and
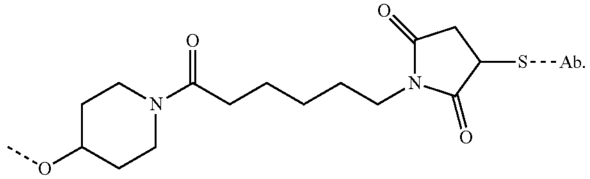
.
In embodiments, the E3LB ligand residue comprises
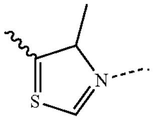
In embodiments, L1 is linked to E3LB ligand residue via the linker selected from the group-consisting of
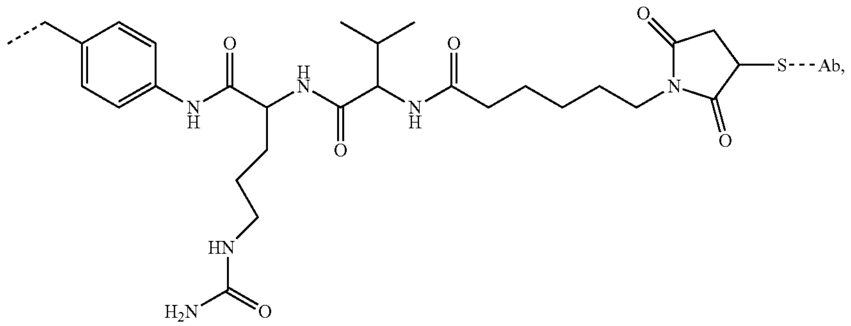
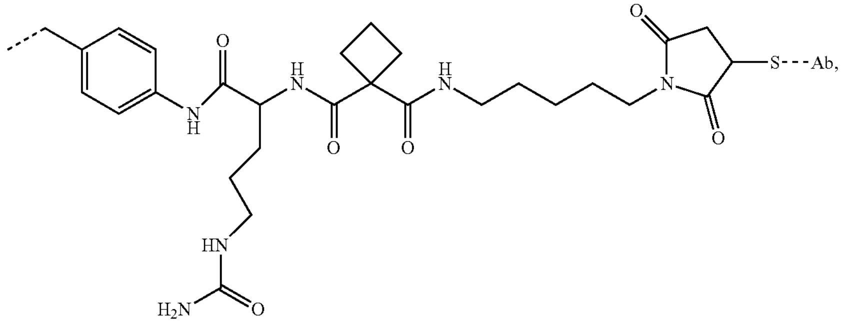

-continued

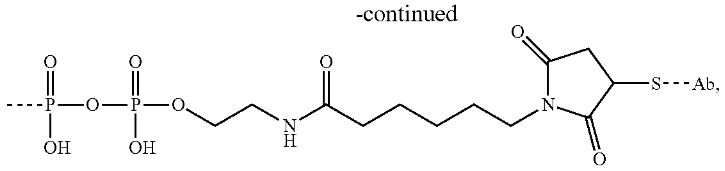

and

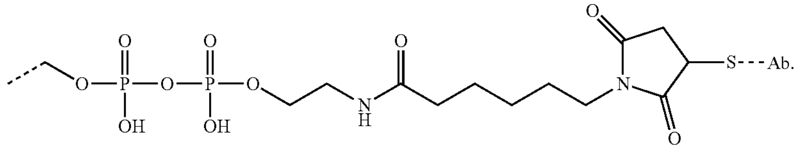

In certain embodiments, the subject matter disclosed herein is directed to a conjugate having the structure.

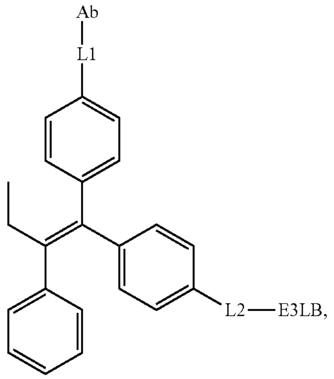

wherein,

Ab is an antibody covalently bound through a disulfide bond to L1;

L2 is a linker covalently bound to E3LB and,

E3LB is a group that binds an E3 ligase, wherein said E3 ligase is von Hippel-Lindau.

In certain embodiments, the subject matter disclosed herein is directed to a conjugate having the structure:

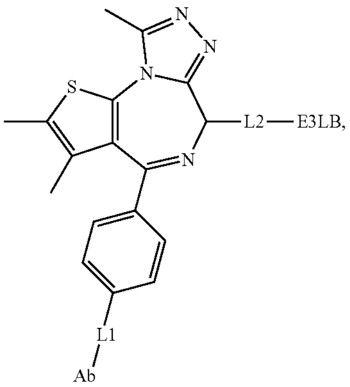

wherein,

Ab is an antibody covalently bound through a disulfide bond to L1;

L2 is a linker covalently bound to E3LB and,

E3LB is a group that binds an E3 ligase, wherein said E3 ligase is von Hippel-Lindau.

In certain embodiments, the subject matter disclosed herein is directed to a conjugate having the structure:

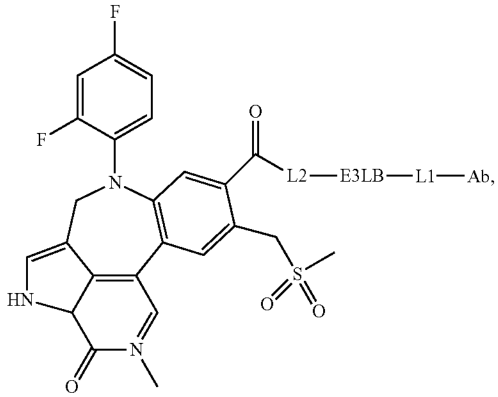

wherein,

Ab is an antibody covalently bound through a disulfide bond to L1;

L1 is a linker covalently bound to E3LB;

E3LB is a group that binds an E3 ligase, wherein said E3 ligase is von Hippel-Lindau, And, Z L2 is a linker covalently bound to E3LB.

The subject matter described herein is also directed to methods of preparing a Ab-CIDE from a L1-CIDE compound, the method comprising contacting an antibody, or variants, mutations, splice variants, indels and fusions thereof, with a L1-CIDE under conditions where the antibody is covalently bound to any available point of attachment on a L1-CIDE, wherein a Ab-CIDE is prepared. The subject matter described herein is also directed to methods of preparing a Ab-CIDE from an Ab-L1 portion, i.e., an antibody, or variants, mutations, splice variants, indels and fusions thereof, covalently attached to a L1, the methods comprising contacting a CIDE with an Ab-L1 under conditions where the CIDE is covalently bound to any available point of attachment on the Ab-L1, wherein a Ab-CIDE is prepared. The methods can further comprise routine isolation and purification of the Ab-CIDEs.

Referring now to a Ab-CIDE and a L1-CIDE compound, as described herein, these can exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes all such solvates.

The skilled artisan will further appreciate that certain compounds and Ab-CIDEs described herein that exist in crystalline form, including the various solvates thereof, may exhibit polymorphism (i.e. the capacity to occur in different crystalline structures). These different crystalline forms are typically known as "polymorphs." The subject matter disclosed herein includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds and Ab-CIDEs described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formula (I) may exist in tautomeric forms other than that shown in the formula and these are also included within the scope of the subject matter disclosed herein. It is to be understood that the subject matter disclosed herein includes all combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes all combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, 17O, $^{18}O$, $^{31}P$, $^{32}P$, $^{35}S$, $^{18}F$, $^{36}Cl$, $^{123}I$ and $^{125}I$.

Compounds and Ab-CIDEs as disclosed herein and pharmaceutically acceptable salts thereof that contain the aforementioned isotopes and/or other isotopes of other atoms are within the scope of the subject matter disclosed herein. Isotopically-labelled compounds are disclosed herein, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{4}C$, isotopes are commonly used for their ease of preparation and detectability. $^{11}C$ and $^{18}F$ isotopes are useful in PET (positron emission tomography), and $^{125}I$ isotopes are useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

The subject matter described herein includes the following embodiments:

1. A conjugate having the chemical structure $Ab\text{-}(L1\text{-}D)_p$, wherein, D is a CIDE having the structure E3LB-L2-PB;

E3LB is covalently bound to L2, and said E3LB is a group that binds an E3 ligase, wherein said E3 ligase is von Hippel-Lindau (VHL);

L2 is a linker covalently bound to E3LB and PB;

PB is a protein binding group covalently bound to L2, and said PB is a group that binds BRD4 or ERα, including all variants, mutations, splice variants, indels and fusions thereof, Ab is an antibody covalently bound to L1;

L1 is a linker, covalently bound to Ab and D; and p has a value from about 1 to about 8.

2. The conjugate of embodiment 1, wherein the EL3B is a residue of a group having the structure:

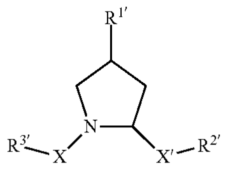

wherein, $R^{1'}$ is an optionally substituted $C_1$-$C_6$ alkyl group, an optionally substituted $-(CH_2)_nOH$, an optionally substituted $-(CH_2)_nSH$, an optionally substituted $(OH_2)_n-O-(C_1\text{-}C_6)$alkyl group, an optionally substituted $(CH_2)_n-WCOCW-(C_0\text{-}C_6)$ alkyl group containing an epoxide moiety WCOCW where each W is independently H or a $C_1$-$C_3$ alkyl group, an optionally substituted $-(CH_2)_nCOOH$, an optionally substituted $-(CH_2)_nC(O)-(C_1\text{-}C_6$ alkyl), an optionally substituted $-(CH_2)_nNHC(O)-R_1$, an optionally substituted $-(CH_2)_nC(O)-NR_1R_2$, an optionally substituted $-(CH_2)_nOC(O)-NR_1R_2$, $-(CH_2O)_nH$, an optionally substituted $-(CH_2)_nOC(O)-(C_1\text{-}C_6$ alkyl), an optionally substituted $-(CH_2)_nC(O)-O-(C_1\text{-}C_6$ alkyl), an optionally substituted $-(CH_2O)_nCOOH$, an optionally substituted $-(OCH_2)_n\ O-(C_1\text{-}C_6$ alkyl), an optionally substituted $-(CH_2)_nC(O)-O-(C_1\text{-}C_6$ alkyl), an optionally substituted $-(OCH_2)_nNHC(O)-R^1$, an optionally substituted $-(CH_2O)_nC(O)-NR_1R_2$, $-(CH_2CH_2O)_nH$, an optionally substituted —$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_s$, an optionally substituted S(O) $R_s$, $NO_2$, CN or halogen (F, Cl, Br, I, preferably F or Cl);

$R_1$ and $R_2$ are each independently H or a $C_1$-$C_6$ alkyl group which may be optionally substituted with one or two hydroxyl groups or up to three halogen groups (preferably fluorine);

$R_s$ is a $C_1$-$C_6$ alkyl group, an optionally substituted aryl, heteroaryl or heterocycle group or a —($CH_2$) $NR_1R_2$ group;

X and X' are each independently C═O, O═S, —S(O), $S(O)_2$, (preferably X and X' are both C═O);

$R^{2'}$ is an optionally substituted —$(CH_2)_n$—$(C{=}O)_u$ $(NR_1)_v(SO_2)_w$alkyl group, an optionally substituted —$(CH_2)_n$—$(C{=}O)_u(NR_1)_v(SO_2)_w$$NR_1NR_2$N group, an optionally substituted —$(CH_2)_n$—$(C{=}O)_u(NR_1)_v(SO_2)_w$-Aryl, an optionally substituted —$(CH_2)_n$—$(C{=}O)_u(NR_1)_v(SO_2)_w$-Heteroaryl, an optionally substituted —$(CH_2)_n$—$(C{=}O)_v$$NR_1(SO_2)_w$-Heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_1NR_2$N, an optionally substituted —$NR^1$—$(CH_2)_n$—$C(O)_u(NR_1)_v(SO_2)_w$—$NR_1$C(O) $R_{1N}$, an optionally substituted —$NR_1$—$(CH_2)_n$—$(C{=}O)_u(NR_1)_v(SO_2)_w$-Aryl, an optionally substituted —$NR_1$—$(CH_2)_n$—$(C{=}O)_u(NR_1)_v(SO_2)_w$-Heteroaryl or an optionally substituted —$NR_1$—$(CH_2)_n$—$(C{=}O)_v$$NR_1(SO_2)_w$-Heterocycle, an optionally substituted —$X^{R2'}$-alkyl group; an optionally substituted —$X^{R2'}$— Aryl group; an optionally substituted —$X^{R2'}$— Heteroaryl group; an optionally substituted —$X^{R2'}$— Heterocycle group; an optionally substituted;

$R^3$ is an optionally substituted alkyl, an optionally substituted —$(CH_2)_n$—$C(O)_u(NR_1)_v(SO_2)_w$-alkyl, an optionally substituted —$(CH_2)_n$—$C(O)_u(NR_1)_v(SO_2)_w$—$NR_1NR_{2N}$, an optionally substituted —$(CH_2)_n$—$C(O)_u(NR_1)_v(SO_2)_w$—$NR_1C(O)R_{1N}$, an optionally substituted —$(CH_2)_n$—$C(O)_u(NR_1)_v(SO_2)_w$—$C(O)NR_1R_2$, an optionally substituted —$(CH_2)_n$—$C(O)_u(NR_1)_v(SO_2)_w$-Aryl, an optionally substituted —$(CH_2)_n$—$C(O)_u(NR_1)_v(SO_2)_w$-Heteroaryl, an optionally substituted —$(CH_2)_n$—$C(O)_u(NR_1)_v(SO_2)_w$-Heterocycle, an optionally substituted —$NR^1$—$(CH_2)_n$—$C(O)_u(NR_1)_v(SO_2)_w$-alkyl, an optionally substituted —NR—$(CH_2)_n$—$C(O)_u(NR_1)_v(SO_2)_w$—$NR_1NR_{2N}$, an optionally substituted —NR—$(CH_2)_n$—$C(O)_u(NR_1)_v(SO_2)_w$—$NR_1C(O)R_{1N}$, an optionally substituted —$NR^1$—$(CH_2)_n$—$C(O)_u(NR_1)_v(SO_2)_w$-Aryl, an optionally substituted —$NR^1$—$(CH_2)_n$—$C(O)_u(NR_1)_v(SO_2)_w$-Heteroaryl, an optionally substituted —$NR^1$—$(CH_2)_n$—$C(O)_u(NR_1)_v(SO_2)_w$-Heterocycle, an optionally substituted O—$(CH_2)_n$—$(C{=}O)_u(NR_1)_v(SO_2)_w$-alkyl, an optionally substituted O—$(CH_2)_n$—$(C{=}O)_u(NR_1)_v(SO_2)_w$—$NR_{1N}R_{2N}$, an optionally substituted —O—$(CH_2)_n$—$(C{=}O)_u(NR_1)_v(SO_2)_w$—$NR_1$C(O) $R_{1N}$, an optionally substituted —O—$(CH_2)_n$—$(C{=}O)_u(NR_1)_v(SO_2)_w$-Aryl, an optionally substituted O—$(CH_2)_n$—$(C{=}O)_u(NR_1)_v(SO_2)_w$-Heteroaryl or an optionally substituted O—$(CH_2)_n$—$(C{=}O)_u(NR_1)_v(SO_2)_w$-Heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-Aryl group, an optionally substituted —$(CH_2)_n$—$(V)_{n'}$—$(CH_2)_n$—$(V)_{n'}$-Heteroaryl group, an optionally substituted —$(CH_2)_n$—$(V)_{n'}$—$(CH_2)_n$—$(V)_{n'}$-Heterocycle group, an optionally substituted —$(CH_2)_n$—$N(R_{1'})(C{=}O)_{m'}$—$(V)_{n'}$-alkyl group, an optionally substituted —$(CH_2)_n$—$N(R_{1'})(C{=}O)_{m'}$—$(V)_{n'}$-Aryl group, an optionally substituted —$(CH_2)_n$—$N(R_{1'})(C{=}O)_{m'}$—$(V)_{n'}$-Heteroaryl group, an optionally substituted —$(CH_2)_n$—$N(R_{1'})(C{=}O)_{m'}$—$(V)_{n'}$-Heterocycle group, an optionally substituted —$X^{R3'}$-alkyl group; an optionally substituted —$X^{R3'}$-Aryl group; an optionally substituted —$X^{R3'}$-Heteroaryl group; an optionally substituted —$X^{R3'}$-Heterocycle group; an optionally substituted;

where $R_{1N}$ and $R_{2N}$ are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

$R^1$ and $R_1$ are each independently H or a $C_1$-$C_3$ alkyl group;

V is O, S or $NR_1$;

$R_1$ is the same as above;

$R^1$ and $R_1$ are each independently H or a $C_1$-$C_3$ alkyl group;

$X^{R2'}$ and $X^{R3'}$ are each independently an optionally substituted —$CH_2)_n$—, —$CH_2)_n$—$CH(X_V){=}CH(X_V)$— (cis or trans), —$CH_2)_n$—CH≡CH—, —$(CH_2CH_2O)_n$— or a $C_3$-$C_6$ cycloalkyl group, where $X_v$ is H, a halo or a $C_1$-$C_3$ alkyl group which is optionally substituted;

Each m is independently 0, 1, 2, 3, 4, 5, 6;

Each m' is independently 0 or 1;

Each n is independently 0, 1, 2, 3, 4, 5, 6;

Each n' is independently 0 or 1;

Each u is independently 0 or 1;

Each v is independently 0 or 1; and

Each w is independently 0 or 1.

3. The conjugate of any above embodiment, wherein the E3LB is a residue of a group having the structure:

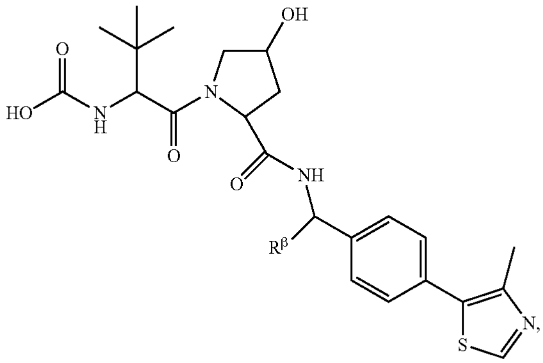
,

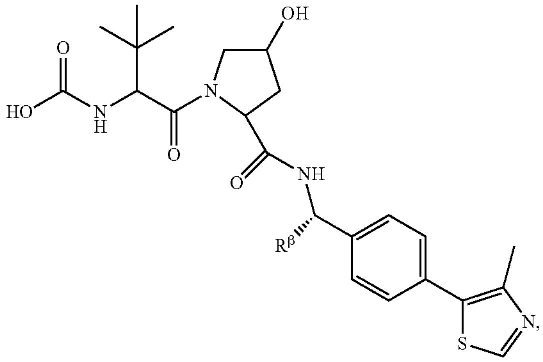
, or

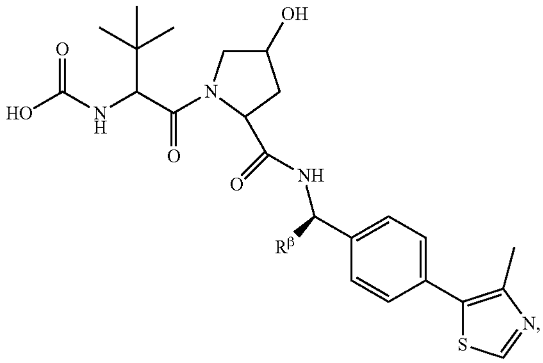
, wherein, $R^{\beta}$ is hydrogen, methyl, ethyl or propyl.

4. The conjugate of any above embodiment, wherein E3LB is a residue of a group having the structure:

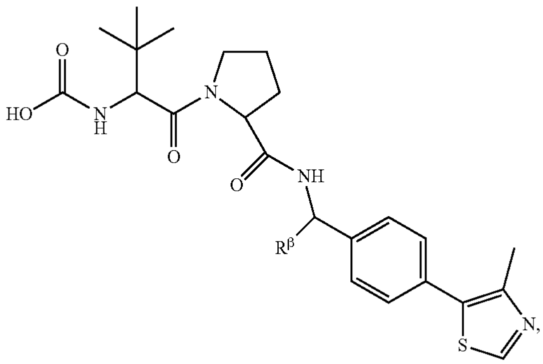
,

-continued

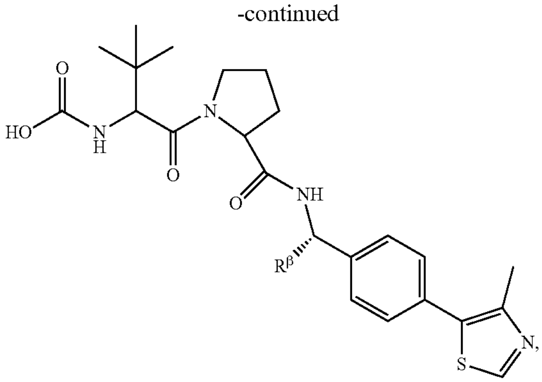
, or

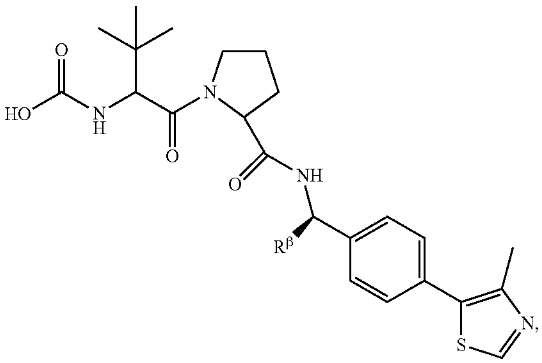
, wherein, $R^{\beta}$ is hydrogen, methyl, ethyl or propyl.

5. The conjugate of any above embodiment, wherein the PB is a residue of a group that binds BRD4.

6. The conjugate of any above embodiment, wherein the PB is a residue of a group that binds BRD4 and has the structure:

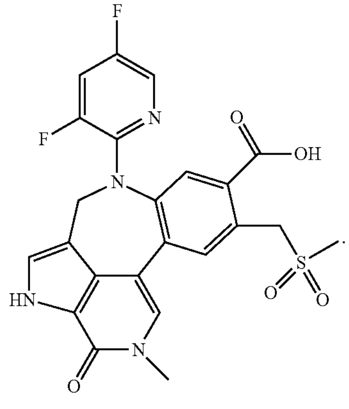 [SMILES: Cn1cc2c3c(c[nH]c3c1=O)CN(c1ncc(F)cc1F)c1cc(C(=O)O)c(CS(C)(=O)=O)cc1-2]
.

7. The conjugate of any above embodiment, wherein the PB is a residue of a group that binds ERα and is an anti-estrogen.

8. The conjugate of any above embodiment, wherein the PB is a residue of a group that binds ERα and is a compound of the following structure:

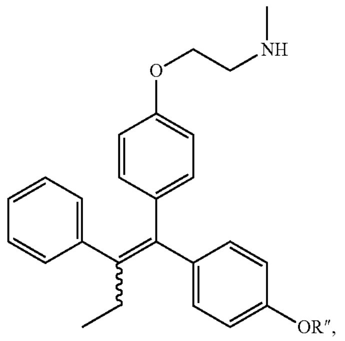

wherein, R'' is hydrogen, $C_1$-$C_6$ alkyl, benzyl, phenyl, or —($PO_3H_2$).

9. The conjugate of any above embodiment, wherein the PB is a residue of a compound of the following structure:

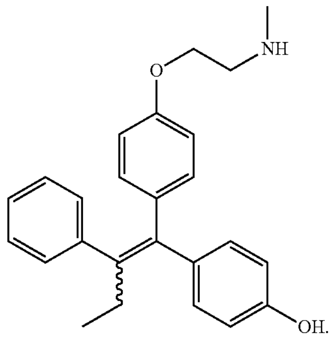 [SMILES: CCC(=C(c1ccc(O)cc1)c1ccc(OCCNC)cc1)c1ccccc1]

10. The conjugate of any above embodiment, wherein said Ab is a cysteine engineered antibody or variant thereof.

11. The conjugate of any above embodiment, wherein Ab binds to one or more of polypeptides selected from the group consisting of DLL3, EDAR, CLL1; BMPR1B; E16; STEAP1; 0772P; MPF; NaPi2b; Sema 5b; PSCA hlg; ETBR; MSG783; STEAP2; TrpM4; CRIPTO; CD21; CD79b; FcRH2; B7-H4; HER2; NCA; MDP; IL20Rα; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; MUC16 and CD33.

12. The conjugate of any above embodiment, wherein Ab binds to one or more of polypeptides selected from the group consisting of CLL1, STEAP1, NaPi2b, STEAP2, TrpM4, CRIPTO, CD21, CD79b, FcRH2, B7-H4, HER2, CD22, CD79a, CD72, LY64, Ly6E, MUC16, and CD33.

13. The conjugate of any above embodiment, wherein Ab is an antibody that binds to one or more polypeptides selected from the group consisting of HER2, B7-H4, and CD22.

14. The conjugate of any above embodiment, wherein the antibody binds to HER2.

15. The conjugate of any above embodiment, wherein the antibody binds to B7-H4 or CD22.

16. The conjugate of any above embodiment, wherein L1 is a peptidomimetic linker.

17. The conjugate of any above embodiment, wherein L1 is a peptidomimetic linker represented by the following formula:

Str-(PM)-Sp wherein,

Str is a stretcher unit covalently attached to Ab;

Ab is an antibody;

Sp is a bond or spacer unit covalently attached to a CIDE moiety;

PM is a non-peptide chemical moiety selected from the group consisting of:

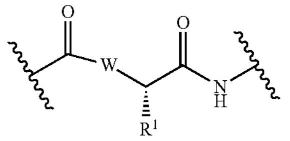

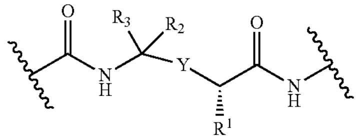 and

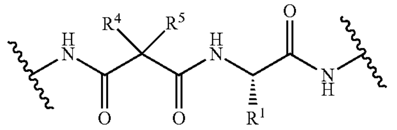

W is —NH-heterocycloalkyl- or heterocycloalkyl;

Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;

each $R^1$ is independently $C_1$-$C_{10}$alkyl, $C_1$-$C_{10}$alkenyl, ($C_1$-$C_6$alkyl)NHC(NH)$NH_2$, ($C_1$-$C_6$alkyl)NHC(O)$NH_2$, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and $R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ together may form a $C_3$-$C_7$cycloalkyl ring.

18. The conjugate of any above embodiment, wherein Str is a chemical moiety represented by the following formula:

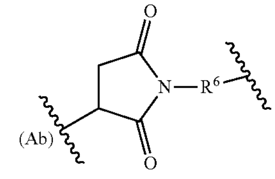

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$ cycloalkyl, $C_4$-$C_7$heterocycloalkyl, heteroarylalkyl, aryl arylalkyl, heteroarylalkyl and heteroaryl each $R^a$ is independently H or $C_1$-$C_6$alkyl; and Sp is —$C_1$-$C_6$alkylene-C(O)NH— or —Ar—$R^b$—, wherein Ar is aryl or heteroaryl, and $R^b$ is ($C_1$-$C_{10}$alkylene)O—.

19. The conjugate of any above embodiment, wherein Str has the formula:

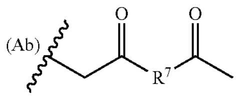

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) and N($R^c$)—($C_2$-$C_6$alkylene); where each $R^c$ is independently H or $C_1$-$C_6$ alkyl; and Sp is —$C_1$-$C_6$alkylene-C(O)NH— or —Ar—$R^b$—, wherein Ar is aryl or heteroaryl, and $R^b$ is ($C_1$-$C_{10}$alkylene)O—.

20. The conjugate of any above embodiment, wherein L1 has the following formula:

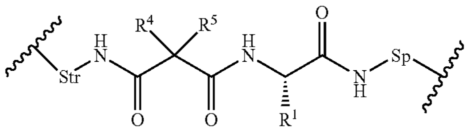

$R^1$ is $C_1$-$C_6$alkyl, ($C_1$-$C_6$alkyl)NHC(NH)$NH_2$ or ($C_1$-$C_6$alkyl)NHC(O)$NH_2$; $R^4$ and $R^5$ together form a $C_3$-$C_7$cycloalkyl ring.

21. The conjugate of any above embodiment, having the formula:

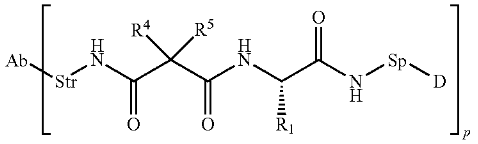

wherein

Sp is a bond or spacer unit covalently attached to CIDE moiety D;

$R^4$ and $R^5$ are each independently $C_1$-$C_{10}$alkyl, $C_1$-$C_{10}$alkenyl, arylalkyl, heteroarylalkyl, ($C_1$—$C_{10}$alkyl)$OCH_2$—, or $R^4$ and $R^5$ together may form a $C_3$-$C_7$cycloalkyl ring $R^1$ is independently $C_1$-$C_{10}$alkyl, $C_1$-$C_{10}$alkenyl, ($C_1$-$C_6$alkyl)NHC(NH)$NH_2$, ($C_1$-$C_6$alkyl)NHC(O)$NH_2$, ($C_1$-$C_{10}$alkyl)NHC(NH)$NH_2$ or ($C_1$-$C_{10}$alkyl)NHC(O)$NH_2$;

Str is a chemical moiety represented by the following formula:

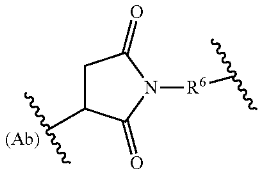

$R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl;

p is 1, 2, 3 or 4.

22. The conjugate of any above embodiment, wherein $R^4$ and $R^5$ together may form a $C_3$-$C_7$cycloalkyl ring and $R^1$ is $C_1$-$C_{10}$alkyl or ($C_1$-$C_6$alkyl)NHC(O)$NH_2$.

23. The conjugate of any above embodiment, wherein $R^4$ and $R^5$ together form cyclobutyl.

24. The conjugate of any above embodiment, wherein the structure of the linker is selected from the group consisting of:

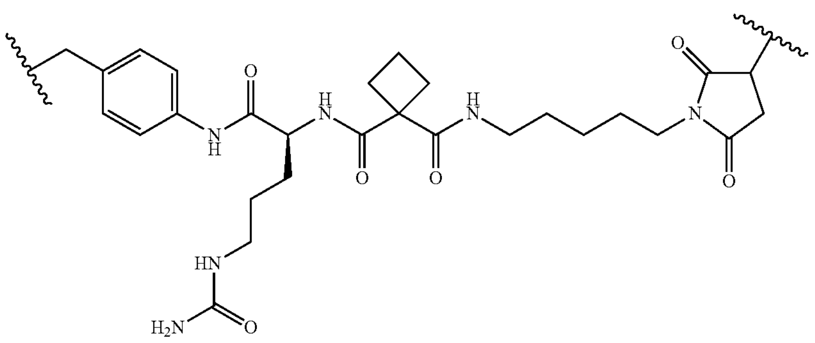

and

-continued

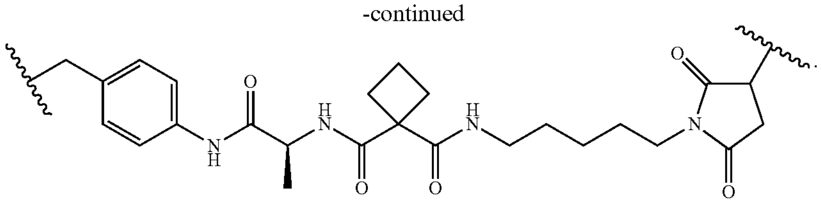

25. The conjugate of any above embodiment, wherein Str is a chemical moiety represented by the following formula:

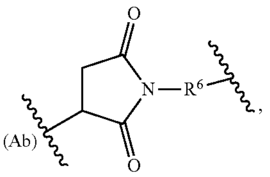

$R^6$ is $C_1$-$C_6$alkylene;

Sp is —$C_1$-$C_6$alkylene-C(O)NH— or —Ar—$R^b$, where Ar is aryl, $R^b$ is ($C_1$-$C_3$alkylene)O—.

26. The conjugate of any above embodiment, having the formula:

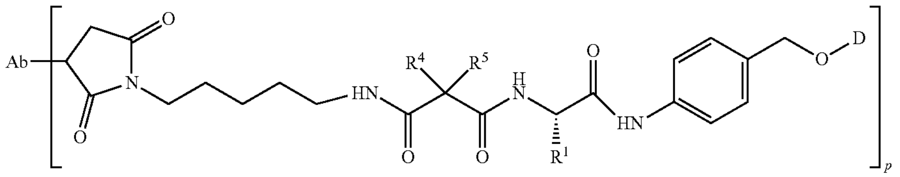

wherein p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

$R^4$ and $R^5$ are each independently $C_1$-$C_6$alkyl, wherein said alkyl are unsubstituted, or $R^4$ and $R^5$ may form a $C_3$-$C_7$cycloalkyl ring.

27. The conjugate of any above embodiment, wherein L1 has the following formula selected from the group consisting of:

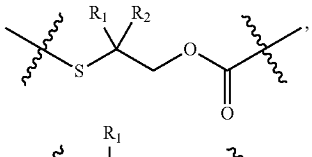

, and

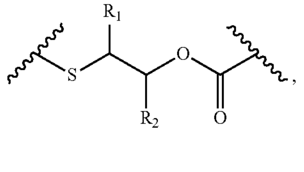

, wherein, $R^1$ and $R^2$ are independently selected from H and $C_1$-$C_6$ alkyl, or $R^1$ and $R^2$ form a 3, 4, 5, or 6-membered cycloalkyl or heterocyclyl group.

28. The conjugate of any above embodiment, wherein L1 has the following formula:

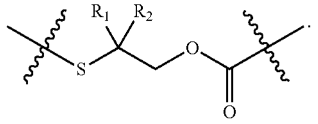

29. The conjugate of any above embodiment, wherein L1 has the following Formula:

$-A_a-W_w—Y_y—$ wherein A is a "stretcher unit", and a is an integer from 0 to 1; W is an "amino acid unit", and w is an integer from 0 to 12; Y is a "spacer unit", and y is 0, 1, or 2.

30. The conjugate of any above embodiment, wherein the stretcher unit A comprises the following formula:

MC

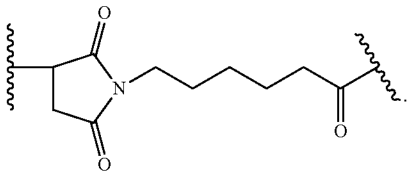

31. The conjugate of any above embodiment, wherein the linker has the following formula:

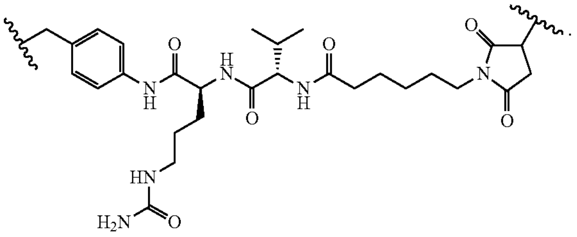 [SMILES: *Cc1ccc(NC(=O)[C@H](CCCNC(N)=O)NC(=O)[C@@H](NC(=O)CCCCCN2C(=O)CC(*)C2=O)C(C)C)cc1]

32. The conjugate of any above embodiment, wherein L1 has the following Formula:

$-A_a-Y_y—$ wherein A and Y are defined as above.

33. The conjugate of any above embodiment, wherein L1 is:

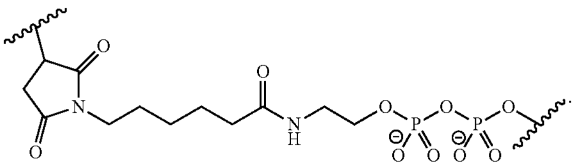 [SMILES: *OP(=O)([O-])OP(=O)([O-])OCCNC(=O)CCCCCN1C(=O)CC(*)C1=O]

34. The conjugate of any above embodiment, wherein p is from about 1.0 to about 3.

35. The conjugate of any above embodiment, wherein p is about 2.

36. The conjugate of any above embodiment, wherein D is a residue covalently linked to L1 and selected from one of the following structures:

36. The conjugate of any above embodiment, wherein D is a residue covalently linked to L1 and selected from one of the following structures:

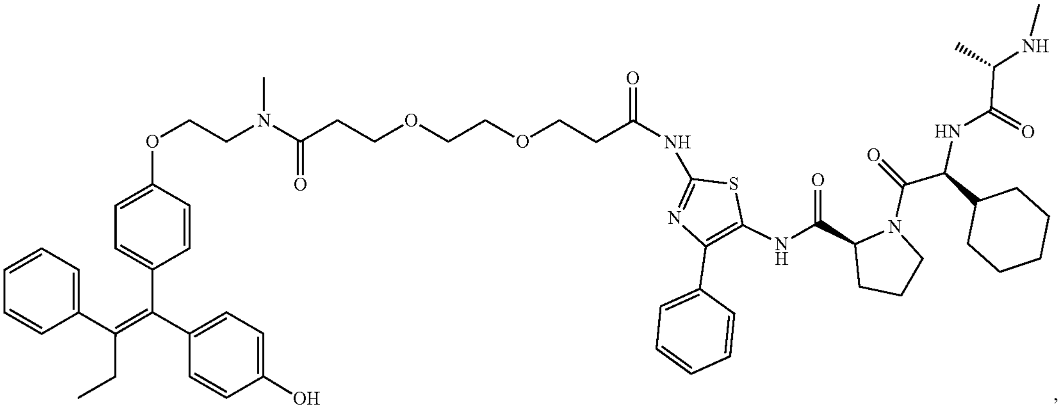

,

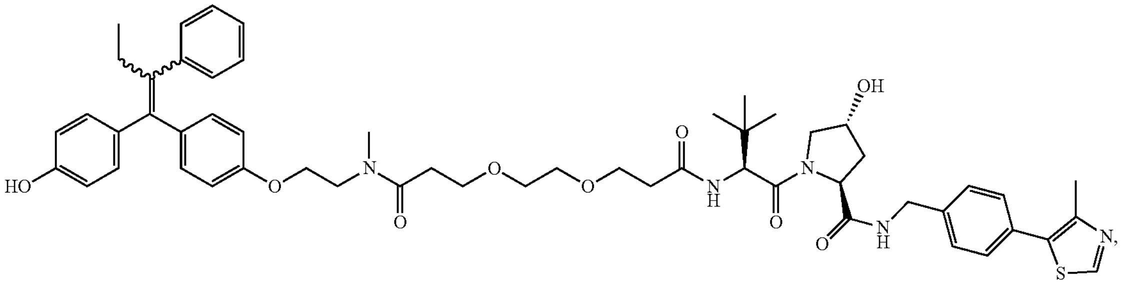

and

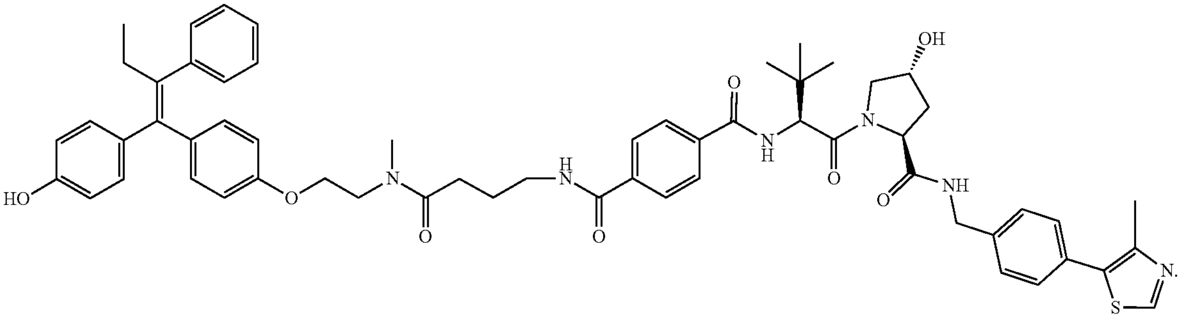

37. The conjugate of any above embodiment, wherein L1-D is a residue covalently linked to said Ab and selected from one of the following structures:
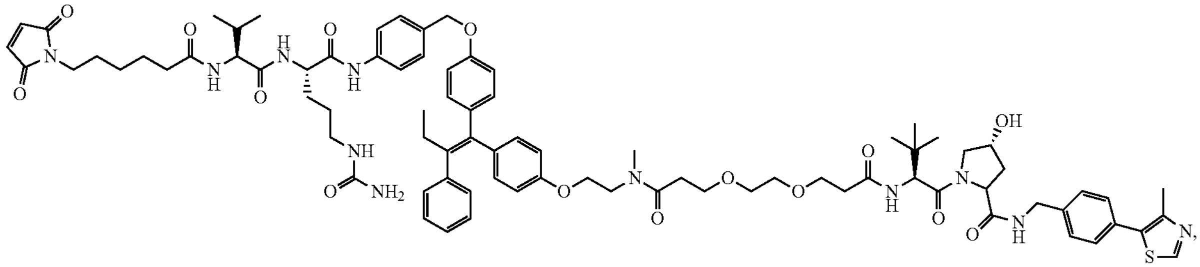
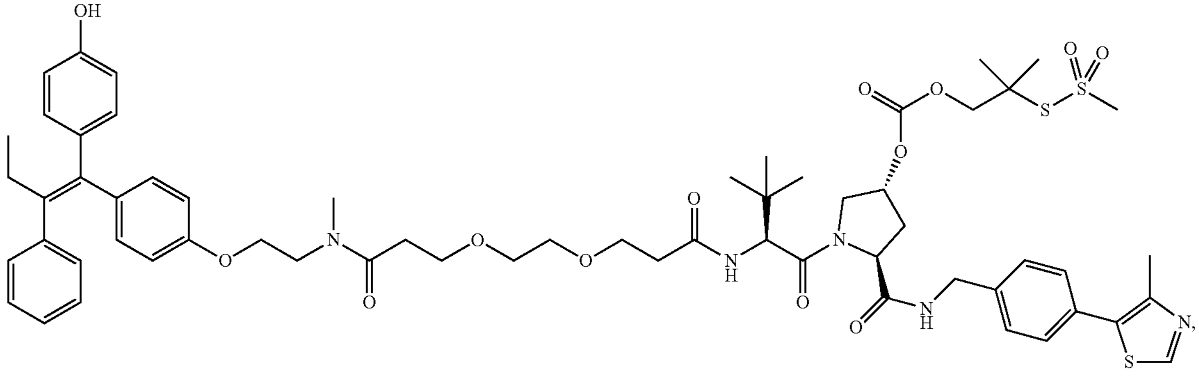
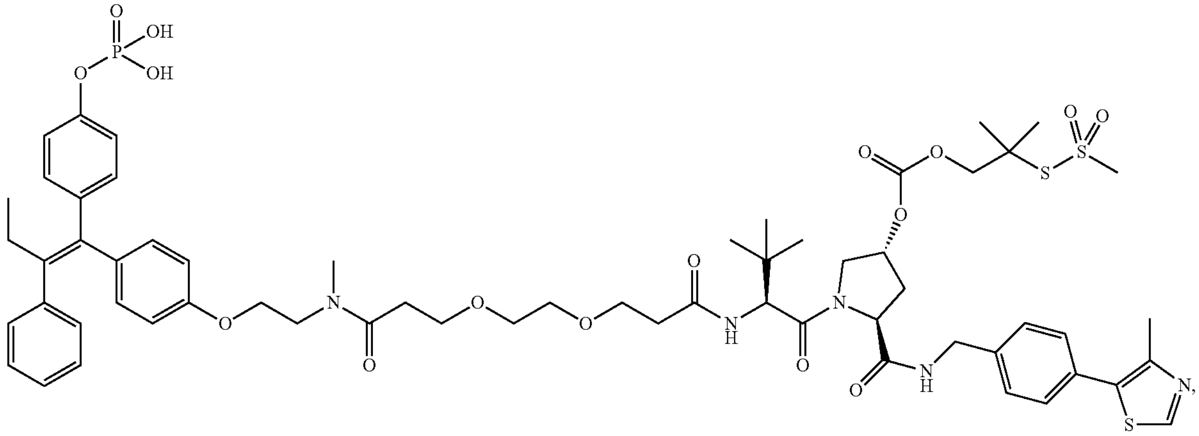
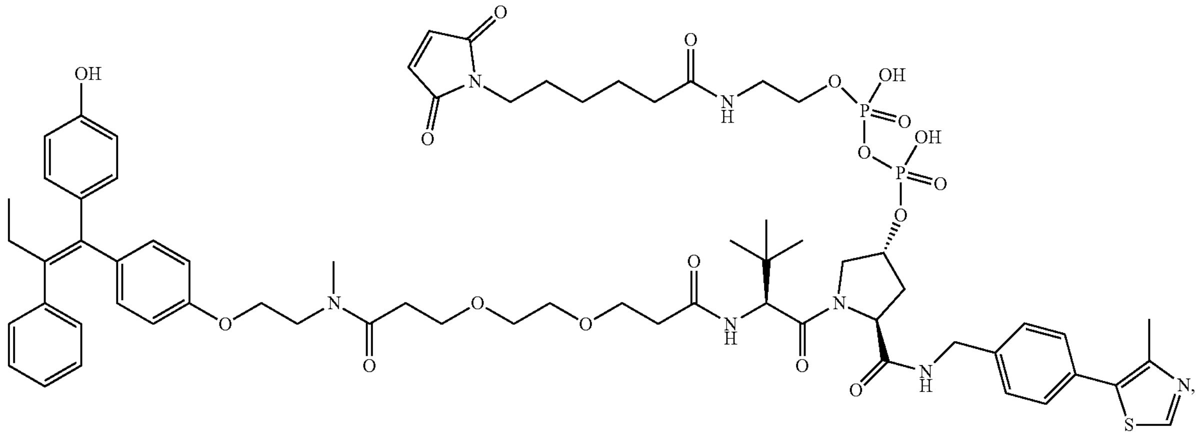

-continued
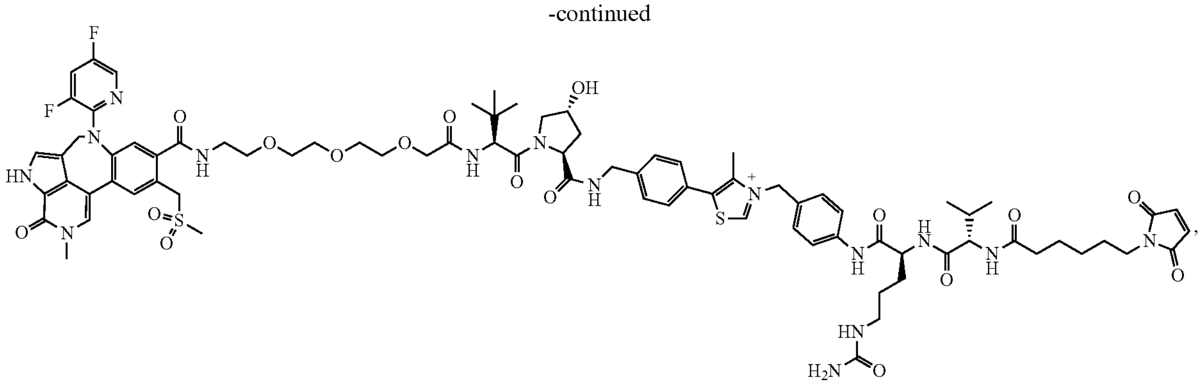
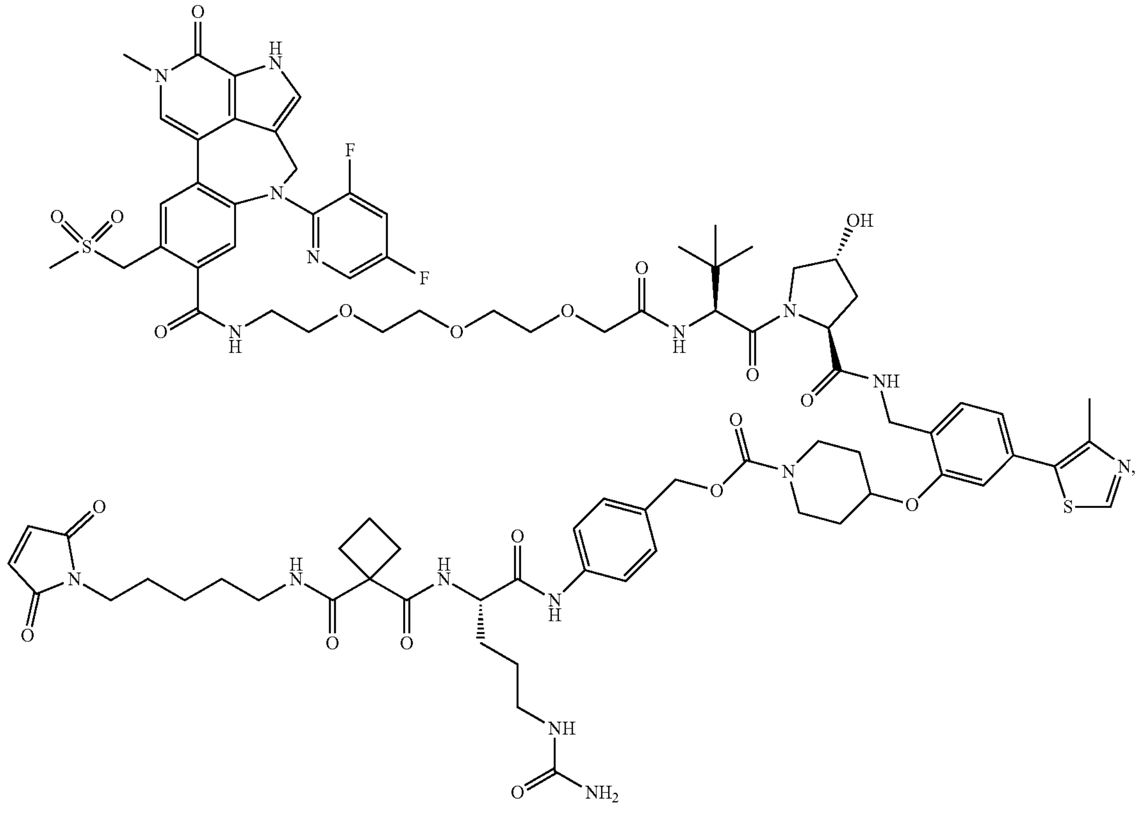
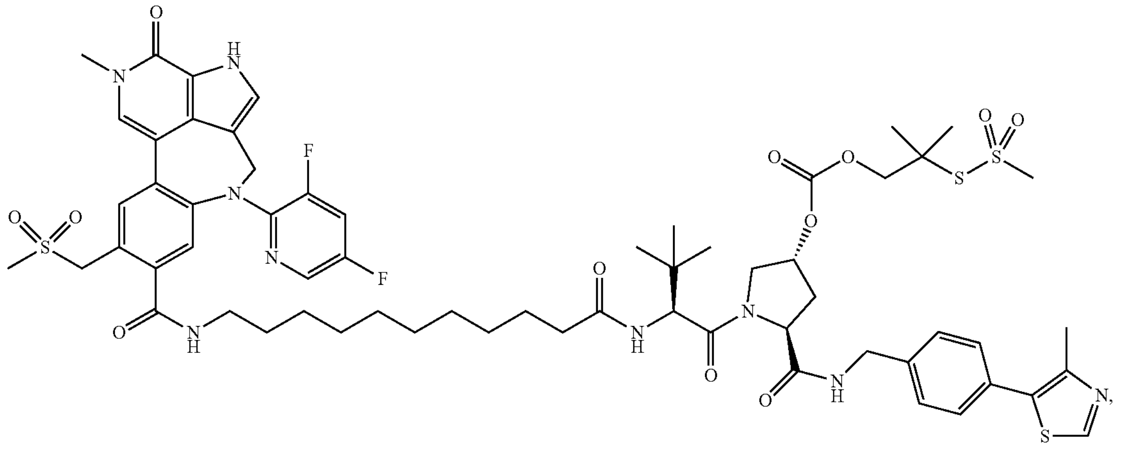

-continued
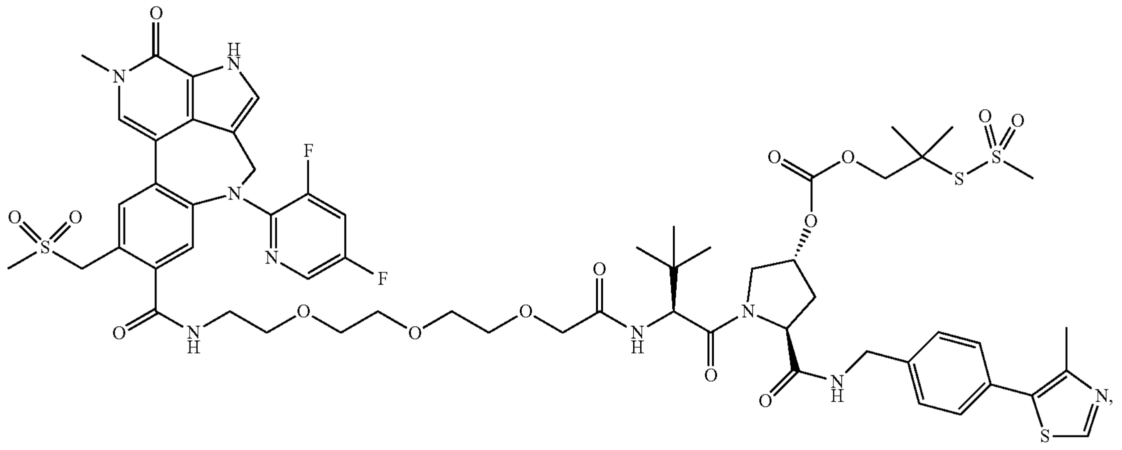
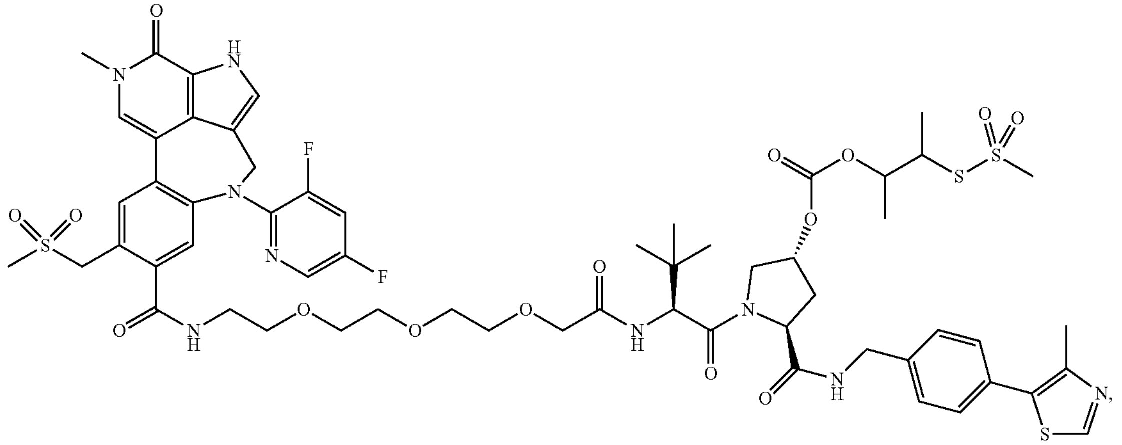
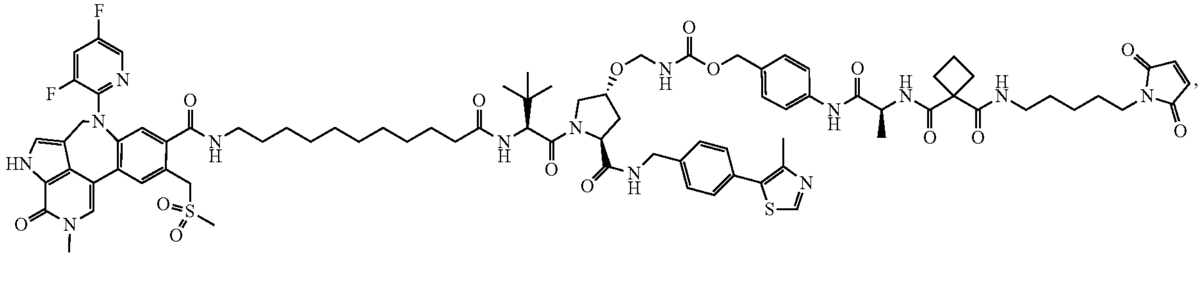

-continued
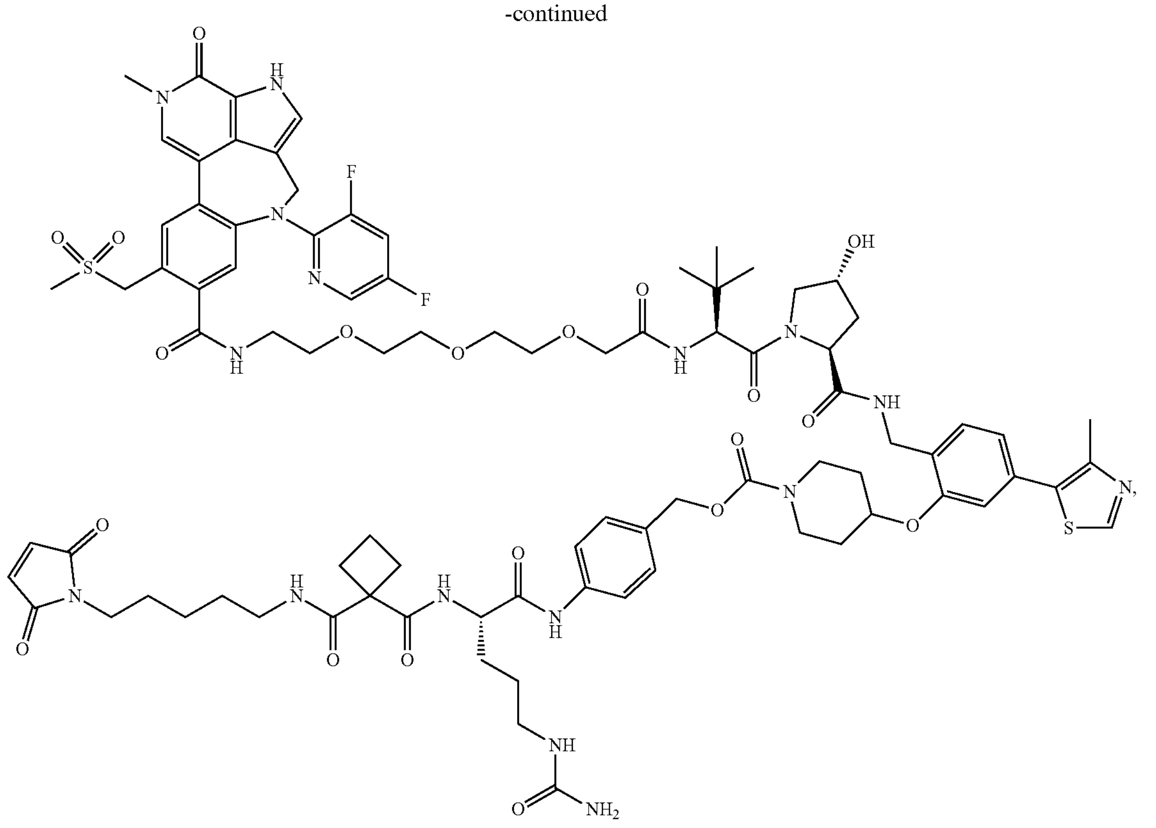
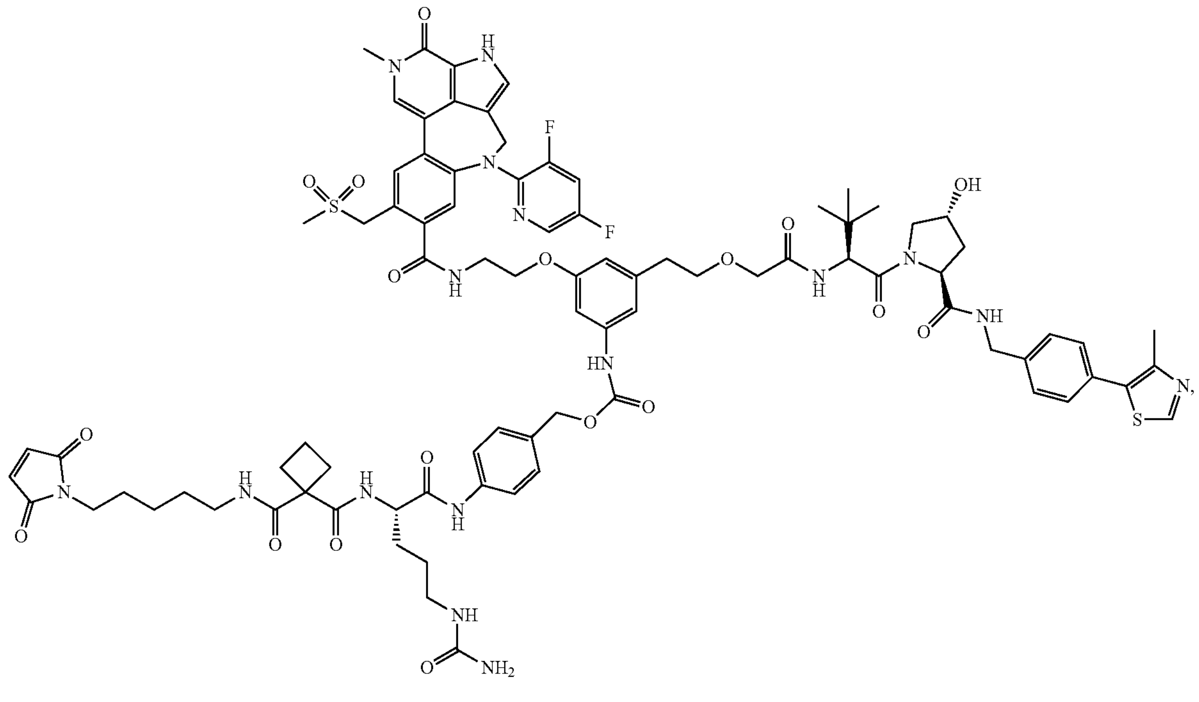

-continued
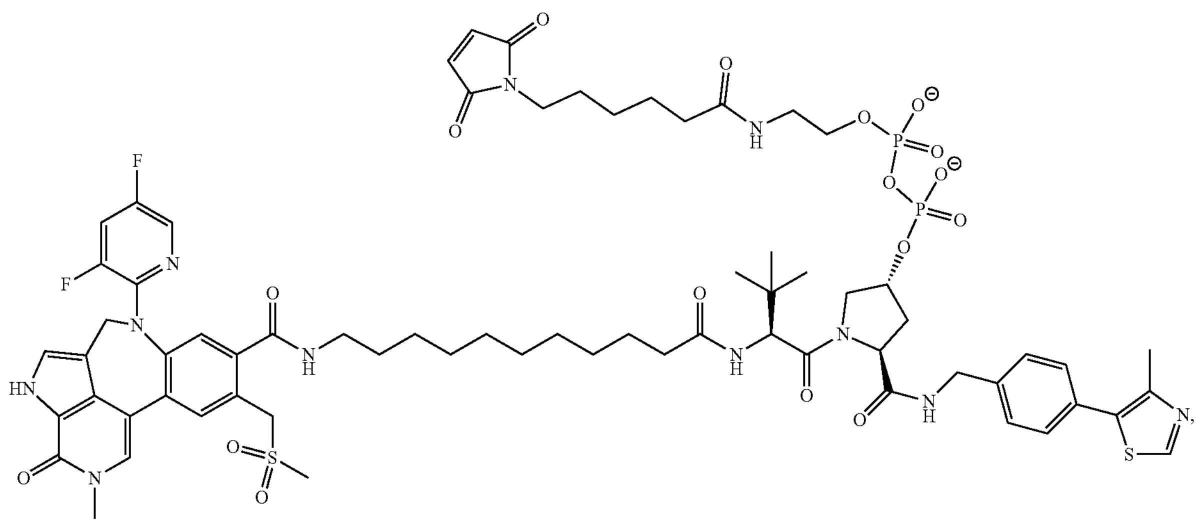
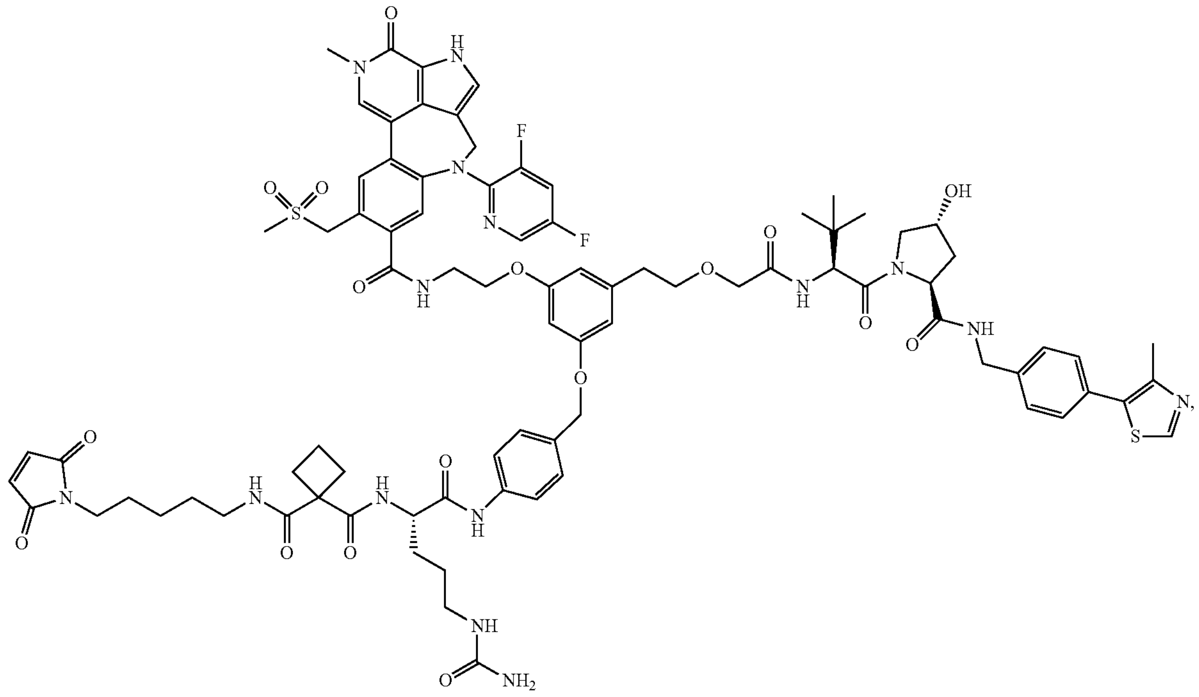
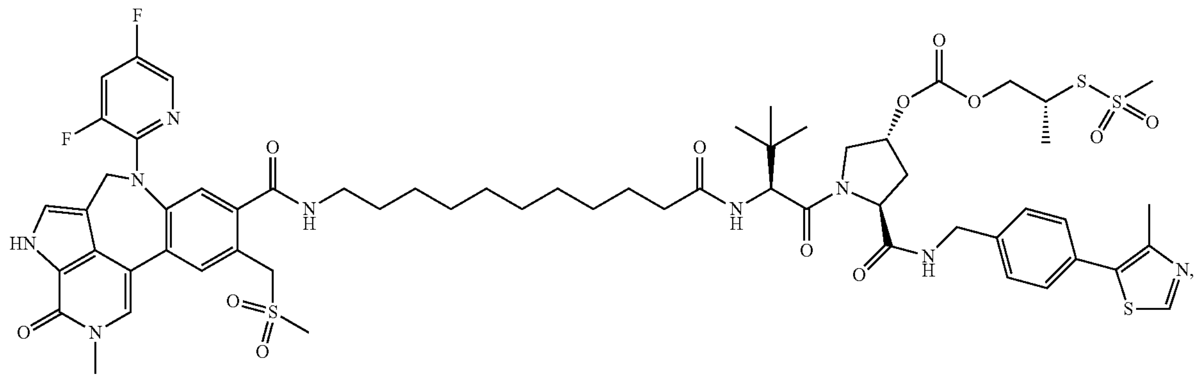

-continued

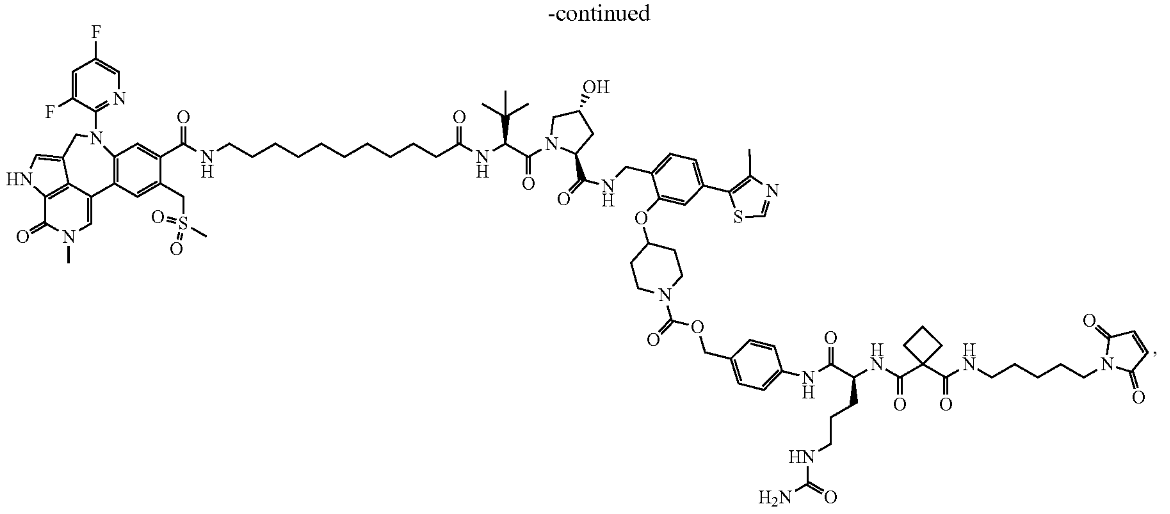

, and

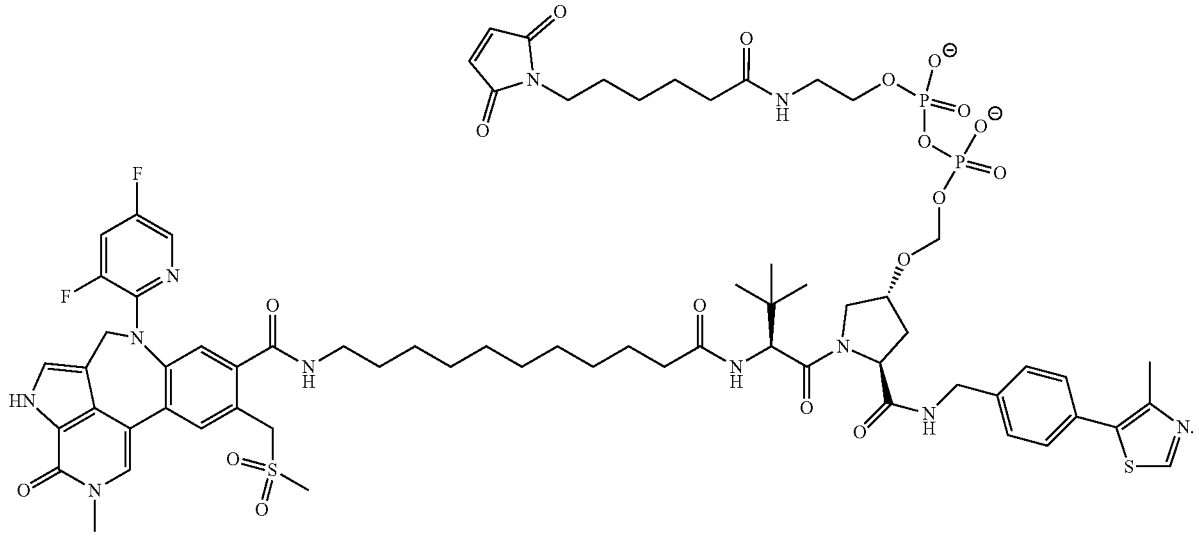

38. The conjugate of any above embodiment, wherein said Ab is an antibody that binds to one or more polypeptides selected from the group consisting of B7-H4, HER2, and CD22.

39. The conjugate of any above embodiment, wherein the PB is a residue of a group that binds BRD4 and has the structure:

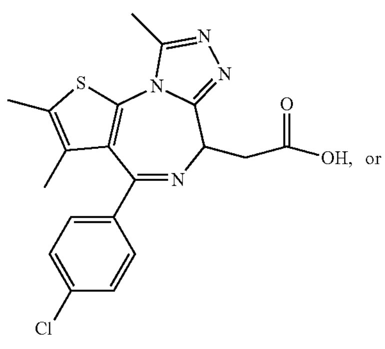

, or

-continued

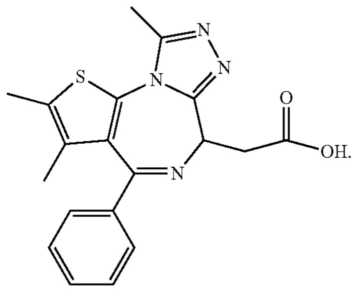

40. The conjugate of any above embodiment, wherein L1-D is a residue covalently linked to said Ab and is selected from one of the following structures:

L1BQ1
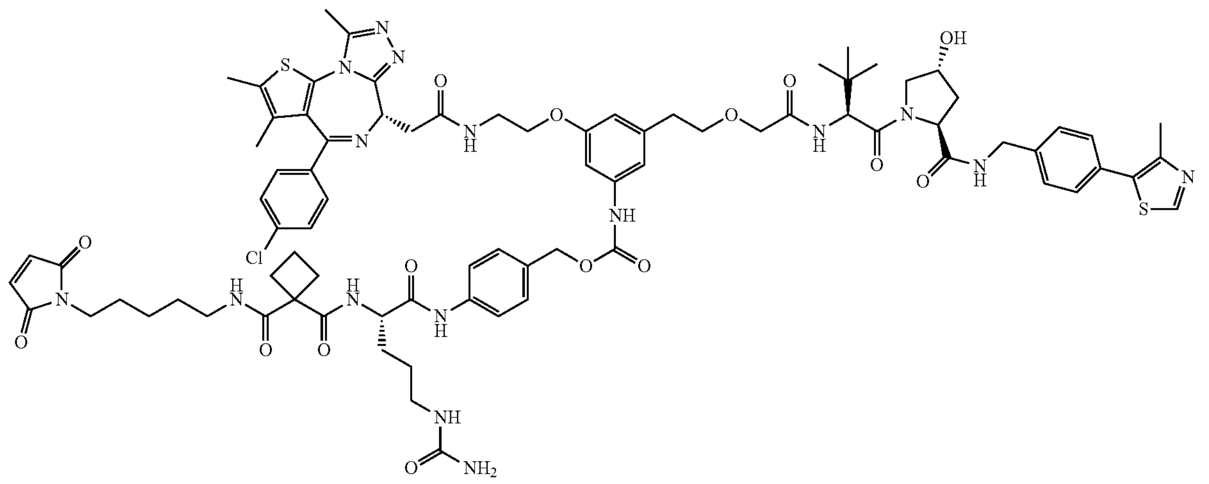
L1BQ2
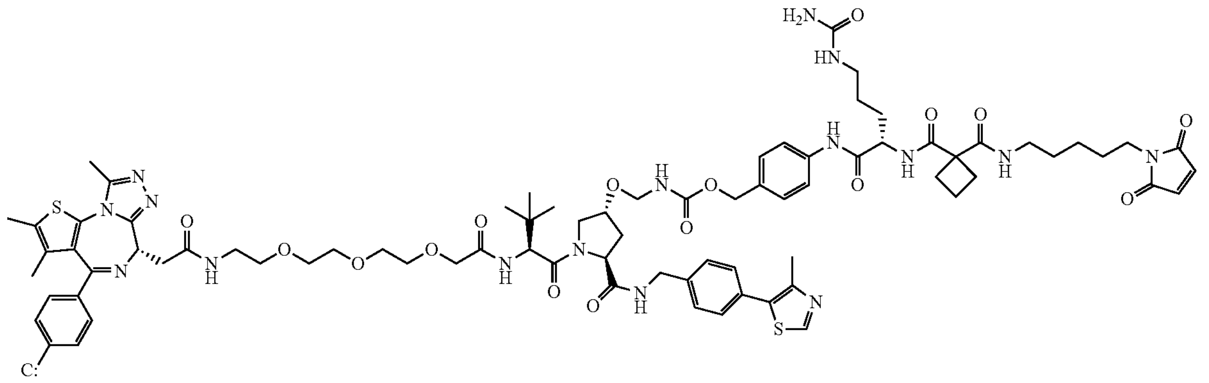
L1BQ3
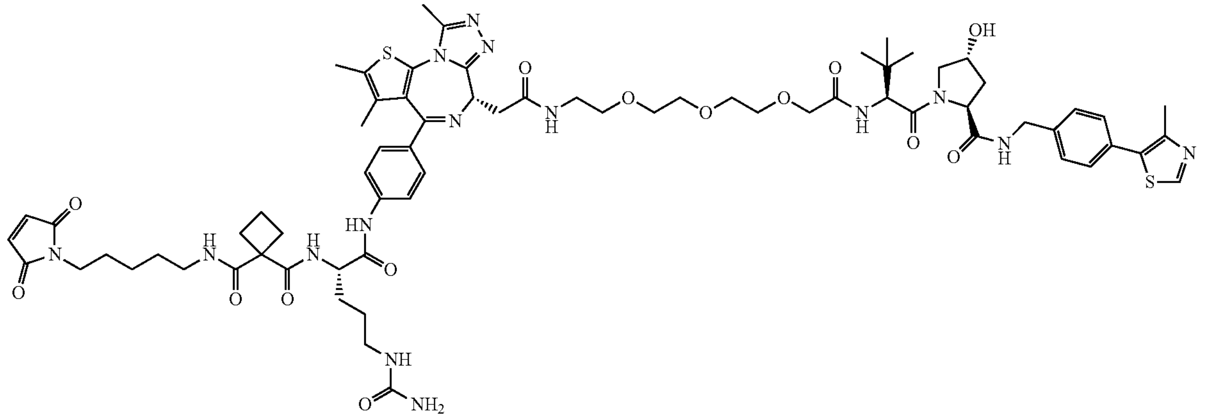

-continued
L1BQ4
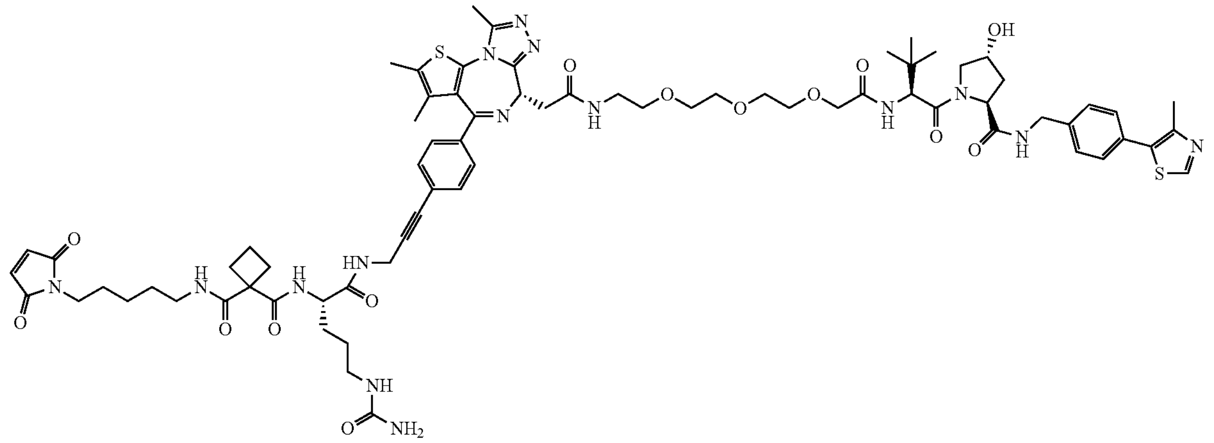
L1BQ5
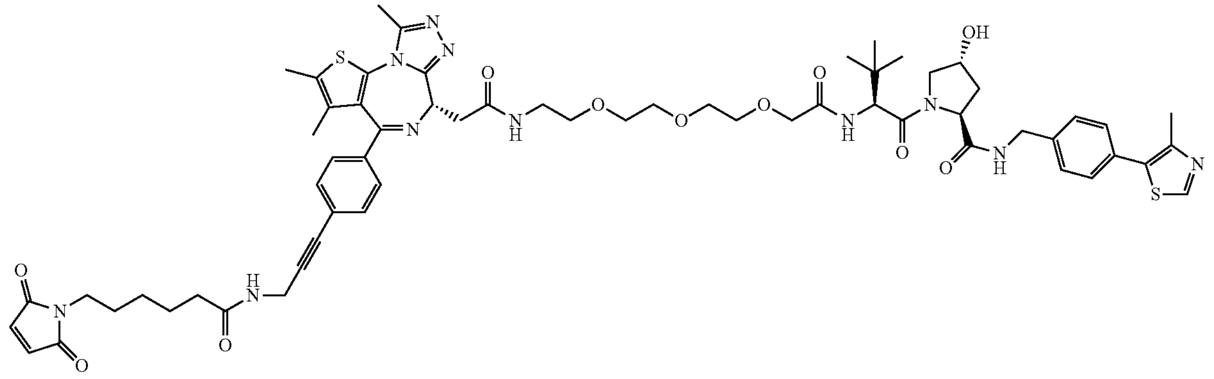
L1BQ6
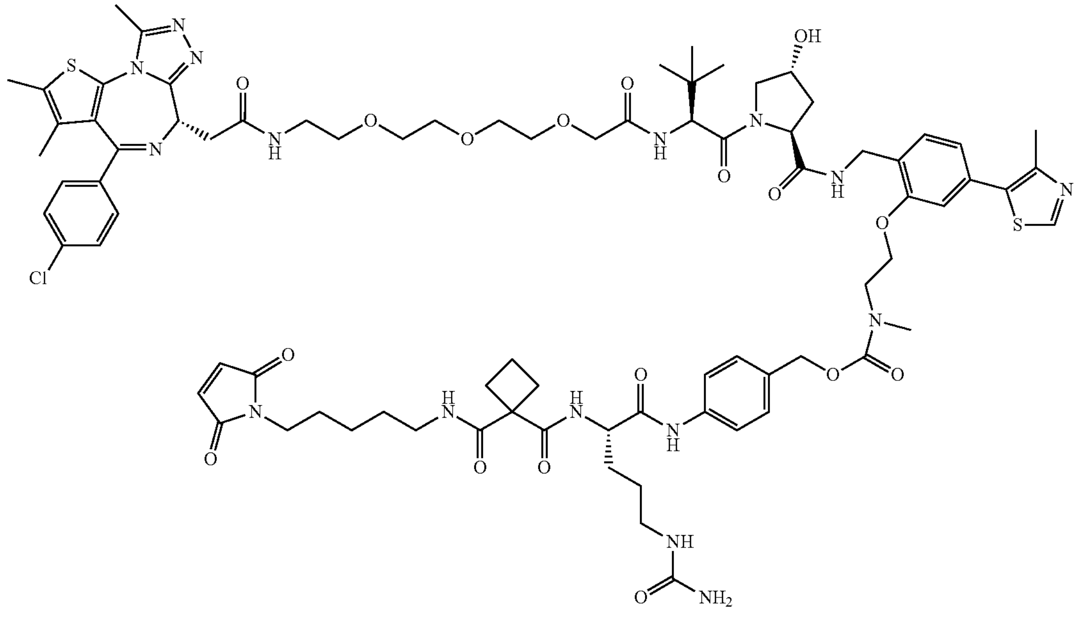

-continued
L1BQ7
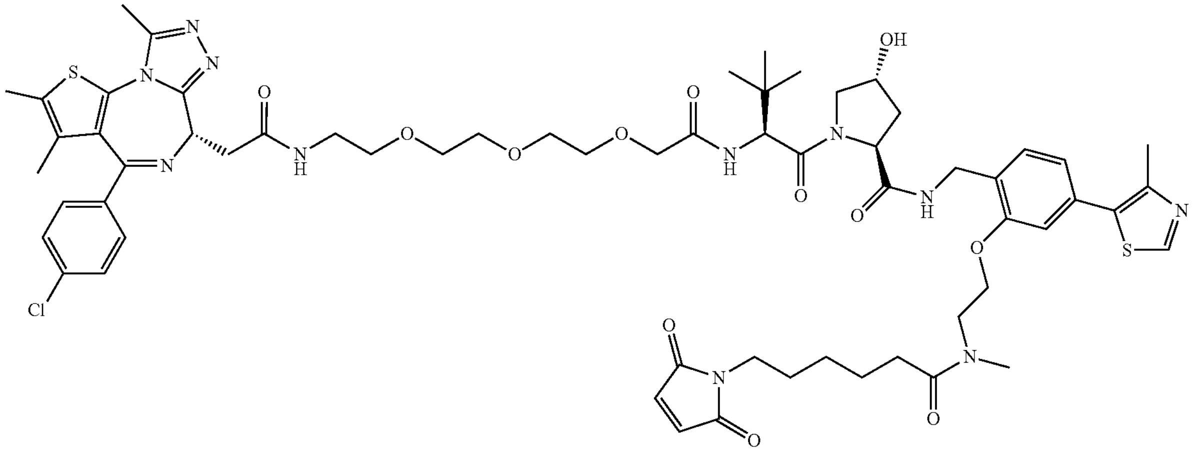
L1BQ8
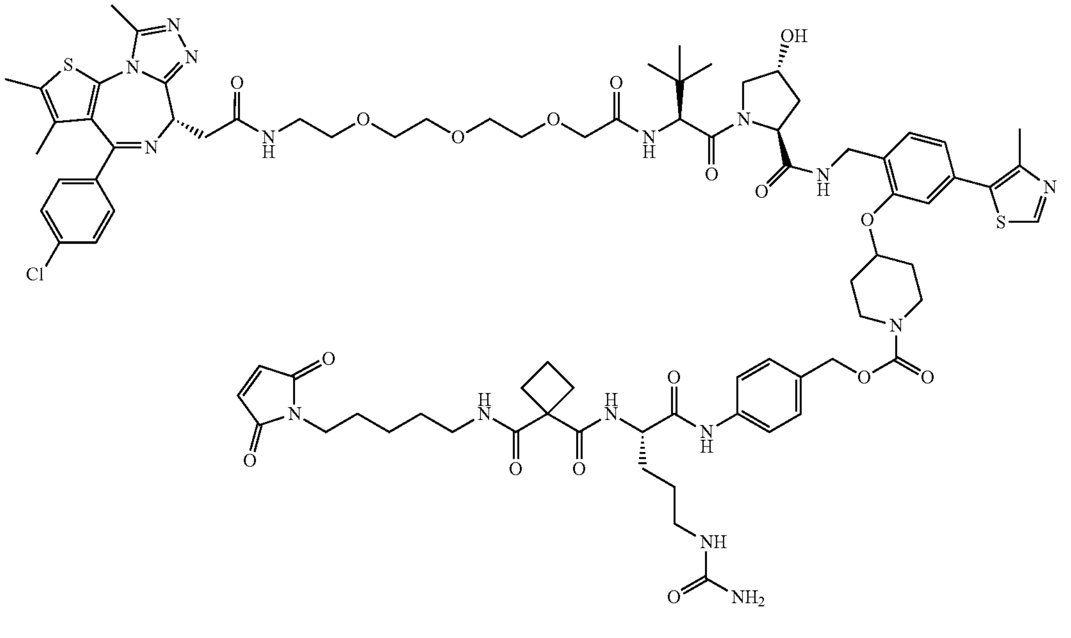
L1BQ9
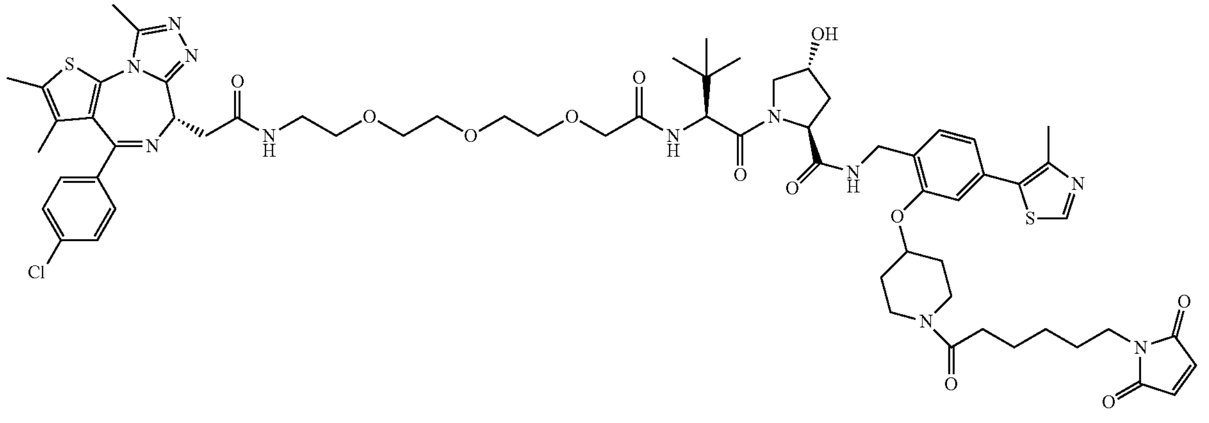

-continued
L1BQ10
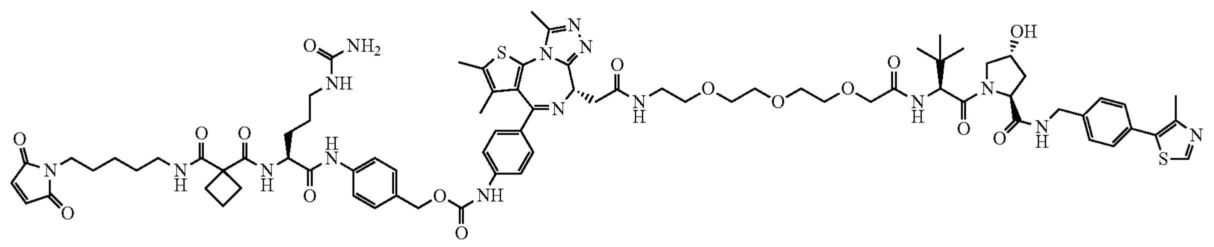
L1BQ11
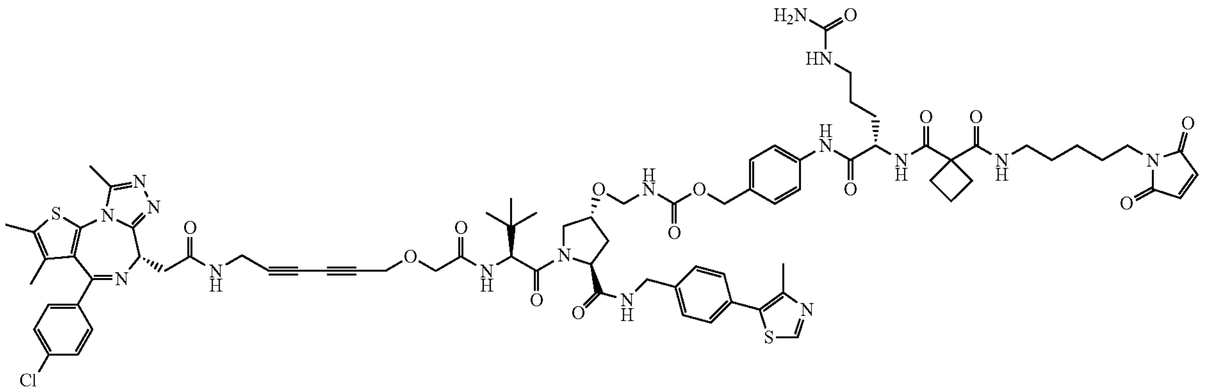
L1BQ12
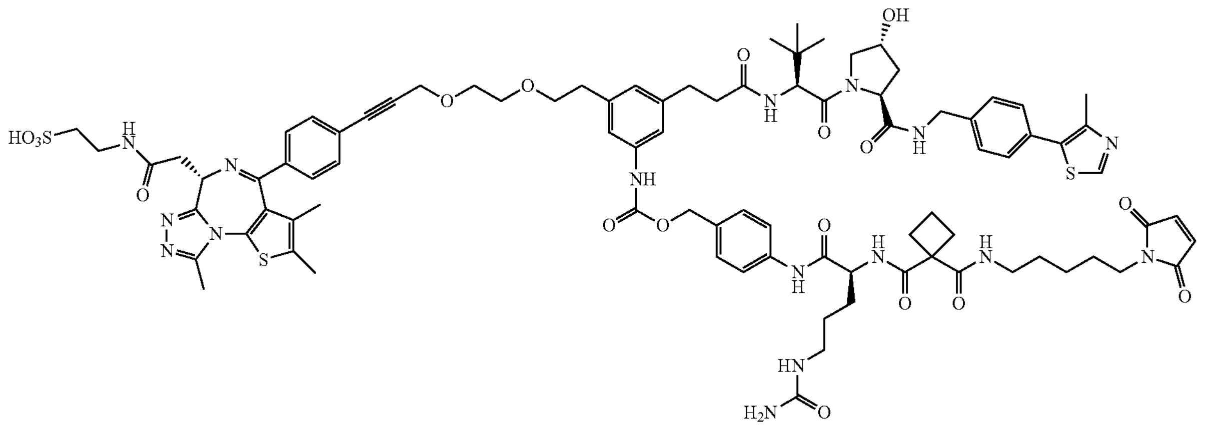
L1BQ13
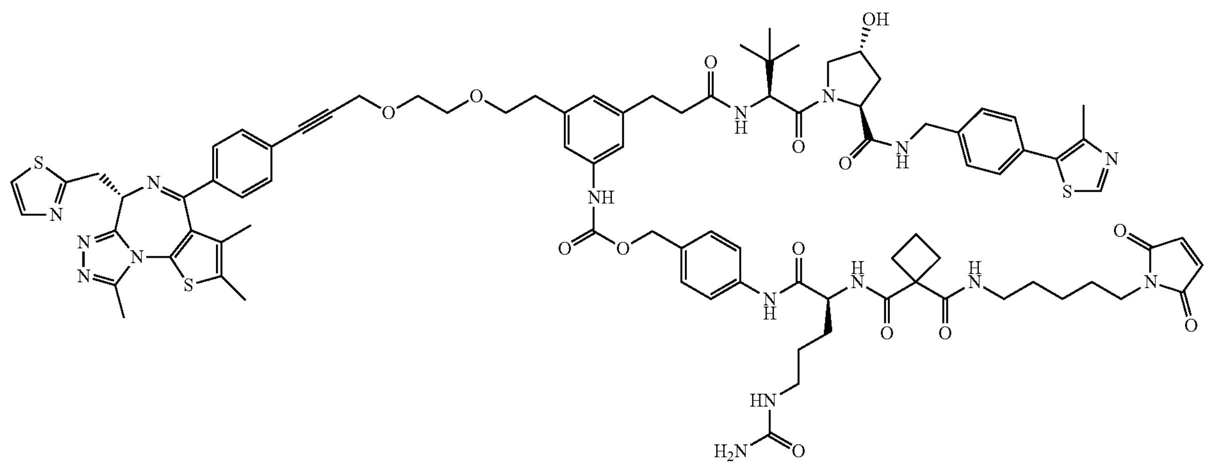

-continued
L1BQ14
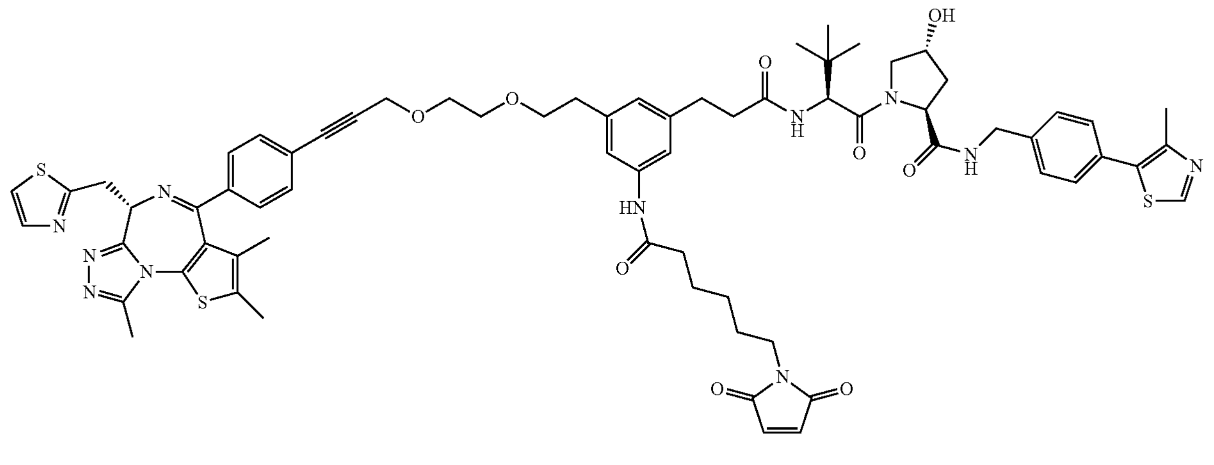
L1BQ15
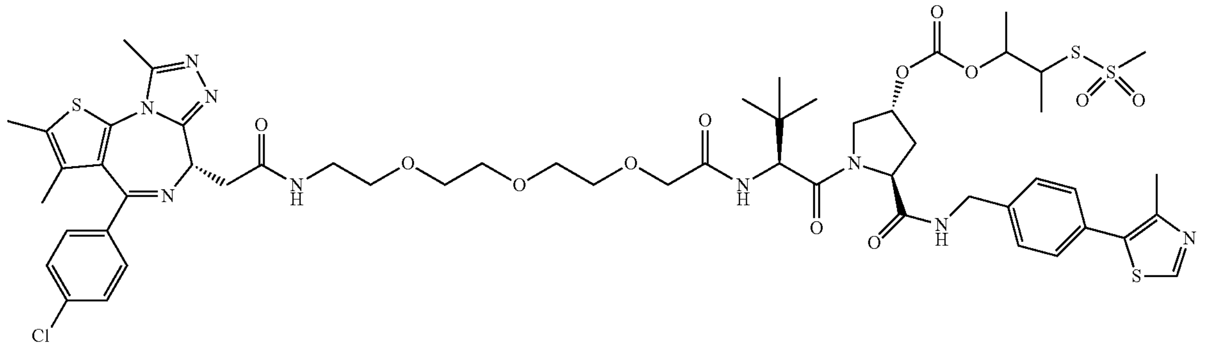
L1BQ16
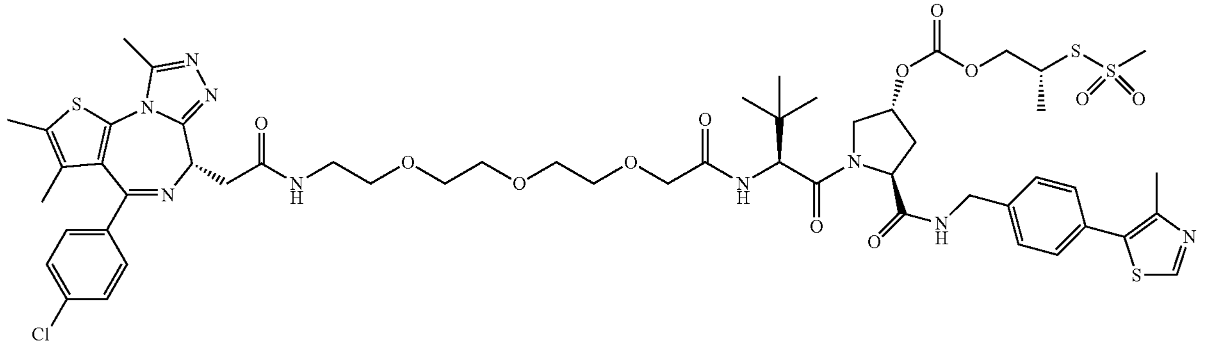
L1BQ17
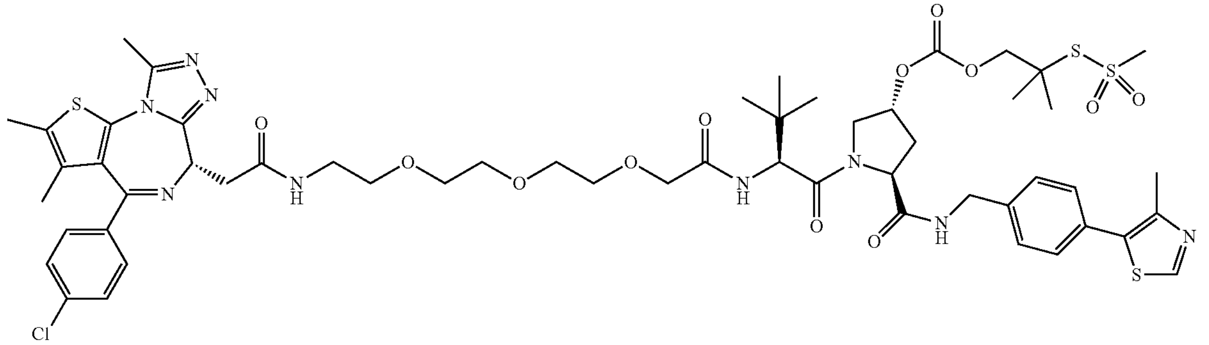

-continued
L1BQ18
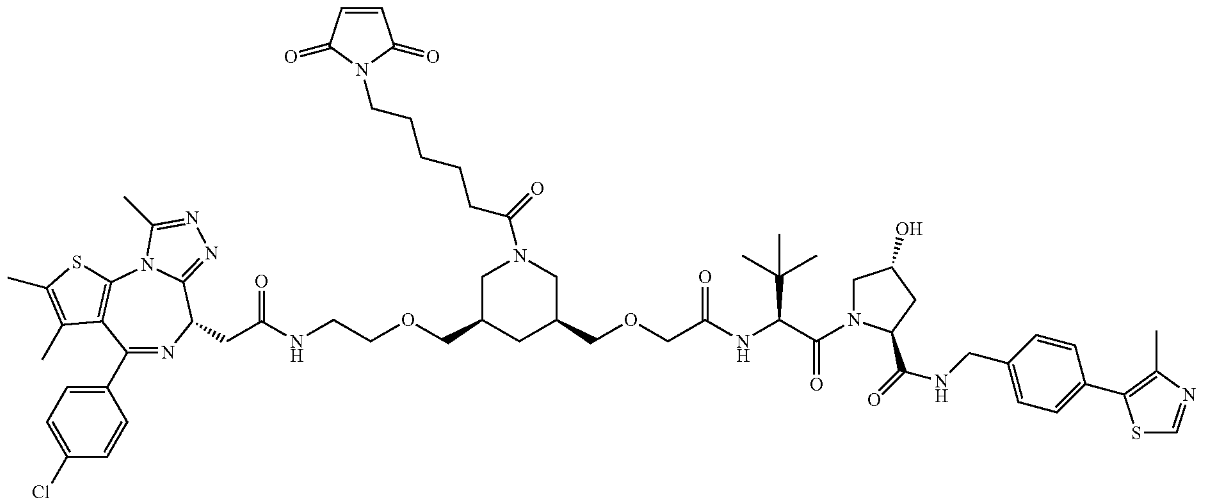
L1BQ19
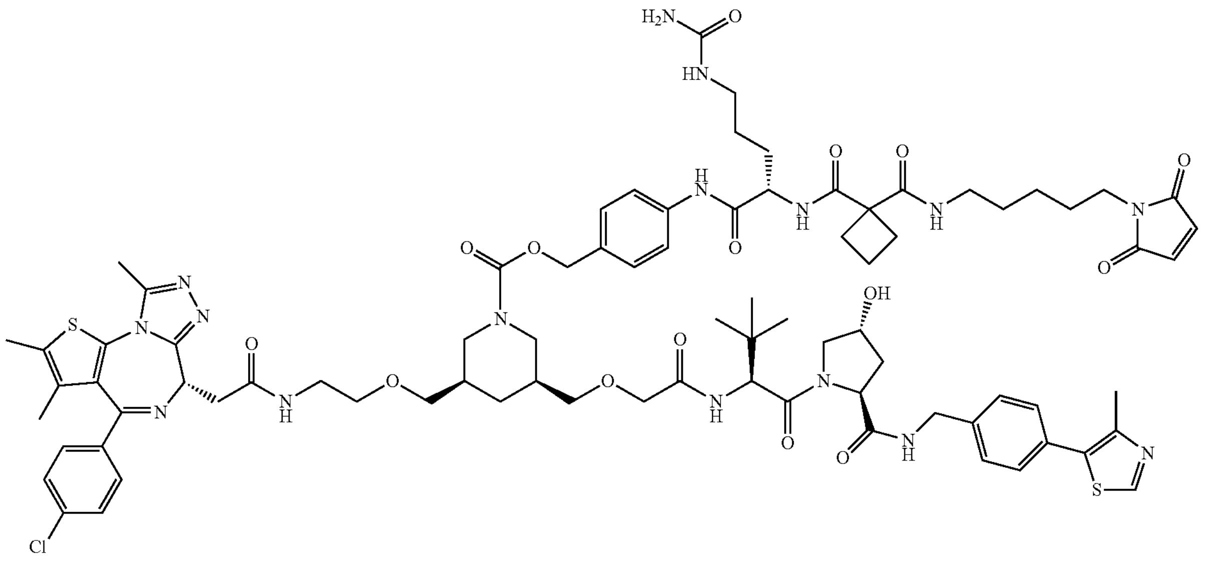
L1BQ20
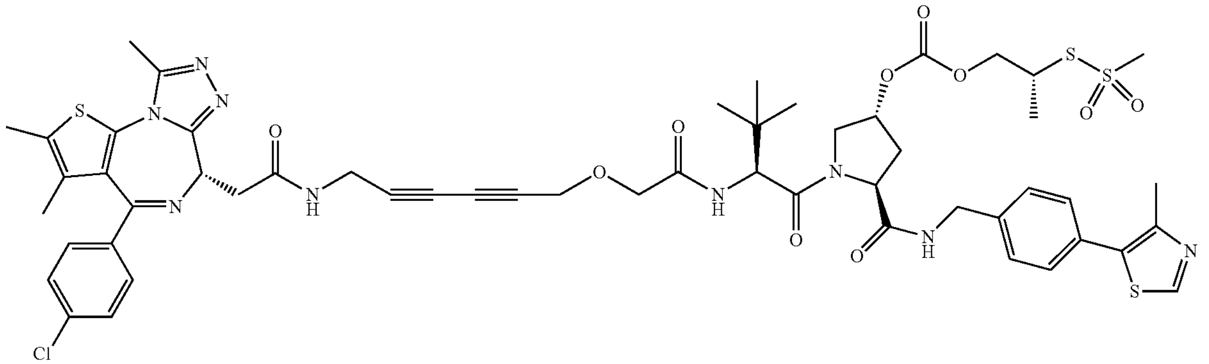

-continued

L1BQ21

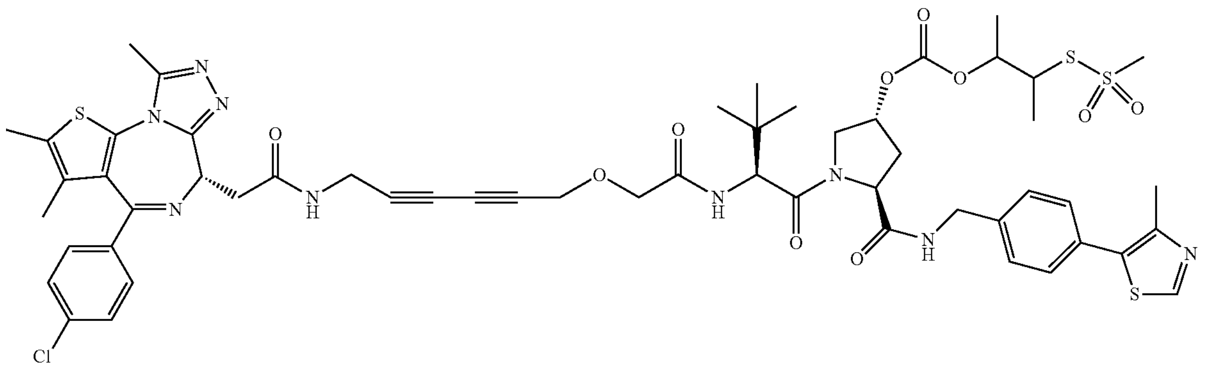

L1BQ22

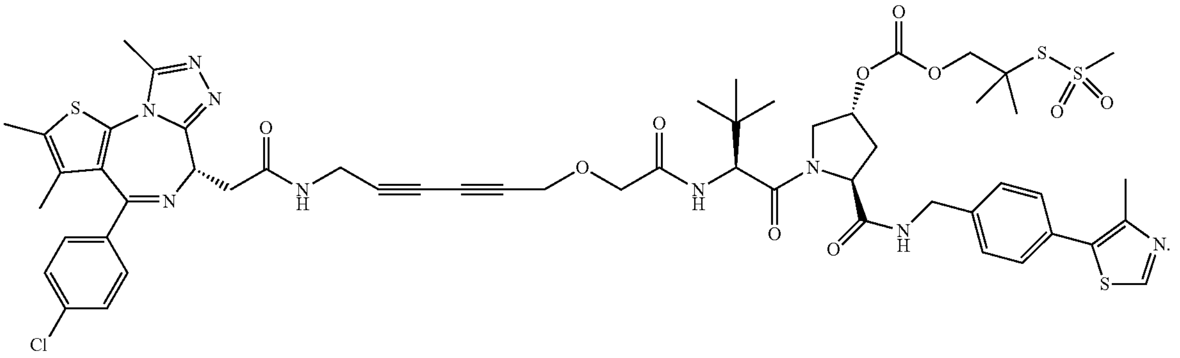

41. A pharmaceutical composition comprising a conjugate of any above embodiment and one or more pharmaceutically acceptable excipients.
42. A method of treating a disease in a human in need thereof, comprising administering to said human an effective amount of a conjugate of any above embodiment or a composition of embodiment 41.
43. The method of embodiment 42, wherein said disease is cancer.
44. The method of embodiment 43, wherein said cancer is selected from the group consisting of prostate, breast, and acute myeloid leukemia.
45. The method of embodiment 44, wherein the cancer is a HER2-positive cancer.
46. The method of embodiment 45, wherein the HER2-positive cancer is breast cancer.
47. A method of preparing a conjugate having the chemical structure Ab-(L1-D)$_p$, wherein,
D is a CIDE having the structure E3LB-L2-PB;
E3LB is covalently bound to L2, and said E3LB is a group that binds an E3 ligase, wherein said E3 ligase is von Hippel-Lindau (VHL);
L2 is a linker covalently bound to E3LB and PB;
PB is a protein binding group covalently bound to L2, and said PB is a group that binds BRD4 or ERα, including all variants, mutations, splice variants, indels and fusions thereof,
Ab is an antibody covalently bound to L1;
L1 is a linker, covalently bound to Ab and D; and
p has a value from about 1 to about 8;

said method comprising:
contacting a L2 with a first solvent, first base, and first coupling reagent to prepare a first solution;
contacting an E3LB with said first solution to prepare an E3LB-L2 intermediate;
contacting a PB with a second solvent, second base, and second coupling reagent to prepare a second solution;
contacting said second solution with said E3LB-L2 intermediate to prepare a CIDE;
contacting said CIDE with L1 and a third base in a third solvent to prepare a L1-CIDE; and
contacting said L1-CIDE with a thiol and a fourth solvent to prepare a fourth solution; and
contacting said fourth solution with an antibody to prepare the conjugate.
48. The method of embodiment 47, wherein said first solvent, second solvent, third solvent, and fourth solvent are each independently selected from the group consisting of dimethylformamide, tetrahydrofuran, ethyl acetate, acetone, acetonitrile, dimethyl sulfoxide, and propylene carbonate.
49. The method of embodiment 47, wherein said first solvent, second solvent, third solvent, and fourth solvent are each dimethylformamide.
50. The method of embodiment 47, wherein said first and second coupling reagents are each 1-[Bis(dimethylamino)methylene]-1H-1,2,3-triazolo[4,5-b]pyridinium 3-oxide hexafluorophosphate (HATU).
51. The method of embodiment 47, wherein said first, second, and third base are each independently selected from the group consisting of N,N-Diisopropylethylamine (DIEA), triethylamine, and 2,2,2,6,6-tetramethylpiperidine.

52. The method of embodiment 47, wherein L1 is selected from the group consisting of:
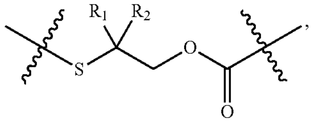
, and
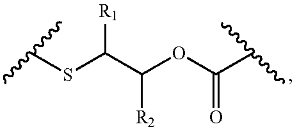
,
wherein, $R^1$ and $R^2$ are independently selected from H and $C_1$-$C_6$ alkyl, or $R^1$ and $R^2$ form a 3, 4, 5, or 6-membered cycloalkyl or heterocyclyl group.
53. The method of embodiment 47, wherein D is a residue covalently linked to L1 and is selected from one of the following structures:
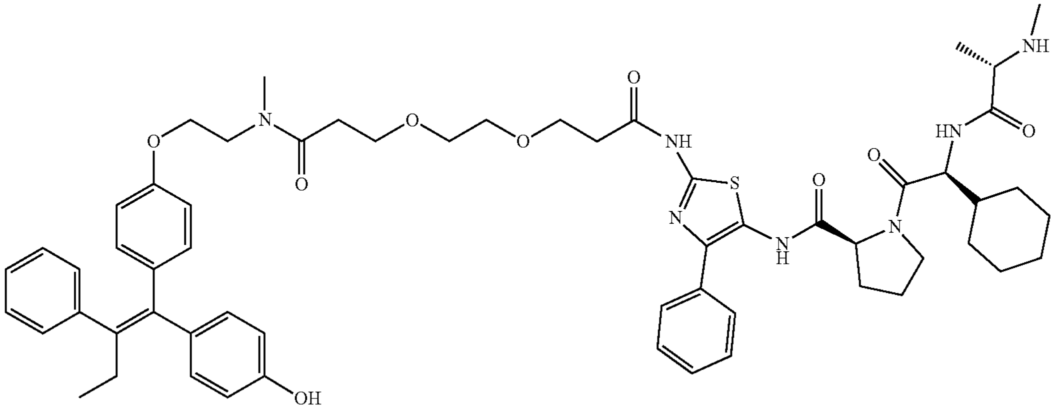
,
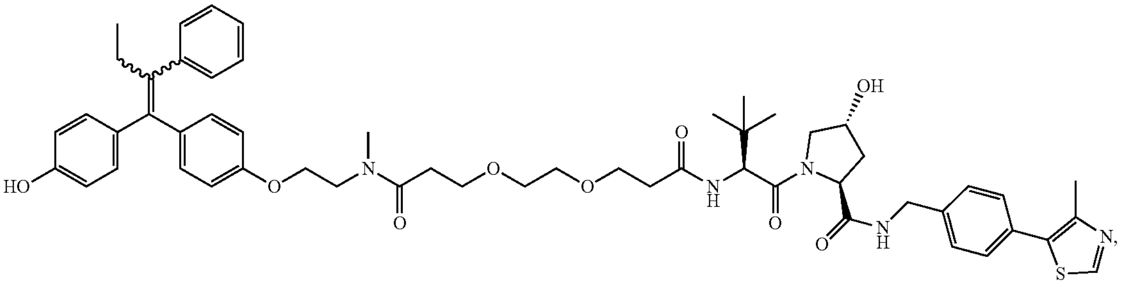
and
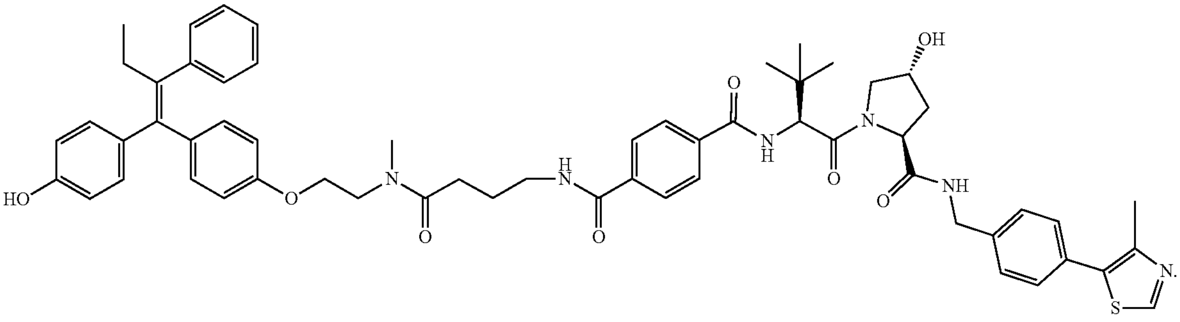

54. The method of embodiment 47, wherein L1-D is a residue covalently linked to said Ab and is selected from one of the following structures:
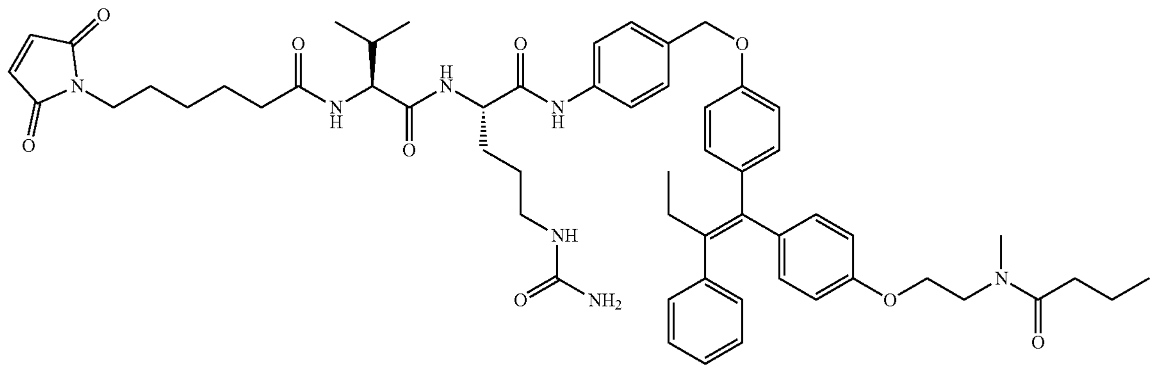
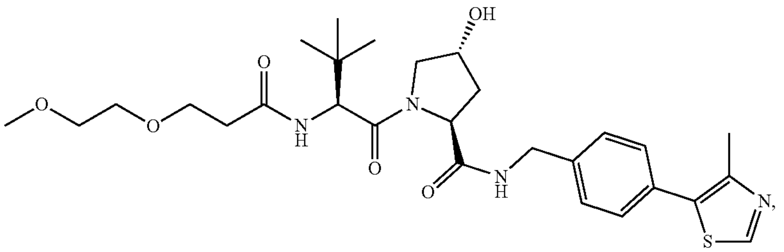
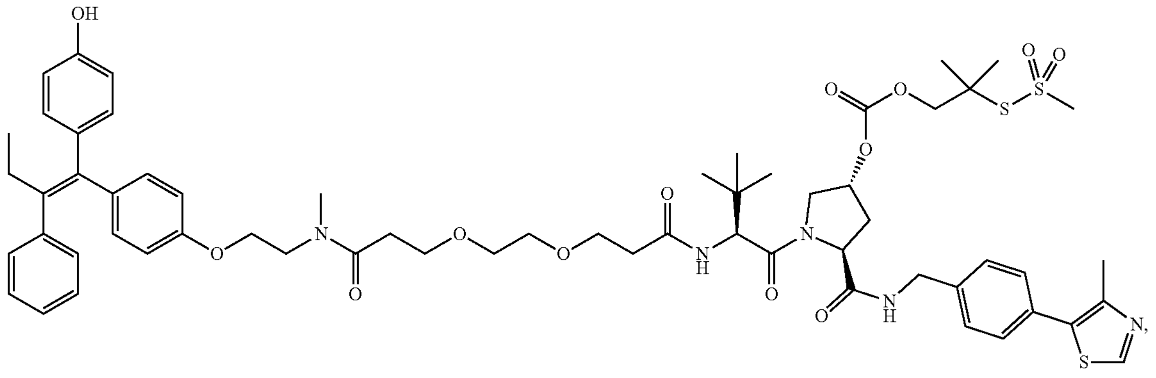
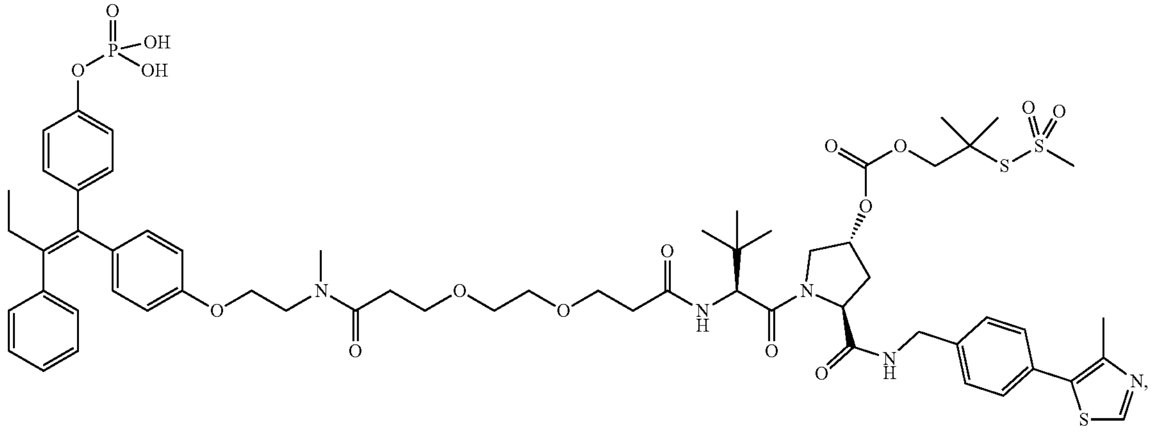

-continued
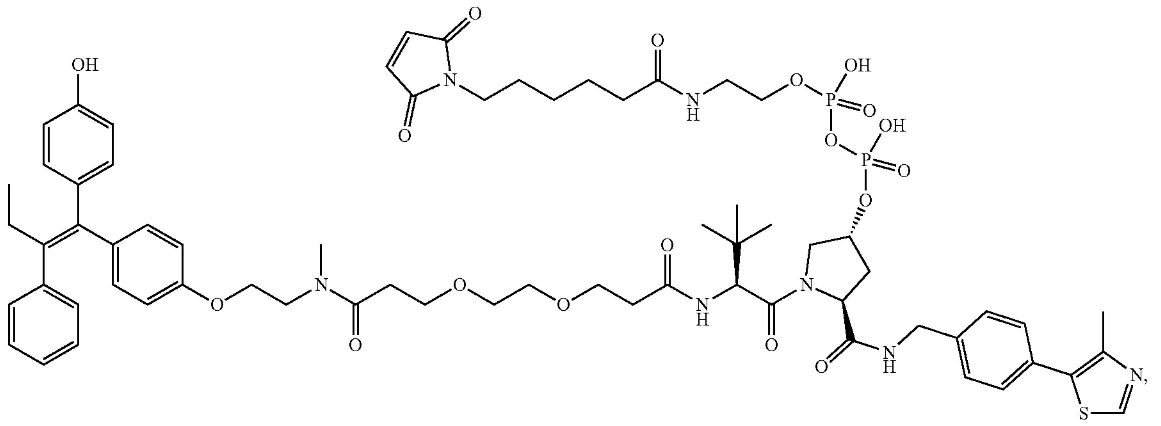
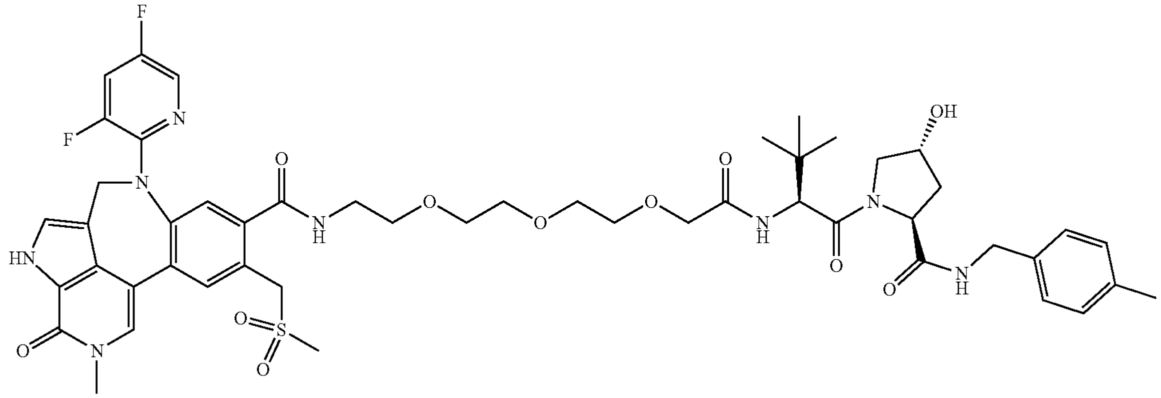
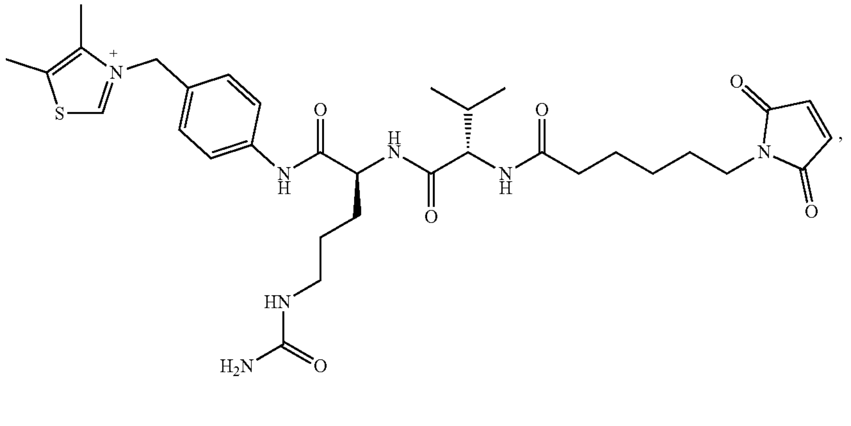

-continued
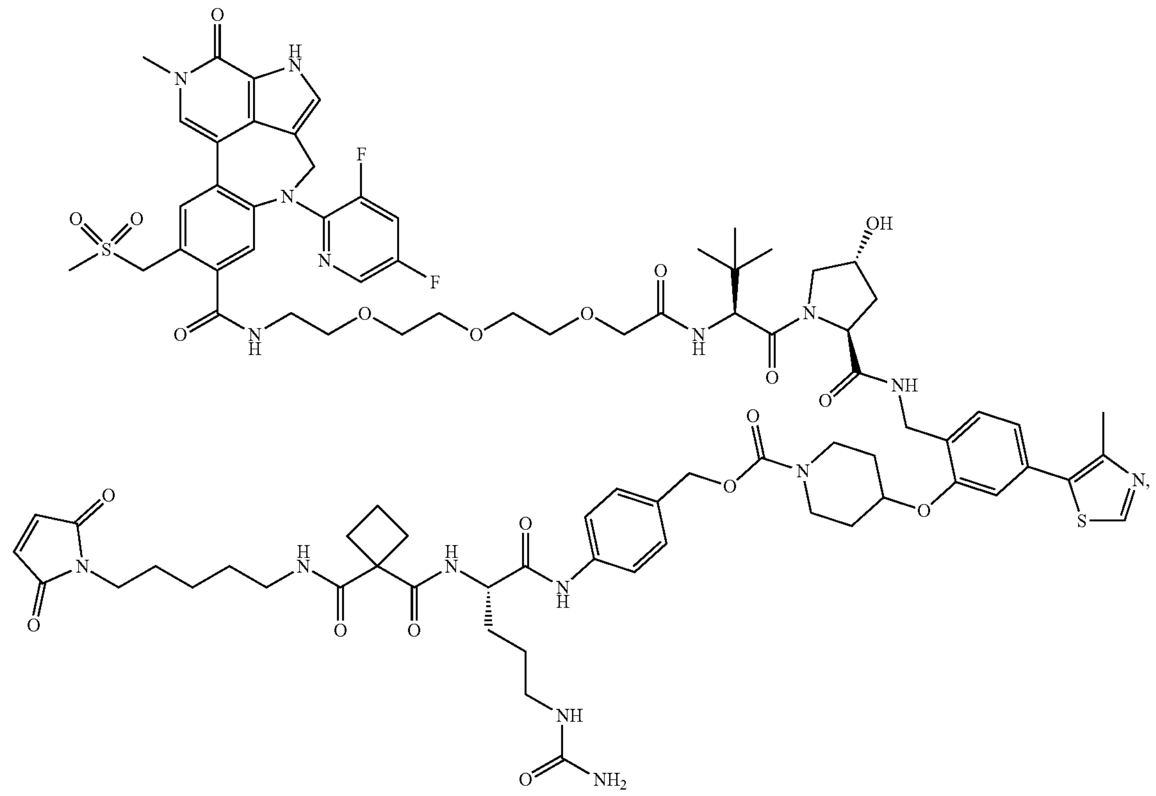
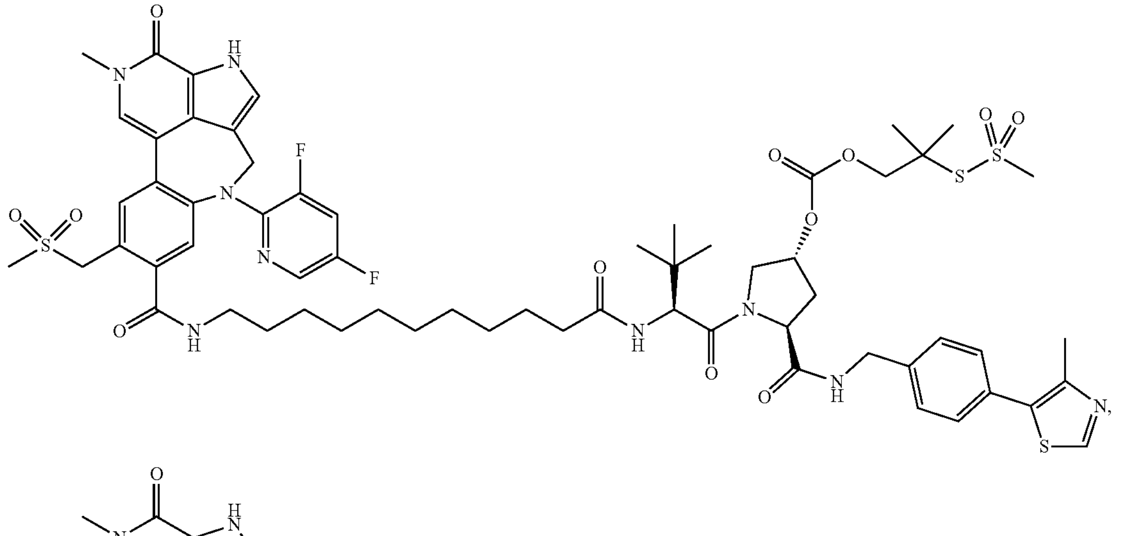
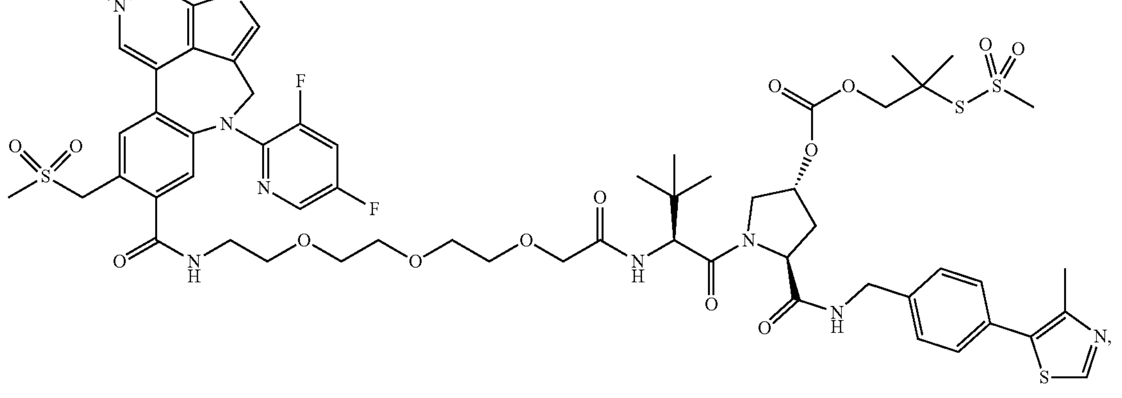

-continued
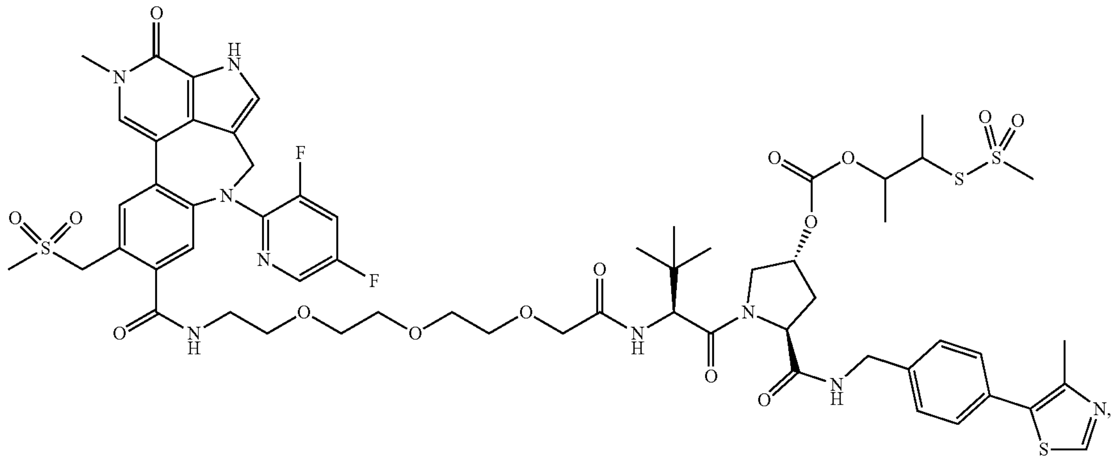
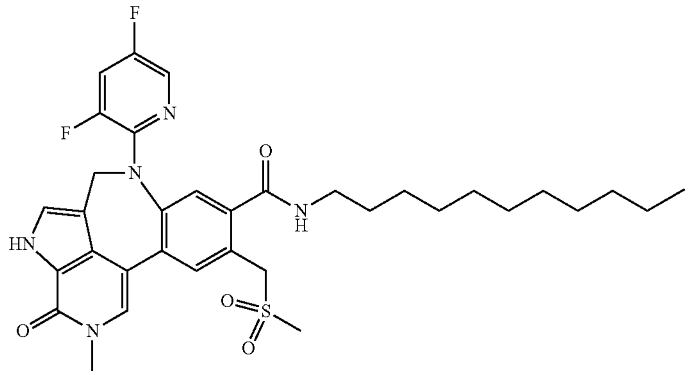
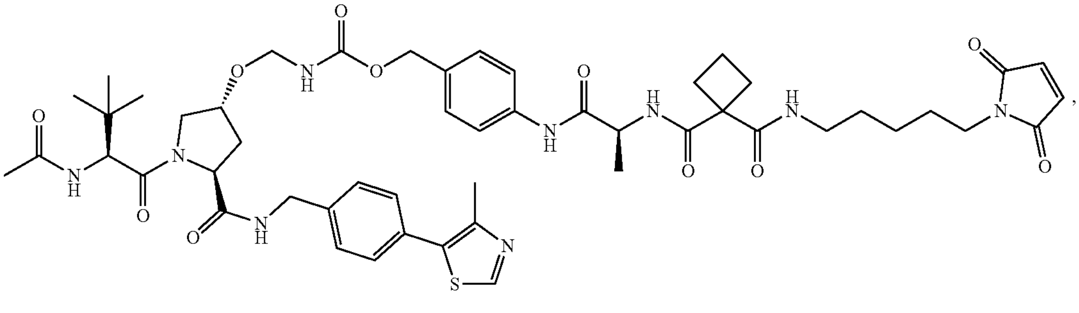
,

-continued
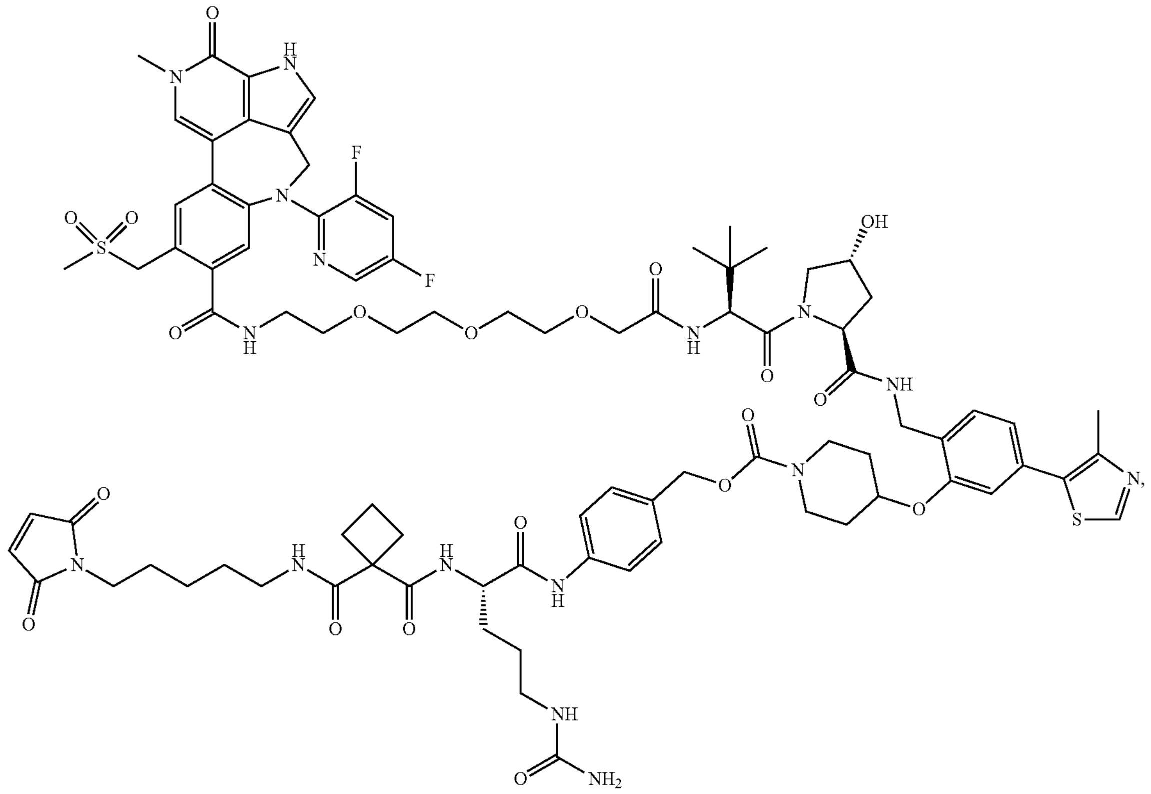
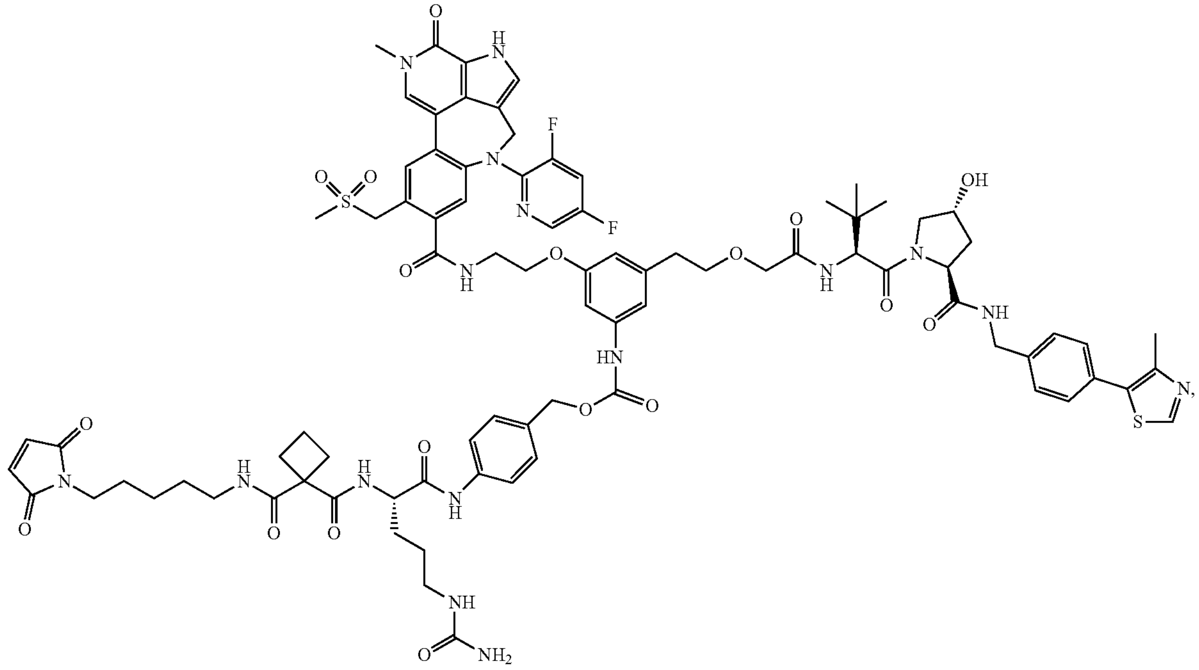

-continued
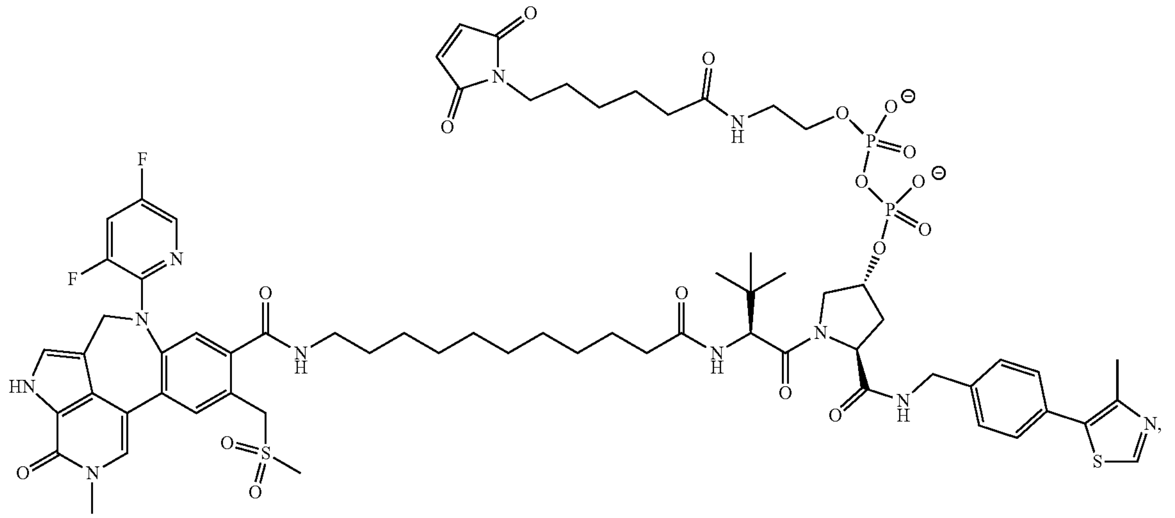
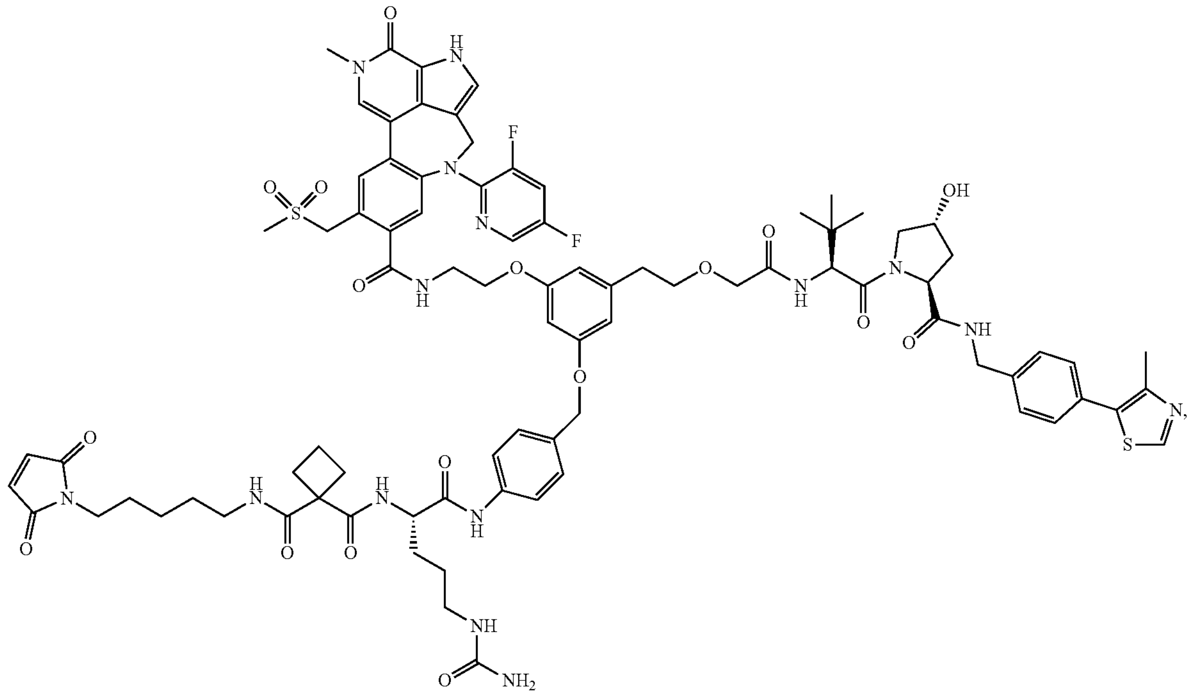
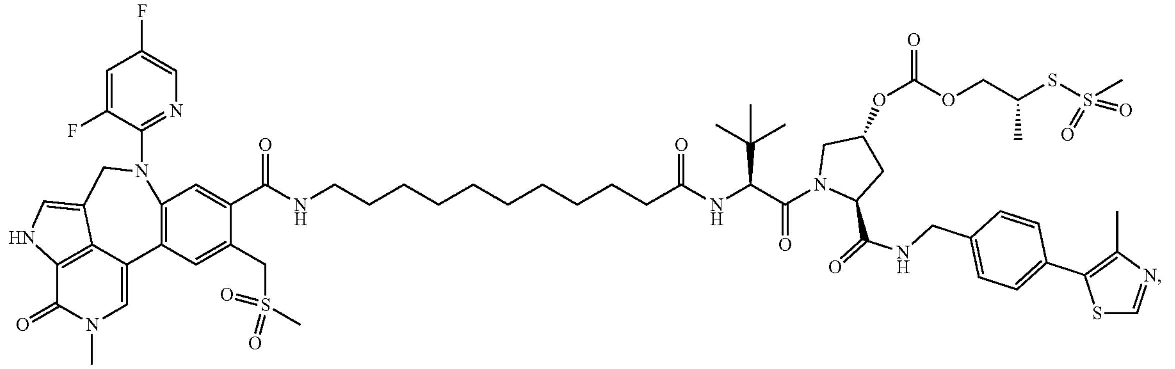

-continued

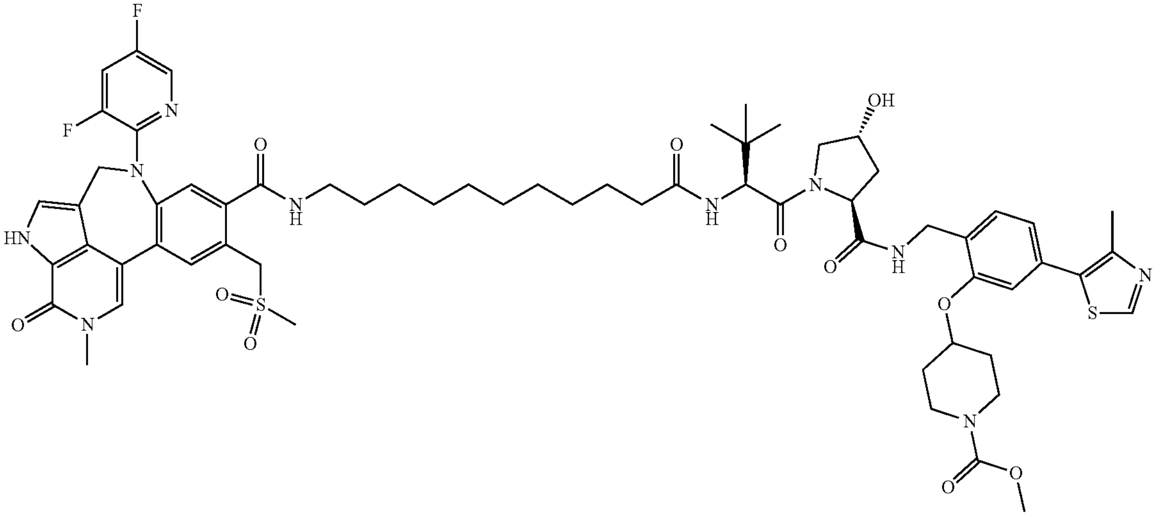

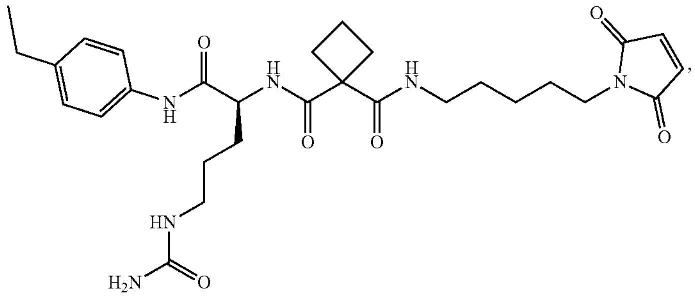
, and

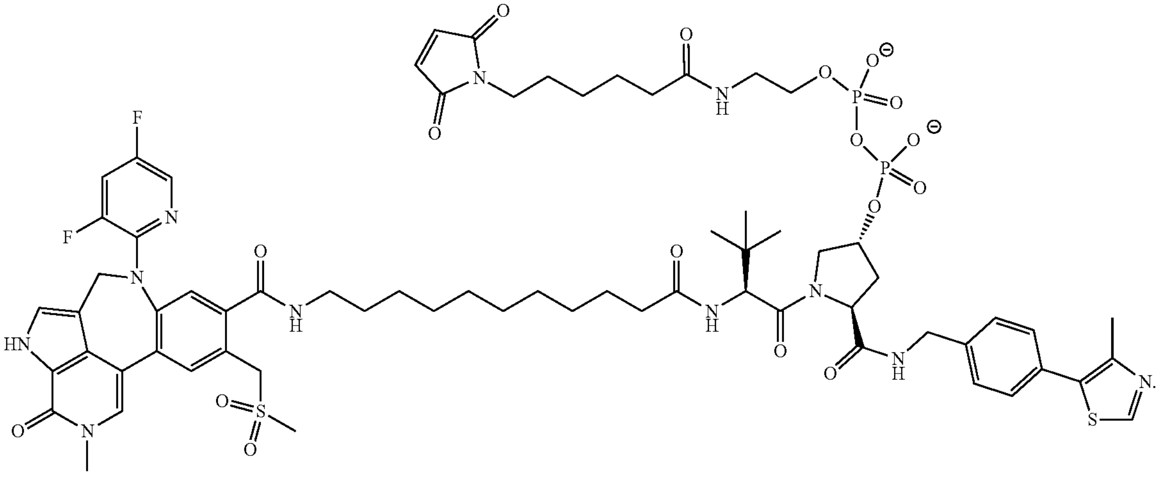

55. An antibody conjugate made by the method of embodiments 47, 48, 49, 50, 51, 52, 53 or 54.

56. An antibody conjugate substantially as described herein.

57. A conjugate having the chemical structure

Ab-(L1-D)$_p$, wherein,

D is a CIDE having the structure E3LB-L2-PB;

E3LB is covalently bound to L2, and said E3LB is a group that binds an E3 ligase, wherein said E3 ligase is von Hippel-Lindau (VHL);

L2 is a linker covalently bound to E3LB and PB;

PB is a protein binding group covalently bound to L2, and said PB is a group that binds BRD4 or ERα, including all variants, mutations, splice variants, indels and fusions thereof, Ab is an antibody covalently bound to L1;

L1 is a linker, covalently bound to Ab and D; and p has a value from about 1 to about 8.

58. The conjugate of embodiment 57, wherein the EL3B is a residue of a group having the structure:

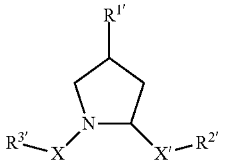

wherein, $R^{1'}$ is an optionally substituted $C_1$-$C_6$ alkyl group, an optionally substituted —$(CH_2)_n$OH, an optionally substituted —$(CH_2)_n$SH, an optionally substituted $(OH_2)_n$—O—($C_1$-$C_6$)alkyl group, an optionally substituted $(CH_2)_n$—WCOCW—($C_0$-$C_6$) alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—($C_1$-$C_6$ alkyl), an optionally substituted —$(CH_2)_n$NHC(O)—$R^1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—($C_1$-$C_6$ alkyl), an optionally substituted —$(CH_2)_n$C(O)—O—($C_1$-$C_6$ alkyl), an optionally substituted
—$(CH_2O)_n$COOH, an optionally substituted —$(OCH_2)_n$O—($C_1$-$C_6$ alkyl), an optionally substituted —$(CH_2)_n$C(O)—O—($C_1$-$C_6$ alkyl), an optionally substituted —$(OCH_2)_n$NHC(O)—$R^1$, an optionally substituted —$(CH_2O)_n$C(O)—$NR_1R_2$, —$(CH_2CH_2O)_n$H, an optionally substituted
—$(CH_2CH_2O)_n$COOH, an optionally substituted —$(OCH_2CH_2)_n$O—($C_1$-$C_6$ alkyl), an optionally substituted —$(CH_2CH_2O)_n$C(O)—($C_1$-$C_6$ alkyl), an optionally substituted
—$(OCH_2CH_2)_n$NHC(O)—$R_1$, an optionally substituted —$(CH_2CH_2O)_n$C(O)—$NR_1R_2$, an optionally substituted —$SO_2R_s$, an optionally substituted S(O)$R_s$, $NO_2$, CN or halogen (F, Cl, Br, I, preferably F or Cl);

$R_1$ and $R_2$ are each independently H or a $C_1$-$C_6$ alkyl group which may be optionally substituted with one or two hydroxyl groups or up to three halogen groups (preferably fluorine);

$R_s$ is a $C_1$-$C_6$ alkyl group, an optionally substituted aryl, heteroaryl or heterocycle group or a —$(CH_2)$ $NR_1R_2$ group;

X and X' are each independently C═O, O═S, —S(O), $S(O)_2$, (preferably X and X' are both C═O);

$R^{2'}$ is an optionally substituted —$(CH_2)_n$—$(C═O)_{uz}$$(NR_1)_v$$(SO_2)_w$alkyl group, an optionally substituted —$(CH_2)_n$—$(C═O)_u$$(NR_1)_v$$(SO_2)_w$$NR_1NR_2$N group, an optionally substituted
—$(CH_2)_n$—$(C═O)_u$$(NR_1)_v$$(SO_2)_w$-Aryl, an optionally substituted
—$(CH_2)_n$—$(C═O)_u$$(NR_1)_v$$(SO_2)_w$-Heteroaryl, an optionally substituted
—$(CH_2)_n$—$(C═O)_v$$NR_1$$(SO_2)_w$-Heterocycle, an optionally substituted
—$NR^1$—$(CH_2)_n$—$C(O)_u$$(NR_1)_v$$(SO_2)_w$-alkyl, an optionally substituted
—$NR^1$—$(CH_2)_n$—$C(O)_u$$(NR_1)_v$$(SO_2)_w$—$NR_1NR_2$N, an optionally substituted
—$NR_1$—$(CH_2)_n$—$C(O)_u$$(NR_1)_v$$(SO_2)_w$—$NR_1$C(O)$R_{1N}$, an optionally substituted
—$NR^1$—$(CH_2)_n$—$(C═O)_u$$(NR_1)_v$$(SO_2)_w$-Aryl, an optionally substituted
—$NR_1$—$(CH_2)_n$—$(C═O)_u$$(NR_1)_v$$(SO_2)_w$-Heteroaryl or an optionally substituted
—$NR_1$—$(CH_2)_n$—$(C═O)_v$$NR_1$$(SO_2)_w$-Heterocycle, an optionally substituted
—$X^{R2'}$-alkyl group; an optionally substituted
—$X^{R2'}$-Aryl group; an optionally substituted
—$X^{R2'}$-Heteroaryl group; an optionally substituted
—$X^{R2'}$-Heterocycle group; an optionally substituted;

$R^3$ is an optionally substituted alkyl, an optionally substituted
—$(CH_2)_n$—$C(O)_u$$(NR_1)_v$$(SO_2)_w$-alkyl, an optionally substituted
—$(CH_2)_n$—$C(O)_u$$(NR_1)_v$$(SO_2)_w$—$NR_{1N}R_{2N}$, an optionally substituted
—$(CH_2)_n$—$C(O)_u$$(NR_1)_v$$(SO_2)_w$—$NR_1$C(O)$R_{1N}$, an optionally substituted
—$(CH_2)_n$—$C(O)_u$$(NR_1)_v$$(SO_2)_w$—C(O)$NR_1R_2$, an optionally substituted
—$(CH_2)_n$—$C(O)_u$$(NR_1)_v$$(SO_2)_w$-Aryl, an optionally substituted
—$(CH_2)_n$—$C(O)_u$$(NR_1)_v$$(SO_2)_w$-Heteroaryl, an optionally substituted
—$(CH_2)_n$—$C(O)_u$$(NR_1)_v$$(SO_2)_w$-Heterocycle, an optionally substituted
—$NR^1$—$(CH_2)_n$—$C(O)_u$$(NR_1)_v$$(SO_2)_w$-alkyl, an optionally substituted
—$NR^1$—$(CH_2)_n$—$C(O)_u$$(NR_1)_v$$(SO_2)_w$—$NR_{1N}R_{2N}$, an optionally substituted
—$NR^1$—$(CH_2)_n$—$C(O)_u$$(NR_1)_v$$(SO_2)_w$—$NR_1$C(O)$R_{1N}$, an optionally substituted
—$NR_1$—$(CH_2)_n$—$C(O)_u$$(NR_1)_v$$(SO_2)_w$-Aryl, an optionally substituted
—$NR^1$—$(CH_2)_n$—$C(O)_u$$(NR_1)_v$$(SO_2)_w$-Heteroaryl, an optionally substituted
—$NR^1$—$(CH_2)_n$—$C(O)_u$$(NR_1)_v$$(SO_2)_w$-Heterocycle, an optionally substituted
—O—$(CH_2)$n-$(C═O)_u$$(NR_1)_v$$(SO_2)_w$-alkyl, an optionally substituted
—O—$(CH_2)$n-$(C═O)_u$$(NR_1)_v$$(SO_2)_w$—$NR_{1N}R_{2N}$, an optionally substituted
—O—$(CH_2)$n-$(C═O)_u$$(NR_1)_v$$(SO_2)_w$—$NR_1$C(O)$R_{1N}$, an optionally substituted
—O—$(CH_2)$n-$(C═O)_u$$(NR_1)_v$$(SO_2)_w$-Aryl, an optionally substituted
—O—$(CH_2)_n$—$(C═O)_u$$(NR_1)_v$$(SO_2)_w$-Heteroaryl or an optionally substituted
—O—$(CH_2)_n$—$(C═O)_u$$(NR_1)_v$$(SO_2)_w$-Heterocycle;
—$(CH_2)_n$—$(V)_{n'}$—$(CH_2)_n$—$(V)_{n'}$-alkyl group, an optionally substituted
—$(CH_2)_n$—$(V)_{n'}$—$(CH_2)_n$—$(V)_{n'}$-Aryl group, an optionally substituted
—$(CH_2)_n$—$(V)_{n'}$—$(CH_2)_n$—$(V)_{n'}$-Heteroaryl group, an optionally substituted
—$(CH_2)_n$—$(V)_{n'}$—$(CH_2)_n$—$(V)_{n'}$-Heterocycle group, an optionally substituted
—$(CH_2)_n$—$N(R_{1'})$$(C═O)_{m'}$—$(V)_{n'}$-alkyl group, an optionally substituted
—$(CH_2)_n$—$N(R_{1'})$$(C═O)_{m'}$—$(V)_{n'}$-Aryl group, an optionally substituted
—$(CH_2)_n$—$N(R_{1'})$$(C═O)_{m'}$—$(V)_{n'}$-Heteroaryl group, an optionally substituted
—$(CH_2)_n$—$N(R_{1'})$$(C═O)_{m'}$—$(V)_{n'}$-Heterocycle group, an optionally substituted
—$X^{R3'}$-alkyl group; an optionally substituted
—$X^{R3'}$-Aryl group; an optionally substituted
—$X^{R3'}$— Heteroaryl group; an optionally substituted
—$X^{R3'}$— Heterocycle group; an optionally substituted;

where $R_{1N}$ and $R_{2N}$ are each independently H, $C_1$-$C_6$ alkyl which is optionally substituted with one or two hydroxyl groups and up to three halogen groups or an optionally substituted —$(CH_2)_n$-Aryl, —$(CH_2)_n$-Heteroaryl or —$(CH_2)_n$-Heterocycle group;

$R^1$ and $R_1$ are each independently H or a $C_1$-$C_3$ alkyl group;

V is O, S or $NR_1$;

$R_1$ is the same as above;

$R^1$ and $R_1$ are each independently H or a $C_1$-$C_3$ alkyl group;

$X^{R2'}$ and $X^{R3'}$ are each independently an optionally substituted —$CH_2)_n$—, —$CH_2)_n$—$CH(X_V)$=$CH(X_V)$— (cis or trans), —$CH_2)_n$—CH≡CH—, —$(CH_2CH_2O)_n$— or a $C_3$-$C_6$ cycloalkyl group, where X, is H, a halo or a $C_1$-$C_3$ alkyl group which is optionally substituted;

Each m is independently 0, 1, 2, 3, 4, 5, 6;

Each m' is independently 0 or 1;

Each n is independently 0, 1, 2, 3, 4, 5, 6;

Each n' is independently 0 or 1;

Each u is independently 0 or 1;

Each v is independently 0 or 1; and

Each w is independently 0 or 1.

59. The conjugate of embodiment 58, wherein the E3LB is a residue of a group having the structure:

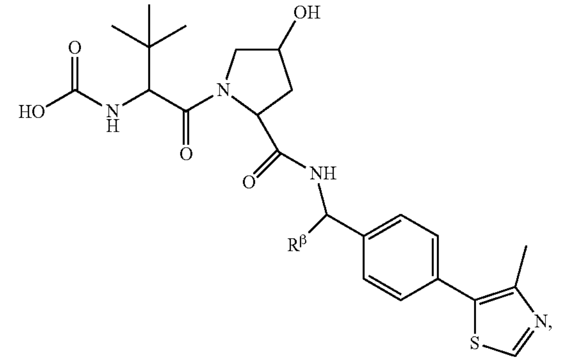

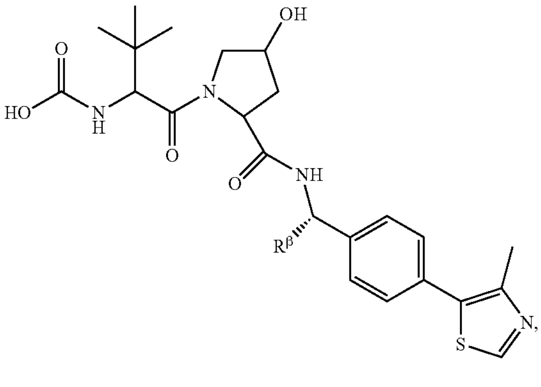

or

-continued

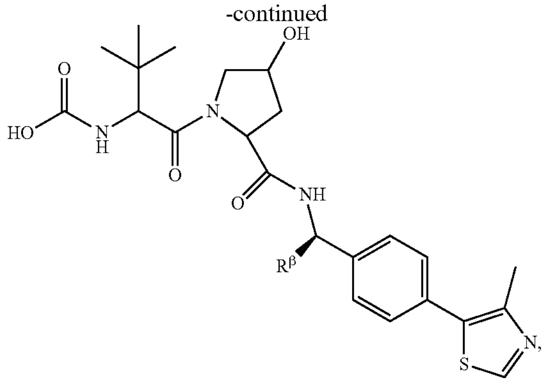

wherein, $R^\beta$ is hydrogen, methyl, ethyl or propyl.

60. The conjugate of embodiment 58, wherein E3LB is a residue of a group having the structure:

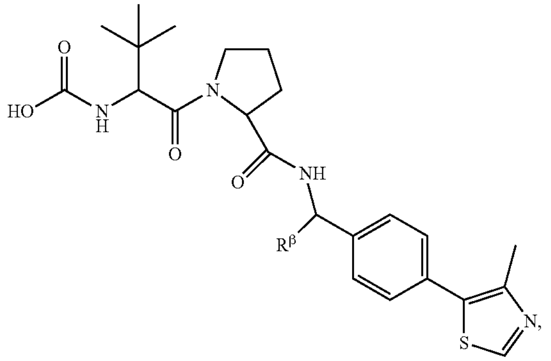

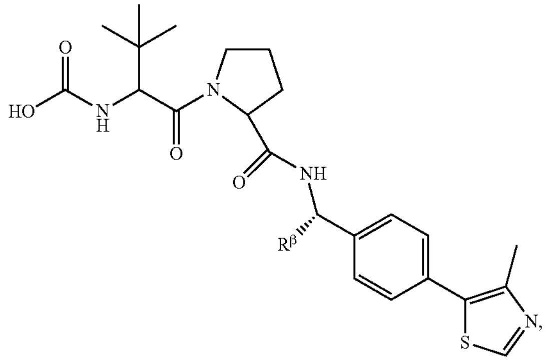

or

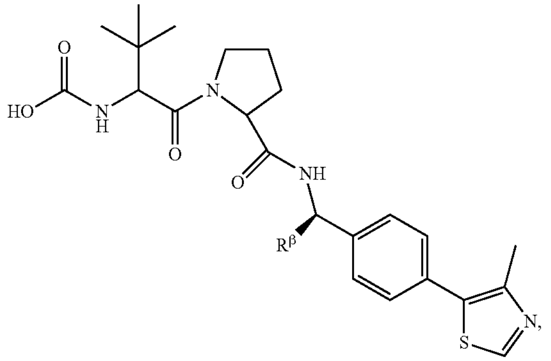

wherein, $R^\beta$ is hydrogen, methyl, ethyl or propyl.

61. The conjugate of embodiment 57, wherein the PB is a residue of a group that binds BRD4.

62. The conjugate of embodiment 61, wherein the PB is a residue of a group that binds BRD4 and has the structure:

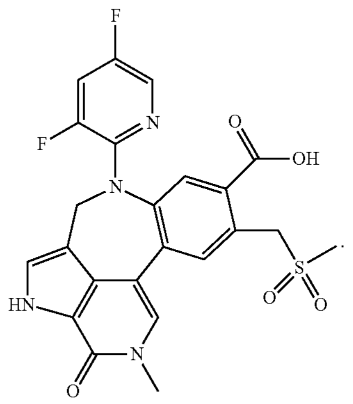 [SMILES: Cn1cc2c3c(c[nH]c3c1=O)CN(c1ncc(F)cc1F)c1cc(C(=O)O)c(CS(C)(=O)=O)cc1-2]

63. The conjugate of embodiment 57, wherein the PB is a residue of a group that binds ERα and is an anti-estrogen.

64. The conjugate of embodiment 63, wherein the PB is a residue of a group that binds ERα and is a compound of the following structure:

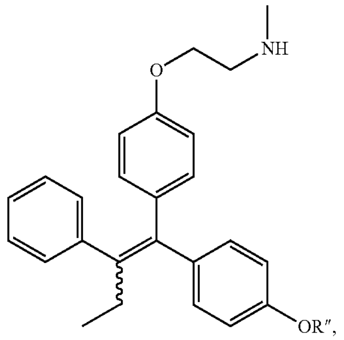

wherein, R" is hydrogen, $C_1$-$C_6$ alkyl, benzyl, phenyl, or —($PO_3H_2$).

65. The conjugate of embodiment 64, wherein the PB is a residue of a compound of the following structure:

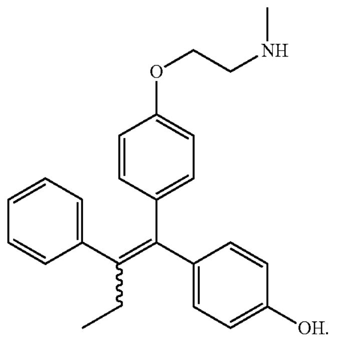 [SMILES: CCC(=C(c1ccc(O)cc1)c1ccc(OCCNC)cc1)c1ccccc1]

66. The conjugate of embodiment 57, wherein said Ab is a cysteine engineered antibody or variant thereof.

67. The conjugate of embodiment 57, wherein Ab binds to one or more of polypeptides selected from the group consisting of DLL3, EDAR, CLL1; BMPR1B; E16; STEAP1; 0772P; MPF; NaPi2b; Sema 5b; PSCA hlg; ETBR; MSG783; STEAP2; TrpM4; CRIPTO; CD21; CD79b; FcRH2; B7-H4; HER2; NCA; MDP; IL220Rα; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; MUC16 and CD33.

68. The conjugate of embodiment 66, wherein Ab binds to one or more of polypeptides selected from the group consisting of CLL1, STEAP1, NaPi2b, STEAP2, TrpM4, CRIPTO, CD21, CD79b, FcRH2, B7-H4, HER2, CD22, CD79a, CD72, LY64, Ly6E, MUC16, and CD33.

69. The conjugate of embodiment 68, wherein Ab is an antibody that binds to one or more polypeptides selected from the group consisting of HER2, B7-H4, and CD22.

70. The conjugate of embodiment 69, wherein the antibody binds to HER2.

71. The conjugate of embodiment 69, wherein the antibody binds to B7-H4 or CD22.

72. The conjugate of embodiment 1, wherein L1 is a peptidomimetic linker.

73. The conjugate of embodiment 72, wherein L1 is a peptidomimetic linker represented by the following formula:

Str-(PM)-Sp wherein,

Str is a stretcher unit covalently attached to Ab;

Ab is an antibody;

Sp is a bond or spacer unit covalently attached to a CIDE moiety;

PM is a non-peptide chemical moiety selected from the group consisting of:

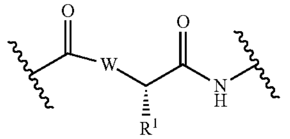

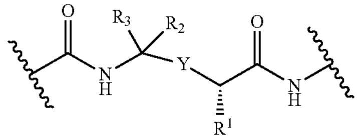 and

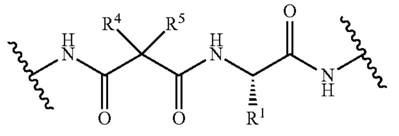

W is —NH-heterocycloalkyl- or heterocycloalkyl;

Y is heteroaryl, aryl, —C(O)$C_1$-$C_6$alkylene, $C_1$-$C_6$alkylene-$NH_2$, $C_1$-$C_6$alkylene-NH—$CH_3$, $C_1$-$C_6$alkylene-N—$(CH_3)_2$, $C_1$-$C_6$alkenyl or $C_1$-$C_6$alkylenyl;

each $R^1$ is independently $C_1$-$C_{10}$alkyl, $C_1$-$C_{10}$alkenyl, ($C_1$-$C_6$alkyl)NHC(NH)$NH_2$, ($C_1$-$C_6$alkyl)NHC(O)$NH_2$, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, $C_1$-$C_{10}$alkenyl, arylalkyl or heteroarylalkyl, or $R^3$ and $R^2$ together may form a $C_3$-$C_7$cycloalkyl; and $R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ together may form a $C_3$-$C_7$cycloalkyl ring.

74. The conjugate of embodiment 73, wherein

Str is a chemical moiety represented by the following formula:

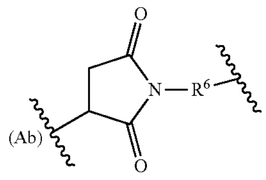

wherein $R^6$ is selected from the group consisting of $C_1$-$C_{10}$alkylene, $C_1$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, heteroarylalkyl, aryl arylalkyl, heteroarylalkyl and heteroaryl each $R^a$ is independently H or $C_1$-$C_6$alkyl; and Sp is —$C_1$-$C_6$alkylene-C(O)NH— or —Ar—$R^b$—, wherein Ar is aryl or heteroaryl, and $R^b$ is ($C_1$-$C_{10}$alkylene)O—.

75. The conjugate of embodiment 73, wherein Str has the formula:

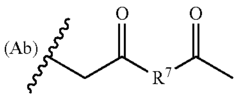

wherein $R^7$ is selected from $C_1$-$C_{10}$alkylene, $C_1$-$C_{10}$alkenyl, ($C_1$-$C_{10}$alkylene)O—, N($R^c$)—($C_2$-$C_6$ alkylene)-N($R^c$) and N($R^c$)—($C_2$-$C_6$alkylene); where each $R^c$ is independently H or $C_1$-$C_6$ alkyl; and Sp is —$C_1$-$C_6$alkylene-C(O)NH— or —Ar—$R^b$—, wherein Ar is aryl or heteroaryl, and $R^b$ is ($C_1$-$C_{10}$alkylene)O—.

76. The conjugate of embodiment 73, wherein L1 has the following formula:

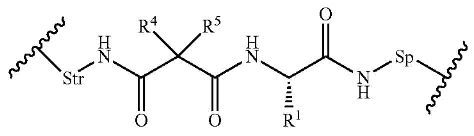

$R^1$ is $C_1$-$C_6$alkyl, ($C_1$-$C_6$alkyl)NHC(NH)$NH_2$ or ($C_1$-$C_6$alkyl)NHC(O)$NH_2$;

$R^4$ and $R^5$ together form a $C_3$-$C_7$cycloalkyl ring.

77. The conjugate of embodiment 57, having the formula:

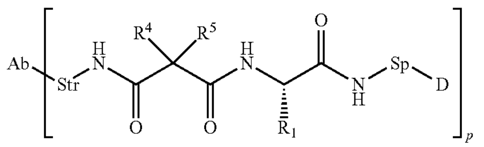

wherein

Sp is a bond or spacer unit covalently attached to CIDE moiety D;

$R^4$ and $R^5$ are each independently $C_1$-$C_{10}$alkyl, $C_1$-$C_{10}$alkenyl, arylalkyl, heteroarylalkyl, ($C_1$-$C_{10}$alkyl)$OCH_2$—, or $R^4$ and $R^5$ together may form a $C_3$-$C_7$cycloalkyl ring;

$R^1$ is independently $C_1$-$C_{10}$alkyl, $C_1$-$C_{10}$alkenyl, ($C_1$-$C_6$alkyl)NHC(NH)$NH_2$, ($C_1$-$C_6$alkyl)NHC(O)$NH_2$, ($C_1$-$C_{10}$alkyl)NHC(NH)$NH_2$ or ($C_1$-$C_{10}$alkyl)NHC(O)$NH_2$;

Str is a chemical moiety represented by the following formula:

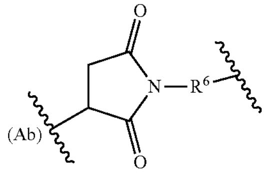

$R^6$ is selected from the group consisting of $C_1$-$C_{10}$alkylene, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio, $C_3$-$C_8$cycloalkyl, $C_4$-$C_7$heterocycloalkyl, aryl, arylalkyl, heteroarylalkyl and heteroaryl each $R^a$ is independently H or $C_1$-$C_6$alkyl;

p is 1, 2, 3 or 4.

78. The conjugate of embodiment 77, wherein $R^4$ and $R^5$ together may form a $C_3$-$C_7$cycloalkyl ring and $R^1$ is $C_1$-$C_{10}$alkyl or ($C_1$-$C_6$alkyl)NHC(O)$NH_2$.

79. The conjugate of embodiment 78, wherein $R^4$ and $R_5$ together form cyclobutyl.

80. The conjugate of embodiment 79, wherein the structure of the linker is selected from the group consisting of:

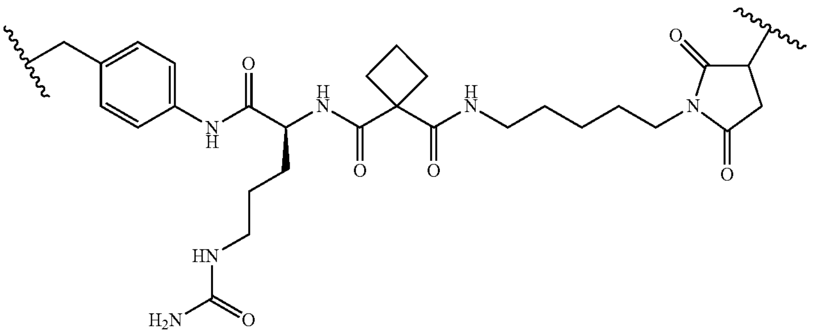

and

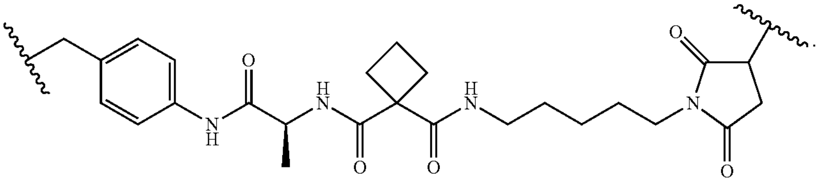

81. The conjugate of embodiment 77, wherein Str is a chemical moiety represented by the following formula:

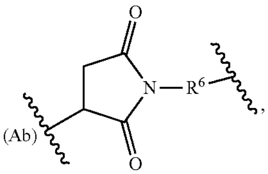

$R^6$ is $C_1$-$C_6$alkylene;

Sp is —$C_1$-$C_6$alkylene-C(O)NH— or —Ar—$R^b$—, where Ar is aryl, $R^b$ is ($C_1$-$C_3$alkylene)O—.

82. The conjugate of embodiment 57, having the formula:

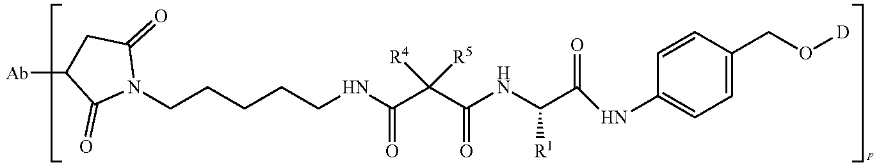

wherein p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$;

$R^4$ and $R^5$ are each independently $C_1$-$C_6$alkyl, wherein said alkyl are unsubstituted, or $R^4$ and $R^5$ may form a $C_3$-$C_7$cycloalkyl ring.

83. The conjugate of embodiment 57, wherein L1 has the following formula selected from the group consisting of:

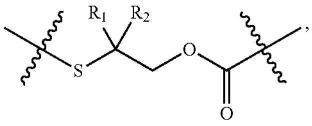

, and

-continued

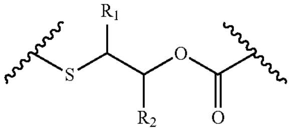

, wherein, $R^1$ and $R^2$ are independently selected from H and $C_1$-$C_6$ alkyl, or $R^1$ and $R^2$ form a 3, 4, 5, or 6-membered cycloalkyl or heterocyclyl group.

84. The conjugate of embodiment 83, wherein L1 has the following formula:

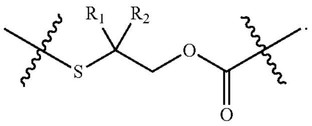

85. The conjugate of embodiment 57, wherein L1 has the following Formula:

$-A_a-W_w—Y_y—$ wherein A is a "stretcher unit", and a is an integer from 0 to 1; W is an "amino acid unit", and w is an integer from 0 to 12; Y is a "spacer unit", and y is 0, 1, or 2.

86. The conjugate of embodiment 85 wherein the stretcher unit A comprises the following formula:

MC

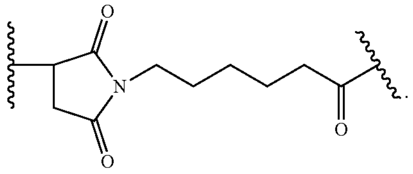

87. The conjugate of embodiment 86, wherein the linker has the following formula:

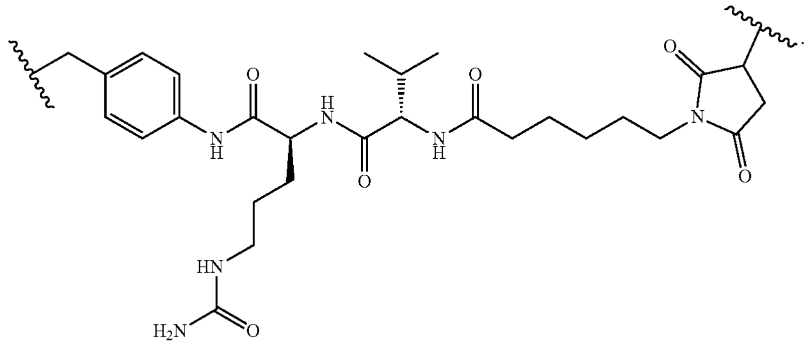 [SMILES: *Cc1ccc(NC(=O)[C@H](CCCNC(N)=O)NC(=O)[C@@H](NC(=O)CCCCCN2C(=O)CC(*)C2=O)C(C)C)cc1]

88. The conjugate of embodiment 57, wherein L1 has the following Formula:

$-A_a-Y_y—$ wherein A and Y are defined as above.

89. The conjugate of embodiment 88, wherein L1 is:

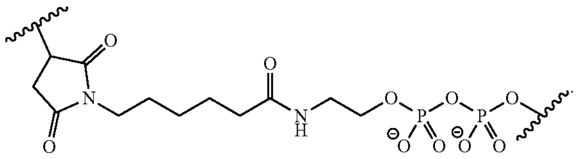 [SMILES: *OP(=O)([O-])OP(=O)([O-])OCCNC(=O)CCCCCN1C(=O)CC(*)C1=O]

90. The conjugate of embodiment 57, wherein p is from about 1.0 to about 3.

91. The conjugate of embodiment 57, wherein p is about 2.

92. The conjugate of embodiment 57, wherein D is a residue covalently linked to L1 and is selected from one of the following structures:

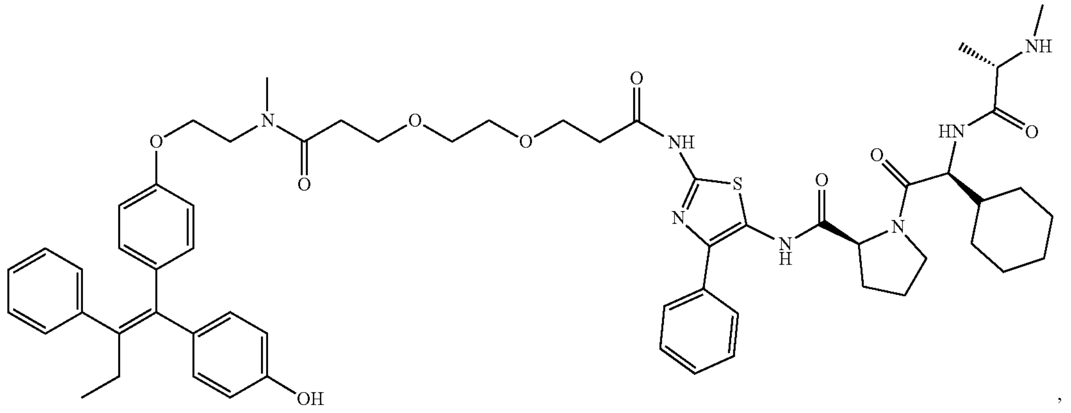

,

-continued
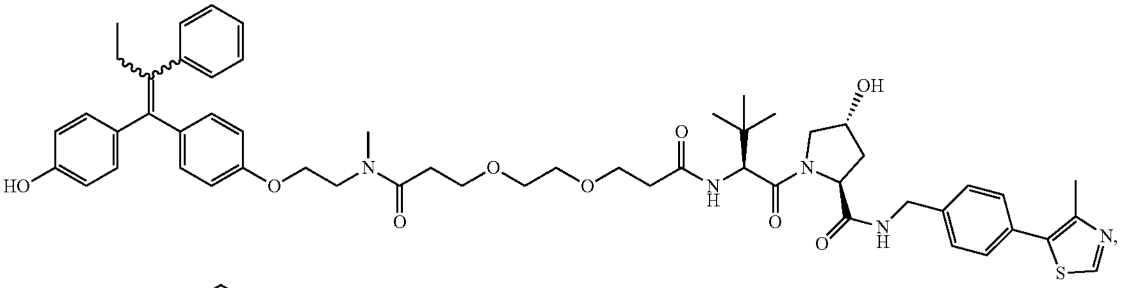
and
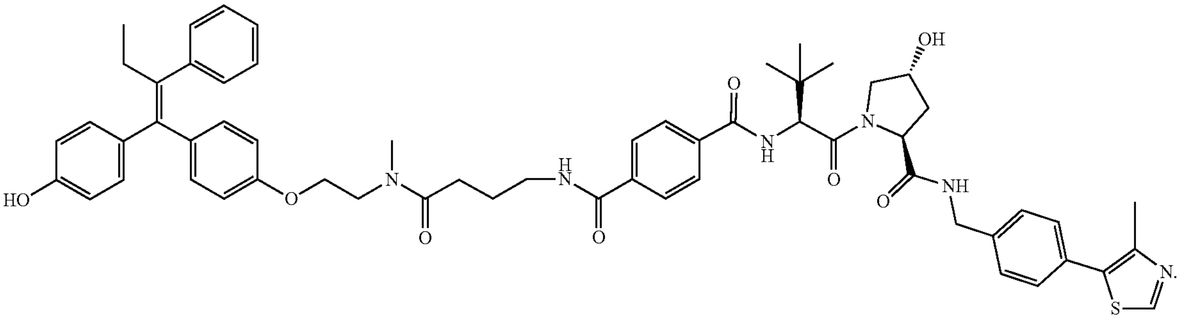
93. The conjugate of embodiment 57, wherein L1-D is a residue covalently linked to said Ab and is selected from one of the following structures:
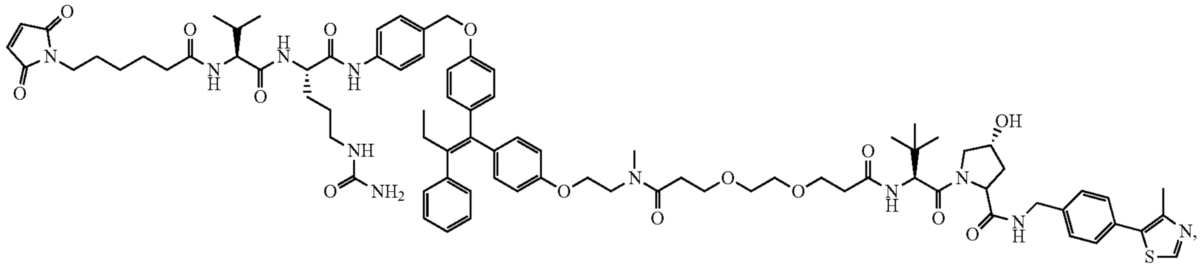
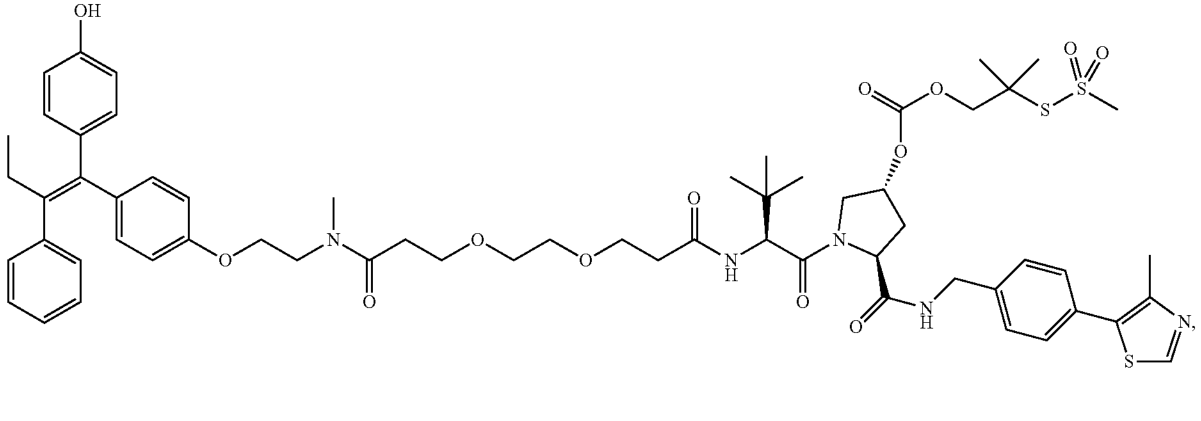

-continued
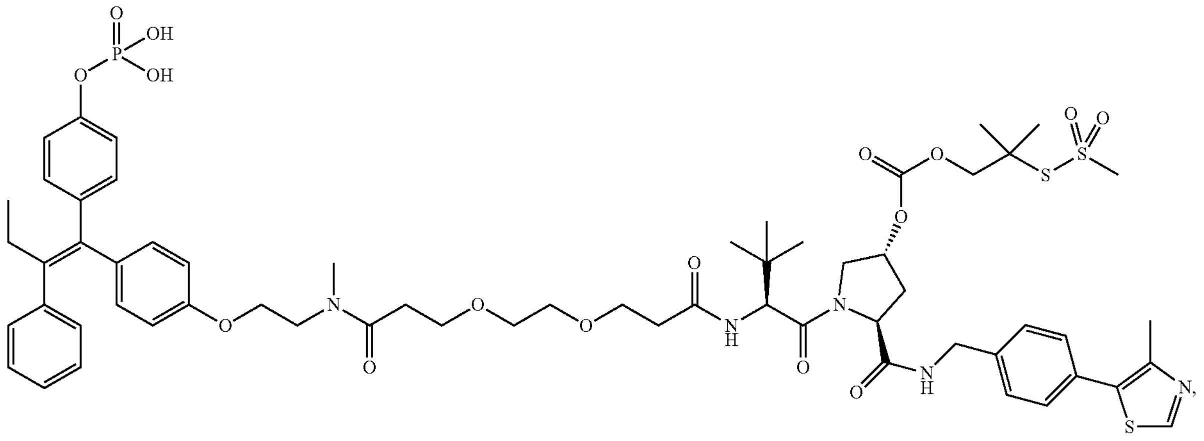
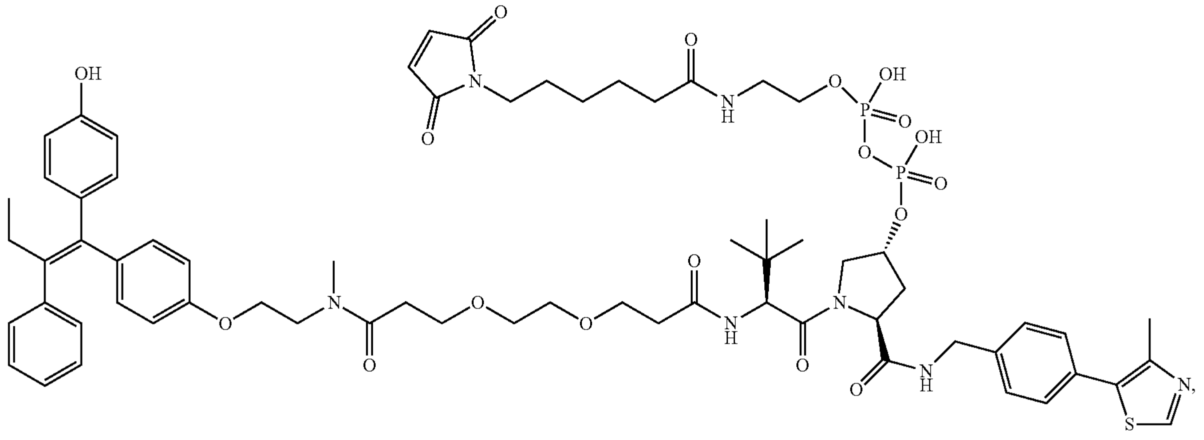
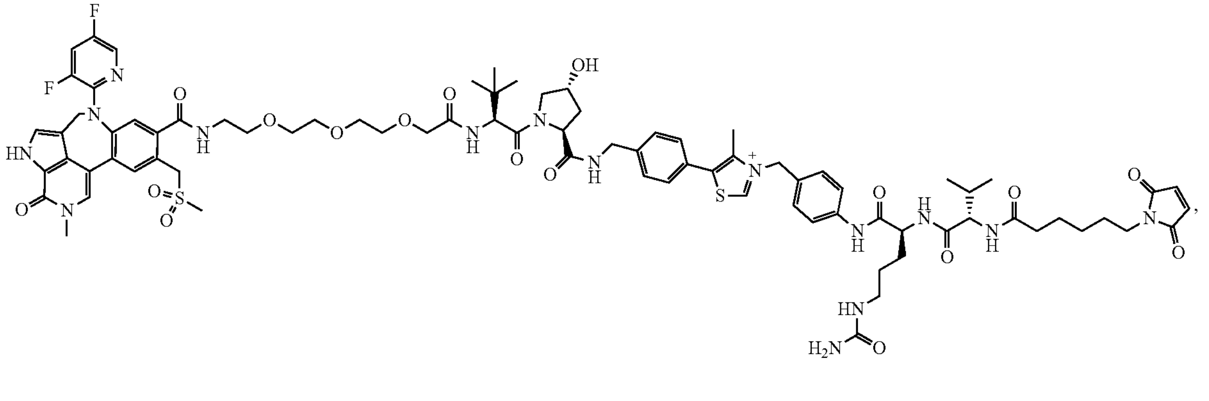

-continued
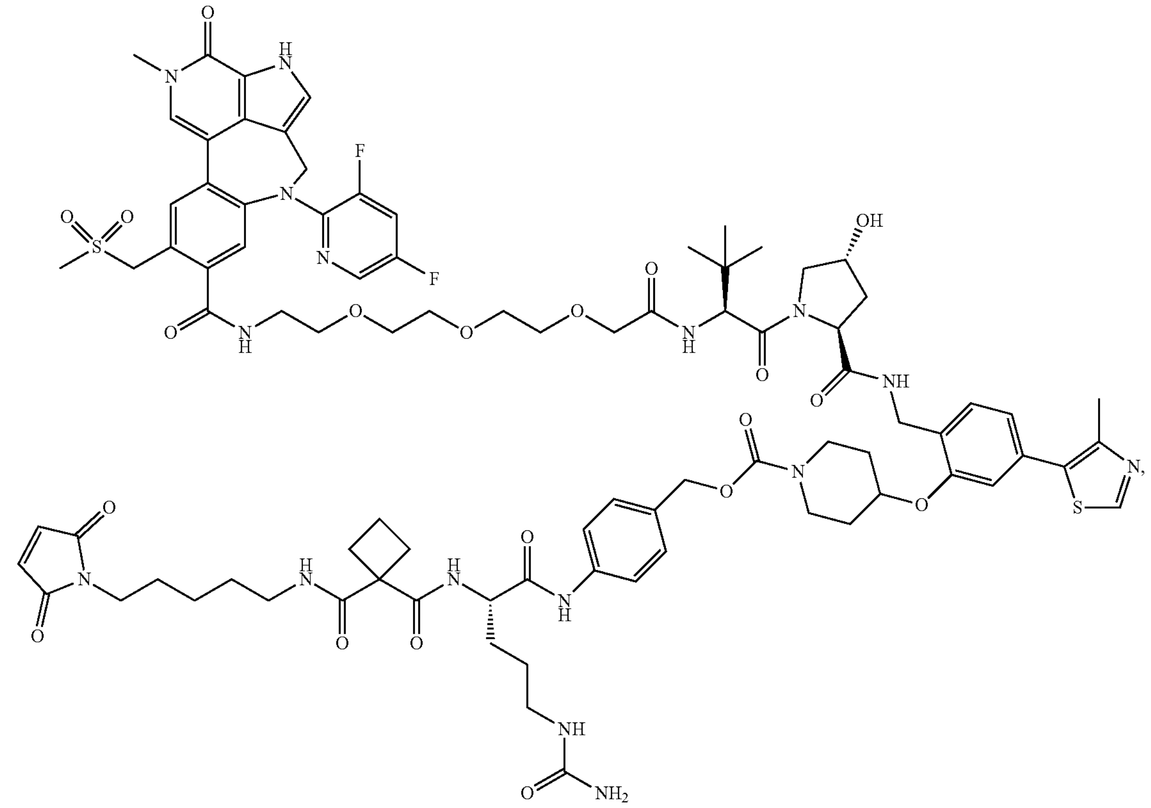
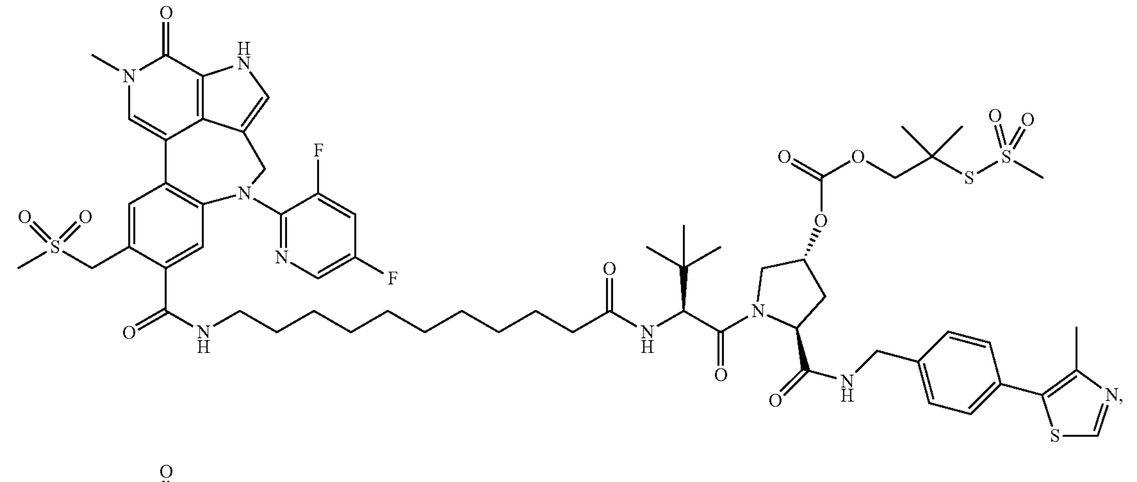
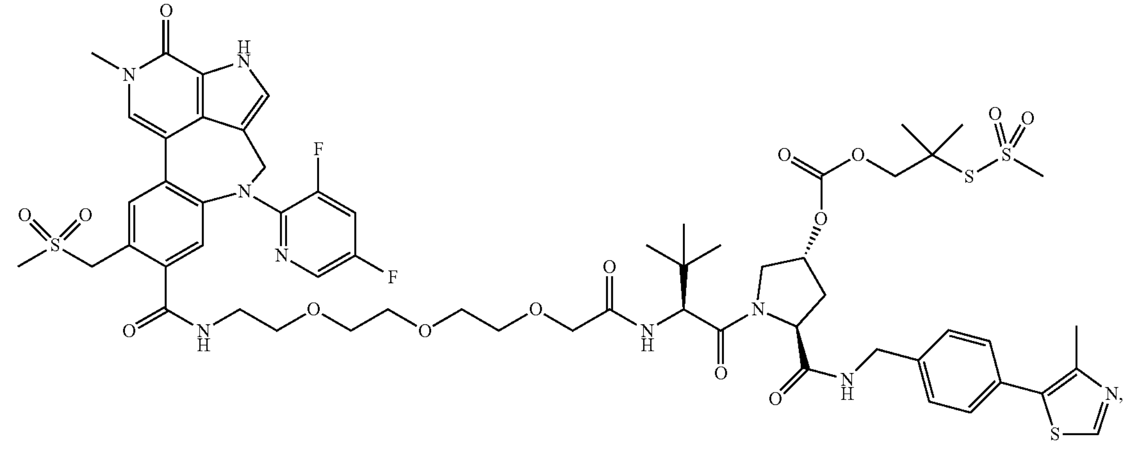

-continued
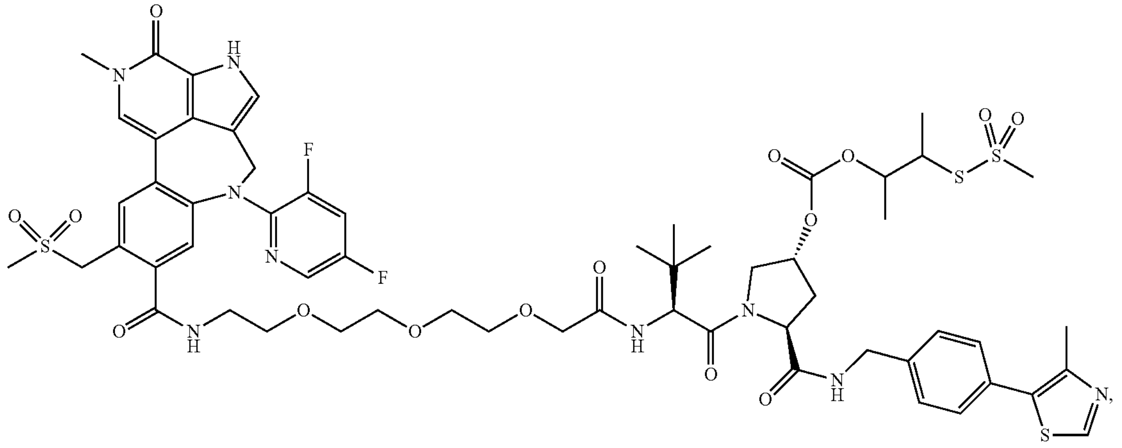
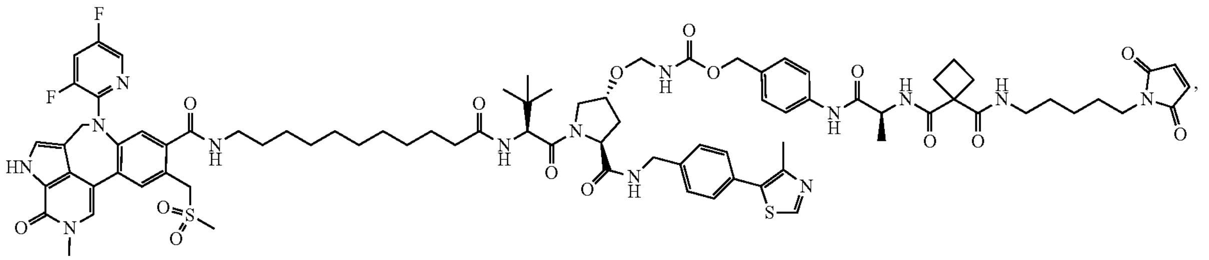
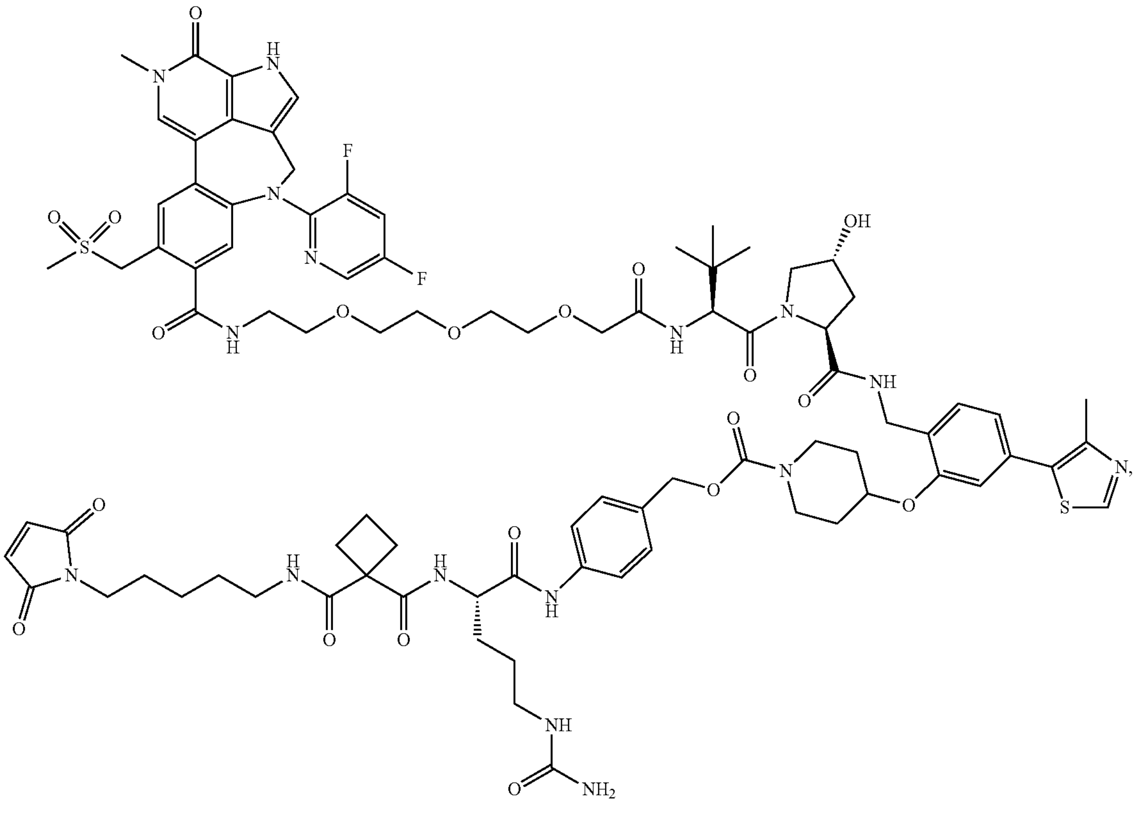

-continued
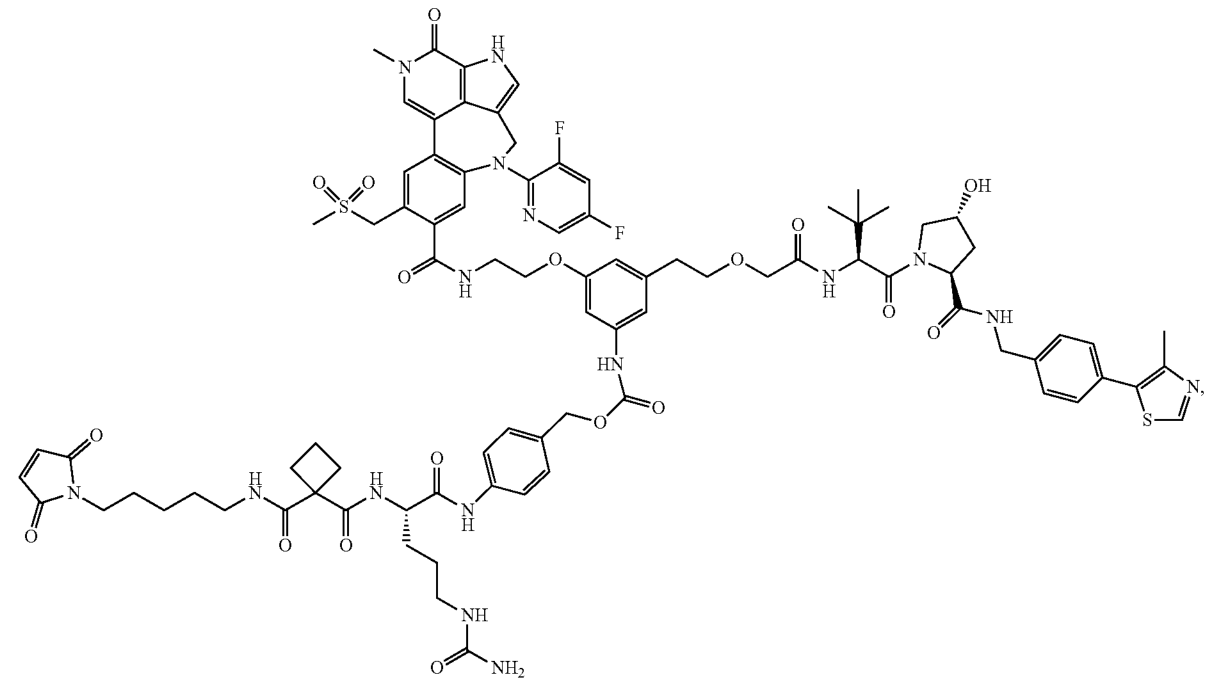
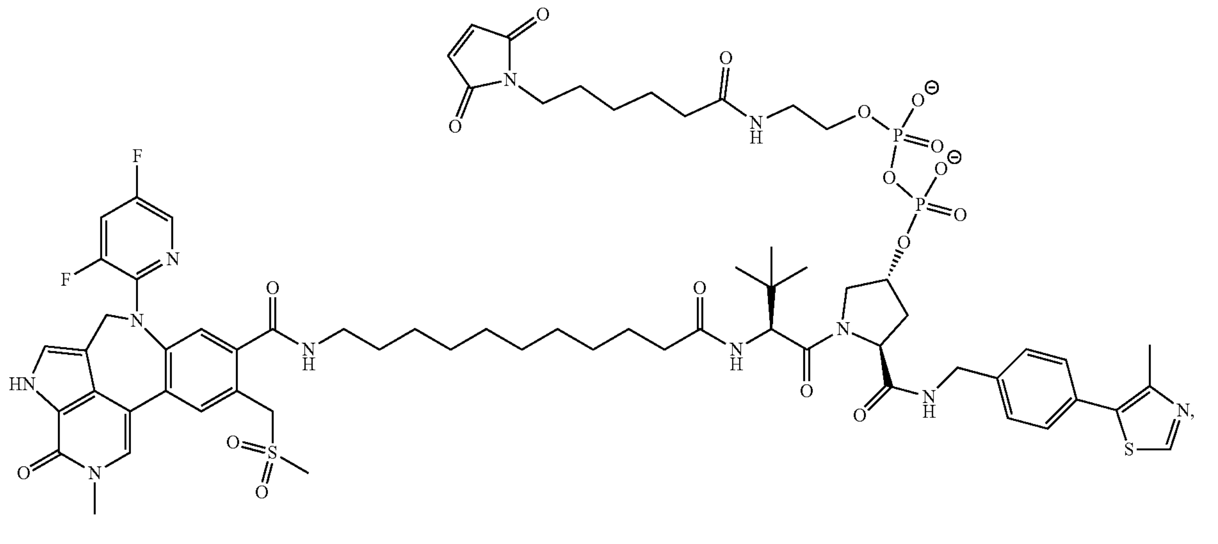

-continued
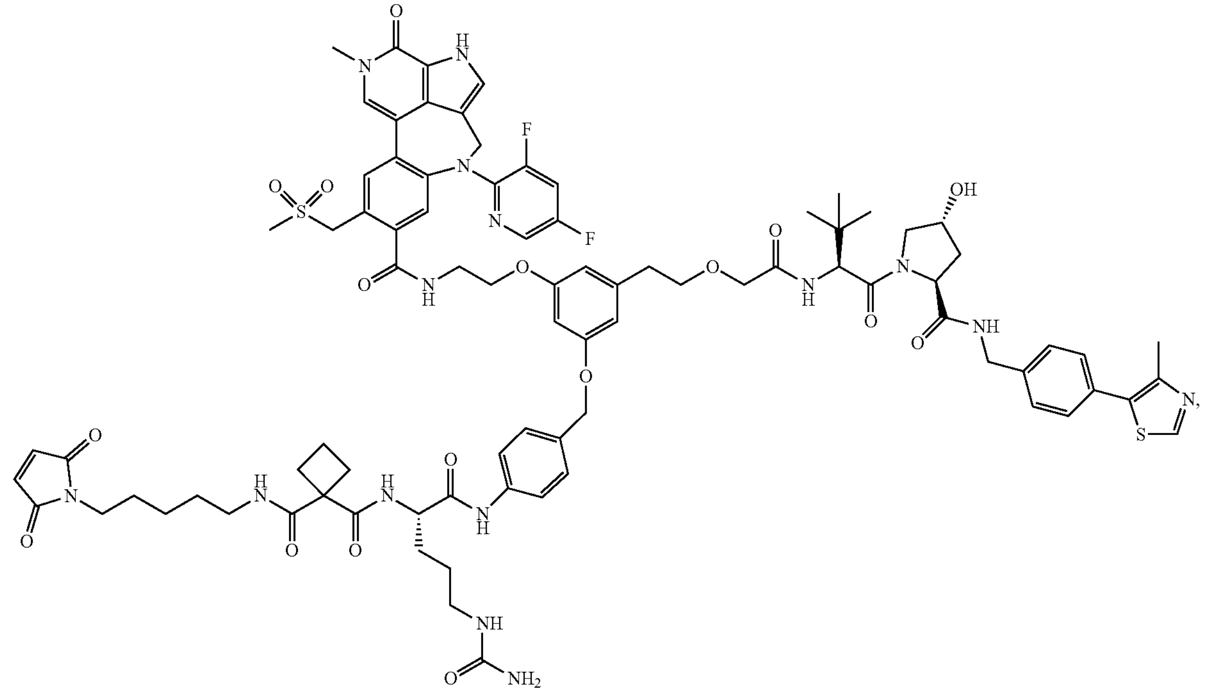
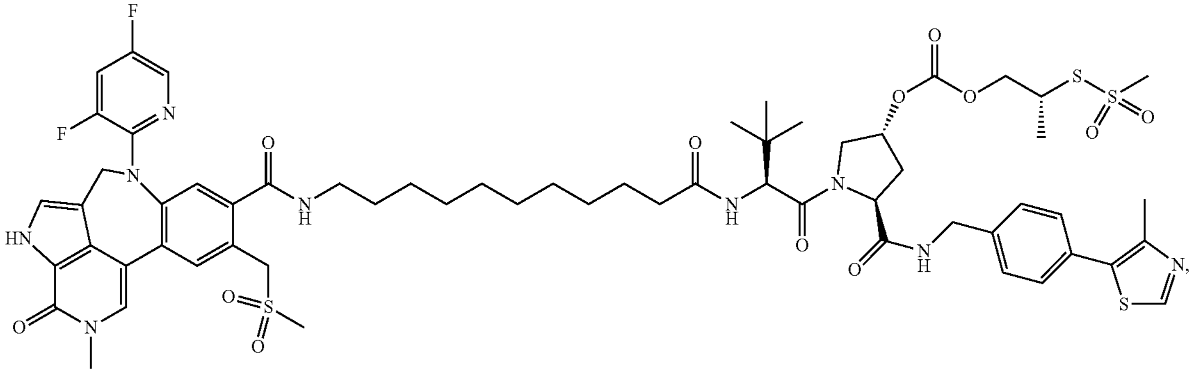
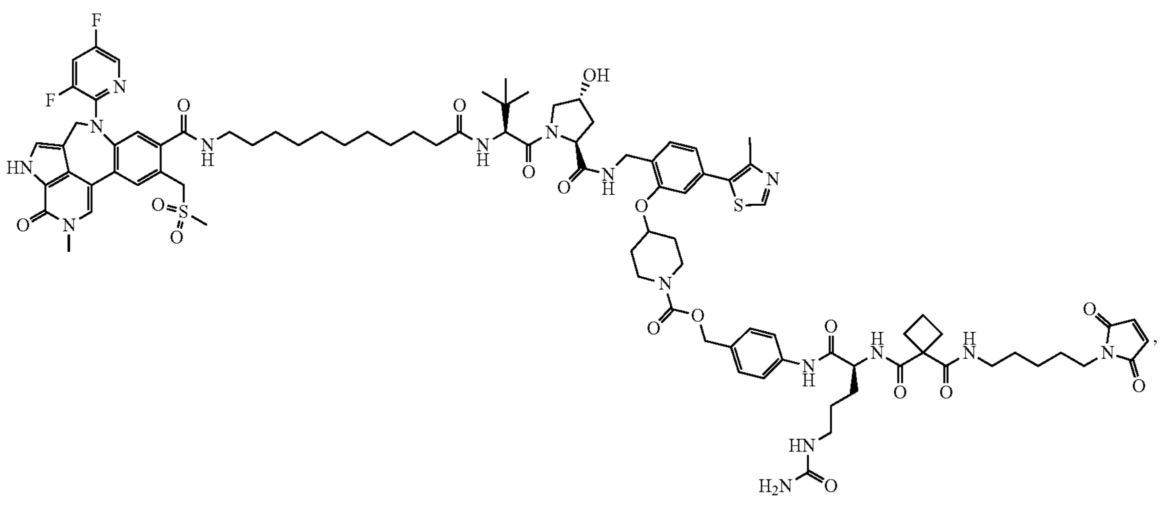
, and

-continued

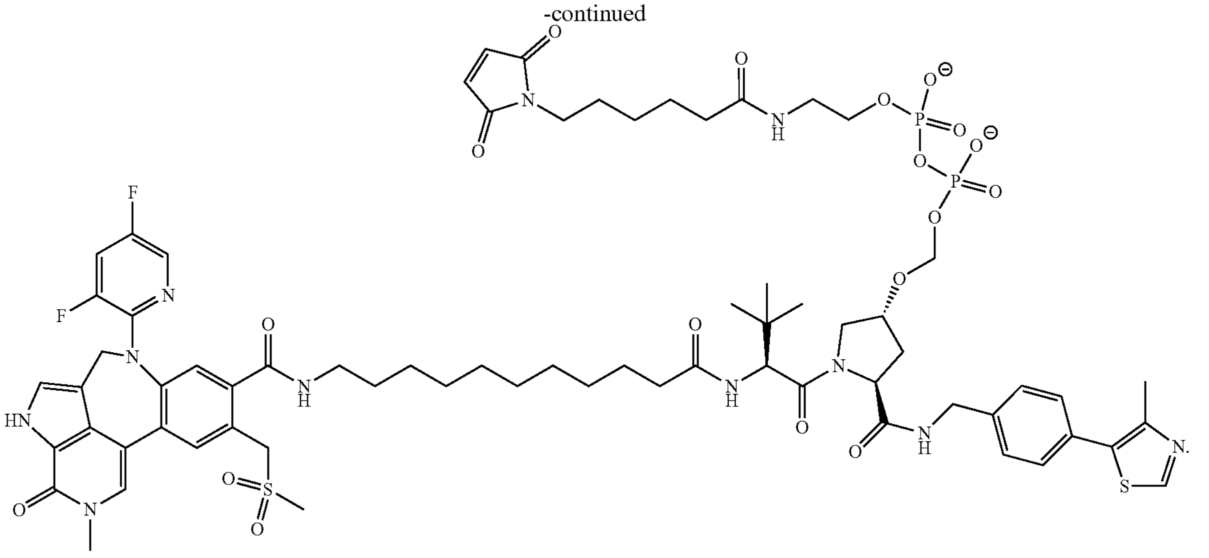

94. The conjugate of embodiment 93, wherein said Ab is an antibody that binds to one or more polypeptides selected from the group consisting of B7-H4, HER2, and CD22.

95. The conjugate of embodiment 61, wherein the PB is a residue of a group that binds BRD4 and has the structure:

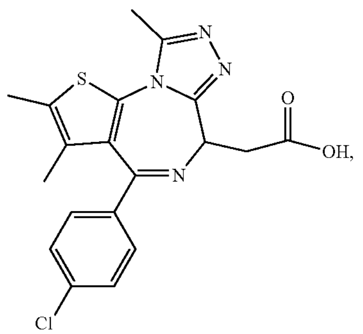

or

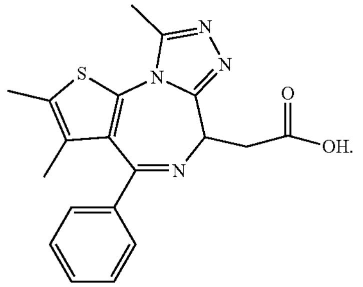

96. The conjugate of embodiment 95, wherein L1-D is a residue covalently linked to said Ab and is selected from one of the following: L1BQ1, L1BQ2, L1BQ3, L1BQ4, LIBQ5, L1BQ6, L1BQ7, L1BQ8, L1BQ9, LIBQ10, L1BQ11, L1BQ12, L1BQ13, L1BQ14, LIBQ15, L1BQ16, L1BQ17, L1BQ18, L1BQ19, LIBQ20, L1BQ21, and L1BQ22.

IV. Synthesis Routes

CIDEs, L1-CIDEs and Ab-CIDEs and other compounds described herein can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990). Starting materials are generally available from commercial sources such as Aldrich Chemicals (Milwaukee, WI) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie,* 4, Aufl. ed. Springer-Verlag, Berlin, including supplements (also available via the Beilstein online database).

Synthetic chemistry transformations and protecting group methodologies (protection and deprotection) useful in synthesizing the CIDEs, L1-CIDEs and Ab-CIDEs and other compounds as described herein and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3d Ed., John Wiley and Sons (1999); and L. Paquette, ed., Encyclopedia of Reagents for Organic Synthesis, John Wiley and Sons (1995) and subsequent editions thereof. In preparing CIDEs, L1-CIDEs and Ab-CIDEs and other compounds, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz or CBZ) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The General Procedures and Examples provide exemplary methods for preparing CIDEs, L1-CIDEs and Ab-CIDEs and other compounds described herein. Those skilled in the art will appreciate that other synthetic routes may be used to synthesize the PACs and compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Generally, an Ab-CIDE can be prepared by connecting a CIDE with a L1 linker reagent according to the procedures of WO 2013/055987; WO 2015/023355; WO 2010/009124; WO 2015/095227, to prepare a L1-CIDE, and conjugating the L1-CIDE with any of the antibodies or variants, mutations, splice variants, indels and fusions thereof, including cysteine engineered antibodies, described herein. Alternatively, an Ab-CIDE can be prepared by first connecting an antibody or variant, mutation, splice variant, indel and fusion thereof, including a cysteine engineered antibody, described herein with a L1 linker reagent, and conjugating it with any CIDE.

The following synthetic routes describe exemplary methods of preparing CIDEs, L1-CIDEs and Ab-CIDEs and other compounds and components thereof. Other synthetic routes for preparing CIDEs, L1-CIDEs and Ab-CIDEs and other compounds and components thereof are disclosed elsewhere herein.

1. Linker L1

With respect to Linker L1, Schemes 1-4 depict synthesis routes to exemplary linkers L1 for disulfide attachment to antibody Ab. The Ab is connected to L1 through a disulfide bond and the CIDE is connected to L1 through any available attachment on the CIDE.

Scheme 1

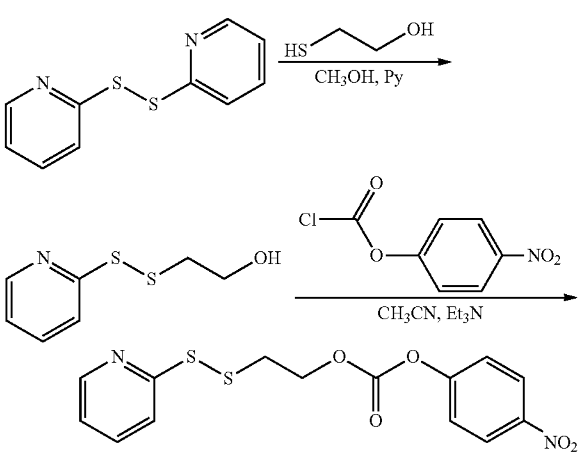

9

Referring to Scheme 1, 1,2-Di(pyridin-2-yl)disulfane and 2-mercaptoethanol were reacted in pyridine and methanol at room temperature to give 2-(pyridin-2-yldisulfanyl)ethanol. Acylation with 4-nitrophenyl carbonochloridate in triethylamine and acetonitrile gave 4-nitrophenyl 2-(pyridin-2-yldisulfanyl)ethyl carbonate 9.

Scheme 2

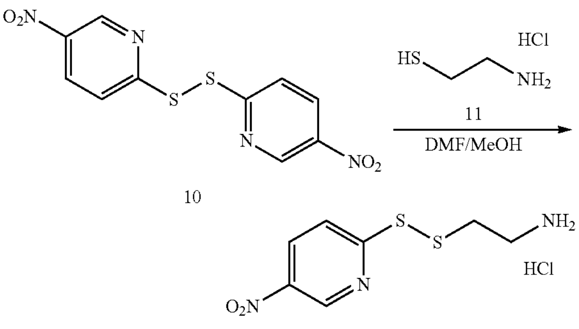

12

Referring to Scheme 2, to a mixture of 1,2-bis(5-nitropyridin-2-yl)disulfane 10 (1.0 g, 3.22 mmol) in anhydrous DMF/MeOH (25 mL/25 mL) was added HOAc (0.1 mL), followed by 2-aminoethanethiol hydrochloride 11 (183 mg, 1.61 mmol). After the reaction mixture was stirred at r.t. overnight, it was concentrated under vacuum to remove the solvent, and the residue was washed with DCM (30 mL×4) to afford 2-((5-nitropyridin-2-yl)disulfanyl)ethanamine hydrochloride 12 as pale yellow solid (300 mg, 69.6%). $^1H$ NMR (400 MHz, DMSO-$d_6$) δ 9.28 (d, J=2.4 Hz, 1H), 8.56 (dd, J=8.8, 2.4 Hz, 1H), 8.24 (s, 4H), 8.03 (d, J=8.8 Hz, 1H), 3.15-3.13 (m, 2H), 3.08-3.06 (m, 2H).

Scheme 3

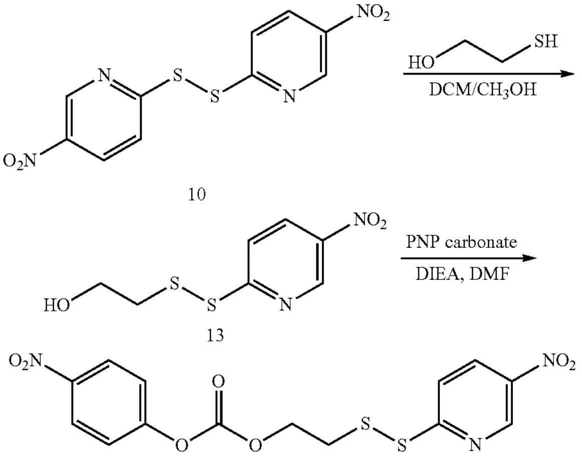

14

Referring to Scheme 3, a solution of 1,2-bis(5-nitropyridin-2-yl)disulfane 10 (9.6 g, 30.97 mmol) and 2-mercaptoethanol (1.21 g, 15.49 mmol) in anhydrous DCM/$CH_3OH$ (250 mL/250 mL) was stirred at r.t. under $N_2$ for 24 h. After the mixture was concentrated under vacuum, and the residue was diluted with DCM (300 mL). $MnO_2$ (10 g) was added and the mixture was stirred at r.t. for another 0.5 h. The mixture was purified by column chromatography on silica gel (DCM/MeOH=100/1 to 100/1) to afford 2-((5-nitropyridin-2-yl)disulfanyl)ethanol 13 (2.2 g, 61.1%) as brown oil.

$^1H$ NMR (400 MHz, $CDCl_3$) δ 9.33 (d, J=2.8 Hz, 1H), 8.38-8.35 (dd, J=9.2, 2.8 Hz, 1H), 7.67 (d, J=9.2 Hz, 1H), 4.10 (t, J=7.2 Hz, 1H), 3.81-3.76 (q, 2H), 3.01 (t, J=5.2 Hz, 2H).

To a solution of 13 (500 mg, 2.15 mmol) in anhydrous DMF (10 mL) was added DIEA (834 mg, 6.45 mmol), followed by PNP carbonate (bis(4-nitrophenyl) carbonate, 1.31 g, 4.31 mmol). The reaction solution was stirred at r.t for 4 h and the mixture was purified by prep-HPLC (FA) to afford 4-nitrophenyl 2-((5-nitropyridin-2-yl)disulfanyl)ethyl carbonate 14 (270 mg, 33.1%) as light brown oil. $^1H$ NMR (400 MHz, $CDCl_3$) δ 9.30 (d, J=2.4 Hz, 1H), 8.43-8.40 (dd, J=8.8, 2.4 Hz, 1H), 8.30-8.28 (m, 2H), 7.87 (d, J=8.8 Hz, 1H), 7.39-7.37 (m, 2H), 4.56 (t, J=6.4 Hz, 2H), 3.21 (t, J=6.4 Hz, 2H).

Scheme 4

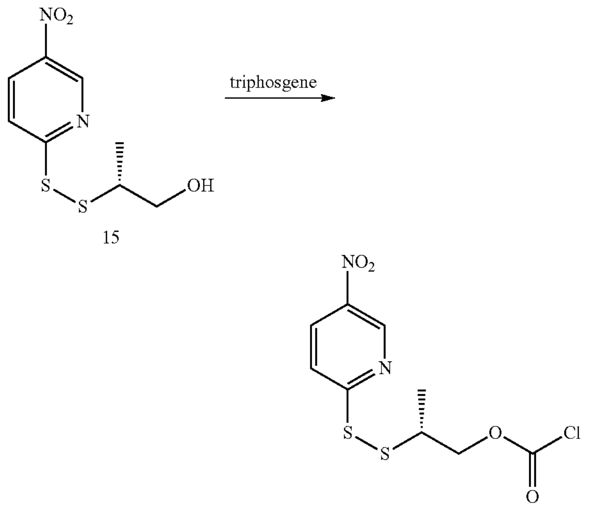

15

16

Referring to Scheme 4, sulfuryl chloride (2.35 mL of a 1.0 M solution in DCM, 2.35 mmol) was added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and was allowed to warm to room temperature then stirred for 2 hours after which time the solvent was removed by evaporation in vacuo to provide a yellow solid. The solid was re-dissolved in DCM (15 mL) and treated drop-wise with a solution of (R)-2-mercaptopropan-1-ol (213 mg, 2.31 mmol) in dry DCM (7.5 mL) at 0° C. under an argon atmosphere. The reaction mixture was allowed to warm to room temperature and stirred for 20 hours at which point analysis by LC/MS revealed substantial product formation at retention time 1.41 minutes (ES+) m/z 247 ($[M+H]^+$, ~100% relative intensity). The precipitate was removed by filtration and the filtrate evaporated in vacuo to give an orange solid which was treated with $H_2O$ (20 mL) and basified with ammonium hydroxide solution. The mixture was extracted with DCM (3×25 mL) and the combined extracts washed with $H_2O$ (20 mL), brine (20 mL), dried ($MgSO_4$), filtered and evaporated in vacuo to give the crude product. Purification by flash chromatography (gradient elution in 1% increments: 100% DCM to 98:2 v/v DCM/MeOH) gave (R)-2-((5-nitropyridin-2-yl)disulfanyl)propan-1-ol 15 as an oil (111 mg, 21% yield).

To a solution of triphosgene, $Cl_3COCOOCCl_3$, Sigma Aldrich, CAS Reg. No. 32315-10-9 (241 mg, 0.812 mmol) in DCM (10 mL) was added a solution of (R)-2-((5-nitropyridin-2-yl)disulfanyl)propan-1-ol 15 (500 mg, 2.03 mmol) and pyridine (153 mg, 1.93 mmol) in DCM (10 mL) dropwise at 20° C. After the reaction mixture was stirred at 20° C. for 30 min, it was concentrated and (R)-2-((5-nitropyridin-2-yl)disulfanyl)propyl carbonochloridate 16 can be used directly without further purification to covalently link through the carbonochloridate group any available group on the CIDE.

2. Cysteine Engineered Antibodies

With regard to cysteine engineered antibodies for conjugation by reduction and reoxidation, they can be prepared generally as follows. Light chain amino acids are numbered according to Kabat (Kabat et al., *Sequences of proteins of immunological interest*, (1991) 5th Ed., US Dept of Health and Human Service, National Institutes of Health, Bethesda, MD). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (THIOMAB™ antibodies) expressed in CHO cells bear cysteine adducts (cystines) or are glutathionylated on the engineered cysteines due to cell culture conditions. As is, THIOMAB™ antibodies purified from CHO cells cannot be conjugated to Cys-reactive linker L1-CIDE intermediates. Cysteine engineered antibodies may be made reactive for conjugation with L1-CIDE intermediates described herein, by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, MA) followed by re-formation of the interchain disulfide bonds (re-oxidation) with a mild oxidant such as dehydroascorbic acid. Full length, cysteine engineered monoclonal antibodies (THIOMAB™ antibodies) expressed in CHO cells (Gomez et al (2010) Biotechnology and Bioeng. 105(4):748-760; Gomez et al (2010) Biotechnol. Prog. 26:1438-1445) were reduced, for example, with about a 50 fold excess of DTT overnight in 50 mM Tris, pH 8.0 with 2 mM EDTA at room temperature, which removes Cys and glutathione adducts as well as reduces interchain disulfide bonds in the antibody. Removal of the adducts was monitored by reverse-phase LCMS using a PLRP-S column. The reduced THIOMAB™ antibody was diluted and acidified by addition to at least four volumes of 10 mM sodium succinate, pH 5 buffer.

Alternatively, the antibody was diluted and acidified by adding to at least four volumes of 10 mM succinate, pH 5 and titration with 10% acetic acid until pH was approximately five. The pH-lowered and diluted THIOMAB™ antibody was subsequently loaded onto a HiTrap S cation exchange column, washed with several column volumes of 10 mM sodium acetate, pH 5 and eluted with 50 mM Tris, pH 8.0, 150 mM sodium chloride. Disulfide bonds were reestablished between cysteine residues present in the parent Mab by carrying out reoxidation. The eluted reduced THIOMAB™ antibody described above is treated with 15× dehydroascorbic acid (DHAA) for about 3 hours or, alternatively, with 200 nM to 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. Reoxidation was monitored by reverse-phase LCMS using a PLRP-S column. The reoxidized THIOMAB™ antibody was diluted with succinate buffer as described above to reach pH approximately 5 and purification on an S column was carried out as described above with the exception that elution was performed with a gradient of 10 mM succinate, pH 5, 300 mM sodium chloride (buffer B) in 10 mM succinate, pH 5 (buffer A). To the eluted THIOMAB™ antibody, EDTA was added to a final concentration of 2 mM and concentrated, if necessary, to reach a final concentration of more than 5 mg/mL. The resulting THIOMAB™ antibody, ready for conjugation, was stored at −20° C. or −80° C. in aliquots. Liquid chromatography/Mass Spectrometric Analysis was performed on a 6200 series TOF or QTOF Agilent LC/MS. Samples were chromatographed on a PRLP-S®, 1000 A, microbore column (50 mm×2.1 mm, Polymer Laboratories, Shropshire, UK) heated to 80° C. A linear gradient from 30-40% B (solvent A: 0.05% TFA in water, solvent B: 0.04% TFA in acetonitrile) was used and the eluent was directly ionized using the electrospray source. Data were collected and deconvoluted by the MassHunter software (Agilent). Prior to LC/MS analysis, antibodies or conjugates (50 micrograms) were treated with PNGase F (2 units/ml; PROzyme, San Leandro, CA) for 2 hours at 37° C. to remove N-linked carbohydrates.

Alternatively, antibodies or conjugates were partially digested with LysC (0.25 μg per 50 μg (microgram) antibody or conjugate) for 15 minutes at 37° C. to give a Fab and Fc fragment for analysis by LCMS. Peaks in the deconvoluted LCMS spectra were assigned and quantitated. CIDE-to-antibody ratios (CAR) were calculated by calculating the ratio of intensities of the peak or peaks corresponding to CIDE-conjugated antibody relative to all peaks observed.

3. Conjugation of Linker L1-CIDE Group to Antibodies

In one method of conjugating Linker L1-CIDE compounds to antibodies, after the reduction and reoxidation procedures above, the cysteine-engineered antibody (THIOMAB™ antibody), in 10 mM succinate, pH 5, 150 mM NaCl, 2 mM EDTA, is pH-adjusted to pH 7.5-8.5 with 1M Tris. An excess, from about 3 molar to 20 equivalents of a linker-CIDE intermediate with a thiol-reactive group (e.g., maleimide or 4-nitropyridy disulfide), is dissolved in DMF, DMA or propylene glycol and added to the reduced, reoxidized, and pH-adjusted antibody. The reaction is incubated at room temperature or 37 C and monitored until completion (1 to about 24 hours), as determined by LC-MS analysis of the reaction mixture. When the reaction is complete, the conjugate is purified by one or any combination of several methods, the goal being to remove remaining unreacted L1-CIDE intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used. The THIOMAB™ antibody CIDE conjugates were formulated into 20 mM His/acetate, pH 5, with 240 mM sucrose using either gel filtration or dialysis. The purified conjugate is concentrated by centrifugal ultrafiltration and filtered through a 0.2-μm filter under sterile conditions and frozen for storage. The PACs were characterized by BCA assay to determine protein concentration, analytical SEC (size-exclusion chromatography) for aggregation analysis and LC-MS after treatment with Lysine C endopeptidase (LysC) to calculate CAR.

Size exclusion chromatography is performed on conjugates using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis may be performed on Ab-CIDE using an Agilent QTOF 6520 ESI instrument. As an example, the CAR is treated with 1:500 w/w Endoproteinase Lys C (Promega) in Tris, pH 7.5, for 30 min at 37° C. The resulting cleavage fragments are loaded onto a 1000 Å (Angstrom), 8 m (micron) PLRP-S (highly cross-linked polystyrene) column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

V. Formulations

Pharmaceutical formulations of therapeutic CIDE-antibody-conjugates (PACs) as described herein can be prepared for parenteral administration, e.g., bolus, intravenous, intratumor injection with a pharmaceutically acceptable parenteral vehicle and in a unit dosage injectable form. A PAC having the desired degree of purity is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

PACs can be formulated in accordance with standard pharmaceutical practice as a pharmaceutical composition. According to this aspect, there is provided a pharmaceutical composition comprising a PAC in association with one or more pharmaceutically acceptable excipients.

A typical formulation is prepared by mixing PACs with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the PAC is being applied. Solvents are generally selected based on solvents recognized by persons skilled in the art as safe (GRAS) to be administered to a mammal.

In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol;

alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

The formulations may also include one or more buffers, stabilizing agents, surfactants, wetting agents, lubricating agents, emulsifiers, suspending agents, preservatives, anti-oxidants, opaquing agents, glidants, processing aids, colorants, sweeteners, perfuming agents, flavoring agents and other known additives to provide an elegant presentation of the PAC or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The PAC formulations can be sterile. In particular, formulations to be used for in vivo administration must be sterile. Such sterilization is readily accomplished by filtration through sterile filtration membranes.

The PAC ordinarily can be stored as a solid composition, a lyophilized formulation or as an aqueous solution.

The pharmaceutical compositions comprising a PAC can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The PAC can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of PAC that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

VI. Indications and Methods of Treatment

It is contemplated that the CIDE-antibody conjugates (PAC) disclosed herein may be used to treat various diseases or disorders. Exemplary hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Also provided herein is a PAC or a composition comprising a PAC for use in therapy. In some embodiments, provided herein is a PAC or a composition comprising a PAC for the treatment or prevention of diseases and disorders as disclosed herein, such as a disease or disorder where it is desirable to degrade a target protein, for example cancer. Also provided herein is the use of a PAC or a composition comprising a PAC in therapy. In some embodiments, provided herein is the use of a PAC for the treatment or prevention of diseases and disorders as disclosed herein. Also provided herein is the use of a PAC or a composition comprising a PAC in the manufacture of a medicament for the treatment or prevention of diseases and disorders as disclosed herein.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the PAC may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

In certain embodiments, a PAC comprising an anti-NaPi2b antibody, such as those described above, is used in a method of treating solid tumor, e.g., ovarian.

In another embodiment, a PAC an anti-CD33 antibody, such as those described herein, is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See: U.S. Pat. No. 8,226,945; Li et al (2013) *Mol. Cancer. Ther.* 12(7):1255-1265; Polson et al (2010) *Leukemia* 24:1566-1573; Polson et al (2011) *Expert Opin. Investig. Drugs* 20(1):75-85.

In another embodiment, a PAC comprising an anti-MUC16 antibody, such as those described herein, is used in a method of treating ovarian, breast and pancreatic cancers. The cancer may be associated with the expression or activity of a MUC16/CA125/0772P polypeptide. See: WO 2007/001851; U.S. Pat. Nos. 7,989,595; 8,449,883; 7,723,485; Chen et al (2007) Cancer Res. 67(10): 4924-4932; Junutula, et al., (2008) *Nature Biotech.,* 26(8):925-932.

In certain embodiments, a PAC comprising an anti-iER2 antibody, such as those described above, is used in a method of treating cancer, e.g., breast or gastric cancer, more specifically HER2+ breast or gastric cancer, wherein the method comprises administering such PAC to a patient in need of such treatment. In one such embodiment, the PAC comprises the anti-HER2 antibody trastuzumab or pertuzumab.

A PAC may be administered by any route appropriate to the condition to be treated. The PAC will typically be administered parenterally, i.e. infusion, subcutaneous, intramuscular, intravenous, intradermal, intrathecal and epidural.

A PAC can be used either alone or in combination with other agents in a therapy. For instance, a PAC may be co-administered with at least one additional therapeutic agent. Such combination therapies noted above encompass combined administration (where two or more therapeutic agents are included in the same or separate formulations), and separate administration, in which case, administration of the PAC can occur prior to, simultaneously, and/or following, administration of the additional therapeutic agent and/or adjuvant. A PAC can also be used in combination with radiation therapy.

A PAC (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of disease, the appropriate dosage of a PAC (when used alone or in combination with one or more other additional therapeutic agents) will depend on the type of disease to be treated, the type of PAC, the severity and course of the disease, whether the PAC is administered for preventive or therapeutic purposes, previous therapy, the patient's clinical history and response to the PAC, and the discretion of the attending physician. The PAC is suitably administered to the patient at one time or over a series of treatments. Depending on the type and severity of the disease, about 1 μg/kg to 15 mg/kg (e.g. 0.1 mg/kg-10 mg/kg) of a PAC can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of a PAC would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses). An initial higher loading dose, followed by one or more lower doses may be administered. However, other dosage regimens may be useful. The progress of this therapy is easily monitored by conventional techniques and assays.

The methods described herein include methods of degrading target proteins. In certain embodiments, the methods comprise administering a PAC to a subject, wherein the target protein is degraded. The level of degradation of the protein can be from about 1% to about 5%; or from about 1% to about 10%; or from about 1% to about 15%; or from about 1% to about 20%; from about 1% to about 30%; or from about 1% to about 40%; from about 1% to about 50%; or from about 10% to about 20%; or from about 10% to about 30%; or from about 10% to about 40%; or from about 10% to about 50%; or at least about 1%; or at least about 10%; or at least about 20%; or at least about 30%; or at least about 40%; or at least about 50%; or at least about 60%; or at least about 70%; or at least about 80%; or at least about 90%; or at least about 95%; or at least about 99%.

The methods described herein include methods of reducing proliferation of a neoplastic tissue. In certain embodiments, the methods comprise administering a PAC to a subject, wherein the proliferation of a neoplastic tissue is reduced. The level of reduction can be from about 1% to about 5%; or from about 1% to about 10%; or from about 1% to about 15%; or from about 1% to about 20%; from about 1% to about 30%; or from about 1% to about 40%; from about 1% to about 50%; or from about 10% to about 20%; or from about 10% to about 30%; or from about 10% to about 40%; or from about 10% to about 50%; or at least about 1%; or at least about 10%; or at least about 20%; or at least about 30%; or at least about 40%; or at least about 50%; or at least about 60%; or at least about 70%; or at least about 80%; or at least about 90%; or at least about 95%; or at least about 99%.

VII. Articles of Manufacture

In another aspect, described herein are articles of manufacture, for example, a "kit," containing materials useful for the treatment of the diseases and disorders described above is provided. The kit comprises a container comprising a PAC. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In one embodiment, the vial is a single-use vial, e.g. a 20-cc single-use vial with a stopper. The container may be formed from a variety of materials such as glass or plastic. The container may hold a PAC or a formulation thereof which is effective for treating the condition and may have a sterile access port (for example, the container may be an intravenous solution bag or a vial having a stopper pierceable by a hypodermic injection needle).

At least one active agent in the composition is a PAC. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a PAC can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the PAC and, if present, the second pharmaceutical formulation. For example, if the kit comprises a first composition comprising a PAC, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a PAC, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a PAC contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a PAC and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Synthetic Methods

General methods for preparing a conjugate having the chemical structure Ab-(L1-D)$_p$ are described below.

1.1 General Synthetic Method for Coupling of L2 to E3LB to Prepare a E3LB-L2 Intermediate In certain embodiments, L2 is first contacted with a first suitable solvent, a first base and a first coupling reagent to prepare a first solution. In certain embodiments, the contacting of L2 with a first suitable solvent, a first base, and a first coupling reagent proceeds for about 15 minutes at room temperature (about 25° C.). The E3LB is then contacted with said first solution. In certain embodiments, the contacting of E3LB with the first solution proceeds for about one hour at room temperature (about 25° C.). The solution is then concentrated and optionally purified.

In certain embodiments, the molar ratio of L2 to first base to first coupling reagent is about 1:4:1.19. In certain embodiments, the molar ratio of L2 to first base to first coupling reagent is about 1:2:0.5, about 1:3:1, about 1:4:2, about 1:5:3, or about 1:6:4.

In certain embodiments, the molar ratio of L2 to E3LB is about 1:1. In certain embodiments, the molar ratio of L2 to E3LB is about 1:0.5, about 1:0.75, about 1:2, or about 0.5:1.

1.2 General Synthetic Method for Coupling E3LB-L2 Intermediate to PB to Prepare a CIDE In certain embodiments, the E3LB-L2 intermediate is coupled to a PB to prepare a CIDE. In certain embodiments, the PB is first contacted with a second suitable solvent, a second base, and second coupling reagent. In certain embodiments, the contacting proceeds for about 10 minutes at room temperature (about 25° C.). The solution is then contacted with the E3LB-L2 intermediate. In certain embodiments, the contacting of the second solution with the E3LB-L2 intermediate proceeds for about 1 hour at room temperature (about 25° C.). The solution is then concentrated and optionally purified to prepare a CIDE.

In certain embodiments, the molar ratio of PB to second base to second coupling reagent is about 1:4:1.2. In certain embodiments, the molar ratio of PB to second base to second coupling reagent is about 1:3:0.75, about 1:5:1, about 1:3:2, or about 1:5:3.

In certain embodiments, the molar ratio of PB to E3LB-L2 intermediate is about 1:1. In certain embodiments, the molar ratio of PB to E3LB-L2 intermediate is about 1:0.5, about 1:0.75, about 1:2, or about 0.5:1.

1.3 General Synthetic Method for Coupling CIDE to L1 to Prepare L1-CIDE

In certain embodiments, the CIDE is contacted with L1 and a third base in a third suitable solvent to prepare a solution. In certain embodiments, the contacting proceeds for about 2 hours at about (about 25° C.). The solution can then be optionally purified to prepare L1-CIDE.

In certain embodiments, the molar ratio of CIDE to L1 is about 1:4. In certain embodiments, the molar ratio of CIDE to L1 is about 1:1, 1:2, 1:3, 1:5, 1:6, 1:7, or about 1:8.

1.4 General Synthetic Method for Coupling L1-CIDE to Antibody

In certain embodiments, the L1-CIDE is contacted with a thiol and a fourth suitable solvent to form a fourth solution. This solution is then contacted with an antibody to prepare the conjugate. In certain embodiments, the In certain embodiments, the thiol is maleimide or 4-nitropyridy disulfide. In certain embodiments, the suitable solvent is selected from the group consisting of dimethylformamide, dimethylacetamide, and propylene glycol.

In certain embodiments, the molar ratio of L1-CIDE to thiol-reactive group is about 3:1 to about 20:1.

In certain embodiments, contacting the solution comprising the L1-CIDE, the thiol-reactive group and the suitable solvent with the antibody proceeds for about 1 to about 24 hours. In certain embodiments, contacting the solution comprising the L1-CIDE, the thiol-reactive group and the suitable solvent with the antibody proceeds at about room temperature (about 25° C.) to about 37° C.

In certain embodiments of the general methods above, the suitable solvent is a polar aprotic solvent, selected from the group consisting of dimethylformamide, tetrahydrofuran, ethyl acetate, acetone, acetonitrile, dimethyl sulfoxide, and propylene carbonate.

In certain embodiments of the general methods above, the base is selected from the group consisting of N,N-Diisopropylethylamine (DIEA), triethylamine, and 2,2,2,6,6-tetramethylpiperidine. In certain embodiments, the coupling reagent is selected from the group consisting of 1-[Bis(dimethylamino)methylene]-1H-1,2,3-triazolo[4,5-b]pyridinium 3-oxide hexafluorophosphate (HATU), (Benzotriazol-1-yloxy)tris(dimethylamino)phosphonium hexafluorophosphate (BOP), (7-Azabenzotriazol-1-yloxy) tripyrrolidinophosphonium hexafluorophosphate (PyAOP), O—(Benzotriazol-1-yl)-N,N,N',N'-tetramethyluronium hexafluorophosphate (HBTU), O—(Benzotriazol-1-yl)-N,N,N',N'-tetramethyluronium tetrafluoroborate (TBTU), O—(6-Chlorobenzotriazol-1-yl)-N,N,N',N'-tetramethyluronium hexafluorophosphate (HCTU), O—(N-Suc-cinimidyl)-1,1,3,3-tetramethyl-uronium tetrafluoroborate (TSTU), O—(5-Norbornene-2,3-dicarboximido)-N,N,N',N'-tetramethyluronium tetrafluoroborate (TNTU), 0-(1,2-Dihydro-2-oxo-1-pyridyl-N,N,N',N'-tetramethyluronium tetrafluoroborate (TPTU), and Carbonyldiimidazole (CDI).

In a preferred embodiment, the solvent is dimethylformamide, the base is N,N-Diisopropylethylamine, and the coupling reagent is HATU.

In certain embodiments of the general methods above, contacting proceeds for about 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 60 minutes, 90 minutes, 120 minutes, 180 minutes, 4 hours, 5 hours, 6 hours, 7 hours, 8 hours, 9 hours, 10 hours, 20 hours, 40 hours, 60 hours, or 72 hours.

In certain embodiments of the general methods above, contacting proceeds at about 20° C., 21° C., 22° C., 23° C., 24° C., 25° C., 26° C., 27° C., 28° C., 29° C., 30° C., 31°

C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 60° C., 70° C., 80° C., 90° C., or 100° C.

The following examples are offered by way of illustration and not by way of limitation.

EXAMPLES

Example 1

Syntheses of a CIDE

A. General Chemical Synthesis of a CIDE:

i. Attachment of a Linker (L2) to an E3 Ligase Binding Group (E3LB)

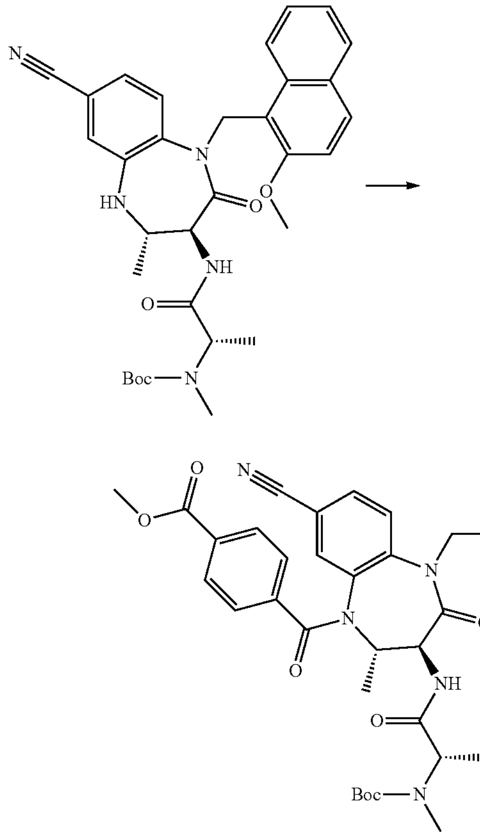

Methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate To a solution of tert-butyl N-[(1S)-1-[[(3S,4S)-7-cyano-1-[(2-methoxynaphthalen-1-yl)methyl]-4-methyl-2-oxo-2,3,4,5-tetrahydro-1H-1,5-benzodiazepin-3-yl]carbamoyl]ethyl]-N-methylcarbamate (3.00 g, 5.25 mmol) in 1,2-dichloroethane (50 mL) was added triethylamine (2.6 g, 25.7 mmol) and methyl 4-(carbonochloridoyl)benzoate (3.10 g, 15.61 mmol) under nitrogen. The resulting solution was stirred for 5 h at 80° C. and allowed to cool to room temperature. Water (100 mL) was added. The resulting solution was extracted with 3x100 mL of dichloromethane and the organic layers combined and dried over anhydrous sodium sulfate and concentrated under vacuum. The residue was purified by flash chromatography on silica gel eluting with ethyl acetate/petroleum ether (1:1). This resulted in 3.10 g (81%) of methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate as a brown solid. MS (ESI): $[M+H]^+=734.4$.

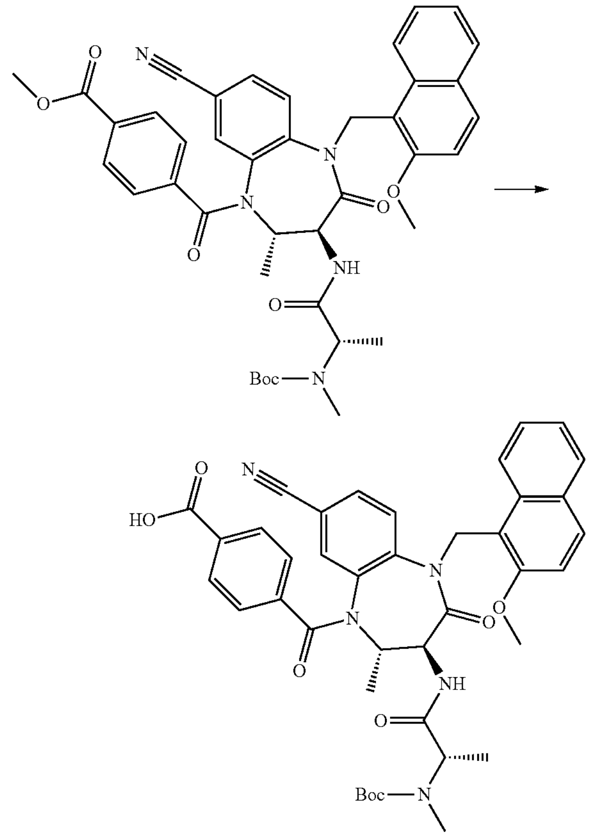

4-[[(2S,3S)-3-[(2S)-2-[[(Tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid Aqueous LiOH solution (30 mL, 1 M) was added to a solution of methyl 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoate (3.10 g, 4.22 mmol) in tetrahydrofuran (30 mL) at room temperature. The resulting solution was stirred for 5 h at room temperature. Ethyl ether (20 mL) was added. Phases were separated. The aqueous phase was acidified with 1 N HCl solution until pH about 7. The resulting mixture was extracted with 2x80 mL of ethyl acetate and the organic layers were combined and dried over anhydrous sodium sulfate and concentrated under vacuum. This resulted in 2.5 g of 4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid as a brown solid. MS (ESI): $[M+H]^+$=720.5.

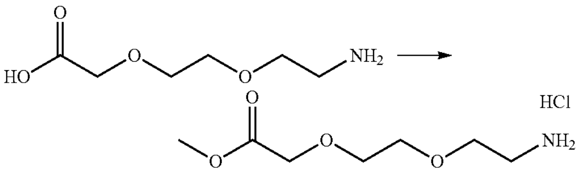

Methyl 2-(2-(2-aminoethoxy)ethoxy)acetate hydrochloride

To a solution of 2-[2-(2-aminoethoxy)ethoxy]acetic acid hydrochloride (500 mg, 2.505 mmol) in 2,2-dimethoxypropane (5 mL, 40.327 mmol) was added dropwise concentrated HCl (0.2 mL) at room temperature. The reaction mixture was stirred for 15 h at 25° C. and concentrated under vacuum. The residue was used directly without further purification.

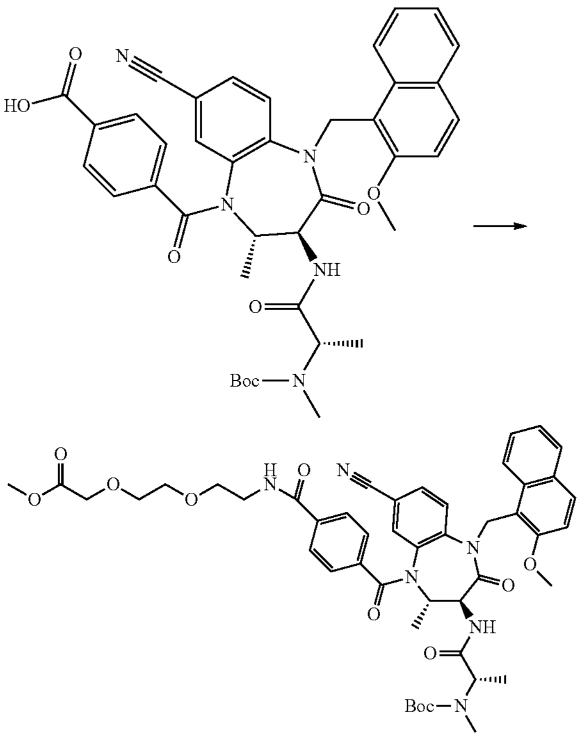

Methyl 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate To a solution of [(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]benzoic acid (500 mg, 0.695 mmol) in N,N-dimethylformamide (6 mL) was added crude methyl 2-[2-(2-aminoethoxy)ethoxy] acetate HCl salt from the previous step (500 mg), HATU (528 mg, 1.389 mmol) and DIPEA (897 mg, 6.94 mmol) under nitrogen at room temperature. The resulting solution was stirred for 1 hour at 25° C., and quenched with water. The resulting solution was extracted with dichloromethane and the organic layers combined. The organic phases were washed with brine and dried over anhydrous sodium sulfate and concentrated under vacuum. The residue was purified by flash chromatography on silica gel eluting with dichloromethane/methanol (20:1). This resulted in 550 mg (90%) of methyl 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate as a yellow solid. MS (ESI): $[M+H]^+$=879.5.

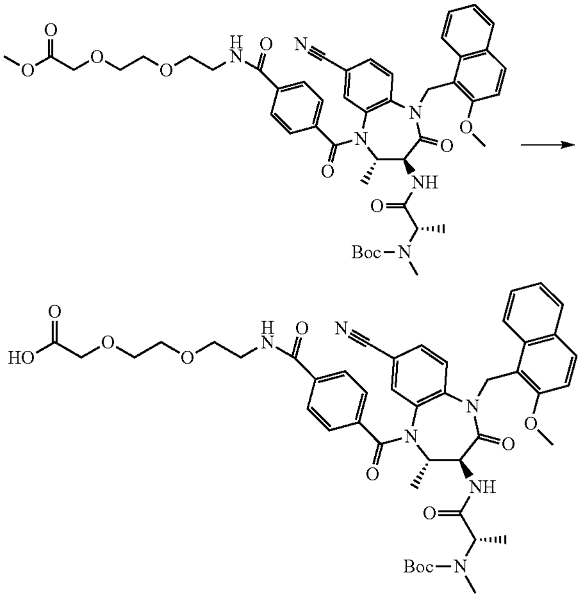

2-(2-[2-[(4-[[(2S,3S)-3-[(2S)-2-[[(Tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetic acid To a solution of methyl 2-(2-[2-[(4-[[(2S,3S)-3-[(2S)-2-[[(tert-butoxy)carbonyl](methyl)amino]propanamido]-8-cyano-5-[(2-methoxynaphthalen-1-yl)methyl]-2-methyl-4-oxo-2,3,4,5-tetrahydro-1H-1,5-benzodiazepin-1-yl]carbonyl]phenyl)formamido]ethoxy]ethoxy)acetate (500 mg, 0.569 mmol) in tetrahydrofuran (8 mL) was added a solution of lithium hydroxide monohydrate (95 mg, 2.26 mmol) in water (1 mL) at room temperature. The mixture was stirred for 1 hour at 25° C. The mixture was diluted with water and acidified with 1 N citric acid to pH about 4, extracted with ethyl acetate (2×). The organic phases were combined and washed with brine, dried over sodium sulfate, and concentrated under reduced pressure. The residue was purified by reverse phase flash chromatography on C18 silica gel, mobile phase: 5 mM aqueous $NH_4HCO_3$ and $CH_3CN$ (0-95%) to afford 370 mg (75%) of 2-(2-[2-[(4-[[(2S,3S)-3-[(2S)-2-[[(tert-butoxy)carbonyl](methyl)amino] propanamido]-8-cyano-5-[(2-methoxynaphthalen-1-yl) methyl]-2-methyl-4-oxo-2,3,4,5-tetrahydro-1H-1,5-benzodiazepin-1-yl]carbonyl]phenyl)formamido]ethoxy] ethoxy)acetic acid as a white solid. MS (ESI): $[M+H]^+$=865.5. $^1H$ NMR (400 MHz, DMSO-$d_6$): δ (ppm) 8.70 (d, J=8.6 Hz, 1H), 8.46 (t, J=5.5 Hz, 1H), 8.21 (d, J=8.7 Hz, 1H), 8.10 (d, J=8.6 Hz, 1H), 7.95 (d, J=9.1 Hz, 1H), 7.89 (dd, J=8.6, 1.9 Hz, 1H), 7.69 (d, J=8.1 Hz, 1H), 7.50 (d, J=9.2 Hz, 1H), 7.30 (m, 1H), 7.18 (d, J=1.9 Hz, 1H), 7.13 (t, J=7.5 Hz, 1H), 7.00 (d, J=8.1 Hz, 2H), 6.13 (d, J=15.1 Hz, 1H), 5.78 (d, J=8.0 Hz, 2H), 5.51 (d, J=15.0 Hz, 1H), 5.04 (brs, 1H), 4.61-4.52 (m, 1H), 4.22 (dd, J=11.9, 8.5 Hz, 1H), 3.99 (s, 2H), 3.96 (s, 3H), 3.68-3.44 (m, 7H), 3.37 (s, 1H), 2.76 (s, 3H), 1.40-1.31 (m, 12H), 1.12 (d, J=6.1 Hz, 3H).

ii. Attachment of a PB to an E3LB Via a Linker (L2)

4-((2S,3S)-8-Cyano-5-((2-methoxynaphthalen-1-yl) methyl)-2-methyl-3-((S)-2-(methylamino)propanamido)-4-oxo-2,3,4,5-tetrahydro-1H-benzo[b][1,4] diazepine-1-carbonyl)-N-(2-(2-(2-((2-(4-(1-(4-hydroxyphenyl)-2-phenylbut-1-en-1-yl)phenoxy) ethyl)(methyl)amino)-2-oxoethoxy)ethoxy)ethyl) benzamide ("compound P1")

To a solution of 2-[2-[2-[[4-[(3S,4S)-3-[[(2S)-2-[tert-butoxycarbonyl(methyl)amino]propanoyl]amino]-7-cyano-1-[(2-methoxy-1-naphthyl)methyl]-4-methyl-2-oxo-3,4-dihydro-1,5-benzodiazepine-5-carbonyl]benzoyl]amino] ethoxy]ethoxy]acetic acid (74 mg, 0.0855 mmol) in 2-methyltetrahydrofuran (0.855 mL) was added HATU (1.1 equiv., 36.5 mg, 0.0941 mmol) and N,N-diisopropylethylamine (3.0 equiv., 0.045 mL, 0.257 mmol). The mixture was stirred at room temperature for 30 minutes, then a solution

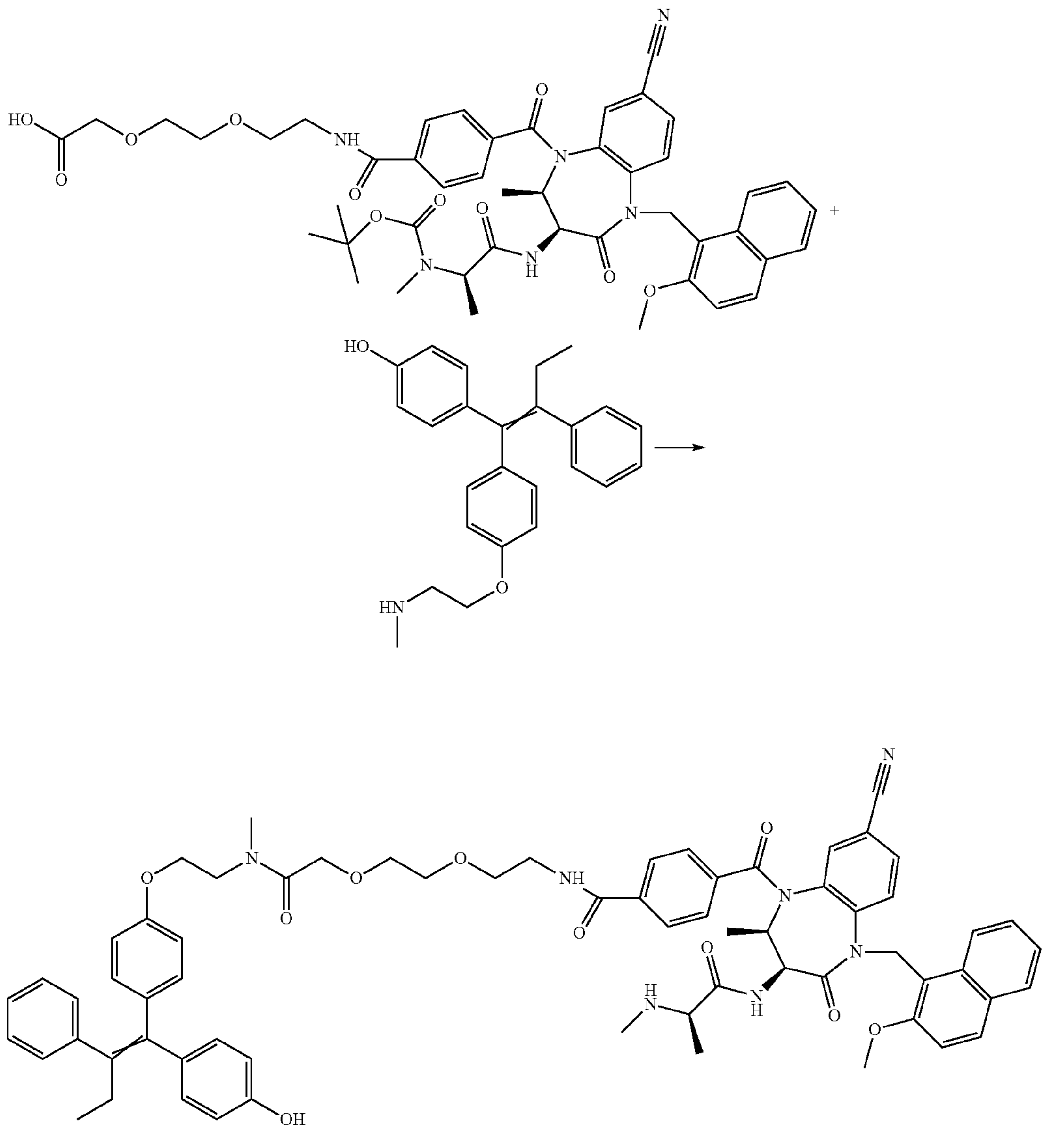

of 4-[1-[4-[2-(methylamino)ethoxy]phenyl]-2-phenyl-but-1-enyl]phenol (1.05 equiv., 33.5 mg, 0.0898 mmol) in 2-methyltetrahydrofuran (60, 0.5 mL, 400 mg, 5 mmol) was added, followed by 0.2 mL DMF. The mixture was stirred at room temperature for 22 h. Water was added and the solution was extracted 3 times with iPrOAc. The organic layers were combined then dried with sodium sulfate and concentrated in vacuo.

The crude material was dissolved in dichloromethane (0.85 mL) and trifluoroacetic acid (0.26 mL) was added dropwise. The reaction was stirred at room temperature until no gas evolution was observed. After 1 h, the solution was concentrated in vacuo and purified by reverse-phase HPLC to obtain 45 mg (45% yield over 2 steps) of the desired product.

M+H=560.9, 1120.7; 6 $^1$H NMR (400 MHz, DMSO-d6) δ 9.39, 9.14 (overlapping s, 1H), 8.85-8.70 (m, 1H), 8.44-8.36 (m, 1H), 8.20 (d, J=8.8 Hz, 1H), 8.10 (d, J=8.6 Hz, 1H), 7.97-7.82 (m, 2H), 7.70-7.64 (m, 1H), 7.50-7.44 (m, 1H), 7.34-7.27 (m, 1H), 7.21-7.04 (m, 9H), 7.03-6.87 (m, 4H), 6.78-6.67 (m, 2H), 6.62-6.54 (m, 2H), 6.44-6.33 (m, 1H), 6.12 (d, J=15.1 Hz, 1H), 5.78 (d, J=8.0 Hz, 2H), 5.52 (d, J=15.0 Hz, 1H), 4.99-4.89 (m, 1H), 4.33-4.04 (m, 4H), 4.00-3.88 (m, 1H), 3.94 (s, 3H), 3.68-3.61 (m, 1H), 3.60-3.42 (m, 5H), 3.38-3.32 (m, 1H), 3.03-2.78 (m, 3H), 2.45-2.35 (m, 2H), 2.32 (s, 3H), 1.23 (d, J=6.4 Hz, 3H), 1.11 (d, J=6.1 Hz, 3H), 0.89-0.76 (m, 4H).

B. Preparation of L1-CIDE i. Attachment of Linker L1 to CIDE

N-[(1S)-1-[[(1S)-4-(Carbamoylamino)-1-[(4-[4-[(1Z)-1-(4-[2-[2-(2-[2-[(4-[[(2S,3S)-8-cyano-5-[(2-methoxynaphthalen-1-yl)methyl]-2-methyl-3-[(2S)-2-(methylamino)propanamido]-4-oxo-2,3,4,5-tetrahydro-1H-1,5-benzodiazepin-1-yl]carbonyl]phenyl)formamido]ethoxy]ethoxy)-N-methylacetamido]ethoxy]phenyl)-2-phenylbut-1-en-1-yl]phenoxymethyl]phenyl)carbamoyl]butyl]carbamoyl]-2-methylpropyl]-6-(2,5-dioxo-2,5-dihydro-1H-pyrrol-1-yl)hexanamide ("compound LP2")

To a solution of (2S)—N-[(3S,4S)-7-cyano-5-[(4-[[2-(2-[[(2-[4-[(1Z)-1-(4-hydroxyphenyl)-2-phenylbut-1-en-1-yl]phenoxy]ethyl)(methyl)carbamoyl]methoxy]ethoxy)ethyl]carbamoyl]phenyl)carbonyl]-1-[(2-methoxynaphthalen-1-yl)methyl]-4-methyl-2-oxo-2,3,4,5-tetrahydro-1H-1,5-benzodiazepin-3-yl]-2-(methylamino)propanamide (compound P1, 48 mg, 0.043 mmol) and N-[(1S)-1-{[(1S)-4-(carbamoylamino)-1-{[4-(chloromethyl)phenyl]carbamoyl}butyl]carbamoyl}-2-methylpropyl]-6-(2,5-di-oxo-2,5-dihydro-1H-pyrrol-1-yl)hexanamide (90 mg, 0.152 mmol) in DMF (0.9 mL) at 0° C. was added $K_2CO_3$ (60 mg, 0.43 mmol). The reaction mixture was stirred for 4 h at 0° C., and diluted with precooled DMF (0.9 mL). The solid was filtered off. The filtrate was purified by Preparative HPLC with the following conditions: Column, SunFire Prep C18 OBD Column, 19*150 mm Sum, 10 nm; mobile phase, water (0.1% TFA) and $CH_3CN$ (5% $CH_3CN$ up to 48% in 10 min); Detector, UV 254/220 nm to afford 22 mg (31%) of N-[(1S)-1-[[(1S)-4-(carbamoylamino)-1-[(4-[4-[(1Z)-1-(4-[2-[2-(2-[2-[(4-[[(2S,3S)-8-cyano-5-[(2-methoxynaphthalen-1-yl)methyl]-2-methyl-3-[(2S)-2-(methylamino)propanamido]-4-oxo-2,3,4,5-tetrahydro-1H-1,5-

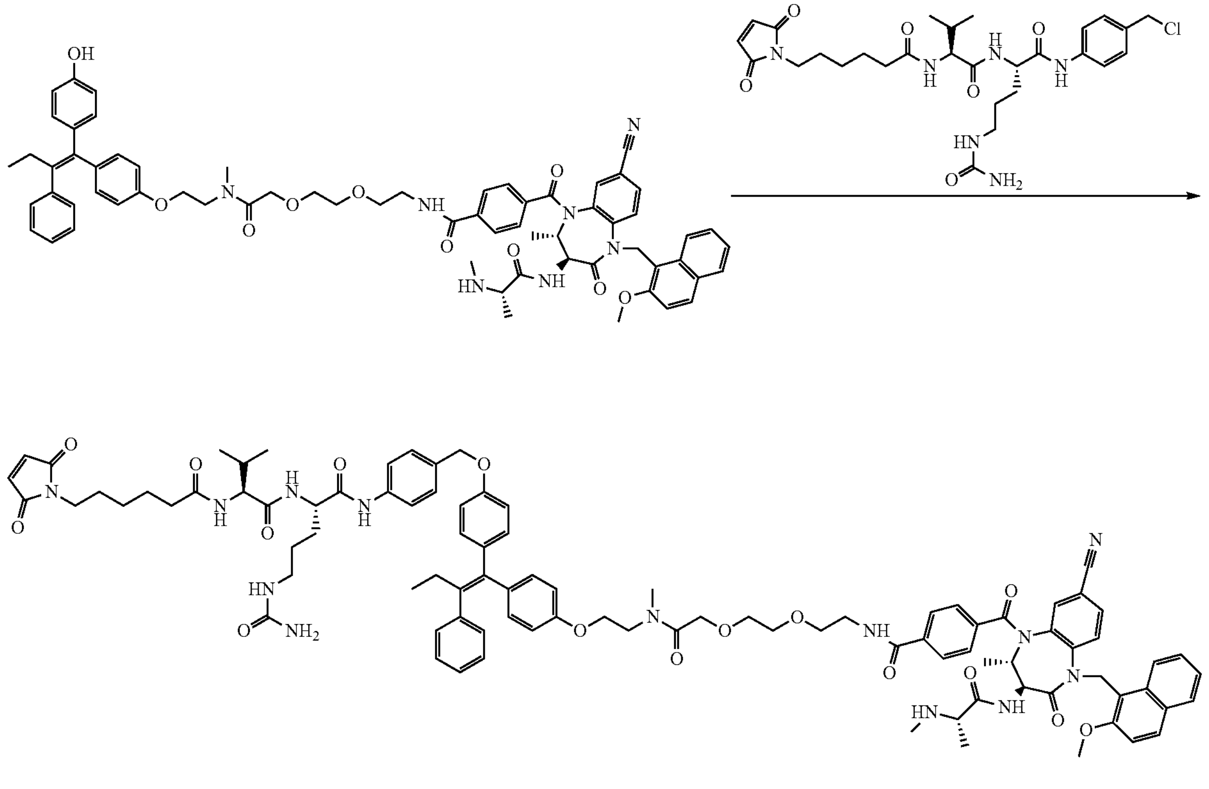

benzodiazepin-1-yl]carbonyl]phenyl)formamido]ethoxy]ethoxy)-N-methylacetamido]ethoxy]phenyl)-2-phenylbut-1-en-1-yl]phenoxymethyl]phenyl)carbamoyl]butyl]carbamoyl]-2-methylpropyl]-6-(2,5-dioxo-2,5-dihydro-1H-pyrrol-1-yl)hexanamide as a white solid. MS (ESI): $[M+H]^+$ =1675.1; $^1$H-NMR (400 MHz, DMSO-$d_6$): δ (ppm) 10.15 (s, 1H), 9.95-9.72 (m, 1H), 9.52-9.41 (m, 1H), 9.31-9.14 (m, 1H), 8.43 (brs, 1H), 8.20-8.18 (m, 1H), 8.17-8.07 (m, 2H), 7.93 (m, 2H), 7.70 (d, J=8 Hz, 1H), 7.70-7.65 (m, 3H), 7.48-7.42 (m, 2H), 7.41-7.36 (m, 1H), 7.33-7.28 (m, 1H), 7.23 (m, 1H), 7.18-7.07 (m, 7H), 7.02-7.01 (m, 1H), 6.99 (s, 3H), 6.96-6.92 (m, 2H), 6.76-6.67 (m, 2H), 6.60-6.58 (m, 2H), 6.40 (d, J=8.4 Hz, 1H), 6.13-6.08 (m, 1H), 5.99 (s, 1H), 5.80 (d, J=7.6 Hz, 2H), 5.55 (d, J=15.2 Hz, 1H), 5.44 (brs, 1H), 5.02-4.93 (m, 1H), 7.43-4.36 (m, 3H), 4.26-4.02 (m, 6H), 3.95-3.88 (m, 4H), 3.66-3.63 (m, 3H), 3.57-3.53 (m, 4H), 3.39-3.36 (m, 4H), 3.05-2.81 (m, 5H), 2.68 (s, 2H), 2.42-2.39 (m, 3H), 2.22-2.07 (m, 2H), 2.03-1.91 (m, 1H), 1.71 (brs, 2H), 1.62 (brs, 3H), 1.50-1.36 (m, 6H), 1.21-1.17 (m, 5H), 0.87-0.82 (m, 10H).

Syntheses of Exemplary ERα Targeting CIDEs

All compounds are mixtures of olefin isomers (approximately 1:1) unless otherwise specified. $^{13}$C resonances listed in parentheses represent olefin isomers and/or alternate N-Me amide bond rotamers of the major isomer of a particular compound.

i. EC1 An exemplary CIDE, EC1, can be synthesized by the following scheme:

Scheme 5

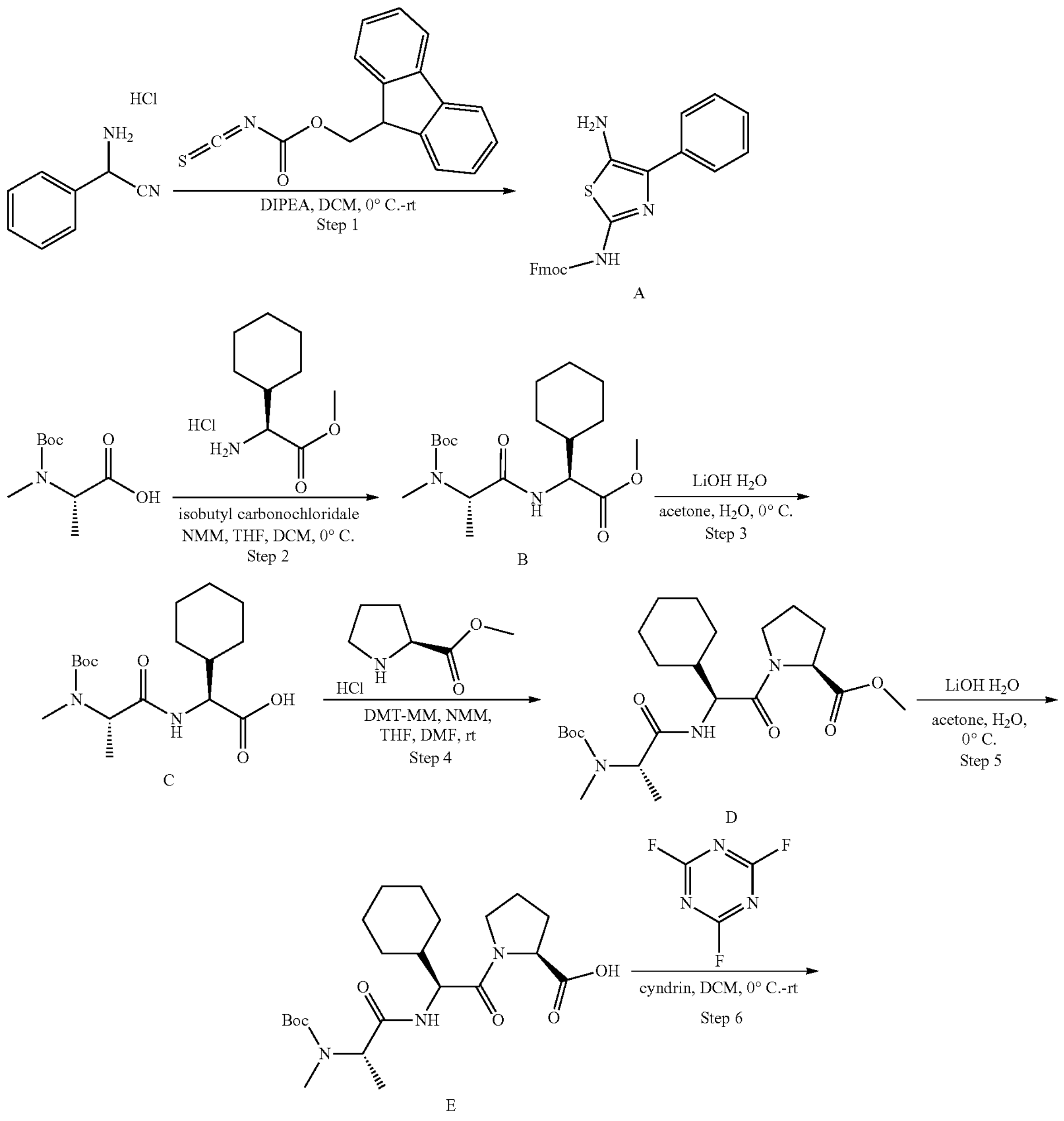

-continued
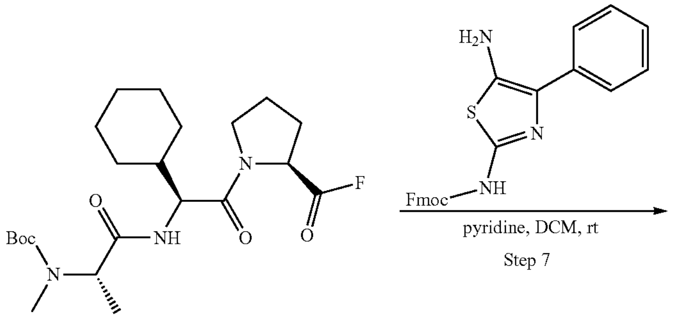
F
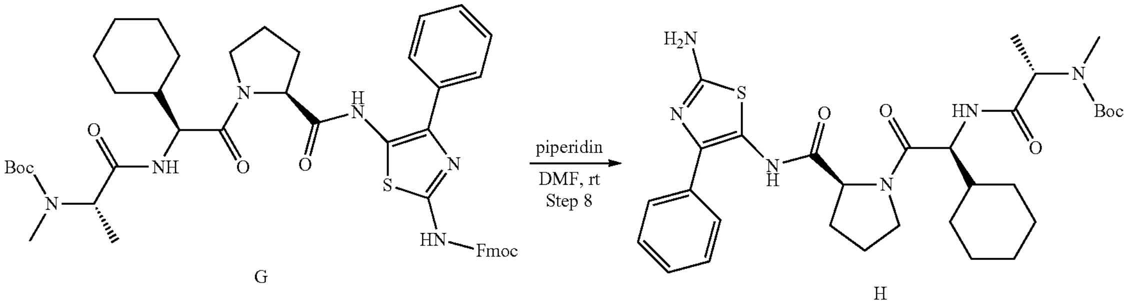
G H
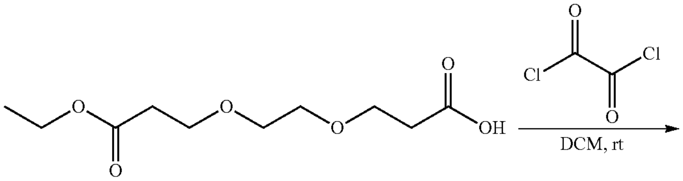
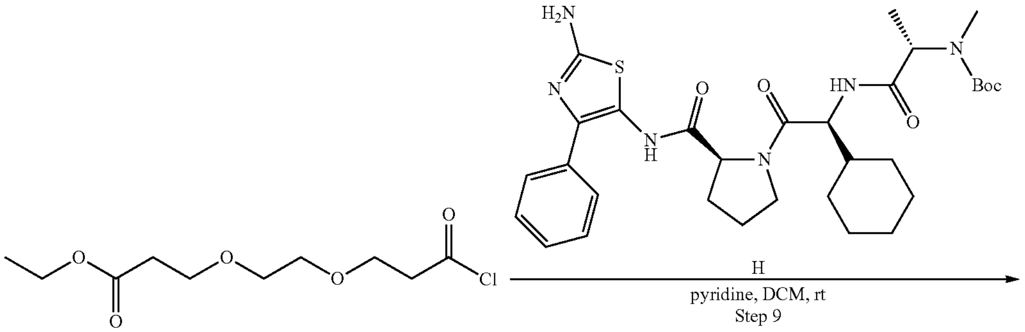
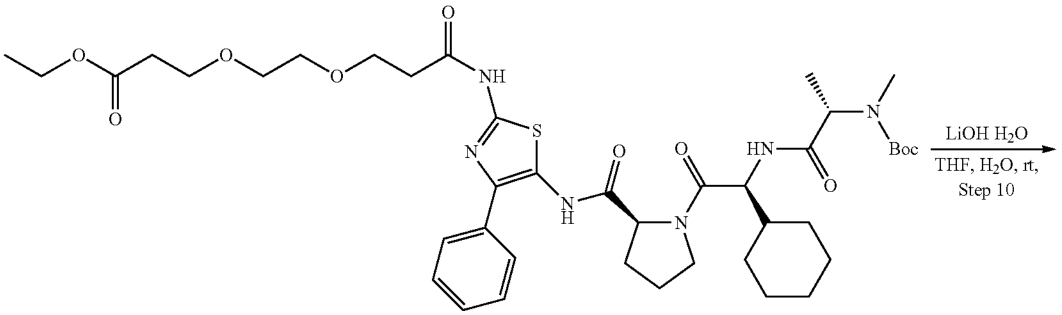
I

-continued

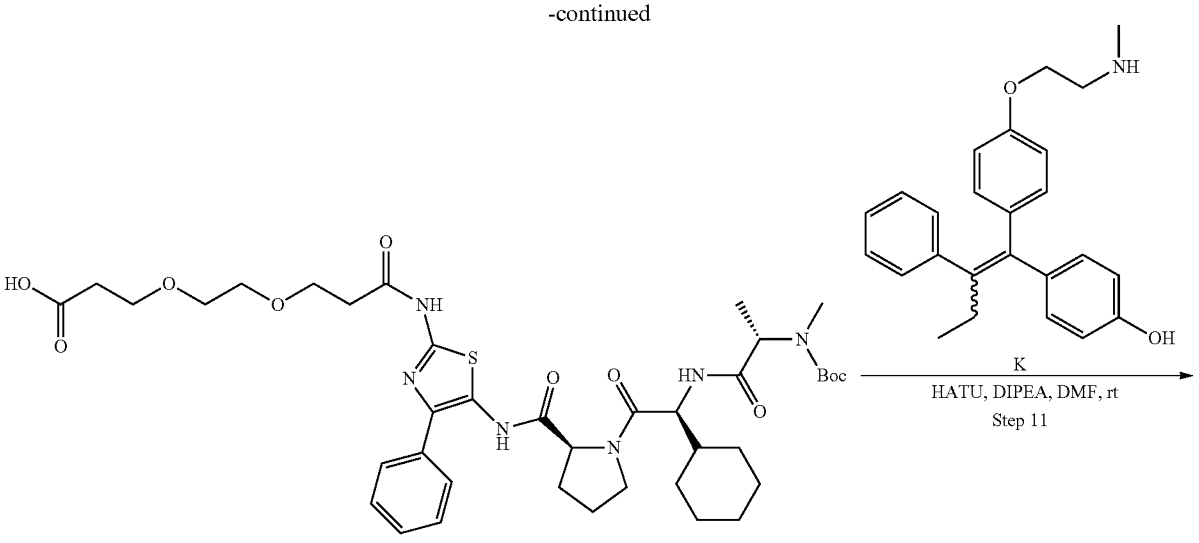

J

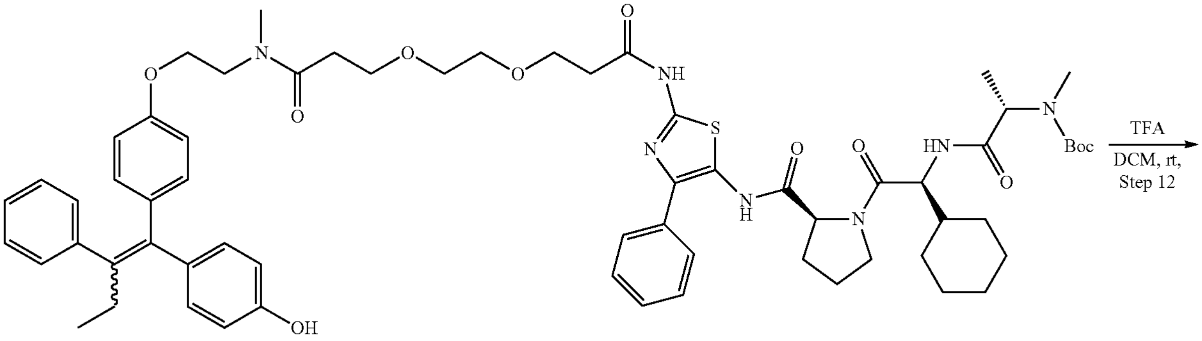

L

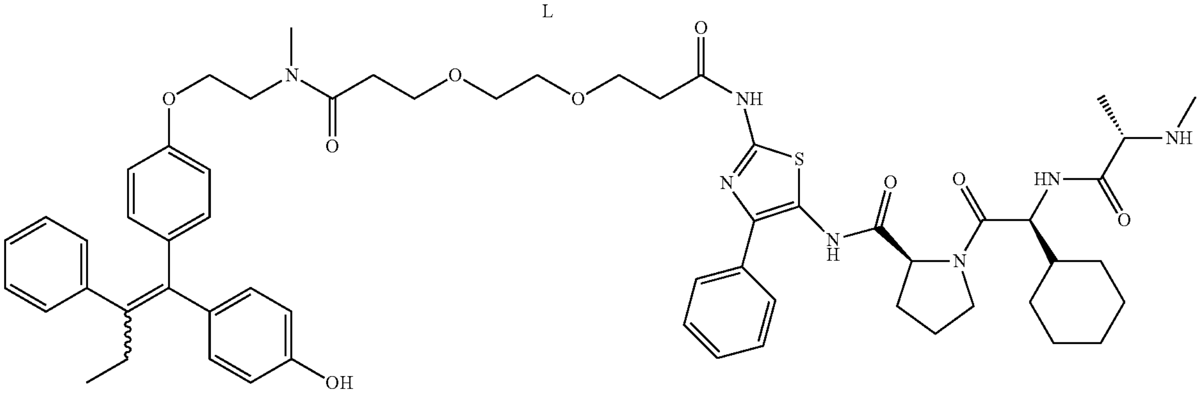

1

Step 1: (9H-Fluoren-9-yl)methyl (5-amino-4-phenylthiazol-2-yl)carbamate (A). A solution of 2-amino-2-phenylacetonitrile hydrochloride (1.20 g, 7.10 mmol), $(iPr)_2NEt$ (1.37 g, 10.6 mmol) and O—((9H-fluoren-9-yl)methyl) carbonisothiocyanatidate (2.00 g, 7.10 mmol) in DCM (10 mL) was stirred at 0° C. for 1 h. The reaction mixture was poured into saturated $NaHCO_3$ solution. The resulting mixture was extracted with EtOAc. The organic layers were washed with brine, dried over anhydrous $Na_2SO_4$, and were concentrated under reduced pressure. The residue was purified by flash chromatography on silica gel (gradient: 0%-80% ethyl acetate in petroleum ether) to yield 996 mg (33%) of compound A as yellow solid. MS (ESI): $[M+H]^+$=414.

Step 2: Methyl (S)-2-((S)-2-((tert-butoxycarbonyl)(methyl)amino)propanamido)-2-cyclohexylacetate (B). A solution of N-(tert-butoxycarbonyl)-N-methyl-L-alanine (2.00 g, 9.90 mmol), 4-methylmorpholine (NMM, 1.99 g, 19.7 mmol) and isobutyl carbonochloridate (1.60 g, 11.8 mmol) in THF (32 mL) was stirred for 0.5 h at 0° C. under nitrogen. A solution of methyl (S)-2-amino-2-cyclohexylacetate hydrochloride (2.00 g, 9.70 mmol) and 4-methylmorpholine (NMM; 1.99 g, 19.7 mmol) in THF (16 mL) and DCM (16 mL) was then added and the resulting solution was stirred at 0° C. for 1 h. The reaction mixture was diluted with EtOAc and quenched by the addition of water. Phases were separated. The aqueous phase was extracted with EtOAc (2×). The combined organic layers were washed with brine, dried over anhydrous $Na_2SO$, and were concentrated under reduced pressure. The residue was purified by flash chromatography on silica gel (gradient: 0%-40% ethyl acetate in petroleum ether) to yield 2.5 g (71%) of compound B as a colorless oil. MS (ESI): $[M+H]^+$=357.

Step 3: (S)-2-((S)-2-((tert-Butoxycarbonyl)(methyl) amino)propanamido)-2-cyclohexylacetic acid (C). To a solution of methyl (S)-2-((S)-2-((tert-butoxycarbonyl) (methyl)amino)-propanamido)-2-cyclohexylacetate (B, 2.50 g, 7.00 mmol) in acetone/water (30 mL, 1:1) was added LiOH—$H_2O$ (1.20 g, 28.6 mmol). The reaction mixture was stirred at 0° C. for 1 h and then was acidified by the addition of a solution of 2 N HCl until the pH was ~4. The mixture was concentrated under reduced pressure to approximate half of the volume and then was diluted with EtOAc. Phases were separated. The aqueous solution was extracted with EtOAc (2×). The combined organic layers were washed sequentially with 5% aqueous $KHSO_4$, brine, and water, then were dried over anhydrous $Na_2SO_4$ and concentrated under reduced pressure to yield 2.0 g (83%) of the compound C as a colorless oil. MS (ESI): $[M+H]^+$=343.

Step 4: Methyl ((S)-2-((S)-2-((tert-butoxycarbonyl) (methyl)amino)propanamido)-2-cyclohexylacetyl)-L-prolinate (D). To a mixture of (S)-2-((S)-2-((tert-butoxycarbonyl) (methyl)amino)propanamido)-2-cyclohexylacetic acid (C, 2.00 g, 5.80 mmol), methyl L-prolinate hydrochloride (0.96 g, 5.80 mmol) and 4-(4,6-dimethoxy-1,3,5-triazin-2-yl)-4-methylmorpholinium chloride (DMT-MM; 3.20 g, 11.6 mmol) in THF (50 mL) and DMF (5 mL) was added 4-methylmorpholine (NMM; 2.4 g, 23.8 mmol) at room temperature. The reaction mixture was stirred at room temperature overnight, then was diluted with EtOAc, followed by the addition of water. Phases were separated. The aqueous phase was extracted with EtOAc (2×). The combined organic layers were washed sequentially with saturated aqueous $NaHCO_3$, 5% aqueous $KHSO_4$, and brine, then were dried over anhydrous $Na_2SO_4$, and concentrated under reduced pressure. The residue was purified by flash chromatography on silica gel (gradient: 0%-80% ethyl acetate in petroleum ether) to yield 1.6 g (60%) of compound D as a white solid. MS (ESI): [M+H]=454.

Step 5: ((S)-2-((S)-2-((tert-Butoxycarbonyl)(methyl) amino)propanamido)-2-cyclohexylacetyl)-L-proline (E). To a solution of methyl ((S)-2-((S)-2-((tert-butoxycarbonyl) (methyl)amino)-propanamido)-2-cyclohexylacetyl)-L-prolinate (D, 1.60 g, 3.50 mmol) in acetone/water (30 mL, 1:1) was added LiOH—$H_2O$ (588 mg, 14.0 mmol). The reaction mixture was stirred at 0° C. for 1 h then was acidified by the addition of a solution of 2 N HCl until the pH was ~4. The mixture was concentrated under reduced pressure to approximate half of the volume and then was diluted with EtOAc. Phases were separated. The aqueous phase was extracted with EtOAc (2×). The combined organic layers were washed sequentially with 5% aqueous $KHSO_4$, brine, and water, then were dried over anhydrous $Na_2SO_4$ and were concentrated under reduced pressure to yield 1.1 g (71%) of compound E as a white solid. MS (ESI): $[M+H]^+$=440.

Step 6: tert-Butyl ((5)-1-(((5)-1-cyclohexyl-2-((S)-2-(fluorocarbonyl)pyrrolidin-1-yl)-2-oxoethyl)amino)-1-oxopropan-2-yl)(methyl)carbamate (F). To a solution of ((S)-2-((S)-2-((tert-butoxycarbonyl)(methyl)amino)propanamido)-2-cyclohexylacetyl)-L-proline (E, 1.10 g, 2.50 mmol) and pyridine (790 mg, 10.0 mmol) in DCM (10 mL) was added cyanuricfluoride (507 mg, 3.80 mmol) at 0° C. The resulting solution was stirred at 0° C. for 1 h then was quenched by the addition of ice water. Phases were separated. The aqueous phase was extracted with DCM. The combined organic layers were dried over anhydrous $Na_2SO_4$ and were concentrated under reduced pressure to yield 1.10 g of the crude product F as colorless oil. This material was used in the next step without further purification. MS (ESI): $[M+H]^+$=442.

Step 7: tert-Butyl ((5)-1-(((5)-2-((S)-2-((2-((((9H-fluoren-9-yl)methoxy)carbonyl)amino)-4-phenylthiazol-5-yl) carbamoyl)pyrrolidin-1-yl)-1-cyclohexyl-2-oxoethyl) amino)-1-oxopropan-2-yl)(methyl)carbamate (G). A mixture of (9H-fluoren-9-yl)methyl (5-amino-4-phenylthiazol-2-yl)carbamate (A, 687 mg, 1.66 mmol), pyridine (525 mg, 6.60 mmol) and tert-butyl ((S)-1-(((S)-1-cyclohexyl-2-((S)-2-(fluorocarbonyl)pyrrolidin-1-yl)-2-oxoethyl)amino)-1-oxopropan-2-yl)(methyl)-carbamate (F, 1.10 g, 2.50 mmol) in DCM (10 mL) was stirred at room temperature for 1 h under nitrogen. Aqueous $NaHCO_3$ solution was then added, and the resulting mixture was extracted with EtOAc (2×). The combined organic layers were dried over anhydrous $Na_2SO_4$ and were concentrated under reduced pressure. The residue was purified by flash chromatography on silica gel (gradient: 0%-100% ethyl acetate in petroleum ether) to yield 845 mg (41%) of compound G as a yellow solid. MS (ESI): $[M+H]^+$=835.

Step 8: tert-Butyl ((S)-1-(((5)-2-((S)-2-((2-amino-4-phenylthiazol-5-yl)carbamoyl)pyrrolidin-1-yl)-1-cyclohexyl-2-oxoethyl)amino)-1-oxopropan-2-yl)(methyl)carbamate (H). A mixture of tert-butyl ((5)-1-(((S)-2-((5)-2-((2-((((9H-fluoren-9-yl)methoxy)carbonyl)amino)-4-phenylthiazol-5-yl) carbamoyl)pyrrolidin-1-yl)-1-cyclohexyl-2-oxoethyl) amino)-1-oxopropan-2-yl)(methyl)carbamate (G, 845 mg, 1.0 mmol) and piperidine (0.5 mL) in DMF (4.5 mL) was stirred at room temperature for 1 h. The reaction mixture was diluted with EtOAc and was washed with water. The organic layer was dried over anhydrous $Na_2SO_4$ and was concentrated under reduced pressure. The residue was purified by flash chromatography on silica gel (gradient: 0%-100% ethyl acetate in petroleum ether) to yield 540 mg (87%) of compound H as a yellow solid. MS (ESI): $[M+H]^+$=613.

Step 9: Ethyl 3-(2-(3-((5-((S)-1-((S)-2-((5)-2-((tert-butoxycarbonyl)(methyl)amino)propanamido)-2-cyclohexylacetyl)pyrrolidine-2-carboxamido)-4-phenylthiazol-2-yl) amino)-3-oxopropoxy)ethoxy)propanoate (I). To a solution of 3-(2-(3-ethoxy-3-oxopropoxy)ethoxy)propanoic acid (491 mg, 2.10 mmol) in DCM (5 mL) was added a solution of oxalyl chloride (1.10 mL, 2.0 M solution in DCM, 2.20 mmol) and catalytic amount of DMF (3.8 mg, 0.05 mmol) at room temperature under nitrogen. The reaction mixture was stirred at room temperature for 1 h. The resulting solution was then added into a pre-mixed solution of tert-butyl ((5)-1-(((S)-2-((S)-2-((2-amino-4-phenylthiazol-5-yl) carbamoyl)pyrrolidin-1-yl)-1-cyclohexyl-2-oxoethyl) amino)-1-oxopropan-2-yl)(methyl)carbamate (H, 320 mg, 0.520 mmol) and pyridine (331 mg, 4.2 mmol) in DCM (3 mL) at 0° C. The resulting mixture was stirred at 0° C. for 1 hour, then was allowed to warm up to room temperature and was stirred at that temperature overnight. The resulting solution was quenched by the addition of water and was subsequently diluted with DCM. Phases were separated. The organic layer was dried over anhydrous $Na_2SO_4$ and was concentrated under reduced pressure. The residue was purified by flash chromatography on silica gel (gradient: 0%-100% ethyl acetate in petroleum ether) to yield 370 mg (85%) of compound I as a white solid. MS (ESI): $[M+H]^+$=829.

Step 10: 3-(2-(3-((5-((S)-1-((S)-2-((S)-2-((tert-Butoxycarbonyl)(methyl)amino)-propanamido)-2-cyclohexylacetyl)pyrrolidine-2-carboxamido)-4-phenylthiazol-2-yl) amino)-3-oxopropoxy)ethoxy)propanoic acid (J). To a mixture of ethyl 3-(2-(3-((5-((S)-1-((S)-2-((S)-2-((tert-butoxycarbonyl)(methyl)amino)propanamido)-2-cyclohexylacetyl)pyrrolidine-2-carboxamido)-4-phenylthiazol-2-yl) amino)-3-oxopropoxy)ethoxy)propanoate (I, 370 mg, 0.450 mmol) in THF (3 mL) and water (3 mL) was added LiOH—$H_2O$ (92.4 mg, 2.20 mmol) at room temperature. The reaction mixture was stirred at room temperature for 1 h, then was acidified with citric acid aqueous solution (1 M) to pH ~2 and subsequently diluted with EtOAc. Phases were separated. The organic layer was washed with water, dried over anhydrous $Na_2SO_4$, and was concentrated under reduced pressure to yield 345 mg (97%) of compound J as a light yellow solid. MS (ESI): $[M+H]^+$=801.

Step 11: tert-Butyl ((S)-1-(((S)-1-cyclohexyl-2-((S)-2-((2-(3-(2-(3-((2-(4-(1-(4-hydroxyphenyl)-2-phenylbut-1-en-1-yl)phenoxy)ethyl)(methyl)amino)-3-oxopropoxy)ethoxy) propanamido)-4-phenylthiazol-5-yl)carbamoyl)pyrrolidin-1-yl)-2-oxoethyl)amino)-1-oxopropan-2-yl)(methyl) carbamate (L). A mixture of 3-(2-(3-((5-((S)-1-((S)-2-((S)-2-((tert-butoxycarbonyl)(methyl)amino)-propanamido)-2-cyclohexylacetyl)-pyrrolidine-2-carboxamido)-4-phenylthiazol-2-yl)amino)-3-oxopropoxy)ethoxy)propanoic acid (J, 345 mg, 0.430 mmol), 4-(1-(4-(2-(methylamino) ethoxy)phenyl)-2-phenylbut-1-en-1-yl)phenol (K, prepared as described in: *Breast Cancer Research and Treatment* 2004, 85, 151; 179 mg, 0.48 mmol), $(iPr)_2NEt$ (224 mg, 1.74 mmol) and HATU (179 mg, 0.470 mmol) in DMF (4 mL) was stirred at room temperature for 1 h. The reaction mixture was loaded directly onto a pre-packed C18 column (40 g, C18, 20-35 μm, 100 Å, Agela Technologies) eluting with acetonitrile/water (solvent gradient: 5-100% acetonitrile in water (0.05% $NH_4HCO_3$), appropriate fractions were collected and concentrated under reduced pressure. The residue was re-purified by flash chromatography on silica gel (gradient: 0%-5% MeOH/DCM) to yield 358 mg (72%) of compound L as a white solid. MS (ESI): $[M+H]=^+1157$.

Step 12: (S)-1-((S)-2-Cyclohexyl-2-((S)-2-(methylamino) propanamido)acetyl)-N-(2-(3-(2-(3-((2-(4-(1-(4-hydroxyphenyl)-2-phenylbut-1-en-1-yl)phenoxy)ethyl)(methyl) amino)-3-oxopropoxy)ethoxy)propanamido)-4-phenylthiazol-5-yl)pyrrolidine-2-carboxamide (1). A solution of tert-butyl ((S)-1-(((S)-1-cyclohexyl-2-((S)-2-((2-(3-(2-(3-((2-(4-(1-(4-hydroxyphenyl)-2-phenylbut-1-en-1-yl)phenoxy)ethyl)(methyl)amino)-3-oxopropoxy)-ethoxy) propanamido)-4-phenylthiazol-5-yl)carbamoyl)pyrrolidin-1-yl)-2-oxoethyl)amino)-1-oxopropan-2-yl)(methyl) carbamate (L, 350 mg, 0.30 mmol) in TFA (1 mL) and DCM (2.5 mL) was stirred at room temperature for 0.5 h. The reaction mixture was concentrated under reduced pressure and the residue was purified by reverse phase flash chromatography (solvent gradient: 5-100% acetonitrile in water (0.05% $NH_4HCO_3$)) to yield 213.2 mg (67%) of compound 1 (Compound ECl) as a white solid. $^1H$ NMR (400 MHz, DMSO-$d_6$) δ 12.07 (s, 1H), 10.30 (s, 1H), 9.41 (9.16) (s, 1H), 7.91 (d, J=8.9 Hz, 1H), 7.75 (d, J=7.7 Hz, 2H), 7.48-7.39 (m, 2H), 7.34 (t, J=7.5 Hz, 1H), 7.23-7.05 (m, 6H), 7.02-6.88 (m, 2H), 6.79-6.67 (m, 2H), 6.63-6.54 (m, 2H), 6.43-6.36 (m, 1H), 4.54 (dd, J=8.3, 5.1 Hz, 1H), 4.42 (t, J=8.2 Hz, 1H), 4.11 (4.04, 3.95, 3.88) (t, J=5.5 Hz, 2H), 3.85-3.75 (m, 1H), 3.75-3.68 (m, 2H), 3.68-3.55 (m, 4H), 3.55-3.40 (m, 5H), 3.05 (2.96, 2.87, 2.80) (s, 3H), 3.02-2.92 (m, 1H), 2.72-2.60 (m, 3H), 2.60-2.55 (m, 1H), 2.45-2.35 (m, 2H), 2.25-1.96 (m, 6H), 1.95-1.80 (m, 2H), 1.80-1.50 (m, 6H), 1.20-0.89 (m, 8H), 0.89-0.79 (m, 3H). $^{13}C$ NMR (75 MHz, DMSO-$d_6$) δ 174.8, 171.5, 171.0 (171.0, 170.9, 170.9), 170.4, 169.9, 157.5 (157.3), 156.6, 156.5, 155.7, 153.0, 142.7, 142.7 (142.7), 140.5 (140.3), 138.3 (138.3), 137.4, 136.5 (136.4, 136.3, 136.1), 134.4 (134.4), 134.1 (134.0), 131.9, 131.9, 130.6, 130.6, 129.9, 128.9, 128.3, 128.3, 128.2, 127.9, 126.4 (126.4), 123.9, 115.4, 114.8, 114.5, 113.8, 70.1, 67.5 (67.4, 67.1, 67.1), 66.7, 66.0 (66.0, 65.8, 65.7), 59.8, 59.6, 54.7, 48.8 (48.7), 47.7, 47.0 (47.0), 36.9 (36.8), 36.2, 34.7, 33.8 (33.7), 33.6 (33.5), 33.2 (33.1), 29.6, 29.4, 29.0 (29.0), 28.4, 26.4, 26.1 (26.0), 25.2, 19.6, 13.9. HRMS (ESI+): m/z calcd for $C_{59}H_{74}N_7O_9S$ (M+H)+ 1056.5269 found 1056.5249.

ii. EC3 An exemplary CIDE, EC3, can be synthesized by the following scheme:

Scheme 6

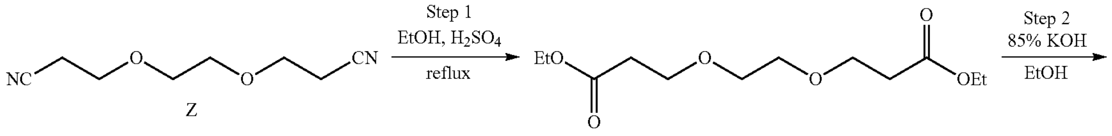

Z

AA

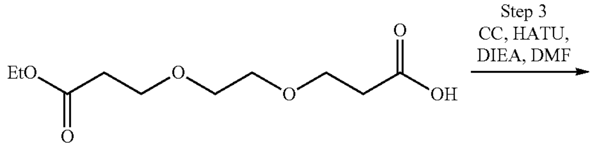

BB

-continued
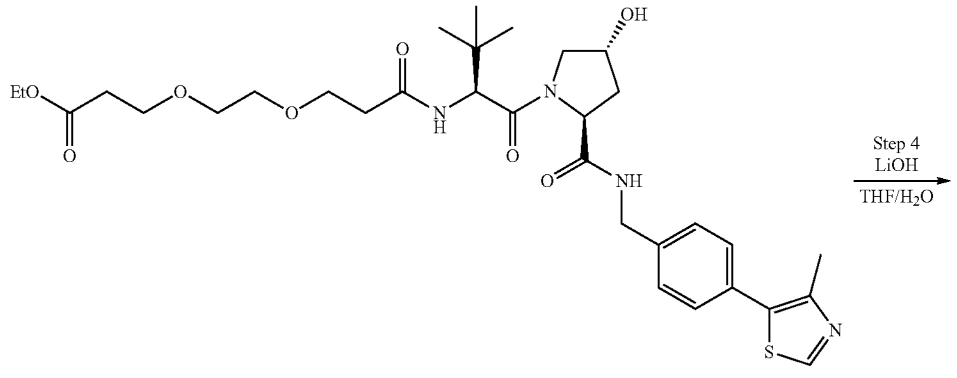
DD
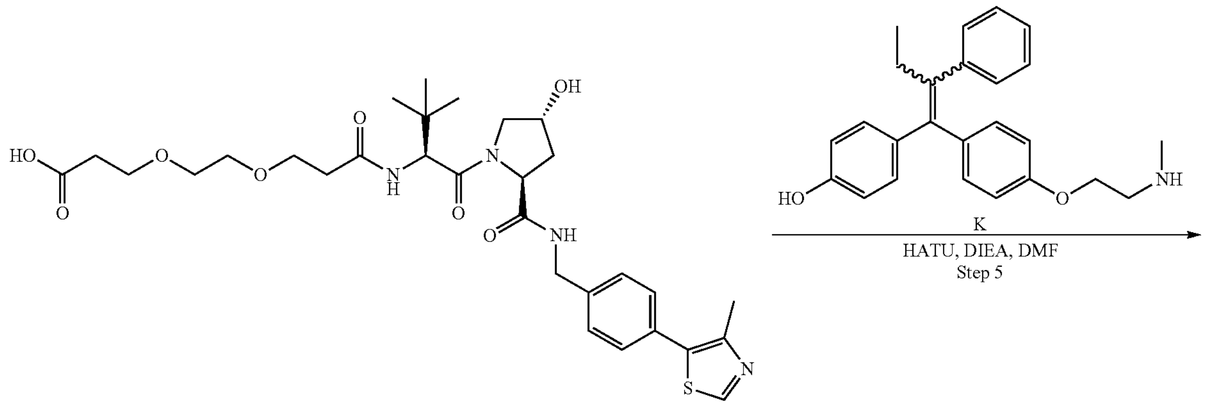
EE
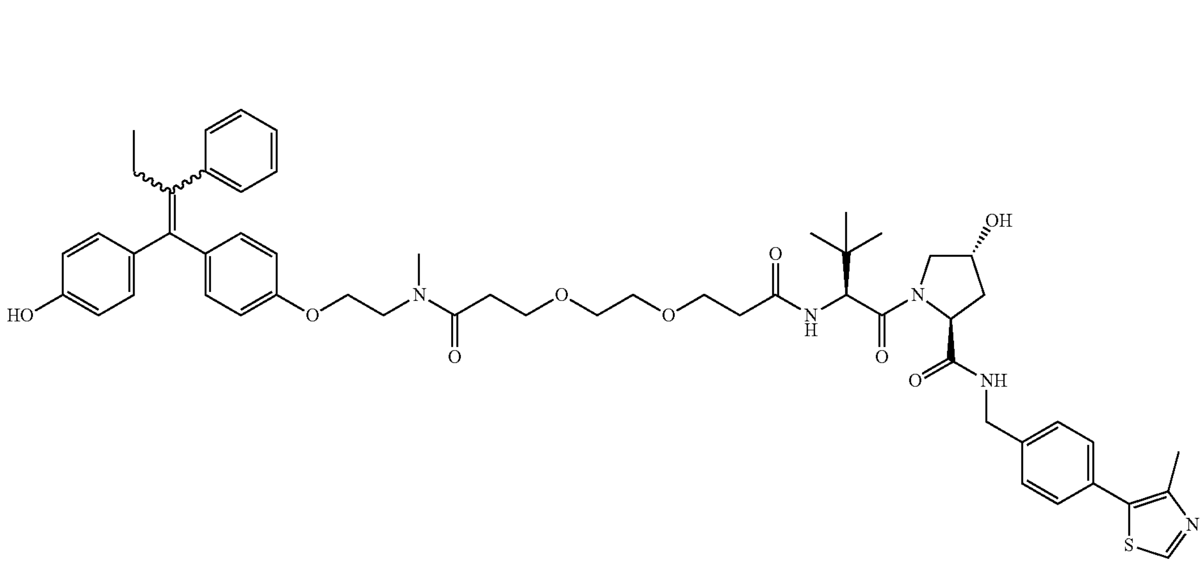
3

-continued

CC

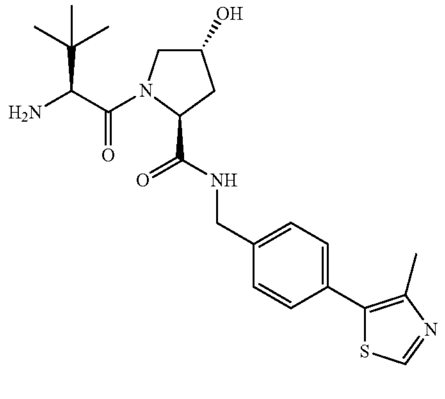

Step 1: Diethyl 3,3'-(ethane-1,2-diylbis(oxy))dipropanoate (AA). To a solution of compound Z (Aldrich, 2.0 g, 11.9 mmol) in EtOH (30 mL) was added $H_2SO_4$ (5.0 mL) dropwise. The reaction solution was stirred at 85° C. for 16 h, then was concentrated in vacuo to remove most of EtOH. The residue was diluted with $H_2O$ (30 mL), and extracted with EtOAc (30 mL×3). The combined organic layers were washed with brine (20 mL), dried over anhydrous $Na_2SO_4$, filtered, and were concentrated to give the crude product. This material was purified by flash chromatography on silica gel (0-30% EtOAc in petroleum ether) to afford compound AA (1.40 g, 45% yield) as a colorless oil. $^1H$ NMR (400 MHz, $CDCl_3$) δ 4.17-4.11 (m, 4H), 3.74 (t, J=6.4 Hz, 4H), 3.60 (s, 4H), 2.58 (t, J=6.4 Hz, 4H), 1.25 (t, J=6.8 Hz, 6H).

Step 2: 3-(2-(3-Ethoxy-3-oxopropoxy)ethoxy)propanoic acid (BB). To a solution of compound AA (1.30 g, 4.96 mmol) in EtOH (20 mL)/$H_2O$ (3.0 mL) was added KOH (278 mg, 4.96 mmol). The reaction solution was stirred at 80° C. for 1 h then was concentrated in vacuo to remove the solvent. The residue was diluted with $H_2O$ (20 mL), and the pH was adjusted to 9.0 to with saturated $NaHCO_3$ solution. The mixture was washed with EtOAc (20 mL×2), and the aqueous phase was adjusted to pH 3.0 with HCl (2.0 M). The acidified aqueous phase was then extracted with EtOAc (30 mL×3). The combined organic layers were dried over $Na_2SO_4$, filtered, and were concentrated in vacuo to afford compound BB (370 mg, 32%) as a colorless oil. $^1H$ NMR (400 MHz, $CD_3OD$) δ 4.16-4.13 (m, 2H), 3.75-3.71 (m, 4H), 3.60-3.59 (m, 4H), 2.56-2.52 (m, 4H), 1.25 (t, J=7.2 Hz, 3H).

Step 3: Ethyl 3-(2-(3-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl)amino)-3-oxopropoxy) ethoxy)-propanoate (DD). To a solution of compound BB (370 mg, 1.58 mmol) in DMF (15 mL) was added $(iPr)_2NEt$ (816 mg, 6.32 mmol) and HATU (720.69 mg, 1.9 mmol). The solution was stirred at 25° C. for 15 min, then VHL ligand CC (TFA salt, prepared as described in: *J. Med. Chem.* 2018, 61, 599; 590 mg, 1.26 mmol) was added. The reaction solution was stirred at 25° C. for additional 1 h then was concentrated in vacuo to remove the solvent. The residue was diluted with EtOAc (40 mL), and this solution was washed with brine (30 mL×3), dried over $Na_2SO_4$, filtered, and was concentrated. The residue was purified by prep-TLC (10% MeOH in DCM, Rf=0.5) to afford compound DD (300 mg, 23%) as a yellow oil. LCMS (5-95, AB, 1.5 min): RT=0.746 min, m/z=669.1 $[M+Na]^+$.

Step 4: 3-(2-(3-(((S)-1-((2S,4R)-4-Hydroxy-2-((4-(4-methylthiazol-5-yl)benzyl)-carbamoyl)pyrrolidin-1-yl)-3,3-dimethyl-1-oxobutan-2-yl)amino)-3-oxopropoxy)ethoxy)-propanoic acid (EE). To a solution of compound DD (300 mg, 0.460 mmol) in THF (6.0 mL)/$H_2O$ (2.0 mL) was added LiOH—$H_2O$ (97 mg, 2.3 mmol). The reaction solution was stirred at 25° C. for 16 h then was concentrated in vacuo to remove most of THF. The residue was acidified to pH 7.0 with HCl (2.0 M) and was subsequently purified by prep-HPLC (Xtimate C18 150*25 mm*5 um, acetonitrile 23-53/0.225% FA in water) to afford compound EE (100 mg, 34%) as a white solid. LCMS (5-95, AB, 1.5 min): RT=0.72 min, m/z=641.1 $[M+Na]^+$.

Step 5: (2S,4R)-1-((S)-2-(tert-Butyl)-16-(4-1-(4-hydroxyphenyl)-2-phenylbut-1-en-1-yl)phenoxy)-14-methyl-4,13-dioxo-7,10-dioxa-3,14-diazahexadecan-1-oyl)-4-hydroxy-N-(4-(4-methylthiazol-5-yl)benzyl)pyrrolidine-2-carboxamide (3). To a solution of compound EE (100 mg, 0.160 mmol) in DMF (4.0 mL) was added HATU (73 mg, 0.190 mmol) and $(iPr)_2NEt$ (83 mg, 0.650 mmol). The mixture was stirred at 25° C. for 10 min, then compound K (prepared as described in: *Breast Cancer Research and Treatment* 2004, 85, 151; 60 mg, 0.16 mmol) was added. The reaction solution was stirred at 25° C. for an additional 1 h then was purified by prep-HPLC (Xtimate C18 150*25 mm*5 um, acetonitrile 60-80.6/0.225% FA in water) to afford compound 3 (Compound EC3) (105 mg, 65%) as a white solid. LCMS (5-95, AB, 1.5 min): RT=0.93 min, m/z=996.4 $[M+Na]^+$. $^1H$ NMR (400 MHz, $CD_3OD$): δ 8.90 (s, 1H), 7.46-7.38 (m, 4H). 7.13-7.04 (m, 7H), 6.90-6.87 (m, 2H), 6.63 (d, J=8.4 Hz, 2H), 6.40 (d, J=8.8 Hz, 2H), 4.65-4.48 (m, 5H), 4.38-4.32 (m, 1H), 4.16-4.09 (m, 2H), 3.91-3.88 (m, 1H), 3.80-3.65 (m, 7H), 3.60-3.54 (m, 4H), 3.16 (s, 1H), 2.99-2.97 (m, 1H), 2.78-2.75 (m, 1H), 2.65-2.62 (m, 1H), 2.53-2.51 (m, 1H), 2.47-2.41 (m, 6H), 2.24-2.19 (m, 1H), 2.11-2.06 (m, 1H), 1.02 (s, 9H), 0.88 (t, J=7.6 Hz, 3H). $^{13}C$ NMR (100 MHz, $CD_3OD$) δ 174.6, 174.3, 174.0, 173.8, 172.2, 158.9, 158.7, 156.5, 153.2, 148.7, 144.3, 141.9, 140.5, 139.7, 133.3, 133.2, 131.8, 131.4, 131.0, 130.6, 130.5, 129.1, 129.0, 127.1, 116.1, 115.3, 114.5, 71.6, 71.5, 71.2, 68.5, 68.4, 66.9, 60.9, 58.1, 43.8, 39.0, 37.5, 36.9, 34.6, 30.0, 27.2, 15.9, 14.2. HRMS (0-95_1_4 min, ESI), m/z 974.4676 $[M+H]^+$.

iii. EC4 An exemplary CIDE, EC4, can be synthesized by the following scheme:
Scheme 7
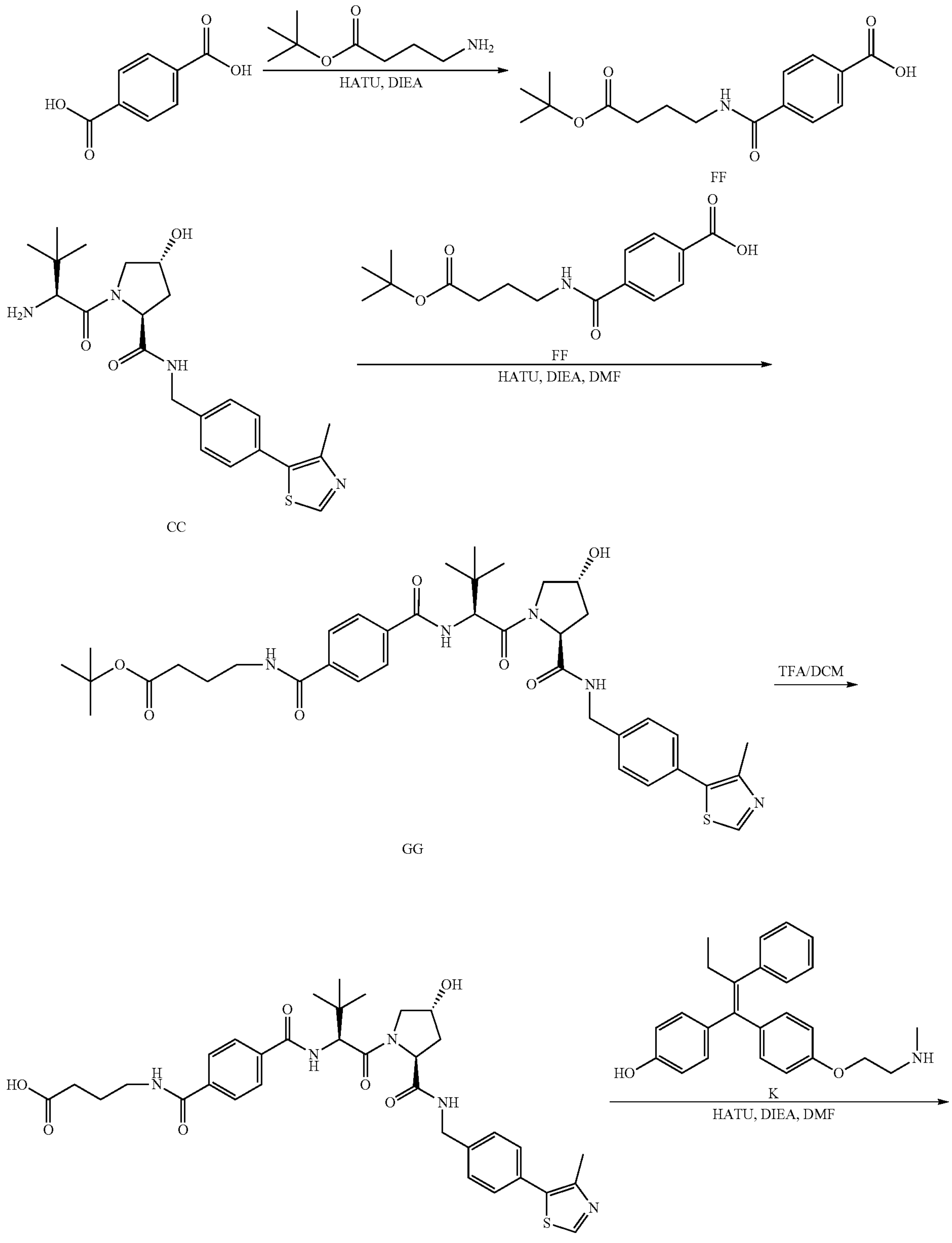

-continued

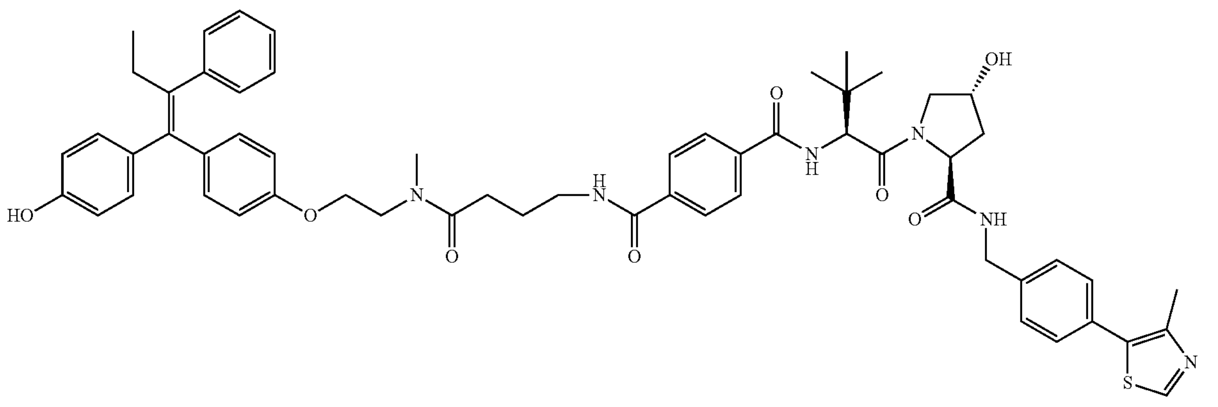

4

Step 1: 4-((4-(tert-butoxy)-4-oxobutyl)carbamoyl)benzoic acid (FF). HATU (144 mg, 0.38 mmol) was added to a solution of terephthalic acid (70 mg, 0.42 mmol) and $(iPr)_2NEt$ (81 mg, 0.63 mmol) in DMF (4 mL) at 25° C. After stirring 10 min at that temperature, tert-butyl-4-aminobutanoate (54 mg, 0.34 mmol) was added and the resulting mixture was stirred at 25° C. for 1 h. LCMS analysis {(5-95AB/1.5 min): RT=0.720 min, m/z=[M+Na]+ 329.9}showed 40% of desired product. The reaction was concentrated in vacuo and purified by Prep-HPLC (Acetonitrile 37-51%/0.225% FA in water) to give compound FF (50 mg, 35%) as a white solid. $^1$H NMR (400 MHz, DMSO-$d_6$) δ 13.18 (brs, 1H), 8.63 (t, J=5.6 Hz, 1H), 8.00 (d, J=8.4 Hz, 2H), 7.92 (d, J=8.4 Hz, 2H), 3.26-3.21 (m, 2H), 2.23 (t, J=7.2 Hz, 2H), 1.74-1.67 (m, 2H), 1.36 (s, 9H). LCMS (5-95, AB, 1.5 min): RT=0.72 min, m/z=$[M+Na]^+$329.9.

Step 2: tert-Butyl 4-(4-(((S)-1-((2S,4R)-4-hydroxy-2-((4-(4-methylthiazol-5-yl)benzyl)carbamoyl) pyrrolidin-1-yl)-3,3-dimethyl-1-oxobutan-2-yl)carbamoyl)benzamido)-butanoate (GG). A mixture of compound CC (TFA salt, prepared as described in: *J. Med. Chem.* 2018, 61, 599; 252 mg, 0.59 mmol), HATU (278 mg, 0.73 mmol), $Et_3N$ (148 mg, 1.46 mmol) and compound FF (150 mg, 0.49 mmol) in DMF (15 mL) was stirred at 25° C. for 2 h. The mixture was concentrated under reduced pressure, and the residue was purified by flash chromatography (0-10% MeOH in DCM, Rf=0.5) to give compound GG (350 mg, 90%) as a yellow solid. LCMS (5-95, AB, 1.5 min): RT=0.845 min, m/z=[M+H]+720.3.

Step 3: 4-(4-(((S)-1-((2S,4R)-4-Hydroxy-2-((4-(4-methylthiazol-5-yl)benzyl)-carbamoyl)pyrrolidin-1-yl)-3,3-dimethyl-1-oxobutan-2-yl)carbamoyl)benzamido)butanoic acid (HH). To a solution of compound GG (350 mg, 0.44 mmol) in DCM (10 mL) at 25° C. was added TFA (10.0 mL, 0.440 mmol). The mixture was stirred at 25° C. for 2 h, then was concentrated in vacuo to afford crude compound HH (290 mg, 99%) as a yellow oil. The crude material was used directly in next step. LCMS (5-95, AB, 1.5 min): RT=0.710 min, m/z=$[M+H]^+$ 664.3.

Step 4: $N^1$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-$N^4$-(4-((2-(4-(1-(4-hydroxyphenyl)-2-phenylbut-1-en-1-yl)phenoxy)ethyl)(methyl)amino)-4-oxobutyl)-terephthalamide (4). A mixture of compound HH (150 mg, 0.23 mmol), HATU (112 mg, 0.29 mmol), compound K (prepared as described in: *Breast Cancer Research and Treatment* 2004, 85, 151; 127 mg, 0.34 mmol) and $Et_3N$ (69 mg, 0.68 mmol) in DMF (10 mL) was stirred at 25° C. for 2 h. The mixture was subsequently purified by prep-HPLC (acetonitrile 51-81%/0.225% FA in water) to give compound 4 (Compound EC4) (90 mg, 39%) as a yellow solid. LCMS (5-95, AB, 1.5 min): RT=0.89 min, m/z=$[M+H]^+$ 1019.5. $^1$H NMR (400 MHz, $CD_3OD$) δ ppm 8.93 (s, 1H), 7.99-7.86 (m, 4H), 7.45-7.39 (m, 4H), 7.12-7.05 (m, 7H), 6.88 (d, J=8.0 Hz, 2H), 6.61 (d, J=8.0 Hz, 2H), 6.38 (d, J=8.0 Hz, 2H), 4.92-4.90 (m, 1H), 4.60-4.52 (m, 3H), 4.35-4.31 (m, 1H), 4.14-4.10 (m, 2H), 3.99-3.93 (m, 1H), 3.87-3.83 (m, 1H), 3.79-3.61 (m, 2H), 3.45-3.38 (m, 2H), 3.15 (s, 1H), 3.05-2.84 (m, 2H), 2.62-2.59 (m, 1H), 2.49-2.39 (m, 6H), 2.26-2.20 (m, 1H), 2.13-2.06 (m, 1H), 2.01-1.86 (m, 2H), 1.30-1.27 (m, 1H), 1.09-1.07 (m, 9H), 0.88-0.84 (m, 3H). $^{13}$C NMR (100 MHz, $CD_3OD$) δ 175.9, 175.5, 174.5, 172.3, 169.2, 158.9, 158.7, 157.3, 156.4, 153.3, 148.6, 144.1, 142.3, 140.5, 138.3, 138.1, 133.2, 131.8, 131.8, 131.0, 130.5, 129.1, 129.0, 128.9, 128.6, 116.0, 115.3, 114.4, 71.3, 67.2, 66.6, 66.3, 61.7, 59.7, 43.8, 39.0, 37.9, 37.4, 34.4, 32.0, 30.0, 27.3, 25.8, 15.9, 14.1. HRMS (0-95_1_4 min, ESI): m/z 1019.4650 $[M+H]^+$.

Syntheses of Exemplary ERα Targeting L1-CIDES iv. L1EC8 An exemplary L1-CIDE, L1EC8, was synthesized as follows:

8

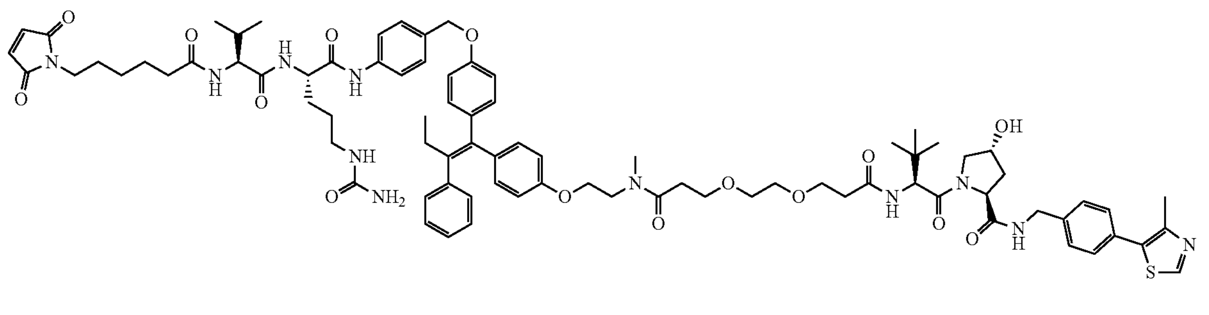

((2S,4R)-1-[(2S)-2-[3-[2-[3-[2-[4-[1-[4-[[4-[[(2S)-2-[[(2S)-2-[6-(2,5-dioxopyrrol-1-yl)hexanoylamino]-3-methyl-butanoyl]amino]-5-ureido-pentanoyl]amino]-phenyl]methoxy]phenyl]-2-phenyl-but-1-enyl]phenoxy] ethyl-methyl-amino]-3-oxo-propoxy]ethoxy]propanoylamino]-3,3-dimethyl-butanoyl]-4-hydroxy-N-[[4-(4-methylthiazol-5-yl)phenyl]methyl]pyrrolidine-2-carboxamide) (8, "L1EC8"). In a small vial, MC-VC-PAB-Cl {N-[(1S)-1-[[(1S)-1-[[4-(chloromethyl)phenyl]carbamoyl]-4-ureido-butyl]carbamoyl]-2-methylpropyl]-6-(2,5-dioxopyrrol-1-yl) hexanamide} (prepared as described in: *Nat. Chem.* 2016, 8, 1112; 35.5 mg, 0.06 mmol) and compound 3 (49.5 mg, 0.051 mmol) were taken up in DMF (0.1 mL) and cooled to 0° C. To the mixture was added potassium carbonate (70 mg, 0.51 mmol), and the reaction was stirred for 1 h at 0° C. then was maintained at 25° C. for 2 h. The mixture was diluted with cold DMF and was filtered. The filtrate was purified directly by HPLC using a 28 min method eluting with a gradient of 40-80% Acetonitrile: 0.01% Formic Acid in Water on a Luna 10 u C18, 250×30 mm column. Isolated compound 8 (L1EC8) (10.8 mg, 14%). M+H=1720.35. $^{1}H$ NMR (500 MHz, DMSO-$d_6$) δ 10.08 (d, J=16.7 Hz, 1H), 8.98 (s, 1H), 8.59 (t, J=6.0 Hz, 1H), 8.17 (t, J=7.4 Hz, 1H), 7.94 (dd, J=9.5, 3.1 Hz, 1H), 7.88-7.83 (m, 1H), 7.64 (d, J=8.3 Hz, 1H), 7.59 (d, J=8.4 Hz, 1H), 7.45-7.34 (m, 5H), 7.29 (d, J=8.5 Hz, 1H), 7.21-7.14 (m, 2H), 7.13-7.04 (m, 5H), 7.00 (d, J=3.5 Hz, 3H), 6.93 (d, J=8.2 Hz, 1H), 6.74-6.68 (m, 2H), 6.68-6.62 (m, 1H), 6.11-5.99 (m, 1H), 5.45 (d, J=4.7 Hz, 2H), 4.85 (s, 1H), 4.56 (d, J=9.4 Hz, 1H), 4.47-4.32 (m, 4H), 4.26-4.16 (m, 2H), 4.13 (t, J=5.4 Hz, 1H), 4.05 (t, J=5.8 Hz, 1H), 3.72 (t, J=5.3 Hz, 1H), 3.70-3.50 (m, 8H), 3.50-3.27 (m, 18H), 3.07 (s, 1H), 3.05-2.90 (m, 3H), 2.88 (s, 1H), 2.62-2.47 (m, 7H), 2.44 (s, 3H), 2.43-2.28 (m, 3H), 2.24-1.84 (m, 6H), 1.75-1.64 (m, 1H), 1.64-1.55 (m, 1H), 1.54-1.31 (m, 7H), 1.23 (s, 1H), 1.22-1.13 (m, 2H), 0.93 (s, 9H), 0.88-0.77 (m, 10H). $^{13}C$ NMR (126 MHz, DMSO-$d_6$) δ 172.7, 172.4, 171.8, 171.5, 171.1, 171.0, 170.4, 170.0, 159.4, 156.8, 151.9, 148.2, 142.5, 140.9, 140.0, 139.2, 137.9, 134.9, 132.1, 131.9, 131.6, 130.7, 130.1, 129.9, 129.3, 129.1, 129.0, 128.4, 127.9, 126.6, 119.5, 119.4, 114.9, 114.6, 114.1, 113.8, 70.1, 69.9, 69.3, 67.4, 67.1, 59.2, 58.0, 56.9, 56.8, 53.6, 47.0, 42.1, 40.5, 40.4, 40.3, 40.2, 40.1, 40.0, 39.8, 39.6, 39.5, 39.4, 38.4, 37.5, 36.9, 36.1, 35.8, 35.4, 33.8, 33.6, 33.2, 30.9, 29.7, 29.0, 28.2, 27.3, 26.8, 26.3, 25.4, 19.7, 18.7, 16.2, 13.9. The $^{1}H$ NMR peak assignments (s, d, t, m, etc.) and integrations are complicated by the presence of amide rotamers and olefin isomers (all peaks are tabulated). $^{13}C$ NMR peak assignments are similarly complicated.

v. L1EC10 An exemplary L1-CIDE, L1EC10, can be synthesized by the following

Scheme 8

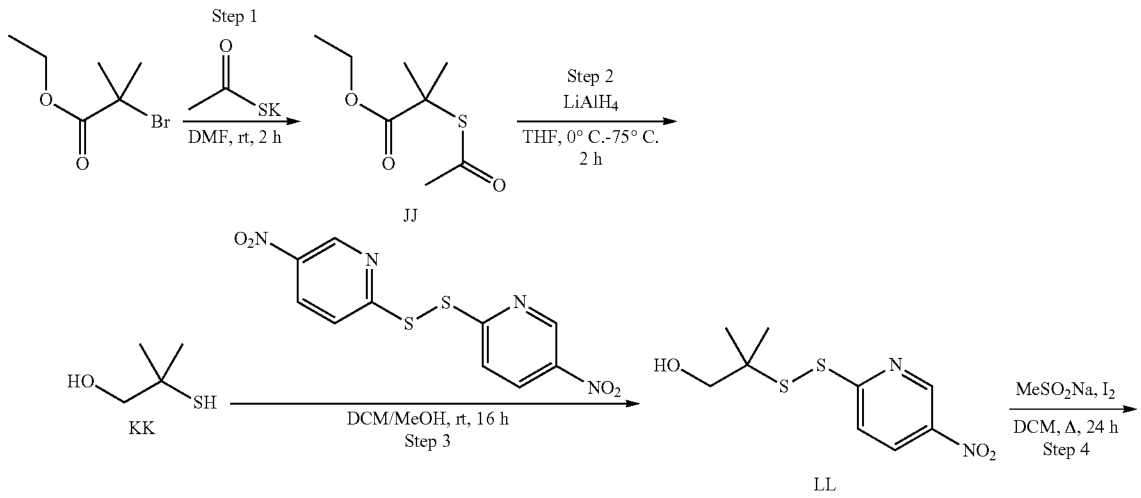

-continued
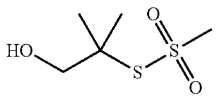
MM
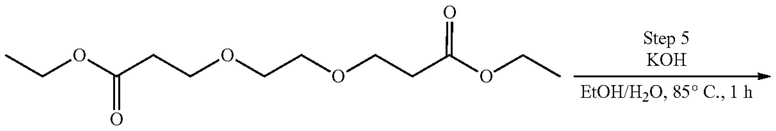
AA
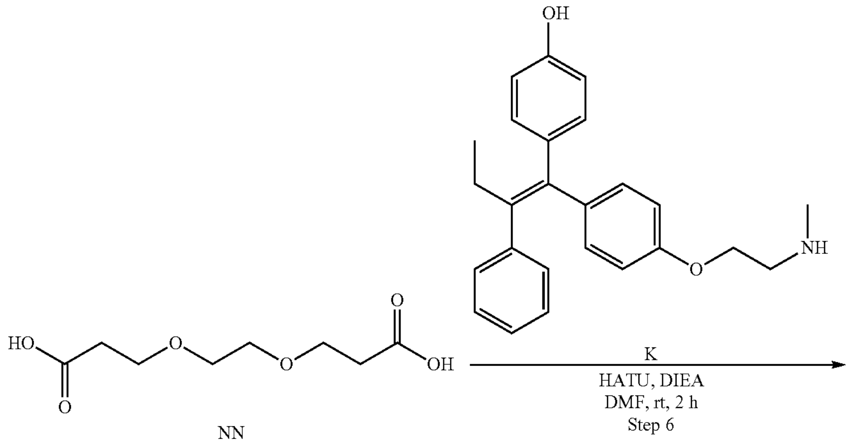
NN
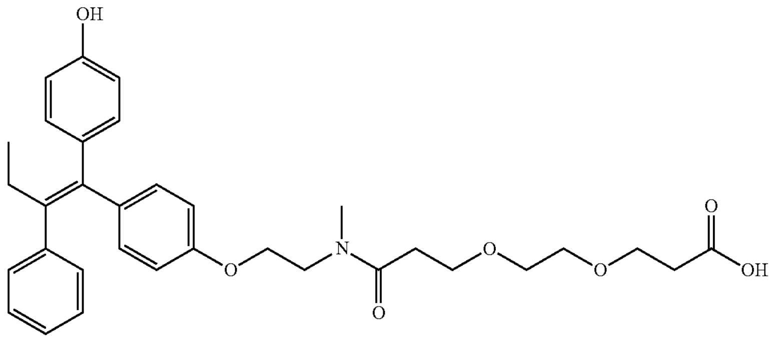
OO
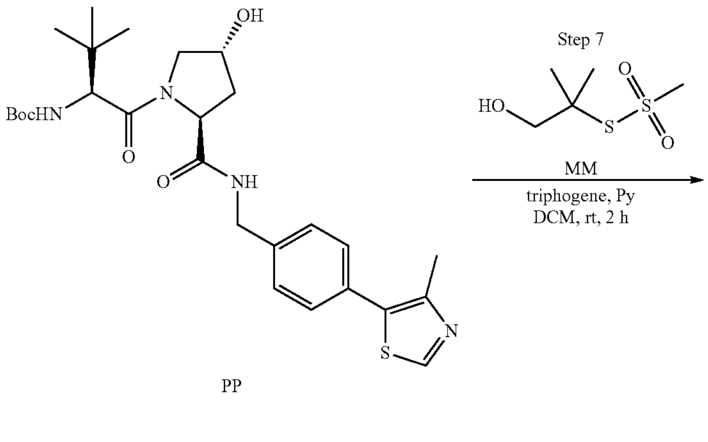
PP -continued

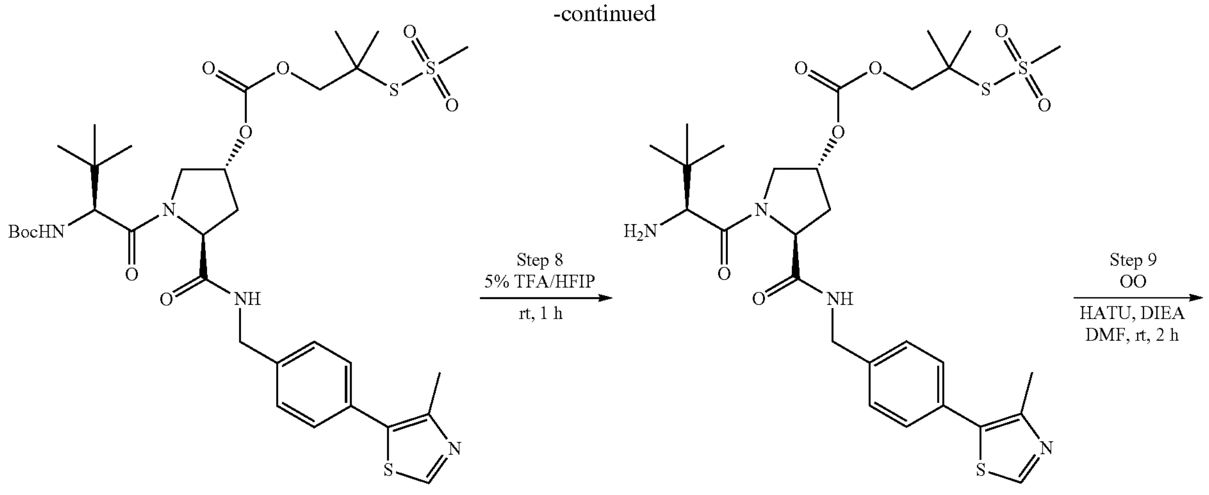

QQ RR

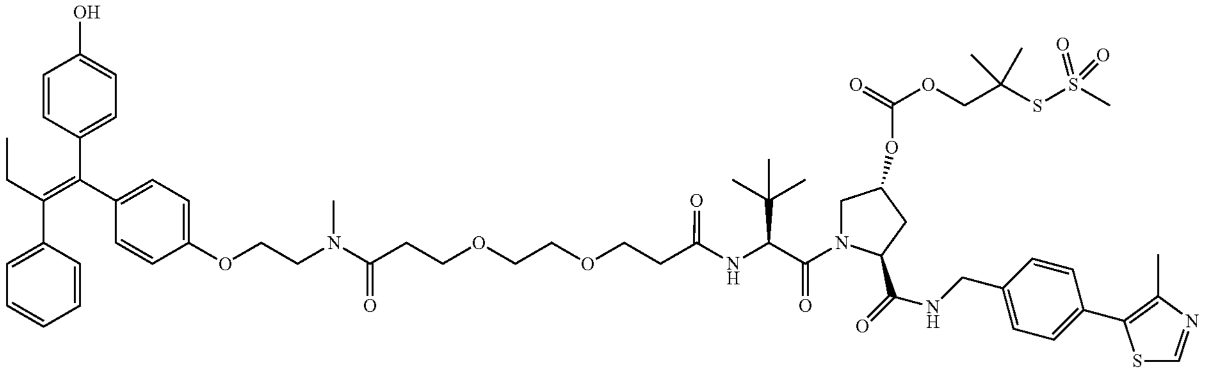

10

Step 1: Ethyl 2-acetylsulfanyl-2-methyl-propanoate (JJ). To a solution of potassium ethanethioate (5.0 g, 44 mmol) in DMF (50 mL) was added ethyl 2-bromoisobutyrate (25.6 g, 131 mmol). The reaction was stirred at room temperature. for 2 h then was concentrated under reduced pressure. The residue was purified by silica gel column chromatography (0-10% EtOAc in petroleum ether) to afford compound JJ (7.00 g, 84%) as a colorless liquid.

Step 2: 2-mercapto-2-methylpropan-1-ol (KK). To a solution of lithium aluminium hydride (2.0 g, 53 mmol) in THF (20 mL) was added dropwise to a solution of ethyl 2-acetylsulfanyl-2-methyl-propanoate (JJ, 2.0 g, 10.5 mmol) in THF (10 mL) at 0° C. The reaction was stirred at 75° C. for 2 h and then was quenched by the addition of EtOAc (20 mL) and HCl (2.0 M, 50 mL) at 0° C. The mixture was separated and the aqueous layer was extracted with EtOAc (20 mL×3). The combined organic layers were washed with brine (10 mL), dried over anhydrous $Na_2SO_4$ and filtered. The filtrate was concentrated to afford crude compound KK (0.90 g) as a yellow oil. This material was directly used in the next step without further purification. $^1$H NMR (400 MHz, $CDCl_3$) δ 4.19-4.09 (m, 1H), 3.43 (s, 2H), 1.63 (s, 1H), 1.35 (s, 6H).

Step 3: 2-methyl-2-((5-nitropyridin-2-yl)disulfanyl)propan-1-ol (LL). To a solution of 2-methyl-2-sulfanyl-propan-1-ol (KK, 0.90 g, 8.40 mmol) in MeOH (30 mL) and DCM (30 mL) was added 2,2'-dithiobis(5-nitropyridine) (2.60 g, 8.50 mmol). The reaction mixture was stirred at room temperature for 16 h. $MnO_2$ (0.20 g) was then added, and the mixture was stirred for an additional 0.5 h. The reaction mixture was filtered, and the filtrate was purified by silica gel column chromatography (0-50% EtOAc in petroleum ether) to afford compound LL (1.10 g, 50%) as a white solid. $^1$H NMR (400 MHz, $CDCl_3$) δ 9.32 (d, J=4.0 Hz, 1H), 8.36-7.34 (m, 1H), 7.60 (d, J=8.0 Hz, 1H), 4.70 (s, 1H), 3.32 (d, J=8.0 Hz, 2H), 1.37 (s, 6H).

Step 4: S-(1-hydroxy-2-methylpropan-2-yl)-methanesulfonothioate (MM). Sodium methane sulfinate (2.20 g, 21 mmol) and iodine (2.10 g, 8.40 mmol) were added sequentially to a solution of 2-methyl-2-[(5-nitro-2-pyridyl)disulfanyl]propan-1-ol (LL, 1.1 g, 4.2 mmol) in DCM (20 mL) at room temperature. After the reaction mixture was stirred at 50° C. for 24 h, it was filtrated, and the filtrate was purified by silica gel column chromatography (0-50% EtOAc in petroleum ether) to give compound MM (660 mg, 85%) as a yellow oil. $^1H$ NMR (400 MHz, $CDCl_3$) δ 3.81 (s, 2H), 3.40 (s, 3H), 1.54 (s, 6H).

Step 5: 3,3'-(ethane-1,2-diylbis(oxy))dipropanoic acid (II). To a solution of ethyl 3,3'-(ethane-1,2-diylbis(oxy)) dipropanoate (AA, prepared as described in the synthesis of compound 3 above; 2.30 g, 8.7 mmol) in EtOH (40 mL) and water (2.0 mL) was added potassium hydroxide (492 mg, 8.7 mmol). The reaction was stirred at 85° C. for 1 h then was concentrated under reduced pressure. The residue was diluted with $H_2O$ (20 mL), and the pH was adjusted to about 9.0 by the addition of saturated $NaHCO_3$ solution (10 mL). The mixture was extracted with EtOAc (20 mL×2), and the aqueous phase was adjusted to pH=3.0 with HCl (2.0 M) solution and extracted with iPrOH/$CHCl_3$ (1:3). The combined organic layers were dried over $Na_2SO_4$, filtered, and were concentrated to afford compound NN (1.30 g, 75%) as a colorless oil. $^1H$ NMR (400 MHz, $CD_3OD$) δ 3.76-3.70 (m, 4H), 3.62-3.58 (m, 4H), 2.58-2.50 (m, 4H).

Step 6: 3-(2-(3-((2-(4-(1-(4-hydroxyphenyl)-2-phenylbut-1-en-1-yl)phenoxy)ethyl)-(methyl)amino)-3-oxopropoxy) ethoxy)propanoic acid (00). To a solution of 3,3'-(ethane-1, 2-diylbis(oxy))dipropanoic acid (NN, 828 mg, 4.0 mmol) in DMF (13 mL) was added $(iPr)_2NEt$ (865 mg, 6.69 mmol) and HATU (559 mg, 1.47 mmol). The solution was stirred at 25° C. for 10 min, then 4-(1-(4-(2-(methylamino)ethoxy) phenyl)-2-phenylbut-1-en-1-yl)phenol (K, prepared as described in: *Breast Cancer Research and Treatment* 2004, 85, 151; 500 mg, 1.3 mmol) was added. The reaction was stirred at room temperature for 1 h then was directly purified by preparative HPLC [Waters Xbridge 150*25 5 u (MeCN 26-46/0.1% $NH_4HCO_3$ in water)] to afford compound 00 (290 mg, 38%) as a white solid. LCMS (ESI) m/z: 562.1 $[M+H]^+$.

Step 7: S-(1-(((((3R,5S)-1-((S)-2-((tert-butoxycarbonyl) amino)-3,3-dimethylbutanoyl)-5-((4-(4-methylthiazol-5-yl) benzyl)carbamoyl)pyrrolidin-3-yl)oxy)carbonyl)oxy)-2-methylpropan-2-yl) methanesulfonothioate (QQ). A solution of triphosgene (0.050 mL, 0.30 mmol) in DCM (2.0 mL) was added dropwise to a solution of pyridine (0.040 mL, 0.50 mmol) and 2-methyl-2-methylsulfonylsulfanyl-propan-1-ol (MM, 100 mg, 0.50 mmol) in DCM (2.0 mL) at room temperature. After the resulting mixture was stirred at room temperature for 30 min, a solution of tert-butyl ((S)-1-((2S, 4R)-4-hydroxy-2-((4-(4-methylthiazol-5-yl)benzyl)carbamoyl) pyrrolidin-1-yl)-3,3-dimethyl-1-oxobutan-2-yl)carbamate (PP, prepared as described in: *J. Med. Chem.* 2018, 61, 599; 220 mg, 0.40 mmol) in DCM (10 mL) and $Et_3N$ (0.11 mL, 0.80 mmol) was added. The reaction mixture was stirred at room temperature for 2 h then was concentrated under reduced pressure. The residue was purified by silica gel column chromatography (0-5% MeOH in DCM) to provide compound QQ (230 mg, 76%) as a yellow oil. LCMS (ESI) m/z: 763.0 [M+H]+.

Step 8: S-(1-(((((3R,5S)-1-((S)-2-amino-3,3-dimethylbutanoyl)-5-((4-(4-methylthiazol-5-yl)benzyl)carbamoyl)pyrrolidin-3-yl)oxy)carbonyl)oxy)-2-methylpropan-2-yl) methanesulfonothioate (RR). Trifluoroacetic acid (0.3 mL, 0.04 mmol) was added dropwise to a solution of S-(1-(((((3R, 5S)-1-((S)-2-((tert-butoxycarbonyl)amino)-3,3-dimethylbutanoyl)-5-((4-(4-methylthiazol-5-yl)benzyl)carbamoyl)pyrrolidin-3-yl)oxy)carbonyl)oxy)-2-methylpropan-2-yl) methanesulfonothioate (QQ, 30 mg, 0.04 mmol) in 1,1,1,3, 3,3-hexafluoro-2-propanol (6 mL, 0.04 mmol) at room temperature. The reaction mixture was stirred at room temperature for 1 h then was concentrated under reduced pressure. The crude product RR (28 mg) was used without further purification in the subsequent step. LCMS (ESI) m/z: 641.1 [M+H]+.

Step 9: S-(1-(((((3R,5S)-1-((S)-2-(tert-butyl)-16-(4-(1-(4-hydroxyphenyl)-2-phenylbut-1-en-1-yl)phenoxy)-14-methyl-4,13-dioxo-7,10-dioxa-3,14-diazahexadecan-1-oyl)-5-((4-(4-methylthiazol-5-yl)benzyl)carbamoyl)pyrrolidin-3-yl)oxy)carbonyl)oxy)-2-methylpropan-2-yl) methanesulfonothioate (10). A solution of 3-(2-(3-((2-(4-(1-(4-hydroxyphenyl)-2-phenylbut-1-en-1-yl)phenoxy)ethyl) (methyl)amino)-3-oxopropoxy)ethoxy)propanoic acid (00, 28 mg, 0.050 mmol), $(iPr)_2NEt$ (0.03 mL, 0.16 mmol) and HATU (19 mg, 0.05 mmol) in anhydrous DMF (1.0 mL) was stirred at room temperature for 20 min. To the resulting mixture was added S-(1-(((((3R,5S)-1-((S)-2-amino-3,3-dimethylbutanoyl)-5-((4-(4-methylthiazol-5-yl)benzyl)carbamoyl)pyrrolidin-3-yl)oxy)carbonyl)oxy)-2-methylpropan-2-yl) methanesulfonothioate (RR, 25 mg, 0.040 mmol) and the reaction was stirred at room temperature for an additional 2 h. The mixture was then filtered, and the filtrate was purified by preparative HPLC [Xtimate C18 150*25 mm*5 um (MeCN 55-85/0.225% formic acid in water)] to afford compound 10 (L1EC10) (4.5 mg, 9.6%) as a white solid. LCMS (ESI) m/z: 641.1 [M+H]+. $^1H$ NMR (400 MHz, DMSO-$d_6$) δ 9.42 (s, 0.3H), 9.17 (s, 0.7H), 8.98 (s, 1H), 8.62 (t, J=6.0 Hz, 1H), 7.95 (d, J=8.8 Hz, 1H), 7.42-7.38 (m, 4H), 7.21-7.14 (m, 2H), 7.13-7.04 (m, 2H), 6.95-6.87 (m, 2H), 6.75-6.69 (m, 1H), 6.65-6.57 (m, 2H), 6.41-6.37 (m, 1H), 5.24 (s, 1H), 4.49-4.37 (m, 3H), 4.36-4.34 (m, 2H), 4.33-4.31 (m, 1H), 4.30 (s, 3H), 4.28-4.21 (m, 2H), 4.20-4.01 (m, 1H), 3.78-3.75 (m, 1H), 3.63-3.57 (m, 4H), 3.54-3.35 (m, 5H), 3.06 (s, 1H), 2.98 (s, 0.5H), 2.87 (s, 1H), 2.80 (s, 0.5H), 2.70-2.52 (m, 3H), 2.43-2.25 (m, 5H), 2.24-1.98 (m, 1H), 1.52 (s, 3H), 1.49 (s, 3H), 1.25-1.22 (m, 2H), 0.94 (s, 9H), 0.85-0.81 (m, 3H). $^{13}C$ NMR (100 MHz, DMSO-$d_6$) 171.2, 170.5, 170.4, 169.7, 163.1, 156.9, 156.1, 156.0, 155.9, 155.2, 153.5, 151.5, 147.7, 142.1, 134.0, 139.8, 139.2, 137.8, 137.7, 135.9, 135.6, 133.9, 133.6, 131.4, 131.1, 130.1, 129.7, 129.4, 128.7, 127.9, 127.8, 127.4, 129.6, 114.9, 114.3, 114.0, 113.2, 77.3, 72.7, 69.6, 69.4, 66.9, 66.5, 65.5, 58.2, 57.0, 55.7, 53.4, 53.0, 48.2, 46.5, 41.7, 36.4, 36.3, 35.5, 34.7, 33.3, 33.20, 33.1, 32.6, 28.9, 28.5, 26.2, 25.0, 15.9, 13.4. HRMS (5-95AB_4MIN_neg, ESI), m/z 1184.4736 $[M+H]^+$.

vi. L1EC11 An exemplary L1-CIDE, L1EC11, was synthesized as follows:

11

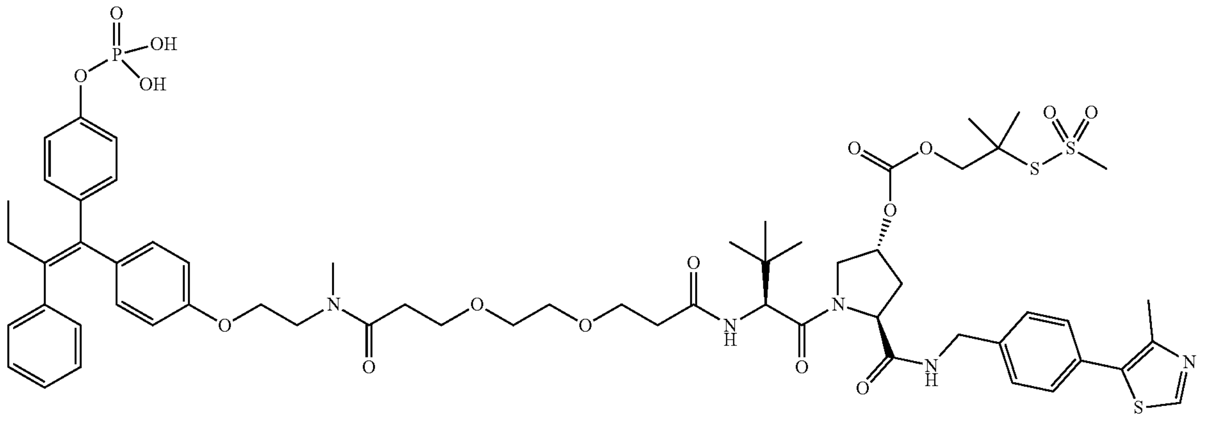

S-(1-(((((3R,5S)-1-((S)-2-(tert-butyl)-14-methyl-4,13-dioxo-16-(4-(2-phenyl-1-(4-(phosphonooxy)phenyl)but-1-en-1-yl)phenoxy)-7,10-dioxa-3,14-diazahexadecan-1-oyl)-5-((4-(4-methylthiazol-5-yl)benzyl)carbamoyl)pyrrolidin-3-yl)oxy)carbonyl)oxy)-2-methylpropan-2-yl) methanesulfonothioate (11, "L1EC11"). Pyrophosphoryl chloride (42 mg, 0.17 mmol) was added dropwise to a solution of S-(1-(((((3R,5S)-1-((S)-2-(tert-butyl)-16-(4-(1-(4-hydroxyphenyl)-2-phenylbut-1-en-1-yl)phenoxy)-14-methyl-4,13-dioxo-7,10-dioxa-3,14-diazahexadecan-1-oyl)-5-((4-(4-methylthiazol-5-yl)benzyl)carbamoyl)pyrrolidin-3-yl)oxy)carbonyl)oxy)-2-methylpropan-2-yl) methanesulfonothioate (10, 80 mg, 0.070 mmol) in THF (1 mL) at −40° C. The reaction mixture was stirred at −40° C. for 2 h then was quenched with ice-water (3 mL). The mixture was treated with saturated aqueous $NaHCO_3$ (5.0 mL) and HCl (1.0 M, 2.0 mL) then was extracted with EtOAc (10 mL×3). The combined organic layers were washed with brine (10 mL×2) and were concentrated. The residue was purified by preparative HPLC [Waters Xbridge 150*25 5 u (MeCN 25-55/0.01% $NH_4HCO_3$ in water)] to afford compound 11 (L1EC11) (25 mg, 30%) as a white solid. LCMS (ESI) m/z: 632.9 [M+H]+. $^1$H NMR (400 MHz, DMSO-$d_6$) δ 8.98 (s, 1H), 8.72-8.67 (m, 1H), 8.01-7.92 (m, 1H), 7.49-7.36 (m, 4H), 7.25-7.18 (m, 5H), 7.17-7.09 (m, 5H), 7.08-6.94 (m, 1H), 6.93-6.90 (m, 1H), 6.75-6.67 (m, 2H), 6.65-6.59 (m, 2H), 5.24 (s, 1H), 4.49-4.31 (m, 6H), 4.30-4.21 (m, 2H), 4.20-4.01 (m, 2H), 3.78-3.71 (m, 1H), 3.60-3.57 (m, 3H), 3.56-3.54 (m, 2H), 3.45-3.35 (m, 6H), 3.06 (s, 1H), 2.98 (s, 0.5H), 2.87 (s, 1H), 2.80 (s, 0.5H), 2.70-2.65 (m, 1H), 2.52-2.49 (m, 1H), 2.43 (s, 3H), 2.41-2.28 (m, 5H), 2.22-2.01 (m, 1H), 1.51 (s, 3H), 1.48 (s, 3H), 0.94 (s, 9H), 0.85-0.81 (m, 3H). $^{13}$C NMR (100 MHz, DMSO-$d_6$) δ 171.4, 170.3, 169.7, 165.0, 160.9, 157.7, 153.5, 153.5, 151.5, 151.1, 147.8, 139.3, 131.2, 129.7, 128.7, 127.4, 113.7, 113.4, 77.4, 72.7, 69.4, 66.9, 65.5, 58.2, 56.9, 55.7, 53.0, 41.7, 40.4, 36.2, 35.5, 34.7, 30.3, 29.1, 29.0, 28.8, 28.7, 28.6, 26.6, 26.3, 25.0, 22.1, 15.9, 13.9. HRMS (50-100AB_4MIN_neg, ESI), m/z 1262.3861 [M−H]−.

vii. L1EC12 An exemplary L1-CIDE, L1EC12, can be synthesized by the following scheme.

Scheme 9

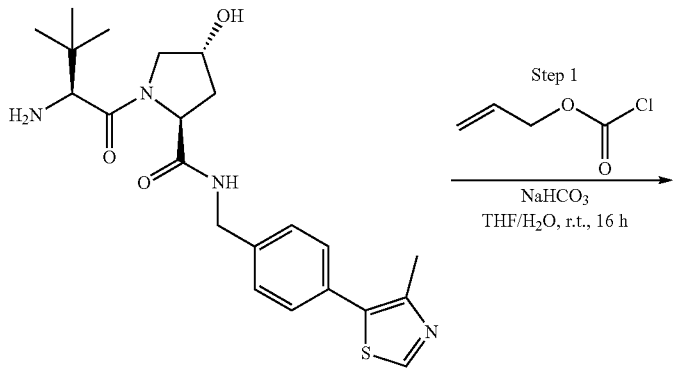

CC

-continued
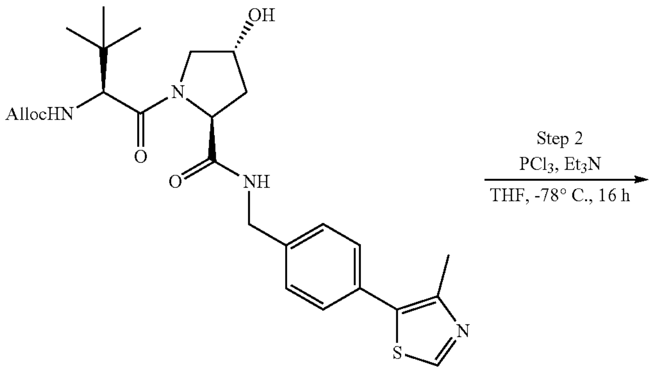
SS
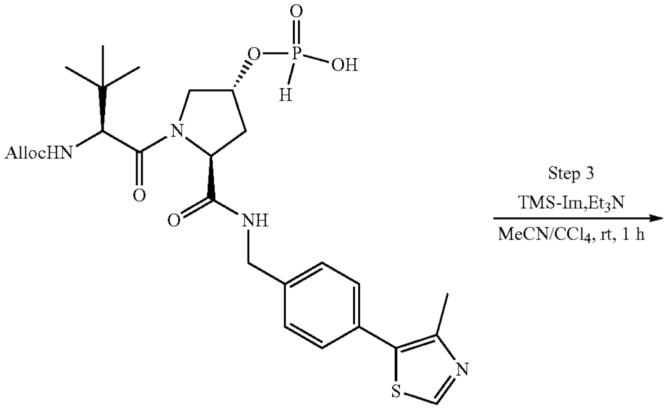
TT
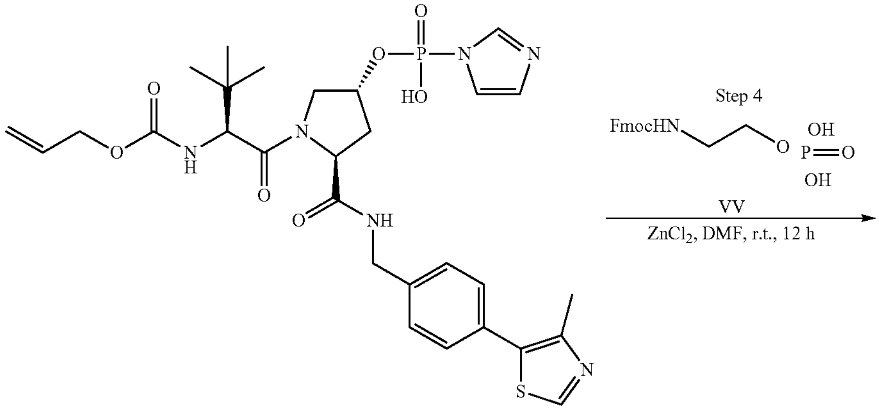
UU

-continued
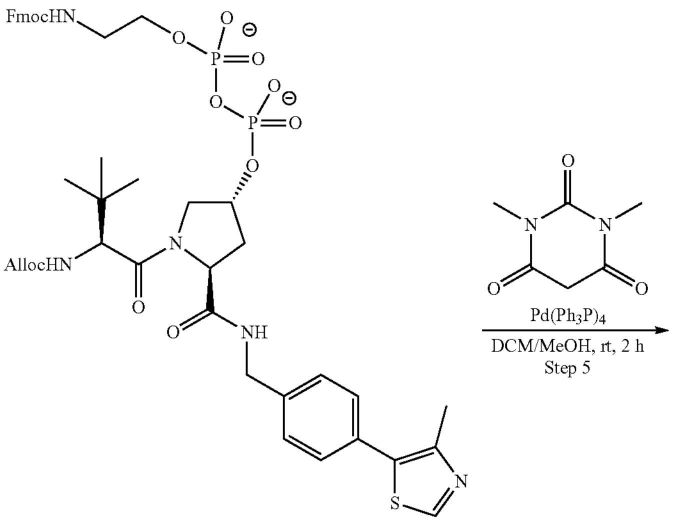
WW
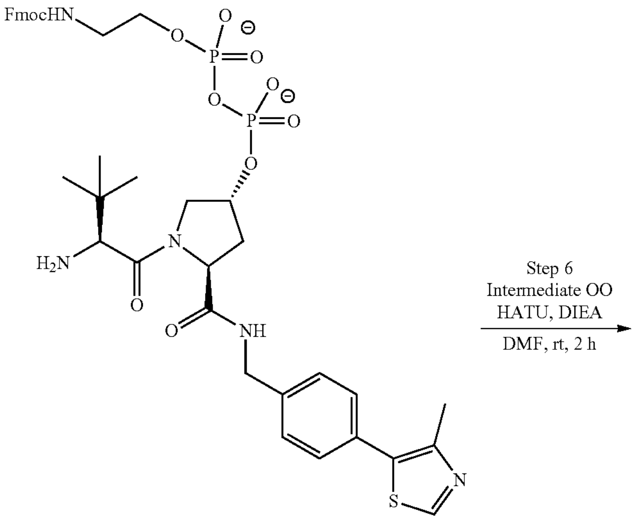
XX
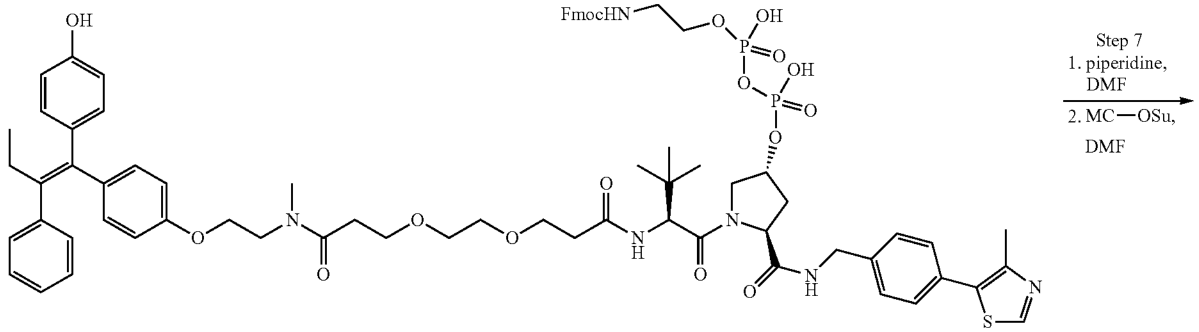
YY

-continued

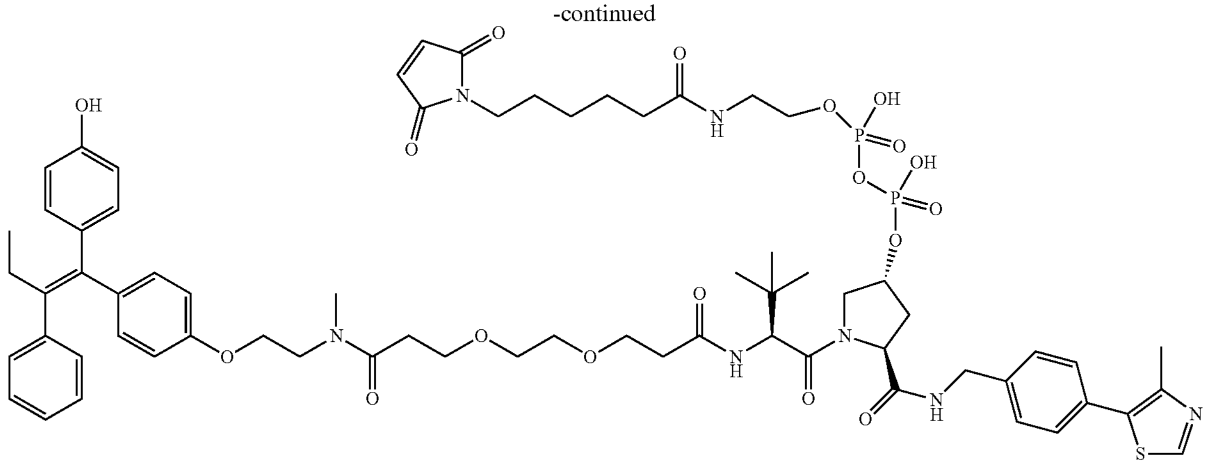

12

Step 1: Allyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (SS). Allyl chloroformate (440 mg, 3.60 mmol) was added dropwise to a solution of (2S,4R)-1-((S)-2-amino-3,3-dimethylbutanoyl)-4-hydroxy-N-(4-(4-methylthiazol-5-yl)benzyl)pyrrolidine-2-carboxamide (CC, TFA salt, prepared as described in: *J. Med. Chem.* 2018, 61, 599; 1.50 g, 3.40 mmol) and $NaHCO_3$ (1.46 g, 17.4 mmol) in water (4.0 mL) and THF (4 mL) at 0° C. The mixture was warmed to 25° C. and was maintained at that temperature for 16 h. The reaction was then diluted with water (10 mL), and the resulting mixture was extracted with EtOAc (15 mL×3). The combined organic layers were washed with brine (10 mL), dried over anhydrous $Na_2SO_4$ and were filtered. The filtrate was concentrated under reduced pressure, and the residue was purified by a silica gel column chromatography (0-5% MeOH in DCM) to give compound SS (1.40 g, 78%) as a gray solid. LCMS (ESI) m/z: 514.0 [M+H]+.

Step 2: Allyl ((2S)-1-((2S,4R)-4-((hydroxyhydrophosphoryl)oxy)-2-((4-(4-methylthiazol-5-yl)benzyl)carbamoyl)pyrrolidin-1-yl)-3,3-dimethyl-1-oxobutan-2-yl)carbamate (TT). A solution of phosphorus trichloride (373 mg, 2.72 mmol) in THF (1.0 mL) and a solution of $Et_3N$ (688 mg, 6.8 mmol) in THF (2.0 mL) were added sequentially to a solution of allyl ((S)-1-((2S,4R)-4-hydroxy-2-((4-(4-methylthiazol-5-yl)benzyl)carbamoyl)-pyrrolidin-1-yl)-3,3-dimethyl-1-oxobutan-2-yl)carbamate (SS, 700 mg, 1.36 mmol) in THF (12 mL) at −78° C. The reaction mixture was stirred at −78° C. for 20 min then was allowed to warm to 25° C. After stirring at that temperature for 16 h, the reaction was quenched by the addition of water (2.0 mL) and aq $NaHCO_3$ (5.0 mL). The resulting mixture was stirred at 25° C. for 10 min, then was acidified with HCl (1.0 M) to pH=3.0 and concentrated under reduced pressure. The residue was purified by prep-TLC (12% MeOH in DCM) to afford compound TT (400 mg, 51%) as a colorless solid. LCMS (ESI) m/z: 579.1 [M+H]+.

Step 3: Allyl ((2S)-1-((2S,4R)-4-((hydroxy(1H-imidazol-1-yl)phosphoryl)oxy)-2-((4-(4-methylthiazol-5-yl)benzyl)carbamoyl)pyrrolidin-1-yl)-3,3-dimethyl-1-oxobutan-2-yl)carbamate (UU). N-Trimethylsilylimidazole (727 mg, 5.2 mmol) was added to a solution of allyl ((2S)-1-((2S,4R)-4-((hydroxyhydrophosphoryl)oxy)-2-((4-(4-methylthiazol-5-yl)benzyl)carbamoyl)pyrrolidin-1-yl)-3,3-dimethyl-1-oxobutan-2-yl)carbamate (TT, 750 mg, 1.3 mmol) and $Et_3N$ (0.72 mL, 5.2 mmol) in carbon tetrachloride (4 mL) and MeCN (4.0 mL) at 25° C. The reaction mixture was stirred at that temperature for 50 min then was treated with MeOH (0.10 mL) and stirred for an additional 10 min. The solvent was removed under reduced pressure, and the residue was washed with 5/1 MTBE/EtOAc (3.0 mL). The resulting precipitate was removed by filtration and was washed with MTBE (3.0 mL). Concentration of the filtrate and washings afforded compound UU (830 mg, 95%) that was used in the next step without additional purification. LCMS (ESI) m/z: 645.3 [M+H]+.

Step 4: 9H-fluoren-9-ylmethyl N-[2-[[[(3R,5S)-1-[(2S)-2-(allyloxycarbonylamino)-3,3-dimethyl-butanoyl]-5-[[4-(4-methylthiazol-5-yl)phenyl]methylcarbamoyl]pyrrolidin-3-yl]oxy-hydroxy-phosphoryl]oxy-hydroxy-phosphoryl]oxyethyl]carbamate (WW). To a room temperature solution of allyl ((2S)-1-((2S,4R)-4-((hydroxy(1H-imidazol-1-yl)phosphoryl)oxy)-2-((4-(4-methylthiazol-5-yl)benzyl)carbamoyl)pyrrolidin-1-yl)-3,3-dimethyl-1-oxobutan-2-yl)carbamate (UU, 830 mg, 1.29 mmol) and (9H-fluoren-9-yl)methyl (2-(phosphonooxy)ethyl)carbamate (VV, prepared as described in: J. Am. Chem. Soc. 2016, 138, 1430; 514 mg, 1.42 mmol) in DMF (3.5 mL) was added zinc chloride solution in toluene (1.0 M, 12.8 mL, 12.8 mmol). The reaction was stirred at room temperature for 12 h, then was directly purified by preparative HPLC [Waters Xbridge 150*25 5 u (MeCN 20-40/10 mM $NH_4HCO_3$ in water)] to afford compound WW (400 mg, 33%) as a white solid. LCMS (ESI) m/z: 940.1 $[M+H]^+$.

Step 5: 9H-fluoren-9-ylmethyl N-[2-[[[(3R,5S)-1-[(2S)-2-amino-3,3-dimethyl-butanoyl]-5-[[4-(4-methylthiazol-5-yl)phenyl]methylcarbamoyl]pyrrolidin-3-yl]oxy-hydroxy-phosphoryl]oxy-hydroxy-phosphoryl]oxyethyl]carbamate (XX). To a solution of 9H-fluoren-9-ylmethyl N-[2-[[[(3R,5S)-1-[(2S)-2-(allyloxycarbonylamino)-3,3-dimethyl-butanoyl]-5-[[4-(4-methylthiazol-5-yl)phenyl]methylcarbamoyl]pyrrolidin-3-yl]oxy-hydroxy-phosphoryl]-oxy-hydroxy-phosphoryl]oxyethyl]carbamate (WW, 150 mg, 0.16 mmol) and 1,3-dimethylbarbituric acid (125 mg, 0.80 mmol) in DCM (6.0 mL) and MeOH (0.60 mL) was added tetrakis(triphenylphosphine)palladium (37 mg, 0.030 mmol) at 25° C. The reaction mixture was stirred at that temperature for 2 h then was directly purified by preparative HPLC [Waters Xbridge 150*25 5 u (MeCN 15-45/10 mM $NH_4HCO_3$ in water)] to afford compound XX (78 mg, 57%) as a yellow solid. LCMS (ESI) m/z: 856.1 [M+H]+.

Step 6: 9H-fluoren-9-ylmethyl N-[2-[hydroxy-[hydroxy-[(3R,5S)-1-[(2S)-2-[3-[2-[3-[2-[4-[1-(4-hydroxyphenyl)-2-phenyl-but-1-enyl]phenoxy]ethyl-methyl-amino]-3-oxo-propoxy]ethoxy]propanoylamino]-3,3-dimethyl-butanoyl]-5-[[4-(4-methylthiazol-5-yl)phenyl]methylcarbamoyl]pyrrolidin-3-yl]oxy-phosphoryl]oxy-phosphoryl]oxyethyl]carbamate (YY). A solution of 3-(2-(3-((2-(4-(1-(4-hydroxyphenyl)-2-phenylbut-1-en-1-yl)phenoxy)ethyl)(methyl)amino)-3-oxopropoxy)ethoxy)propanoic acid (00, prepared as described above in the synthesis of compound 10; 210 mg, 0.37 mmol), $(iPr)_2NEt$ (0.12 mL, 0.75 mmol) and HATU (142 mg, 0.37 mmol) in anhydrous DMF (3.0 mL) was stirred at 25° C. for 20 min. 9H-fluoren-9-ylmethyl N-[2-[[[(3R,5S)-1-[(2S)-2-amino-3,3-dimethyl-butanoyl]-5-[[4-(4-methylthiazol-5-yl)phenyl]methylcarbamoyl]-pyrrolidin-3-yl]oxy-hydroxy-phosphoryl]oxy-hydroxy-phosphoryl]oxyethyl]carbamate (XX, 80 mg, 0.09 mmol) was then added, and the resulting mixture was stirred at 25° C. for 2 h. The reaction mixture was subsequently purified directly by prepartive HPLC [Waters Xbridge 150*25 5 u (MeCN 32-62/10 mM $NH_4HCO_3$ in water)] to afford compound TT (60 mg, 45%) as a white solid. LCMS (ESI) m/z: 1400.2 [M+H]+.

Step 7: [2-[6-(2,5-dioxopyrrol-1-yl)hexanoylamino]ethoxy-hydroxy-phosphoryl][(3R,5S)-1-[(2S)-2-[3-[2-[3-[2-[4-[1-(4-hydroxyphenyl)-2-phenyl-but-1-enyl]phenoxy]ethyl-methyl-amino]-3-oxo-propoxy]ethoxy]propanoylamino]-3,3-dimethyl-butanoyl]-5-[[4-(4-methylthiazol-5-yl)phenyl]methylcarbamoyl]pyrrolidin-3-yl] hydrogen phosphate (12). Part A. Piperidine (14 mg, 0.16 mmol) was added dropwise to a solution of 9H-fluoren-9-ylmethyl N-[2-[hydroxy-[hydroxy-[(3R,5S)-1-[(2S)-2-[3-[2-[3-[2-[4-[1-(4-hydroxy-phenyl)-2-phenyl-but-1-enyl]phenoxy]ethyl-methyl-amino]-3-oxo-propoxy]ethoxy]-propanoylamino]-3,3-dimethyl-butanoyl]-5-[[4-(4-methylthiazol-5-yl)phenyl]methyl-carbamoyl]pyrrolidin-3-yl]oxy-phosphoryl]oxy-phosphoryl]oxyethyl]carbamate (YY, 46 mg, 0.030 mmol) in DMF (0.50 mL) at 25° C. The reaction mixture was stirred at that temperature for 1 h then was concentrated under reduced pressure. The resulting residue was purified by preparative HPLC [Waters Xbridge 150*25 5 u (MeCN 25-55/10 mM $NH_4HCO_3$ in water)] to afford [2-aminoethoxy(hydroxy)phosphoryl] [(3R,5S)-1-[(2S)-2-[3-[2-[3-[2-[4-[1-(4-hydroxyphenyl)-2-phenyl-but-1-enyl]phenoxy]ethyl-methyl-amino]-3-oxo-propoxy]ethoxy]propanoylamino]-3,3-dimethyl-butanoyl]-5-[[4-(4-methylthiazol-5-yl)phenyl]methylcarbamoyl]pyrrolidin-3-yl]hydrogen phosphate (not shown in scheme; 30 mg, 78%) as a white solid. LCMS (ESI) m/z: 1177.4 [M+H]+.

Part B. To a solution of $(iPr)_2NEt$ (6.6 mg, 0.05 mmol) and [2-aminoethoxy(hydroxy)phosphoryl] [(3R,5S)-1-[(2S)-2-[3-[2-[3-[2-[4-[1-(4-hydroxyphenyl)-2-phenyl-but-1-enyl]phenoxy]ethyl-methyl-amino]-3-oxo-propoxy]ethoxy]propanoylamino]-3,3-dimethyl-butanoyl]-5-[[4-(4-methylthiazol-5-yl)phenyl]methylcarbamoyl]pyrrolidin-3-yl]hydrogen phosphate (prepared in part A above; 30 mg, 0.030 mmol) in DMF (1.0 mL) was added 6-maleimido-hexanoic acid N-hydroxysuccinimide ester (MC-OSu, Aldrich; 19.6 mg, 0.06 mmol) at 25° C. The reaction mixture was stirred at that temperature for 8 h then was filtered. The filtrate was purified by prepartive HPLC [Waters Xbridge 150*25 5 u (MeCN 25-55%/10 mM $NH_4HCO_3$ in water)] to afford compound 12 ("L1EC12") (9.5 mg, 26%) as a white solid. LCMS (ESI) m/z: 641.5 [M+H]+. $^1H$ NMR (400 MHz, DMSO-$d_6$) δ 8.97 (s, 1H), 8.85 (s, 1H), 8.72 (s, 1H), 7.96 (t, J=8.0 Hz, 1H), 7.46-7.36 (m, 6H), 7.18-7.14 (m, 2H), 7.13-7.04 (m, 5H), 6.98 (s, 2H), 6.95-6.92 (m, 2H), 6.76-6.68 (m, 1H), 6.67-6.61 (m, 1H), 6.59-6.55 (m, 2H), 6.42-6.40 (m, 1H), 4.78-4.71 (s, 1H), 4.57-4.52 (m, 1H), 4.51-4.41 (m, 2H), 4.28-4.21 (m, 1H), 4.20-4.01 (m, 1H), 3.78-3.75 (m, 1H), 3.63-3.57 (m, 5H), 3.54-3.49 (m, 8H), 3.48-3.41 (m, 6H), 3.38-3.35 (m, 2H), 3.07 (s, 1H), 2.98 (s, 1H), 2.80 (s, 1H), 2.75 (s, 1H), 2.65-2.62 (m, 1H), 2.44 (s, 3H), 2.05-1.98 (m, 2H), 1.95-1.85 (m, 1H), 1.54-1.43 (m, 6H), 1.26-1.12 (m, 3H), 0.92 (s, 9H), 0.85-0.81 (m, 3H). $^{13}C$ NMR (100 MHz, DMSO-$d_6$) δ 171.7, 171.1, 159.3, 158.4, 155.3, 151.5, 147.7, 142.2, 139.4, 134.5, 131.4, 131.2, 130.2, 130.1, 129.7, 129.4, 128.7, 127.8, 127.4, 115.0, 114.3, 113.3, 69.6, 69.4, 67.0, 66.6, 63.5, 62.5, 59.9, 57.6, 57.6, 56.4, 55.1, 41.7, 36.5, 35.7, 35.5, 34.9, 33.1, 32.6, 30.9, 29.1, 28.7, 28.6, 27.8, 26.3, 25.9, 24.8, 15.9, 15.9, 13.4. HRMS (50-100AB_4MIN_neg, ESI), m/z 1385.4942 [M−H+NH3]−.

Syntheses of Exemplary BRD4 Targeting CIDEs and BRD4 Targeting L1-CIDES viii. L1BC1 An exemplary L1-CIDE, L1BC1, can be synthesized by the following scheme:

Scheme 10

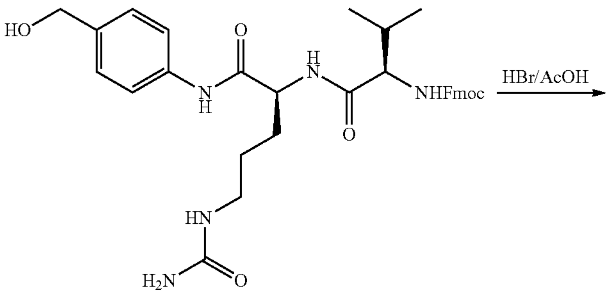

1

-continued
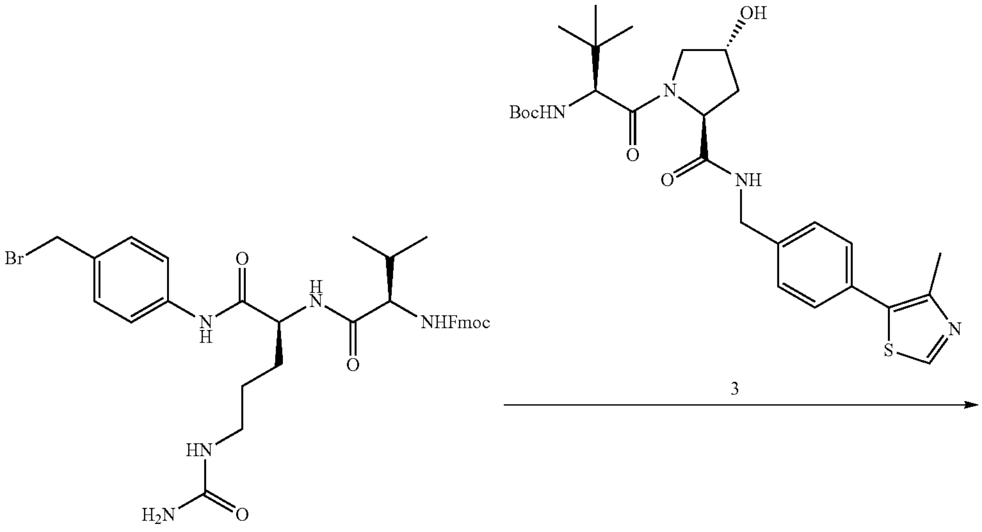
2
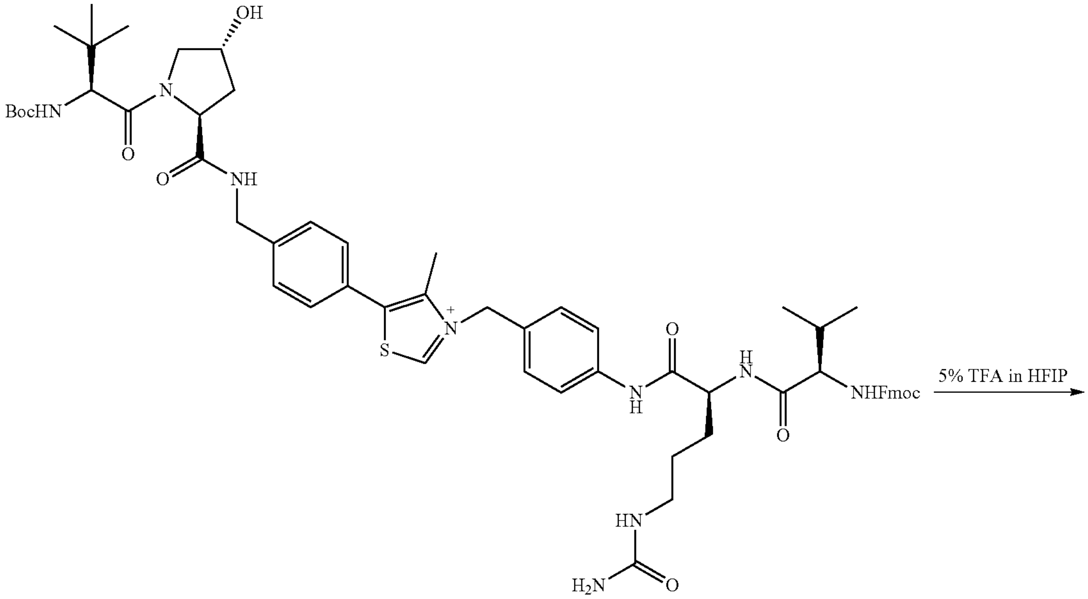
4
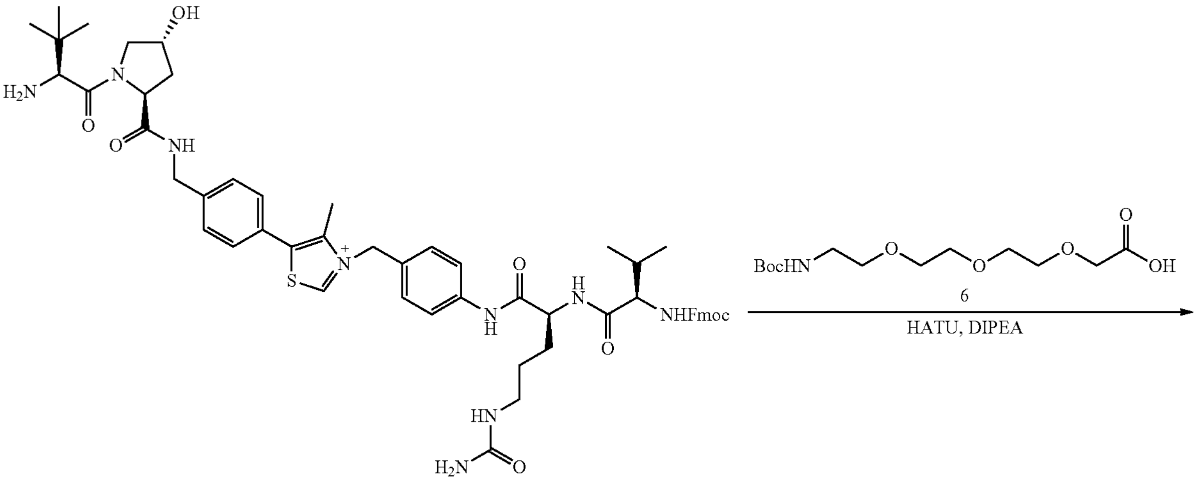
5

-continued
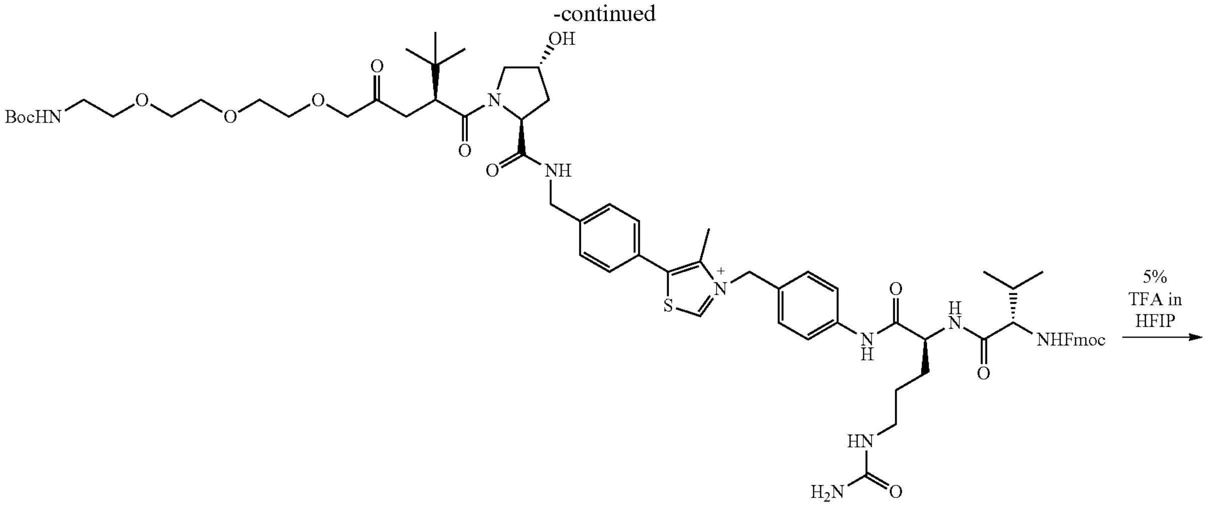
7
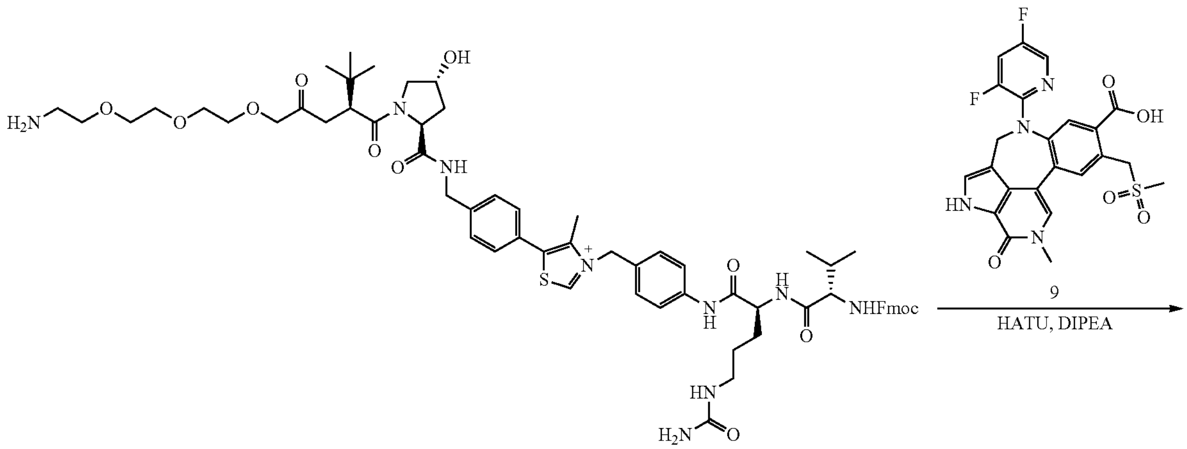
9
8
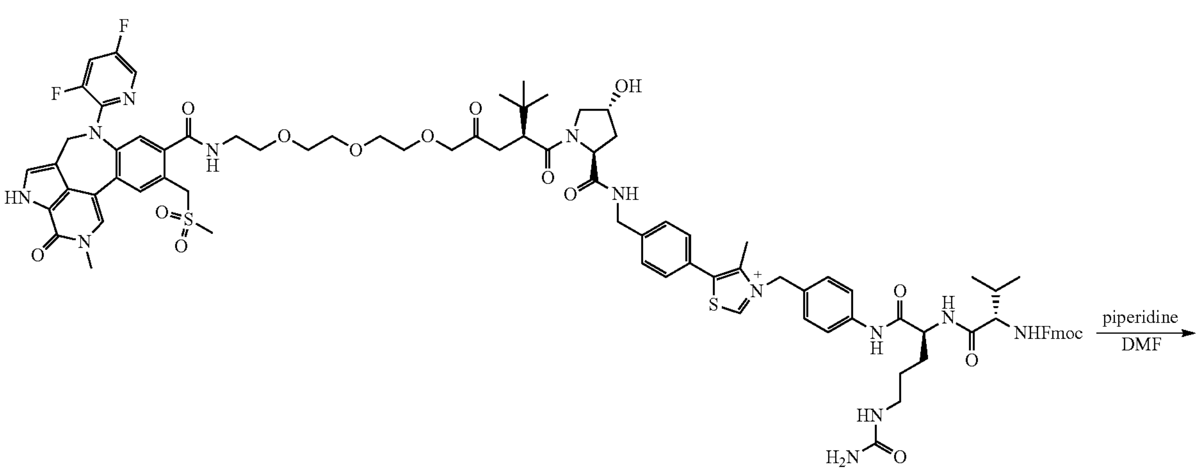
10

-continued
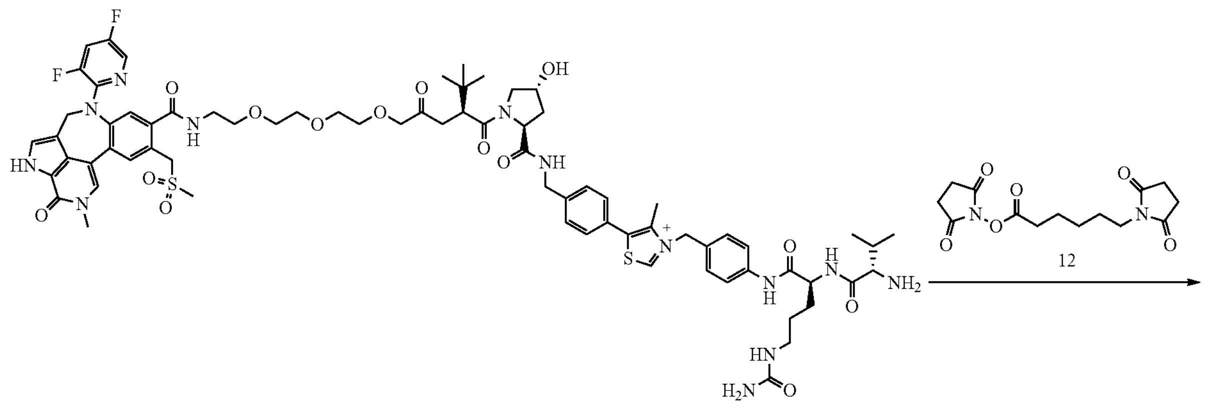
11
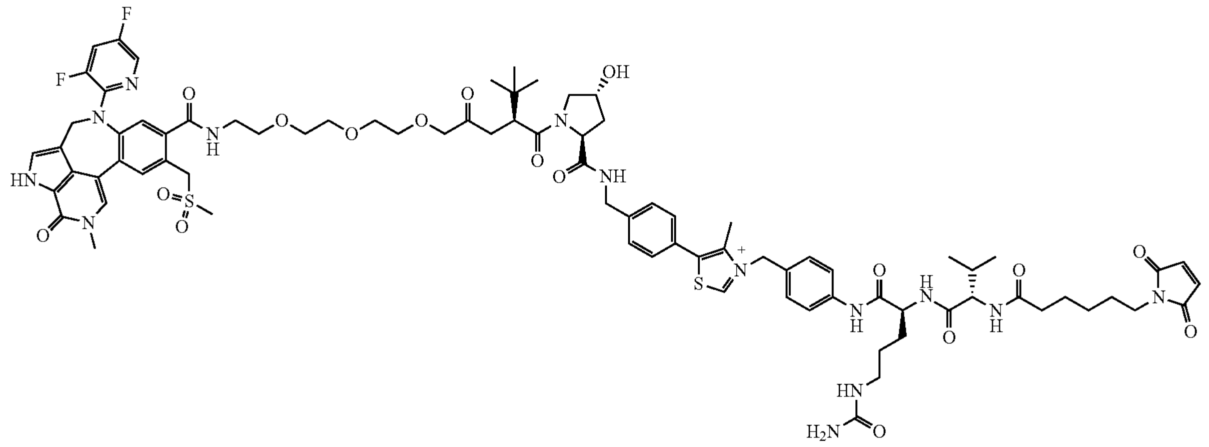
L1BC1
-continued
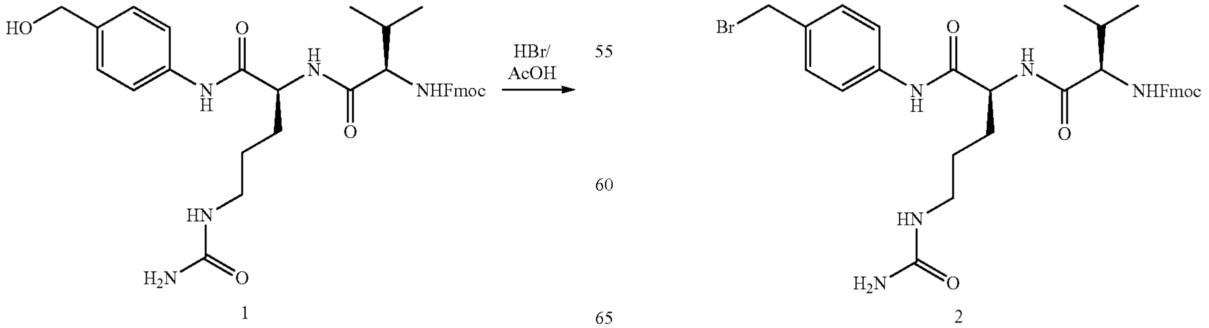
1 2

Compound 1 (1.000 g, 1.66 mmol) was dissolved in HBr/HOAc (10 mL), and the mixture was stirred at 25° C. for 2 h. The reaction mixture was put into ice water (20 mL). The precipitate was filtered and washed with water (10 mL×2), MTBE (20 mL), and dried under vacuum for 24 h to give the crude product compound 2 (1.100 g, 99.6%) as a gray solid, which was used directly in the next step.

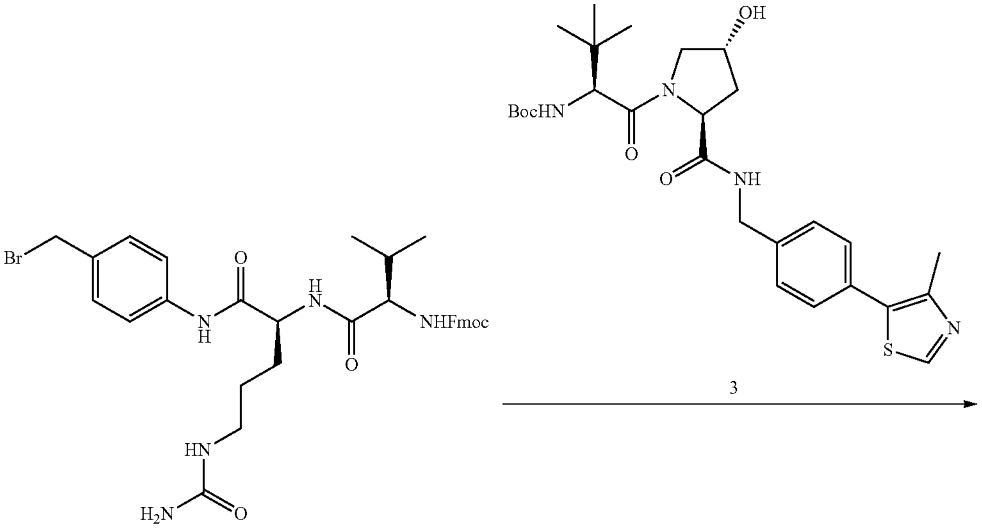

2

3

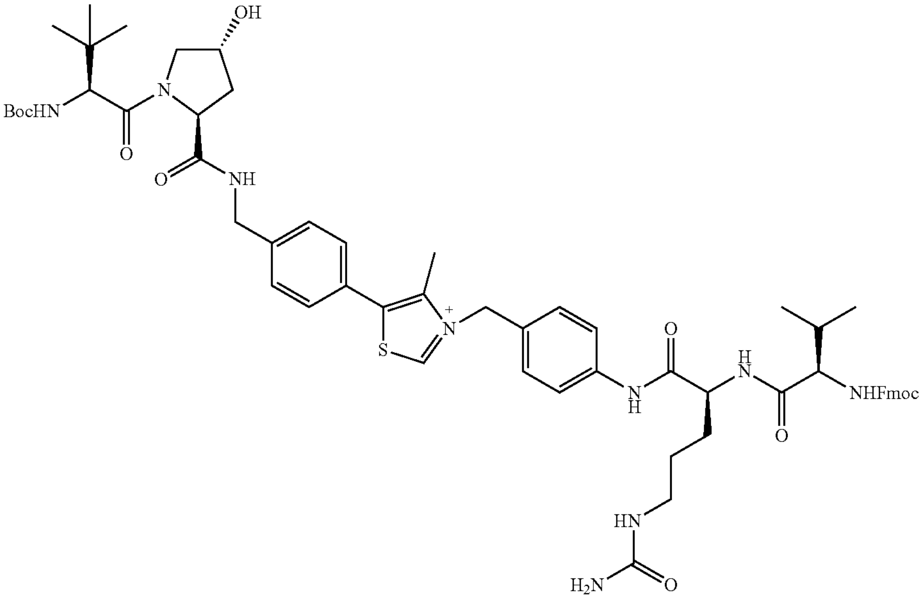

4

A solution of compound 3 (500.0 mg, 0.9400 mmol) and compound 2 (1.064 g, 1.6 mmol) in anhydrous DMF (8.0 mL) was stirred at 80° C. for 2 h. The reaction was filtered and the resulting residue was purified by prep-HPLC (acetonitrile 34-64/0.225% FA in water) to afford compound 4 (150 mg, 14%) as a white solid. LCMS (5-95, AB, 1.5 min): $R_T$=0.738 min, m/z=1114.6 $[M]^+$.

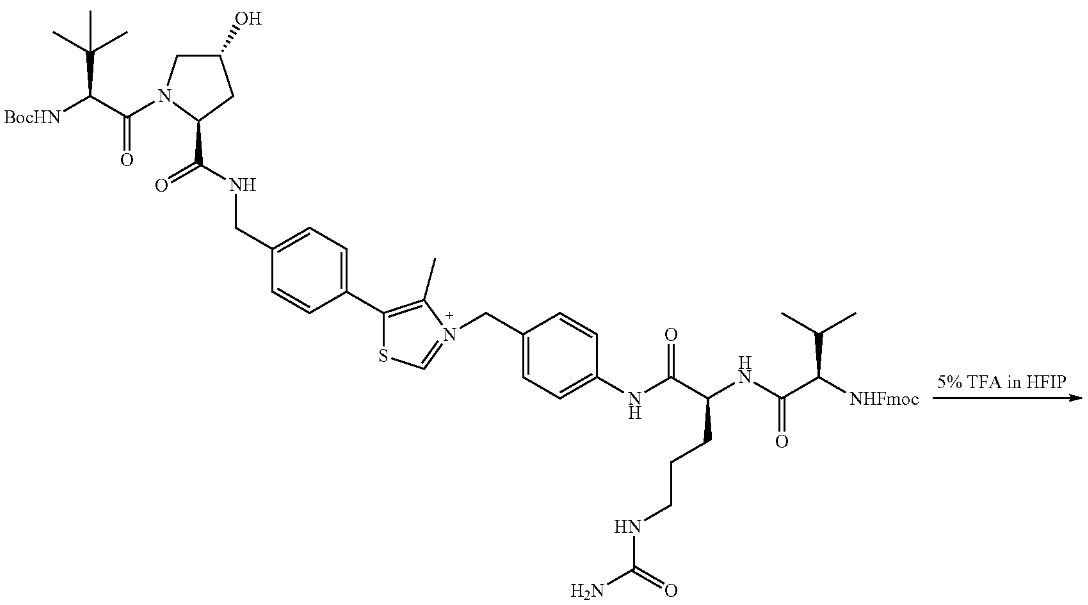
4
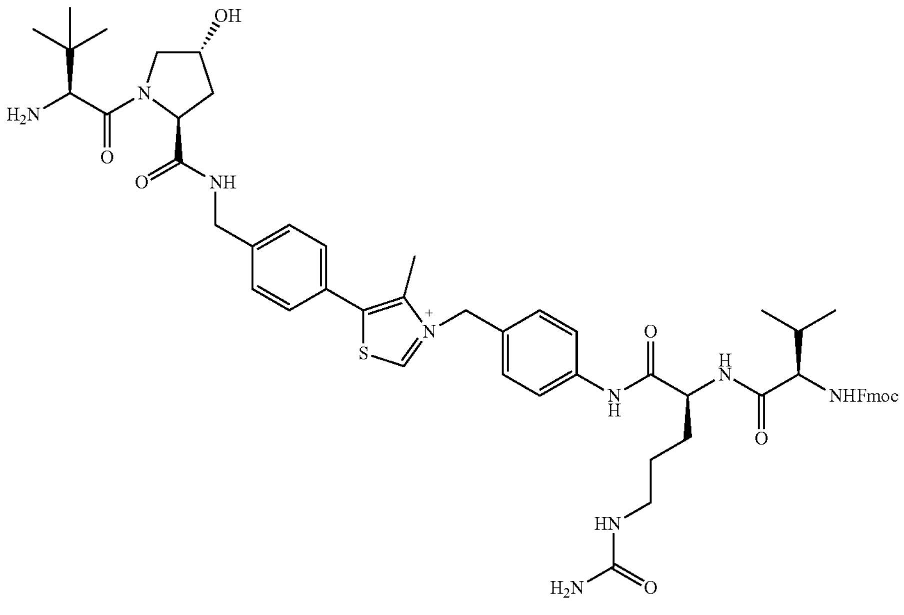
5

Compound 4 (30.0 mg, 0.0300 mmol) was dissolved in a solution of TFA in HFIP (5%, 1.5 mL) at 25° C., and the mixture stirred at 25° C. for 1 h. The mixture was concentrated to give the crude product compound 5 (30 mg, 98.8%) as a gray solid, which was used directly in the next step.

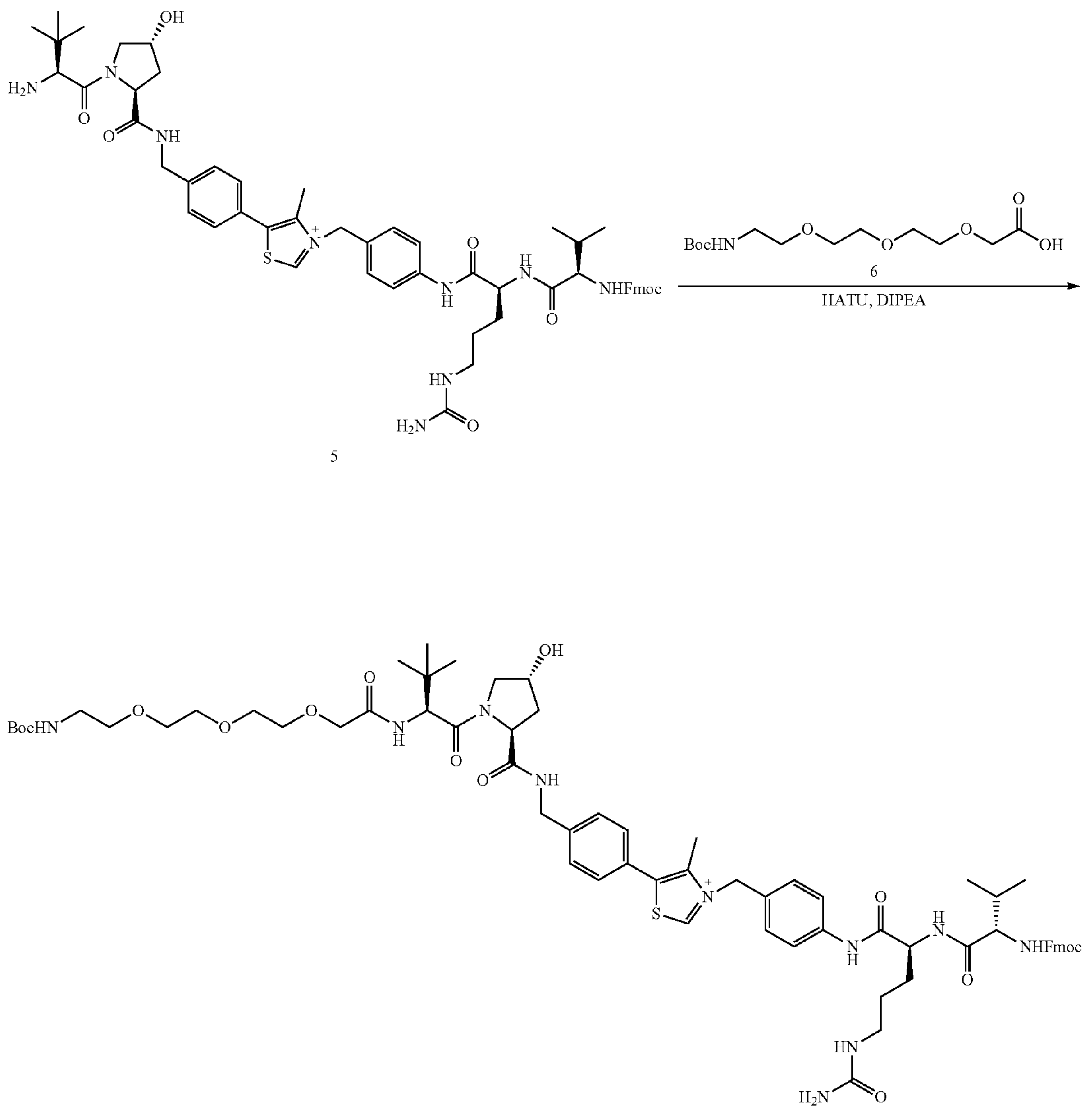

5

7

A solution of compound 6 (9.8 mg, 0.0300 mmol), DIEA (10.3 mg, 0.0800 mmol) and HATU (12.12 mg, 0.0300 mmol) in anhydrous DMF (2.0 mL) was stirred at 25° C. for 20 min, and then compound 5 (30.0 mg, 0.0300 mmol) was added. The resulted mixture was stirred at 25° C. for 2 h. The reaction was concentrated and the resulting residue was washed with EtOAc (2.0 mL×2) to afford compound 7 (34 mg, 98%) as a gray solid, which was used directly in the next step. LCMS (5-95, AB, 1.5 min): RT=0.848 min, m/z=1305.3 $[M]^+$.

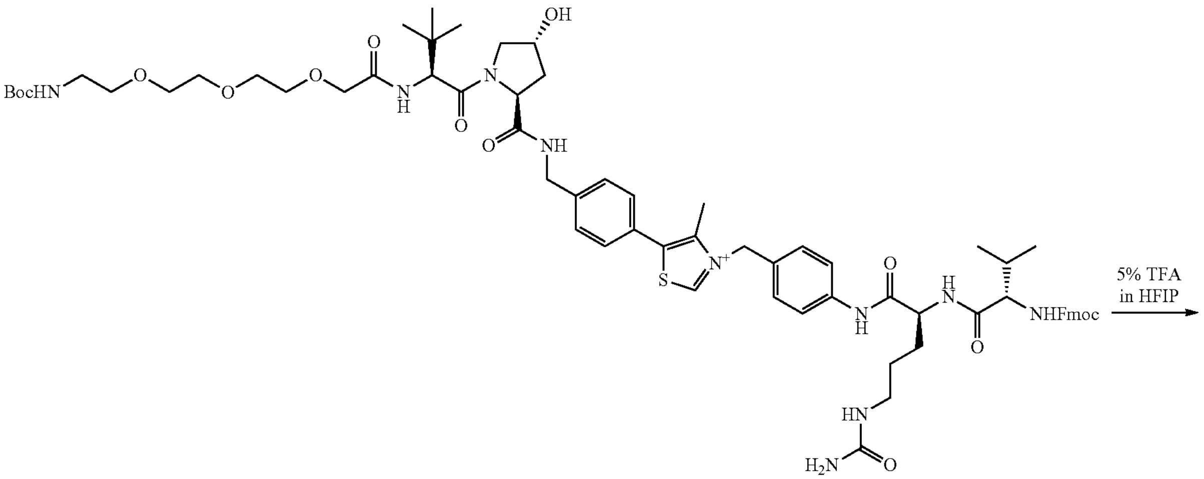
7
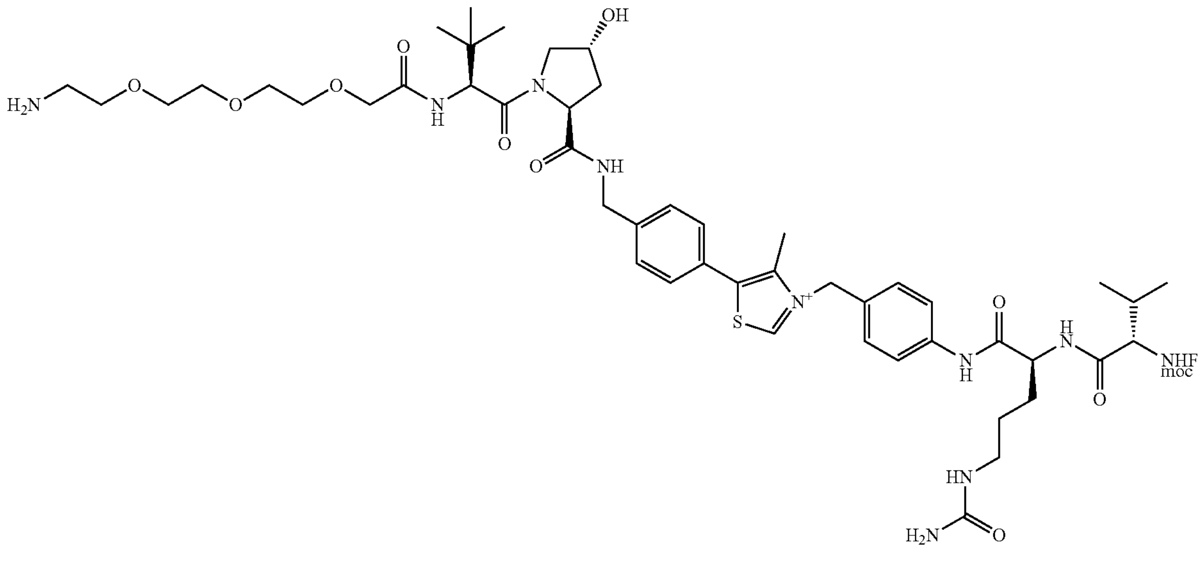
8

Compound 7 (34.0 mg, 0.0300 mmol) was dissolved in a solution of TFA in HFIP (5%, 1.5 mL) at 25° C., and the mixture stirred at 25° C. for 1 h. The mixture was concentrated and the residue was washed with EtOAc (1.0 mL×2) to give the crude product compound 8 (34 mg, 98.9%) as a gray solid, which was used directly in the next step.

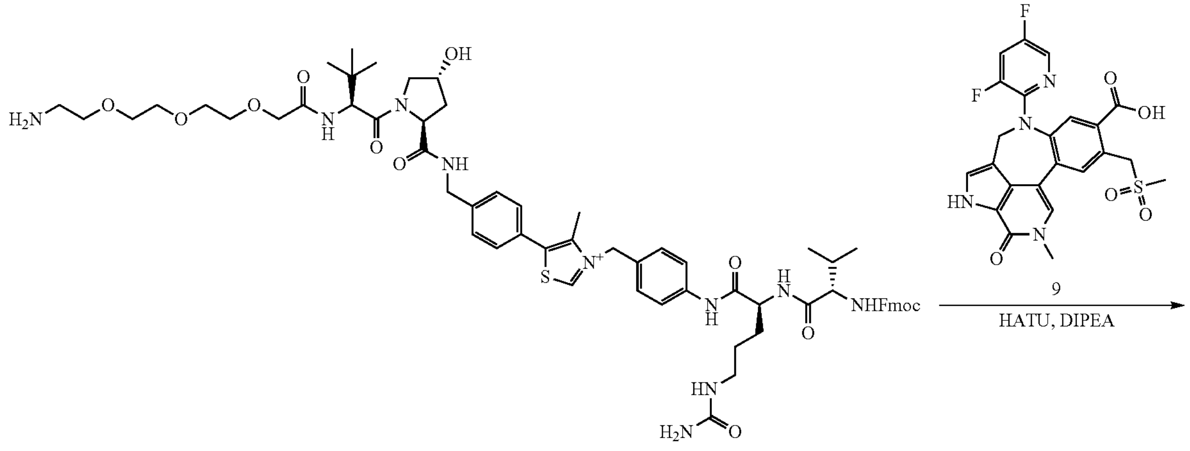

8

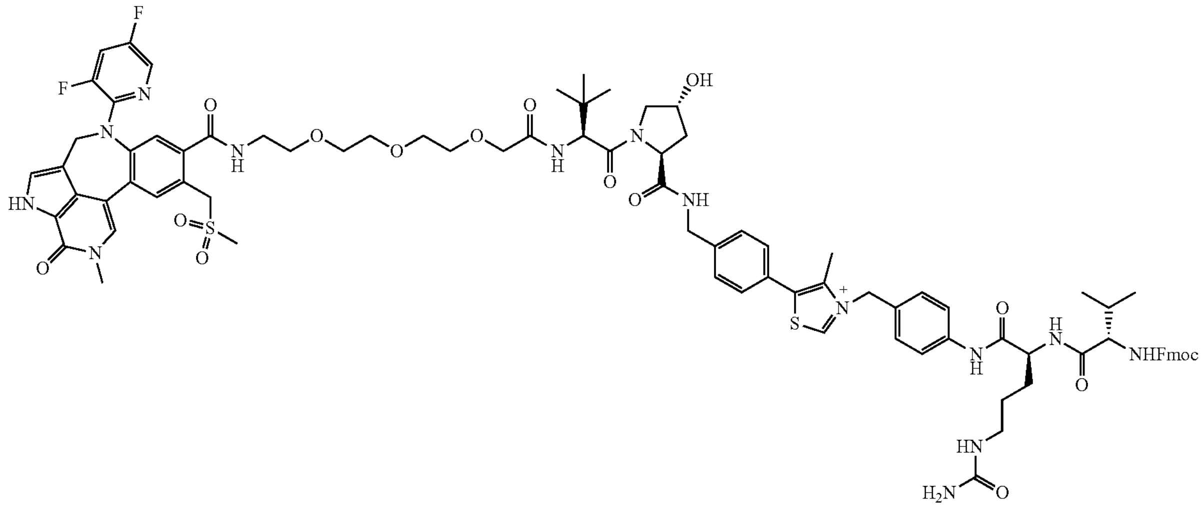

10

A solution of compound 9 (15.49 mg, 0.0300 mmol), HATU (10.79 mg, 0.0300 mmol) and DIEA (13.33 mg, 0.1000 mmol) in anhydrous DMF (3.0 mL) was stirred at 25° C. for 20 min, and compound 8 (34.0 mg, 0.0300 mmol) was added. The resulted mixture was stirred at 25° C. for 2 h. The mixture was concentrated and the residue was washed with EtOAc (2.0 mL×2) to give compound 10 (43 mg, 98.8%) as a light yellow solid, which was used directly in the next step. LCMS (5-95, AB, 1.5 min): RT=0.828 min, m/z=843.4 [M/2+1]+.

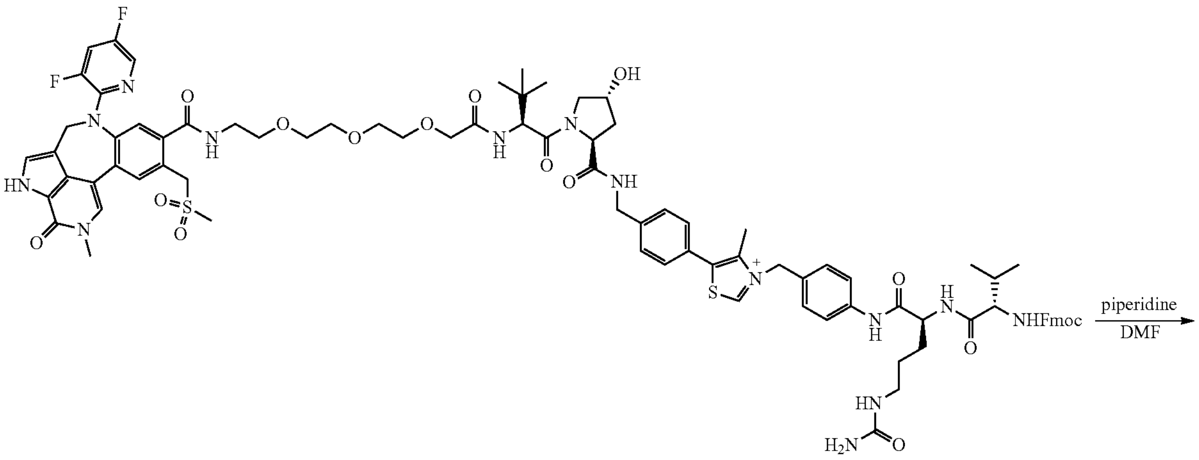
10
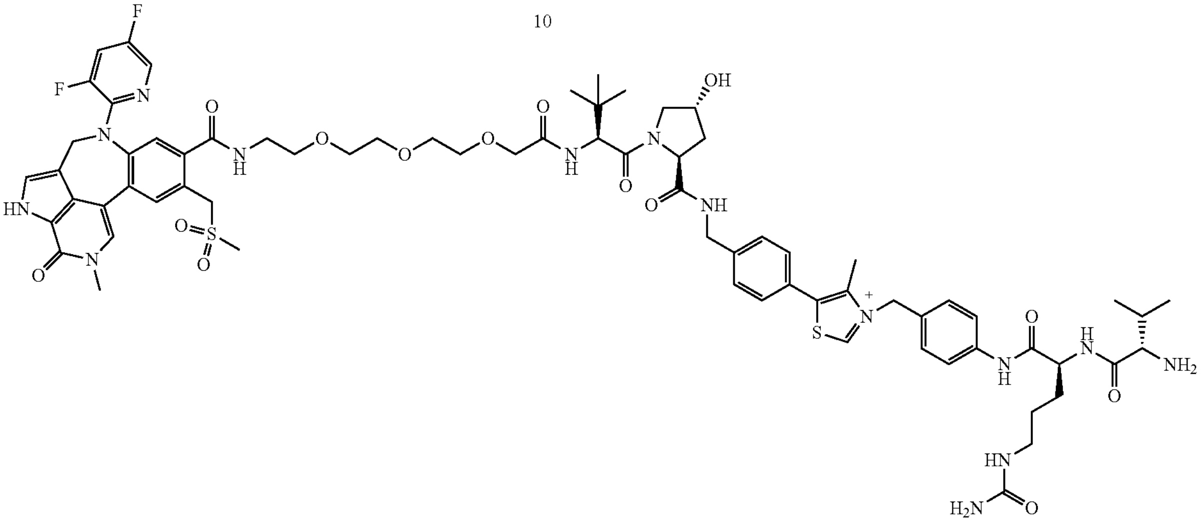
11
To a solution of compound 10 (43.0 mg, 0.0300 mmol) in DMF (1.0 mL) was added piperidine (10.85 mg, 0.1300 mmol) at 25° C. The mixture was stirred at 25° C. for 30 min. The mixture was concentrated and the residue was washed with EtOAc (1.0 mL×2) to afford compound 11 (37 mg, 99.1%) as a gray solid, which was used directly in the next step.
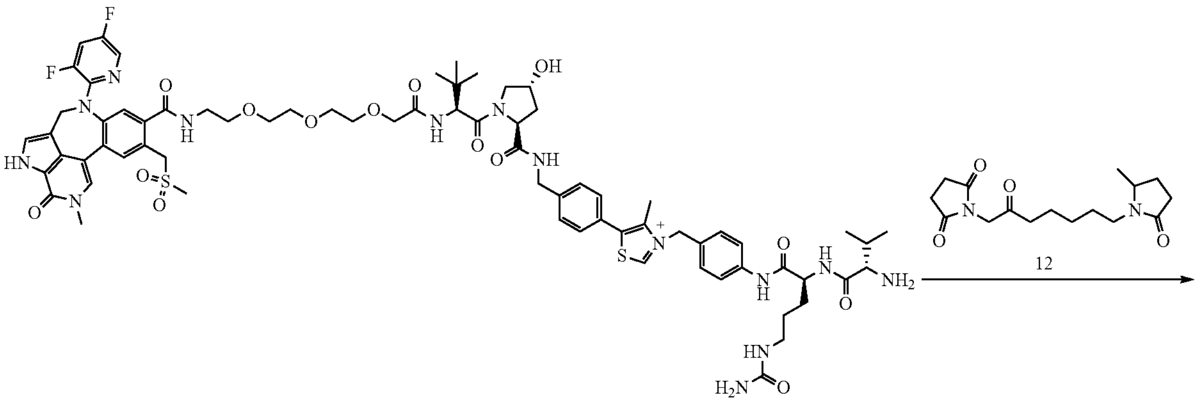
11

-continued
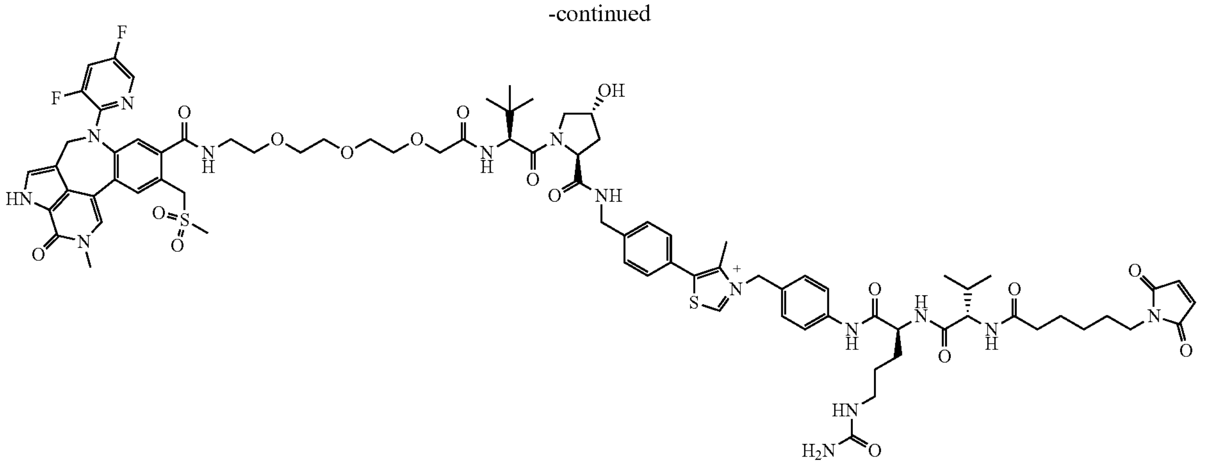
L1BC1
To a solution of compound 11 ("BC1"), (37.0 mg, 0.0300 mmol) in DMF (1.0 mL) was added compound 12 (11.68 mg, 0.0400 mmol) at 25° C. The mixture was stirred at 25° C. for 12 h. The mixture was filtered and purified by prep-HPLC (acetonitrile 22-52%/0.225% FA in water) to afford L1BC1 (3.95 mg, 7.5%) as a white solid. LCMS (5-95, AB, 1.5 min): RT=0.757 min, m/z=828.8[M/2+1]$^+$.
ix. L1BC2 An exemplary L1-CIDE, L1BC2, can be synthesized by the following scheme.
Scheme 11
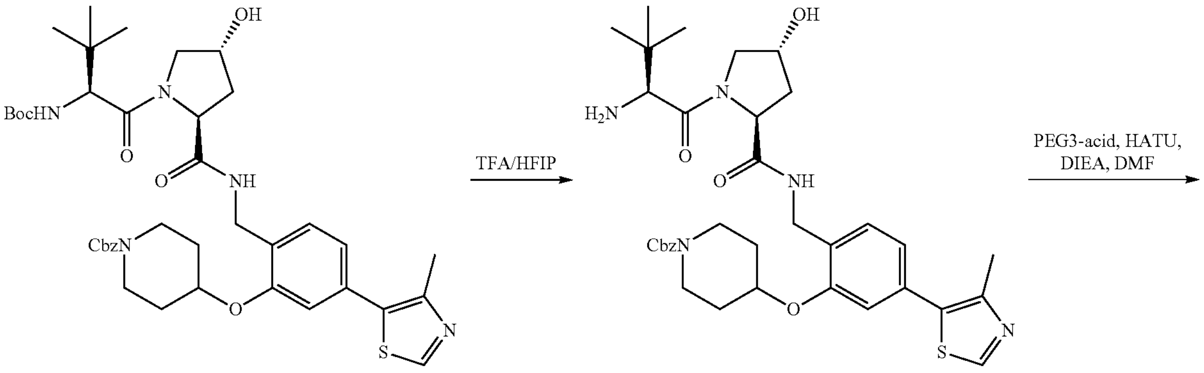
1
2
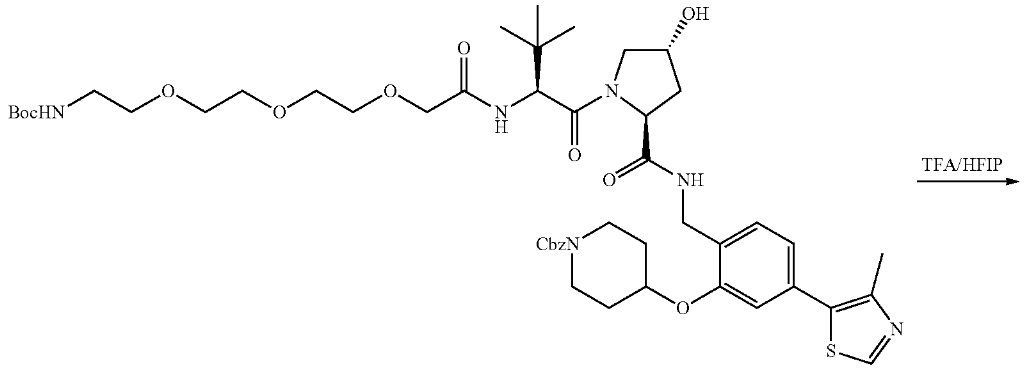
3

-continued
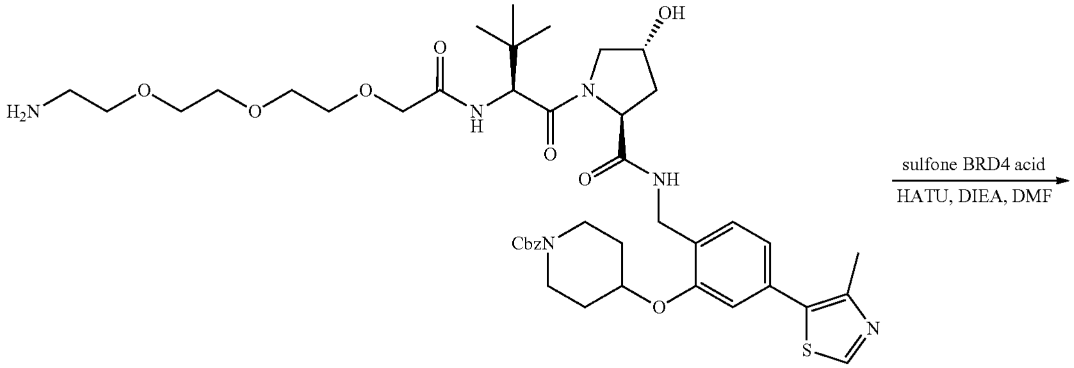
4
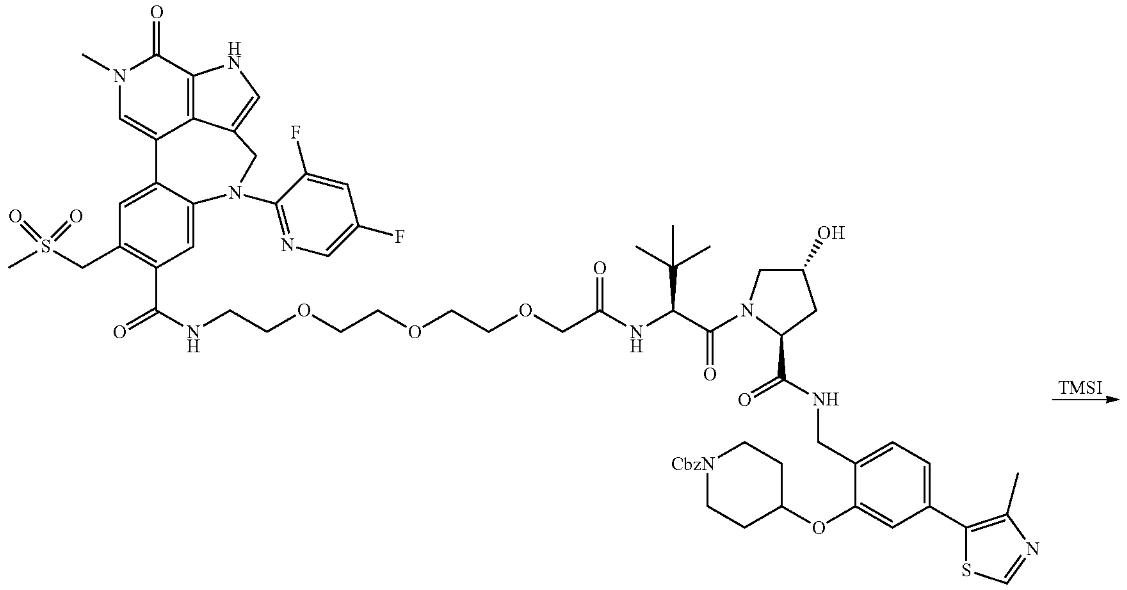
5
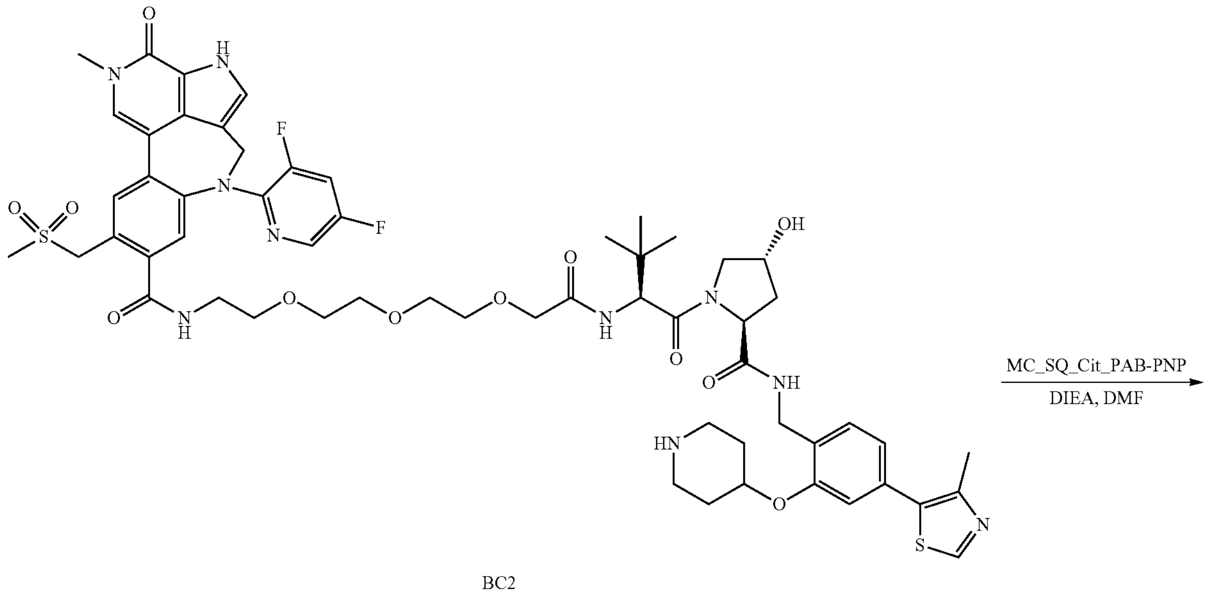
BC2

-continued
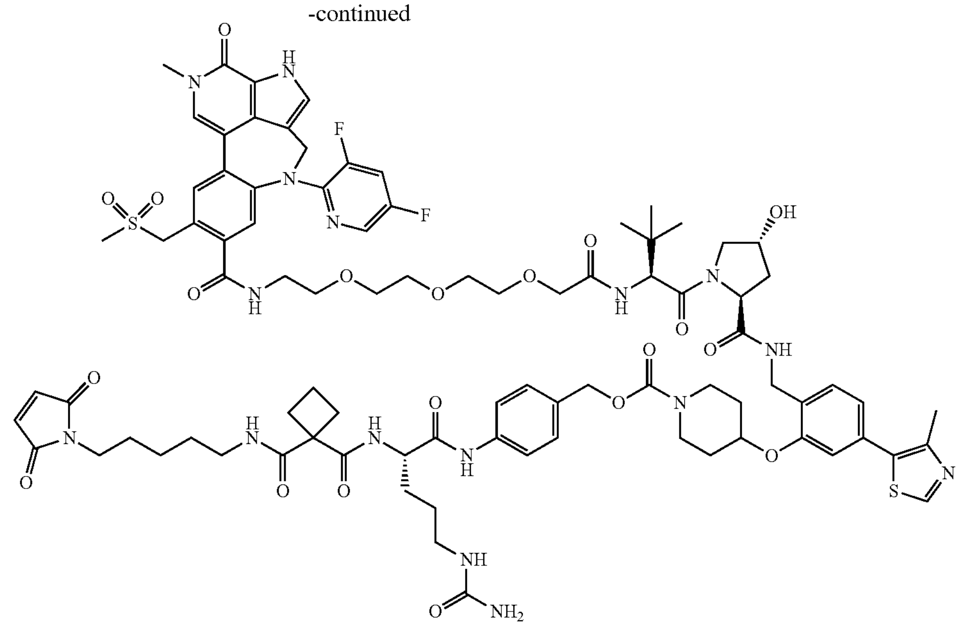
L1BC2
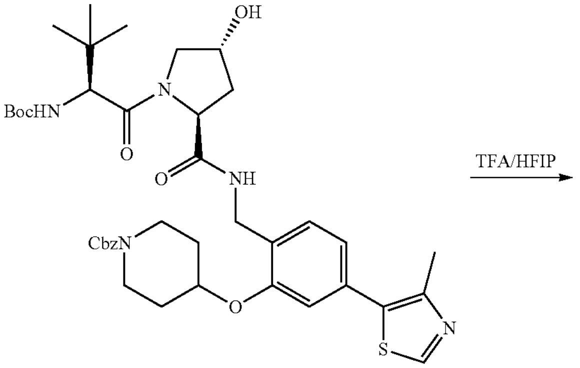
1
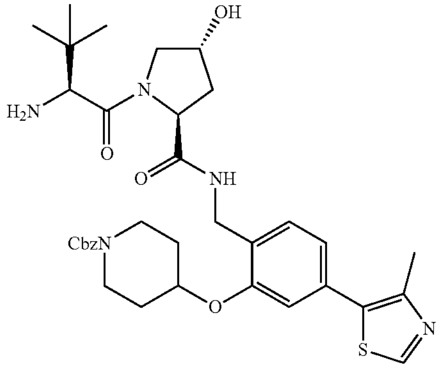
2
A solution of Compound 1 (200.0 mg, 0.2600 mmol) in a mixture of TFA (0.30 mL) and HFIP (6.0 mL) was stirred at 25° C. for 1 h. The solution was concentrated and the residue was diluted with DMF (5.0 mL), and concentrated again to afford Compound 2 (200 mg, 98%) as colorless oil, which was used in the next step directly.

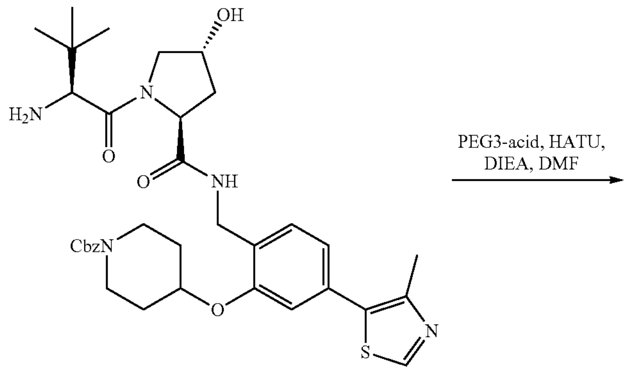

2

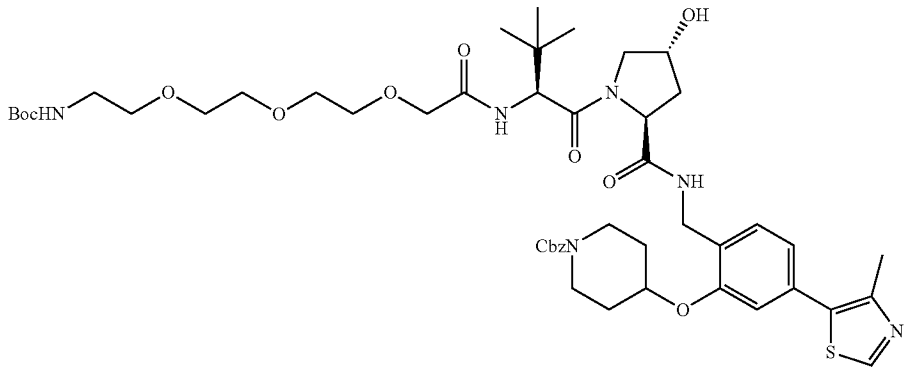

3

To a solution of BocNH_PEG3-acid (80.0 mg, 0.2600 mmol) in DMF (5.0 mL) was added DIEA (134.56 mg, 1.04 mmol) and HATU (118.77 mg, 0.3100 mmol). The solution was stirred at 25° C. for 15 min, then Compound 2 (200.0 mg, 0.260 mmol) was added. The reaction solution was stirred at 25° C. for another 1 h. The solution was concentrated and the residue was purified by prep-TLC (10% MeOH in DCM, $R_f$=0.5) to afford Compound 3 (150 mg, 59% yield) as a yellow oil. LCMS (5-95, AB, 1.5 min): $R_T$=0.883 min, m/z=975.6 $[M+23]^+$.

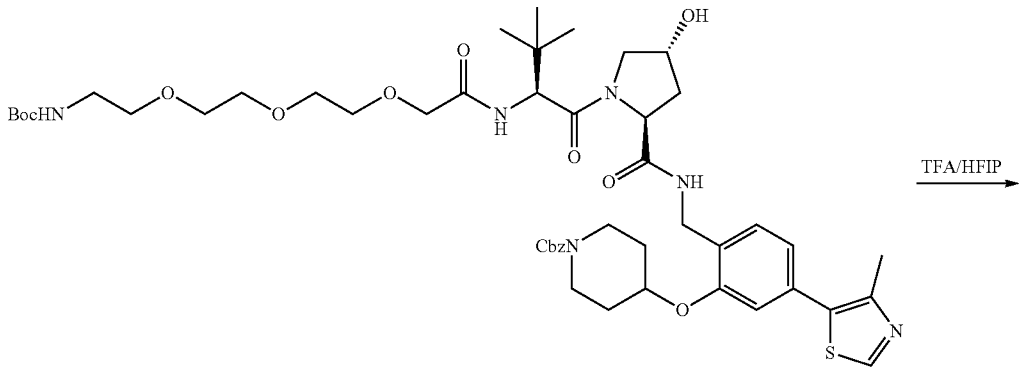

3

-continued
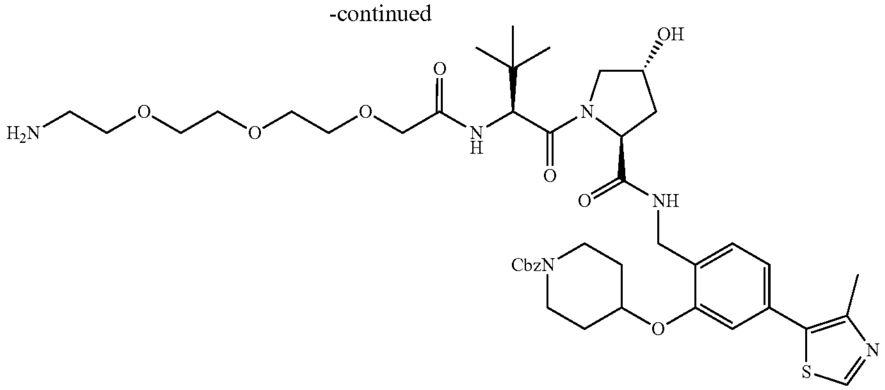
4
A solution of Compound 3 (150.0 mg, 0.1600 mmol) in a mixture of TFA (0.20 mL) and HFIP (4.0 mL) was stirred at 25° C. for 1 h. The solution was concentrated and the residue was diluted with DMF (5.0 mL), and concentrated again to afford Compound 4 (150 mg 98.6%) as colorless oil, which was used in the next step directly.
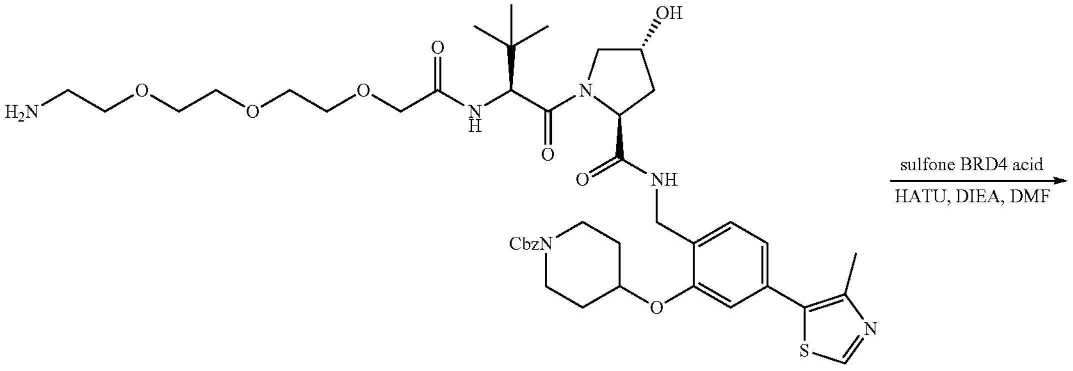
4
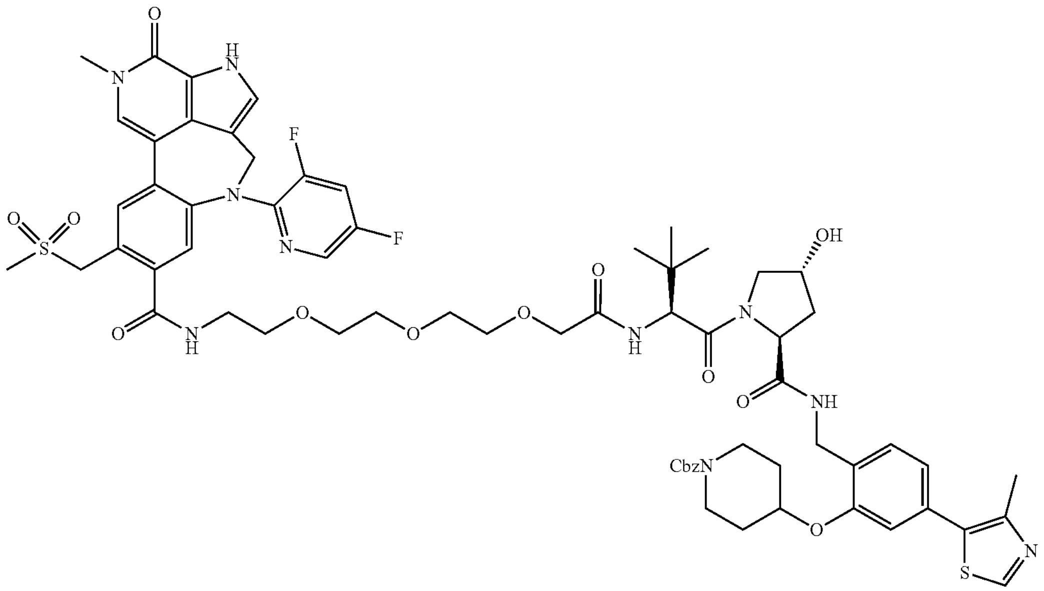
5

To a solution of sulfone BRD4 acid (75.0 mg, 0.1500 mmol) in DMF (5.0 mL) was added DIEA (77.47 mg, 0.600 mmol) and HATU (68.38 mg, 0.1800 mmol). The solution was stirred at 25° C. for 10 min, then Compound 4 (144.92 mg, 0.1500 mmol) was added. The resulting reaction solution was stirred at 25° C. for 1 h. The solution was concentrated and the residue was purified by prep-TLC (10% MeOH in DCM, $R_f$=0.5) to afford Compound 5 (198 mg, 97.9%) as a pale yellow oil. LCMS (5-95, AB, 1.5 min): RT=0.847 min, m/z=1358.0 [M+1]$^+$.

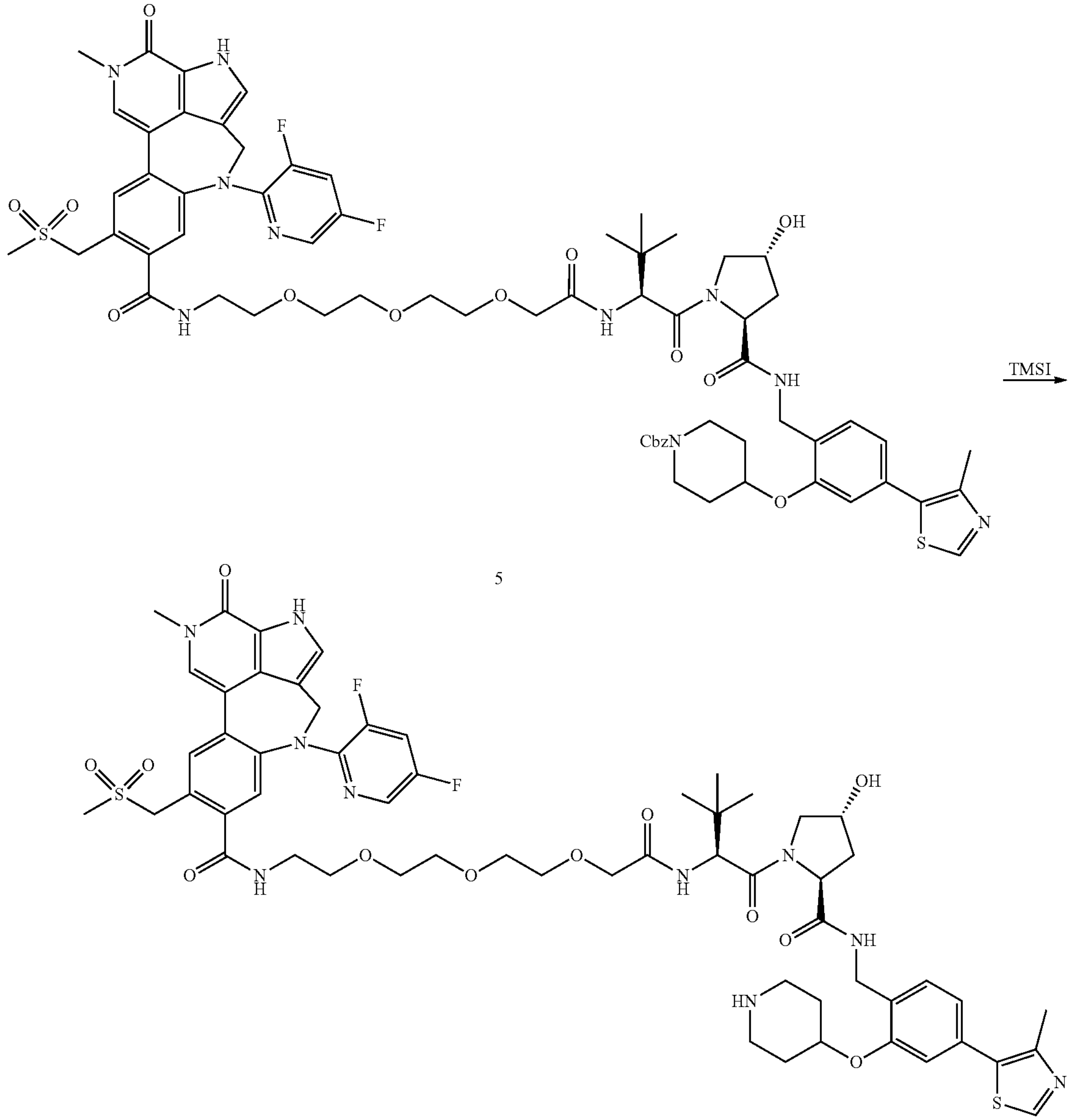

5

BC2

To a solution of Compound 5 (160.0 mg, 0.1200 mmol) in DCM (4.0 mL) was added TMSI (239.72 mg, 1.2 mmol). The reaction mixture was stirred at 25° C. for 1 h. MeOH (20 mL) was added, and the solution was stirred at 25° C. for another 10 min. The solution was concentrated and the residue was purified by prep-HPLC (acetonitrile 0-40/0.1% HCl in water) to afford BC2 (42 mg, 27%) as a white solid. LCMS (5-95, AB, 1.5 min): RT=0.773 min, m/z=1201.6 [M+1]$^+$; $^1$H NMR (400 MHz, $CDCl_3$) δ 8.86 (s, 1H), 8.53 (s, 1H), 7.94 (s, 1H), 7.88 (s, 1H), 7.69 (s, 1H), 7.47 (d, J=7.6 Hz, 1H), 7.36 (s, 1H), 7.23-7.21 (m, 2H), 7.05-7.00 (m, 2H), 4.88-4.82 (br, 2H), 4.69 (s, 1H), 4.60-4.49 (m, 5H), 4.38-4.34 (m, 1H), 4.02-3.98 (m, 2H), 3.88-3.79 (m, 2H), 3.71-3.63 (m, 13H), 3.51-3.44 (m, 4H), 3.24-3.20 (m, 2H), 2.99 (s, 3H), 2.46 (s, 3H), 2.13-2.07 (m, 6H), 1.02 (s, 9H).

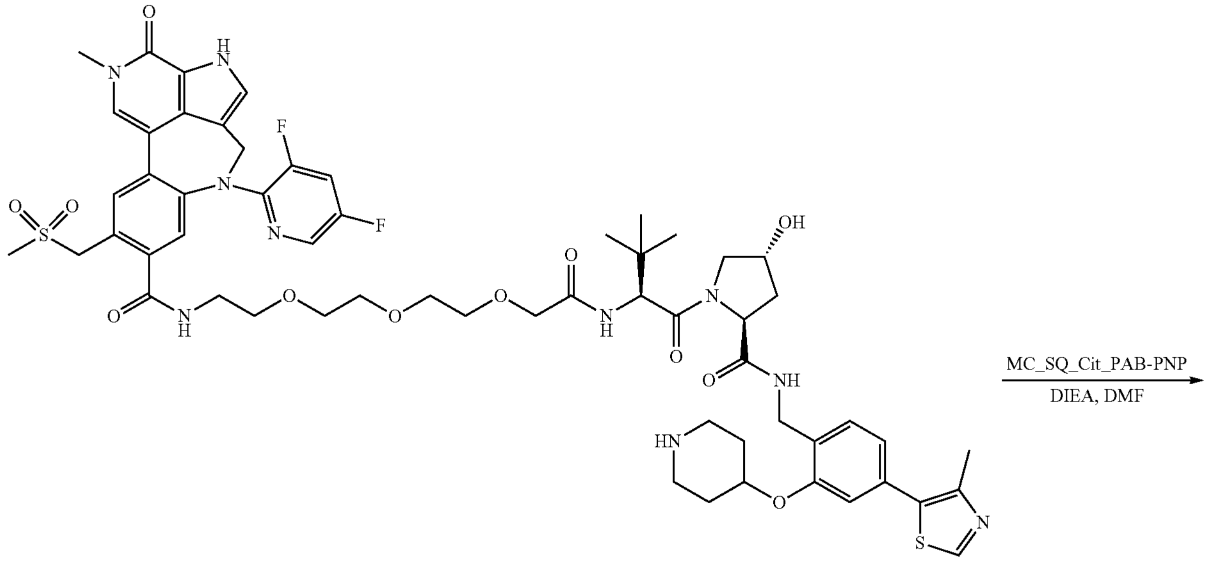

BC2

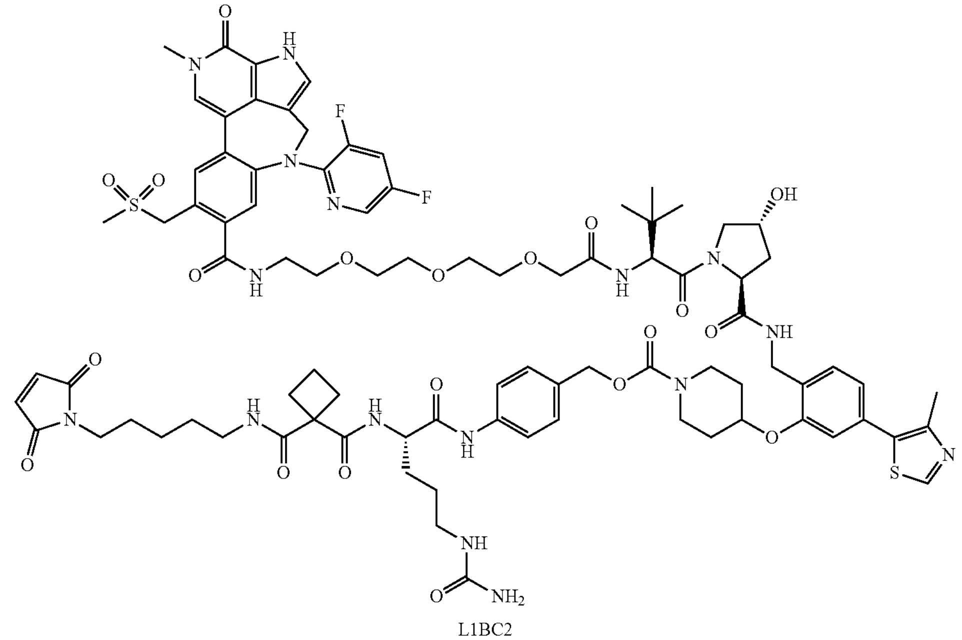

L1BC2

A solution of BC2 (25.0 mg, 0.0200 mmol) and MC_SQ_Cit_PAB-PNP in DMF (2.0 mL) was added DIEA (10.36 mg, 0.0800 mmol). The reaction solution was stirred at 25° C. for 2 h. The solution was purified by prep-HPLC (Xtimate C18 150*25 mm*5 um, acetonitrile 35-65/0.225% FA in water) to afford L1BC2 (16.89 mg, 45%) as a white solid. LCMS (5-95, AB, 1.5 min): RT=0.803 min, m/z=900.4 [M/2+H]+. $^1$H NMR (400 MHz, $CDCl_3$) δ 8.85 (s, 1H), 7.93 (s, 1H), 7.87 (s, 1H), 7.86 (s, 1H), 7.69-7.68 (m, 3H), 7.43 (d, J=7.6 Hz, 1H), 7.35 (s, 1H), 7.30 (d, J=8.8 Hz, 2H), 7.26 (s, 1H), 7.21 (s, 1H), 7.01-6.94 (m, 1H), 6.75 (s, 2H), 5.06 (brs, 1H), 4.89-4.67 (m, 12H), 4.65-4.61 (m, 1H), 4.01 (d, J=4.8 Hz, 2H), 3.71-3.61 (m, 15H), 3.49-3.42 (m, 5H), 3.31-3.22 (m, 3H), 3.25-3.21 (m, 4H), 3.16-3.13 (m, 2H), 2.97 (s, 3H), 2.56-2.51 (m, 2H), 2.45 (s, 3H), 1.94-1.92 (m, 3H), 1.78-1.74 (m, 2H), 1.55-1.51 (m, 6H), 1.28-1.26 (m, 4H), 1.00 (s, 9H).

x. L1BC3 An exemplary L1-CIDE, L1BC3, can be synthesized by the following scheme:
Scheme 12
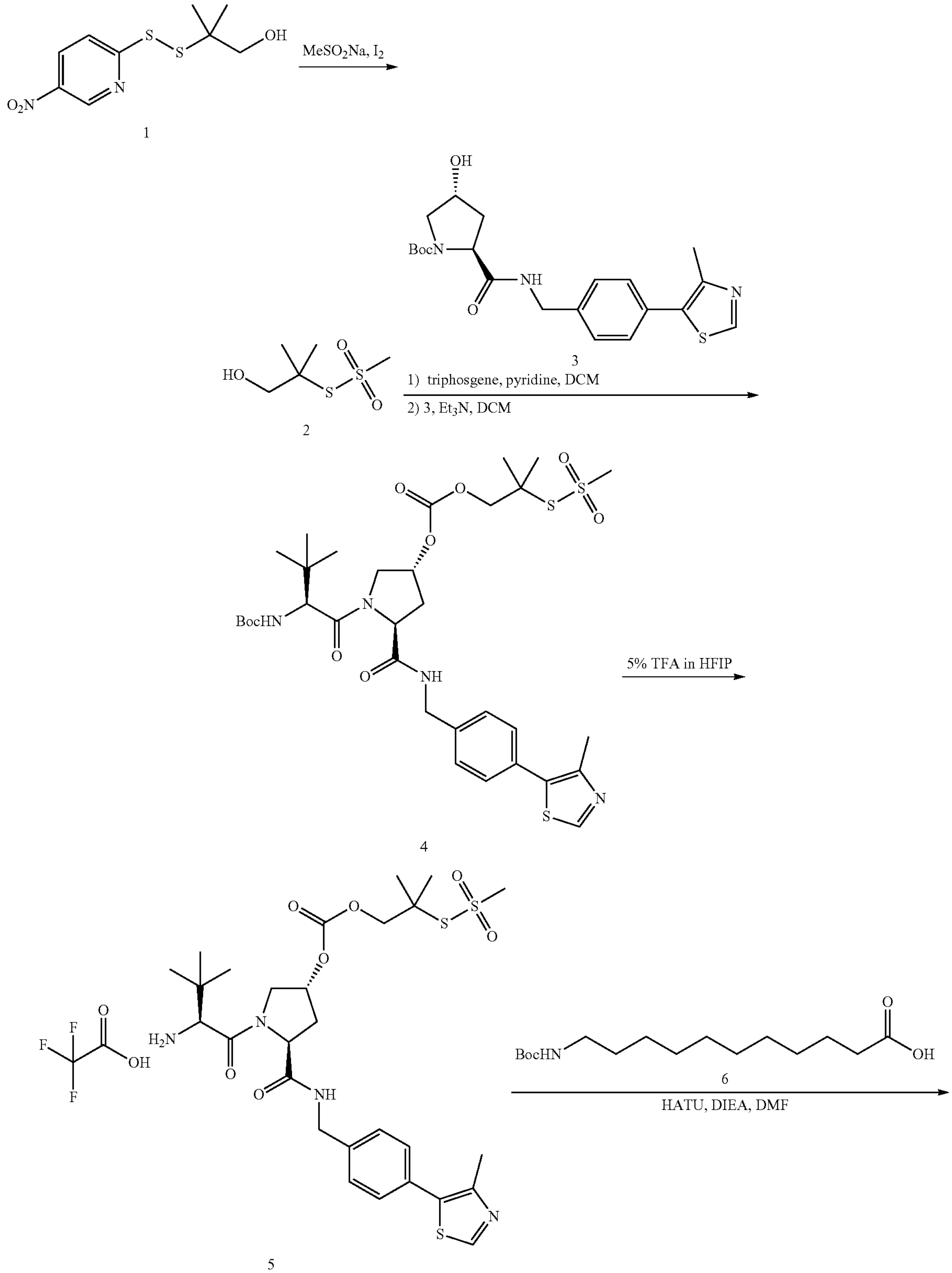
1
3
2
4
6
5

-continued
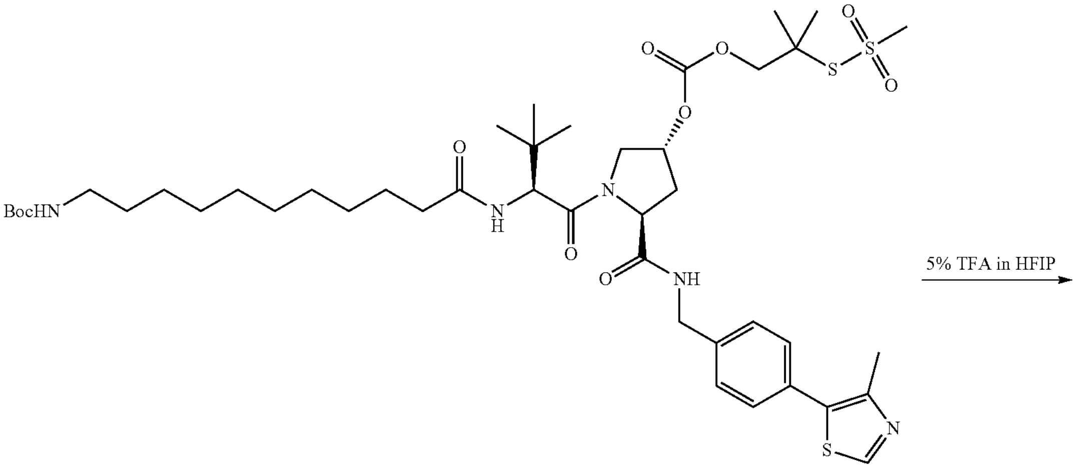
7
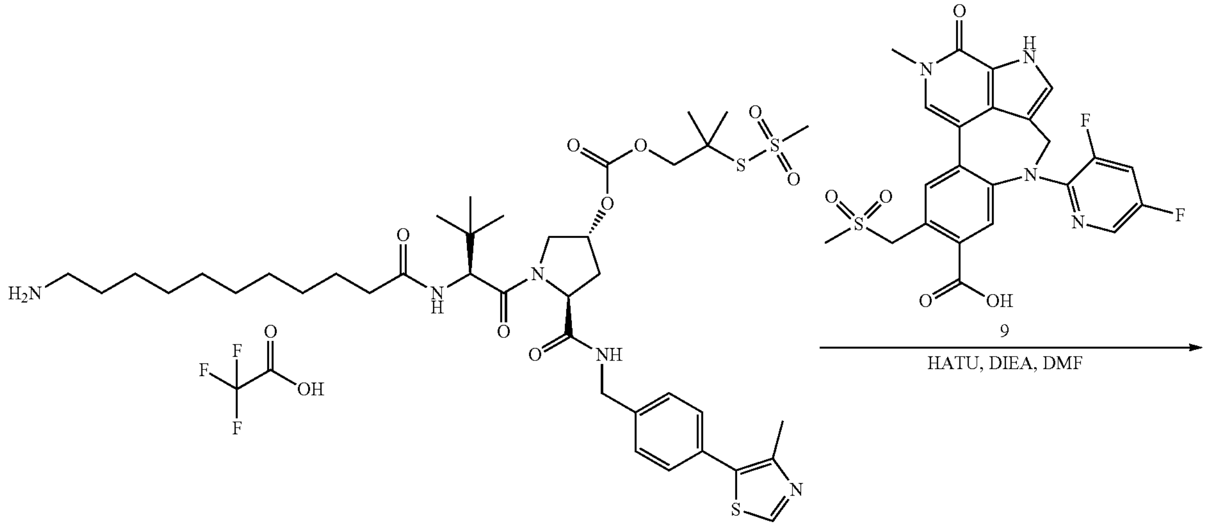
8
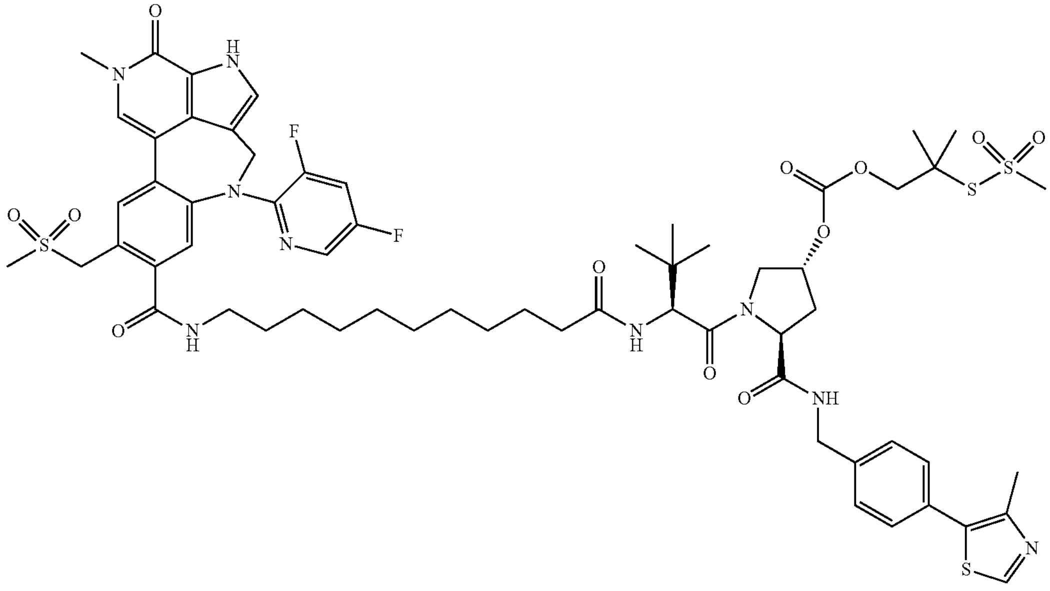
L1BC3

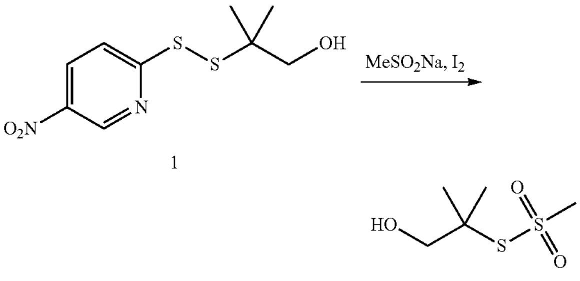

1

2

To a solution of t (2.00 g, 7.68 mmol) in DCM (20 mL) was added $MeSO_2Na$ (3.92 g, 38.41 mmol) and $I_2$ (3.90 g, 15.37 mmol) at 25° C. After the reaction mixture was stirred at 50° C. for 24 h, it was filtrated and the filtration was concentrated. It was purified by column chromatography (0-33% EtOAc in petroleum ether, $R_f$=0.3) to give 2 (400 mg, 28.3%) as a yellow oil. $^1$HNMR (400 MHz, $CDCl_3$) δ 3.81 (s, 2H), 3.40 (s, 3H), 1.54 (s, 6H).

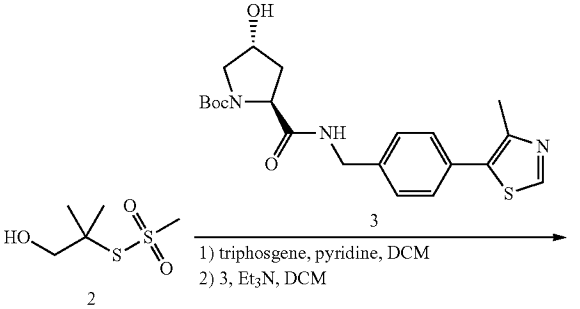

3

2

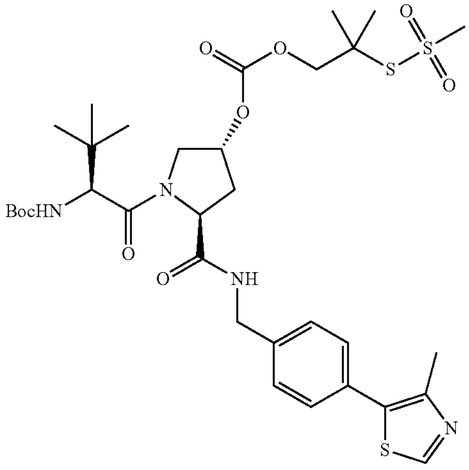

4

To a solution of triphosgene (322.06 mg, 1.09 mmol) in DCM (2.0 mL) was added a solution of pyridine (171.70 mg, 2.17 mmol) and Compound 2 (400.00 mg, 2.17 mmol) in DCM (2.0 mL). After the reaction was stirred at 25° C. for 30 min, it was concentrated and re-dissolved in DCM (20 mL). A solution of $Et_3N$ (438.83 mg, 4.34 mmol) and Compound 3 (1.73 g, 3.25 mmol) was added, and the reaction was stirred at 25° C. for 2 h. The mixture was concentrated in vacuum and purified by column chromatography (0-10% MeOH in DCM, $R_f$=0.5) to give Compound 4 (100.00 mg, 6.2%) as a yellow oil. LCMS (5-95, AB, 1.5 min): $R_T$=0.962 min, m/z=741.1 [M+1]$^+$.

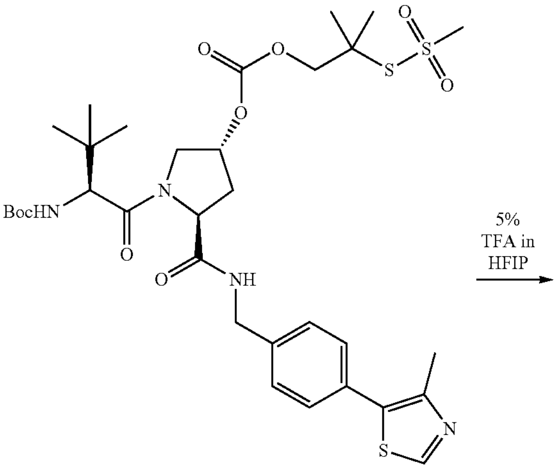

4

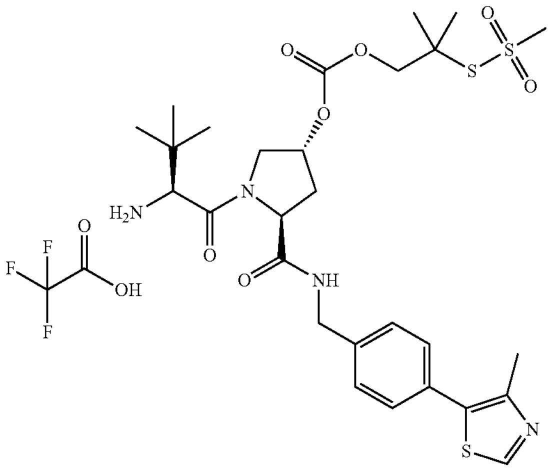

5

To a solution of Compound 4 (100.00 mg, 0.13 mmol) in HFIP (6.00 mL) was added TFA (0.30 mL). After the reaction solution was stirred at 25° C. for 1 h, it was concentrated in vacuo to afford Compound 5 (a TFA salt, 101.00 mg, 99.1%) as colorless oil, which was used in the next step directly.

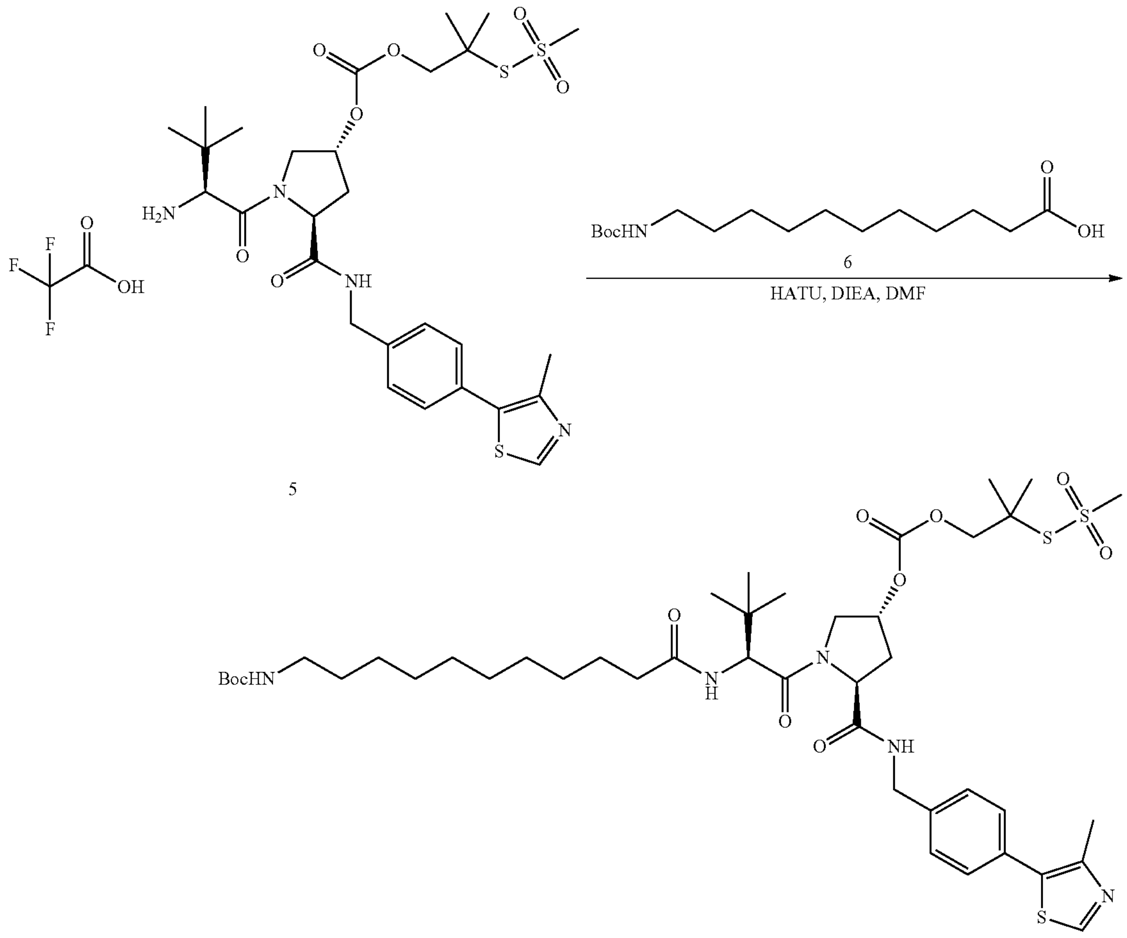

5

7

To a solution of Compound 6 (44.36 mg, 0.15 mmol) and HATU (67.15 mg, 0.18 mmol) in DMF (5.0 mL) was added DIEA (86.46 mg, 0.67 mmol). After the mixture was stirred at 25° C. for 10 min, compound 5 (101.00 mg, 0.13 mmol) was added. The mixture was stirred at 25° C. for 30 min. The mixture was concentrated in vacuo and purified by column chromatography (solvent gradient: 0-10% MeOH in DCM Rf=0.6) and then by prep-TLC (10% MeOH in DCM, Rf=0.6) to give Compound 7 (100.00 mg, 74.4%) as a yellow oil. LCMS (5-95, AB, 1.5 min): RT=1.066 min, m/z=924.5 $[M+1]^+$;

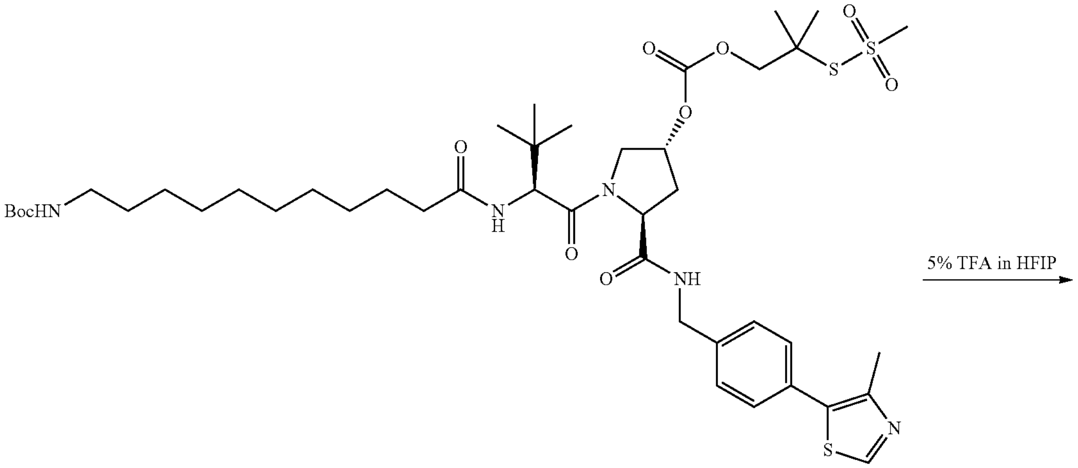

7

-continued
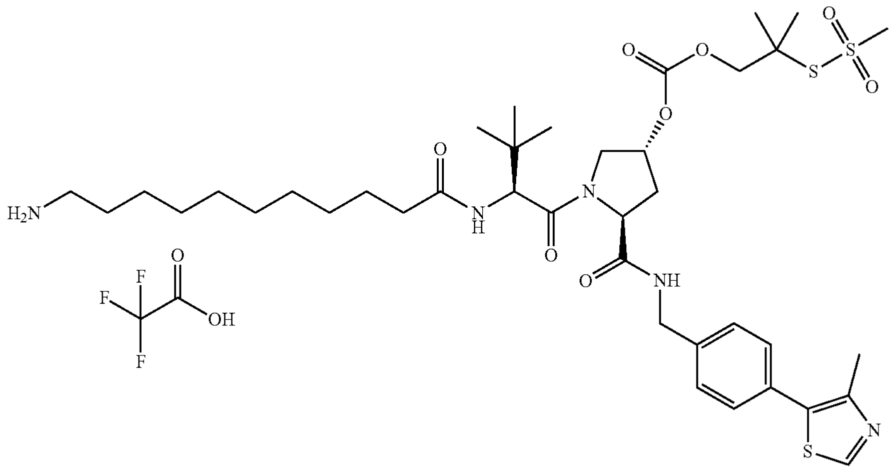
8
To a solution of Compound 7 (44.36 mg, 0.05 mmol) in HFIP (6.00 mL) was added TFA (0.30 mL). The reaction solution was stirred at 25° C. for 1 h. The solution was concentrated in vacuo to afford Compound 8 (TFA salt, 45.00 mg, 94%) as a colorless oil.
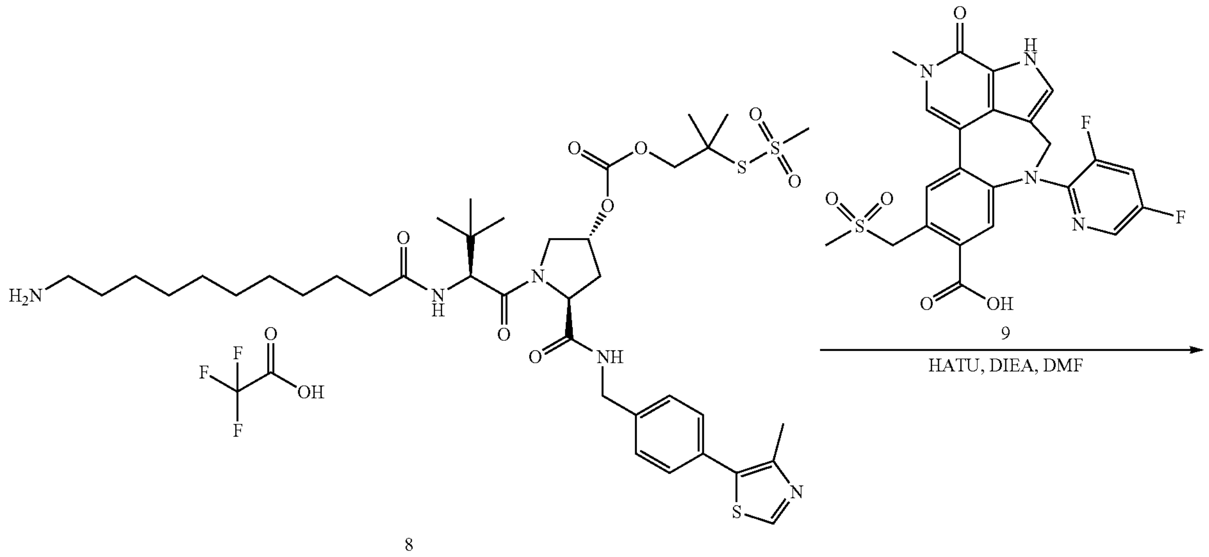
8

-continued

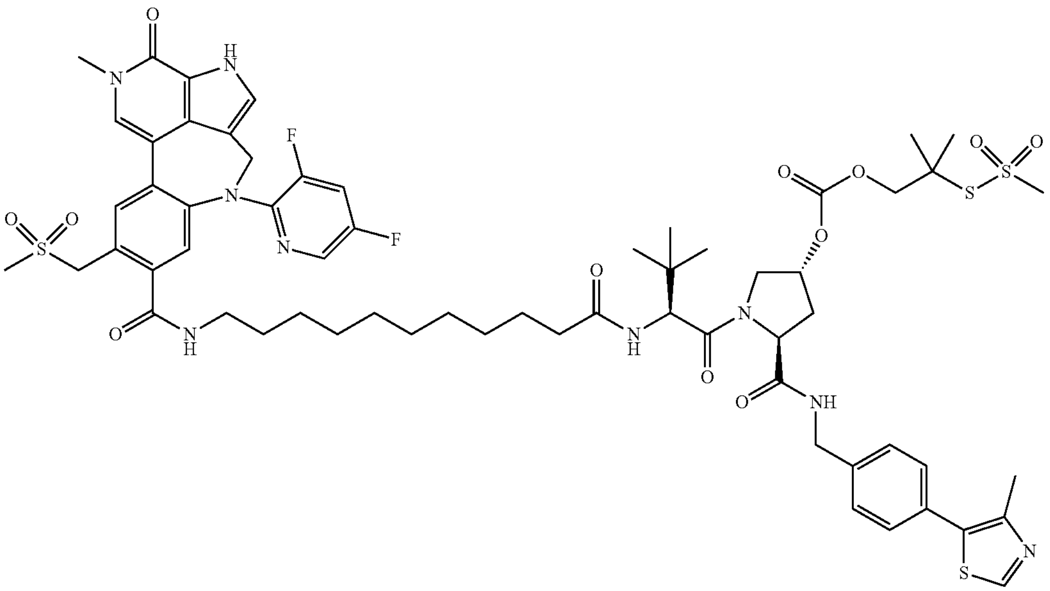

L1BC3

To a solution of Compound 9 (20.00 mg, 0.04 mmol) and HATU (19.75 mg, 0.05 mmol) in DMF (15 mL) was added DIEA (25.82 mg, 0.20 mmol). After the mixture was stirred at 25° C. for 10 min, compound 8 (45 mg, 0.05 mmol) was added. The mixture was stirred at 25° C. for 30 min. The mixture was purified by prep-HPLC (acetonitrile 50-80/0.225% FA in water) to afford L1BC3 (35.00 mg, 67%) as a white solid. LCMS (5-95, AB, 1.5 min): RT=0.854 min, m/z=654.1 $[M/2+1]^+$; $^1H$ NMR (400 MHz, DMSO-$d_6$) δ 11.92 (brs, 2H), 8.98 (s, 1H), 8.61-8.58 (m, 1H), 8.40-8.36 (m, 1H), 8.06 (s, 1H), 7.89-7.86 (m, 2H), 7.75 (s, 1H), 7.63-7.60 (m, 2H), 7.39-7.33 (m, 4H), 7.26-7.23 (m, 2H), 5.24 (brs, 2H), 4.48-4.39 (m, 3H), 4.37-4.29 (m, 4H), 4.28-4.25 (m, 1H), 4.24-4.08 (m, 4H), 3.84-3.81 (m, 2H), 3.62 (s, 2H), 3.53 (s, 3H), 3.14 (brs, 3H), 2.90 (s, 3H), 2.44 (s, 2H), 1.60-1.48 (m, 10H), 1.21 (brs, 12H), 0.95 (s, 9H).

xi. L1BC4 An exemplary L1-CIDE, L1BC4, can be synthesized by the following scheme.

Scheme 13

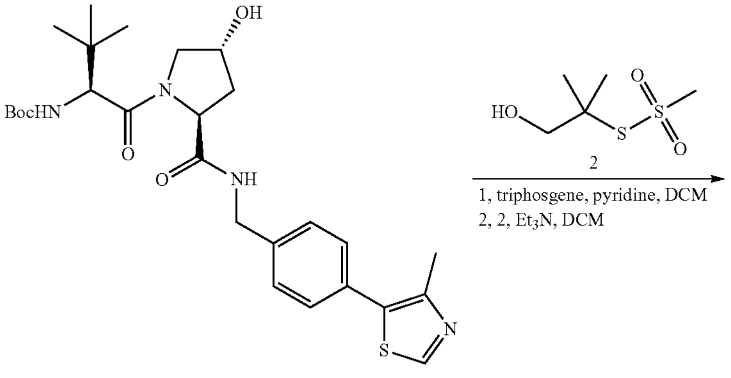

1

-continued
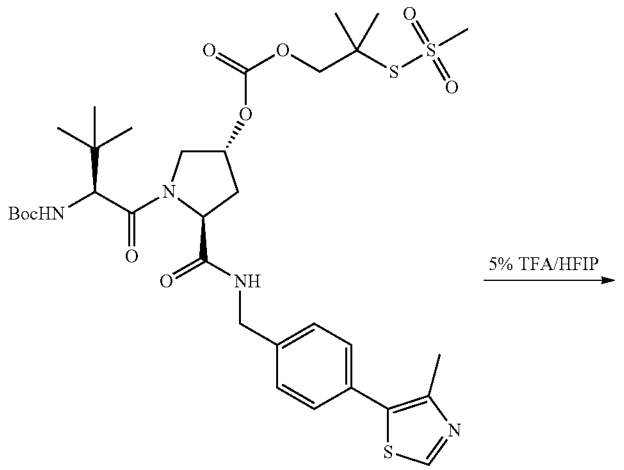
3
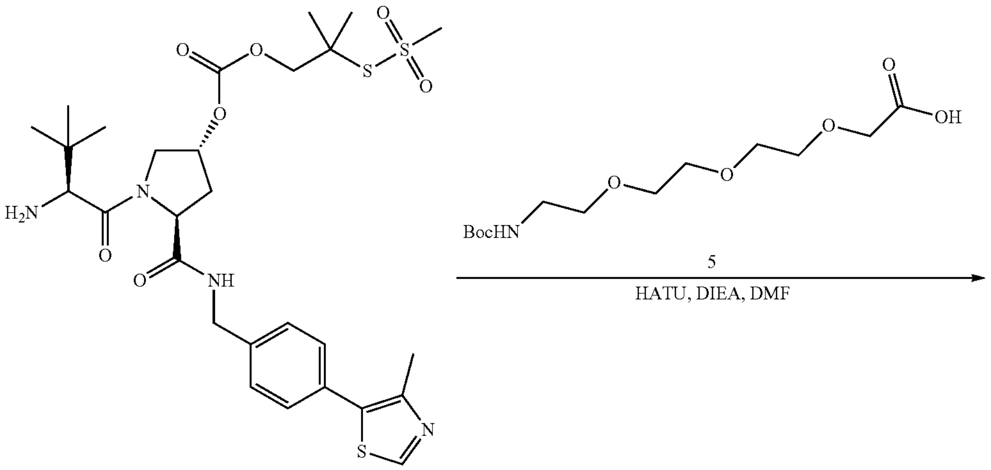
4
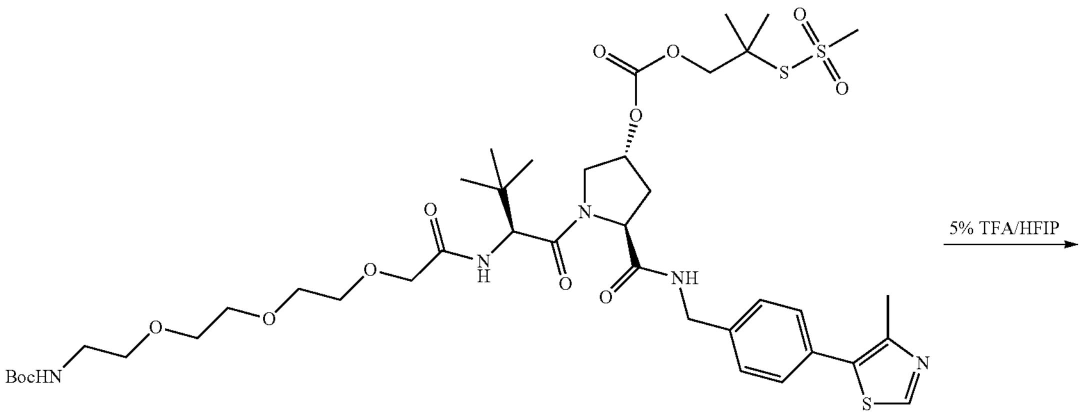
6

-continued
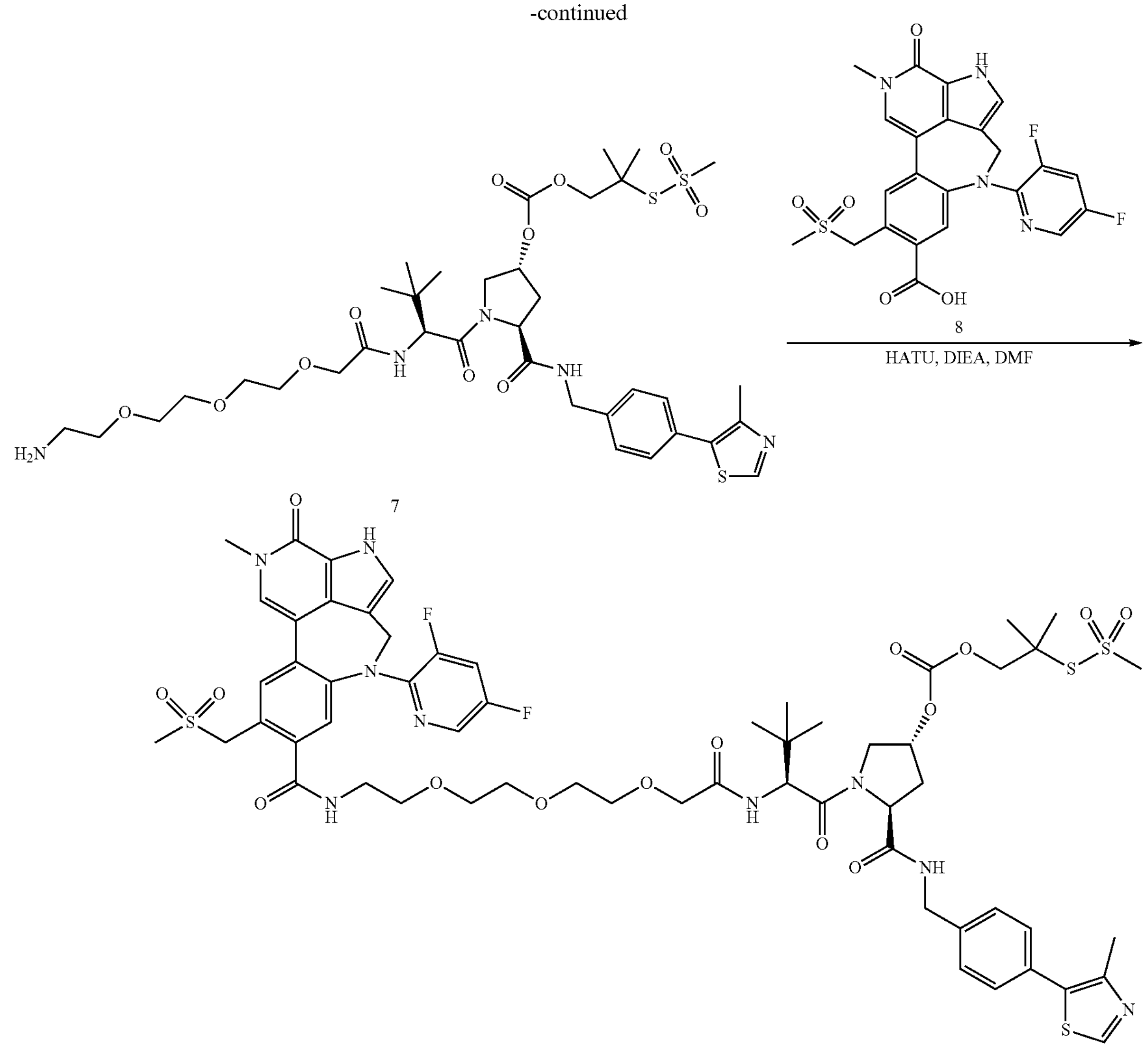
7
8
L1BC4
-continued
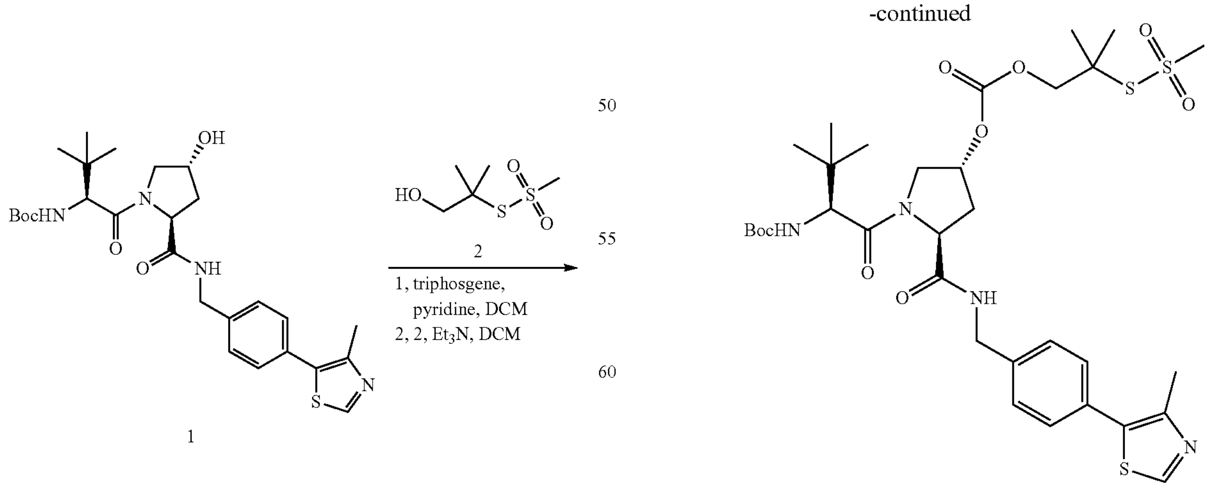
1
2
3

To a solution of triphosgene (88.57 mg, 0.3000 mmol) in DCM (2.0 mL) was added a solution pyridine (47.22 mg, 0.600 mmol), followed by a solution of Compound 2 (110.0 mg, 0.600 mmol) in DCM (2.0 mL). The reaction was stirred at 25° C. for 30 min. The reaction mixture was concentrated to dryness to give the crude product (140 mg) as a white solid. To the solution of this crude product in DCM (8.0 mL) was added a solution of $Et_3N$ (76.27 mg, 0.7500 mmol) and compound 1 (200.0 mg, 0.380 mmol) in DCM (2.0 mL), and the reaction was stirred at 25° C. for 2 h. The mixture was concentrated and purified by column chromatography (0-10% MeOH in DCM Rf=0.5) to give compound 3 (110 mg, 36%) as a yellow oil. LCMS (5-95, AB, 1.5 min): RT=0.955 min, m/z=741.3 $[M+1]^+$.

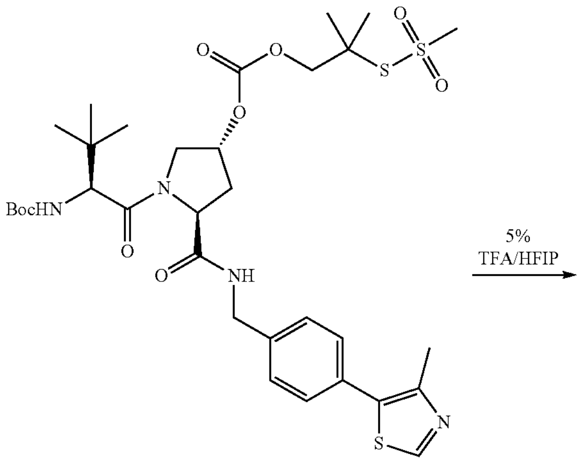

3

-continued

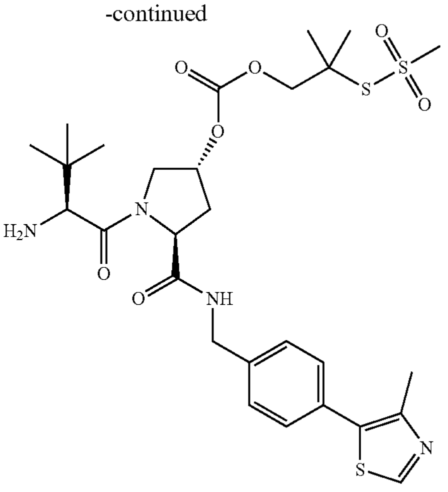

4

To a solution of Compound 3 (55.0 mg, 0.0700 mmol) in HFIP (6.0 mL) was added TFA (0.30 mL). The reaction solution was stirred at 25° C. for 1 h. The solution was concentrated to afford compound 4 TFA salt (56.0 mg) as a yellow oil, which was used in the next step directly. LCMS (5-95, AB, 1.5 min): RT=0.697 min, m/z=641.1 $[M+1]^+$.

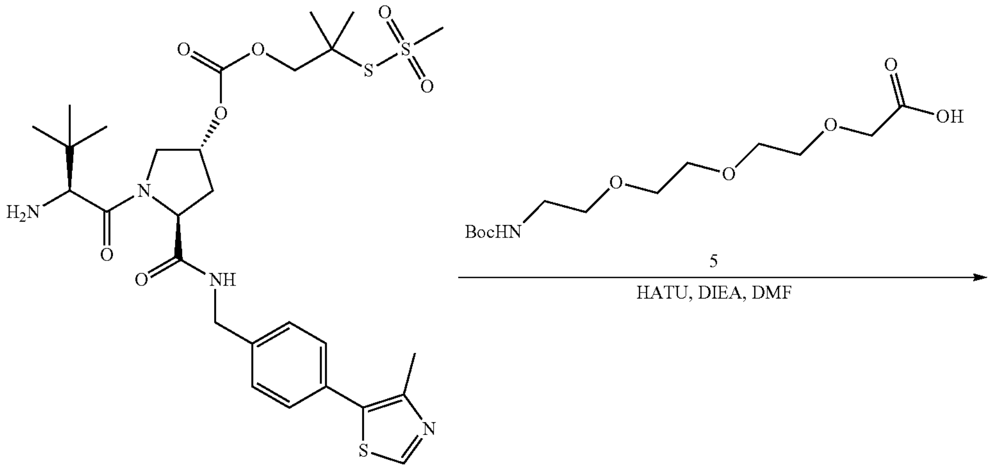

4

-continued

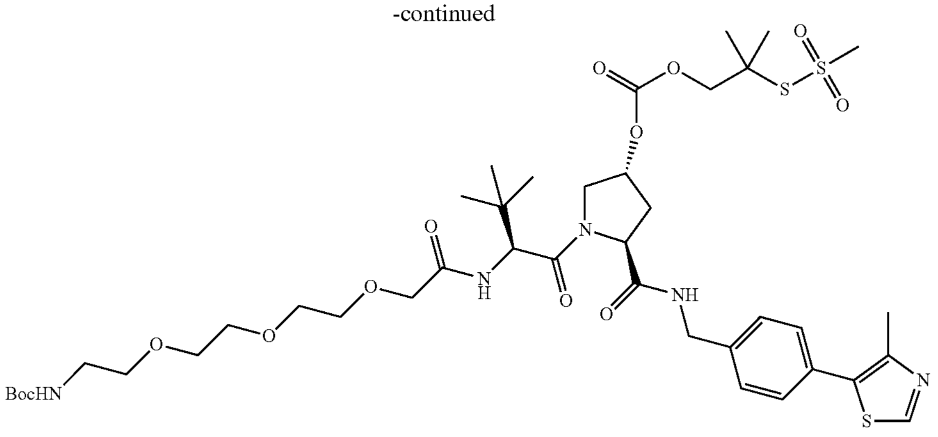

6

To a solution of compound 5 (29.64 mg, 0.1000 mmol) and HATU (42.31 mg, 0.1100 mmol) in DMF (5.0 mL) was added DIEA (47.94 mg, 0.370 mmol). The mixture was stirred at 25° C. for 10 min. To above reaction mixture was added TFA salt of Compound 4 (56.0 mg, 0.0700 mmol). The mixture was stirred at 25° C. for 1 h. The mixture was concentrated and the resulting residue was purified by prep-TLC (5% MeOH in DCM, Rf=0.5) to afford compound 6 (65 mg, 82%) as a yellow solid. LCMS (5-95, AB, 1.5 min): $R_T$=0.850 min, m/z=952.3 $[M+23]^+$.

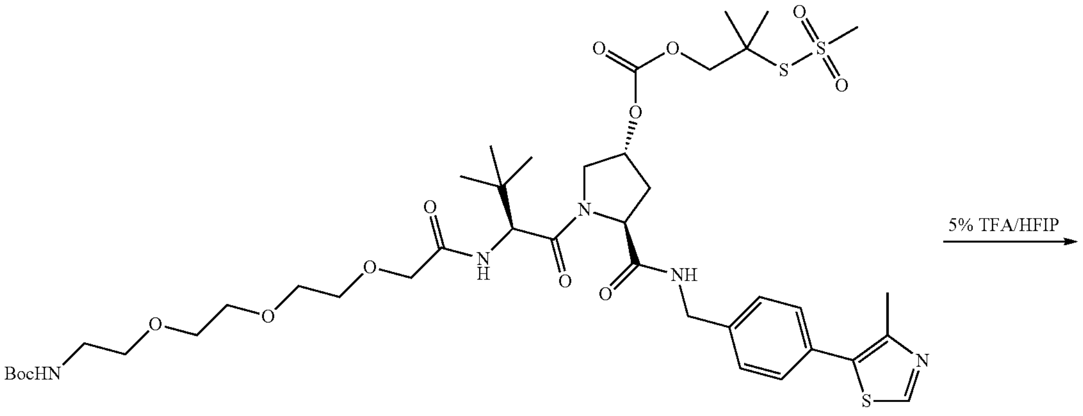

6

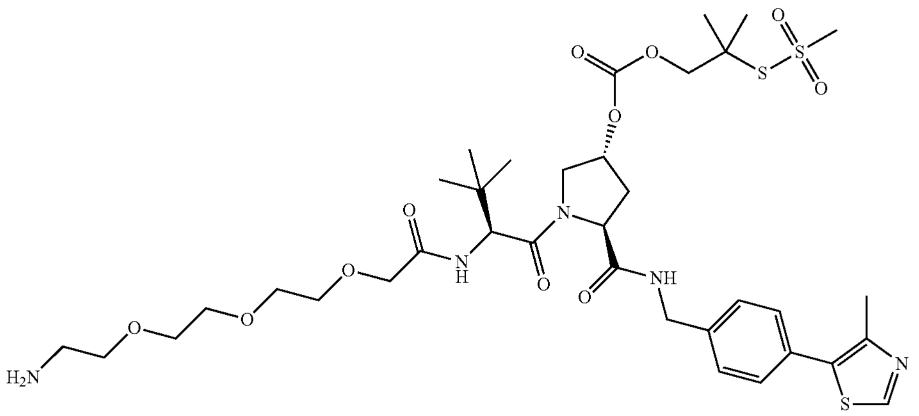

7

To a solution of Compound 6 (65.0 mg, 0.0600 mmol) in HFIP (6.0 mL) was added TFA (0.30 mL). The reaction solution was stirred at 25° C. for 1 h. The solution was concentrated to afford compound 7 TFA salt (57 mg, 99.7%) as a yellow oil which was used in next step directly. LCMS (5-95, AB, 1.5 min): $R_T$=0.720 min, m/z=852.2 [M+23]$^+$.

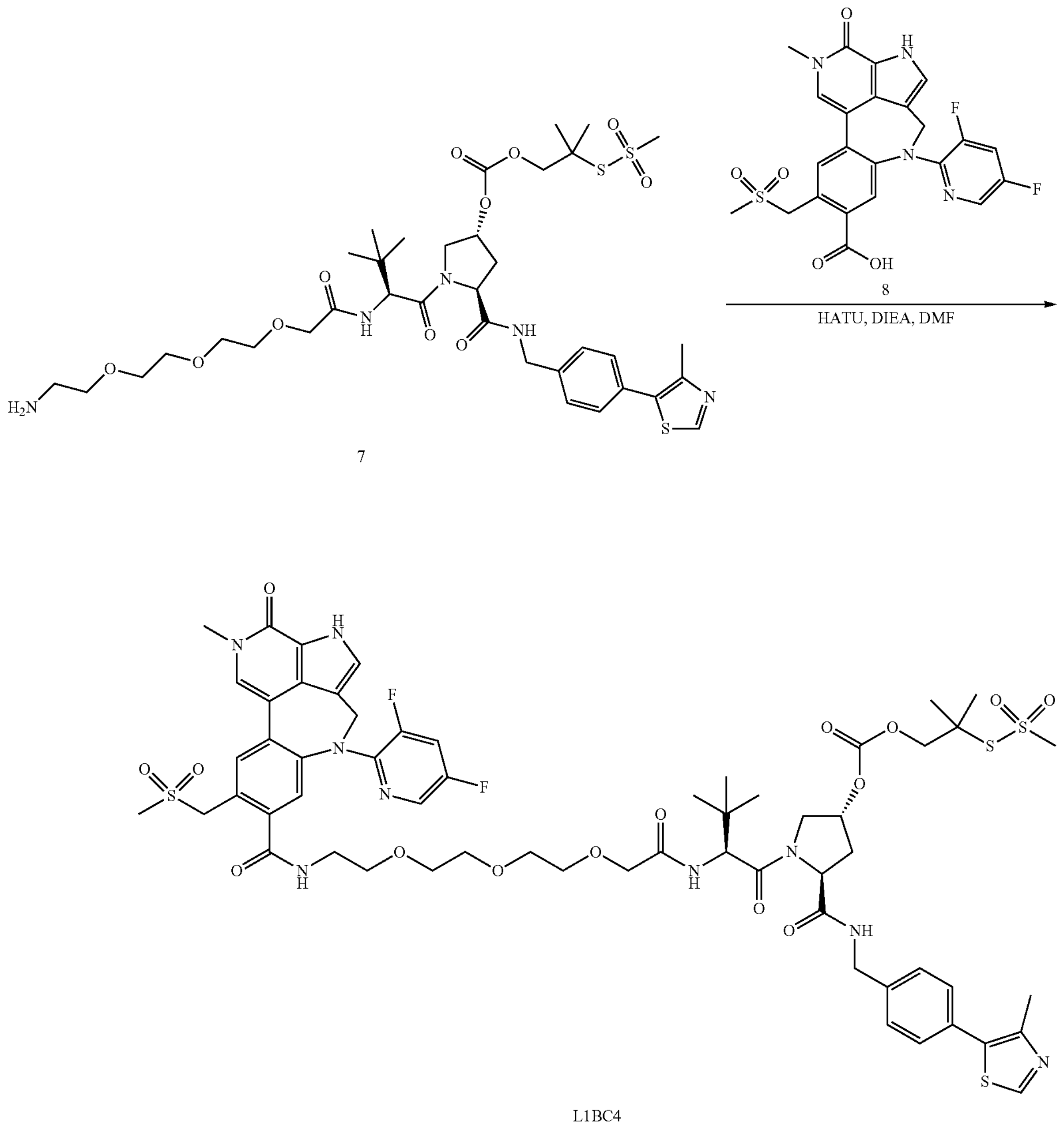

7

8

L1BC4

To a solution of compound 8 (20.0 mg, 0.0400 mmol) and HATU (19.75 mg, 0.0500 mmol) in DMF (5.0 mL) was added DIEA (22.46 mg, 0.1700 mmol). The mixture was stirred at 25° C. for 10 min. To above mixture was added Compound 7 TFA salt (32.8 mg, 0.030 mmol), and the mixture was stirred at 25° C. for 1 h. The mixture was concentrated and the resulting residue was purified by prep-HPLC (41-71 water (0.225% FA)-ACN) to afford to the desired product L1BC4 (21.79 mg, 42% yield) as a white solid. LCMS (5-95, AB, 1.5 min): RT=0.819 min m/Z=1313.6[M+1]$^+$; $^1$H NMR (400 MHz, DMSO-d6) δ 11.91 (s, 1H), 8.97 (s, 1H), 8.65 (brs, 1H), 8.48 (brs, 1H), 8.06 (s, 1H), 7.92 (s, 1H), 7.76 (s, 1H), 7.62-7.57 (m, 1H), 7.45-7.39 (m, 5H), 7.28 (brs, 2H), 5.95 (brs, 1H), 5.26-5.17 (m, 2H), 4.62-4.26 (m, 7H), 4.07-3.86 (m, 4H), 3.62 (brs, 5H), 3.53 (brs, 10H), 2.90 (s, 3H), 2.43-2.33 (m, 7H), 2.15-2.11 (m, 1H), 1.49 (d, J=6.8 Hz, 6H), 1.23 (brs, 1H), 0.91 (s, 9H).

xii. L1BC5 An exemplary L1-CIDE, L1BC5, can be synthesized by the following scheme:
Scheme 14
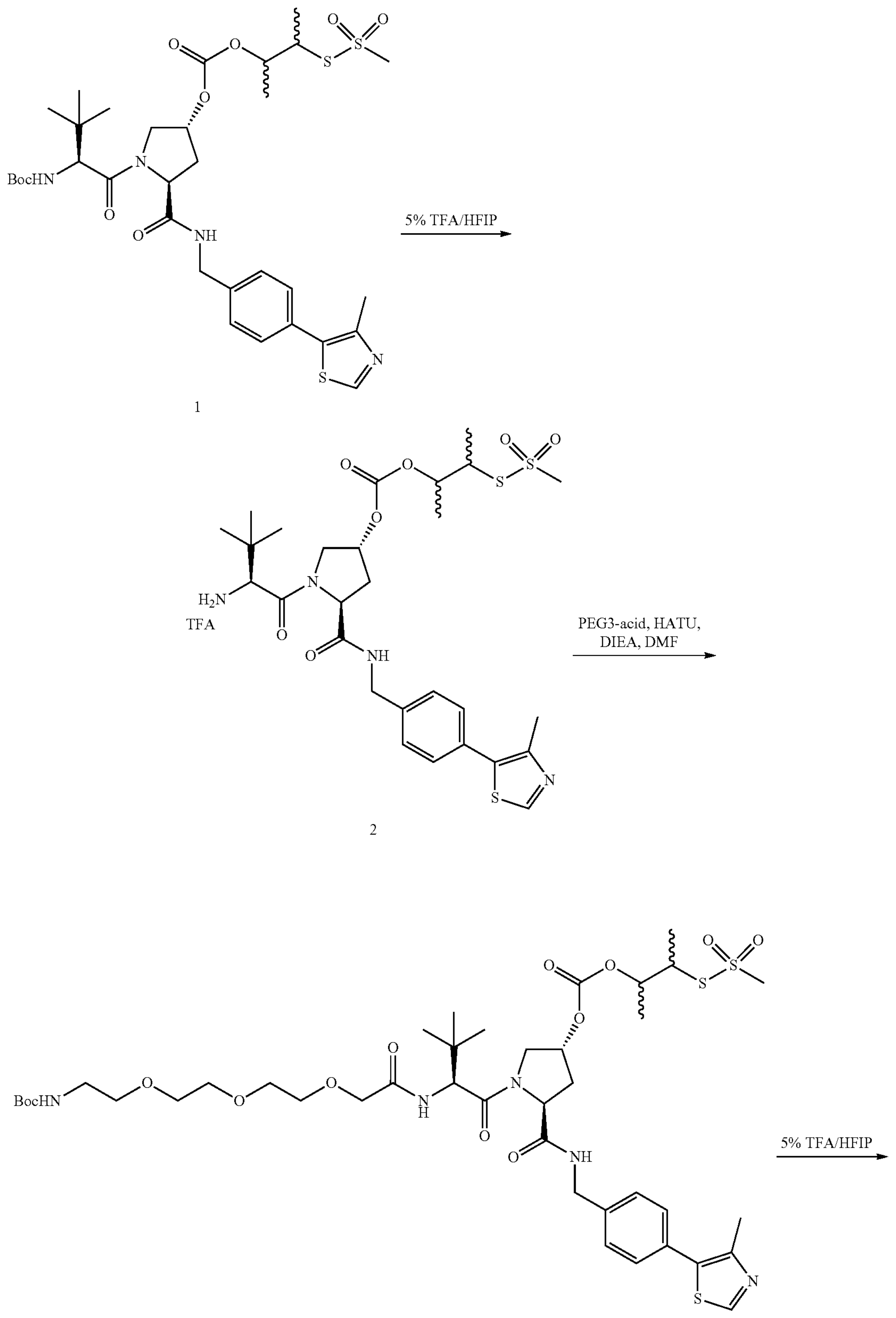

-continued
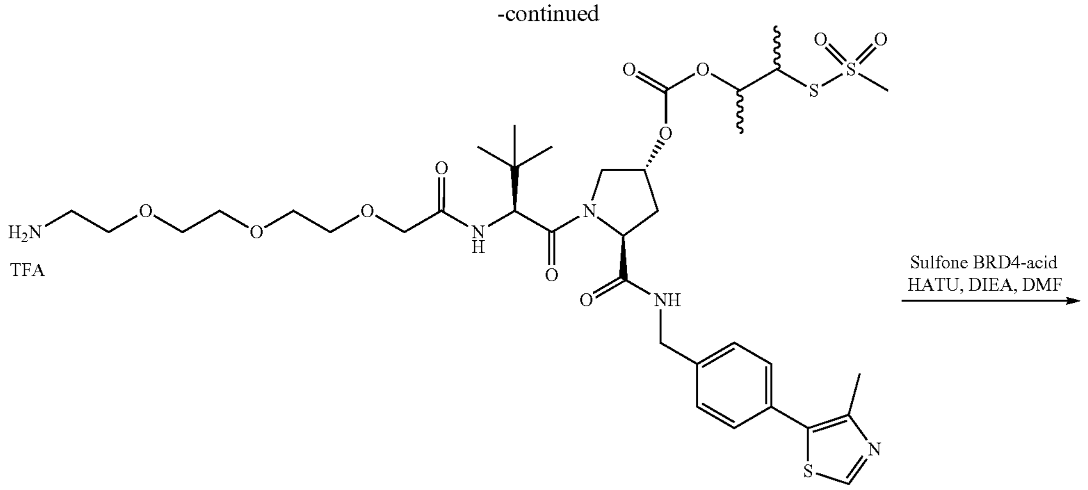
4
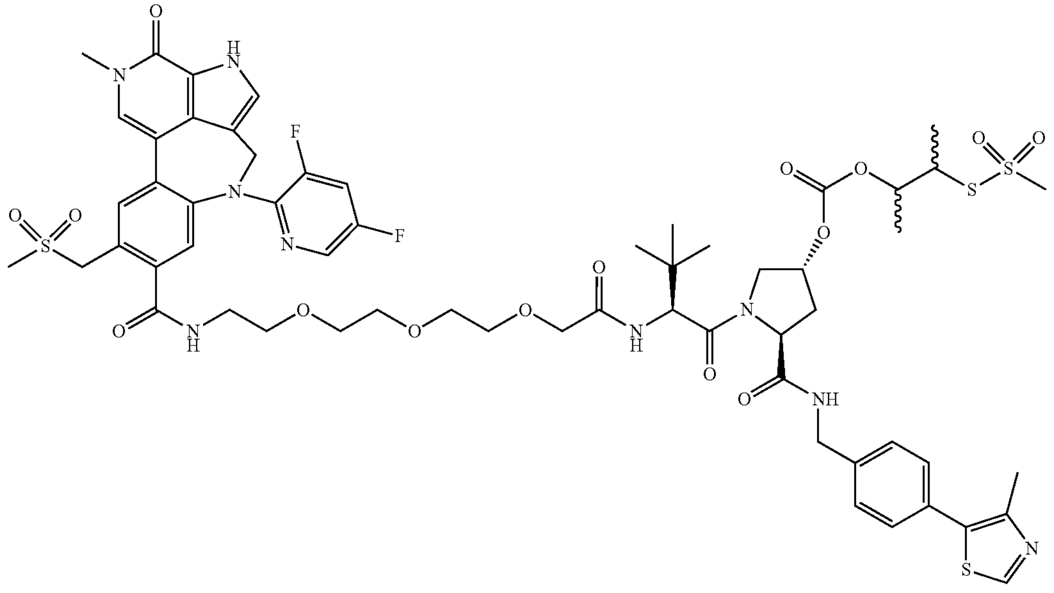
L1BC5
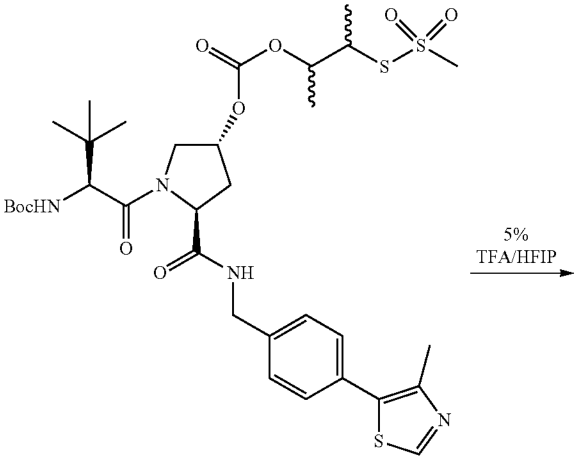
1
-continued
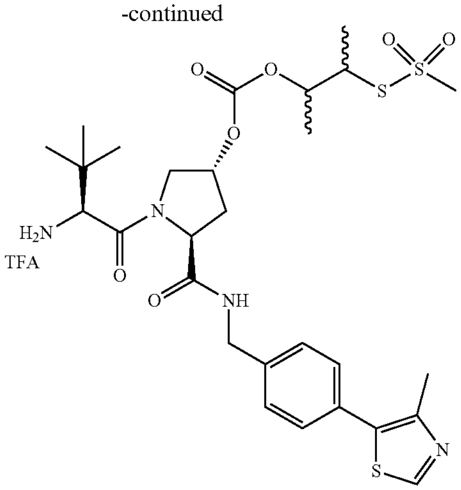
2

A solution of compound 1 (100.0 mg, 0.1300 mmol) in a mixture of TFA (0.2 mL) and HFIP (4.0 mL) was stirred at 20° C. for 1 h. The solution was concentrated, the residue was diluted with DMF (8 mL). It was concentrated in vacuo again to afford compound 2 (100 mg, 98.2% o) as crude colorless oil, which was used for the next step directly. LCMS (5-95, AB, 1.5 min). RT=0.705 min, m/z=663.1 $[M+23]^+$.

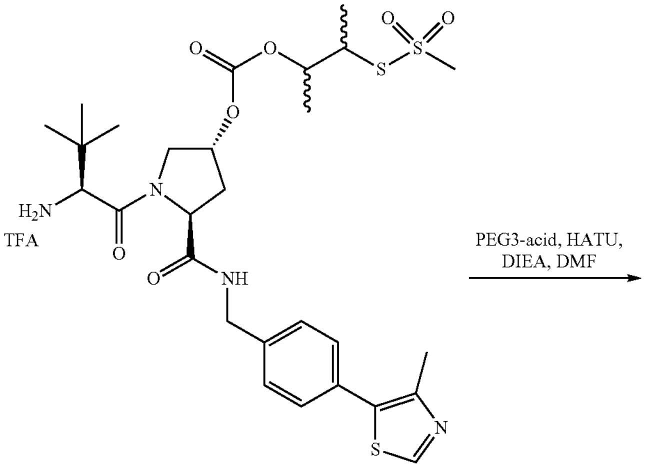

2

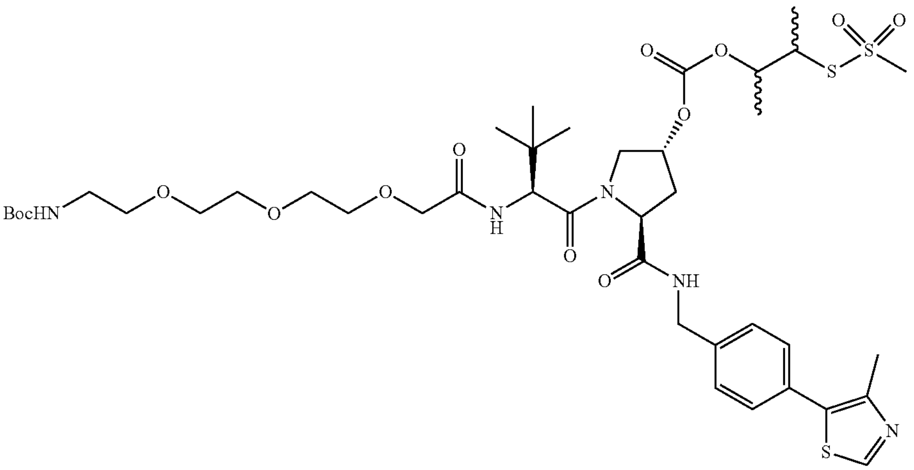

3

To a solution of 2-[2-[2-[2-(tert-butoxycarbonylamino)ethoxy]ethoxy]ethoxy]acetic acid (40.71 mg, 0.1300 mmol) in DMF (5.0 mL) was added DIEA (68.48 mg, 0.530 mmol) and HATU (60.45 mg, 0.1600 mmol). The solution was stirred at 25° C. for 10 min, then compound 2 (100.0 mg, 0.1300 mmol) was added. The resulting reaction solution was stirred at 25° C. for another 1 h. The solution was concentrated and the residue was purified by prep-TLC (10% MeOH in DCM, Rf=0.5) to afford compound 3 (110 mg, 77%) as a white solid. LCMS (5-95, AB, 1.5 min): RT=0.942 min, m/z=952.4 $[M+23]^+$.

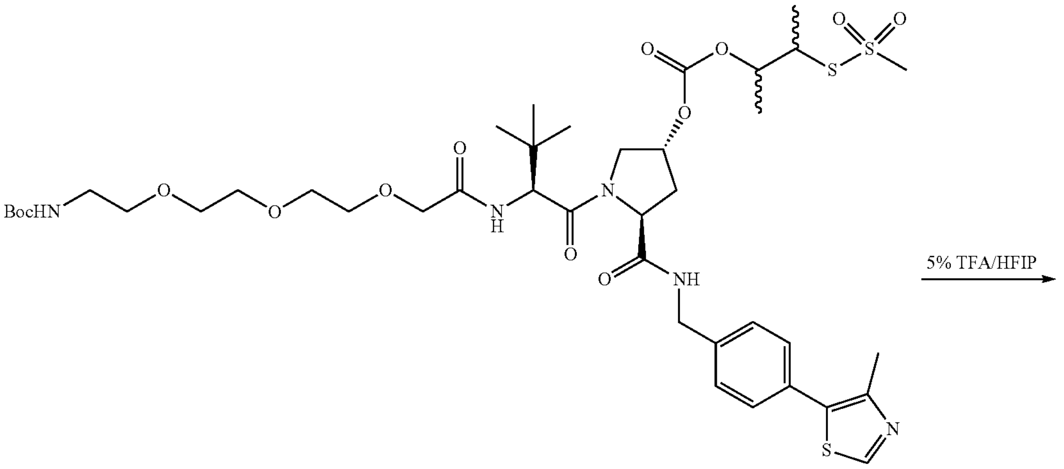
3
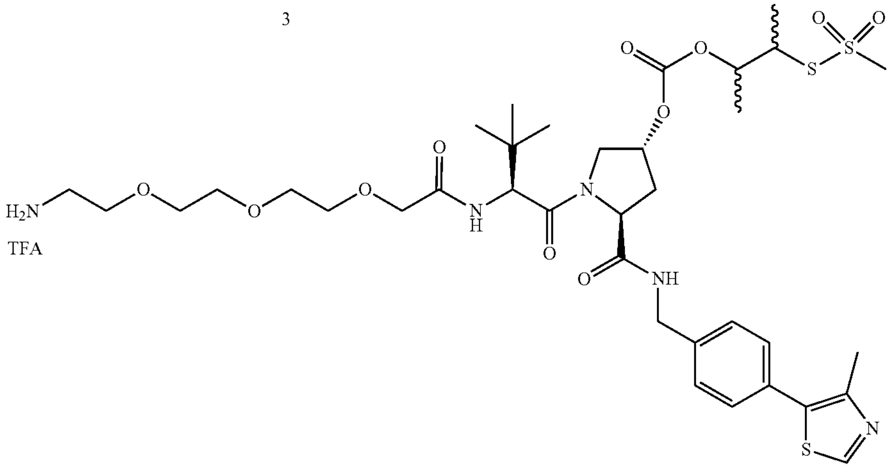
4
A solution of compound 3 (50.0 mg, 0.0500 mmol) in a mixture of TFA (0.20 mL) and HFIP (4.0 mL) was stirred at 25° C. for 1 h. The solution was concentrated, and the residue was diluted with DMF (6.0 mL). It was concentrated again to remove the remaining TFA to afford compound 4 (50 mg, 98.5%) as crude colorless oil. LCMS (5-95, AB, 1.5 min): RT=0.740 min, m/z=830.3 $[M+1]^+$.
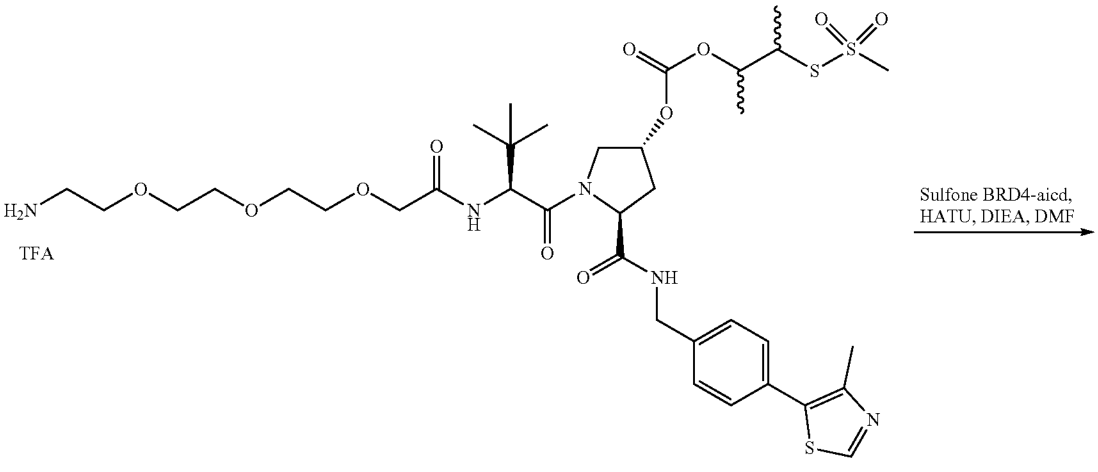
4

-continued

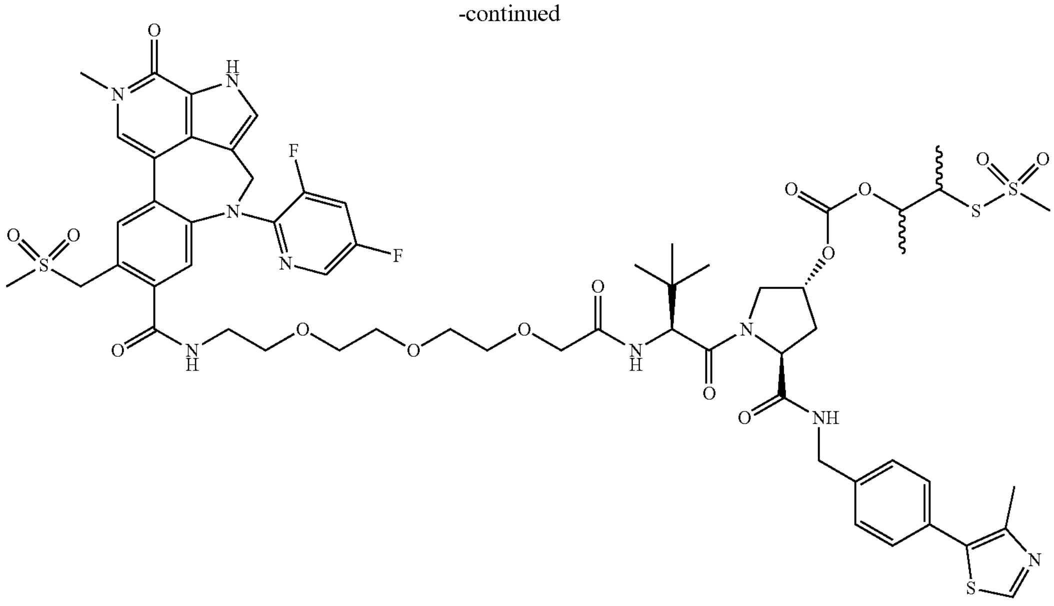

L1BC5

To a solution of sulfone BRD4-acid (20.0 mg, 0.0400 mmol) in DMF (4.0 mL) was added DIEA (20.66 mg, 0.1600 mmol) and HATU (18.23 mg, 0.0500 mmol). The solution was stirred at 25° C. for 10 min, then compound 4 (45.27 mg, 0.0500 mmol) was added. After the reaction solution was stirred at 25° C. for another 1 h, it was concentrated and purified by prep-HPLC (Xtimate C18 150*25 mm*5 um, acetonitrile 36-66/0.225% FA in water) to afford L1BC5 (15 mg, 29%) as a white solid. LCMS (5-95, AB, 1.5 min): $R_T$=0.839 min, m/z=1334.2 $[M+23]^+$; $^1H$ NMR (400 MHz, $CD_3OD$) δ 8.87 (s, 1H), 7.94 (s, 1H), 7.88 (s, 1H), 7.69 (s, 2H), 7.62-7.58 (m, 1H), 7.43-7.35 (m, 3H), 7.25-7.22 (m, 2H), 5.29 (s, 1H), 4.62-4.51 (m, 4H), 4.34-4.22 (m, 4H), 4.04-3.92 (m, 4H), 3.71-3.64 (m, 11H), 3.51-3.49 (m, 2H), 3.43-3.38 (m, 3H), 2.98 (s, 3H), 2.47-2.45 (m 4H), 2.29-2.26 (m, 2H), 1.46-1.43 (m, 2H), 1.38-1.25 (m, 4H), 1.03-1.00 (m, 9H).

xiii. L1BC6 An exemplary L1-CIDE, L1BC6, can be synthesized by the following scheme:

Scheme 15

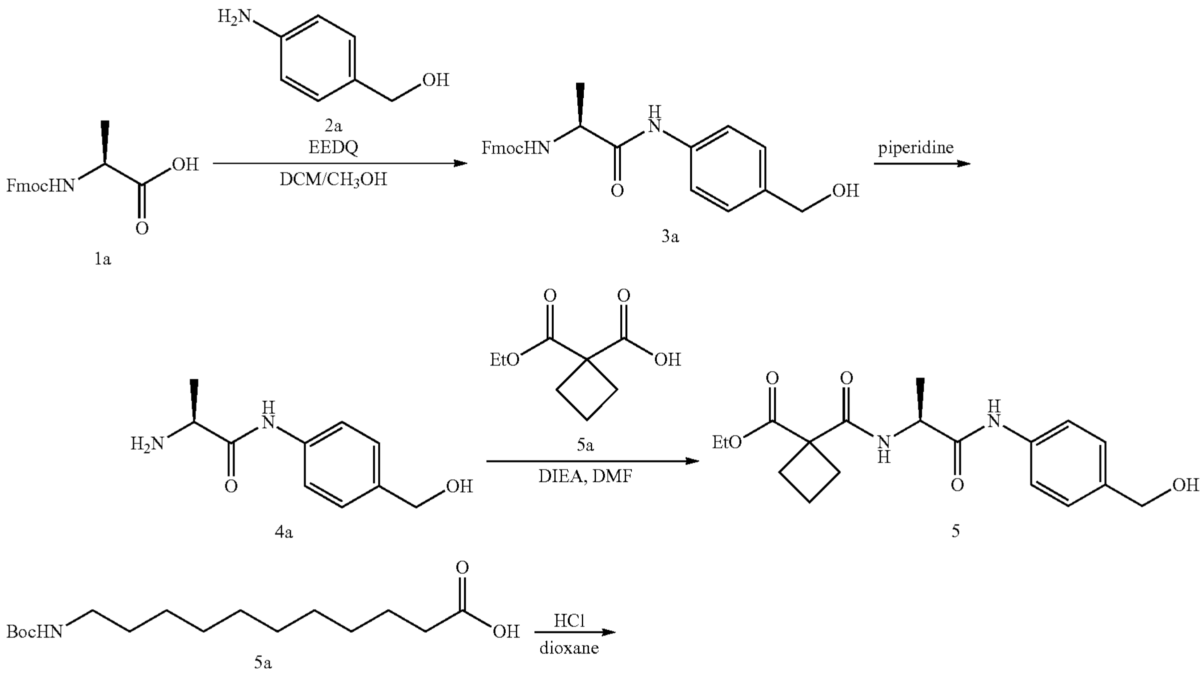

-continued
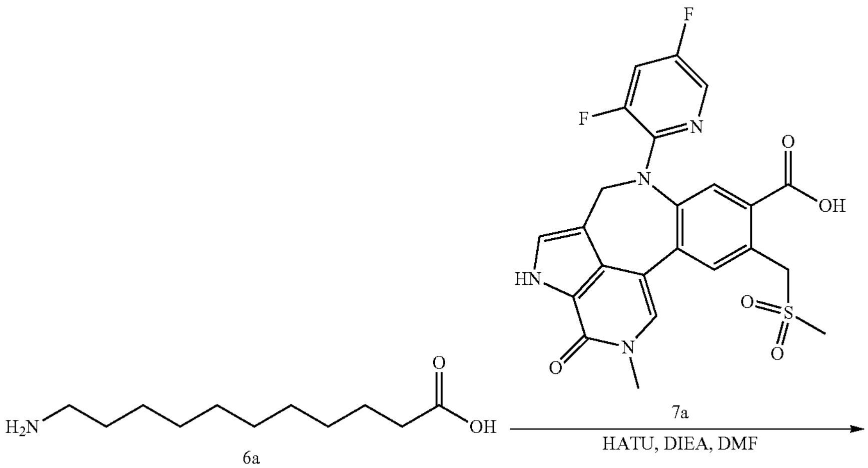
6a
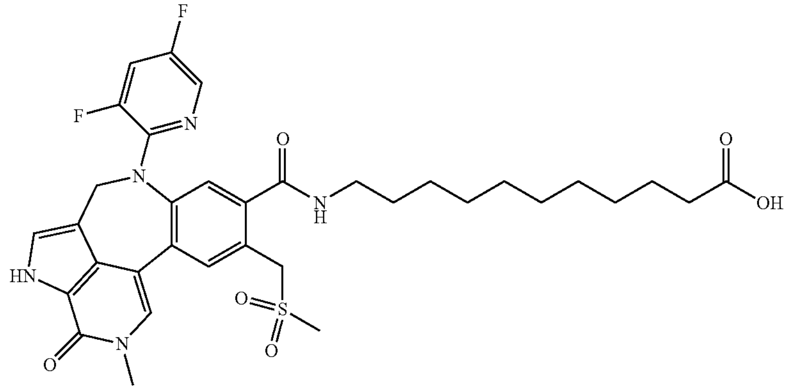
8
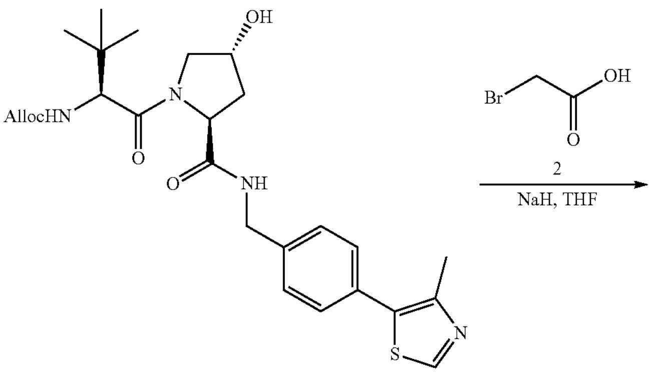
1

-continued
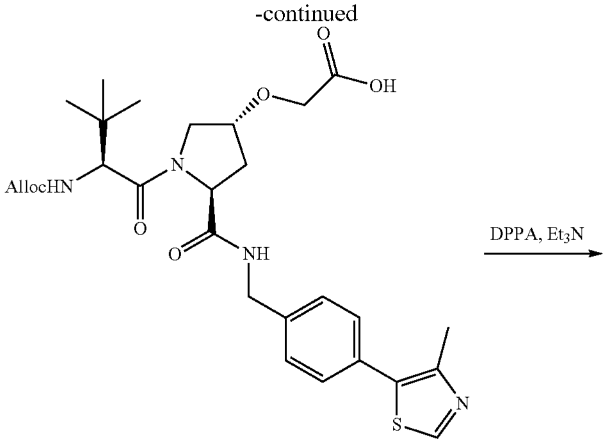
3
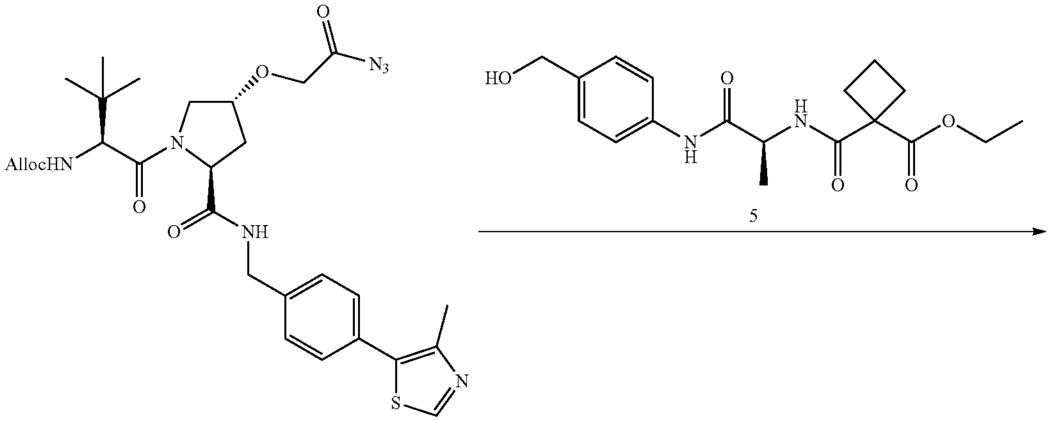
4
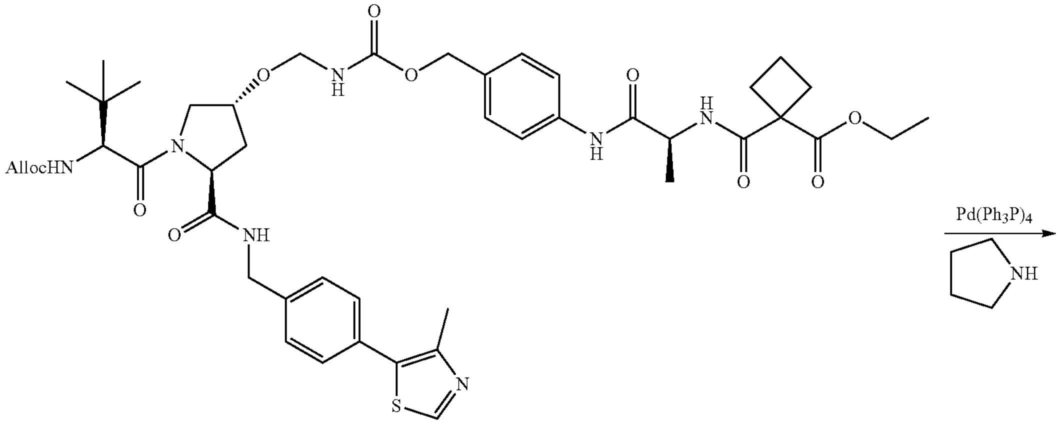
6

-continued
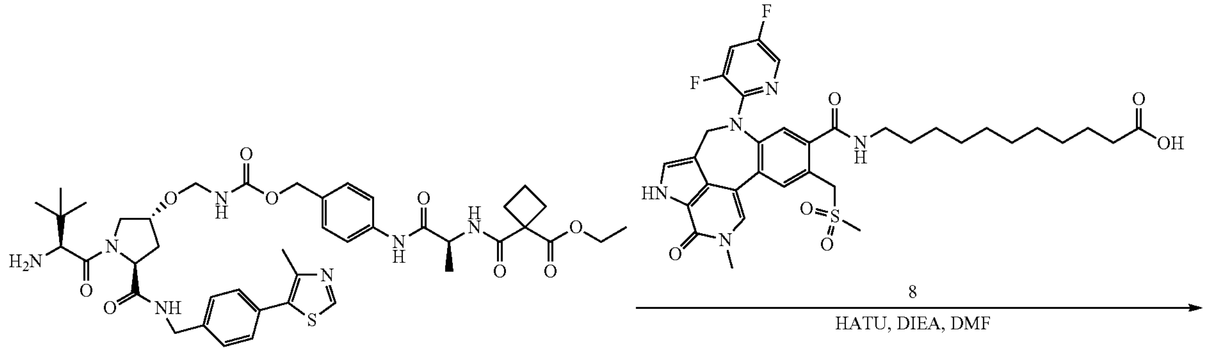
7
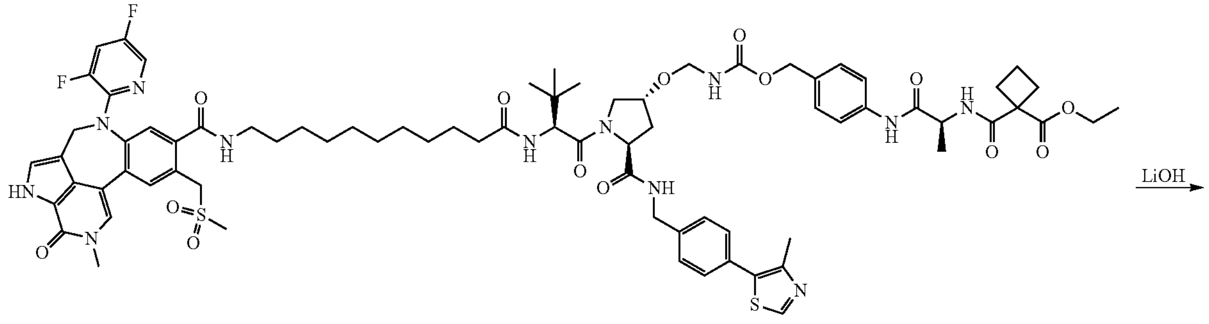
9
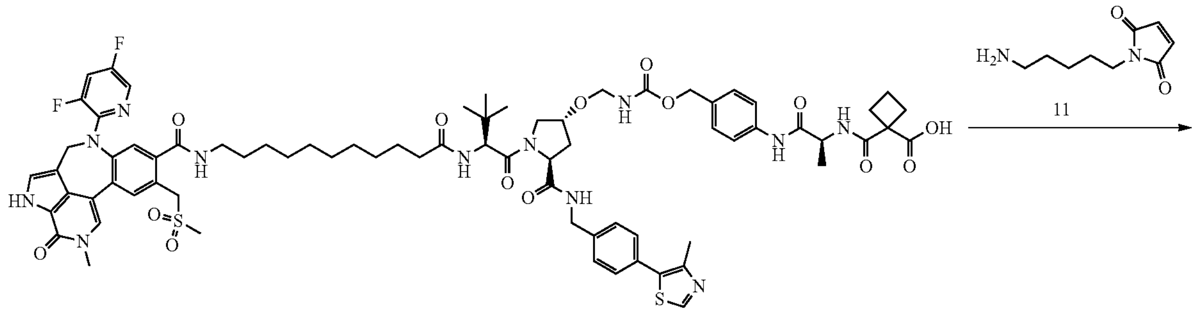
10
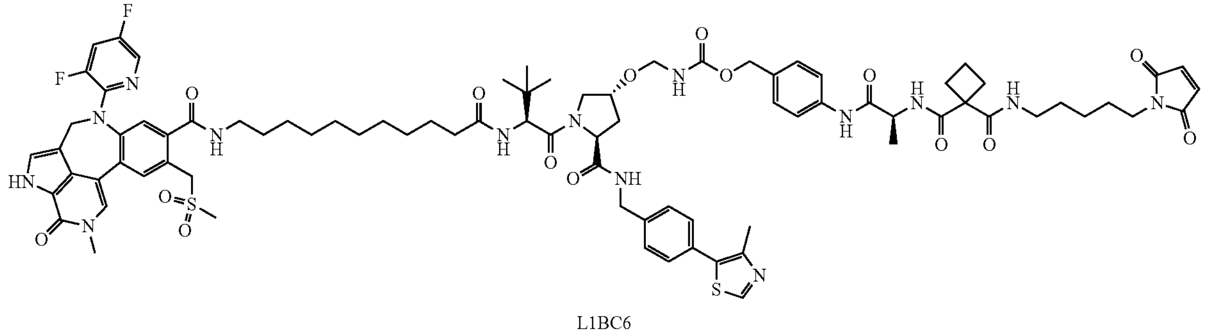
L1BC6

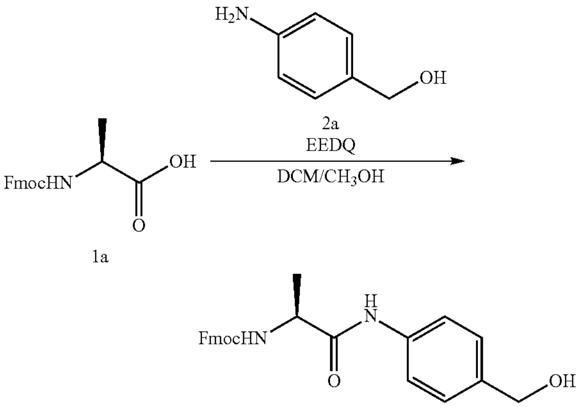

1a

3a

To a stirred solution of compound 1a (5.000 g, 16.06 mmol) in DCM (50 ML) and MeOH (10 mL) was added EEDQ (7.943 g, 32.12 mmol). After it was stirred for 10 min, compound 2a (2.967 g, 24.1 mmol) was added under $N_2$ at 20° C. After the mixture was stirred at 20° C. for 12 h, it was concentrated, and washed by methyl tert-butyl ether (20 mL×3) and DCM (20 mL) to afford compound 3a (5.000 g, 75%) as a white solid. LCMS (5-95, AB, 1.5 min): $R_T$=0.876 min, m/z=439.2 $[M+23]^+$; $^1H$ NMR (400 MHz, DMSO-d6) δ 9.92 (s, 1H), 7.85 (d, J=7.6 Hz, 2H), 7.73-7.62 (m, 3H), 7.51 (d, J=8.4 Hz, 2H), 7.38-7.19 (m, 6H), 5.08 (t, J=5.6 Hz, 1H), 4.39 (d, J=5.6 Hz, 2H), 4.29-4.21 (m, 2H), 4.18-4.15 (m, 2H), 1.28-1.23 (m, 3H).

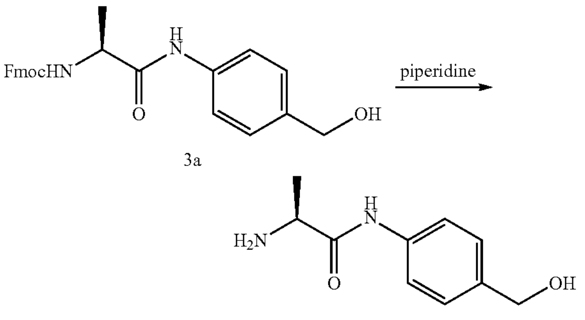

3a

4a

To a solution of piperidine (3.066 g, 36.02 mmol) in DMF (50 mL) was added compound 3a (3.000 g, 7.2 mmol) at 25° C. The reaction mixture was stirred at 25° C. for 1 h and concentrated to give the crude product which was washed with methyl tert-butyl ether (10 mL×3) to afford the compound 4a (1.390 g, 99.3%) as a white solid which was used directly in next step.

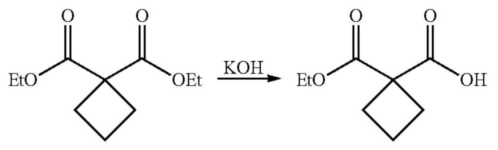

4b

5a

To a stirred solution of compound 4b (20.00 g, 99.89 mmol) in EtOH (100 mL) was added KOH (5.6 g, 99.89 mmol)/water (10 mL) at 18° C. The reaction mixture was stirred at 80° C. for 4 h. The mixture was concentrated to dryness and partitioned between EtOAc (100 mL) and $H_2O$ (130 mL). The aqueous phase was acidified with HCl (1.0 M) to pH=3.0 and extracted with EtOAc (120 mL×2). The organic layers were dried over $Na_2SO_4$, filtered and concentrated to give compound 5a (13.5 g, 78.5%) as a colorless oil. The crude was used directly in the next step. LCMS (5-95, AB, 1.5 min): $R_T$=0.560 min, m/z=172.8 $[M+1]^+$.

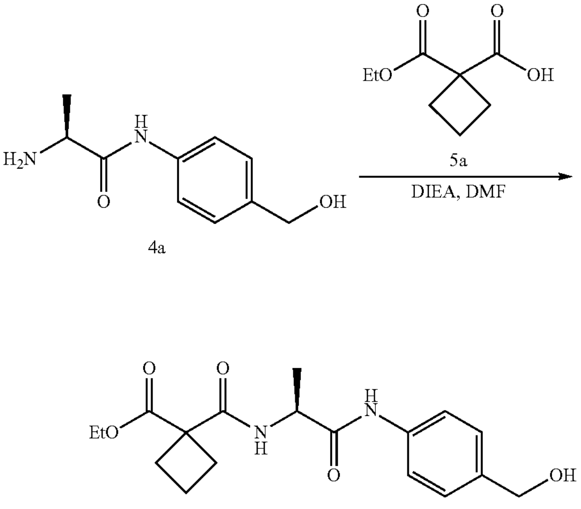

4a

5

To a mixture of compound 5a (1.478, 8.59 mmol) in DMF (20 mL) was added HATU (4.081 g, 10.73 mmol) and DIEA (4.624 g, 35.78 mmol). The mixture was stirred for 30 min, then compound 4a (1.390 g, 7.16 mmol) was added at 25° C. The mixture was stirred for 2 h. The mixture was concentrated and purified by column chromatography on silica (0-10% MeOH in DCM, $R_f$=0.6) to give compound 5 (1.900 g, 70.7%) as a white solid. LCMS (5-95, AB, 1.5 min): $R_T$=0.766 min, m/z=371.1 $[M+23]^+$;

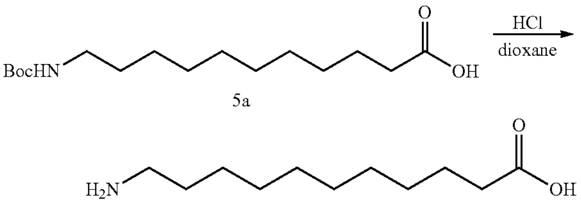

5a

6a

Compound 5a (30.0 mg, 0.1000 mmol) was dissolved in 4M HCl in dioxane (2.0 mL) at 25° C., the mixture was stirred at 25° C. for 1 h. The mixture was concentrated to give the crude product compound 6a (23.66 mg, 100%) as a gray solid, which was used directly in the next step.

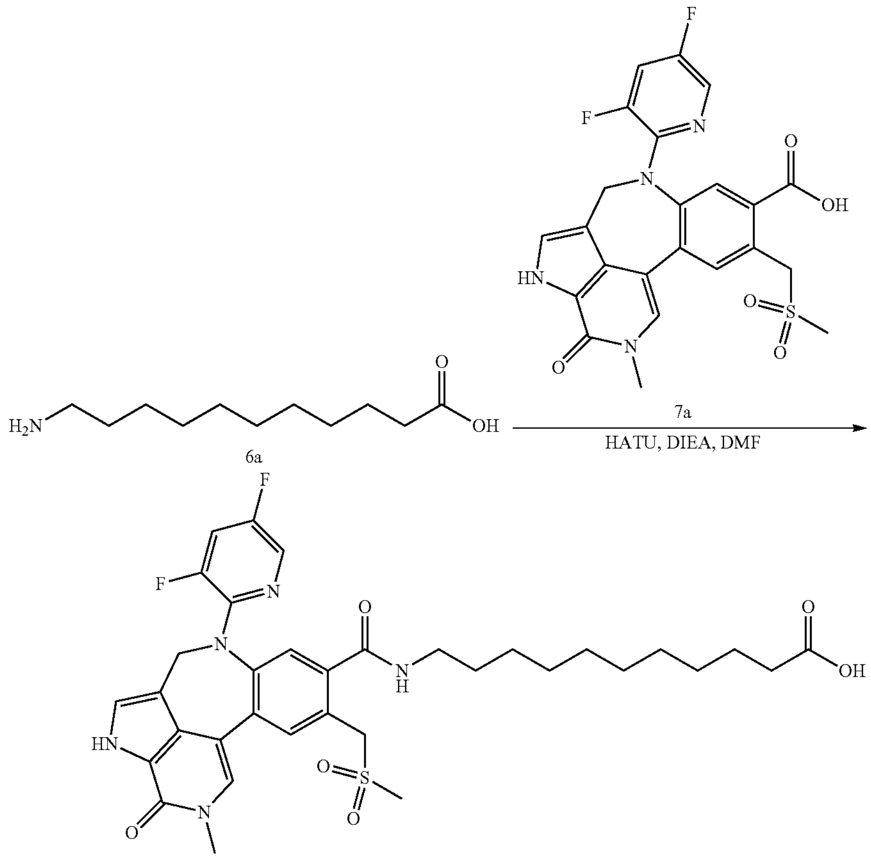

6a

7a

8

A solution of compound 7a (25.0 mg, 0.0500 mmol), DIEA (19.37 mg, 0.1500 mmol) and HATU (22.79 mg, 0.0600 mmol) in anhydrous DMF (3.0 mL) was stirred at 25° C. for 50 min. Compound 6a (17.82 mg, 0.0700 mmol) was added and the reaction mixture was stirred at 25° C. for 2 h. The reaction mixture was concentrated and the residue was purified by prep-TLC (12% MeOH in DCM, Rf=0.4) to give the product compound 8 (34 mg, 99.5%) as a gray solid. LCMS (5-95, AB, 1.5 min): $R_T$=0.817 min, m/z=684.3 $[M+1]^+$.

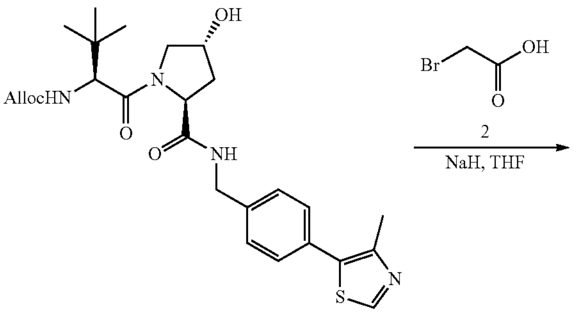

1

2

-continued

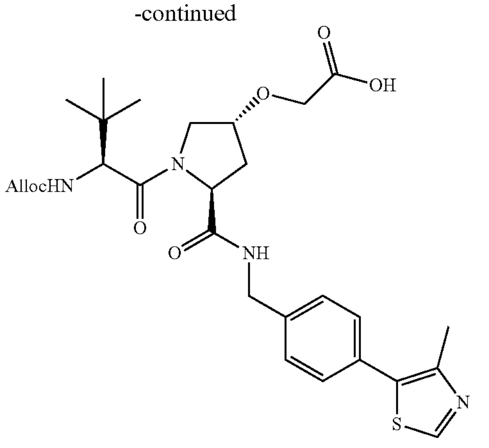

3

NaH (60%, 240.95 mg, 6.02 mmol) was suspended in THF (4.0 mL) and compound 1 (310.0 mg, 0.600 mmol) in THF (3.0 mL) was added dropwise at 25° C., and the reaction mixture was stirred at 25° C. for 2 h. Then compound 2 (125.55 mg, 0.900 mmol) in THF (3.0 mL) was added. After the resulted reaction mixture was stirred at 25° C. for 12 h, it was quenched with water (10 mL) and extracted with EtOAc (10 mL). The aqueous layer was separated and acidified with HCl (2.0 M) to pH=3.0 and extracted with a solution of 10% of MeOH in DCM (10 mL×2). The DCM layer was dried and concentrated to give the crude product compound 3 (320 mg, 92.8%) as a brown solid, which was used directly in the next step.

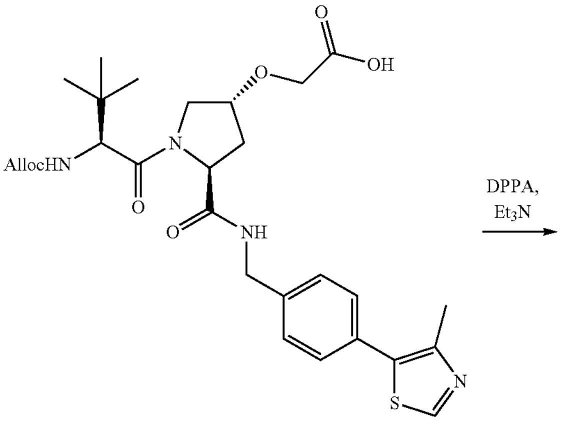

3

-continued

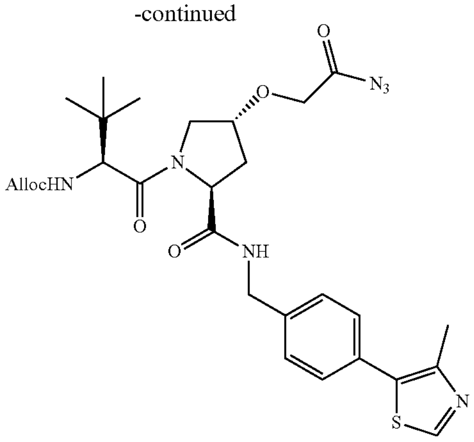

4

To a solution of compound 3 (100.0 mg, 0.1700 mmol) and DPPA (96.11 mg, 0.350 mmol) in DMF (2.0 mL) was added $Et_3N$ (70.68 mg, 0.7000 mmol). The resulted mixture was stirred at 25° C. for 1 h. The mixture was diluted with water (5.0 mL) and extracted with toluene (3.0 mL×2). The toluene layer was dried over $Na_2SO_4$ and 4A molecular sieves, filtered, and the filtrate was used directly in the next step.

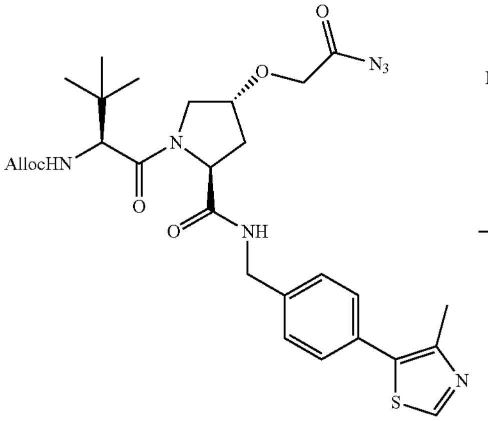

4

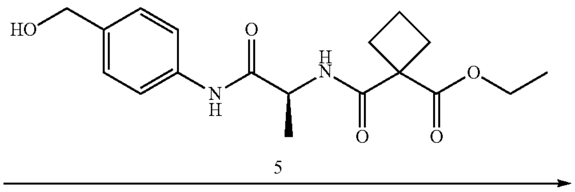

5

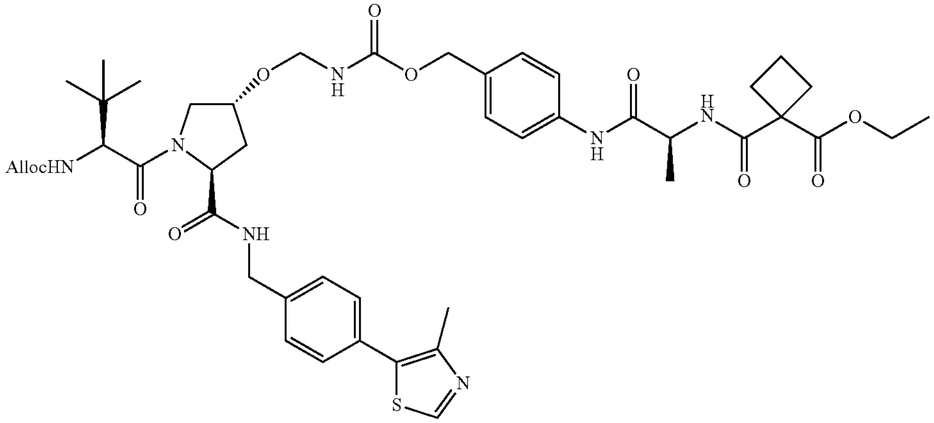

6

To the above solution of compound 4 (100.0 mg, 0.1700 mmol) in toluene (6.0 mL) and DMF (1.0 mL) was added compound 5 (58.29 mg, 0.1700 mmol) and dibutyltin dilaurate (10.57 mg, 0.0200 mmol), and the mixture stirred at 80° C. for 1 h. The reaction mixture was filtered and the filtrate was concentrated and purified by prep-TLC (8% of MeOH in DCM, Rf=0.5) to afford compound 6 (100 mg, 65%) as a light yellow oil. LCMS (5-95, AB, 1.5 min): RT=0.769 min, m/z=918.4 [M+1]$^+$.

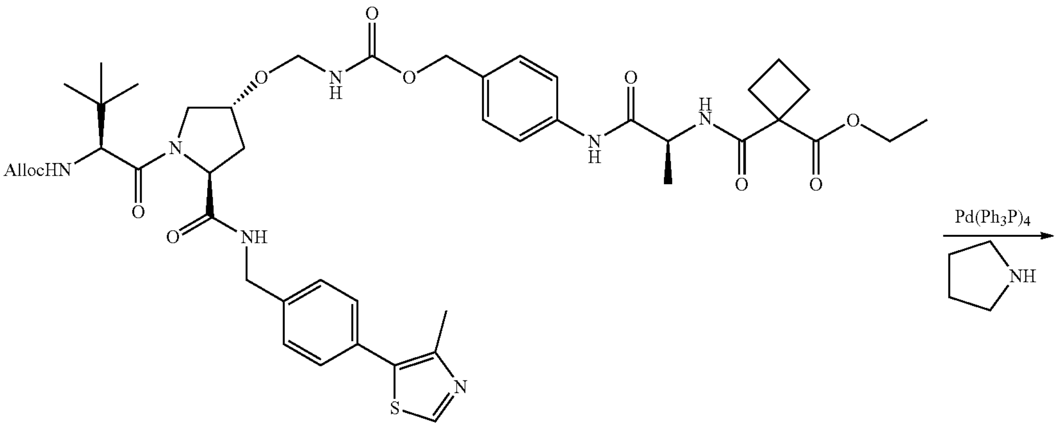

6

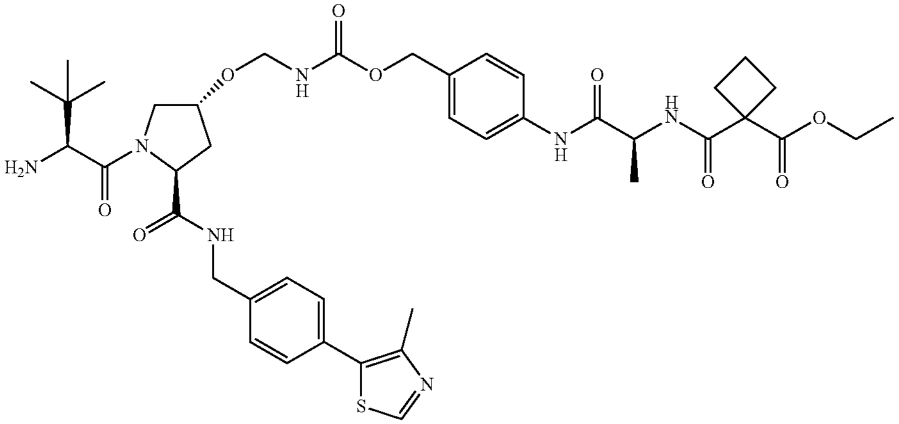

7

To a solution of compound 6 (80.0 mg, 0.0900 mmol) in DCM (3.0 mL) and MeOH (0.30 mL) was added $Pd(Ph_3P)_4$ (10.07 mg, 0.0100 mmol) and pyrrolidine (30.99 mg, 0.440 mmol), the mixture stirred at 25° C. for 1 h under $N_2$. The reaction mixture was concentrated and the residue was purified by prep-TLC (12% of MeOH in DCM, Rf=0.4) to give compound 7 (46 mg, 63%) as a brown solid. LCMS (5-95, AB, 1.5 min): RT=0.671 min, m/z=834.2 [M+1]$^+$.

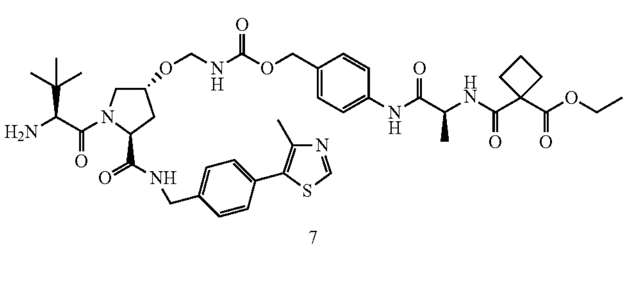

7

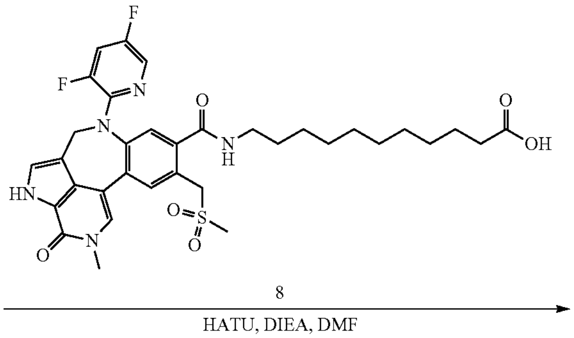

8

HATU, DIEA, DMF

-continued

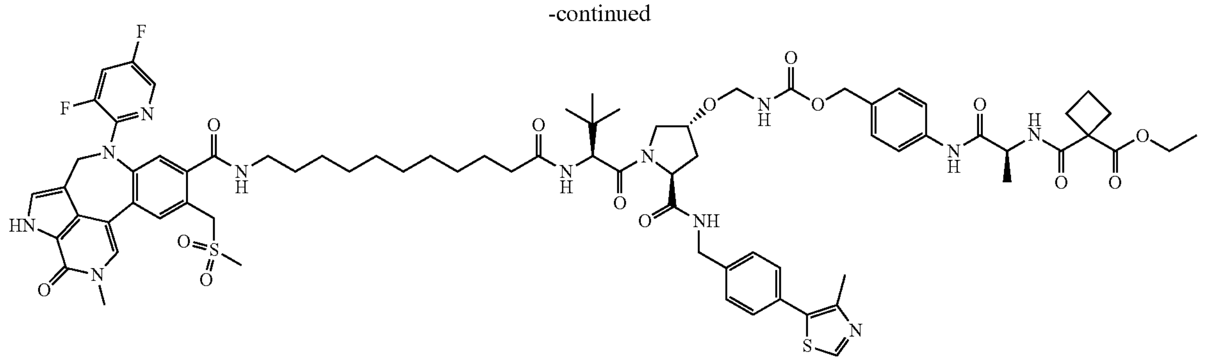

9

A solution of compound 8 (34.0 mg, 0.0500 mmol), DIEA (19.28 mg, 0.150 mmol) and HATU (28.36 mg, 0.0700 mmol) in anhydrous DMF (3.0 mL) was stirred at 25° C. for 50 min, and then compound 7 (45.62 mg, 0.0500 mmol) was added. The resulted mixture was stirred at 25° C. for 2 h. The reaction mixture was concentrated and the residue was purified by prep-TLC (10% MeOH in DCM, Rf=0.5) to give the product compound 9 (60 mg, 81%) as a gray solid. LCMS (5-95, AB, 1.5 min): RT=0.814 min, m/z=750.7 $[M/2+1]^+$.

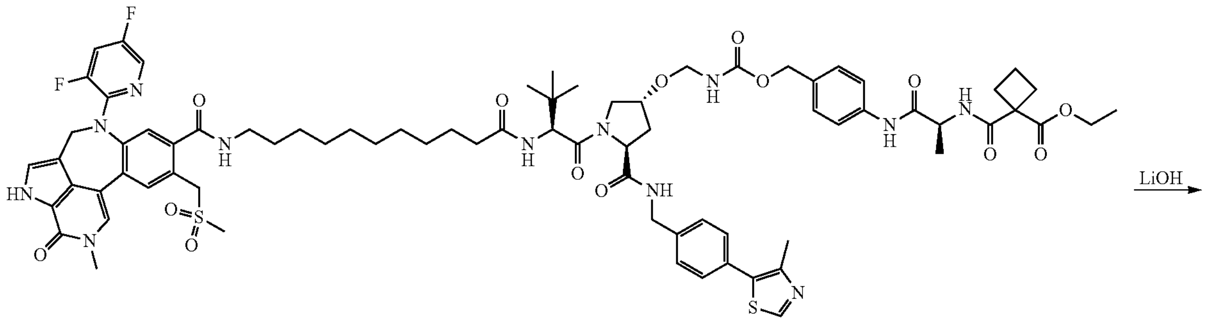

9

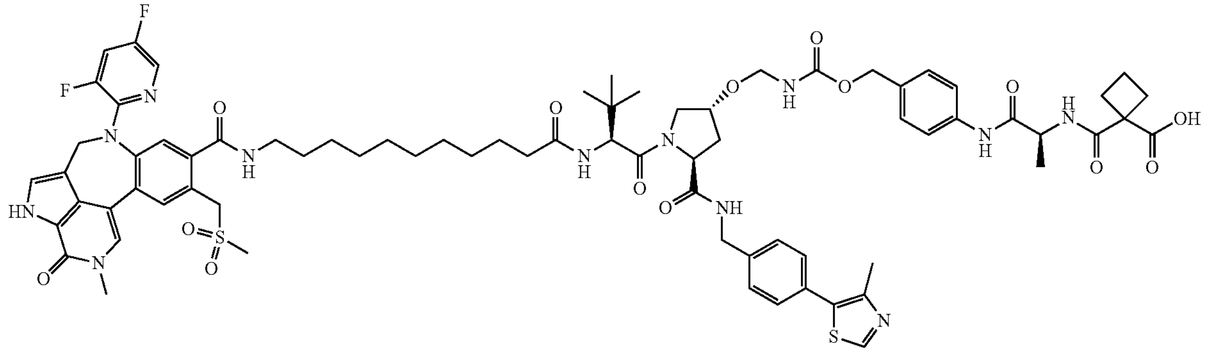

10

Compound 9 (60.0 mg, 0.0400 mmol) was dissolved in THF (2.0 mL) and MeOH (1.0 mL), and LiOH $H_2O$ (8.39 mg, 0.200 mmol) in water (1.0 mL) was added at 25° C. The reaction mixture was stirred at 25° C. for 2 h. The reaction mixture was concentrated and purified by prep-HPLC (acetonitrile 27-47/water) to afford compound 10 (11 mg, 19%) as a white solid, which was used directly in the next step. LCMS (5-95, AB, 1.5 min): RT=0.700 min, m/z=1097.5 [M (fragment)+1]+.

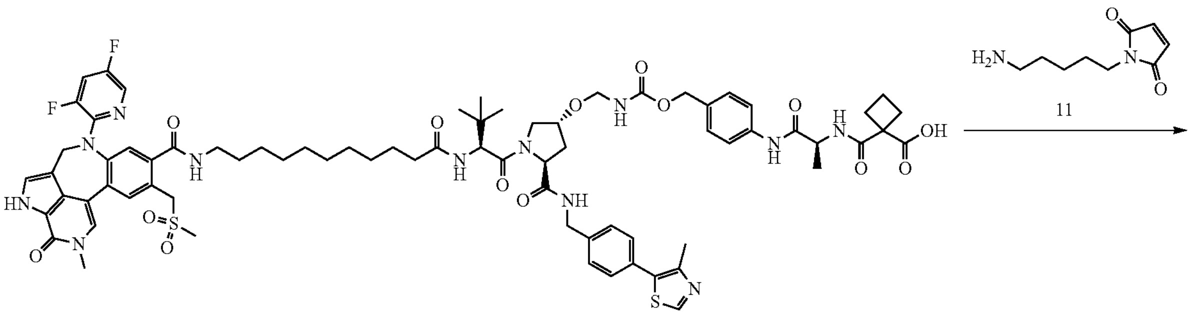

10

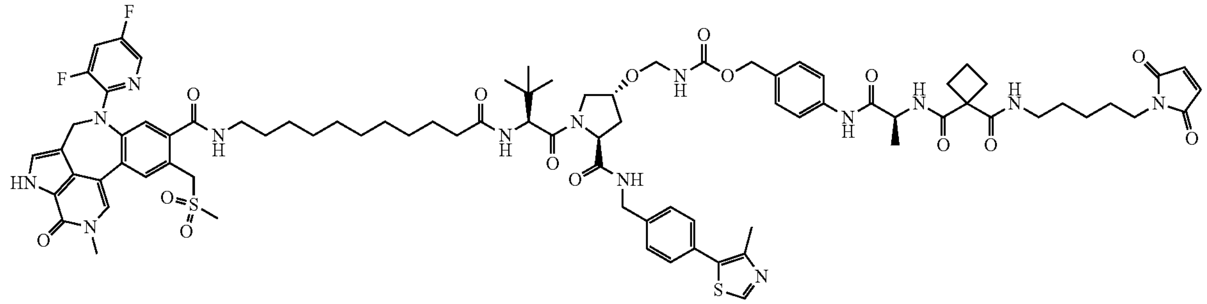

L1BC6

The solution of compound 10 (10.0 mg, 0.010 mmol), DIEA (2.63 mg, 0.020 mmol) and HATU (3.88 mg, 0.0100 mmol) in anhydrous DMF (3.0 mL) was stirred at 25° C. for 20 min, and then compound 11 (1.86 mg, 0.0100 mmol) was added. The resulted mixture was stirred at 25° C. for 2 h. The reaction mixture was filtered and the resulting residue was purified by prep-HPLC (acetonitrile 45-65/water) to afford the product L1BC6 (2.5 mg, 23%) as a white solid. LCMS (10-80, CD, 3.0 min): RT=1.950 min, m/z=818.5 [M/2+H]$^+$.

xiv. L1BC8 An exemplary L1-CIDE, L1BC8, can be synthesized by the following

Scheme 16

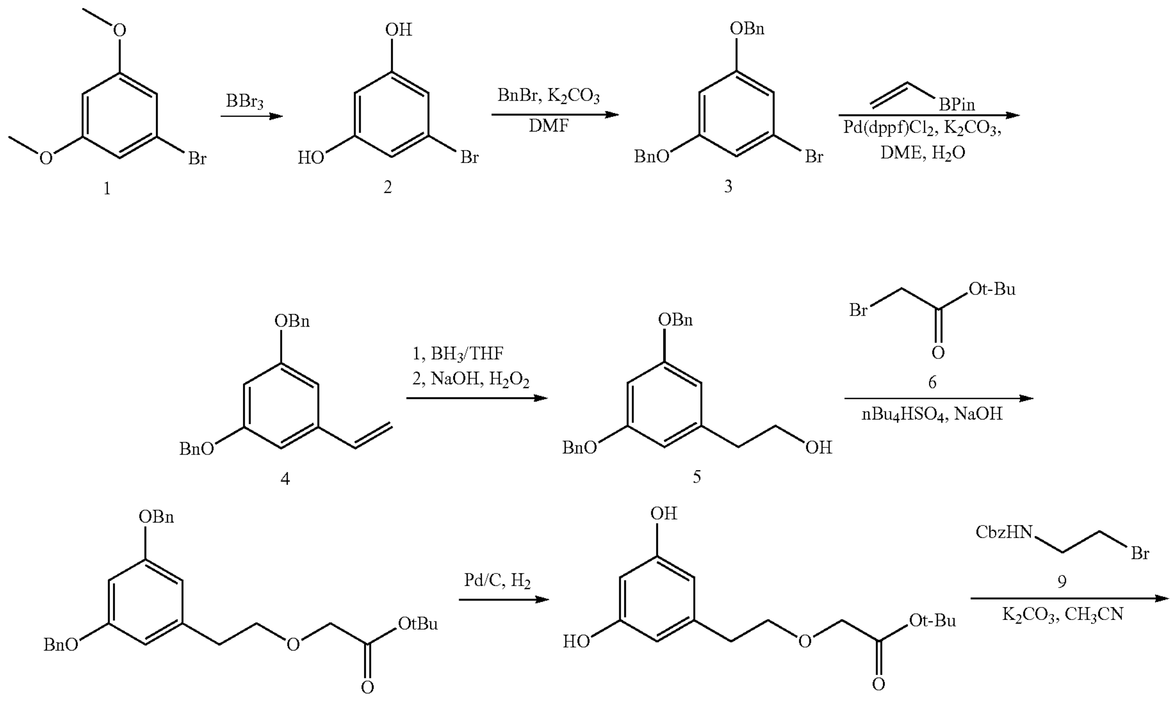

-continued
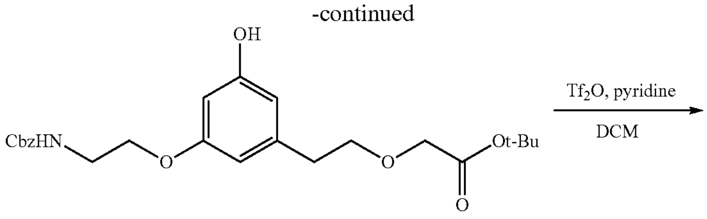
10
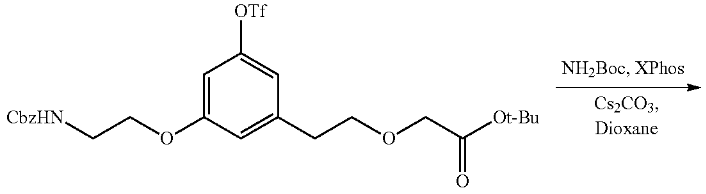
11
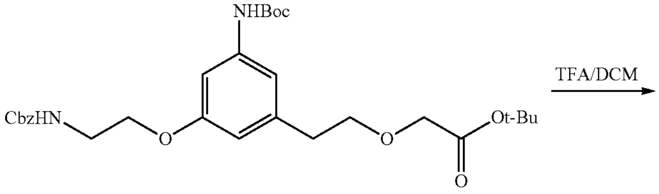
12
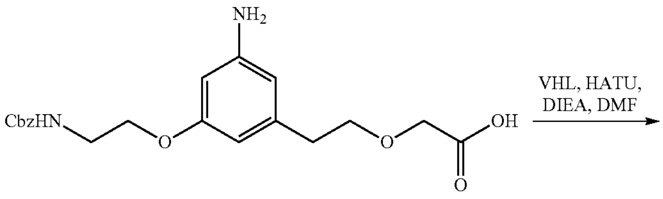
13
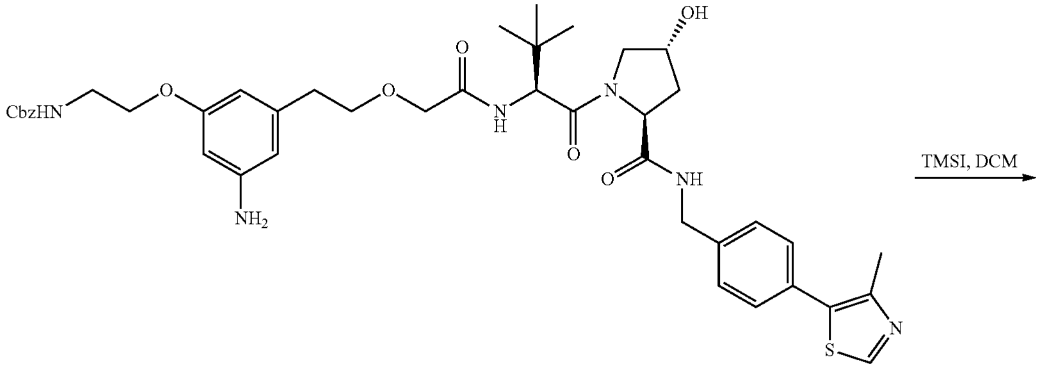
14
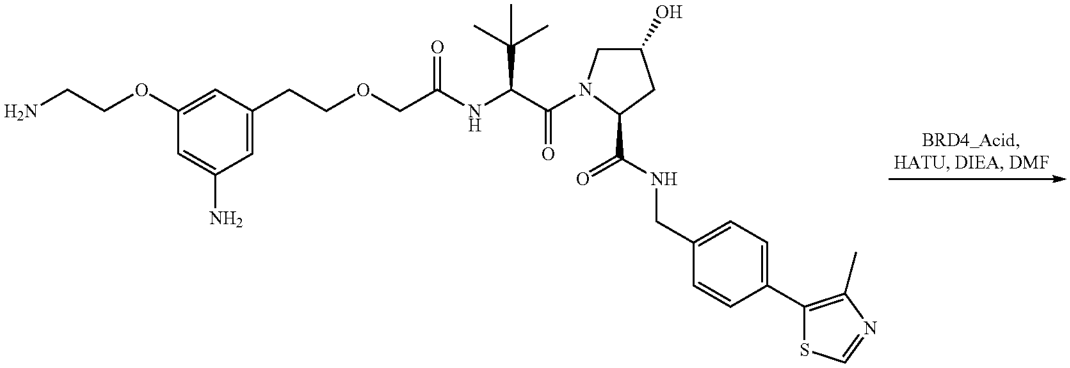
15

-continued

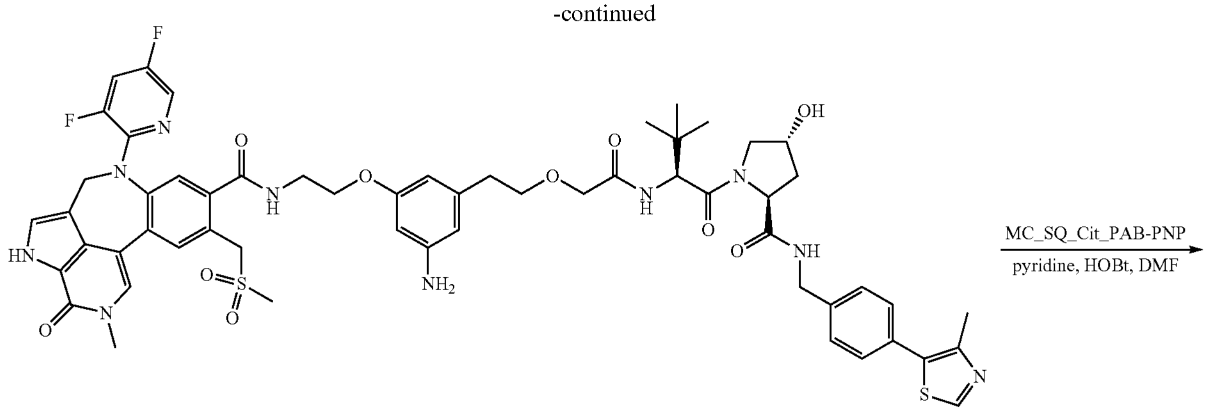

16

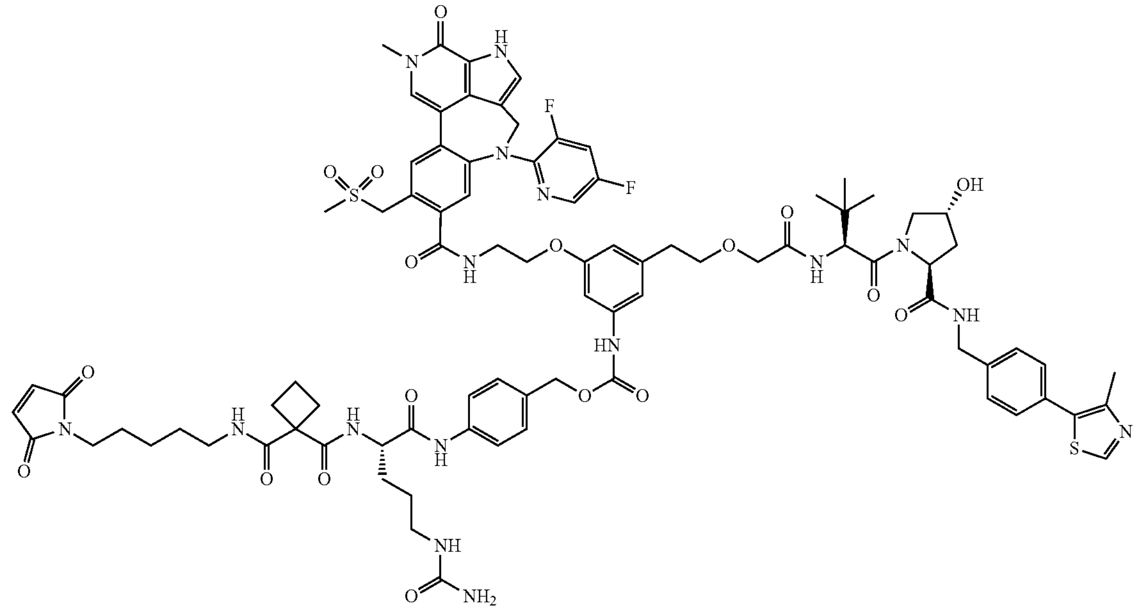

L1BC8

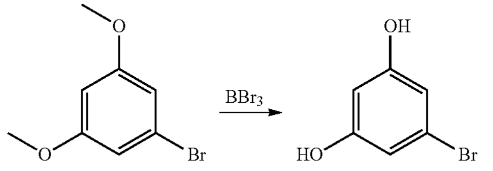

1 2

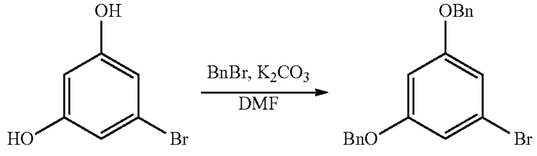

2 3

To a solution of 1 (25.0 g, 115.18 mmol) in DCM (200 mL) was added dropwise $BBr_3$ (21.45 mL, 230.35 mmol) at 0° C., and the mixture was stirred at 25° C. for 16 h. The reaction was quenched by MeOH (50 mL) and concentrated under vacuum to afford 2 (21.7 g, 99.7%) as a red oil, which was used directly without further purification.

The solution of 2 (6.0 g, 31.74 mmol) in DMF (150 mL) was added $K_2CO_3$ (8.77 g, 63.49 mmol) and BnBr (7.55 mL, 63.49 mmol). The mixture was stirred at 25° C. for 16 h. The mixture was filtrated and the organic layer was concentrated and purified by column chromatography (0-10% EtOAc in petroleum ether) to afford 3 (11.0 g, 94%) as a white solid. $^1$HNMR (400 MHz, $CDCl_3$) δ 7.40-7.35 (m, 10H), 6.76 (s, 4H), 6.54 (s, 1H), 5.00 (s, 4H).

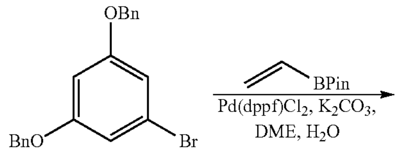

3

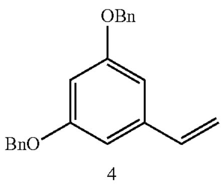

4

To a solution of 3 (11.0 g, 29.79 mmol) in 1,4-dioxane (100 mL) and water (20 mL) was added Pd(dppf)$Cl_2$ (2.18 g, 2.98 mmol), $Cs_2CO_3$ (19.41 g, 59.58 mmol), vinylboronic acid pinacolester (6.88 g, 44.69 mmol), the mixture was stirred at 100° C. for 16 h under $N_2$. The solution was filtered and extracted with EtOAc (40 mL×3) and washed with water (50 mL). The organic was dried over $Na_2SO_4$, filtrated, concentrated, and purified by column chromatography (0-10% EtOAc in petroleum ether) to give 4 (6.6 g, 70%) as a white solid. $^1$H NMR (400 MHz, $CDCl_3$) δ 7.44-7.29 (m, 10H), 6.67 (s, 2H), 6.55-6.54 (m, 1H), 5.70 (d, J=17.2 Hz, 1H), 5.24 (d, J=10.8 Hz, 1H), 5.04 (s, 4H).

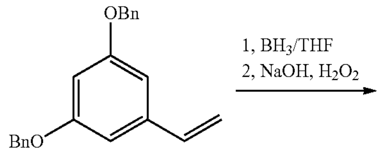

4

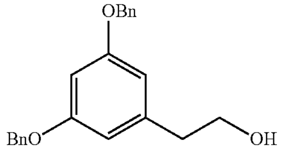

5

To a solution of 4 (6.60 g, 20.86 mmol) in THF (20 mL) was added $BH_3$/THF (31.29 mL, 31.29 mmol) at 0° C. under $N_2$, and the mixture was stirred at 25° C. for 3 h. Then an aq NaOH solution (3.0 M, 10.43 mL, 31.29 mmol) was added at 0° C., follow by $H_2O_2$ (31.39 mL, 312.9 mmol). The resulting mixture was stirred at 25° C. for 1 h. The reaction was quenched with a solution of $Na_2SO_3$, and extracted with EtOAc (30 mL×3) and water (30 mL). The organic was dried over $Na_2SO_4$, filtered, concentrated, and purified with column chromatography (0-50% EtOAc in petroleum ether) to afford 5 (4.8 g, 69%) as a white solid. $^1$HNMR (400 MHz, $CDCl_3$) δ 7.79 (s, 1H), 7.43-7.32 (m, 10H), 6.52-6.49 (m, 1H), 6.48 (s, 2H), 5.02 (s, 4H), 3.84 (t, J=6.4 Hz, 2H), 2.80 (d, J=7.6 Hz, 2H).

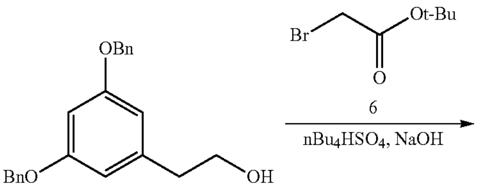

6

5

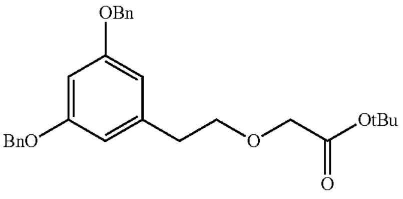

7

To a mixture of 5 (4.800 g, 14.35 mmol) in toluene (100 mL) was added a solution of NaOH (22.965 g, 574.15 mmol) in water (25 mL), $^{n}Bu_4HSO_4$ (487.35 mg, 1.44 mmol), and compound 6 (5.599 g, 28.71 mmol). The mixture was stirred at 25° C. for 16 h. The mixture was separated and the water layer was extracted with EtOAc (30 mL×2), washed with water (50 mL) and brine (20 mL×2). The combined organic layer was concentrated and the resulting residue was purified by column chromatography (0-20% EtOAc in petroleum ether) to afford 7 (4.00 g, 62.1%) as a white solid. LCMS (5-95, AB, 1.5 min): $R_T$=1.186 min, m/z=471[M+23]$^+$.

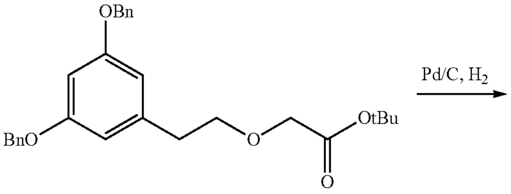

7

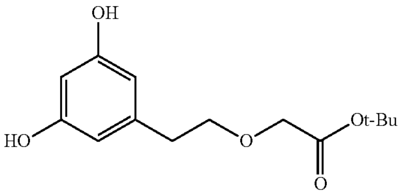

8

To a solution of 7 (4.000 g, 8.92 mmol) in MeOH (50 mL) was added 10% Pd on carbon (104.39 mg, 0.980 mmol). The mixture was stirred at 25° C. for 16 h under $H_2$ (15 psi). The solution was filtered, concentrated and purified by column chromatography (0-50% EtOAc in petroleum ether) to give 8 (2.100 g, 88%) as a colorless oil. LCMS (5-95, AB, 1.5 min): $R_T$=0.855 min, m/z=314 k[M+46]$^+$.

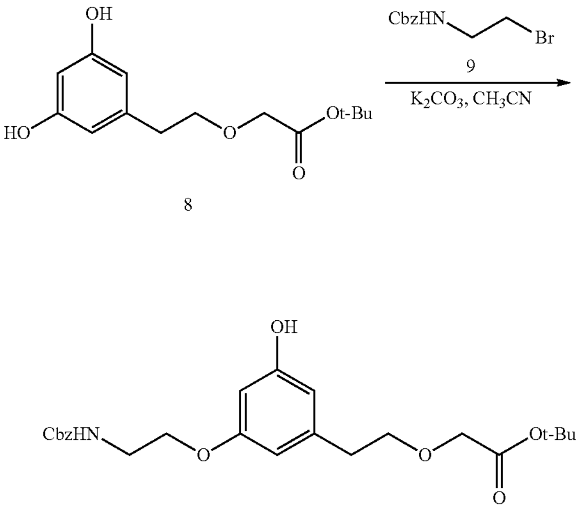

8

9

10

To a solution of compound 9 (2.222 mg, 8.61 mmol) and compound 8 (2.100 g, 7.83 mmol) in acetonitrile (50 mL) were added $K_2CO_3$ (1.73 g, 12.52 mmol) and KI (129.92 mg, 0.7800 mmol). The mixture was stirred at 70° C. for 12 h. The mixture was concentrated, diluted with EtOAc (40 mL), and washed with water (20 mL×2). The combined organic layer was dried over $Na_2SO_4$, and concentrated. The residue was purified by prep-HPLC (acetonitrile 20-80%/0.225% FA in water) to give 10 (1.100 g, 32%) as colorless oil. LCMS (5-95, AB, 1.5 min): $R_T$=0.978 min, m/z=468.1 [M+23].

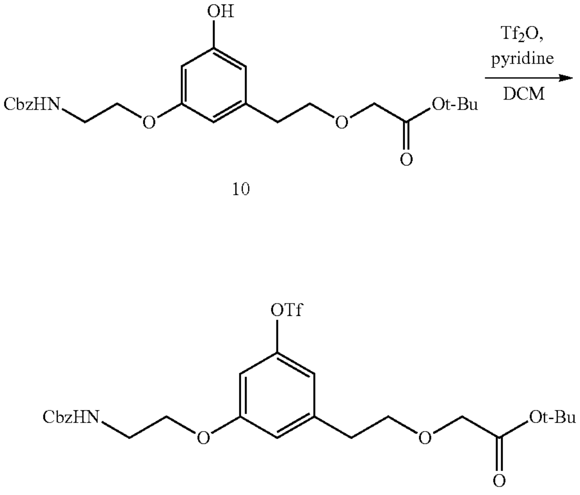

10

11

To a solution of compound 10 (330.0 mg, 0.740 mmol) in DCM (10 mL) was added pyridine (0.30 mL, 3.7 mmol) and $Tf_2O$ (0.25 mL, 1.48 mmol). The mixture was stirred at 20° C. for 1 h. The mixture was diluted with EtOAc (50 mL) and partitioned. The organic was washed with citric acid (10 mL×3) and concentrated to give the crude product compound 11 (427 mg, 99.8%) as a yellow oil, which was used in next step directly. LCMS (5-95, AB, 1.5 min): $R_T$=0.985 min, m/z=600.3 $[M+23]^+$.

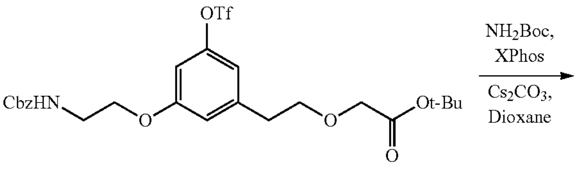

11

12

To a solution of compound 11 (427.0 mg, 0.7400 mmol) in 1,4-Dioxane (20 mL) and was added tert-butyl carbamate (129.91 mg, 1.11 mmol), $Cs_2CO_3$ (481.8 mg, 1.48 mmol), XPhos (35.24 mg, 0.0700 mmol) and $Pd(OAc)_2$ (8.3 mg, 0.0400 mmol) at 25° C. The reaction mixture was stirred at 110° C. for 16 h under $N_2$. The mixture was concentrated and purified by column chromatography (0-40% EtOAc in petroleum ether, Rf=0.5) to give compound 12 (220 mg, 55%) as a yellow oil. LCMS (5-95, AB, 1.5 min): $R_T$=0.948 min m/z=567.1 $[M+23]^+$.

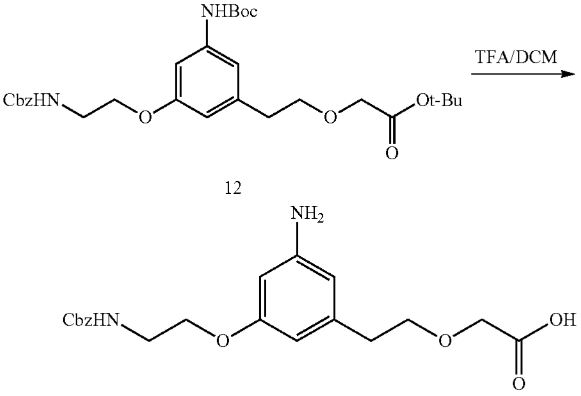

12

13

A solution of compound 12 (220.0 mg, 0.400 mmol) in DCM (3.0 mL) was added TFA (2.0 mL). The mixture was stirred at 25° C. for 1 h. The mixture was concentrated and purified by prep-HPLC (acetonitrile 19-49%/0.225% FA in water) to give the product compound 13 (110 mg, 54%) as a white solid. LCMS (5-95, AB, 1.5 min): RT=0.640 min, m/z=389.0 $[M+1]^+$.

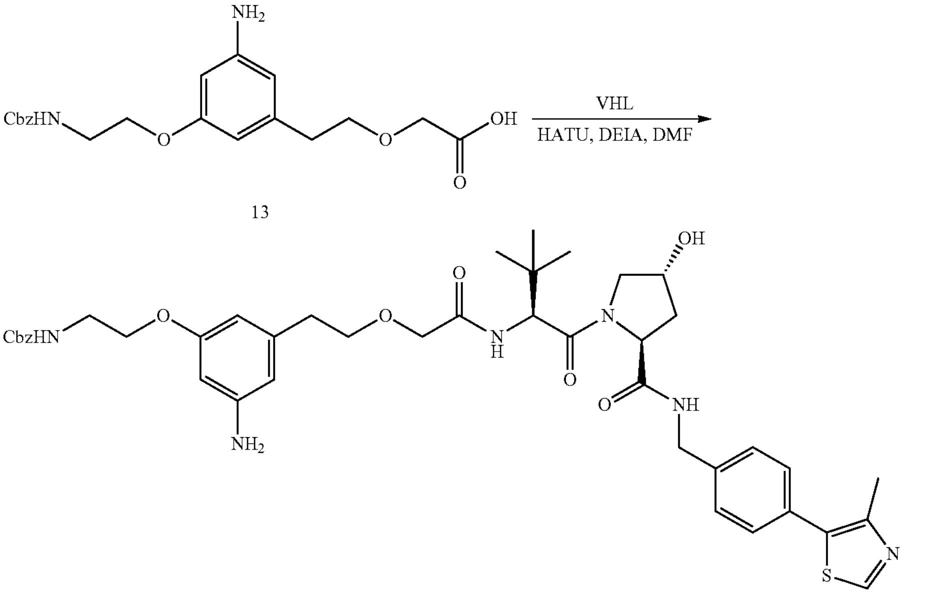
13
14
To a solution of VHL ligand (256.07 mg, 0.590 mmol), compound 13 (110.0 mg, 0.2800 mmol) and HATU (118.45 mg, 0.3100 mmol) in DMF (5.0 mL) was added DIEA (0.23 mL, 1.42 mmol). The mixture was stirred at 25° C. for 1 h. The mixture was concentrated and purified by prep-TLC (10% MeOH in DCM, Rf=0.5) to give the product compound 15 (120 mg, 53%) as a yellow solid. LCMS (5-95, AB, 1.5 min): $R_T$=0.855 min, m/z=823.3 [M+23]$^+$.
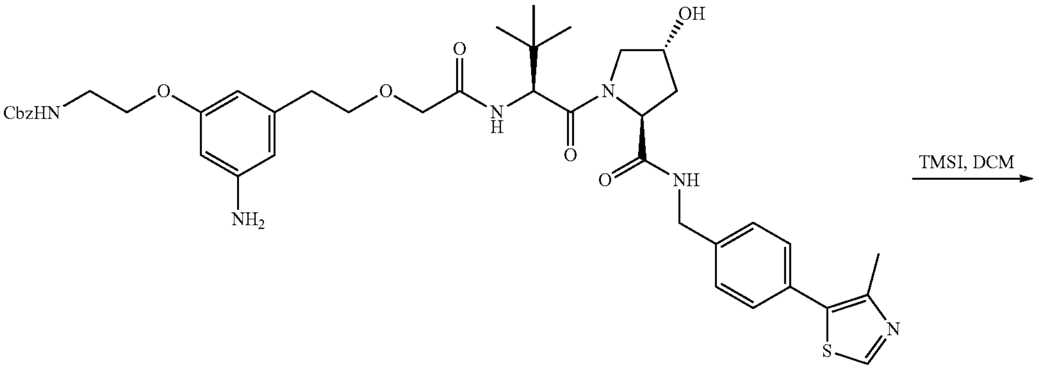
14
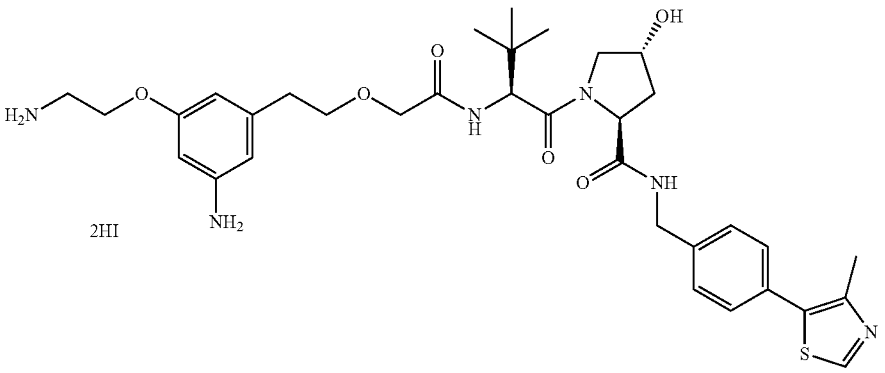
2HI
15

TMSI (99.93 mg, 0.50 mmol) was added to a solution of Compound 14 (80.00 mg, 0.10 mmol) in DCM (5.0 mL) at 25° C., and the resulting mixture was stirred at 25° C. for 1 h. The solvent was removed and the resulting residue was washed with EtOAc (10 mL×3) and used for next step directly. LCMS (5-95, AB, 1.5 min): $R_T$=0.661 min, m/z=667.5 $[M+1]^+$.

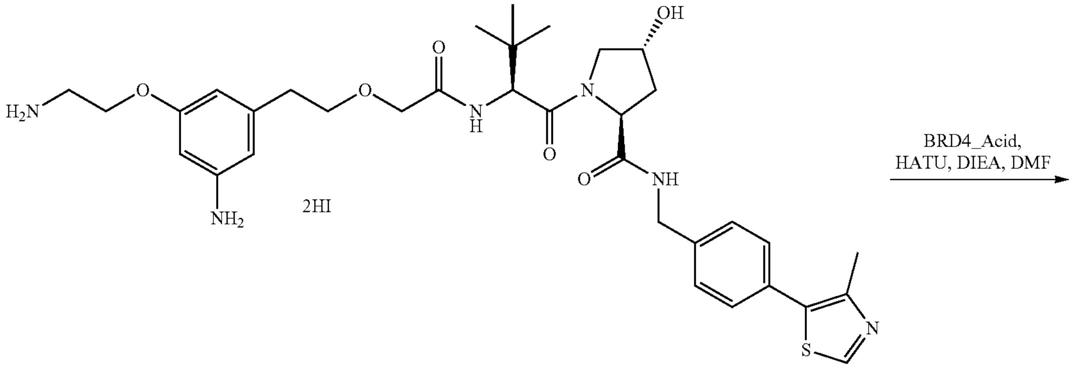

15

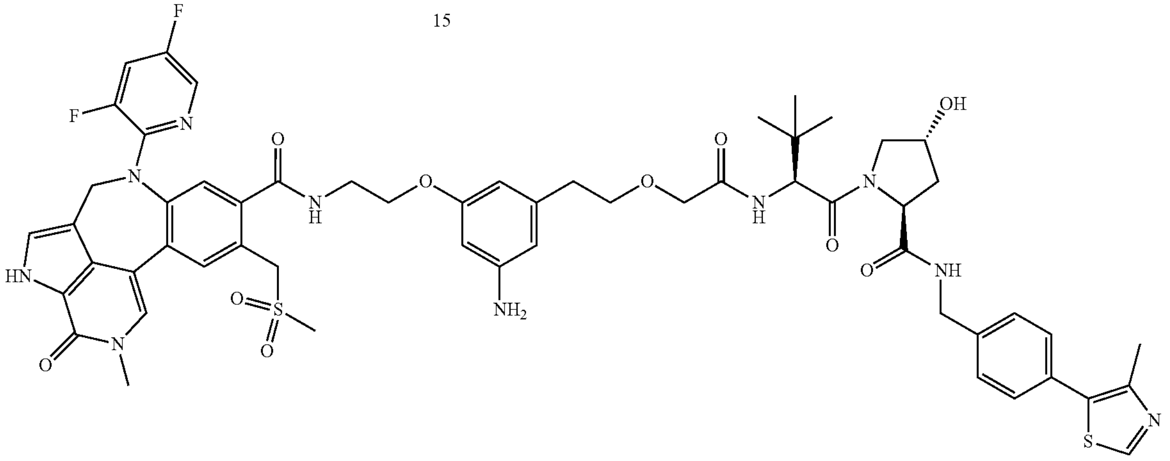

16

To a solution of the BRD4 acid (50.00 mg, 0.10 mmol) and HATU (41.79 mg, 0.11 mmol) in DMF (8.0 mL) was added DIEA (64.56 mg, 0.50 mmol). The mixture was stirred at 25° C. for 10 min. To above solution was added a solution of Compound 15 (90.00 mg, 0.10 mmol). The mixture was stirred at 25° C. for 1 h. The mixture was concentrated and purified by prep-TLC (10% MeOH in DCM, Rf=0.5) to give Compound 16 (80 mg, 70%) as a yellow solid. LCMS (5-95, AB, 1.5 min): $R_T$=0.750 min, m/z=575.8 $[M/2+H]^+$.

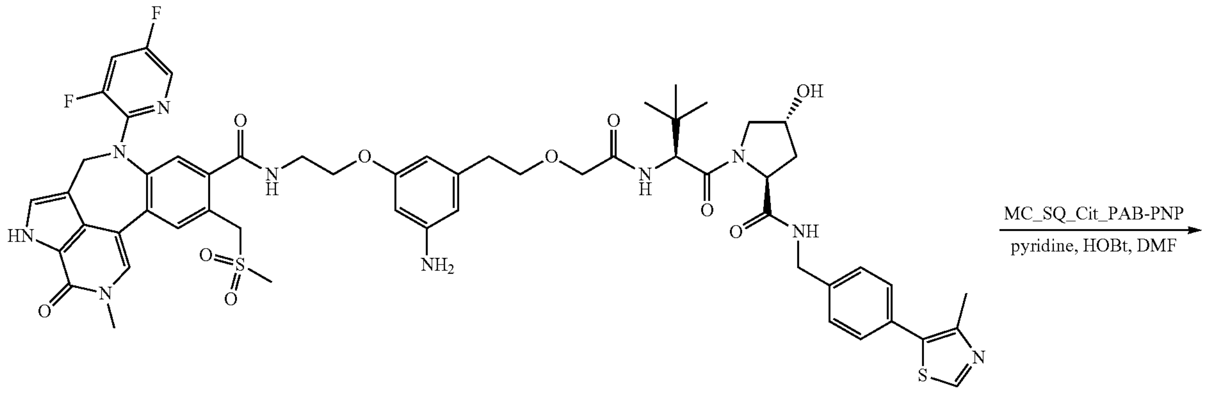

16

-continued

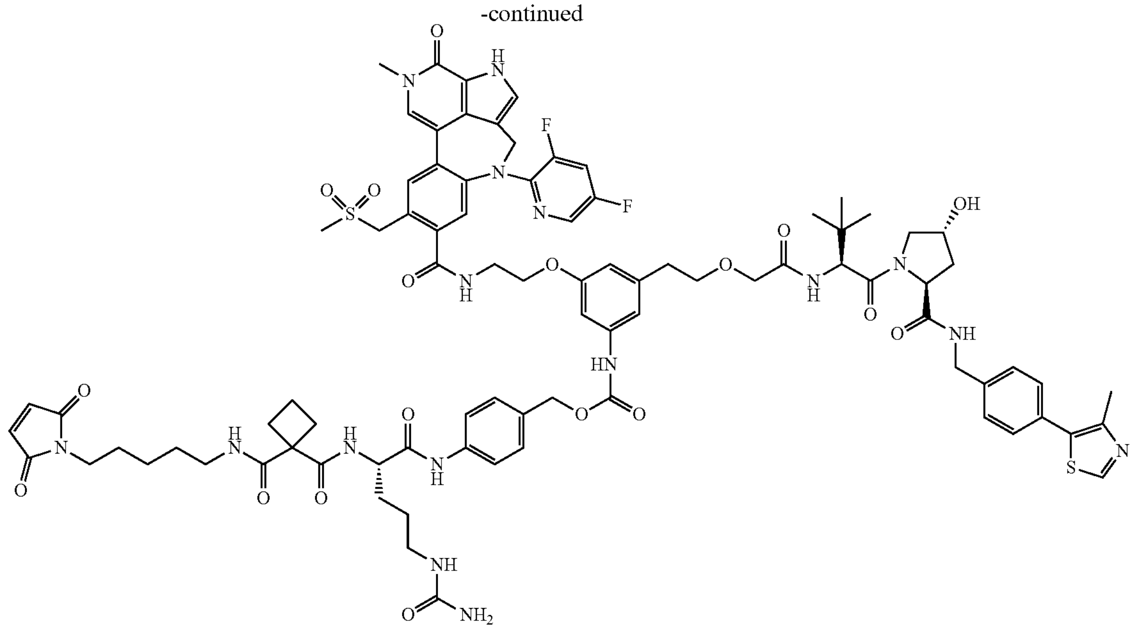

L1BC8

To a solution of Compound 15 (50.00 mg, 0.040 mmol) and MC_SQ_Cit_PAB-PNP (96.03 mg, 0.13 mmol) in DMF (10 mL) was added HOBt (11.75 mg, 0.09 mmol) and pyridine (34.41 mg, 0.44 mmol). The mixture was stirred at 38° C. for 1 h. The mixture was concentrated and purified by prep-HPLC (acetonitrile 32-62/0.225% FA in water) to give L1BC8 (15.00 mg, 19%) as a white solid. LCMS (5-95, AB, 1.5 min): $R_T$=0.706 min, m/z=873.8 [M/2+H]$^+$.

xv. L1BC9 An exemplary L1-CIDE, L1BC9, can be synthesized by the following scheme.

Scheme 17

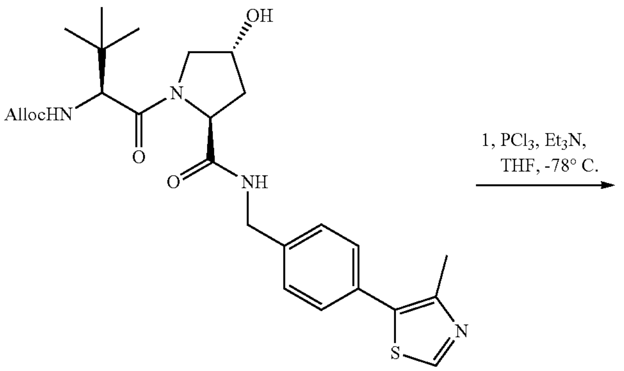

1

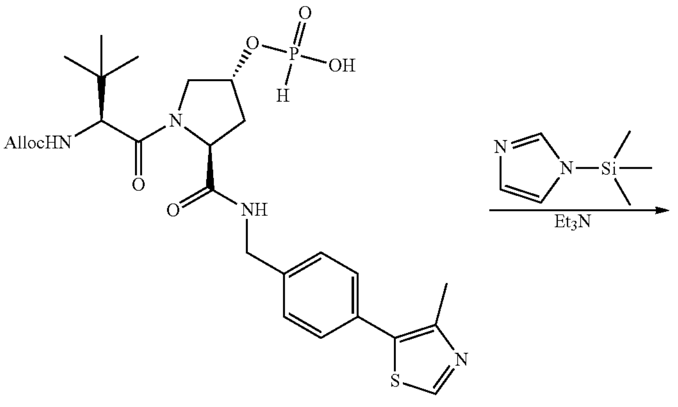

2

-continued
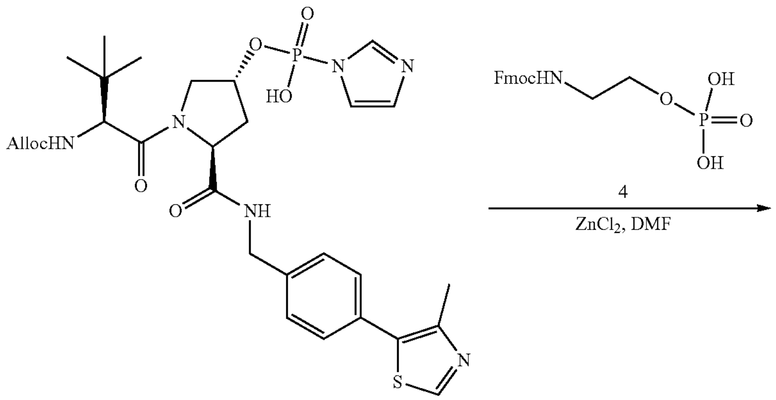
3
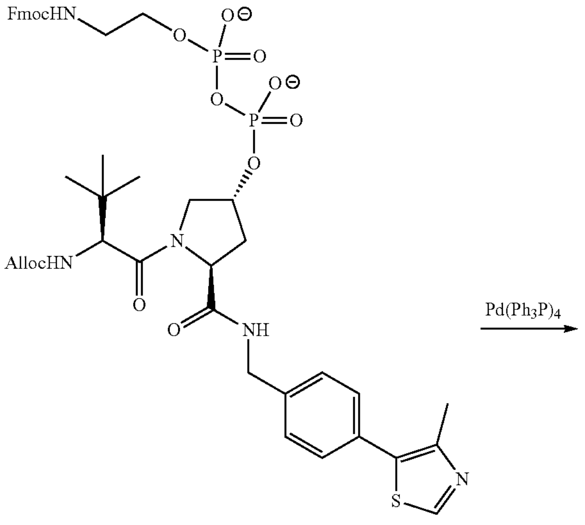
5
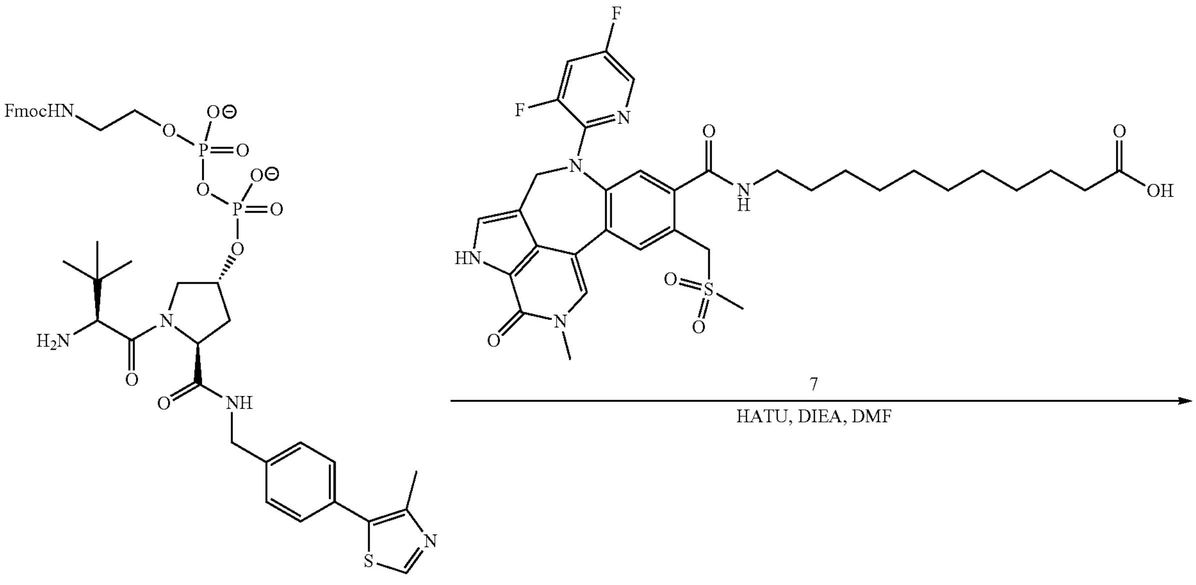
6

-continued
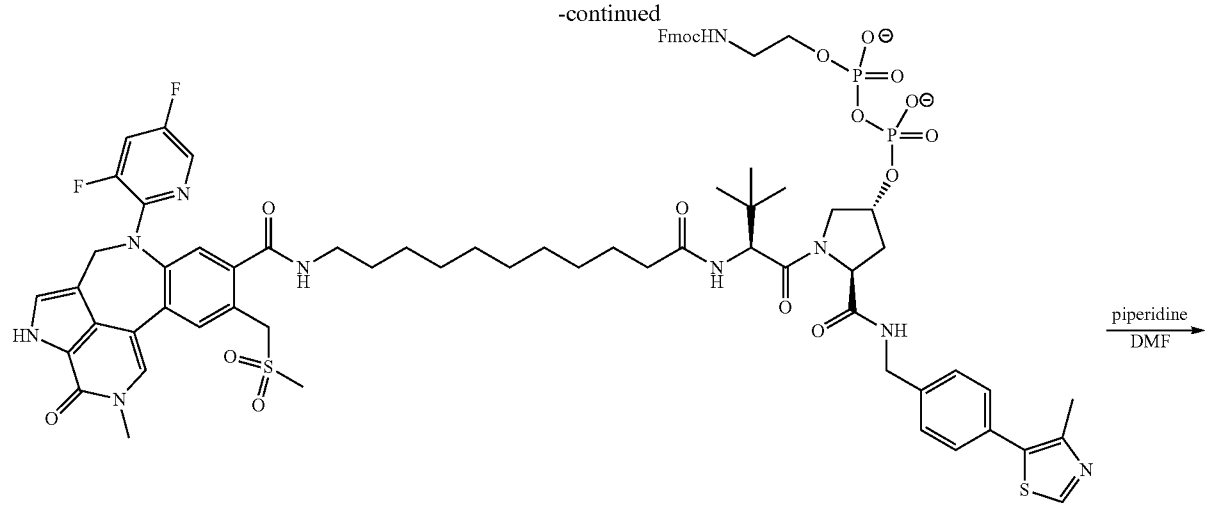
8
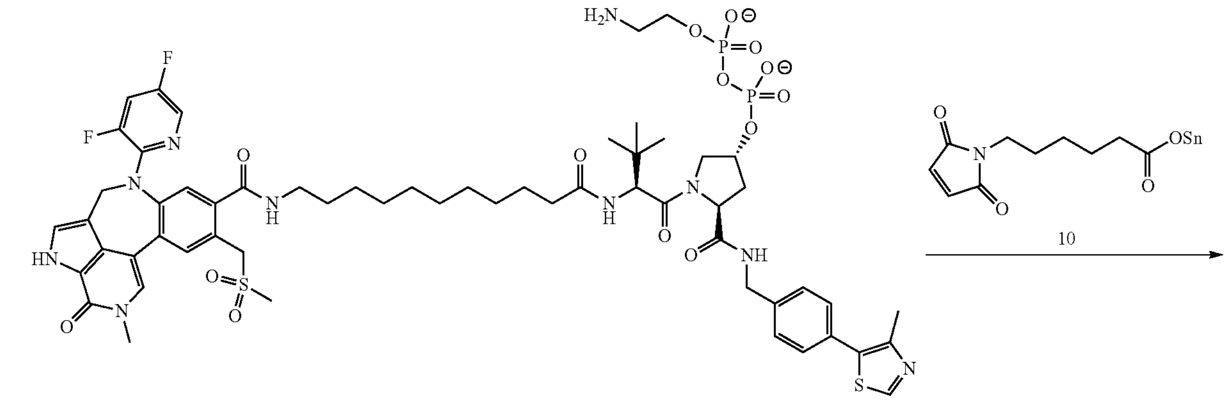
9
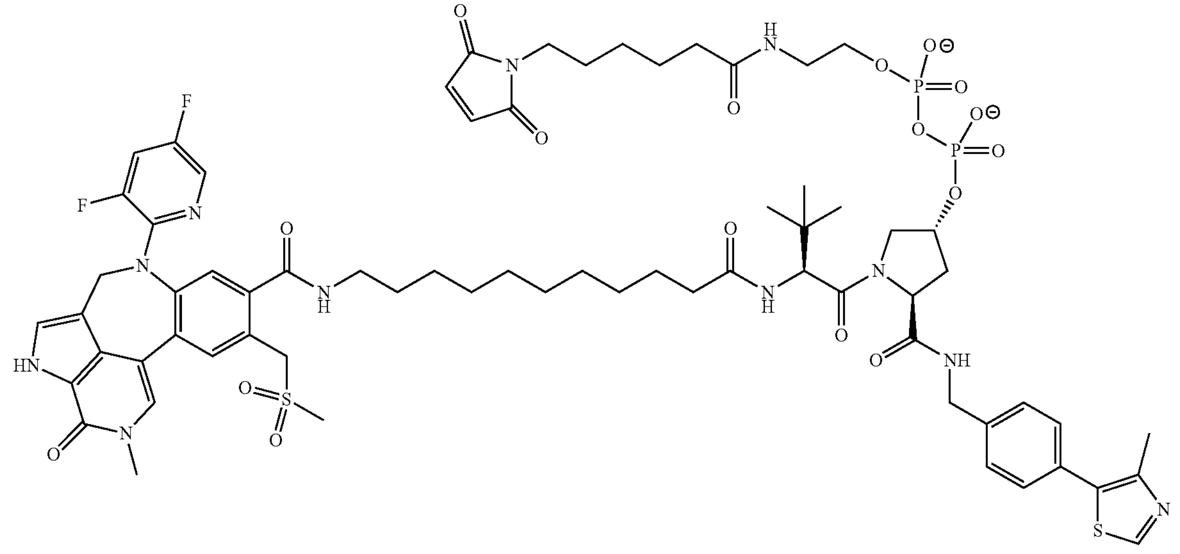
L1BC9

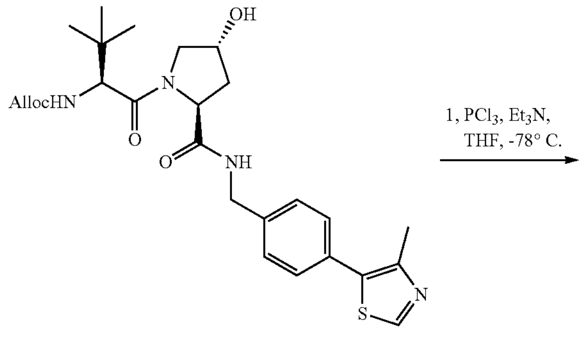

1

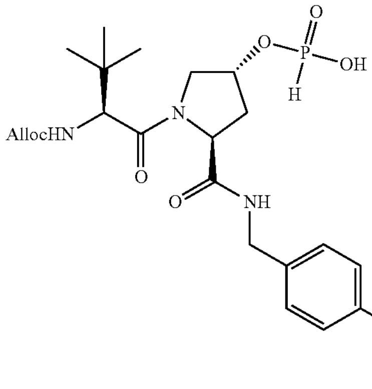

2

To a solution of compound 1 (450.0 mg, 0.870 mmol) in THF (5.0 mL) was added $PCl_3$ (500.0 mg, 3.64 mmol) in THF (2.0 mL) and $Et_3N$ (0.73 mL, 5.25 mmol) in THF (2.0 mL) at −78° C. The reaction mixture was stirred at −78° C. for 20 min then allowed warm to 25° C. After the mixture was stirred at 25° C. for 12 h, it was quenched with water (2.0 mL) and aq $NaHCO_3$ (5.0 mL), and the mixture was stirred at 25° C. for 10 min. It was acidified with HCl (1.0 M) to pH=3.0, the resulted mixture was concentrated and purified by prep-TLC (12% MeOH in DCM, Rf=0.4) to afford compound 2 (450 mg, 89%) as a colorless crystal. LCMS (0-60, CD, 3.0 min): RT=1.421 min, m/z=579.2 $[M+1]^+$.

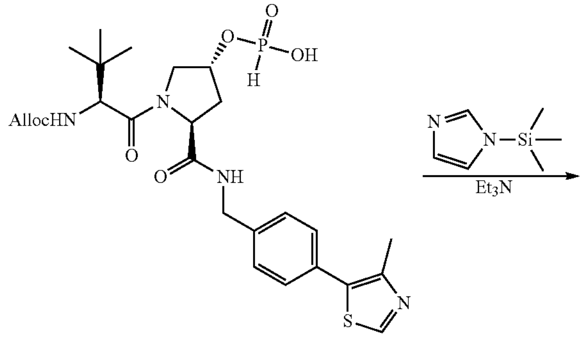

2

-continued

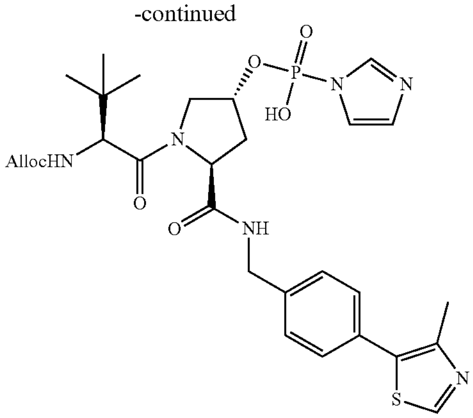

3

To a solution of compound 2 (450.0 mg, 0.7800 mmol) and $Et_3N$ (0.43 mL, 3.11 mmol) in $CCl_4$ (4.0 mL) and acetonitrile (4.0 mL) was added N-TMS-imidazole (436.33 mg, 3.11 mmol) at 25° C. The reaction mixture was stirred at 25° C. for 40 min. The mixture was treated with MeOH (0.1 mL) and stirred at 25° C. for 10 min. The solvent was removed and the residue was washed with MTBE/EtOAc=5/1 (3 mL), the precipitate was filtered and washed with MTBE (3 mL) to afford the product compound 3 (450 mg, 90%) as a white solid. LCMS (5-95, AB, 1.5 min): RT=0.725 min, m/z=645.3 $[M+1]^+$.

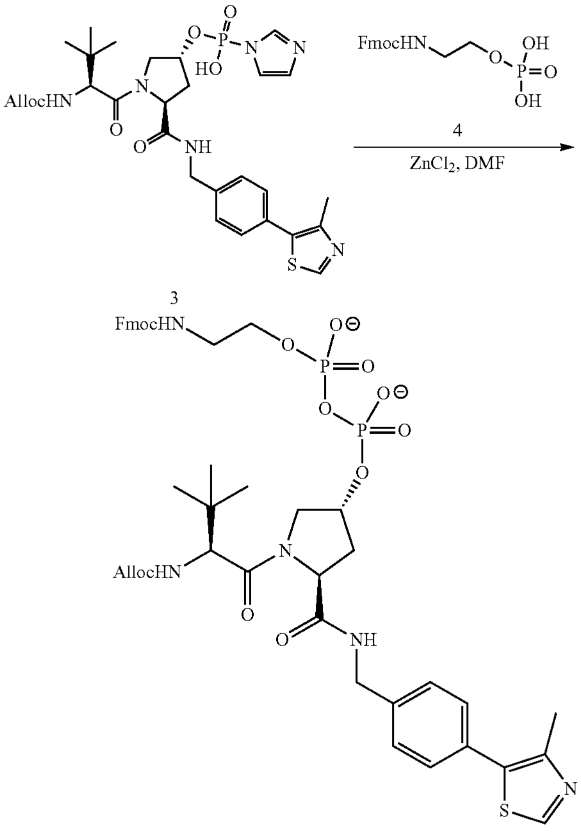

3

4

5

To a solution of compound 3 (450.0 mg, 0.700 mmol) and compound 4 (355.03 mg, 0.980 mmol) in DMF (5.0 mL)

was added $ZnCl_2$ solution (1.0 mol/L in toluene, 6.98 mL, 6.98 mmol) at 25° C. The reaction mixture was stirred at 25° C. for 12 h. The reaction mixture was quenched with HCl (1.0 M), concentrated, and purified by prep-HPLC (acetonitrile 22-42/10 mM $NH_4HCO_3$ in water) to afford the product compound 5 (250 mg, 38%) as a white solid. LCMS (5-95, AB, 1.5 min): RT=1.751 min, m/z=940.3 $[M+1]^+$.

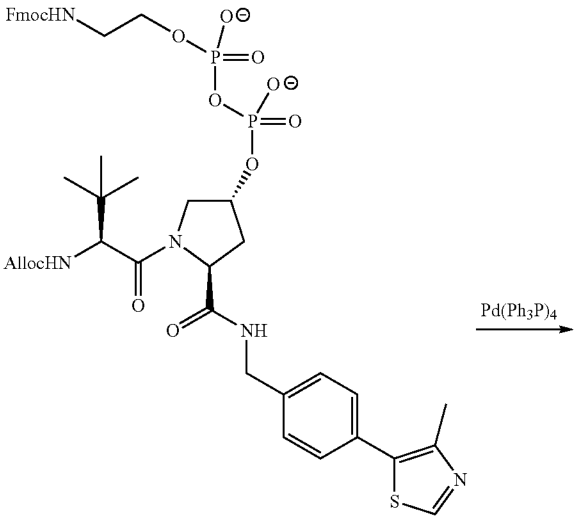

5

-continued

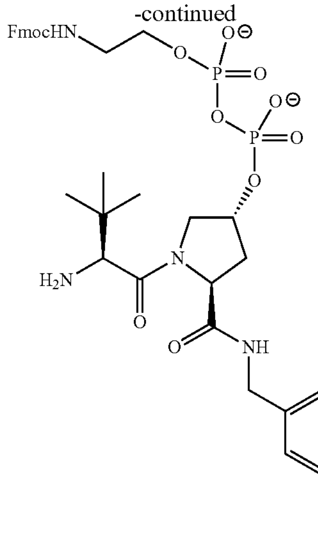

6

To a solution of compound 5 (100.0 mg, 0.1100 mmol) and 1,3-dimethylbarbituric acid (83.06 mg, 0.530 mmol) in DCM (1.0 mL) and MeOH (0.20 mL) was added $Pd(Ph_3P)_4$ (24.59 mg, 0.0200 mmol) at 25° C. The reaction mixture was stirred under $N_2$ at 25° C. for 2 h. The reaction mixture was concentrated and the resulting residue was purified by prep-HPLC (acetonitrile 18-48/10 mM $NH_4HCO_3$ in water) to afford compound 6 (55 mg, 60.4%) as a white solid. LCMS (0-60, CD, 3.0 min): RT=1.450 min m/z=856.1 [M+1].

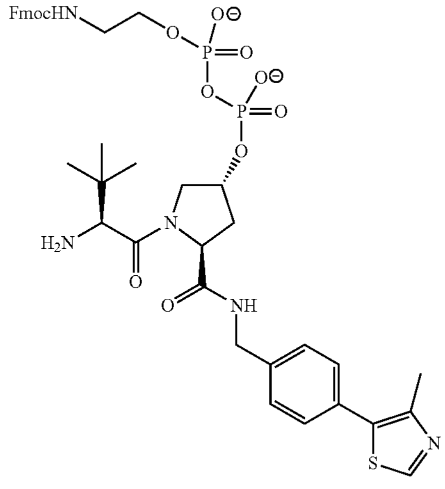

6

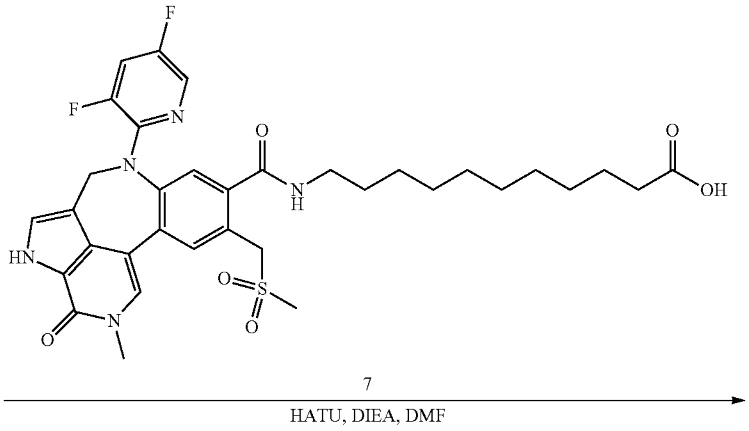

7

-continued

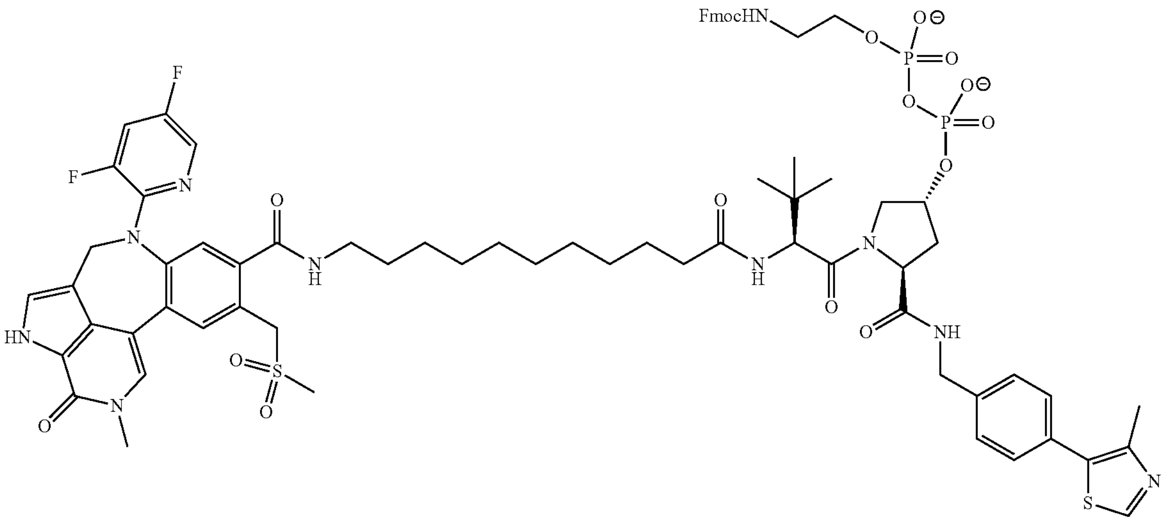

8

The solution of compound 7 (119.84 mg, 0.1800 mmol), DIEA (7.55 mg, 0.0600 mmol) and HATU (22.21 mg, 0.0600 mmol) in anhydrous DMF (2.0 mL) was stirred at 25° C. for 20 min, and then compound 6 (50.0 mg, 0.0600 mmol) was added. The resulted mixture was stirred at 25° C. for 2 h. The reaction was filtered and the resulting residue was purified by prep-HPLC (acetonitrile 27-57/0.05% $NH_4OH$ in water) to afford compound 8 (40 mg, 45%) as a white solid. LCMS (0-60, CD, 3.0 min): RT=1.968 min, m/z=761.3[M/2+1]$^+$.

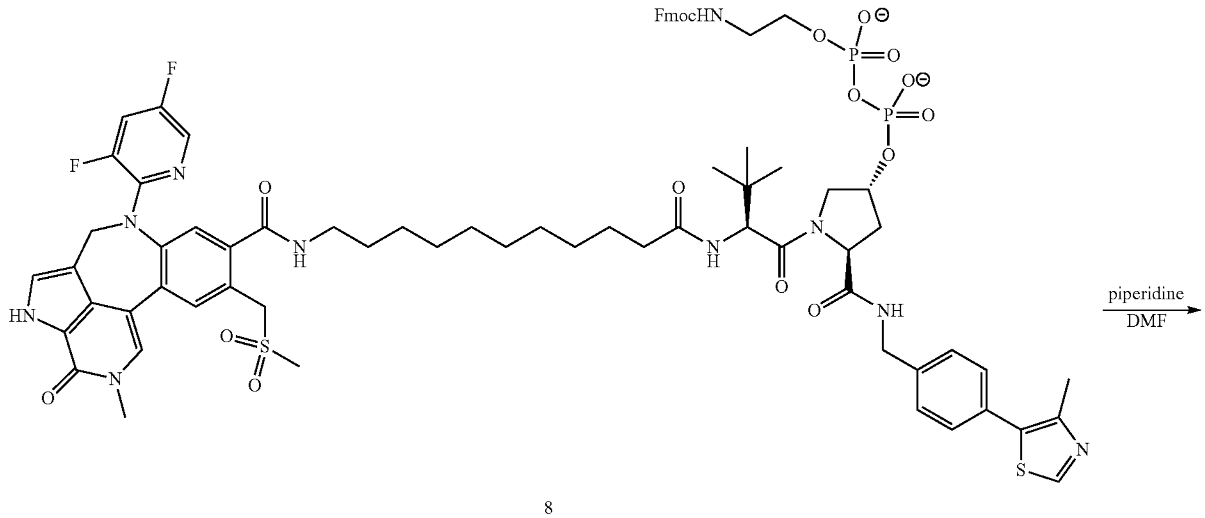

8

-continued
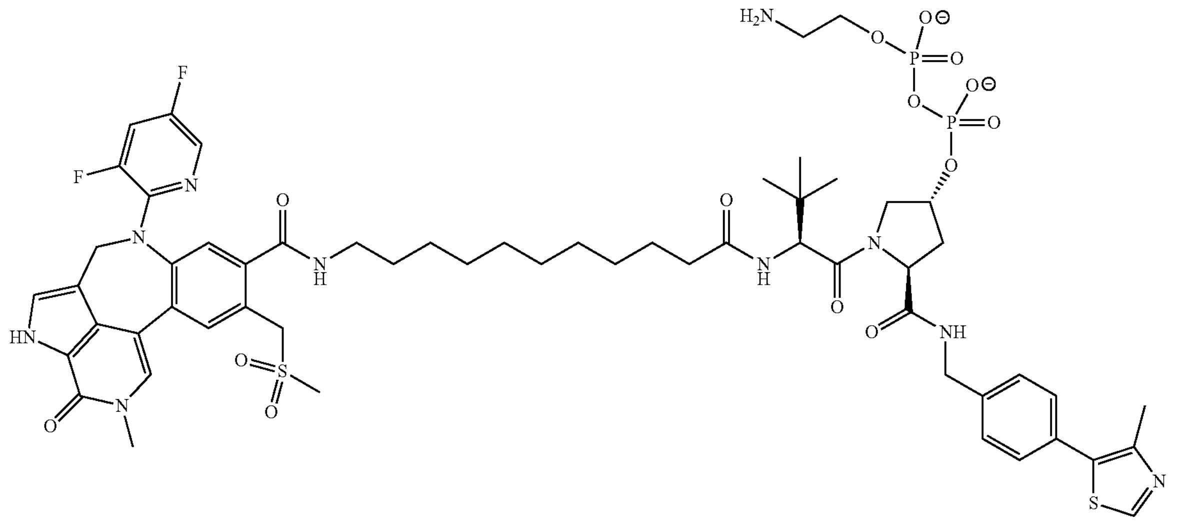
9
To a solution of compound 8 (40.0 mg, 0.0300 mmol) in DMF (1.0 mL) was added piperidine (11.19 mg, 0.1300 mmol) at 25° C. The reaction mixture was stirred at 25° C. for 1 h. The mixture was filtered and the filtrate was purified by prep-HPLC (acetonitrile 23-53%/10 mM $NH_4HCO_3$ in water) to afford compound 9 (20 mg, 59%) as a white solid. LCMS (0-60, CD, 3.0 min): RT=1.729 min, m/z=650.3 $[M/2+1]^+$.
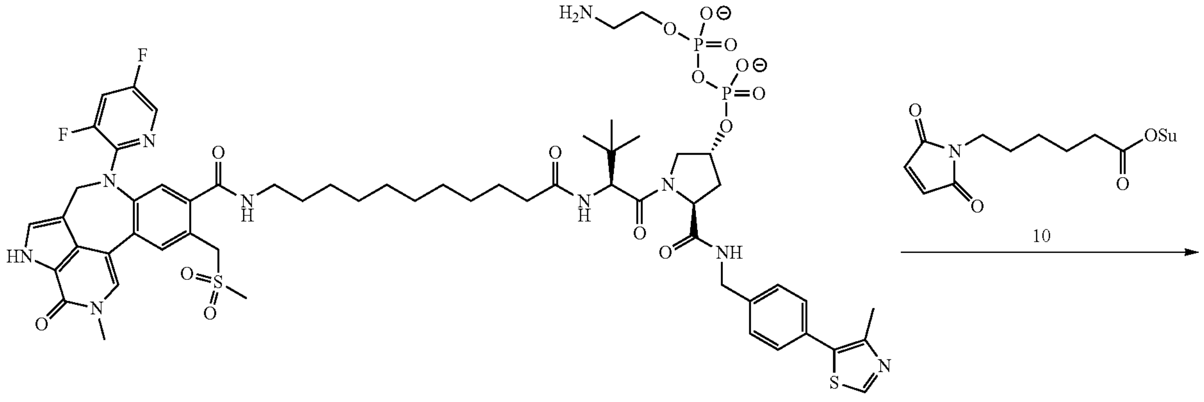
9

-continued

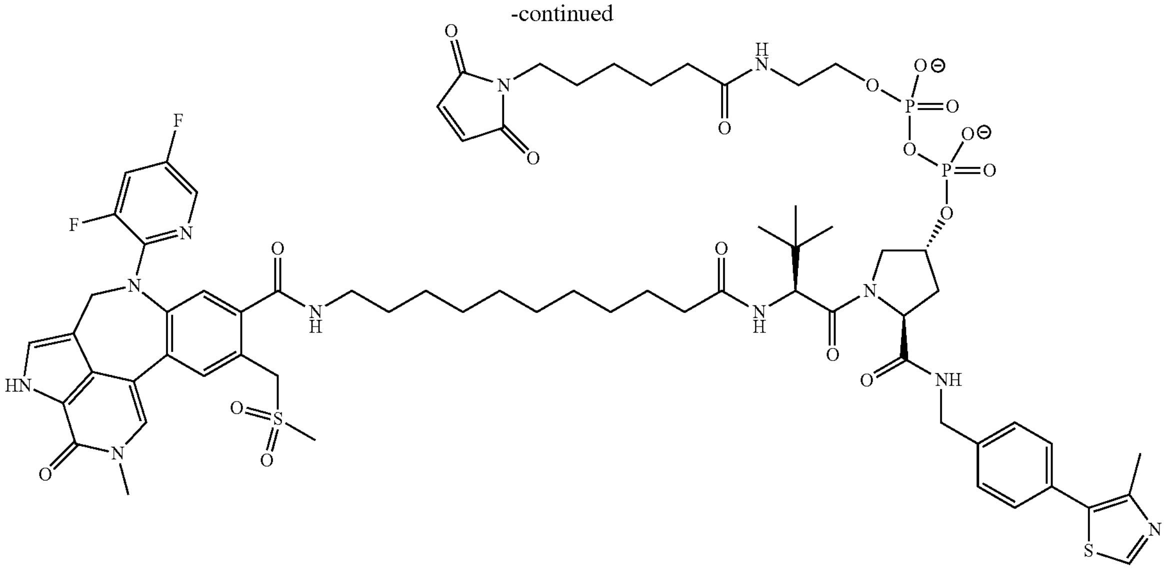

L1BC9

To a solution of compound 10 (5.93 mg, 0.0200 mmol) and DIEA (1.99 mg, 0.0200 mmol) in DMF (1.0 mL) was added compound 9 (10.0 mg, 0.0100 mmol) at 25° C. The mixture was stirred at 25° C. for 6 h. The mixture was filtered and the filtrate was purified by prep-HPLC (acetonitrile 25-55%/0.1% TFA in water) to afford L1BC9 (2.7 mg, 24%) as a white solid. LCMS (0-60, CD, 3.0 min): RT=1.635 min, m/z=746.8 [M/2+1]$^+$.

xvi. L1BC10 An exemplary L1-CIDE, L1BC10, can be synthesized by the following scheme:

Scheme 18

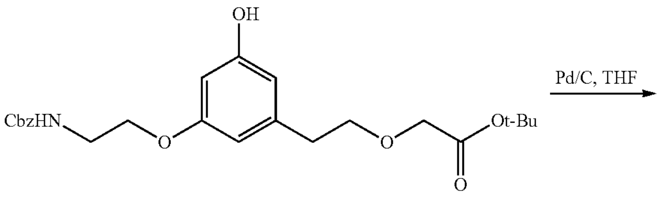

1

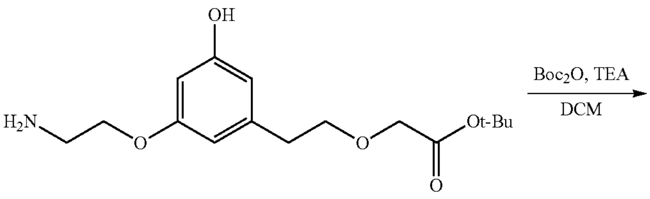

2

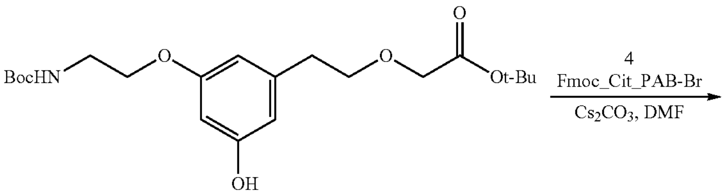

3

-continued
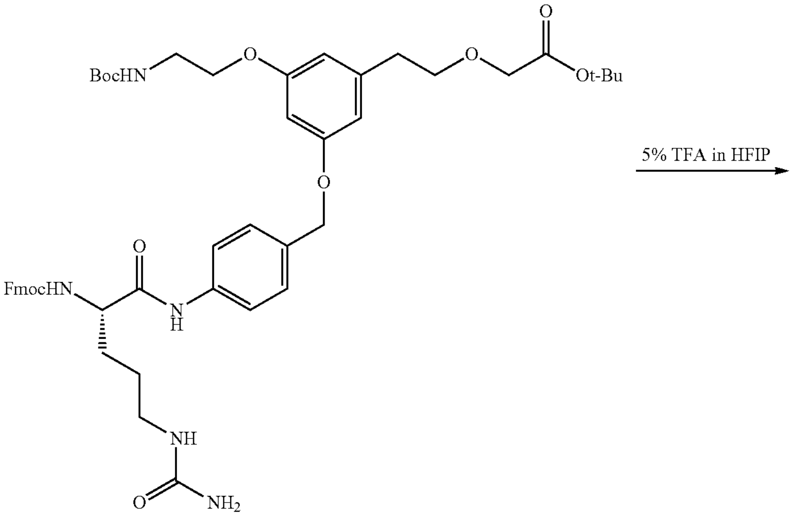
5
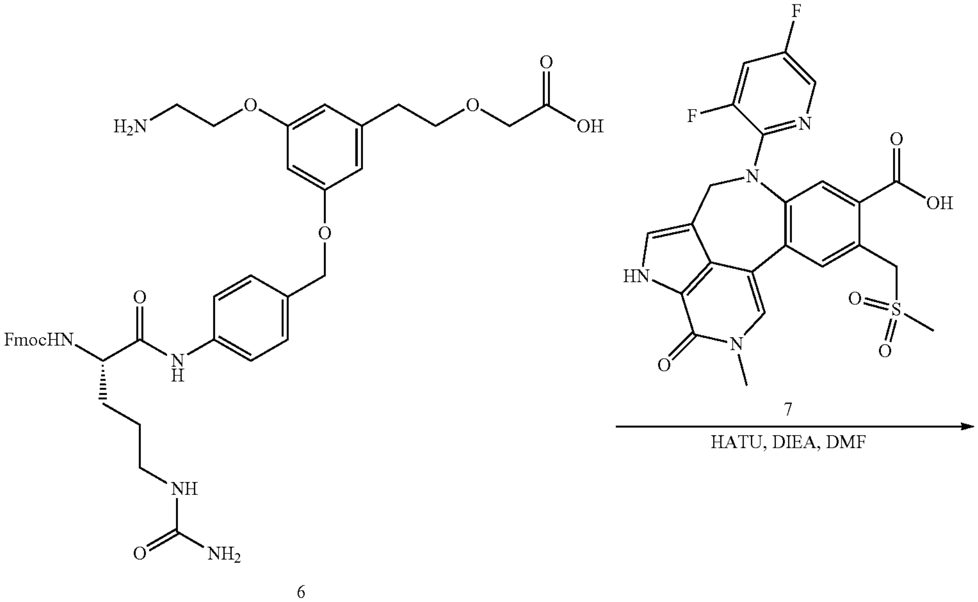
6

-continued
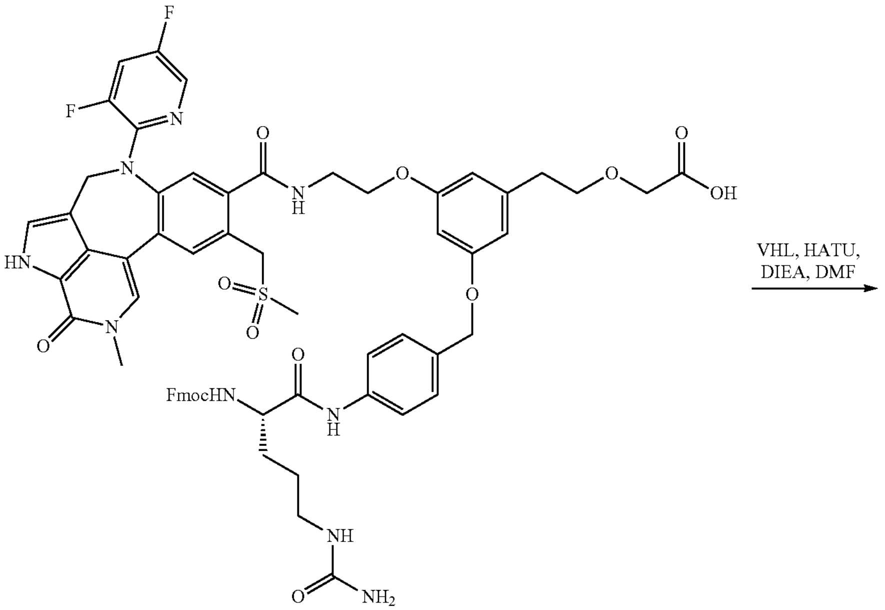
8
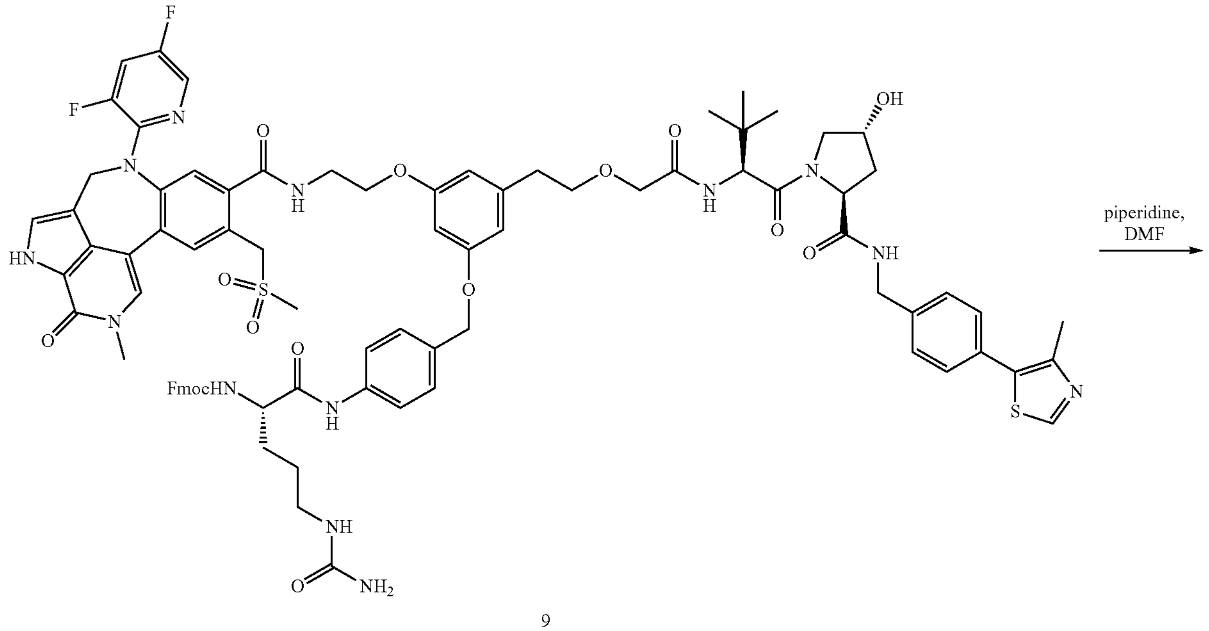
9

-continued
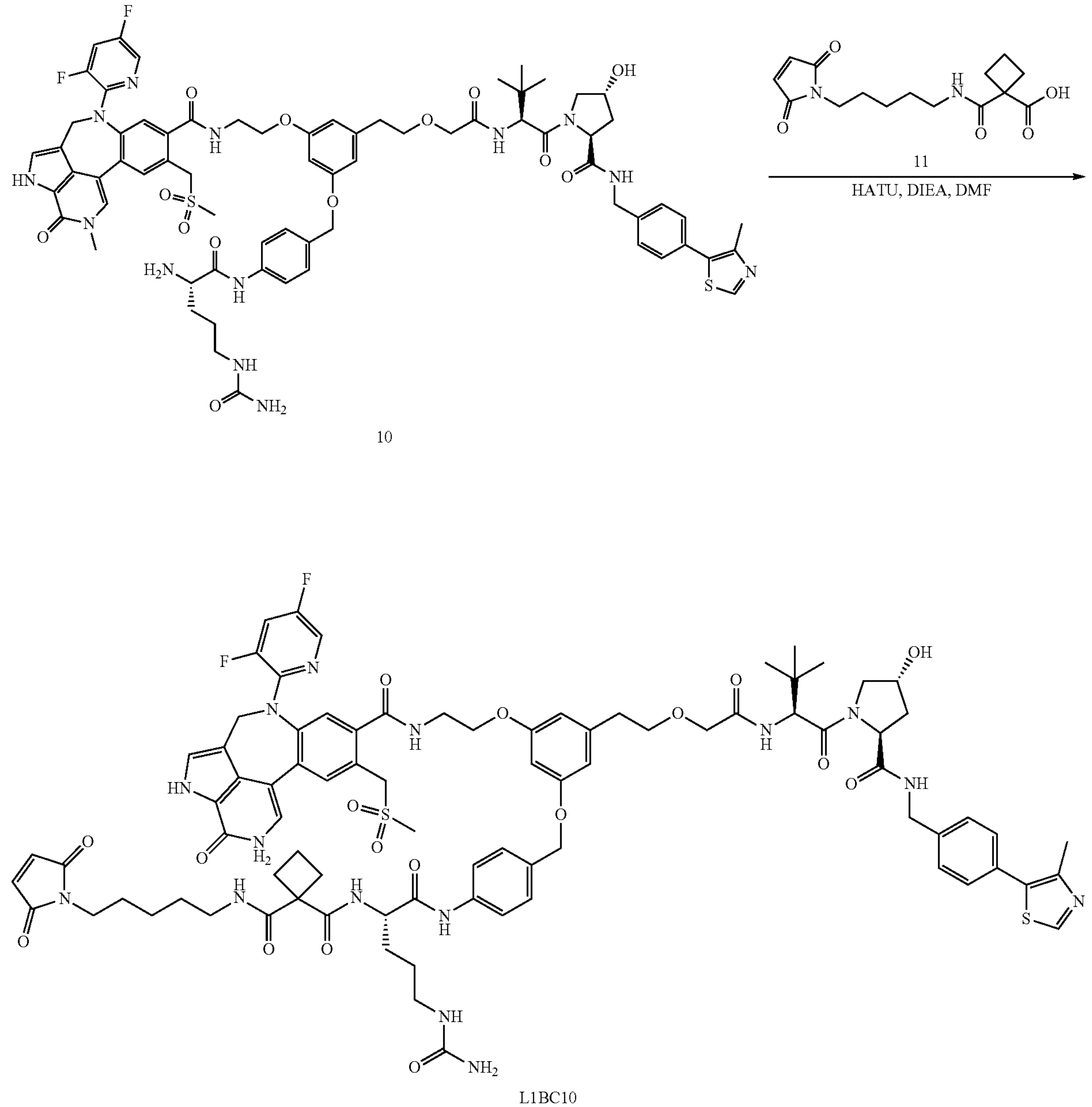
10
L1BC10
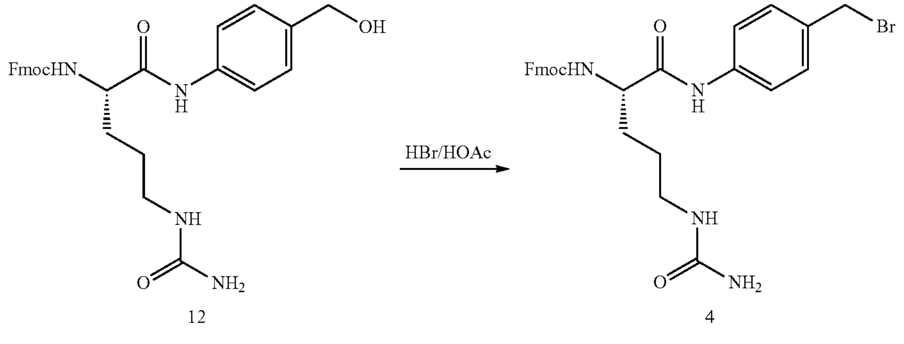
12
4

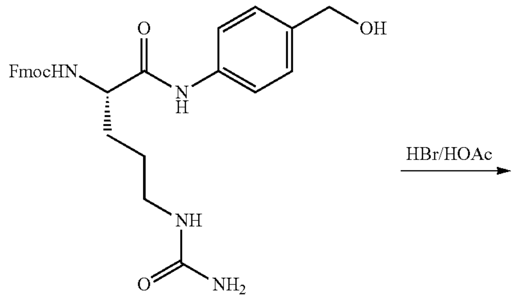

12

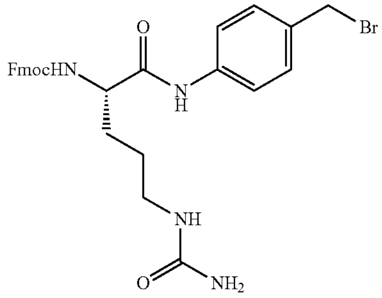

4

Compound 12 (1.000 g, 1.99 mmol) was added to a HBr solution in HOAc (35%, 15.0 mL). After the mixture was stirred at 25° C. for 2 h, it was poured into ice water (20 mL). The precipitate was filtered and washed with MTBE (20 mL×2) to give the crude product 4 (1000 mg, 89%) as a gray solid, which was used directly in the next step. LCMS (5-95, AB, 1.5 min): RT=0.783 min, m/z=566.8 $[M+1+2]^+$.

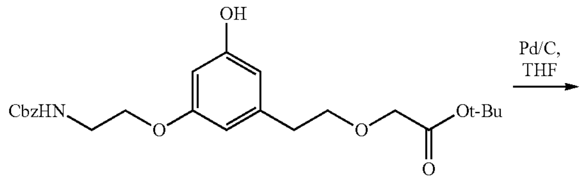

1

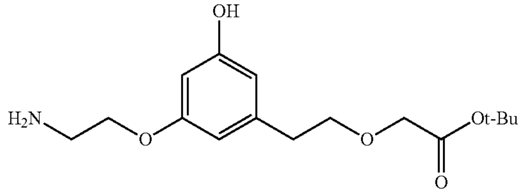

2

To a solution of Compound 1 (0.300 g, 0.6700 mmol) in THF (15 mL) was added Pd/C (359 mg) and stirred under $H_2$ (15 psi) at 25° C. for 2 h. The solid were filtered, and the filtrate was concentrated under reduced pressure to give the crude product 2 (200 mg, 95%) as a yellow solid, which was used directly in next step.

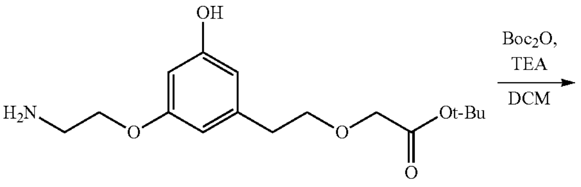

2

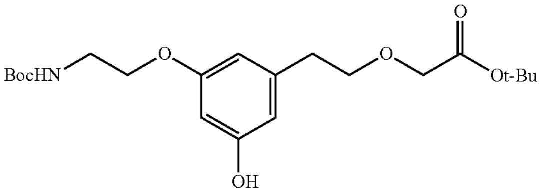

3

To a solution of Compound 2 (200 mg, 0.64 mmol) and $Et_3N$ (0.13 mL, 0.960 mmol) in DCM (10 mL) was added $Boc_2O$ (140.19 mg, 0.640 mmol) at 25° C. After the reaction was stirred at 25° C. for 1 h, it was concentrated and the residue was purified by prep-TLC (5% MeOH in DCM, Rf=0.5) to give compound 3 (260 mg, 87%) as a yellow oil. LCMS (5-95, AB, 1.5 min): RT 0.933 min, m/z=434.2 $[M+23]^+$.

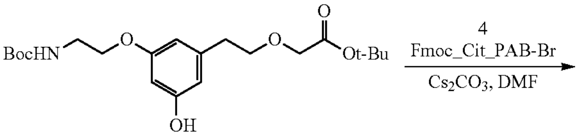

3

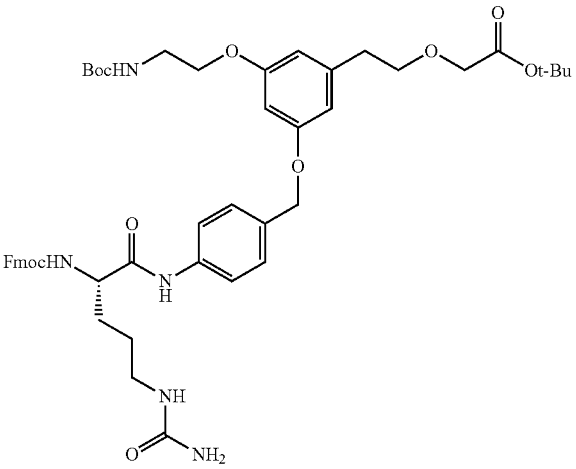

5

A mixture of $Cs_2CO_3$ (285.05 mg, 0.870 mmol) and Compound 3 (120.0 mg, 0.290 mmol) in anhydrous DMF (5.0 mL) was stirred at 25° C. for 10 min, and then Compound 4 (494.7 mg, 0.870 mmol) was added. The resulted mixture was stirred at 25° C. for 1 h. The mixture was diluted with water (15 mL), and extracted with EtOAc (10 mL×3). The organic layer was washed with brine (10 mL×2), dried over $Na_2SO_4$, concentrated, and purified by prep-TLC (10% MeOH in DCM, Rf=0.4) to afford compound 5 (50 mg, 19%) as a white solid. LCMS (5-95, AB, 1.5 min): $R_T$=1.021 min, m/z=897.4 $[M+1]^+$.

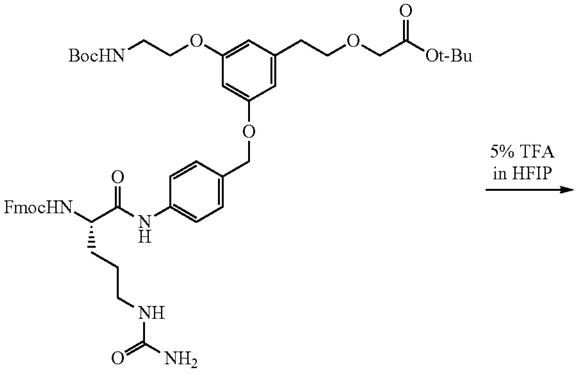

5

-continued

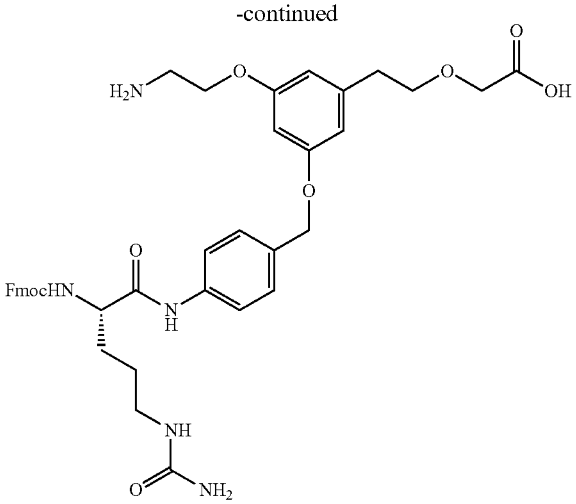

6

To a solution of Compound 5 (50 mg, 0.0547 mmol) in HFIP (4.0 mL) was added TFA (0.20 mL). The reaction solution was stirred at 25° C. for 1 h. The solution was concentrated to afford compound 6 TFA salt (72 mg, 99.4%) as a yellow oil. The crude product was used in next step directly. LCMS (5-95, AB, 1.5 min): RT=0.663 min, m/z=740.2 $[M+1]^+$.

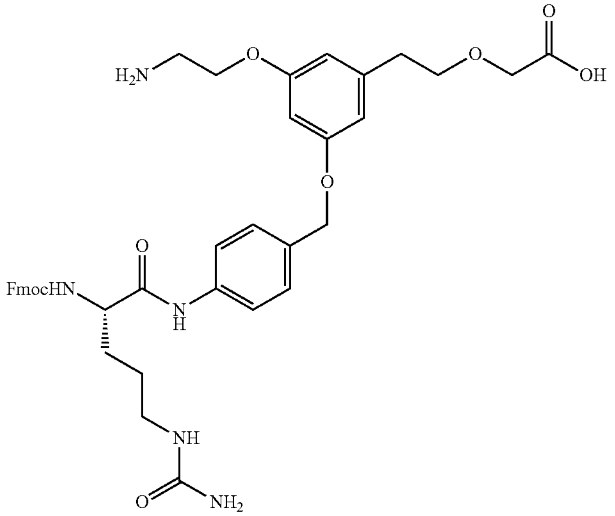

6

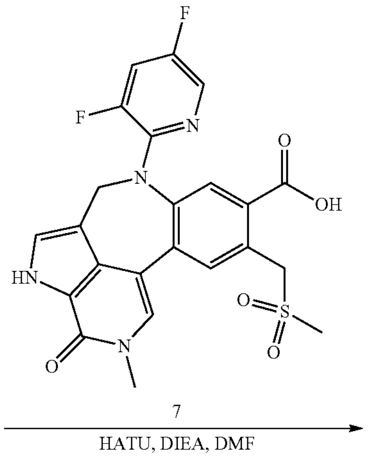

7

-continued

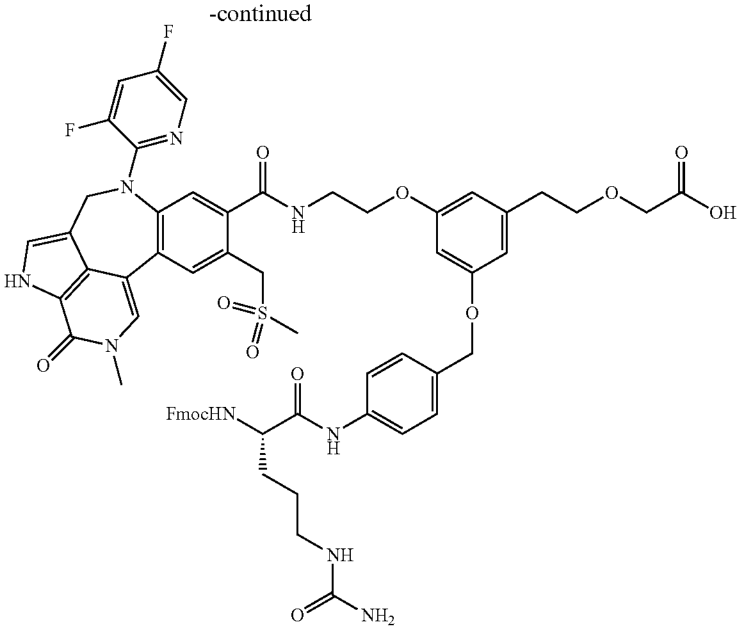

8

A solution of Compound 7 (50.0 mg, 0.1000 mmol), DIEA (0.05 mL, 0.300 mmol) and HATU (41.79 mg, 0.1100 mmol) in anhydrous DMF (5.0 mL) was stirred at 25° C. for 10 min, and then TFA salt of Compound 6 (68.24 mg, 0.0800 mmol) was added. The resulted mixture was stirred at 25° C. for 1 h. The reaction was concentrated and DCM (10 mL) was added, the precipitate was collected, washed with DCM (5.0 mL) and dried in vacuum to afford compound 8 (50 mg, 41%) as a yellow solid. The crude was used in next step directly. LCMS (5-95, AB, 1.5 min): RT=0.872 min, m/z=1224.3[M+1]$^+$.

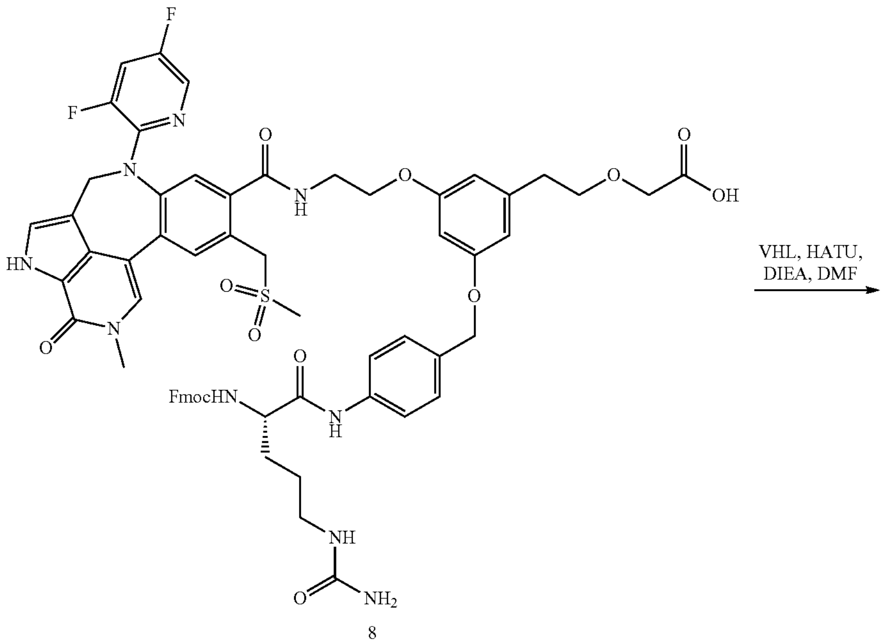

8

-continued
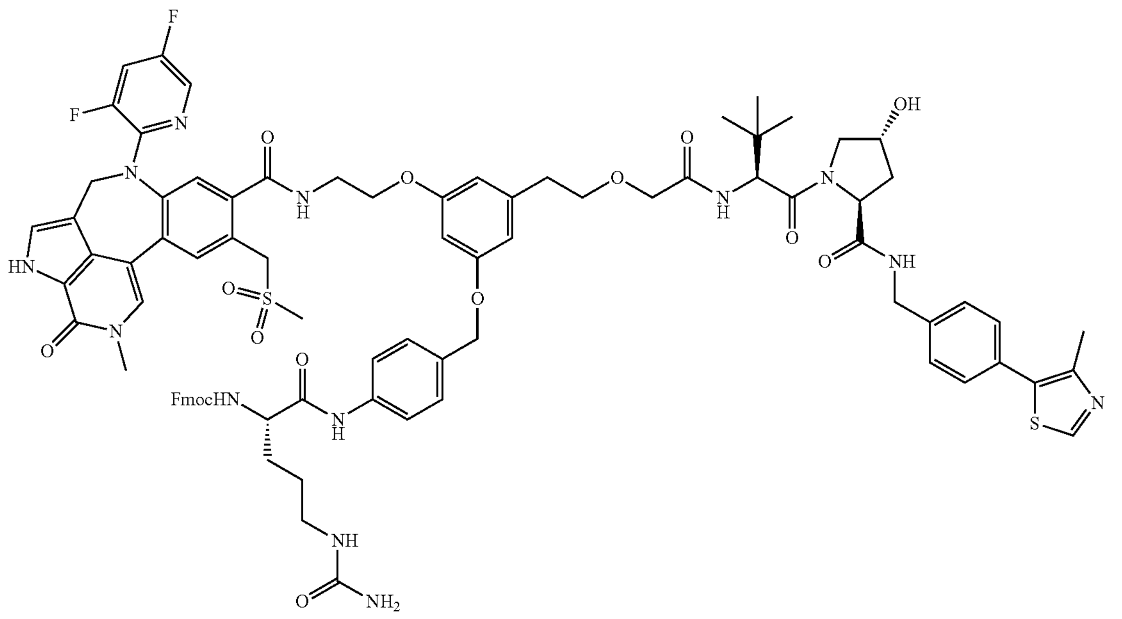
9
To a solution of Compound 8 (50.0 mg, 0.0400 mmol) in DMF (4.0 mL) was added VHL ligand (21.14 mg, 0.0500 mmol), HATU (17.11 mg, 0.0400 mmol) and DIEA (15.86 mg, 0.1200 mmol). The mixture was stirred at 25° C. for 2 h. The mixture was concentrated and purified by prep-TLC (10% MeOH in DCM Rf=0.3) to give compound 9 (15 mg, 22%) as a white solid. LCMS (5-95, AB, 1.5 min): RT=0.753 min m/z=817.8 $[M/2+1]^+$.
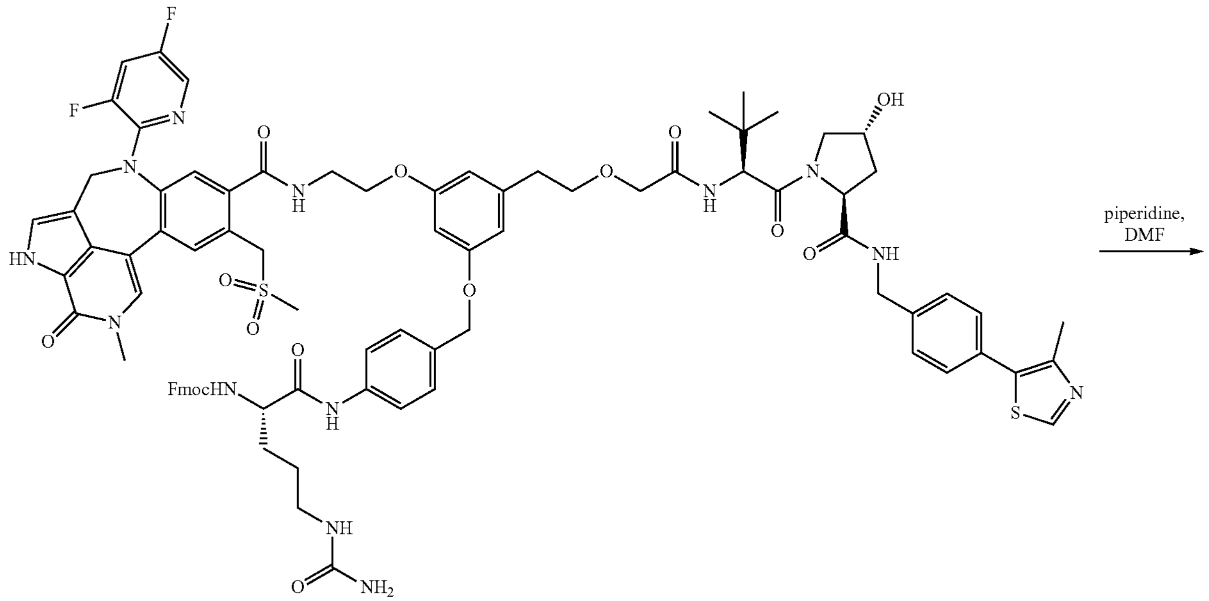
9

-continued
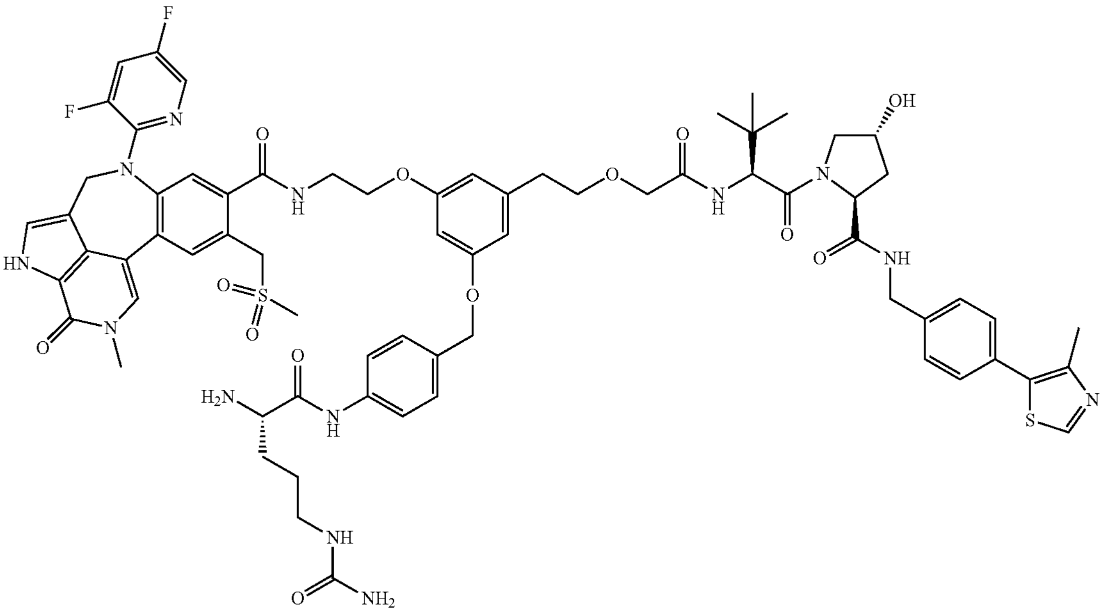
10
A mixture of Compound 9 (15.0 mg, 0.0100 mmol) and piperidine (0.010 mL, 0.0200 mmol) in DMF (2.0 mL) was stirred at 25° C. for 2 h. The mixture was concentrated to give crude compound 10 (12 mg, 930 yield) as a white solid, which was used directly in the next step. LCMS (5-95, AB, 1.5 min): RT=0.769 min m/z=707.0[M/2+1]$^+$.
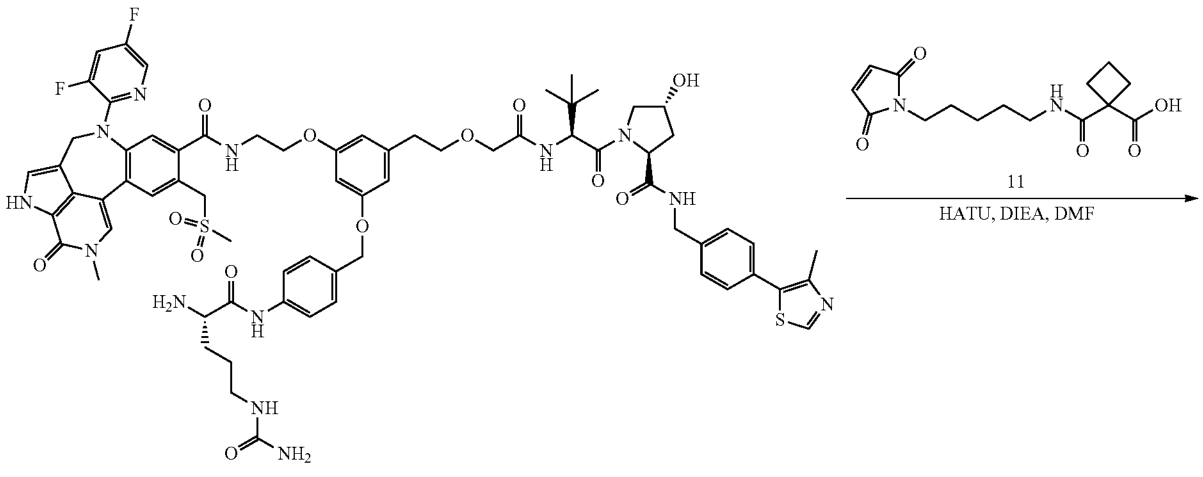
10

-continued

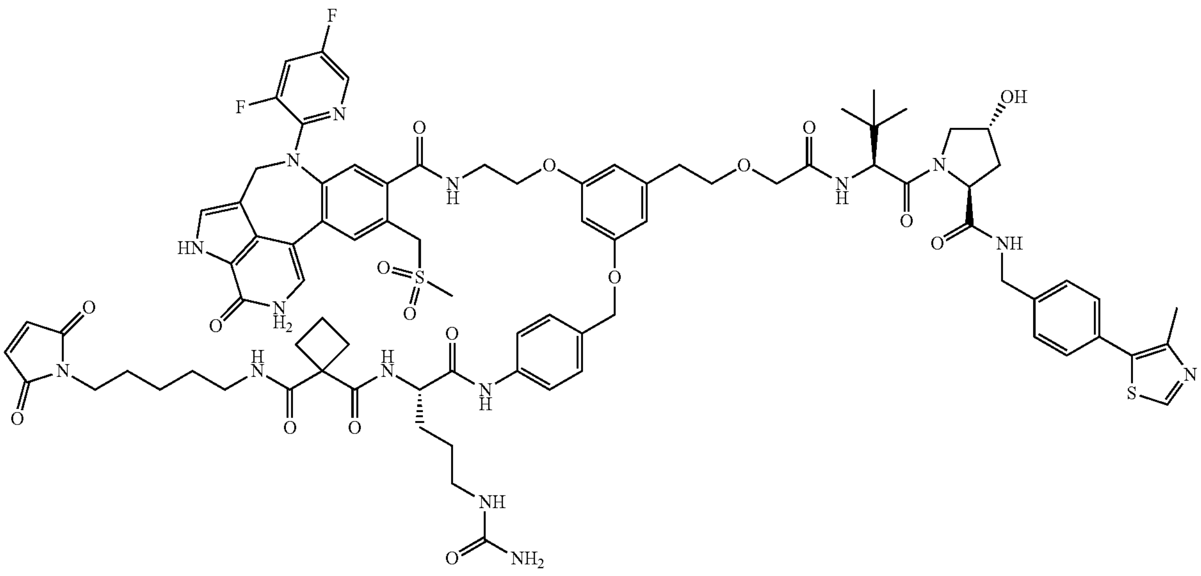

L1BC10

To a solution of Compound 10 (12.0 mg, 0.0100 mmol) in DMF (4.0 mL) was added compound 11 (3.14 mg, 0.0100 mmol) and HATU (4.85 mg, 0.0100 mmol) and DIEA (3.29 mg, 0.0300 mmol). The mixture was stirred at 25° C. for 1 h. The mixture was concentrated and purified by prep-HPLC (37-67 water (0.225% FA)-ACN) to afford the desired product L1BC10 (4.92 mg, 33%) as a white solid. LCMS (5-95, AB, 1.5 min): RT=0.839 min, m/z=852.3 $[M/2+1]^+$; HRMS (0-95_1_4 min): RT=2.561-2.643 min, m/z=1702.6758 $[M+1]^+$.

xvii. L1BC11 An exemplary L1-CIDE, L1BC11, can be synthesized by the following scheme:

Scheme 19

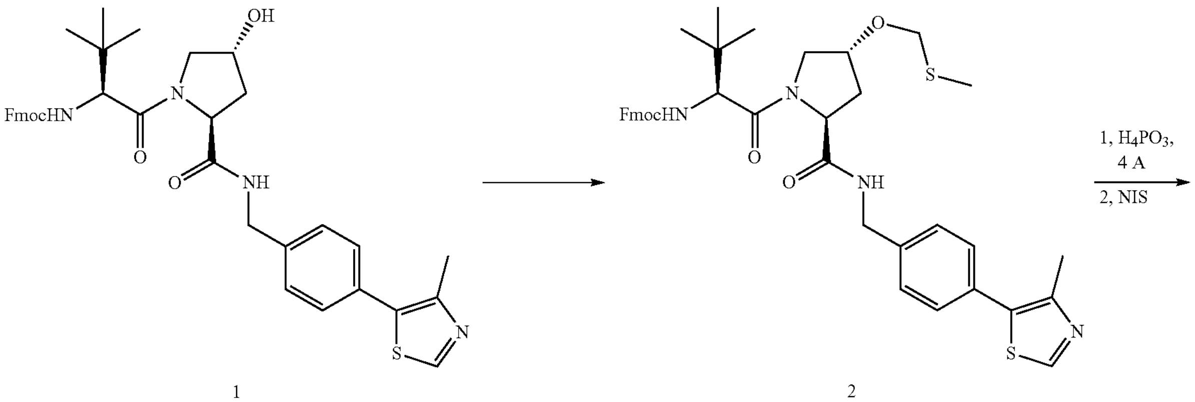

1

2

-continued
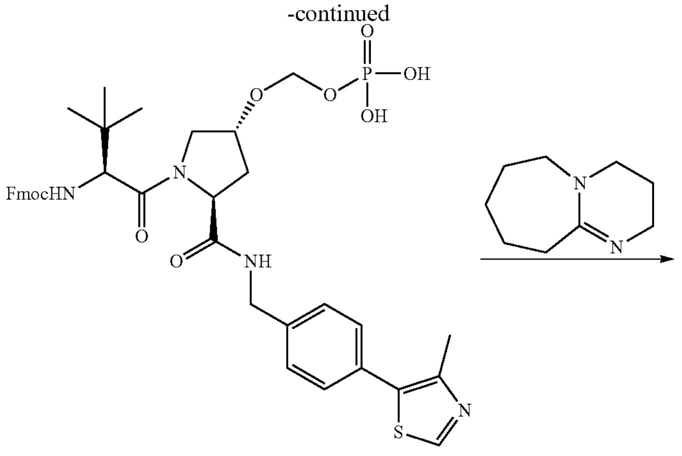
3
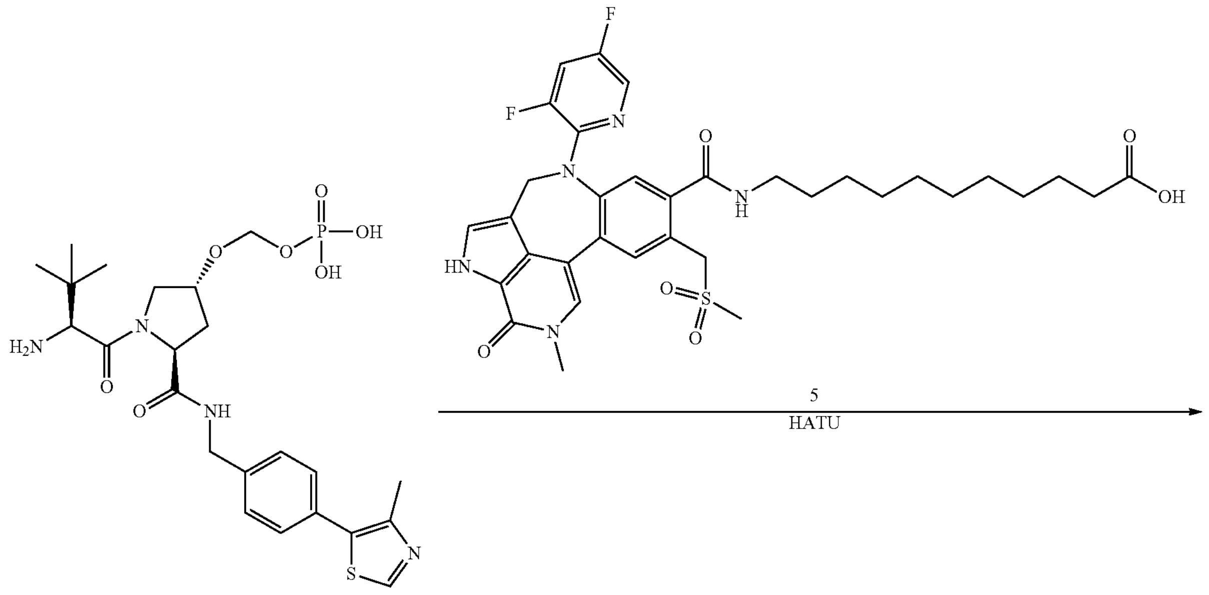
4
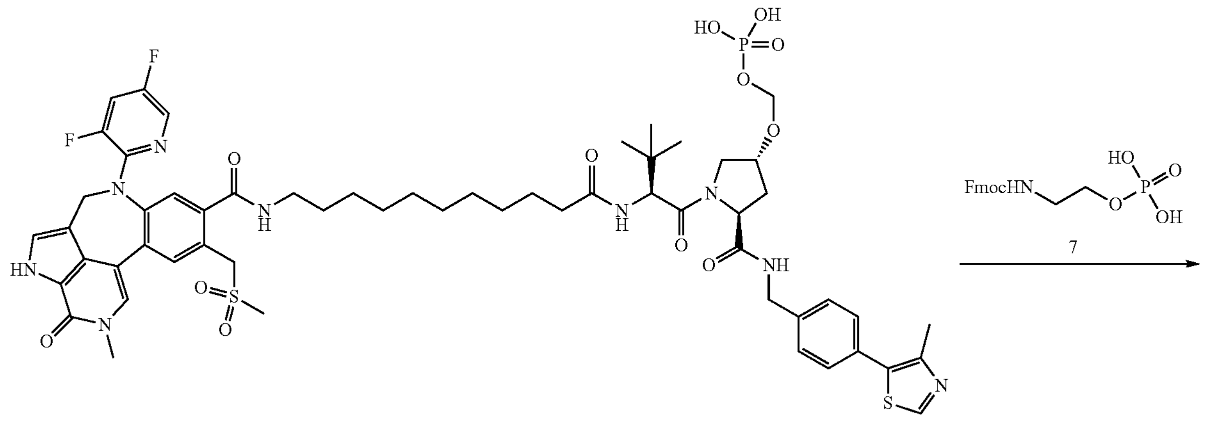
6

-continued
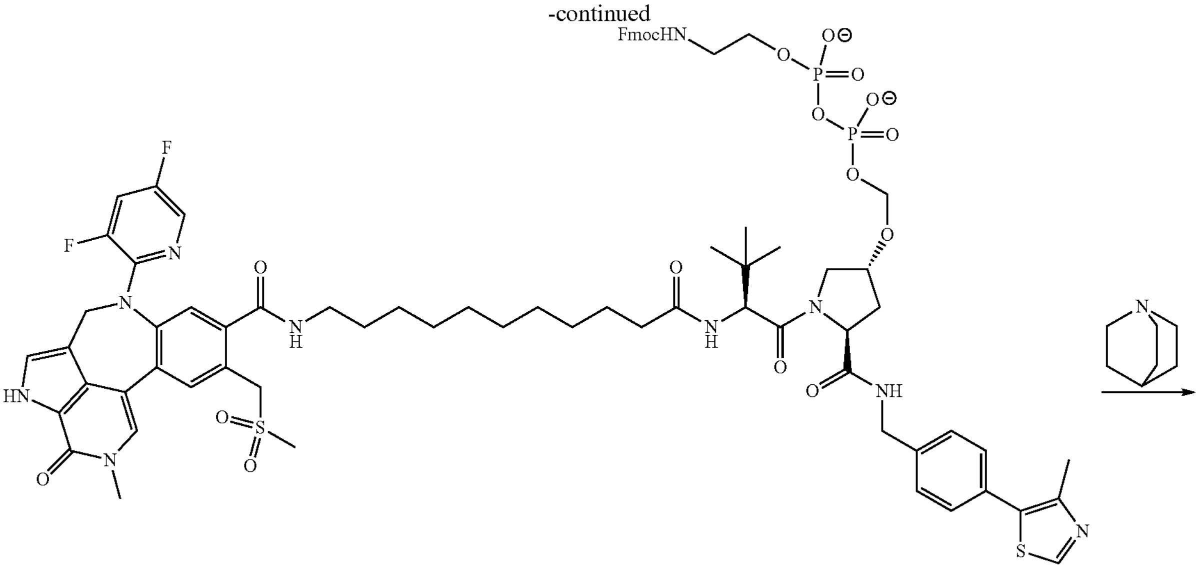
8
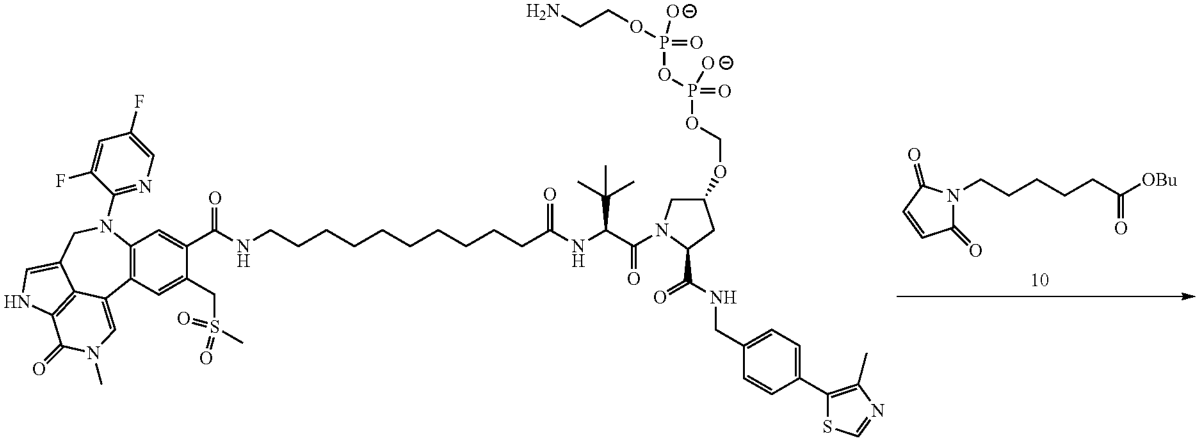
9
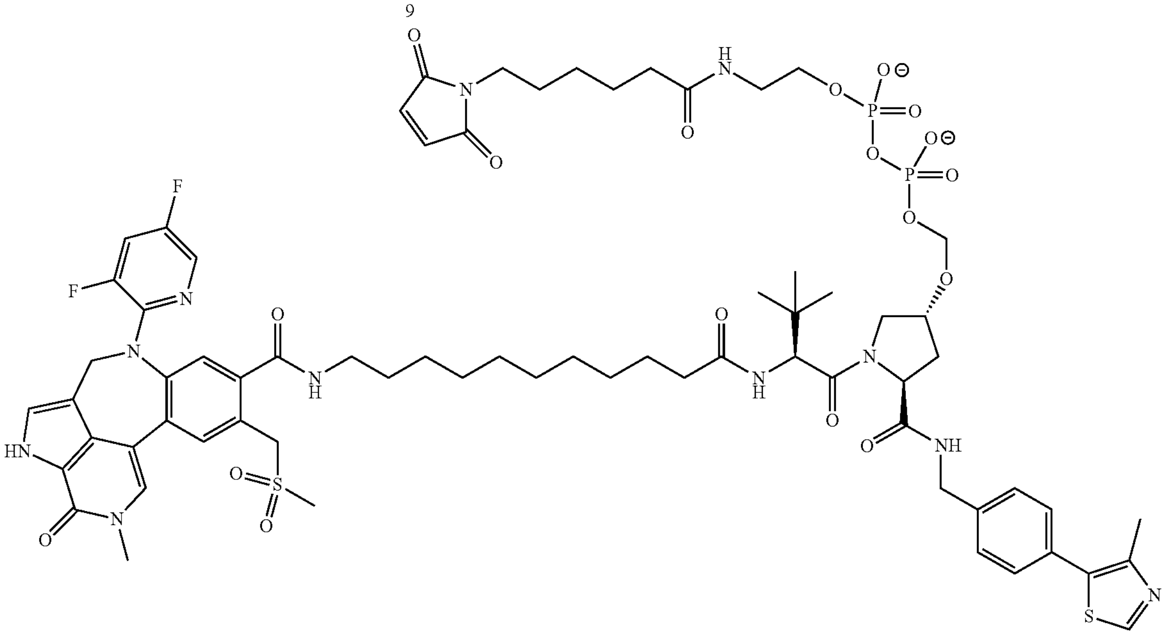
L1BC11

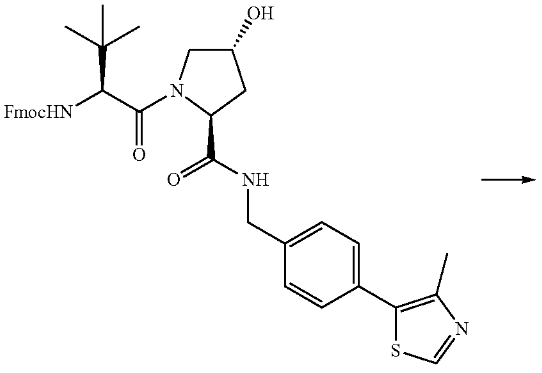

1

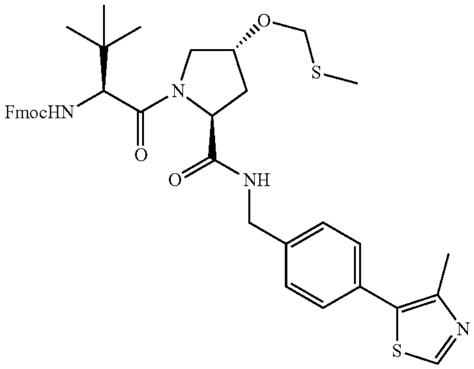

2

A solution of compound 1 (2.4 g, 3.68 mmol) in DMSO (6.74 mL, 94.87 mmol) was added HOAc (6.74 mL, 117.83 mmol) and $Ac_2O$ (4.51 mL, 47.67 mmol). The mixture was stirred at 40° C. for 48 h. The mixture was added water (30 mL) and treated with aq. $NaHCO_3$ (50 mL). The mixture was extracted with EtOAc (40 mL×3), and the organic layers were concentrated. The residue was purified by a column chromatography (0%-5% MeOH in DCM, Rf=0.4) to afford compound 2 (2.03 g, 65%) as a light yellow oil. LCMS (5-95, AB, 1.5 min): $R_T$=1.007 min, m/z=713.1 [M+1]+.

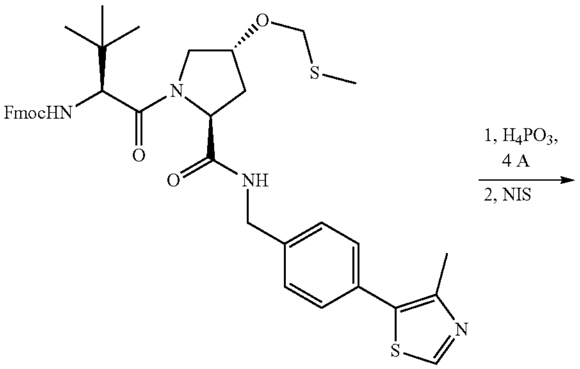

2

-continued

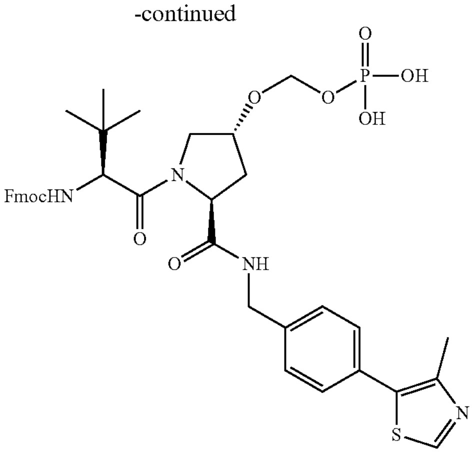

3

Phosphoric acid (481.12 mg, 4.91 mmol) was heated at 120° C. for 20 min and cooled to 25° C. Then molecular sieves (4A, 50 mg) and a solution of compound 2 (500.0 mg, 0.700 mmol) in THF (10 mL) was added, followed by NIS (236.68 mg, 1.05 mmol). The resulted mixture was stirred at 25° C. for 2 h. Then the mixture was concentrated and the resulting residue was purified by prep-HPLC (acetonitrile 22-52/0.05% $NH_3H_2O$ in water) to afford compound 3 (200 mg, 37%) as a gray solid, which was used directly in next step. LCMS (10-80, CD, 3.0 min): $R_T$=1.001 min, m/z=763.2 [M+1]+.

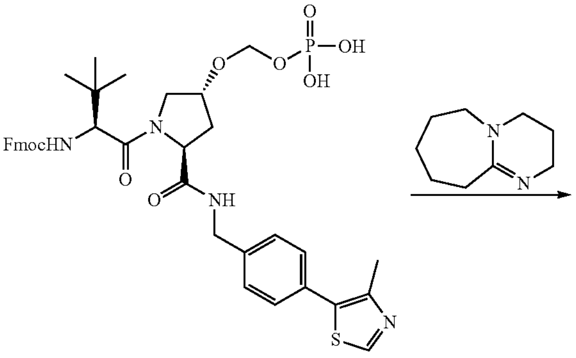

3

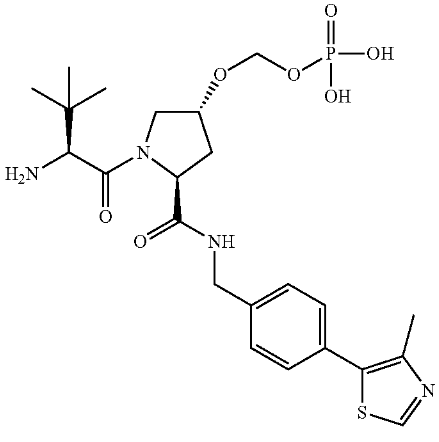

4

To a solution of compound 3 (200.0 mg, 0.2600 mmol) in DMF (3.0 mL) was added DBU (119.75 mg, 0.790 mmol). The mixture was stirred for 30 min at 25° C. Then the mixture was concentrated and the residue was washed with EtOAc (2.0 mL×2) to give the crude product compound 4 (141 mg, 99.5%) as a gray solid, which was used directly in next step. LCMS (5-95, AB, 1.5 min): $R_T$=0.554 min, m/z=541.2 $[M+1]^+$.

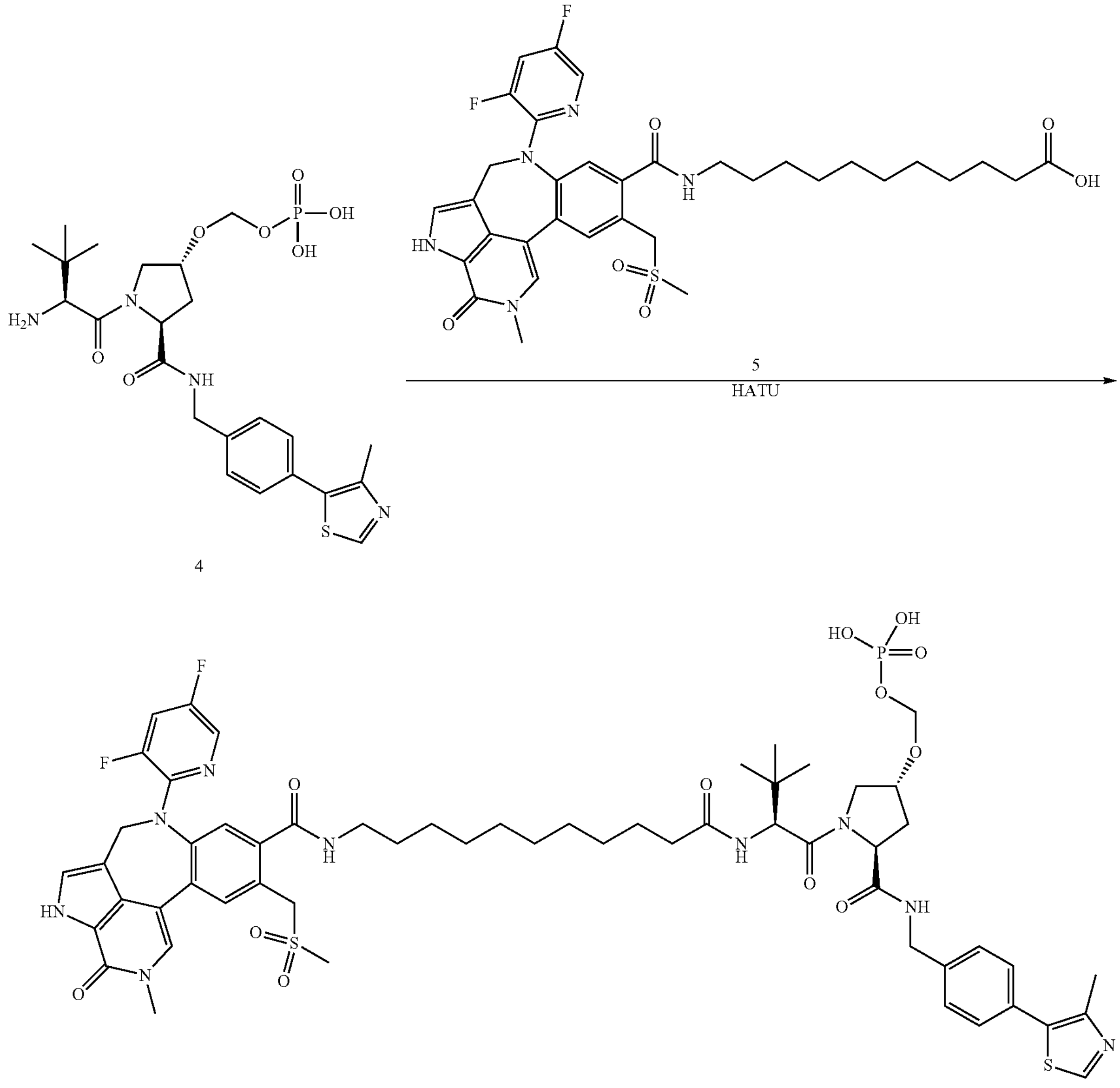

4

6

A solution of compound 5 (178.35 mg, 0.260 mmol), DIEA (101.13 mg, 0.780 mmol) and HATU (99.18 mg, 0.2600 mmol) in anhydrous DMF (3.0 mL) was stirred at 25° C. for 20 min, and then compound 4 (141.0 mg, 0.260 mmol) was added. The resulted mixture was stirred at 25° C. for 2 h. The reaction mixture was filtered and the filtrate was purified by prep-HPLC (acetonitrile 20-50/0.05% $NH_4OH$ in water) to afford compound 6 (130 mg, 41%) as a white solid. LCMS (10-80, CD, 3.0 min): RT=1.144 min, m/z=1206.3 $[M+1]^+$.

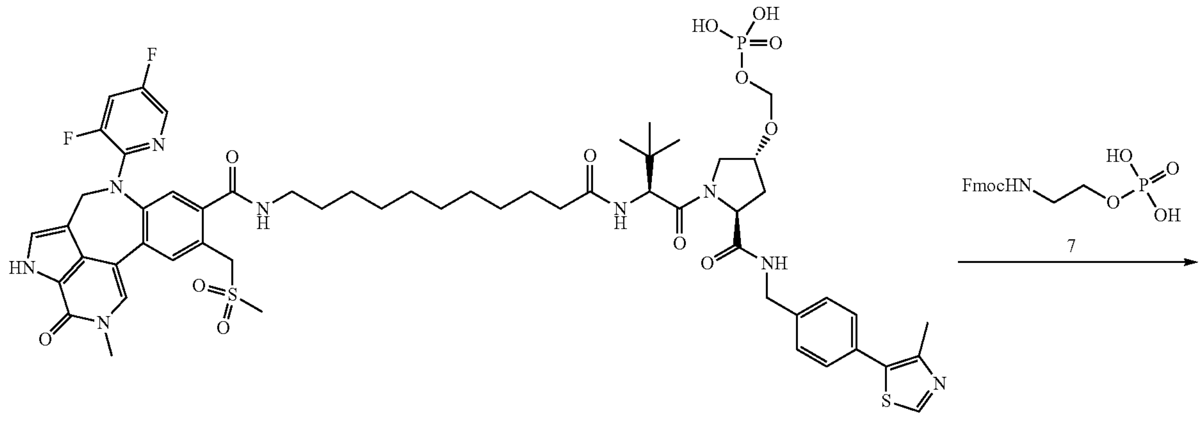

6

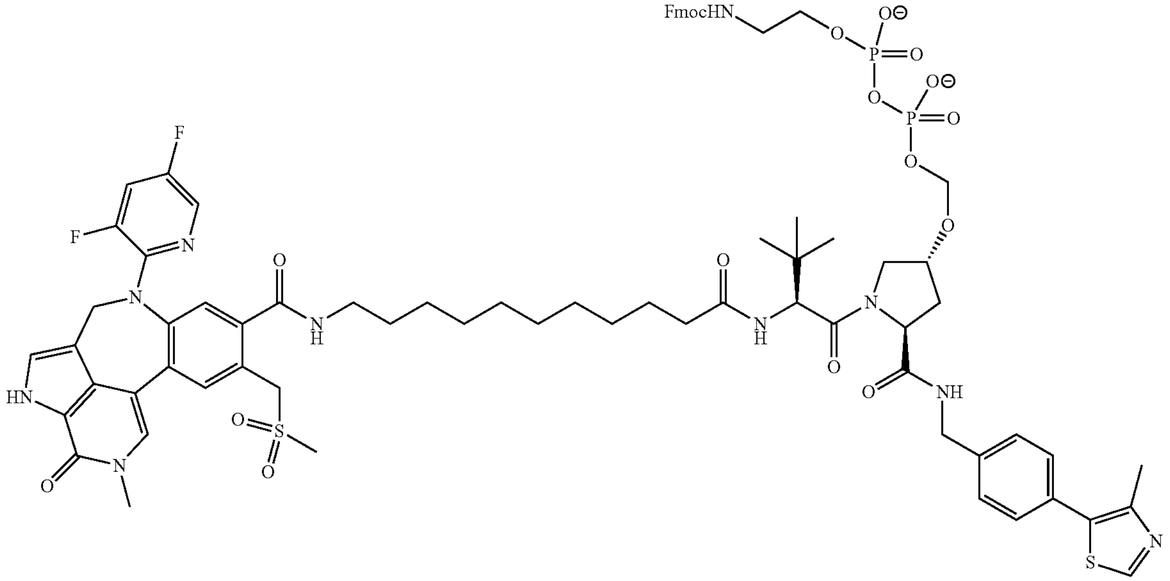

8

To a solution of compound 7 (54.21 mg, 0.1500 mmol) in anhydrous DMF (3.0 mL) was added $Et_3N$ (15.1 mg, 0.150 mmol) and CDI (30.92 mg, 0.1900 mmol) at 25° C. The reaction mixture was stirred at 25° C. for 20 min, and then compound 6 (100.0 mg, 0.0800 mmol) and $ZnCl_2$ solution (0.83 mL, 1.0 mol/L in toluene, 0.830 mmol) was added. The resulted mixture was stirred at 25° C. for 12 h. The reaction mixture was filtered and the filtrate was purified by prep-HPLC (acetonitrile 25-55/0.05% $NH_4OH$ in water) to afford the product compound 8 (35 mg, 27.2%) as a white solid. LCMS (10-80, CD, 3.0 min): $R_T$=1.498 min, m/z=776.3[M/2+]$^+$.

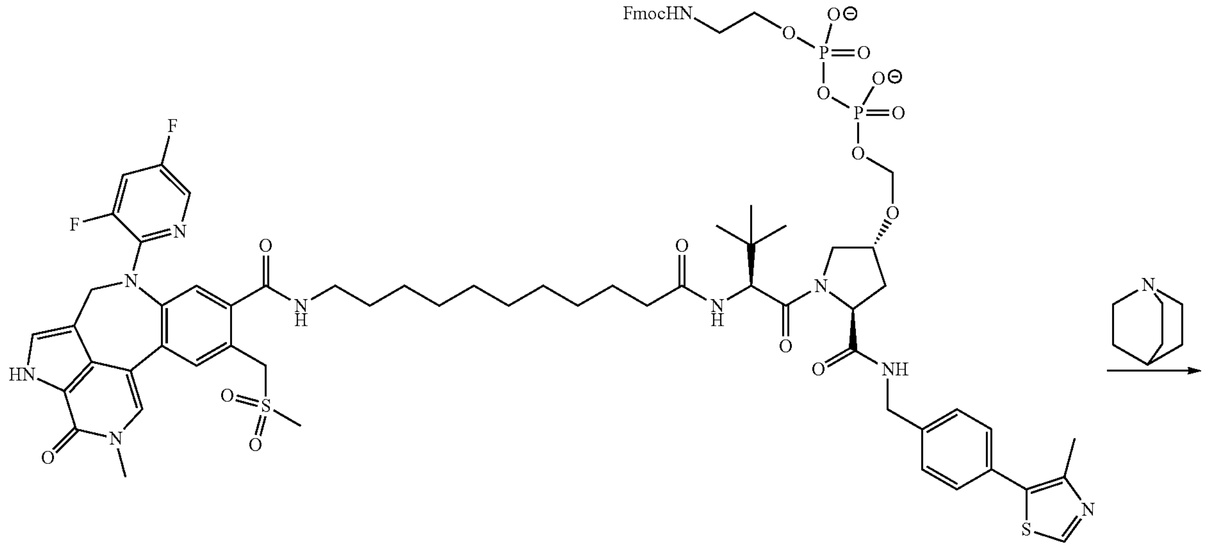
8
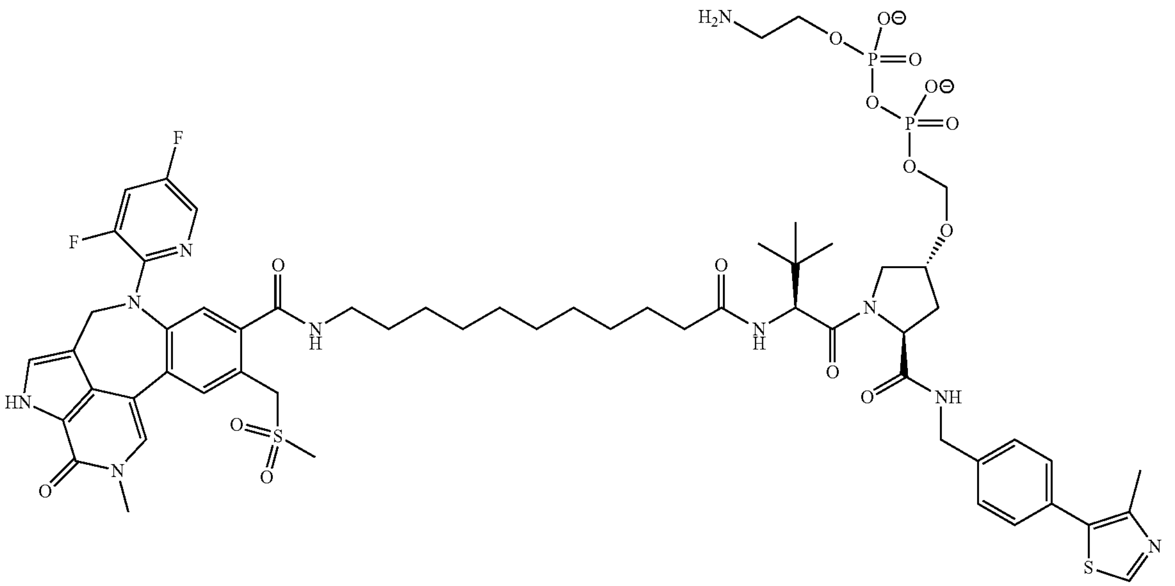
9

To a solution of compound 8 (35.0 mg, 0.020 mmol) in DMF (1.0 mL) was added quinuclidine (12.54 mg, 0.110 mmol). The mixture was stirred for 4 h at 25° C. The mixture solution was used directly in next step. LCMS (10-80, CD, 3.0 min): $R_T$=1.299 min, m/z=665.4 $[M/2+1]^+$.

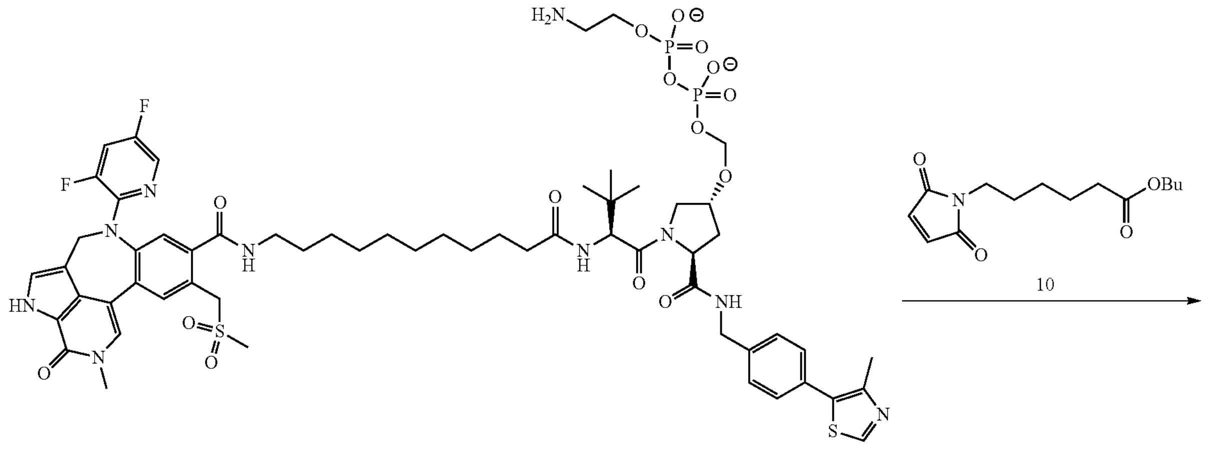

9

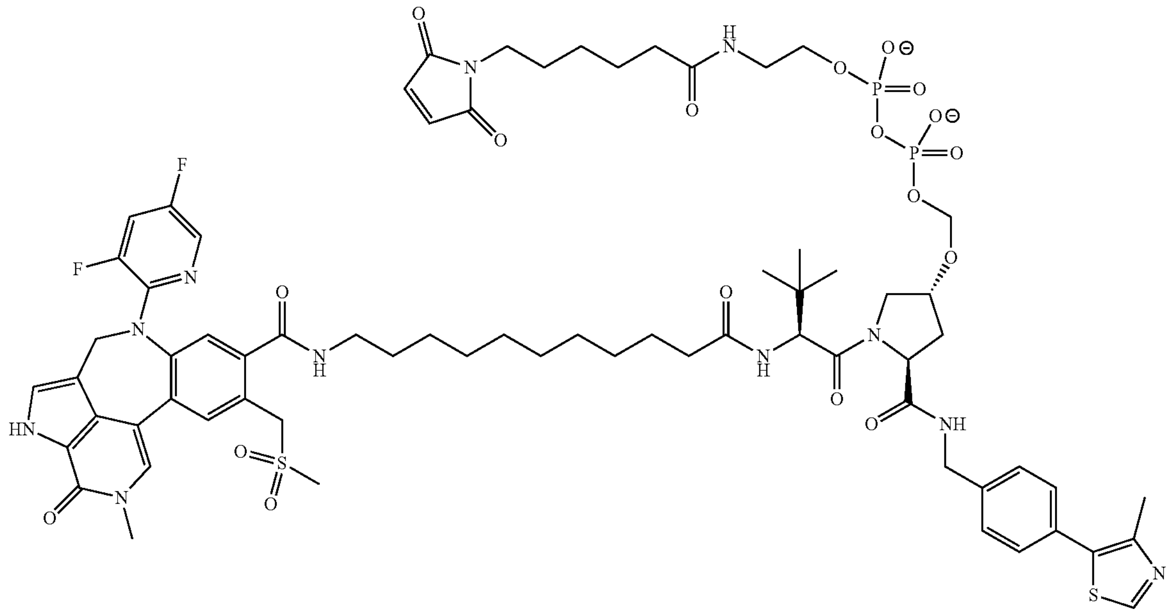

L1BC11

To a solution of compound 9 (29.0 mg, 0.020 mmol) in anhydrous DMF (2.0 mL) was added compound 10 (6.73 mg, 0.0200 mmol) at 25° C. After the reaction mixture was stirred at 25° C. for 12 h, it was filtered and the filtrate was concentrated. It was purified by prep-HPLC twice (acetonitrile 18-48/in water, then acetonitrile 25-48/10 mM $NH_4HCO_3$ in water) to afford L1BC11 (2.4 mg, 7.2%) as a white solid. LCMS (10-80, CD, 3.0 min): $R_T$=1.202 min, m/z=761.8 $[M/2+1]^+$.

xviii. L1BC12 An exemplary L1-CIDE, L1BC12, can be synthesized by the following scheme:

Scheme 20
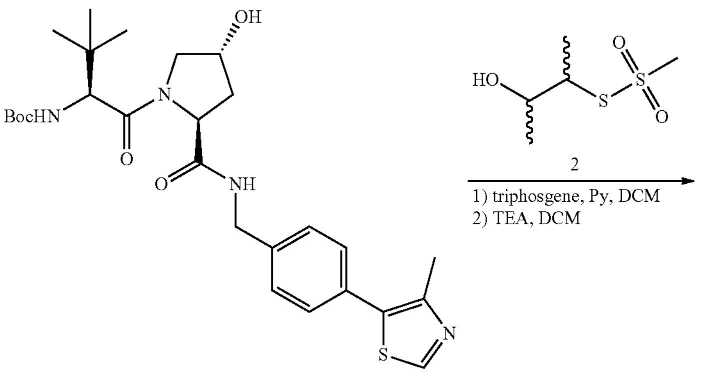
1
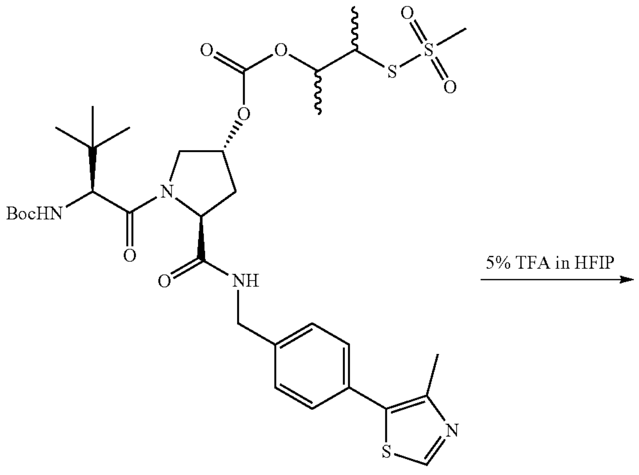
3
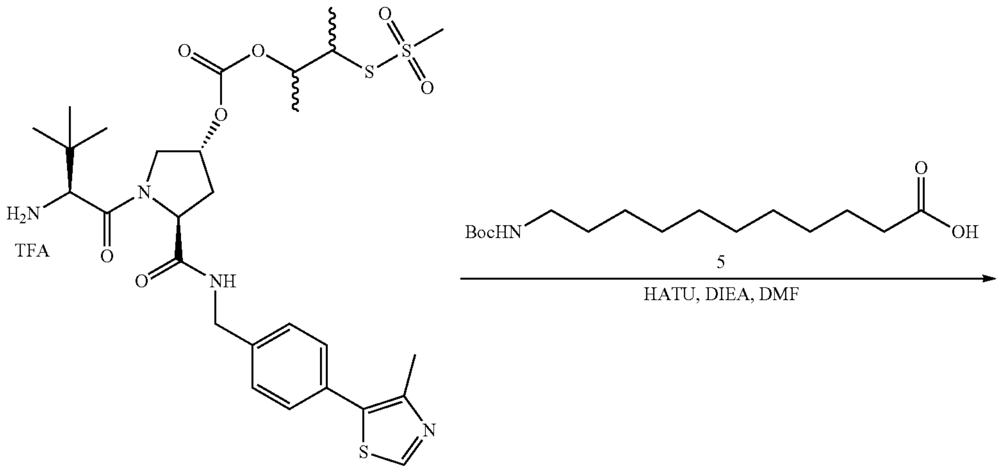
4

-continued
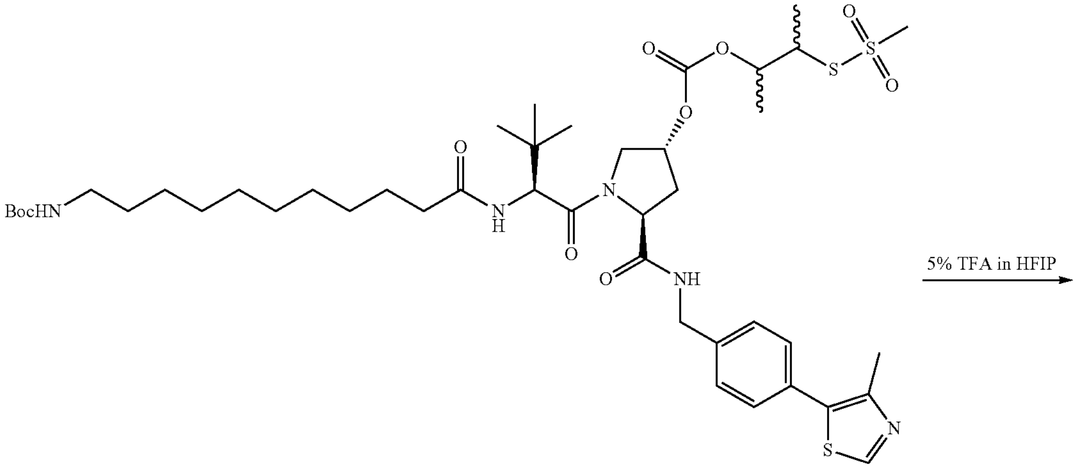
6
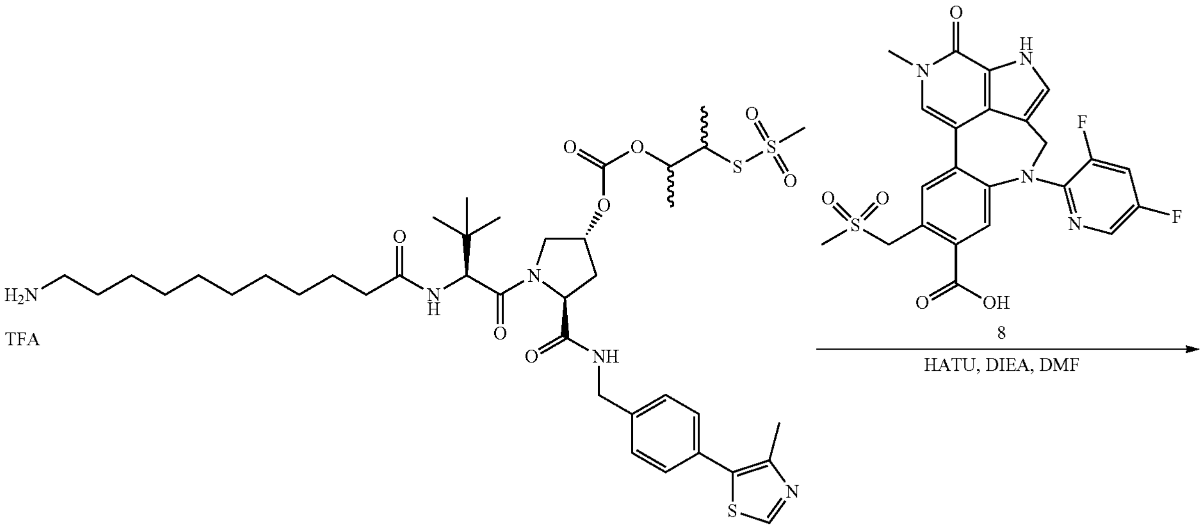
7
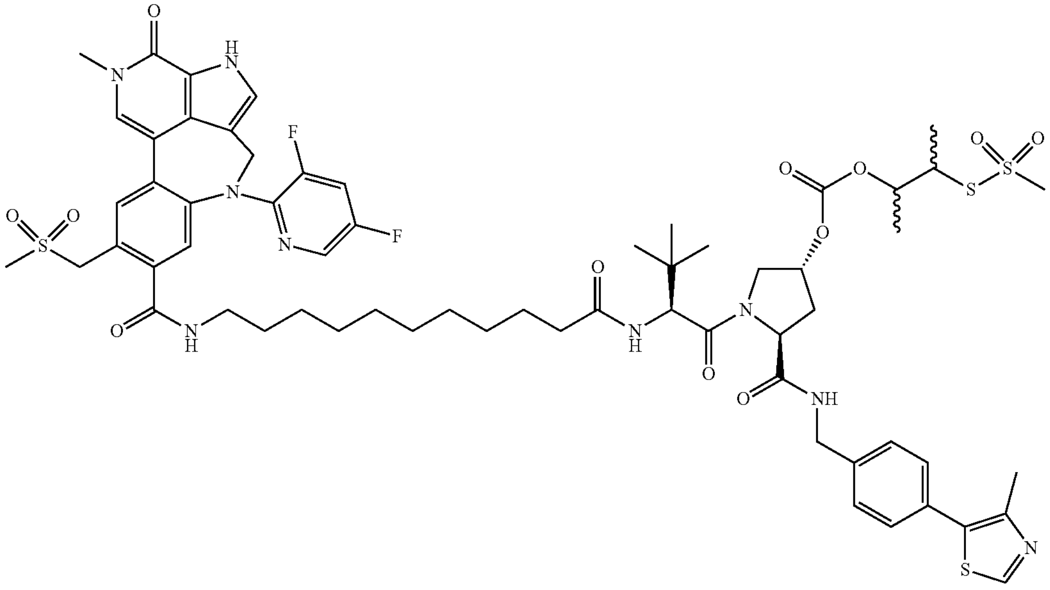
L1BC12

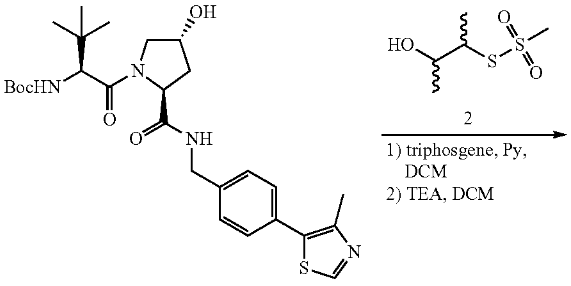

1

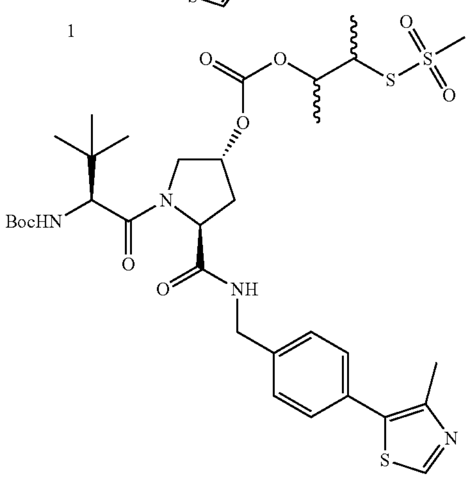

3

To a mixture of triphosgene (240.45 mg, 0.810 mmol) and 4 Å molecular sieves (100 mg) in anhydrous DCM (20 mL) was added a solution of compound 2 (300.0 mg, 1.63 mmol) in pyridine (256.37 mg, 3.24 mmol) in anhydrous DCM (6.0 mL) slowly at 20° C. The reaction mixture was stirred at 20° C. for 0.5 h. Then the mixture was concentrated in vacuo, and the residue was diluted with anhydrous DCM (25 mL). $Et_3N$ (245.98 mg, 2.43 mmol) was added, followed by a solution of compound 1 (430.0 mg, 0.810 mmol) in anhydrous DCM (8.0 mL). The reaction mixture was stirred at 20° C. for another 16 h. The mixture was diluted with DCM (30 mL), washed with $H_2O$ (20 mL×3), dried over $Na_2SO_4$, filtered, and concentrated. The residue was purified by prep-TLC (7% MeOH in DCM, Rf=0.6) to afford compound 3 (480 mg, 74%) as a pale yellow solid. LCMS (5-95, AB, 1.5 min): $R_T$=0.877 min, m/z=763.3 $[M+23]^+$;

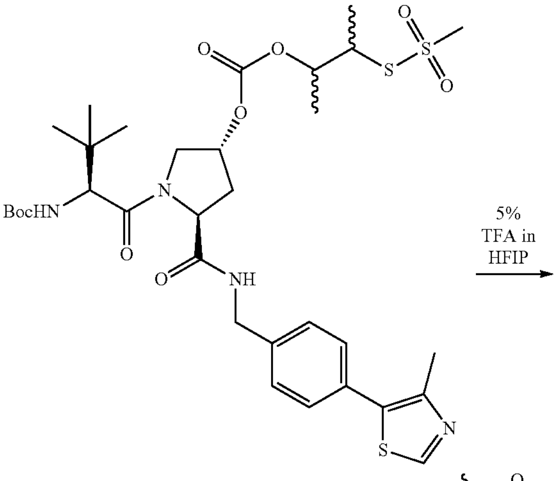

3

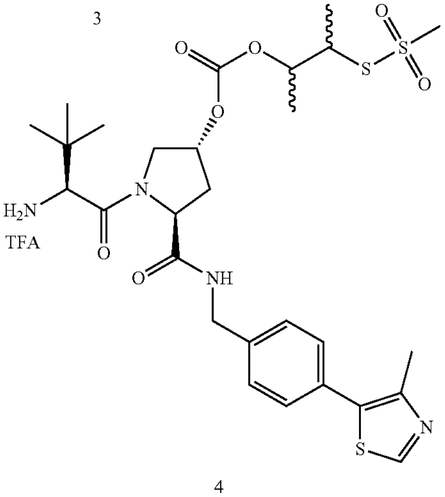

4

A solution of compound 3 (100.0 mg, 0.1300 mmol) in a mixture of TFA (0.20 mL)/HFIP (4.0 mL) was stirred at 20° C. for 1 h. The solution was concentrated in vacuo, the residue was diluted with DMF (10 mL), and concentrated in vacuo again to afford compound 4 (100 mg, 98.2%) as crude colorless oil, which was used for the next step directly. LCMS (5-95, AB, 1.5 min): $R_T$=0.723 min, m/z=641.1 $[M+1]^+$.

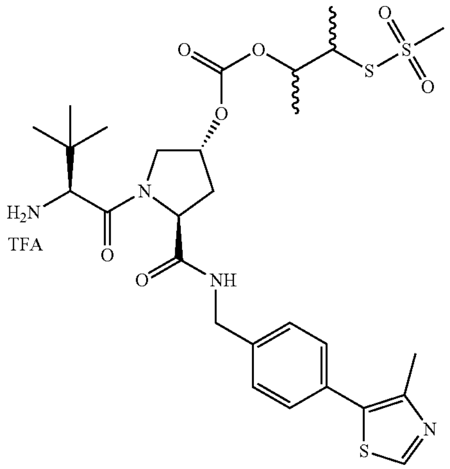

4

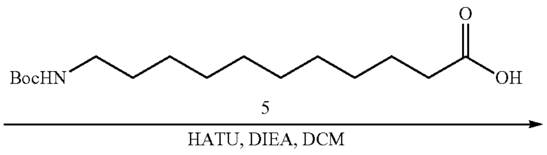

-continued

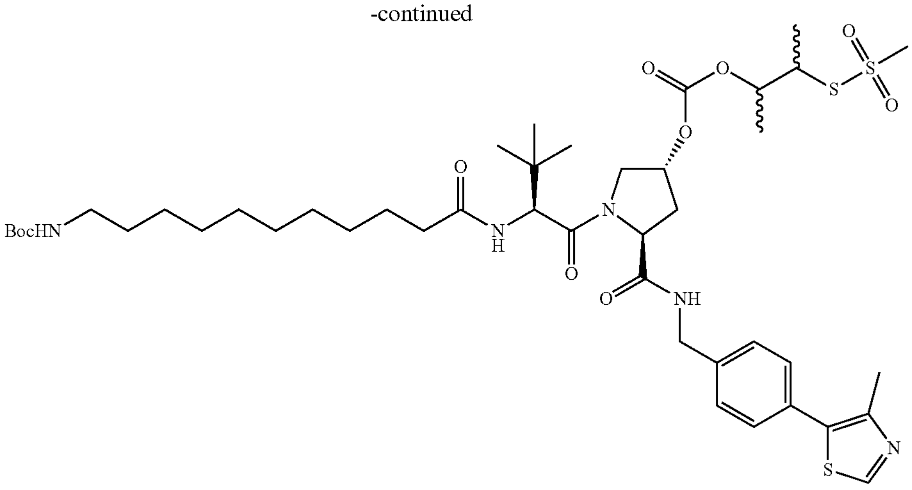

6

To a solution of compound 5 (40.0 mg, 0.1300 mmol) in anhydrous DCM (10 mL) was added HATU (60.55 mg, 0.1600 mmol) and N,N-diisopropylethylamine (68.6 mg, 0.530 mmol). The mixture was stirred at 20° C. for 15 min, then a solution of compound 4 (100.0 mg, 0.1300 mmol) in anhydrous DCM (5 mL) was added. The resulting reaction mixture was stirred at 20° C. for another 1 h. The mixture was concentrated in vacuo, and the residue was purified by prep-TLC (10% MeOH in DCM, $R_f$=0.5) to afford compound 6 (85 mg, 61%) as a white solid. LCMS (5-95, AB, 1.5 min): $R_T$=0.964 min, m/z=946.3 [M+23]$^+$.

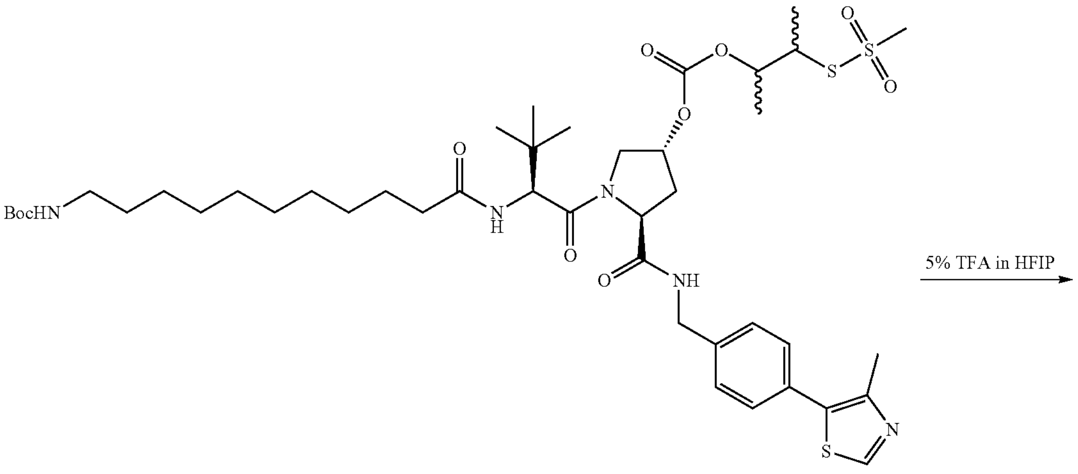

6

-continued
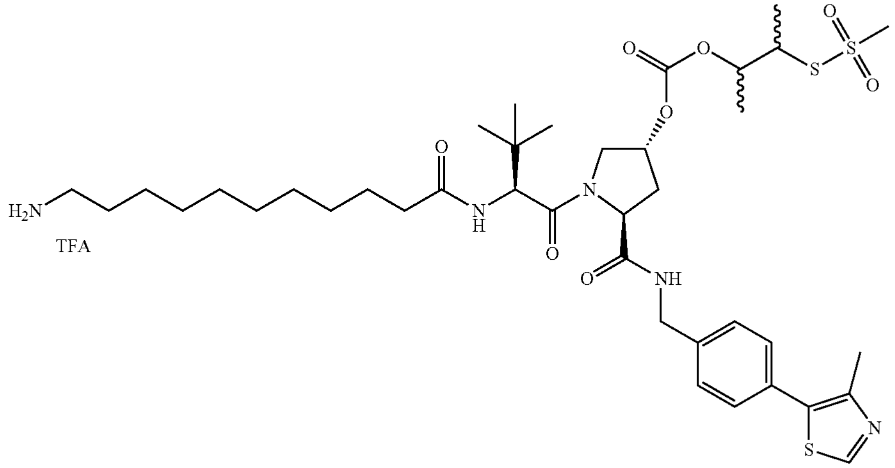
7
A solution of compound 6 (85.0 mg, 0.090 mmol) in a mixture of TFA (0.20 mL)/HFIP (4.0 mL) was stirred at 20° C. for 1 h. The solution was concentrated in vacuo, diluted with DMF (10 mL), and concentrated in vacuo again to remove the remaining TFA, to afford compound 7 (86 mg, 99.7%) as a crude colorless oil, which was used in the next step directly. LCMS (5-95, AB, 1.5 min): $R_T$=0.777 min, m/z=824.4 $[M+1]^+$.
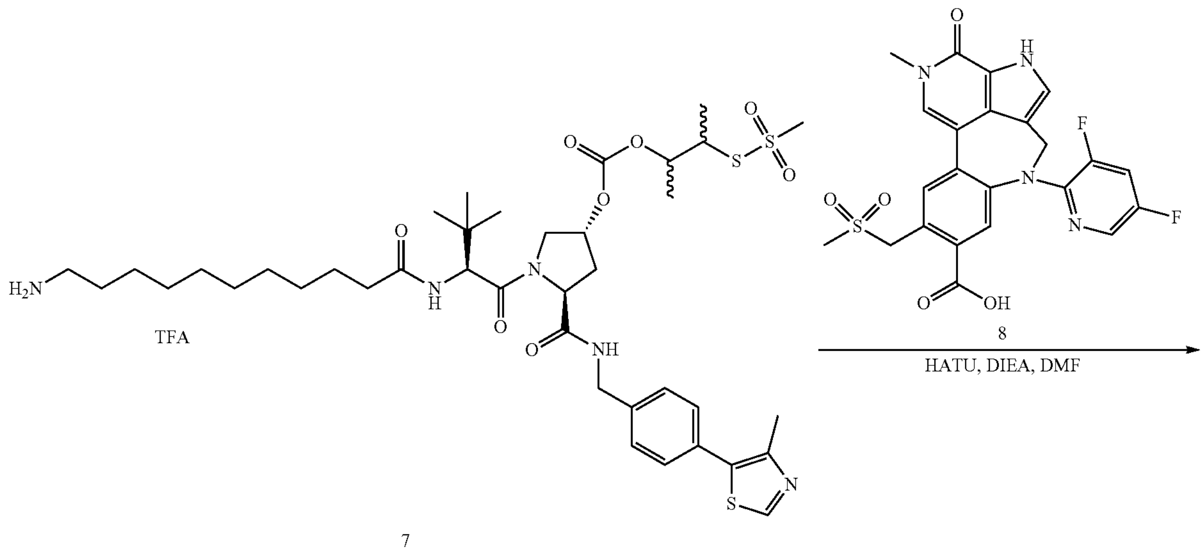
7

-continued

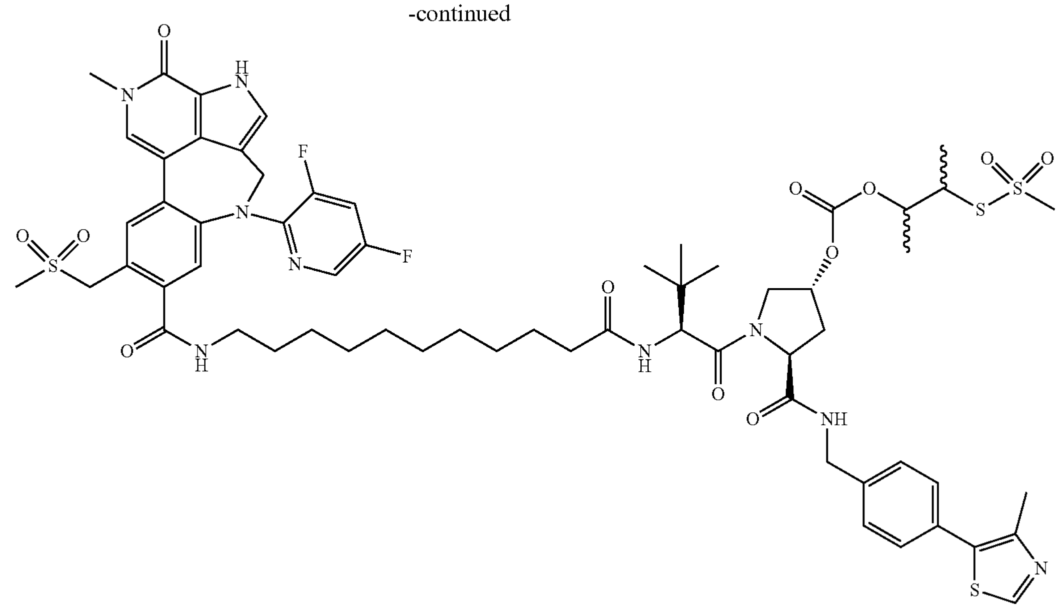

L1BC12

To a solution of compound 8 (20.0 mg, 0.0400 mmol) in DMF (4.0 mL) was added HATU (19.75 mg, 0.0500 mmol) and DIEA (25.82 mg, 0.200 mmol). After the solution was stirred at 20° C. for 10 min, compound 7 (48.74 mg, 0.0500 mmol) was added. The resulting reaction solution was stirred at 20° C. for another 1 h. The solution was purified by prep-HPLC (Xtimate C18 150*25 mm*5 um, acetonitrile 50-80/0.225% FA in water) to afford L1BC12 (23 mg, 43.2%) as a white solid. LCMS (5-95, AB, 1.5 min): $R_T$=0.892 min, m/z=1329.1 $[M+23]^+$; $^1H$ NMR (400 MHz, DMSO-$d_6$) δ 11.93 (s, 1H), 8.98 (s, 1H), 8.62-8.60 (m, 1H), 8.41-8.39 (m, 1H), 8.06 (d, J=2.4 Hz, 1H), 7.91-7.87 (m, 2H), 7.75 (s, 1H), 7.63-7.57 (m, 2H), 7.43-7.37 (m, 3H), 7.27-7.26 (m, 2H), 5.21 (d, J=12.0 Hz, 2H), 4.98-4.94 (m, 2H), 4.47-4.35 (m, 4H), 4.27-4.09 (m, 4H), 3.84-3.80 (m, 2H), 3.75-3.70 (m, 2H), 3.62 (s, 3H), 3.54 (d, J=2.8 Hz, 3H), 3.13 (brs, 3H), 2.90 (s, 3H), 2.67 (brs, 1H), 2.44 (s, 3H), 2.33-2.09 (m, 3H), 1.45-1.32 (m, 10H), 1.21 (s, 8H), 0.94 (s, 9H).

xix. L1BQ1 An exemplary L1-CIDE, L1BQ1, can be synthesized by the following scheme:

Scheme 21

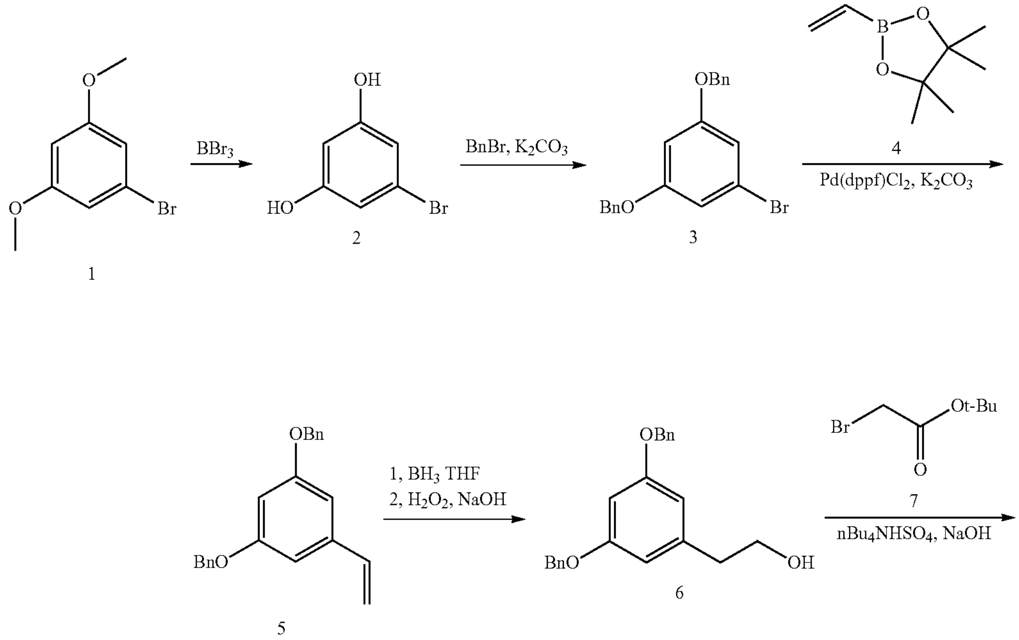

-continued
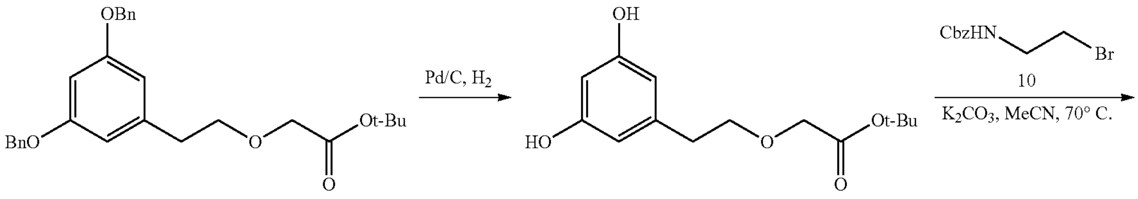
8 9
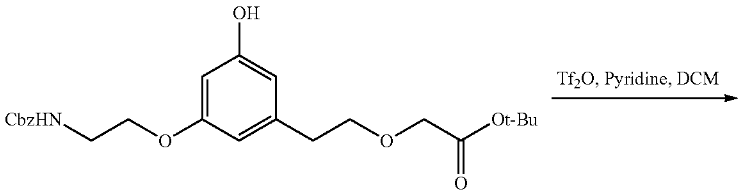
11
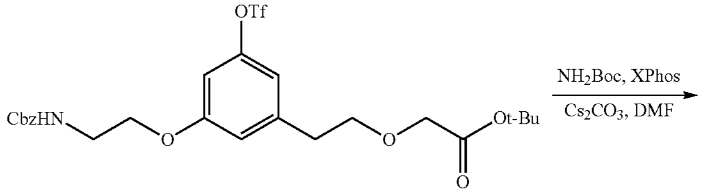
12
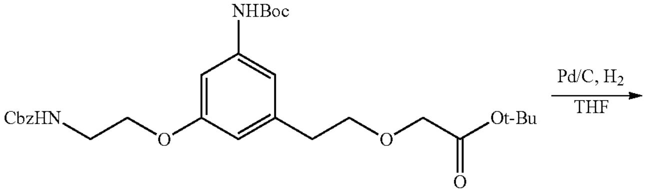
13
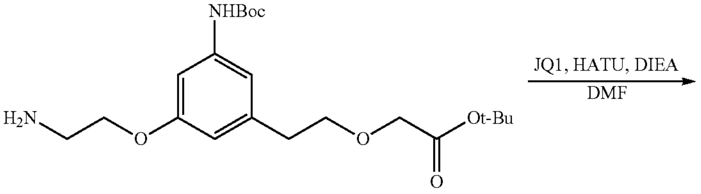
14
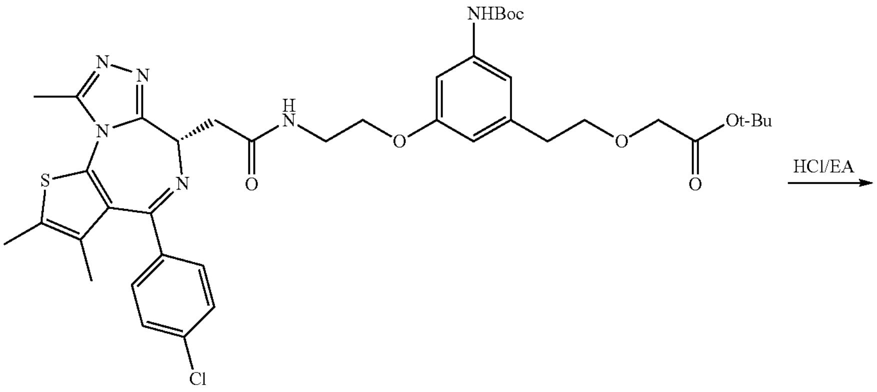
15

-continued
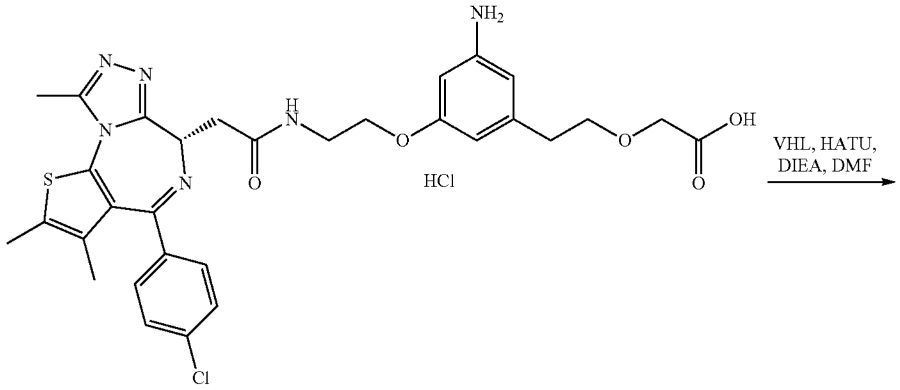
16
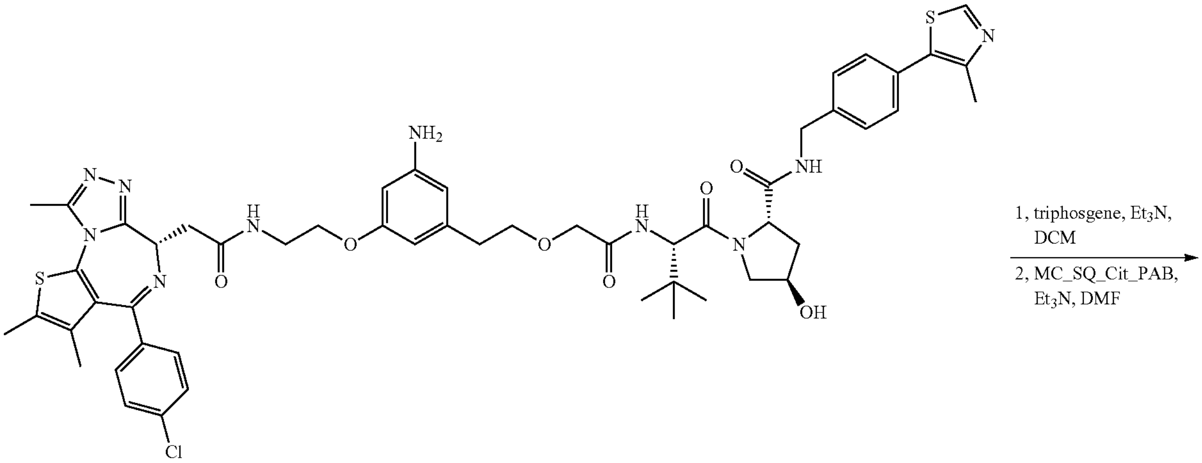
17
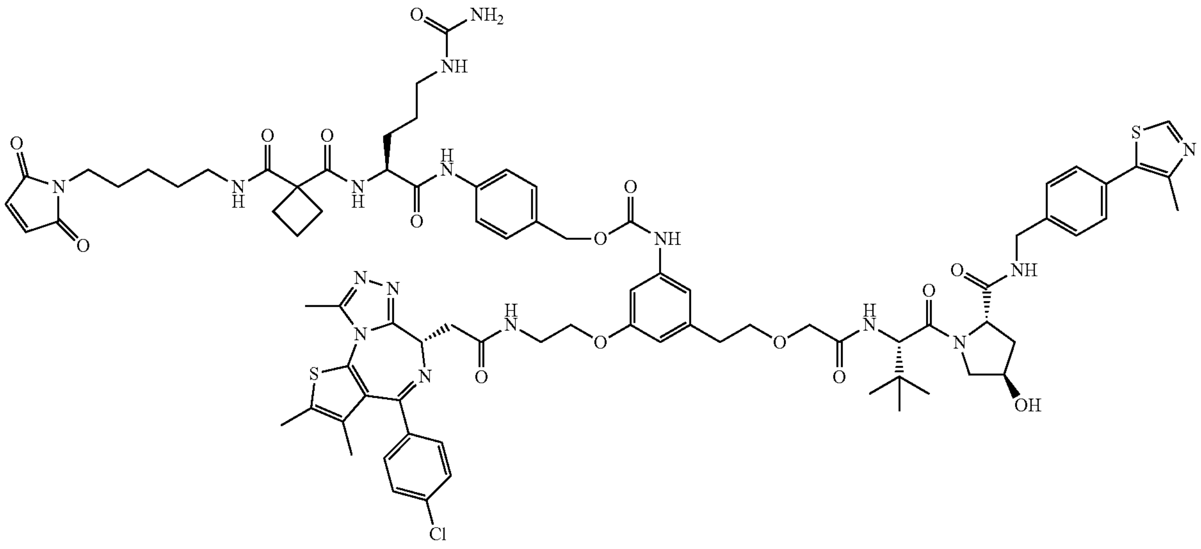
L1BQ1

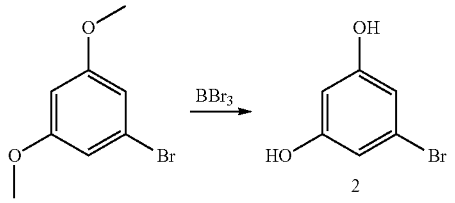

1 2

To a solution compound 1 (15.0 g, 69.11 mmol) in DCM (150 mL) was added $BBr_3$ (19.25 mL, 207.32 mmol). The mixture was stirred at 20° C. for 10 hrs. The TLC (10% ethyl acetate in petroleum ether, Rf=0.4) showed the reaction was completed. The reaction was quenched by MeOH (20 mL), and then DCM (100 mL) was added. The organic layer was washed with water (60 m) and brine (60 mL). The organics were then separated and dried over $Na_2SO_4$, filtered and concentrated to give the crude product (9.6 g, 74%) as yellow oil which was used directly without further purification. $^1$H NMR (400 MHz, MeOD): δ 6.37 (s, 2H), 6.14 (m, J=2.4 Hz, 1H).

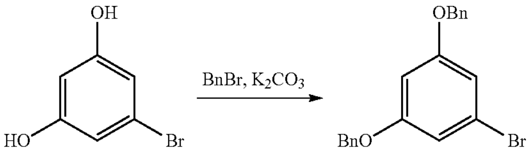

2 3

To a solution compound 2 (9.6 g, 50.79 mmol) in DMF (200 mL) was added $K_2CO_3$ (42.12 g, 304.75 mmol) and BnBr (34.75 g, 203.16 mmol). The mixture was stirred at 20° C. for 12 hrs. The reaction mixture was filtered and the filtrate was concentrated to afford the residue was purified by column chromatography (0-10% ethyl acetate in petroleum ether, Rf=0.8) to give compound 3 (12.5 g, 63%) as a white powder. $^1$H NMR (400 MHz, $CDCl_3$): δ 7.38-7.32 (m, 10H), 6.76 (d, J=2.0 Hz, 2H), 6.52 (d, J=1.6 Hz, 1H), 4.99 (s, 4H).

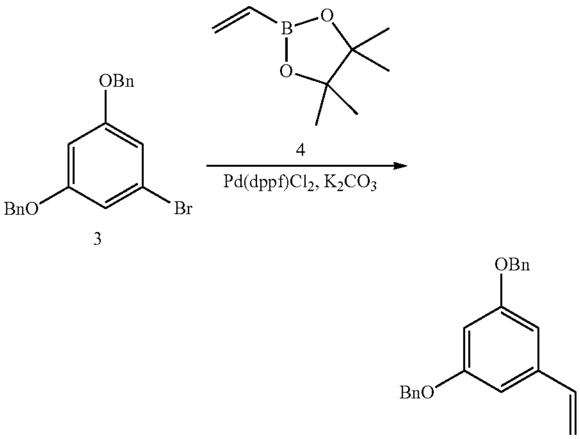

3 4 5

To a solution of compound 3 (9.9 g, 26.81 mmol) and $K_2CO_3$ (14.82 g, 107.24 mmol) in 1,4-Dioxane (200 mL) and Water (50 mL) was added compound 4 (5.78 g, 37.54 mmol) and Pd(dppf)$Cl_2$ (1.57 g, 2.14 mmol). The mixture was stirred at 100° C. for 15 hrs under nitrogen. The mixture was extracted with EtOAc (50 mL×3). The combined organic layers were dried over $Na_2SO_4$ and concentrated to give the residue which was purified by column chromatography (10% ethyl acetate in petroleum ether, Rf=0.8) to compound 5 (5.6 g, 66%) as colorless oil. $^1$H NMR (400 MHz, $CDCl_3$): δ 7.44-7.31 (m, 10H), 6.76 (d, J=2.0 Hz, 2H), 6.48-6.32 (m, 1H), 6.55 (d, J=1.6 Hz, 1H), 5.72 (d, J=17.6 Hz, 1H), 5.25 (d, J=13.6 Hz, 1H), 5.05 (s, 4H).

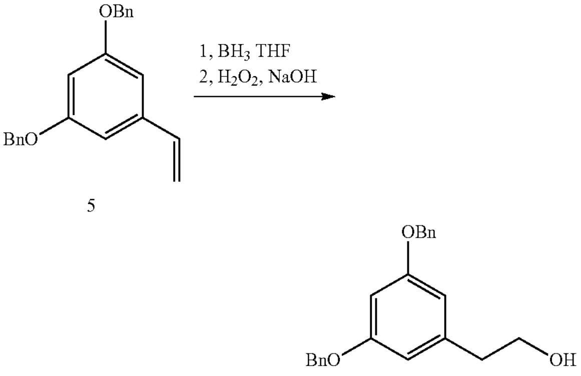

5 6

To a solution of compound 5 (5.6 g, 17.7 mmol) in THF (100 mL) was added $BH_3$ in THF (23.01 mL, 23.01 mmol) at 0° C. under nitrogen, the mixture was stirred at 20° C. for 1 hr. Then aqueous NaOH (1 mL, 1 mol/L) was added, follow by $H_2O_2$ (26.64 mL, 265.5 mmol), the resulting mixture was stirred at 20° C. for 2 hrs. The reaction was quenched with $Na_2SO_3$ solution, and extracted with ethyl acetate (50 mL×3), washed with brine (15 mL×3), dried over $Na_2SO_4$, filtered, and concentrated. The residue obtained was purified with column chromatography (25% ethyl acetate in petroleum ether, Rf=0.4) to give compound 6 (2.9 g, 49%) as colorless oil. $^1$HNMR (400 MHz, $CDCl_3$) δ 7.41-7.29 (m, 10H), 6.50-6.47 (m, 3H), 5.02 (s, 4H), 3.83 (t, J=6.4 Hz, 2H), 2.79 (t, J=6.4 Hz, 2H).

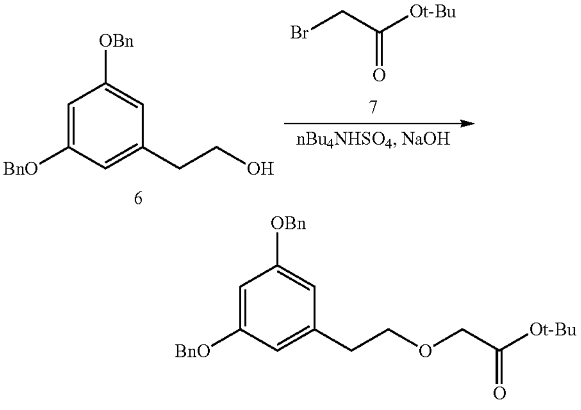

6 7 8

To a solution of compound 6 (4.1 g, 12.26 mmol), compound 7 (15.81 mL, 98.08 mmol) in Toluene (100 mL) was added aqueous NaOH (39.2 g, 980.83 mmol) in Water (40 mL) and $nBu_4NHSO_4$ (3.35 g, 9.81 mmol) at 20° C. The mixture was stirred at 20° C. for 3 hrs. TLC (20% ethyl acetate in petroleum ether, Rf=0.5) showed the start material was consumed. The reaction mixture was extracted with EtOAc (50 mL×3). The organic layer was combined, dried over anhydrous sodium sulfate and concentrated under vacuum, then purified by flash chromatography on silica (0-20% EtOAC in petroleum ether) to give compound 8 (4840 mg, 64%) as a white solid. LCMS (5-95, AB, 1.5 min): RT (220/254 nm)=1.064 min, m/z=471.0 $[M+23]^+$. $^1H$ NMR (400 MHz, $CDCl_3$): δ 7.42-7.30 (m, 10H), 6.50-6.47 (m, 3H), 5.00 (s, 4H), 3.94 (s, 2H), 3.72 (t, J=7.2 Hz, 2H), 2.88 (t, J=7.2 Hz, 2H), 1.46 (s, 9H).

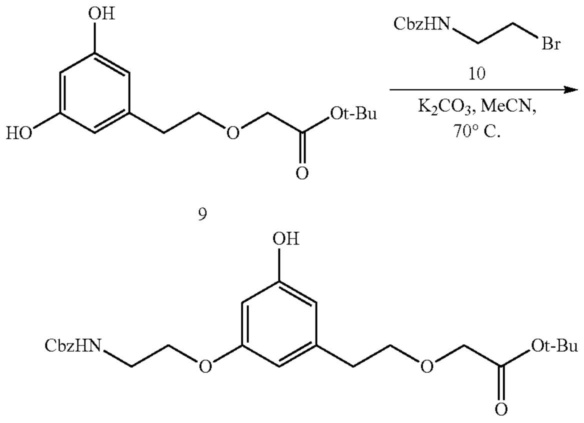

9

11

To a solution of compound 9 (2.60 g, 9.69 mmol) and compound 10 (2.50 g, 9.69 mmol) in Acetonitrile (80 mL) was added $K_2CO_3$ (2.14 g, 15.5 mmol) and KI (160.86 mg, 0.97 mmol). The mixture was stirred at 70° C. for 12 hrs. The mixture was diluted with EtOAc (250 mL) and washed with water (50 mL*3). The organic layer was concentrated and purified by Pre-HPLC (acetonitrile 25-70%/0.225% FA in water) to give Compound 3 (2.13 g, 49%) as a colorless oil. LCMS (5-95, AB, 1.5 min): RT (220/254 nm)=0.887 min, m/z=468.1 $[M+23]^+$.

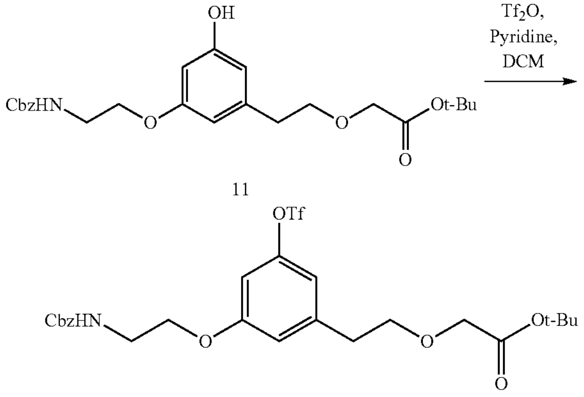

11

12

To a solution of Compound 11 (2.13 g, 4.78 mmol) and pyridine (1.93 mL, 23.91 mmol) in DCM (20 mL) was added $Tf_2O$ (1.61 mL, 9.56 mmol). The mixture was stirred at 20° C. for 1 h. The mixture was diluted with EtOAc (120 mL) and washed with citric acid (30 mL*3). The organic layer was concentrated to give the crude product 12, which was used for next step directly. LCMS (5-95, AB, 1.5 min): RT (220/254 nm)=1.066 min, m/z=600.3 $[M+23]^+$.

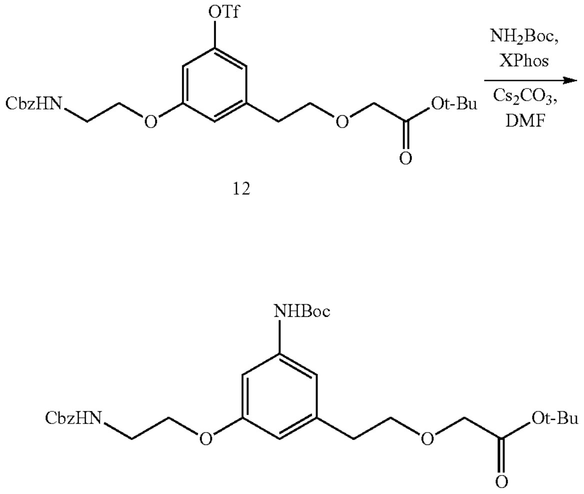

12

13

To a solution of Compound 12 (2.74 g, 23.37 mmol) in 1,4-Dioxane (50 mL) was added $Pd(OAc)_2$ (104.95 mg, 0.47 mmol), Xphos (445.71 mg, 0.93 mmol) and $Cs_2CO_3$ (4.57 g, 14.02 mmol). The mixture was stirred at 100° C. under $N_2$ for 12 h. The mixture was concentrated and purified by flash column (eluting 0-40% EtOAc in Petroleum ether) to give Compound 13 (2.20 g, 76%) as a white solid. LCMS (5-95, AB, 1.5 min): RT (220/254 nm)=0.971 min, m/z=567.1 $[M+23]^+$.

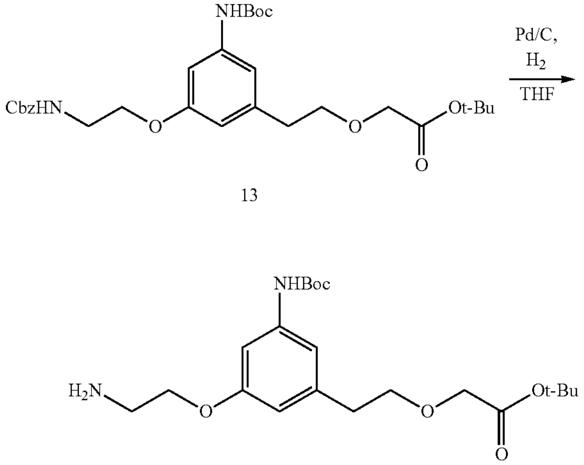

13

14

To a solution of Compound 13 (2.20 g, 4.04 mmol) in THF (80 mL) was added Pd/C (429.87 mg). The mixture was stirred at 20° C. under $H_2$ for 2 hrs. The mixture was filtered and concentrated to give the crude product 14, which was used for next step directly. LCMS (5-95, AB, 1.5 min): RT (220/254 nm)=0.773 min, m/z=411.1 [M+1]$^+$.

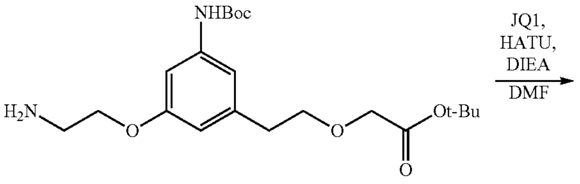

14

-continued

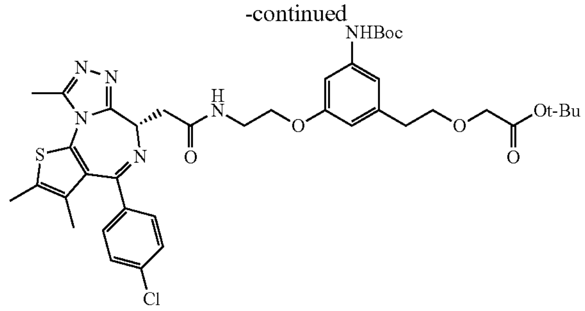

15

To a solution of JQ1 (2.20 g, 5.48 mmol), Compound 14 (1.50 g, 3.65 mmol) and HATU (1.81 g, 4.75 mmol) in DMF (20 mL) was added DIEA (2.55 mL, 14.62 mmol). The mixture was stirred at 20° C. for 1 h. The mixture was purified by reverse phase chromatography (acetonitrile 30-90/0.225% FA in water) to afford Compound 14 (1.13 g, 39%) as a yellow solid. LCMS (5-95, AB, 1.5 min): RT (220/254 nm)=0.969 min, m/z=815.0 [M+23]$^+$.

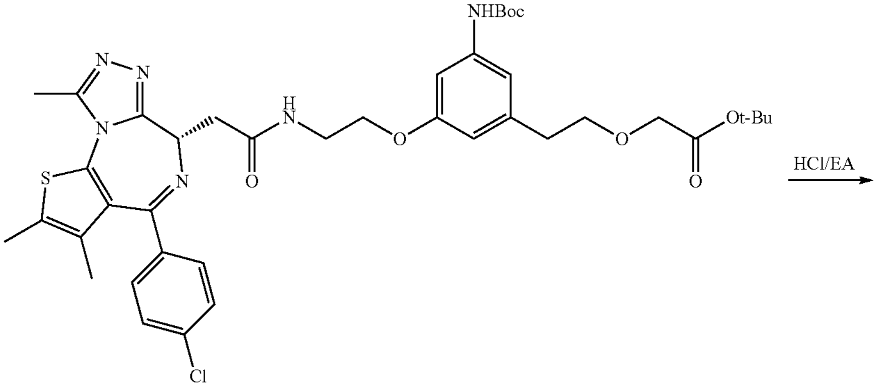

15

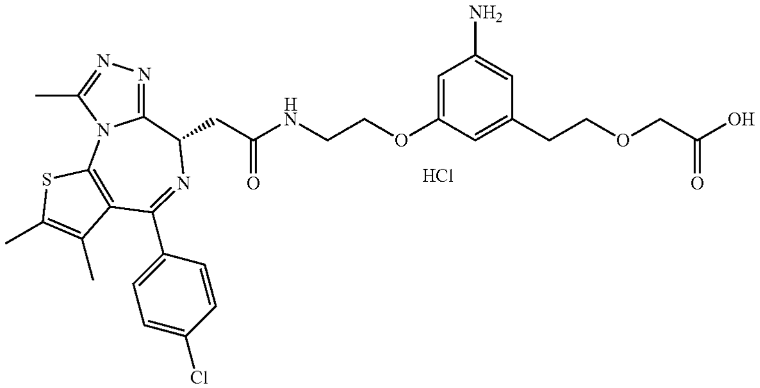

16

A mixture of Compound 15 (1.13 g, 1.42 mmol) in HCl/EtOAc (10 mL) was stirred at 20° C. for 1 h. The mixture was concentrated to give compound 16 (959 mg, 100%) as a white solid, which was used for next step directly. LCMS (5-95, AB, 1.5 min): RT (220/254 nm)=0.786 min, m/z=637.3 [M+1]$^+$.

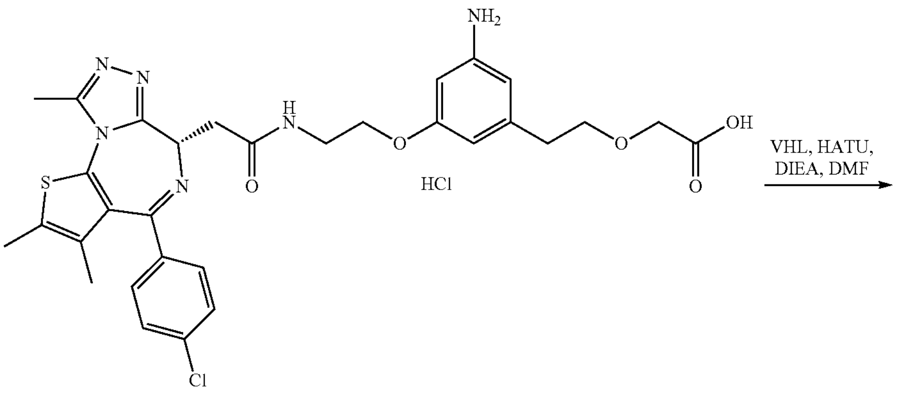

16

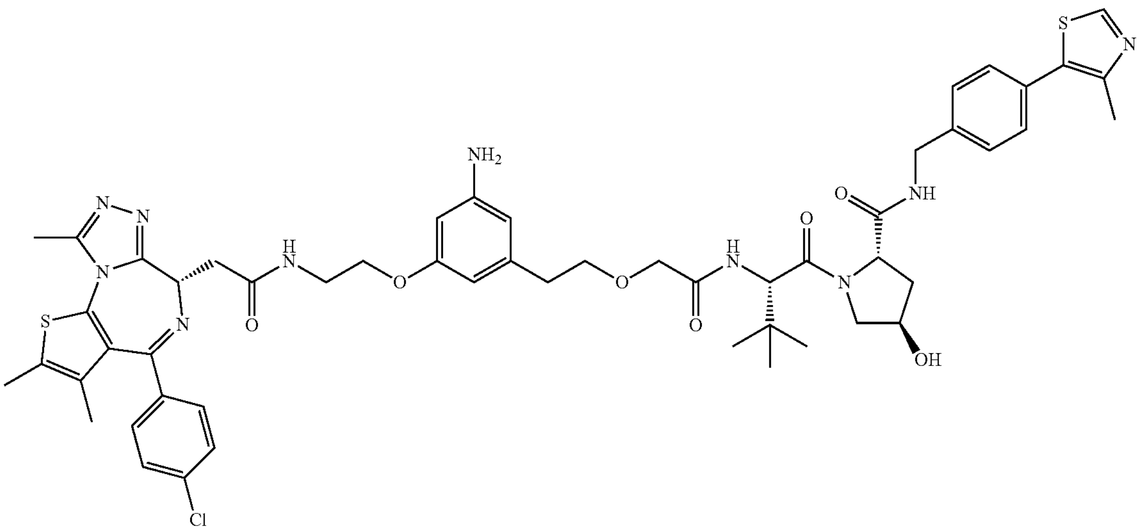

17

To a solution of Compound 16 (959 mg, 1.42 mmol), VHL (1287 mg, 2.99 mmol) and DIEA (919.98 mg, 7.12 mmol) in DMF (15 mL) was added HATU (595.46 mg, 1.57 mmol). The mixture was stirred at 20° C. for 1 h. The mixture was purified by reverse phase chromatography (acetonitrile 10-50/0.225% FA in water) to afford Compound 17 (1.10 g, 71.4%) as a yellow solid. LCMS (5-95, AB, 1.5 min): RT (220/254 nm)=0.817 min, m/z=1049.0 [M+1]$^+$.

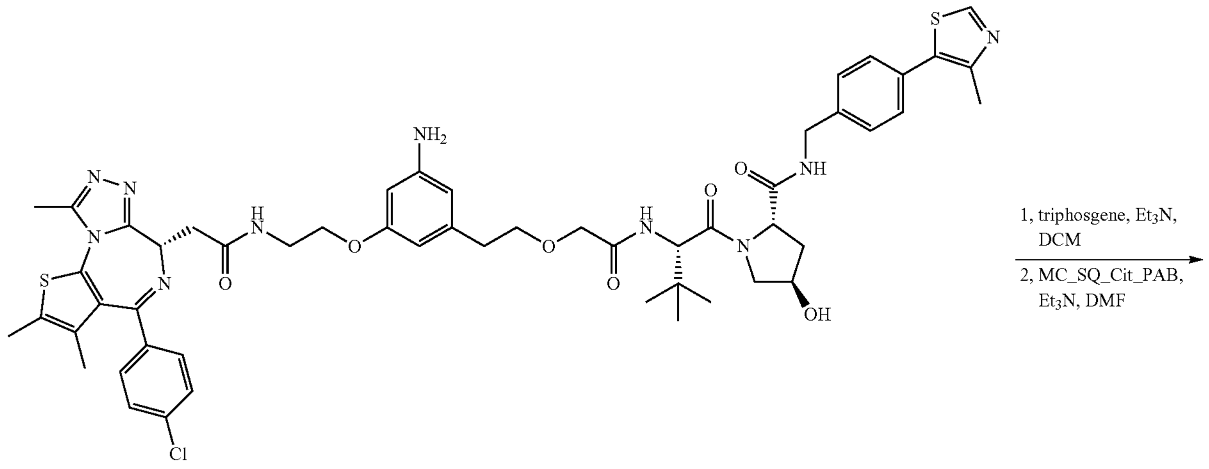

17

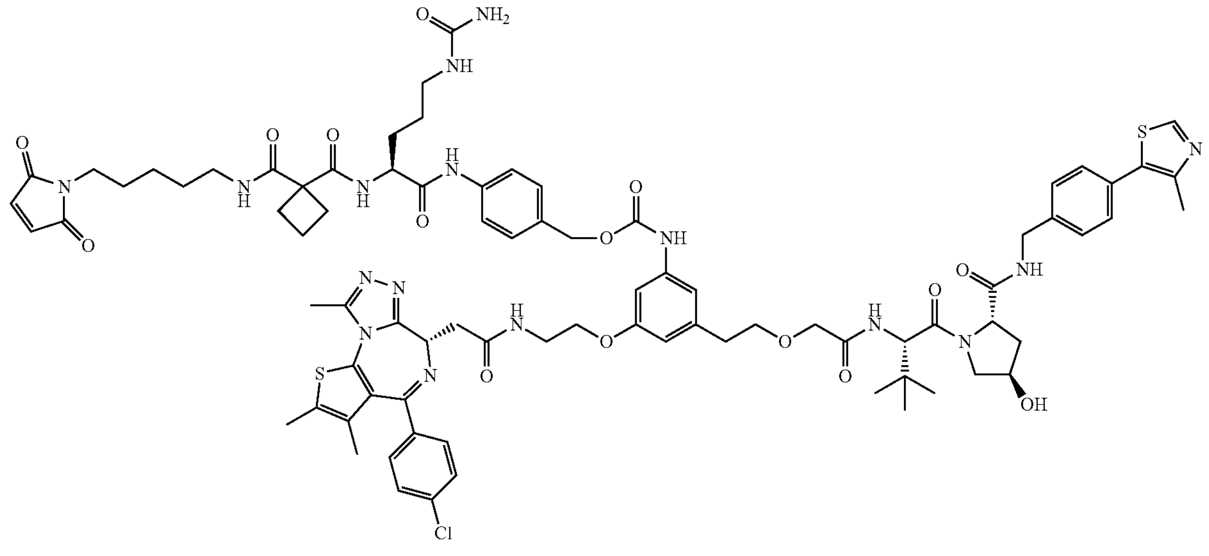

L1BQ1

To a mixture of Triphosgene (14.13 mg, 0.05 mmol) and 4A molecular sieve in DCM (2 mL) was added a solution Compound 17 (50.00 mg, 0.05 mmol) and $Et_3N$ (14.46 mg, 0.14 mmol) in DCM (2 mL). The mixture was stirred at 20° C. for 0.5 h. The mixture was concentrated and resolved in DCM (5 mL) and used for next step directly.

To above solution was added a solution of Compound MC_SQ_Cit_PAB (81.53 mg, 0.14 mmol) and $Et_3N$ (14.46 mg, 0.14 mmol) in DMF (2 mL). The mixture was stirred at 15° C. for 12 hrs. The mixture was concentrated and the resulting residue was purified by reverse phase chromatography (acetonitrile 38-68/0.225% FA in water) to give L1BQ1 (5.0 mg, 6%) as a white solid. LCMS (10-80, AB, 7.0 min): RT (220/254 nm)=3.928 min, m/z=824.5 $[M/2+1]^+$.

xx. L1BQ2 An exemplary L1-CIDE, L1BQ2, can be synthesized by the following scheme:
Scheme 22
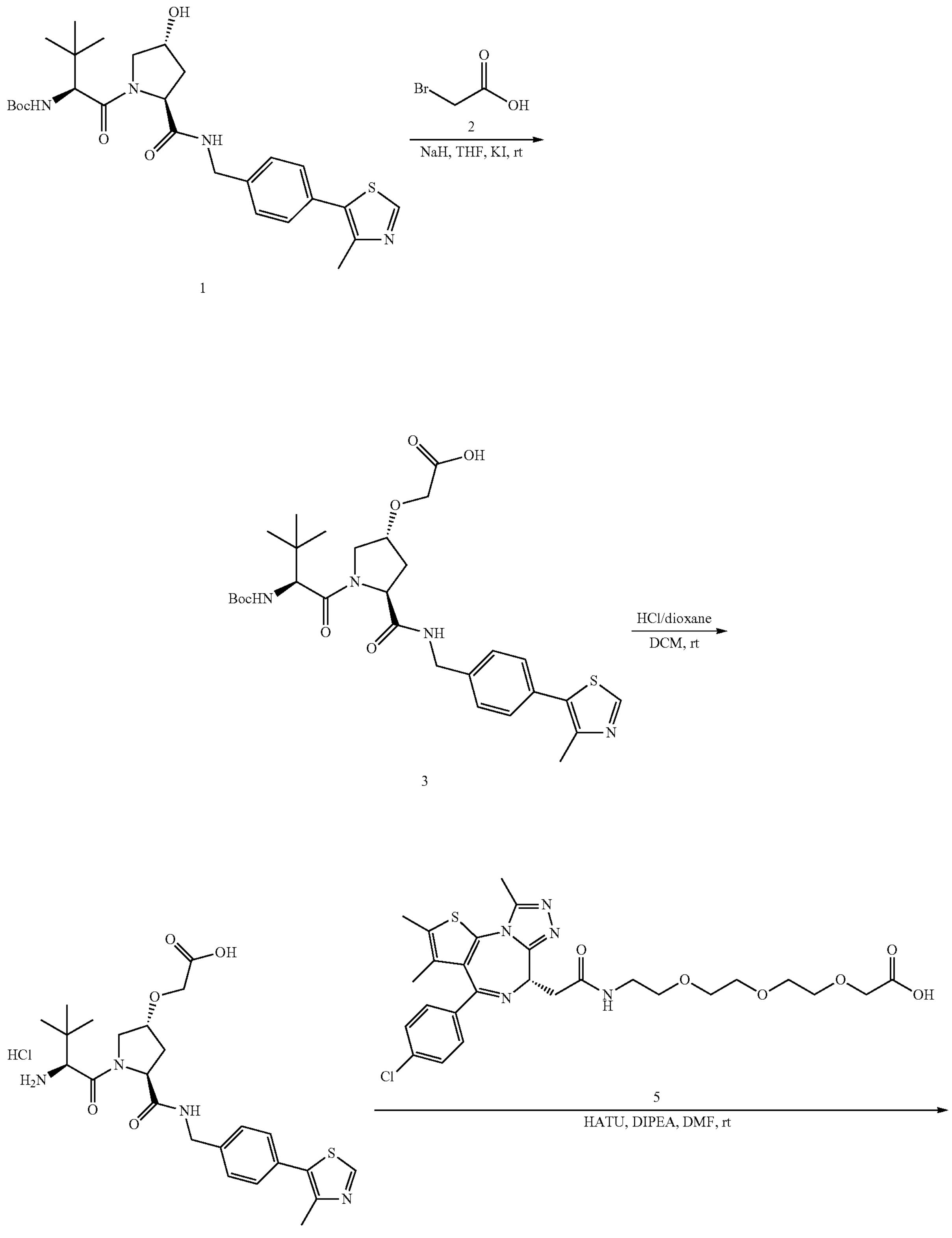
1
3
4

-continued

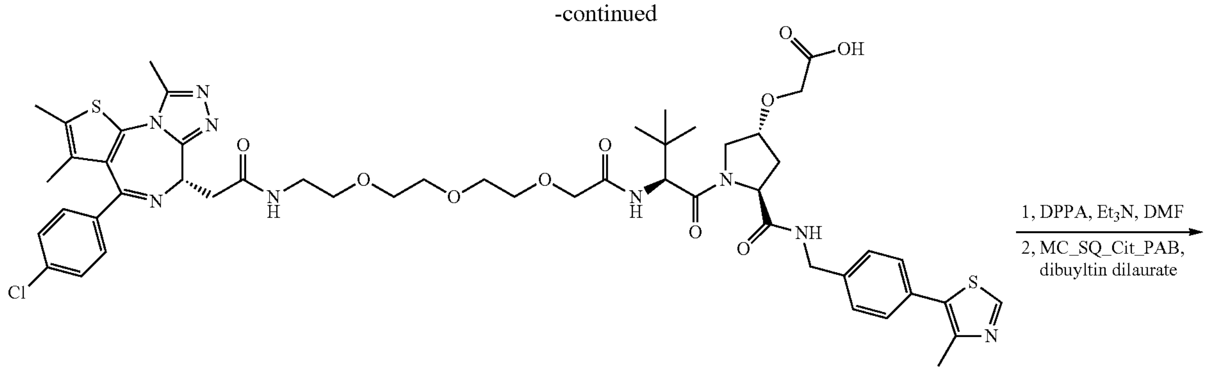

6

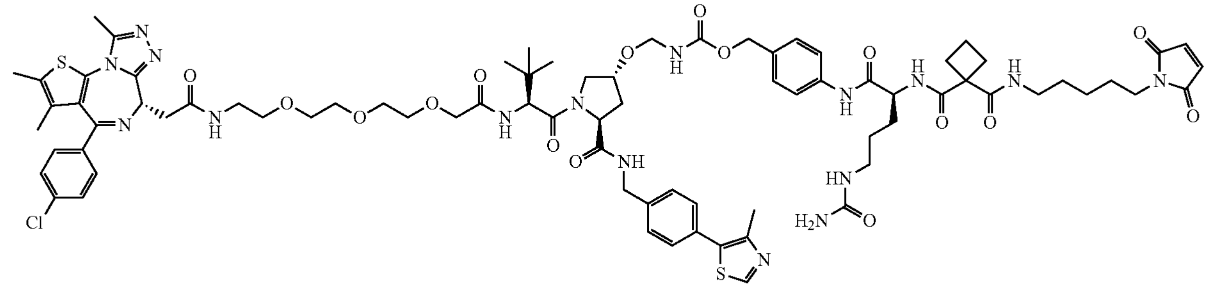

L1BQ2

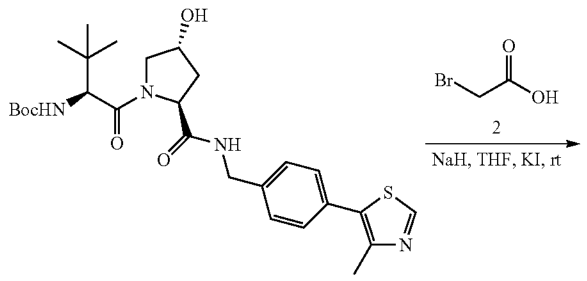

1

NaH (226.12 mg, 5.65 mmol) was suspended in THF (4.0 mL) and compound 1 (300.0 mg, 0.5700 mmol) in THF (3.0 mL) was added drop-wise at 20° C. The reaction mixture was stirred at 20° C. for 2 h. Then compound 2 (117.83 mg, 0.8500 mmol) in THF (3.0 mL) was added. After the reaction mixture was stirred at 20° C. for 2 h, it was quenched with water (10 mL) and extracted with EtOAc (10 mL). The aqueous layer was separated and acidified with HCl (2.0 M) to pH=3.0 and extracted with a MeOH solution in DCM (10 mL×2). The combined organic layers were dried and concentrated to give the crude product compound 3 (190 mg, 57%) as a brown oil, which was used directly in the next step. LCMS (5-95, AB, 1.5 min): RT=0.735 min, m/z=589.1 [M+1]$^+$.

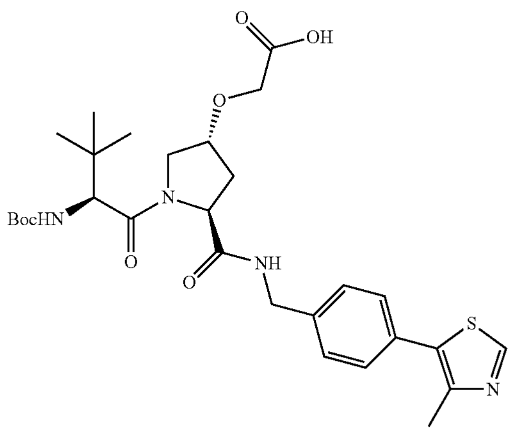

3

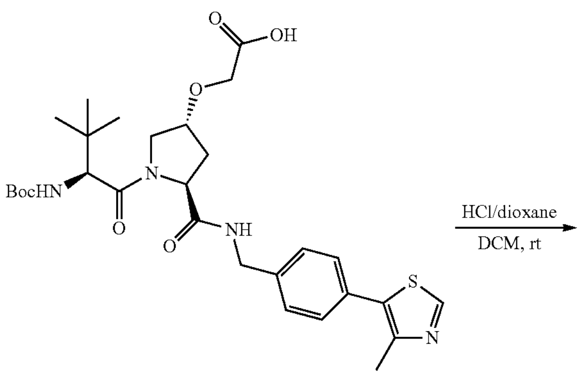

3

-continued
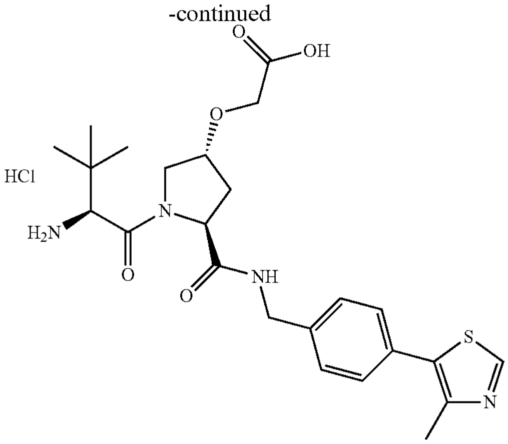
4
To a solution of compound 3 (190.0 mg, 0.3600 mmol) in DCM (5.0 mL) was added a solution of HCl in EtOAc (4.0 M, 5.0 mL). After the reaction mixture was stirred at 20° C. for 2 h, it was concentrated to give the crude product compound 4 (120 mg, 64%) as a gray solid, which was used directly in the next step.
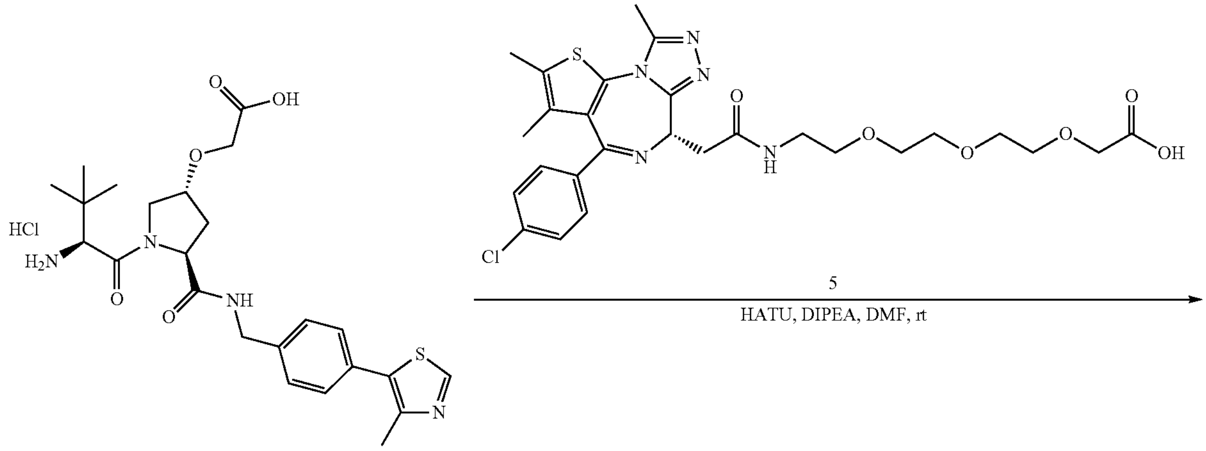
4
5
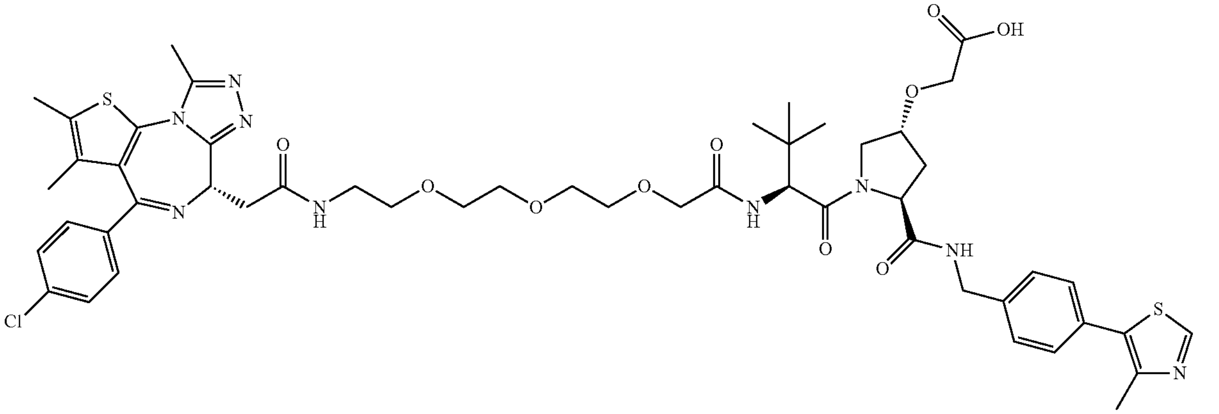
6

A solution of compound 5 (151.72 mg, 0.2600 mmol), DIEA (66.46 mg, 0.5100 mmol) and HATU (97.76 mg, 0.2600 mmol) in anhydrous DMF (3.0 mL) was stirred at 20° C. for 50 min, and then compound 4 (90.0 mg, 0.1700 mmol) was added. The resulted mixture was stirred at 20° C. for 2 h, filtered and the filtrate was purified by prep-HPLC (acetonitrile 40-60/0.225% FA in water) to afford compound 6 (35 mg, 19.3%) as a gray solid. LCMS (5-95, AB, 1.5 min): RT=0.881 min, m/z=1060.7 $[M+1]^+$.

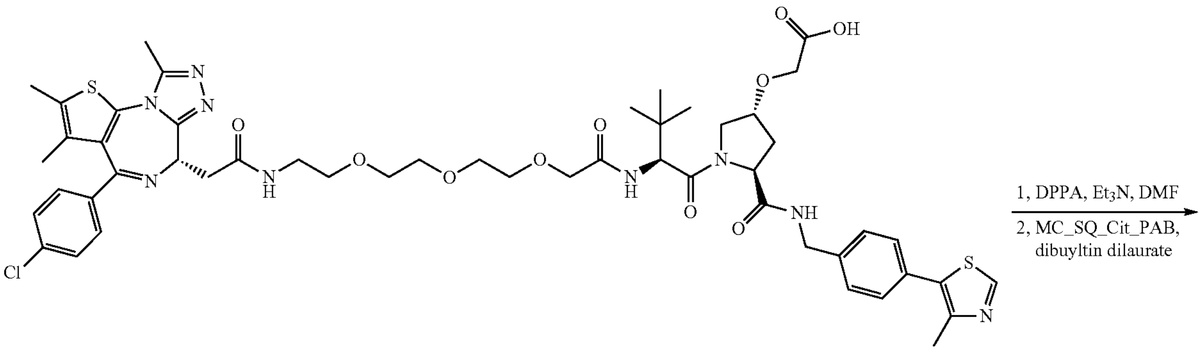

6

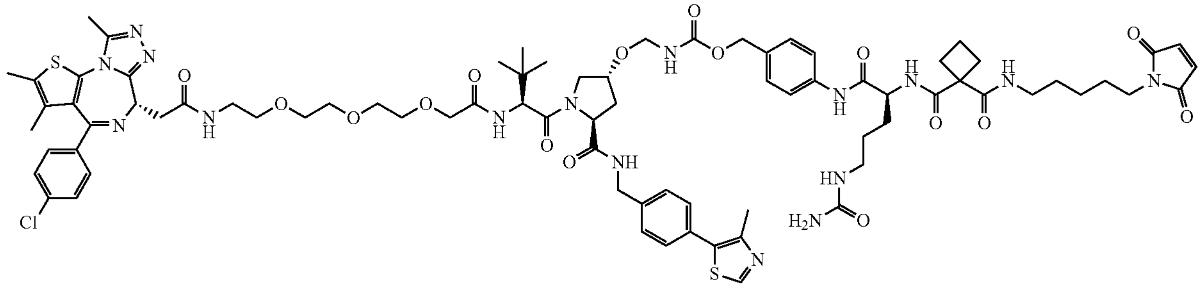

L1BQ2

To a solution of compound 6 (30.0 mg, 0.0300 mmol) and DPPA (11.68 mg, 0.0400 mmol) in DMF (2.0 mL) was added $Et_3N$ (8.59 mg, 0.0800 mmol). After the mixture was stirred at 20° C. for 1 h, it was diluted with water (5.0 mL) and extracted with toluene (3 mL×2). The toluene layer was dried over $Na_2SO_4$, and dried with 4A molecular sieves. To a solution in toluene (6.0 mL) was added compound 8 (15.77 mg, 0.0300 mmol) in DMF (1.0 mL), dibutyltin dilaurate (1.75 mg, 0.0028 mmol), and the mixture stirred at 80° C. for 1 h. The reaction mixture was filtered, concentrated, and purified by prep-TLC (10% of MeOH in DCM, Rf=0.3) to afford L1BQ2 (2.5 mg, 5.6%) as a gray solid. LCMS (5-95, AB, 1.5 min): RT=0.755 min, m/z=815.1 $[M/2+1]^+$.

xxi. L1BQ3 An exemplary L1-CIDE, L1BQ3, can be synthesized by the following scheme:

Scheme 23

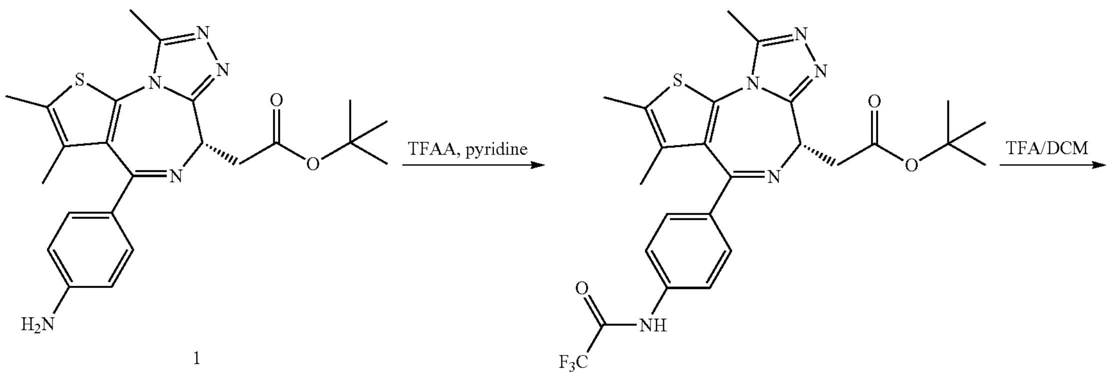

1

2

-continued
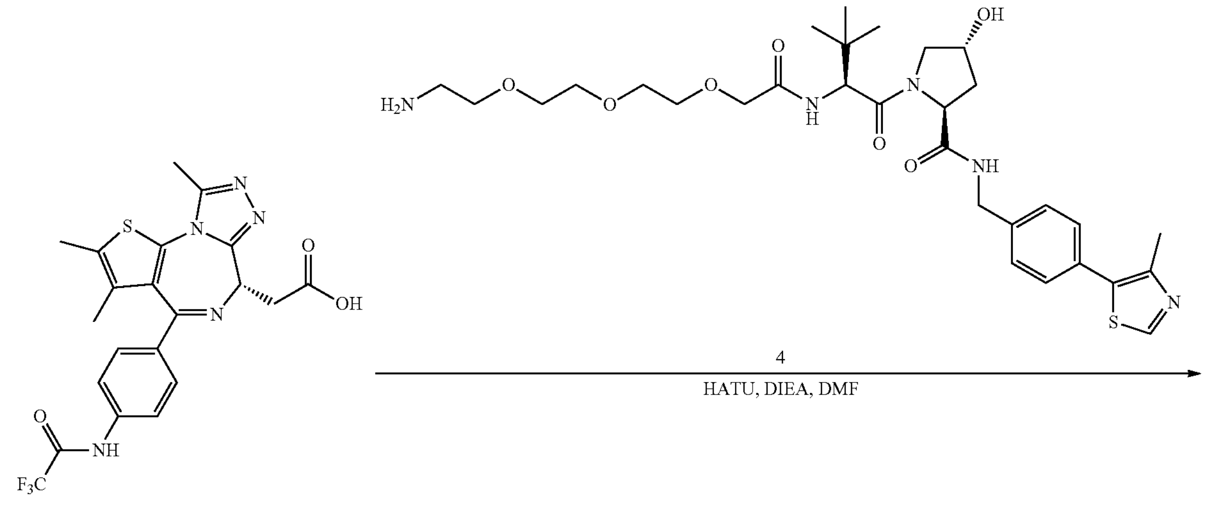
3
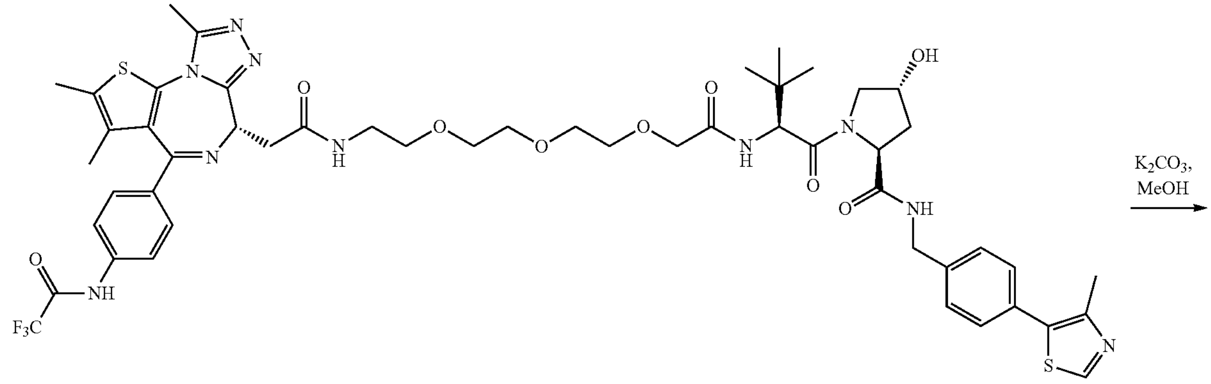
5
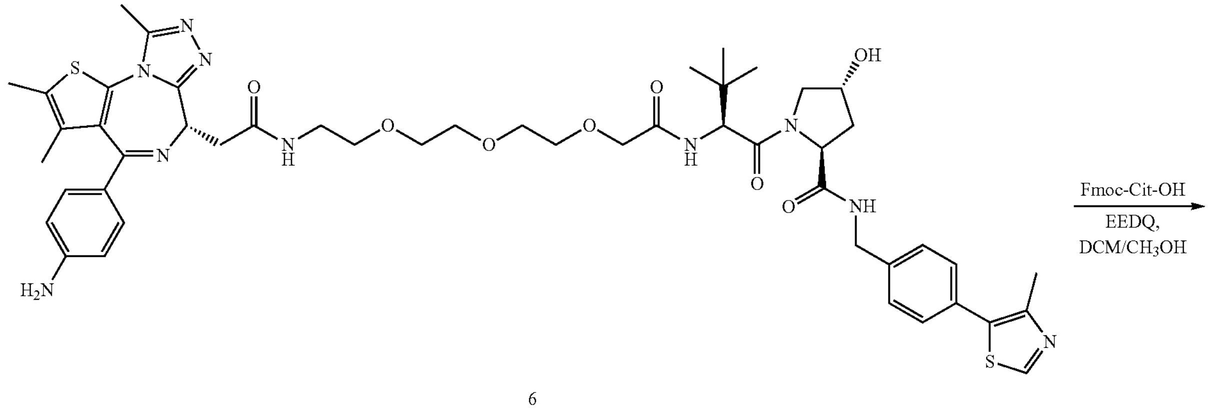
6

-continued
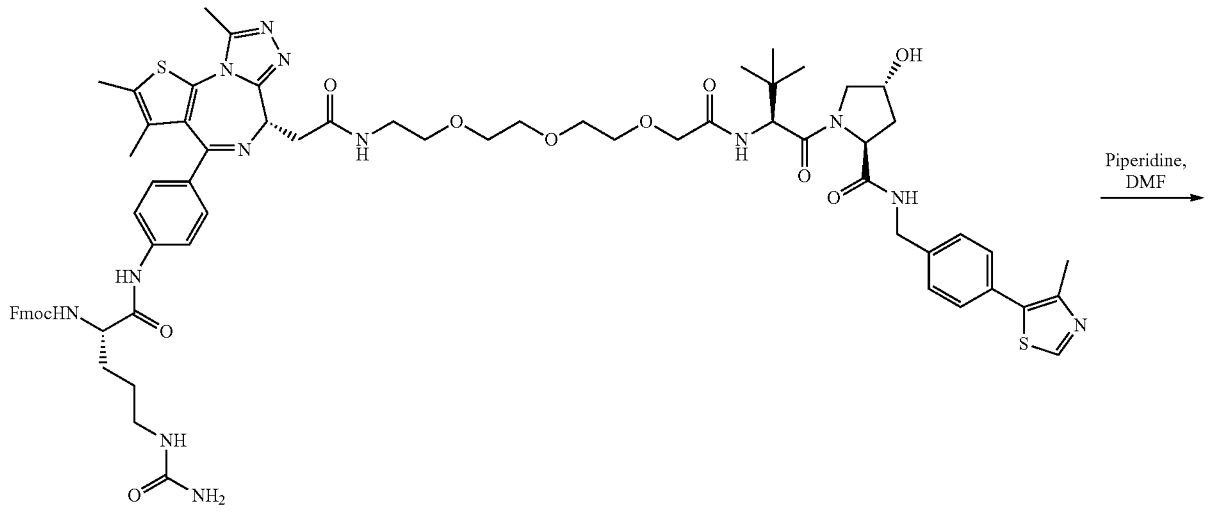
7
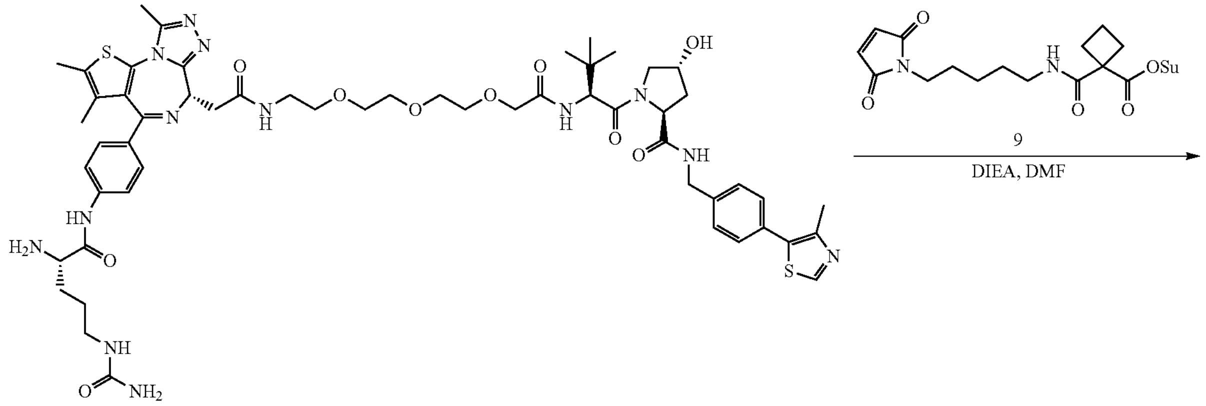
8
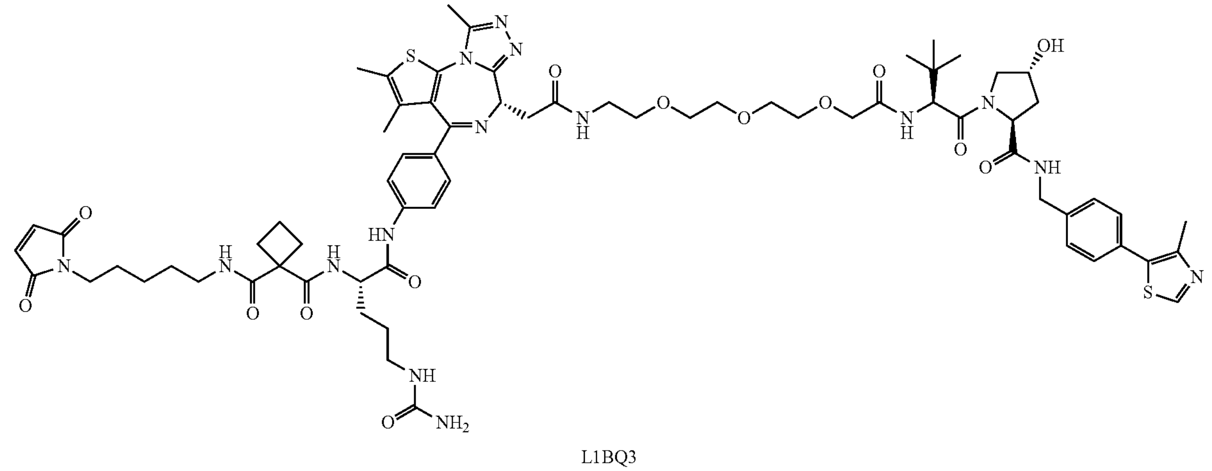 [SMILES: Cc1ncsc1-c1ccc(CNC(=O)[C@@H]2C[C@@H](O)CN2C(=O)[C@@H](NC(=O)COCCOCCOCCNC(=O)C[C@@H]2N=C(c3ccc(NC(=O)[C@H](CCCNC(N)=O)NC(=O)C4(C(=O)NCCCCCN5C(=O)C=CC5=O)CCC4)cc3)c3c(sc(C)c3C)-n3c(C)nnc32)C(C)(C)C)cc1]
L1BQ3

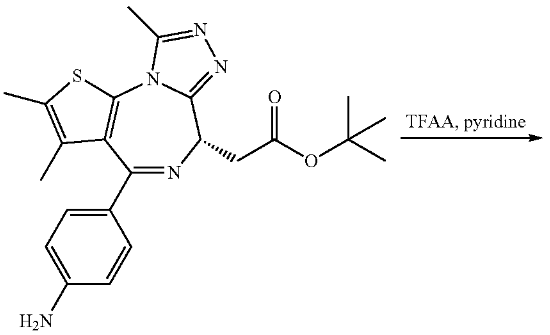

1

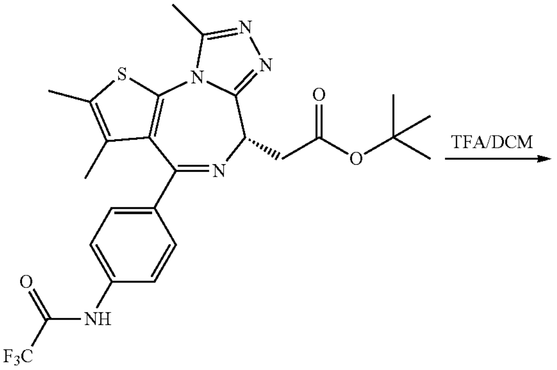

2

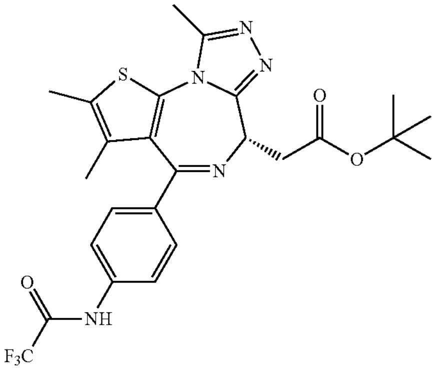

2

To a solution of compound 1 (100.0 mg, 0.230 mmol) in pyridine (10.0 mL) was added TFAA (144.0 mg, 0.6900 mmol). The reaction mixture was stirred at 50° C. for 12 h. The reaction diluted with EtOAc (20 mL) and washed with water (20 mL×2) and brine (20 mL). The organics were dried over $Na_2SO_4$, filtered and concentrated and purified by prep-TLC (500 MeOH in DCM, Rf=0.3) to afford compound 2 (65 mg, 52%) as a yellow solid. LCMS (5-95, AB, 1.5 min): RT (220/254 nm)=0.752 min, m/z=534.2 $[M+1]^+$.

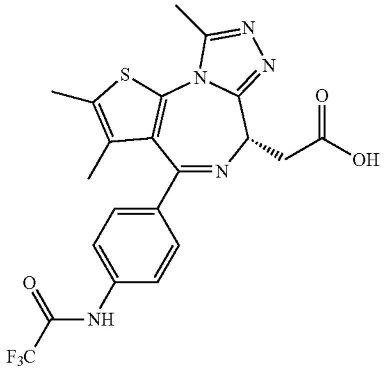

3

A solution of compound 2 (65.0 mg, 0.1200 mmol) in TFA (5 mL)/DCM (5 mL) was stirred at 25° C. for 0.5 h. The reaction mixture was concentrated to give compound 3 (55 mg, 95%) as a yellow solid, which was used directly in the next step.

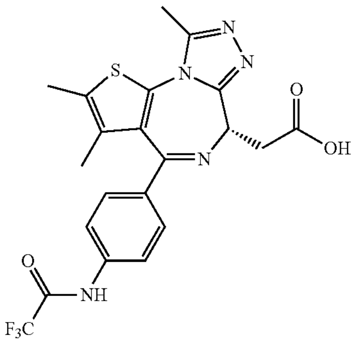

3

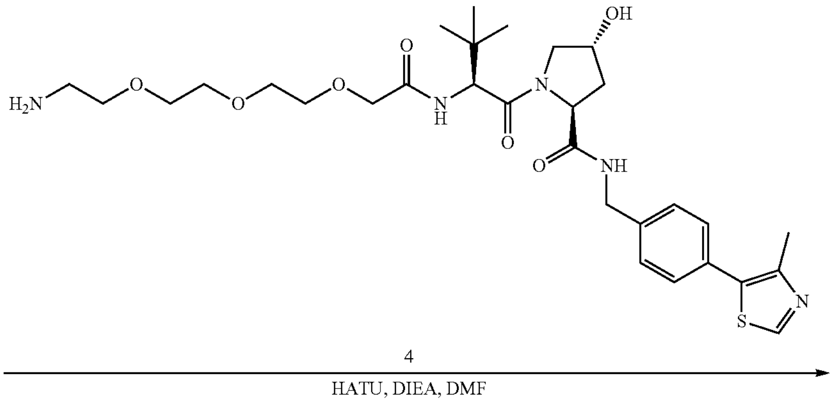

4

-continued

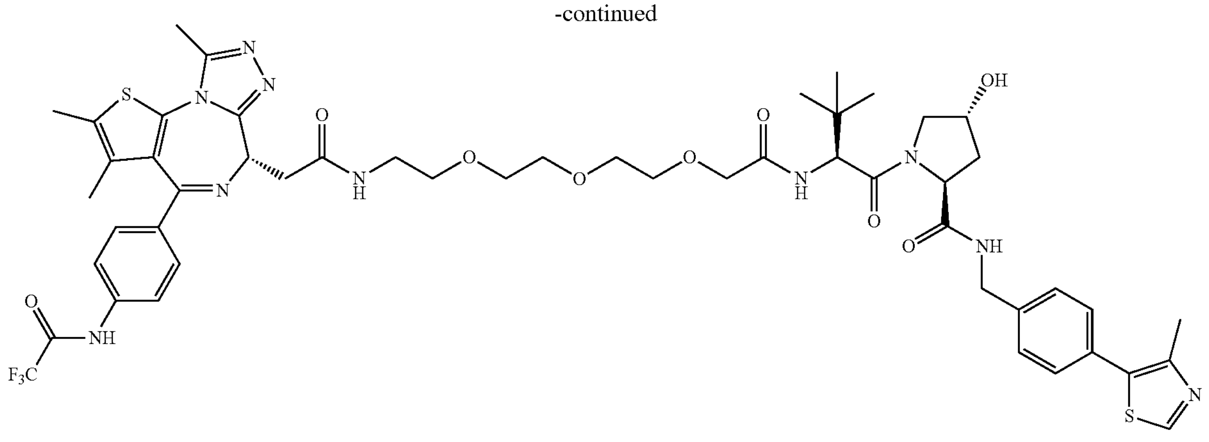

5

To a solution of compound 3 (55.0 mg, 0.1200 mmol) in DMF (5.0 mL) was added HATU (87.6 mg, 0.2300 mmol) and DIEA (44.66 mg, 0.3500 mmol) at 20° C. After the reaction mixture was stirred at 20° C. for 10 min, compound 4 (80.0 mg, 0.1300 mmol) was added. The reaction mixture was stirred at 20° C. for 2 h. The reaction mixture was diluted with water (10 mL), extracted with EtOAc (10 mL×3), dried over $Na_2SO_4$, filtered and concentrated. It was purified by prep-TLC (10% MeOH in DCM, Rf=0.3) to afford compound 5 (100 mg, 73%) as a yellow solid. LCMS (5-95, AB, 1.5 min): RT (220/254 nm)=0.684 min, m/z=1101.6 $[M+23]^+$.

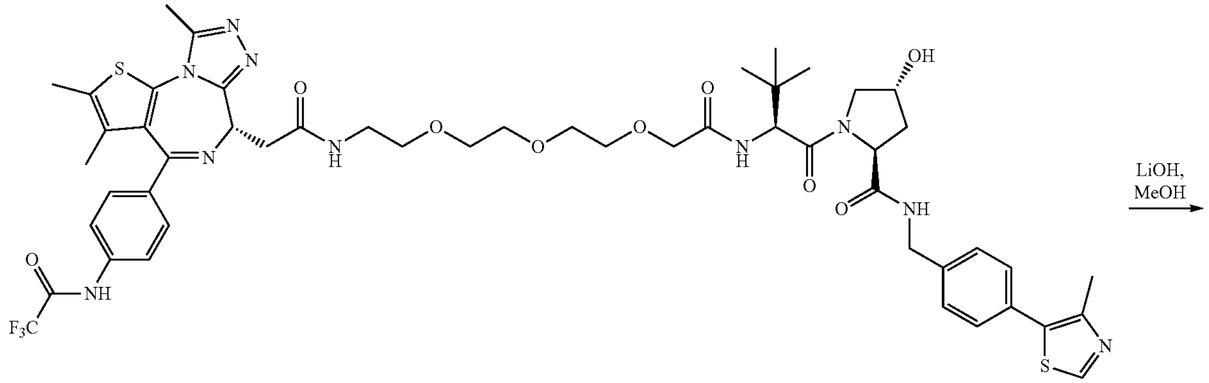

5

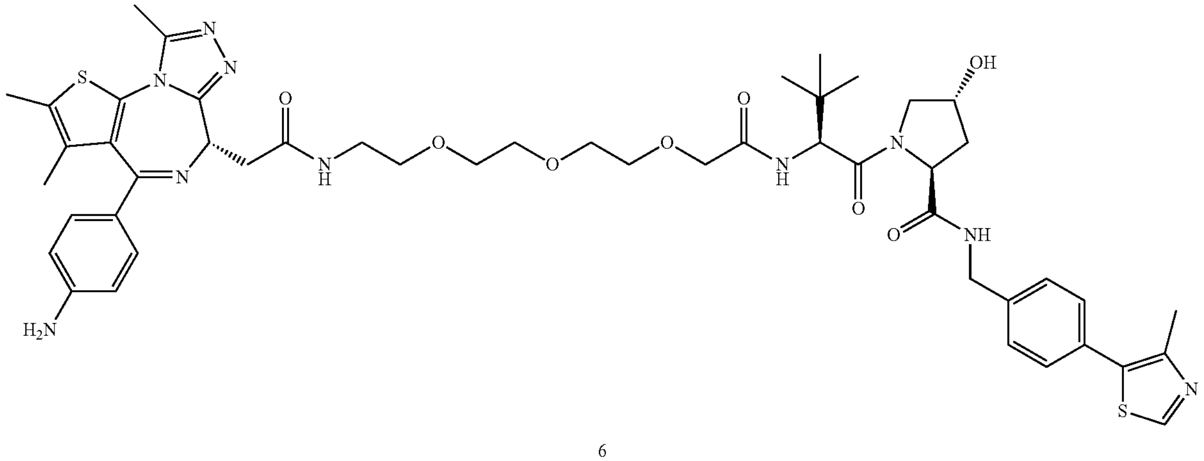

6

To a solution of compound 5 (100.0 mg, 0.0900 mmol) in MeOH (4.0 mL), THF (2.0 mL) was added LiOH (19.44 mg, 0.4600 mmol). The reaction mixture was stirred at 50° C. for 12 h. The reaction was concentrated and purified by prep-HPLC (acetonitrile 20-50%/0.225% EA in ACN) to afford compound 6 (40 mg, 44%) as a yellow solid, which was used directly in the next step. LCMS (5-95, AB, 1.5 min): RT (220/254 nm)=0.591 min, m/z=1105.6 [M+23]$^+$.

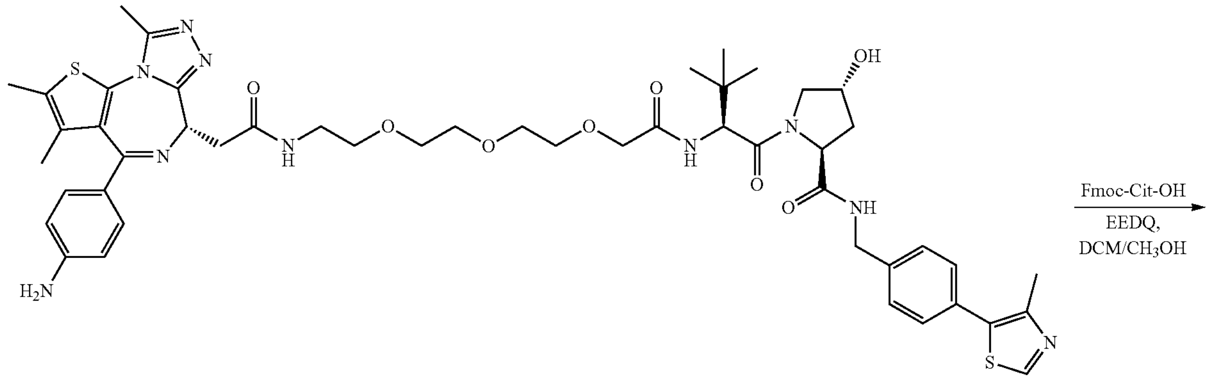

6

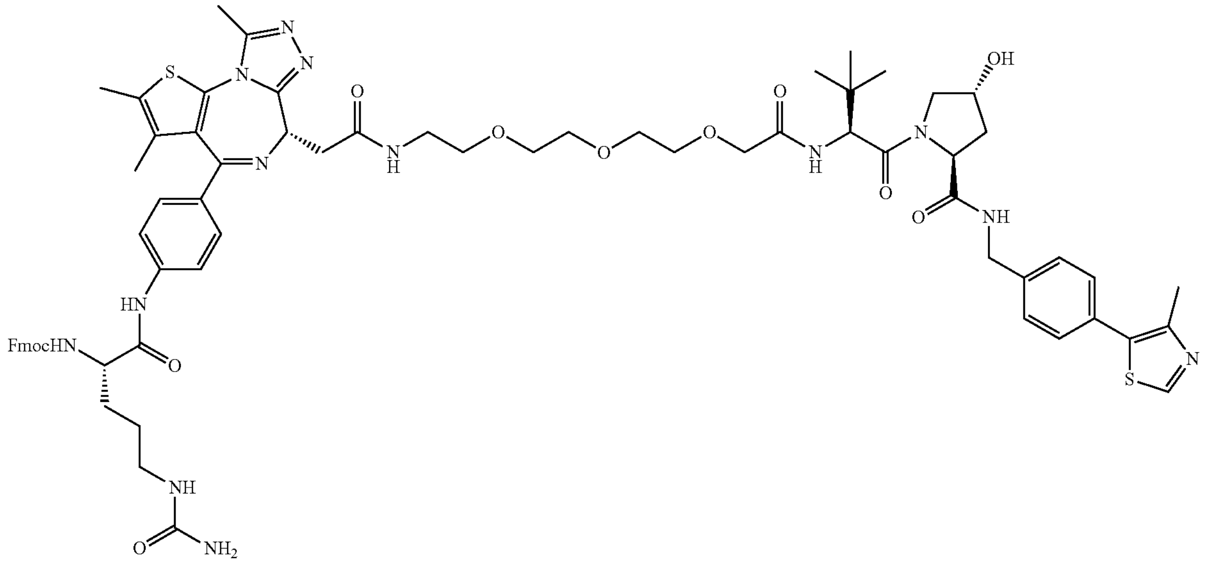

7

A mixture of Fmoc-Cit-OH (18.19 mg, 0.0500 mmol) and EEDQ (15.09 mg, 0.0600 mmol) in DMF (2.0 mL) was stirred at 25° C. for 30 min. The mixture was added to a solution of compound 6 (15.0 mg, 0.0200 mmol) in DMF (2.0 mL). The reaction mixture was stirred at 25° C. for 48 h. The mixture was filtered and the filtrate was purified by prep-HLC (acetonitrile 33-63/0.225% FA in water) to give the compound 7 (10 mg, 48%) as a white solid. LCMS (10-80, AB, 7.0 min): RT=3.695 min, m/z=682.1 [M/2+1]$^+$.

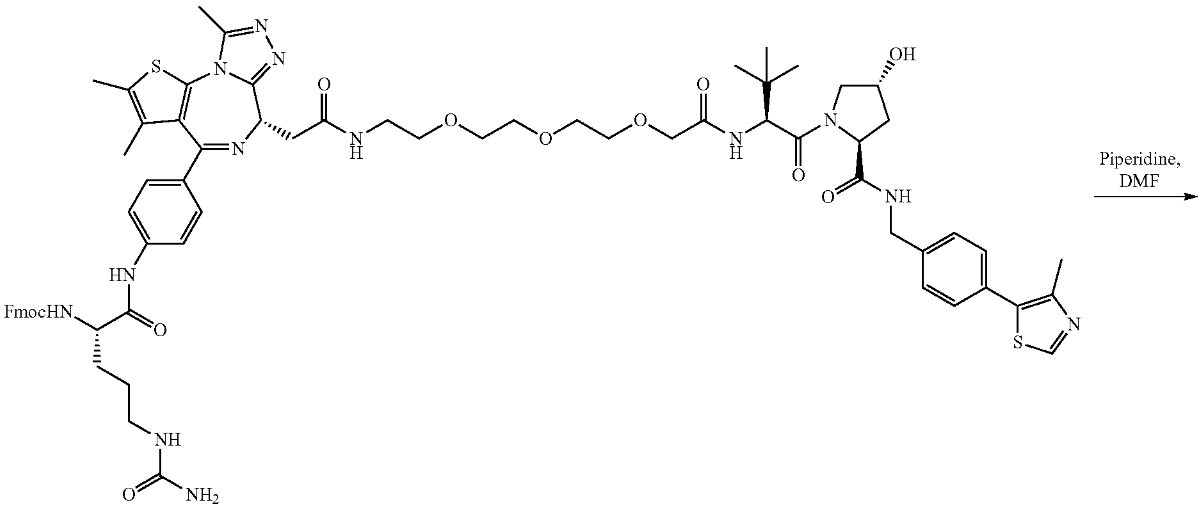
7
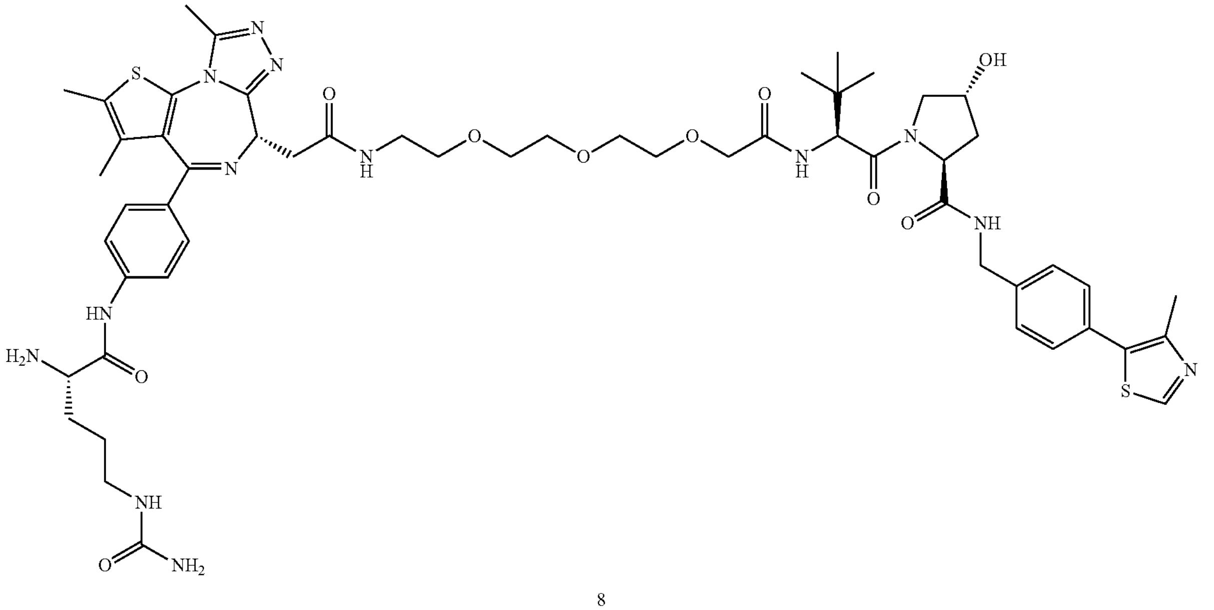
8
To a solution of compound 7 (10.0 mg, 0.0100 mmol) in DMF (2.0 mL) was added piperidine (2.5 mg, 0.0300 mmol) at 25° C. The reaction mixture was stirred at 25° C. for 2 h. The mixture was concentrated, washed with MTBE (2 mL×2) to give the compound 8 (8 mg, 95.6%) as a gray solid, which was used directly. LCMS (5-95, AB, 1.5 min): RT=0.611 min, m/z=571.1[M/2+1]$^+$.

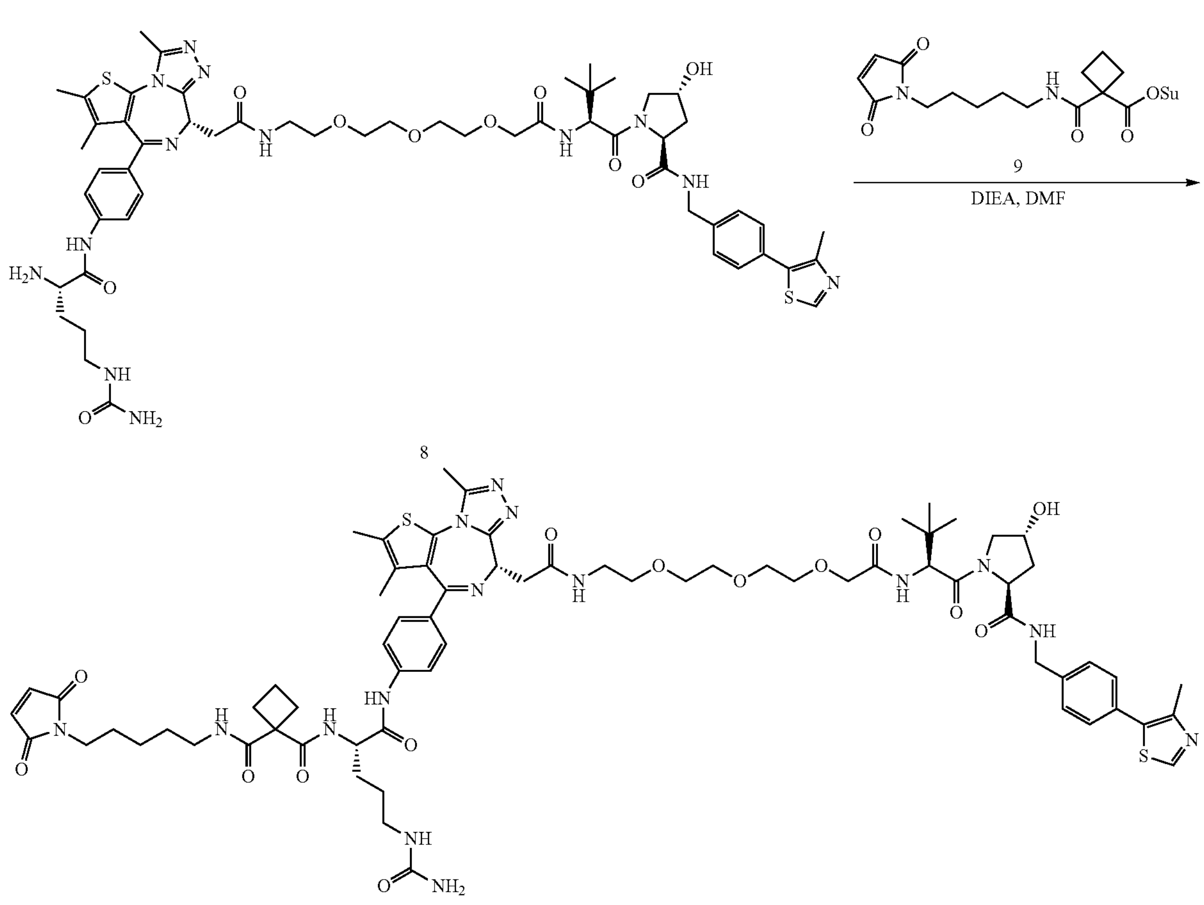

8

LABQ3

To a solution of DIEA (0.95 mg, 0.0100 mmol) and compound 8 (10.0 mg, 0.0100 mmol) in DMF (2.0 mL) was added compound 9 (11.9 mg, 0.0300 mmol). The reaction mixture was stirred at 20° C. for 12 h. The mixture was filtered and the filtrate was purified by prep-HPLC (acetonitrile 31-51/0.225% FA in water) to give L1BQ3 (2.5 mg, 23.6%) as a white solid. LCMS (5-95, AB, 1.5 min): RT=0.663 min, m/z=716.3[M/2+1]$^+$.

xxii. L1BQ4 An exemplary L1-CIDE, L1BQ4, can be synthesized by the following

Scheme 24

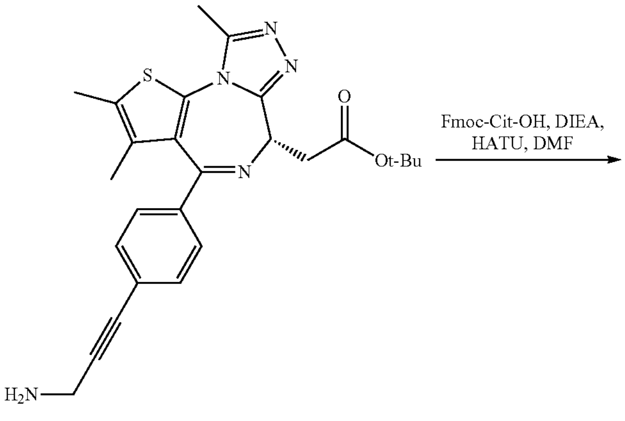

1
GNT_C439_22

-continued
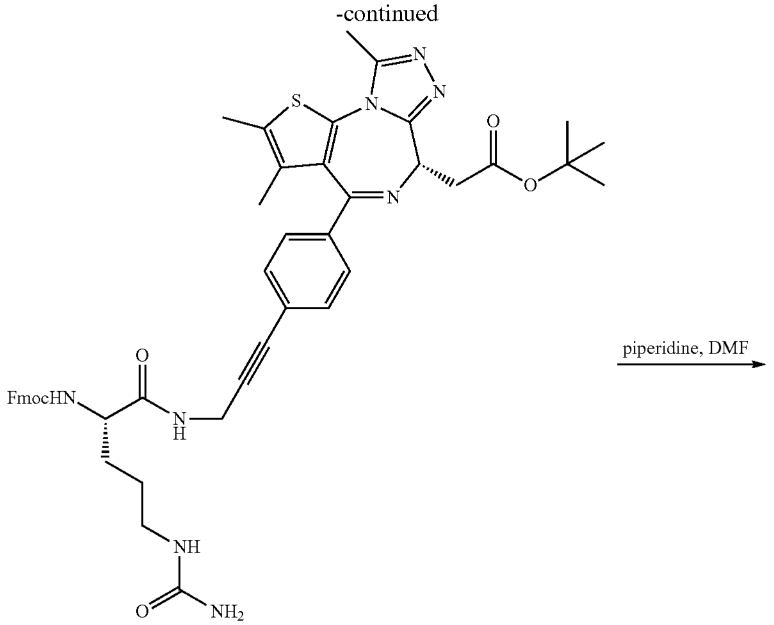
2
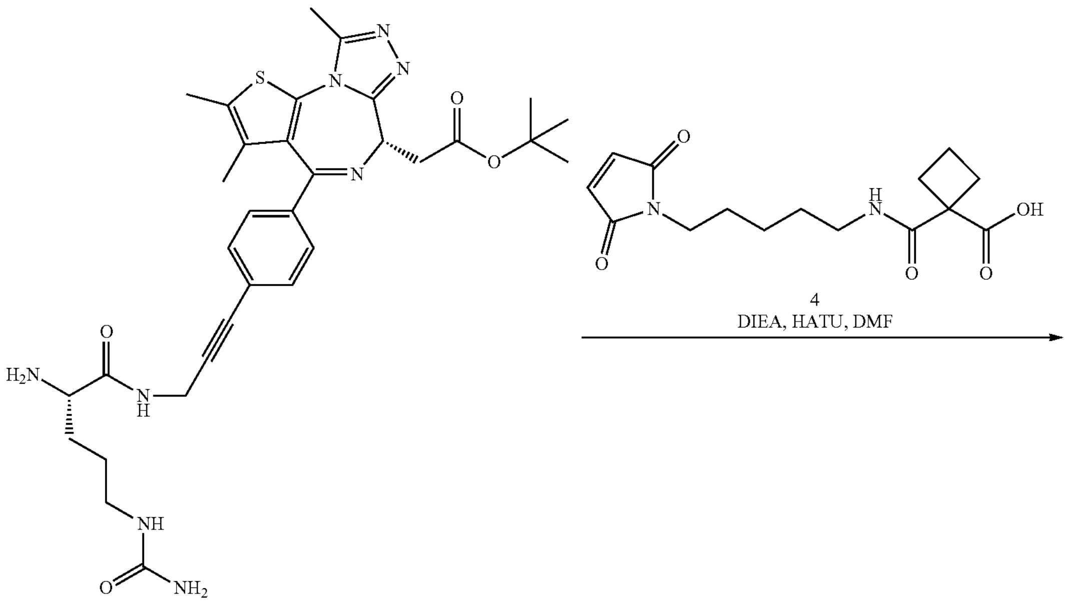
3

-continued
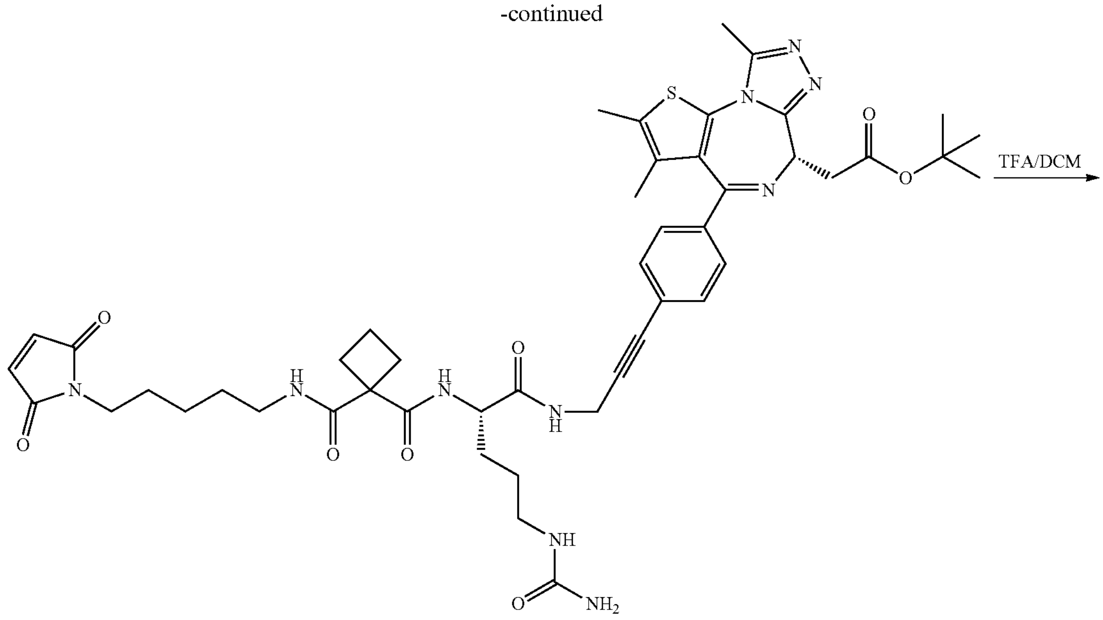
5
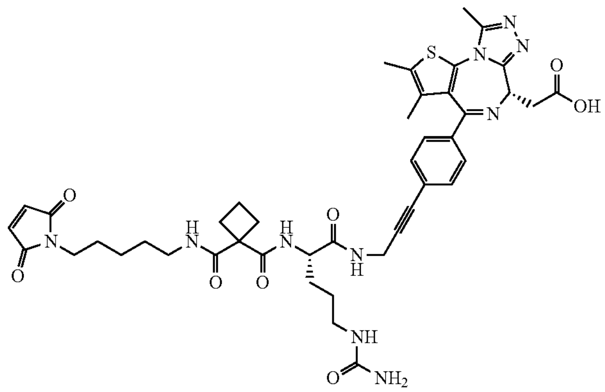
6
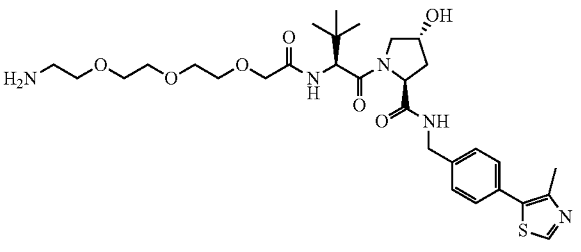
7
DIEA, HATU, DMF
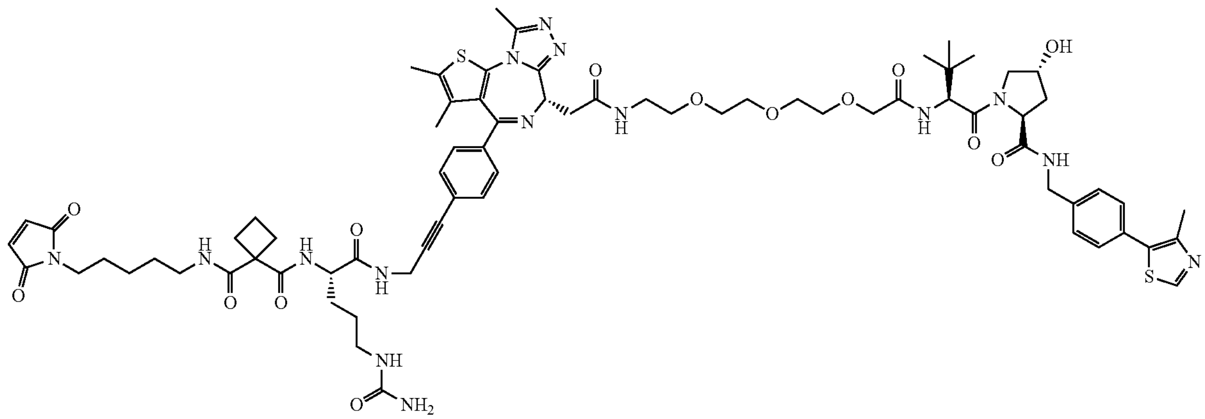
L1BQ4

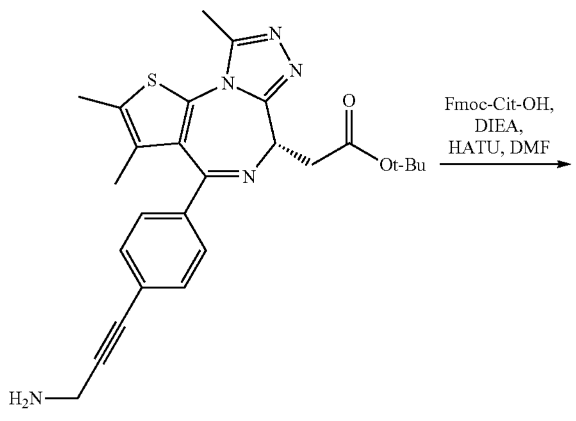

1

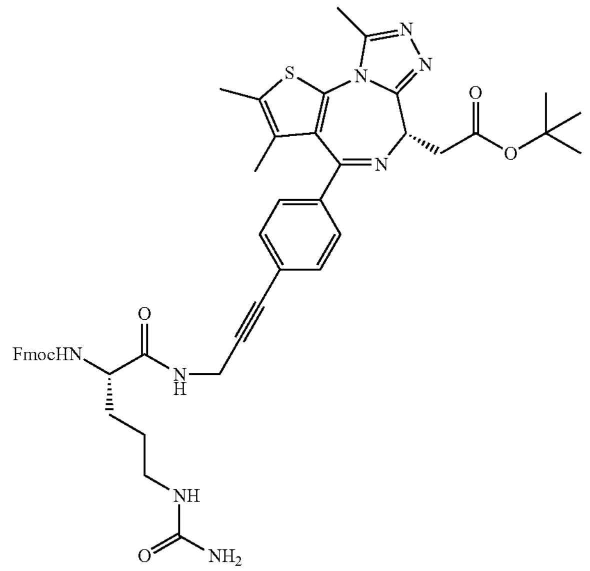

2

To a solution of Fmoc-Cit-OH (30.08 mg, 0.0800 mmol) in DMF (10.0 mL) was added HATU (47.97 mg, 0.1300 mmol) and DIEA (20.38 mg, 0.1600 mmol) at 20° C. The reaction mixture was stirred at 20° C. for 10 min. Then Compound 1 (30.0 mg, 0.0600 mmol) was added. After the reaction mixture was stirred at 20° C. for 12 h, it was diluted with water (10 mL), extracted with EtOAc (10 mL). The organic layer was washed with water (10 mL×2), brine (10 mL), dried over $Na_2SO_4$, filtered and concentrated. It was purified by prep-TLC (10% MeOH in DCM, $R_f$=0.4) to afford Compound 2 (45 mg, 78.4%) as a yellow solid. LCMS (5-95, AB, 1.5 min): RT (220/254 nm)=0.885 min, m/z=877.1 $[M+23]^+$.

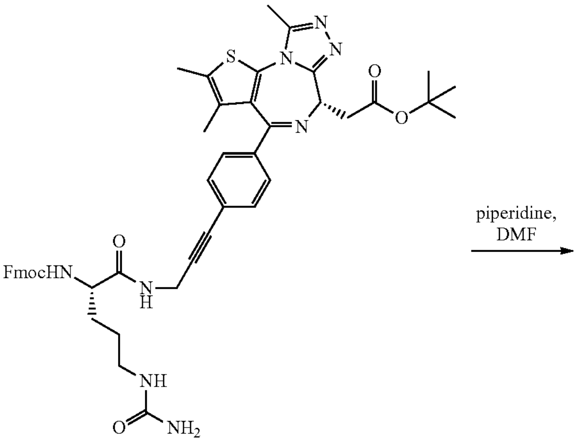

2

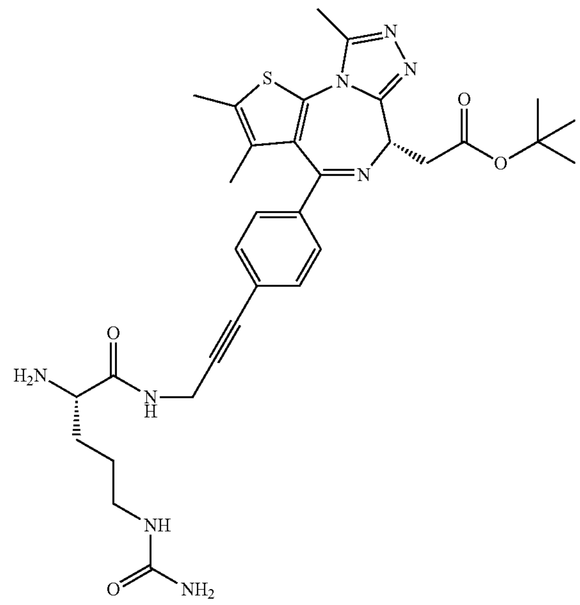

3

To solution of Compound 2 (45.0 mg, 0.0500 mmol) in DMF (5.0 mL) at 20° C. was added piperidine (0.02 mL, 0.1600 mmol). The mixture was stirred at 20° C. for 2 h, and concentrated to give Compound 3 (33 mg, 99.1%) as a yellow solid, which was used directly in the next step. LCMS (5-95, AB, 1.5 min): RT (220/254 nm)=0.742 min, m/z=655.1 $[M+23]^+$.

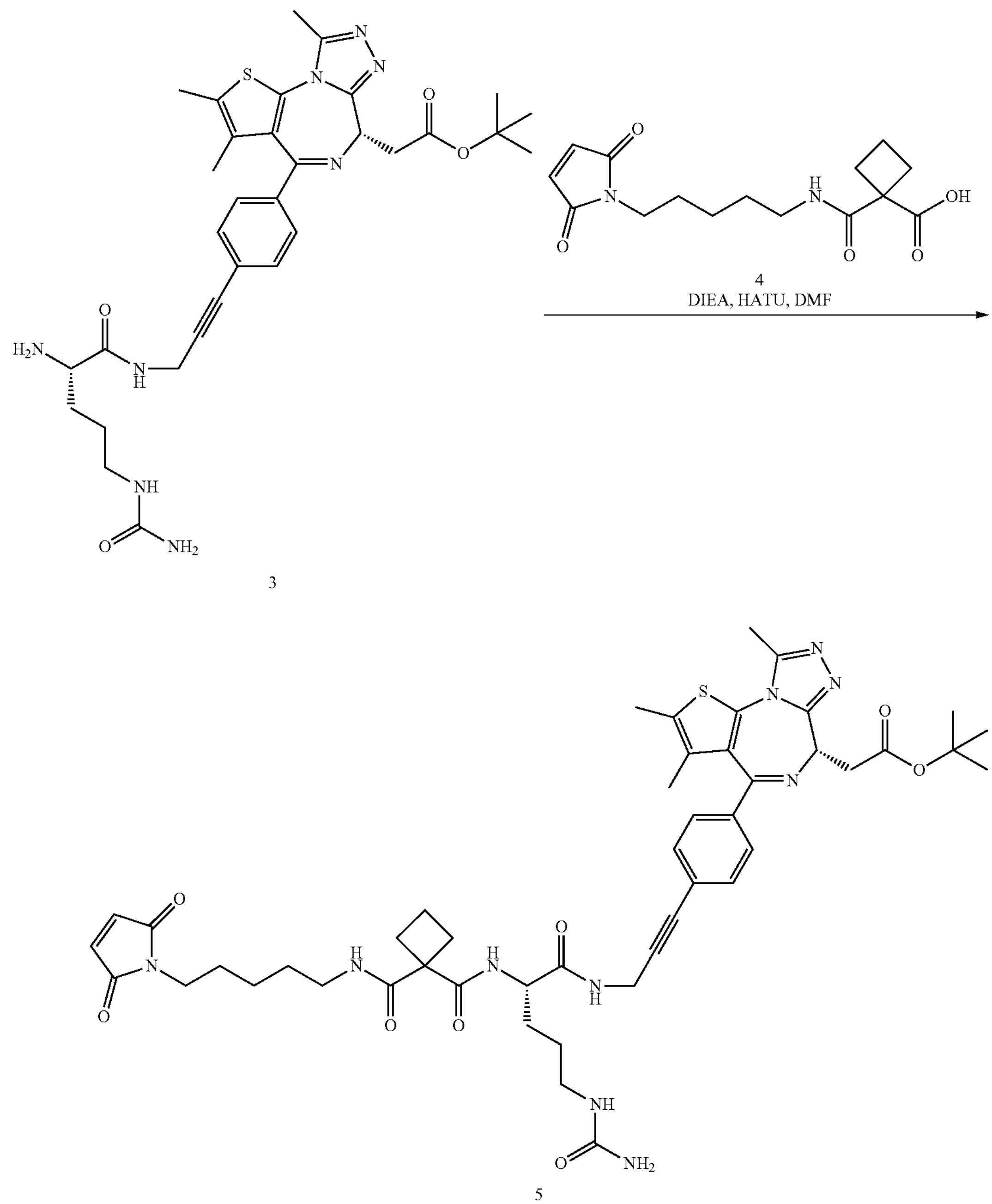

3

5

To a solution of Compound 4 (19.3 mg, 0.0600 mmol) in DMF (2.0 mL) was added HATU (39.66 mg, 0.1000 mmol) and DIEA (20.22 mg, 0.1600 mmol) at 20° C. The reaction mixture was stirred at 20° C. for 10 min. Then Compound 3 (33.0 mg, 0.0500 mmol) was added. The reaction mixture was stirred at 20° C. for 12 h. The reaction was quenched with water (10 mL), extracted with EtOAc (10 mL). The organic layer was washed with water (5 mL×2), brine (5 mL), dried over $Na_2SO_4$, filtered and concentrated. It was purified by prep-TLC (10% MeOH in DCM, Rf=0.2) to afford Compound 5 (30 mg, 58%) as a yellow solid. LCMS (5-95, AB, 1.5 min): RT (220/254 nm)=0.826 min, m/z=945.1 $[M+23]^+$.

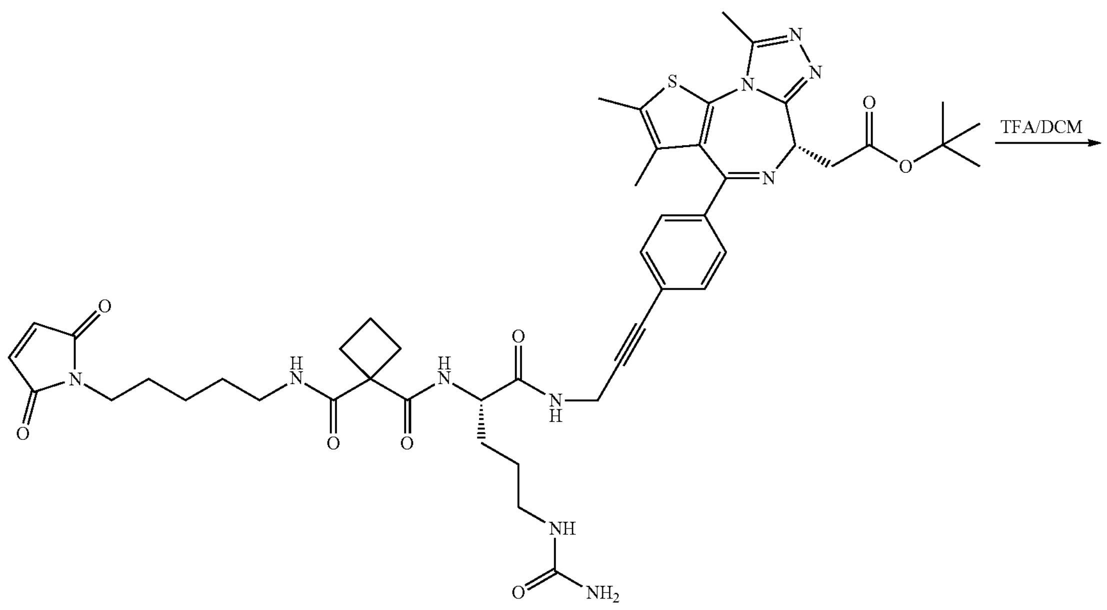
5
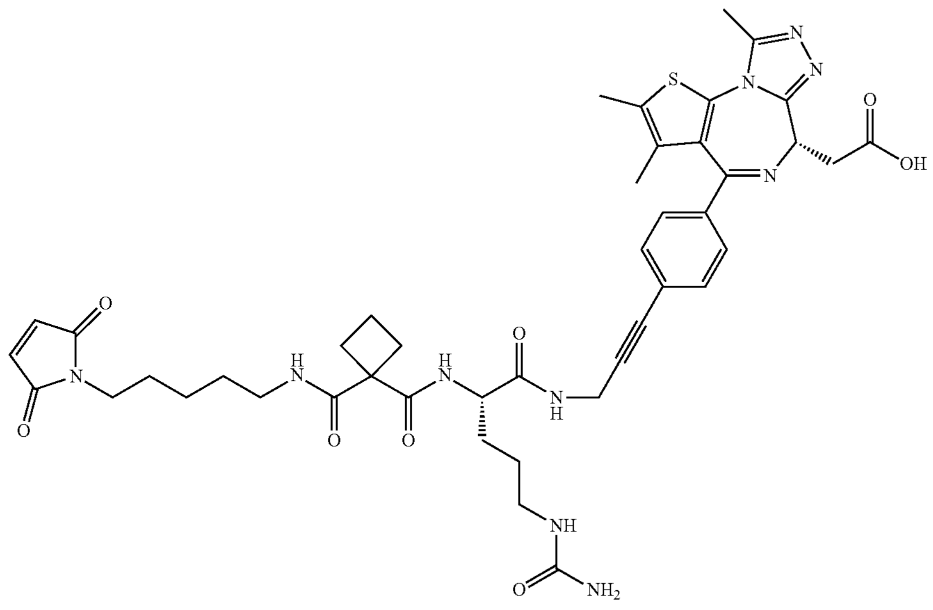
6
A solution of Compound 5 (30.0 mg, 0.0300 mmol) in TFA (3 mL)/DCM (3 mL) was stirred at 20° C. for 2 hrs. TLC (50% ethyl acetate in petroleum ether, Rf=0.1) showed the reaction was completed. The reaction mixture concentrated to give Compound 6 (28 mg, 99.4%) as a yellow solid, which was used directly in the next step. LCMS (5-95, AB, 1.5 min): RT (220/254 nm)=0.601 min, m/z=869.5 $[M+23]^+$.

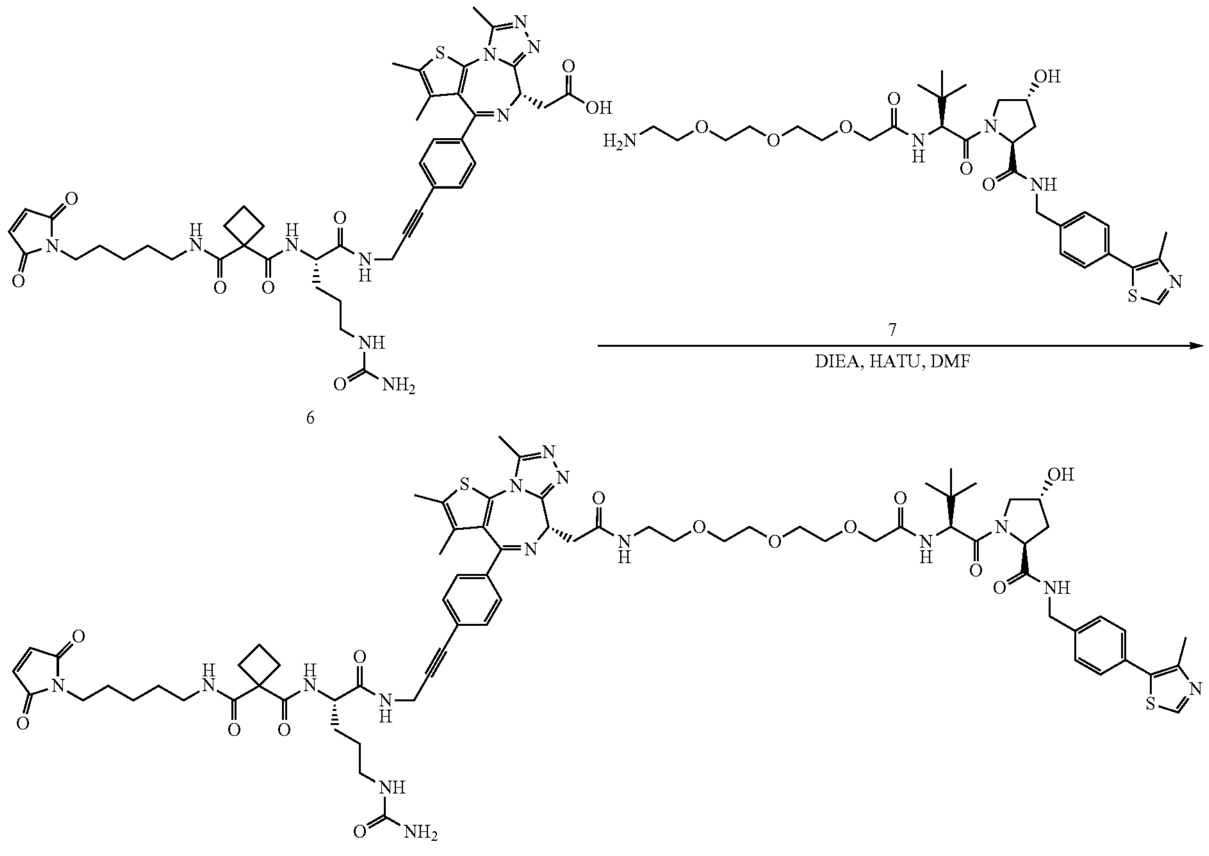

6

7

L1BQ4

To a solution of Compound 6 (28.0 mg, 0.0300 mmol) in DMF (5.0 mL) was added HATU (24.56 mg, 0.0600 mmol) and DIEA (12.52 mg, 0.1000 mmol) at 20° C. The reaction mixture was stirred at 20° C. for 10 min. Then Compound 7 (20.0 mg, 0.0300 mmol) was added. The reaction mixture was stirred at 20° C. for 12 h. The reaction mixture was diluted with EtOAc (15 mL), washed with water (5 mL×2) and brine (5 mL). The organic layer was dried over $Na_2SO_4$, filtered, concentrated, and purified by prep-TLC (20% MeOH in DCM, Rf=0.5) to afford L1BQ4 (20.9 mg, 42.6%) as a white solid. LCMS (5-95, AB, 1.5 min): RT (220/254 nm)=0.788 min, m/z=734.8 $[M/2+1]^+$.

xxiii. L1BQ5 An exemplary L1-CIDE, L1BQ5, can be synthesized by the following scheme:

Scheme 25

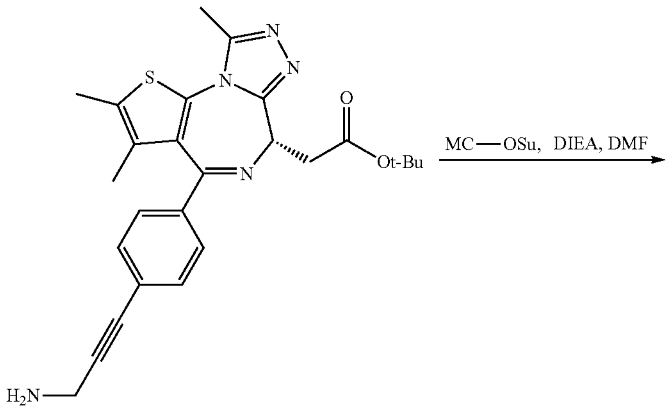

1

-continued
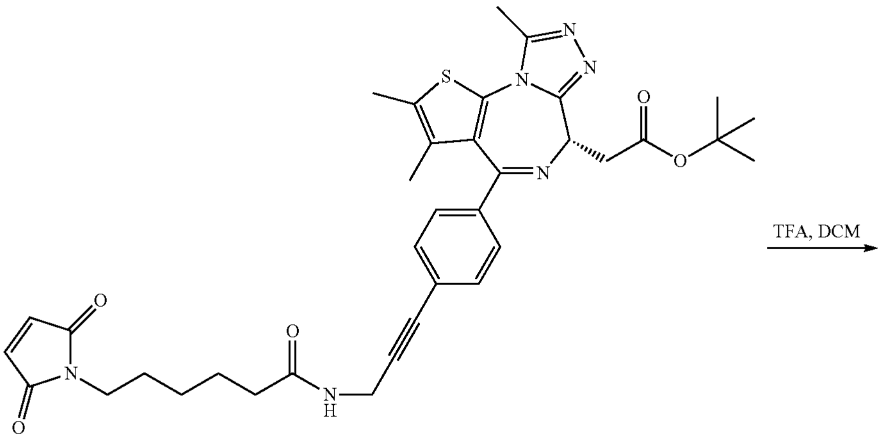
2
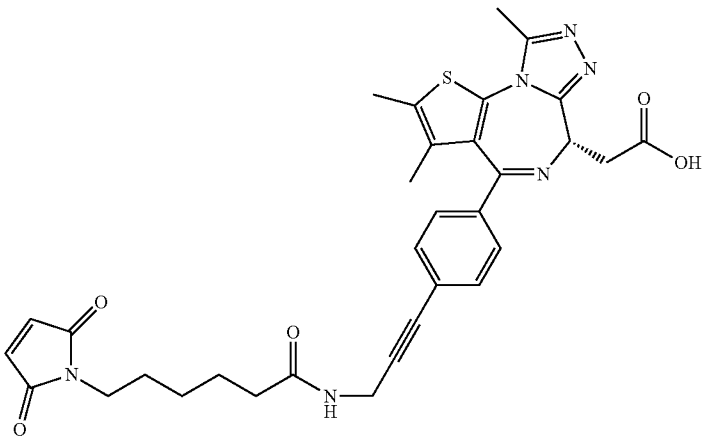
3
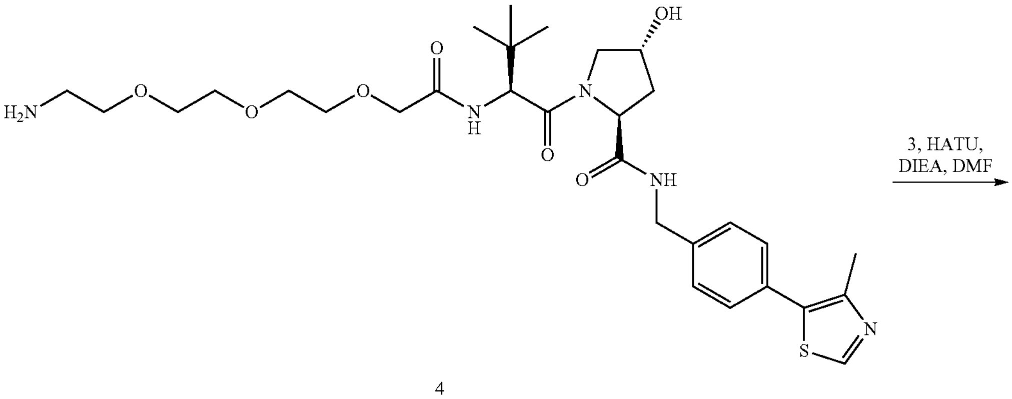
4

-continued
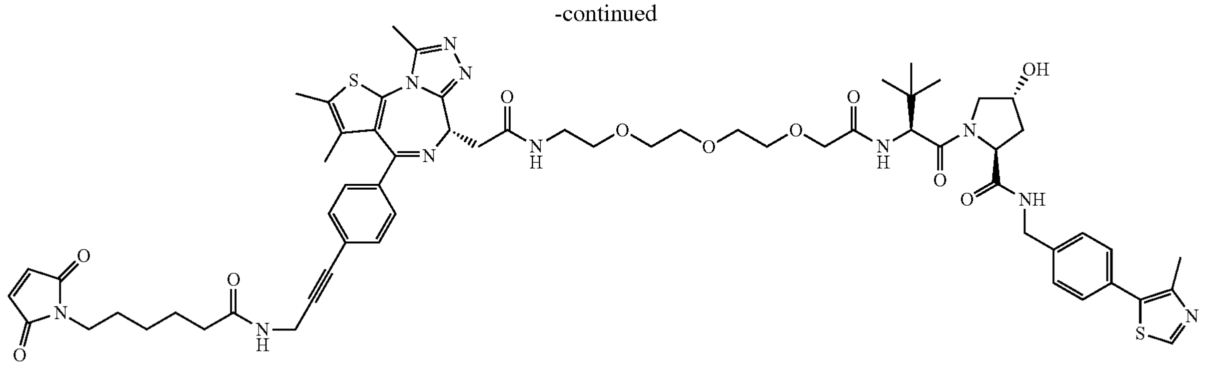
L1BQ5
-continued
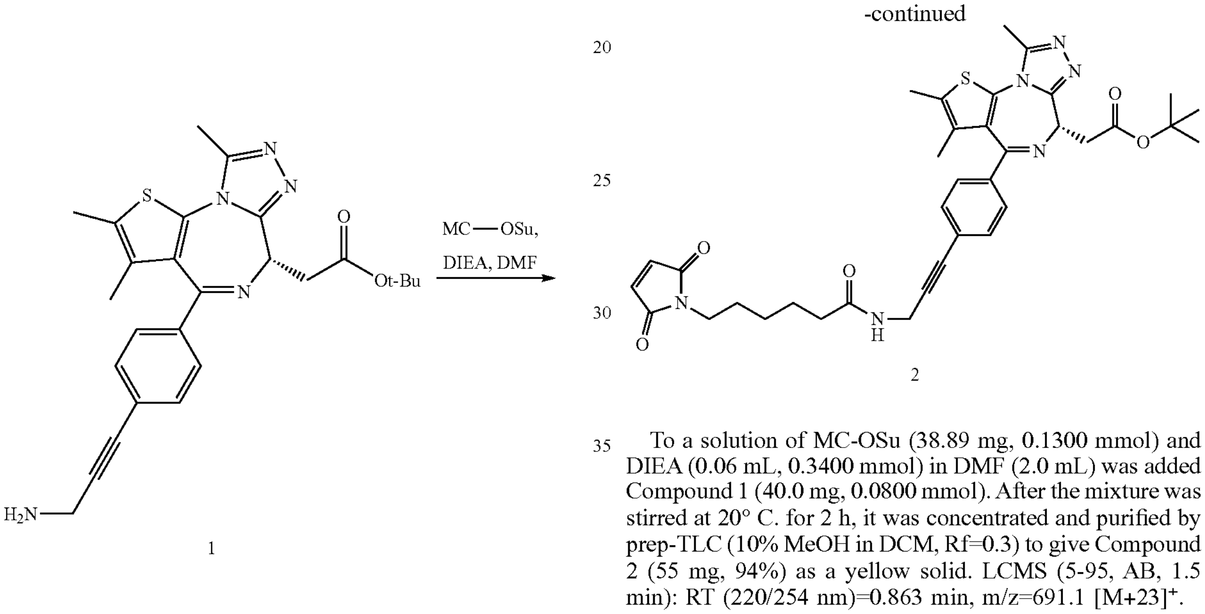
1
2
To a solution of MC-OSu (38.89 mg, 0.1300 mmol) and DIEA (0.06 mL, 0.3400 mmol) in DMF (2.0 mL) was added Compound 1 (40.0 mg, 0.0800 mmol). After the mixture was stirred at 20° C. for 2 h, it was concentrated and purified by prep-TLC (10% MeOH in DCM, Rf=0.3) to give Compound 2 (55 mg, 94%) as a yellow solid. LCMS (5-95, AB, 1.5 min): RT (220/254 nm)=0.863 min, m/z=691.1 $[M+23]^+$.
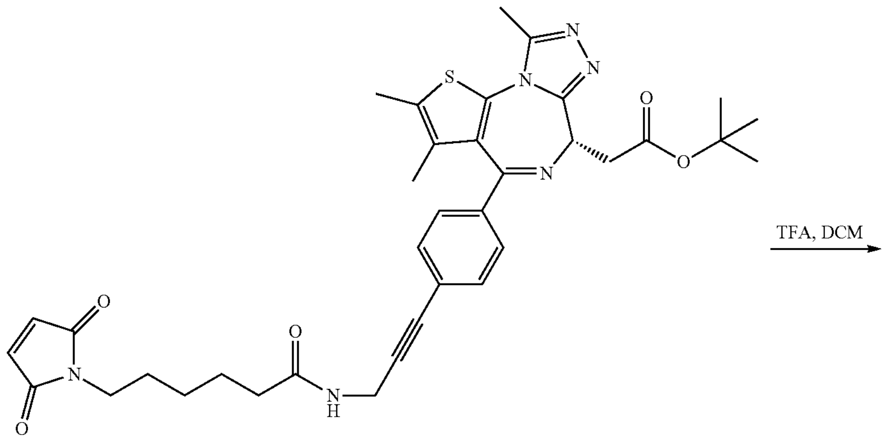
2

-continued
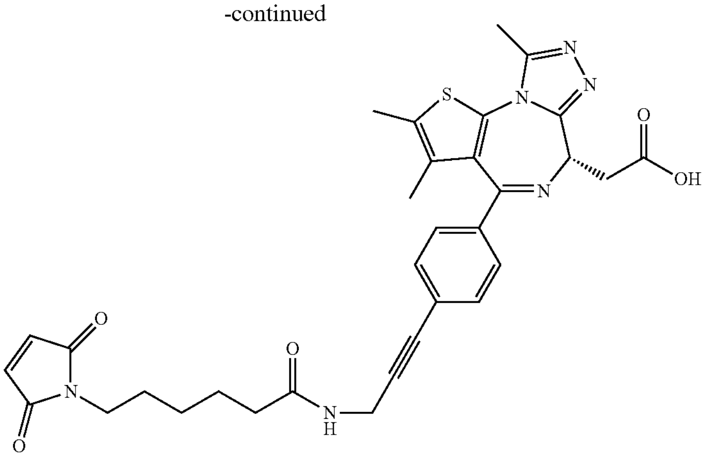
3
A solution of Compound 2 (55.0 mg, 0.0800 mmol) in TFA (1.0 mL)/DCM (3.0 mL) was stirred at 20° C. for 0.5 h. The reaction mixture concentrated to give compound 3 (49 mg, 97%) as a colorless oil, which was used directly in the next step. LCMS (5-95, AB, 1.5 min): RT (220/254 nm)=0.796 min, m/z=613.4 $[M+1]^+$.
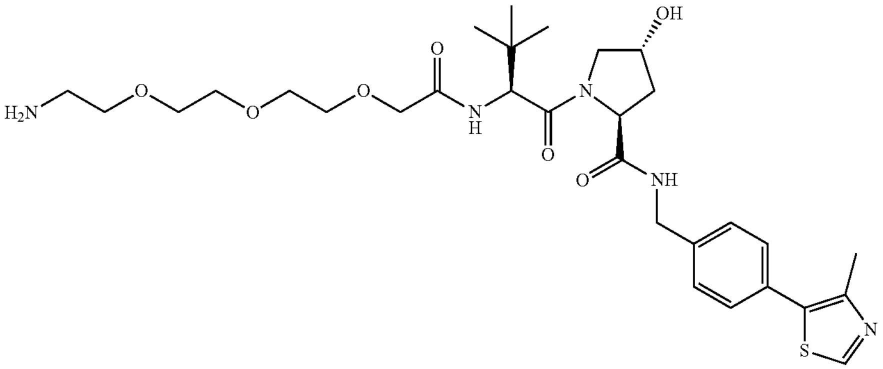
4
+
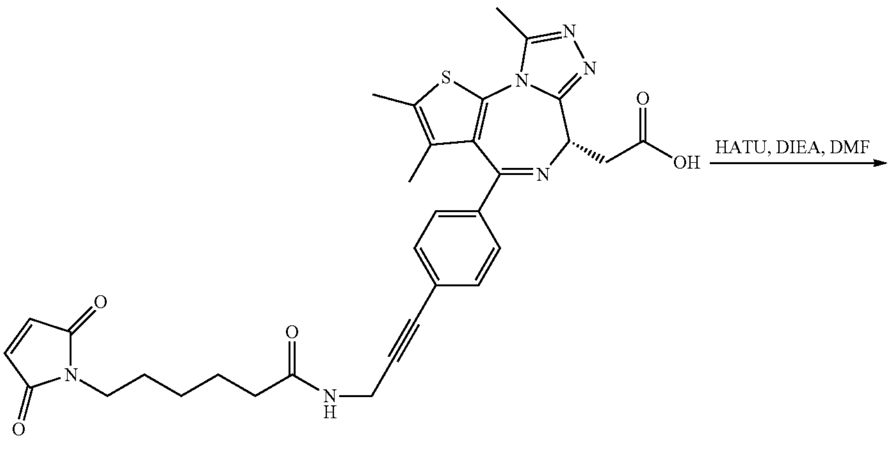
3

-continued

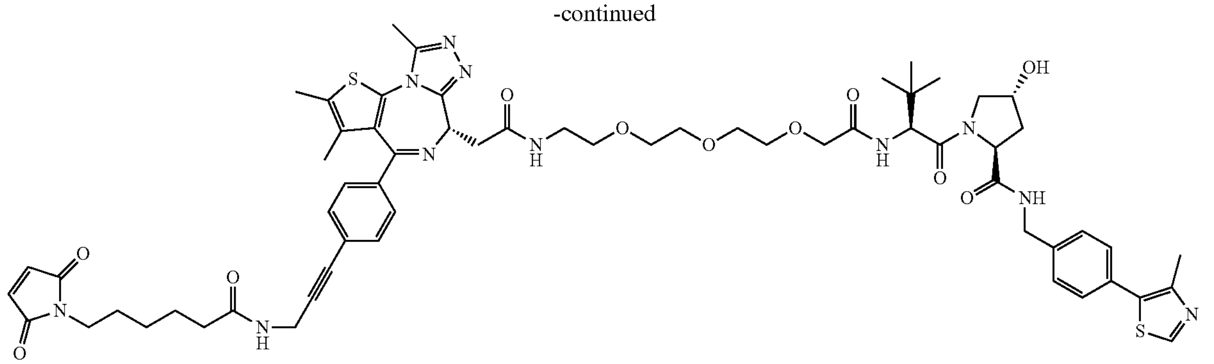

L1BQ5

A solution of Compound 3 (49.0 mg, 0.0800 mmol) in DMF (5.0 mL) was added HATU (60.82 mg, 0.1600 mmol) and DIEA (31.01 mg, 0.2400 mmol) at 20° C. The reaction mixture was stirred at 20° C. for 10 min, and compound 4 (55.0 mg, 0.090 mmol) was added. The reaction mixture was stirred at 20° C. for 12 h. The reaction mixture was diluted with water (5.0 mL) extracted EtOAc (10 mL×3). The organic layer was dried over $Na_2SO_4$, concentrated, and purified by prep-TLC (100% MeOH in DCM, Rf=0.2 to afford L1BQ5 (33.7 mg, 330%) as a white solid. $^1H$ NMR (400 MHz, $CDCl_3$) δ11.04 (brs, 1H), 8.60 (s, 1H), 7.85 (brs, 1H), 7.41-7.36 (m, 1H), 7.30-7.25 (m, 6H), 7.19 (s, 2H), 6.59 (s, 2H), 5.87 (brs, 1H), 4.72 (t, J=7.50 Hz, 1H), 4.61-4.51 (m, 2H), 4.46-4.38 (m, 2H), 4.25-4.15 (m, 3H), 4.09-4.02 (m, 1H), 3.62-3.51 (m, 12H), 3.43 (t, J=7.2 Hz, 2H), 3.38 (d, J=8.8 Hz, 1H), 3.38-3.30 (m, 2H), 3.07-3.01 (m, 3H), 2.54 (s, 2H), 2.43 (s, 2H), 2.31 (s, 2H), 2.14 (t, J=7.6 Hz, 2H), 1.61-1.49 (m, 5H), 1.41-1.37 (m, 12H), 1.32 (d, J=6.8 Hz, 8H), 1.28-1.18 (m, 4H), 0.9 (s, 9H). LCMS (5-95, AB, 1.5 min): RT (220/254 nm)=0.823 min, m/z=1214.6 $[M+1]^+$.

xxiv. L1BQ6 An exemplary L1-CIDE, L1BQ6, can be synthesized by the following scheme:

Scheme 26

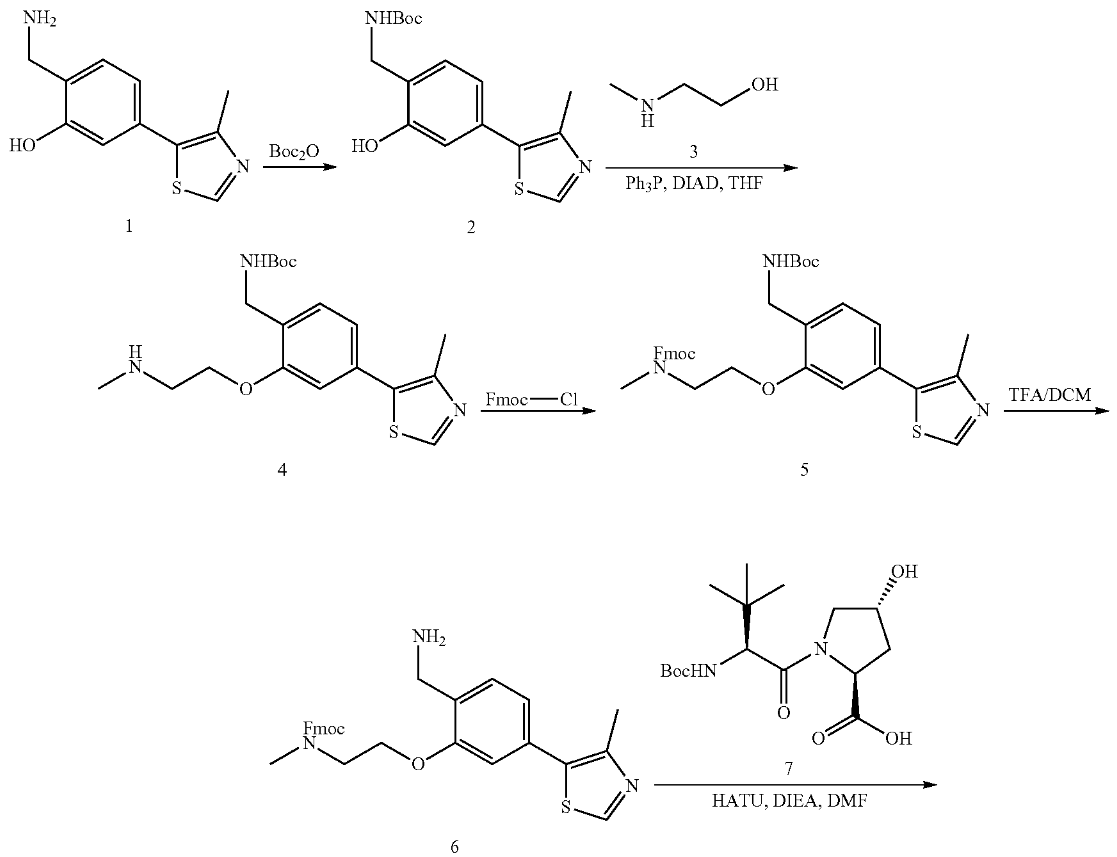

1 2 4 5 6

-continued
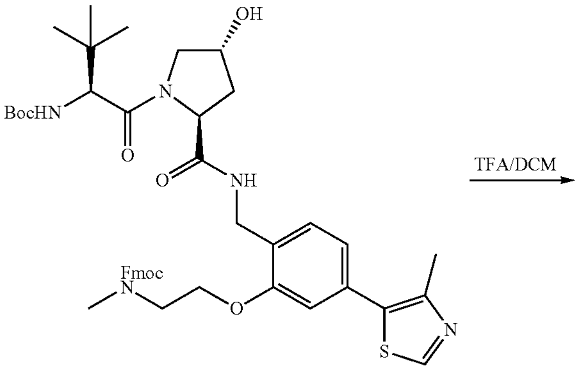
8
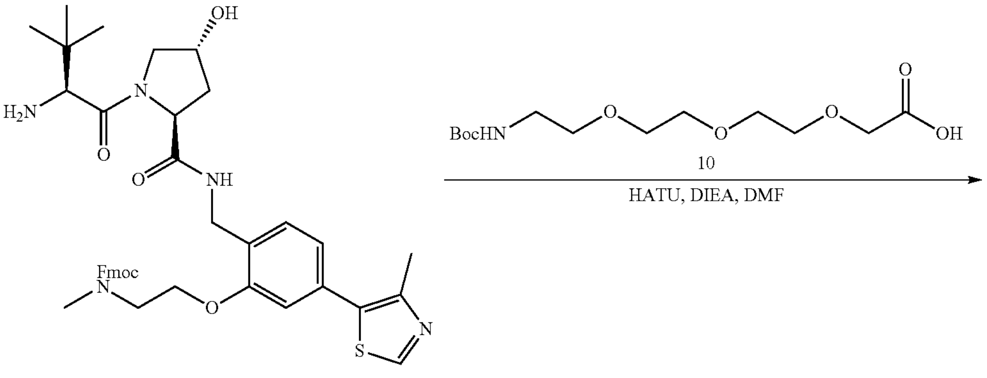
9
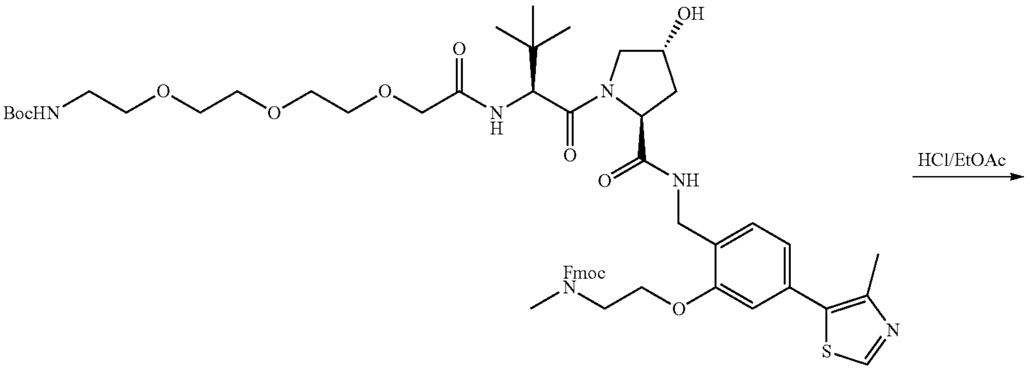
11
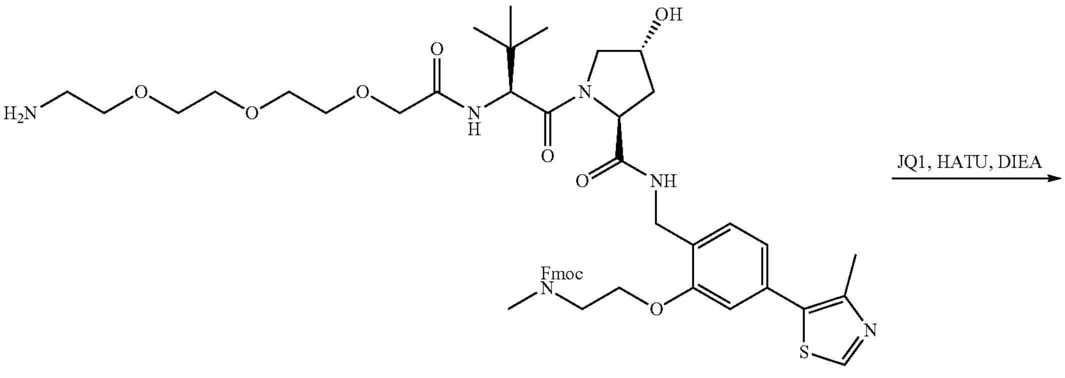
12

-continued
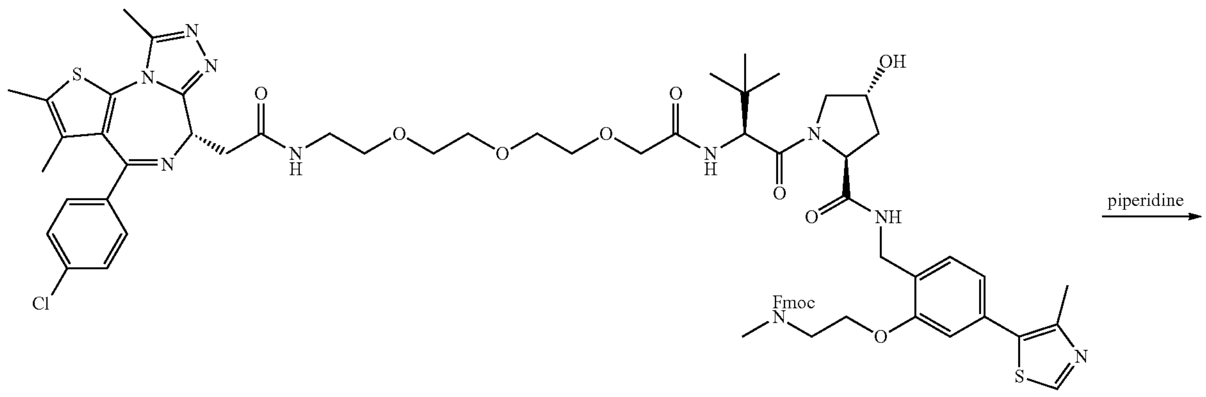
13
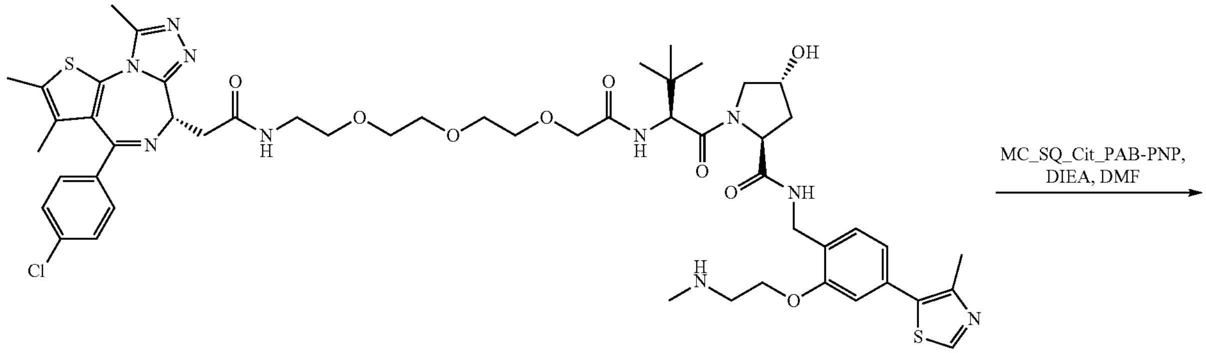
14
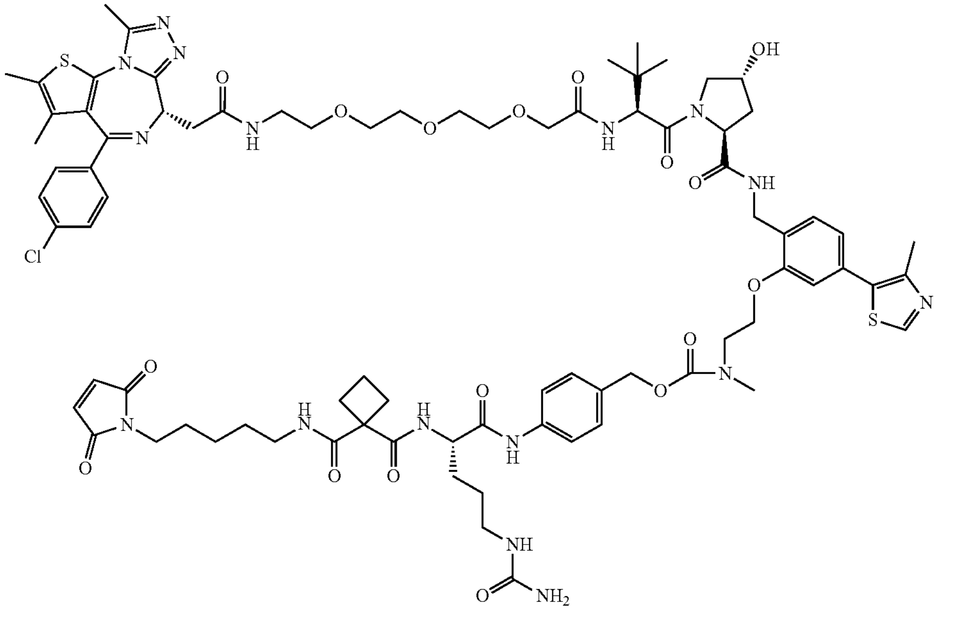
L1BQ6

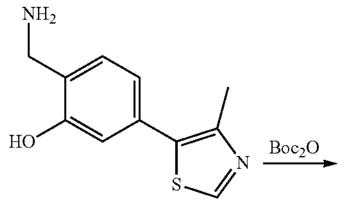

1

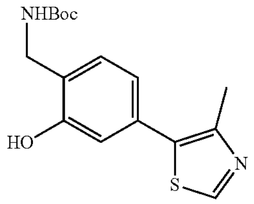

2

To a solution of Compound 1 (1.0 g, 4.54 mmol) in THF (5.0 mL) was added $Boc_2O$ (1.25 mL, 5.45 mmol). Then the mixture was stirred at 20° C. for 4 h. Then the mixture was concentrated and purified by column chromatography (30% EtOAc in petroleum ether, Rf=0.7) to get Compound 2 (1.1 g, 76%). LCMS (5-95, AB, 1.5 min): RT (220/254 nm)=0.697 min, m/z=321.2 $[M+1]^+$.

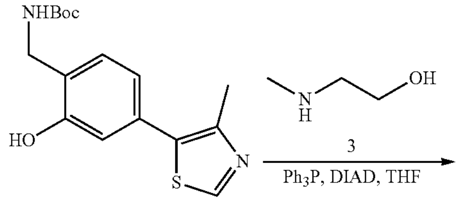

2

3

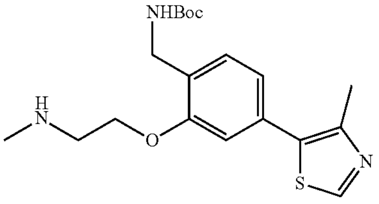

4

To a solution of Compound 2 (600.0 mg, 1.87 mmol) $Ph_3P$ (982.33 mg, 3.75 mmol) and compound 3 (210.98 mg, 2.81 mmol) in THF (20 mL) was added DIAD (757.32 mg, 3.75 mmol) slowly at 0° C. After the reaction mixture was stirred at 70° C. for 12 h, it was diluted with DCM (50 mL), washed with water (40 mL×2), dried over anhydrous sodium sulfate, and concentrated in vacuo. The residue was purified by flash chromatography on silica gel (0-10% MeOH in DCM, Rf=0.5) to compound 4 (100 mg, 14%) as a yellow solid. LCMS (5-95, AB, 1.5 min): RT=0.713 min, m/z=378.0 $[M+1]^+$.

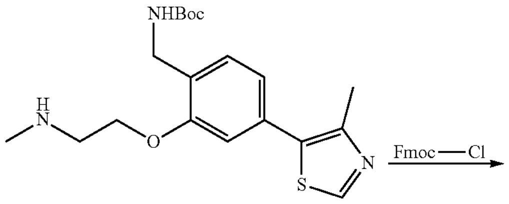

4

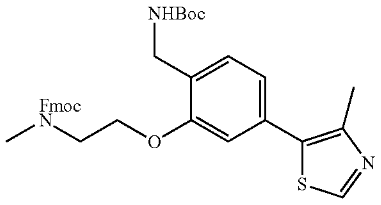

5

To a solution of Compound 4 (100.0 mg, 0.2600 mmol) in THF (10 mL) was added a solution of $Na_2CO_3$ (56.15 mg, 0.530 mmol) in water (4.0 mL) and Fmoc-Cl (96.44 mg, 0.4000 mmol). The mixture was stirred at 20° C. for 8 h. The reaction mixture was diluted with water (20 mL), extracted with EtOAc (20 mL×3), dried over anhydrous sodium sulfate, and concentrated in vacuo. The residue was purified by silica flash chromatography (10%-80% EtOAc/petroleum ether to afford Compound 5 (130 mg, 81%) as a white solid. LCMS (5-95, AB, 1.5 min): RT (220/254 nm)=0.986 min, m/z=622.0 $[M+23]^+$.

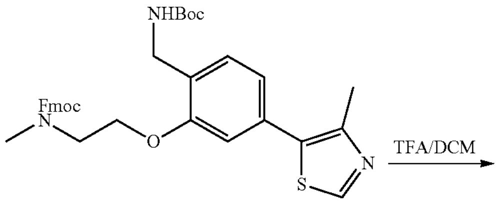

5

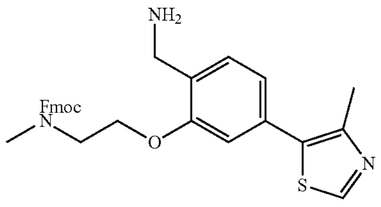

6

A solution of Compound 5 (130.0 mg, 0.2200 mmol) in TFA (1.0 mL)/DCM (4.0 mL) was stirred at 20° C. for 0.5 h. The reaction mixture concentrated to give Compound 6 (105 mg, 97%) as a white solid, which was used directly in the next step.

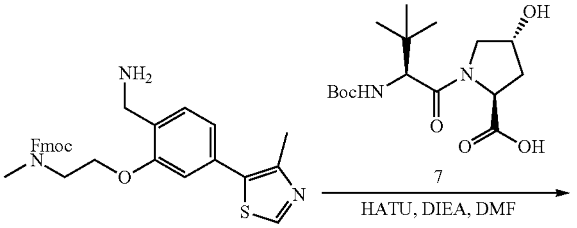

6

7

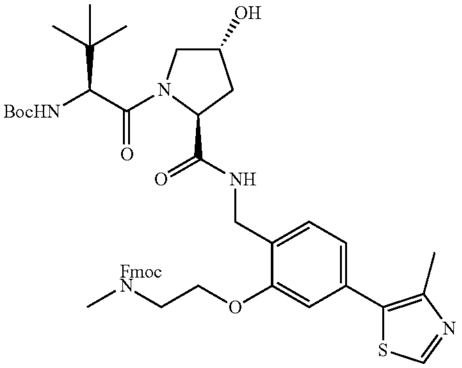

8

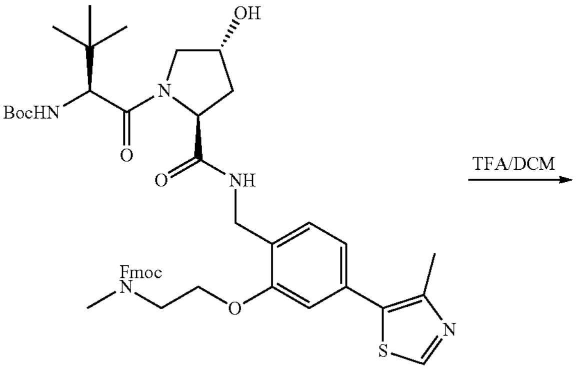

8

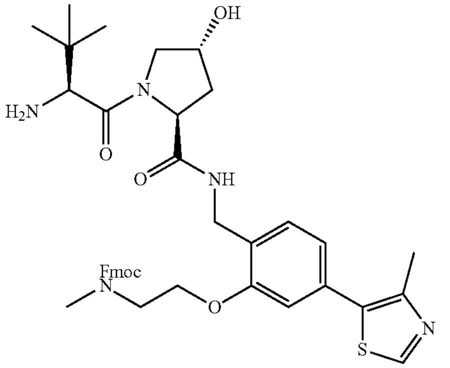

9

To a solution of Compound 7 (115.0 mg, 0.330 mmol) in DMF (10.0 mL) was added HATU (159.8 mg, 0.420 mmol) and DIEA (81.48 mg, 0.630 mmol) at 20° C. The reaction mixture was stirred at 20° C. for 10 min. Then Compound 6 (105.0 mg, 0.210 mmol) was added. The reaction mixture was stirred at 20° C. for 2 h. The reaction mixture was diluted with water (30 mL) and extracted with EtOAc (30 mL). The organic layer was dried over $Na_2SO_4$, filtered, concentrated, and purified by prep-TLC (10% methanol in DCM, Rf=0.5) to afford Compound 8 (170 mg, 98%) as a yellow solid, which was used directly in the next step. LCMS (5-95, AB, 1.5 min): RT (220/254 nm)=0.935 min, m/z=848.2 $[M+23]^+$.

A solution of Compound 8 (170.0 mg, 0.210 mmol) in TFA (1.0 mL)/DCM (4.0 mL) was stirred at 20° C. for 0.5 h. The reaction mixture concentrated to give Compound 9 (149 mg, 99.7%) as a colorless oil, which was used directly in the next step. LCMS (5-95, AB, 1.5 min): RT (220/254 nm)=0.801 min, m/z=726.1 $[M+1]^+$.

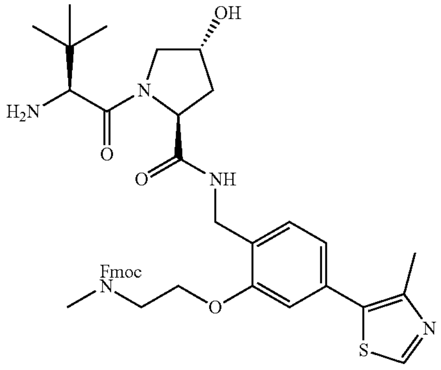

9

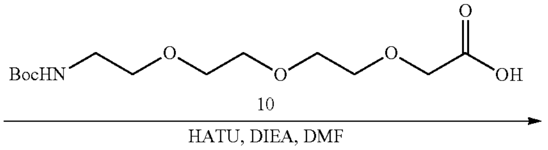

10

-continued

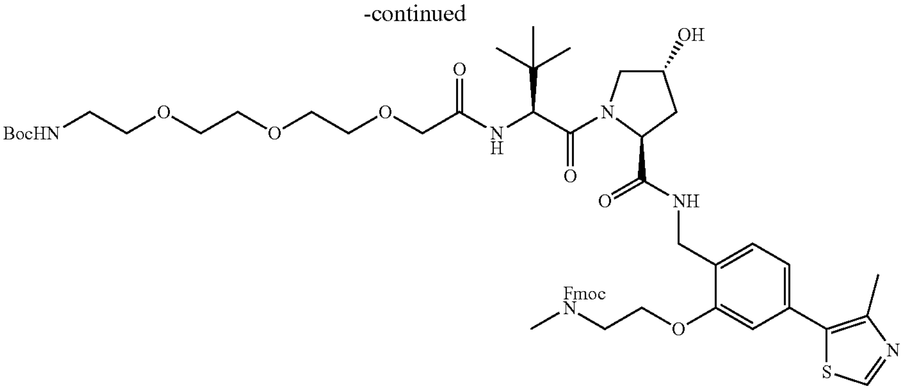

11

To a solution of Compound 10 (75.7 mg, 0.250 mmol) in DMF (5.0 mL) was added HATU (156.1 mg, 0.410 mmol) and DIEA (79.58 mg, 0.6200 mmol) at 20° C. The reaction mixture was stirred at 20° C. for 10 min. Then Compound 9 (149.0 mg, 0.210 mmol) was added. The reaction mixture was stirred at 20° C. for 2 h. The reaction was diluted with water (10 mL) and extracted with DCM (10 mL×3). The organic layer was dried over $Na_2SO_4$, filtered, concentrated, and purified by prep-TLC (10% MeOH in DCM, Rf=0.4) to afford Compound 11 (208 mg, 99.8%) as a yellow solid, which was used directly in the next step. LCMS (5-95, AB, 1.5 min): RT (220/254 nm)=0.920 min, m/z=1037.3 $[M+23]^+$.

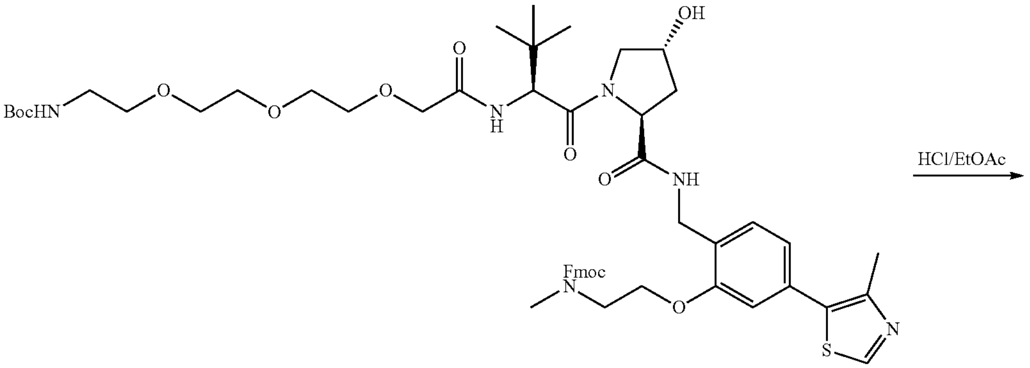

11

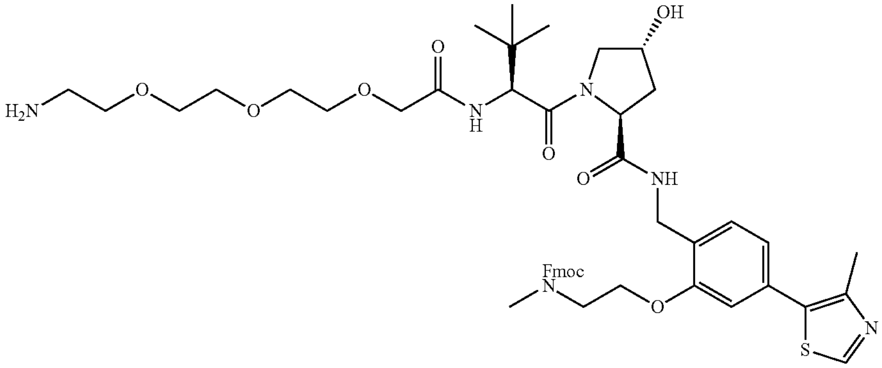

12

To a solution of Compound 11 (40.0 mg, 0.0400 mmol) in DCM (1.0 mL) was added HCl/EtOAc (4.0 M, 2.0 mL, 8 mmol) and the mixture was stirred at 20° C. for 2 h. The reaction mixture concentrated to give Compound 12 (37.11 mg, 99%) as a yellow solid, which was used directly in the next step. LCMS (5-95, AB, 1.5 min): RT (220/254 nm)=0.685 min, m/z=915.3 [M+1]$^+$.

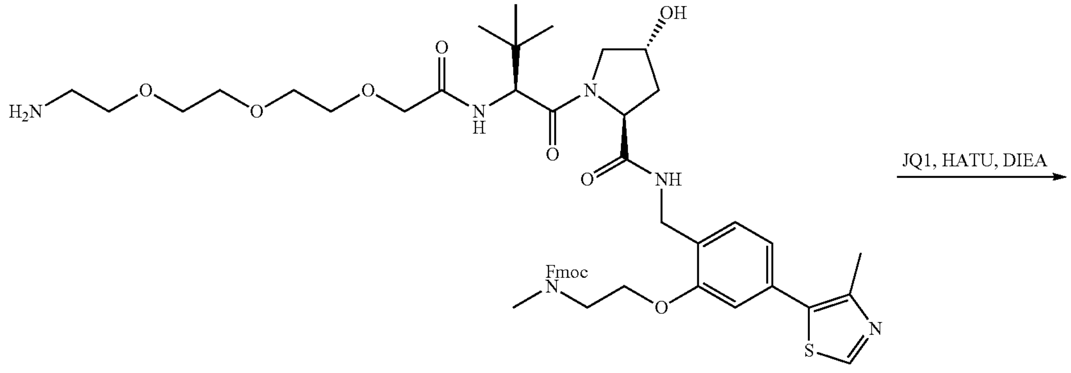

12

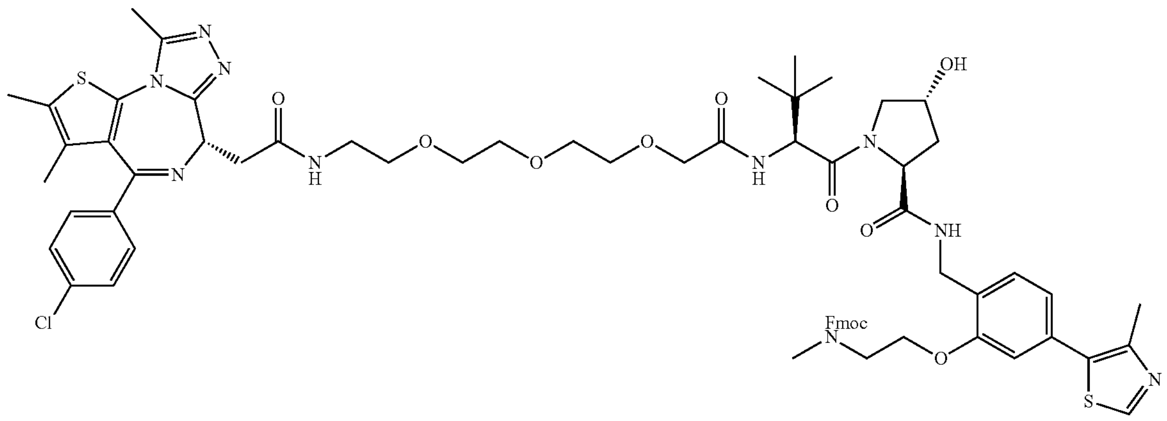

13

To a solution of JQ1 (23.45 mg, 0.0600 mmol) in DMF (2.0 mL) was added HATU (29.66 mg, 0.0800 mmol) and DIEA (20.16 mg, 0.1600 mmol) at 20° C. After the reaction mixture was stirred at 20° C. for 10 min, compound 12 (37.11 mg, 0.0400 mmol) was added at 20° C. for 2 h.

The mixture was concentrated and purified by prep-TLC (10% MeOH in DCM, Rf=0.5) to afford Compound 13 (40 mg, 66%) as a yellow solid. LCMS (5-95, AB, 1.5 min): RT (220/254 nm)=0.922 min, m/z=1297.2[M+1]$^+$.

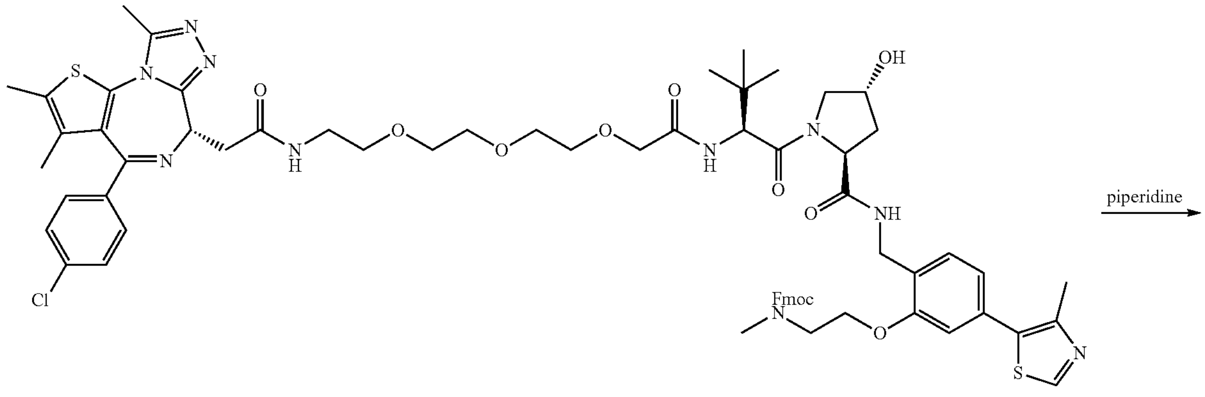

13

-continued
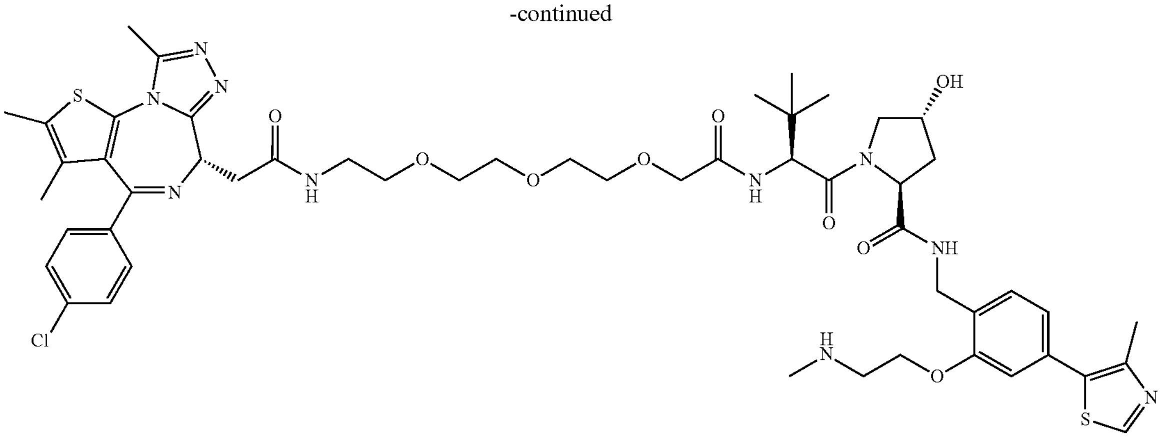
14
To a solution of Compound 13 (40.0 mg, 0.0300 mmol) in DMF (2.0 mL) was added piperidine (13.12 mg, 0.1500 mmol) and the mixture was stirred at 20° C. for 1 h. The mixture was concentrated and purified by prep-HPLC (acetonitrile 33-63/0.225% FA in water) to afford Compound 14 (8.4 mg, 25%) as white solid. LCMS (5-95, AB, 1.5 min): RT (220/254 nm)=0.773 min, m/z=1075.0 $[M+1]^+$.
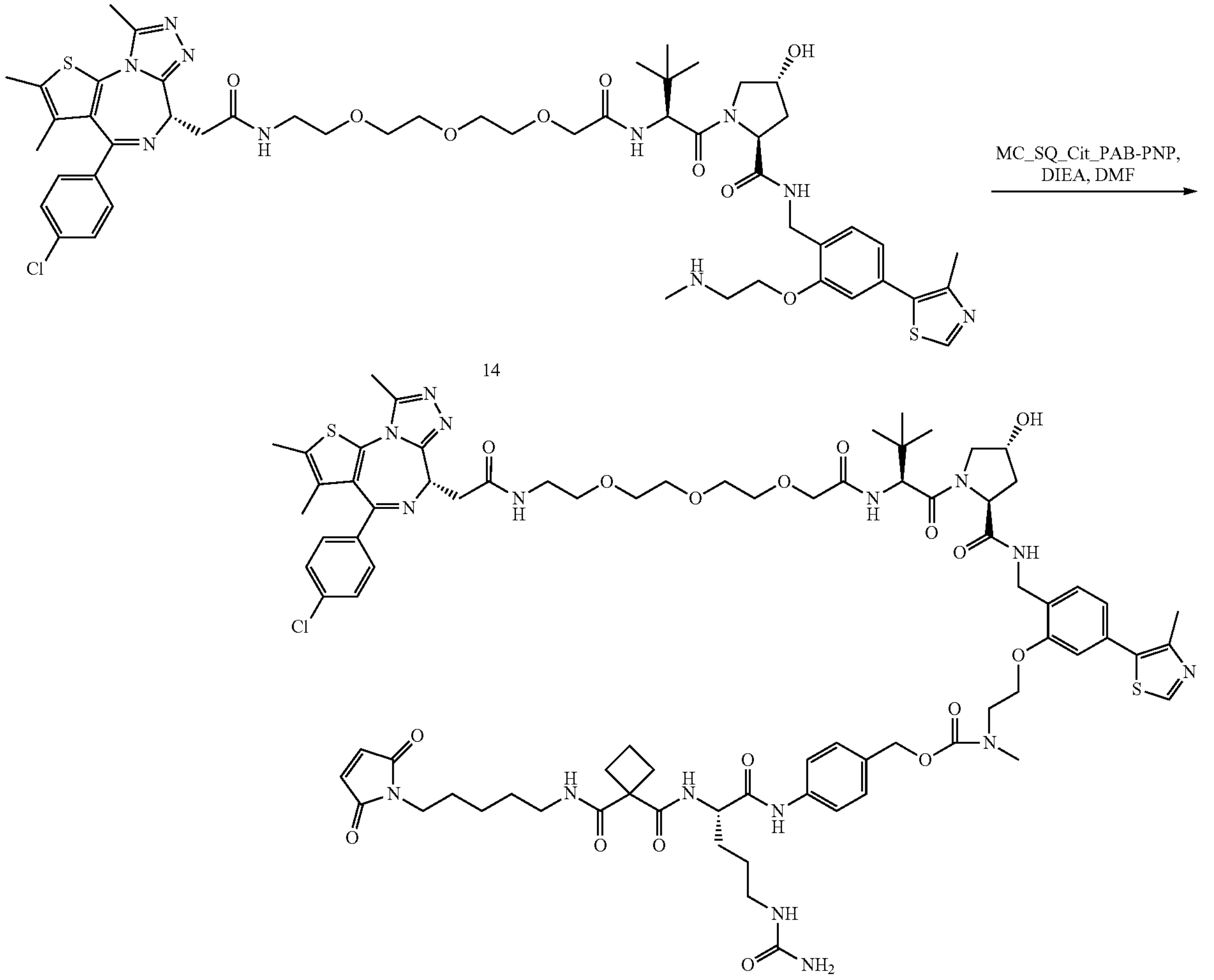
14
L1BQ6

To a solution of MC_SQ_Cit_PAB-PNP (3.08 mg, 0.0042 mmol) and Compound 14 (3.0 mg, 0.0028 mmol) in DMF (2.0 mL) was added DIEA (1.44 mg, 0.0100 mmol). The mixture was stirred at 20° C. for 12 h. The mixture was purified by prep-HPLC (acetonitrile 38-68/0.225% FA in water) to afford L1BQ6 (2.19 mg, 46%) as a white solid. LCMS (5-95, AB, 1.5 min): RT (220/254 nm)=0.842 min, m/z=858.9[M/2+23]*. HRMS (0-95_1_4 min.m): m/z=1671.66 $[M+1]^+$.

xxv. L1BQ7 An exemplary L1-CIDE, L1BQ7, can be synthesized by the following scheme:

Scheme 27

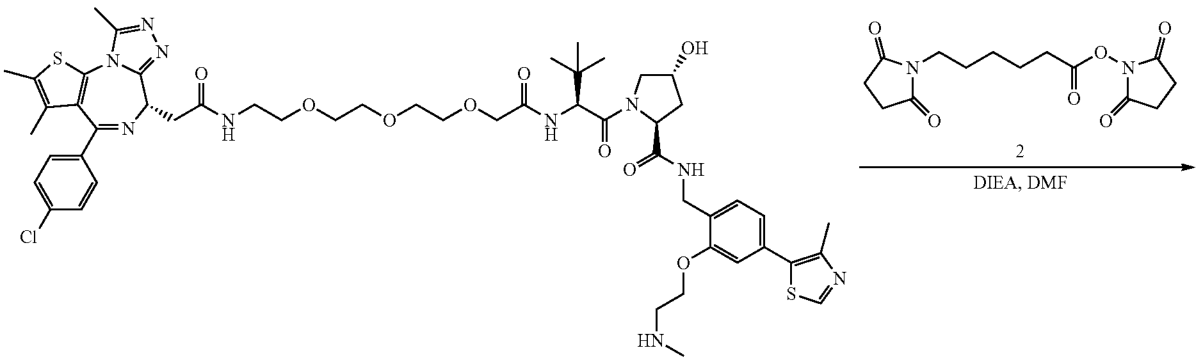

1

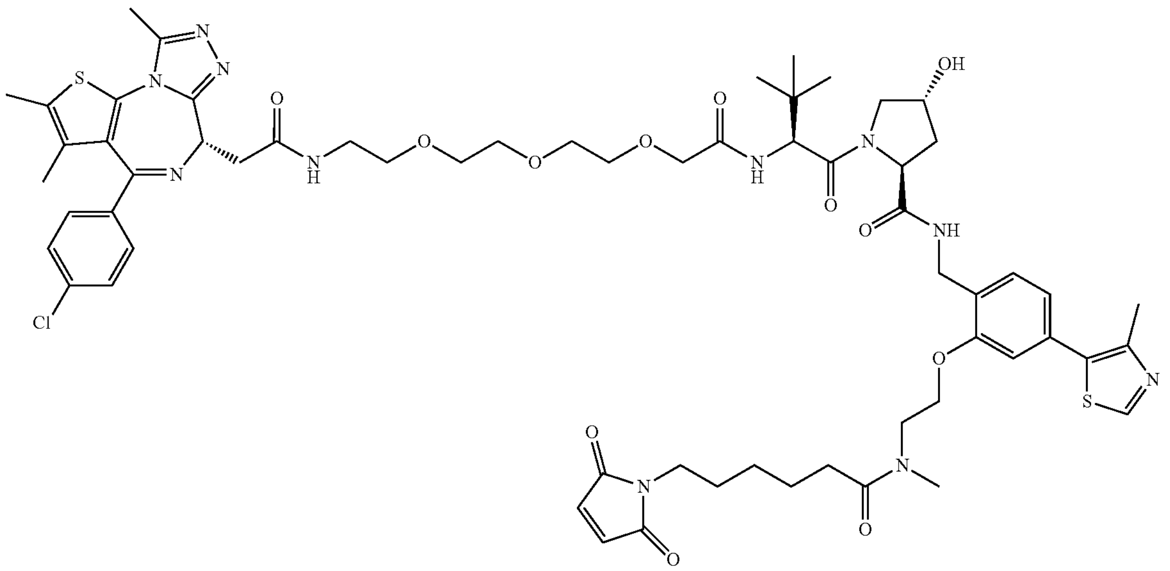

L1BQ7

To a solution of Compound 2 (1.29 mg, 0.0028 mmol) and Compound 1 (3.0 mg, 0.0028 mmol) in DMF (2.0 mL) was added DIEA (1.5 mg, 0.0100 mmol). The mixture was stirred at 20° C. for 12 h. The mixture was purified by prep-HPLC (acetonitrile 38-68/0.225% FA in water) to afford L1BQ7 (2.41 mg, 68%) as a white solid. LCMS (5-95, AB, 1.5 min): RT (220/254 nm)=0.850 min, m/z=1291.7 $[M+23]^+$. HRMS (0-95_1_4 min.m): m/z=1290.4777 $[M+23]^+$.

xxvi. L1BQ8 An exemplary L1-CIDE, L1BQ8, can be synthesized by the following scheme:
Scheme 38
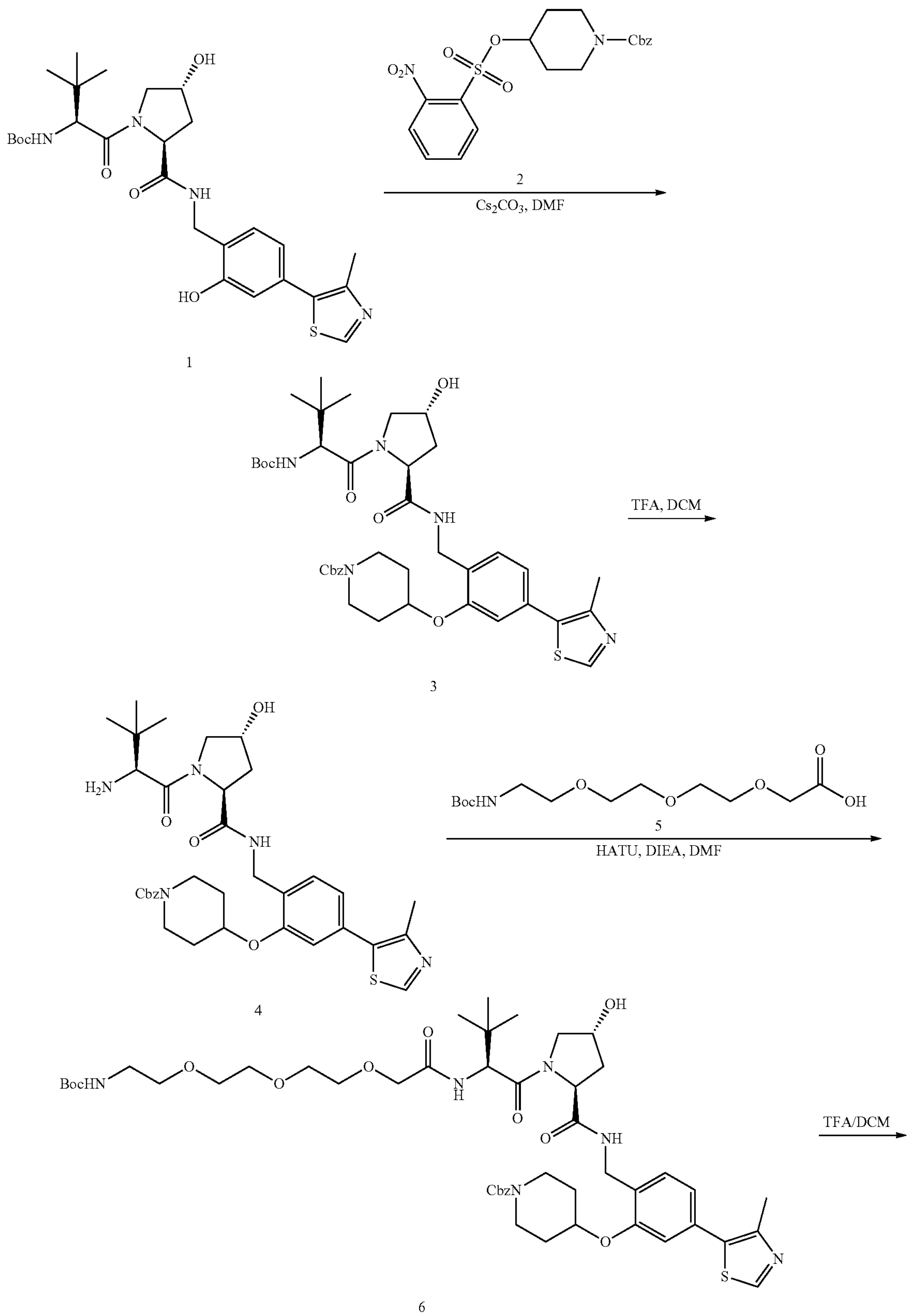

-continued
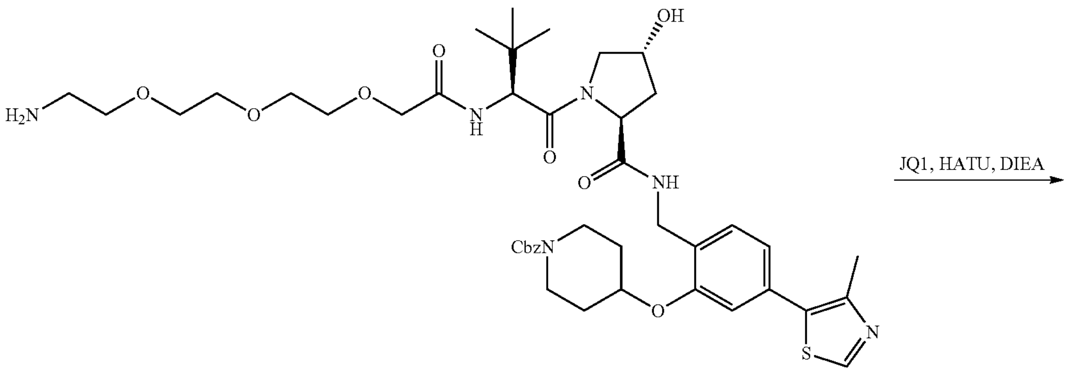
7
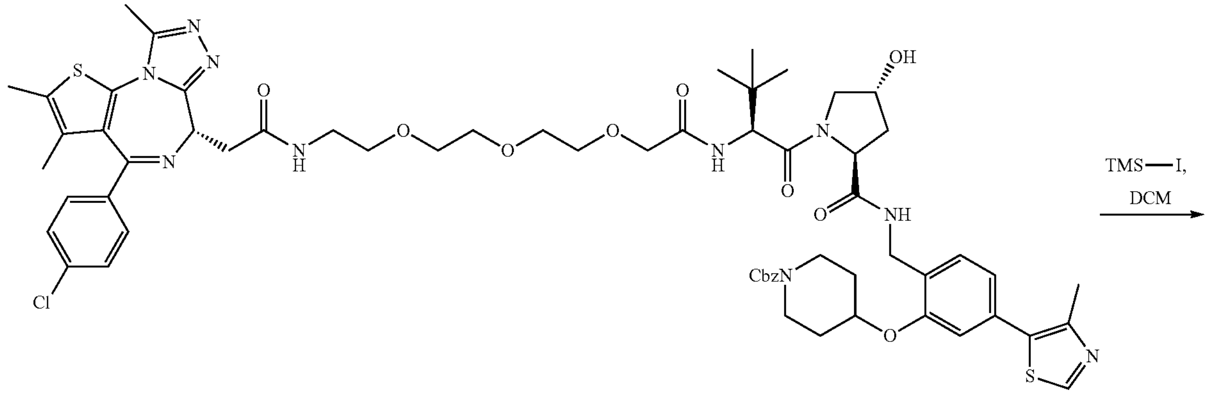
8
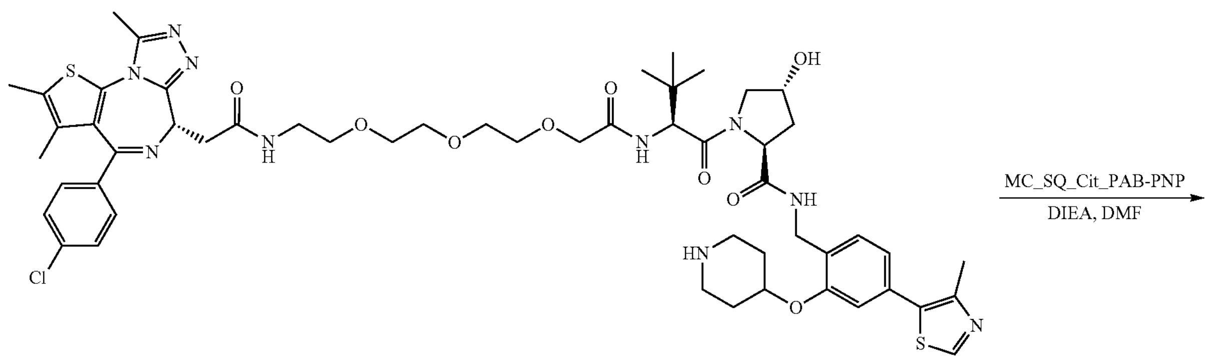
9

-continued

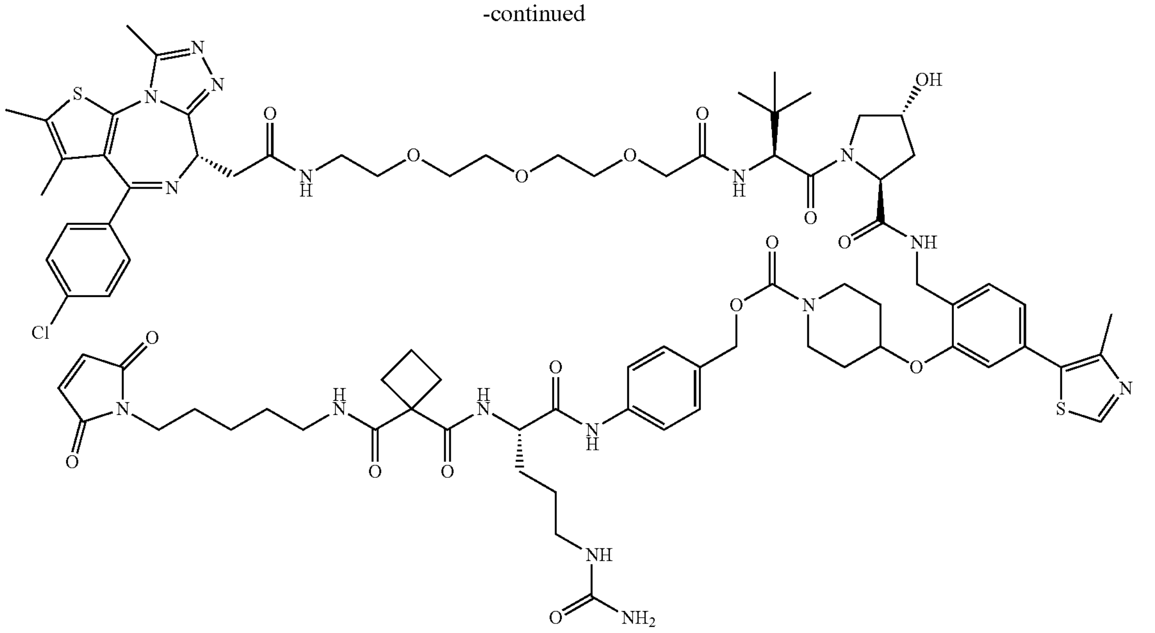

L1BQ8

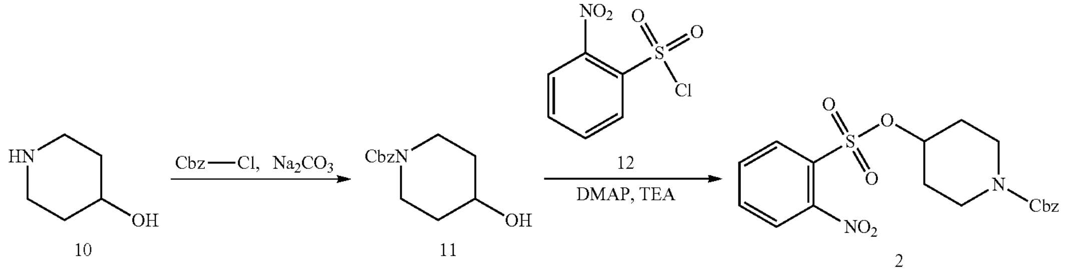

10 11 2

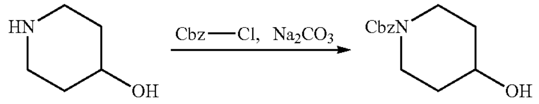

10 11

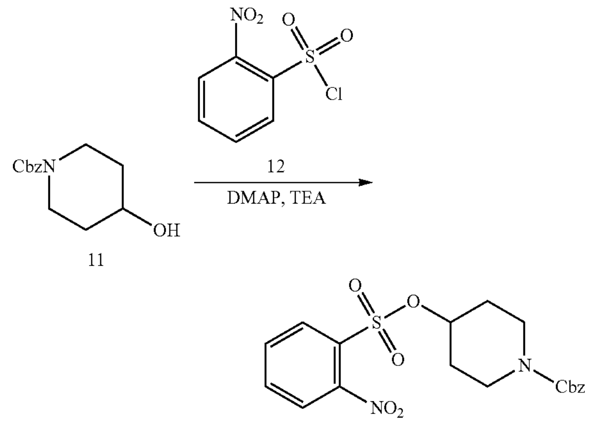

11 2

A solution of Compound 10 (5.000 g, 49.43 mmol), $NaHCO_3$ (10.478 g, 98.86 mmol) in THE (50 mL) was cooled to 0° C., and then Cbz-Cl (9.275 g, 54.37 mmol) was added drop-wise. The mixture was warmed to 20° C. for 12 h. The mixture was concentrated, diluted with aq. $NaHCO_3$ (5%, 30 mL), and extracted with EtOAc (100 mL×2). The organic layer was washed with brine (100 mL×3), dried over $Na_2SO_4$, filtered and concentrated. It was purified by flash chromatography on silica gel (0-60% EtOAc in petroleum ether) to give compound 11 (11.00 g, 95%) as a yellow oil. $^1H$ NMR (400 MHz, $CDCl_3$) δ 7.37-7.30 (m, 5H), 5.13 (s, 2H), 3.93-3.84 (m, 3H), 3.18-3.11 (m, 2H), 1.87 (brs, 2H), 1.50-1.48 (br, 2H).

Compound 12 (2.260 g, 10.2 mmol) in DCM (10 mL) was added drop-wise to a solution of Compound 11 (2.000 g, 8.5 mmol) and TEA (2.150 g, 21.25 mmol), DMAP (51.93 mg, 0.4300 mmol) in DCM (50 mL) at 0° C. The reaction mixture was stirred at 20° C. for 12 h. The reaction was concentrated and purified by flash chromatography on silica gel (0-50% EtOAc in petroleum ether, Rf=0.5) to afford Compound 12 (1.300 g, 36%) as a colorless oil. LCMS (5-95, AB, 1.5 min): RT (220/254 nm)=0.888 min, m/z=442.9 $[M+23]^+$.

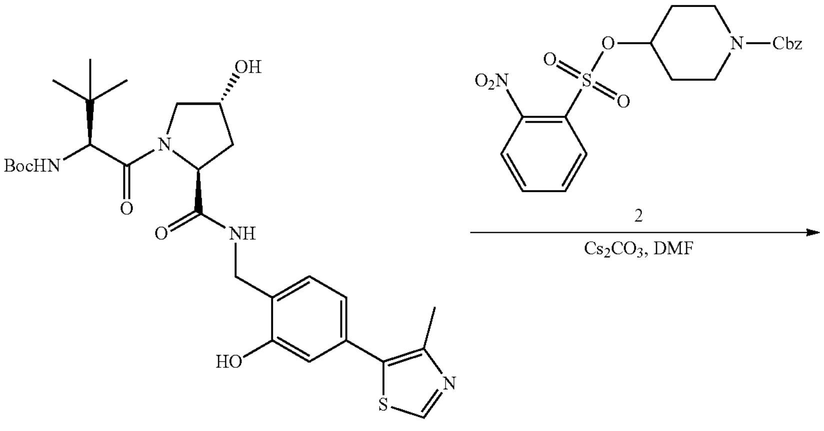

1

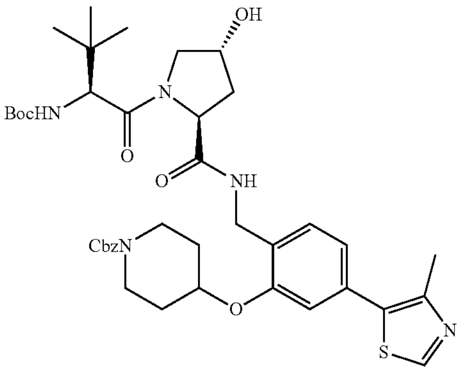

3

A mixture of $Cs_2CO_3$ (596.0 mg, 1.83 mmol), Compound 1 (500.0 mg, 0.9100 mmol) and Compound 2 (1.153 g, 2.74 mmol) in DMF (20 mL) was stirred at 50° C. for 13 h. The reaction solution was diluted with water (10 mL), extracted with EtOAc (50 mL). The organic layer was concentrated and purified by flash chromatography on silica gel (0-90% EtOAc in petroleum ether) to give compound 3 (370 mg, 53%) as a yellow solid. LCMS (5-95, AB, 1.5 min): RT (220/254 nm)=0.897 min, m/z=786.1[M+23]$^+$.

-continued

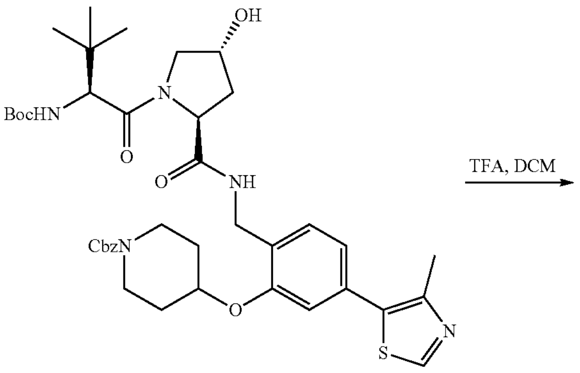

3

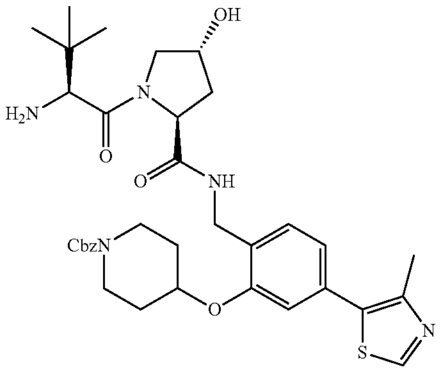

4

A solution of compound 3 (50.0 mg, 0.0700 mmol) in a mixture of TFA (1.0 mL)/DCM (5.0 mL) was stirred at 20° C. for 2 h. The reaction mixture concentrated to give Compound 4 (50 mg, 98.2%) as a yellow solid, which was used directly in the next step. LCMS (5-95, AB, 1.5 min): RT (220/254 nm)=0.763 min, m/z=664.1[M+1]$^+$.

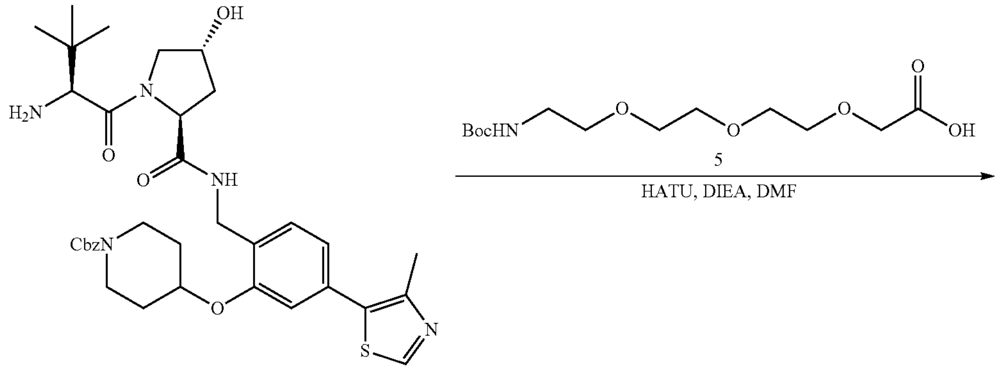

4

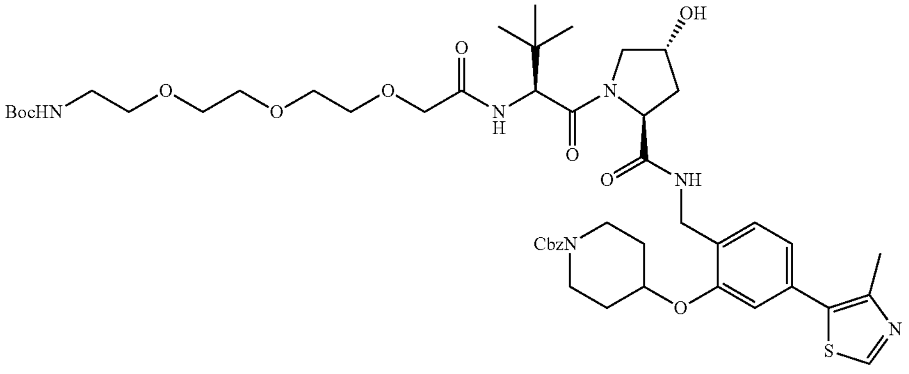

6

To a solution of Compound 5 (23.71 mg, 0.0800 mmol) in DMF (10 mL) was added HATU (48.88 mg, 0.1300 mmol) and DIEA (24.92 mg, 0.1900 mmol) at 20° C. The reaction mixture was stirred at 20° C. for 10 min. Then Compound 4 (50.0 mg, 0.0600 mmol) was added. The reaction mixture was stirred at 20° C. for 12 h. The reaction mixture was added to water (5.0 mL), then extracted with EtOAc (30 mL). The organics was washed with water (10 mL×2), followed by brine (10 mL). The organic layer was dried over $Na_2SO_4$, filtered, concentrated and purified by prep-TLC (10% MeOH in DCM, Rf=0.3) to afford Compound 6 (60 mg, 98%) as a yellow solid. LCMS (5-95, AB, 1.5 min): RT (220/254 nm)=0.886 min, m/z=975.2 $[M+23]^+$.

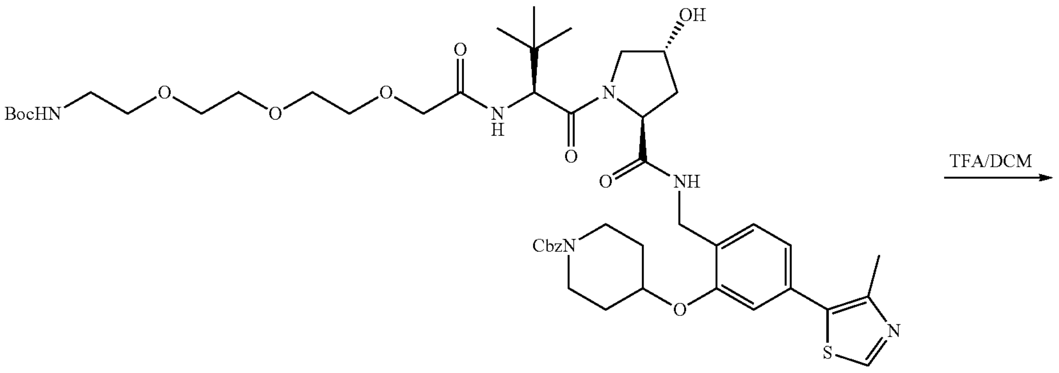

6

-continued

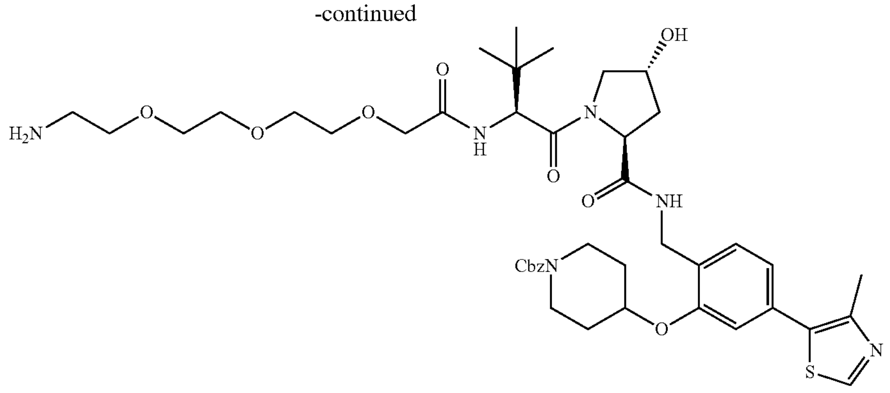

7

A solution of Compound 6 (60.0 mg, 0.0600 mmol) in TFA (1.0 mL)/DCM (4.0 mL) was stirred at 20° C. for 0.5 h. The reaction mixture concentrated to give Compound 7 (52 mg, 85%) as a colorless oil, which was used directly in the next step. LCMS (5-95, AB, 1.5 min): RT (220/254 nm)=0.781 min, m/z=875.1 [M+23]$^+$.

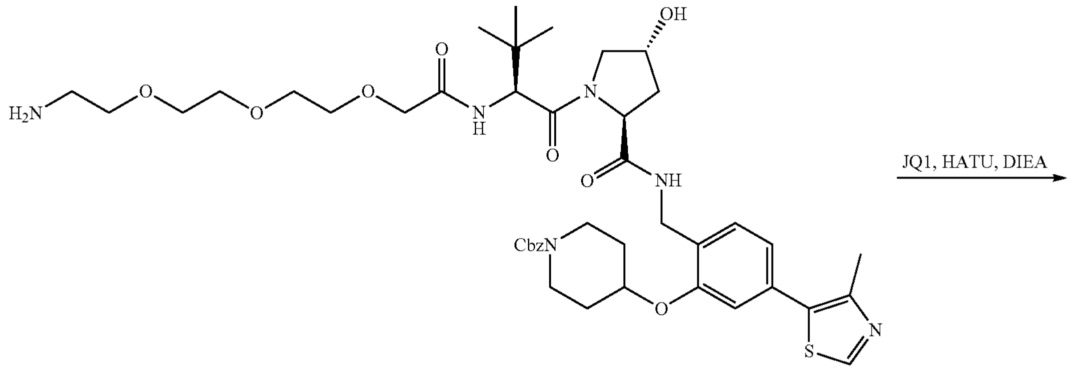

7

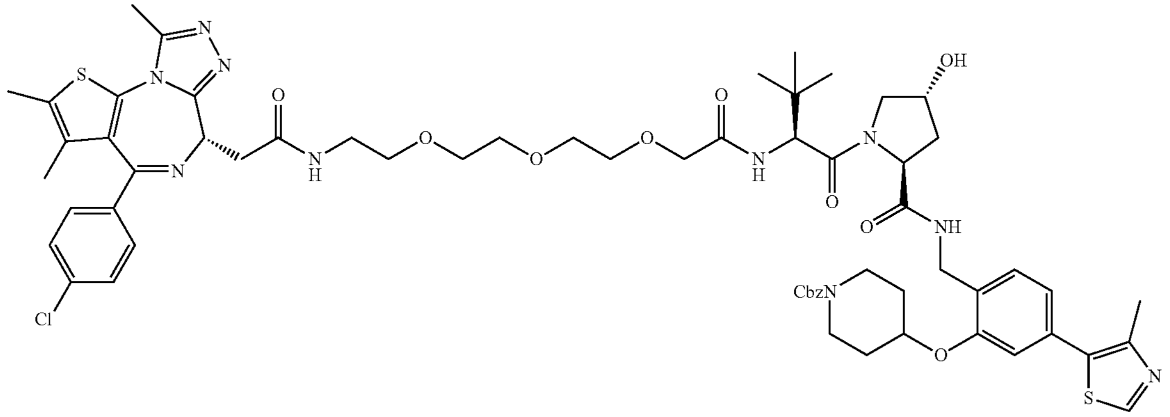

8

To a solution of JQ1 (26.46 mg, 0.0700 mmol) in DMF (10 mL) was added of HATU (40.89 mg, 0.1100 mmol) and DIEA (20.85 mg, 0.1600 mmol) at 20° C. The reaction mixture was stirred at 20° C. for 10 min. Then Compound 7 (52.0 mg, 0.0500 mmol) was added. The reaction mixture was stirred at 20° C. for 12 h. The reaction mixture was diluted with water (5 mL) and extracted with EtOAc (10 mL×3). The organic layer was washed with water (10 mL×2) and brine (10 mL). It was dried over $Na_2SO_4$, filtered, concentrated, and purified by prep-TLC (10% MeOH in DCM, Rf=0.2) to afford Compound 8 (66 mg, 97%) as a yellow solid. LCMS (5-95, AB, 1.5 min): RT (220/254 nm)=0.906 min, m/z=1257.9 [M+23]$^+$.

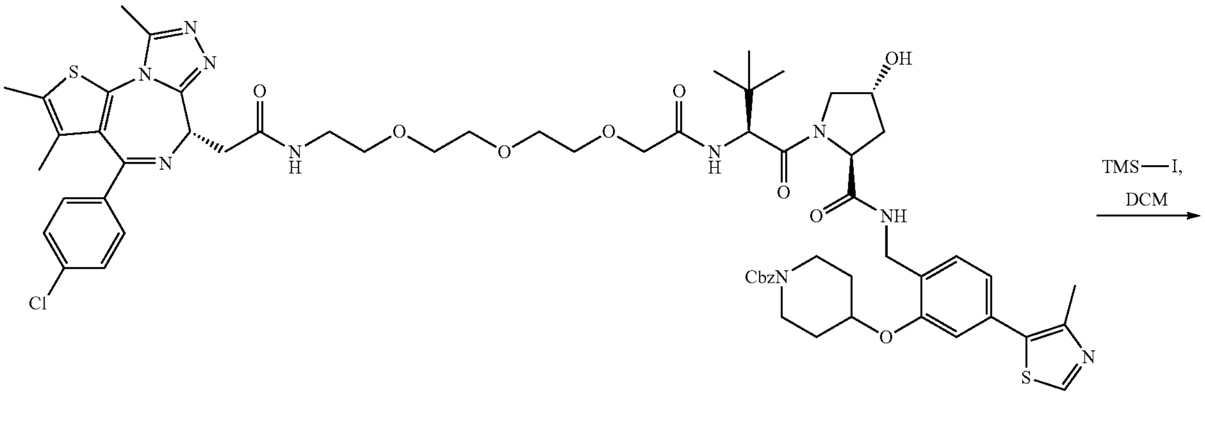
8
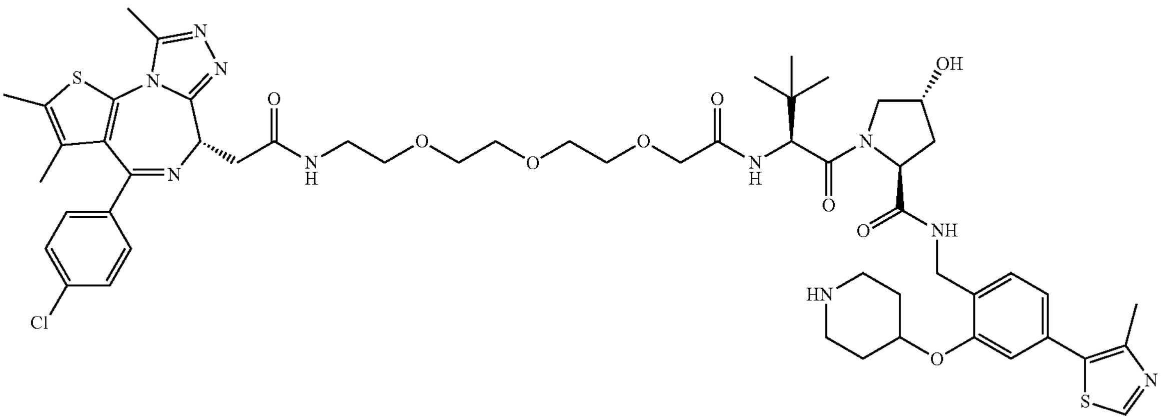
9
TMSI (110.09 mg, 0.5500 mmol) was added to a solution of Compound 8 (68.0 mg, 0.0600 mmol) in DCM (15 mL) at 20° C., and the resulting mixture was stirred at 20° C. for 12 h. $Et_3N$ (2.0 mL) was added and the mixture was stirred at 20° C. for 15 min. The solvents were removed, and the residue was purified by prep-HPLC (acetonitrile 21-51%/0.225% FA in water) to give Compound 9 (15 mg, 24%) as a white solid. LCMS (5-95, AB, 1.5 min): RT (220/254 nm)=0.792 min, m/z=1101.2 $[M+1]^+$.
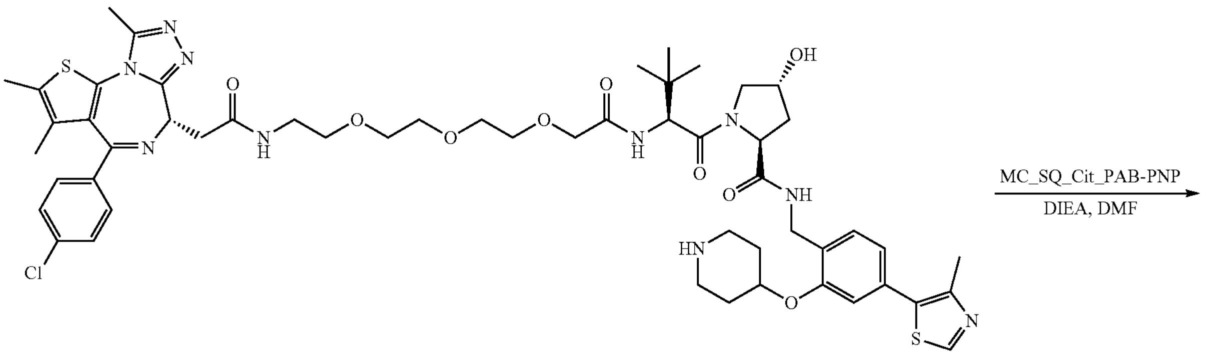
9

-continued
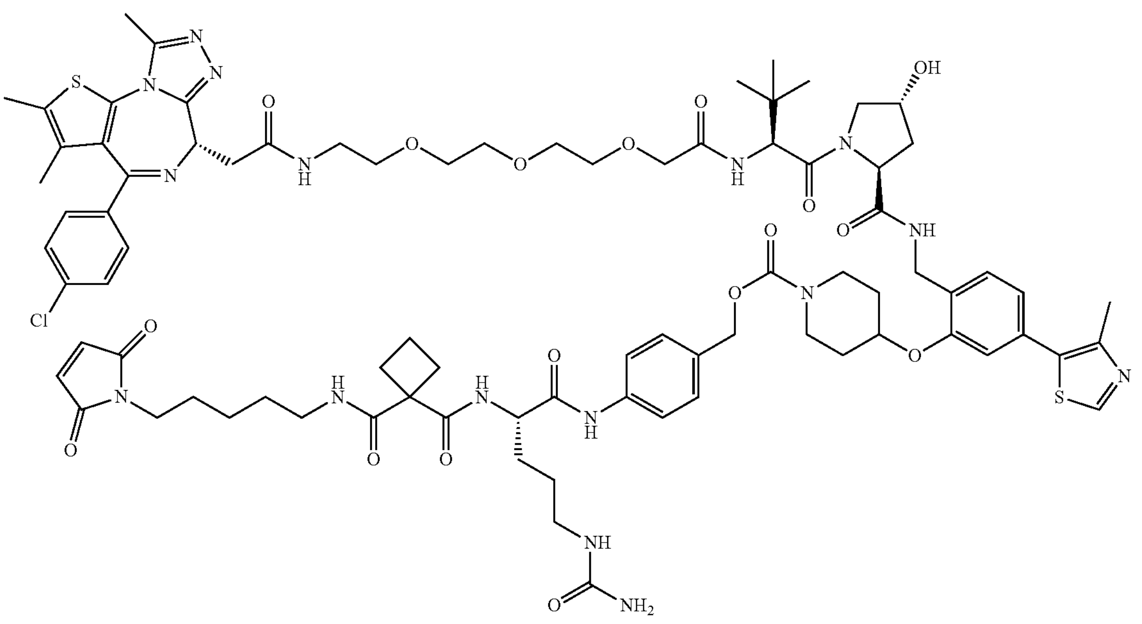
L1BQ8
To a solution of MC_SQ_Cit_PAB-PNP (8.51 mg, 0.0100 mmol) and Compound 9 (8.5 mg, 0.0100 mmol) in DMF (2.0 mL) was added DIEA (0.01 mL, 0.0300 mmol). The mixture was stirred at 20° C. for 12 h. The mixture was purified by prep-HPLC (acetonitrile 12-47/0.225% FA in water) to afford L1BQ8 (1.6 mg, 12%) as a white solid. LCMS (5-95, AB, 1.5 min): RT (220/254 nm)=0.852 min, m/z=850.2 [M/2+1]$^+$.
xxvii. L1BQ9 An exemplary L1-CIDE, L1BQ9, can be synthesized by the following scheme:
Scheme 29
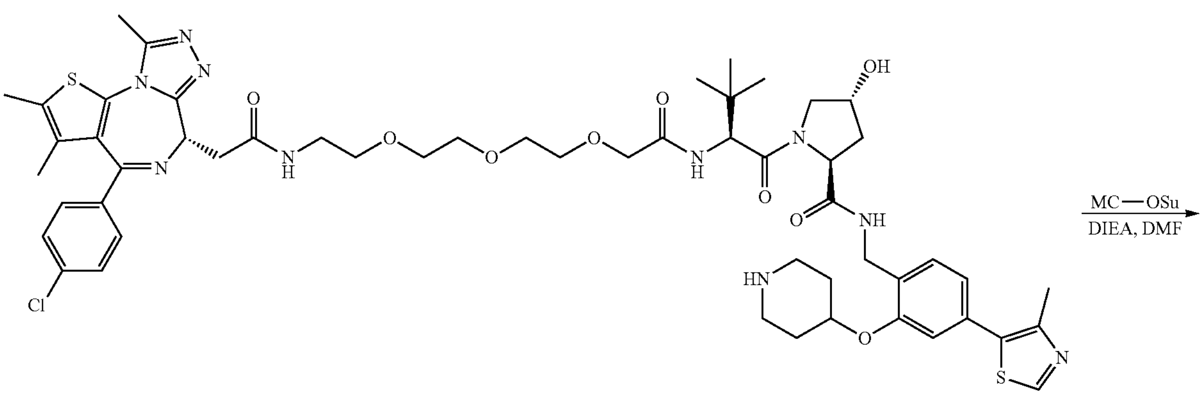

-continued
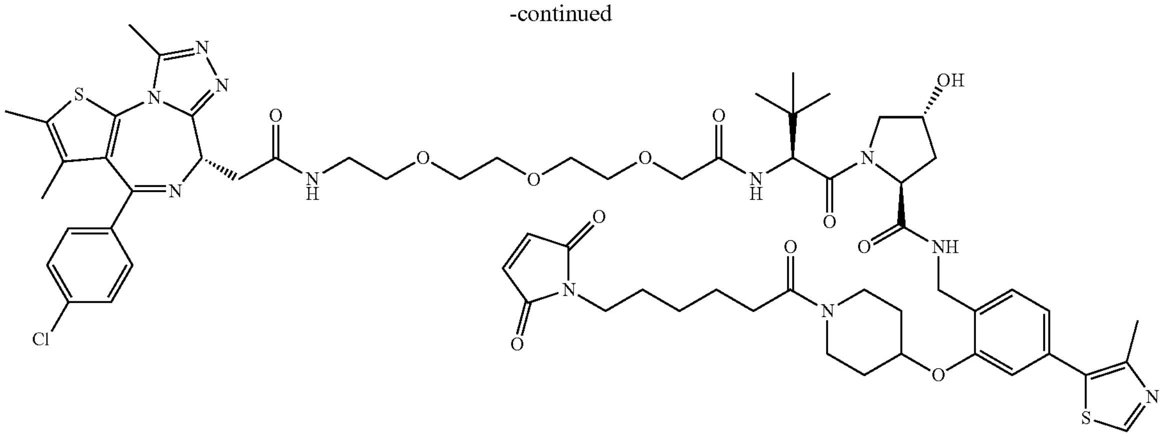
L1BQ9
To a solution of Compound 1 (22.0 mg, 0.0200 mmol) and MC-OSu (9.23 mg, 0.0300 mmol) in DMF (2.0 mL) was added DIEA (7.74 mg, 0.0600 mmol). The mixture was stirred at 20° C. for 3 h. The mixture was purified by prep-HPLC (acetonitrile 38-68/0.225% FA in water) to afford L1BQ9 (4.5 mg, 16.7%) as a white solid. LCMS (5-95, AB, 1.5 min): RT (220/254 nm)=0.867 min, m/z=1294.4 $[M+1]^+$.
xxviii. L1B 10 An exemplary L1-CIDE, L1BQ10, can be synthesized by the following scheme:
Scheme 30
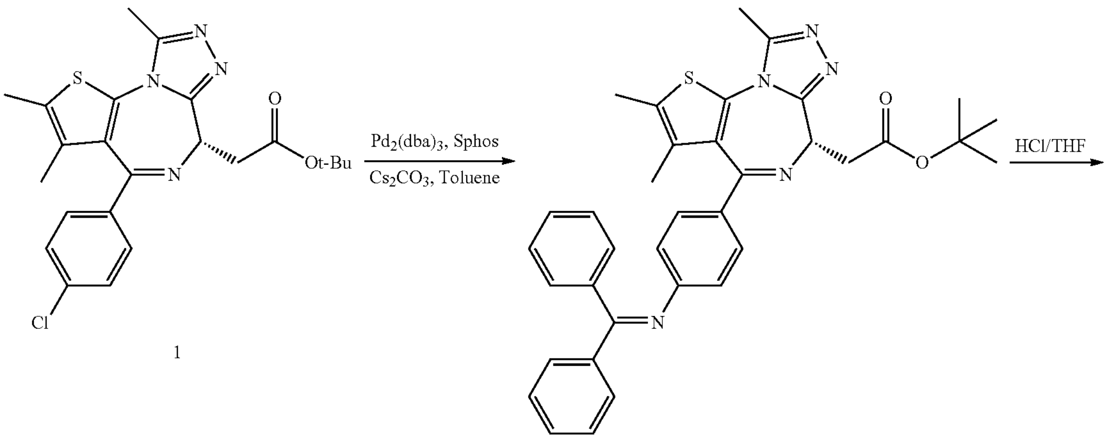
1
2
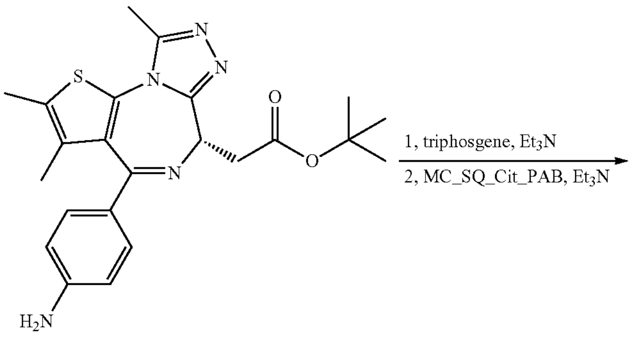
3

-continued
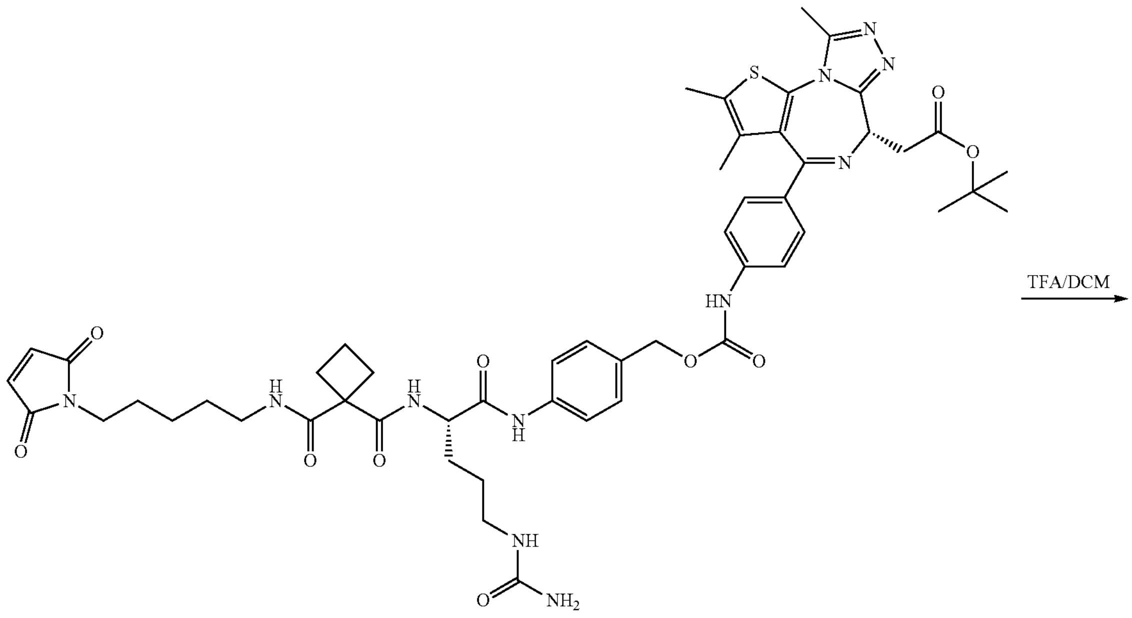
4
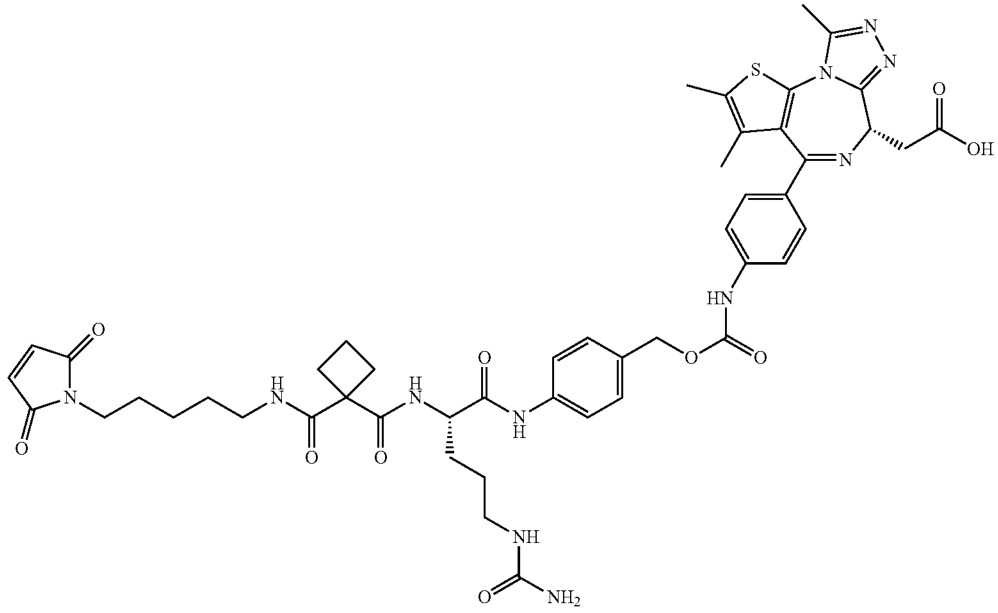
5
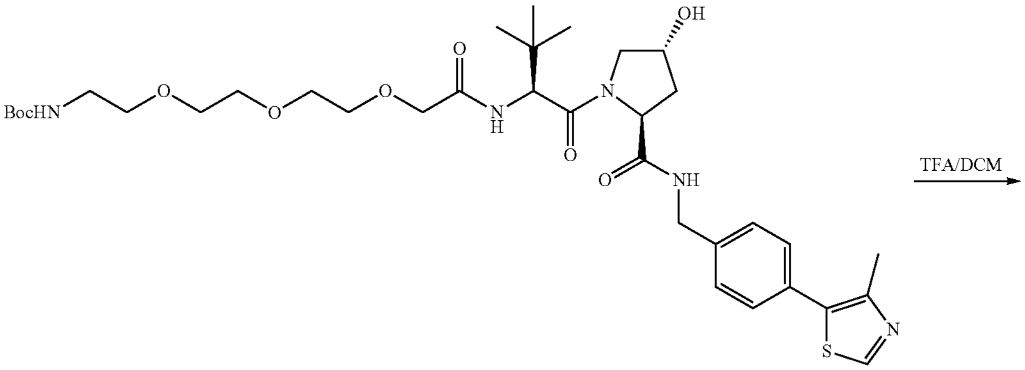
6

-continued
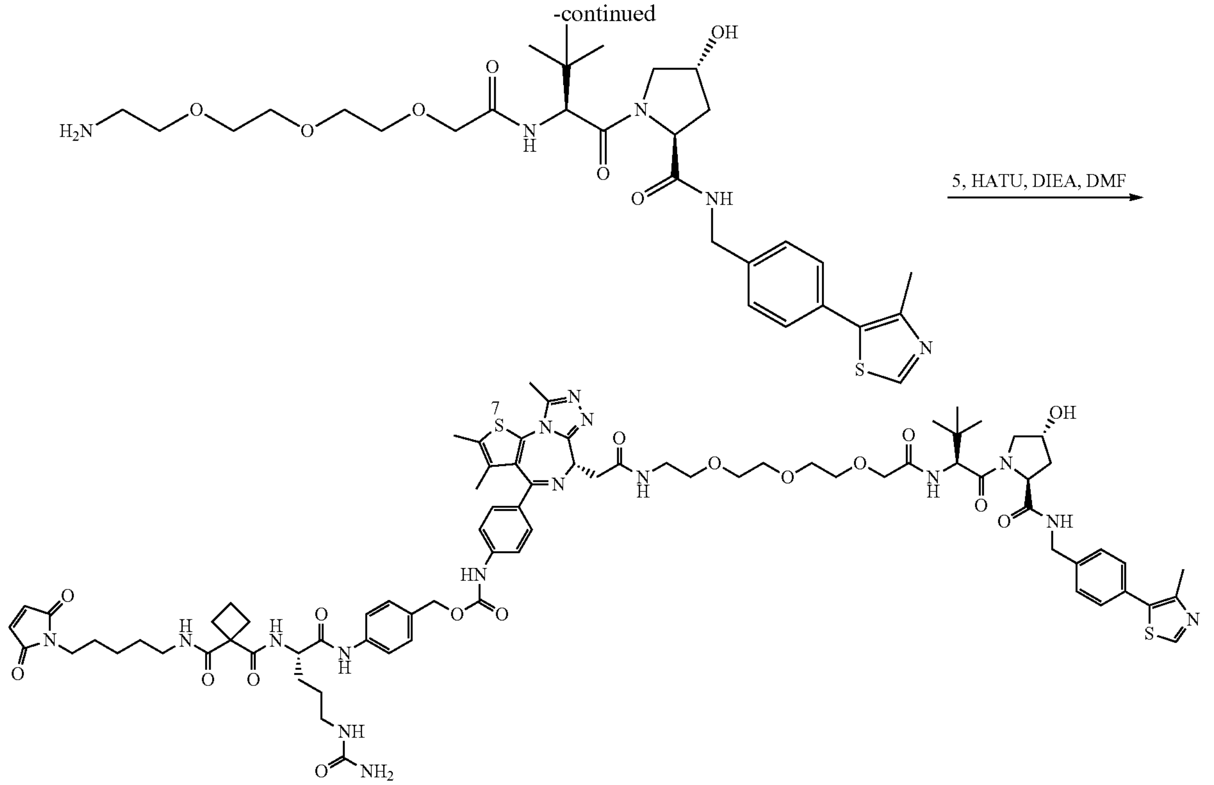
L1BQ10
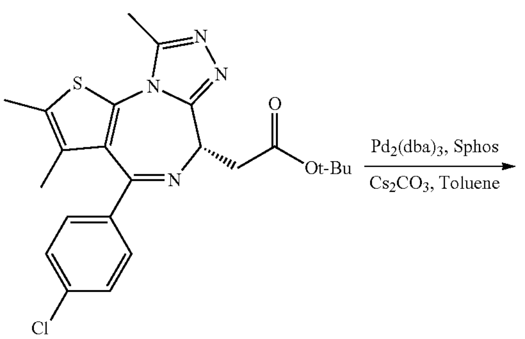
1
A mixture of Compound 1 (300.0 mg, 0.660 mmol), benzophenone imine (178.46 mg, 0.980 mmol), $Pd_2(dba)_3$ (60.11 mg, 0.0700 mmol), S-Phos (26.95 mg, 0.0700 mmol), $Cs_2CO_3$ (641.7 mg, 1.97 mmol) in toluene (20 mL) was stirred for 16 h at 110° C. under $N_2$. Solvent was removed to give the crude product which was purified by flash column (0-50% EtOAc in petroleum) to give compound 2 (350 mg, 60%) as a yellow oil. LCMS (5-95, AB, 1.5 min): RT (220/254 nm)=1.050 min, m/z=602.2 $[M+1]^+$.
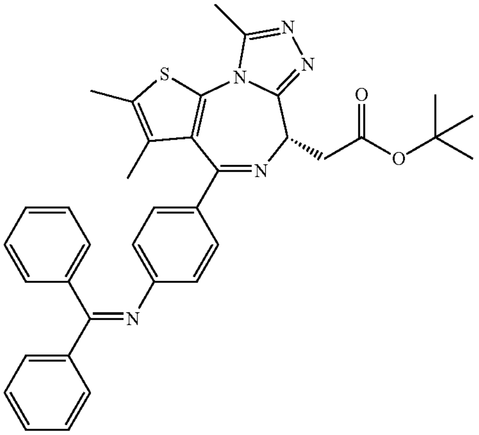
2
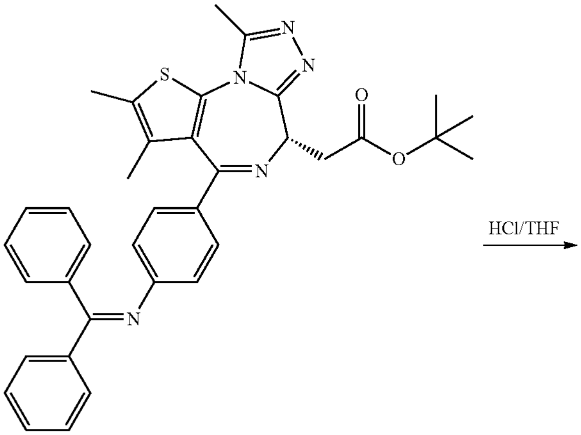
2

-continued
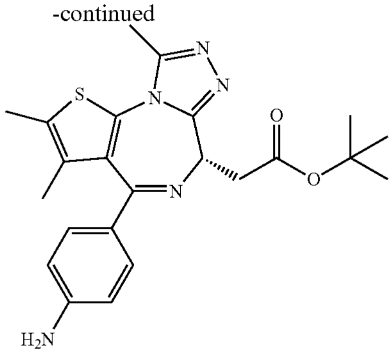
3
A mixture of Compound 2 (350.0 mg, 0.580 mmol) in THF (20 mL) and HCl (1.0 M, 5.0 mL) was stirred at 20° C. for 3 h. The mixture was diluted with EtOAc (20 mL) and the organic layer was separated. The organic layer was concentrated and purified by prep-TLC (5% MeOH in DCM, Rf=0.5) to give Compound 3 (250 mg, 94.5%) as a yellow oil. LCMS (5-95, AB, 1.5 min): RT (220/254 nm)=0.739 min, m/z=460.0 $[M+23]^+$.
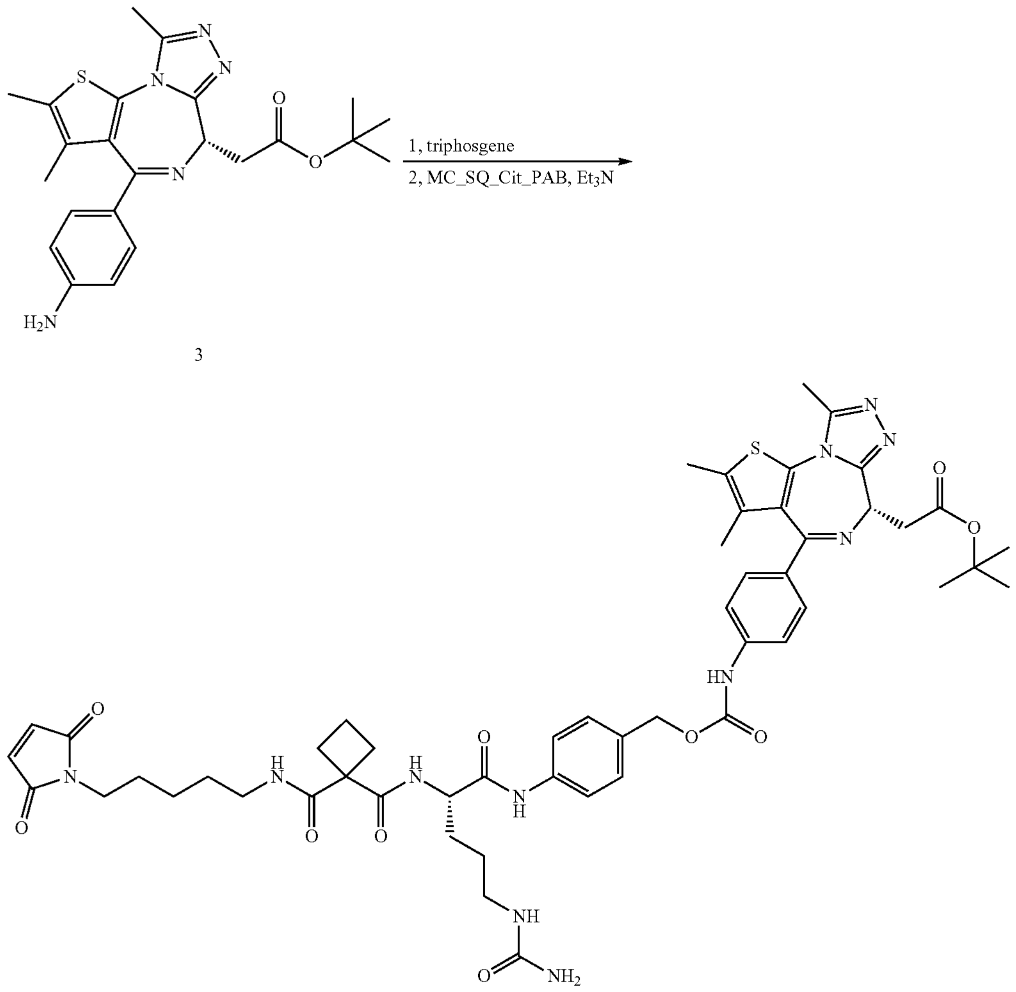
3
4

To a solution of triphosgene (27.13 mg, 0.0900 mmol) in THF (5.0 mL) was added a solution of Compound 3 (40.0 mg, 0.0900 mmol) in THF (5.0 mL) at 20° C. under $N_2$. The reaction mixture was stirred at 40° C. for 2 h. This reaction mixture was concentrated to give the crude product (40 mg) as a yellow solid, which was used directly in the next step. LCMS (5-95, AB, 1.5 min): RT (220/254 nm)=0.849 min, m/z=496.1 $[M+1]^+$ (quenched with MeOH). To solution of above product (40.0 mg, 0.0900 mmol) in DCM (5.0 mL) was added a solution of MC_SQ_Cit_PAB (59.09 mg, 0.1000 mmol) and $Et_3N$ (26.2 mg, 0.260 mmol) in DMF (1 mL) at 20° C. The reaction mixture was stirred at 20° C. for 4 h. This reaction was concentrated and purified by prep-HPLC (acetonitrile 44-74%/0.225% FA in water) to give Compound 4 (7 mg, 8%) as a yellow solid. LCMS (5-95, AB, 1.5 min): RT (220/254 nm)=0.856 min, m/z=1056.2 $[M+23]^+$.

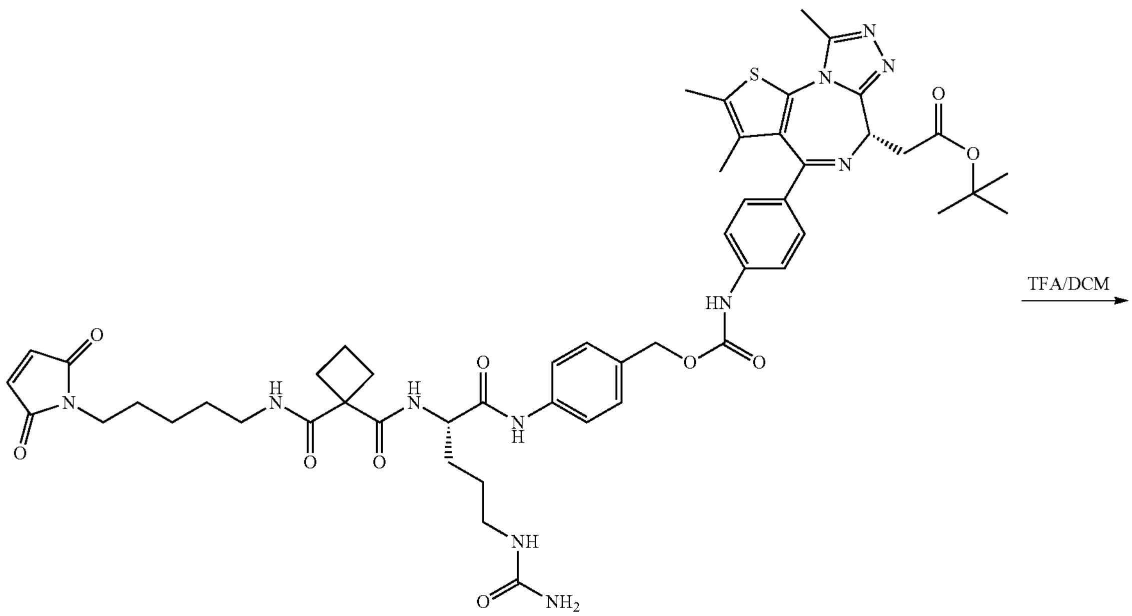

4

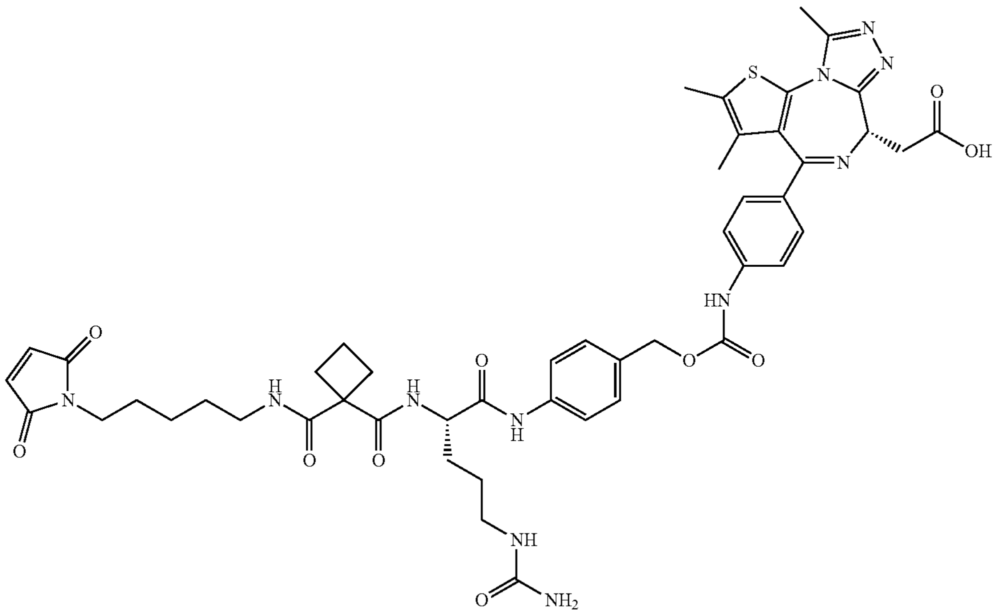

5

A solution of Compound 4 (10.0 mg, 0.0100 mmol) in TFA (2.0 mL)/DCM (2 mL) was stirred at 20° C. for 2 h. The reaction mixture concentrated to give Compound 5 (9.4 mg, 100%) as a yellow solid, which was used directly in the next step. LCMS (5-95, AB, 1.5 min): RT (220/254 nm)=0.780 min, m/z=978.2 $[M+1]^+$.

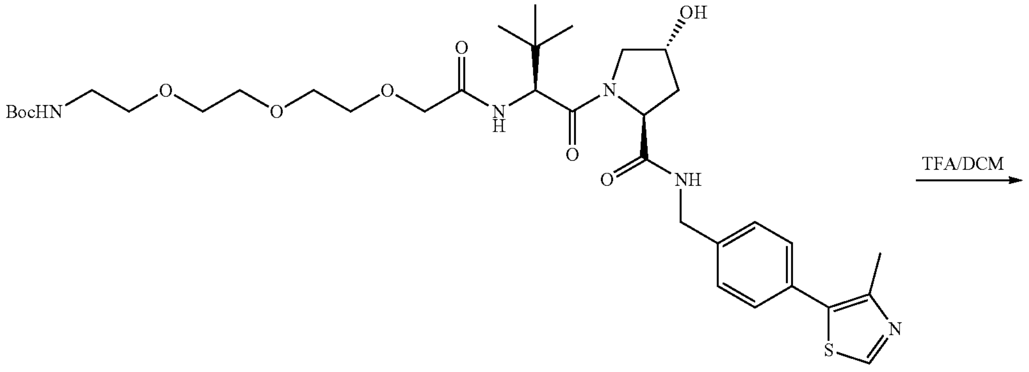

6

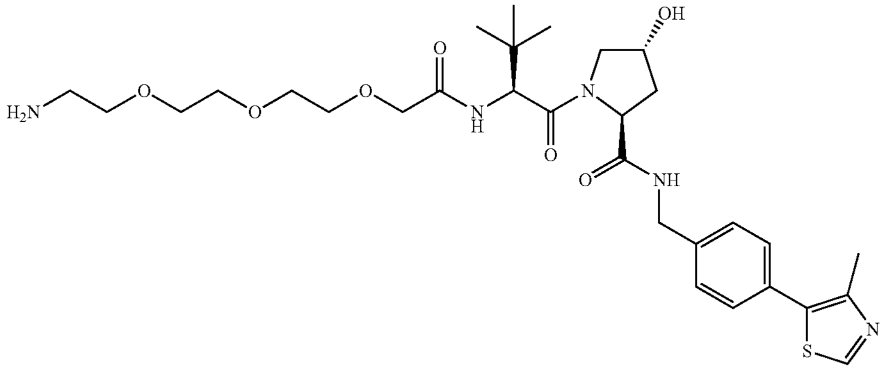

7

A solution of Compound 6 (45.0 mg, 0.0600 mmol) in TFA (1 mL)/DCM (5 mL) was stirred at 20° C. for 2 h. The reaction mixture was concentrated to give Compound 7 with TFA salt (38.7 mg, 85%) as a yellow solid, which was used directly in the next step. LCMS (5-95, AB, 1.5 min): RT (220/254 nm)=0.692 min, m/z=620.1 $[M+1]^+$.

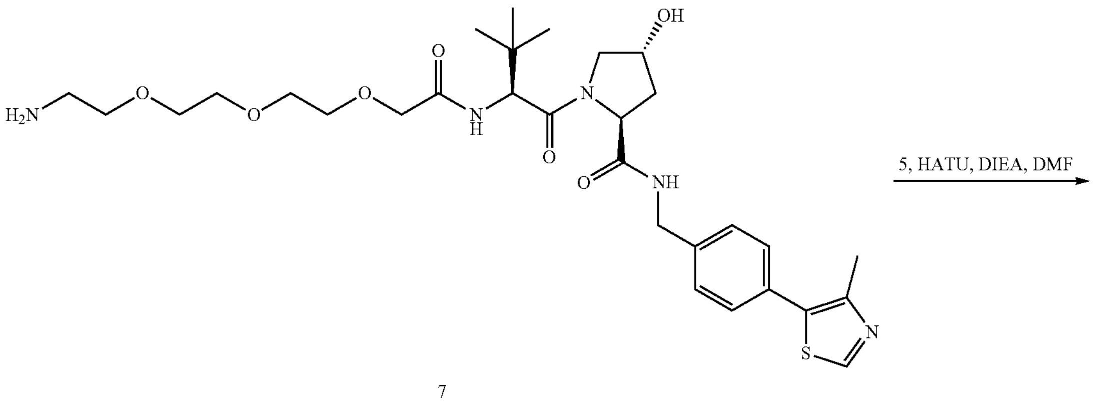

7

-continued

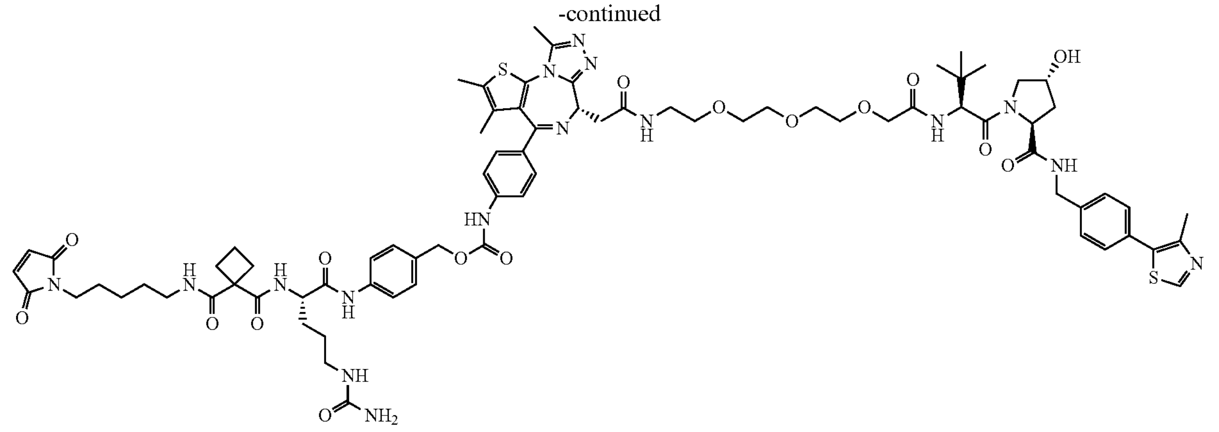

L1BQ10

To a solution of Compound 5 (9.4 mg, 0.0100 mmol) in DMF (5.0 mL) was added HATU (4.39 mg, 0.0100 mmol) and DIEA (3.73 mg, 0.0300 mmol) at 20° C. The reaction mixture was stirred at 20° C. for 10 min. Then Compound 7 (8.46 mg, 0.0100 mmol) was added and the formed mixture was stirred at 20° C. for 12 h. The mixture was purified by prep-HPLC (acetonitrile 30-60%/0.225% FA in MeCN) to afford L1BQ10 (1.8 mg, 12%) as a yellow solid. LCMS (5-95, AB, 1.5 min): RT (220/254 nm)=0.823 min, m/z=790.6 [M/2+1]$^+$.

xxix. L1BQ11 An exemplary L1-CIDE, L1BQ11, can be synthesized by the following

Scheme 31

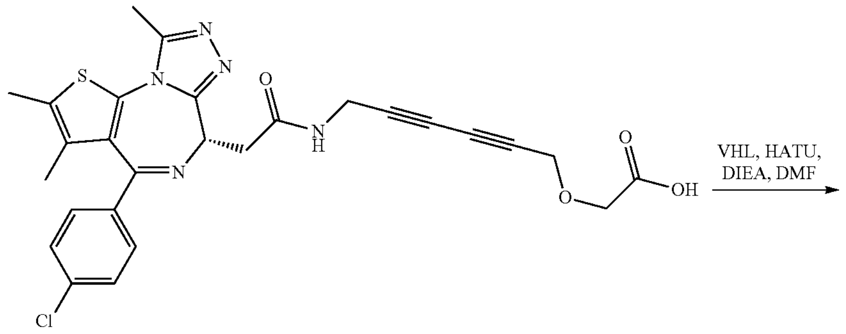

1

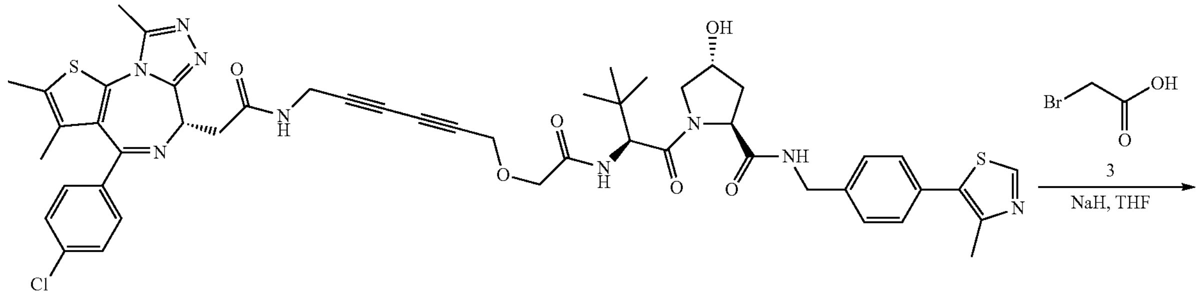

2

-continued
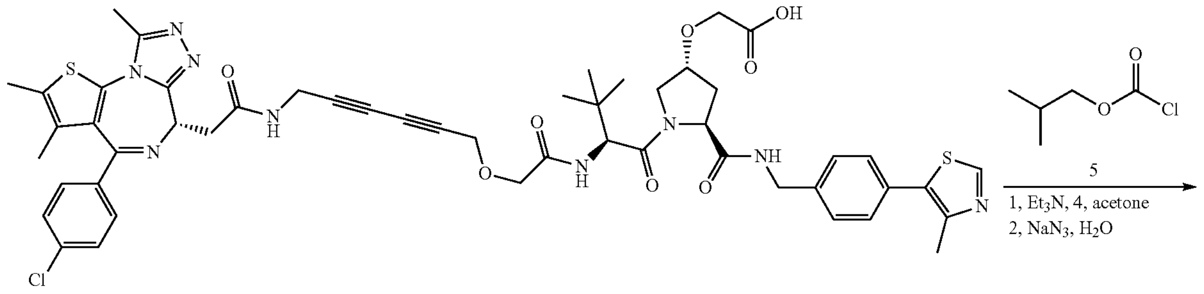
4
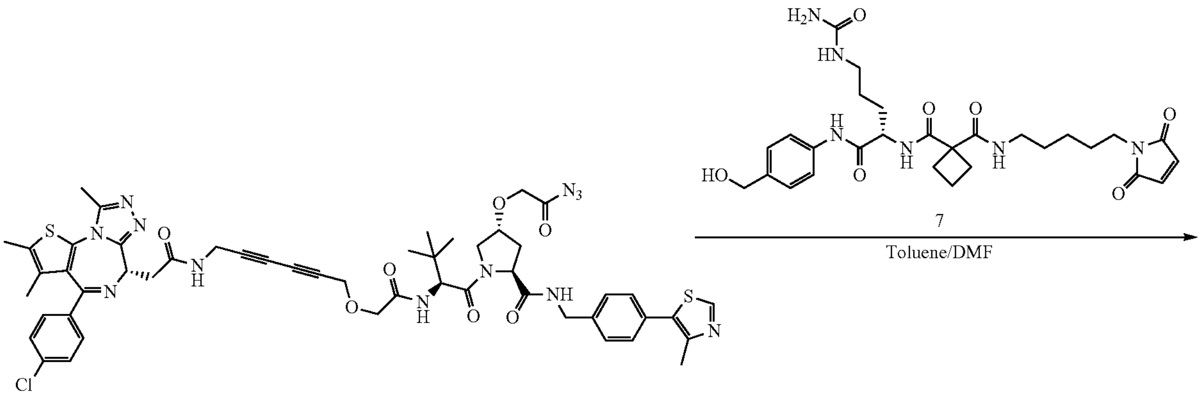
6
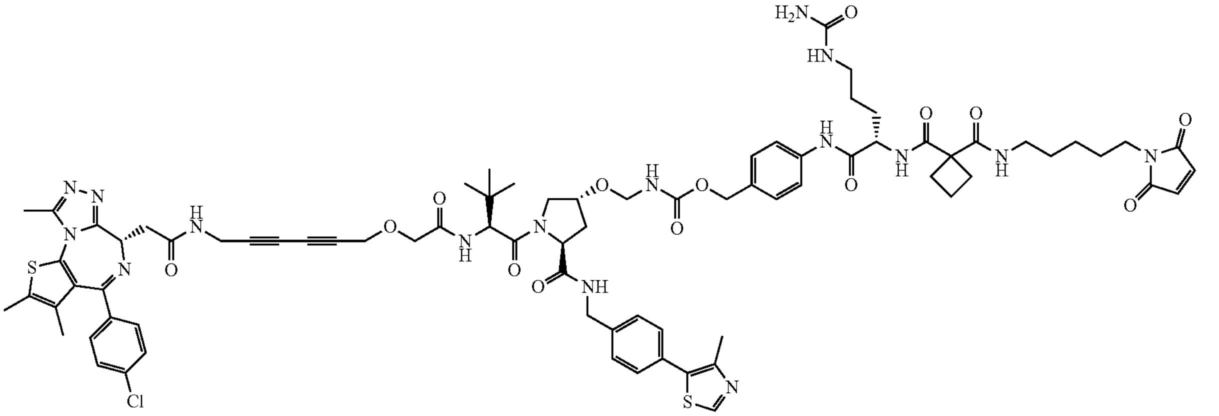
L1BQ11
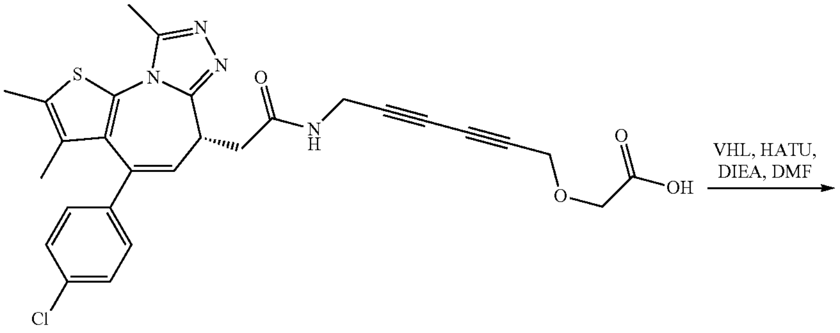
1

-continued

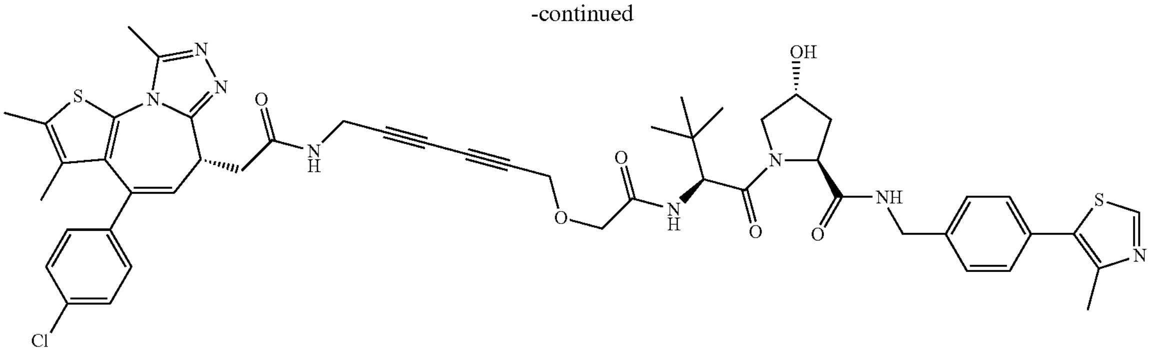

2

To a solution of compound 1 (45.0 mg, 0.0800 mmol) in anhydrous DMF (4.0 mL) was added HATU (37.33 mg, 0.1000 mmol) and DIEA (31.72 mg, 0.2500 mmol). The solution was stirred at 25° C. for 15 min, then VHL ligand (42.03 mg, 0.0900 mmol) was added. The resulting reaction solution was stirred at 25° C. for another 1 h. The mixture was purified by prep-HPLC (Xtimate C18 150*25 mm*5 um, acetonitrile 40-70/0.225% FA in water) to afford compound 2 (46 mg, 58%) as a pale yellow solid. LCMS (5-95, AB, 1.5 min): RT=0.835 min, m/z=962.3 $[M+1]^+$. $^1$H NMR (400 MHz, DMSO-d6) δ 8.98 (s, 1H), 8.78 (t, J=4.2 Hz, 1H), 8.60 (t, J=6.0 Hz, 1H), 7.55 (d, J=9.6 Hz, 1H), 7.49-7.40 (m, 8H), 4.57-4.35 (m, 6H), 4.27-4.21 (m, 1H), 4.11-4.01 (m, 4H), 3.68-3.59 (m, 3H), 3.31-3.19 (m, 2H), 2.59 (s, 3H), 2.52-2.51 (m, 1H), 2.44 (m, 3H), 2.40 (s, 3H), 2.08-2.03 (m, 1H), 1.92-1.86 (m, 1H), 1.61 (s, 3H), 0.93 (s, 9H).

A mixture of compound 2 (100.0 mg, 0.1000 mmol) and NaH (16.62 mg, 0.420 mmol) in THF (5.0 mL) was stirred at 20° C. for 1 h and then compound 3 (21.65 mg, 0.1600 mmol) in THF (1.0 mL) was added dropwise. The mixture was stirred at 20° C. for 2 h. The reaction was quenched with Sat.aq $NH_4Cl$ (10 mL) and acidified to pH=4.0 with HCl solution (2.0 M). The resulting mixture was extracted with a solution of MeOH in DCM (10%, 20 mL×3). The organic layers were washed with brine (20 mL), dried over anhydrous $Na_2SO_4$ and filtered. The filtrate was concentrated to give the crude compound 4 (100 mg, 94.3%) as a light yellow oil. LCMS (5-95, AB, 1.5 min): RT=0.885 min, m/z=1042.1 $[M+23]^+$.

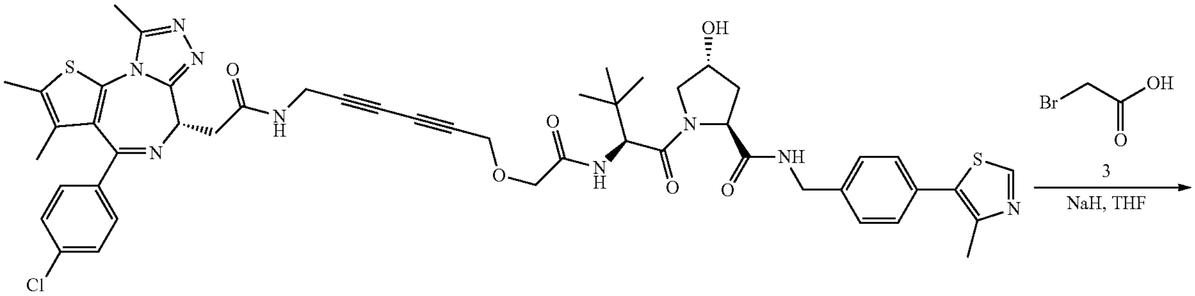

2

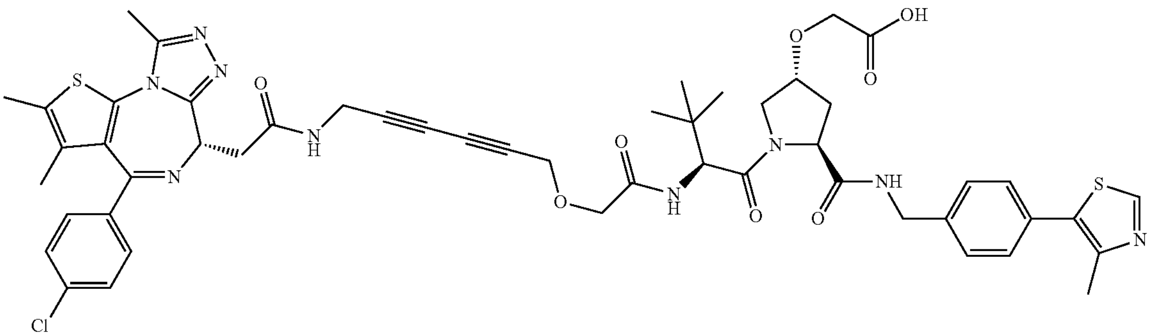

4

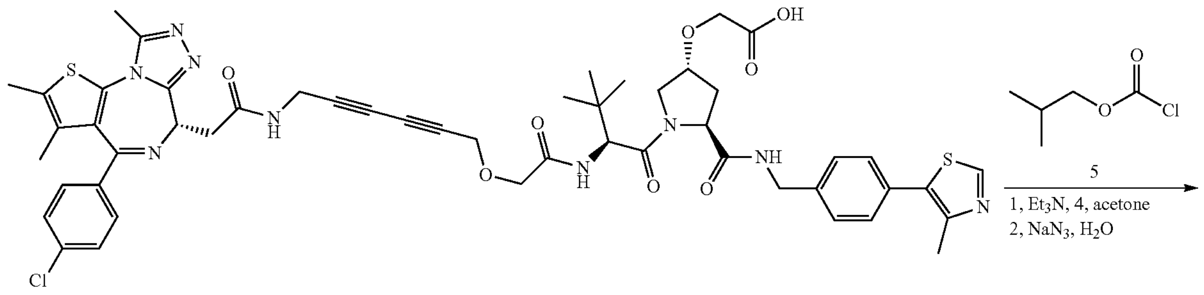

4

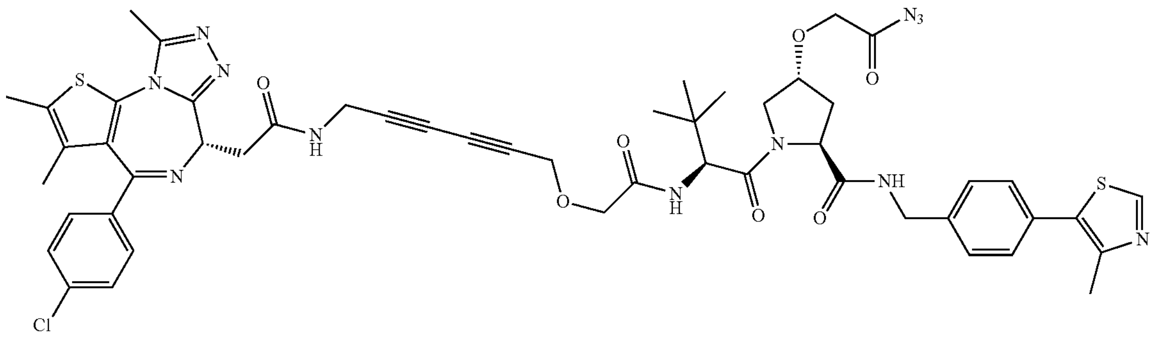

6

To a solution of compound 4 (60.0 mg, 0.0600 mmol) and $Et_3N$ (7.14 mg, 0.0700 mmol) in acetone (3.0 mL) was added compound 5 (9.64 mg, 0.0700 mmol) at 20° C., and the mixture was stirred at 20° C. for 10 min, then $NaN_3$ (7.64 mg, 0.1200 mmol) in water (1.0 mL) was added dropwise. The resulted mixture was stirred at 20° C. for 1 h and water (5.0 mL) was added. The mixture was extracted with toluene (2 mL×2). The combined toluene layers were dried over $Na_2SO_4$ and filtered. The filtrate was treated with 4 A molecular sieves and used directly in the next step.

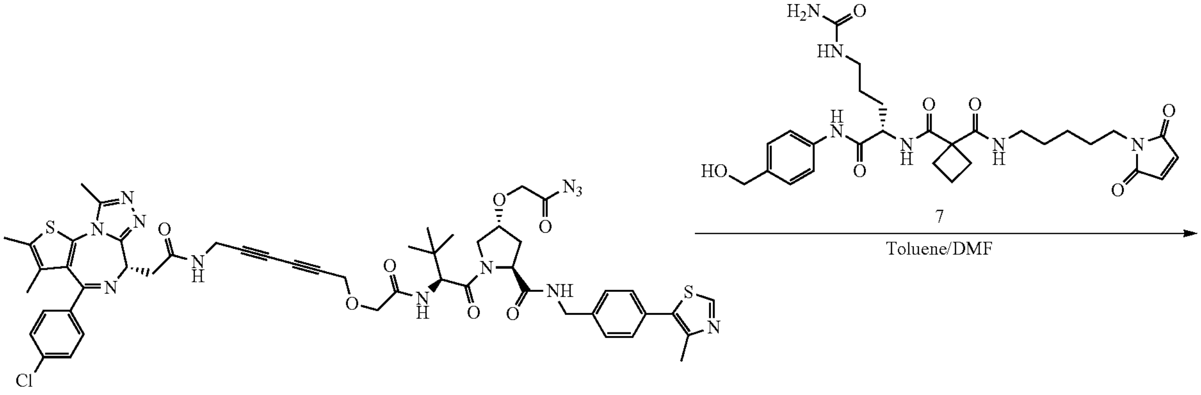

6

-continued

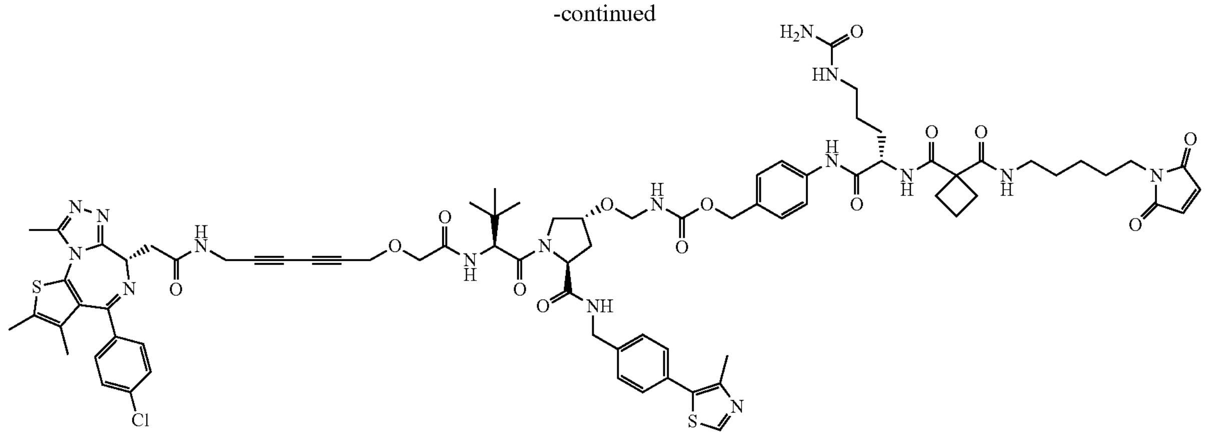

L1BQ11

To above toluene solution was added compound 7 (33.29 mg, 0.0600 mmol) in DMF (1.0 mL) and dibutyltin dilaurate (3.68 mg, 0.0100 mmol) at 20° C. The reaction mixture was stirred at 60° C. for 1 h, concentrated, and purified by prep-TLC (10% MeOH in DCM, Rf=0.4) and prep-HPLC (acetonitrile 28-53/10 mM $NH_4HCO_3$ in water) to afford L1BQ11 (3 mg, 3.2%) as a white solid. LCMS (5-95, AB, 1.5 min): RT=0.783 min, m/z=794.6 $[M/2+1]^+$.

xxx. L1BQ12 An exemplary L1-CIDE, L1BQ12, can be synthesized by the following scheme.

Scheme 32

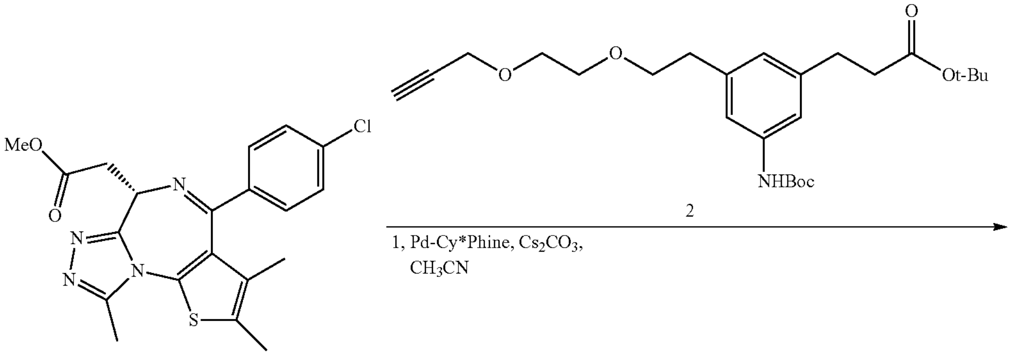

1

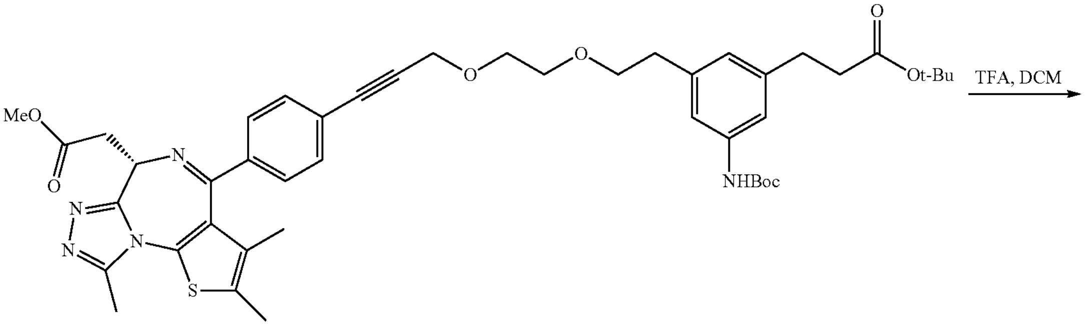

3

-continued
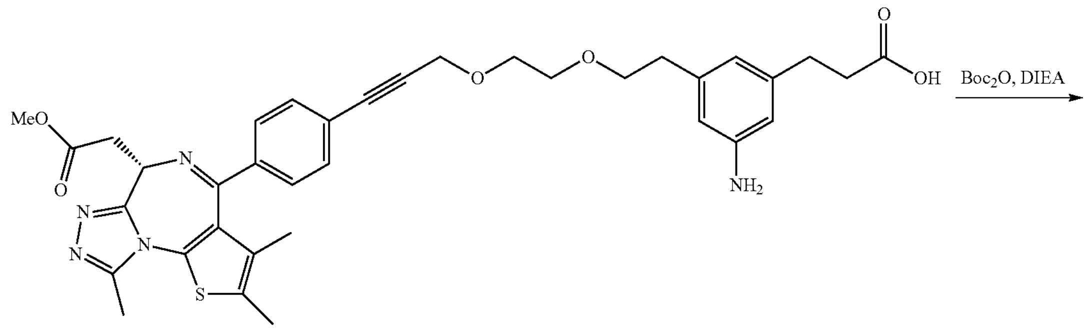
4
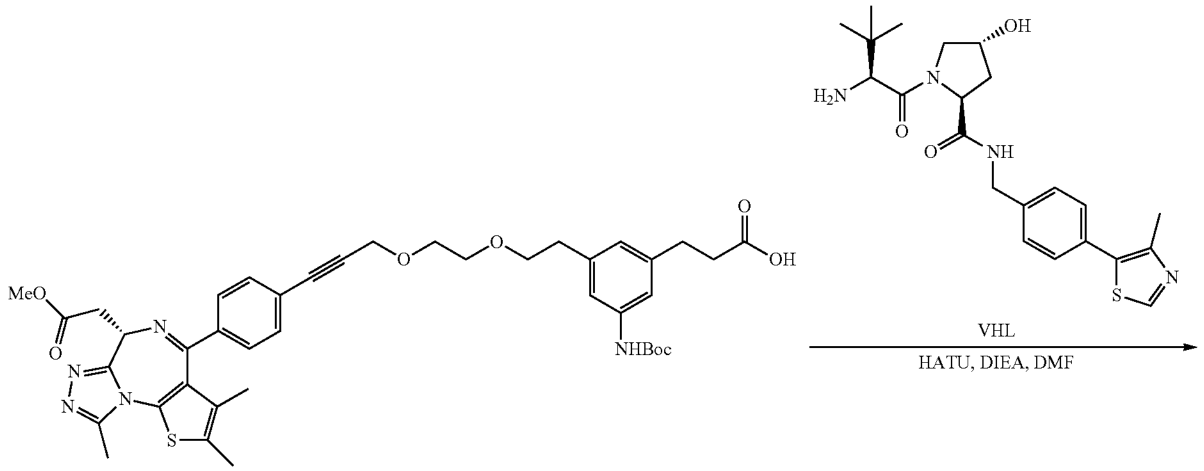
5
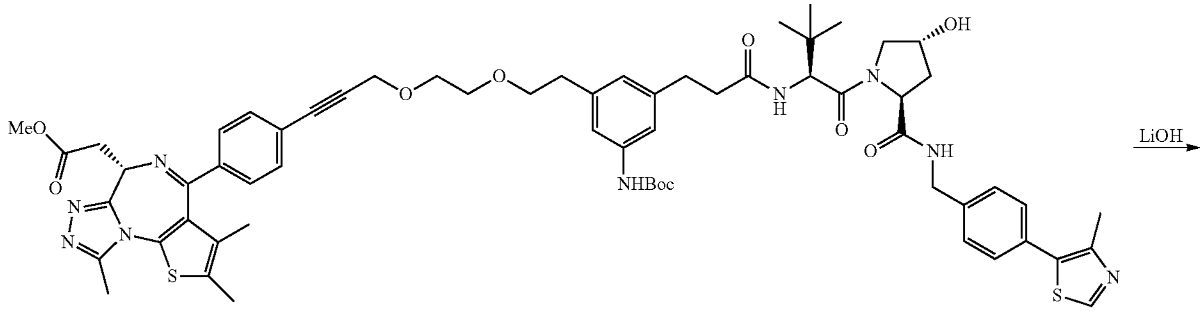
6
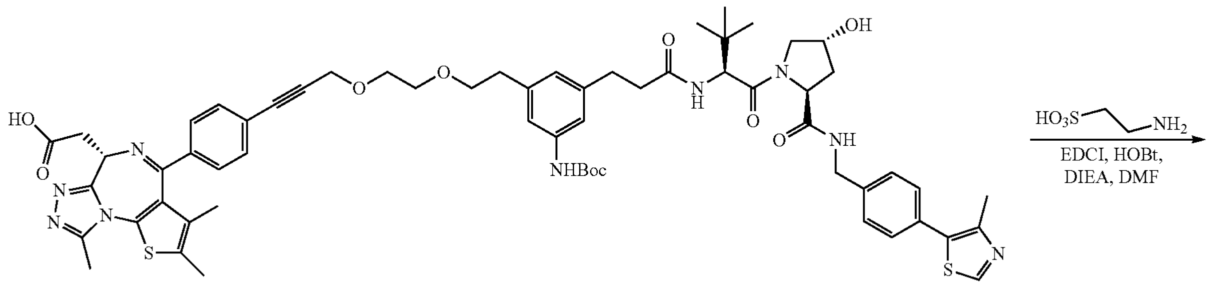
7

-continued
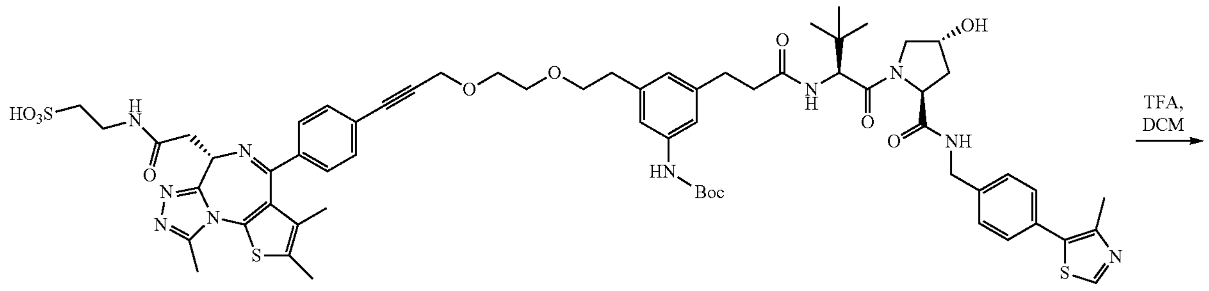
8
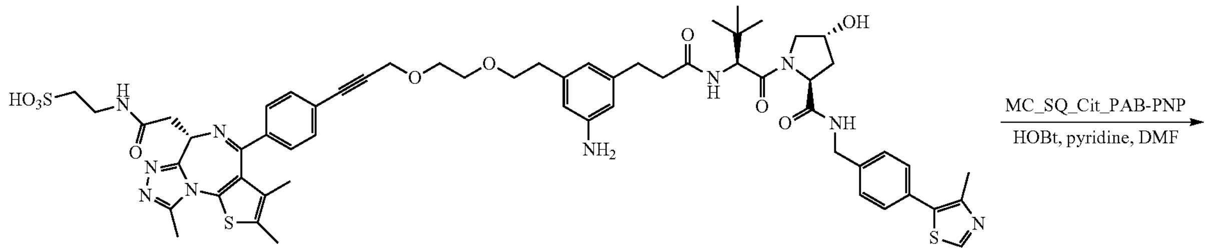
9
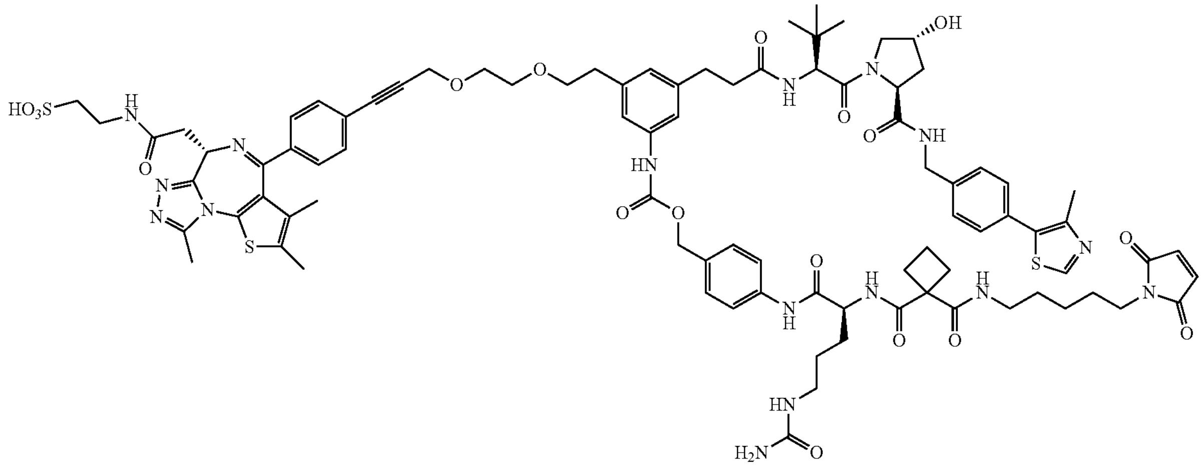
L1BQ12
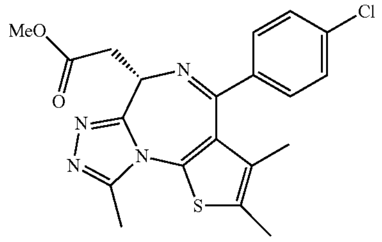
1
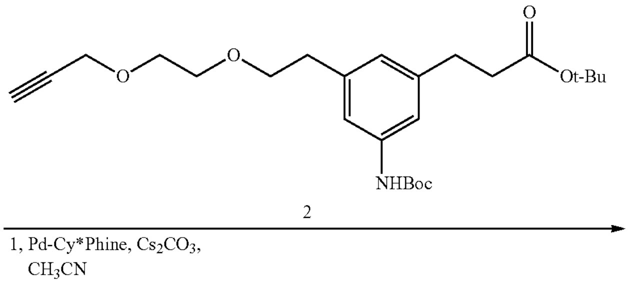

-continued

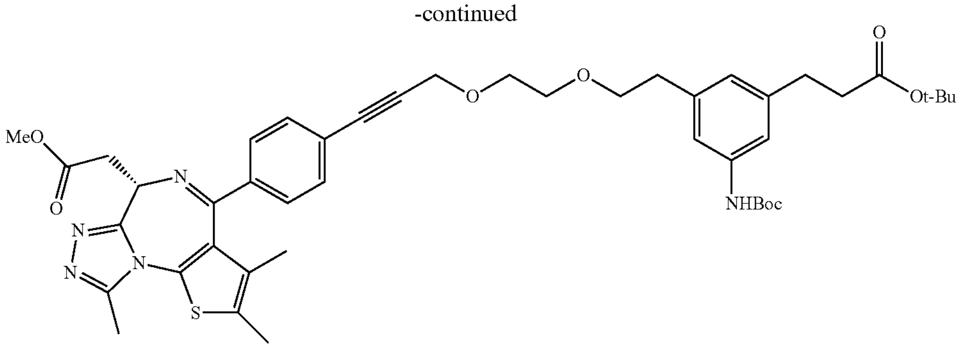

3

To a mixture of Compound 1 (45.0 mg, 0.1100 mmol) in $CH_3CN$ (4.0 mL) was added Pd-Cy*Phine (6.96 mg, 0.0100 mmol), $Cs_2CO_3$ (106.01 mg, 0.3300 mmol) and Compound 2 (97.08 mg, 0.2200 mmol). After the mixture was stirred at 100° C. in microwave under $N_2$ for 1 h, it was filtered, concentrated and purified by flash chromatography on silica (0-100% EtOAc in petroleum ether, Rf=0.3) to give Compound 3 (70 mg, 74%) as a brown solid. LCMS (5-95, AB, 1.5 min): RT (220/254 nm)=1.017 min, m/z=848.1 $[M+23]^+$.

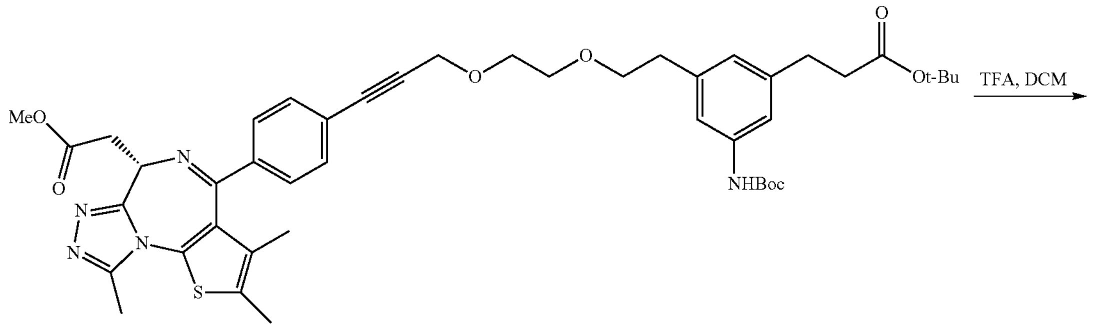

3

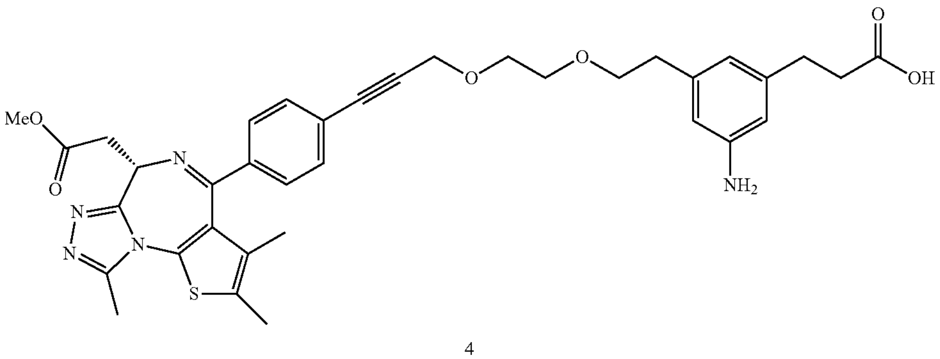

4

A mixture of Compound 3 (70.0 mg, 0.0800 mmol) in DCM (4.5 mL) was added TFA (1.5 mL, 0.1700 mmol) at 0° C. and stirred at 25° C. for 2 h. The reaction mixture was concentrated to give Compound 4 (56 mg, 98.7%) as a brown oil. LCMS (5-95, AB, 1.5 min): RT (220/254 nm)=0.775 min, m/z=692.1 $[M+23]^+$.

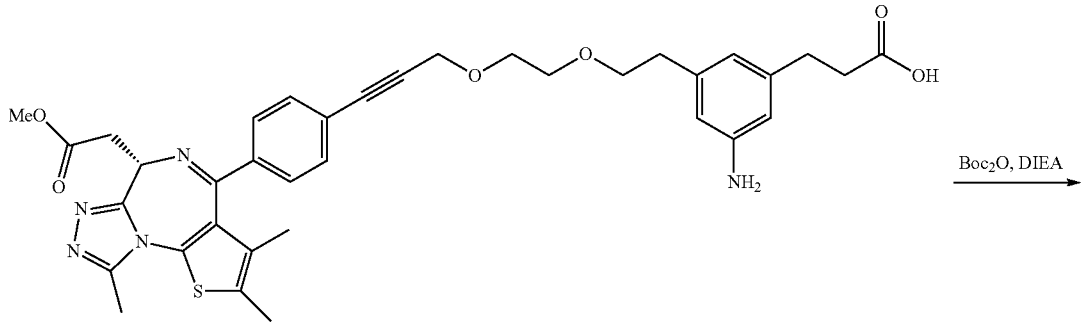
4
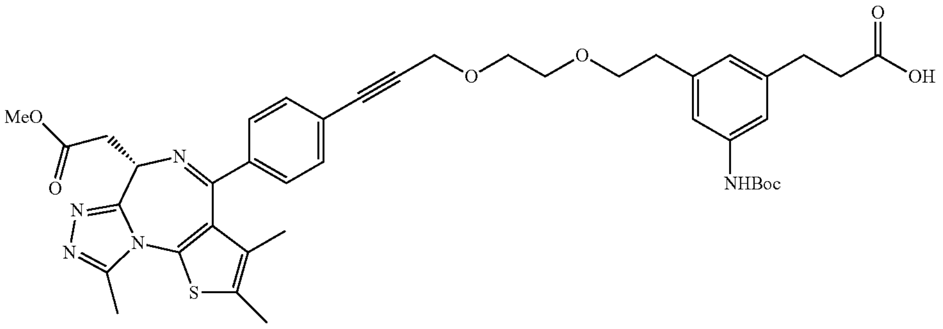
5
To a solution of Compound 4 (40.0 mg, 0.0600 mmol) in DCM (5.0 mL) was added DIEA (23.15 mg, 0.1800 mmol) and $Boc_2O$ (26.07 mg, 0.1200 mmol). The mixture was stirred at 25° C. for 16 h. The mixture was concentrated and purified by flash column chromatography (0-5% MeOH in DCM, Rf=0.5) to afford Compound 5 (35 mg, 62%) as a colorless oil. LCMS (5-95, AB, 1.5 min): RT (220/254 nm)=0.908 min, m/z=770.1 $[M+1]^+$.
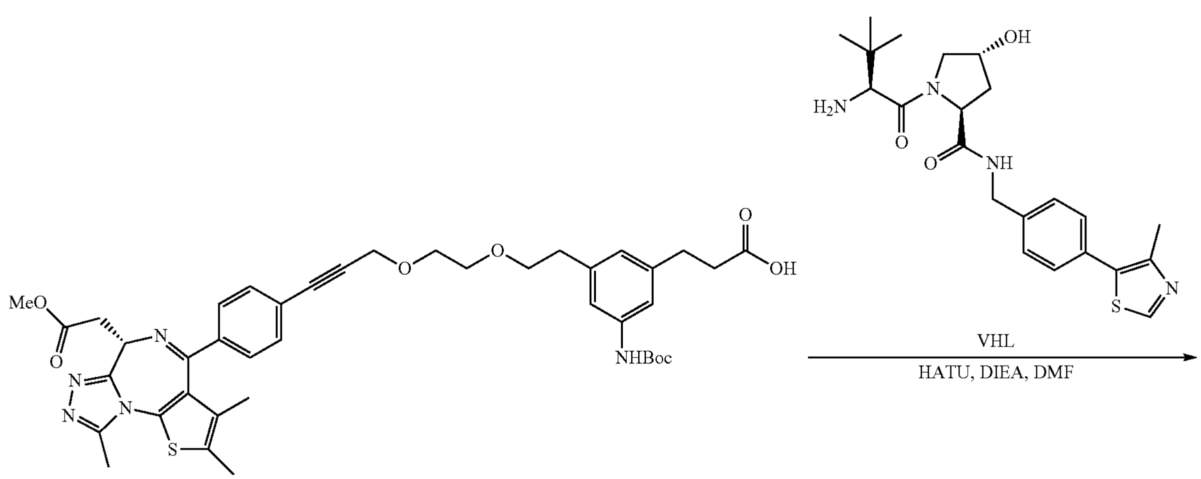
5

-continued

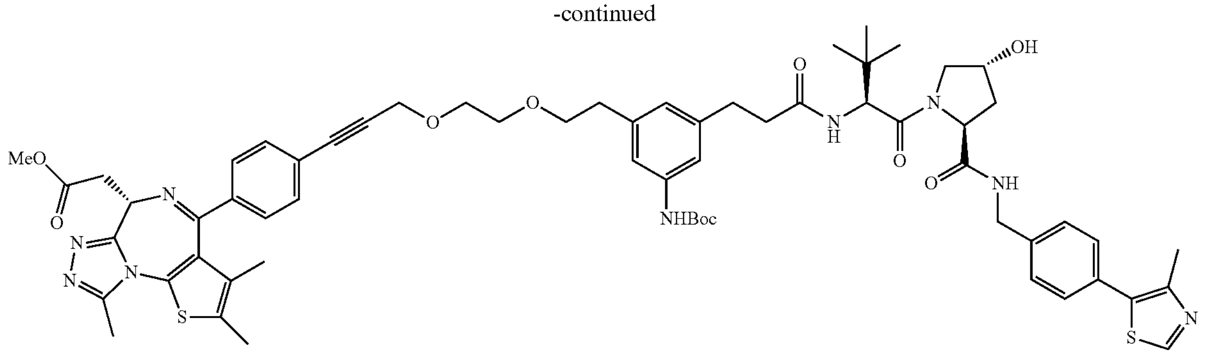

6

To a solution of Compound 5 (35.0 mg, 0.050 mmol), VHL ligand (29.36 mg, 0.0700 mmol) and HATU (20.74 mg, 0.0500 mmol) in DMF (5 mL) was added DIEA (0.04 mL, 0.230 mmol) and the reaction solution was stirred at 25° C. for 2 h. The reaction mixture was filtered and concentrated and purified by prep-TLC (10% MeOH in DCM, Rf=0.4) to give Compound 6 (30 mg, 48%) as a white solid. LCMS (5-95, AB, 1.5 min): RT (220/254 nm)=0.933 min, m/z=1205.1 [M+23]$^+$.

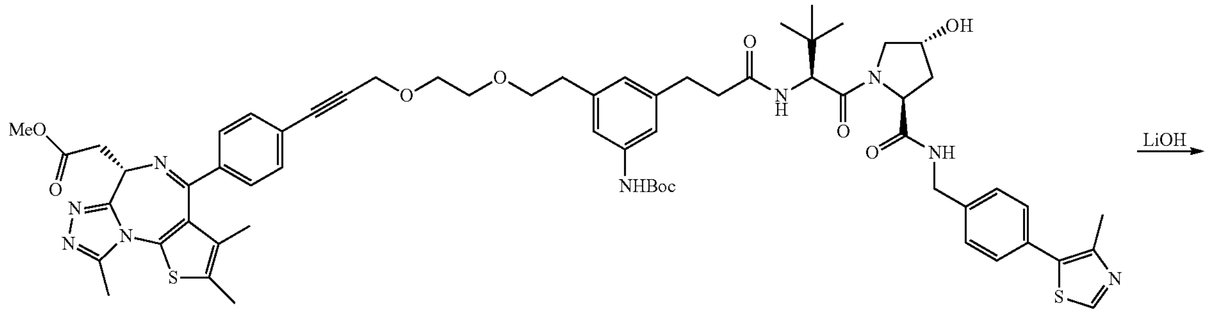

6

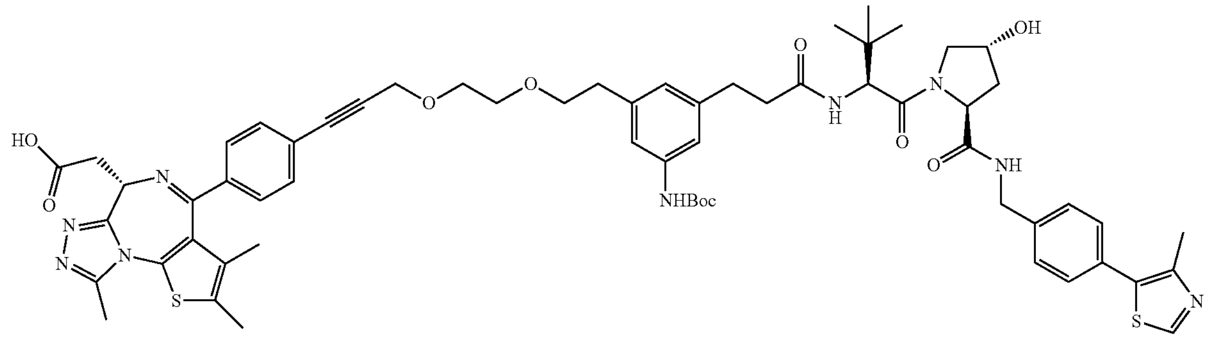

7

A mixture of Compound 6 (30.0 mg, 0.0300 mmol) and LiOH (2.43 mg, 0.1000 mmol) in THF (3.0 mL) and water (0.600 mL) was stirred at 20° C. for 2 h. The mixture was diluted with water (10 mL) and adjusted to pH=5 with HCl solution (2.0 M). The mixture was filtrated, and the solid was washed with water (10 mL), concentrated to give Compound 7 (15 mg, 51%) as a yellow solid, which was used directly in the next step. LCMS (5-95, AB, 1.5 min): RT=0.775 min, m/z=[M+1]$^+$.

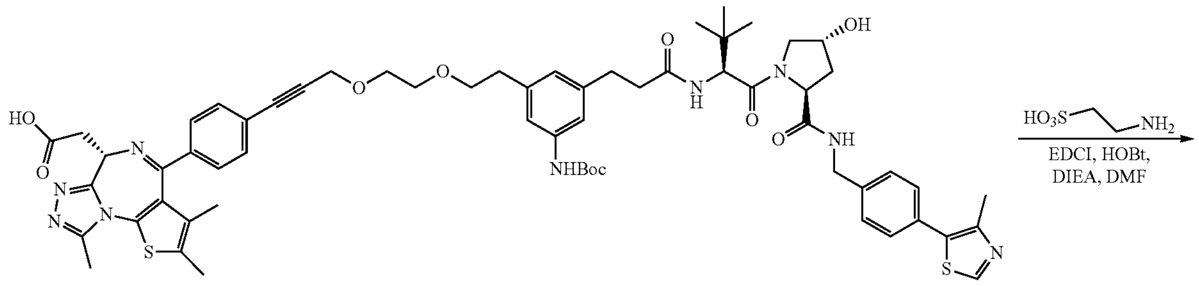
7
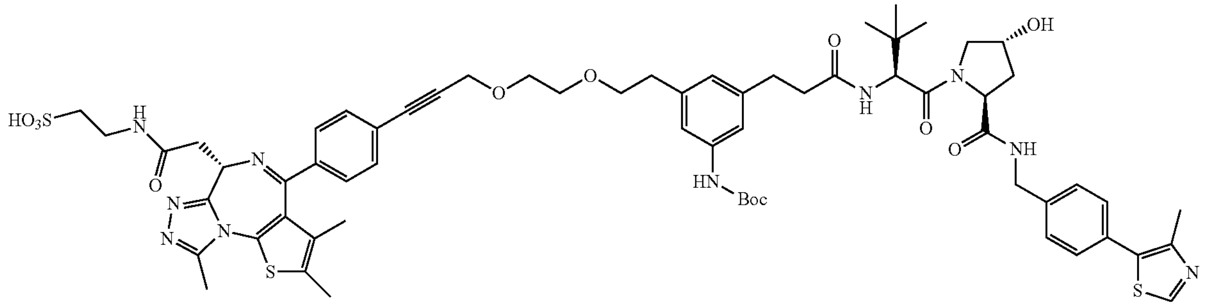
8
To a solution of Compound 7 (15.0 mg, 0.0100 mmol) in DMF (3.0 mL) was added 2-aminoethanesulfonic acid (3.21 mg, 0.0300 mmol), DIEA (8.3 mg, 0.0600 mmol), EDCI (4.92 mg, 0.0300 mmol) and HOBt (3.47 mg, 0.0300 mmol). The mixture was stirred at 20° C. for 18 h.
The reaction mixture was concentrated and purified by prep-HPLC (acetonitrile 35-65%/0.1% TFA in water) to give Compound 8 (8.0 mg, 47%) as a yellow solid. LCMS (5-95, AB, 1.5 min): RT (220/254 nm)=0.738 min, m/z=1276.4 $[M+1]^+$.
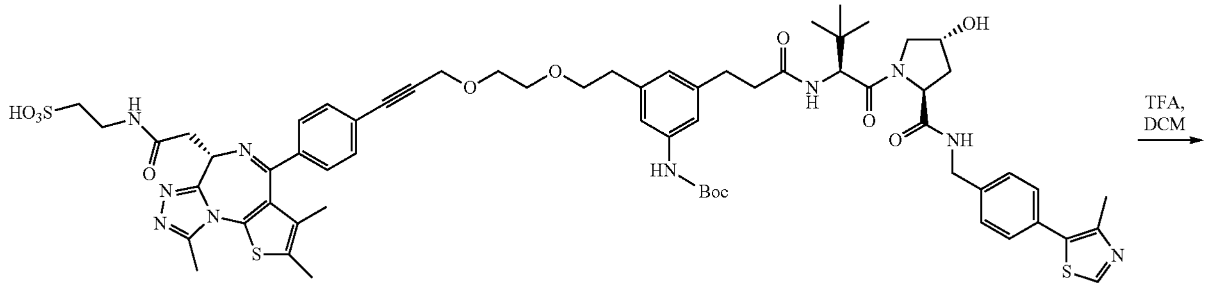
8
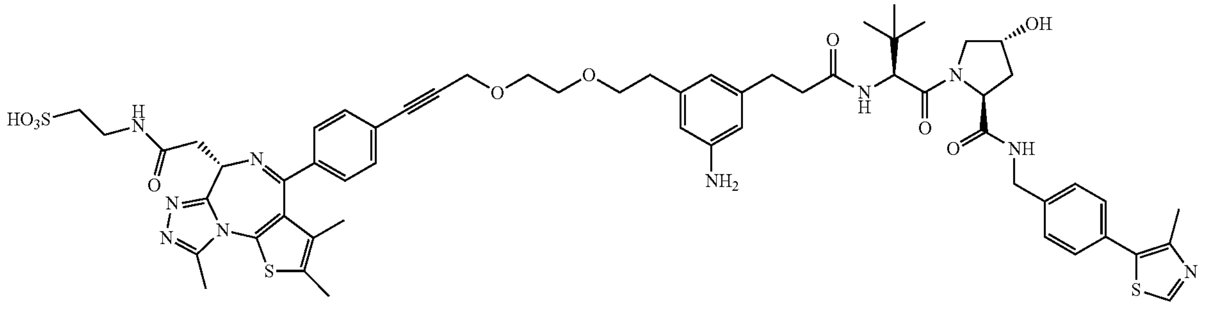
9

A mixture of Compound 8 (8.0 mg, 0.0100 mmol) in DCM (5.0 mL) was added TFA (1.0 mL) at 0° C. and stirred at 25° C. for 2 h. The reaction mixture was concentrated and purified by prep-HPLC (acetonitrile 19-49%/0.1% TFA in water) to give compound 9 (6.57 mg, 80%) as a yellow solid. LCMS (5-95, AB, 1.5 min): RT (220/254 nm)=0.662 min, m/z=1175.5 [M+1]$^+$.

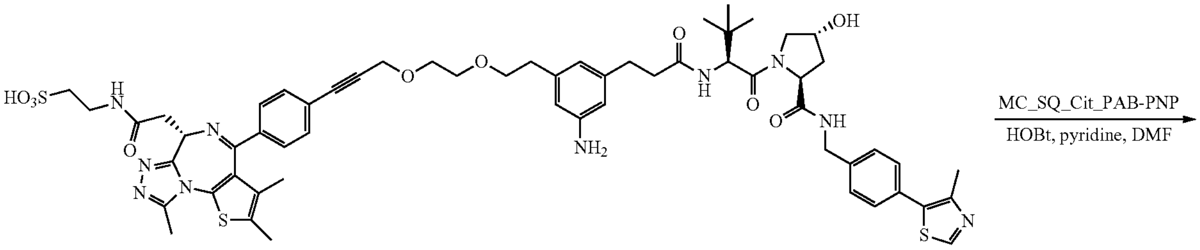

9

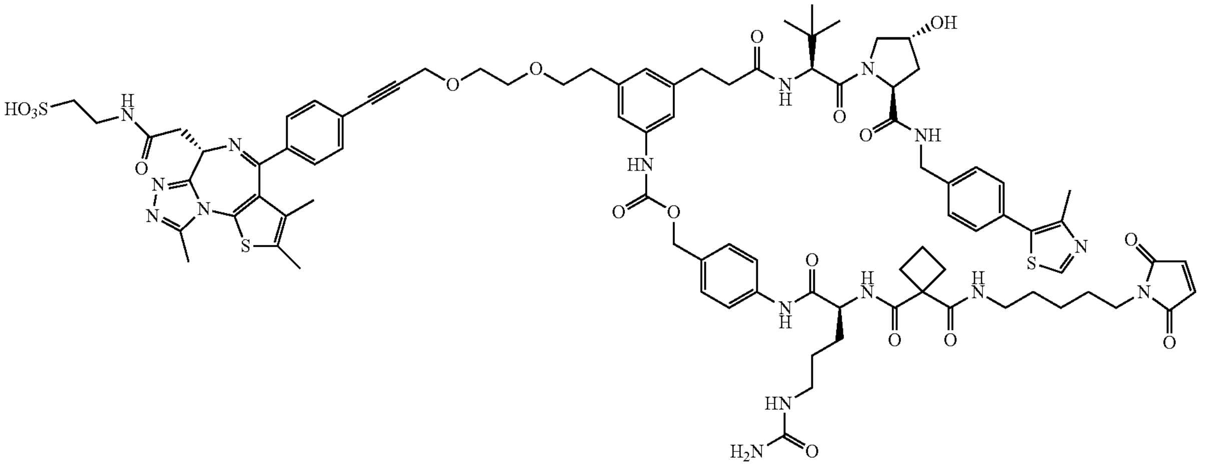

L1BQ12

To a solution of compound 9 (7.0 mg, 0.0100 mmol) in DMF (2.0 mL) was added pyridine (4.71 mg, 0.0600 mmol), HOBt (1.05 mg, 0.0100 mmol), and MC_SQ_Cit_PAB-PNP (5.7 mg, 0.0100 mmol). The reaction solution was stirred at 50° C. for 24 h. The solution was concentrated and purified by prep-HPLC (acetonitrile 0-40/0.1% HCl in water) to afford L1BQ12 (2.01 mg, 19%) as a pale yellow solid. LCMS (10-80, AB, 7 min): $R_T$=3.717 min, m/z=886.6 [M/2+1]$^+$. HRMS: 0-95_1_4 min.m, m/z=1771.70 [M+1]$^+$.

xxxi. L1BQ13 An exemplary L1-CIDE, L1BQ13, can be synthesized by the following scheme:

Scheme 33

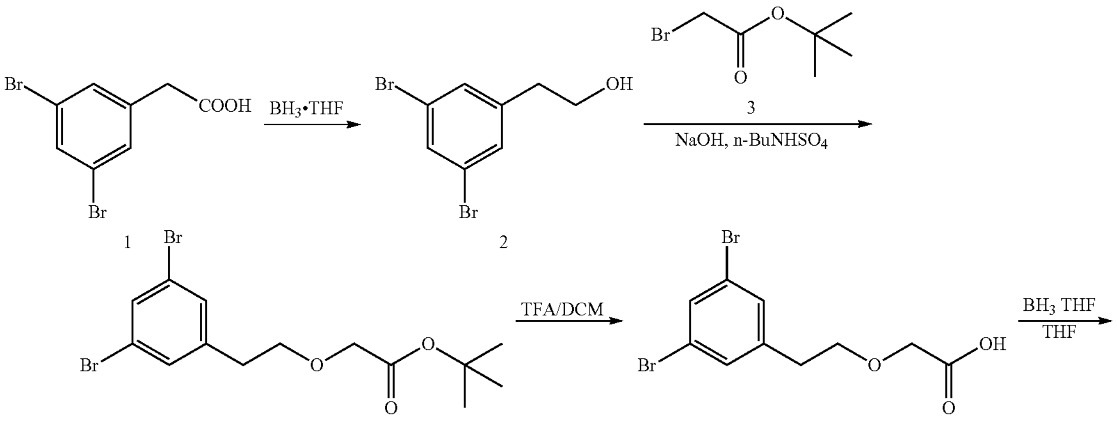

1 2 4 5

-continued
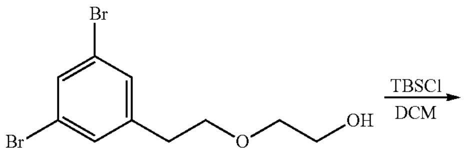
6
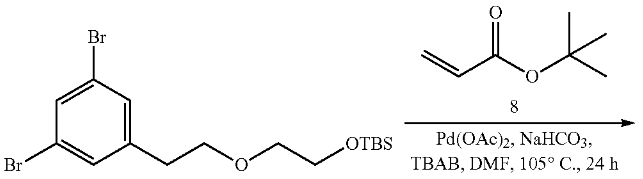
7
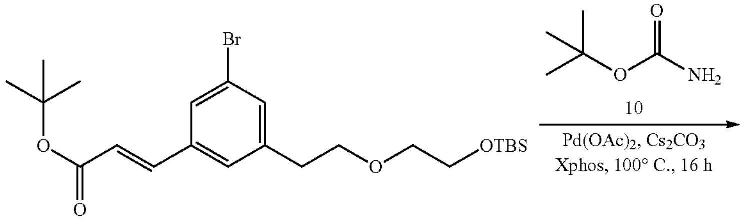
9
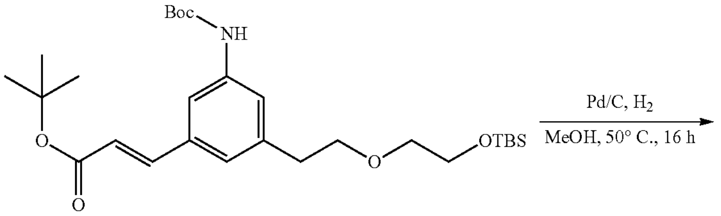
11
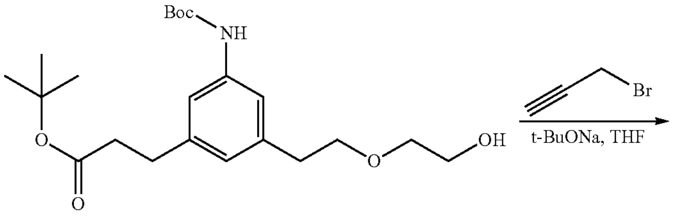
12
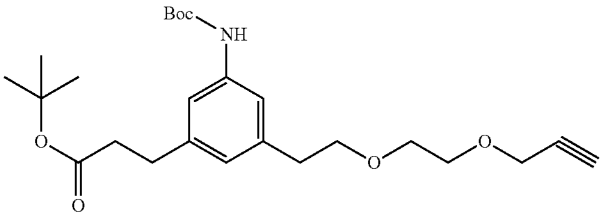
13
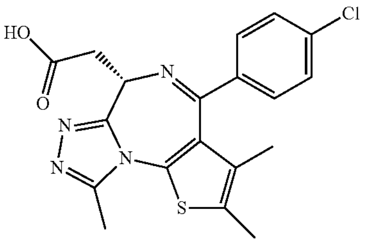
15
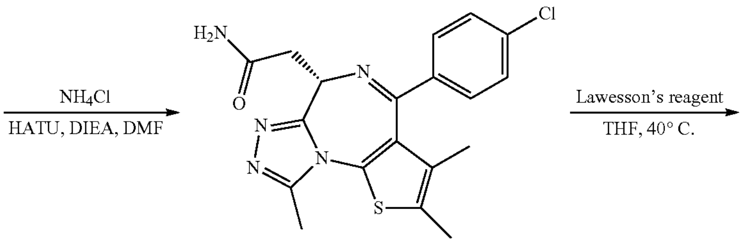
16

-continued
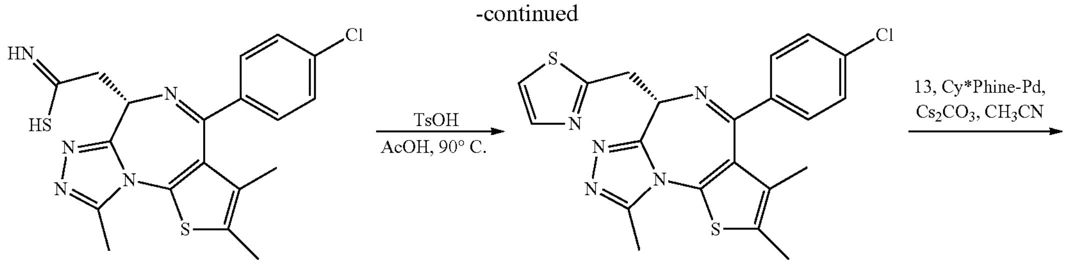
17 18
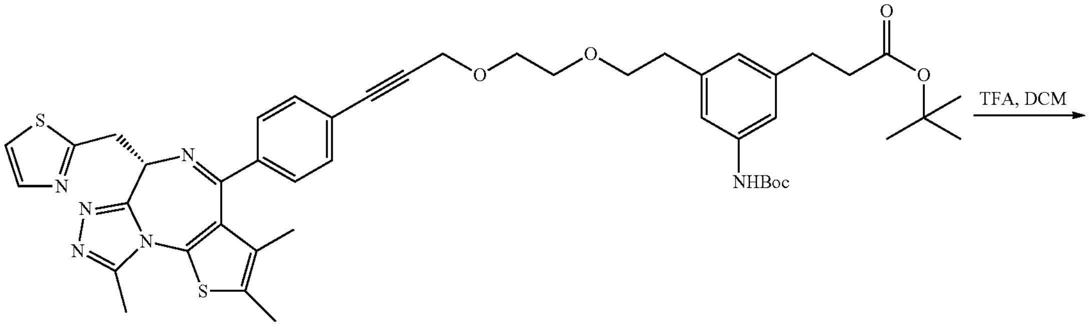
19
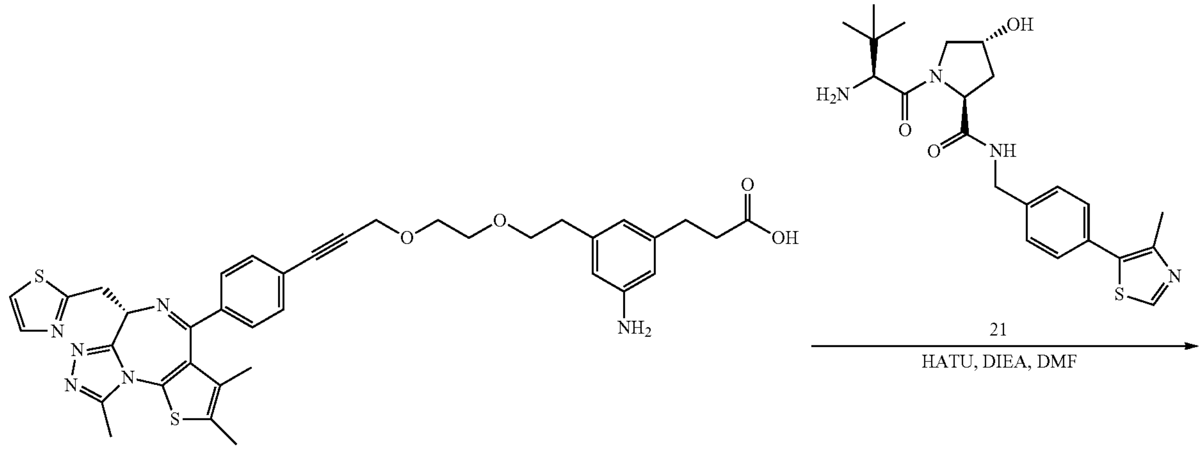
20
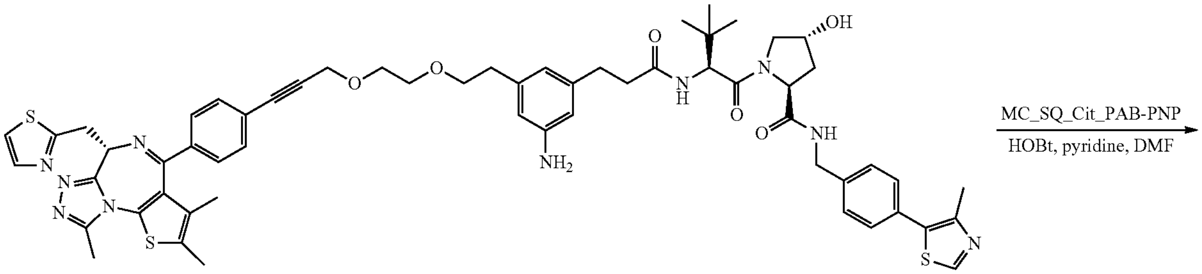
22

-continued

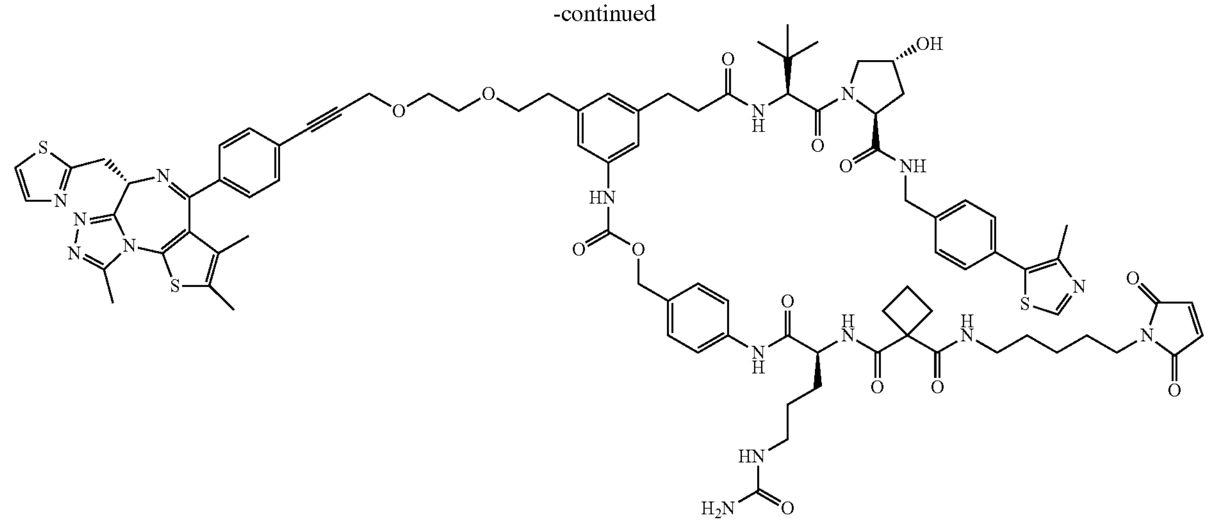

L1BQ13

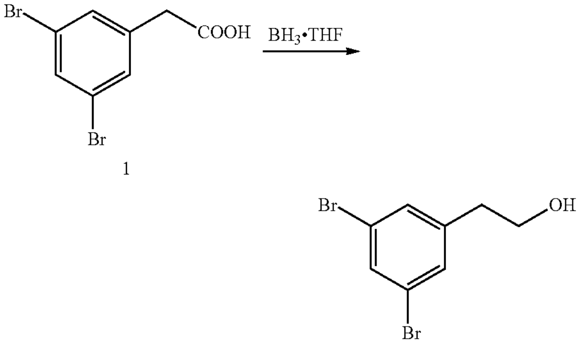

1

2

To a mixture of compound 1 (5.00 g, 17.01 mmol) in THF (75 mL) was added $BH_3$ THF (705.76 mg, 51.03 mmol) at 25° C. under $N_2$. The mixture was stirred at 20° C. for 12 h. The reaction was quenched with MeOH (10 mL), and concentrated to dryness. The residue was diluted with EtOAc (60 mL) and washed with brine (20 mL×3). The organic layer was then dried over $Na_2SO_4$, concentrated, and purified by flash column chromatography (0-30% EtOAc in petroleum ether, $R_f$=0.5) to give compound 2 (4.722 g, 99%) as an off white solid. H NMR (400 MHz, MeOD) δ 7.53 (s, 1H), 7.39 (s, 2H), 3.72 (t, J=6.8 Hz, 2H), 2.76 (t, J=6.8 Hz, 2H).

-continued

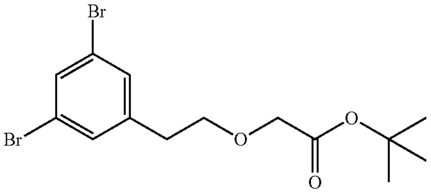

4

To a solution of compound 2 (4.00 g, 14.29 mmol), compound 3 (22.294 g, 114.3 mmol) in toluene (80 mL) and water (228 mL) was added TBAI (3.904 g, 11.43 mmol) and NaOH (45.72 g, 1143 mmol) at 25° C. The mixture was stirred at 25° C. for 3 h. The reaction mixture was extracted with MTBE (50 mL×3). The organic layer was combined, dried over anhydrous sodium sulfate, and concentrated. The crude product was purified by flash chromatography (0-10% EtOAC in petroleum ether, $R_f$=0.6) to give compound 4 (5.550 g, 98.6%) as colorless oil. $^1$H NMR (400 MHz, MeOD) δ 7.51 (d, J=1.6 Hz, 1H), 7.42 (d, J=2.0 Hz, 2H), 3.93 (s, 2H), 3.70 (t, J=6.4 Hz, 2H), 2.84 (t, J=6.4 Hz, 2H), 1.44 (s, 9H).

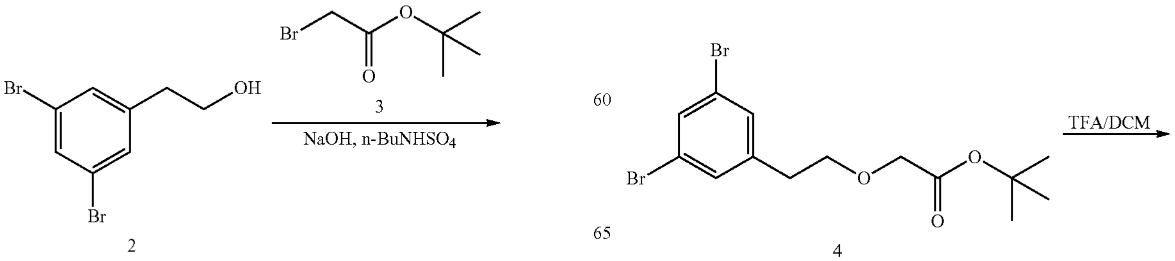

2

3

4

-continued

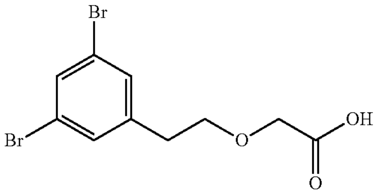

5

To a solution of compound 4 (4.500 g, 11.42 mmol) in DCM (180 mL) was added TFA (36.0 mL). The mixture was stirred at 25° C. for 16 h. The mixture was concentrated to give the crude product which was diluted with EtOAc (60 mL) and washed with water (20 mL×8). The organic layer was dried over $Na_2SO_4$ and concentrated to give compound 5 (3650 mg, 95%) as a yellow oil which was used in next step directly. $^1$H NMR (400 MHz, $CDCl_3$) δ 7.54 (s, 1H), 7.32 (s, 2H), 4.24-4.16 (m, 2H), 3.78 (t, J=7.2 Hz, 2H), 2.89 (t, J=6.8 Hz, 2H).

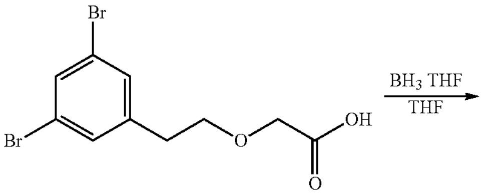

5

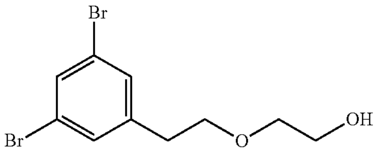

6

To a solution of compound 5 (5.300 g, 15.68 mmol) in THF (70 mL) was added borane in $Me_2S$ (10.0 M, 4.7 mL, 47.04 mmol) at 20° C. under $N_2$. The mixture was stirred at 20° C. for 12 h. The reaction was quenched with MeOH (30 mL). The mixture was concentrated and diluted with a.q. $NaHCO_3$ (60 mL), extracted with EtOAc (30 mL×3), and washed with brine (30 mL×3). The organic layer was separated, dried over $Na_2SO_4$, and concentrated to give compound 6 (4.60 g, 90.5%) as a yellow oil, which was used in next step directly. $^1$H NMR (400 MHz, $CDCl_3$) δ 7.52 (t, J=1.6 Hz, 1H), 7.32 (d, J=2.0 Hz, 2H), 3.74-3.67 (m, 4H), 3.56 (t, J=4.8 Hz, 2H), 2.85 (t, J=6.4 Hz, 2H).

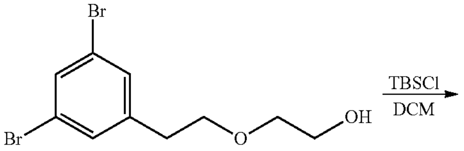

6

-continued

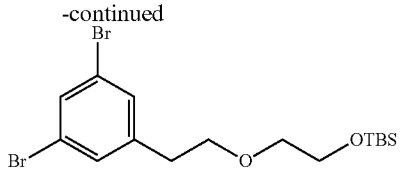

7

A mixture of compound 6 (4.600 g, 14.2 mmol), TBSCI (3.209 g, 21.3 mmol), and imidazole (2.899 g, 42.59 mmol) in DCM (50 mL) was stirred at 20° C. for 4 h. Water (30 mL) was added, extracted with DCM (30 mL×3), and washed with brine (30 mL×3). The organic layer was separated, dried over $Na_2SO_4$, concentrated, and purified by flash column chromatography (0-5% EtOAc in petroleum ether, Rf=0.6) to give compound 7 (5.200 g, 84%) as a yellow oil. $^1$H NMR (400 MHz, MeOD) δ 7.48 (t, J=2.0 Hz, 1H), 7.36 (d, J=2.0 Hz, 2H), 3.70-3.63 (m, 4H), 3.45 (t, J=4.8 Hz, 2H), 2.79 (t, J=6.0 Hz, 2H), 0.84 (s, 9H), 0.00 (m, 6H).

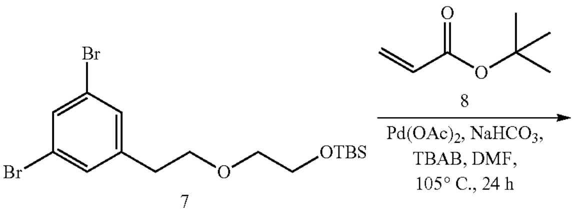

7

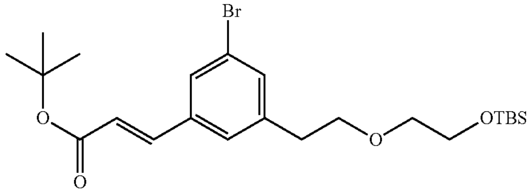

9

To a solution of compound 7 (1.380 g, 3.15 mmol) in DMF (20 mL) was added TBAB (1.015 g, 3.15 mmol), compound 8 (605.36 mg, 4.72 mmol), $NaHCO_3$ (1.058 g, 12.59 mmol) and $Pd(OAc)_2$ (70.69 mg, 0.3100 mmol). The mixture was stirred at 105° C. under $N_2$ for 24 h. The mixture was filtered, water was added, extracted with EtOAc (30 mL×3), washed with brine (30 mL×3). The organic layer was separated, dried over $Na_2SO_4$, concentrated and purified by prep-HPLC (0-10% EtOAc in petroleum ether, $R_f$=0.5) to give compound 9 (1.230 g, 81%) as light yellow oil. $^1$H NMR (400 MHz, MeOD) δ 7.52 (d, J=1.6 Hz, 1H), 7.42-7.38 (m, 3H), 6.38 (d, J=16 Hz, 1H), 3.71-3.65 (m, 4H), 3.46 (t, J=4.8 Hz, 2H), 2.83 (t, J=6.4 Hz, 2H), 1.49 (s, 9H), 0.84 (s, 9H), 0.00 (s, 6H).

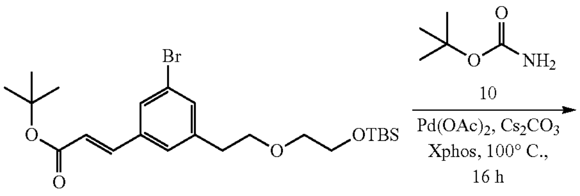

9

-continued

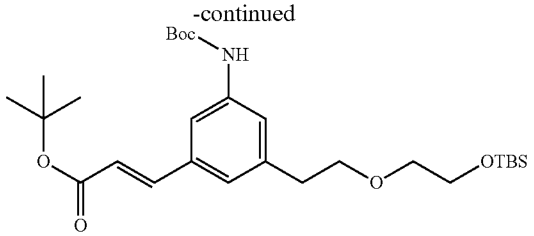

11

To a solution of compound 9 (1.230 g, 2.53 mmol) and compound 10 (445.17 mg, 3.8 mmol) in 1,4-dioxane (20 mL) was added $Cs_2CO_3$ (1.650 g, 5.07 mmol), Xphos (120.77 mg, 0.2500 mmol) and $Pd(OAc)_2$ (28.44 mg, 0.1300 mmol). The mixture was purged and stirred at 100° C. for 16 h under $N_2$. The mixture was filtered, and water (20 mL) was added. It was extracted with EtOAc (30 mL×3), washed with brine (30 mL×3). The organic layer was separated, dried over $Na_2SO_4$, concentrated, and purified by prep-HPLC (0-17% EtOAc in petroleum ether, Rf=0.5) to give compound 11 (1180 mg, 89%) as yellow oil. $^1$H NMR (400 MHz, MeOD) δ 7.47-7.43 (m, 2H), 7.30 (brs, 1H), 7.05 (s, 1H), 6.33 (d, J=16 Hz, 1H), 3.71-3.65 (m, 4H), 3.47 (t, J=4.8 Hz, 2H), 2.82-2.80 (m, 2H), 1.48 (s, 18H), 0.84 (s, 9H), 0.00 (m, 6H).

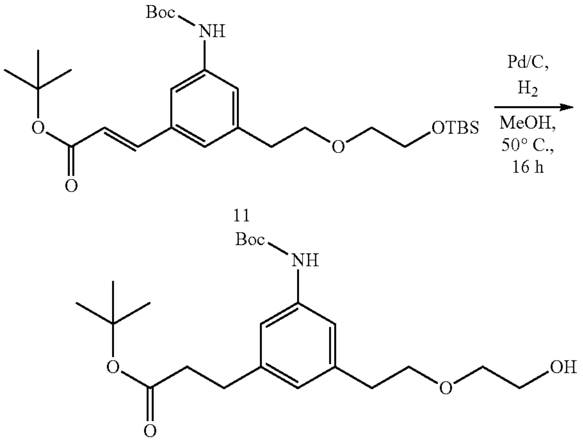

11

12

A mixture of compound 11 (2.000 g, 3.83 mmol) in MeOH (20 mL) was added 10% Pd/C (407.93 mg) at 20° C. under $N_2$. The mixture was stirred at 50° C. under $H_2$ (50 psi) for 16 h. The mixture was filtered and the filtrate was concentrated to give compound 12 (1.750 g) as a colorless oil used in next step directly. LCMS (5-95, AB, 1.5 min): $R_T$ (220/254 nm)=0.781 min, m/z=432.1 [M+23]$^+$.

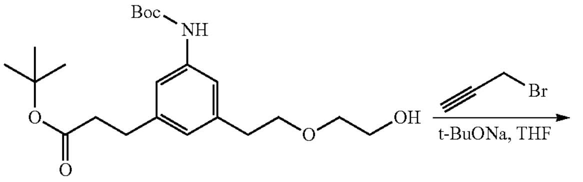

12

-continued

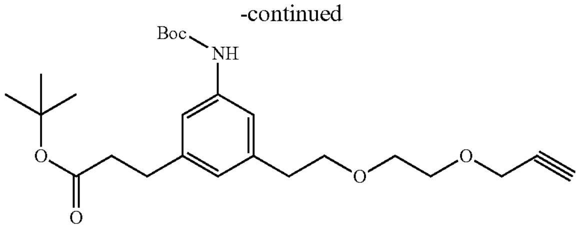

13

To a solution of compound 12 (1.560 g, 3.81 mmol) in THF (20 mL) was added tBuONa (439.29 mg, 4.57 mmol) at 0° C. under $N_2$. The mixture was stirred at 0° C. for 30 minutes, then propargyl bromide (0.51 mL, 4.57 mmol) was added drop-wise. The mixture was stirred at 25° C. for 12 h under $N_2$. The reaction was quenched with water (10 mL), extracted with EtOAc (30 mL×2), washed with brine (20 mL×3), and concentrated. It was purified by flash column chromatography (0-30% EtOAc in petroleum ether, $R_f$=0.4) to obtained compound 13 (1.150 g, 68%) as a light-colored oil. $^1$H NMR (400 MHz, $CD_3OD$) δ 7.11-7.09 (m, 2H), 6.74 (s, 1H), 4.15 (s, 2H), 3.65-3.59 (m, 6H), 2.82-2.76 (m, 5H), 2.49 (t, J=7.6 Hz, 2H), 1.54 (s, 9H), 1.43 (s, 9H). LCMS (10-80, AB, 7 min): $R_T$(220/254 nm)=4.259 min, m/z=470.2 [M+23]$^+$.

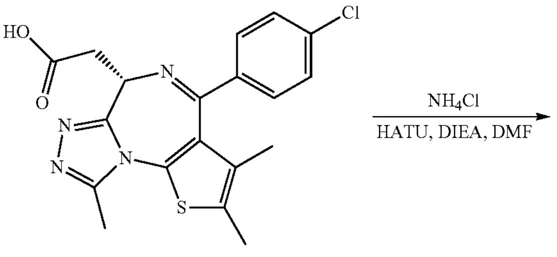

15

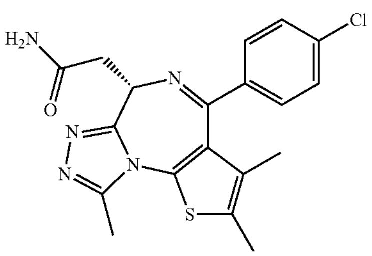

16

To a mixture of Compound 15 (0.870 g, 2.11 mmol), $NH_4Cl$ (337.81 mg, 6.32 mmol) and HATU (1.600 g, 4.21 mmol) in DMF (20 mL) was added DIEA (1.74 mL, 10.53 mmol). The mixture was stirred at 20° C. for 2 h. The mixture was concentrated and purified by flash column chromatography (0-5% MeOH in DCM) to give Compound 16 (0.84 g, 98.5%) as a yellow solid. LCMS (5-95, AB, 1.5 min): $R_T$ (220/254 nm)=0.771 min, m/z=421.9 [M+23]$^+$.

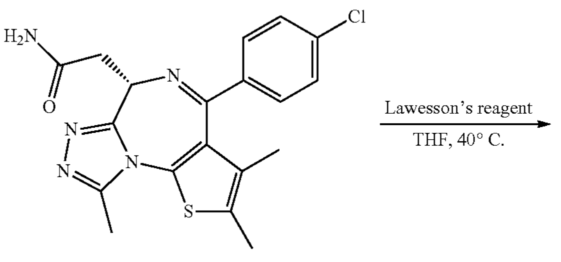

16

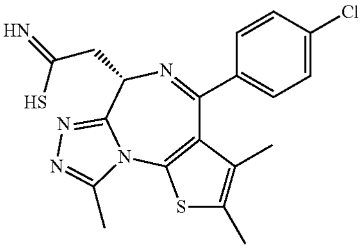

17

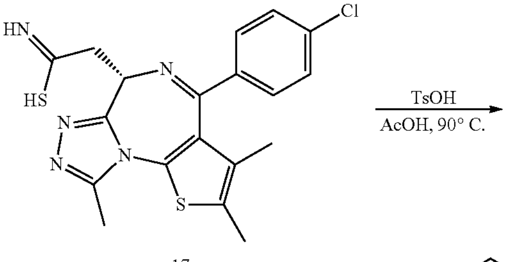

17

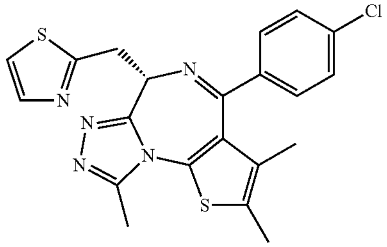

18

To a solution of Compound 17 (630.00 mg, 1.51 mmol) and 2-bromo-1,1-diethoxyethane (447.71 mg, 2.27 mmol) in acetic acid (5 mL) was added TsOH (26.08 mg, 0.15 mmol). The mixture was stirred at 90° C. for 1 h. The mixture was concentrated and purified by flash column chromatography eluting 5-10% MeOH in DCM to give the Compound 18 (600 mg, 87%) as a yellow solid. LCMS (5-95, AB, 1.5 min): $R_T$ (220/254 nm)=0.845 min, m/z=461.9 [M+23]$^+$.

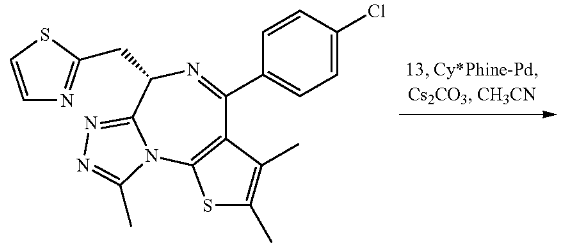

18

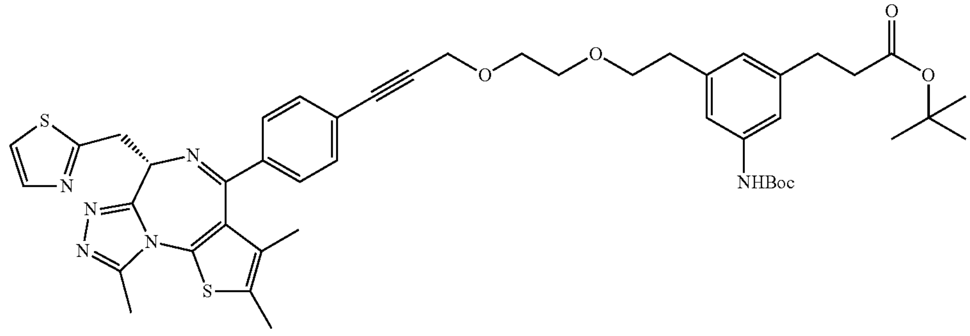

19

To a solution of Compound 16 (840.00 mg, 2.10 mmol) in THF (50 mL) was added Lawesson's reagent (1.700 g, 4.20 mmol). The mixture was stirred at 40° C. for 2 h. The mixture was diluted with EtOAc (250 mL), washed with $H_2O$ (50 mL×3) and brine (50 mL). The organic layer was concentrated and purified by flash column chromatography (5-10% MeOH in DCM) to give Compound 4 (630.00 mg, 71.4%) as a yellow solid. LCMS (5-95, AB, 1.5 min): RT (220/254 nm)=0.888 min, m/z=416.0 [M+1]$^+$.

To a mixture of Compound 18 (30.0 mg, 0.0700 mmol) in Acetonitrile (3 mL) was added Pd-Cy*Phine (4.37 mg, 0.05 mmol), $Cs_2CO_3$ (66.65 mg, 0.2000 mmol) and Compound 13 (61.03 mg, 0.1400 mmol). The mixture was stirred at 105° C. in microwave under the atmosphere of $N_2$ for 1 hr. LCMS showed the reaction was completed. The reaction mixture was filtered, concentrated and purified by prep-TLC (10% methanol in DCM, Rf=0.3) to afford Compound 19 (26 mg, 45%) as a yellow solid. LCMS (5-95, AB, 1.5 min): RT (220/254 nm)=1.065 min, m/z=851.3 [M+1]+

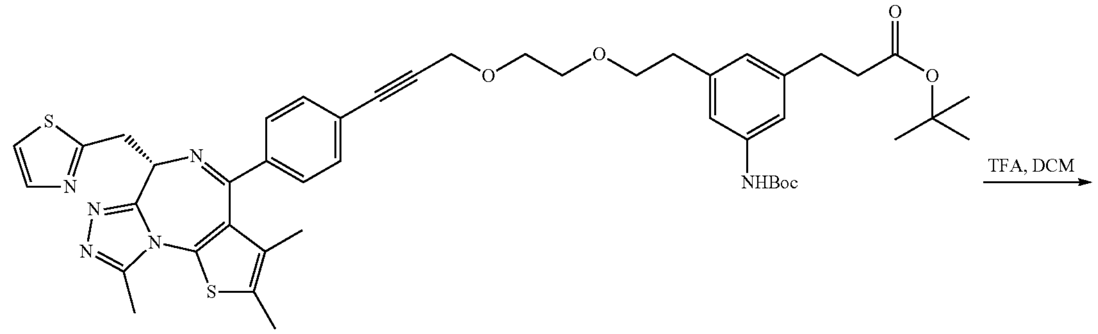
19
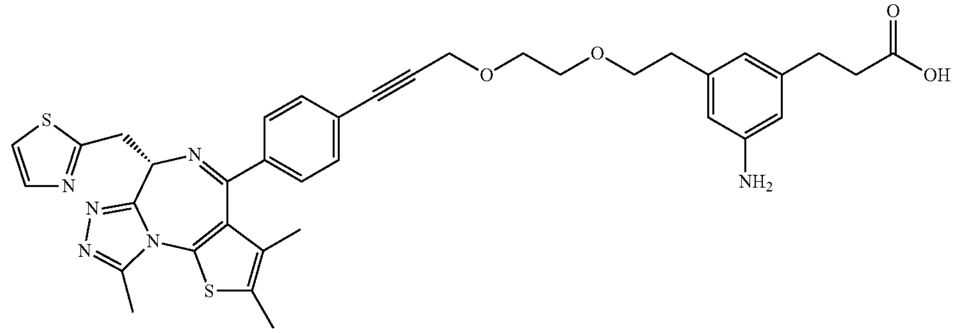
20
To a solution of 19 (47.0 mg, 0.0600 mmol) in DCM (3 mL) was added TFA (0.6 mL) at 25° C. The mixture was stirred for 2 h at 25° C. The mixture was concentrated to give 20 (38 mg, 99%) as a yellow oil, which was used in next step directly. LCMS (5-95, AB, 1.5 min): RT 220/254 nm)=0.801 min, m/z=695.2 [M+1]+.
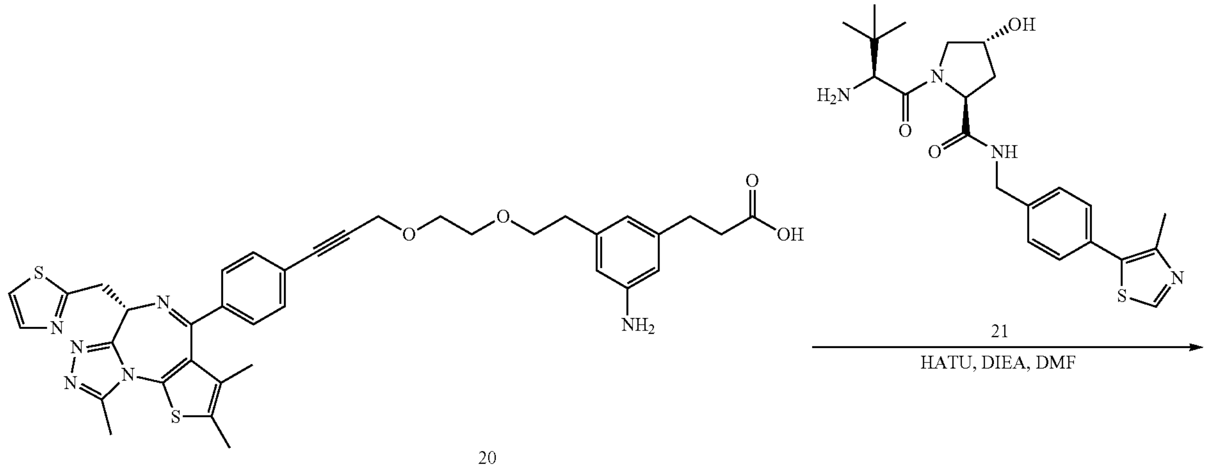
20

-continued

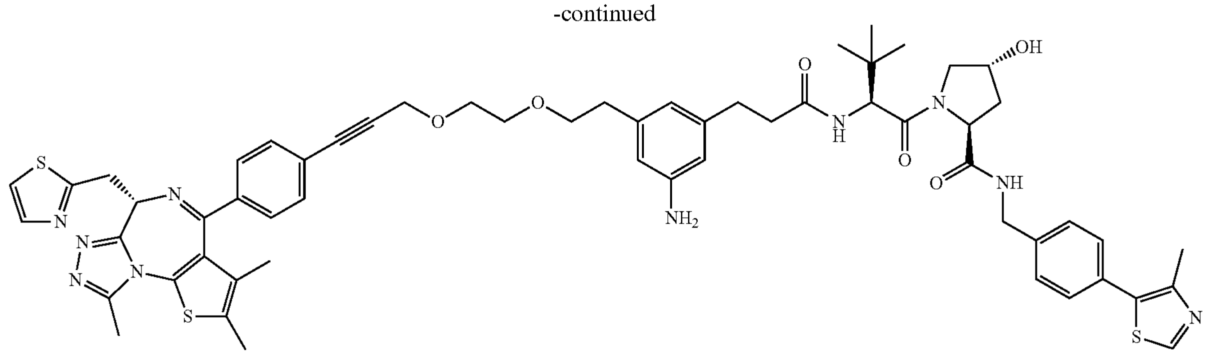

22

A mixture of 20 (21.0 mg, 0.0300 mmol), 21 (14.31 mg, 0.0300 mmol), DIEA (11.72 mg, 0.0900 mmol) and HATU (12.64 mg, 0.0300 mmol) in DMF (3.0 mL) was stirred at 20° C. for 1 h. The mixture was concentrated to give crude product, which was purified by prep-HPLC (acetonitrile 25-55/0.05% TFA in water), and the product fraction was treated with a.q. HCl (1.0 M, 0.10 mL), then lyophilized to give 22 (3.82 mg, 11.1%) as a light yellow solid. LCMS (5-95, AB, 1.5 min): $R_T$ (220/254 nm)=0.835 min, m/z=1107.7 $[M+1]^+$. $^1H$ NMR (400 MHz, MeOD): δ 8.86 (s, 1H), 7.72 (d, J=3.6 Hz, 1H), 7.54 (d, J=3.2 Hz, 1H), 7.46-7.39 (m, 10H), 6.52-6.46 (m, 3H), 4.65-4.60 (m, 7H), 4.56-4.51 (m, 2H), 4.40 (s, 1H), 4.35-4.26 (m, 1H), 4.25-4.15 (m, 1H), 4.14-4.10 (m, 1H), 3.80-3.76 (m, 1H), 3.73-3.72 (m, 2H), 3.71-3.64 (m, 5H), 2.78-2.75 (m, 4H), 2.71 (s, 3H), 2.55-2.51 (m, 2H), 2.46 (s, 3H), 2.43 (s, 3H), 2.40-2.36 (m, 1H), 2.09-2.07 (m, 1H), 1.64 (s, 2H), 0.95 (s, 9H).

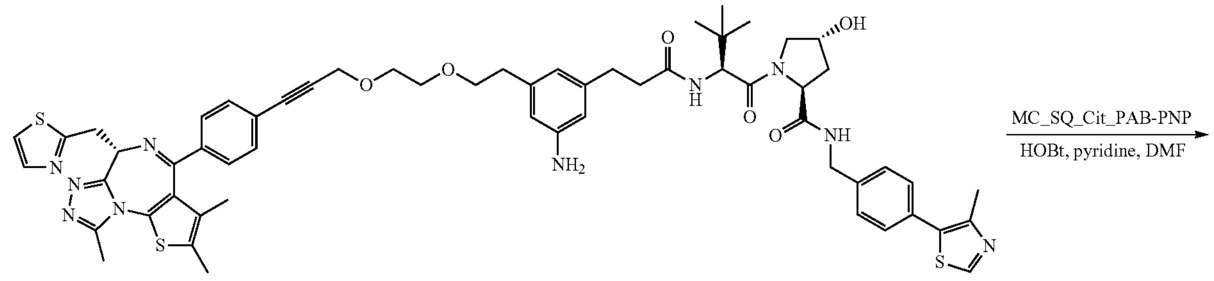

22

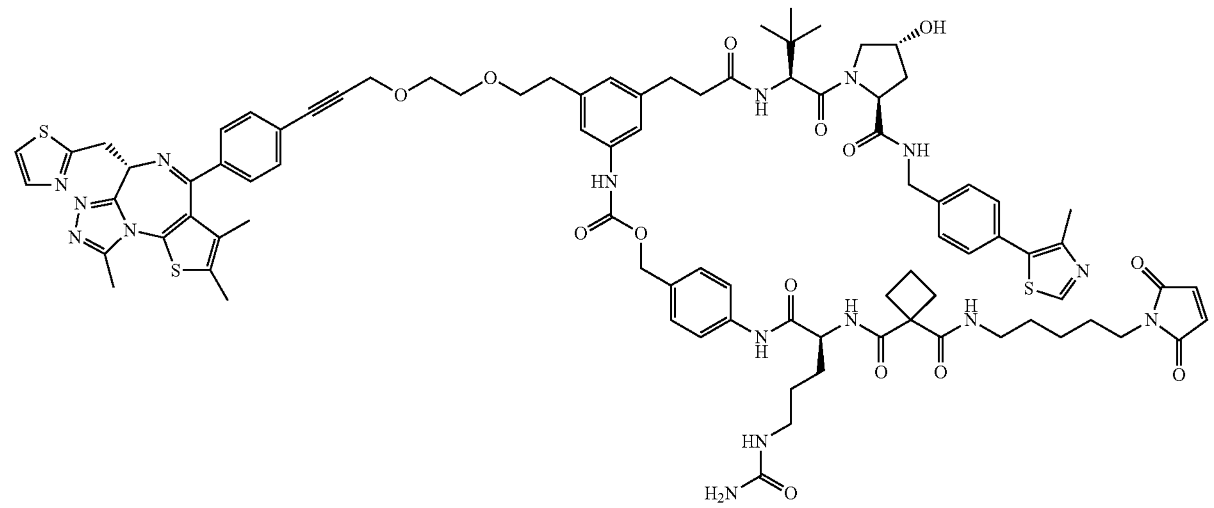

L1BQ13

To a solution of 22 (20.0 mg, 0.0200 mmol) in anhydrous DMF (2.0 mL) was added Pyridine (14.29 mg, 0.1800 mmol), HOBt (3.17 mg, 0.0200 mmol), and MC_SQ_Cit_PAB-PNP (17.27 mg, 0.0200 mmol). The reaction solution was stirred at 50° C. for 16 h. The reaction mixture was filtered and the filtrate was purified by prep-HPLC (acetonitrile 46-56/0.225% FA in water) to afford L1BQ13 (8.5 mg, 27%) as a white solid. LCMS (5-95, AB, 1.5 min): $R_T$ (220/254 nm)=0.756 min, m/z=852.9 $[M/2+1]^+$.

xxxii. L1BQ14 An exemplary L1-CIDE, L1BQ14, can be synthesized by the following scheme:

Scheme 34

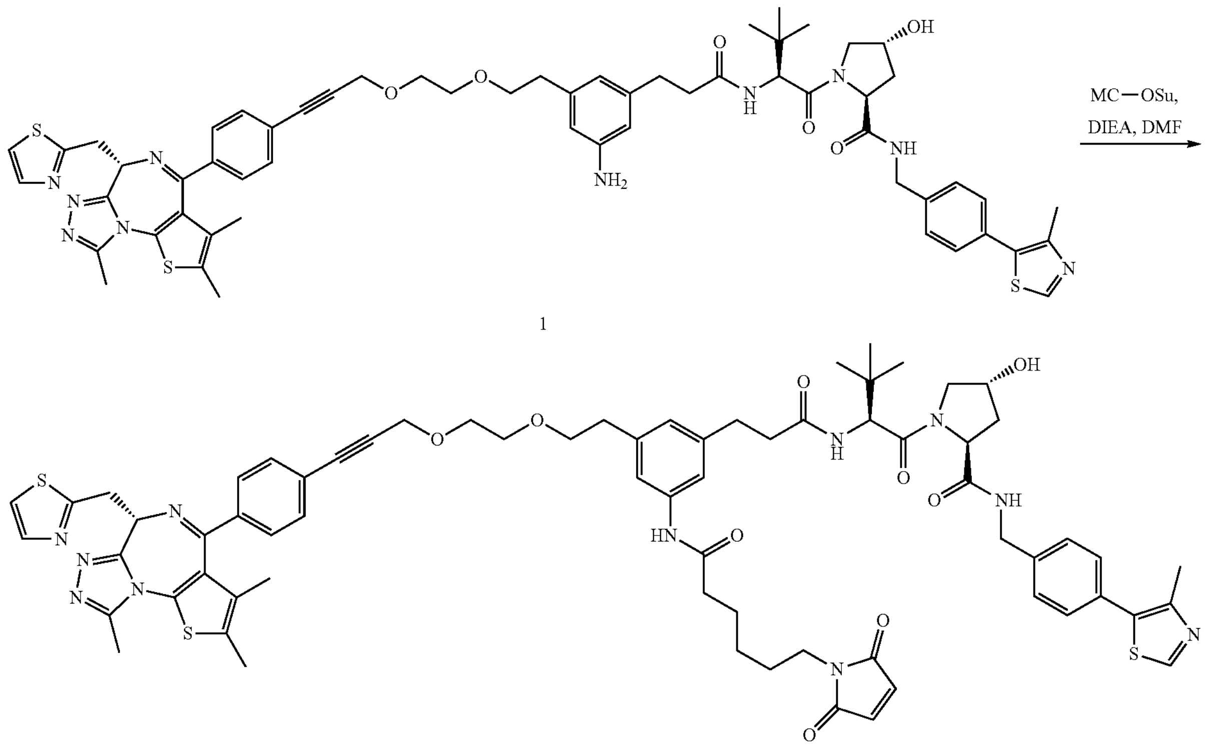

1

L1BQ14

To a solution of 1 (15.0 mg, 0.0100 mmol) and MC_OSu (6.26 mg, 0.0200 mmol) in DMF (8.0 mL), was added DIEA (5.25 mg, 0.0400 mmol). The mixture was stirred at 60° C. for 48 h. The mixture was purified by prep-HPLC (acetonitrile 38-68/0.225% FA in water) to afford L1BQ14 (1.68 mg, 9.4%) as a white solid. LCMS (5-95, AB, 7 min): RT (220/254 nm)=4.218 min, m/z=1322.0 $[M+23]^+$.

xxxiii. L1BQ15 An exemplary L1-CIDE, L1BQ15, can be synthesized by the following scheme:

Scheme 35

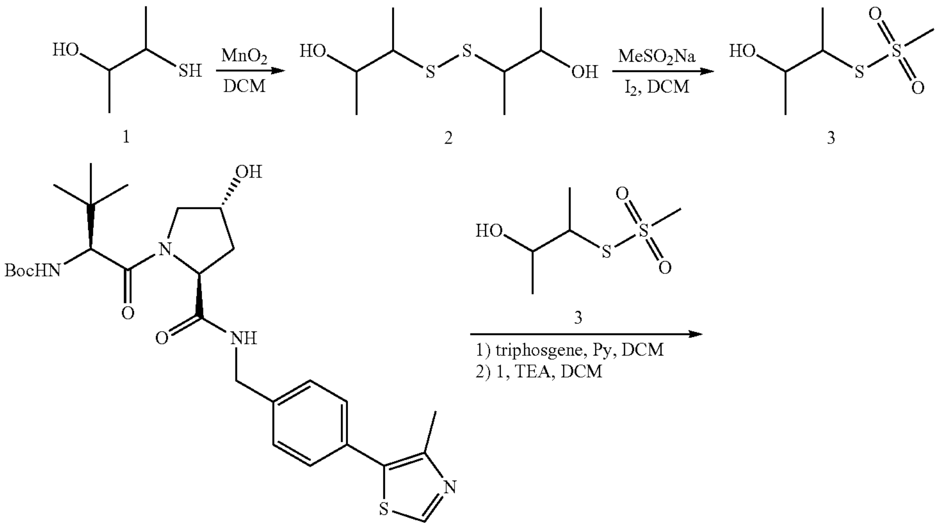

1 2 3 3 4

-continued
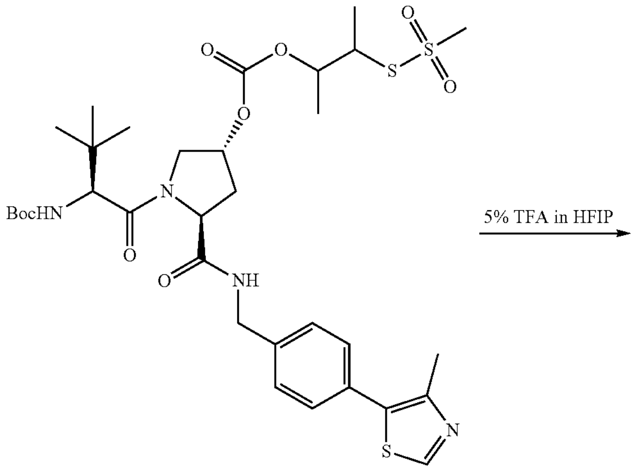
5
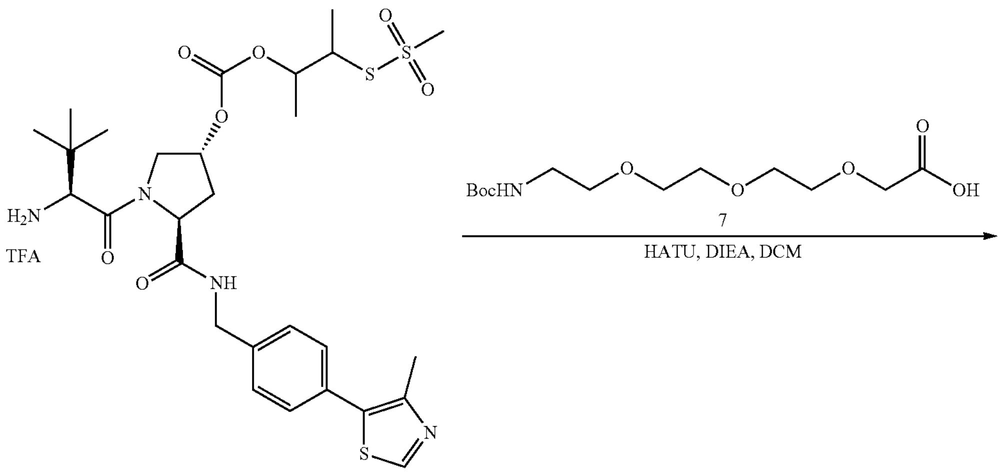
6
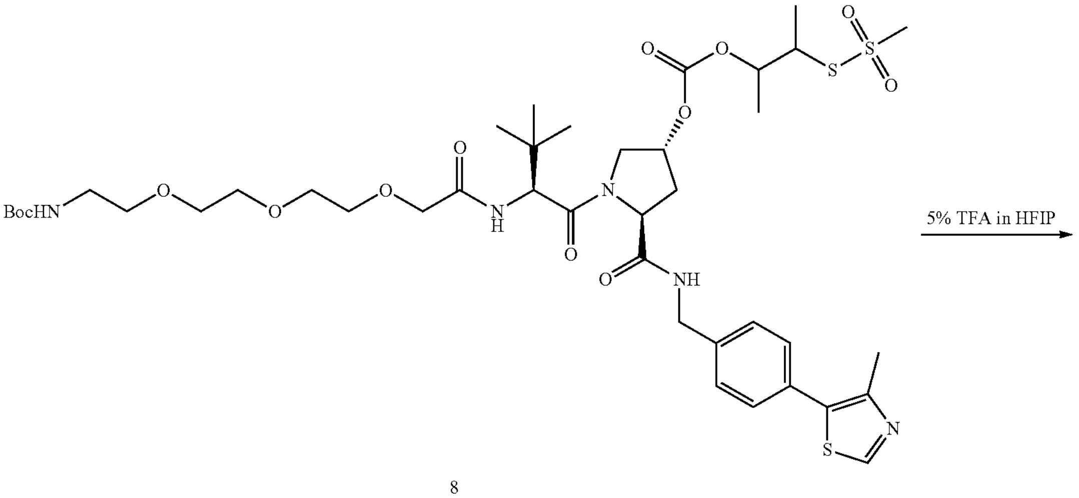
8

-continued

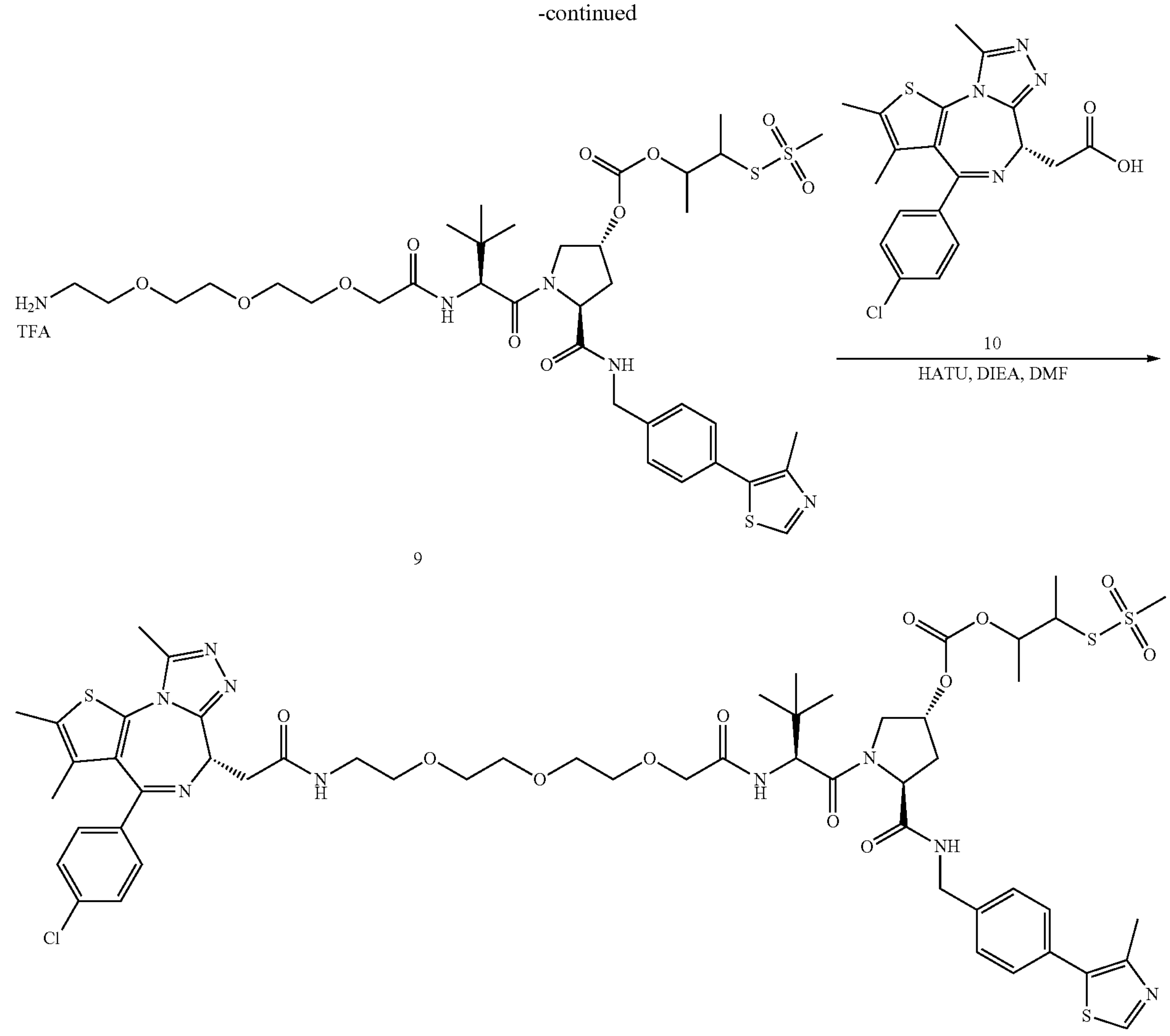

9

10

L1BQ15

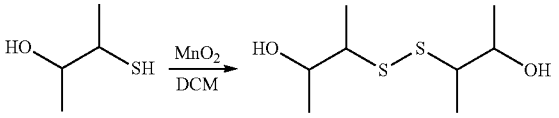

1

2

To a solution of compound 1 (2.000 g, 18.84 mmol) in anhydrous DCM (40 mL) was added $MnO_2$ (2.456 g, 28.25 mmol). The reaction mixture was stirred at 20° C. for 1 h. The mixture was filtered, the filtrate was concentrated in vacuo to afford compound 2 (1.970 g, 99.4%) as a colorless oil, which was used in the next step directly.

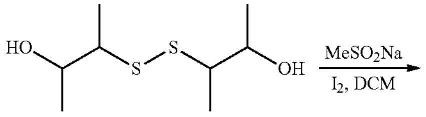

2

-continued

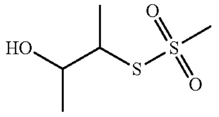

3

To a solution of compound 2 (1.970 g, 9.36 mmol) in anhydrous DCM (50 mL) was added $MeSO_2Na$ (1.912 g, 18.73 mmol) and iodine (2.376 g, 9.36 mmol). The reaction mixture was stirred in dark at 20° C. for 24 h. The mixture was filtered, the filtrate was concentrated and purified by chromatography on silica (0-5% MeOH in DCM) to afford compound 3 (1.200 g, 70%) as a pale yellow oil. $^1H$ NMR (400 MHz, $CDCl_3$) δ 4.13-4.11, 3.96-3.93 (m, 1H), 3.77-3.70 and 3.51-3.47 (m, 1H), 3.42 and 3.39 (s, 3H), 2.04 and 1.96 (s, 1H), 1.53 and 1.42 (d, J=7.2 Hz, 3H), 1.33, and 1.22 (d, J=6.0 Hz, 3H).

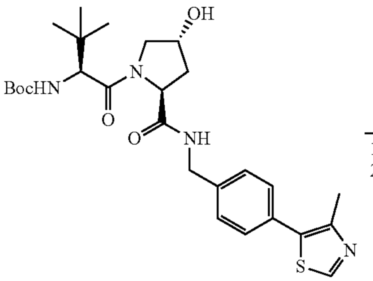

4

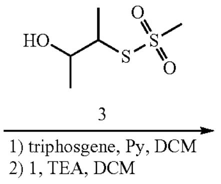

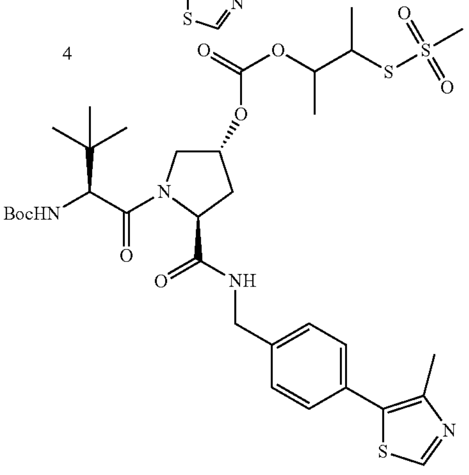

5

To a mixture of triphosgene (111.84 mg, 0.3800 mmol) and 4 Å molecular sieves (100 mg) in anhydrous DCM (10 mL) was added a solution of compound 3 (138.9 mg, 0.750 mmol) and a solution of pyridine (178.86 mg, 2.26 mmol) in anhydrous DCM (5.0 mL) slowly at 20° C. The reaction mixture was stirred at 20° C. for 0.5 h. Then the mixture was concentrated to the give the crude product, which was used in the next step directly. To above product in anhydrous DCM (15 mL) was added $Et_3N$ (114.41 mg, 1.13 mmol), and compound 4 (200.0 mg, 0.3800 mmol) was added. The reaction mixture was stirred at 20° C. for another 2 h, and was diluted with DCM (20 mL), washed with $H_2O$ (20 mL×3), dried over $Na_2SO_4$, filtered, and concentrated. The residue was purified by prep-TLC (8% MeOH in DCM, Rf=0.6) to afford compound 5 (100 mg, 35%) as a white solid. LCMS (5-95, AB, 1.5 min): $R_T$=0.883 min, m/z=763.0 $[M+23]^+$.

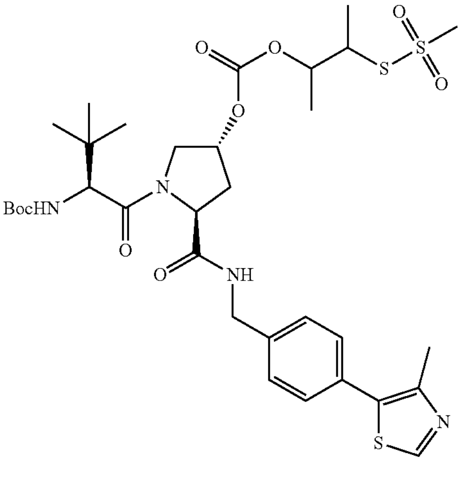

5

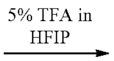

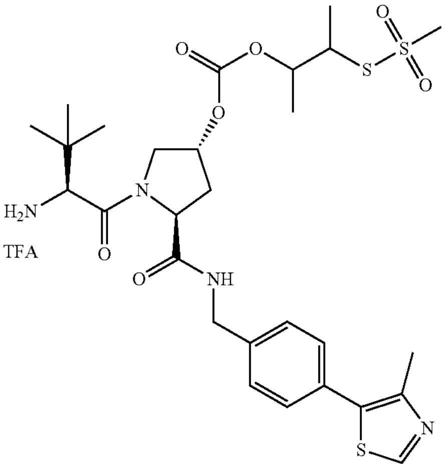

6

To a solution of compound 5 (90.0 mg, 0.1200 mmol) in hexafluoroisopropanol (6.0 mL) was added TFA (0.30 mL, 0.1200 mmol). The reaction solution was stirred at 20° C. for 1 h. The solution was concentrated to afford compound 6 (90 mg, 98.2%) as a crude colorless oil. LCMS (5-95, AB, 1.5 min): RT=0.744 min, m/z=641.1 $[M+1]^+$.

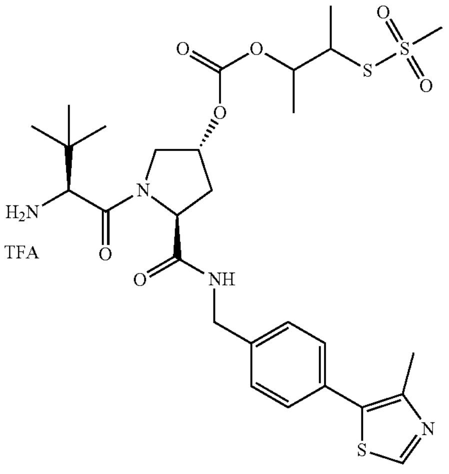

6

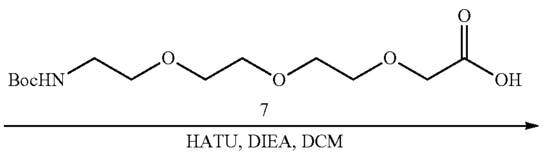

-continued

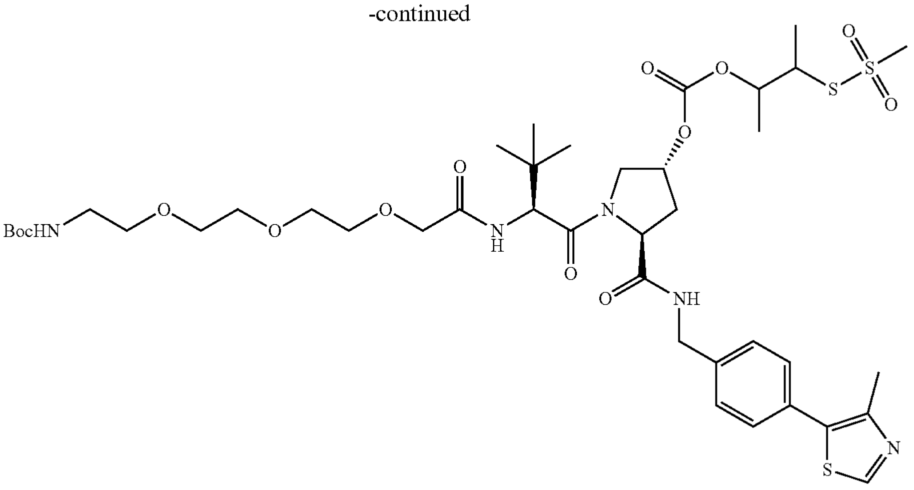

8

To a solution of compound 7 (54.97 mg, 0.1800 mmol) in DMF (6 mL) was added N,N-diisopropylethylamine (77.04 mg, 0.600 mmol) and HATU (90.67 mg, 0.240 mmol). The solution was stirred at 20° C. for 15 min, then compound 6 (90.0 mg, 0.1200 mmol) was added. The resulting reaction solution was stirred at 20° C. for 0.5 h. The mixture was concentrated and purified by prep-TLC (10% MeOH in DCM, Rf=0.7) to afford compound 8 (100 mg, 83%) as a white solid. LCMS (10-80, AB, 7 min): $R_T$=4.028 min, m/z=952.3 $[M+23]^+$.

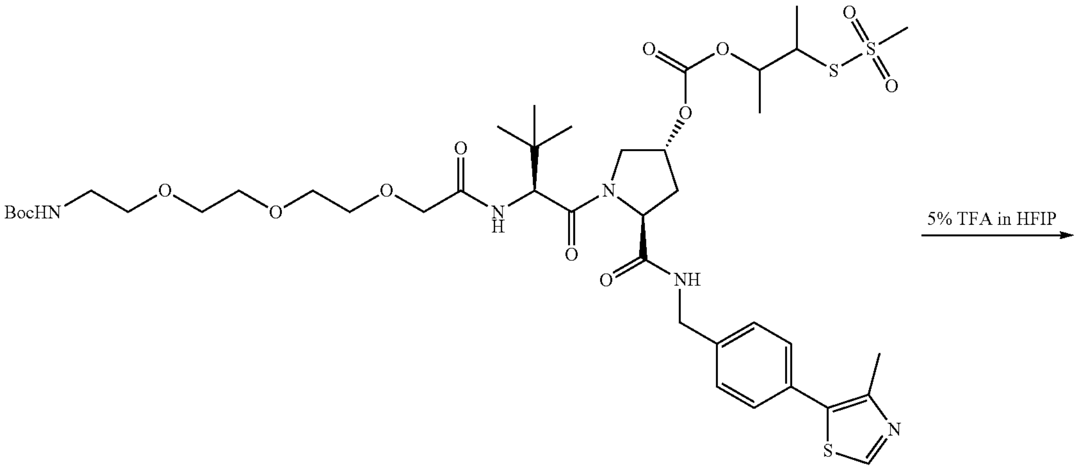

8

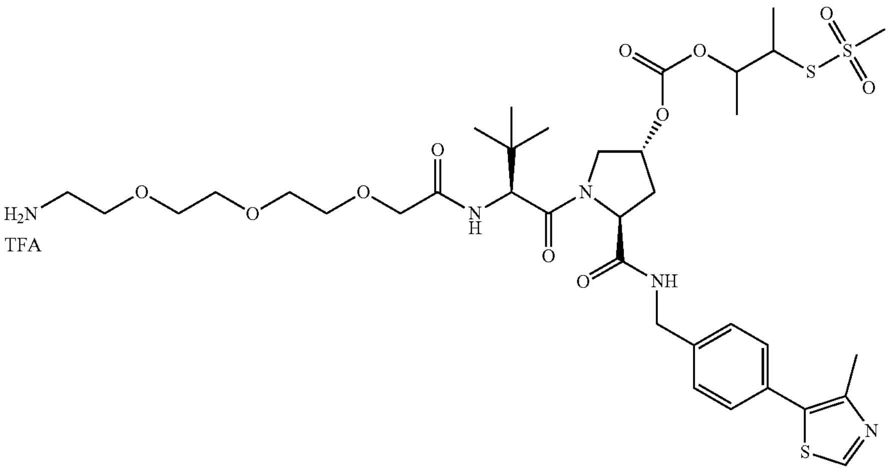

9

To a solution of compound 8 (90.0 mg, 0.1000 mmol) in HFIP (7.0 mL) was added TFA (0.35 mL). The reaction solution was stirred at 20° C. for 1 h. The mixture was concentrated in vacuo to remove the solvent to afford compound 9 (90 mg, 99%) as colorless oil. LCMS (5-95, AB, 1.5 min): $R_T$=0.760 min, m/z=830.5 [M+1]$^+$.

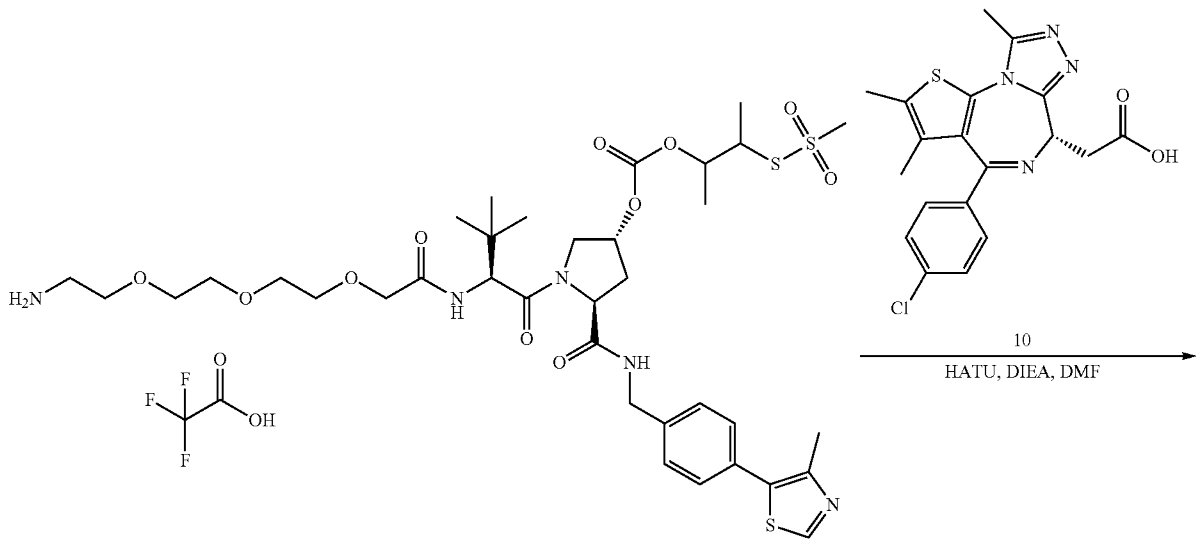

9

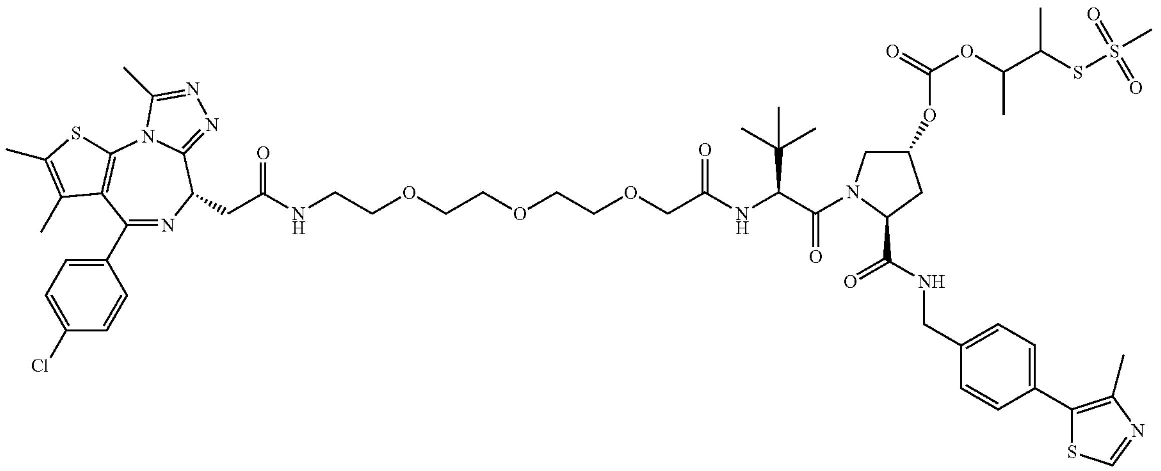

L1BQ15

To a solution of compound 10 (57.32 mg, 0.1400 mmol) in DMF (4.0 mL) was added DIEA (61.6 mg, 0.4800 mmol) and HATU (61.62 mg, 0.1600 mmol). The solution was stirred at 20° C. for 15 min, then compound 9 (90.0 mg, 0.1000 mmol) was added. The reaction solution was stirred at 20° C. for 1 h. The mixture was purified by prep-HPLC (Xtimate C18 150*25 mm*5 um, acetonitrile 56-66/0.225% FA in water) to afford L1BQ15 (30 mg, 250%) as a white solid. H NMR (400 MHz, DMSO-$d_6$) δ 8.99-8.98 (m, 1H), 8.64 (brs, 1H), 8.29 (t, J=5.6 Hz, 1H), 7.45-7.40 (m, 9H), 5.23 (brs, 1H), 4.98-4.95 (m, 1H), 4.53-4.43 (m, 4H), 4.30-4.24 (m, 1H), 4.07 (t, J=12.4 Hz, 1H), 3.96 (s, 2H), 3.86-3.84 (m, 1H), 3.74-3.71 (m, 1H), 3.59-3.53 (m, 12H), 3.31-3.18 (m, 3H), 2.59 (s, 3H), 2.45-2.44 (m, 3H), 2.40 (s, 3H), 2.37-2.33 (m, 1H), 2.17-2.10 (m, 1H), 1.61 (s, 3H), 1.44-1.37 (m, 3H), 1.34-1.25 (m, 3H), 0.95 (s, 9H). LCMS (10-80, AB, 7 min): $R_T$=4.328 min, m/z=607.4 [M/2+1]$^+$.

xxxiv. L1BQ17 An exemplary L1-CIDE, L1BQ17, can be synthesized by the following scheme.
Scheme 36
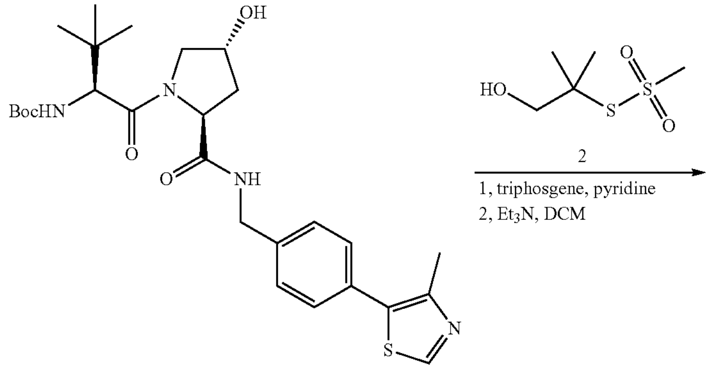
1
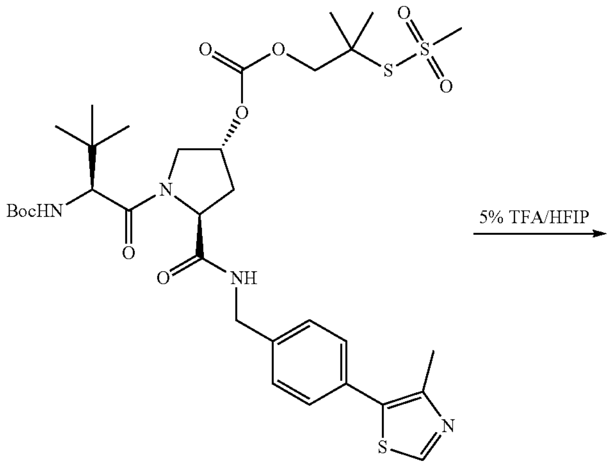
3
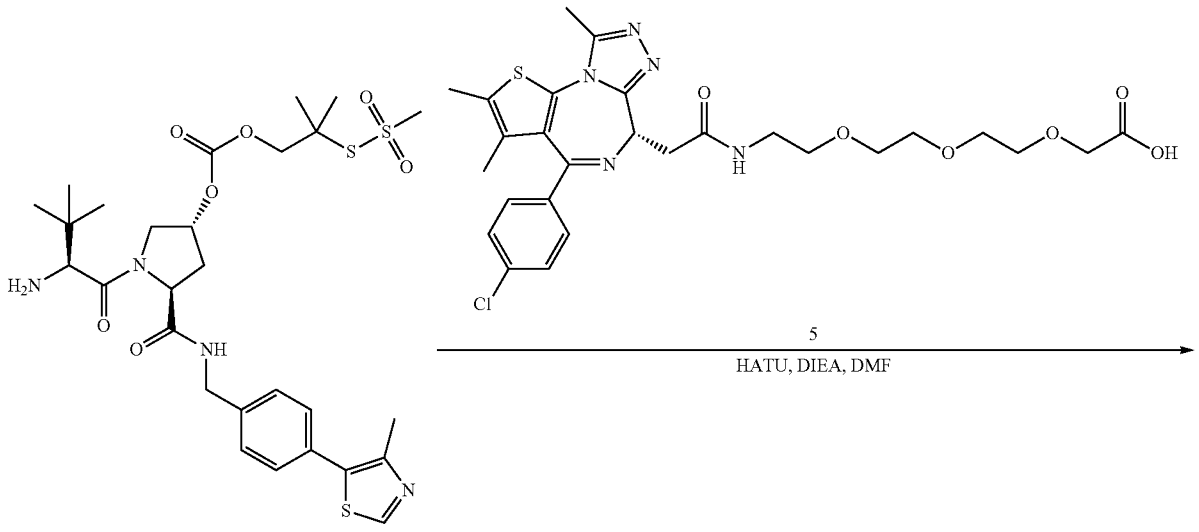
4

-continued

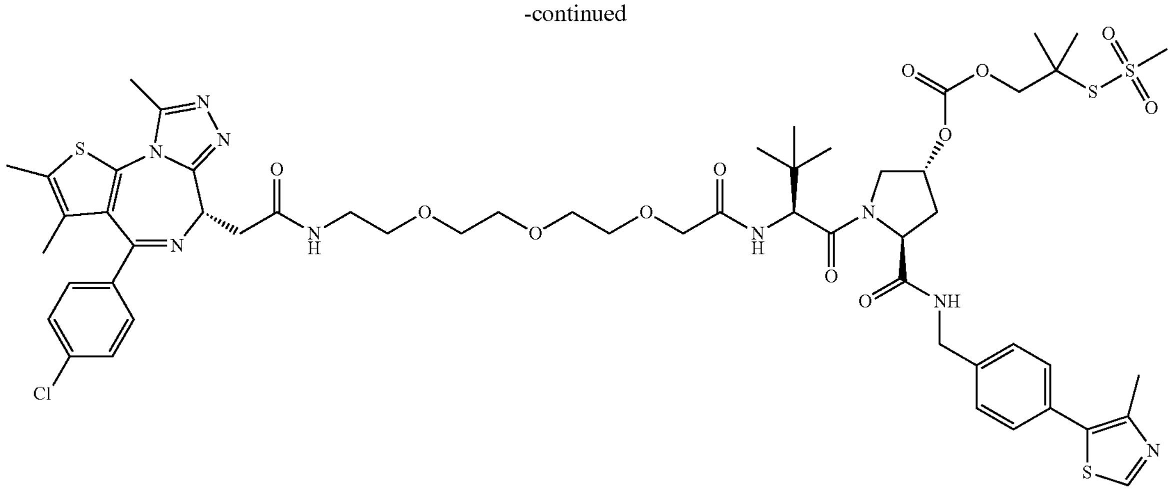

L1BQ17

Synthesis of 2:

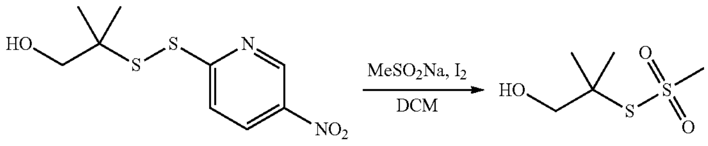

6 2

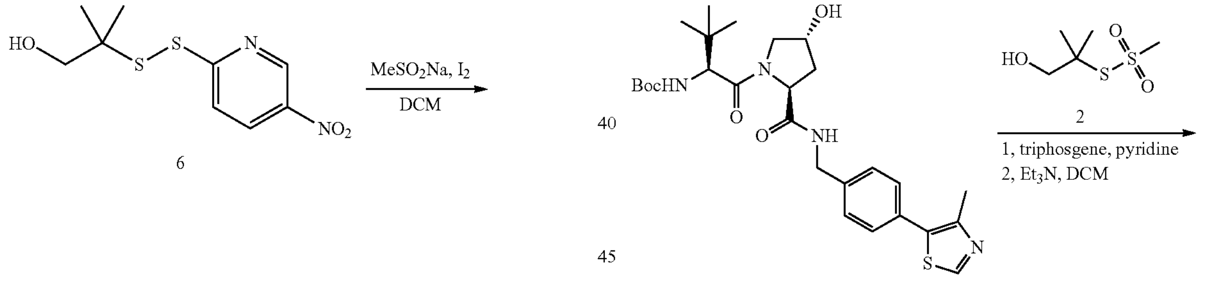

6 1

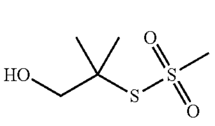

2

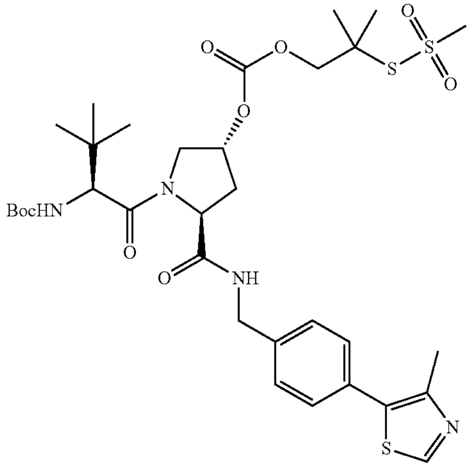

3

A solution of 2-methyl-2-[(5-nitro-2-pyridyl)disulfanyl] propan-1-ol (1.1 g, 4.2 mmol) in DCM (20 mL) was added sodium methane sulfinate (2.20 g, 21.1 mmol) and iodine (2.10 g, 8.40 mmol) at r.t. After it was stirred at 50° C. for 24 h, the reaction mixture was filtrated and the filtrate was purified by silica gel column chromatography (0-50% EtOAc in PE) to give the title compound (660 mg, 85%) as a yellow oil. $^1$HNMR (400 MHz, $CDCl_3$) δ 3.77 (s, 2H), 3.37 (s, 3H), 1.54 (s, 6H).

To a solution of Triphosgene (95.01 mg, 0.3200 mmol) in DCM (2.0 mL) was added a solution of pyridine (50.65 mg, 0.6400 mmol) and compound 2 (118.0 mg, 0.6400 mmol) in DCM (2.0 mL), and the reaction was stirred at 15° C. for 30 min. The reaction mixture was concentrated to dryness to give compound 3 (156 mg, 98%) as a white solid. To a solution of the above product (90.66 mg, 0.370 mmol) in DCM (8 mL) was added a solution of $Et_3N$ (49.58 mg, 0.490 mmol) and compound 1 (130.0 mg, 0.240 mmol) in DCM (2.0 mL). The reaction mixture was stirred at 20° C. for 2 h. The mixture was concentrated and purified by flash column (0-10% MeOH in DCM Rf=0.5) to give compound 3 (107 mg, 44%) as colorless oil. LCMS (5-95, AB, 1.5 min): RT=0.811 min, m/z=741.1 $[M+1]^+$.

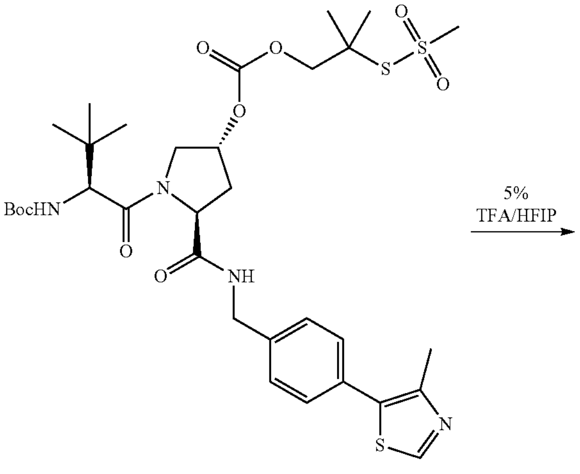

3

-continued

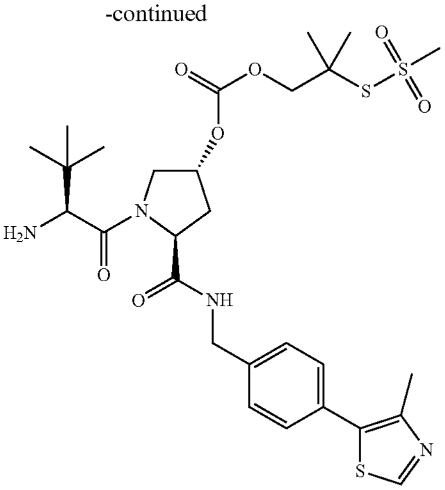

4

To a solution of compound 3 (107.0 mg, 0.1400 mmol) in hexafluoroisopropanol (1.9 mL) was added TFA (0.10 mL). The reaction solution was stirred at 20° C. for 1 h. The mixture was concentrated to give compound 4 with TFA salt (109 mg, 100%) as a colorless oil, which was used for the next step directly. LCMS (5-95, AB, 1.5 min): RT=0.632 min, m/z=641.0 $[M+1]^+$.

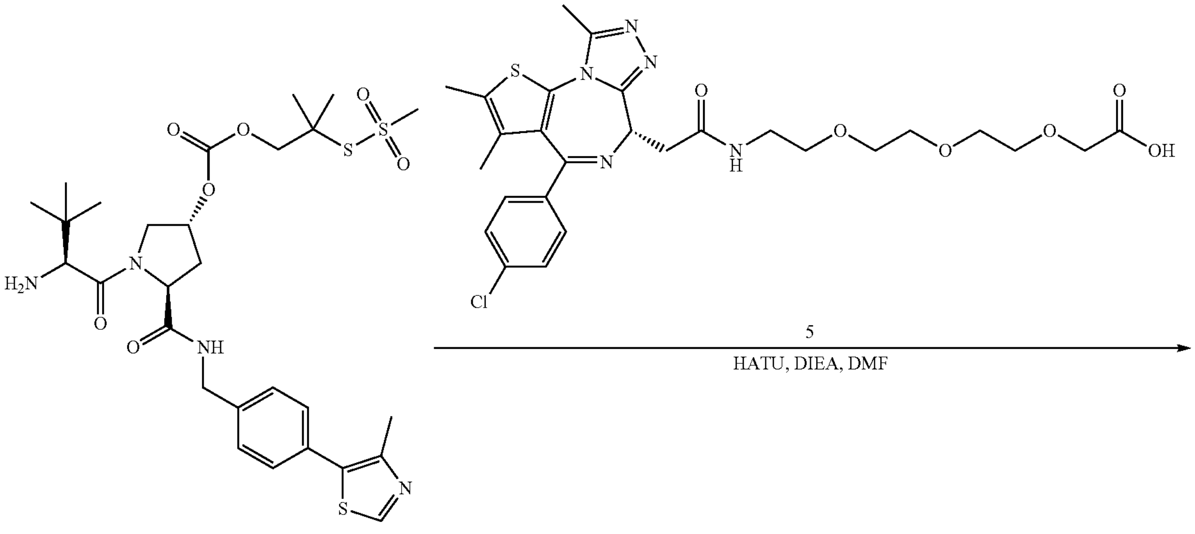

4

5

-continued

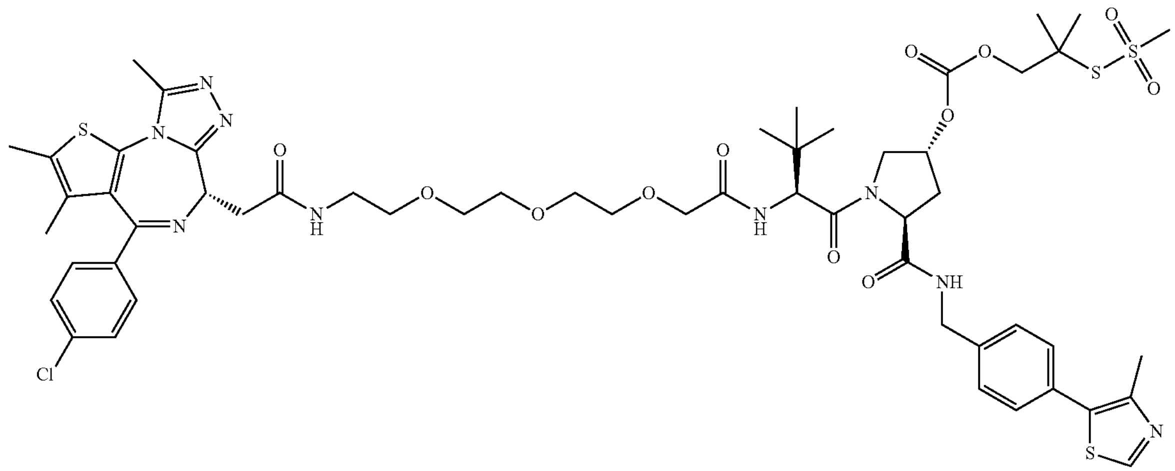

L1BQ17

A solution of compound 5 (60.0 mg, 0.1000 mmol), DIEA (39.42 mg, 0.3100 mmol) and HATU (57.99 mg, 0.1500 mmol) in anhydrous DMF (10 mL) was stirred at 25° C. for 10 min, and then compound 4 (99.78 mg, 0.1300 mmol) was added. The resulted mixture was stirred at 25° C. for 2 h. The mixture was purified by prep-HPLC (acetonitrile 39-69%/0.1% TFA in water) to give L1BQ17 (43.09 mg, 32.5%) as a white solid. LCMS (10-80, AB, 7 min): RT=4.305 min, m/z=1212.6 $[M+1]^+$.

xxxv. L1BQ18 An exemplary L1-CIDE, L1BQ18, can be synthesized by the following scheme:

Scheme 37

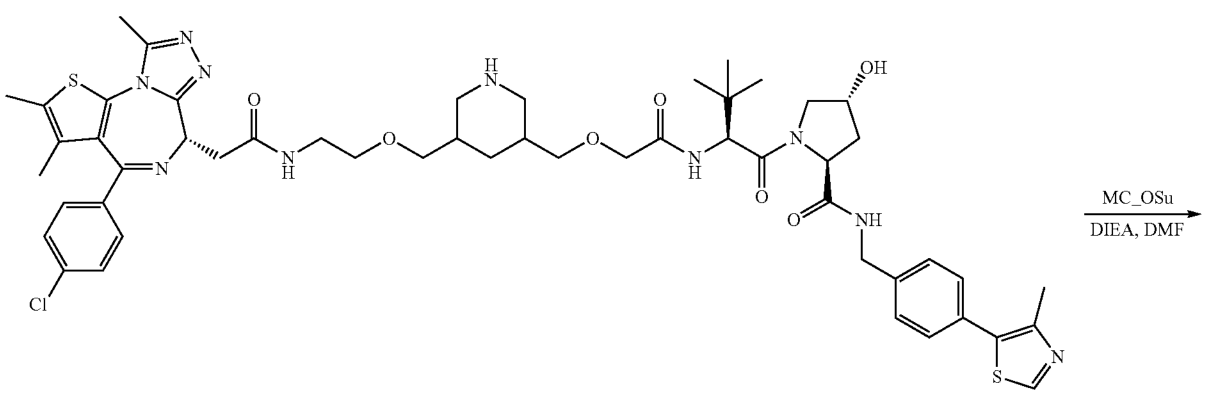

1

-continued
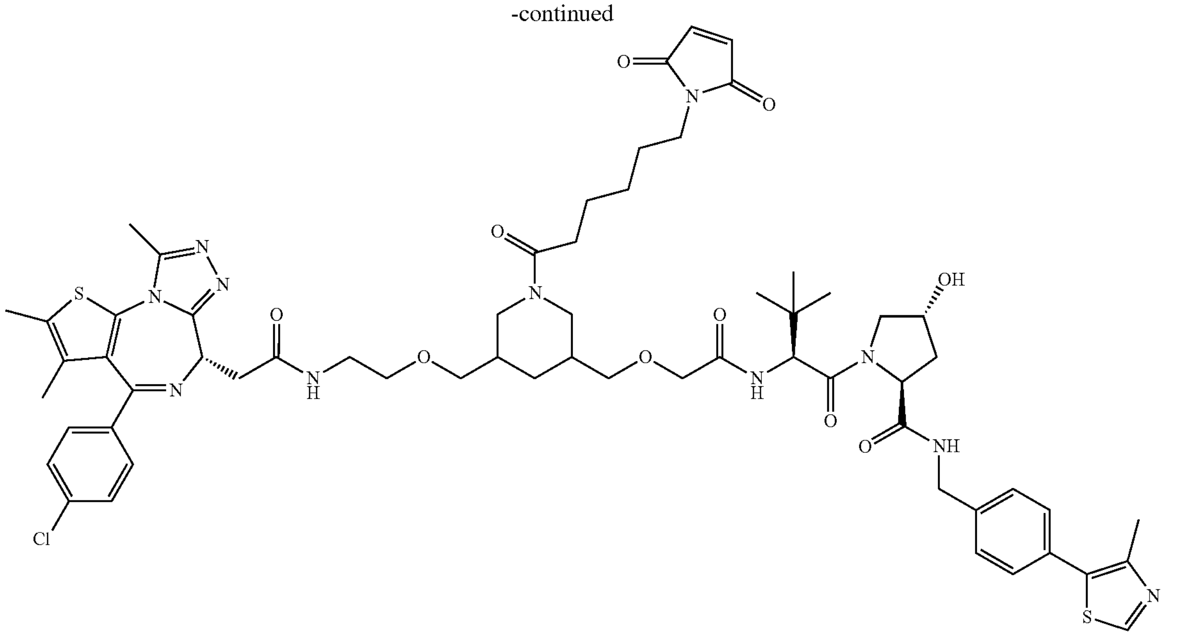
L1BQ18
To a solution of MC_OSu (6.43 mg, 0.020 mmol) in anhydrous DMF (2.0 mL) was added 1 (15.0 mg, 0.0100 mmol) and DIEA (8.99 mg, 0.0700 mmol). The mixture was stirred at 20° C. for 12 h. The solution was concentrated and purified by prep-HPLC (45-75 water (0.225% FA)-ACN) to afford L1BQ18 (4.02 mg, 23%) as a white solid. LCMS (5-95, AB, 1.5 min): $R_T$=0.847 min, m/z=1234.4 $[M+1]^+$.
xxxvi. L1BQ19 An exemplary L1-CIDE, L1BQ19, can be synthesized by the following
Scheme 38
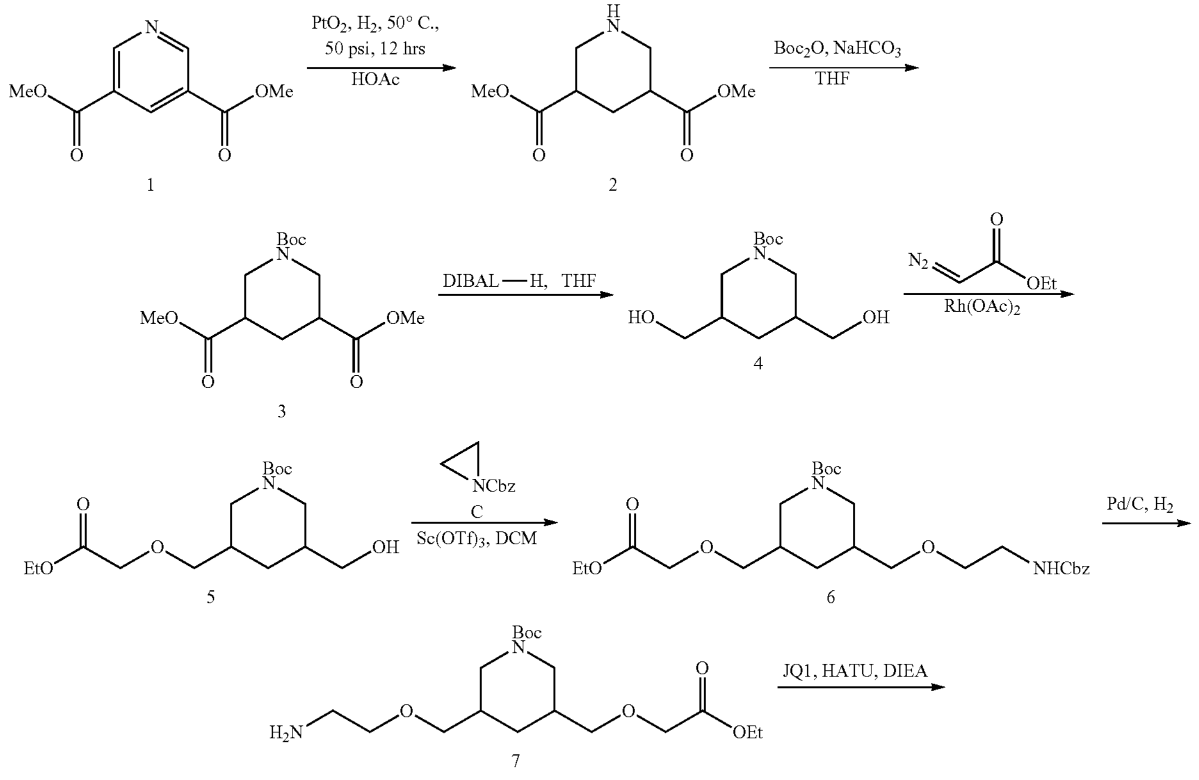

-continued
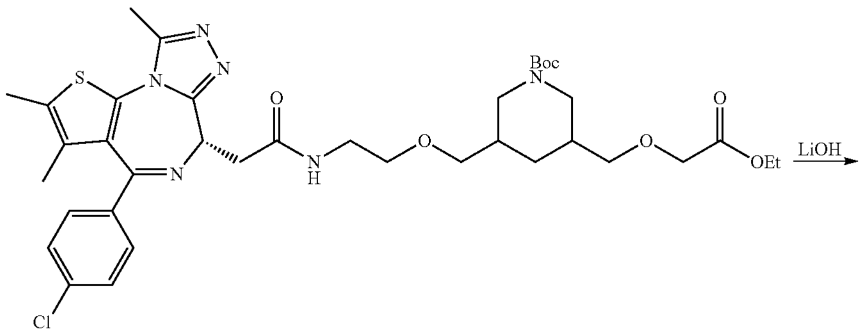
8
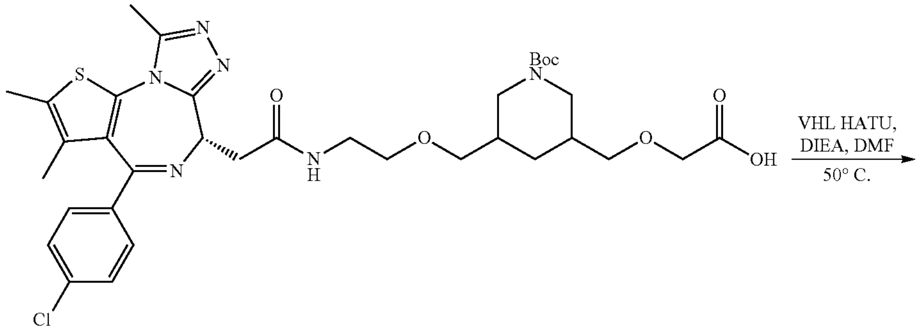
9
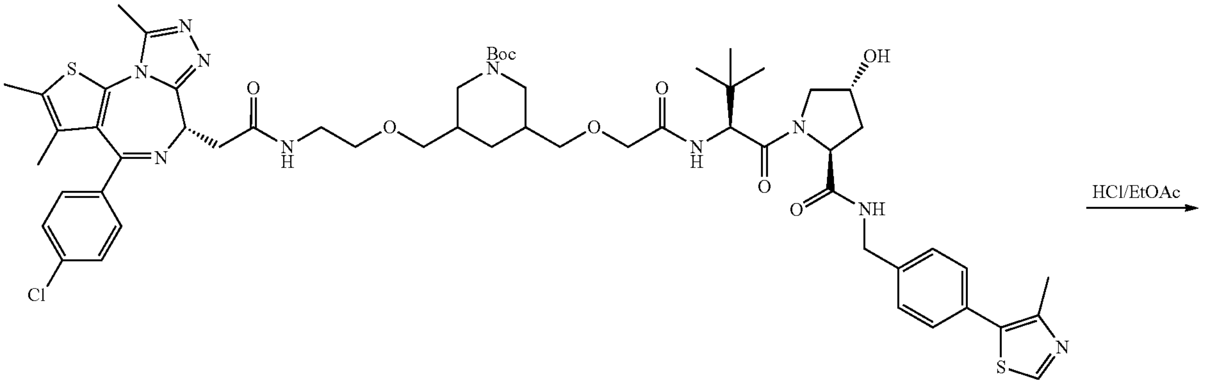
10
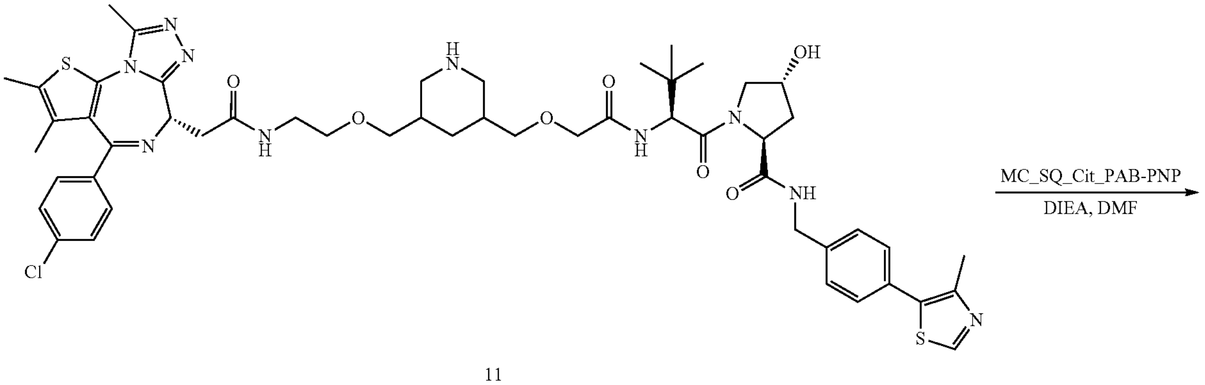
11

-continued

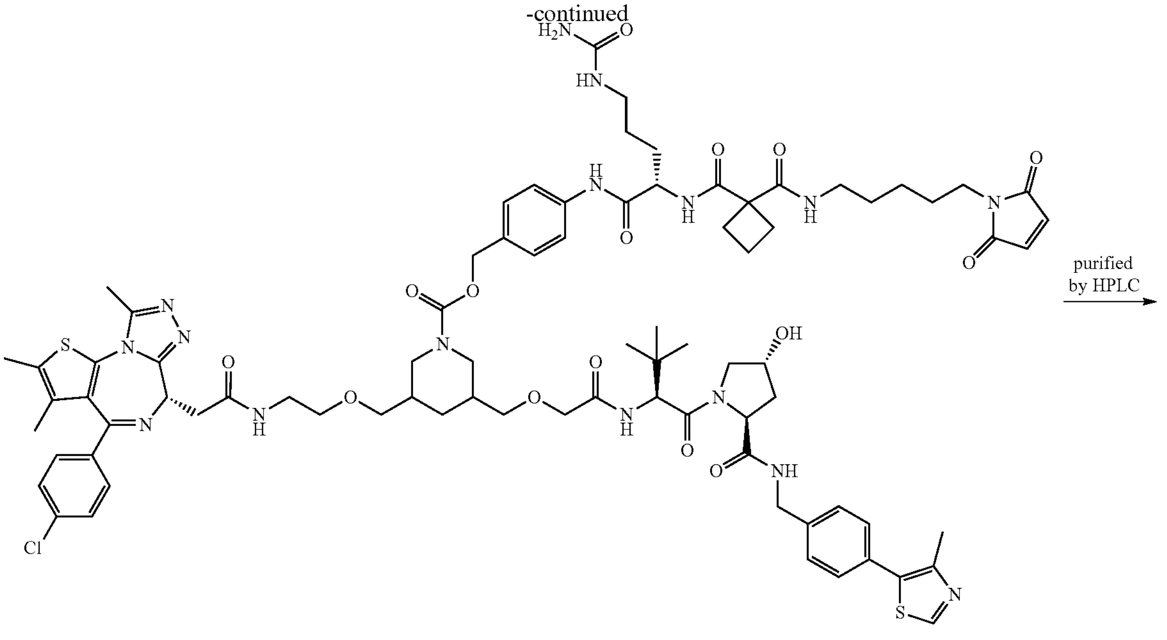

12

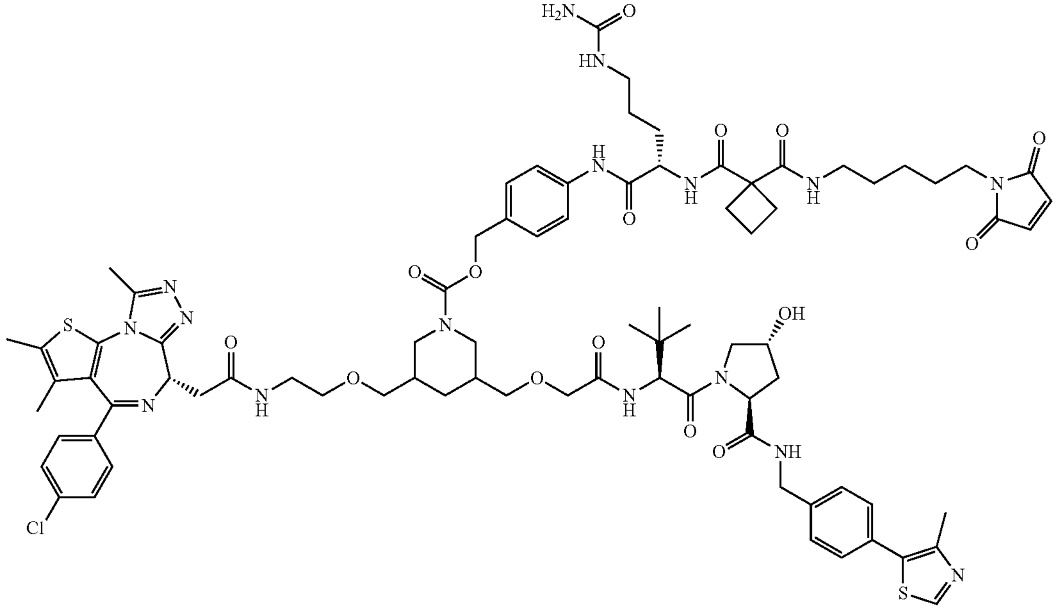

L1BQ19

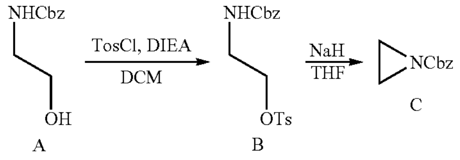

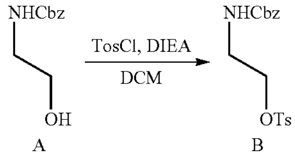

To a solution of Compound A (5.0 g, 25.61 mmol) and DIEA (6.35 mL, 38.42 mmol) in DCM (50 mL) was added TsCl (7.32 g, 38.42 mmol) at 0° C. The mixture was warmed to 25° C. and stirred for 16 h. The mixture was quenched with water (20 mL), extracted with EtOAc (20 mL×2). The organic layer was washed with brine (20 mL), dried over $Na_2SO_4$, filtered and concentrated. The residue was purified by column chromatography (0-50% EtOAc in petroleum ether) to give the desired product B (5.20 g, 58%) as a white solid. LCMS (5-95, AB, 1.5 min): RT=0.879 min, m/z=371.9 [M+23]+.

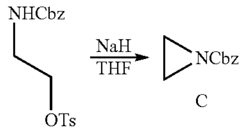

B C

To a suspension of NaH (480.82 mg, 12.02 mmol) in THF (40 mL) was added Compound B (3.500 g, 10.02 mmol) in THF (5.0 mL) at 40° C., and the reaction mixture was stirred at 40° C. for 4.5 h and quenched with water. EtOAc (10 mL) was added, and the organic layer was separated and washed with water (10 mL×2) and brine (10 mL). The organics were dried over $MgSO_4$, concentrated, and purified by flash column chromatography (0-20% EtOAc in petroleum ether, Rf=0.4) to give compound C (1.200 g, 68%) as a colorless oil. H NMR (400 MHz, $CDCl_3$) δ 7.40-7.32 (m, 5H), 5.15 (s, 2H), 2.24 (s, 4H).

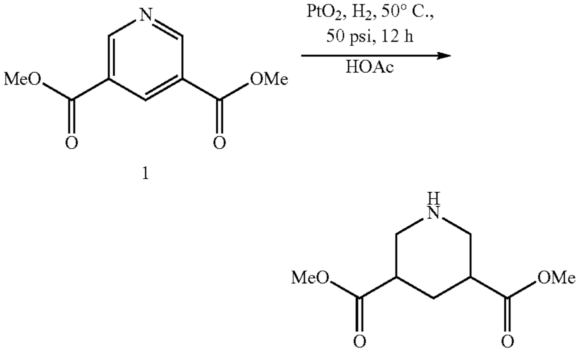

1

2

To a solution of Compound 1 (6.000 g, 30.74 mmol) in acetic acid (50 mL) was added $PtO_2$ (698.1 mg, 3.07 mmol), and the resulting suspension was stirred under $H_2$ (50 psi) at 45° C. for 12 h. After the catalyst was removed by filtration through celite, the filtrate was concentrated to afford compound 2 (6.000 g, 97%) as a colorless oil. The crude was used directly without further purification.

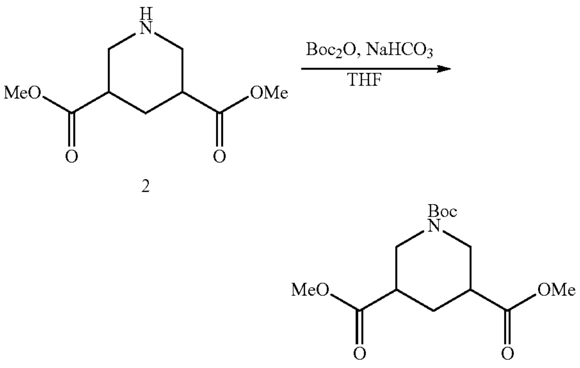

2

3

To a solution of Compound 2 (6.00 g, 29.82 mmol) in THF (20 mL) and water (5.00 mL) was added $NaHCO_3$ (10.020 g, 119.27 mmol) and $Boc_2O$ (10.28 mL, 44.73 mmol). The mixture was stirred at 18° C. for 2 h. The mixture was diluted with water (15 mL), and extracted with EtOAc (15 mL×3). The organic layer was dried, concentrated and purified by column chromatography (5%-30% EtOAc in petroleum ether, Rf=0.5) to afford compound 3 (7.200 g, 75%) as a white solid. LCMS (5-95, AB, 1.5 min): RT (220/254 nm)=0.873 min, m/z=201.9 [M+1-100]+.

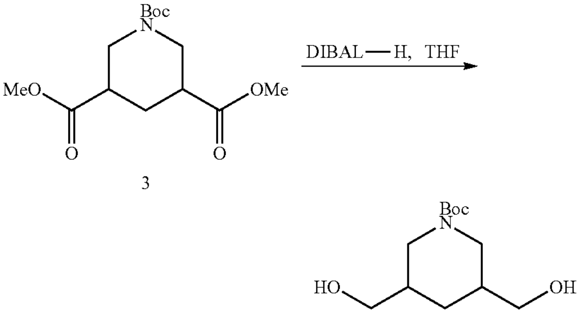

3

4

To a solution of Compound 3 (7.200 g, 23.89 mmol) in THF (40.0 mL) was added DIBAL-H (95.57 mL, 95.57 mmol) (1.0 M in toluene) at −78° C. under $N_2$, and the mixture was stirred at −78° C. for 2 h. The reaction was quenched with MeOH (5.0 mL) at −25° C. and stirred for 5 min. A Rochelle salt solution (60 mL 20% w/w) was added and stirred at 25° C. for 1 h. The residue was extracted with EtOAc (15 mL×2). The combined organic layers were washed with water (30 mL×2), brine (30 mL×2) and dried over sodium sulfate. The crude was purified by flash column chromatography (0-10% MeOH in DCM, Rf=0.5) to give compound 4 (2.70 g, 38%) as a colorless oil. LCMS (5-95, AB, 1.5 min): RT=0.840 min, m/z=268.0 [M+23]+. 1

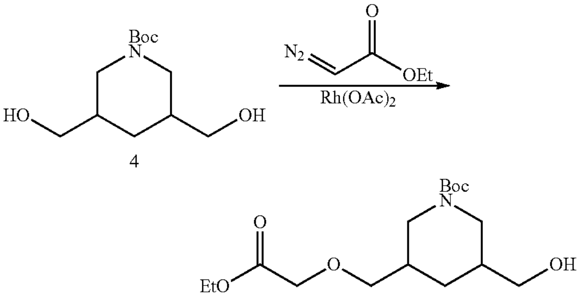

4

5

To a solution of $Rh(OAc)_2$ (0.45 g, 2.04 mmol) and Compound 4 (2.50 g, 10.19 mmol) in DCM (40 mL) was added ethyl diazoacetate (1.07 mL, 10.19 mmol) at 0° C. under $N_2$. Then the mixture was warmed to 15° C. and stirred for 12 h. The mixture was quenched with water (10 mL), extracted with DCM (10 mL×3). The organic layer was washed with water (10 mL×3), brine (10 mL×3), dried over $Na_2SO_4$, concentrated and purified by column chromatography (0-1% MeOH in DCM, Rf=0.3) to afford compound 5 (1.00 g, 30%) as a colorless oil. LCMS (5-95, AB, 1.5 min): RT (220/254 nm)=0.805 min, m/z=354.1[M+23]+.

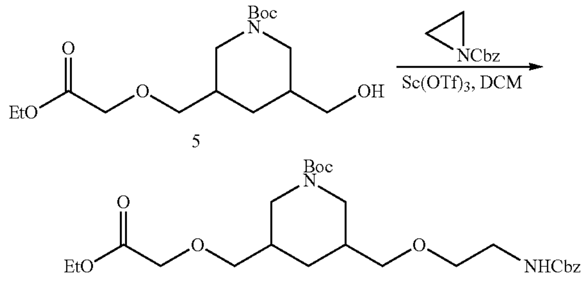

5

6

A mixture of Compound 5 (1000.0 mg, 3.02 mmol) and $Sc(OTf)_3$ (148.51 mg, 0.3000 mmol) in DCM (10 mL) was stirred at −78° C. under $N_2$, then a solution of benzyl aziridine-1-carboxylate (802.05 mg, 4.53 mmol) in DCM (3.0 mL) was added drop-wise. The mixture was stirred at −78° C. for 4 h and warmed to 15° C. for 12 h. The mixture was concentrated and purified by flash chromatography on silica gel (0-5% MeOH in DCM, Rf=0.4) and prep-HPLC (50%-80% water (10 mM $NH_4HCO_3$)-ACN) to afford compound 6 (200 mg, 13%) as a brown oil. LCMS (5-95, AB, 1.5 min): RT (220/254 nm)=0.896 min, m/z=409.0 $[M+1-100]^+$.

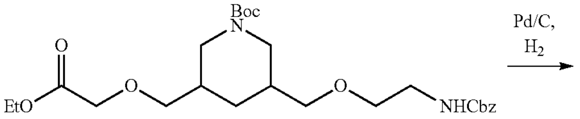

6

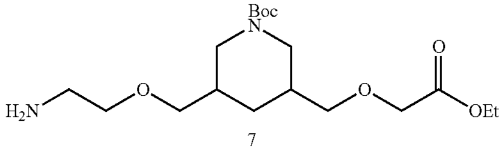

7

To a solution of Pd/C (35.57 mg) in THF (10 mL) was added Compound 6 (170.0 mg, 0.3300 mmol). The mixture was stirred at 15° C. under $H_2$ (15 psi) for 1 h. The mixture was filtered, washed with MeOH (10 mL×3), and the filtrate was concentrated to afford compound 7 (125 mg, 99.9%) as a yellow oil, which was used in the next step without further purification.

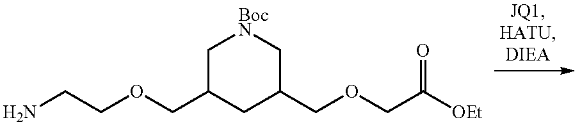

7

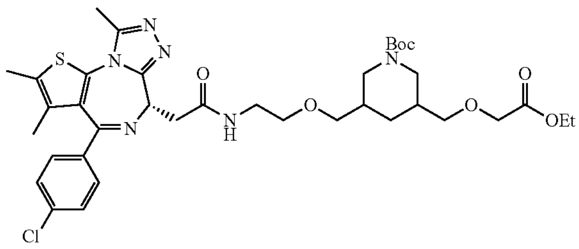

8

A solution of JQ1 (160.58 mg, 0.4000 mmol), HATU (190.38 mg, 0.5000 mmol) and DIEA (0.17 mL, 1 mmol) in DMF (5.0 mL) was added Compound 7 (125.0 mg, 0.3300 mmol) at 0° C. The reaction mixture was stirred at 15° C. for 1 h. The mixture was concentrated and purified by prep-TLC (5% MeOH in DCM, Rf=0.3) to afford compound 8 (240 mg, 92%) as a yellow solid. LCMS (5-95, AB, 1.5 min): RT=0.920 min, m/z=757.0 $[M+1]^+$.

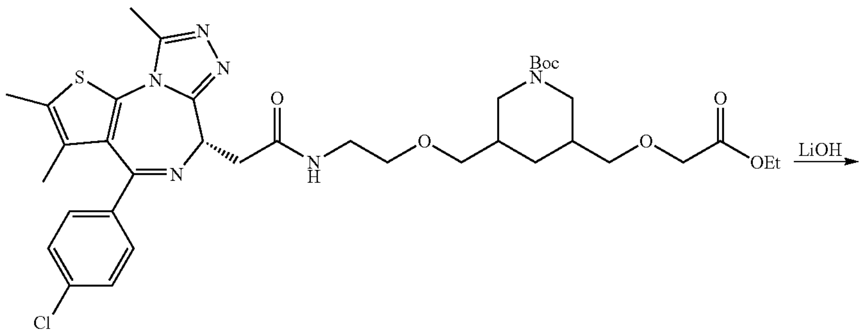

8

-continued

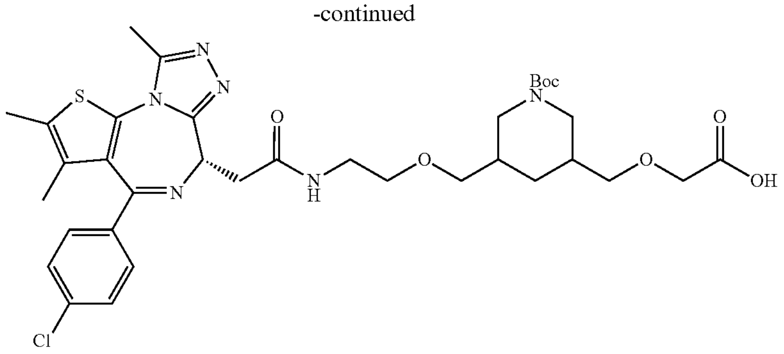

9

To a solution of Compound 8 (180.0 mg, 0.2400 mmol) in THF (5.0 mL), MeOH (1.0 mL) and water (1 mL) was added LiOH $H_2O$ (49.86 mg, 1.19 mmol). The mixture was stirred at 15° C. for 1 h. The mixture was quenched with water (10 mL), washed with EtOAc (10 mL×3). The aqueous layer was acidified with citric acid to pH=4, extracted with EtOAc (10 mL×2). The organic layer was dried, concentrated, and purified by prep-HPLC (25%-55% water (10 mM NH4HCO3)-ACN) to afford compound 9 (100 mg, 58%) as a white solid. LCMS (5-95, AB, 1.5 min): RT (220/254 nm)=0.843 min, m/z=751.1 $[M+23]^+$.

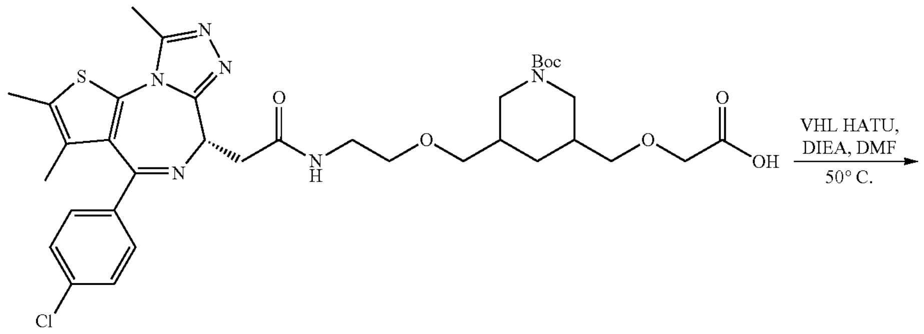

9

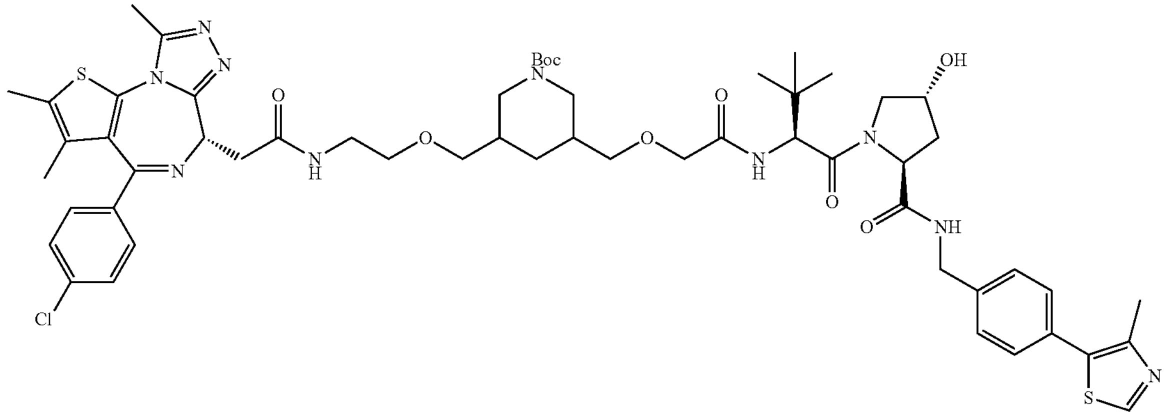

10

A solution of Compound 9 (30.0 mg, 0.0300 mmol), VHL (26.58 mg, 0.0600 mmol), DIEA (5.31 mg, 0.0300 mmol) and HATU (15.63 mg, 0.0300 mmol) in DMF (4.0 mL) was stirred at 50° C. for 6 h. The mixture was concentrated and purified by prep-HPLC (45%-75% water (10 mM and $NH_4HCO_3$)-ACN, 25 ml/min) to afford compound 10 (25 mg, 72%) as a yellow solid. LCMS (5-95, AB, 1.5 min): RT=0.894 min, m/z=1142.3 $[M+1]^+$.

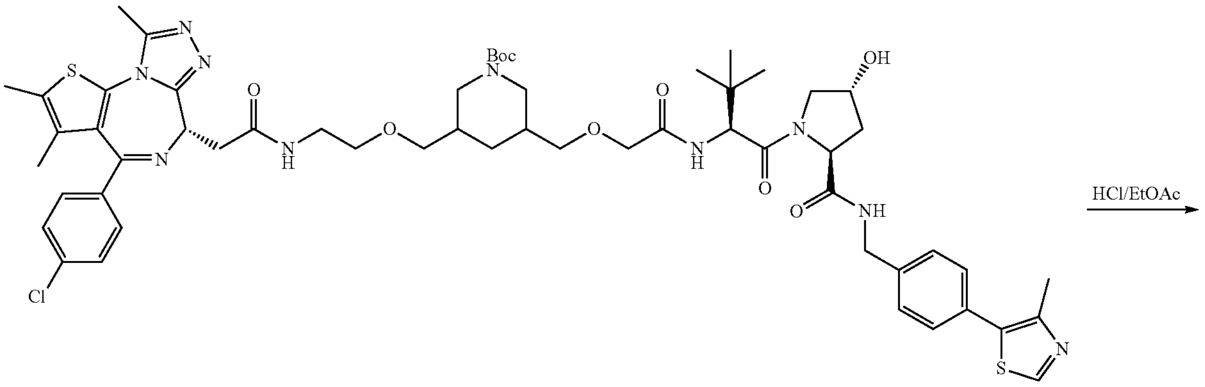

10

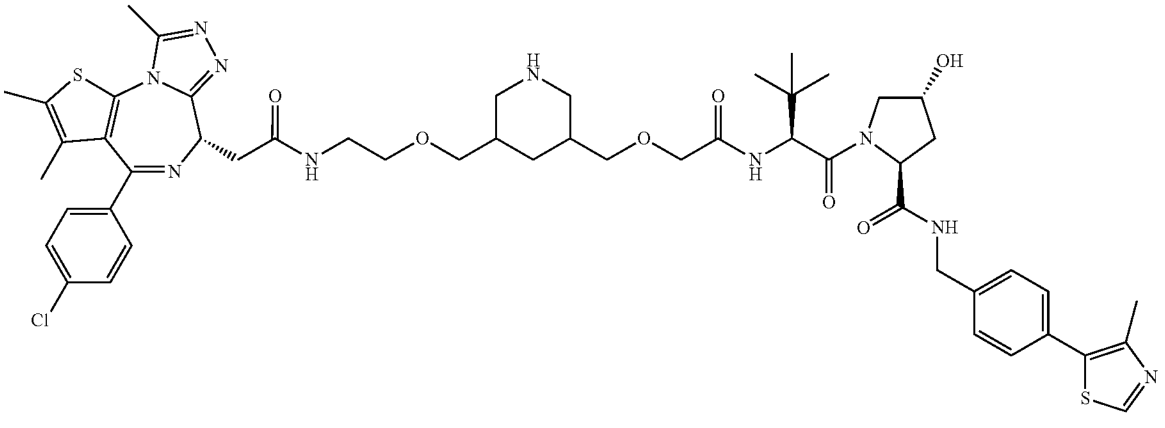

11

A mixture of Compound 10 (25.0 mg, 0.0200 mmol) in a solution of HCl in EtOAc (4.0 M, 9.83 mL) was stirred at 15° C. for 1 h. The mixture was concentrated and the resulting residue was washed with EtOAc (10 mL×2) and DCM (10 mL×2) to afford GNT_C439_45-1 HCl salt as a yellow solid (20 mg, 85%). $^1$H NMR (400 MHz, $D_2O$) δ 9.56 (s, 1H), 7.43-7.41 (m, 4H), 7.38-7.33 (m, 4H), 4.53-4.46 (m, 3H), 4.38-4.37 (m, 2H), 4.05-3.96 (m, 2H), 3.90-3.87 (m, 1H), 3.77-3.75 (m, 1H), 3.59-3.57 (m, 3H), 3.49-3.32 (m, 9H), 2.69-2.65 (m, 4H), 2.46 (s, 3H), 2.33-1.88 (m, 10H), 1.67-1.63 (m, 1H), 1.52 (s, 3H), 1.19-1.09 (m, 1H), 0.88 (s, 9H). LCMS (10-80, AB, 7 min): RT=3.233 min, m/z=1041.5 [M+1]$^+$. Chiral HPLC (CD-PH_10-80_B_08ML_30 min): RT=16.05 min, 16.44 min, showed 68% and 32% of desired product.

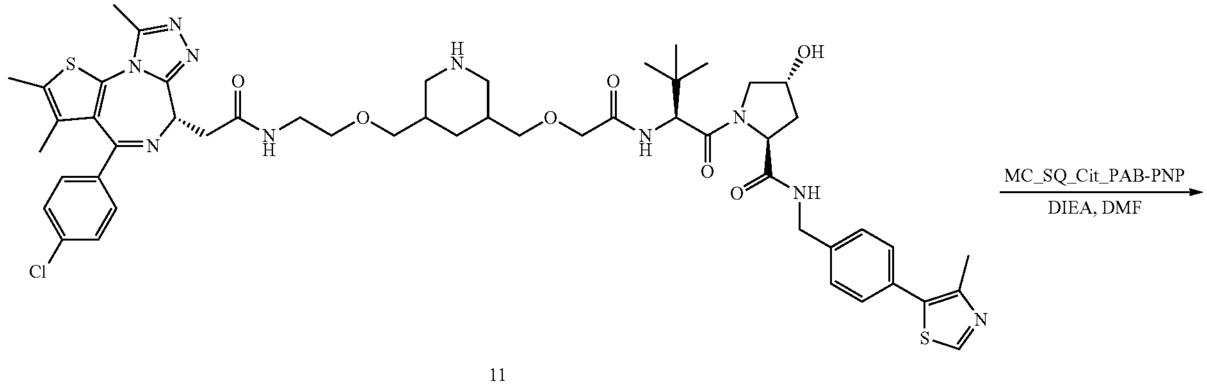

11

-continued

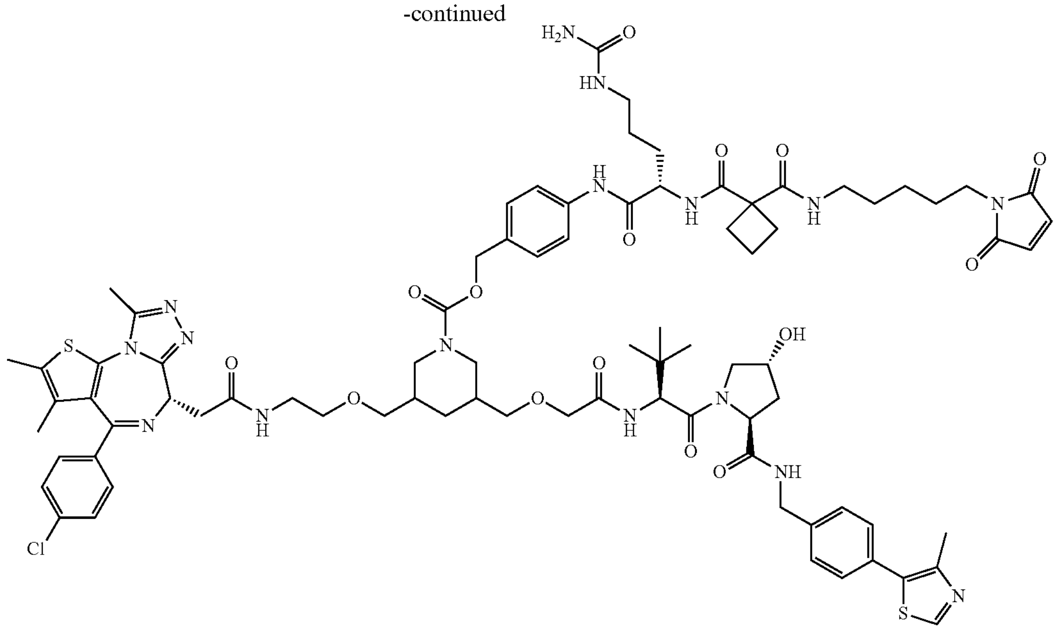

L1BQ19

To a solution of MC_SQ_Cit_PAB-PNP (9.11 mg, 0.0100 mmol) in anhydrous DMF (2.0 mL) was added 11 (8.9 mg, 0.0100 mmol) and DIEA (5.33 mg, 0.0400 mmol). The reaction solution was stirred at 20° C. for 12 h. The mixture was concentrated and purified by prep-HPLC (38-58 water (10 mM $NH_4HCO_3$)-ACN) to afford product (15 mg, with 89% purity), which was further purified by prep-HPLC (39-59 water (0.225% FA)-ACN) to afford two L1BQ19 products: (4.11 mg, 43%) and (4.62 mg, 47%) both as a white solid. LCMS (5-95, AB, 1.5 min): RT=0.841 min, m/z=820.0 $[M2+1]^+$; and LCMS (5-95, AB, 1.5 min): RT=0.844 min, m/z=820.1$[M/2+1]^+$.

xxxvii. L1BQ20 An exemplary L1-CIDE, L1BQ20, can be synthesized by the following Scheme 39

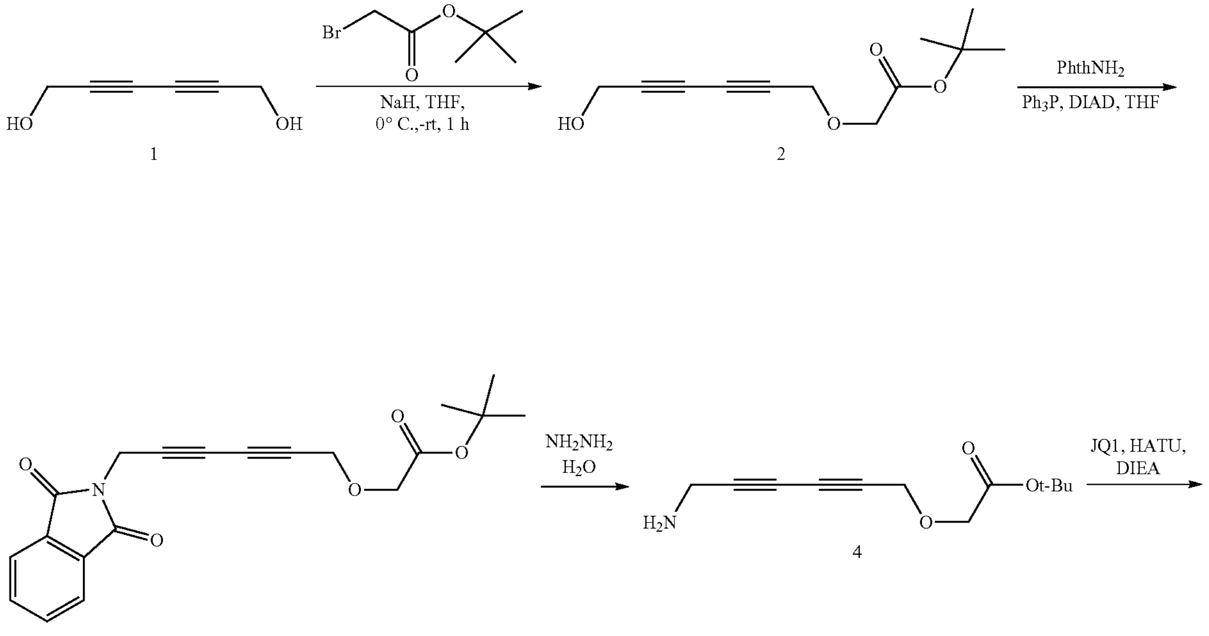

1

2

3

4

-continued
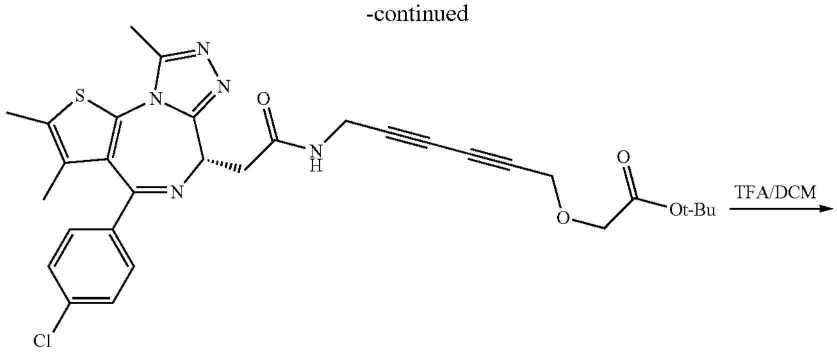
5
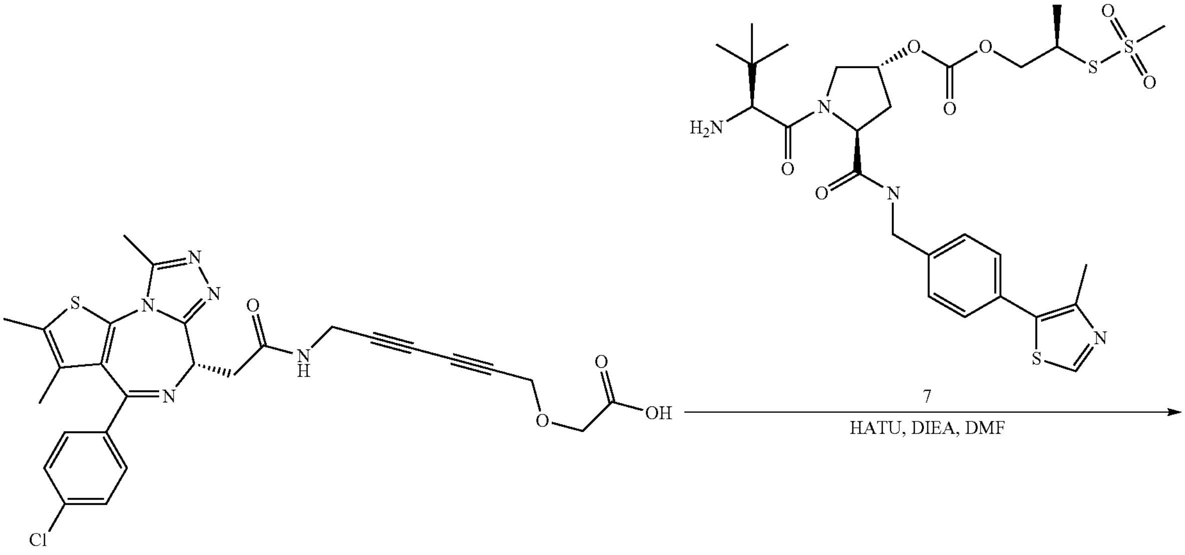
6
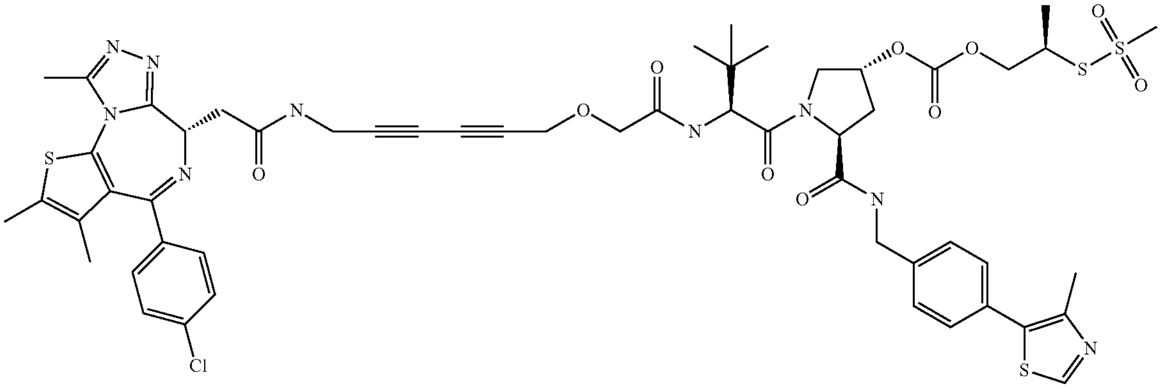
L1BQ20
-continued
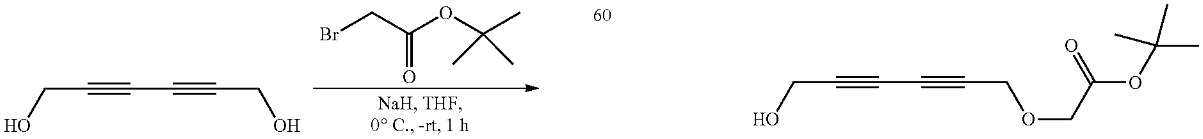
1 2

To a suspension of NaH (59.94 mg, 1.5 mmol) in THF (10 mL) was added compound 1 (0.070 mL, 1 mmol) at 0° C. under $N_2$. The mixture was stirred for 0.5 h. Then tert-butyl bromoacetate (0.11 mL, 0.950 mmol) in THF (5.0 mL) was added to the above mixture slowly. The reaction was quenched with water (10 mL), and extracted with EtOAc (20 mL×2), washed with brine (10 mL×2). The organic layer was concentrated and purified by flash column chromatography (20% EtOAc in petroleum ether, Rf=0.5) to give compound 2 (90 mg, 40.2%) as light yellow oil. $^1H$ NMR (400 MHz, $CD_3OD$) δ 4.34 (s, 2H), 4.24 (s, 2H), 4.03 (s, 2H), 1.48 (s, 9H).

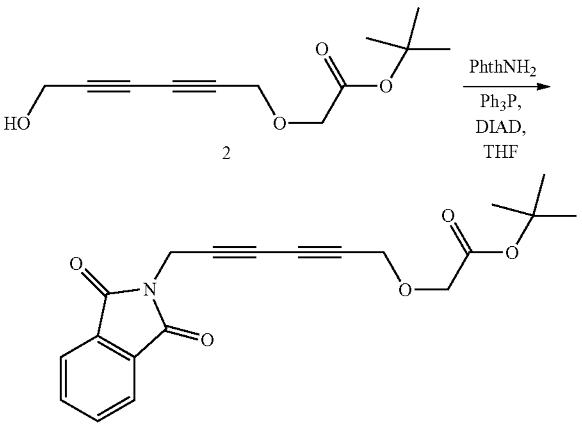

2

3

To a stirred solution of compound 2 (512.0 mg, 2.28 mmol), $PhthNH_2$ (369.51 mg, 2.51 mmol) and $Ph_3P$ (718.62 mg, 2.74 mmol) in THF (10 mL) was added DIAD (554.0 mg, 2.74 mmol) at 20° C. The mixture was stirred at r.t. for 12 h. The reaction solvent was removed and the residue was purified by flash chromatography on silica gel (0-30% EtOAc in petroleum ether) to give compound 3 (1.1 g, >100%) as yellow oil. $^1H$ NMR (400 MHz, $CDCl_3$) δ 7.89-7.86 (m, 2H), 7.75-7.73 (m, 2H), 4.52 (s, 2H), 4.32 (s, 2H), 4.01 (s, 2H), 1.45 (s, 9H).

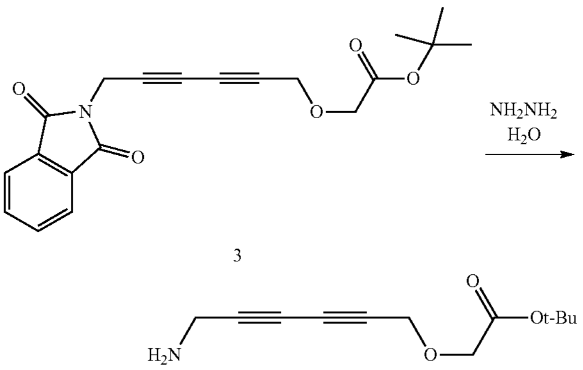

3

4

To a stirred solution of compound 3 (200.0 mg, 0.570 mmol) in EtOH (5.0 mL) was added hydrazine hydrate (0.010 mL, 0.680 mmol), and the mixture was stirred at 80° C. for 1 h. The mixture was concentrated, extracted with DCM/MeOH (10:1) (20 mL×3), and washed with brine (10 mL). The organic layer was concentrated to give compound 4 (120 mg, 95%) as a brown oil which was used in next step directly.

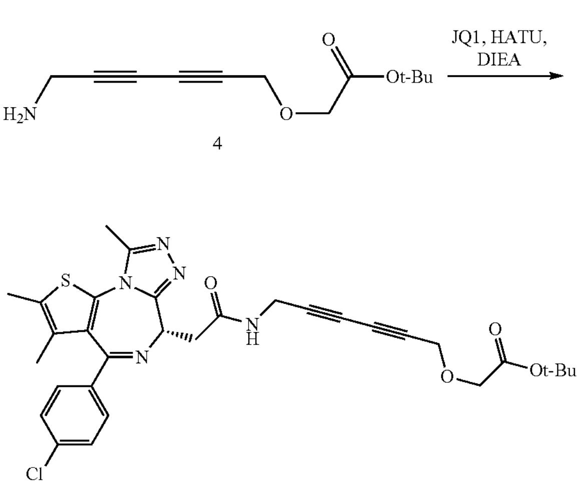

4

5

To a mixture of JQ1 (2.05 g, 5.11 mmol) and compound 4 (0.95 g, 4.25 mmol) in DMF (10 mL) was added DIEA (1.099 g, 8.51 mmol) and HATU (2.426 g, 6.38 mmol) at 25° C. The mixture was stirred for 2 h. The mixture was concentrated and purified by chromatography on silica (0-10% MeOH in DCM Rf=0.6) to give compound 5 (1.56 g, 61%) as a yellow oil. LCMS (5-95, AB, 1.5 min): RT=0.905 min, m/z=606.0 [M+1]$^+$.

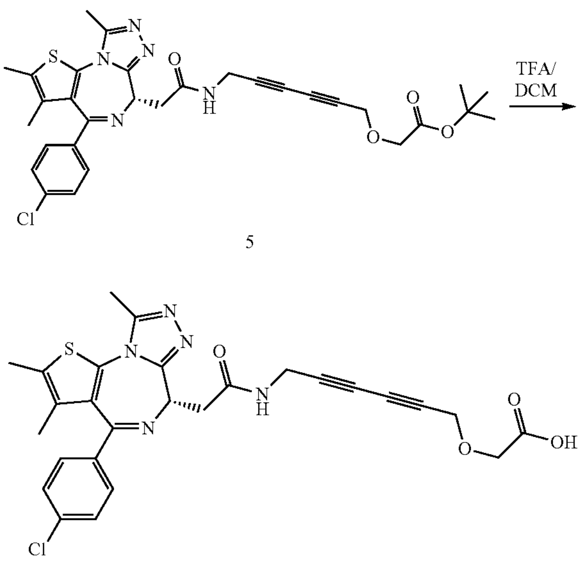

5

6

To a stirred solution of compound 5 (1.37 g, 2.26 mmol) in DCM (20 mL) was added TFA (20.0 mL) at 20° C. The mixture was stirred at 20° C. for 2 h. The solvent was removed to give compound 6 (1.2 g, 82%) as a yellow oil. LCMS (5-95, AB, 1.5 min): RT=0.804 min, m/z=550.1 [M+1]$^+$.

7
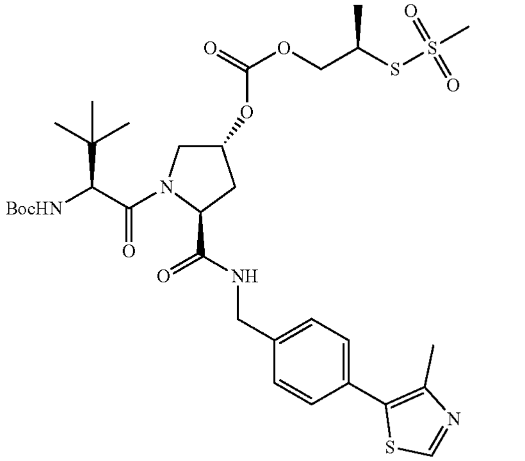
LCMS (5-95, AB, 1.5 min): RT=0.942 min, m/z=727.2 [M+1]+.
8
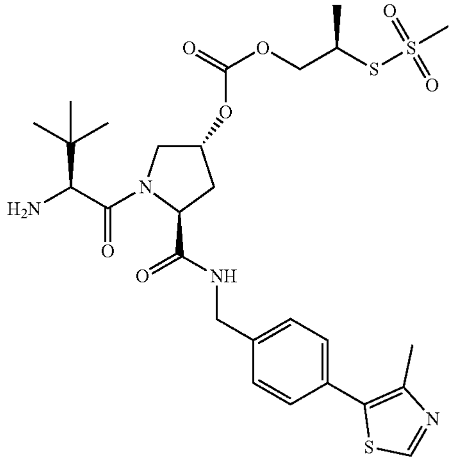
LCMS (5-95, AB, 1.5 min): RT=0.748 min, m/z=627.3 [M+1]+.
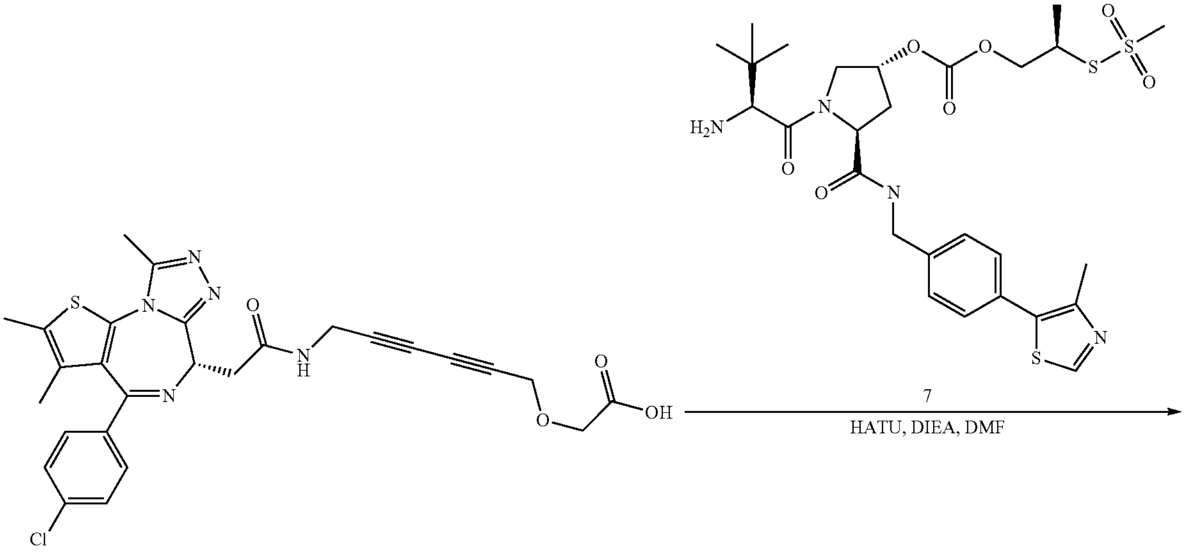
6
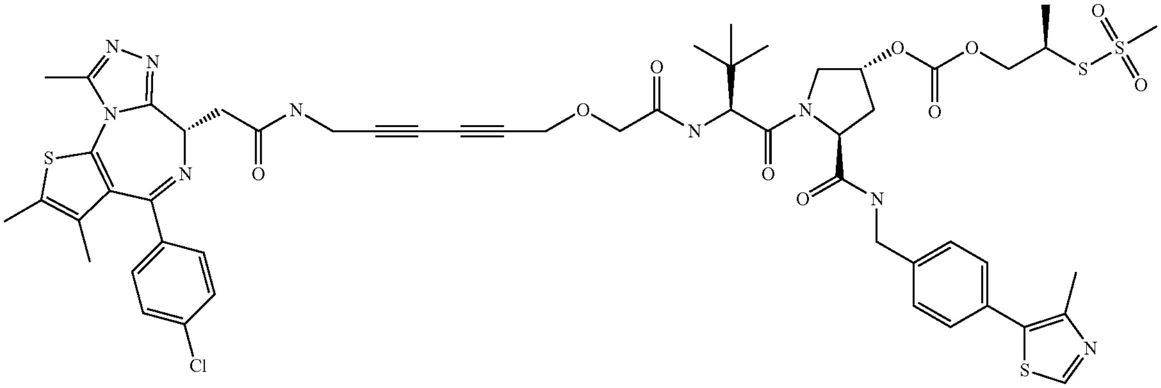
L1BQ20

A mixture of compound 6 (96.52 mg, 0.1800 mmol), DIEA (52.34 mg, 0.400 mmol) and HATU (66.72 mg, 0.1800 mmol) in anhydrous DMF (5.0 mL) was stirred at 25° C. for 10 min, and compound 7 (100.0 mg, 0.1300 mmol) was added. The mixture was stirred at 25° C. for 2 h. The crude product was purified by prep-HPLC (acetonitrile 32-62%/0.225% FA in water) to give L1BQ20 (18.75 mg, 12%) as a white solid. LCMS (10-80, AB, 7 min): RT=4.380 min, m/z=1158.2 $[M+1]^+$.

xxxviii. L1BQ21 An exemplary L1-CIDE, L1BQ21, can be synthesized by the following scheme:

Scheme 40

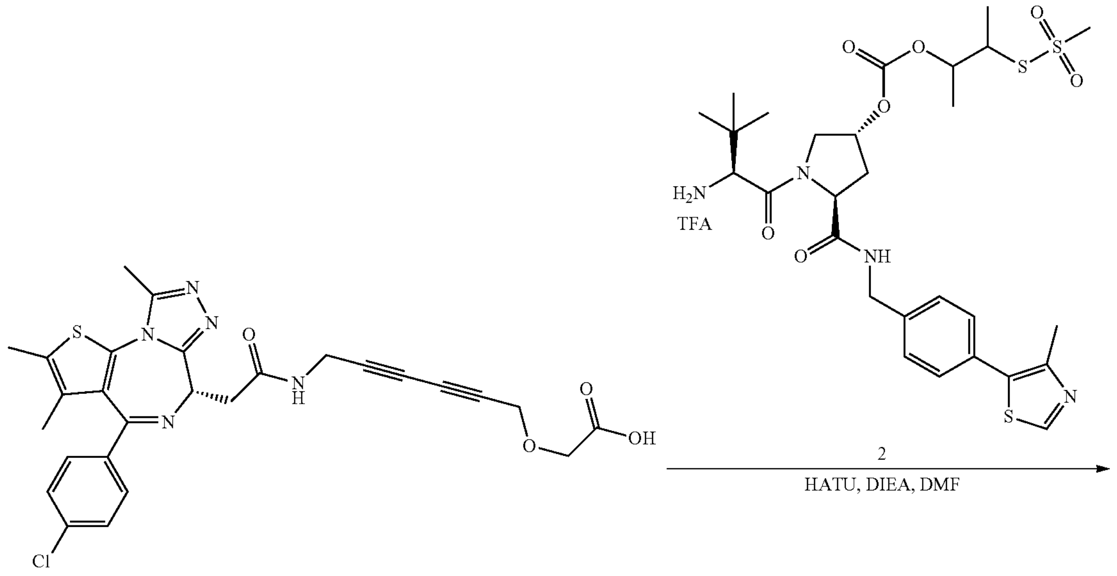

1

2

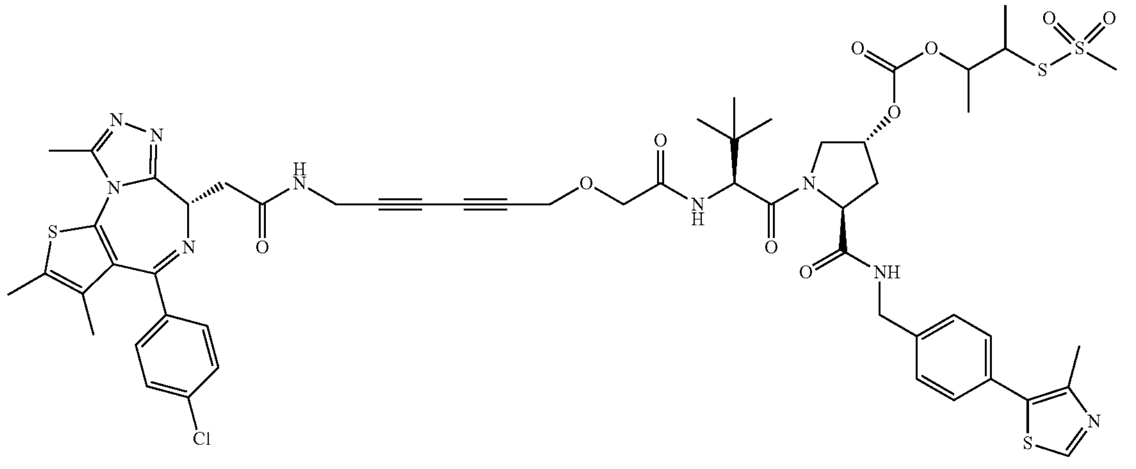

L1BQ21

To a solution of compound 1 (45.0 mg, 0.0800 mmol) in DMF (4.0 mL) was added HATU (34.22 mg, 0.0900 mmol) and DIEA (31.72 mg, 0.2500 mmol). The solution was stirred at 25° C. for 15 min, then compound 2 (91.0 mg, 0.1200 mmol) was added. The resulting reaction solution was stirred at 25° C. for another 1 h, and was purified by prep-HPLC (Xtimate C18 150*25 mm*5 um, acetonitrile 54-74/0.225% FA in water) to afford L1BQ21 (22 mg, 23%) as a white solid. LCMS (5-95, AB, 1.5 min): $R_T$=0.889 min, m/z=1172.2$[M+1]^+$. $^1$H NMR (400 MHz, DMSO-$d_6$) δ 8.98 (s, 1H), 8.78 (t, J=5.2 Hz, 1H), 8.64 (brs, 1H), 7.63 (t, J=8.8 Hz, 1H), 7.49-7.40 (m, 8H), 5.23 (brs, 1H), 4.97-4.94 (m, 1H), 4.52-4.38 (m, 4H), 4.28-4.23 (m, 1H), 4.16-3.98 (m, 4H), 3.86-3.82 (m, 2H), 3.76-3.71 (m, 2H), 3.55 (brs, 2H), 3.29-3.17 (m, 1H), 2.59 (s, 3H), 2.44 (s, 3H), 2.40 (s, 3H), 2.33 (brs, 1H), 2.17-2.11 (m, 1H), 1.61 (s, 3H), 1.44-1.37 (m, 3H), 1.34-1.23 (m, 3H), 0.95 (s, 9H).

xxxix. L1BQ22 An exemplary L1-CIDE, L1BQ22, can be synthesized by the following scheme:

Scheme 41

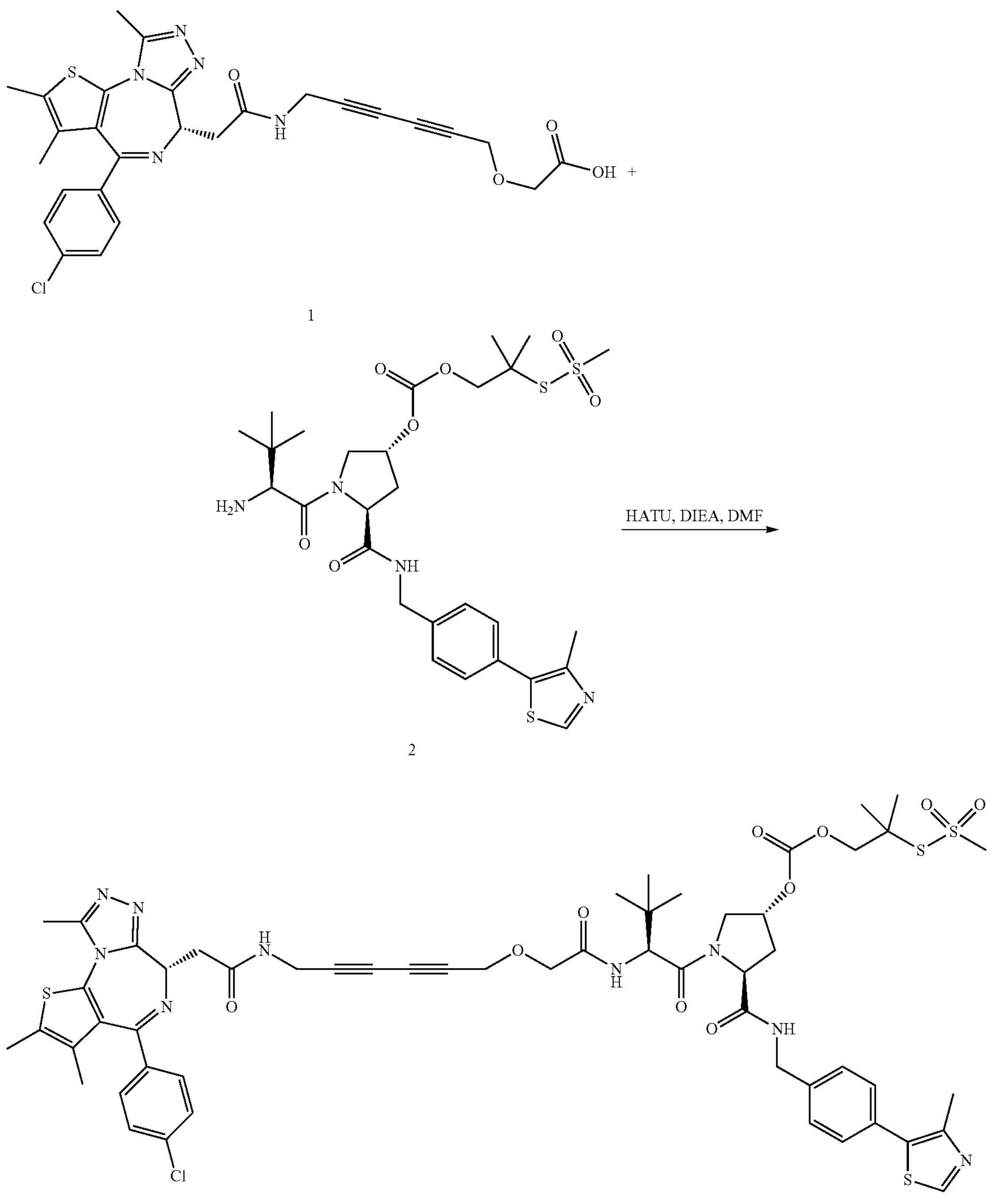

L1BQ22

To a solution of Compound 1 (37.71 mg, 0.0700 mmol) and HATU (29.47 mg, 0.0800 mmol) in DMF (5.0 mL) was added DIEA (38.52 mg, 0.3000 mmol). The mixture was stirred at 25° C. for 10 min. Compound 2 (45.0 mg, 0.0600 mmol) was added and the mixture was stirred at 25° C. for 1 h. The mixture was concentrated and the residue was purified by prep-HPLC (51-71 water (0.225% FA)-ACN) to afford L1BQ22 (20.95 mg, 30%) as a white solid. $^1$H NMR (400 MHz, DMSO-d6) δ ppm 8.95 (s, 1H), 8.76-8.73 (m, 1H), 8.63-8.60 (m, 1H), 7.61 (d, J=8.8 Hz, 1H), 7.45-7.36 (m, 8H), 4.47-4.20 (m, 9H), 4.06-3.96 (m, 5H), 3.97-3.82 (m, 1H), 3.51 (s, 3H), 3.27-3.23 (m, 1H), 3.18-3.13 (m, 1H), 2.64-2.63 (m, 1H), 2.56 (s, 3H), 2.40 (s, 3H), 2.37 (s, 3H), 2.32-2.29 (m, 1H), 2.18-2.04 (m, 1H), 1.58 (s, 3H) 1.438-1.45 (m, 6H), 0.92 (s, 9H). LCMS (5-95_1.5 min): RT (220/254 nm)=0.888 min, $[M+H]^+$ 1172.2.

C. Preparation of Ab-CIDEs i. Attachment of Antibody (Ab) to CIDE Via Linker L1

Conjugation of a L1-CIDEs to several antibodies to yield Ab-CIDEs was accomplished as follows.

Anti-HER2 7C2 LC-K149C and B7-H4 LC K149C were conjugated to compounds 6-8 and Anti-HER2 7C2 LC-K149C and Anti-CD22 10F4.v3 LC K149C to compounds 10-12 via engineered LC-K149C, HC-A140, HC-L174C, and/or HC—Y373C cysteine residues. The cysteine-engineered antibody (THIOMAB™), in 10 mM succinate, pH 5, 150 mM NaCl, 2 mM EDTA, was pH-adjusted to pH 7.5-8.5 with 1M Tris. 3-16 equivalents of compounds 6-8 and 10-12 (each containing a thiol-reactive maleimide group) were dissolved in DMF or DMA (concentration=10 mM) and were added to the reduced, reoxidized, and pH-adjusted antibodies. The reactions were incubated at room temperature or 37° C. and were monitored until completion (1 to about 24 hours) as determined by LC-MS analysis of the reaction mixtures. When the reactions were complete, the Ab-CIDEs were purified by one or any combination of several methods, the goal being to remove remaining unreacted linker-drug intermediates and aggregated proteins (if present at significant levels). In one example, the Ab-CIDEs were diluted with 10 mM histidine-acetate, pH 5.5 until the final pH was approximately 5.5 and were purified by S cation exchange chromatography using either HiTrap S columns connected to an Akta purification system (GE Healthcare) or S maxi spin columns (Pierce). Alternatively, the Ab-CIDEs were purified by gel filtration chromatography using an S200 column connected to an Akta purification system or Zeba spin columns. Dialysis was used to purify the conjugates.

The THIOMAB™ Ab-CIDEs were formulated into 20 mM His/acetate, pH 5, with 240 mM sucrose using either gel filtration or dialysis. The purified Ab-CIDEs were concentrated by centrifugal ultrafiltration and filtered through a 0.2-μm filter under sterile conditions and were frozen at −20° C. for storage.

Example 2

Characterization of Ab-CIDEs

The Ab-CIDEs were characterized to determine protein concentration (e.g., by BCA assay), aggregation level (by analytical SEC), CAR (e.g., by LC-MS).

Size exclusion chromatography was performed on the conjugates using a Shodex KW802.5 column in 0.2 M potassium phosphate pH 6.2 with 0.25 mM potassium chloride and 15% IPA at a flow rate of 0.75 mL/min. The aggregation state of the Ab-CIDEs was determined by integration of eluted peak area absorbance at 280 nm. LC-MS analysis was performed on the conjugates using an Agilent TOF 6530 ESI instrument. As an example, an Ab-CIDE was treated with 1:500 w/w Endoproteinase Lys C (Promega) in Tris, pH 7.5, for 30 min at 37° C. The resulting cleavage fragments were loaded onto a 1000 Å (Angstrom), 8 m (micron) PLRP-S (highly cross-linked polystyrene) column heated to 80° C. and eluted with a gradient of 30% B to 40% B in 10 minutes. Mobile phase A was $H_2O$ with 0.05% TFA and mobile phase B was acetonitrile with 0.04% TFA. The flow rate was 0.5 mL/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments. Detailed characterization data for several Ab-CIDEs conjugate are provided in Table 1 below.

TABLE 1

Characterization of several Ab-CIDES.

| Ab-CIDE (antigen-site-L1-CIDE) | Site[a] | CAR[b] | Aggregation[c] (%) | Free LD[d] (%) | Yield (%) |
|---|---|---|---|---|---|
| B7H4-lc-6 | LC-K149 | NA | >50 | NA | 0[e] |
| B7H4-lc-7 | LC-K149 | 2.0 | 4.7 | <5 | 34 |
| B7H4-hc-7 | HC-A140 | 1.7 | 6.3 | <5 | 35 |
| CD22-lc-L1EC8 | LC-K149 | NA | NA | NA | 0[f] |
| HER2-ms-L1EC10 | LC-K149<br>HC-L174<br>HC-Y373 | 5.6 | 0.91 | <2 | 44 |
| CD22-ms-L1EC10 | LC-K149<br>HC-L174<br>HC-Y373 | 5.5 | 0 | <2 | 39 |
| HER2-ms-L1EC11 | LC-K149<br>HC-L174<br>HC-Y373 | 5.8 | 3.0 | <5 | 55 |
| CD22-ms-L1EC11 | LC-K149<br>HC-L174<br>HC-Y373 | 5.8 | 3.6 | <2 | 66 |
| HER2-ms-L1EC12 | LC-K149<br>HC-L174<br>HC-Y373 | 5.7 | 9.1 | <2 | 49 |
| CD22-ms-L1EC12 | LC-K149<br>HC-L174<br>HC-Y373 | 5.7 | 1.5 | <2 | 61 |

[a]Site of Cys mutation used for linker attachment. The nomenclature used to depict the mAb attachment sites follows that described in: E. A. Kabat, T. T. Wu, C. Foeller, H. M. Perry, K. S. Gottesman "Sequences of Proteins of Immunological Interest" Diane Publishing, 1992 ISBN 094137565X.

[b]CIDE-antibody ratio.

[c]Percent aggregated material observed during conjugation process. Such aggregates were separated from the conjugates during subsequent purification process.

[d]Amount of unconjugated linker-drug present in purified conjugates.

[e]High aggregation and/or poor solubility prevented isolation of purified conjugate.

[f]No conjugation of linker-drug observed using DMF or PG as co-solvents.

Example 3

In Vivo Degradation of ERα

FIG. 1 depicts the activity of two Ab-CIDEs. The structures are shown in Table 2.

TABLE 2

| L1-CIDE | Ab-CIDE | $DC_{50}$ |
|---|---|---|
| 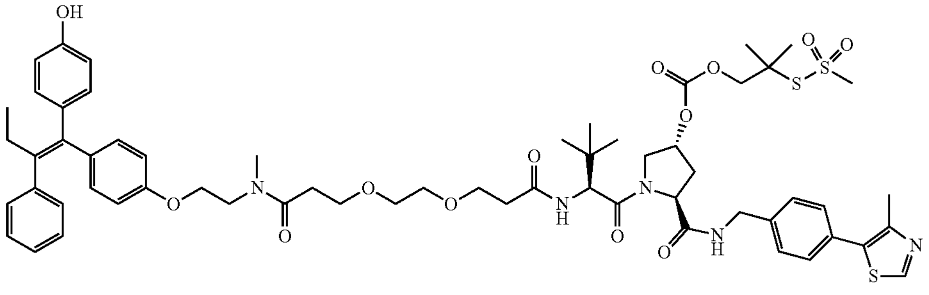 [SMILES: CC/C(=C(\c1ccc(O)cc1)c1ccc(OCCN(C)C(=O)CCOCCOCCC(=O)N[C@H](C(=O)N2C[C@H](OC(=O)OCC(C)(C)SS(C)(=O)=O)C[C@H]2C(=O)NCc2ccc(-c3scnc3C)cc2)C(C)(C)C)cc1)c1ccccc1]<br>L1EC10 | Thio Hu Anti-Her2 7C2 high DAR [LC:K149C HC:L174C HC:Y373C] MTS diMe-carbonate ER CIDE<br>Thio Hu Anti-CD22 10F4v3 high DAR [LC:K149C HC:L174C Y373C] MTS diMe-carbonate ER CIDE | 0.033 μg/mL Sinf −93%<br>0.36 μg/mL Sinf −92% |

FIG. 2 depicts the activity of two Ab-CIDEs. The structures are shown in Table 3.

TABLE 3

| L1-CIDE | Ab-CIDE | $DC_{50}$ |
|---|---|---|
| 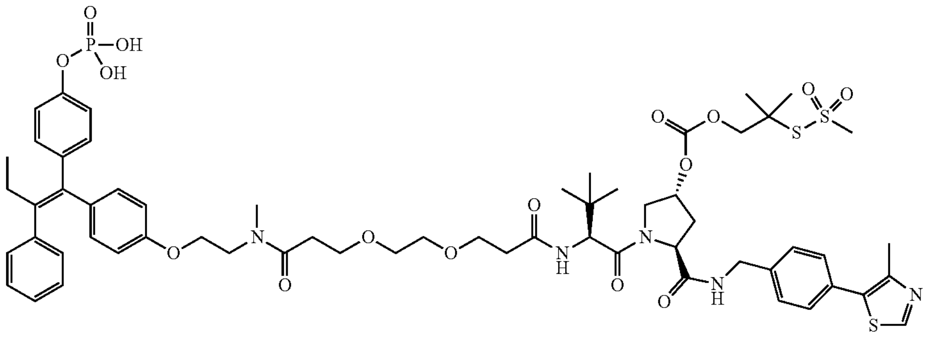 [SMILES: CC/C(=C(/c1ccc(OCCN(C)C(=O)CCOCCOCCC(=O)N[C@H](C(=O)N2C[C@H](OC(=O)OCC(C)(C)SS(C)(=O)=O)C[C@H]2C(=O)NCc2ccc(-c3scnc3C)cc2)C(C)(C)C)cc1)c1ccc(OP(=O)(O)O)cc1)c1ccccc1]<br>L1EC11 | Thio Hu Anti-Her2 7C2 high DAR [LC:K149C HC:L174C HC:Y373C] MTS diMe-carbonate phoshorylated ER CIDE<br>Thio Hu Anti-CD22 10F4v3 high DAR [LC:K149C HC:L174C HC:Y373C] MTS diMe-carbonate phoshorylated ER CIDE | 0.06 μg/mL Sinf −94%<br>1.6 μg/mL Sinf −92% |

FIG. 3 depicts the activity of two Ab-CIDEs. The structures are shown in Table 4.

TABLE 4

| L1-CIDE | Ab-CIDE | $DC_{50}$ |
|---|---|---|
| 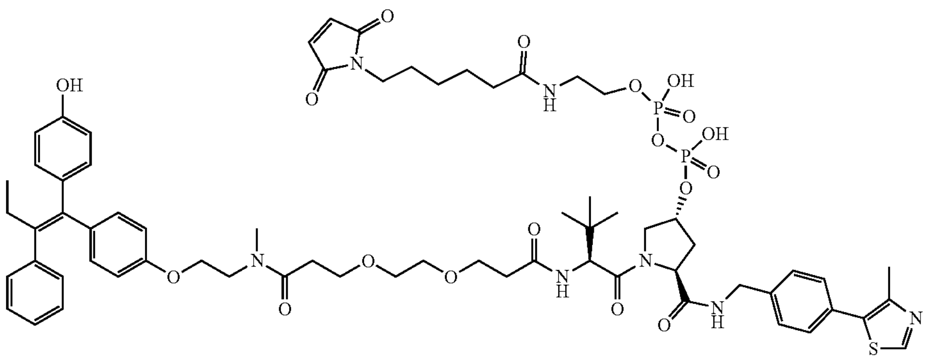 L1EC12 | Thio Hu Anti-Her2 7C2 high DAR [LC:K149C HC:L174C HC:Y373C] MC-pyrophosphate ER CIDE | 0.03 µg/mL Sinf −95% |
| | Thio Hu Anti-CD22 10F4v3 high DAR [LC:K149C HC:L174C HC:Y373C] MC-pyrophosphate ER CIDE | 2.7 µg/mL Sinf −81% |

Example 4

Quantitation of BRD4 Degradation by CIDEs in PC3-Steap 1 Cells

PC3 Steap-1 overexpressing prostate cancer cells were seeded on day-1 at a density of 9000 cells per well in CellCarrier-384 Ultra Microplates, tissue culture treated (Perkin Elmer #6057300) in 45 ul/well of assay media (RPM1, 10% FBS, containing 2 mM L-glutamine). On day-2 compounds were serially diluted ⅓ in dimethylsulfoxide (DMSO) to create 20-point dilutions across a 384 well v-bottom polypropylene microplate (Greiner #781091). 2 ul of each sample from the serial dilution was transferred to 98 ul of assay media as an intermediate dilution. 5 ul of intermediate dilution was added to 45 ul of cell plate. Columns 1, 2, 23 and 24 were treated with only 0.2% w/v final concentration of DMSO for data normalization as "neutral controls". After compound treatment cell plates were stored in a 37 C incubator for 4 hours. After 4 hours cells were fixed in 3.7% final concentration of paraformaldehyde by addition of 15 ul of 16% w/v paraformaldehyde (Electron Microscopy Sciences #15710-S) directly to the 50 ul media and compound in the cell plate. Cell plate was incubated at RT for 20 minutes. Well contents were aspirated and washed with 100 ul/well PBS 3 times. 50 ul/well of Phosphate Buffered Saline (PBS) containing 0.5% w/v bovine serum albumen, 0.5% w/v Triton X-100 (Antibody Dilution Buffer) was added to each well. Samples were incubated for 30 minutes. Samples were incubated for 20 minutes. Well contents were aspirated and washed 3 times with 100 ul/well of PBS. PBS was aspirated from the wells. Immunofluorescence staining of BRD4 was carried out by diluting mAB Anti-BRD4 [EPR5150] antibody (Abcam 128874) 1:500 into Antibody Dilution Buffer (PBS, Triton X100 0.5%, BSA 0.5%). 25 ul per well of BRD4 antibody diluted in buffer was added and incubated overnight at 4 C.

On day-3 samples were washed 3 times with 100 ul/well of PBS. 25 ul/well of secondary antibody solution (Goat Anti-Rabbit IgG, DyLight 488 Conjugated Highly Cross-adsorbed Thermo Fisher #35553) and Hoechst 33342 1 ug/ml diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 ul PBS. Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response used to define the inflexion point of curve (EC50) and the plateau of the maximal effect.

Example 5

Quantitation of BRD4 Degradation by CIDEs in EoL-1 Cells

PC3 Steap-1 overexpressing prostate cancer cells were seeded on day-1 at a density of 9000 cells per well in CellCarrier-384 Ultra Microplates EoL-1 eosinophilic leukemia cells were seeded on day 1 at a density of 45,000 cells per well in Corning PureCoat Amine Microplates, (Corning #354719) in 45 ul/well of assay media (RPMI, 10% FBS, containing L-glutamine). After cells attached to cell plate, compounds were serially diluted ⅓ in dimethylsulfoxide (DMSO) to create 20-point dilutions across a 384 well v-bottom polypropylene microplate (Greiner #781091). 2 ul of each sample from the serial dilution was transferred to 98 ul of assay media as an intermediate dilution. 5 ul of each well of the intermediate dilution was added to 45 ul of cell plate. Columns 1, 2, 23 and 24 were treated with only 0.2% final concentration of DMSO for data normalization as "neutral controls". After compound treatment, cell plates were stored in a 37 C incubator for 4 hours. After 4 hours cells were fixed in 3.7% w/v final concentration of paraformaldehyde by addition of 15 ul of 16% w/v paraformaldehyde (Electron Microscopy Sciences #15710-S) directly to the 50 ul media and compound in the cell plate. Cell plate was incubated at RT for 20 minutes. Well contents were aspirated and washed with 100 ul/well PBS 3 times. 50 ul/well of phosphate Buffered Saline (PBS) (pH7.5) containing 0.5% w/v bovine serum albumen, 0.5% w/v Triton X-100 (Block/Permeabilzation Buffer) was added to each well. Samples were incubated for 20 minutes. Well contents were aspirated and washed 3 times with 100 ul/well of PBS. PBS was aspirated from the well and 50 ul per well of EoL-1 Block Buffer (PBS containing 10% Normal Goat Serum (AbCam #ab7481)) was added to each well. Plates were incubated at room temperature for 30 minutes. Block buffer was decanted from the wells. Immunofluorescence staining of BRD4 was carried out by diluting mAB Anti-BRD4 [EPR5150] antibody (Abcam 128874) 1:500 into Antibody Dilution Buffer (PBS, 2% Normal Goat Serum). 25 ul per well of BRD4 antibody diluted in buffer was added and incubated overnight at 4 C.

On day-2 samples were washed 3 times with 100 ul/well of PBS. 25 ul/well of secondary antibody solution (Goat Anti-Rabbit IgG, DyLight 488 Conjugated Highly Cross-adsorbed Thermo Fisher #35553) and Hoechst 33342 1 ug/ml diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 ul PBS. Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response used to define the inflexion point of curve (EC50) and the plateau of the maximal effect.

Example 6

Quantitation of BRD4 Degradation by CIDE Antibody Conjugates in PC3-Steap 1 Cells PC3 Steap-1 over expressing prostate cancer cells were seeded on day 1 at a density of 1000 cells per well in CellCarrier-384 Ultra Microplates, tissue culture treated (Perkin Elmer #6057300) in 45 ul/well of assay media (RPMI, 10% FBS, 1% Glutamax, methionine supplemented on day of assay with 50 uM cystine). On day-2, antibody conjugates were serially diluted ⅓ in antibody buffer (20 mM histidine acetate pH 5.5, 240 m M sucrose, 0.02% Tween 20) to create 20-point dilutions across a 384 well v-bottom polypropylene microplate (Greiner #781091). 5 ul of each well of antibody conjugate was transferred to 45 ul of cell plate. Columns 1, 2, 23 and 24 were treated with only antibody buffer for data normalization as "neutral controls". After antibody treatment cell plates were stored in a 37 C incubator for 72 hours. After 4 hours cells were fixed in 3.7% final concentration of paraformaldehyde by addition of 15 ul of 16% paraformaldehyde (Electron Microscopy Sciences #15710-S) directly to the 50 ul media and compound in the cell plate. Cell plate was incubated at RT for 20 minutes. Well contents were aspirated and washed with 100 ul/well PBS 3 times. 50 ul/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Samples were incubated for 20 minutes. Well contents were aspirated and washed 3 times with 100 ul/well of PBS. PBS was aspirated from the wells. Immunofluorescence staining of BRD4 was carried out by diluting mAB Anti-BRD4 [EPR5150] antibody (Abcam 128874) 1:500 into Antibody Dilution Buffer (PBS, Triton X100 0.5%, BSA 0.5%). 25 ul per well of BRD4 antibody diluted in buffer was added and incubated overnight at 4 C.

On day-3 samples were washed 3 times with 100 ul/well of PBS. 25 ul/well of secondary antibody solution (Goat Anti-Rabbit IgG, DyLight 488 Conjugated Highly Cross-adsorbed Thermo Fisher #35553) and Hoechst 33342 1 ug/ml diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 u PBS. Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 00 and 1000 changes in BRD4. The dose-response log(inhibitor) vs. response used to define the inflexion point of curve (EC50) and the plateau of the maximal effect. Data are provided in Table 5 below.

TABLE 5

BRD4 Degradation Results.

| Antigen | L1-CIDE | DAR[a] | BRD4 $DC_{50}$ (PC3, ug/mL)[b] | BRD4 $DC_{50}$ (PC3, nM)[c] | BRD4 $S_{inf}$ (PC3, %)d |
|---|---|---|---|---|---|
| STEAP1 | L1BQ1 | 5.9 | 0.11 | 4.4 | 43 |
| CLL1 | L1BQ1 | 5.8 | >100 | >3000 | NA |
| STEAP1 | L1BQ2 | 5.7 | 0.21 | 7.9 | 70 |
| CLL1 | L1BQ2 | 5.4 | 54 | 1900 | 65 |
| STEAP1 | L1BQ3 | 5.4 | 1.6 | 58 | 24 |
| HER2 | L1BQ3 | 5.9 | >100 | >3900 | NA |
| STEAP1 | L1BQ4 | 6.0 | 0.017 | 0.67 | 48 |
| CLL1 | L1BQ4 | 6.0 | 0.26 | 10 | 46 |
| HER2 | L1BQ4 | 5.9 | >100 | >3900 | NA |
| STEAP1 | L1BQ5 | 5.7 | 0.034 | 1.3 | 71 |
| CLL1 | L1BQ5 | 5.7 | 33 | 1300 | 59 |
| HER2 | L1BQ5 | 5.6 | 58 | 2100 | 80 |
| STEAP1 | L1BQ6 | 5.8 | 2.9 | 113 | 88 |
| HER2 | L1BQ6 | 5.9 | 26 | 1000 | 91 |
| STEAP1 | L1BQ7 | 5.9 | 3.8 | 149 | 34 |
| CLL1 | L1BQ7 | 6.0 | >100 | >3900 | NA |
| HER2 | L1BQ7 | 6.0 | >100 | >3900 | NA |
| STEAP1 | L1BQ8 | 6.0 | 0.25 | 10 | 78 |
| CLL1 | L1BQ8 | 6.0 | 100 | 4000 | 29 |
| HER2 | L1BQ8 | 6.0 | >100 | >3900 | NA |
| STEAP1 | L1BQ9 | 6.0 | 1.3 | 52 | 87 |
| CLL1 | L1BQ9 | 6.0 | >100 | >3900 | NA |
| HER2 | L1BQ9 | 6.0 | 38 | 1500 | 80 |
| STEAP1 | L1BQ10 | 6.0 | 100 | 3900 | 100 |
| HER2 | L1BQ10 | 6.0 | >100 | >3900 | NA |
| STEAP1 | L1BQ11 | 5.4 | 1.2 | 43 | 40 |
| CLL1 | L1BQ11 | 5.7 | >100 | >3700 | NA |
| STEAP1 | L1BQ12 | 5.9 | >100 | >3900 | NA |
| CLL1 | L1BQ12 | 6.0 | >100 | >3900 | NA |
| STEAP1 | L1BQ13 | 5.7 | 1.3 | 48 | 33 |
| CLL1 | L1BQ13 | 5.5 | >100 | >3600 | NA |
| HER2 | L1BQ13 | 5.7 | >100 | >3700 | NA |
| STEAP1 | L1BQ14 | 6.0 | 21 | 835 | 55 |
| CLL1 | L1BQ14 | 5.9 | 25 | 974 | 50 |
| STEAP1 | L1BQ15 | 5.9 | 0.71 | 27 | 91 |
| CLL1 | L1BQ15 | 5.9 | 2.9 | 115 | 91 |
| STEAP1 | L1BQ16 | 5.9 | 0.051 | 2.0 | 95 |
| CLL1 | L1BQ16 | 6.0 | 0.40 | 16 | 93 |
| STEAP1 | L1BQ17 | 5.8 | 0.29 | 11 | 95 |
| CLL1 | L1BQ17 | 5.8 | 0.74 | 28 | 93 |

TABLE 5-continued

BRD4 Degradation Results.

| Antigen | L1-CIDE | DAR[a] | BRD4 $DC_{50}$ (PC3, ug/mL)[b] | BRD4 $DC_{50}$ (PC3, nM)[c] | BRD4 $S_{inf}$ (PC3, %)d |
|---|---|---|---|---|---|
| STEAP1 | L1BQ18 | 6.0 | 23 | 942 | 74 |
| CLL1 | L1BQ18 | 6.0 | 100 | 3900 | 17 |
| STEAP1 | L1BQ19 | 6.0 | 15 | 591 | 72 |
| CLL1 | L1BQ19 | 5.8 | 100 | 3900 | 15 |
| STEAP1 | L1BQ20 | 5.9 | 0.038 | 1.5 | 91 |
| CLL1 | L1BQ20 | 5.9 | 0.17 | 6.8 | 96 |
| STEAP1 | L1BQ21 | 5.9 | 0.22 | 8.4 | 93 |
| CLL1 | L1BQ21 | 5.9 | 1.1 | 42 | 94 |
| STEAP1 | L1BQ22 | 5.6 | 0.078 | 2.9 | 93 |
| CLL1 | L1BQ22 | 5.6 | 0.27 | 10 | 93 |
| STEAP1 | L1BC1 | 5.4 | 0.024 | 0.87 | 92 |
| CLL1 | L1BC1 | 5.6 | 8.3 | 306 | 88 |
| STEAP1 | L1BC12 | 2.0 | 0.030 | 0.39 | 97 |
| CLL1 | L1BC12 | 1.9 | 0.019 | 0.24 | 96 |
| STEAP1 | L1BC3 | 1.9 | 0.034 | 0.44 | 96 |
| CLL1 | L1BC3 | 2.0 | 0.061 | 0.81 | 95 |
| STEAP1 | L1BC13 | 2.0 | 0.017 | 0.23 | 96 |
| CLL1 | L1BC13 | 2.0 | 0.029 | 0.38 | 96 |
| STEAP1 | L1BC14 | 1.9 | 0.11 | 1.4 | 87 |
| CLL1 | L1BC14 | 2.0 | 6.7 | 88 | 88 |
| STEAP1 | L1BC4 | 5.9 | 0.022 | 0.86 | 94 |
| CLL1 | L1BC4 | 5.5 | 0.19 | 7.6 | 94 |
| STEAP1 | L1BC5 | 5.9 | 0.034 | 1.3 | 96 |
| CLL1 | L1BC5 | 5.9 | 0.46 | 18 | 93 |
| STEAP1 | L1BC2 | 6.1 | 0.011 | 0.46 | 90 |
| CLL1 | L1BC2 | 6.0 | 5.1 | 205 | 84 |
| STEAP1 | L1BC8 | 5.9 | 0.04 | 1.6 | 90 |
| CLL1 | L1BC8 | 5.9 | 8.0 | 313 | 89 |
| STEAP1 | L1BC9 | 2.0 | 0.025 | 0.33 | 94 |
| CLL1 | L1BC9 | 2.0 | 0.61 | 8.3 | 96 |
| STEAP1 | L1BC9 | 5.9 | 0.00063 | 0.025 | 92 |
| CLL1 | L1BC9 | 6.0 | 0.15 | 6.0 | 95 |
| STEAP1 | L1BC10 | 5.8 | 0.0066 | 0.26 | 94 |
| CLL1 | L1BC10 | 5.8 | 14 | 549 | 75 |
| STEAP1 | L1BC11 | 5.3 | 0.0025 | 0.088 | 97 |
| CLL1 | L1BC11 | 5.5 | 0.0054 | 0.20 | 97 |
| STEAP1 | L1BC6 | 2.0 | 0.0080 | 0.11 | 95 |
| CLL1 | L1BC6 | 2.0 | 0.32 | 4.3 | 96 |

[a]Drug-antibody ratio.

[b]BRD4 degradation potency (concentration of conjugate).

[c]BRD4 degradation potency (concentration of conjugated CIDE).

dMaximum BRD4 degradation observed.

Example 7

Quantitation of BRD4 Degradation by CIDE Antibody Conjugates in EoL-1 Cells

EoL-1 eosinophilic leukemia cells were seeded on day 1 at a density of 45,000 cells per well in Corning PureCoat Amine Microplates, (Corning #354719) in 45 ul/well of assay media (RPMI, 10% FBS, containing L-glutamine). After cells attached to cell plate, antibody conjugates were serially diluted ⅓ in antibody buffer (20 mM histidine acetate pH 5.5, 240 mM sucrose, 0.02% Tween 20) to create 20-point dilutions across a 384 well v-bottom polypropylene microplate (Greiner #781091). 5 ul of each well of antibody conjugate was transferred to 45 ul of cell plate. Columns 1, 2, 23 and 24 were treated with only antibody buffer for data normalization as "neutral controls". After antibody treatment cell plated were stored in a 37 C incubator for 20 hours. After 20 hours cells were fixed in 3.7% final concentration of paraformaldehyde by addition of 15 ul of 16% paraformaldehyde (Electron Microscopy Sciences #15710-S) directly to the 50 ul media and compound in the cell plate. Cell plate was incubated at RT for 20 minutes. Well contents were aspirated and washed with 100 ul/well PBS 3 times. 50 ul/well of phosphate Buffered Saline (PBS) (pH7.5) containing 0.5% w/v bovine serum albumen, 0.5% v/v Triton X-100 (Block/Permeabilzation Buffer) was added to each well. Samples were incubated for 20 minutes. Well contents were aspirated and washed 3 times with 100 ul/well of PBS. PBS was aspirated from the well and 50 ul per well of EoL-1 Block Buffer (PBS containing 10% Normal Goat Serum (AbCam #ab7481)) was added to each well. Plates were incubated at room temperature for 30 minutes. Block buffer was decanted from the wells. Immunofluorescence staining of BRD4 was carried out by diluting mAB Anti-BRD4 [EPR5150] antibody (Abcam 128874) 1:500 into Antibody Dilution Buffer (PBS, Triton X100 0.5%, BSA 0.1%). 25 ul per well of BRD4 antibody diluted in buffer was added and incubated overnight at 4 C.

On day-2 samples were washed 3 times with 100 ul/well of PBS. 25 ul/well of secondary antibody solution (Goat Anti-Rabbit IgG, DyLight 488 Conjugated Highly Cross-adsorbed Thermo Fisher #35553) and Hoechst 33342 1 ug/ml diluted in Antibody Dilution Buffer) were dispensed into each well. Hoechst 33342 only was added to bottom 3 columns for data normalization as "inhibitor controls". Samples were incubated for 2 hours at room temperature. Samples were washed 3 times with 100 ul PBS. Quantitative fluorescence imaging of BRD4 was carried out using an Opera Phenix High-Content Screening System. Fluorescent images of the samples were captured using 488 nm and 405 nm channels. Hoechst channel was used to identify nuclear region. Mean 488 intensity of BRD4 quantitated in nuclear region. Data analysis was carried out using Genedata Screener, with DMSO and no primary antibody control treated samples being used to define the 0% and 100% changes in BRD4. The dose-response log(inhibitor) vs. response used to define the inflexion point of curve (EC50) and the plateau of the maximal effect.

Example 8

Cell Proliferation Assays for BRD4 Targeted CIDEs

To determine the anti-proliferative effects of small molecule degraders of BRD4, individually or as payload conjugated to an antibody, a standard cell viability assessment protocol was employed. As antibody conjugates were targeted to either STEAP-1 or CLL-1 antigens, cell lines assayed included LNCaP (clone FGC), PC-3-STEAP1 (PC-3 cells stably expressing STEAP-1), EOL-1 and HL-60.

Culture media used for all cell lines was RPM-1640 with reduced cysteine concentration (50 uM), plus 10% FBS and antibiotics. Cell seeding density was determined for each line to enable a 6 day treatment with test compounds or antibodies without overgrowth of cells. All incubations were at 37° C. in a humidified $CO_2$ incubator.

On day 1, cells were harvested by either centrifugation of suspension cells or by Acutase treatment of adherent cells, then seeded in 50 uL of fresh culture media in 384 well black/clear tissue culture plates at the following densities: LNCaP (1250 cells/well), PC-3-STEAP-1 (400 cells/well), EOL-1 and HL-60 (2500 cells/well). Treatment with various concentrations of test molecules was started the following day by the addition of either small molecules diluted in DMSO or antibody conjugates in dilution buffer (20 mM histidine acetate, 240 mM sucrose, 0.02% polysorbate 20, pH 5.5), using an Echo acoustic dispenser (Labcyte).

After 6 days of treatment with the test molecules, assay plates were allowed to equilibrate to room temperature and the level of viable cells was assessed by addition of 40 uL of CellTiterGlo (Promega) according to manufacturer's instruction and luminescence read on an Envision instrument (PerkinElmer).

Level of luminescence is a direct correlation to ATP from the lysed cells and reflects the number of viable cells. Reduced signal as compared to control wells (DSMO or antibody diluent) was used as an indication of inhibition of proliferation or of cell death due to loss of BRD4. Results are shown in Table 6.

TABLE 6

Antiproliferation Results.

| Antigen | Linker-Drug | CAR[a] | LnCap $IC_{50}$ (ug/mL)[b] | LnCap $IC_{50}$ (nM)[c] | PC3 $IC_{50}$ (ug/mL)[d] | PC3 $IC_{50}$ (nM)[e] |
|---|---|---|---|---|---|---|
| STEAP1 | L1BC1 | 5.4 | 0.89 | 32 | 0.74 | 27 |
| CLL1 | L1BC1 | 5.6 | 2.7 | 101 | 2.7 | 101 |
| STEAP1 | L1BC12 | 2.0 | 0.23 | 3.0 | 1.5 | 20 |
| CLL1 | L1BC12 | 1.9 | 0.26 | 3.3 | 0.97 | 12 |
| STEAP1 | L1BC3 | 1.9 | 0.43 | 5.5 | 0.69 | 8.7 |
| CLL1 | L1BC3 | 2.0 | 0.41 | 5.5 | 0.96 | 13 |
| STEAP1 | L1BC13 | 2.0 | 0.32 | 4.3 | 0.86 | 11 |
| CLL1 | L1BC13 | 2.0 | 0.16 | 2.1 | 1.0 | 13 |
| STEAP1 | L1BC14 | 1.9 | >20 | >250 | >20 | >250 |
| CLL1 | L1BC14 | 2.0 | >20 | >250 | >20 | >250 |
| STEAP1 | L1BC4 | 5.9 | 1.2 | 48 | 1.5 | 61 |
| CLL1 | L1BC4 | 5.5 | 2.7 | 106 | 5.4 | 211 |
| STEAP1 | L1BC5 | 5.9 | 2.4 | 95 | 1.8 | 70 |
| CLL1 | L1BC5 | 5.9 | 7.5 | 294 | >20 | >780 |
| STEAP1 | L1BC2 | 6.1 | 0.36 | 15 | 0.19 | 7.5 |
| CLL1 | L1BC2 | 6.0 | 11 | 448 | 11 | 448 |
| STEAP1 | L1BC8 | 5.9 | 0.72 | 28 | 0.32 | 13 |
| CLL1 | L1BC8 | 5.9 | >20 | >780 | >20 | >780 |
| STEAP1 | L1BC9 | 2.0 | 1.3 | 17 | 3.4 | 45 |
| CLL1 | L1BC9 | 2.0 | 2.0 | 28 | 7.4 | 100 |
| STEAP1 | L1BC9 | 5.9 | 1.4 | 56 | 0.16 | 6.4 |
| CLL1 | L1BC9 | 6.0 | 12 | 488 | 17 | 670 |
| STEAP1 | L1BC10 | 5.8 | 0.81 | 31 | 2.8 | 108 |
| CLL1 | L1BC10 | 5.8 | >20 | >775 | >20 | >775 |
| STEAP1 | L1BC11 | 5.3 | 0.17 | 5.9 | 0.11 | 3.8 |
| CLL1 | L1BC11 | 5.5 | 0.17 | 6.1 | 0.22 | 8.0 |
| STEAP1 | L1BC6 | 2.0 | 1.2 | 15 | 2.6 | 35 |
| CLL1 | L1BC6 | 2.0 | 4.7 | 63 | 9.3 | 125 |

[a]CIDE-antibody ratio.
[b]potency (LnCap cells; concentration of conjugate).
[c]Antiproliferation potency (LnCap cells; concentration of conjugated CIDE).
[d]Antiproliferation potency (PC3 cells; concentration of conjugate).
[e]Antiproliferation potency (PC3 cells; concentration of conjugated CIDE).

PK and Tumor Model Examples 9-11

Materials and Methods

In vivo experiments. All animal studies were carried out in compliance with the National Institutes of Health guidelines for the care and use of laboratory animals and were approved by the Institutional Animal Care and Use Committee (IACUC) at Genentech, Inc.

Two human AML cell lines, EOL-1 (DSMZ; Braunschweig, Germany) and HL-60 (ATCC, Manassas, VA) were used to establish subcutaneous xenograft models for efficacy evaluation of the degrader-antibody conjugates. Tumor cells (5 million cells suspended in 0.1 mL of Hanks' Balanced Salt Solution supplemented with Matrigel) were inoculated to the flanks of female CB-17 Fox Chase SCID mice (Charles River Lab, Hollister, CA). When mean tumor size reached the desired volume (200-300 $mm^3$), animals were randomized into groups of n=5, each with similar tumor volume distributions, and each animal received an intraperitoneal dose of a mouse IgG2a anti-ragweed antibody in excess amount (30 mg/kg; to block Fcγ receptors frequently expressed on the surface of AML cells). Four hours later, vehicle or degrader-antibody conjugates were administered to the animals via single intravenous (IV) bolus injections through the tail vein. Tumors were measured in two dimensions (length and width) using calipers and the tumor volume was calculated using the formula: Tumor size ($mm^3$) =0.5×(length×width×width). The results were plotted as mean tumor volume+/−SEM of each group over time. Treatment groups were not blinded during tumor measurement.

To assess levels of released degraders and BRD4 degradation in vivo, tumor tissues (200-300 $mm^3$; n=4-5/group) from additional xenograft animals were collected at day 4 following administration of single IV doses of the degrader-antibody conjugates plus anti-ragweed as described above. For pharmacokinetic and in vivo stability analysis, plasma samples (n=3/time point) were collected from naive animals at indicated time points following single IV doses of the degrader-antibody conjugates. All samples were stored at −70° C. until analysis.

Example 9

Pharmacokinetics of the CLL1-targeting Ab-CIDE (PAC) having the structure shown in FIG. 10 was compared to the corresponding unconjugated CIDE having the structure:

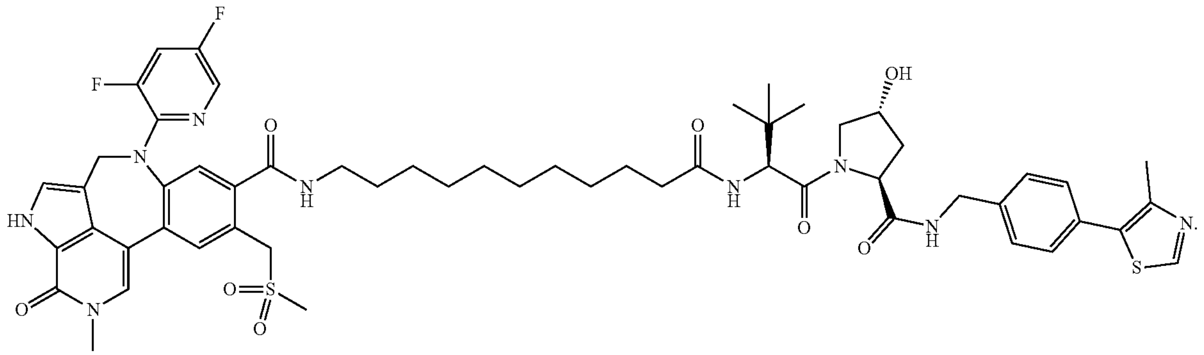 [SMILES: Cc1ncsc1-c1ccc(CNC(=O)[C@@H]2C[C@@H](O)CN2C(=O)[C@@H](NC(=O)CCCCCCCCCCNC(=O)c2cc3c(cc2CS(C)(=O)=O)-c2cn(C)c(=O)c4[nH]cc(c24)CN3c2ncc(F)cc2F)C(C)(C)C)cc1]

Figure 6A:
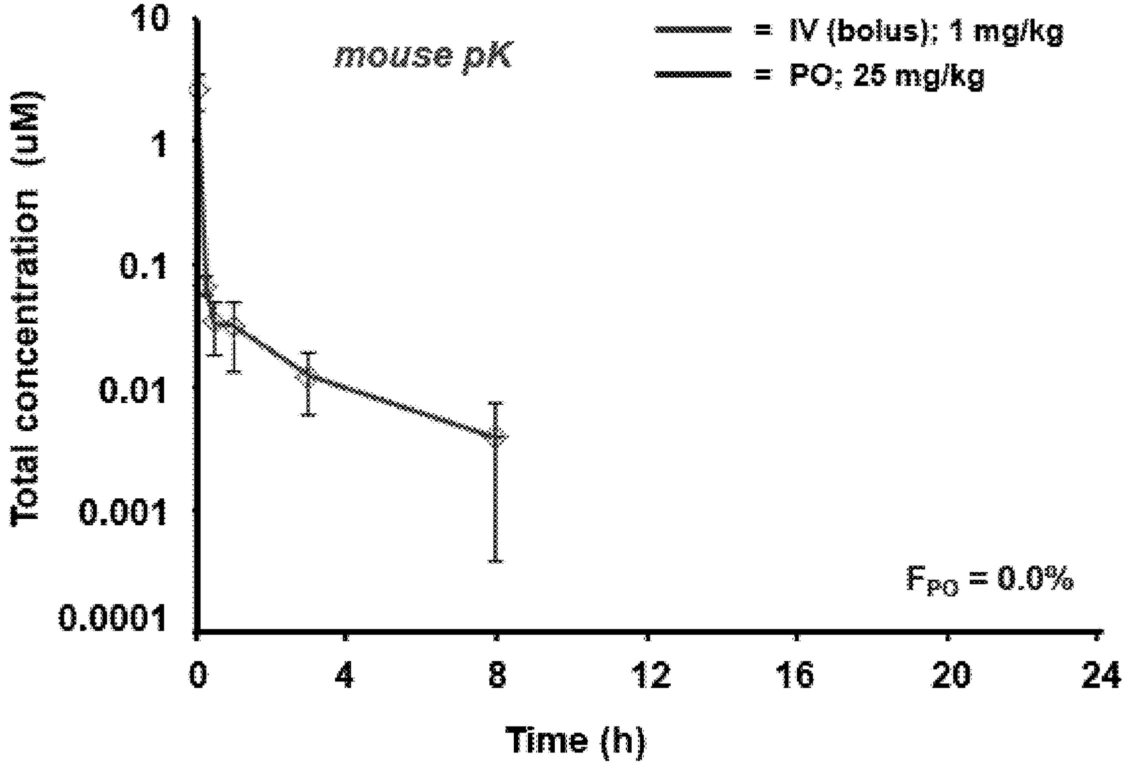
FIGS. 6*a* and 6*b* depict pharmacokinetic properties of an Ab-CIDE and a corresponding unconjugated CIDE.
Figure 6B:
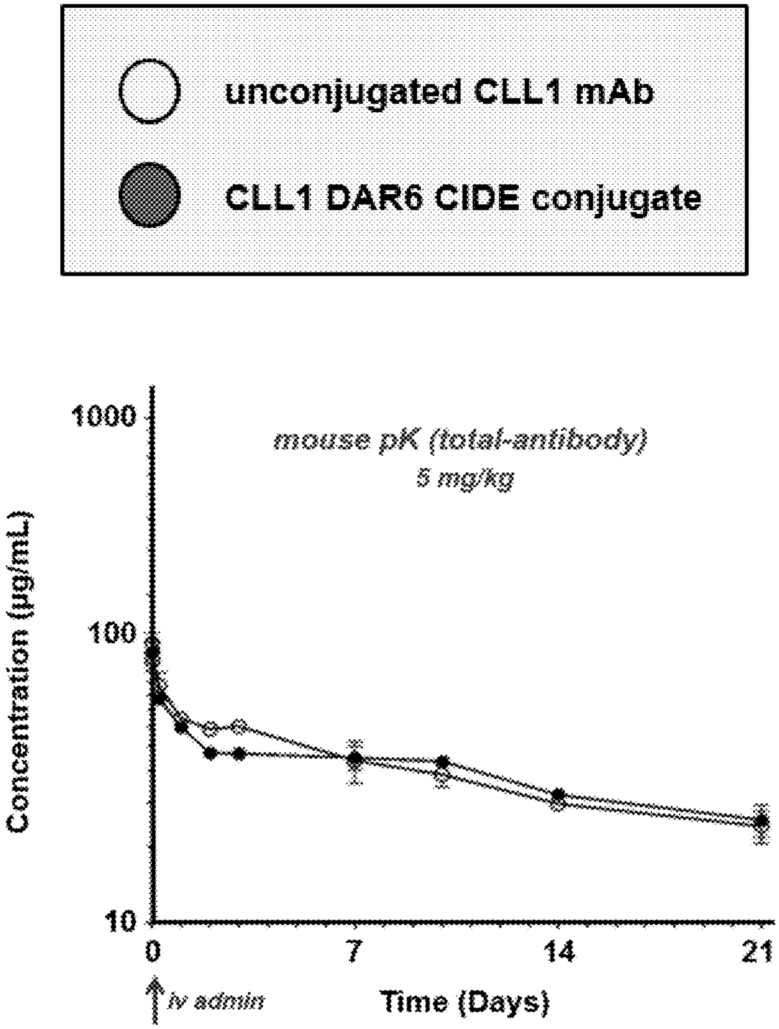

Mouse PK for the unconjugated CIDE is shown in FIG. 6*a*. Mouse PK for the CLL1-targeting PAC is shown in FIG. 6*b*.

Example 10

Antibody Conjugate Exhibited Potent, Antigen-Dependent Efficacy in Mouse Xenograft Models Single intravenous (IV) administration of the CLL1-targeting PAC having the structure shown in FIG. 10 to mice bearing HL-60 AML xenografts afforded dose-dependent tumor growth inhibition activity that was well-separated from the vehicle control (data not shown). At a matched dose level of 5 mg/kg, the CLL1-targeting PAC exhibited significantly stronger HL-60 efficacy outcomes relative to the HER2-targeting control conjugate (HER2-5, data not shown). This result was consistent with the antigen-dependent delivery of the corresponding CIDE (unconjugated) to the AML tumors via the CLL1-targeted PAC. Similar dose-dependent antitumor activity and even more profound antigen-dependent delivery effects were observed when CLL1-targeted PAC and HER2-5 were assessed via single IV administrations in mice bearing EOL-1 AML xenografts (FIG. 7). In a separate experiment, measurable levels of unconjugated CIDE were detected in EOL-1 tumors four days following IV administration of CLL1-targeted PAC to xenografted mice (data not shown). The measured intratumor amounts of unconjugated CIDE correlated well with the administered doses of CLL1-targeted PAC as well as with the EOL-1 tumor growth inhibition activity displayed by the conjugate (compare dose levels 1.5, 5.0, and 10 mg/kg). The described relationships between xenograft efficacy and intratumor degrader concentrations for the CLL1-targeted PAC paralleled related outcomes observed for several other previously-studied ADCs bearing cytotoxic payloads. Importantly, CLL1-targeted PAC and HER2-5 conjugates were well tolerated in all of these in vivo studies with minimal reductions detected in the associated mouse body-weights (data not shown).

Example 11

Antibody Conjugation of CIDE Afforded Significantly Improved In Vivo Efficacy Properties Relative to the Unconjugated CIDE To determine whether conjugation of the unconjugated CIDE depicted in Example 9 enhanced the molecule's ability to provide favorable xenograft outcomes, the unconjugated compound was assessed in the EOL-1 tumor model via administration of a single IV dose (0.4 mg/kg). The amount of unconjugated unconjugated CIDE employed in this experiment was equivalent to that associated with a 10 mg/kg dose of the corresponding CLL1-targeted PAC (note the large molecular weight differences between unconjugated CIDE and the CLL1-targeted PAC; 1096 and 156,690 g/mole, respectively). As shown in FIG. 8, administration of the unconjugated CIDE afforded no efficacy in the EOL-1 model. In contrast, the matched dose of the CLL1-targeted PAC (10 mg/kg) exhibited strong antitumor activity in the same experiment (FIG. 8). These outcomes clearly demonstrated the ability of antibody conjugation to enable the in vivo activity of the chimeric degrader molecule and thereby significantly enhance its efficacy performance relative to results obtained with the unconjugated compound. The stability and pharmacokinetic analyses conducted CLL1-targeted PAC supports a prolonged in vivo exposure of CLL1-targeted PAC; and, this property may have contributed to the favorable efficacy outcomes observed with the conjugate. In addition, single IV administration of the unconjugated CLL1 antibody at both the 5 and 10 mg/kg dose levels resulted in no EOL-1 in vivo efficacy (FIG. 8). These results confirmed that the efficacy observed for CLL1-targeted PAC in the EOL-1 model did not result from the mAb portion of the conjugate.

Example 12

Antibody Conjugation of CIDE Shows Higher Reduction of ERα Levels Compared to Unconjugated CIDE MCF7-neo/HER2 cells were seeded into 12-well cell culture plates at a density of 200,000 cells/well in phenol red free RPMI, supplemented with 10% charcoal stripped Fetal Bovine Serum. After 16 hours, cells were treated with a serial dilution of conjugates or compounds for 72 or 4 hours, respectively. Cells were washed once with PBS and lysed in 100 uL lysis buffer (20 mM Tris pH7.5, 12.5 mM NaCl, 2.5 mM $MgCl_2$, 0.1% Triton X-100, 6 M Urea, protease inhibitor (Roche)). Total protein concentrations were determined by BCA assay (ThermoFisher). For each sample, 10 μg total protein was separated on a 4-12% Bis-Tris gel and transferred to a PVDF membrane. Membranes were incubated with antibodies against Estrogen Receptor alpha (Cell Signaling; 8644S) and GAPDH (Cell Signaling; 8884S) and protein bands were visualized using chemiluminescence (Perkin Elmer). The resulting data are depicted in FIG. 9. The structures of test compounds are.

2

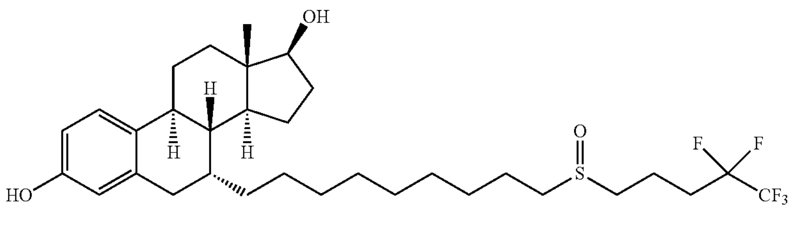

-continued

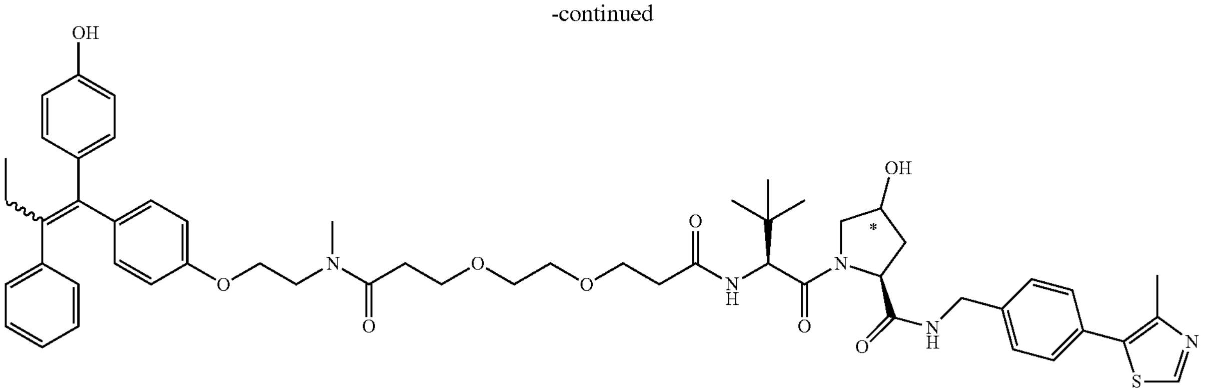

6* = (R)
7* = (S)

9

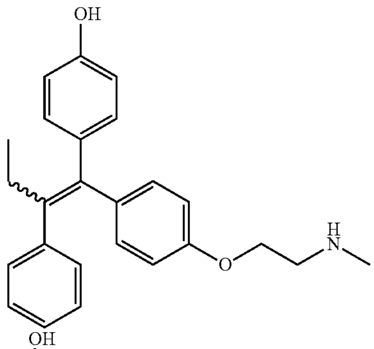

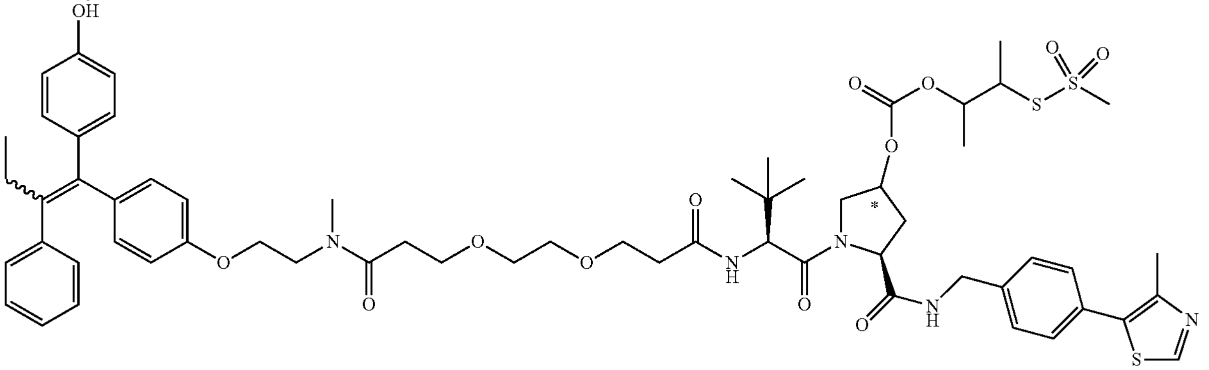

12* = (R)
13* = (S)

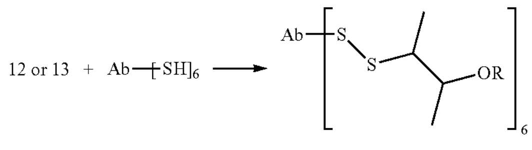

HER2-12
CD22-12
HER2-13

Efforts have been made to ensure accuracy with respect to numbers used (e.g. amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A conjugate having the chemical structure:

Ab-(L1-D)$_p$, wherein,

D is a CIDE having the structure;

E3LB-L2-PB, wherein:

E3LB is covalently bound to L1 and L2, having the structure of

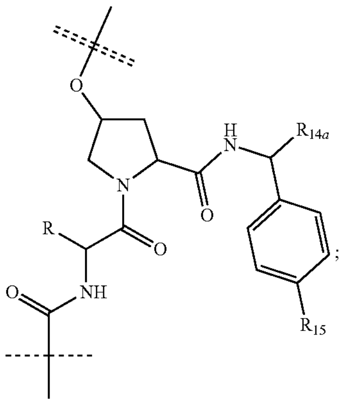

;

wherein ┬ indicates the attachment point to L2 and ====== indicates the attachment point to L1;

L2 is a linker covalently bound to E3LB and PB;

PB is a protein binding group covalently bound to L2 and the PB binds BRD4 or Estrogen Receptor alpha (ERα), or variants, mutations, splice variants, indels or fusions thereof;

Ab is an antibody covalently bound to L1;

L1 is a linker covalently bound to the Ab and the E3LB, wherein L1 has the formula selected from the group consisting of:

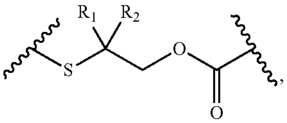

,

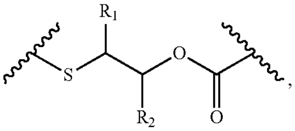

,

-continued

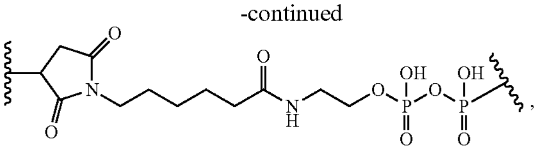

, and

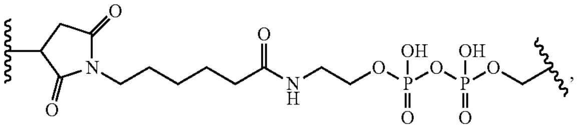

, wherein, $R_1$ and $R_2$ are independently selected from H and $C_1$-$C_6$ alkyl, or $R_1$ and $R_2$ together with the carbon to which each is attached form a 3, 4, 5, or 6-membered cycloalkyl or heterocyclyl group; $R_{14a}$ is H, haloalkyl, optionally substituted alkyl, methyl, fluoromethyl, hydroxymethyl, ethyl, isopropyl, or cyclopropyl; $R_{15}$ is optionally substituted heteroaryl or optionally substituted aryl; and R is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl; and p has a value of from 1 to 8.

2. The conjugate of claim 1, wherein $R_1$ and $R_2$ are each independently hydrogen or methyl.

3. The conjugate of claim 1, wherein $R_1$ and $R_2$ are each methyl.

4. The conjugate of claim 1, wherein $R_2$ is methyl.

5. The conjugate of claim 1, wherein L1 is covalently bound to a cysteine thiol group of the antibody.

6. The conjugate of claim 5, wherein the structure of L1 covalently bound to the cysteine thiol group of the antibody is selected from the group consisting of:

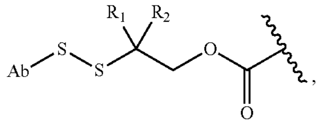

,

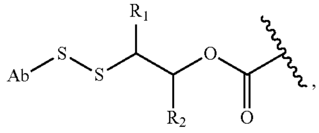

,

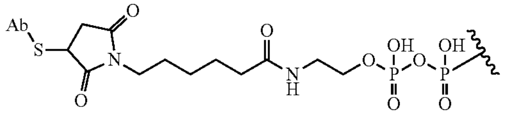

and

-continued
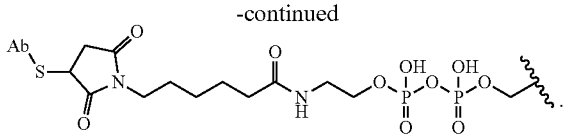
7. The conjugate of claim 6, wherein the L1-D to which the antibody is conjugated is selected from the group consisting of:
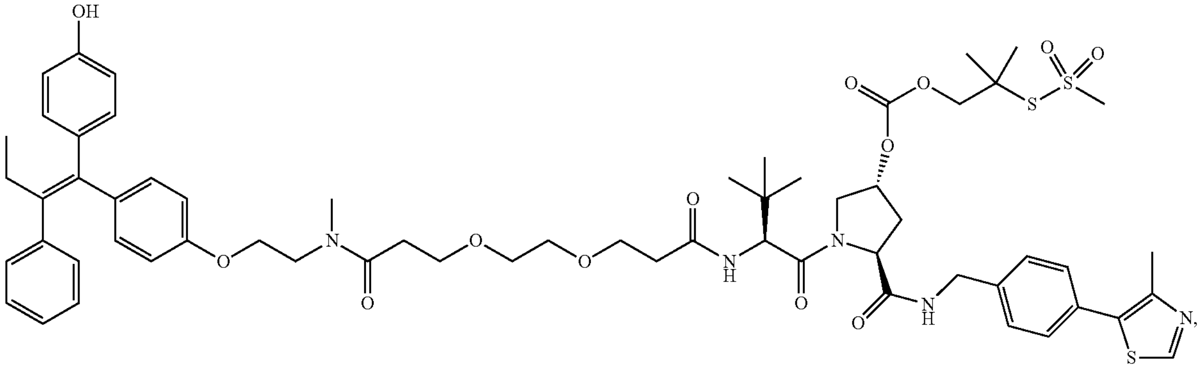
L1EC11
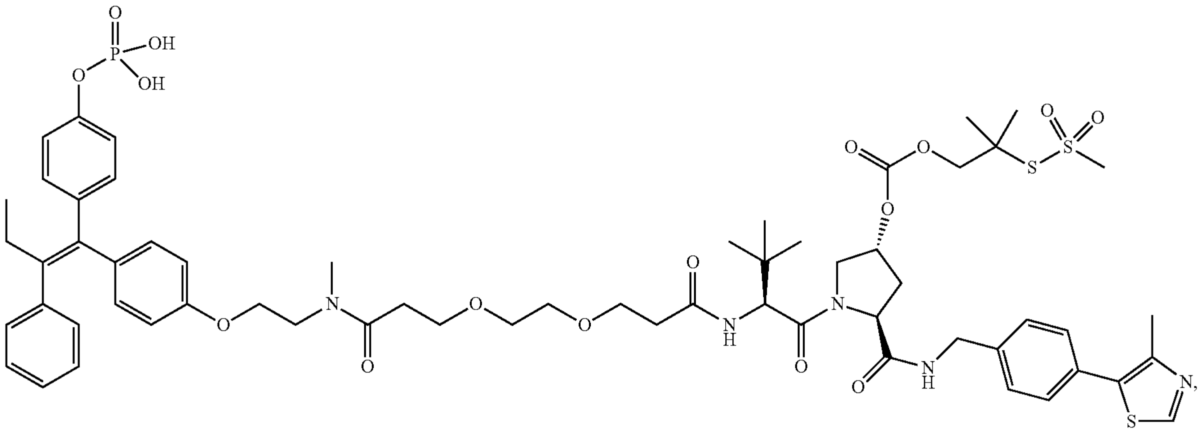
L1BC3
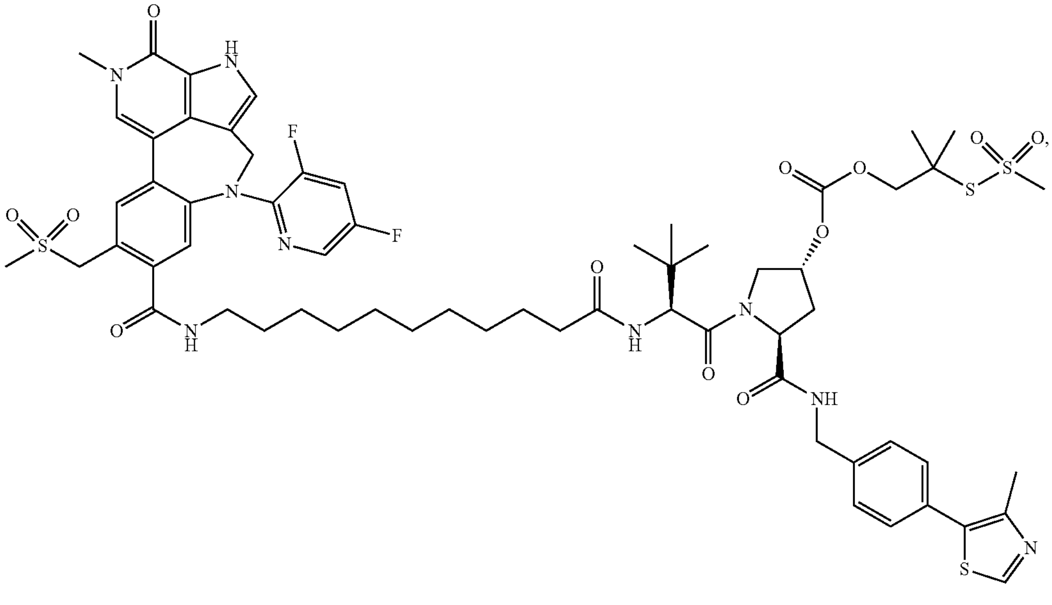

-continued
L1BC4
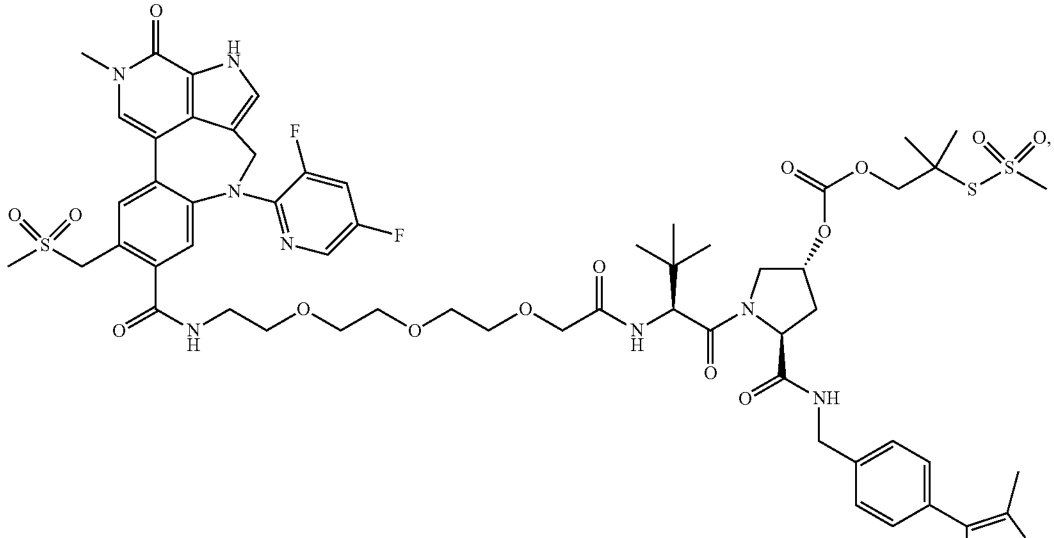
L1BC5
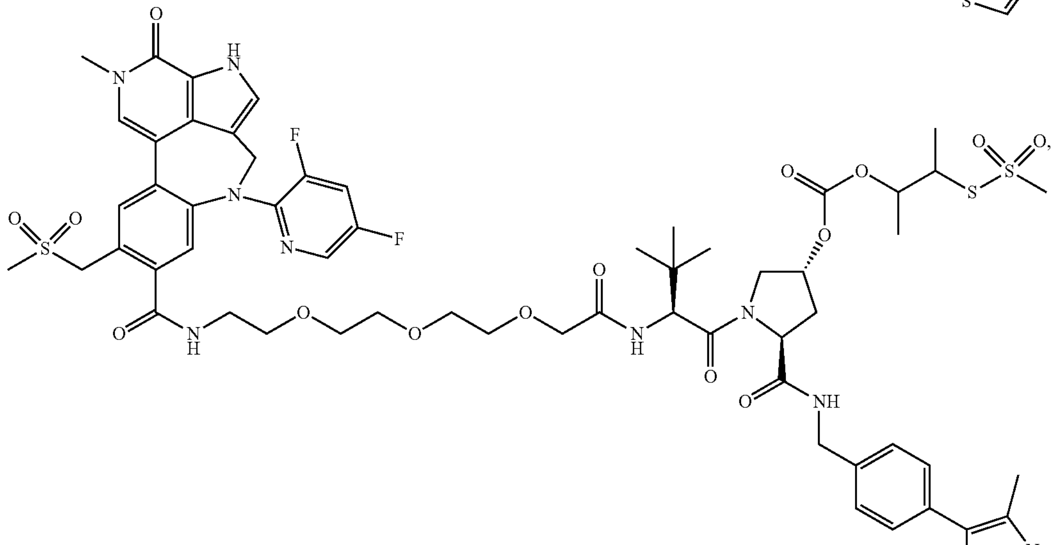
L1BC12
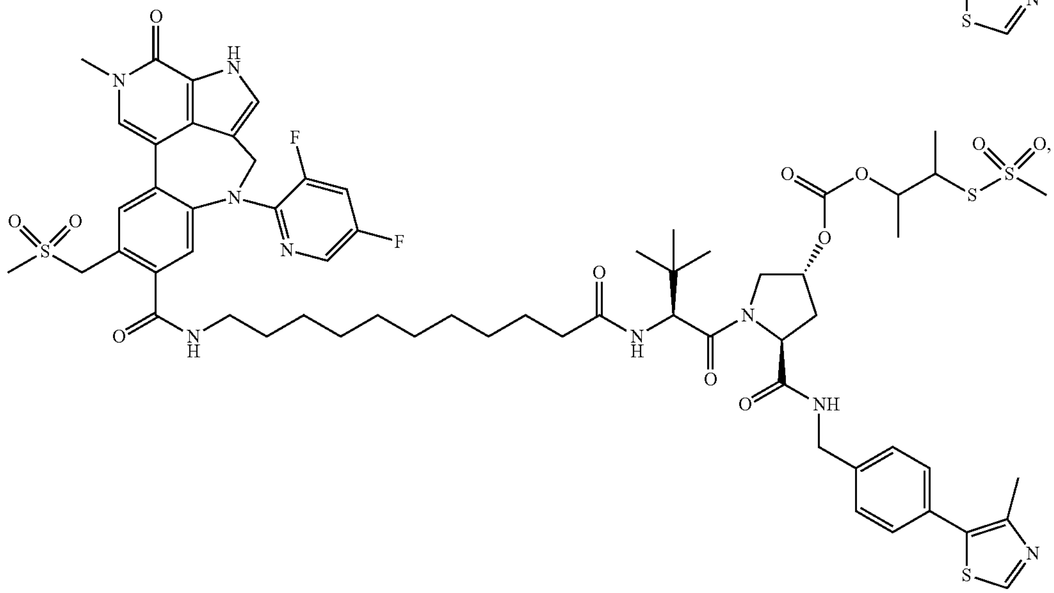

-continued
L1BQ15
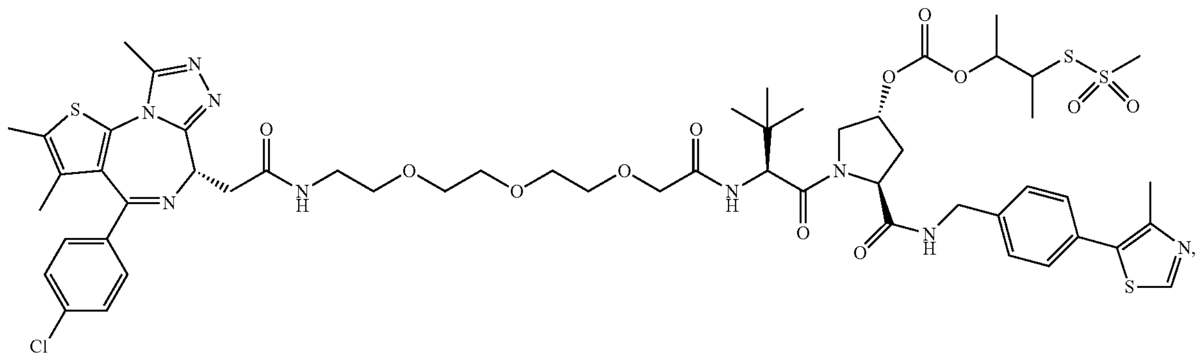
L1BQ16
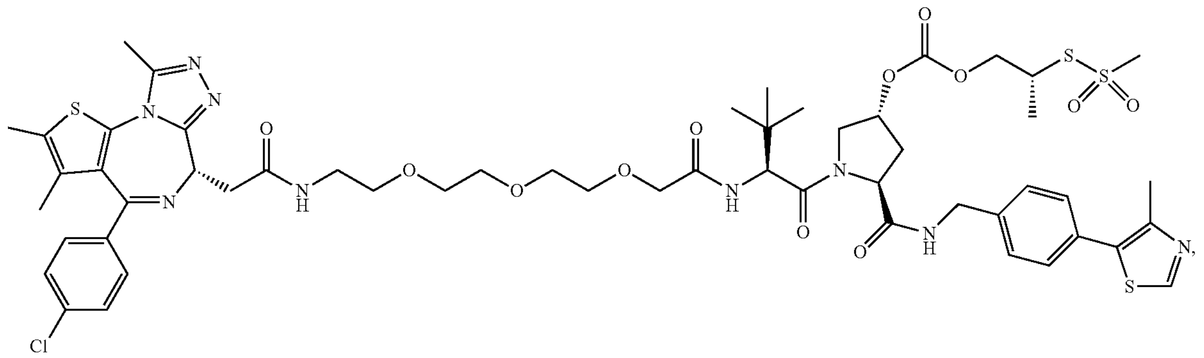
L1BQ17
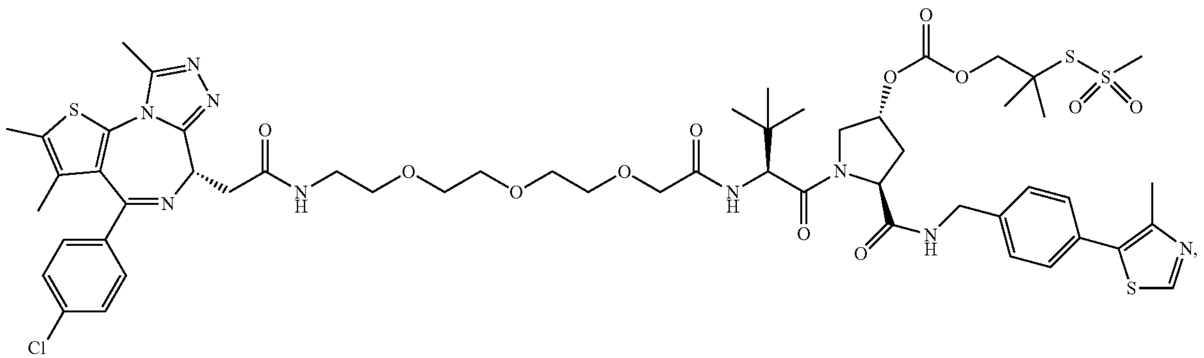
L1BQ20
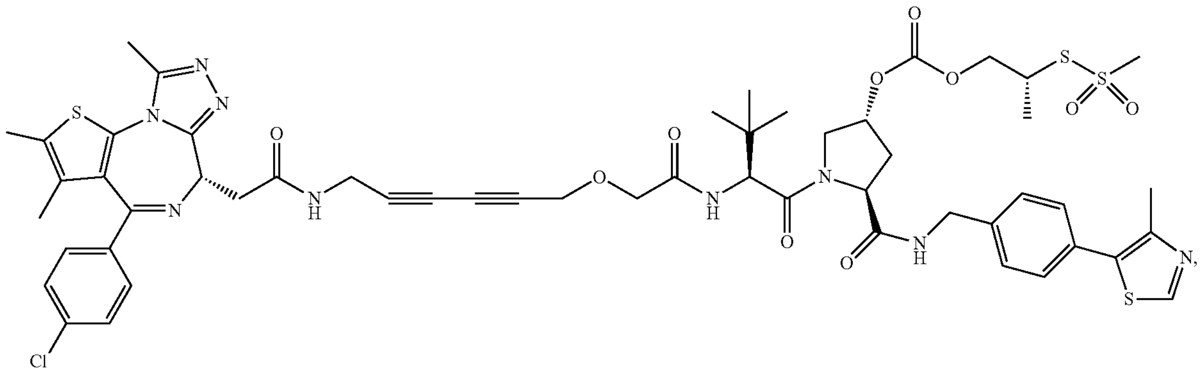

-continued
L1BQ21
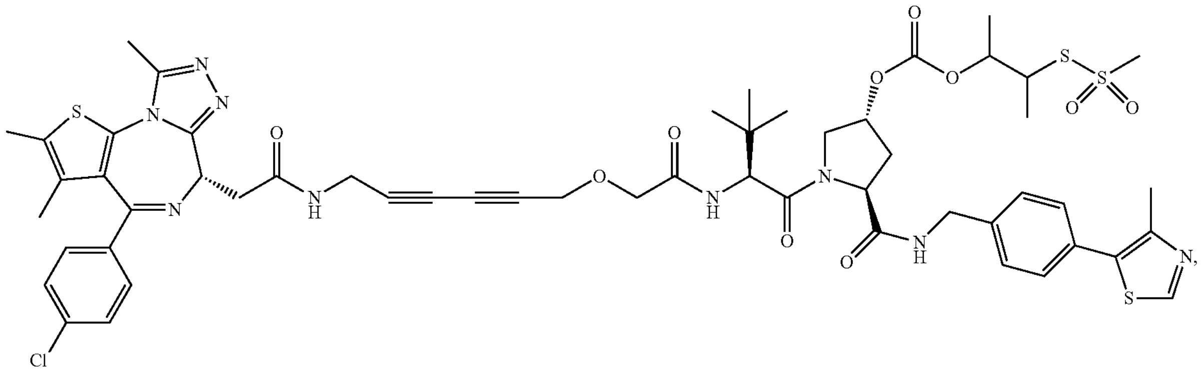
L1BQ22
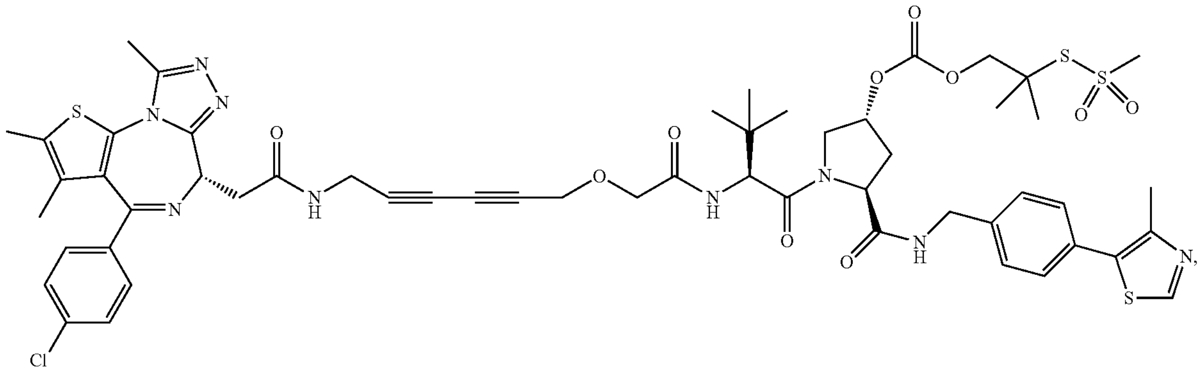
LIEC12
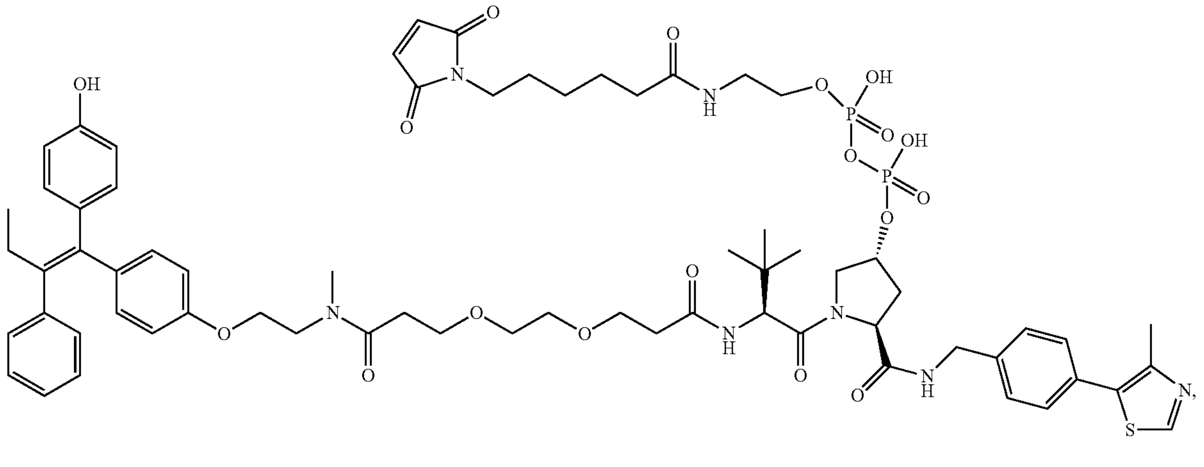

-continued

L1BC9

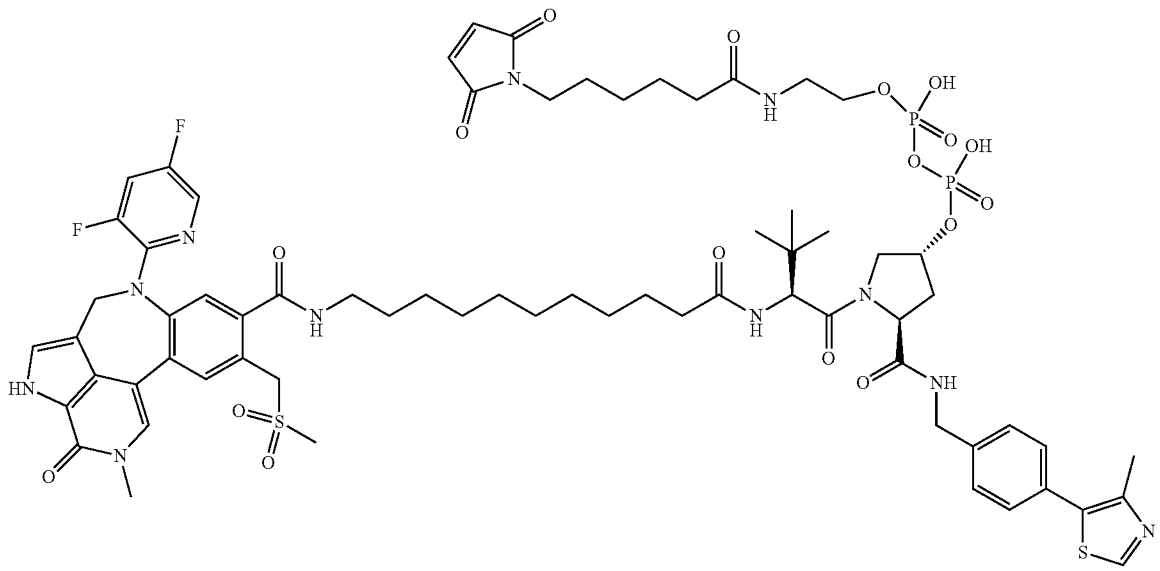

and

L1BC11

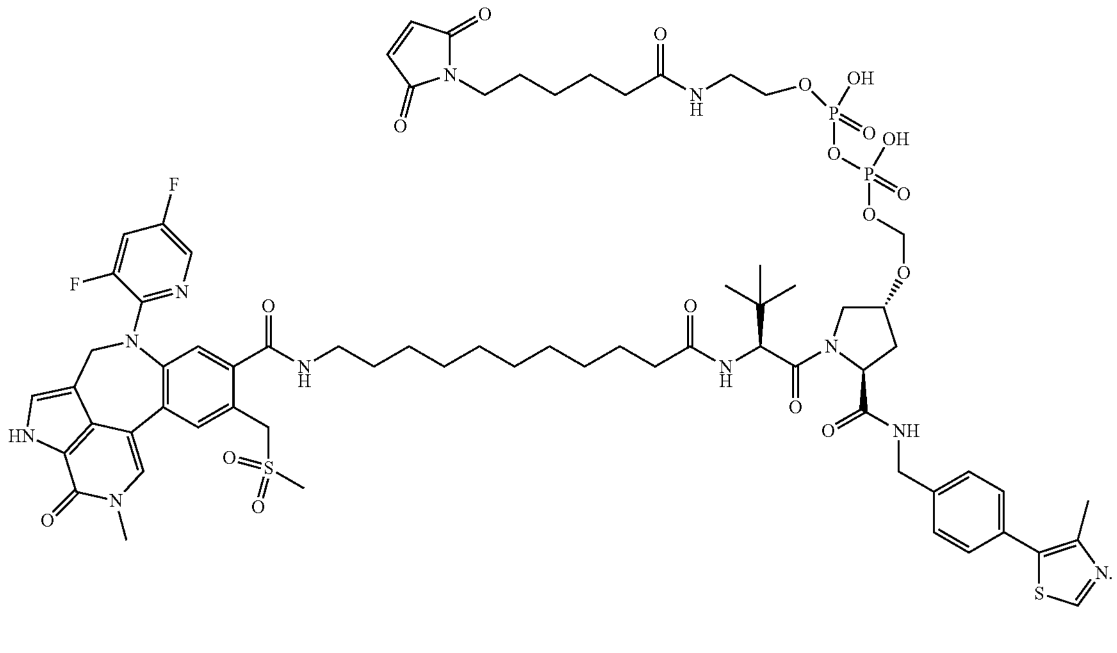

.

8. The conjugate of claim 6, wherein the cysteine of the antibody is engineered.

9. The conjugate of claim 8, wherein the engineered cysteine is selected from the group consisting of LC-K149C, HC-A140, HC-L174C, and HC—Y373C.

10. The conjugate of claim 1, wherein p is between 1 and 6.

11. The conjugate of claim 10, wherein p is 2 or 6.

12. A pharmaceutical composition comprising the conjugate of claim 1, and at least one pharmaceutical excipient.

13. A method of treating a subject having a condition modulated by the protein bound by the PB of the conjugate of claim 1, comprising administering an effective amount of the conjugate to said subject.

14. The method of claim 13, wherein the conjugate is co-administered with at least one additional therapeutic agent.

15. A compound having the formula L1-D, wherein D is a CIDE having the structure;

E3LB-L2-PB, wherein:

E3LB is covalently bound to L1 and L2, having the structure of

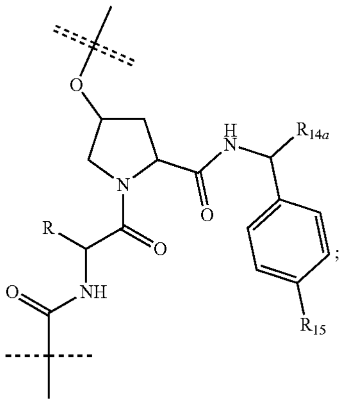

wherein indicates the attachment point to L2 and ====== indicates the attachment point to L1;

L2 is a linker covalently bound to E3LB and PB; and

PB is a protein binding group covalently bound to L2 and the PB binds BRD4 or Estrogen Receptor alpha (ERα), or variants, mutations, splice variants, indels or fusions thereof; and L1 is covalently bound to E3LB and has the formula selected from the group consisting of:

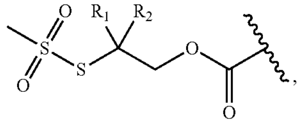

,

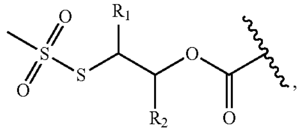

,

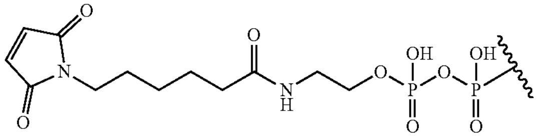

and

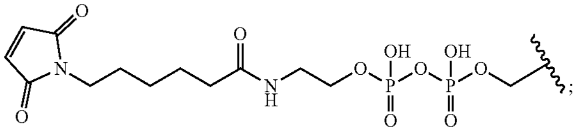

;

wherein, $R_1$ and $R_2$ are independently selected from H and $C_1$-$C_6$ alkyl, or $R_1$ and $R_2$ together with the carbon to which each is attached form a 3, 4, 5, or 6-membered cycloalkyl or heterocyclyl group; $R_{14a}$ is H, haloalkyl, optionally substituted alkyl, methyl, fluoromethyl, hydroxymethyl, ethyl, isopropyl, or cyclopropyl; $R_{15}$ is optionally substituted heteroaryl or optionally substituted aryl; and R is H, ethyl, isopropyl, tert-butyl, sec-butyl, cyclopropyl, cyclobutyl, cyclopentyl, or cyclohexyl; optionally substituted alkyl, optionally substituted cycloalkyl, optionally substituted hydroxyalkyl, optionally substituted heteroaryl, or haloalkyl.

16. The compound of claim 15, wherein said compound is selected from the group consisting of:

L1EC10

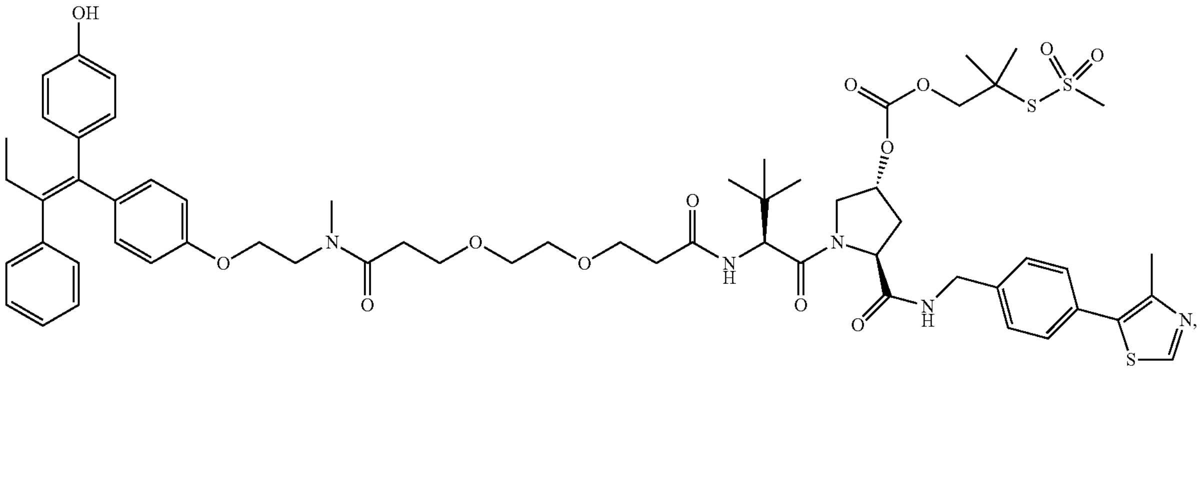

,

-continued
L1EC11
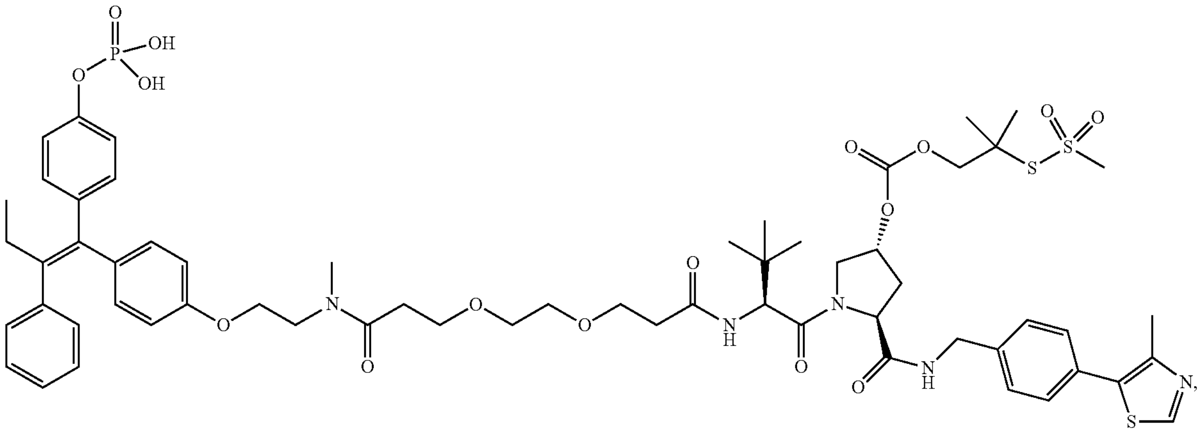
L1BC3
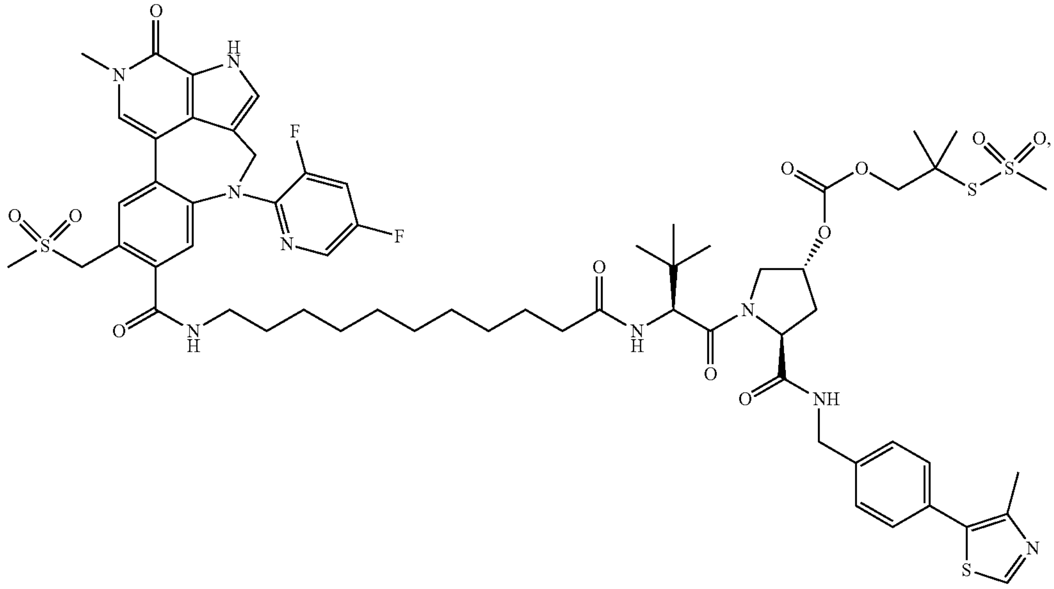
L1BC4
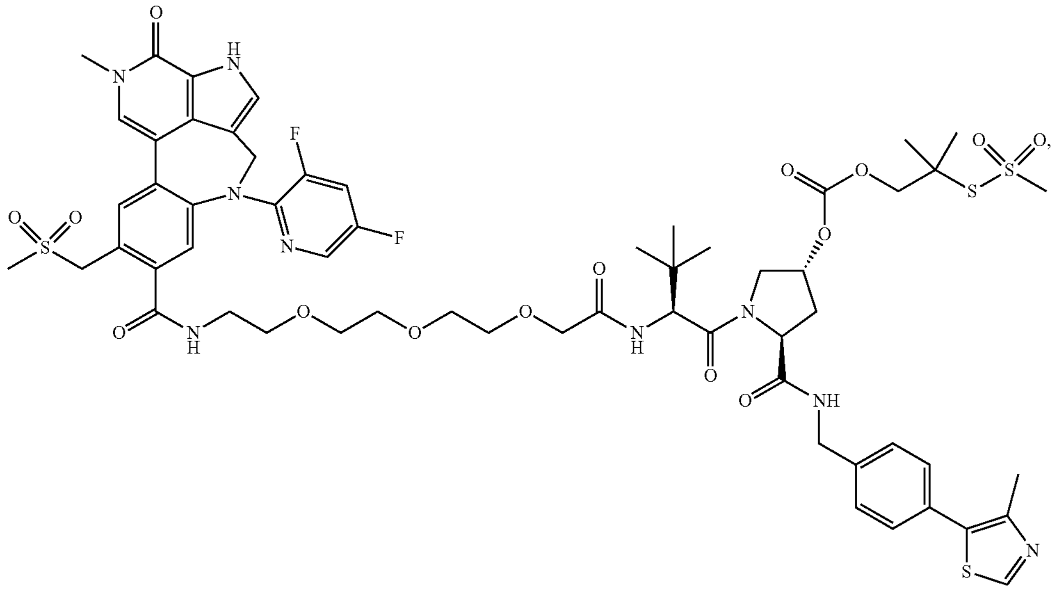

-continued
L1BC5
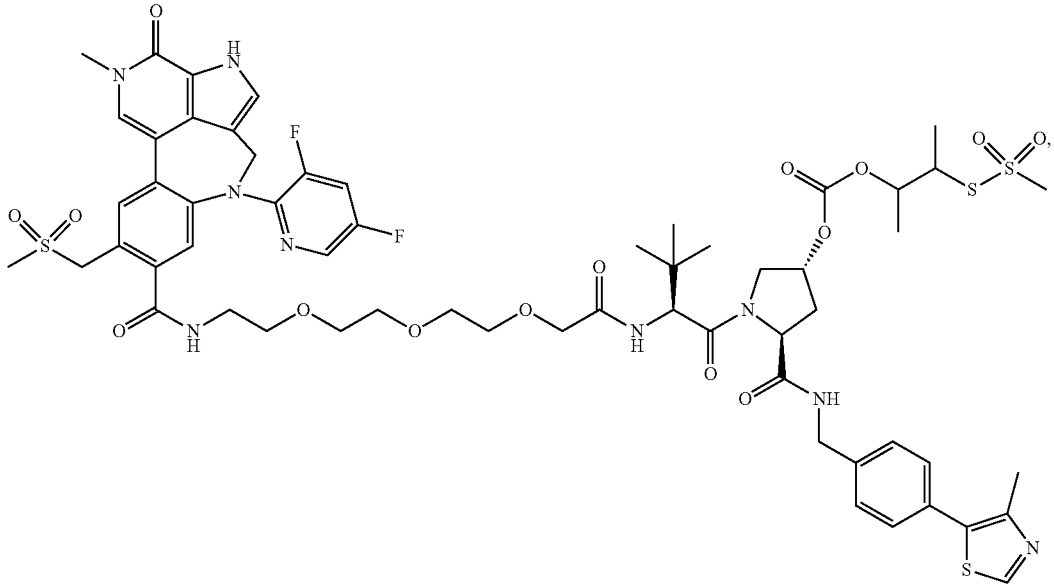
L1BC12
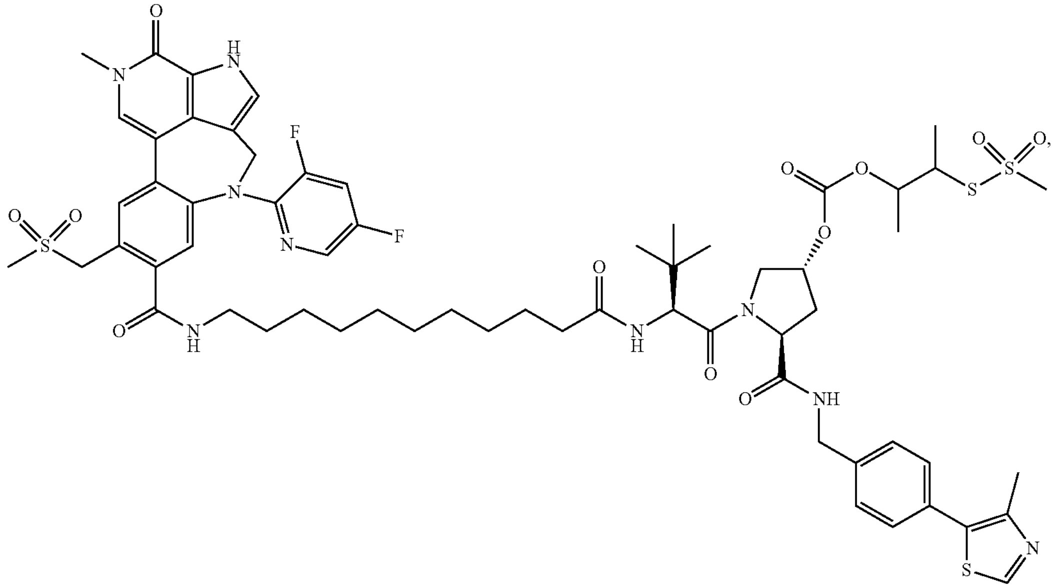
L1BQ15
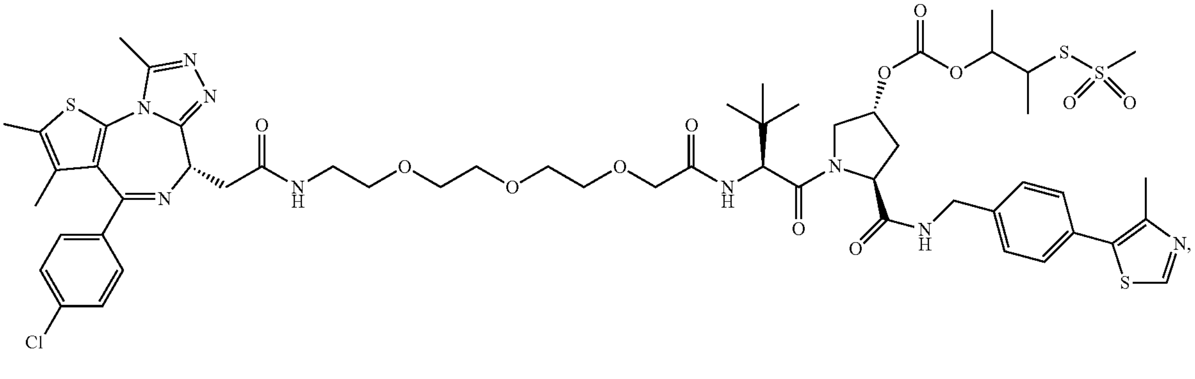

-continued
L1BQ16
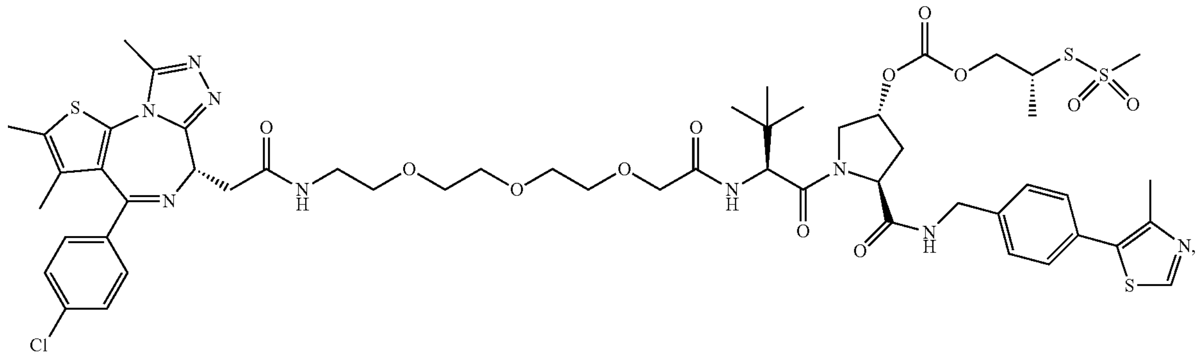
L1BQ17
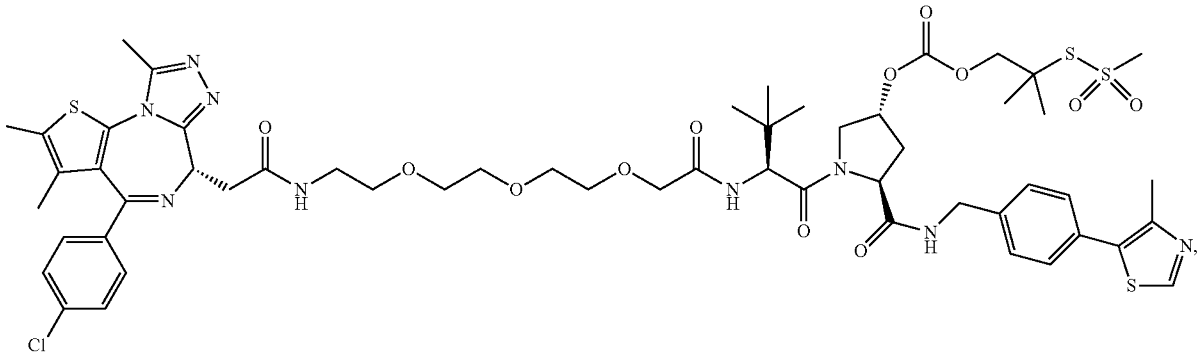
L1BQ20
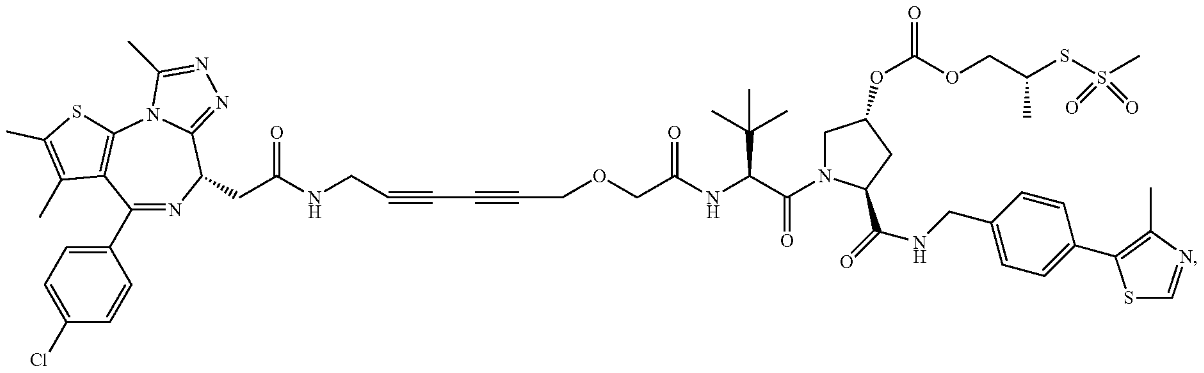
L1BQ21
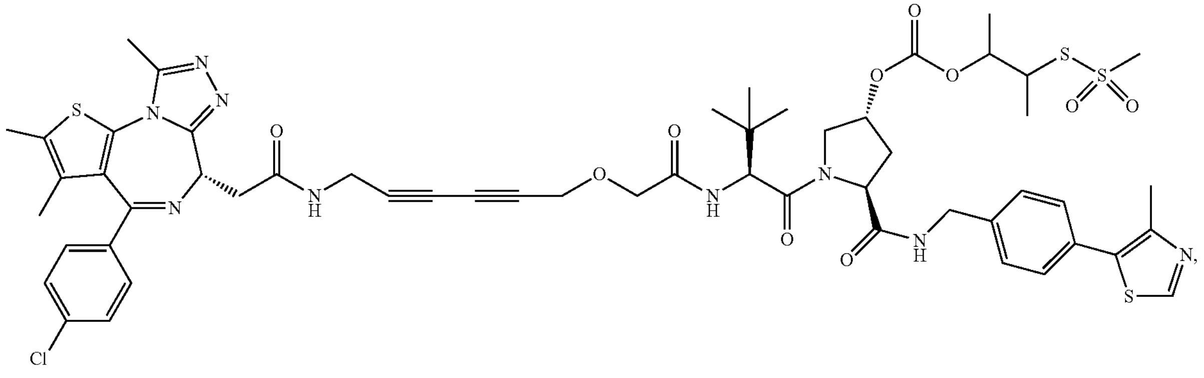

-continued
L1BQ22
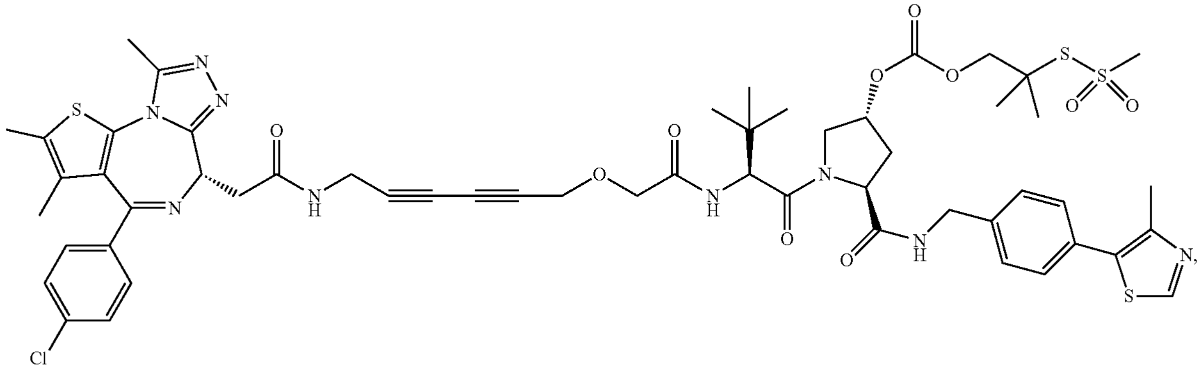
LIEC12
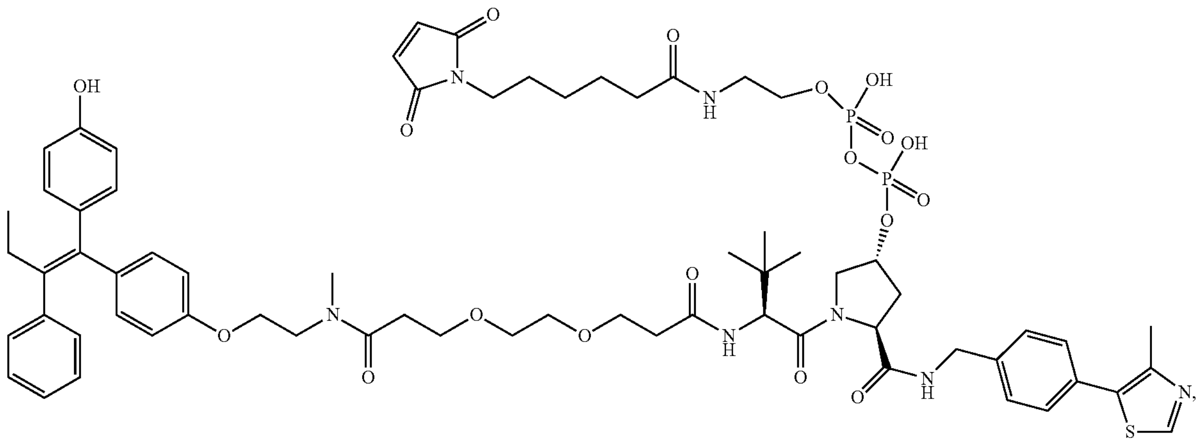
L1BC9
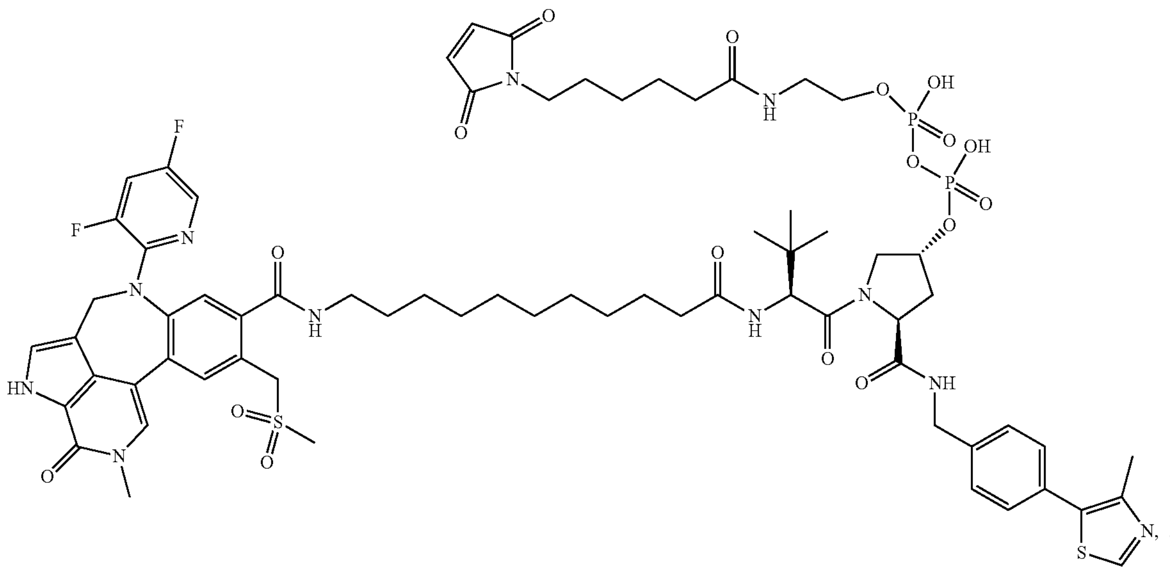
and

-continued
L1BC11
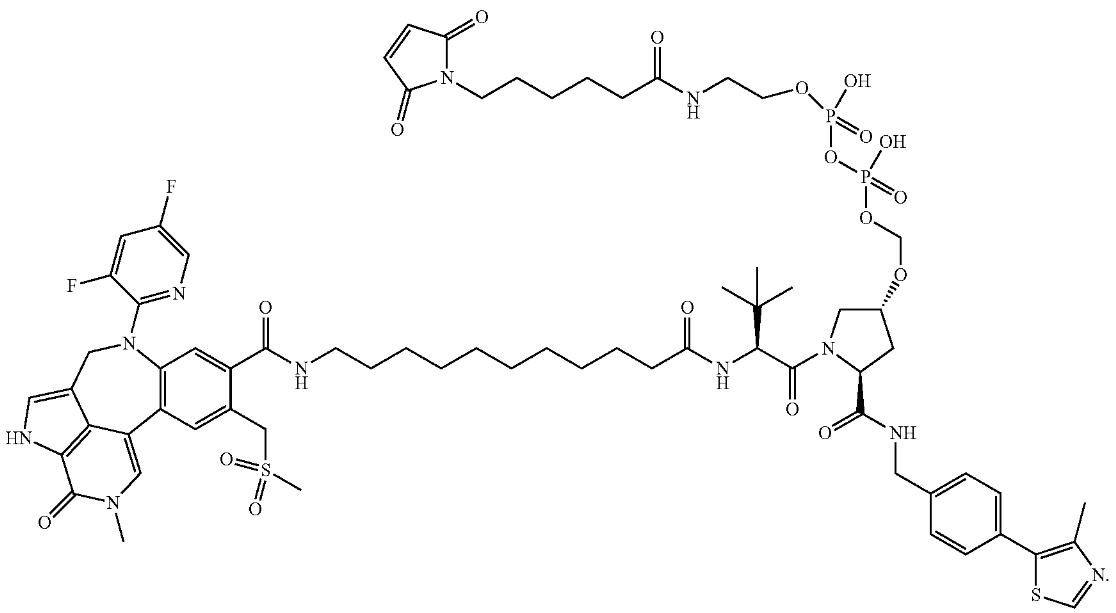
17. The compound of claim 15, wherein between 2 and about 6 compounds are linked to an antibody.
* * * * *

SEQUENCE LISTING

```
<160> NUMBER OF SEQ ID NOS: 258

<210> SEQ ID NO 1
<211> LENGTH: 108
<212> TYPE: PRT
<213> ORGANISM: Human
<220> FEATURE:
<221> NAME/KEY: misc_feature
<222> LOCATION: (1)..(108)
<223> OTHER INFORMATION: hukI

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys Arg
            100                 105


<210> SEQ ID NO 2
<211> LENGTH: 112
<212> TYPE: PRT
<213> ORGANISM: Human
<220> FEATURE:
<221> NAME/KEY: misc_feature
<222> LOCATION: (1)..(112)
<223> OTHER INFORMATION: huVH1

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80
```

Leu Glu Leu Ser Ser Leu Arg Ser Glu Asp Thr Ala Val Tyr Tyr Cys
85 90 95

Ala Arg Phe Asp Tyr Trp Gly Gln Gly Thr Leu Val Thr Val Ser Ser
100 105 110

<210> SEQ ID NO 3
<211> LENGTH: 108
<212> TYPE: PRT
<213> ORGANISM: Mouse
<220> FEATURE:
<221> NAME/KEY: misc_feature
<222> LOCATION: (1)..(108)
<223> OTHER INFORMATION: mu1D11 light chain variable region

<400> SEQUENCE: 3

Asp Ile Gln Met Thr Gln Ser Pro Ser Ser Leu Ser Ala Ser Leu Gly
1 5 10 15

Gly Lys Val Thr Ile Thr Cys Lys Ala Ser Gln Gly Phe Asn Lys Tyr
20 25 30

Val Ala Trp Tyr Gln His Lys Pro Gly Gln Cys Pro Arg Leu Leu Ile
35 40 45

His Tyr Thr Ser Thr Leu Gln Pro Gly Ile Pro Ala Arg Phe Ser Gly
50 55 60

Ser Gly Ser Gly Arg Asp Tyr Ser Phe Ser Ile Ser Asn Leu Glu Pro
65 70 75 80

Glu Asp Ser Ala Thr Tyr Phe Cys Leu Gln Tyr Gly Asn Leu Leu Tyr
85 90 95

Ala Phe Gly Gly Gly Thr Lys Leu Glu Ile Lys Arg
100 105

<210> SEQ ID NO 4
<211> LENGTH: 121
<212> TYPE: PRT
<213> ORGANISM: Mouse
<220> FEATURE:
<221> NAME/KEY: misc_feature
<222> LOCATION: (1)..(121)
<223> OTHER INFORMATION: mu1D11 heavy chain variable region

<400> SEQUENCE: 4

Gln Val Gln Leu Gln Gln Ser Gly Ala Glu Leu Val Arg Pro Gly Thr
1 5 10 15

Ser Val Lys Met Ser Cys Lys Ala Ser Gly Tyr Thr Phe Thr Ser Tyr
20 25 30

Trp Ile Gly Trp Ala Lys Gln Arg Pro Gly His Gly Phe Glu Trp Ile
35 40 45

Gly Asp Ile Tyr Pro Gly Gly Gly Tyr Thr Asn Tyr Asn Glu Lys Phe
50 55 60

Lys Gly Lys Ala Thr Leu Thr Ala Asp Lys Ser Ser Ser Thr Ala Tyr
65 70 75 80

Met Gln Phe Ser Ser Leu Thr Ser Glu Asp Ser Ala Ile Tyr Tyr Cys
85 90 95

Ala Arg Leu Asp Gly Ser Ser Tyr Arg Gly Ala Met Asp Ser Trp Gly
100 105 110

Gln Gly Thr Ser Ile Thr Val Ser Ser
115 120

<210> SEQ ID NO 5
<211> LENGTH: 10
<212> TYPE: PRT

<213> ORGANISM: Mouse
<220> FEATURE:
<221> NAME/KEY: misc_feature
<222> LOCATION: (1)..(10)
<223> OTHER INFORMATION: mu1D11 HVR H1

<400> SEQUENCE: 5

Gly Tyr Thr Phe Thr Ser Tyr Tyr Ile His
1               5                   10

<210> SEQ ID NO 6
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu1D11 HVR H2

<400> SEQUENCE: 6

Asp Ile Tyr Pro Gly Gly Gly Tyr Thr Asn Tyr Asn Glu Lys Phe Lys
1               5                   10                  15

Gly

<210> SEQ ID NO 7
<211> LENGTH: 107
<212> TYPE: PRT
<213> ORGANISM: homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: homo sapiens

<400> SEQUENCE: 8

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

-continued

```
Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120


<210> SEQ ID NO 9
<211> LENGTH: 11
<212> TYPE: PRT
<213> ORGANISM: homo sapiens

<400> SEQUENCE: 9

Ser Ala Ser Gln Gly Ile Ser Asn Tyr Leu Asn
1               5                   10


<210> SEQ ID NO 10
<211> LENGTH: 7
<212> TYPE: PRT
<213> ORGANISM: homo sapiens

<400> SEQUENCE: 10

Tyr Thr Ser Asn Leu His Ser
1               5


<210> SEQ ID NO 11
<211> LENGTH: 9
<212> TYPE: PRT
<213> ORGANISM: homo sapiens

<400> SEQUENCE: 11

Gln Gln Tyr Ser Glu Leu Pro Trp Thr
1               5


<210> SEQ ID NO 12
<211> LENGTH: 10
<212> TYPE: PRT
<213> ORGANISM: homo sapiens

<400> SEQUENCE: 12

Gly Phe Ser Leu Thr Gly Tyr Ser Val Asn
1               5                   10


<210> SEQ ID NO 13
<211> LENGTH: 16
<212> TYPE: PRT
<213> ORGANISM: homo sapiens

<400> SEQUENCE: 13

Met Ile Trp Gly Asp Gly Ser Thr Asp Tyr Asn Ser Ala Leu Lys Ser
1               5                   10                  15


<210> SEQ ID NO 14
<211> LENGTH: 12
<212> TYPE: PRT
<213> ORGANISM: homo sapiens

<400> SEQUENCE: 14

Asp Tyr Tyr Val Asn Tyr Ala Ser Trp Phe Ala Tyr
1               5                   10


<210> SEQ ID NO 15
<211> LENGTH: 214
```

<212> TYPE: PRT
<213> ORGANISM: homo sapiens

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 16
<211> LENGTH: 450
<212> TYPE: PRT
<213> ORGANISM: homo sapiens

<400> SEQUENCE: 16

```
Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125
```

-continued

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 112
<212> TYPE: PRT
<213> ORGANISM: homo sapiens

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50              55              60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

<210> SEQ ID NO 18
<211> LENGTH: 118
<212> TYPE: PRT
<213> ORGANISM: homo sapiens

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser
        115

<210> SEQ ID NO 19
<211> LENGTH: 15
<212> TYPE: PRT
<213> ORGANISM: homo sapiens

<400> SEQUENCE: 19

Arg Ala Ser Gln Ser Val Ser Gly Ser Arg Phe Thr Tyr Met His
1               5                   10                  15

<210> SEQ ID NO 20
<211> LENGTH: 7
<212> TYPE: PRT
<213> ORGANISM: homo sapiens

<400> SEQUENCE: 20

Tyr Ala Ser Ile Leu Glu Ser
1               5

<210> SEQ ID NO 21
<211> LENGTH: 10
<212> TYPE: PRT
<213> ORGANISM: homo sapiens

<400> SEQUENCE: 21

Gln His Ser Trp Glu Ile Pro Pro Trp Thr
1               5                   10

<210> SEQ ID NO 22
<211> LENGTH: 5
<212> TYPE: PRT
<213> ORGANISM: homo sapiens

<400> SEQUENCE: 22

Gly Tyr Trp Met Asn
1               5

<210> SEQ ID NO 23
<211> LENGTH: 17
<212> TYPE: PRT
<213> ORGANISM: homo sapiens

<400> SEQUENCE: 23

Met Ile His Pro Leu Asp Ala Glu Ile Arg Ala Asn Gln Lys Phe Arg
1               5                   10                  15

Asp

<210> SEQ ID NO 24
<211> LENGTH: 9
<212> TYPE: PRT
<213> ORGANISM: homo sapiens

<400> SEQUENCE: 24

Gly Thr Tyr Asp Gly Gly Phe Glu Tyr
1               5

<210> SEQ ID NO 25
<211> LENGTH: 219
<212> TYPE: PRT
<213> ORGANISM: homo sapiens

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser 195 200 205

Pro Val Thr Lys Ser Phe Asn Arg Gly Glu Cys
210 215

<210> SEQ ID NO 26
<211> LENGTH: 448
<212> TYPE: PRT
<213> ORGANISM: homo sapiens

<400> SEQUENCE: 26

Glu Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Gly Tyr
20 25 30

Trp Met Asn Trp Val Arg Gln Ala Pro Gly Gln Gly Leu Glu Trp Ile
35 40 45

Gly Met Ile His Pro Leu Asp Ala Glu Ile Arg Ala Asn Gln Lys Phe
50 55 60

Arg Asp Arg Val Thr Ile Thr Val Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Gly Thr Tyr Asp Gly Gly Phe Glu Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 27
<211> LENGTH: 17
<212> TYPE: PRT
<213> ORGANISM: homo sapiens

<400> SEQUENCE: 27

Met Ile His Pro Met Asp Ser Glu Ile Arg Ala Asn Gln Lys Phe Arg
1               5                   10                  15

Asp


<210> SEQ ID NO 28
<211> LENGTH: 17
<212> TYPE: PRT
<213> ORGANISM: homo sapiens

<400> SEQUENCE: 28

Met Ile His Pro Leu Asp Ser Glu Ile Arg Ala Asn Gln Lys Phe Arg
1               5                   10                  15

Asp


<210> SEQ ID NO 29
<211> LENGTH: 9
<212> TYPE: PRT
<213> ORGANISM: homo sapiens

<400> SEQUENCE: 29

Gly Thr Tyr Asp Gly Gly Phe Lys Tyr
1               5


<210> SEQ ID NO 30
<211> LENGTH: 219
<212> TYPE: PRT
<213> ORGANISM: homo sapiens

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
```

```
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 31
<211> LENGTH: 448
<212> TYPE: PRT
<213> ORGANISM: homo sapiens

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 32
<211> LENGTH: 448
<212> TYPE: PRT
<213> ORGANISM: homo sapiens

<400> SEQUENCE: 32

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 33
<211> LENGTH: 8
<212> TYPE: PRT
<213> ORGANISM: homo sapiens

<400> SEQUENCE: 33

Tyr Gly Ala Thr Ser Leu Glu Thr
1 5

<210> SEQ ID NO 34
<211> LENGTH: 9
<212> TYPE: PRT
<213> ORGANISM: homo sapiens

<400> SEQUENCE: 34

Gln Gln Tyr Trp Thr Thr Pro Phe Thr
1 5

<210> SEQ ID NO 35
<211> LENGTH: 11
<212> TYPE: PRT
<213> ORGANISM: homo sapiens

<400> SEQUENCE: 35

Gly Tyr Ser Ile Thr Asn Asp Tyr Ala Trp Asn
1 5 10

<210> SEQ ID NO 36
<211> LENGTH: 17
<212> TYPE: PRT
<213> ORGANISM: homo sapiens

<400> SEQUENCE: 36

Gly Tyr Ile Ser Tyr Ser Gly Tyr Thr Thr Tyr Asn Pro Ser Leu Lys
1 5 10 15

Ser

<210> SEQ ID NO 37
<211> LENGTH: 9
<212> TYPE: PRT
<213> ORGANISM: homo sapiens

<400> SEQUENCE: 37

Ala Arg Trp Ala Ser Gly Leu Asp Tyr
1 5

<210> SEQ ID NO 38
<211> LENGTH: 108
<212> TYPE: PRT
<213> ORGANISM: homo sapiens

<400> SEQUENCE: 38

Asp Ile Gln Met Thr Gln Ser Pro Ser Ser Leu Ser Ala Ser Val Gly
1 5 10 15

Asp Arg Val Thr Ile Thr Cys Lys Ala Ser Asp Leu Ile His Asn Trp
20 25 30

Leu Ala Trp Tyr Gln Gln Lys Pro Gly Lys Ala Pro Lys Leu Leu Ile
35 40 45

Tyr Gly Ala Thr Ser Leu Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Trp Thr Thr Pro Phe
85 90 95

Thr Phe Gly Gln Gly Thr Lys Val Glu Ile Lys Arg
100 105

<210> SEQ ID NO 39
<211> LENGTH: 116
<212> TYPE: PRT
<213> ORGANISM: homo sapiens

<400> SEQUENCE: 39

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Ser Ile Thr Asn Asp
20 25 30

Tyr Ala Trp Asn Trp Val Arg Gln Ala Pro Gly Lys Gly Leu Glu Trp
35 40 45

Val Gly Tyr Ile Ser Tyr Ser Gly Tyr Thr Thr Tyr Asn Pro Ser Leu
50 55 60

-continued

```
Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115


<210> SEQ ID NO 40
<211> LENGTH: 11
<212> TYPE: PRT
<213> ORGANISM: homo sapiens

<400> SEQUENCE: 40

Gly Tyr Ser Ile Thr Ser Asp Tyr Ala Trp Asn
1               5                   10


<210> SEQ ID NO 41
<211> LENGTH: 17
<212> TYPE: PRT
<213> ORGANISM: homo sapiens

<400> SEQUENCE: 41

Gly Tyr Ile Ser Asn Ser Gly Ser Thr Ser Tyr Asn Pro Ser Leu Lys
1               5                   10                  15

Ser


<210> SEQ ID NO 42
<211> LENGTH: 15
<212> TYPE: PRT
<213> ORGANISM: homo sapiens

<400> SEQUENCE: 42

Glu Arg Asn Tyr Asp Tyr Asp Asp Tyr Tyr Tyr Ala Met Asp Tyr
1               5                   10                  15


<210> SEQ ID NO 43
<211> LENGTH: 17
<212> TYPE: PRT
<213> ORGANISM: homo sapiens

<400> SEQUENCE: 43

Lys Ser Ser Gln Ser Leu Leu Tyr Arg Ser Asn Gln Lys Asn Tyr Leu
1               5                   10                  15

Ala


<210> SEQ ID NO 44
<211> LENGTH: 7
<212> TYPE: PRT
<213> ORGANISM: homo sapiens

<400> SEQUENCE: 44

Trp Ala Ser Thr Arg Glu Ser
1               5


<210> SEQ ID NO 45
<211> LENGTH: 9
<212> TYPE: PRT
<213> ORGANISM: homo sapiens

<400> SEQUENCE: 45
```

-continued

```
Gln Gln Tyr Tyr Asn Tyr Pro Arg Thr
1               5


<210> SEQ ID NO 46
<211> LENGTH: 124
<212> TYPE: PRT
<213> ORGANISM: homo sapiens

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Asp Tyr Tyr Tyr Ala Met Asp
            100                 105                 110

Tyr Trp Gly Gln Gly Thr Leu Val Thr Val Ser Ser
        115                 120


<210> SEQ ID NO 47
<211> LENGTH: 113
<212> TYPE: PRT
<213> ORGANISM: homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys


<210> SEQ ID NO 48
<211> LENGTH: 10
<212> TYPE: PRT
<213> ORGANISM: homo sapiens

<400> SEQUENCE: 48

Gly Phe Ser Phe Ser Asp Phe Ala Met Ser
1               5                   10


<210> SEQ ID NO 49
```

<211> LENGTH: 18
<212> TYPE: PRT
<213> ORGANISM: homo sapiens

<400> SEQUENCE: 49

```
Ala Thr Ile Gly Arg Val Ala Phe His Thr Tyr Tyr Pro Asp Ser Met
1               5                   10                  15

Lys Gly
```

<210> SEQ ID NO 50
<211> LENGTH: 13
<212> TYPE: PRT
<213> ORGANISM: homo sapiens

<400> SEQUENCE: 50

```
Ala Arg His Arg Gly Phe Asp Val Gly His Phe Asp Phe
1               5                   10
```

<210> SEQ ID NO 51
<211> LENGTH: 16
<212> TYPE: PRT
<213> ORGANISM: homo sapiens

<400> SEQUENCE: 51

```
Arg Ser Ser Glu Thr Leu Val His Ser Ser Gly Asn Thr Tyr Leu Glu
1               5                   10                  15
```

<210> SEQ ID NO 52
<211> LENGTH: 7
<212> TYPE: PRT
<213> ORGANISM: homo sapiens

<400> SEQUENCE: 52

```
Arg Val Ser Asn Arg Phe Ser
1               5
```

<210> SEQ ID NO 53
<211> LENGTH: 9
<212> TYPE: PRT
<213> ORGANISM: homo sapiens

<400> SEQUENCE: 53

```
Phe Gln Gly Ser Phe Asn Pro Leu Thr
1               5
```

<210> SEQ ID NO 54
<211> LENGTH: 120
<212> TYPE: PRT
<213> ORGANISM: homo sapiens

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120
```

<210> SEQ ID NO 55
<211> LENGTH: 113
<212> TYPE: PRT
<213> ORGANISM: homo sapiens

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg
```

<210> SEQ ID NO 56
<211> LENGTH: 117
<212> TYPE: PRT
<213> ORGANISM: homo sapiens

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115
```

<210> SEQ ID NO 57
<211> LENGTH: 112
<212> TYPE: PRT
<213> ORGANISM: homo sapiens

<400> SEQUENCE: 57

Asp Ile Gln Leu Thr Gln Ser Pro Ser Ser Leu Ser Ala Ser Val Gly
1 5 10 15

Asp Arg Val Thr Ile Thr Cys Lys Ala Ser Gln Ser Val Asp Tyr Glu
20 25 30

Gly Asp Ser Phe Leu Asn Trp Tyr Gln Gln Lys Pro Gly Lys Ala Pro
35 40 45

Lys Leu Leu Ile Tyr Ala Ala Ser Asn Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln Gln Ser Asn
85 90 95

Glu Asp Pro Leu Thr Phe Gly Gln Gly Thr Lys Val Glu Ile Lys Arg
100 105 110

<210> SEQ ID NO 58
<211> LENGTH: 10
<212> TYPE: PRT
<213> ORGANISM: homo sapiens

<400> SEQUENCE: 58

Gly Tyr Thr Phe Ser Ser Tyr Trp Ile Glu
1 5 10

<210> SEQ ID NO 59
<211> LENGTH: 18
<212> TYPE: PRT
<213> ORGANISM: homo sapiens

<400> SEQUENCE: 59

Gly Glu Ile Leu Pro Gly Gly Gly Asp Thr Asn Tyr Asn Glu Ile Phe
1 5 10 15

Lys Gly

<210> SEQ ID NO 60
<211> LENGTH: 10
<212> TYPE: PRT
<213> ORGANISM: homo sapiens

<400> SEQUENCE: 60

Thr Arg Arg Val Pro Ile Arg Leu Asp Tyr
1 5 10

<210> SEQ ID NO 61
<211> LENGTH: 15
<212> TYPE: PRT
<213> ORGANISM: homo sapiens

<400> SEQUENCE: 61

Lys Ala Ser Gln Ser Val Asp Tyr Glu Gly Asp Ser Phe Leu Asn
1 5 10 15

<210> SEQ ID NO 62
<211> LENGTH: 7
<212> TYPE: PRT
<213> ORGANISM: homo sapiens

<400> SEQUENCE: 62

Ala Ala Ser Asn Leu Glu Ser
1 5

<210> SEQ ID NO 63
<211> LENGTH: 9
<212> TYPE: PRT
<213> ORGANISM: homo sapiens

<400> SEQUENCE: 63

Gln Gln Ser Asn Glu Asp Pro Leu Thr
1 5

<210> SEQ ID NO 64
<211> LENGTH: 219
<212> TYPE: PRT
<213> ORGANISM: homo sapiens

<400> SEQUENCE: 64

Asp Ile Gln Met Thr Gln Ser Pro Ser Ser Leu Ser Ala Ser Val Gly
1 5 10 15

Asp Arg Val Thr Ile Thr Cys Arg Ser Ser Glu Thr Leu Val His Ser
20 25 30

Ser Gly Asn Thr Tyr Leu Glu Trp Tyr Gln Gln Lys Pro Gly Lys Ala
35 40 45

Pro Lys Leu Leu Ile Tyr Arg Val Ser Asn Arg Phe Ser Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Phe Gln Gly
85 90 95

Ser Phe Asn Pro Leu Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 65
<211> LENGTH: 450
<212> TYPE: PRT
<213> ORGANISM: homo sapiens

<400> SEQUENCE: 65

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Phe Ser Asp Phe
20 25 30

Ala Met Ser Trp Val Arg Gln Ala Pro Gly Lys Gly Leu Glu Trp Val
35 40 45

Ala Thr Ile Gly Arg Val Ala Phe His Thr Tyr Tyr Pro Asp Ser Met
50 55 60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 66
<211> LENGTH: 16

<212> TYPE: PRT
<213> ORGANISM: homo sapiens

<400> SEQUENCE: 66

Arg Ser Ser Gln Ser Ile Val His Ser Val Gly Asn Thr Phe Leu Glu
1 5 10 15

<210> SEQ ID NO 67
<211> LENGTH: 7
<212> TYPE: PRT
<213> ORGANISM: homo sapiens

<400> SEQUENCE: 67

Lys Val Ser Asn Arg Phe Ser
1 5

<210> SEQ ID NO 68
<211> LENGTH: 9
<212> TYPE: PRT
<213> ORGANISM: homo sapiens

<400> SEQUENCE: 68

Phe Gln Gly Ser Gln Phe Pro Tyr Thr
1 5

<210> SEQ ID NO 69
<211> LENGTH: 10
<212> TYPE: PRT
<213> ORGANISM: homo sapiens

<400> SEQUENCE: 69

Gly Tyr Glu Phe Ser Arg Ser Trp Met Asn
1 5 10

<210> SEQ ID NO 70
<211> LENGTH: 17
<212> TYPE: PRT
<213> ORGANISM: homo sapiens

<400> SEQUENCE: 70

Arg Ile Tyr Pro Gly Asp Gly Asp Thr Asn Tyr Ser Gly Lys Phe Lys
1 5 10 15

Gly

<210> SEQ ID NO 71
<211> LENGTH: 11
<212> TYPE: PRT
<213> ORGANISM: homo sapiens

<400> SEQUENCE: 71

Asp Gly Ser Ser Trp Asp Trp Tyr Phe Asp Val
1 5 10

<210> SEQ ID NO 72
<211> LENGTH: 113
<212> TYPE: PRT
<213> ORGANISM: homo sapiens

<400> SEQUENCE: 72

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Ile Val His Ser
20 25 30

```
Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg


<210> SEQ ID NO 73
<211> LENGTH: 120
<212> TYPE: PRT
<213> ORGANISM: homo sapiens

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser
        115                 120


<210> SEQ ID NO 74
<211> LENGTH: 219
<212> TYPE: PRT
<213> ORGANISM: homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
```

```
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 75
<211> LENGTH: 450
<212> TYPE: PRT
<213> ORGANISM: homo sapiens

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 76
<211> LENGTH: 16
<212> TYPE: PRT
<213> ORGANISM: homo sapiens

<400> SEQUENCE: 76

Arg Ser Ser Gln Ser Leu Leu His Ser Asn Gly Tyr Asn Tyr Leu Asp
1               5                   10                  15


<210> SEQ ID NO 77
<211> LENGTH: 7
<212> TYPE: PRT
<213> ORGANISM: homo sapiens

<400> SEQUENCE: 77

Leu Gly Val Asn Ser Val Ser
1               5


<210> SEQ ID NO 78
<211> LENGTH: 5
<212> TYPE: PRT
<213> ORGANISM: homo sapiens

<400> SEQUENCE: 78

Asn His Ala Ile Ser
1               5


<210> SEQ ID NO 79
<211> LENGTH: 17
<212> TYPE: PRT
<213> ORGANISM: homo sapiens

<400> SEQUENCE: 79

Gly Ile Ile Pro Ile Phe Gly Thr Ala Asn Tyr Ala Gln Lys Phe Gln
1               5                   10                  15
```

Gly

<210> SEQ ID NO 80
<211> LENGTH: 8
<212> TYPE: PRT
<213> ORGANISM: homo sapiens

<400> SEQUENCE: 80

Glu Trp Ala Asp Val Phe Asp Ile
1               5

<210> SEQ ID NO 81
<211> LENGTH: 8
<212> TYPE: PRT
<213> ORGANISM: homo sapiens

<400> SEQUENCE: 81

Glu Trp Ala Asp Val Phe Asp Ile
1               5

<210> SEQ ID NO 82
<211> LENGTH: 112
<212> TYPE: PRT
<213> ORGANISM: homo sapiens

<400> SEQUENCE: 82

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 83
<211> LENGTH: 117
<212> TYPE: PRT
<213> ORGANISM: homo sapiens

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Phe
65                  70                  75                  80

Met Glu Leu Ser Ser Leu Arg Ser Glu Asp Thr Ala Val Tyr Tyr Cys
                85                  90                  95

```
Ala Arg Glu Trp Ala Asp Val Phe Asp Ile Trp Gly Gln Gly Thr Met
            100                 105                 110

Val Thr Val Ser Ser
        115


<210> SEQ ID NO 84
<211> LENGTH: 11
<212> TYPE: PRT
<213> ORGANISM: homo sapiens

<400> SEQUENCE: 84

Arg Ala Ser Gln Gly Ile Arg Asn Asp Leu Gly
1               5                   10


<210> SEQ ID NO 85
<211> LENGTH: 7
<212> TYPE: PRT
<213> ORGANISM: homo sapiens

<400> SEQUENCE: 85

Ala Ala Ser Ser Leu Gln Ser
1               5


<210> SEQ ID NO 86
<211> LENGTH: 5
<212> TYPE: PRT
<213> ORGANISM: homo sapiens

<400> SEQUENCE: 86

Gly Asn Tyr Met Ser
1               5


<210> SEQ ID NO 87
<211> LENGTH: 5
<212> TYPE: PRT
<213> ORGANISM: homo sapiens

<400> SEQUENCE: 87

Gly Asn Tyr Met Ser
1               5


<210> SEQ ID NO 88
<211> LENGTH: 16
<212> TYPE: PRT
<213> ORGANISM: homo sapiens

<400> SEQUENCE: 88

Leu Ile Tyr Ser Gly Asp Ser Thr Tyr Tyr Ala Asp Ser Val Lys Gly
1               5                   10                  15


<210> SEQ ID NO 89
<211> LENGTH: 10
<212> TYPE: PRT
<213> ORGANISM: homo sapiens

<400> SEQUENCE: 89

Asp Gly Tyr Tyr Val Ser Asp Met Val Val
1               5                   10


<210> SEQ ID NO 90
<211> LENGTH: 107
<212> TYPE: PRT
<213> ORGANISM: homo sapiens
```

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 91
<211> LENGTH: 118
<212> TYPE: PRT
<213> ORGANISM: homo sapiens

<400> SEQUENCE: 91

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115

<210> SEQ ID NO 92
<211> LENGTH: 107
<212> TYPE: PRT
<213> ORGANISM: homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp

```
                85                  90                  95

Thr Phe Gly Gln Gly Thr Lys Leu Glu Ile Lys
            100                 105


<210> SEQ ID NO 93
<211> LENGTH: 118
<212> TYPE: PRT
<213> ORGANISM: homo sapiens

<400> SEQUENCE: 93

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115


<210> SEQ ID NO 94
<211> LENGTH: 107
<212> TYPE: PRT
<213> ORGANISM: homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105


<210> SEQ ID NO 95
<211> LENGTH: 118
<212> TYPE: PRT
<213> ORGANISM: homo sapiens

<400> SEQUENCE: 95

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30
```

```
Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115


<210> SEQ ID NO 96
<211> LENGTH: 107
<212> TYPE: PRT
<213> ORGANISM: homo sapiens

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105


<210> SEQ ID NO 97
<211> LENGTH: 118
<212> TYPE: PRT
<213> ORGANISM: homo sapiens

<400> SEQUENCE: 97

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ala Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115
```

<210> SEQ ID NO 98
<211> LENGTH: 1255
<212> TYPE: PRT
<213> ORGANISM: homo sapiens

<400> SEQUENCE: 98

Met Glu Leu Ala Ala Leu Cys Arg Trp Gly Leu Leu Leu Ala Leu Leu
1 5 10 15

Pro Pro Gly Ala Ala Ser Thr Gln Val Cys Thr Gly Thr Asp Met Lys
20 25 30

Leu Arg Leu Pro Ala Ser Pro Glu Thr His Leu Asp Met Leu Arg His
35 40 45

Leu Tyr Gln Gly Cys Gln Val Val Gln Gly Asn Leu Glu Leu Thr Tyr
50 55 60

Leu Pro Thr Asn Ala Ser Leu Ser Phe Leu Gln Asp Ile Gln Glu Val
65 70 75 80

Gln Gly Tyr Val Leu Ile Ala His Asn Gln Val Arg Gln Val Pro Leu
85 90 95

Gln Arg Leu Arg Ile Val Arg Gly Thr Gln Leu Phe Glu Asp Asn Tyr
100 105 110

Ala Leu Ala Val Leu Asp Asn Gly Asp Pro Leu Asn Asn Thr Thr Pro
115 120 125

Val Thr Gly Ala Ser Pro Gly Gly Leu Arg Glu Leu Gln Leu Arg Ser
130 135 140

Leu Thr Glu Ile Leu Lys Gly Gly Val Leu Ile Gln Arg Asn Pro Gln
145 150 155 160

Leu Cys Tyr Gln Asp Thr Ile Leu Trp Lys Asp Ile Phe His Lys Asn
165 170 175

Asn Gln Leu Ala Leu Thr Leu Ile Asp Thr Asn Arg Ser Arg Ala Cys
180 185 190

His Pro Cys Ser Pro Met Cys Lys Gly Ser Arg Cys Trp Gly Glu Ser
195 200 205

Ser Glu Asp Cys Gln Ser Leu Thr Arg Thr Val Cys Ala Gly Gly Cys
210 215 220

Ala Arg Cys Lys Gly Pro Leu Pro Thr Asp Cys Cys His Glu Gln Cys
225 230 235 240

Ala Ala Gly Cys Thr Gly Pro Lys His Ser Asp Cys Leu Ala Cys Leu
245 250 255

His Phe Asn His Ser Gly Ile Cys Glu Leu His Cys Pro Ala Leu Val
260 265 270

Thr Tyr Asn Thr Asp Thr Phe Glu Ser Met Pro Asn Pro Glu Gly Arg
275 280 285

Tyr Thr Phe Gly Ala Ser Cys Val Thr Ala Cys Pro Tyr Asn Tyr Leu
290 295 300

Ser Thr Asp Val Gly Ser Cys Thr Leu Val Cys Pro Leu His Asn Gln
305 310 315 320

Glu Val Thr Ala Glu Asp Gly Thr Gln Arg Cys Glu Lys Cys Ser Lys
325 330 335

Pro Cys Ala Arg Val Cys Tyr Gly Leu Gly Met Glu His Leu Arg Glu
340 345 350

Val Arg Ala Val Thr Ser Ala Asn Ile Gln Glu Phe Ala Gly Cys Lys
355 360 365

Lys Ile Phe Gly Ser Leu Ala Phe Leu Pro Glu Ser Phe Asp Gly Asp

-continued

```
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800
```

```
Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200
```

-continued

```
Ala Pro  Gln Pro His Pro Pro  Pro Ala Phe Ser Pro  Ala Phe Asp
    1205                 1210                 1215

Asn Leu  Tyr Tyr Trp Asp Gln  Asp Pro Pro Glu Arg  Gly Ala Pro
    1220                 1225                 1230

Pro Ser  Thr Phe Lys Gly Thr  Pro Thr Ala Glu Asn  Pro Glu Tyr
    1235                 1240                 1245

Leu Gly  Leu Asp Val Pro Val
    1250                 1255


<210> SEQ ID NO 99
<211> LENGTH: 121
<212> TYPE: PRT
<213> ORGANISM: Artificial Sequence
<220> FEATURE:
<223> OTHER INFORMATION: Synthetic:  hu1D11.v1.5 heavy chain variable
      region

<400> SEQUENCE: 99

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 100
<211> LENGTH: 121
<212> TYPE: PRT
<213> ORGANISM: Artificial Sequence
<220> FEATURE:
<223> OTHER INFORMATION: Synthetic:  hu1D11.v1.4 heavy chain variable
      region

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110
```

```
Gln Gly Thr Leu Val Thr Val Ser Ser
        115                 120


<210> SEQ ID NO 101
<211> LENGTH: 121
<212> TYPE: PRT
<213> ORGANISM: Artificial Sequence
<220> FEATURE:
<223> OTHER INFORMATION: Synthetic:  hu1D11.v1, v2, v1.1, v1.2, v1.3
      heavy chain variable region

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 102
<211> LENGTH: 121
<212> TYPE: PRT
<213> ORGANISM: Artificial Sequence
<220> FEATURE:
<223> OTHER INFORMATION: Synthetic:  hu1D11.v3 heavy chain variable
      region

<400> SEQUENCE: 102

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Leu Thr Ala Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 103
<211> LENGTH: 121
<212> TYPE: PRT
<213> ORGANISM: Artificial Sequence
<220> FEATURE:
```

<223> OTHER INFORMATION: Synthetic: hu1D11.v4 heavy chain variable region

<400> SEQUENCE: 103

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Leu Thr Ala Asp Lys Ser Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120
```

<210> SEQ ID NO 104
<211> LENGTH: 106
<212> TYPE: PRT
<213> ORGANISM: Artificial Sequence
<220> FEATURE:
<223> OTHER INFORMATION: Synthetic: hu22C10.v1 light chain variable region

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105
```

<210> SEQ ID NO 105
<211> LENGTH: 106
<212> TYPE: PRT
<213> ORGANISM: Artificial Sequence
<220> FEATURE:
<223> OTHER INFORMATION: Synthetic: hu22C10.v2.1 light chain variable region

<400> SEQUENCE: 105

```
Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Leu Trp Ile Tyr
```

```
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105


<210> SEQ ID NO 106
<211> LENGTH: 106
<212> TYPE: PRT
<213> ORGANISM: Artificial Sequence
<220> FEATURE:
<223> OTHER INFORMATION: Synthetic:  hu22C10.v2.2 light chain variable
      region; hu22C10.v2.8 light chain variable region

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Leu Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys
            100                 105


<210> SEQ ID NO 107
<211> LENGTH: 116
<212> TYPE: PRT
<213> ORGANISM: Artificial Sequence
<220> FEATURE:
<223> OTHER INFORMATION: Synthetic:  hu22C10.v2.6 heavy chain variable
      region

<400> SEQUENCE: 107

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser
```

115

<210> SEQ ID NO 108
<211> LENGTH: 116
<212> TYPE: PRT
<213> ORGANISM: Artificial Sequence
<220> FEATURE:
<223> OTHER INFORMATION: Synthetic: hu22C10.v2.5 heavy chain variable region

<400> SEQUENCE: 108

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Leu Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 109
<211> LENGTH: 116
<212> TYPE: PRT
<213> ORGANISM: Artificial Sequence
<220> FEATURE:
<223> OTHER INFORMATION: Synthetic: hu22C10.v2.4 heavy chain variable region

<400> SEQUENCE: 109

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Ile Thr Val Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 110
<211> LENGTH: 116
<212> TYPE: PRT
<213> ORGANISM: Artificial Sequence
<220> FEATURE:
<223> OTHER INFORMATION: Synthetic: hu22C10.v2.3 heavy chain variable region

<400> SEQUENCE: 110

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Val Thr Leu Thr Val Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 111
<211> LENGTH: 116
<212> TYPE: PRT
<213> ORGANISM: Artificial Sequence
<220> FEATURE:
<223> OTHER INFORMATION: Synthetic: hu22C10.v1, v2, v2.1, v2.2 heavy chain variable region

<400> SEQUENCE: 111

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Leu Thr Val Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 112
<211> LENGTH: 116
<212> TYPE: PRT
<213> ORGANISM: Artificial Sequence
<220> FEATURE:
<223> OTHER INFORMATION: Synthetic: hu22C10.v3 heavy chain variable region

<400> SEQUENCE: 112

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Leu Thr Val Asp Lys Ser Thr Ser Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 113
<211> LENGTH: 116
<212> TYPE: PRT
<213> ORGANISM: Artificial Sequence
<220> FEATURE:
<223> OTHER INFORMATION: Synthetic: hu22C10.v4 heavy chain variable region

<400> SEQUENCE: 113

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Leu Thr Val Asp Lys Ser Thr Asn Thr Ala Tyr
65 70 75 80

Leu Glu Leu Ser Ser Leu Arg Ser Glu Asp Thr Ala Val Tyr Tyr Cys
85 90 95

Ser Arg Glu Ile Thr Thr Val Asp Tyr Trp Gly Gln Gly Thr Leu Val
100 105 110

Thr Val Ser Ser
115

<210> SEQ ID NO 114
<211> LENGTH: 116
<212> TYPE: PRT
<213> ORGANISM: Artificial Sequence
<220> FEATURE:
<223> OTHER INFORMATION: Synthetic: hu22C10.v5 heavy chain variable region

<400> SEQUENCE: 114

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Ala Thr Leu Thr Val Asp Lys Ser Ser Asn Thr Ala Tyr
65 70 75 80

```
Leu Glu Leu Ser Ser Leu Arg Ser Glu Asp Thr Ala Val Tyr Tyr Cys
                85                  90                  95

Ser Arg Glu Ile Thr Thr Val Asp Tyr Trp Gly Gln Gly Thr Leu Val
            100                 105                 110

Thr Val Ser Ser
        115


<210> SEQ ID NO 115
<211> LENGTH: 15
<212> TYPE: PRT
<213> ORGANISM: Artificial Sequence
<220> FEATURE:
<223> OTHER INFORMATION: Synthetic:  hu22C10.v2.1 LC FR2

<400> SEQUENCE: 115

Trp Tyr Gln Gln Lys Pro Gly Lys Ala Pro Lys Leu Trp Ile Tyr
1               5                   10                  15


<210> SEQ ID NO 116
<211> LENGTH: 15
<212> TYPE: PRT
<213> ORGANISM: Artificial Sequence
<220> FEATURE:
<223> OTHER INFORMATION: Synthetic:  hu22C10.v2.2 LC FR2

<400> SEQUENCE: 116

Trp Tyr Gln Gln Lys Pro Gly Lys Ala Pro Lys Gly Leu Ile Tyr
1               5                   10                  15


<210> SEQ ID NO 117
<211> LENGTH: 32
<212> TYPE: PRT
<213> ORGANISM: Artificial Sequence
<220> FEATURE:
<223> OTHER INFORMATION: Synthetic:  hu22C10.v1 LC FR3

<400> SEQUENCE: 117

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30


<210> SEQ ID NO 118
<211> LENGTH: 32
<212> TYPE: PRT
<213> ORGANISM: Artificial Sequence
<220> FEATURE:
<223> OTHER INFORMATION: Synthetic:  hu22C10.v2.6 HC FR3

<400> SEQUENCE: 118

Arg Ala Thr Leu Thr Val Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30


<210> SEQ ID NO 119
<211> LENGTH: 32
<212> TYPE: PRT
<213> ORGANISM: Artificial Sequence
<220> FEATURE:
<223> OTHER INFORMATION: Synthetic:  hu22C10.v2.5 HC FR3

<400> SEQUENCE: 119

Arg Ala Thr Leu Thr Arg Asp Thr Ser Thr Ser Thr Ala Tyr Leu Glu
```

1 5 10 15

Leu Ser Ser Leu Arg Ser Glu Asp Thr Ala Val Tyr Tyr Cys Ser Arg
20 25 30

<210> SEQ ID NO 120
<211> LENGTH: 32
<212> TYPE: PRT
<213> ORGANISM: Artificial Sequence
<220> FEATURE:
<223> OTHER INFORMATION: Synthetic: hu22C10.v2.4 HC FR3

<400> SEQUENCE: 120

Arg Ala Thr Ile Thr Val Asp Thr Ser Thr Ser Thr Ala Tyr Leu Glu
1 5 10 15

Leu Ser Ser Leu Arg Ser Glu Asp Thr Ala Val Tyr Tyr Cys Ser Arg
20 25 30

<210> SEQ ID NO 121
<211> LENGTH: 32
<212> TYPE: PRT
<213> ORGANISM: Artificial Sequence
<220> FEATURE:
<223> OTHER INFORMATION: Synthetic: hu22C10.v2.3 HC FR3

<400> SEQUENCE: 121

Arg Val Thr Leu Thr Val Asp Thr Ser Thr Ser Thr Ala Tyr Leu Glu
1 5 10 15

Leu Ser Ser Leu Arg Ser Glu Asp Thr Ala Val Tyr Tyr Cys Ser Arg
20 25 30

<210> SEQ ID NO 122
<211> LENGTH: 32
<212> TYPE: PRT
<213> ORGANISM: Artificial Sequence
<220> FEATURE:
<223> OTHER INFORMATION: Synthetic: hu22C10.v1, v2, v2.1, v2.2 HC FR3

<400> SEQUENCE: 122

Arg Ala Thr Leu Thr Val Asp Thr Ser Thr Ser Thr Ala Tyr Leu Glu
1 5 10 15

Leu Ser Ser Leu Arg Ser Glu Asp Thr Ala Val Tyr Tyr Cys Ser Arg
20 25 30

<210> SEQ ID NO 123
<211> LENGTH: 32
<212> TYPE: PRT
<213> ORGANISM: Artificial Sequence
<220> FEATURE:
<223> OTHER INFORMATION: Synthetic: hu22C10.v3 HC FR3

<400> SEQUENCE: 123

Arg Ala Thr Leu Thr Val Asp Lys Ser Thr Ser Thr Ala Tyr Leu Glu
1 5 10 15

Leu Ser Ser Leu Arg Ser Glu Asp Thr Ala Val Tyr Tyr Cys Ser Arg
20 25 30

<210> SEQ ID NO 124
<211> LENGTH: 32
<212> TYPE: PRT
<213> ORGANISM: Artificial Sequence
<220> FEATURE:
<223> OTHER INFORMATION: Synthetic: hu22C10.v4 HC FR3

<400> SEQUENCE: 124

```
Arg Ala Thr Leu Thr Val Asp Lys Ser Thr Asn Thr Ala Tyr Leu Glu
1               5                   10                  15

Leu Ser Ser Leu Arg Ser Glu Asp Thr Ala Val Tyr Tyr Cys Ser Arg
            20                  25                  30


<210> SEQ ID NO 125
<211> LENGTH: 32
<212> TYPE: PRT
<213> ORGANISM: Artificial Sequence
<220> FEATURE:
<223> OTHER INFORMATION: Synthetic:  hu22C10.v5 HC FR3

<400> SEQUENCE: 125

Arg Ala Thr Leu Thr Val Asp Lys Ser Ser Asn Thr Ala Tyr Leu Glu
1               5                   10                  15

Leu Ser Ser Leu Arg Ser Glu Asp Thr Ala Val Tyr Tyr Cys Ser Arg
            20                  25                  30


<210> SEQ ID NO 126
<211> LENGTH: 108
<212> TYPE: PRT
<213> ORGANISM: Artificial Sequence
<220> FEATURE:
<223> OTHER INFORMATION: Synthetic:  hu1D11.v1.9 varC2 and varD light
      chain variable region

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg
            100                 105


<210> SEQ ID NO 127
<211> LENGTH: 121
<212> TYPE: PRT
<213> ORGANISM: Artificial Sequence
<220> FEATURE:
<223> OTHER INFORMATION: Synthetic:  hu1D11.v1.9 varC2 heavy chain
      variable region

<400> SEQUENCE: 127

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80
```

```
Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 128
<211> LENGTH: 12
<212> TYPE: PRT
<213> ORGANISM: Artificial Sequence
<220> FEATURE:
<223> OTHER INFORMATION: Synthetic:  hu1D11.v1.9 varC2 HVR H3

<400> SEQUENCE: 128

Leu Ala Gly Ser Ser Tyr Arg Gly Ala Met Asp Ser
1               5                   10


<210> SEQ ID NO 129
<211> LENGTH: 9
<212> TYPE: PRT
<213> ORGANISM: Artificial Sequence
<220> FEATURE:
<223> OTHER INFORMATION: Synthetic:  hu1D11.v1.9 varC2 and varD HVR L3

<400> SEQUENCE: 129

Leu Gln Tyr Gly Asp Leu Leu Tyr Ala
1               5


<210> SEQ ID NO 130
<211> LENGTH: 451
<212> TYPE: PRT
<213> ORGANISM: Artificial Sequence
<220> FEATURE:
<223> OTHER INFORMATION: Synthetic:  hu1D11.v1.9 varC2 IgG1 heavy chain

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ser Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 131
<211> LENGTH: 451
<212> TYPE: PRT
<213> ORGANISM: Artificial Sequence
<220> FEATURE:
<223> OTHER INFORMATION: Synthetic: hu1D11.v1.9 varD IgG1 heavy chain

<400> SEQUENCE: 131

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Gly Trp Val Arg Gln Ala Pro Gly Gln Gly Leu Glu Trp Ile
35 40 45

Gly Asp Ile Tyr Pro Gly Gly Gly Tyr Thr Asn Tyr Asn Glu Lys Phe
50 55 60

Lys Gly Arg Val Thr Ile Thr Arg Asp Thr Ser Thr Ser Thr Ala Tyr
65 70 75 80

```
Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser Ser Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 132
<211> LENGTH: 451
<212> TYPE: PRT
<213> ORGANISM: Artificial Sequence
<220> FEATURE:
<223> OTHER INFORMATION: Synthetic: hu1D11.v1.9 varC2 IgG1 A118C heavy chain

<400> SEQUENCE: 132

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Gly Trp Val Arg Gln Ala Pro Gly Gln Gly Leu Glu Trp Ile
35 40 45

Gly Asp Ile Tyr Pro Gly Gly Gly Tyr Thr Asn Tyr Asn Glu Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Leu Ala Gly Ser Ser Tyr Arg Gly Ala Met Asp Ser Trp Gly
100 105 110

Gln Gly Thr Leu Val Thr Val Ser Ser Cys Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 133
<211> LENGTH: 451
<212> TYPE: PRT
<213> ORGANISM: Artificial Sequence
<220> FEATURE:
<223> OTHER INFORMATION: Synthetic:  hu1D11.v1.9 varD IgG1 A118C heavy
      chain

<400> SEQUENCE: 133

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser Cys Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 134
<211> LENGTH: 214
<212> TYPE: PRT
<213> ORGANISM: Artificial Sequence
<220> FEATURE:
<223> OTHER INFORMATION: Synthetic:  hu1D11.v1.9 varC2 and varD IgK
      light chain

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
        195                 200                 205

Phe Asn Arg Gly Glu Cys
    210


<210> SEQ ID NO 135
<211> LENGTH: 330
<212> TYPE: PRT
<213> ORGANISM: Artificial Sequence
<220> FEATURE:
<223> OTHER INFORMATION: Synthetic:  IgG1 S400C heavy chain constant
      region

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Cys Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 136
<211> LENGTH: 106
<212> TYPE: PRT
<213> ORGANISM: Artificial Sequence
<220> FEATURE:
<223> OTHER INFORMATION: Synthetic: IgK V205C light chain constant region

<400> SEQUENCE: 136

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105
```

<210> SEQ ID NO 137
<211> LENGTH: 446
<212> TYPE: PRT
<213> ORGANISM: Artificial Sequence
<220> FEATURE:
<223> OTHER INFORMATION: Synthetic: hu22C10.v2.7 IgG1 A118C heavy chain

<400> SEQUENCE: 137

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Cys Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 138
<211> LENGTH: 213
<212> TYPE: PRT
<213> ORGANISM: Artificial Sequence
<220> FEATURE:
<223> OTHER INFORMATION: Synthetic:  hu22C10.v2.7 IgK light chain

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Ser Ala Thr Ser Ser Ile Ser Tyr Met
            20                  25                  30

His Trp Tyr Gln Gln Lys Pro Gly Lys Ala Pro Lys Gly Trp Ile Tyr
        35                  40                  45

Asp Thr Ser Lys Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
```

```
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 139
<211> LENGTH: 106
<212> TYPE: PRT
<213> ORGANISM: Artificial Sequence
<220> FEATURE:
<223> OTHER INFORMATION: Synthetic:  IgK K149C light chain constant
      region

<400> SEQUENCE: 139

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Cys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 140
<211> LENGTH: 233
<212> TYPE: PRT
<213> ORGANISM: Artificial Sequence
<220> FEATURE:
<223> OTHER INFORMATION: Synthetic:  hu1D11.v1.9 varC2 and varD IgK
      K149C light chain precursor

<400> SEQUENCE: 140

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Gly Phe
        35                  40                  45

Asn Lys Tyr Val Ala Trp Tyr Gln Gln Lys Pro Gly Lys Ala Pro Lys
    50                  55                  60

Leu Leu Ile Tyr Tyr Thr Ser Thr Leu Gln Pro Gly Val Pro Ser Arg
65                  70                  75                  80

Phe Ser Gly Ser Gly Ser Gly Arg Asp Tyr Thr Leu Thr Ile Ser Ser
```

```
                85                  90                  95

Leu Gln Pro Glu Asp Phe Ala Thr Tyr Tyr Cys Leu Gln Tyr Gly Asp
            100                 105                 110

Leu Leu Tyr Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Cys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 141
<211> LENGTH: 233
<212> TYPE: PRT
<213> ORGANISM: Artificial Sequence
<220> FEATURE:
<223> OTHER INFORMATION: Synthetic:  hu1D11.v1.9 varC2 and varD IgK
      V205C light chain precursor

<400> SEQUENCE: 141

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Lys Ala Ser Gln Gly Phe
        35                  40                  45

Asn Lys Tyr Val Ala Trp Tyr Gln Gln Lys Pro Gly Lys Ala Pro Lys
    50                  55                  60

Leu Leu Ile Tyr Tyr Thr Ser Thr Leu Gln Pro Gly Val Pro Ser Arg
65                  70                  75                  80

Phe Ser Gly Ser Gly Ser Gly Arg Asp Tyr Thr Leu Thr Ile Ser Ser
                85                  90                  95

Leu Gln Pro Glu Asp Phe Ala Thr Tyr Tyr Cys Leu Gln Tyr Gly Asp
            100                 105                 110

Leu Leu Tyr Ala Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205
```

-continued

```
Lys Val Tyr Ala Cys Glu Val Thr His Gln Gly Leu Ser Ser Pro Cys
    210                 215                 220

Thr Lys Ser Phe Asn Arg Gly Glu Cys
225                 230


<210> SEQ ID NO 142
<211> LENGTH: 232
<212> TYPE: PRT
<213> ORGANISM: Artificial Sequence
<220> FEATURE:
<223> OTHER INFORMATION: Synthetic:  hu22C10.v2.7 IgK K149C light chain
      precursor

<400> SEQUENCE: 142

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Thr Ser Ser Ile
        35                  40                  45

Ser Tyr Met His Trp Tyr Gln Gln Lys Pro Gly Lys Ala Pro Lys Gly
    50                  55                  60

Trp Ile Tyr Asp Thr Ser Lys Leu Ala His Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys His Gln Arg Arg Ser Tyr
            100                 105                 110

Pro Phe Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Cys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 143
<211> LENGTH: 232
<212> TYPE: PRT
<213> ORGANISM: Artificial Sequence
<220> FEATURE:
<223> OTHER INFORMATION: Synthetic:  hu22C10.v2.7 IgK V205C light chain
      precursor

<400> SEQUENCE: 143

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30
```

```
Ser Val Gly Asp Arg Val Thr Ile Thr Cys Ser Ala Thr Ser Ser Ile
        35                  40                  45

Ser Tyr Met His Trp Tyr Gln Gln Lys Pro Gly Lys Ala Pro Lys Gly
    50                  55                  60

Trp Ile Tyr Asp Thr Ser Lys Leu Ala His Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys His Gln Arg Arg Ser Tyr
            100                 105                 110

Pro Phe Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Cys Thr
    210                 215                 220

Lys Ser Phe Asn Arg Gly Glu Cys
225                 230


<210> SEQ ID NO 144
<211> LENGTH: 446
<212> TYPE: PRT
<213> ORGANISM: Artificial Sequence
<220> FEATURE:
<223> OTHER INFORMATION: Synthetic:  hu22C10.v2.7 IgG1 heavy chain

<400> SEQUENCE: 144

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ser Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 145
<211> LENGTH: 214
<212> TYPE: PRT
<213> ORGANISM: Artificial Sequence
<220> FEATURE:
<223> OTHER INFORMATION: Synthetic:  hu1D11.v1.9 varC2 and varD IgK
      K149C light chain

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80
```

```
Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 146
<211> LENGTH: 214
<212> TYPE: PRT
<213> ORGANISM: Artificial Sequence
<220> FEATURE:
<223> OTHER INFORMATION: Synthetic:  hu1D11.v1.9 varC2 and varD IgK
      V205C light chain

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Leu Tyr
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
```

210

<210> SEQ ID NO 147
<211> LENGTH: 213
<212> TYPE: PRT
<213> ORGANISM: Artificial Sequence
<220> FEATURE:
<223> OTHER INFORMATION: Synthetic: hu22C10.v2.7 IgK K149C light chain

<400> SEQUENCE: 147

Asp Ile Gln Met Thr Gln Ser Pro Ser Ser Leu Ser Ala Ser Val Gly
1 5 10 15

Asp Arg Val Thr Ile Thr Cys Ser Ala Thr Ser Ser Ile Ser Tyr Met
20 25 30

His Trp Tyr Gln Gln Lys Pro Gly Lys Ala Pro Lys Gly Trp Ile Tyr
35 40 45

Asp Thr Ser Lys Leu Ala His Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys His Gln Arg Arg Ser Tyr Pro Phe Thr
85 90 95

Phe Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Cys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 148
<211> LENGTH: 213
<212> TYPE: PRT
<213> ORGANISM: Artificial Sequence
<220> FEATURE:
<223> OTHER INFORMATION: Synthetic: hu22C10.v2.7 IgK V205C light chain

<400> SEQUENCE: 148

Asp Ile Gln Met Thr Gln Ser Pro Ser Ser Leu Ser Ala Ser Val Gly
1 5 10 15

Asp Arg Val Thr Ile Thr Cys Ser Ala Thr Ser Ser Ile Ser Tyr Met
20 25 30

His Trp Tyr Gln Gln Lys Pro Gly Lys Ala Pro Lys Gly Trp Ile Tyr
35 40 45

Asp Thr Ser Lys Leu Ala His Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

```
Asp Phe Ala Thr Tyr Tyr Cys His Gln Arg Arg Ser Tyr Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Cys Thr Lys Ser Phe
        195                 200                 205

Asn Arg Gly Glu Cys
    210


<210> SEQ ID NO 149
<211> LENGTH: 459
<212> TYPE: PRT
<213> ORGANISM: Artificial Sequence
<220> FEATURE:
<223> OTHER INFORMATION: Synthetic:  hu1D11.v1.9 varD heavy chain knob
      pHIS

<400> SEQUENCE: 149

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly His His His His His His
    450                 455


<210> SEQ ID NO 150
<211> LENGTH: 1380
<212> TYPE: DNA
<213> ORGANISM: Artificial Sequence
<220> FEATURE:
<223> OTHER INFORMATION: Synthetic: Exemplary hu1D11.v1.9 varD heavy
      chain knob pHIS coding sequence

<400> SEQUENCE: 150

gaggttcagc tggtgcagtc tggcgccgaa gtgaaaaaac caggggcctc agtgaaagtg     60

tcctgtaaag cttctggata caccttcact agctactgga taggttgggt gcgtcaggcc    120

ccgggtcagg gcctggaatg gatcggcgat atttaccctg gaggtggtta tactaactac    180

aatgagaagt tcaagggccg tgttactatc acccgtgaca cctccaccag cacagcctac    240

ctagaactga gcagcttaag aagcgaggac actgccgtct attattgcgc gcgtctcgct    300

ggtagtagtt acagaggggc tatggactcc tggggtcaag gaaccctggt caccgtctcc    360

tcggcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg actgtgccct ctagcagctt gggcacccag    600

acctacatct gcaacgtgaa tcacaagccc agcaacacca aggtggacaa gaaagttgag    660
```

```
cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggaa   1080

gagatgacca agaaccaggt cagcctgtgg tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt ggcggtggac atcatcacca tcaccactga   1380


<210> SEQ ID NO 151
<211> LENGTH: 461
<212> TYPE: PRT
<213> ORGANISM: Artificial Sequence
<220> FEATURE:
<223> OTHER INFORMATION: Synthetic:  hu1D11.v1.9 varD heavy chain hole
      FLAG

<400> SEQUENCE: 151

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Asp Tyr Lys Asp Asp Asp Asp Lys
    450                 455                 460
```

<210> SEQ ID NO 152
<211> LENGTH: 1386
<212> TYPE: DNA
<213> ORGANISM: Artificial Sequence
<220> FEATURE:
<223> OTHER INFORMATION: Synthetic: Exemplary hu1D11.v1.9 varD heavy chain hole FLAG coding sequence

<400> SEQUENCE: 152

```
gaggttcagc tggtgcagtc tggcgccgaa gtgaaaaaac caggggcctc agtgaaagtg     60

tcctgtaaag cttctggata caccttcact agctactgga taggttgggt gcgtcaggcc    120

ccgggtcagg gcctggaatg gatcggcgat atttaccctg gaggtggtta tactaactac    180

aatgagaagt tcaagggccg tgttactatc acccgtgaca cctccaccag cacagcctac    240

ctagaactga gcagcttaag aagcgaggac actgccgtct attattgcgc gcgtctcgct    300

ggtagtagtt acagaggggc tatggactcc tggggtcaag gaaccctggt caccgtctcc    360

tcggcctcca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg actgtgccct ctagcagctt gggcacccag    600

acctacatct gcaacgtgaa tcacaagccc agcaacacca aggtggacaa gaaagttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780
```

```
cctgaggtca catgcgtggt ggtggacgtg agccacgaag accctgaggt caagttcaac     840

tggtacgtgg acggcgtgga ggtgcataat gccaagacaa agccgcggga ggagcagtac     900

aacagcacgt accgtgtggt cagcgtcctc accgtcctgc accaggactg gctgaatggc     960

aaggagtaca agtgcaaggt ctccaacaaa gccctcccag cccccatcga gaaaaccatc    1020

tccaaagcca aagggcagcc ccgagaacca caggtgtaca ccctgccccc atcccgggaa    1080

gagatgacca agaaccaggt cagcctgagc tgcgcggtca aaggcttcta tcccagcgac    1140

atcgccgtgg agtgggagag caatgggcag ccggagaaca actacaagac cacgcctccc    1200

gtgctggact ccgacggctc cttcttcctc gtcagcaagc tcaccgtgga caagagcagg    1260

tggcagcagg ggaacgtctt ctcatgctcc gtgatgcatg aggctctgca caaccactac    1320

acgcagaaga gcctctccct gtctccgggt ggcggtggcg attataagga cgatgacgat    1380

aaatga                                                               1386
```

<210> SEQ ID NO 153
<211> LENGTH: 645
<212> TYPE: DNA
<213> ORGANISM: Artificial Sequence
<220> FEATURE:
<223> OTHER INFORMATION: Synthetic: Exemplary hu1D11.v1.9 varD Igk K149C light chain coding sequence

<400> SEQUENCE: 153

```
gatatccaga tgacccagtc cccgagctcc ctgtccgcct ctgtgggcga tagggtcacc      60

atcacctgca aggcaagcca aggctttaac aagtatgtag cttggtatca acagaaacca     120

ggaaaagctc cgaagcttct gatttactat acatctacat tacagccagg agtcccttct     180

cgcttctctg gtagcggttc cgggagagat tatactctga ccatcagcag tctgcagccg     240

gaagacttcg caacttatta ctgtctacag tatggtgacc ttctgtacgc gttcggacag     300

ggtaccaagg tggagatcaa acgaactgtg gctgcaccat ctgtcttcat cttcccgcca     360

tctgatgagc agttgaaatc tggaactgcc tctgttgtgt gcctgctgaa taacttctat     420

cccagagagg ccaaagtaca gtggtgcgtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gttaa                     645
```

<210> SEQ ID NO 154
<211> LENGTH: 454
<212> TYPE: PRT
<213> ORGANISM: Artificial Sequence
<220> FEATURE:
<223> OTHER INFORMATION: Synthetic: hu22C10.v2.7 heavy chain knob pHIS

<400> SEQUENCE: 154

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
```

-continued

```
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

His His His His His His
    450
```

<210> SEQ ID NO 155
<211> LENGTH: 1365
<212> TYPE: DNA
<213> ORGANISM: Artificial Sequence
<220> FEATURE:
<223> OTHER INFORMATION: Synthetic: Exemplary hu22C10.v2.7 heavy chain knob pHIS coding sequence

<400> SEQUENCE: 155

```
gaggttcagc tggtgcagtc tggcgccgaa gtgaaaaaac caggggcctc agtgaaagtg     60

tcctgtaaag cttctggcta cacgttcacc aacttctgga tacactgggt gcgtcaggcc    120

ccgggtcagg gcctggaatg gatcggcgag attgatcctt ctgatagtta tactaactac    180

aatcaaaagt tcaagggccg tgttactatc acccgtgaca cctccaccag cacagcctac    240

ctagaactga gcagcttaag aagcgaggac actgccgtct attattgcgc tagagagatt    300

actacggtgg actactgggg tcaaggaacc ctggtcaccg tctcctcggc ctccaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgactgt gccctctagc agcttgggca cccagaccta catctgcaac    600

gtgaatcaca agcccagcaa caccaaggtg gacaagaaag ttgagcccaa atcttgtgac    660

aaaactcaca catgcccacc gtgcccagca cctgaactcc tggggggacc gtcagtcttc    720

ctcttccccc caaaacccaa ggacaccctc atgatctccc ggacccctga ggtcacatgc    780

gtggtggtgg acgtgagcca cgaagaccct gaggtcaagt tcaactggta cgtggacggc    840

gtggaggtgc ataatgccaa gacaaagccg cgggaggagc agtacaacag cacgtaccgt    900

gtggtcagcg tcctcaccgt cctgcaccag gactggctga atggcaagga gtacaagtgc    960

aaggtctcca acaaagccct cccagccccc atcgagaaaa ccatctccaa agccaaaggg   1020

cagccccgag aaccacaggt gtacaccctg cccccatccc gggaagagat gaccaagaac   1080

caggtcagcc tgtggtgcct ggtcaaaggc ttctatccca gcgacatcgc cgtggagtgg   1140

gagagcaatg ggcagccgga gaacaactac aagaccacgc ctcccgtgct ggactccgac   1200

ggctccttct tcctctacag caagctcacc gtggacaaga gcaggtggca gcaggggaac   1260

gtcttctcat gctccgtgat gcatgaggct ctgcacaacc actacacgca gaagagcctc   1320

tccctgtctc cgggtggcgg tggacatcat caccatcacc actga                   1365
```

<210> SEQ ID NO 156
<211> LENGTH: 456
<212> TYPE: PRT
<213> ORGANISM: Artificial Sequence
<220> FEATURE:
<223> OTHER INFORMATION: Synthetic: hu22C10.v2.7 heavy chain hole FLAG

<400> SEQUENCE: 156

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Asp Tyr Lys Asp Asp Asp Asp Lys
    450                 455
```

<210> SEQ ID NO 157
<211> LENGTH: 1371
<212> TYPE: DNA
<213> ORGANISM: Artificial Sequence
<220> FEATURE:
<223> OTHER INFORMATION: Synthetic: Exemplary hu22C10.v2.7 heavy chain
hole FLAG coding sequence

<400> SEQUENCE: 157
gaggttcagc tggtgcagtc tggcgccgaa gtgaaaaaac caggggcctc agtgaaagtg 60
tcctgtaaag cttctggcta cacgttcacc aacttctgga tacactgggt gcgtcaggcc 120
ccgggtcagg gcctggaatg gatcggcgag attgatcctt ctgatagtta tactaactac 180
aatcaaaagt tcaagggccg tgttactatc acccgtgaca cctccaccag cacagcctac 240
ctagaactga gcagcttaag aagcgaggac actgccgtct attattgcgc tagagagatt 300
actacggtgg actactgggg tcaaggaacc ctggtcaccg tctcctcggc ctccaccaag 360
ggcccatcgg tcttcccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgactgt gccctctagc agcttgggca cccagaccta catctgcaac 600
gtgaatcaca agcccagcaa caccaaggtg gacaagaaag ttgagcccaa atcttgtgac 660
aaaactcaca catgcccacc gtgcccagca cctgaactcc tggggggacc gtcagtcttc 720
ctcttccccc caaaacccaa ggacaccctc atgatctccc ggacccctga ggtcacatgc 780
gtggtggtgg acgtgagcca cgaagaccct gaggtcaagt tcaactggta cgtggacggc 840
gtggaggtgc ataatgccaa gacaaagccg cgggaggagc agtacaacag cacgtaccgt 900
gtggtcagcg tcctcaccgt cctgcaccag gactggctga atggcaagga gtacaagtgc 960
aaggtctcca acaaagccct cccagccccc atcgagaaaa ccatctccaa agccaaaggg 1020
cagccccgag aaccacaggt gtacaccctg cccccatccc gggaagagat gaccaagaac 1080
caggtcagcc tgagctgcgc ggtcaaaggc ttctatccca gcgacatcgc cgtggagtgg 1140
gagagcaatg ggcagccgga gaacaactac aagaccacgc ctcccgtgct ggactccgac 1200
ggctccttct tcctcgtcag caagctcacc gtggacaaga gcaggtggca gcaggggaac 1260
gtcttctcat gctccgtgat gcatgaggct ctgcacaacc actacacgca gaagagcctc 1320
tccctgtctc cgggtggcgg tggcgattat aaggacgatg acgataaatg a 1371

<210> SEQ ID NO 158
<211> LENGTH: 642
<212> TYPE: DNA
<213> ORGANISM: Artificial Sequence
<220> FEATURE:
<223> OTHER INFORMATION: Synthetic: Exemplary hu22C10.v2.7 Igk K149C light chain coding sequence

<400> SEQUENCE: 158
gatatccaga tgacccagtc cccgagctcc ctgtccgcct ctgtgggcga tagggtcacc 60
atcacctgca gtgccacttc aagtataagt tacatgcact ggtatcaaca gaaaccagga 120
aaagctccga agggatggat ttatgacaca tccaaactgg ctcatggagt cccttctcgc 180
ttctctggta gcggttccgg gacggatttc actctgacca tcagcagtct gcagccggaa 240
gacttcgcaa cttattactg tcatcagcgg agaagttacc cattcacgtt cggacagggt 300
accaaggtgg agatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gtgcgtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgtt aa 642

<210> SEQ ID NO 159
<211> LENGTH: 451
<212> TYPE: PRT
<213> ORGANISM: Artificial Sequence
<220> FEATURE:
<223> OTHER INFORMATION: Synthetic: hu1D11.v1.9 varD heavy chain knob

<400> SEQUENCE: 159

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Gly Trp Val Arg Gln Ala Pro Gly Gln Gly Leu Glu Trp Ile
35 40 45

Gly Asp Ile Tyr Pro Gly Gly Gly Tyr Thr Asn Tyr Asn Glu Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Leu Ala Gly Ser Ser Tyr Arg Gly Ala Met Asp Ser Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser

```
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 160
<211> LENGTH: 451
<212> TYPE: PRT
<213> ORGANISM: Artificial Sequence
<220> FEATURE:
<223> OTHER INFORMATION: Synthetic:  hu1D11.v1.9 varD heavy chain hole

<400> SEQUENCE: 160

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 161
<211> LENGTH: 446
<212> TYPE: PRT
<213> ORGANISM: Artificial Sequence
<220> FEATURE:
<223> OTHER INFORMATION: Synthetic:  hu22C10.v2.7 heavy chain knob

<400> SEQUENCE: 161

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 162
<211> LENGTH: 446
<212> TYPE: PRT
<213> ORGANISM: Artificial Sequence
<220> FEATURE:
<223> OTHER INFORMATION: Synthetic:  hu22C10.v2.7 heavy chain hole

<400> SEQUENCE: 162

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
```

-continued

```
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 163
<211> LENGTH: 450
<212> TYPE: PRT
<213> ORGANISM: Artificial Sequence
<220> FEATURE:
<223> OTHER INFORMATION: Synthetic:  hu1D11.v1.9 varD heavy chain knob

<400> SEQUENCE: 163

Glu Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Ala Gly Ser Ser Tyr Arg Gly Ala Met Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
435 440 445

Pro Gly
450

<210> SEQ ID NO 164
<211> LENGTH: 450
<212> TYPE: PRT
<213> ORGANISM: Artificial Sequence
<220> FEATURE:
<223> OTHER INFORMATION: Synthetic: hu1D11.v1.9 varD heavy chain hole

<400> SEQUENCE: 164

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Gly Trp Val Arg Gln Ala Pro Gly Gln Gly Leu Glu Trp Ile
35 40 45

Gly Asp Ile Tyr Pro Gly Gly Gly Tyr Thr Asn Tyr Asn Glu Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Leu Ala Gly Ser Ser Tyr Arg Gly Ala Met Asp Ser Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys
210 215 220

Asp Lys Thr His Thr Cys Pro Pro Cys Pro Ala Pro Glu Leu Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Glu Glu Met Thr Lys Asn Gln Val Ser
355 360 365

Leu Ser Cys Ala Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Val Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 165
<211> LENGTH: 445
<212> TYPE: PRT
<213> ORGANISM: Artificial Sequence
<220> FEATURE:
<223> OTHER INFORMATION: Synthetic: hu22C10.v2.7 heavy chain knob

<400> SEQUENCE: 165

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Glu Ile Thr Thr Val Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 166
<211> LENGTH: 445
<212> TYPE: PRT
<213> ORGANISM: Artificial Sequence
<220> FEATURE:
<223> OTHER INFORMATION: Synthetic:  hu22C10.v2.7 heavy chain hole

<400> SEQUENCE: 166

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Phe
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Glu Ile Thr Thr Val Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 167
<211> LENGTH: 12
<212> TYPE: PRT
<213> ORGANISM: Mouse
<220> FEATURE:
<221> NAME/KEY: misc_feature
<222> LOCATION: (1)..(12)
<223> OTHER INFORMATION: mu1D11 HVR H3

<400> SEQUENCE: 167

```
Leu Asp Gly Ser Ser Tyr Arg Gly Ala Met Asp Ser
1               5                   10
```

<210> SEQ ID NO 168
<211> LENGTH: 11
<212> TYPE: PRT
<213> ORGANISM: Mouse
<220> FEATURE:
<221> NAME/KEY: misc_feature
<222> LOCATION: (1)..(11)
<223> OTHER INFORMATION: mu1D11 HVR L1

<400> SEQUENCE: 168

Lys Ala Ser Gln Gly Phe Asn Lys Tyr Val Ala
1 5 10

<210> SEQ ID NO 169
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu1D11 HVR L2

<400> SEQUENCE: 169

Tyr Thr Ser Thr Leu Gln Pro
1 5

<210> SEQ ID NO 170
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu1D11 HVR L3

<400> SEQUENCE: 170

Leu Gln Tyr Gly Asn Leu Leu Tyr Ala
1 5

<210> SEQ ID NO 171
<211> LENGTH: 113
<212> TYPE: PRT
<213> ORGANISM: Mouse
<220> FEATURE:
<221> NAME/KEY: misc_feature
<222> LOCATION: (1)..(113)
<223> OTHER INFORMATION: mu32D6 light chain variable region

<400> SEQUENCE: 171

Asp Ile Val Met Thr Gln Ser Pro Ser Ser Leu Ile Val Thr Ala Gly
1 5 10 15

Glu Lys Val Thr Met Ser Cys Arg Ser Ser Gln Ser Leu Phe Asp Ser
20 25 30

Gly Ser Gln Arg Asn Tyr Leu Thr Trp Phe His Gln Lys Pro Gly Arg
35 40 45

Pro Pro Lys Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Thr Glu Asp Leu Ala Val Tyr Phe Cys Gln Asn
85 90 95

Asp Tyr Ser Phe Pro Phe Thr Phe Gly Ser Gly Thr Lys Leu Glu Glu
100 105 110

Lys

<210> SEQ ID NO 172
<211> LENGTH: 120
<212> TYPE: PRT
<213> ORGANISM: Mouse
<220> FEATURE:
<221> NAME/KEY: misc_feature
<222> LOCATION: (1)..(120)

<223> OTHER INFORMATION: mu32D6 heavy chain variable region

<400> SEQUENCE: 172

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Ile His Trp Met Lys Gln Ser His Gly Lys Ser Leu Glu Trp Ile
        35                  40                  45

Gly Arg Val Asn Pro Asn Asn Gly Asp Pro Ile Tyr Asn Gln Lys Phe
    50                  55                  60

Arg Gly Lys Ala Ile Leu Thr Val Asp Gln Ser Ser Asn Thr Ala Tyr
65                  70                  75                  80

Met Glu Leu Arg Ser Leu Thr Ser Glu Ala Ser Ala Val Tyr Tyr Cys
                85                  90                  95

Ala Arg Val Leu Phe Tyr Tyr Gly Ser Pro Phe Ala Tyr Trp Gly Gln
            100                 105                 110

Gly Thr Leu Val Thr Val Ser Ala
        115                 120

<210> SEQ ID NO 173
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu32D6 HVR H1

<400> SEQUENCE: 173

Gly Tyr Ser Phe Thr Gly Tyr Tyr Ile His
1               5                   10

<210> SEQ ID NO 174
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu32D6 HVR H2

<400> SEQUENCE: 174

Arg Val Asn Pro Asn Asn Gly Asp Pro Ile Tyr Asn Gln Lys Phe Arg
1               5                   10                  15

Gly

<210> SEQ ID NO 175
<211> LENGTH: 11
<212> TYPE: PRT
<213> ORGANISM: Mouse
<220> FEATURE:
<221> NAME/KEY: misc_feature
<222> LOCATION: (1)..(11)
<223> OTHER INFORMATION: mu32D6 HVR H3

<400> SEQUENCE: 175

Val Leu Phe Tyr Tyr Gly Ser Pro Phe Ala Tyr
1               5                   10

<210> SEQ ID NO 176
<211> LENGTH: 17
<212> TYPE: PRT

<213> ORGANISM: Mouse
<220> FEATURE:
<221> NAME/KEY: misc_feature
<222> LOCATION: (1)..(17)
<223> OTHER INFORMATION: mu32D6 HVR L1

<400> SEQUENCE: 176

Arg Ser Ser Gln Ser Leu Phe Asp Ser Gly Ser Gln Arg Asn Tyr Leu
1 5 10 15

Thr

<210> SEQ ID NO 177
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu32D6 HVR L2

<400> SEQUENCE: 177

Trp Ala Ser Thr Arg Glu Ser
1 5

<210> SEQ ID NO 178
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu32D6 HVR L3

<400> SEQUENCE: 178

Gln Asn Asp Tyr Ser Phe Pro Phe Thr
1 5

<210> SEQ ID NO 179
<211> LENGTH: 107
<212> TYPE: PRT
<213> ORGANISM: Mouse
<220> FEATURE:
<221> NAME/KEY: misc_feature
<222> LOCATION: (1)..(107)
<223> OTHER INFORMATION: mu9B9 light chain variable region

<400> SEQUENCE: 179

Gln Ala Val Val Thr Gln Glu Ser Ala Leu Thr Thr Ser Pro Gly Asp
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Thr Asn Asn Arg Val Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Met Tyr Phe Cys Ala Leu Trp Tyr Asn Asn
85 90 95

His Trp Val Phe Gly Gly Gly Thr Lys Leu Glu
100 105

<210> SEQ ID NO 180
<211> LENGTH: 121

<212> TYPE: PRT
<213> ORGANISM: Mouse
<220> FEATURE:
<221> NAME/KEY: misc_feature
<222> LOCATION: (1)..(121)
<223> OTHER INFORMATION: mu9B9 heavy chain variable region

<400> SEQUENCE: 180

Gln Val Gln Leu Gln Gln Ser Gly Ala Glu Leu Met Lys Pro Gly Ala
1 5 10 15

Ser Val Lys Met Ser Cys Lys Ala Thr Gly Tyr Thr Phe Ser Ser Tyr
20 25 30

Trp Ile Glu Trp Val Lys Gln Arg Pro Gly His Gly Leu Glu Trp Ile
35 40 45

Gly Glu Ile Leu Pro Gly Thr Ser Ile Thr Thr Tyr Asn Ala Lys Phe
50 55 60

Lys Val Lys Ala Thr Phe Thr Ala Asp Thr Ser Ser Asn Thr Ala Tyr
65 70 75 80

Met Gln Leu Ser Ser Leu Thr Ser Glu Asp Ser Ala Val Tyr Phe Cys
85 90 95

Ala Arg Tyr Tyr Phe Gly Ser Ser Ser Phe Tyr Phe Asp Tyr Trp Gly
100 105 110

Gln Gly Thr Ser Leu Thr Val Ser Ser
115 120

<210> SEQ ID NO 181
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu9B9 HVR H1

<400> SEQUENCE: 181

Gly Tyr Thr Phe Ser Ser Tyr Trp Ile Glu
1 5 10

<210> SEQ ID NO 182
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu9B9 HVR H2

<400> SEQUENCE: 182

Glu Ile Leu Pro Gly Thr Ser Ile Thr Thr Tyr Asn Ala Lys Phe Lys
1 5 10 15

Val

<210> SEQ ID NO 183
<211> LENGTH: 14
<212> TYPE: PRT
<213> ORGANISM: Mouse
<220> FEATURE:
<221> NAME/KEY: misc_feature
<222> LOCATION: (1)..(14)
<223> OTHER INFORMATION: mu9B9 HVR H3

<400> SEQUENCE: 183

Ala Arg Tyr Tyr Phe Gly Ser Ser Ser Phe Tyr Phe Asp Tyr
1 5 10

<210> SEQ ID NO 184
<211> LENGTH: 14
<212> TYPE: PRT
<213> ORGANISM: Mouse
<220> FEATURE:
<221> NAME/KEY: misc_feature
<222> LOCATION: (1)..(14)
<223> OTHER INFORMATION: mu9B9 HVR L1

<400> SEQUENCE: 184

```
Arg Ser Ser Thr Gly Ala Val Thr Thr Ser Asn Tyr Ala Asn
1               5                   10
```

<210> SEQ ID NO 185
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu9B9 HVR L2

<400> SEQUENCE: 185

```
Gly Thr Asn Asn Arg Val Pro
1               5
```

<210> SEQ ID NO 186
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu9B9 HVR L3

<400> SEQUENCE: 186

```
Ala Leu Trp Tyr Asn Asn His Trp Val
1               5
```

<210> SEQ ID NO 187
<211> LENGTH: 106
<212> TYPE: PRT
<213> ORGANISM: Mouse
<220> FEATURE:
<221> NAME/KEY: misc_feature
<222> LOCATION: (1)..(106)
<223> OTHER INFORMATION: mu22C10 light chain variable region

<400> SEQUENCE: 187

```
Gln Ile Val Leu Thr Gln Ser Pro Thr Ile Met Ser Ala Ser Pro Gly
1               5                   10                  15

Glu Lys Val Thr Leu Thr Cys Ser Ala Thr Ser Ser Ile Ser Tyr Met
            20                  25                  30

His Trp Tyr Gln Gln Lys Pro Gly Thr Ser Pro Lys Gly Trp Ile Tyr
        35                  40                  45

Asp Thr Ser Lys Leu Ala His Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Arg Ser Tyr Pro Phe Thr
                85                  90                  95

Phe Gly Ser Gly Thr Lys Leu Glu Ile Lys
            100                 105
```

<210> SEQ ID NO 188
<211> LENGTH: 116
<212> TYPE: PRT
<213> ORGANISM: Mouse
<220> FEATURE:
<221> NAME/KEY: misc_feature
<222> LOCATION: (1)..(116)
<223> OTHER INFORMATION: mu22C10 heavy chain variable region

<400> SEQUENCE: 188

```
Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Asn Phe
            20                  25                  30

Trp Ile His Trp Val Ile Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ser Arg Glu Ile Thr Thr Val Asp Tyr Trp Gly Gln Gly Thr Thr Leu
            100                 105                 110

Thr Val Ser Ser
        115
```

<210> SEQ ID NO 189
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu22C10 HVR H1

<400> SEQUENCE: 189

```
Gly Tyr Thr Phe Thr Asn Phe Trp Ile His
1               5                   10
```

<210> SEQ ID NO 190
<211> LENGTH: 17
<212> TYPE: PRT
<213> ORGANISM: Mouse
<220> FEATURE:
<221> NAME/KEY: misc_feature
<222> LOCATION: (1)..(17)
<223> OTHER INFORMATION: mu22C10 HVR H2

<400> SEQUENCE: 190

```
Glu Ile Asp Pro Ser Asp Ser Tyr Thr Asn Tyr Asn Gln Lys Phe Lys
1               5                   10                  15

Gly
```

<210> SEQ ID NO 191
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu22C10 HVR H3

<400> SEQUENCE: 191

Glu Ile Thr Thr Val Asp Tyr
1 5

<210> SEQ ID NO 192
<211> LENGTH: 10
<212> TYPE: PRT
<213> ORGANISM: Mouse
<220> FEATURE:
<221> NAME/KEY: misc_feature
<222> LOCATION: (1)..(10)
<223> OTHER INFORMATION: mu22C10 HVR L1

<400> SEQUENCE: 192

Ser Ala Thr Ser Ser Ile Ser Tyr Met His
1 5 10

<210> SEQ ID NO 193
<211> LENGTH: 7
<212> TYPE: PRT
<213> ORGANISM: Mouse
<220> FEATURE:
<221> NAME/KEY: misc_feature
<222> LOCATION: (1)..(7)
<223> OTHER INFORMATION: mu22C10 HVR L2

<400> SEQUENCE: 193

Asp Thr Ser Lys Leu Ala His
1 5

<210> SEQ ID NO 194
<211> LENGTH: 9
<212> TYPE: PRT
<213> ORGANISM: Mouse
<220> FEATURE:
<221> NAME/KEY: misc_feature
<222> LOCATION: (1)..(9)
<223> OTHER INFORMATION: mu22C10 HVR L3

<400> SEQUENCE: 194

His Gln Arg Arg Ser Tyr Pro Phe Thr
1 5

<210> SEQ ID NO 195
<211> LENGTH: 108
<212> TYPE: PRT
<213> ORGANISM: Artificial Sequence
<220> FEATURE:
<223> OTHER INFORMATION: Synthetic: hu1D11.v1.7, v1.8, v1.9 light chain variable region;

<400> SEQUENCE: 195

Asp Ile Gln Met Thr Gln Ser Pro Ser Ser Leu Ser Ala Ser Val Gly
1 5 10 15

Asp Arg Val Thr Ile Thr Cys Lys Ala Ser Gln Gly Phe Asn Lys Tyr
20 25 30

Val Ala Trp Tyr Gln Gln Lys Pro Gly Lys Ala Pro Lys Leu Leu Ile
35 40 45

Tyr Tyr Thr Ser Thr Leu Gln Pro Gly Val Pro Ser Arg Phe Ser Gly
50 55 60

Ser Gly Ser Gly Arg Asp Tyr Thr Leu Thr Ile Ser Ser Leu Gln Pro
65 70 75 80

Glu Asp Phe Ala Thr Tyr Tyr Cys Leu Gln Tyr Gly Asn Leu Leu Tyr
85 90 95

Ala Phe Gly Gln Gly Thr Lys Val Glu Ile Lys Arg

```
            100                 105


<210> SEQ ID NO 196
<211> LENGTH: 121
<212> TYPE: PRT
<213> ORGANISM: Artificial Sequence
<220> FEATURE:
<223> OTHER INFORMATION: Synthetic:  hu1D11.v1.6 heavy chain variable
      region; hu1D11.v1.7 heavy chain variable region

<400> SEQUENCE: 196

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 197
<211> LENGTH: 121
<212> TYPE: PRT
<213> ORGANISM: Artificial Sequence
<220> FEATURE:
<223> OTHER INFORMATION: Synthetic:  hu1D11.v1.8 heavy chain variable
      region

<400> SEQUENCE: 197

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile Gly Trp Val Arg Gln Ala Pro Gly Gln Gly Leu Glu Trp Ile
        35                  40                  45

Gly Asp Ile Tyr Pro Gly Gly Gly Tyr Thr Asn Tyr Asn Glu Lys Phe
    50                  55                  60

Lys Gly Arg Ala Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Leu Asp Gly Ser Ser Tyr Arg Gly Ala Met Asp Ser Trp Gly
            100                 105                 110

Gln Gly Thr Leu Val Thr Val Ser Ser
        115                 120


<210> SEQ ID NO 198
<211> LENGTH: 121
<212> TYPE: PRT
<213> ORGANISM: Artificial Sequence
<220> FEATURE:
<223> OTHER INFORMATION: Synthetic:  hu1D11.v1.9 heavy chain variable
```

region; hu1D11.v1.9 varD heavy chain variable region

<400> SEQUENCE: 198

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Ile Gly Trp Val Arg Gln Ala Pro Gly Gln Gly Leu Glu Trp Ile
35 40 45

Gly Asp Ile Tyr Pro Gly Gly Gly Tyr Thr Asn Tyr Asn Glu Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Leu Asp Gly Ser Ser Tyr Arg Gly Ala Met Asp Ser Trp Gly
100 105 110

Gln Gly Thr Leu Val Thr Val Ser Ser
115 120

<210> SEQ ID NO 199
<211> LENGTH: 10
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HVR H1

<400> SEQUENCE: 199

Gly Tyr Thr Phe Thr Ser Tyr Trp Ile Gly
1 5 10

<210> SEQ ID NO 200
<211> LENGTH: 17
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HVR H2

<400> SEQUENCE: 200

Asp Ile Tyr Pro Gly Gly Gly Tyr Thr Asn Tyr Asn Glu Lys Phe Lys
1 5 10 15

Gly

<210> SEQ ID NO 201
<211> LENGTH: 12
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varD HVR H3

<400> SEQUENCE: 201

Leu Asp Gly Ser Ser Tyr Arg Gly Ala Met Asp Ser
1 5 10

<210> SEQ ID NO 202
<211> LENGTH: 11
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HVR L1

<400> SEQUENCE: 202

Lys Ala Ser Gln Gly Phe Asn Lys Tyr Val Ala
1 5 10

<210> SEQ ID NO 203
<211> LENGTH: 7
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HVR L2

<400> SEQUENCE: 203

Tyr Thr Ser Thr Leu Gln Pro
1 5

<210> SEQ ID NO 204
<211> LENGTH: 9
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9 HVR L3

<400> SEQUENCE: 204

Leu Gln Tyr Gly Asn Leu Leu Tyr Ala
1 5

<210> SEQ ID NO 205
<211> LENGTH: 23
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD light chain (LC) framework 1 (FR1)

<400> SEQUENCE: 205

Asp Ile Gln Met Thr Gln Ser Pro Ser Ser Leu Ser Ala Ser Val Gly
1 5 10 15

Asp Arg Val Thr Ile Thr Cys
20

<210> SEQ ID NO 206
<211> LENGTH: 15
<212> TYPE: PRT
<213> ORGANISM: Artificial Sequence
<220> FEATURE:
<223> OTHER INFORMATION: Synthetic: hu1D11.v1.1, v1.7, v1.8, v1.9, v1.9 varC2, v1.9 varD LC FR2

<400> SEQUENCE: 206

Trp Tyr Gln Gln Lys Pro Gly Lys Ala Pro Lys Leu Leu Ile Tyr
1 5 10 15

<210> SEQ ID NO 207
<211> LENGTH: 32
<212> TYPE: PRT
<213> ORGANISM: Artificial Sequence
<220> FEATURE:
<223> OTHER INFORMATION: Synthetic: hu1D11.v1, v1.4, v1.5, v1.6, v1.7, v1.8, v1.9, v1.9 varC2, v1.9 LC FR3

<400> SEQUENCE: 207

Gly Val Pro Ser Arg Phe Ser Gly Ser Gly Ser Gly Arg Asp Tyr Thr
1 5 10 15

Leu Thr Ile Ser Ser Leu Gln Pro Glu Asp Phe Ala Thr Tyr Tyr Cys
20 25 30

<210> SEQ ID NO 208
<211> LENGTH: 11
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD LC FR4

<400> SEQUENCE: 208

Phe Gly Gln Gly Thr Lys Val Glu Ile Lys Arg
1 5 10

<210> SEQ ID NO 209
<211> LENGTH: 25
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD heavy chain (HC) framework 1 (FR1)

<400> SEQUENCE: 209

Glu Val Gln Leu Val Gln Ser Gly Ala Glu Val Lys Lys Pro Gly Ala
1 5 10 15

Ser Val Lys Val Ser Cys Lys Ala Ser
20 25

<210> SEQ ID NO 210
<211> LENGTH: 14
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HC FR2

<400> SEQUENCE: 210

Trp Val Arg Gln Ala Pro Gly Gln Gly Leu Glu Trp Ile Gly
1 5 10

<210> SEQ ID NO 211
<211> LENGTH: 32
<212> TYPE: PRT
<213> ORGANISM: Artificial Sequence
<220> FEATURE:
<223> OTHER INFORMATION: Synthetic: hu1D11.v1.6 and v1.7 HC FR3

<400> SEQUENCE: 211

Arg Ala Thr Leu Thr Arg Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 212
<211> LENGTH: 32
<212> TYPE: PRT
<213> ORGANISM: Artificial Sequence
<220> FEATURE:

<223> OTHER INFORMATION: Synthetic: hu1D11.v1.8 HC FR3

<400> SEQUENCE: 212

Arg Ala Thr Ile Thr Arg Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 213
<211> LENGTH: 32
<212> TYPE: PRT
<213> ORGANISM: Artificial Sequence
<220> FEATURE:
<223> OTHER INFORMATION: Synthetic: hu1D11.v1.9, v1.9 varC2, v1.9 varD HC FR3

<400> SEQUENCE: 213

Arg Val Thr Ile Thr Arg Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 214
<211> LENGTH: 11
<212> TYPE: PRT
<213> ORGANISM: Artificial Sequence
<220> FEATURE:
<223> OTHER INFORMATION: Synthetic: hu1D11.v1, v2, v3, v4, v1.1, v1.2, v1.3, v1.4, v1.5, v1.6, v1.7, v1.8, v1.9, v1.9 varC2, v1.9 varD HC FR4

<400> SEQUENCE: 214

Trp Gly Gln Gly Thr Leu Val Thr Val Ser Ser
1 5 10

<210> SEQ ID NO 215
<211> LENGTH: 106
<212> TYPE: PRT
<213> ORGANISM: Artificial Sequence
<220> FEATURE:
<223> OTHER INFORMATION: Synthetic: hu22C10.v2, v3, v4, v5, v2.3, v2.4, v2.5, v2.6, v2.7 light chain variable region

<400> SEQUENCE: 215

Asp Ile Gln Met Thr Gln Ser Pro Ser Ser Leu Ser Ala Ser Val Gly
1 5 10 15

Asp Arg Val Thr Ile Thr Cys Ser Ala Thr Ser Ser Ile Ser Tyr Met
20 25 30

His Trp Tyr Gln Gln Lys Pro Gly Lys Ala Pro Lys Gly Trp Ile Tyr
35 40 45

Asp Thr Ser Lys Leu Ala His Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys His Gln Arg Arg Ser Tyr Pro Phe Thr
85 90 95

Phe Gly Gln Gly Thr Lys Val Glu Ile Lys
100 105

<210> SEQ ID NO 216
<211> LENGTH: 116
<212> TYPE: PRT
<213> ORGANISM: Artificial Sequence
<220> FEATURE:
<223> OTHER INFORMATION: Synthetic: hu22C10.v2.7 heavy chain variable region; hu22C10.v2.8 heavy chain variable region

<400> SEQUENCE: 216

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Phe
20 25 30

Trp Ile His Trp Val Arg Gln Ala Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Arg Val Thr Ile Thr Arg Asp Thr Ser Thr Ser Thr Ala Tyr
65 70 75 80

Leu Glu Leu Ser Ser Leu Arg Ser Glu Asp Thr Ala Val Tyr Tyr Cys
85 90 95

Ala Arg Glu Ile Thr Thr Val Asp Tyr Trp Gly Gln Gly Thr Leu Val
100 105 110

Thr Val Ser Ser
115

<210> SEQ ID NO 217
<211> LENGTH: 106
<212> TYPE: PRT
<213> ORGANISM: Artificial Sequence
<220> FEATURE:
<223> OTHER INFORMATION: Synthetic: hu22C10.v2.8 light chain variable region

<400> SEQUENCE: 217

Asp Ile Gln Met Thr Gln Ser Pro Ser Ser Leu Ser Ala Ser Val Gly
1 5 10 15

Asp Arg Val Thr Ile Thr Cys Ser Ala Thr Ser Ser Ile Ser Tyr Met
20 25 30

His Trp Tyr Gln Gln Lys Pro Gly Lys Ala Pro Lys Gly Leu Ile Tyr
35 40 45

Asp Thr Ser Lys Leu Ala His Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys His Gln Arg Arg Ser Tyr Pro Phe Thr
85 90 95

Phe Gly Gln Gly Thr Lys Val Glu Ile Lys
100 105

<210> SEQ ID NO 218
<211> LENGTH: 10
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR H1

<400> SEQUENCE: 218

Gly Tyr Thr Phe Thr Asn Phe Trp Ile His
1 5 10

<210> SEQ ID NO 219
<211> LENGTH: 17

<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR H2

<400> SEQUENCE: 219

Glu Ile Asp Pro Ser Asp Ser Tyr Thr Asn Tyr Asn Gln Lys Phe Lys
1 5 10 15

Gly

<210> SEQ ID NO 220
<211> LENGTH: 7
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR H3

<400> SEQUENCE: 220

Glu Ile Thr Thr Val Asp Tyr
1 5

<210> SEQ ID NO 221
<211> LENGTH: 10
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR L1

<400> SEQUENCE: 221

Ser Ala Thr Ser Ser Ile Ser Tyr Met His
1 5 10

<210> SEQ ID NO 222
<211> LENGTH: 7
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR L2

<400> SEQUENCE: 222

Asp Thr Ser Lys Leu Ala His
1 5

<210> SEQ ID NO 223
<211> LENGTH: 9
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HVR L3

<400> SEQUENCE: 223

His Gln Arg Arg Ser Tyr Pro Phe Thr
1 5

<210> SEQ ID NO 224
<211> LENGTH: 23
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 LC FR1

<400> SEQUENCE: 224

```
Asp Ile Gln Met Thr Gln Ser Pro Ser Ser Leu Ser Ala Ser Val Gly
1               5                   10                  15

Asp Arg Val Thr Ile Thr Cys
            20


<210> SEQ ID NO 225
<211> LENGTH: 15
<212> TYPE: PRT
<213> ORGANISM: Artificial Sequence
<220> FEATURE:
<223> OTHER INFORMATION: Synthetic:  hu22C10.v1, v2, v3, v4, v5, v2.1,
      v2.2, v2.3, v2.4, v2.5, v.2.6, v2.7 LC FR2

<400> SEQUENCE: 225

Trp Tyr Gln Gln Lys Pro Gly Lys Ala Pro Lys Gly Trp Ile Tyr
1               5                   10                  15


<210> SEQ ID NO 226
<211> LENGTH: 15
<212> TYPE: PRT
<213> ORGANISM: Artificial Sequence
<220> FEATURE:
<223> OTHER INFORMATION: Synthetic:  hu22C10.v2.8 LC FR2

<400> SEQUENCE: 226

Trp Tyr Gln Gln Lys Pro Gly Lys Ala Pro Lys Gly Leu Ile Tyr
1               5                   10                  15


<210> SEQ ID NO 227
<211> LENGTH: 32
<212> TYPE: PRT
<213> ORGANISM: Artificial Sequence
<220> FEATURE:
<223> OTHER INFORMATION: Synthetic:  hu22C10.v2, v3, v4, v5, v2.1, v2.2,
      v2.3, v2.4, v2.5, v.2.6, v2.7, v2.8 LC FR3

<400> SEQUENCE: 227

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30


<210> SEQ ID NO 228
<211> LENGTH: 11
<212> TYPE: PRT
<213> ORGANISM: Artificial Sequence
<220> FEATURE:
<223> OTHER INFORMATION: Synthetic:  hu22C10.v1, v2, v3, v4, v5, v2.1,
      v2.2, v2.3, v2.4, v2.5, v.2.6, v2.7, v2.8 LC FR4

<400> SEQUENCE: 228

Phe Gly Gln Gly Thr Lys Val Glu Ile Lys Arg
1               5                   10


<210> SEQ ID NO 229
<211> LENGTH: 25
<212> TYPE: PRT
<213> ORGANISM: Artificial Sequence
<220> FEATURE:
<223> OTHER INFORMATION: Synthetic:  hu22C10.v1, v2, v3, v4, v5, v2.1,
      v2.2, v2.3, v2.4, v2.5, v.2.6, v2.7, v2.8 HC FR1

<400> SEQUENCE: 229

Glu Val Gln Leu Val Gln Ser Gly Ala Glu Val Lys Lys Pro Gly Ala
1               5                   10                  15
```

Ser Val Lys Val Ser Cys Lys Ala Ser
20 25

<210> SEQ ID NO 230
<211> LENGTH: 14
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HC FR2

<400> SEQUENCE: 230

Trp Val Arg Gln Ala Pro Gly Gln Gly Leu Glu Trp Ile Gly
1 5 10

<210> SEQ ID NO 231
<211> LENGTH: 32
<212> TYPE: PRT
<213> ORGANISM: Artificial Sequence
<220> FEATURE:
<223> OTHER INFORMATION: Synthetic: hu22C10.v2.7 and v2.8 HC FR3

<400> SEQUENCE: 231

Arg Val Thr Ile Thr Arg Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 232
<211> LENGTH: 11
<212> TYPE: PRT
<213> ORGANISM: Artificial Sequence
<220> FEATURE:
<223> OTHER INFORMATION: Synthetic: hu22C10.v1, v2, v3, v4, v5, v2.1, v2.2, v2.3, v2.4, v2.5, v.2.6, v2.7, v2.8 HC FR4

<400> SEQUENCE: 232

Trp Gly Gln Gly Thr Leu Val Thr Val Ser Ser
1 5 10

<210> SEQ ID NO 233
<211> LENGTH: 282
<212> TYPE: PRT
<213> ORGANISM: Human
<220> FEATURE:
<221> NAME/KEY: misc_feature
<222> LOCATION: (1)..(282)
<223> OTHER INFORMATION: Human B7_H4 precursor; signal sequence = amino acids 1-28

<400> SEQUENCE: 233

Met Ala Ser Leu Gly Gln Ile Leu Phe Trp Ser Ile Ile Ser Ile Ile
1 5 10 15

Ile Ile Leu Ala Gly Ala Ile Ala Leu Ile Ile Gly Phe Gly Ile Ser
20 25 30

Gly Arg His Ser Ile Thr Val Thr Thr Val Ala Ser Ala Gly Asn Ile
35 40 45

Gly Glu Asp Gly Ile Leu Ser Cys Thr Phe Glu Pro Asp Ile Lys Leu
50 55 60

Ser Asp Ile Val Ile Gln Trp Leu Lys Glu Gly Val Leu Gly Leu Val
65 70 75 80

His Glu Phe Lys Glu Gly Lys Asp Glu Leu Ser Glu Gln Asp Glu Met
85 90 95

Phe Arg Gly Arg Thr Ala Val Phe Ala Asp Gln Val Ile Val Gly Asn

```
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280


<210> SEQ ID NO 234
<211> LENGTH: 254
<212> TYPE: PRT
<213> ORGANISM: Human
<220> FEATURE:
<221> NAME/KEY: misc_feature
<222> LOCATION: (1)..(254)
<223> OTHER INFORMATION: Human B7-H4 mature, without signal sequence;
      amino acids 29 to 282

<400> SEQUENCE: 234

Phe Gly Ile Ser Gly Arg His Ser Ile Thr Val Thr Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Leu Gly Leu Val His Glu Phe Lys Glu Gly Lys Asp Glu Leu Ser Glu
    50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
```

```
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser Leu Cys Val Ser Ser Phe Phe Ala Ile
225                 230                 235                 240

Ser Trp Ala Leu Leu Pro Leu Ser Pro Tyr Leu Met Leu Lys
                245                 250


<210> SEQ ID NO 235
<211> LENGTH: 282
<212> TYPE: PRT
<213> ORGANISM: Cynomolgus monkey
<220> FEATURE:
<221> NAME/KEY: misc_feature
<222> LOCATION: (1)..(282)
<223> OTHER INFORMATION: Cynomolgus monkey B7-H4 precursor; signal
      sequence = amino acids 1-28

<400> SEQUENCE: 235

Met Ala Ser Leu Gly Gln Ile Leu Phe Trp Ser Ile Ile Ser Ile Ile
1               5                   10                  15

Phe Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
```

```
            260                 265                 270

Leu Pro Leu Ala Pro Tyr Leu Met Leu Lys
        275                 280


<210> SEQ ID NO 236
<211> LENGTH: 254
<212> TYPE: PRT
<213> ORGANISM: Cynomolgus monkey
<220> FEATURE:
<221> NAME/KEY: misc_feature
<222> LOCATION: (1)..(254)
<223> OTHER INFORMATION: Cynomolgus monkey B7-H4 mature, without signal
      sequence; amino acids 29-282

<400> SEQUENCE: 236

Phe Gly Ile Ser Gly Arg His Ser Ile Thr Val Thr Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Ile Gly Leu Val His Glu Phe Lys Glu Gly Lys Asp Glu Leu Ser Glu
    50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser Leu Cys Val Ser Ser Phe Leu Ala Ile
225                 230                 235                 240

Ser Trp Ala Leu Leu Pro Leu Ala Pro Tyr Leu Met Leu Lys
                245                 250


<210> SEQ ID NO 237
<211> LENGTH: 282
<212> TYPE: PRT
<213> ORGANISM: Rat
<220> FEATURE:
<221> NAME/KEY: misc_feature
<222> LOCATION: (1)..(282)
<223> OTHER INFORMATION: Rat B7-H4 precursor; signal sequence = amino
      acids 1-28

<400> SEQUENCE: 237
```

```
Met Ala Ser Leu Gly Gln Ile Ile Phe Trp Ser Ile Ile Asn Val Ile
1               5                   10                  15

Ile Ile Leu Ala Gly Ala Ile Val Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile His Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Glu Leu Leu Asn Ser
                245                 250                 255

Gly Pro Ser Pro Cys Val Ser Ser Val Ser Ala Ala Gly Trp Ala Leu
            260                 265                 270

Leu Ser Leu Ser Cys Cys Leu Met Leu Arg
        275                 280
```

<210> SEQ ID NO 238
<211> LENGTH: 254
<212> TYPE: PRT
<213> ORGANISM: Rat
<220> FEATURE:
<221> NAME/KEY: misc_feature
<222> LOCATION: (1)..(254)
<223> OTHER INFORMATION: Rat B7-H4 mature, without signal sequence; amino acids 29-282

<400> SEQUENCE: 238

```
Phe Gly Ile Ser Gly Lys His Phe Ile Thr Val Thr Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
        35                  40                  45

Lys Gly Leu Val His Glu Phe Lys Glu Gly Lys Asp Asp Leu Ser Gln
    50                  55                  60
```

-continued

```
Gln His Glu Met Phe Arg Gly Arg Thr Ala Val Phe Ala Asp Gln Val
65                  70                  75                  80

Val Val Gly Asn Ala Ser Leu Arg Leu Lys Asn Val Gln Leu Thr Asp
                85                  90                  95

Ala Gly Thr Tyr Thr Cys Tyr Ile His Thr Ser Lys Gly Lys Gly Asn
            100                 105                 110

Ala Asn Leu Glu Tyr Lys Thr Gly Ala Phe Ser Met Pro Glu Ile Asn
        115                 120                 125

Val Asp Tyr Asn Ala Ser Ser Glu Ser Leu Arg Cys Glu Ala Pro Arg
    130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Glu
    210                 215                 220

Leu Leu Asn Ser Gly Pro Ser Pro Cys Val Ser Ser Val Ser Ala Ala
225                 230                 235                 240

Gly Trp Ala Leu Leu Ser Leu Ser Cys Cys Leu Met Leu Arg
                245                 250
```

<210> SEQ ID NO 239
<211> LENGTH: 283
<212> TYPE: PRT
<213> ORGANISM: Mouse
<220> FEATURE:
<221> NAME/KEY: misc_feature
<222> LOCATION: (1)..(283)
<223> OTHER INFORMATION: Mouse B7-H4 precursor; signal sequence = amino acids 1-28

<400> SEQUENCE: 239

```
Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160
```

-continued

```
Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Ala Ala Gly Trp Ala
            260                 265                 270

Leu Leu Ser Leu Ser Cys Cys Leu Met Leu Arg
        275                 280


<210> SEQ ID NO 240
<211> LENGTH: 255
<212> TYPE: PRT
<213> ORGANISM: Mouse
<220> FEATURE:
<221> NAME/KEY: misc_feature
<222> LOCATION: (1)..(255)
<223> OTHER INFORMATION: Mouse B7-H4 mature, without signal sequence;
      amino acids 29 to 283

<400> SEQUENCE: 240

Phe Gly Ile Ser Gly Lys His Phe Ile Thr Val Thr Thr Phe Thr Ser
1               5                   10                  15

Ala Gly Asn Ile Gly Glu Asp Gly Thr Leu Ser Cys Thr Phe Glu Pro
            20                  25                  30

Asp Ile Lys Leu Asn Gly Ile Val Ile Gln Trp Leu Lys Glu Gly Ile
        35                  40                  45

Lys Gly Leu Val His Glu Phe Lys Glu Gly Lys Asp Asp Leu Ser Gln
    50                  55                  60

Gln His Glu Met Phe Arg Gly Arg Thr Ala Val Phe Ala Asp Gln Val
65                  70                  75                  80

Val Val Gly Asn Ala Ser Leu Arg Leu Lys Asn Val Gln Leu Thr Asp
                85                  90                  95

Ala Gly Thr Tyr Thr Cys Tyr Ile Arg Thr Ser Lys Gly Lys Gly Asn
            100                 105                 110

Ala Asn Leu Glu Tyr Lys Thr Gly Ala Phe Ser Met Pro Glu Ile Asn
        115                 120                 125

Val Asp Tyr Asn Ala Ser Ser Glu Ser Leu Arg Cys Glu Ala Pro Arg
    130                 135                 140

Trp Phe Pro Gln Pro Thr Val Ala Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Asp Ser Glu Val Lys Arg Arg Ser Gln Leu Gln
    210                 215                 220
```

```
Leu Leu Asn Ser Gly Pro Ser Pro Cys Val Phe Ser Ser Ala Phe Ala
225                 230                 235                 240

Ala Gly Trp Ala Leu Leu Ser Leu Ser Cys Cys Leu Met Leu Arg
                245                 250                 255


<210> SEQ ID NO 241
<211> LENGTH: 278
<212> TYPE: PRT
<213> ORGANISM: Chimpanzee
<220> FEATURE:
<221> NAME/KEY: misc_feature
<222> LOCATION: (1)..(278)
<223> OTHER INFORMATION: Chimp B7-H4 precursor; signal sequence = amino
      acids 1-24

<400> SEQUENCE: 241

Met Lys Pro Leu Thr Ser Arg Ile Ile Ser Ile Ile Ile Ile Leu Ala
1               5                   10                  15

Gly Ala Ile Arg Leu Ile Ile Gly Phe Gly Ile Ser Gly Arg His Ser
            20                  25                  30

Ile Thr Val Thr Thr Val Ala Ser Ala Gly Asn Ile Gly Glu Asp Gly
        35                  40                  45

Ile Leu Ser Cys Thr Phe Glu Pro Asp Ile Lys Leu Ser Asp Ile Val
    50                  55                  60

Ile Gln Trp Leu Lys Glu Gly Val Leu Gly Leu Val His Glu Phe Lys
65                  70                  75                  80

Glu Gly Lys Asp Glu Leu Ser Glu Gln Asp Glu Met Phe Arg Gly Arg
                85                  90                  95

Thr Ala Val Phe Ala Asp Gln Val Ile Val Gly Asn Ala Ser Leu Arg
            100                 105                 110

Leu Lys Asn Val Gln Leu Thr Asp Ala Gly Thr Tyr Lys Cys Tyr Ile
        115                 120                 125

Ile Thr Ser Lys Gly Lys Gly Asn Ala Asn Leu Glu Tyr Lys Thr Gly
    130                 135                 140

Ala Phe Ser Met Pro Glu Val Asn Val Asp Tyr Asn Ala Ser Ser Glu
145                 150                 155                 160

Thr Leu Arg Cys Glu Ala Pro Arg Trp Phe Pro Gln Pro Thr Val Val
                165                 170                 175

Trp Ala Ser Gln Ile Asp Gln Gly Ala Asn Phe Ser Glu Val Ser Asn
            180                 185                 190

Thr Ser Phe Glu Leu Asn Ser Glu Asn Val Thr Met Lys Val Val Ser
        195                 200                 205

Val Leu Tyr Asn Ala Thr Ile Asn Asn Thr Tyr Ser Cys Met Ile Glu
    210                 215                 220

Asn Asp Ile Ala Lys Ala Thr Gly Asp Ile Lys Val Thr Glu Ser Glu
225                 230                 235                 240

Ile Lys Arg Arg Ser His Leu Gln Leu Leu Asn Ser Lys Ala Ser Leu
                245                 250                 255

Cys Val Ser Ser Phe Phe Ala Ile Ser Trp Ala Leu Leu Pro Leu Ser
            260                 265                 270

Pro Tyr Leu Met Leu Lys
        275


<210> SEQ ID NO 242
<211> LENGTH: 254
<212> TYPE: PRT
<213> ORGANISM: Chimpanzee
<220> FEATURE:
```

<221> NAME/KEY: misc_feature
<222> LOCATION: (1)..(254)
<223> OTHER INFORMATION: Chimp B7-H4 mature, without signal sequence; amino acids 25 to 278

<400> SEQUENCE: 242

```
Phe Gly Ile Ser Gly Arg His Ser Ile Thr Val Thr Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Leu Gly Leu Val His Glu Phe Lys Glu Gly Lys Asp Glu Leu Ser Glu
    50                  55                  60

Gln Asp Glu Met Phe Arg Gly Arg Thr Ala Val Phe Ala Asp Gln Val
65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Ile Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Ala Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser Leu Cys Val Ser Ser Phe Phe Ala Ile
225                 230                 235                 240

Ser Trp Ala Leu Leu Pro Leu Ser Pro Tyr Leu Met Leu Lys
                245                 250
```

<210> SEQ ID NO 243
<211> LENGTH: 15
<212> TYPE: PRT
<213> ORGANISM: Artificial Sequence
<220> FEATURE:
<223> OTHER INFORMATION: Synthetic: hu1D11.v1, v2, v3, v4, v1.2, v.1.3, v1.4, v1.5, v.1.6 LC FR2

<400> SEQUENCE: 243

```
Trp Tyr Gln Gln Lys Pro Gly Lys Ala Pro Lys Leu Leu Ile His
1               5                   10                  15
```

<210> SEQ ID NO 244
<211> LENGTH: 32
<212> TYPE: PRT
<213> ORGANISM: Artificial Sequence
<220> FEATURE:
<223> OTHER INFORMATION: Synthetic: hu1D11.v2 LC FR3

<400> SEQUENCE: 244

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Thr Tyr Tyr Cys
20 25 30

<210> SEQ ID NO 245
<211> LENGTH: 32
<212> TYPE: PRT
<213> ORGANISM: Artificial Sequence
<220> FEATURE:
<223> OTHER INFORMATION: Synthetic: hu1D11.v3 and v4 LC FR3

<400> SEQUENCE: 245

Gly Ile Pro Ser Arg Phe Ser Gly Ser Gly Ser Gly Arg Asp Tyr Thr
1 5 10 15

Leu Thr Ile Ser Ser Leu Gln Pro Glu Asp Phe Ala Thr Tyr Tyr Cys
20 25 30

<210> SEQ ID NO 246
<211> LENGTH: 32
<212> TYPE: PRT
<213> ORGANISM: Artificial Sequence
<220> FEATURE:
<223> OTHER INFORMATION: Synthetic: hu1D11.v1.2 LC FR3

<400> SEQUENCE: 246

Gly Val Pro Ser Arg Phe Ser Gly Ser Gly Ser Gly Thr Asp Tyr Thr
1 5 10 15

Leu Thr Ile Ser Ser Leu Gln Pro Glu Asp Phe Ala Thr Tyr Tyr Cys
20 25 30

<210> SEQ ID NO 247
<211> LENGTH: 32
<212> TYPE: PRT
<213> ORGANISM: Artificial Sequence
<220> FEATURE:
<223> OTHER INFORMATION: Synthetic: hu1D11.v1.3 LC FR3

<400> SEQUENCE: 247

Gly Val Pro Ser Arg Phe Ser Gly Ser Gly Ser Gly Arg Asp Phe Thr
1 5 10 15

Leu Thr Ile Ser Ser Leu Gln Pro Glu Asp Phe Ala Thr Tyr Tyr Cys
20 25 30

<210> SEQ ID NO 248
<211> LENGTH: 32
<212> TYPE: PRT
<213> ORGANISM: Artificial Sequence
<220> FEATURE:
<223> OTHER INFORMATION: Synthetic: hu1D11.v1, v2, v1.1, v1.2, v1.3 HC
FR3

<400> SEQUENCE: 248

Arg Ala Thr Leu Thr Ala Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 249
<211> LENGTH: 32
<212> TYPE: PRT
<213> ORGANISM: Artificial Sequence
<220> FEATURE:
<223> OTHER INFORMATION: Synthetic: hu1D11.v3 HC FR3

<400> SEQUENCE: 249

Arg Ala Thr Leu Thr Ala Asp Lys Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 250
<211> LENGTH: 32
<212> TYPE: PRT
<213> ORGANISM: Artificial Sequence
<220> FEATURE:
<223> OTHER INFORMATION: Synthetic: hu1D11.v4 HC FR3

<400> SEQUENCE: 250

Arg Ala Thr Leu Thr Ala Asp Lys Ser Ser Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 251
<211> LENGTH: 32
<212> TYPE: PRT
<213> ORGANISM: Artificial Sequence
<220> FEATURE:
<223> OTHER INFORMATION: Synthetic: hu1D11.v1.4 HC FR3

<400> SEQUENCE: 251

Arg Val Thr Leu Thr Ala Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 252
<211> LENGTH: 32
<212> TYPE: PRT
<213> ORGANISM: Artificial Sequence
<220> FEATURE:
<223> OTHER INFORMATION: Synthetic: hu1D11.v1.5 HC FR3

<400> SEQUENCE: 252

Arg Ala Thr Ile Thr Ala Asp Thr Ser Thr Ser Thr Ala Tyr Leu Glu
1 5 10 15

Leu Ser Ser Leu Arg Ser Glu Asp Thr Ala Val Tyr Tyr Cys Ala Arg
20 25 30

<210> SEQ ID NO 253
<211> LENGTH: 108
<212> TYPE: PRT
<213> ORGANISM: Artificial Sequence
<220> FEATURE:
<223> OTHER INFORMATION: Synthetic: hu1D11.v1, v1.4, v1.5, v1.6 light chain variable region;

<400> SEQUENCE: 253

Asp Ile Gln Met Thr Gln Ser Pro Ser Ser Leu Ser Ala Ser Val Gly
1 5 10 15

Asp Arg Val Thr Ile Thr Cys Lys Ala Ser Gln Gly Phe Asn Lys Tyr
20 25 30

Val Ala Trp Tyr Gln Gln Lys Pro Gly Lys Ala Pro Lys Leu Leu Ile
35 40 45

His Tyr Thr Ser Thr Leu Gln Pro Gly Val Pro Ser Arg Phe Ser Gly
50 55 60

-continued

```
Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105


<210> SEQ ID NO 254
<211> LENGTH: 108
<212> TYPE: PRT
<213> ORGANISM: Artificial Sequence
<220> FEATURE:
<223> OTHER INFORMATION: Synthetic:  hu1D11.v1.3 light chain variable
      region

<400> SEQUENCE: 254

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105


<210> SEQ ID NO 255
<211> LENGTH: 108
<212> TYPE: PRT
<213> ORGANISM: Artificial Sequence
<220> FEATURE:
<223> OTHER INFORMATION: Synthetic:  hu1D11.v1.2 light chain variable
      region

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Phe Asn Lys Tyr
            20                  25                  30

Val Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105


<210> SEQ ID NO 256
<211> LENGTH: 108
<212> TYPE: PRT
<213> ORGANISM: Artificial Sequence
<220> FEATURE:
```

<223> OTHER INFORMATION: Synthetic: hu1D11.v1.1 light chain variable region

<400> SEQUENCE: 256

Asp Ile Gln Met Thr Gln Ser Pro Ser Ser Leu Ser Ala Ser Val Gly
1 5 10 15

Asp Arg Val Thr Ile Thr Cys Lys Ala Ser Gln Gly Phe Asn Lys Tyr
20 25 30

Val Ala Trp Tyr Gln Gln Lys Pro Gly Lys Ala Pro Lys Leu Leu Ile
35 40 45

Tyr Tyr Thr Ser Thr Leu Gln Pro Gly Val Pro Ser Arg Phe Ser Gly
50 55 60

Ser Gly Ser Gly Arg Asp Tyr Thr Leu Thr Ile Ser Ser Leu Gln Pro
65 70 75 80

Glu Asp Phe Ala Thr Tyr Tyr Cys Leu Gln Tyr Gly Asn Leu Leu Tyr
85 90 95

Ala Phe Gly Gln Gly Thr Lys Val Glu Ile Lys Arg
100 105

<210> SEQ ID NO 257
<211> LENGTH: 108
<212> TYPE: PRT
<213> ORGANISM: Artificial Sequence
<220> FEATURE:
<223> OTHER INFORMATION: Synthetic: hu1D11.v2 light chain variable region

<400> SEQUENCE: 257

Asp Ile Gln Met Thr Gln Ser Pro Ser Ser Leu Ser Ala Ser Val Gly
1 5 10 15

Asp Arg Val Thr Ile Thr Cys Lys Ala Ser Gln Gly Phe Asn Lys Tyr
20 25 30

Val Ala Trp Tyr Gln Gln Lys Pro Gly Lys Ala Pro Lys Leu Leu Ile
35 40 45

His Tyr Thr Ser Thr Leu Gln Pro Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Gly Asn Leu Leu Tyr
85 90 95

Ala Phe Gly Gln Gly Thr Lys Val Glu Ile Lys Arg
100 105

<210> SEQ ID NO 258
<211> LENGTH: 108
<212> TYPE: PRT
<213> ORGANISM: Artificial Sequence
<220> FEATURE:
<223> OTHER INFORMATION: Synthetic: hu1D11.v3 light chain variable region; hu1D11.v4 light chain variable region

<400> SEQUENCE: 258

Asp Ile Gln Met Thr Gln Ser Pro Ser Ser Leu Ser Ala Ser Val Gly
1 5 10 15

Asp Arg Val Thr Ile Thr Cys Lys Ala Ser Gln Gly Phe Asn Lys Tyr
20 25 30

Val Ala Trp Tyr Gln Gln Lys Pro Gly Lys Ala Pro Lys Leu Leu Ile
35 40 45

His Tyr Thr Ser Thr Leu Gln Pro Gly Ile Pro Ser Arg Phe Ser Gly

-continued

```
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Gly Asn Leu Leu Tyr
                85                  90                  95

Ala Phe Gly Gln Gly Thr Lys Val Glu Ile Lys Arg
            100                 105
```